US009718790B2

(12) United States Patent
Kai et al.

(10) Patent No.: US 9,718,790 B2
(45) Date of Patent: Aug. 1, 2017

(54) TRIAZINE DERIVATIVE AND PHARMACEUTICAL COMPOSITION HAVING AN ANALGESIC ACTIVITY COMPRISING THE SAME

(75) Inventors: Hiroyuki Kai, Toyonaka (JP); Tohru Horiguchi, Toyonaka (JP); Kentaro Asahi, Toyonaka (JP); Yasuhiko Fujii, Toyonaka (JP)

(73) Assignee: SHIONOGI & CO., LTD., Osaka (JP)

(*) Notice: Subject to any disclaimer, the term of this patent is extended or adjusted under 35 U.S.C. 154(b) by 431 days.

(21) Appl. No.: 13/814,346

(22) PCT Filed: Aug. 9, 2011

(86) PCT No.: PCT/JP2011/068113
§ 371 (c)(1),
(2), (4) Date: Aug. 27, 2013

(87) PCT Pub. No.: WO2012/020749
PCT Pub. Date: Feb. 16, 2012

(65) Prior Publication Data
US 2013/0172317 A1 Jul. 4, 2013

(30) Foreign Application Priority Data

Aug. 10, 2010 (JP) ................. 2010-179350
Aug. 18, 2010 (JP) ................. 2010-182803
Mar. 30, 2011 (JP) ................. 2011-074763

(51) Int. Cl.
*C07D 251/46* (2006.01)
*C07D 401/12* (2006.01)
(Continued)

(52) U.S. Cl.
CPC ......... *C07D 251/46* (2013.01); *C07D 251/52* (2013.01); *C07D 401/06* (2013.01); *C07D 401/12* (2013.01); *C07D 401/14* (2013.01); *C07D 403/04* (2013.01); *C07D 403/06* (2013.01); *C07D 403/12* (2013.01);
(Continued)

(58) Field of Classification Search
CPC .. C07D 251/46; C07D 251/52; C07D 401/06; C07D 401/12; C07D 401/14; C07D 403/04; C07D 403/06; C07D 403/12; C07D 405/06; C07D 405/12; C07D 405/14; C07D 409/06; C07D 413/06; C07D 413/12;
(Continued)

(56) References Cited

U.S. PATENT DOCUMENTS 3,598,815 A    8/1971 Gilles
4,021,249 A    5/1977 Noguchi et al.
(Continued)

FOREIGN PATENT DOCUMENTS

EP    0 005 911 A1    12/1979
EP    0 547 461 A1    6/1993
(Continued)

OTHER PUBLICATIONS

English-language International Search Report for International Application No. PCT/JP2011/068113 from the Japanese Patent Office mailed Nov. 1, 2011.
Kennedy, "P2X Receptors: Targets for Novel Analgesics?", The Neuroscientist, vol. 11 No. 4, pp. 345-356, (2005).
Cockayne, et al., "P2X$_2$ knockout mice and P2X$_2$/P2X$_3$ double knockout mice reveal a role for the P2X$_2$ receptor subunit in mediating multiple sensory effects of ATP", J. Physiol vol. 567, No. 2, pp. 621-639, (2005).
Shieh, et al., "P2X receptor ligands and pain", Expert Opinion Ther. Patens, vol. 16, No. 8, pp. 1113-1127, (2006).
North, "P2X$_3$ receptors and peripheral pain mechanisms", Symposium Report, J. Physiol, vol. 554, No. 2, pp. 301-308, (2003).
Kennedy, et al., "Topical Review, Crossing the pain barrier: P2 receptors as targets for novel analgesics", J. Physiol, vol. 553, No. 3, pp. 683-694, (2003).
Gever, et al., "Pharmacology of P2X channels", Pflugers Arch—Eur J Physiol, vol. 452, pp. 513-537, (2006).
Jarvis, et al., "A-317491, a novel potent and selective non-nucleotide antagonist of P2X$_3$ and P2X$_{2/3}$ receptors, reduces chronic inflammatory and neuropathic pain in the rat", PNAS, vol. 99, No. 26, pp. 17179-17184, (Dec. 24, 2002).
Balboni, et al., "Triazine Compounds as Antagonists at Bv8-Prokineticin Receptors", J. Med. Chem., vol. 51, No. 23, pp. 7635-7639, (2008).
(Continued)

*Primary Examiner* — Irina Neagu
(74) *Attorney, Agent, or Firm* — Finnegan, Henderson, Farabow, Garrett & Dunner, LLP

(57) ABSTRACT

The present invention provides novel compounds having a P2X$_3$ and/or P2X$_{2/3}$ receptor antagonistic effect.
A pharmaceutical composition having an analgesic effect or an improving effect of urination disorder comprising a compound of the formula (I):

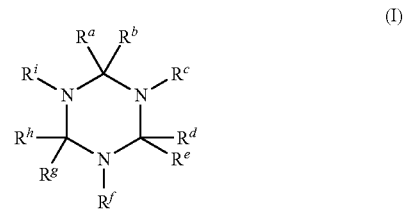

wherein
R$^h$ and R$^i$ are taken together to form a bond; R$^a$ and R$^b$ and/or R$^d$ and R$^e$ are taken together to form oxo or the like; R$^c$ is hydrogen, substituted or unsubstituted alkyl or the like; R$^f$ is —(CR$^{4a}$R$^{4b}$)$_n$—R$^2$; R$^{4a}$ and R$^{4b}$ are hydrogen, substituted or unsubstituted alkyl or the like; R$^2$ is substituted or unsubstjtuted cycloalkyl or the like; n is an integer of 1 to 4; —R$^g$ is —X—R$^3$; —X— is —O—, —S— or the like; R$^3$ is substituted or unsubstituted cycloalkyl or the like,
or its pharmaceutically acceptable salt or a solvate thereof.

10 Claims, No Drawings

(51) Int. Cl.

| | | |
|---|---|---|
| *C07D 401/14* | (2006.01) | |
| *C07D 403/12* | (2006.01) | |
| *C07D 413/12* | (2006.01) | |
| *C07D 417/12* | (2006.01) | |
| *A61P 25/02* | (2006.01) | |
| *C07D 401/06* | (2006.01) | |
| *C07D 403/06* | (2006.01) | |
| *C07D 405/06* | (2006.01) | |
| *C07D 405/12* | (2006.01) | |
| *C07D 409/06* | (2006.01) | |
| *C07D 413/06* | (2006.01) | |
| *C07D 413/14* | (2006.01) | |
| *C07D 417/06* | (2006.01) | |
| *C07D 417/14* | (2006.01) | |
| *C07D 251/52* | (2006.01) | |
| *C07D 403/04* | (2006.01) | |
| *C07D 405/14* | (2006.01) | |

(52) U.S. Cl.
CPC ......... *C07D 405/06* (2013.01); *C07D 405/12* (2013.01); *C07D 405/14* (2013.01); *C07D 409/06* (2013.01); *C07D 413/06* (2013.01); *C07D 413/12* (2013.01); *C07D 413/14* (2013.01); *C07D 417/06* (2013.01); *C07D 417/12* (2013.01); *C07D 417/14* (2013.01)

(58) Field of Classification Search
CPC .. C07D 413/14; C07D 417/06; C07D 417/12; C07D 417/14
USPC .......................... 544/211, 212, 223; 514/245
See application file for complete search history.

(56) References Cited

U.S. PATENT DOCUMENTS

| | | | |
|---|---|---|---|
| 4,127,718 A | 11/1978 | Illy et al. | |
| 4,156,002 A | 5/1979 | Brown et al. | |
| 4,158,724 A | 6/1979 | Illy et al. | |
| 4,254,122 A | 3/1981 | Brown | |
| 4,317,911 A | 3/1982 | Rasberger et al. | |
| 4,518,688 A | 5/1985 | Leppard et al. | |
| 5,232,924 A | 8/1993 | Watanabe et al. | |
| 5,389,599 A | 2/1995 | Schallner et al. | |
| 6,177,437 B1 | 1/2001 | Wright | |
| 7,745,451 B2 | 6/2010 | Kelly et al. | |
| 7,858,632 B2 | 12/2010 | Broka et al. | |
| 9,150,546 B2* | 10/2015 | Kai ..................... | C07D 251/46 |
| 2002/0049320 A1 | 4/2002 | Gopalsamy et al. | |
| 2007/0037974 A1 | 2/2007 | Brotherton-Pleiss et al. | |
| 2007/0049534 A1 | 3/2007 | Dillon et al. | |
| 2007/0049609 A1 | 3/2007 | Broka et al. | |
| 2007/0049610 A1 | 3/2007 | Dillon et al. | |
| 2007/0049758 A1 | 3/2007 | Dillon et al. | |
| 2009/0099195 A1 | 4/2009 | Bayrakdarian et al. | |
| 2009/0270369 A1 | 10/2009 | Ozaki et al. | |
| 2010/0317676 A1 | 12/2010 | Kelly et al. | |
| 2011/0077242 A1 | 3/2011 | Broka et al. | |
| 2011/0237578 A1 | 9/2011 | Wei et al. | |
| 2011/0319414 A1* | 12/2011 | Kai et al. .................. | 514/236.2 |
| 2013/0225596 A1 | 8/2013 | Kai et al. | |
| 2016/0024072 A1 | 1/2016 | Kai et al. | |
| 2016/0115151 A1 | 4/2016 | Kai | |

FOREIGN PATENT DOCUMENTS

| | | |
|---|---|---|
| EP | 2 399 910 A1 | 12/2011 |
| JP | 57-144269 | 9/1982 |
| JP | 62-156110 | 7/1987 |
| JP | 11-189577 | 7/1999 |
| JP | 2000-72757 | 3/2000 |
| JP | 2001-131156 | 5/2001 |
| JP | 2006528640 | 2/2005 |
| JP | 2007-526268 | 9/2007 |
| JP | 2008-546639 | 12/2008 |
| JP | 2009-007258 | 1/2009 |
| JP | 2010-526138 | 7/2010 |
| JP | 2010523667 | 7/2010 |
| RU | 867303 | 9/1981 |
| RU | 2057754 | 4/1996 |
| WO | WO-99/52881 | 10/1999 |
| WO | WO-00/39101 | 7/2000 |
| WO | WO-00/51990 | 9/2000 |
| WO | WO-01/55093 | 8/2001 |
| WO | WO 02/094767 A2 | 11/2002 |
| WO | WO-2004/054617 | 7/2004 |
| WO | WO 2005/009980 A1 | 2/2005 |
| WO | WO 2005/095359 A1 | 10/2005 |
| WO | WO 2006/012639 | 2/2006 |
| WO | WO-2006/074057 | 7/2006 |
| WO | WO 2006/102112 A2 | 9/2006 |
| WO | WO 2006/104713 A1 | 10/2006 |
| WO | WO 2006/104715 A1 | 10/2006 |
| WO | WO 2006/119502 A2 | 11/2006 |
| WO | WO 2006/119504 | 11/2006 |
| WO | WO 2007/079163 A2 | 7/2007 |
| WO | WO 2007/079214 A2 | 7/2007 |
| WO | WO 2008/005538 | 1/2008 |
| WO | WO 2008/016522 | 2/2008 |
| WO | WO-2008/089051 | 7/2008 |
| WO | WO 2008/089051 A1 | 7/2008 |
| WO | WO 2008/127591 A2 | 10/2008 |
| WO | WO 2008/136756 A1 | 11/2008 |
| WO | WO 2009/058653 A1 | 5/2009 |
| WO | WO 2010/051188 A1 | 5/2010 |
| WO | WO 2010/092966 | 8/2010 |
| WO | WO 2010/149578 | 12/2010 |
| WO | WO 2011/017347 | 2/2011 |
| WO | WO-2012/016182 | 2/2012 |
| WO | WO 2012/020749 | 2/2012 |
| WO | WO 2012/135800 | 10/2012 |
| WO | WO 2013/089212 | 6/2013 |

OTHER PUBLICATIONS

Bernatowicz, et al., 1*H*-Pyrazole-1-carboxamidine Hydrochloride: An Attractive Reagent for Guanylation of Amines and Its Application to Peptide Synthesis, J. Org. Chem., vol. 57, pp. 2497-2502, (1992).

Schriof-Grégoire, et al., "Preparation of *N*-alkyl-*N'*-carboalkoxy guanidines: unexpected effective trans-alkoxylation transforming the 2,2,2-trichloroethoxycarbonyl into various carbamates", Tetrahedron Letters, vol. 48, pp. 2357-2359, (2007).

Dräger, et al., "A new reagent and its polymer-supported variant for the amidination of amines", Tetrahedron Letters, vol. 43, pp. 1401-1403, (2002).

Pecchi, et al., "Identification and structure-activity relationship of 2-morpholino 6-(3-hydroxyphenyl) pyrimidines, a class of potent and selective PI3 kinase inhibitors", Bioorganic & Medicinal Chemistry Letters, vol. 20, No. 23, pp. 6895-6898, (2010).

Knotz, "1-Chloromethylisatin, an excellent reagent for the identification of carboxylic acids and NH-acid compounds", Scientia Pharmaceutica, vol. 38, No. 4, pp. 227-233, (1970).

Esayan, et al., Synthesis and sulfuric acid hydrolysis Y-chlorocrotylbenzyl (alkyl) isocyanurates, Armyanskii Khimicheskii Zhurnal, vol. 28, No. 4, pp. 332-337, (1975).

Lerchova, et al., "Antioxidants and Stabilizers, L. Transformation of the 1,3,5-Tris(4-hydroxy-3,5-di-tert-butylbenzyl)cyanuric acid into Alkylperoxycyclohexadienones, their Properties and Effects on the Oxidation of Tetralin and Polypropylene", Angewandte Makromolekulare Chemie, vol. 39, No. 1, pp. 107-118, (1974).

Zuen, et al., "Crystalline furanic polyisocyanates", Polymer Bulletin 26, vol. 26, No. 4, pp. 383-390, (1991).

Shao, et al., "Strapped porphyrin rosettes based on the melamine-cyanuric acid motif. Self-assembly and supramolecular recognition", Tetrahedron, vol. 60, No. 41, pp. 9155-9162, (2004).

Akteries et al., "Reactions of Carbonyl Diisocyanate With Amides and Acids," Chem. Ber., vol. 119, pp. 669-682 (1986).

(56) References Cited

OTHER PUBLICATIONS

Carter et al., "Identification and SAR of novel diaminopyrimidines. Part 1: The discovery of RO-4, a dual $P2X_3/P2X_{2/3}$ antagonist for the treatment of pain", Bioorganic & Medicinal Chemistry Letters, vol. 19, pp. 1628-1631, (2009).
Gopalsamy et al., "Combinatorial Synthesis of Heterocycles: Solid-Phase Synthesis of 6-Amino-2,4-Dihydro-1,3,5-Triazine Derivatives," J. Comb. Chem., vol. 3, pp. 278-283 (2001).
Simov et al., "Triazines and Other 6-Membered Rings," Chemical Abstracts, Heterocyclic Compounds, vol. 67, p. 10245 (1967).
Somogyi, L. et al., "Cyclisierungsreaktionen von mono- und disubstituierten Biguaniden mit Phenylisothiocyanat," Chem. Ber., vol. 100; pp. 1975-1982 (1967).
Suyama et al., "The Reaction of 3-Cyano-2-Methyl-1-Phenylisothiourea With Isocyanate, Isothiocyanate and Carbodiimide," Nippon Kagaku Kaishi, No. 9. pp. 845-848 (1996).
English-language International Search Report from the Japanese Patent Office for International Application No. PCT/JP2010/051920 (Mail date Mar. 30, 2010).
Notification of Transmittal of Translation of the International Preliminary Report on Patentability, International Preliminary Report on Patentability, and Translation of the Written Opinion of the International Searching Authority, for International Patent Application No. PCT/JP2010/051920, mailed Sep. 22, 2011 (14 pages).
Supplementary European Search Report for European Application No. 10741243, mailed Sep. 13, 2012.
Adriaensen et al., "Functional Morphology of Pulmonary Neuroepithelial Bodies: Extremely Complex Airway Receptors", The Anatomical Record Part A, vol. 270A, pp. 25-40 (2003).
Basoglu, MD, et al., "Effects of Aerosolized Adenosine 5'—Triphosphate vs Adenosine 5'—Monophosphate on Dyspnea and Airway Caliber in Healthy Nonsmokers and Patients with Asthma", Chest, vol. 128, No. 4, pp. 1905-1909 (2005).
Brouns et al., "Intraepithelial Vagal Sensory Nerve Terminals in Rat Pulmonary Neuroepithelial Bodies Express P2X3 Receptors", Am. J. Respir. Cell Mol. Biol., vol. 23, pp. 52-61 (2000).
English-language Abstract of Okano, Natsuko et al., "Preparation of 2-phenylaminopyrimidinones, intermediates as pesticides and herbicides in agriculture", Chem. Abstracts Service, Columbus, OH (1999); STN Accession No. 1999-672770.
English-language Abstract of Fukuchi, T et al., "Novel 2-aminopyrimidinone derivatives, useful as insecticide and acaricide", Thomson Scientific, London, GB (May 15, 2001); STN Accession No. 2001-468100.
English-language Abstract of Fukuchi, T et al., "2-anilino-4(3H)-pyrimidinone derivatives, pesticidally/herbicidally active, useful in agriculture/horticulture and their preparation", Thomson Scientific, London, GB (2003); STN Accession No. 2003-318151.
Engish-language Abstract of Fukuchi, T et al., "A novel 2-substituted amoni-5,6-dihydro-4(3H)-pyrimidinone derivative", Thomson Scientific, London, GB (2001); STN Accession No. 2001-491646.
English Abstract of WO 9952881 A1 (1999), (via Espacenet).
English Abstract of JP 11-189577 (1999), (Patent Abstracts of Japan).
English Abstract of JP 2009-7258 (2009), (Patent Abstracts of Japan).
English Abstract of WO 01/55093 (2001), (via WIPO Patentscope).

English Abstract of WO 04/054617 (2004), (via WIPO Patentscope).
English Abstract of WO 10/092966 (2010), (via WIPO Patentscope).
English Abstract of WO 12/020749 (2012), (via WIPO Patentscope).
International Search Report from the Japanese Patent Office for International Application No. PCT/JP2013/052991 mailed Mar. 12, 2013.
Ji-Zhen, Li et al., "Polymer Supported Synthesis of Multi-substituted Pyrimidine-4-one Derivatives via Pbf-activated Thiourea", Chem. Research in Chinese Universities, vol. 27, No. 2, (2011) pp. 221-223.
Kennedy et al., "Crossing the pain barrier: P2 receptors as targets for novel anaigesics", J. Physiology, vol. 553, No. 3, pp. 683-694 (2003).
Notification of Transmittal of Translation of the International Preliminary Report on Patentability (PCT/IB/338); English-language translation of International Preliminary Report on Patentability (PCT/IB/373) issued Aug. 12, 2014, and Written Opinion from The International Searching Authority (PCT/ISA/237) mailed Mar. 12, 2013, for International Application No. PCT/JP2013/052991.
Office Action dated Nov. 7, 2014 in U.S. Appl. No. 13/201,209.
Office Action dated Jan. 28, 2015 in U.S. Appl. No. 13/816,085.
Supplementary European Search Report for European Application No. 11816406, mailed Oct. 20, 2014.
CAS RN 857972-98-6 (entered into STN Aug. 3, 2005).
Han, Jun, "Advances in Characterization of Pharmaceutical Hydrates," Trends in Bio/Pharmaceutical Industry, pp. 25-29, Mar. 2006.
Notification of Transmittal of Translation of the International Preliminary Report on Patentability, International Preliminary Report on Patentability, and Translation of the Written Opinion of the International Searching Authority, for International Patent Application No. PCT/JP2011/068097, mailed Mar. 21, 2013 (10 pages).
Notification of Transmittal of Translation of the International Preliminary Report on Patentability, International Preliminary Report on Patentability, and Translation of the Written Opinion of the International Searching Authority, for International Patent Application No. PCT/JP2011/068113, mailed Mar. 21, 2013 (15 pages).
Vippagunta, Sudha R., "Crystalline Solids," Advanced Drug Delivery Reviews 48 (2001) pp. 3-26.
English-language International Search Report for International Application No. PCT/JP2011/068097 from the Japanese Patent Office mailed Nov. 15, 2011.
Office Action dated Apr. 2, 2013 in U.S. Appl. No. 13/201,209.
Office Action dated Dec. 4, 2012 in U.S. Appl. No. 13/201,209.
Cantin, L. et al., Bioorganic & Medicinal Chemistry Letters, vol. 22, p. 2565-2571 (2012).
Jahangir, A. et al., Bioorganic & Medicinal Chemistry Letters, vol. 19, p. 1632-1635 (2009).
Kong, K.H., et al., Chem. Eur. J., vol. 18, p. 1476-1486 (2012).
CAS Registry No. RN 343346-65-6 (Entered STN: Jun. 26, 2001).
CAS Registry No. RN 887418-38-4 (Entered STN: Jun. 12, 2006).
T. Kappe et al., Chemische Berichte, vol. 112, pp. 3424-3421 (1979).

* cited by examiner

TRIAZINE DERIVATIVE AND PHARMACEUTICAL COMPOSITION HAVING AN ANALGESIC ACTIVITY COMPRISING THE SAME

The instant application is a national stage entry of International Application No. PCT/JP2011/068113, filed on Aug. 9, 2011, which claims priority from Japanese Patent Application No. JP 2011 074763, filed on Mar. 30, 2011, from Japanese Patent Application No. JP 2010 182803, filed on Aug. 18, 2010, and from Japanese Patent Application No. JP 2010 179350, filed on Aug. 10, 2010.

TECHNICAL FIELD

The invention relates to a compound useful for the treatment of diseases or conditions associated with P2X receptor, specifically to $P2X_3$ and/or $P2X_{2/3}$ receptor, and a pharmaceutical composition having an analgesic effect, an improving effect of urination disorder comprising such compound.

BACKGROUND ART

Adenosine triphosphate (ATP) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. ATP thus released mediates various extracellular signal transductions through an ATP receptor (Non-Patent Document 4, Non-Patent Document 5).

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel (Non-Patent Document 6).

ATP is known to cause pain, and studies with $P2X_3$ knockout and knockdown methodologies have shown that $P2X_3$ receptor mediates transmission of chronic pain. $P2X_3$ receptors are expressed in a specific manner on peripheral sensory nerve to form a homo-complex or hetero-complex with $P2X_2$ ($P2X_{2/3}$) (Non-Patent Document 1).

Later, the compound A-317491 was reported as a specific antagonist to $P2X_3$ and $P2X_{2/3}$ receptors. A-317491 is tri-substituted-N-[(1S)-1,2,3,4-tetrahydro-1-naphthalenyl]benzamide derivative represented by the formula:

[Chemical Formula 1]

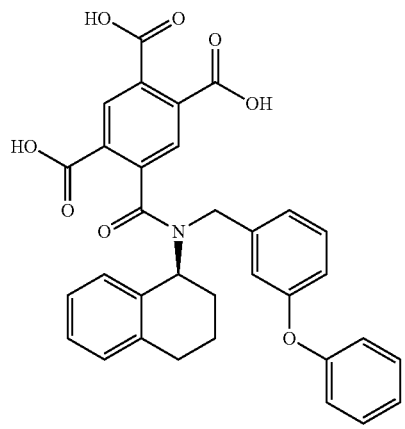

(Patent Document 1). It was reported to exhibit an antagonist activity to $P2X_3$ and $P2X_{2/3}$ receptors and analgesic action in neuropathic pain model and inflammatory pain model (Non-Patent Document 7). This indicates that pain sensation is transmitted via $P2X_3$ or $P2X_{2/3}$ receptor and that a compound having a $P2X_3$ or $P2X_{2/3}$ receptor antagonistic effect is useful as an analgesic. Also, compounds that exhibit $P2X_3$ or $P2X_{2/3}$ receptor antagonistic effect are described in Patent Documents 2-7.

Additionally, it was recently reported that vesical reflex was strongly reduced in $P2X_3$ knockout mouse (Non-Patent Document 2), suggesting that a compound having $P2X_3$ antagonistic effect is useful in the treatment of diseases caused by overactive bladder.

Patent Documents 8, 9, 10 and 11 disclose compounds having similar structure to the compounds of the present invention but they do not disclose analgesic effect and $P2X_3$ or $P2X_{2/3}$ receptor antagonistic effect. Non-Patent Document 8 discloses compounds having similar structure to the compounds of the present invention and having analgesic effect, but it does not discloses $P2X_3$ or $P2X_{2/3}$ receptor antagonistic effect. Patent Document 12 discloses compounds having $P2X_3$ receptor antagonistic effect but the structures are different with those of the compounds of the present invention. Patent Document 13 discloses compounds having $P2X_3$ or $P2X_{2/3}$ receptor antagonistic effect with a triazine structure but in case that a ring corresponding to ring B of the present application is a cyclopentane ring, a benzene ring, a tetrahydropyrane ring or a piperizine ring, then the ring is unsubstituted, and therefore, the structures are different with those of the present invention.

Patent Document 14 discloses compounds having a pyrazolyl-substituted triazine ring but the structures are different with those of the compound of the formula (XII) of the present invention. Patent Document 14 does not disclose a process for converting a pyrazolyl group on a triazine ring into an anilino group by using a pyrazolyl group as a leaving group.

Non-Patent Documents 9, 10, 11 and 12 disclose a process for converting a pyrazolyl group to an anilino group by using a pyrazolyl group as a leaving group, but do not disclose a process for converting a pyrazolyl group on a triazine ring into an anilino group.

3
PRIOR ART

[Patent Document]
  [Patent Document 1] WO02/094767
  [Patent Document 2] WO2005/095359
  [Patent Document 3] US20070037974
  [Patent Document 4] US20070049758
  [Patent Document 5] US20070049610
  [Patent Document 6] US20070049609
  [Patent Document 7] US20070049534
  [Patent Document 8] JP12-072757A
  [Patent Document 9] WO2006/104713
  [Patent Document 10] WO2006/104715
  [Patent Document 11] WO2006/102112
  [Patent Document 12] WO2010/051188
  [Patent Document 13] WO2010/092966
  [Patent Document 14] EP547461A

[Non-Patent Document]
  [Non-Patent Document 1] Neuroscientist 11 (2005) pp. 345-356
  [Non-Patent Document 2] J. Physiol. 567.2 (2005) pp. 621-689
  [Non-Patent Document 3] Expert Opin. Ther. Patens (2006) 16(8), p. 113-1127
  [Non-Patent Document 4] J. Physiology (2003), 554(2), p. 301-808
  [Non-Patent Document 5] A. Physiology (2003), 553(3), p. 683-694
  [Non-Patent Document 6] Pflungers Arch Eur J physiol (2006), p. 452, 513-537
  [Non-Patent Document 7] PNAS (2002), 99(26), p. 17179-17184
  [Non-Patent Document 8] Journal of Medicinal Chemistry (2008), 51(23), p. 7635-7639
  [Non-Patent Document 9] J. Org. Chem. (1992), 57, p. 2497-2502
  [Non-Patent Document 10] Tetrahedron Lett. (2007), 48, p. 2357-2359
  [Non-Patent Document 11] Tetrahedron Lett. (2002), 43, p. 1401-1403
  [Non-Patent Document 12] Bioorganic & Medicinal Chemistry Letters (2010), 20(23), p. 6895-6898

SUMMARY OF THE INVENTION

[Problems to be Solved by the Invention]

The present invention provides a novel compound having a P2X$_3$ and/or P2X$_{2/3}$ receptor antagonistic effect. It also provides a pharmaceutical composition having a P2X$_3$ and/or P2X$_{2/3}$ receptor antagonistic effect and having an analgesic effect or an improving effect of urination disorder. Furthermore, it provides methods of producing the above-mentioned compound or pharmaceutical composition and important intermediates for the producing methods.

[Means for Solving the Problem]

Through their extensive research to solve the aforementioned problems, the inventors have found novel compounds that bind specifically to P2X$_3$ and/or P2X$_{2/3}$ receptor and exhibit an antagonistic effect, and novel compounds that bind specifically to P2X$_3$ and/or P2X$_{2/3}$ receptor. Additionally, they have discovered pharmaceutical compositions that have P2X$_3$ and/or P2X$_{2/3}$ antagonistic effect and having an analgesic effect or an improving effect of urination disorder. Furthermore, they have found methods for producing the above-mentioned compound or pharmaceutical composition and important intermediates for the producing methods.

The compounds and pharmaceutical compositions encompassed by the present invention produced excellent results of P2X$_3$ receptor inhibitory effect, P2X$_3$ receptor inhibitory effect in the presence of rat serum albumin (hereinafter referred to as RSA) and the like. The compounds encompassed by the present invention or the pharmaceutical compositions encompassed by the present invention also produced excellent results in CYP enzyme inhibition assay, FAT assay, solubility assay, metabolic stability assay, hERG inhibitory activity assay, bioavailability assay and/or protein binding assay and the like. The compounds encompassed by the present invention or the pharmaceutical composition encompassed by the present invention showed potent analgesic effect or improving effect of urination disorder.

This invention relates to (1) A compound of the formula (VIII):

[Chemical Formula 2]

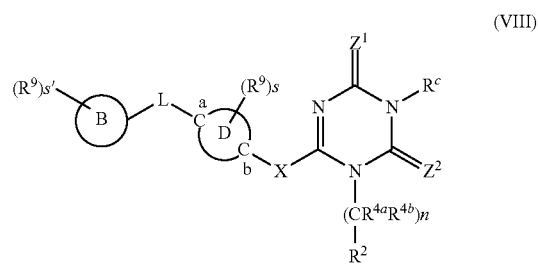

wherein $Z^1$ and $Z^2$ are each independently an oxygen atom, a sulfur atom or $=$N—$R^x$;

$R^x$ is a hydrogen atom, substituted or unsubstituted alkyl, substituted or unsubstituted alkenyl, substituted, or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^c$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;

n is an integer of 1 to 4;

$R^2$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

—X— is —O—, —S—, —N($R^5$)— or —(C$R^{5a}R^{5b}$)—;

—L— is —O—, —S—, —N($R^{5'}$)— or —(C$R^{5a'}R^{5b'}$)—;

$R^5$ and $R^{5'}$ are each independently a hydrogen atom, substituted or unsubstituted alkyl, substituted or unsubstituted alkenyl, substituted or unsubstituted alkynyl, or substituted or unsubstituted acyl;

$R^{5a}$, $R^{5b}$, $R^{5a'}$ and $R^{5b'}$ each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy or substituted or unsubstituted alkenyloxy;

ring D is a benzene ring, a pyridine ring, a pyrimidine ring, a pyrazine ring or a pyridazine ring;

carbon atom a and carbon atom b are carbon atoms which constitute ring D;

ring B is an aromatic carbocyclic ring, a non-aromatic carbocyclic ring, an aromatic heterocyclic ring or a non-aromatic heterocyclic ring;

s and s' are each independently an integer of 0 to 3; and $R^9$ and $R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsulystituted amino, substituted or unsubstituted sulfamoyl, substituted sulfonyl, substituted sulfinyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy;

provided that s' is an integer of 1 to 3 when ring B is a cyclopentane ring, a benzene ring, a tetrahydropyran ring or a piperidine ring, or its pharmaceutically acceptable salt or a solvate thereof.

(2) The compound according to the above (1), wherein —L— is —O—, or its pharmaceutically acceptable salt or a solvate thereof.

(3) The compound according to the above (1) or (2), wherein ring B is an aromatic heterocyclic ring, or its pharmaceutically acceptable salt or a solvate thereof.

(4) The compound according to any one of the above (1) to (3), wherein ring B is a thiazole ring, an isothiazole ring, an oxazole ring, an isoxazole ring, a pyrazole ring, an imidazole ring, a triazole ring, a furan ring, a thiophene ring, a thiadiazole ring, an oxadiazole ring, a pyridine ring, a pyrimidine ring, a pyrazine ring, a pyridazine ring, a triazine ring or a benzoxazole ring, or its pharmaceutically acceptable salt or a solvate thereof.

(5) The compound according to any one of the above (1) to (4), wherein ring B is a thiazole ring, an isothiazole ring, an oxazole ring, an isoxazole ring, a thiadiazole ring, an oxadiazole ring, a pyridine ring, a pyrimidine ring, a pyrazine ring or a pyridazine ring, or its pharmaceutically acceptable salt or a solvate thereof.

(6) The compound according to any one of the above (1) to (5), wherein s' is an integer of 1 to 2, and at least one of $R^{9'}$ is hydroxy, carboxy, cyano, substituted alkyl, substituted or unsubstituted carbamoyl, substituted or unsubstituted amino, substituted or unsubstituted sulfamoyl, substituted sulfonyl or substituted sulfinyl, or its pharmaceutically acceptable salt or a solvate thereof.

(7) The compound according to any one of the above (1) to (6), wherein s' is 1, and $R^{9'}$ is carboxy or substituted or unsubstituted carbamoyl, or its pharmaceutically acceptable salt or a solvate thereof.

(8) A compound of the formula (IX):

[Chemical Formula 3]

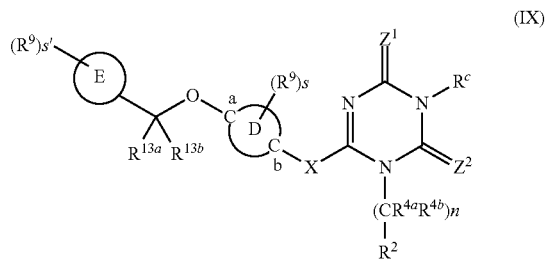

wherein $Z^1$ and $Z^2$ are each independently an oxygen atom, a sulfur atom or =N—$R^x$;

$R^x$ is a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^c$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;

n is an integer of 1 to 4;

$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

—X— is —O—, —S—, —N($R^5$)— or —($CR^{5a}R^{5b}$)—;

$R^5$ is a hydrogen atom, substituted or unsubstituted alkyl, substituted or unsubstituted alkenyl, substituted or unsubstituted alkynyl, or substituted or unsubstituted acyl;

$R^{5a}$ and $R^{5b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;

ring D is a benzene ring, a pyridine ring, a pyrimidine ring, a pyrazine ring or a pyridazine ring;

carbon atom a and carbon atom b are carbon atoms which constitute ring D;

$R^{13a}$ and $R^{13b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy, or $R^{13a}$ and $R^{13b}$ attached to the same carbon atom are taken together to form oxo or thioxo;

ring E is a cycloalkane ring or a cycloalkene ring;

s and s' are each independently an integer of 0 to 3; and $R^9$ and $R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, or its pharmaceutically acceptable salt or a solvate thereof.

(9) The compound according to the above (8) wherein $R^{13a}$ and $R^{13b}$ are both hydrogen atoms, or its pharmaceutically acceptable salt or a solvate thereof.

(10) The compound according to the above (8) or (9), wherein ring E is a cyclopropane ring, or its pharmaceutically acceptable salt or a solvate thereof.

(11) The compound according to any one of the above (1) to (10), wherein ring D is a benzene ring, or its pharmaceutically acceptable salt or a solvate thereof.

(12) The compound according to any one of the above (1) to (11), wherein carbon atom a is positioned on ring D in a 1,4 relationship with respect to carbon atom b, or its pharmaceutically acceptable salt or a solvate thereof.

(13) The compound according to any one of the above (1) to (12), wherein s and s' are each independently an integer of 0 to 2; and $R^9$ and $R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstittded alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl or substituted sulfinyl, or its pharmaceutically acceptable salt or a solvate thereof.

(14) A compound of the formula (VII):

[Chemical Formula 4]

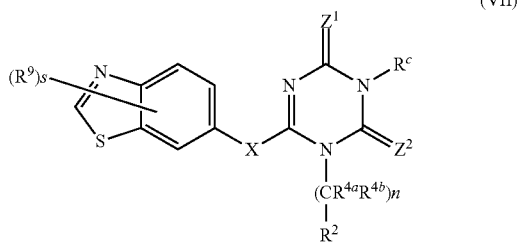

(VII)

wherein
$Z^1$ and $Z^2$ are each independently an oxygen atom, a sulfur atom or =N—$R^x$;
$R^x$ is a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^c$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;
n is an integer of 1 to 4;
$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
—X— is —O—, —S—, —N($R^5$)— or —($CR^{5a}R^{5b}$)—;
$R^5$ is a hydrogen atom, substituted or unsubstituted alkyl, substituted or unsubstituted alkenyl, substituted or unsubstituted alkynyl, or substituted or unsubstituted acyl;
$R^{5a}$ and $R^{5b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;
s is an integer of 0 to 3; and
$R^9$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, or its pharmaceutically acceptable salt or a solvate thereof.

(15) The compound according to the above (14), wherein s is an integer of 0 to 2; and $R^9$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl or substituted sulfinyl, or its pharmaceutically acceptable salt or a solvate thereof.

(16) The compound according to any one of the above (1) to (15), wherein $Z^1$ and $Z^2$ are both oxygen atoms or both sulfur atoms, or its pharmaceutically acceptable salt or a solvate thereof.

(17) The compound according to any one of the above (1) to (16), wherein $Z^1$ and $Z^2$ are both oxygen atoms, or its pharmaceutically acceptable salt or a solvate thereof.

(18) The compound according to any one of the above (1) to (17), wherein $R^c$ is unsubstituted alkyl, alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), unsubstituted alkenyl, alkenyl substituted with one or more substituents selected from Substituent Group A, unsubstituted alkynyl or alkynyl substituted with one or more substituents selected from Substituent Group A, or its pharmaceutically acceptable salt or a solvate thereof.

(19) The compound according to any one of the above (1) to (18), wherein $R^c$ is unsubstituted alkyl, alkyl substituted with one or more substituents selected from Substituent Group B" (Substituent Group B": hydroxy, carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), unsubstituted alkenyl, alkenyl substituted with one or more substituents selected from Substituent Group B", unsubstituted alkynyl or alkynyl substituted with one or more substituents selected from Substituent Group B", or its pharmaceutically acceptable salt or a solvate thereof.

(20) The compound according to any one of the above (1) to (19), wherein $R^c$ is unsubstituted alkyl, or its pharmaceutically acceptable salt or a solvate thereof.

(21) The compound according to any one of the above (1) to (19), wherein $R^c$ is —$(CR^{11a}R^{11b})$m—OH; $R^{11a}$ and $R^{11b}$ are each independently a hydrogen atom, substituted or unsubstituted alkyl, substituted or unsubstituted alkenyl, or substituted or unsubstituted alkynyl, and $R^{11a}$ and $R^{11b}$ together with the carbon atom to which they are attached form a substituted or unsubstituted cycloalkane ring, a substituted or unsubstituted cycloalkene ring, or a substituted or unsubstituted non-aromatic heterocyclic ring; and m is an integer of 2 to 4, or its pharmaceutically acceptable salt or a solvate thereof.

(22) The compound according to any one of the above (1) to (19) and (21), wherein $R^c$ is —$(CR^{11a}R^{11b})$m—OH; $R^{11a}$ is a hydrogen atom, substituted or unsubstituted alkyl, substituted or unsubstituted alkenyl, or substituted or unsubstituted alkynyl; $R^{11b}$ is —$(CR^{12a}R^{12b})$u—OH; $R^{12a}$ $R^{12b}$ are each independently a hydrogen atom, substituted or unsubstituted alkyl, substituted or unsubstituted alkenyl, or substituted or unsubstituted alkynyl; u is an integer of 0 to 2; and m is an integer of 2 to 4, or its pharmaceutically acceptable salt or a solvate thereof.

(23) The compound according to any one of the above (1) to (19), (21) and (22), wherein $R^c$ is a group of the formula:

[Chemical Formula 5]

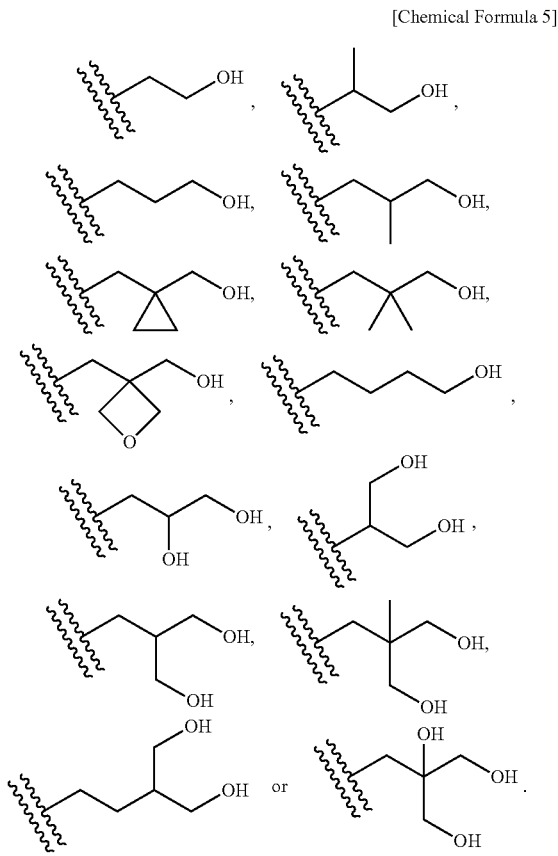

or its pharmaceutically acceptable salt or a solvate thereof.

(24) The compound according to any one of the above (1) to (19), wherein $R^c$ is —$(CR^{14a}R^{14b})$t—$N(R^{15a})(R^{15b})$; $R^{14a}$ and $R^{14b}$ are each independently a hydrogen atom, substituted or unsubstituted alkyl, substituted or unsubstituted alkenyl, substituted or unsubstituted alkynyl, or $R^{14a}$ and $R^{14b}$ together with the carbon atom to which they are attached form a substituted or unsubstituted cycloalkane ring, a substituted or unsubstituted cycloalkene ring, or a substituted or unsubstituted non-aromatic hetercyclic ring; t is an integer of 2 to 4; and $R^{15a}$ and $R^{15b}$ are each independently a hydrogen atom, substituted or unsubstituted alkyl, substituted or unsubstituted alkenyl, substituted or unsubstituted alkynyl, substituted or unsubstituted carbamoyl, substituted or an substituted sulfamoyl, substituted or unsubstituted acyl, substituted sulfonyl or substituted sulfinyl; or —(CR$^{14a'}$R$^{14b'}$)t'—C(=O)N(R$^{15a'}$)(R$^{15b'}$); R$^{14a'}$ and R$^{14b'}$ are each independently a hydrogen atom, substituted or unsubstituted alkyl, substituted or unsubstituted alkenyl, or substituted or unsubstituted alkynyl or R$^{14a'}$ and R$^{14b'}$ together with the carbon atom to which they are attached form a substituted or unsubstituted cycloalkane ring, a substituted or unsubstituted cycloalkone ring, or a substituted or unsubstituted non-aromatic heterocyclic ring; t' is an integer of 1 to 4; and R$^{15a'}$ and R$^{15b'}$ are each independently a hydrogen atom, cyano, substituted or unsubstituted alkyl, substituted or unsubstituted alkenyl, substituted or unsubstituted alkynyl, substituted or unsubstituted carbamoyl, substituted or unsubstituted sulfamoyl, substituted or unsubstituted acyl, substituted sulfonyl or substituted sulfinyl, or its pharmacentically acceptable salt or a solvate thereof.

(25) The compound according to any one of the above (1) to (19), and (24), wherein R$^c$ is a group of the formula:

[Chemical Formula 6]

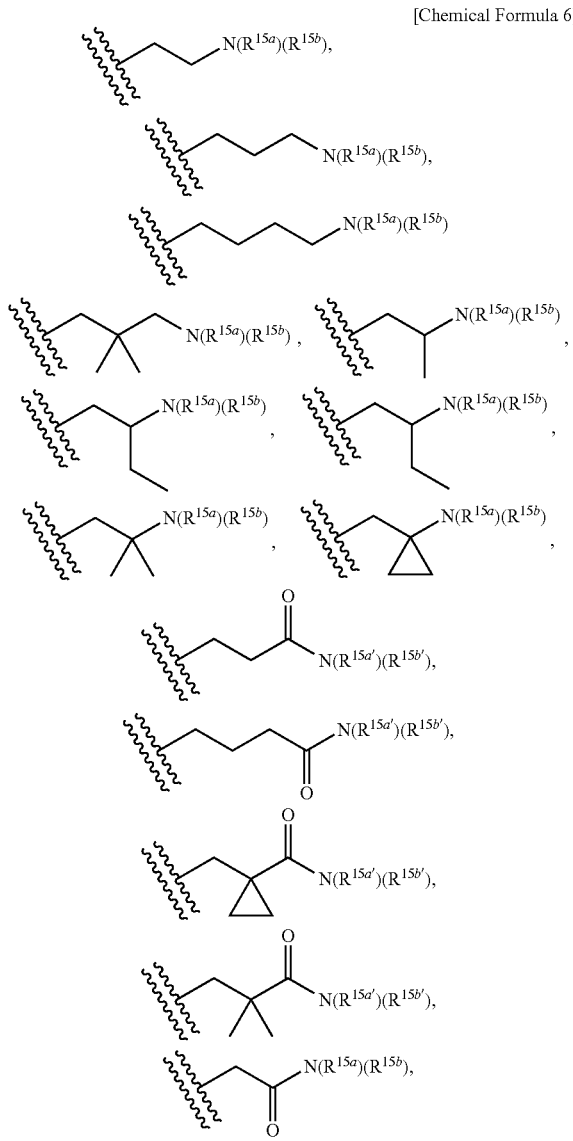

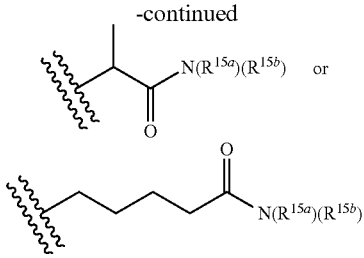

wherein R$^{15a}$, R$^{15b}$, R$^{15a'}$ and R$^{15b'}$ are as defined in the above (24), or its pharmaceutically acceptable salt or a solvate thereof.

(26) The compound according to any one of the above (1) to (25), wherein n is 1, or its pharmaceutically acceptable salt or a solvate thereof.

(27) The compound according to any one of the above (1) to (26), wherein R$^{4a}$ and R$^{4b}$ are both hydrogen atoms, or R$^{4a}$ and R$^{4b}$ attached to the same carbon atom are taken together to form oxo, or its pharmaceutically acceptable salt or a solvate thereof.

(28) The compound according to any one of the above (1) to (27), wherein n is 1, and R$^{4a}$ and R$^{4b}$ are both hydrogen atoms, or its pharmaceutically acceptable salt or a solvate thereof.

(29) The compound according to an one of the above (1) to (28), wherein R$^2$ is substituted or unsubstituted cycloalkyl, substituted or unsubstituted aryl, or substituted or unsubstituted heteroaryl, or its pharmaceutically acceptable salt or a solvate thereof.

(30) The compound according to any one of the above (1) to (29), wherein R$^2$ is cycloalkyl optionally substituted with one or more substituents select from Substituent Group C (Substituent Group C: halogen, alkyl, alkenyl, alkynyl, alkyloxy, alkenyloxy, alkynyloxy, cycloalkyl, cycloalkenyl, cycloalkynyl, and alkylsilylalkynyl), aryl optionally substituted with one or more substituents selected from Substituent Group C, or heteroaryl optionally substituted with one or more substituents selected from Substituent Group C, or its pharmaceutically acceptable salt or a solvate thereof.

(31) The compound according to any one of the above (1) to (30), wherein —X— is —N(R$^5$)—, and R$^5$ is as defined in the above (1), or its pharmaceutically acceptable salt or a solvate thereof.

(32) The compound according to any one of the above (1) to (31), wherein —X— is —NH—, or its pharmaceutically acceptable salt or a solvate thereof.

(33) A compound of the formula (IV):

[Chemical Formula 7]

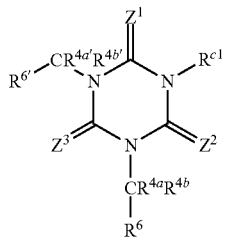

(IV)

wherein
Z$^1$, Z$^2$ and Z$^3$ are each independently an oxygen atom or a sulfur atom;

$R^{c1}$ is unsubstituted alkyl, unsubstituted alkynyl, alkyl substituted with one or more substituents selected from Substituent Group B (Substituent Group B: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, and nitro), alkenyl substituted with one or more substituents selected from Substituent Group B, alkynyl substituted with one or more substituents selected from Substituent Group B;

$R^{4a}$ is a hydrogen atom or substituted or unsubstituted alkyl;
$R^{4b}$ is a hydrogen atom;
$R^6$ is substituted or unsubstituted cycloalkyl, substituted or unsubstituted aryl or substituted or unsubstituted heteroaryl;
$R^{4a'}$ is a hydrogen atom or substituted or unsubstituted alkyl;
$R^{4b'}$ is a hydrogen atom; and
$R^{6'}$ is substituted or unsubstituted aryl or substituted or unsubstitnted heteroaryl; provided that 1) a compound wherein $R^{c1}$ is ethyl substituted with substituted or unsubstituted amino, or propyl substituted with substituted or unsubstituted amino, and $R^6$ and $R^{6'}$ are both substituted or unsubstituted phenyl, and 2) a compound wherein $R^{c1}$ is unsubstituted oxirane, substituted or unsubstituted phenyl, or alkyl substituted with unsubstituted acetyl,
are excluded,
or its pharmaceutically acceptable salt or a solvate thereof.

(34) The compound according to the above (33), wherein $Z^1$, $Z^2$ and $Z^3$ are oxygen atoms, or its pharmaceutically acceptable salt or a solvate thereof.

(35) The compound according to the above (33) or (34), wherein $R^6$ is cycloalkyl optionally substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl and alkylsilylalkynyl), aryl optionally substituted with one or more substituents selected from Substituent Group C, or heteroaryl optionally substituted with one or more substituents selected from Substituent Group C, or its pharmaceutically acceptable salt or a solvate thereof.

(36) The compound according to any one of the above (33) to (35), wherein $R^6$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryl optionally substituted with one or more substituents selected from Substituent Group D, or its pharmaceutically acceptable salt or a solvate thereof.

(37) A pharmaceutical composition comprising the compound according to any one of the above (1) to (36), or its pharmaceutically acceptable salt, or a solvate thereof.

(38) The pharmaceutical composition according to the above (37), wherein the composition has a $P2X_3$ and/or $P2X_{2/3}$ receptor antagonistic effect.

(39) A compound according to any one of the above (1) to (36), or its pharmaceutically acceptable salt, or a solvate thereof for use in a method for treating and/or preventing a disease related $P2X_3$ and/or $P2X_{2/3}$ receptor.

(40) A method for treating and/or preventing a disease related to $P2X_3$ and/or $P2X_{2/3}$ receptor comprising administering the compound according to any one of the above (1) to (36), or its pharmaceutically acceptable salt, or a solvate thereof.

(41) A pharmaceutical composition having an analgesic effect or an improving effect of urination disorder comprising a compound of the formula (I):

[Chemical Formula 8]

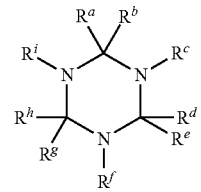

(I)

wherein
(i)
$R^h$ and $R^i$ are taken together to form a bond;
$R^a$ and $R^b$ and/or $R^d$ and $R^e$ are taken together to form oxo, thioxo or $=N-R^x$;
$R^x$ is a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^c$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
—$R^f$ is —$(CR^{4a}R^{4b})n$—$R^2$;
$R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;
n is an integer of 1 to 4;
$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^g$ is —X—$R^3$;
—X— is —O—, —S—, —N($R^5$)— or —$(CR^{5a}R^{5b})$—;

$R^8$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^5$ is a hydrogen atom, substituted or unsubstituted alkyl, substituted or unsubstituted alkenyl, substituted or unsubstituted alkynyl, or substituted or unsubstituted acyl;

$R^{5a}$ and $R^{5b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;

(ii)

$R^h$ and $R^j$ are taken together to form a bond;

$R^a$ is a group of $-Y-R^{1a}$;

$R^{1a}$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$-Y-$ is $-O-$, $-S-$, $-N(R^7)-$ or $(CR^{8a}R^{8b})-$;

$R^7$ is a hydrogen atom, substituted or unsubstituted alkyl, substituted or unsubstituted acyl;

$R^{8a}$ and $R^{8b}$ are each independently a hydrogen atom, halogen or substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^b$ and $R^c$ are taken together to form a bond;

$R^d$ and $R^e$ are taken together to form oxo or thioxo; and $R^f$ and $R^g$ are as defined in the above (i); or (iii)

$R^a$ and $R^b$, $R^d$ and $R^e$, and/or $R^g$ and $R^h$ are taken together to form oxo or thioxo;

$R^c$ is unsubstituted alkyl, unsubstituted alkynyl, alkyl substituted with one or more substituents selected from Substituent Group B (Substituent Group B: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, and nitro), alkenyl substituted with one or more substituents selected from Substituent Group B, or alkynyl substituted with one or more substituents selected from Substituent Group B;

$R^f$ is $-(CR^{4a}R^{4b})-R^6$;

$R^j$ is $-(CR^{4a'}R^{4b'})-R^{6'}$;

$R^6$ is substituted or unsubstituted cycloalkyl, substituted or unsubstituted aryl, or substituted or unsubstituted heteroaryl;

$R^{6'}$ is substituted or unsubstituted, aryl, or substituted or unsubstituted heteroaryl;

and $R^{4a}$, $R^{4b}$, $R^{4a'}$ and $R^{4b'}$ are each independently a hydrogen atom, or substituted or unsubstituted alkyl; or (iv) $R^j$ and $R^b$ are taken together to form a bond;

$R^a$ is a group of $-Y-R^{1a}$;

$-Y-$ is $-O-$, $-S-$, $-N(R^7)-$ or $(CR^{8a}R^{8b})-$;

$R^{1a}$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^c$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^d$ and $R^e$ are taken together to form oxo, thioxo or $=N-R^x$;

$R^x$ is a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$-R^f$ is $-(CR^{4a}R^{4b})n-R^2$;

$R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;

n is an integer of 1 to 4;

$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^g$ and $R^h$ are taken together to form $=N-R^8$; and $R^8$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl, provided that 1) a compound wherein, in (i), $-X-$ is $-NH-$, and $R^8$ is cyclohexyl substituted with guanidyl, and 2) a compound wherein, in (ii), $R^a$ is substituted phenyl, $R^d$ and $R^e$ are taken together to form thioxo, $R^{4a}$ and $R^{4b}$ are taken together to form oxo, and $R^8$ is unsubstituted cyclohexyl, are excluded, or its pharmaceutically acceptable salt or a solvate thereof.

(42) The pharmaceutical composition having an analgesic effect or an improving effect of urination disorder according to the above (41), comprising the compound of the formula (II):

[Chemical Formula 9]

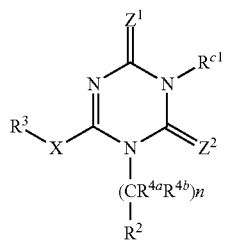

(II)

wherein $Z^1$ and $Z^2$ are each independently an oxygen atom, a sulfur atom or $=N-R^x$;

$R^x$, $R^{4a}$, $R^{4b}$, n, $R^2$, X, and $R^3$ are as defined in the above (41); and $R^{c1}$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl, or its pharmaceutically acceptable salt or a solvate thereof.

(43) The pharmaceutical composition having an analgesic effect or an improving effect of urination disorder according to the above (42), comprising the compound wherein $Z^1$ and $Z^2$ are both oxygen atoms or both sulfur atoms, or its pharmaceutically acceptable salt or a solvate thereof.

(44) The pharmaceutical composition having an analgesic effect or an improving effect of urination disorder according to the above (42) or (43), comprising the compound wherein $Z^1$ and $Z^2$ are both oxygen atoms or its pharmaceutically acceptable salt or a solvate thereof.

(45) The pharmaceutical composition having an analgesic effect or an improving effect of urination disorder according to the above (42) or (44), comprising the compound wherein $R^{c1}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), alkenyl substituted with one or more substituents selected from Substituent Group A, or alkynyl substituted with one or more substituents selected from Substituent Group A, or its pharmaceutically acceptable salt or a solvate thereof.

(46) The pharmaceutical composition having an analgesic effect or an improving effect of urination disorder according to the above (42) or (45), comprising the compound wherein $R^{c1}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group B', or alkynyl substituted with one or more substituents selected from Substituent Group B', or its pharmaceutically acceptable salt or a solvate thereof.

(47) The pharmaceutical composition having an analgesic effect or an improving effect of urination disorder according to the above (41), comprising the compound of the formula (III):

[Chemical Formula 10]

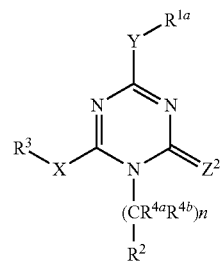

(III)

wherein $Z^2$ is an oxygen atom, a sulfur atom or $=N-R^x$; and $R^x$, $-Y-$, $R^{1a}$, $R^{4a}$, $R^{4b}$, n, $R^2$, $-X-$, and $R^3$ are as defined in the above (41), or its pharmaceutically acceptable salt or a solvate thereof.

(48) The pharmaceutical composition having an analgesic effect or an improving effect of urination disorder according to the above (47), comprising the compound wherein $Z^2$ is an oxygen atom or a sulfur atom, or its pharmaceutically acceptable salt or a solvate thereof.

(49) The pharmaceutical composition having an analgesic effect or an improving effect of urination disorder according to the above (47) or (48), comprising the compound wherein $-Y-$ is $-O-$, or its pharmaceutically acceptable salt or a solvate thereof.

(50) The pharmaceutical composition having an analgesic effect or an improving effect of urination disorder according to the above (47) or (49), comprising the compound wherein $R^{1a}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), alkenyl substituted with one or more substituents selected from Substituent Group A, or alkynyl substituted with one or more substituents selected from Substituent Group A, or its pharmaceutically acceptable salt or a solvate thereof.

(51) The pharmaceutical composition having an analgesic effect or an improving effect of urination disorder according to the above (47) or (50), comprising the compound wherein $R^{1a}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group B', or alkynyl substituted with one or more substituents selected from Substituent Group B', or its pharmaceutically acceptable salt or a solvate thereof.

(52) The pharmaceutical composition having an analgesic effect or an improving effect of urination disorder according to any one of the above (42) to (51), comprising the compound wherein n is 1, or its pharmaceutically acceptable salt or a solvate thereof.

(53) The pharmaceutical composition having an analgesic effect or an improving effect of urination disorder according to any one of the above (42) to (52), comprising the compound wherein $R^{4a}$ and $R^{4b}$ are both hydrogen atoms, or $R^{4a}$ and $R^{4b}$ attached to the same carbon atom are taken together to form oxo, or its pharmaceutically acceptable salt or a solvate thereof.

(54) The pharmaceutical composition having an analgesic effect or an improving effect of urination disorder according to any one of the above (42) to (53), comprising the compound wherein $R^2$ substituted or unsubstituted cycloalkyl, substituted or unsubstituted aryl, or substituted or unsubstituted heteroaryl, or its pharmaceutically acceptable salt or a solvate thereof.

(55) The pharmaceutical composition having an analgesic effect or an improving effect of urination disorder according to any one of the above (42) to (54), comprising the compound wherein $R^2$ cycloalkyl optionally substituted with one or more substituents selected from Substituent Group C (Substituent Group C: halogen, alkyl, alkenyl, alkynyl, alkyloxy, alkenloxy, alkynyloxy, cycloalkyl, cycloalkenyl, cycloalkynyl, and alkylsilylalkynyl), aryl optionally substituted with one or more substituents selected from Substituent Group C, or heteroaryl optionally substituted with one or more substituents selected from Substituent Group C, or its pharmaceutically acceptable salt or a solvate thereof.

(56) The pharmaceutical composition having an analgesic effect or an improving effect of urination disorder according to any one of the above (42) to (55), comprising the compound wherein —X— is —N($R^5$)—, and $R^5$ is as defined in the above (41), or its pharmaceutically acceptable salt or a solvate thereof.

(57) The pharmaceutical composition having an analgesic effect or an improving effect of urination disorder according to any one of the above (42) to (56), comprising the compound wherein —X— is —NH—, or its pharmaceutically acceptable salt or a solvate thereof.

(58) The pharmaceutical composition having an analgesic effect or an improving effect of urination disorder according to any one of the above (42) to (57), comprising the compound wherein $R^8$ is a group of the formula:

[Chemical Formula 11]

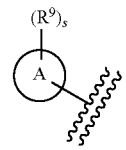

wherein ring A is an aromatic carbocyclic ring or an aromatic heterocyclic ring;
s is an integer of 0 to 3; and
$R^9$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted sulfonyl, substituted sulfinyl, substituted or unsubstituted cycloalkyl substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, or its pharmaceutically acceptable salt or a solvate thereof.

(59) The pharmaceutical composition having an analgesic effect or an improving effect of urination disorder according to any one of the above (42) to (58), comprising the compound wherein $R^8$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryl optionally substituted with one or more substituents selected from Substituent Group D, or its pharmaceutically acceptable salt or a solvate thereof.

(60) A method of producing a compound of the formula (XI):

[Chemical Formula 12]

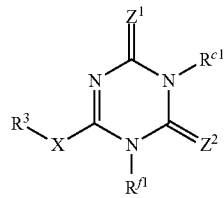

(XI)

wherein $Z^1$ and $Z^2$ are each independently an oxygen atom or a sulfur atom, $R^{f1}$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^{c1}$ is substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^8$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
X is $-N(R^5)-$;
$R^5$ is a hydrogen atom, substituted or unsubstituted alkyl, substituted or unsubstituted alkenyl, substituted or unsubstituted alkynyl or substituted or unsubstituted acyl, or its pharmaceutically acceptable salt or a solvate thereof. characterized by reacting a compound of the formula (X):

[Chemical Formula 13]

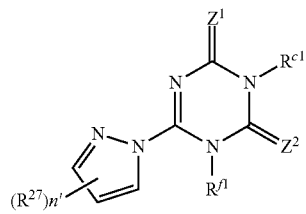

(X)

wherein $Z^1$, $Z^2$, $R^{f1}$ and $R^{c1}$ are as defined above;
$R^{27}$ is substituted or unsubstituted alkyl; and
n' is an integer of 0 to 3 or its salt,
with a compound of the formula: $R^3-X'$
wherein $R^3$ is as defined above;
$-X'$ is $-NH(R^5)$; and
$R^5$ is as defined above.
In the above (60), the following compound of the formula (XII), its pharmaceutically acceptable salt or a solvate thereof can be used instead of the compound of the formula (X), its pharmaceutically acceptable salt or a solvate thereof.

(60') A method of producing a compound of the formula (XVII):

[Chemical Formula 14]

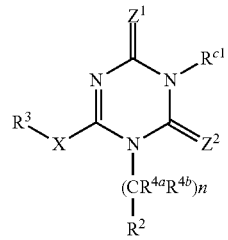

(XVII)

wherein $Z^1$, $Z^2$, $R^{c1}$, $R^{4a}$, $R^{4b}$, n, $R^2$, X and $R^3$ are as defined in the (62) mentioned below, or its pharmaceutically acceptable salt or a solvate thereof comprising the steps of i) reacting a compound of the formula (XIII);

[Chemical Formula 15]

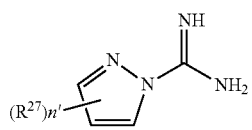

(XIII)

wherein $R^{27}$ and n' are as defined in the above (60) or its salt with a compound of the formula:

[Chemical Formula 16]

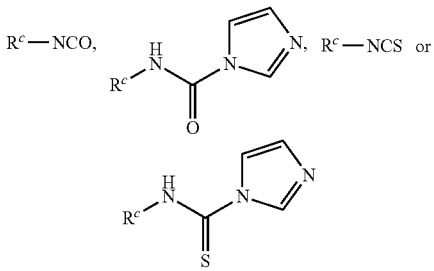

wherein $R^c$ is substituted or unsubstituted alkyl, substituted or unsubstituted alkenyl, substituted or unsubstituted alkynyl, substituted or an substituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl or its salt in the presence of a base to give a compound of the formula (XIV):

[Chemical Formula 17]

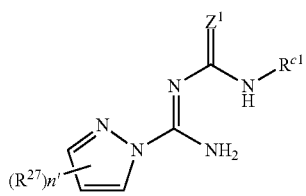

(XIV)

wherein $Z^1$, $R^{c1}$, $R^{27}$ and n' are as defined in the above (60) or its salt, ii) reacting the compound of the formula (XIV) or its salt with a carbonylating agent or a thiocarbonylating agent in the presence of a base to give a compound of the formula (XV):

[Chemical Formula 18]

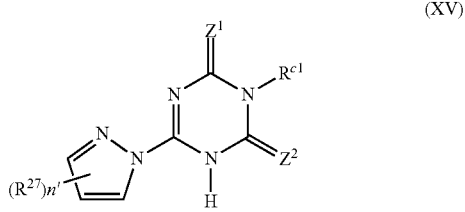

(XV)

wherein $Z^1$, $Z^2$, $R^{c1}$, $R^{27}$ and n' are as defined in the above (60) or its salt,
iii) reacting the compound of the formula (XV) with a compound of the formula:
$R^2$—$(CR^{4a}R^{4b})n$—Y
wherein $R^2$, $R^{4a}$, $R^{4b}$ and n are as defined in the (62) mentioned below and Y is a leaving group or its salt in the presence of a base to give a compound of the formula (XVI):

[Chemical Formula 19]

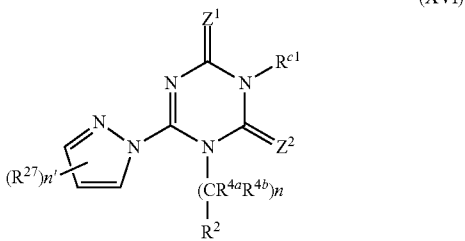

(XVI)

wherein $Z^1$, $Z^2$, $R^{c1}$, $R^{27}$ and n' are as defined in the (62) mentioned below or its salt,
and
iv) reacting the compound of the formula (XVI) or its salt with a compound of the formula:
$R^8$—X'
wherein and $R^8$ and —X' are as defined in the above (60) or its salt.
In the above (60'). "to give a compound or its salt" includes a case that the compound or its salt are presence in a reaction system and a case that the compound or its salt are isolated. In the above (60'), a compound of the following formula (XII):

[Chemical Formula 20]

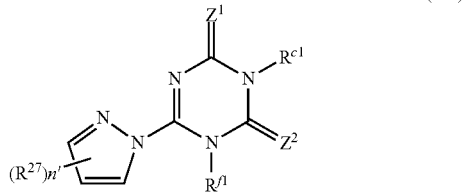

(XII)

wherein $R^{c1}$ is —$(CR^{4a}R^{Rb})n$—$R^2$ wherein $R^{4a}$, $R^{4b}$, n and $R^2$ are as defined in the (68) mentioned below; $Z^1$, $Z^2$, $R^{c1}$, $R^{27}$ and n' are as defined in the (66) mentioned below, or its pharmaceutically acceptable salt or a solvate thereof can be used instead of the compound of the formula (XVI) or its pharmaceutically acceptable salt or a solvate thereof.
(61) The method according to the above (60) or (60'), wherein $Z^1$ and $Z^2$ are oxygen atoms.
(62) The method according to any one or the above (60) or (60') and (61), wherein $R^{f1}$ is a group of —$(CR^{4a}R^{4b})n$—$R^2$;
wherein $R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;
n is an integer of 1 to 4; and
$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl.
(63) The method according to any one of the above (60), (60'), (61) and (62), wherein $R^{c1}$ is substituted or unsubstituted alkyl.
(64) The method according to any one of the above (60), (60'), and (61) to (63), wherein $R^5$ is a hydrogen atom.
(65) The method according to any one of the above (60), (61'), and (61) to (64), wherein $R^8$ is substituted or unsubstituted aryl or substituted or unsubstituted heteroaryl,
(66) A compound of the formula (XII):

[Chemical Formula 21]

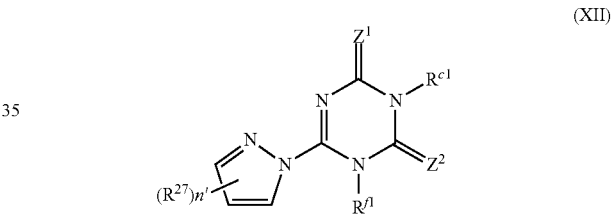

(XII)

wherein $Z^1$ and $Z^2$ are each independently an oxygen atom or a sulfur atom;
$R^{f1}$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^{c1}$ is substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
provided that $R^{c1}$ not unsubstituted alkyl, unsubstituted alkenyl or unsubstituted cycloalkyl, when $R^{f1}$ is a hydrogen atom;
$R^{27}$ is substituted or unstibstituted alkyl; and
n' is an integer of 0 to 3, or its pharmaceutically acceptable salt, or a solvate thereof.
(67) The compound according to the above (66), wherein $Z^1$ and $Z^2$ are oxygen atoms, or its pharmaceutically acceptable salt or a solvate thereof.
(68) The compound according to the above (66) or (67) wherein $R^{f1}$ is a group of —$(CR^{4a}R^{4b})n$—$R^2$;

wherein $R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;
n is an integer of 1 to 4; and
$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl, or its pharmaceutically acceptable salt or a solvate thereof.

(69) The compound according to any one of the above (66) to (68), wherein $R^{c1}$ is substituted or unsubstituted alkyl, or its pharmaceutically acceptable salt or a solvate thereof.

(70) The compound according to any one of the above (06) to (09), wherein $R^5$ is a hydrogen atom, or its pharmaceutically acceptable salt, or a solvate thereof.

Furthermore, the present invention relates to the followings:

(1B) A pharmaceutical composition having an analgesic effect and/or an improving effect of urination disorder comprising a compound of the formula (I):

[Chemical Formula 22]

(I)

wherein
(i)
$R^h$ and $R^j$ are taken together to form a bond;
$R^a$ and $R^b$ and/or $R^d$ and $R^e$ are taken together to form oxo, thioxo or $=N-R^x$;
$R^x$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^c$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
—$R^f$ is —$(CR^{4a}R^{4b})n$—$R^2$;
$R^{4a}$ and $R^{4b}$ are each independently a hydrogen atom or substituted or unsubstituted alkyl, or $R^{4a}$ and $R^{4b}$ attached to the same carbon atom are taken together to form oxo or thioxo;
n is an integer of 1 to 4;
$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^g$ is —$X$—$R^3$;
—$X$— is —$O$—, —$S$—, —$N(R^5)$— or —$(CR^{5a}R^{5b})$—;
$R^3$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^5$ is hydrogen, substituted or unsubstituted alkyl, substituted or unsubstituted alkenyl, substituted or unsubstituted alkynyl, substituted or unsubstituted acyl;
$R^{5a}$ and $R^{5b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;
(ii)
$R^h$ and $R^j$ are taken together to form a bond;
$R^a$ is a group of —$Y$—$R^{1a}$;
$R^{1a}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
—$Y$— is —$O$—, —$S$—, —$N(R^7)$— or $(CR^{8a}R^{8b})$—;
$R^7$ is hydrogen, substituted or unsubstituted alkyl, substituted or unsubstituted acyl;
$R^{8a}$ and $R^{8b}$ are each independently hydrogen, halogen or substituted or unsubstituted alkyl; hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^b$ and $R^c$ are taken together to form a bond;
$R^d$ and $R^e$ are taken together to form oxo or thioxo;
$R^f$ and $R^g$ are as defined in the above (i); or
(iii)
$R^a$ and $R^b$, $R^d$ and $R^e$, and/or $R^g$ and $R^h$ are taken together to form oxo or thioxo;
$R^c$ is unsubstituted alkyl, unsubstituted alkynyl, alkyl substituted with one or more substituents selected from Substituent Group B (Substituent Group B: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, and nitro), alkenyl substituted with one or more substituents selected from Substituent Group B, or alkynyl substituted with one or more substituents selected from Substituent Group B;
$R^f$ is —$(CR^{4a}R^{4b})$—$R^6$;
$R^j$ is —$(CR^{4a'}R^{4b'})$—$R^{6'}$;
$R^6$ is substituted or unsubstituted cycloalkyl, substituted or unsubstituted aryl, or substituted or unsubstituted heteroaryl;

$R^{6'}$ is substituted or unsubstituted, aryl, or substituted or unsubstituted heteroaryl;

$R^{4a}$, $R^{4b}$, $R^{4a'}$ and $R^{4b'}$ are each independently a hydrogen atom, or substituted or unsubstituted alkyl;

(iv)

$R^j$ and $R^b$ are taken together to form a bond;

$R^a$ is a group of —Y—$R^{1a}$;

—Y— is —O—, —S—, —N($R^7$)— or ($CR^{8a}R^{8b}$)—;

$R^{1a}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^c$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

$R^d$ and $R^e$ are taken together to form oxo, thioxo or =N—$R^x$;

$R^x$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

—$R^f$ is —($CR^{4a}R^{4b}$)n—$R^2$;

$R^{4a}$ and $R^{4b}$ are each independently hydrogen, substituted or unsubstituted alkyl, or $R^{4a}$ and $R^{4b}$ are taken together to form oxo or thioxo;

n is an integer of 1 to 4;

$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^g$ and $R^h$ are taken together to form =N—$R^8$; and $R^3$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl, provided that 1) a compound wherein, in (i), —X— is —NH—, and $R^3$ is cyclohexyl substituted with guanidyl, and 2) a compound wherein, in (ii), $R^a$ is substituted phenyl, $R^d$ and $R^e$ are taken together to form thioxo, $R^{4a}$ and $R^{4b}$ are taken together to form oxo, and $R^3$ is unsubstituted cyclohexyl, are excluded, or its pharmaceutically acceptable salt or a solvate thereof as an active ingredient.

Furthermore, the present invention relates to the mentioned below.

(2) A pharmaceutical composition having an analgesic effect and/or an improving effect of urination disorder comprising the compound of the formula (II):

[Chemical Formula 23]

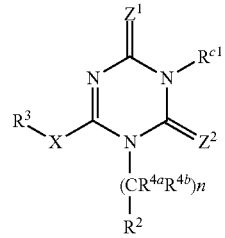

(II)

wherein $Z^1$ and $Z^2$ are each independently an oxygen atom, a sulfur atom or =N—$R^x$;

$R^x$, $R^{4a}$, $R^{4b}$, n, $R^2$, X, and $R^3$ are as defined in the above (1B);

$R^{c1}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl, or its pharmaceutically acceptable salt or a solvate thereof as an active ingredient.

(3B) The pharmaceutical composition having an analgesic effect or an improving effect of urination disorder according comprising the compound according to the above (2B) wherein $Z^1$ and $Z^2$ is an oxygen atom or a sulfur atom or its pharmaceutically acceptable salt or a solvate thereof as an active ingredient.

(4B) The pharmaceutical composition having an analgesic effect and/or an improving effect of urination disorder comprising the compound according to the above (2B) or (3B) wherein $Z^1$ and $Z^2$ are both oxygen atoms, its pharmaceutically acceptable salt or a solvate thereof as an active ingredient.

(5B) The pharmaceutical composition having an analgesic effect and/or an improving effect of urination disorder comprising the compound according to any one of the above (2B) to (4B) wherein $R^{c1}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), alkenyl substituted with one or more substituents selected from Substituent Group A, or alkynyl substituted with one or more substituents selected from Substituent Group A, or its pharmaceutically acceptable salt or a solvate thereof as an active ingredient.

(6B) The pharmaceutical composition having an analgesic effect and/or an improving effect of urination disorder comprising the compound according to any one of the above (2B) to (5B) wherein $R^{c1}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group B', or alkynyl substituted with one or more substituents selected from Substituent Group B', or its pharmaceutically acceptable salt or a solvate thereof as an active ingredient.

(7B) The pharmaceutical composition having an analgesic effect and/or an improving effect of urination disorder according to the above (1B) comprising the compound of the formula (III):

[Chemical Formula 24]

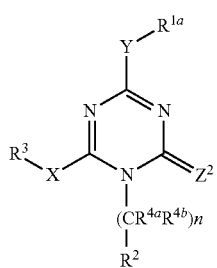

(III)

wherein $Z^2$ is an oxygen atom, a sulfur atom or (=)N—$R^x$; and $R^x$, —Y—, $R^{1a}$, $R^{4a}$, $R^{4b}$, n, $R^2$, —X—, and $R^3$ are as defined in the above (1B) or its pharmaceutically acceptable salt or a solvate thereof as an active ingredient.

(8B) The pharmaceutical composition having an analgesic effect and/or an improving effect of urination disorder comprising the compound according to the above (7B) wherein $Z^2$ is an oxygen atom or a sulfur atom or its pharmaceutically acceptable salt or a solvate thereof as an active ingredient.

(9B) The pharmaceutical composition having an analgesic effect and/or an improving effect of urination comprising the compound according to the above (7B) or (8B) wherein —Y— is —O—, or its pharmaceutically acceptable salt or a solvate thereof as an active ingredient.

(10B) The pharmaceutical composition having an analgesic effect and/or an improving effect of urination disorder comprising the compound according to any one of the above (7B) to (9B) wherein $R^{1a}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), alkenyl substituted with one or more substituents selected from Substituent Group A, or alkynyl substituted with one or more substituents selected from Substituent Group A, or its pharmaceutically acceptable salt or a solvate thereof as an active ingredient.

(11B) The pharmaceutical composition having an analgesic effect and/or an improving effect of urination disorder comprising the compound according to any one of the above (7B) to (10B) wherein $R^{1a}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group B', or alkynyl substituted with one or more substituents selected from Substituent Group B', or its pharmaceutically acceptable salt or a solvate thereof as an active ingredient.

(12B) The pharmaceutical composition having an analgesic effect and/or an improving effect of urination disorder comprising the compound according to any one of the above (2B) to (11B) wherein n is 1, or its pharmaceutically acceptable salt or a solvate thereof as an active ingredient.

(13B) The pharmaceutical composition having an analgesic effect and/or an improving effect of urination disorder comprising the compound according to any one of the above (2B) to (12B) wherein $R^{4a}$ and $R^{4b}$ are both hydrogen atoms or $R^{4a}$ and $R^{4b}$ are taken together to form oxo, or its pharmaceutically acceptable salt or a solvate thereof as an active ingredient.

(14B) The pharmaceutical composition having an analgesic effect and/or an improving effect of urination disorder comprising the compound according to any one of the above (2B) to (13B) wherein $R^2$ substituted or unsubstituted cycloalkyl, substituted or unsubstituted aryl, or substituted or unsubstituted heteroaryl, or its pharmaceutically acceptable salt or a solvate thereof as an active ingredient.

(15B) The pharmaceutical composition having an analgesic effect and/or an improving effect of urination disorder comprising the compound according to any one of the above (2B) to (14B) wherein $R^2$ cycloalkyl optionally substituted with one or more substituents selected from Substituent Group C (Substituent Group C: halogen, alkyl, alkenyl, alkynyl, alkyloxy, alkenloxy, alkynyloxy, cycloalkyl, cycloalkenyl, cycloalkynyl and alkylsilylalkynyl), heteroaryl optionally substituted with one or more substituents selected from Substituent Group C or heteroaryl optionally substituted with one or more substituents selected from Substituent Group C, its pharmaceutically acceptable salt or a solvate thereof as an active ingredient.

(16B) The pharmaceutical composition having an analgesic effect and/or an improving effect of urination disorder comprising the compound according to any one of the above (2B) to (15B) wherein —X— is —N($R^5$)— wherein and $R^5$ is as defined in the above (1B), its pharmaceutically acceptable salt or a solvate thereof as an active ingredient.

(17B) The pharmaceutical composition having an analgesic effect and/or an improving effect of urination disorder comprising the compound according to any one of the above (2B) to (16B) wherein —X— is —NH—, or its pharmaceutically acceptable salt or a solvate thereof as an active ingredient.

(18B) The pharmaceutical composition having an analgesic effect and/or an improving effect of urination disorder comprising the compound according to any one of the above (2B) to (17B) wherein $R^3$ is a group of the formula:

[Chemical Formula 25]

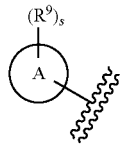

wherein ring A is aryl or heteroaryl;
s is an integer of 0 to 3;
$R^9$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or its pharmaceutically acceptable salt or a solvate thereof as an active ingredient.

(19B) The pharmaceutical composition having an analgesic effect and/or an improving effect of urination disorder comprising the compound according to any one of the above (2B) to (18B) wherein $R^8$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryl optionally substituted with one or more substituents selected from Substituent Group D, or its pharmaceutically acceptable salt or a solvate thereof as an active ingredient.

(20B) A compound of the formula (IV):

[Chemical Formula 26]

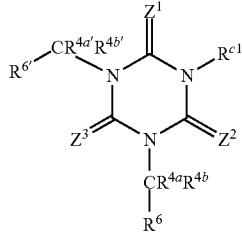

(IV)

wherein
$Z^1$, $Z^2$ and/or $Z^3$ is an oxygen atom or a sulfur atom;
$R^{c1}$ is unsubstituted alkyl, unsubstituted alkynyl, alkyl substituted with one or more substituents selected from Substituent Group B (Substituent Group B: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, and nitro), alkenyl substituted with one or more substituents selected from Substituent Group B, alkynyl substituted with one or more substituents selected from Substituent Group B;
$R^{4a}$ is hydrogen or substituted or unsubstituted alkyl;
$R^{4b}$ is hydrogen;
$R^6$ is substituted or unsubstituted cycloalkyl, substituted or unsubstituted aryl, or substituted or unsubstituted heteroaryl;
$R^{4a'}$ is hydrogen or substituted or unsubstituted alkyl;
$R^{4b'}$ is hydrogen;
$R^{6'}$ is substituted or unsubstituted aryl or substituted or unsubstitnted heteroaryl, or its pharmaceutically acceptable salt or a solvate thereof.

(21B) The compound according to the above (20B), wherein $Z^1$, $Z^2$ and $Z^3$ are oxygen atoms, or its pharmaceutically acceptable salt or solvate thereof.

(22B) The compound according to the above (20B) or (21B), wherein $R^6$ is cycloalkyl optionally substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl and alkylsilylalkynyl), aryl optionally substituted with one or more substituents selected from Substituent Group C, or heteroaryl optionally substituted with one or more substituents selected from Substituent Group C, or its pharmaceutically acceptable salt or a solvate thereof.

(23B) The compound according to any one of the above (20B) to (22B), wherein $R^{6'}$ is aryl optionally substituted with one or more substituents selected from Substituent Group D (Substituent Group D: halogen; hydroxy; alkyl optionally substituted with halogen, hydroxy, cyano, alkyloxyimino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryl optionally substituted with one or more substituents selected from Substituent Group D, or its pharmaceutically acceptable salt or a solvate thereof.

(24B) A compound of the formula (II):

[Chemical Formula 27]

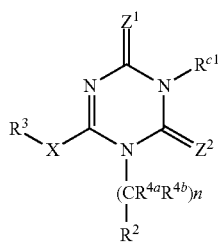

(II)

wherein $Z^1$ and/or $Z^2$ is an oxygen atom, a sulfur atom, or (=N)—$R^x$;

$R^x$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^{c1}$ is hydrogen, alkyl substituted with one or more substituents selected from Substituent Group E (Substituent Group E: sulfo; substituted or unsubstituted sulfamoyl; substituted or unsubstituted imino; substituted or unsubstituted guanidyl; a substituted or unsubstituted non-aromatic heterocyclic group provided that morpholinyl, imidazolidinyl, tetrahydropyranyl and piperidinyl are excluded: substituted or unsubstituted heteroaryl provided that pyridyl is excluded), alkenyloxy substituted with one or more substituents selected from Substituent Group E, or alkynyl substituted with one or more substituents selected from Substituent Group E;

$R^{4a}$ and $R^{4b}$ are each independently hydrogen, substituted or unsubstituted alkyl, or $R^{4b}$ and $R^{4b}$ are taken together to form oxo or thioxo;

n is an integer of 1 to 4;

$R^2$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

—X— is —O—, —S—, —N($R^5$)— or —(C$R^{5a}R^{5b}$)—;

$R^5$ is hydrogen, substituted or unsubstituted alkyl, substituted or unsubstituted alkenyl, substituted or unsubstituted alkynyl, or substituted or unsubstituted acyl;

$R^{5a}$ and $R^{5b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;

$R^3$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt or a solvate thereof.

(25B) The compound according to the above (24B) wherein $Z^1$ and/or $Z^2$ is an oxygen atom or a sulfur atom, or its pharmaceutically acceptable salt or a solvate thereof.

(26B) The compound according to the above (24B) wherein $Z^1$ and/or $Z^2$ is an oxygen atom or a sulfur atom, or its pharmaceutically acceptable salt or a solvate thereof.

(27B) The compound according to any one of the above (24B) to (26B) wherein $R^{c1}$ is alkyl substituted with one or more substituents selected from Substituent Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), alkenyl substituted with one or more substituents selected from Substituent Group A, or alkynyl substituted with one or more substituents selected from Substituent Group A, or its pharmaceutically acceptable salt or a solvate thereof.

(28B) The compound according to any one of the above (24B) to (27B) wherein $R^{c1}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group B', or alkynyl substituted with one or more substituents selected from Substituent Group B', or its pharmaceutically acceptable salt or a solvate thereof.

(29B) The compound according to any one of the above (24B) to (28B) wherein n is 1, or its pharmaceutically acceptable salt or a solvate thereof.

(30B) The compound according to any one of the above (24B) to (29B) wherein $R^{4a}$ and $R^{4b}$ are both hydrogen atoms or $R^{4a}$ and $R^{4b}$ are taken together to form oxo, or its pharmaceutically acceptable salt or a solvate thereof.

(31B) The compound according to any one of the above (24B) to (30B) wherein $R^2$ is substituted or unsubstituted cycloalkyl, substituted or unsubstituted aryl, or substituted or unsubstituted heteroaryl, or its pharmaceutically acceptable salt or a solvate thereof.

(32B) The compound according to any one of the above (24B) to (31B) wherein $R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkenyl, cycloalkynyl and alkylsilylalkynyl), heteroaryl optionally substituted with one or more substituents selected from Substituent Group C or cycloalkyl optionally substituted with one or more substituents selected from Substituent Group C, or its pharmaceutically acceptable salt or a solvate thereof.

(33B) The compound according to any one of the above (24B) to (33B) wherein —X— is —N($R^5$)— (wherein is as defined in the above (1B)), or its pharmaceutically acceptable salt or a solvate thereof.

(34B) The compound according to any one of the above (24B) to (33B) wherein X— is —NH—, or its pharmaceutically acceptable salt or a solvate thereof.

(35B) The compound according to any one of the above (24B) to (34B) wherein $R^3$ is a group of the formula:

[Chemical Formula 28]

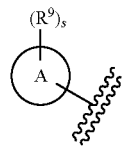

wherein ring A is aryl or heteroaryl;
s is an integer of 0 to 3; and
$R^9$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstittded alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted heteroaryloxy, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy), or its pharmaceutically acceptable salt or a solvate thereof.

(36B) The compound according to any one of the above (24B) to (35B) wherein $R^3$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy; a non-aromatic heterocyclic group; and alkylamino) or heteroaryl optionally substituted with one or more substituents selected from Substituent Group D, or its pharmaceutically acceptable salt or a solvate thereof.

(37B) A compound of the formula (VII):

[Chemical Formula 29]

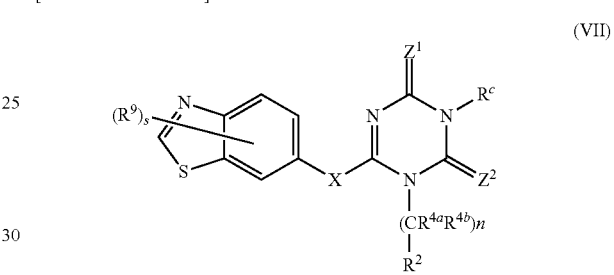

wherein
$Z^1$ and/or $Z^2$ is oxo, thioxo, or (=N)—$R^x$;
$R^x$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^c$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^{4a}$ and $R^{4b}$ are each independently hydrogen, substituted or unsubstituted alkyl, or
$R^{4b}$ and $R^{4b}$ are taken together to form oxo or thioxo;
n is an integer of 1 to 4;
$R^2$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
—X— is —O—, —S—, —N($R^5$)— or —(C$R^{5a}R^{5b}$)—;
$R^5$ is hydrogen, substituted or unsubstituted alkyl, substituted or unsubstituted alkenyl, substituted or unsubstituted alkynyl, or substituted or unsubstituted acyl;
$R^{5a}$ and $R^{5b}$ are each independently hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;
s is an integer of 0 to 3; and $R^9$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, or its pharmaceutically acceptable salt or a solvate thereof.

(38B) The compound according to the above (37B) wherein $Z^1$ and $Z^2$ are both oxygen atoms, or its pharmaceutically acceptable salt or a solvate thereof.

(39B) The compound according to any one of the above (37B) to (38B) wherein $R^c$ is unsubstituted alkyl, alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), unsubstituted alkenyl, alkenyl substituted with one or more substituents selected from Substituent Group A, unsubstituted alkynyl, alkynyl substituted with one or more substituents selected from Substituent Group A, or its pharmaceutically acceptable salt or a solvate thereof.

(40B) The compound according to any one of the above (37B) to (39B) wherein $R^c$ is unsubstituted alkyl, alkyl substituted with one or more substituents selected from Substituent Group B" (Substituent Group B": hydroxy, carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), unsubstituted alkenyl, alkenyl substituted with one or more substituents selected from Substituent Group B", unsubstituted alkynyl, alkynyl substituted with one or more substituents selected from Substituent Group B", or its pharmaceutically acceptable salt or a solvate thereof.

(41B) The compound according to any one of the above (37B) to (39B) wherein n is 1, and $R^{4a}$ and $R^{4b}$ are both hydrogen atoms, or its pharmaceutically acceptable salt or a solvate thereof.

(42B) The compound according to any one of the above (37B) to (41B) wherein $R^2$ is substituted or unsubstituted cycloalkyl, substituted or unsubstituted aryl, or substituted or unsubstituted heteroaryl, or its pharmaceutically acceptable salt or a solvate thereof.

(43B) The compound according to any one of the above (37B) to (42B) wherein $R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkenyl, cycloalkynyl and alkylsilylalkynyl), heteroaryl optionally substituted with one or more substituents selected from Substituent Group C or cycloalkyl optionally substituted with one or more substituents selected from Substituent Group C, or its pharmaceutically acceptable salt or a solvate thereof.

(44B) The compound according to any one of the above (37B) to (43B) wherein —X— is —N($R^5$)— wherein $R^5$ is as defined in the above (37B), or its pharmaceutically acceptable salt or a solvate thereof.

(45B) The compound according to any one of the above (37B) to (44B) wherein X— is —NH—, its pharmaceutically acceptable salt or a solvate thereof.

(46B) The compound according to any one of the above (37B) to (45B) wherein s is an integer of 0 to 2; and $R^9$ is each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, and substituted or unsubstituted sulfamoyl), or its pharmaceutically acceptable salt or a solvate thereof.

In (46B), a compound wherein s is an integer of 0 to 1, or its pharmaceutically acceptable salt or a solvate thereof is preferable.

(47B) A compound of the formula (VIII):

[Chemical Formula 30]

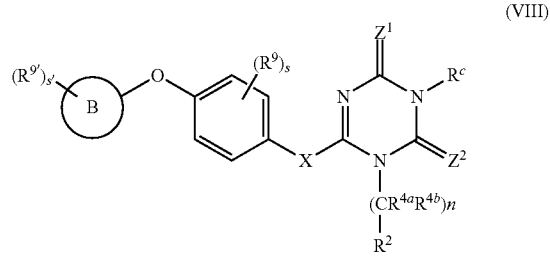

wherein
$Z^1$ and/or $Z^2$ is oxo, thioxo, or =N—$R^x$;
$R^x$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^c$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^{4a}$ and $R^{4b}$ are each independently hydrogen, substituted or unsubstituted alkyl, or $R^{4b}$ and $R^{4b}$ are taken together to form oxo or thioxo;

n is an integer of 1 to 4;

$R^2$ is substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;

—X— is —O—, —S—, —N($R^5$)— or —($CR^{5a}R^{5b}$)—;

ring B is heteroaryl;

s and s' are each independently is an integer of 0 to 3;

$R^9$ and $R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsulystituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, or its pharmaceutically acceptable salt or a solvate thereof.

(48B) The compound according to the above (47B) wherein $Z^1$ and $Z^2$ are both oxygen atoms, or its pharmaceutically acceptable salt or a solvate thereof.

(49B) The compound according to the above (47B) or (48B) wherein $R^c$ is unsubstituted alkyl, alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), unsubstituted alkenyl, alkenyl substituted with one or more substituents selected from Substituent Group A, unsubstituted alkynyl, alkynyl substituted with one or more substituents selected from Substituent Group A, or its pharmaceutically acceptable salt or a solvate thereof.

(50B) The compound according to any one of the above (47B) to (49B) wherein $R^c$ is unsubstituted alkyl, alkyl substituted with one or more substituents selected from Substituent Group B" (Substituent Group B": hydroxy, carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), unsubstituted alkenyl, alkenyl substituted with one or more substituents selected from Substituent Group B", unsubstituted alkynyl, alkynyl substituted with one or more substituents selected from Substituent Group B", or its pharmaceutically acceptable salt or a solvate thereof.

(51B) The compound according to any one of the above (47B) to (50B) wherein n is 1, and $R^{4a}$ and $R^{4b}$ are both hydrogen atoms, or its pharmaceutically acceptable salt or a solvate thereof.

(52B) The compound according to any one of the above (47B) to (51B) wherein $R^2$ is substituted or unsubstituted cycloalkyl, substituted or unsubstituted aryl, or substituted or unsubstituted heteroaryl, or its pharmaceutically acceptable salt or a solvate thereof.

(53B) The compound according to any one of the above (47B) to (52B) wherein $R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkenyl, cycloalkynyl and alkylsilylalkynyl), heteroaryl optionally substituted with one or more substituents selected from Substituent Group C or cycloalkyl optionally substituted with one or more substituents selected from Substituent Group C, or its pharmaceutically acceptable salt or a solvate thereof.

(54B) The compound according to any one of the above (47B) to (53B) wherein X— is —N($R^5$)— wherein $R^5$ is as defined in the above (47B), or its pharmaceutically acceptable salt or a solvate thereof.

(55B) The compound according to any one of the above (47B) to (54B) wherein X— is —NH—, or its pharmaceutically acceptable salt or a solvate thereof.

(56B) The compound according to any one of the above (47B) to (55B) wherein s and s' are each independently an integer of 0 to 2; and $R^9$ and $R^{9'}$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, or substituted or unsubstituted sulfamoyl, or its pharmaceutically acceptable salt or a solvate thereof.

In (57B), a compound wherein s is 0, s' is 0 or 1, and R9'' is halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, or substituted or unsubstituted sulfamoyl, or its pharmaceutically acceptable salt or a solvate thereof is preferable.

(58B) A pharmaceutical composition comprising the compound according to any one of the above (20B) to (57B), or its pharmaceutically acceptable salt or a solvate thereof.

(59B) The pharmaceutical composition according to the above (58B) wherein the composition has a $P2X_3$ and/or $P2X_{2/3}$ receptor antagonistic effect.

(60B) A compound according to any one of the above (20B) to (57B) for use in a method for treating and/or preventing a disease related $P2X_3$ and/or $P2X_{2/3}$ receptor, or its pharmaceutically acceptable salt or a solvate thereof.

(61B) A compound according to any one of the above (20B) to (57B) for use in method for treating and/or preventing a disease related to $P2X_3$ and/or $P2X_{2/3}$ receptor, or its pharmaceutically acceptable salt, or a solvate thereof.

(62B) A method for treating or preventing a disease related to $P2X_3$ and/or $P2X_{2/3}$ receptor, comprising administering the compound according to any one of the above (20B) to (57B), or its pharmaceutically acceptable salt, or a solvate thereof.

(1A) A pharmaceutical composition having an analgesic effect and/or an improving effect of urination disorder comprising a compound of the formula (I):

[Chemical Formula 31]

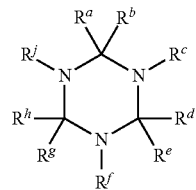

(I)

wherein
(i)
$R^h$ and $R^j$ are taken together to form a bond;
$R^a$ and $R^b$ and/or $R^d$ and $R^e$ are taken together to form oxo, thioxo or =N—$R^x$;
$R^x$ is a hydrogen atom, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

$R^c$ is a hydrogen atom, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
—$R^f$ is —$(CR^{4a}R^{4b})$n—$R^2$;
$R^{4a}$ and $R^{4b}$ are each independently substituted or unsubstituted alkyl, or $R^{4a}$ and $R^{4b}$ are taken together to form oxo or thioxo;
$R^2$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
—$R^g$ is —X—$R^3$;
—X— is —O—, —S—, —N($R^5$)— or —$(CR^{5a}R^{5b})$—;
$R^3$ is substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;
$R^5$ is a hydrogen atom, substituted or unsubstituted alkyl, substituted or unsubstituted alkenyl, substituted or unsubstituted alkynyl, or substituted or unsubstituted acyl;
$R^{5a}$ and $R^{5b}$ are each independently a hydrogen atom, halogen, hydroxy, substituted or unsubstituted alkyl, substituted or unsubstituted alkenyl, substituted or unsubstituted alkynyl, substituted or unsubstituted alkyloxy, substituted or unsubstituted alkynyloxy, or substituted or unsubstituted alkenyloxy;
(ii)
$R^h$ and $R^j$ are taken together to form a bond;
$R^a$ is a group of —Y—$R^{1a}$;
$R^{1a}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
—Y— is —O—, —S—, —N($R^7$)— or $(CR^{8a}R^{8b})$—;
$R^7$ is hydrogen, substituted or unsubstituted alkyl, substituted or unsubstituted acyl;
$R^{8a}$ and $R^{8b}$ are each independently hydrogen, halogen or substituted or unsubstituted alkyl; hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl;
$R^b$ and $R^c$ are taken together to form a bond;
$R^d$ and $R^e$ are taken together to form oxo or thioxo;
$R^f$ and $R^g$ are as defined in the above (i); or
(iii)
$R^a$ and $R^b$, $R^d$ and $R^e$, and/or $R^g$ and $R^h$ are taken together to form oxo or thioxo;
$R^c$ is unsubstituted alkyl, unsubstituted alkynyl, alkyl substituted with one or more substituents selected from Substituent Group B (Substituent Group B: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, and nitro), alkenyl substituted with one or more substituents selected from Substituent Group B, or alkynyl substituted with one or more substituents selected from Substituent Group B;

$R^f$ is —$(CR^{4a}R^{4b})$—$R^6$;

$R^j$ is —$(CR^{4a'}R^{4b'})$—$R^{6'}$;

$R^6$ is substituted or unsubstituted cycloalkyl, substituted or unsubstituted aryl, or substituted or unsubstituted heteroaryl;

$R^{6'}$ is substituted or unsubstituted, aryl, or substituted or unsubstituted heteroaryl;

$R^{4a}$, $R^{4b}$, $R^{4a'}$ and $R^{4b'}$ are each independently a hydrogen atom, or substituted or unsubstituted alkyl, provided that 1) a compound wherein, in (i), —X— is —NH—, and $R^3$ is cyclohexyl substituted with guanidyl, and 2) a compound wherein, in (ii), $R^a$ is substituted phenyl, $R^d$ and $R^e$ are taken together to form thioxo, $R^{4a}$ and $R^{4b}$ are taken together to form oxo, and $R^3$ is unsubstituted cyclohexyl, are excluded, or its pharmaceutically acceptable salt or solvate thereof as an active ingredient.

[Chemical Formula 32]

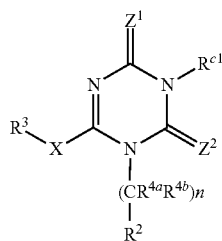

(II)

wherein $Z^1$ and/or $Z^2$ is oxo, thioxo, or =N—$R^x$;

$R^x$, $R^{4a}$, $R^{4b}$, n, $R^2$, X, and $R^3$ are as defined in the above (1A);

$R^{c1}$ is hydrogen, substituted or unsubstituted alkyl, substituted or unsubstituted alkenyl, substituted or unsubstituted alkynyl, substituted or unsubstituted acyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl, or its pharmaceutically acceptable salt or a solvate thereof as an active ingredient.

(3A) The pharmaceutical composition having an analgesic effect and/or an improving effect of urination disorder comprising the compound according to the above (2A) wherein $Z^1$ and/or $Z^2$ is oxo or thioxo, or its pharmaceutically acceptable salt or a solvate thereof as an active ingredient.

(4A) The pharmaceutical composition having an analgesic effect and/or an improving effect of urination disorder comprising the compound according to the above (2A) or (3A) wherein $Z^1$ and/or $Z^2$ are both oxo, or its pharmaceutically acceptable salt or a solvate thereof as an active ingredient.

(5A) The pharmaceutical composition having an analgesic effect and/or an improving effect of urination disorder comprising the compound according to any one of the above (2A) or (4A) wherein $R^{c1}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), alkenyl substituted with one or more substituents selected from Substituent Group A, or alkynyl substituted with one or more substituents selected from Substituent Group A, or its pharmaceutically acceptable salt or a solvate thereof as an active ingredient.

(6A) The pharmaceutical composition having an analgesic effect and/or an improving effect of urination disorder comprising the compound according to any one of the above (2A) or (5A) wherein $R^{c1}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group B', or alkynyl substituted with one or more substituents selected from Substituent Group B', or its pharmaceutically acceptable salt or a solvate thereof as an active ingredient.

(7A) A pharmaceutical composition having an analgesic effect and/or an improving effect of urination disorder comprising the compound of the formula (III):

[Chemical Formula 33]

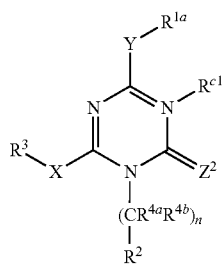

(III)

wherein $Z^2$ is oxo, thioxo, or =N—$R^x$; $R^x$, —Y—, $R^{1a}$, $R^{4a}$, $R^{4a}$, n, $R^2$, —X—, and $R^3$ are as defined in the above (1A); or its pharmaceutically acceptable salt or a solvate thereof as an active ingredient.

(8A) The pharmaceutical composition having an analgesic effect and/or an improving effect of urination disorder comprising the compound according to the above (7A) wherein $Z^2$ is oxo or thioxo or its pharmaceutically acceptable salt or a solvate thereof as an active ingredient.

(9A) The pharmaceutical composition having an analgesic effect and/or an improving effect of urination disorder comprising the compound according to the above (7A) or (8A) wherein —Y— is —O—, or its pharmaceutically acceptable salt or a solvate thereof as an active ingredient.

(10A) The pharmaceutical composition having an analgesic effect and/or an improving effect of urination disorder comprising the compound according to any one of the above (7A) or (9A) wherein $R^{1a}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxycarbonyl, substituted or unsubstituted heteroaryloxycarbonyl, nitro, oxo, and thioxo), alkenyl substituted with one or more substituents selected from Substituent Group A, or alkynyl substituted with one or more substituents selected from Substituent Group A, or its pharmaceutically acceptable salt or a solvate thereof as an active ingredient.

(11A) The pharmaceutical composition having an analgesic effect and/or an improving effect of urination disorder comprising the compound according to the above (7A) or (10A) wherein $R^{1a}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and guanidyl), alkenyl substituted with one or more substituents selected from Substituent Group B', or alkynyl substituted with one or more substituents selected from Substituent Group B', or its pharmaceutically acceptable salt or a solvate thereof as an active ingredient.

(12A) The pharmaceutical composition having an analgesic effect and/or an improving effect of urination disorder comprising the compound according to any one of the above (2A) to (16A) wherein n is 1, or its pharmaceutically acceptable salt or a solvate thereof as an active ingredient.

(13A) The pharmaceutical composition having an analgesic effect and/or an improving effect of urination disorder comprising the compound according to any one of the above (2A) to (12A) wherein $R^{4a}$ and $R^{4b}$ are both hydrogen, or $R^{4a}$ and $R^{4b}$ are taken together to form oxo, or its pharmaceutically acceptable salt or a solvate thereof as an active ingredient.

(14A) The pharmaceutical composition having an analgesic effect and/or an improving effect of urination disorder comprising the compound according to any one above (2A) to (13A) wherein $R^2$ is substituted or unsubstituted cycloalkyl, substituted or unsubstituted aryl, or substituted or unsubstituted heteroaryl, or its pharmaceutically acceptable salt or a solvate thereof as an active ingredient.

(15A) The pharmaceutical composition having an analgesic effect and/or an improving effect of urination disorder comprising the compound according to the above (2A) to (14A) wherein $R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl and alkylsilylalkynyl), heteroaryl optionally substituted with one or more substituents selected from Substituent Group C or cycloalkyl optionally substituted with one or more substituents selected from Substituent Group C, or its pharmaceutically acceptable salt or a solvate thereof as an active ingredient.

(16A) The pharmaceutical composition having an analgesic effect and/or an improving effect of urination disorder comprising the compound according to the above (2A) to (15A) wherein —X— is —N($R^5$)— wherein $R^5$ is as defined in the above (1A), or its pharmaceutically acceptable salt or a solvate thereof as an active ingredient.

(17A) The pharmaceutical composition having an analgesic effect and/or an improving effect of urination disorder comprising the compound according to any one of the above (2A) to (16A) wherein —X— is —NH—, or its pharmaceutically acceptable salt or a solvate thereof as an active ingredient.

(18A) The pharmaceutical composition having an analgesic effect and/or an improving effect of urination disorder comprising the compound according to any one of the above (2A) to (17A) wherein $R^3$ is a group of the formula:

[Chemical Formula 34]

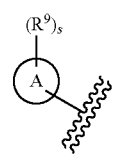

wherein ring A is aryl or heteroaryl;
s is an integer of 0 to 3;
$R^9$ are each independently halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstittded alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or its pharmaceutically acceptable salt or a solvate thereof as an active ingredient.

(18A') The pharmaceutical composition having an analgesic effect and/or an improving effect of urination disorder comprising the compound according to any one of the above (2A) to (18A) wherein $R^3$ is a group of the formula:

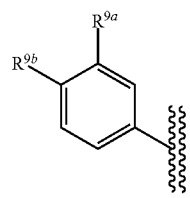

[Chemical Formula 35]

$R^{9a}$ is hydrogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted non-aromatic heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy;
$R^{9b}$ is halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy, or its pharmaceutically acceptable salt or a solvate thereof as an active ingredient.

(18A") The pharmaceutical composition having an analgesic effect and/or an improving effect of urination disorder comprising the compound according to any one of the above (2A) to (18A) and (18A') wherein $R^3$ is a group of the formula:

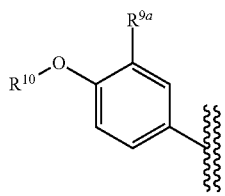

[Chemical Formula 36]

$R^{9a}$ is as defined in the above (18A'); $R^{10}$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt or a solvate thereof as an active ingredient.

(19A) The pharmaceutical composition having an analgesic effect and/or improving effect of urination disorder comprising the compound according to any one of the above (2A) to (18A) and (18A') wherein $R^3$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryl optionally substituted with one or more substituents selected from Substituent Group D, or its pharmaceutically acceptable salt or a solvate thereof as an active ingredient.

(19A') The pharmaceutical composition having an analgesic effect and/or an improving effect of urination, disorder comprising the compound according to any one of the above (2A) to (18A) wherein $R^3$ is a group of the formula(A):

[Chemical Formula 37]

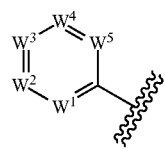
(A)

wherein =W¹—W²=W³—W⁴=W⁵— is any one selected from the following (a) to (h):

(a): =C(H)—C(R^{10a})=C(R^{10b})—C(H)—;
(b): =N—C(R^{10a})=C(R^{10b})—C(R^{10c})=C(H)—;
(c): =C(H)—N=C(R^{10b})—C(R^{10c})=C(H)—;
(d): =C(H)—C(R^{10a})=N—C(R^{10c})=C(H)—;
(e): =C(H)—C(R^{10a})=C(R^{10b})—N=C(H)—;
(f): =N—C(R^{10a})=C(R^{10b})—C(R^{10c})=(N)—;
(g): =C(H)—C(R^{10a})=N—C(R^{10c})=C(H)—; and
(h): =C(H)—N=C(R^{10b})—N=C(H)—;

$R^{10a}$, $R^{10b}$, amd $R^{10c}$ is each independently hydrogen, halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, substituted or unsubstituted heteroaryloxy; or $R^{10a}$ and $R^{10b}$ or $R^{10b}$ and $R^{10c}$ together with the ring atom to which they are attached form a non-aromatic carbocyclic ring, a non-aromatic heterocyclic ring, an aromatic carbocyclic ring or an aromatic heterocyclic ring, or its pharmaceutically acceptable salt or a solvate thereof as an active ingredient.

(19A") A compound described in any one of the above (1A) to (19A), (18A'), (18A") and (19A') for use in a method for treating, preventing and/or improving pain and/or urination disorder, or its pharmaceutically acceptable salt or a solvate thereof.

(19A''') A method for treating, preventing and/or improving pain and/or urination disorder comprising administering the compound described in any one of the above (1A) to (19A), (18A'),(18A") and (19A'), or its pharmaceutically acceptable salt or a solvate thereof.

(20A) A compound of the formula (IV):

[Chemical Formula 38]

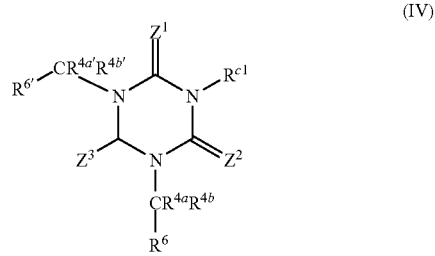
(IV)

wherein
$R^{c1}$ is unsubstituted alkyl, unsubstituted alkynyl, alkyl substituted with one or more substituents selected from Substituent Group B, alkenyl substituted with one or more substituents selected from Substituent Group B, or alkynyl substituted with one or more substituents selected from Substituent Group B;
$R^{4a}$ is hydrogen or substituted or unsubstituted alkyl;
$R^{4b}$ is hydrogen;
$R^6$ is substituted or unsubstituted cycloalkyl, substituted or unsubstituted aryl, or substituted or unsubstituted heteroaryl;
$R^{4a'}$ is hydrogen or substituted or unsubstituted alkyl;
$R^{4b'}$ is hydrogen; and
$R^{6'}$ is substituted or unsubstituted aryl or substituted or unsubstitnted heteroaryl, or its pharmaceutically acceptable salt or a solvate thereof.

(21A) The compound according to the above (20A) wherein $Z^1$, $Z^2$, and $Z^3$ are oxygen atoms, or its pharmaceutically acceptable salt or a solvate thereof.

(22A) The compound according to the above (20A) or (22A) wherein $R^6$ is cycloalkyl optionally substituted with one or more substituents selected from Substituent Group C, aryl optionally substituted with one or more substituents selected from Substituent Group C, or heteroaryl optionally substituted with one or more substituents selected from Substituent Group C, or its pharmaceutically acceptable salt or a solvate thereof.

(23A) The compound according to any one of the above (20A) to (22A) wherein $R^{6'}$ is aryl optionally substituted with one or more substituents selected from Substituent Group D, or heteroaryl optionally substituted with one or more substituents selected from Substituent Group D, or its pharmaceutically acceptable salt or a solvate thereof.

(24A) A compound of the formula (II):

[Chemical Formula 39]

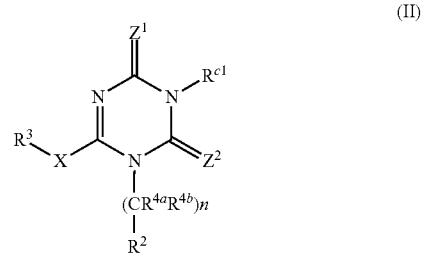
(II)

wherein

Z¹ and/or Z² is an oxygen atom, a sulfur atom, or (=N)—R$^x$;
R$^x$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl or substituted or unsubstituted heteroaryl;

R$^{c1}$ is hydrogen, alkyl substituted with one or more substituents selected from Substituent Group E (Substituent Group E: sulfo; substituted or unsubstituted sulfamoyl; substituted or unsubstituted imino; substituted or unsubstituted guanidyl; a substituted or unsubstituted non-aromatic heterocyclic group provided that morpholinyl, imidazolidinyl, tetrahydropyranyl and piperidinyl are excluded: substituted or unsubstituted heteroaryl provided that pyridyl is excluded), alkenyloxy substituted with one or more substituents selected from Substituent Group E, or alkynyl substituted with one or more substituents selected from Substituent Group E, or its pharmaceutically acceptable salt or a solvate thereof.

(25A) The compound according to the above (24A) wherein Z¹ and Z² is oxo or thioxo, or its pharmaceutically acceptable salt or a solvate thereof.

(26A) The compound according to the above (24A) or (25A) wherein Z¹ and Z² are both oxo, or its pharmaceutically acceptable salt or a solvate thereof.

(27A) The compound according to any one of the above (24A) to (26A) wherein R$^{c1}$ is alkyl substituted with one or more substituents selected from Substituent Group B' (Substituent Group B': carboxy, sulfo, a substituted or unsubstituted non-aromatic heterocyclic group, tetrazolyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group B', or alkynyl substituted with one or more substituents selected from Substituent Group B', or its pharmaceutically acceptable salt or a solvate thereof.

(28A) The compound according to any one of the above (24A) to (27A) wherein n is 1, or its pharmaceutically acceptable salt or a solvate thereof.

(29A) The compound according to any one of the above (24A) to (28A) wherein R$^{4a}$ and R$^{4b}$ are both hydrogen atoms or R$^{4a}$ and R$^{4b}$ are taken together to form oxo, or its pharmaceutically acceptable salt or a solvate thereof.

(30A) The compound according to any one of the above (24A) to (29A) wherein R² is substituted or unsubstituted cycloalkyl, substituted or unsubstituted aryl, or substituted or unsubstituted heteroaryl, or its pharmaceutically acceptable salt or a solvate thereof.

(31A) The compound according to any one of the above (24A) to (30A), wherein R² is aryl substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl, and alkylsilylalkynyl), heteroaryl optionally substituted with one or more substituents selected from Substituent Group C or cycloalkyl optionally substituted with one or more substituents selected from Substituent Group C, or its pharmaceutically acceptable salt or a solvate thereof.

(32A) The compound according to any one of the above (24A) to (31A) wherein —X— is —N(R⁵)—wherein R⁵ is defined in the above (1A), or its pharmaceutically acceptable salt or a solvate thereof.

(33A) The compound according to any one of the above (24A) to (32A) wherein X— is —NH—, or its pharmaceutically acceptable salt or a solvate thereof.

(34A) The compound according to any one of the above (24A) to (33A) wherein
R³ is a group of the formula;

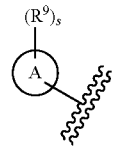

[Chemical Formula 40]

wherein ring A is aryl or heteroaryl;
s is an integer of 0 to 1;
R⁹ are each independently halogen, hydroxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted aryl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy, or its pharmaceutically acceptable salt or a solvate thereof according to any one of the above (24A) to (33A).

(34A') The compound according to any one of the above (24A) to (34A) wherein R³ is a group of the formula:

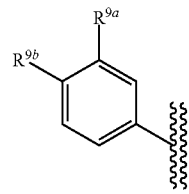

[Chemical Formula 41]

wherein R$^{9a}$ is hydrogen, hydroxy, cyano, nitro, substituted or unsubstituted substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted aryl, carboxy, substituted or unsubstituted alkyloxyoarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy, or substituted or unsubstituted heteroaryloxy: $R^{9b}$ halogen, hydroxy, cyano, nitro, substituted or unsubstituted alkyl, substituted or unsubstituted alkenyl, substituted or unsubstituted alkynyl, substituted or unsubstituted alkyloxy, substituted or unstrbstituted alkenyloxy, substituted or unsubstituted alkynyloxy, substituted or unsubstituted alkylthio, substituted or unsubstituted alkenylthio, substituted or unsubstituted alkynylthio, substituted or unstibstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted substituted or unsubstituted heteroaryl, substituted or unsubstituted cycloalkyloxy, substituted or unsubstituted cycloalkenyloxy, substituted or unsubstituted non-aromatic heterocyclyloxy, substituted or unsubstituted aryloxy or substituted or unsubstituted heteroaryloxy, or its pharmaceutically acceptable salt or a solvate thereof.

(34A") The compound according to any one of the above (24A) to (34A) and (34A') wherein $R^3$ is a group of the formula:

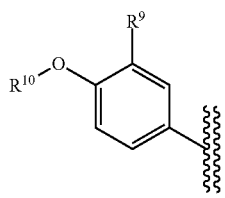

[Chemical Formula 42]

wherein
$R^9$ is as defined in the above (7A); $R^{10}$ is substituted or unsubstituted alkyl, substituted or unsubstituted alkenyl, substituted or unsubstituted alkynyl, substituted or unsubstituted cycloalkyl, substituted or unsubstituted cycloalkenyl, a substituted or unsubstituted non-aromatic heterocyclic group, substituted or unsubstituted aryl, or substituted or unsubstituted heteroaryl, or its pharmaceutically acceptable salt or a solvate thereof.

(35A) The compound according to any one of the above (24A) to (34A), (34A') and (34A") wherein $R^8$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryl optionally substituted with one or more substituents selected from Substituent Group D, or its pharmaceutically acceptable salt or a solvate thereof.

(36A) A compound of the following formula:

[Chemical Formula 43]

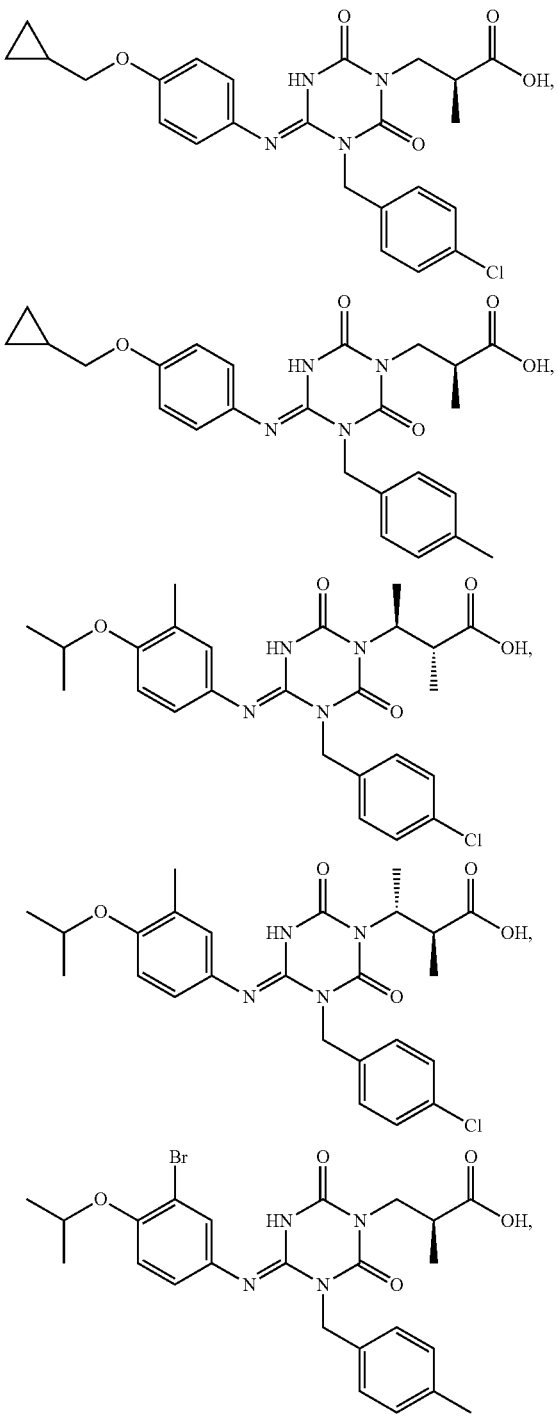

55
-continued
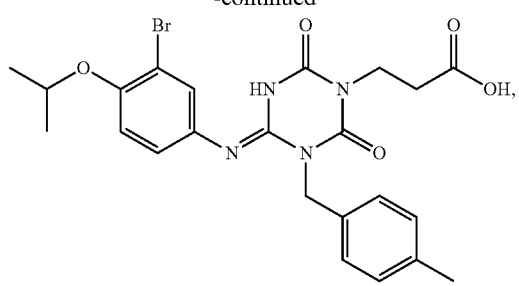
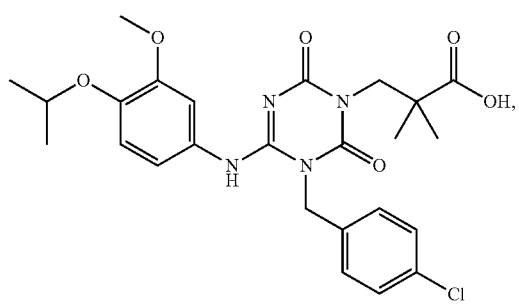
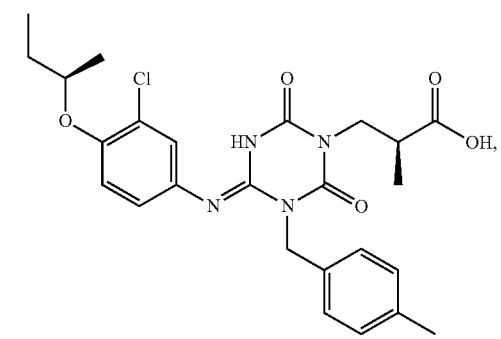
[Chemical Formula 44]
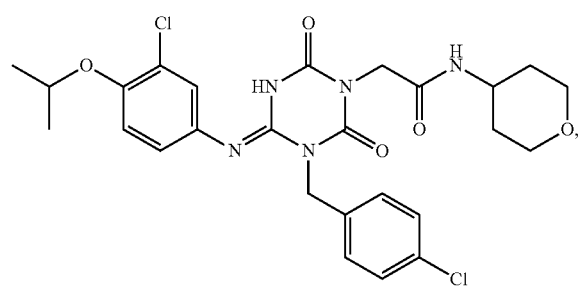
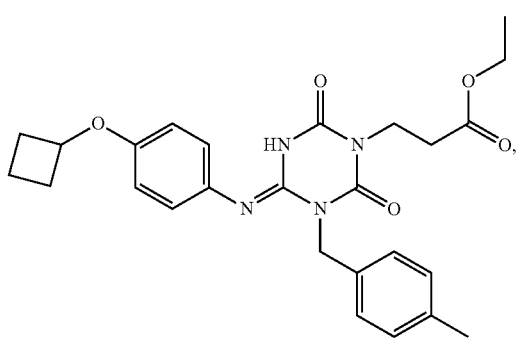
56
-continued
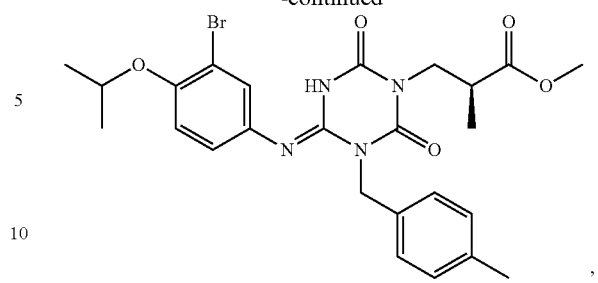
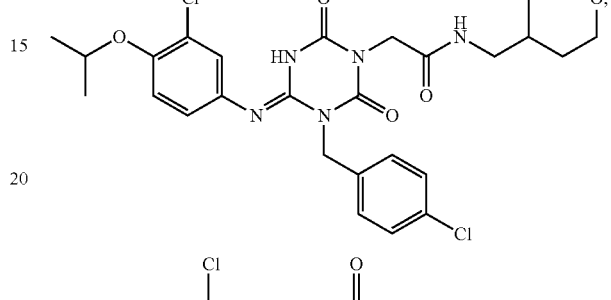
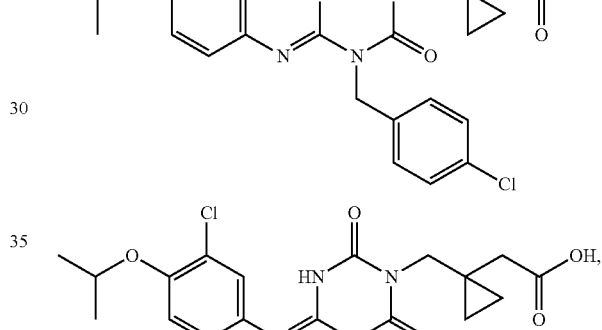
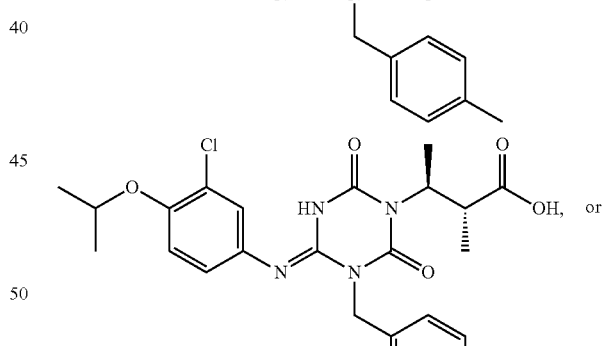
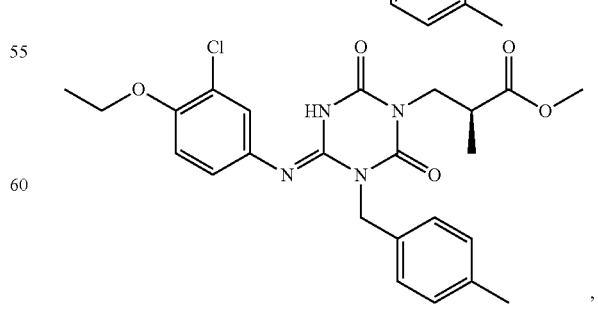
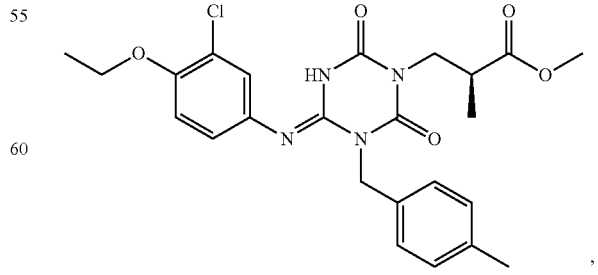
or pharmaceutically acceptable salt or a solvate thereof.

(36A') A compound of the following formula:
[Chemical Formula 45]
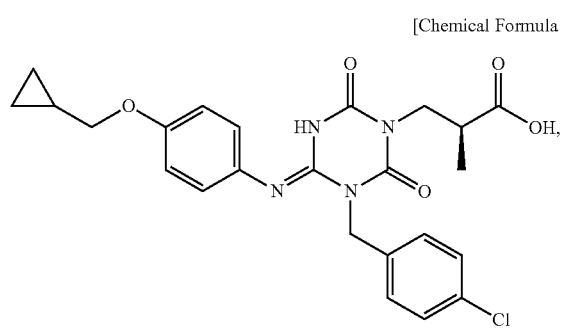
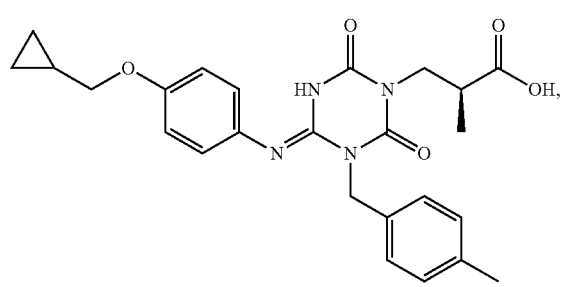
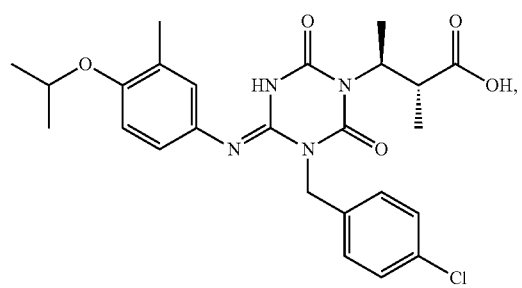
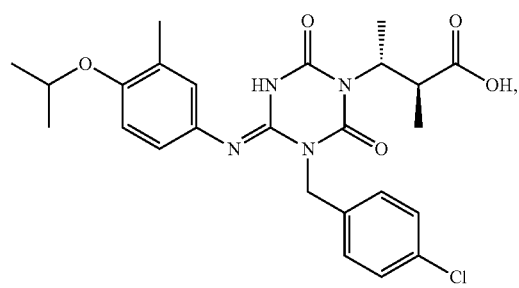
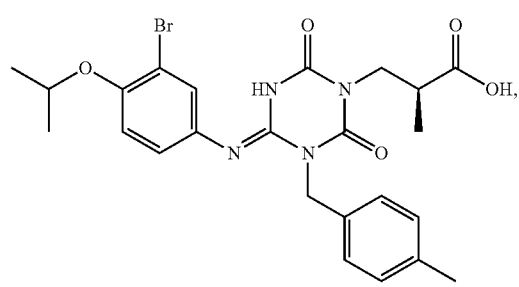
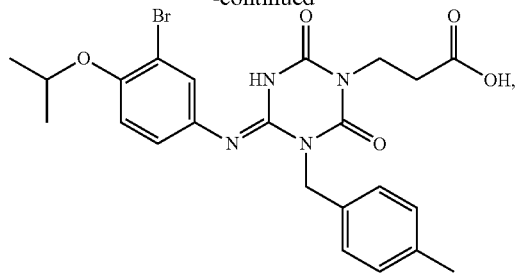
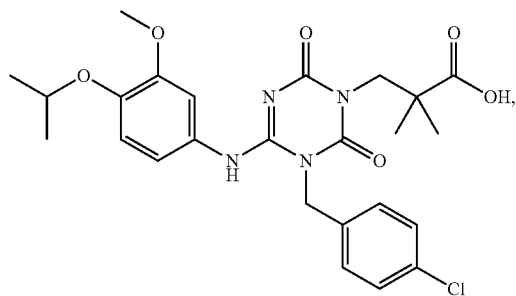
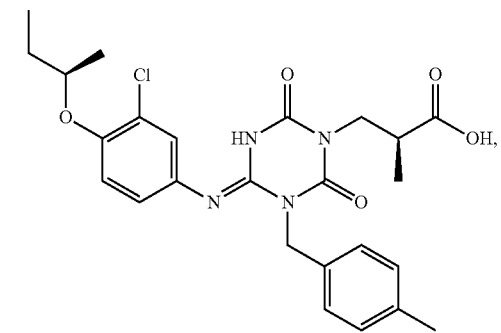
or its pharmaceutically acceptable salt or a solvate thereof.
(36A") A compound of the following formula:
[Chemical Formula 46]
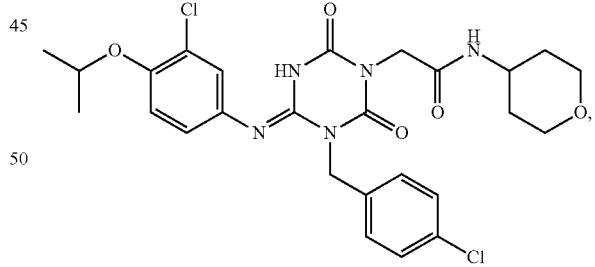
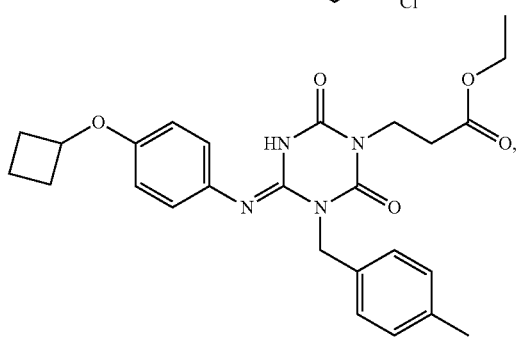

-continued
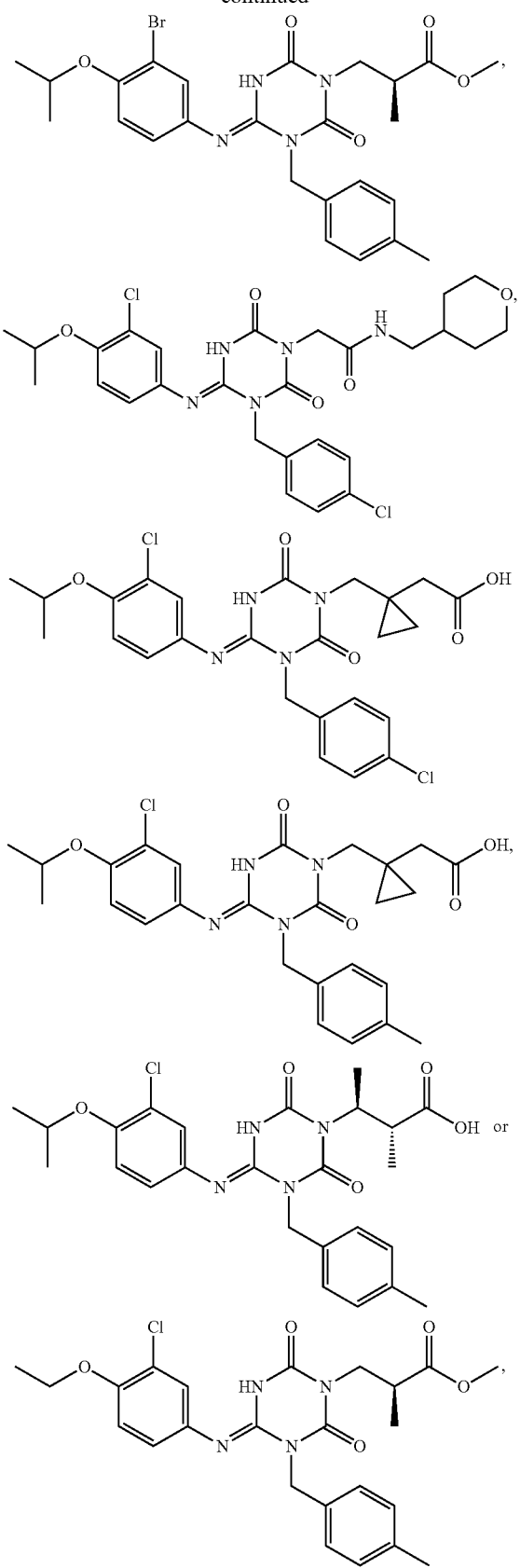
its pharmaceutically acceptable salt or solvate thereof.
(36A''') A pharmaceutical composition having an analgesic effect and/or an improving effect of urination disorder comprising the compound of the following formula:
[Chemical Formula 47]
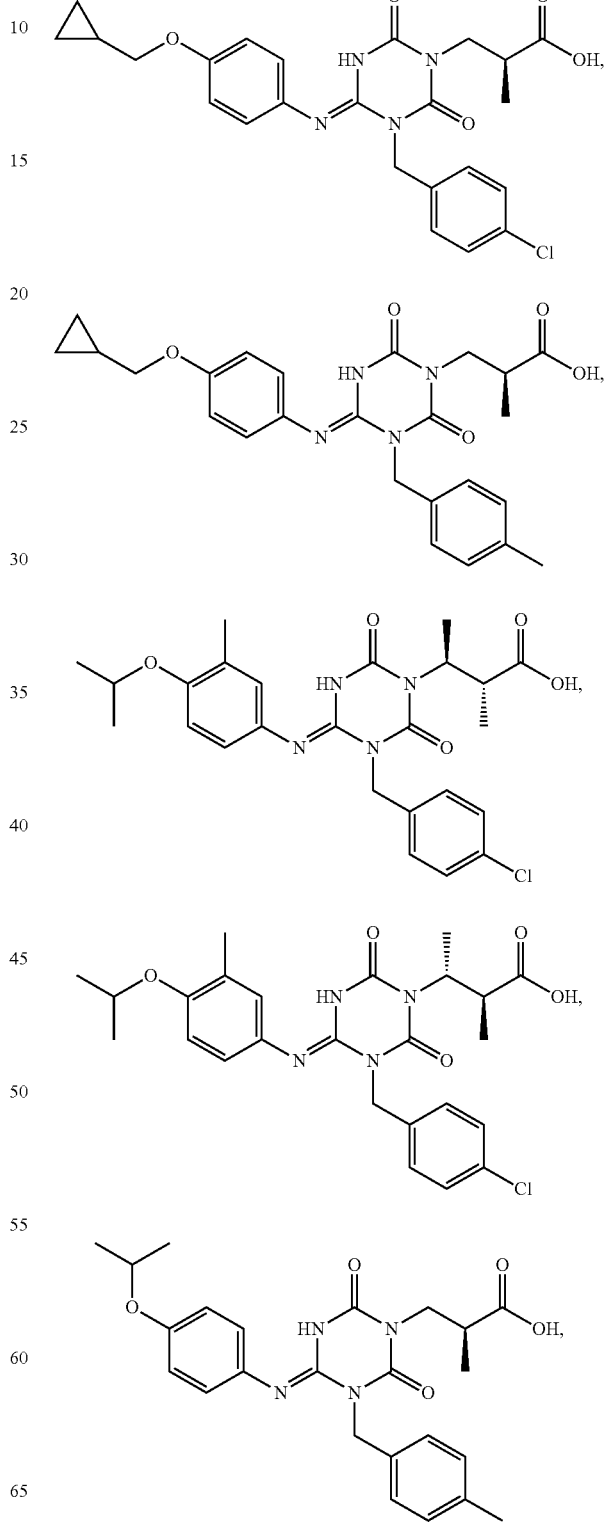

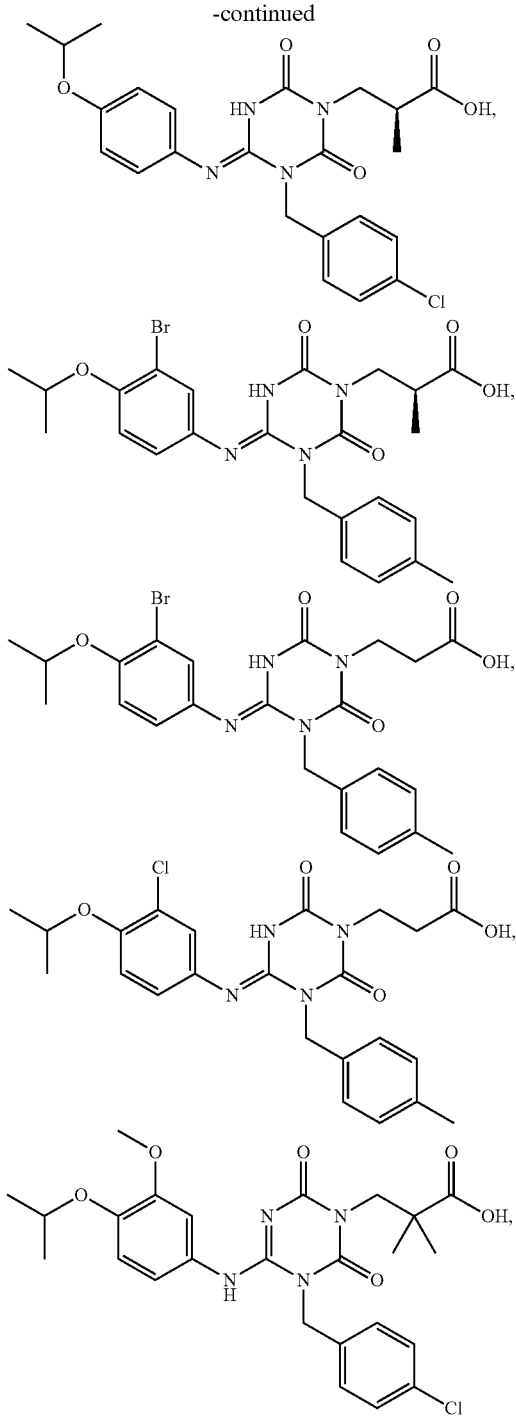
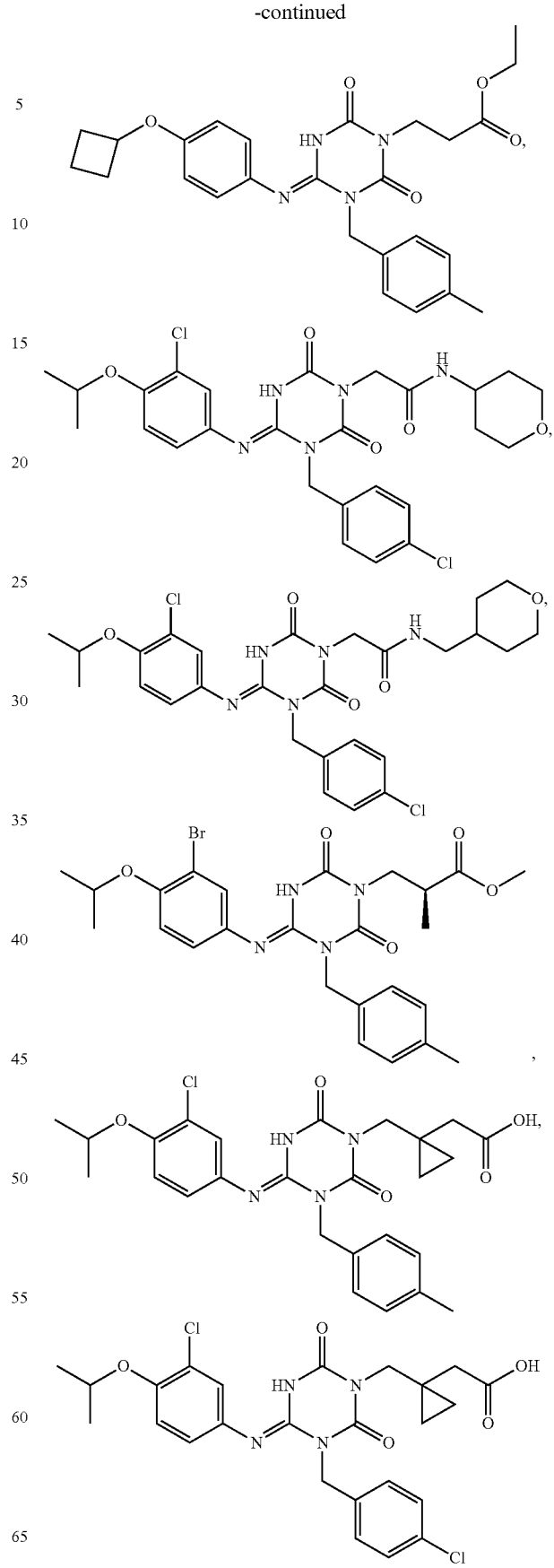

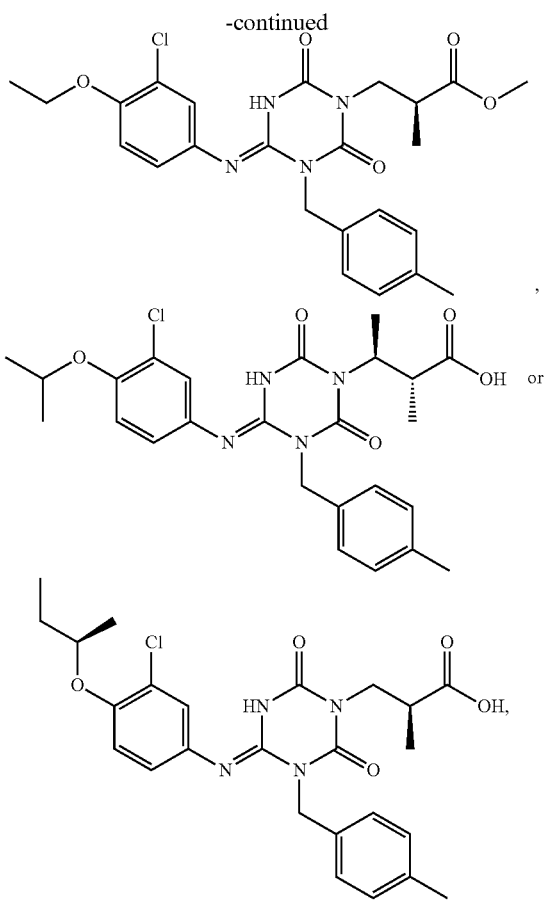

or its pharmaceutically acceptable salt or a solvate thereof as an active ingredient.

(37A) A pharmaceutical composition comprising the compound according to any one of the above (20A) to (36A), (35A'), (36A'), (35A") and (36A"), or its pharmaceutically acceptable salt or a solvate thereof.

(37A') A pharmaceutical composition comprising the compound according to any one of the above (20A) to (36A), (35A'), (36A'), (35A") and (36A"), or its pharmaceutically acceptable salt or a solvate thereof wherein the composition has a $P2X_3$ and/or $P2X_{2/3}$ receptor antagonistic effect.

(38A) The pharmaceutical composition according to (37A) which has a $P2X_3$ and/or $P2X_{2/3}$ receptor antagonistic effect.

(39A) A compound according to any one of the above (20A) to (36A), (35A'), (36A'), (35A") and (36A"), or its pharmaceutically acceptable salt or a solvate thereof for use in a method for treating and/or preventing a disease related to $P2X_3$ and/or $P2X_{2/3}$ receptor.

(40A) A method for treating and/or preventing a disease related to $P2X_3$ and/or $P2X_{2/3}$ receptor comprising administering the compound according to (20A) to (36A), (35A'), (36A'), (35A") and (36A") and (36A'''), or its pharmaceutically acceptable salt or a solvate thereof.

(41A) A compound according to any one of the above (20A) to (36A), (35A'), (36A'), (35A"), (36A") and (36A'''), or its pharmaceutically acceptable salt or a solvate thereof for use in a method for treating pain and/or urination disorder.

(42A) A method for relieving pain and/or treating urination disorder comprising administering the compound according to (20A) to (36A), (35A'), (36A'), (35A"), (36A") and (36A''') or its pharmaceutically acceptable salt or a solvate thereof.

[Effect of the Invention]

The compound of the invention has an antagonistic effect on $P2X_3$ and/or $P2X_{2/3}$ receptor and is useful in the treatment of diseases or conditions associated with a $P2X_3$ and/or $P2X_{2/3}$ receptor, especially chronic pain, overactive bladder, etc.

[Mode for Carrying Out the Invention]

As used throughout the specification, the following terms have the following meaning unless specifically indicated.

The term "halogen" means fluoro, chloro, bromo and iodo.

The halogen moiety in said "haloalkyl", "haloalkylcarbamoyl" and "haloalkyloxy" is as defined above for "halogen".

The term "alkyl" includes a straight or branched chain monovalent hydrocarbon group of a carbon number of 1 in 15, as one embodiment a carbon number of 1 to 10, and as another embodiment a carbon number of 1 in 6. Example include methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl, n-decyl, n-undecanyl, dodecanyl, tridecanyl, and the like.

The alkyl moiety in said "haloalkyl", "hydroxyalkyl", "aminoalkyl", "alkylaminoalkyl", "alkylamino", "alkylimino", "alkylsulfonyl", "alkylsulfamoyl", "alkylcarbamoyl", "arylalkyl", "alkylsilylalkynyl", "alkylsulfonyl", "alkylsulfinyl", "alkylcarbamoyl", "alkylcarbamoylalkyl", "alkylsulfamoyl", "alkylsulfamoylalkyl", "haloalkylcarbamoyl", "hydroxyalkylcarbamoyl", "alkyloxycarbonylalkyl" and "arylalkylamino" is as defined above for "alkyl".

The term "alkyloxy" includes an alkyloxy group of which alkyl moiety is as defined above for "alkyl". For example, methoxy, ethoxy, propoxy, isopropoxy, butoxy, isobutoxy, sec-butoxy, tert-butoxy, pentyloxy, isopentyloxy, neopentyloxy, hexyloxy, etc are exemplified as alkyloxy.

The alkyloxy moiety in said "haloalkyloxy", "arylalkyloxy", "alkyloxycarbonyl", "alkyloxycarbonylalkyl", and "alkyloxylmino" is as defined above for "alkyloxy".

For example, methylthio, ethylthio, propylthio, isopropylthio, butylthio, isobutylthio, sec-butylthio, tert-butylthio, pentylthio, isopentylthio, neopentylthio, hexylthio, and the like are exemplified as "alkylthio".

For example, methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, and the like are exemplified as "alkyloxycarbonyl".

For example, mono- or di-alkylcarbamoyl, such as methylcarbamoyl, ethylcarbamoyl, d-propylcarbamoyl, isopropylcarbamoyl, cyclopropylcarbamoyl, n-butylcarbamoyl, dimethylcarbamoyl, diethylcarbamoyl, dipropylcarbamoyl, and the like are exemplified as "alkylcarbamoyl".

The term "alkenyl" includes linear or branched alkenyl of a carbon number of 2 to 15, as one embodiment a carbon number of 2 to 10, and as another embodiment a carbon number of 2 to 6 having one or more double bonds at any available position. Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octonyl, nonenyl, decenyl, undecenyl, dodecenyl, tridecanyl and the like.

The alkenyl moiety in said "alkenyloxy", "alkenylthio", "alkenylcarbamoyl", "alkenylsulfamoyl" and "alkenyloxycarbonyl" is as defined above for "alkenyl".

The term "alkenyl" includes a linear or branched alkynyl of a carbon number of 2 to 15, as one embodiment a carbon number of 2 to 10, as another embodiment a carbon number 2 to 6. Examples include ethynyl, propynyl, butynyl, pentynyl, hexynyl, heptynyl, octynyl, nonynyl and decynyl. These have one or more triple bonds at any available position and may further a double bond.

The alkynyl moiety in said "alkynyloxy", "alkynylthio" and "alkynyloxycarbonyl" is as defined above for "alkynyl".

The term "acyl" includes a group of the formula R—C(=O)—, wherein R is, for example, "hydrogen", "alkyl", "alkenyl" or "alkynyl" as defined above and "cycloalkyl", "cycloalkenyl", "non-aromatic heterocyclic group", "aryl" or "heteroaryl" as defined below.

The acyl moiety in "acylamino" and "acylimino" is as defined above for "acyl"

The term "cycloalkane" includes a monocyclic polycyclic saturated cyclic carbocyclic ring containing from 3 to 10 carbons. Monocyclic cycloalkane includes, for example, cyclopropane, cyclobutane, cyclopentane, cyclohexane, cycloheptane, cyclooctane, cyclononane, cyclodecane, etc. Polycyclic cycloalkane includes norbornanane, tetrahydronaphthalene, etc.

The term "cycloalkyl" includes a monovalent group derived from "cycloalkane" as defined above. Monocyclic cycloalkyl includes, for example, cyclopropyl, cyclobutyl, cyclopentyl, cyclohexyl, cycloheptyl, cyclooctyl, cyclononyl, cyclodecyl, etc. As one embodiment, C3 to C8 cycloalkane is exemplified. As another embodiment, C3 to C7 cycloalkane is exemplified. Polycyclic cycloalkyl includes norbornyl, tetrahydronaphthalene-5-yl, tetrahydronaphthalene-6-yl, etc.

Examples of "cycloalkyl" for $R^2$ are cyclopentyl, cyclohexyl, cycloheptyl, cyclooctyl and the like.

Examples of "cycloalkyl" for $R^3$ are cyclopentyl, cyclohexyl, cycloheptyl, cyclooctyl and the like.

The cycloalkyl moiety in said "cycloalkyloxycarbonyl" and "cycloalkyloxy" is as defined above for "cycloalkyl".

The term "cycloalkene" includes a non-aromatic monocyclic or polycyclic ring of 3 to 10 carbons containing at least one carbon-carbon double bond. As one embodiment C3 to C8 cycloalkene is exemplified. As another embodiment C3 to C7 cycloalkene is exemplified. Monocyclic cycloalkene includes, for example, cyclopentene, cyclohexene, etc. Polycyclic cycloalkene includes norbornene, indene, etc.

The term "cycloalkenyl" includes a monovalent group derived from "cycloalkene" as defined above. Monocyclic cycloalkenyl includes cyclopentenyl, cyclohexenyl, etc. As one embodiment, C3 to C8 cycloalkane is exemplified. As another embodiment, C3 to C7 cycloalkane is exempt cycloalkenyl includes norbornenyl, indene-1-yl, indene-2-yl, indene-3-yl, etc.

The cycloalkenyl moiety in said "cycloalkenyloxycarbonyl" and "cyclolalkenyloxy" is as defined above for "cycloalkenyl".

The term "aromatic carbocyclic ring" includes an aromatic hydrocarbocyclic ring which is monocyclic or fused-cyclic, such as benzene ring, naphthalene ring, anthracene ring, phenanthrene ring, etc.

The term "aryl" includes a monovalent group derived from "aromatic carbocyclic ring" as defined above. For example, phenyl, 1-naphthyl, 2-naphthyl, anthryl, phenanthryl, etc. are exemplified.

Preferable "aryl" for $R^3$ is phenyl.

The aryl moiety in said "aryloxy", "arylthio" and "aryloxycarbonyl" is as defined above for "aryl".

The term "heterocyclic ring" includes an aromatic or a non-aromatic monocyclic or fused-cyclic ring, which includes a five- to seven-membered ring having at least one nitrogen, atom, oxygen atom, and/or sulfur atom in the ring; a fused ring consisting of two or more said five- to seven-membered rings; or a fused ring consisting of said five- to seven-membered ring having at least one nitrogen atom, oxygen atom, and/or sulfur atom in the ring fused to one or more "aromatic carbocyclic ring", "cycloalkane" "cycloalkene" as defined above.

For example, a monocyclic non-aromatic heterocyclic ring such as pyrroline, pyrrolidine, piperidine, piperazine, morpholine, thiomorpholine, tetrahydropyrane, dihydropyridine, dihydropyridazine, dioxane, oxathiolane, thiane, tetrahydrofuran, tetrahydropyran, tetrahydrathiazole, tetrahydraisothiazole, etc.;

a monocyclic aromatic heterocyclic ring such as pyrrole, pyrazine, pyrazole, tetrazole, furan, thiophene, pyridine, imidazole, triazole, tetrazole, triazine, pyridazine, pyrimidine, isoxazole, thiazole, isothiazole, thiadiazole, oxazole, oxadiazole, etc; and a fused heterocyclic ring such as indole, isoindole, indazole, indolizine, indoline, isoindoline, quinoline, isoquinoline, cinnoline, phthalazine, quinazoline, naphthyridine, quinoxaline, purine, pteridine, benzopyrane, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridiazole, triazolopyridine, imidazothiazole, pyrazinopyridazine, benzimidazole, benzodioxane, tetrahydroquinoline, tetrahydrabenzothiophene, etc. are exemplified.

The term "heterocyclic group" includes a monovalent group derived from "heterocyclic ring" as defined above.

For example, monocyclic non-aromatic heterocyclic groups such as pyrrolinyl, pyrrolidine, pyrrolidinyl, imidazolidinyl, pyrazolinyl, pyrazolidinyl, piperidino, piperidyl, piperazino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl, etc.;

monocyclic aromatic heterocyclic groups such as pyrrolyl, pyrazinyl, pyrazolyl, tetrazolyl, furyl, thienyl, pyridyl, imidazolyl, tetrazolyl, triazolyl, pyridazinyl, pyrimidinyl, pyrazinyl, isoxazolyl, thiazolyl, isothiazolyl, thiadiazolyl, oxazolyl, oxadiazolyl, etc; and fused heterocyclic groups such indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolinyl, benzodioxanyl, tetrahydroquinoline, tetrahydrobenzothienyl, etc. are exemplified.

The term "non-aromatic carbocyclic ring" includes "cycloalkane" as defined above, "cycloalkene" as defined above, a fused ring consisting of "aromatic carbocyclic ring" as defined above fused to "cycloalkane" or "cycloalkene" as defined above. As a fused ring, indene and the like are exemplified.

The term "non-aromatic carbocyclic ring" includes a monovalent group defined from "non-aromatic carbocyclic ring" as defined above. For example, cyclopropyl, cyclobutyl, cyclopentyl, cyclohexyl, cycloheptyl, cyclooctyl, cyclononyl, cyclodecyl, cyclopentenyl, cyclohexenyl, norbornenyl, inden-1-yl, inden-2-yl, inden-3-yl and the like are exemplified.

The non-aromatic carbocyclyl moiety in said "non-aromatic carbocyclyloxy" and "non-aromatic carbocyclylalkyloxy" is as defined above for "non-aromatic carbocyclic ring".

The term "aromatic heterocyclic ring" includes aromatic rings of "heterocyclic ring" as defined above.

"Aromatic heterocyclic ring" includes a five- to seven-membered aromatic ring having at least one nitrogen atom, oxygen atom, and/or sulfur atom in the ring;
a fused ring consisting of two or more of a five- to seven-membered rings; or
a fused ring consisting of a five- to seven-membered ring having at least one nitrogen atom, oxygen atom, and/or sulfur atom in the ring fused to one or more "aromatic carbocyclic ring", as defined above.

For example, a monocyclic aromatic heterocyclic ring such as pyrazine, pyrazole, tetrazole, furan, thiophene, pyridine, imidazole, triazole, triazine, pyridazine, pyrimidine, pyrazine, isoxazole, thiazole, isothiazole, thiadiazole, oxazole, oxadiazole, etc; and
a fused aromatic heterocyclic ring such as indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridiazole, triazolopyridine, imidazothiazole, pyrazinopyridazine, benzimidazoline, etc. are exemplified.

"Five- or six-membered aromatic heterocyclic ring" includes five- or six-membered rings of "aromatic heterocyclic ring" as defined above. Examples are thiazole, isothiazole, oxazole, isoxazole, thiadiazole, oxadiazole, pyrazole, furan, thiophene, imidazole, triazole, tetrazole, pyridine, pyrimidine, pyrazine, pyridazine, triazine, etc.

"Five membered-aromatic heterocyclic ring" includes 6-membered rings of "aromatic heterocyclic ring" as defined above. Examples are thiazole, isothiazole, oxazole, isoxazole, thiadiazole, oxadiazole, pyrazole, furan, thiophen, imidazole, triazole, tetrazole.

"Six-membered aromatic heterocyclic ring" includes six-membered rings of "aromatic heterocyclic ring" as defined above. Examples are pyridine, pyrimidine, pyrazine, pyridazine, triazine, etc.

The term "heteroaryl" includes a monovalent group derived from "aromatic heterocyclic ring" as defined above. "Heteroaryl" includes a five- to seven-membered aromatic group having at least one nitrogen atom, oxygen atom, and/or sulfur atom in the ring;
a fused aromatic group consisting of two or more said rings; and
a fused ring consisting of a five- to seven-membered aromatic group having at least one nitrogen atom, oxygen atom, and/or sulfur atom in the ring fused to one or more "aromatic carbocyclic ring" as defined above.

For example, monocyclic heteroaryl such as pyrrolyl, pyrazinyl, pyrazolyl, indolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl, oxadiazolyl, etc; and
fused heteroaryl such as isoindolyl, indazolyl, indolizinyl, isoindolinyl, quinolyl, isoquinolyl, cinnolinyl, phthalazinyl, quinazolinyl, naphthyridinyl, quinoxnlinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolinyl, etc. are exemplified.

One of examples of "heteroaryl" for $R^2$ is pyridyl.

Examples of "heteroaryl" for $R^3$ are pyridyl, pyrimidyl, benzofuryl, benzothienyl, indolyl, benzisoxazolyl etc.

One of examples of "heteroaryl" for $R^3$ is pyridyl.

The heteroaryl moiety in said "heteroaryloxy" and "heteroaryloxycarbonyl" is as defined above for "heteroaryl".

The term "non-aromatic heterocyclic ring" includes non-aromatic rings of "heterocyclic ring" as defined above.

"Non-aromatic heterocyclic ring" includes, a four- to seven-membered non-aromatic ring having at least one nitrogen atom, oxygen atom, and/or sulfur atom in the ring;
a fused non-aromatic ring consisting of two or more said rings;
a fused ring consisting of a five- to seven-membered aromatic group having at least one nitrogen atom, oxygen atom, and/or sulfur atom in the ring fused to one or more "cycloalkane" or "cycloalkene" as defined above.
a fused ring consisting of a five- to seven-membered non-aromatic heterocyclic ring having at least one nitrogen atom, oxygen atom, and/or sulfur atom in the ring fused to one or more "aromatic carbocyclic ring" and "non-aromatic carbocyclic ring" as defined above.

For example, a monocyclic non-aromatic heterocyclic ring such as oxetane, thietane, azetidine, pyrroline, pyrrolidine, imidazoline, imidazolidine, pyrazoline, pyrazolidine, piperidine, piperazine, morpholine, thiomorpholine, thiomorpholine, tetrahydropyrane, dihydropyridine, dihydropyridazine, dihydropyrazine, dioxane, oxathiolane, thiane, tetrahydrofuran, tetrahydropyran, tetrahydrathiazoline, tetrahydraisothiazole, etc.;
a fused non-aromatic heterocyclic ring such a indoline, isoindoline, benzopyrane, benzodioxane, tetrahydroquinoline, benzo[d]oxazole-2(3H)-one, tetrahydrobenzothiophene etc. are exemplified.

"Non-aromatic heterocyclic group" includes a monovalent group derived from "non-aromatic heterocyclic ring" as defined above.

Examples are monocyclic non-aromatic heterocyclic group such as pyrrolinyl, pyrrolidine, pyrrolidinyl, imidazolinyl, imidazolidinyl, pyrazolinyl, pyrazolidinyl, piperidino, piperidyl, piperazine, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydrlisothiazolinyl etc. and
a fused heterocyclic group such as benzodioxane, tetrahydroquinoline, benzo[d]-oxazole-2(3H)-one, tetrahydfobenzothiophene etc.

The non-aromatic heterocyclyl moiety in said "non-aromatic heterocycloxy" and "non-aromatic heterocyclyloxycarbonyl" is as defined above for "non-aromatic heterocyclic ring".

The term "nitrogen-containing non-aromatic heterocyclic group" includes a group derived from a four- to seven-membered non-aromatic ring which containing at least one nitrogen atom in the ring and may contain one or more atoms arbitrarily selected from an oxygen atom and an sulfur atom in the ring and a fused ring consisting of two or more said rings. Examples are pyrrolinyl, pyrrolidino, pyrrolidinyl, piperidino, piperidyl, piperazino, piperazinyl, morpholinyl, morpholino, thiomorpholino etc.

The non-aromatic heterocyclyl moiety in said "non-aromatic heterocyclyloxycarbonyl" is as defined above for "non-aromatic heterocyclic ring".

Substituents for "substituted alkyl", "substituted alkenyl", "substituted alkynyl", "substituted alkyloxy", "substituted alkenyloxy", "substituted alkynyloxy", "substituted alkylthio", "substituted alkenylthio", "substituted alkynylthio", "substituted alkyloxycarbonyl", "substituted alkenyloxycarbonyl" and "substituted alkynyloxycarbonyl" include but are not limited to one or more same or different substituents selected from the group consisting of:

hydroxy, carboxy, halogen (F, Cl, Br, I), haloalkyloxy (e.g., CF$_3$O), cycloalkyl (e.g., cyclopropyl), cycloalkenyl (e.g., cyclopropenyl), lower alkyloxy (e.g., methoxy, ethoxy, propoxy, butoxy, etc.), alkenyloxy (e.g., vinyloxy, allyloxy, etc.), alkyloxycarbonyl (e.g., methoxycarbonyl, ethoxycarbonyl, tert-butoxycarbonyl, etc.), nitro, nitroso, amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, alkylsulfonylamino (e.g., methanesulfonylamino), alkylsulfinylamino (e.g., methanesulfinylamino), imino, hydroxylmino, alkylimino (e.g, methylimino, ethylimino, dimethylimino, etc.) , alkyloxylmino (e.g., methoxylmino, ethoxylmino, etc.) acylimino (e.g., acetylimino, benzoylimino, etc.), azido, aryl (e.g., phenyl, etc.) , arylalkyl (e.g., benzyl, phenylethyl etc.), arylalkyloxy (e.g., benzyloxy) , a non-aromatic heterocyclic group (e.g., pyrrolinyl, piperidyl, piperazinopyrrolidino, pyrrolidinyl, morpholinyl, morpholino etc.) heteroaryl (e.g., furyl, thienyl, pyridyl, isoxazolyl, thiazolyl, thiadiazolyl, oxazolyl, oxadiazolyl, tetrazolyl, indolyl, benzofuryl etc.) heteroarylalkyl (e.g., pyridylmethyl, pyridylethyl etc.), cyano, isocyano, isocyanato, thiocyanato, isothiocyanato, mercapto, alkylthio (e.g., methylthio, etc.), alkylsulfonyl (e.g., methanesulfonyl, ethanesulfonyl), carbamoyl, alkylcarbamoyl (e.g., methylcarbamoyl, ethylcarbamoyl, dimethylcarbamoyl, etc.) , sulfamoyl, alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, tri-alkylsilyl (e.g., trimethylsilyl, etc.) , and oxo.

As a substituent for "substituted alkyl", "substituted alkenyl", and "substituted alkynyl" for $R^c$ and $R^{c1}$, the followings are exemplified.

carboxy; hydroxy; oxo; thioxo; halogen; alkyloxy; alkenyloxy; alkynyloxy; alkyloxyalkyloxy; carbamoyl optionally substituted with hydroxy, cyano, alkenyl, alkynyl, hydroxyalkyl, hydroxyalkenyl, hydroxyalkynyl, haloalkyl, haloalkynyl, cycloalkylalkyl, cycloalkenylalkyl, non-aromatic heterocyclylalkyl, a non-aromatic heterocyclic group, aryl or heteroaryl; sulfamoyl optionally substituted with hydroxy, cyano, alkyl, alkenyl, alkynyl, hydroxyalkyl, haloalkyl, haloalkenyl, haloalkynyl, cycloalkylalkyl, cycloalkenylalkyl, non-aromatic heterocyclylalkyl, arylalkyl, heteroarylalkyl, cycloalkyl, cycloalkenyl, heteroaryl, aryl, or heteroaryl; amino optionally substituted with hydroxy, alkyloxycarbonyl, alkenyloxycarbonyl, alkynyloxycarbonyl; imino optionally substituted with hydroxy, alkyloxy, alkenyloxy, or alkynyloxy; guanidyl optionally substituted with cyanoalkyl;

cycloalkyl optionally substituted with carboxy, alkyl, hydroxyalkyl, carboxyalkyl, arylalkyl, heteroarylalkyl, alkyloxyarylmethyl, alkyloxycarbonyl, alkenyloxycarbonyl, alkynyloxycarbonyl, cycloalkyloxycarbonyl, cycloalkenyloxyalkyl, non-aromatic heterocyclyloxyalkyl, aryloxyalkyl, heteroaryloxyalkyl, oxo or thioxo;

a non-aromatic heterocyclic group optionally substituted with carboxy, alkyl, hydroxyalkyl, carboxyalkyl, alkyloxycarbonyl, arylalkyl, alkyloxyarylmethyl, non-aromatic heterocyclyloxyalkyl, or oxo;
aryl optionally substituted with halogen or alkyloxycarbonyl;
heteroaryl optionally substituted with carboxy, alkyloxy, alkyloxycarbonyl, non-aromatic heterocyclyloxyalkyloxy; alkyloxycarbonyl; alkenyloxycarbonyl; alkynyloxycarbonyl; cycloalkyloxycarbonyl; cycloalkenyloxycarbonyl; non-aromatic heterocyclyloxycarbonyl; aryloxycarbonyl; or heteroaryloxycarbonyl etc.

As a substituent for "substituted alkyl", "substituted alkenyl", and "substituted alkynyl" for $R^c$ and $R^{c1}$, the followings are exemplified.

halogen; hydroxy; carboxy; alkyloxy; alkyloxyalkyloxy; sulfo;
cycloalkyl optionally substituted with carboxy, alkyl, hydroxyalkyl, carboxyalkyl, alkyloxycarbonyl, arylalkyl, alkyloxyarylmethyl, non-aromatic heterocyclyloxyalkyl, or oxo;
a non-aromatic heterocyclic group optionally substituted with carboxy, alkyl, hydroxyalkyl, carboxyalkyl, alkyloxycarbonyl, arylalkyl, alkyloxyarylmethyl, non-aromatic heterocyclyloxyalkyl, or oxo;
aryl optionally substituted with halogen or alkyloxycarbonyl;
heteroaryl optionally substituted with carboxy, alkyloxy, alkyloxycarbonyl, non-aromatic heterocyclyloxyalkyloxy; alkyloxycarbonyl; alkenyloxycarbonyl; alkynyloxycarbonyl; cycloalkyloxycarbonyl;
cycloalkenyloxycarbonyl; non-aromatic heterocyclyloxycarbonyl; aryloxycarbonyl; heteroaryloxycarbonyl;
carbamoyl optionally substituted with hydroxy, cyano, alkyl, hydroxyalkyl, haloalkyl, non-aromatic heterocyclylalkyl or a non-aromatic heterocyclic group;
sulfamoyl optionally substituted with hydroxy, cyano, alkyl, hydroxyalkyl, haloalkyl, non-aromatic heterocyclylalkyl or a non-aromatic heterocyclic group;
amino optionally substituted with hydroxy, alkyloxycarbonyl, alkenyloxycarbonyl, alkynyloxycarbonyl;
imino optionally substituted with hydroxy, alkyloxy, alkenyloxy, alkynyloxy;
guanidyl optionally substituted with cyanoalkyl; oxo; thioxo etc.

As a substituent for "substituted alkyl", "substituted alkenyl", and "substituted alkynyl" for and $R^c$ and $R^{c1}$, the followings are exemplified.

halogen; hydroxy; carboxy; alkyloxy; alkyloxyalkyloxy; sulfo; cycloalkyl;
a non-aromatic heterocyclic group optionally substituted with carboxy, alkyl, hydroxyalkyl, carboxyalkyl, alkyloxycarbonyl, arylalkyl, alkyloxyarylmethyl, non-aromatic heterocyclyloxyalkyl, or oxo;
aryl optionally substituted with halogen, or alkyloxycarbonyl;
heteroaryl optionally substituted with carboxy, alkyloxy, alkyloxycarbonyl, non-aromatic heterocyclyloxyalkyloxy; alkyloxycarbonyl; alkenyloxycarbonyl; alkynyloxycarbonyl; cycloalkyloxycarbonyl;
cycloalkenyloxycarbonyl; non-aromatic heterocyclyloxycarbonyl; aryloxycarbonyl; heteroaryloxycarbonyl;
carbamoyl optionally substituted with hydroxy, cyano, alkyl, hydroxyalkyl, haloalkyl, non-aromatic heterocyclylalkyl or a non-aromatic heterocyclic group;
sulfamoyl;

amino optionally substituted with hydroxy, or alkyloxycarbonyl;
imino optionally substituted with hydroxy, or alkyloxycarbonyl;
guanidyl optionally substituted with cyanoalkyl;
oxo; thioxo etc.

As a substituent for "substituted alkyl", "substituted alkenyl", and "substituted alkynyl" for and $R^c$ and $R^{c1}$, the followings are exemplified.

fluoro, hydroxy, carboxy, methyloxy, methyloxymethyloxy, sulfo, methyloxycarbonyl, ethyloxycarbonyl, t-butyloxycarbonyl, tetrahydropyranylmethyloxycarbonyl, methylcarbonyl, hydroxycarbamoyl, dihydroxylsopropylcarbamoyl, aminocarbamoyl, cyanocarbamoyl, trifluoromethylcarbamoyl, hydroxyethylcarbamoyl, tetrahydropyranylcarbamoyl, tetrnhydropyranylethylcarbamoyl, sulfamoyl, hydroxyamino, methyloxycarbonylamino, t-butyloxycarbonylamino, hydroxylmino, methyloxylmino, guanidyl, cyanomethylguanidyl, cyclopropyl, carboxypyrrolidinyl, oxetanyl, oxodihydrooxadiazolyl, dimethyldioxaranyl, oxopyrrolidinyl, methyloxopyrrolidinyl, hydroxyethyloxopyrrolidinyl, carboxmethyloxopyrrolidinyl, oxodihydropyrrolidinyl, methyloxycarbonylmethyloxopyrrolidinyl, morpholinyl, piperazinyl, t-butyloxycarbonylpiperazinyl, oxo (phenylmethyl) (methyl) piperazinyl, oxo (methyloxyphenylmethyl) (methyl) piperazinyl, tetrahydropyranyloxyethyloxopiperazinyl, phenyl, chlorophenyl, ethyloxycarbonylphenyl, triazolyl, tetrazolyl, carboxylsoxazolyl, methyloxycarbonylisoxazotyl, ethyloxycarbonylisoxazolyl, oxazolyl, carboxyfuranyl, methyloxycarbonylfuryl, methyloxypyridyl, carboxypyridyl, methyloxycarbonylpyridyl, hydroxymethyloxypyridyl, ethyloxycarbonylthiazolyl, tetrahydropyranyloxyethyloxypyridinyl, oxo etc.

Substituents for "substituted acyl" are selected from the substituents as defined above for "substituted alkyl", the above "alkyl", the above "alkenyl" and the above "alkynyl". If R in acyl (R—C(=O)—) is "cycloalkyl", "cycloalkenyl", "non-aromatic heterocyclic group", "aryl", or "heteroaryl", then each ring may be substituted with alkyl (e.g., methyl, ethyl, isopropyl, tert-butyl, etc.), haloalkyl (e.g., $CF_3$, $CH_2CF_3$, $CH_2CCl_3$, etc.). alkenyl, alkynyl (e.g., ethynyl), alkyloxy (e.g., methoxy, ethoxy, isopropyloxy), halogen (e.g., fluoro, chloro etc.) or the like.

Substituents for "substituted carbamoyl", "substituted thiocarbamoyl" and "substituted sulfamoyl" are one or more same or different groups selected from, but are not limited to, the group consisting of:
hydroxy, carboxy, halogen (F, Cl, Br, I), alkyl (e.g., methyl, ethyl), (e.g., vinyl), alkenyl (e.g., ethynyl), cycloalkyl (e.g., cyclopropyl), cycloalkenyl (e.g., cyclopropenyl), alkyloxycarbonyl (e.g., methoxycarbonyl, ethoxycarbonyl, tert-butoxycarbonyl, etc.), amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, aryl (e.g., phenyl, etc.), cyano, isocyano, isocyanato, thiocyanato, isothiocyanato and acyl (e.g., formyl, acetyl, etc.).

Substituents for "substituted sulfonyl" or "substituted sulfinyl" are selected from the above "substituted or unsubstituted alkyl", the above "substituted or unsubstituted alkenyl", the above "substituted or unsubstituted alkynyl", the after-mentioned "substituted or unsubstituted cycloalkyl", the after-mentioned "substituted or unsubstituted cycloalkenyl", the after-mentioned "substituted or unsubstituted non-aromatic heterocyclic group", "substituted or unsubstituted aryl", and the after-mentioned "substituted or unsubstituted heteroaryl". If R in R—S(=O)$_2$— or R—S(=O)— is "cycloalkyl", "cycloalkenyl", "non-aromatic heterocyclic group", "aryl", "heteroaryl" or the like, then each ring may be substituted with alkyl (e.g., methyl, ethyl, (e.g., ethynyl), alkyloxy (e.g., methoxy, ethoxy, isopropyloxy), halogen (e.g., fluoro, chloro etc.) or the like.

Substituents (or "substituted amino", "substituted imino" and "substituted guanidyl" are one or more same or different groups selected from, but are not limited to, the group consisting of:
alkyl (e.g., methyl, ethyl, isopropyl, tert-butyl etc.), haloalkyl (e.g., $CF_3$, $CH_2CF_3$, $CH_2CCl_3$, etc.), hydroxyalkyl (e.g., hydroxyethyl, —C(CH$_3$)$_2$CH$_2$OH, etc.), alkenyl (e.g., vinyl), alkynyl (e.g., ethynyl), cycloalkyl (e.g., cyclopropyl), cycloalkenyl (e.g., cyclopropenyl), alkyloxy (e.g., methoxy, ethoxy, propoxy, butoxy, etc.), haloalkyloxy (e.g., $CF_3O$), alkenyloxy (e.g., vinyloxy, allyloxy, etc.), alkyloxycarbonyl (methoxycarbonyl, tert-butyloxycarbonyl, etc.), alkyloxycarbonylalkyl, amino, alkylamino (e.g., methylamino, ethylamino, dimethylamino, etc.), acylamino (e.g., acetylamino, benzoylamino, etc.), arylalkylamino (e.g., benzylamino, tritylamino), hydroxyamino, imino, hydroxyimino, alkylimino (e.g., methylimino, ethylimino, dimethylimino, etc.), alkyloxyimino (e.g., methoxyimino, ethoxyimino, etc.), acylimino (e.g., acetylimino, benzoylimino, etc.), aryl (e.g., phenyl, etc.), arylalkyl (e.g., benzyl, etc.), aryloxy (e.g., phenoxy etc.), a non-aromatic heterocyclic group (e.g., pyrrolinyl, pyrrolidino, piperidino, piperidyl, piperazino, piperazinyl, morpholinyl, morpholino etc.), heteroaryl (e.g., pyridyl, thienyl, thiazolyl, furyl etc.), heteroarylalkyl (e.g., pyridylmethyl, thienylmethyl, thiazolylmethyl, furylmethyl etc.), non-aromatic heterocyclyloxy (pipierazinooxy, piperidinooxy etc.), heteroaryloxy (pyridyloxy etc.), hydroxy, halogen, (F, Cl, Br, I), cyano, acyl (e.g., formyl, acetyl, etc.), alkylsulfonyl (e.g., methanesulfonyl etc.), alkylsulfinyl (e.g., methanaulfinyl), carbamoyl, alkylcarbamoyl (e.g., methylcarbamoyl etc.), alkylcarbamoylalkyl (e.g., methylcarbamoylmethyl etc), carbamoylalkyl (e.g., carbamoylmethyl etc.), carboxyalkyl (e.g., carboxymethyl etc.), sulfamoyl, alkylsulfamoyl (e.g., methylsulfamoyl etc.), alkylsulfamoylalkyl (e.g., methylsulfamoylmethyl etc.), and sulfamoylalkyl (e.g., sulfamoylmethyl etc.).

Substituents for "substituted cycloalkyl", "substituted cycloalkenyl", "substituted aryl", "substituted phenyl", "substituted heterocyclic group", "substituted heteroaryl", "a substituted non-aromatic carbocyclic group", "a substituted not-aromatic heterocyclic group", "a substituted nitrogen-containing non-aromatic heterocyclic group", "substituted cycloalkyloxycarbonyl", "substituted cycloalkyenyloxycarbonyl", "substituted non-aromatic heterocyclyloxycarbonyl", "substituted aryloxycarbonyl", "substituted heteroaryloxycarbonyl", "a substituted cyclopropane ring", "a substituted cyclopropene ring", "a substituted oxetane ring", "a substituted thietane ring" and "a substituted azetizine ring" are one or more same or different groups selected from, but are not limited to, the group consisting of:
alkyl (e.g., methyl, ethyl, isopropyl, tert-butyl etc.), haloalkyl (e.g., $CF_3$, $CH_2CF_3$, $CH_2CCl_3$, etc.), haloalkyloxy (e.g., $CF_3O$, $CHCF_2O$ etc.), alkenyl (e.g., vinyl), alkynyl (e.g., ethynyl), cycloalkyl (e.g., cyclopropyl), cycloalkenyl (e.g., cyclopropenyl), alkyloxy (e.g., methoxy, ethoxy, propoxy, butoxy, etc.), alkenyloxy (e.g., vinyloxy, allyloxy, etc.), alkyloxycarbonyl (e.g., methoxycarbonyl, ethoxycarbonyl, tert-butoxycarbonyl, etc.), nitro, nitroso, amino, alkylamino (e.g., methylamino, ethylamino, dimethylamino, etc.). acylamino (e.g., acetylamino, benzoylamino, etc.), arylalkylamino (e.g., benzylamino, tritylamino), hydroxyamino, amino substituted with one or two same or different substituent selected from the after-mentioned substituent Group Y, imino, hydroxy imino, alkylimino (e.g., methylimino, ethylimino, dimethylimino etc.), alkyloxyimino (e.g., methoxyimino, ethoxyimino etc.), acylimino (e.g., acetylimino, benzoylimino etc.), azido, aryl (e.g., phenyl etc.), arylalkyl (e.g., benzyl etc.), unsubstituted non-aromatic carbocyclyloxy (e.g., cyclopropyloxy etc.), non-aromatic carbocyclyloxy substituted with one or more same or different substituents selected from the after-mentioned Substituent Group Z, unsubstituted non-aromatic carbocyclylalkyloxy (e.g., cyclopropylmethyloxy etc.), non-aromatic carbocyclylalkyloxy substituted with one or more same or different substituents selected from the after-mentioned Substituent Group Z, unsubstituted aryloxy (e.g., phenoxy etc.), aryloxy substituted with one or more same or different substituents selected from the after-mentioned Substituent Group Z, unsubstituted arylalkyloxy (e.g., benzyloxy etc.), arylalkyloxy substituted with one or more same or different substituents selected from the after-mentioned Substituent Group Z, a non-aromatic heterocyclic group (e.g., pyrrolinyl, pyrrolidino, piperidino, piperidyl, piperazino, piperazinyl, morpholinyl, morpholino etc.), heteroaryl (e.g., pyridyl, thienyl, thiazolyl, furyl etc.), heteroarylalkyl (e.g., pyridylmethyl, thienylmethyl, thiazolylmethyl, furylmethyl etc.), unsubstituted non-aromatic heterocyclyloxy (e.g., piperazinooxy, piperizinooxy etc.), non-aromatic heterocyclyloxy substituted with one or more same or different substituents selected from the after-mentioned Substituent Group Z, unsubstituted heteroaryloxy (e.g., pyridyloxy etc.), heteroaryloxy substituted with one or more same or different substituents selected from the after-mentioned Substituent Group Z, cyano, isocyano, isocyanato, thiocyanato, isothiocyanato, mercapto, alkylthio (e.g., methylthio etc.), alkylsulfonyl (e.g., methanesulfonyl, ethanesulfonyl), substituted or unsubstituted carbamoyl (e.g., carbamoyl, N-methyl—N-methoxycarbamoyl etc.), substituted or unsubstituted alkylcarbamoyl (e.g., methylcarbamoyl, ethylcarbamoyl, dimethylcarbamoyl, hydroxyethylcarbamoyl, trifluoromethylcarbamoyl, trifluoroethylcarbamoyl etc.), sulfamoyl, hydroxy, carboxy, halogen (F, Cl, Br, I), acyl (e.g., formyl, acetyl etc.), formyloxy, thioformyl, thiocarboxy, dithiocarboxy, thiocarbamoyl, sulfino, sulfo, hydrazino, azido, ureido, amidino, guanidino, phthalimido and oxo.

A substituent Group Y includes hydroxy alkyl (e.g., hydroxyethyl, —C(CH$_3$)$_2$CH$_2$OH etc.), alkyloxycarbonyl (methoxycarbonyl, tert-butoxycarbonyl etc.), alkyloxycarbonylalkyl, alkylsulfonyl (e.g., methanesulfonyl etc.), alkylsulfinyl (e.g., methanesulfinyl etc.), carbamoyl, alkylcarbamoyl (e.g., methylcarbamoyl etc.), alkylcarbamoylalkyl (e.g., methylcarbamoylmethyl etc.), carbamoylalkyl (e.g., carbamoylmethyl etc.), carboxyalkyl (e.g., carboxymethyl etc.), sulfamoyl, alkylsulfamoyl (e.g., methanesulfamoyl etc.), alkylsulfamoylalkyl (e.g., methylsulfamoylmethyl etc.), and sulfamoylalkyl (e.g., sulfamoylmethyl etc.).

A substituent Group Z includes halogen, hydroxy, carboxy, cyano, nitro, alkyl hydroxyalkyl, aminoalkyl, alkylaminoalkyl, alkenyl, alkynyl, alkyloxy, alkenyloxy, alkynyloxy, alkylthio, alkenylthio, alkynylthio, acyl, alkyloxycarbonyl, alkenyloxycarbonyl, alkynyloxycarbonyl, carbamoyl, alkylcarbamoyl, haloalkylcarbamoyl, hydroxyalkylcarbamoyl, cyanocarbamoyl, amino, acylamino, amino substituted with one or two same or different substituent selected from the above substituent Group Y, sulfamoyl, methylsulfonyl, methylsulfinyl, cycloalkyl, cycloalkenyl, a non-aromatic heterocyclic group, aryl, heteroaryl, cycloalkyloxy, cycloalkenyloxy, a non-aromatic heterocycloxy, aryloxy and heteroaryloxy.

As substituents for "substituted aryl" and "substituted heteroaryl" for $R^2$, halogen, alkyl, alkenyl, alkynyl, alkyloxy, alkenyloxy, alkynyloxy, cycloalkyl, cycloalkenyl, a non-aromatic heterocyclic group, alkylsilylalkynyl and the like are exemplified.

As substituents for "substituted aryl" and "substituted heteroaryl" for $R^2$, halogen, alkyl, alkenyl, alkynyl, alkyloxy, cycloalkyl, alkylsilylalkynyl and the like are exemplified.

As substituents for "substituted aryl" and "substituted heteroaryl" for $R^2$, halogen, chloro, bromo, iodo, methyl, ethyl, propyl, isopropyl, propenyl, vinyl, ethynyl, methyloxy, cyclopropyl, trimethylsilylethynyl and the like are exemplified.

As substituents for "substituted aryl" and "substituted heteroaryl" for $R^3$, halogen; hydroxy;
alkyl optionally substituted with halogen, hydroxy, cyano, alkyloxylmino, alkenyloxylmino, alkynyloxylmino, dialkylamino, alkyloxy, alkenyloxy, alkynyloxy, cycloalkyl, cycloalkenyl, aryl, heteroaryl, arylalkyl or heteroarylalkyl;
alkenyl optionally substituted with cycloalkyl, cycloalkenyl or a non-aromatic heterocyclic group;
alkynyl optionally substituted with cycloalkyl, cycloalkenyl or a non-aromatic heterocyclic group;
unsubstituted alkyloxy;
alkyloxy substituted with a non-aromatic heterocyclic group optionally substituted with halogen, alkyloxy, alkenyloxy, alkynyloxy, aryl, alkyl, alkenyl or alkynyl;
alkylthio; alkenylthio; alkynylthio; cycloalkyl; cycloalkenyl; a non-aromatic heterocyclic group; alkylamino; alkenyl amino; alkynylamino and the like are exemplified.

As substituents for "substituted aryl" and "substituted heteroaryl" for $R^3$ are halogen; hydroxy;
alkyl optionally substituted with halogen, hydroxy, cyano, alkyloxylmino, dialkylamino, alkyloxy, cycloalkyl or heteroarylalkyl;
alkenyl optionally substituted with cycloalkyl;
alkynyl optionally substituted with cycloalkyl;
alkyloxy optionally substituted with a non-aromatic heterocyclic group optionally substituted with halogen, alkyloxy, aryl, or alkyl;
alkylthio; cycloalkyl; cycloalkenyl; a non-aromatic heterocyclic group; alkylamino and the like are exemplified.

As substituents for "substituted aryl" and "substituted heteroaryl" for $R^3$, chloro, bromo, fluoro, hydroxy, methyl, trifluoromethyl, methyloxymethyl, cyanomethyl, difluoroethyl, methyloxylminomethyl, isopropyl, propyl, trifluoroisopropyl, dimethylaminomethyl, butyl, isobutyl, isopropyloxymethyl, pentyl, cyclopropylethyl, cyclopentylmethyl, pyridylmethyl, methylisopropenyl, vinyl, cyclopropylvinyl, methyl propenyl, cyclopentylidenemethyl, cyclopropylethynyl, hydroxyethyl, methyloxy, difluoromethyloxy, trifluoromethyloxy, ethyloxy, propyloxy, methyloxy ethyloxy, oxetanyloxy, cyclobutyloxy, cyclopentyloxy, s-butyloxy, isobutyloxy, cyclopropylmethyloxy, tetrahydropyranyloxy, 2-methylbutyloxy, dimethylbutyloxy, pentanyloxy, pentane-3-yloxy, dimethylpyridyloxy, methyl pyridyloxy, pyridyloxy, phenyloxy, methylthio, ethylthio, cyclopentyl, cyclopentenyl, cyclohexyl, piperazinyl, piperidinyl, azepanyl and the like are exemplified.

Examples of "heteroaryloxy" as substituents for "substituted aryl" and "substituted heteroaryl" for $R^3$ include pyrrolyloxy, pyrazinyloxy, pyrazolyloxy, indolyloxy, tetrazolyloxy, furyloxy, thienyloxy, pyridyloxy, imidazolyloxy, triazolyloxy, tetrazolyloxy, triazinyloxy, pyridazinyloxy, pyrimidinyloxy, pyrazinyloxy, isooxazolyloxy, thiazolyloxy, isothiazolyloxy, thiadiazolyloxy, oxazolyloxy, oxadiazolyloxy and the like.

As substituents for "substituted aryl" and "substituted heteroaryl" for $R^3$, unsubstituted heteroaryloxyl, heteroaryloxyl substituted with one or more same or different substituents selected from the above Substituent Group Z and the like are exemplified. Further, halogen, hydroxy, carboxy, cyano, nitro, alkyl, haloalkyl, haloalkyloxy, alkyloxy, amino and the like are exemplified. The above heteroaryloxyl includes the following groups which are unsubstituted or substituted with one or more same or different substituents selected from the above Substituent Group Z:

pyrrolyloxy, pyrazinyloxy, pyrazolyloxy, indolyloxy, tetrazolyloxy, furyloxy, thienyloxy, pyridyloxy, imidazolyloxy, triazolyloxy, tetrazolyloxy, triazinyloxy, pyridazinyloxy, pyrimidinyloxy, pyrazinyloxy, isooxazolyloxy, thiazolyloxy, isothiazolyloxy; thiadiazolyloxy, oxazolyloxy, and oxadiazolyloxy and the like.

As substituents for "substituted heteroaryl" for $R^3$, halogen; alkyl; alkenyl; alkynyl; alkyloxy; alkenyloxy; alkynyloxy; cycloalkyloxy; cycloalkenyloxy; aryloxyl; heteroaryloxyl and the like are exemplified.

As substituents for "substituted heteroaryl" for $R^3$, halogen; alkyl; alkyloxy; cycloalkyloxy and the like are exemplified.

As substituents for "substituted non-aromatic heterocyclic group" for $R^3$, arylalkyl, heteroarylalkyl, aryl, heteroaryl and the like are exemplified.

As substituents for "substituted non-aromatic heterocyclic group" for $R^3$, arylalkyl, aryl and the like are exemplified.

As substituents for "substituted non-aromatic heterocyclic group" for $R^3$, phenylmethyl, phenyl and the like are exemplified.

As substituents for "substituted amino" for $R^{9'}$, carbamoyl, alkylcarbamoyl (e.g., methylcarbamoyl etc.), alkylcarbamoylalkyl (e.g., methylcarbamoylmethyl etc.), carbamoylalkyl (e.g., carbamoylmethyl etc.), carboxyalkyl (e.g., carboxymethyl etc.) and the like are exemplified.

Examples of "substituted or unsubstituted alkyl" for $R^{30}$ and $R^{31}$ are methyl, monofluoromethyl, difluoromethyl, trifluoromethyl, ethyl and the like.

Examples of $R^{9'}$ are halogen, hydroxy, carboxy, cyano, nitro, alkyl, hydroxyalkyl, aminoalkyl, alkylaminoalkyl, alkenyl, alkynyl, alkyloxy, alkenyloxy, alkynyloxy, alkylthio, alkenylthio, alkynylthio, acyl, alkyloxycarbonyl, alkenyloxycarbonyl, alkynyloxycarbonyl, carbamoyl, alkylcarbamoyl, haloalkylcarbmoyl, hydroxyalkylcarbamoyl, cyanocarbamoyl, amino, acylamino, amino substituted with one or two same or different substituents selected from the above Substituent Group Y, sulfamoyl, methylsulfonyl, methylsulfinyl and the like.

In general formula (VIII), general formula (IX), general formula (VII), general formula (IV), general formula (I), general formula (II) or general formula (III), "$R^{4a}$ and $R^{4b}$ attached to the same carbon atom are taken together to form oxo or thioxo" includes the followings:

[Chemical Formula 49]

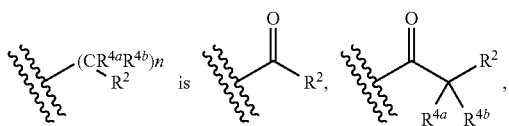

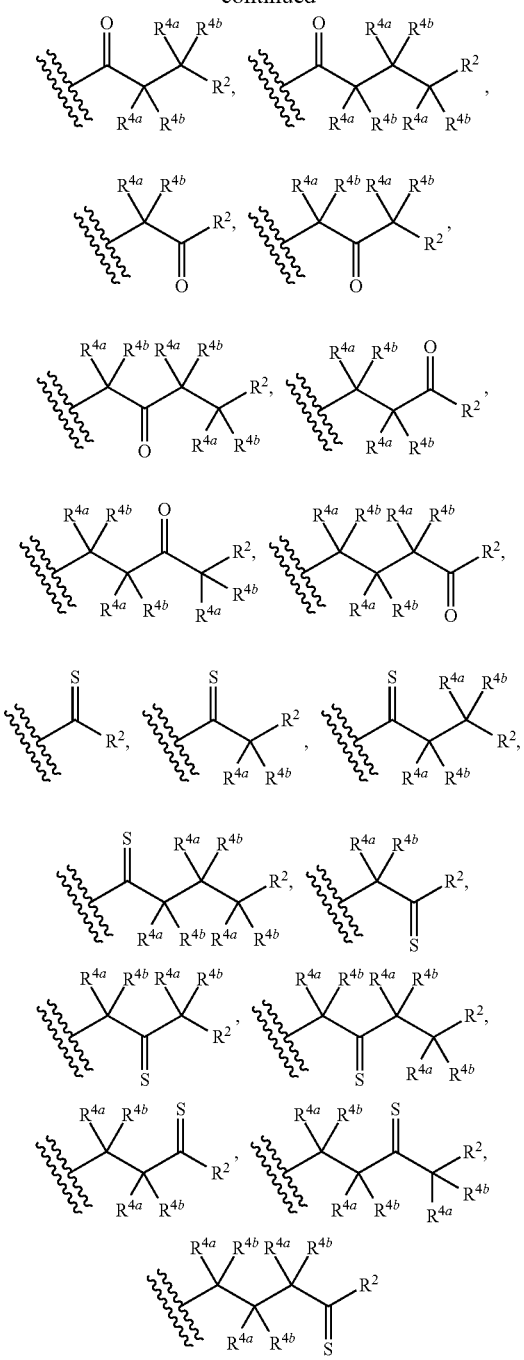

wherein n, $R^{4a}$, $R^{4b}$ and $R^2$ defined in the above (1) and the like.

In a formula (VIII), the positions of carbon atom a, $Q^a$ atom, $Q^b$ atom, carbon atom b, $Q^c$ atom and $Q^d$ atom which constitute a benzene ring, a pyridine ring, a pyrimidine ring, a pyrazine ring or a pyridazine ring as ring D is defined as 1-position, 2-position, 3-position, 4-position, 5-position and 6-position, respectively. Each of the position numbers of these atoms is different from position number based on IUPAC nomenclature. That is, "carbon atom a is positioned on ring D in a 1,4 relationship with respect to carbon atom b" includes the followings:

[Chemical Formula 50]

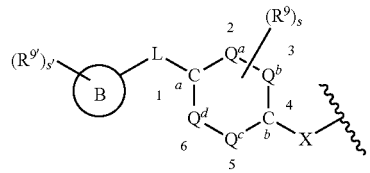

wherein $Q^a$ atom, $Q^b$ atom, $Q^c$ atom and $Q^d$ atom are each independently a carbon atom or a nitrogen atom, —X—, —L—, ring D, ring B, s, s', $R^9$ and $R^{9'}$ are as defined in the above (1).

In general formula (VIII), the positions of carbon atom a, $Q^a$ atom, $Q^b$ atom, carbon atom b, $Q^c$ atom and $Q^d$ atom which constitute a benzene ring, a pyridine ring, a pyrimidine ring, a pyrazine ring or a pyridazine ring as ring D is defined as 1-position, 2-position, 3-position, 4-position, 5-position and 6-position, respectively. Each of the position numbers of these atoms is different from position number based on IUPAC nomenclature. That is, "carbon atom a is positioned on ring D in a 1,3 relationship with respect to carbon atom b" includes the followings:

[Chemical Formula 51]

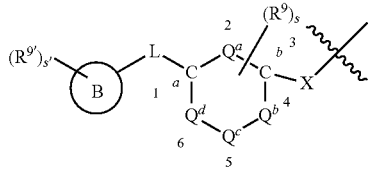

wherein atom, $Q^a$ atom, $Q^b$ atom, $Q^c$ atom and $Q^d$ atom are each independently a carbon atom or a nitrogen atom, —X—, —L—, ring D, ring B, s, s', $R^9$ and $R^{9'}$ are as defined in the above (1).

In general formula (IX), the positions of carbon atom a, $Q^a$ atom, $Q^b$ atom, carbon atom b, $Q^c$ atom and $Q^d$ atom which constitute a benzene ring, a pyridine ring, a pyrimidine ring, a pyrazine ring or a pyridazine ring as ring D is defined as 1-position, 2-position, 3-position, 4-position, 5-position and 6-position, respectively. Each of the position numbers of these atoms is different from position number based on IUPAC nomenclature. That is, "carbon atom a is positioned on ring D in a 1,4 relationship with respect to carbon atom b" includes the followings:

[Chemical Formula 52]

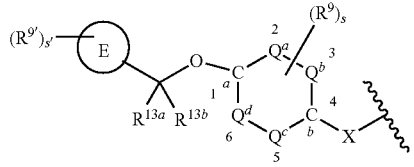

wherein atom, $Q^a$ atom, $Q^b$ atom, $Q^c$ atom and $Q^d$ atom are each independently a carbon atom or a nitrogen atom, —X—, —L—, ring D, $R^{13a}$, $R^{13b}$, ring E, s, s', $R^9$ and $R^{9'}$ are as defined in the above (8).

In general formula (IX), each of the position of carbon atom a, $Q^a$ atom, $Q^b$ atom, carbon atom b, $Q^c$ atom and $Q^d$ atom which constitute a benzene ring, a pyridine ring, a pyrimidine ring, a pyrazine ring or a pyridazine ring as ring D is defined as 1-position, 2-position, 3-position, 4-position, 5-position and 6-position, respectively. Each of the position numbers of these atoms is different from position number based on IUPAC nomenclature. That is, "carbon atom a is positioned on ring D in a 1,3 relationship with respect to carbon atom b" includes the followings:

[Chemical Formula 53]

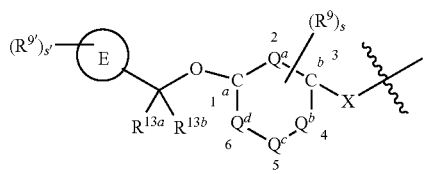

wherein $Q^a$ atom, $Q^b$ atom, $Q^c$ atom and $Q^d$ atom are each independently a carbon atom or a nitrogen atom, —X—, —L—, ring D, $R^{13a}$, $R^{13b}$, ring E, s, s', $R^9$ and $R^{9'}$ are as defined in the above (8).

In general formula (VIII), general formula (IX), and general formula (VII), "$R^{11a}$ and $R^{11b}$ together with the carbon atom to which they are attached form a substituted or unsubstituted cycloalkane ring, a substituted or unsubstituted cycloalkene ring, or a substituted or unsubstituted non-aromatic, heterocyclic ring" includes the followings:

[Chemical Formula 54]

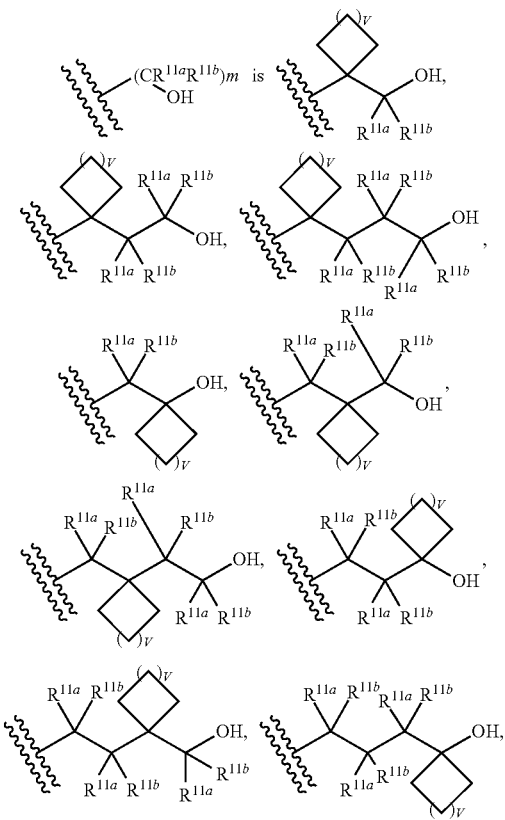

-continued

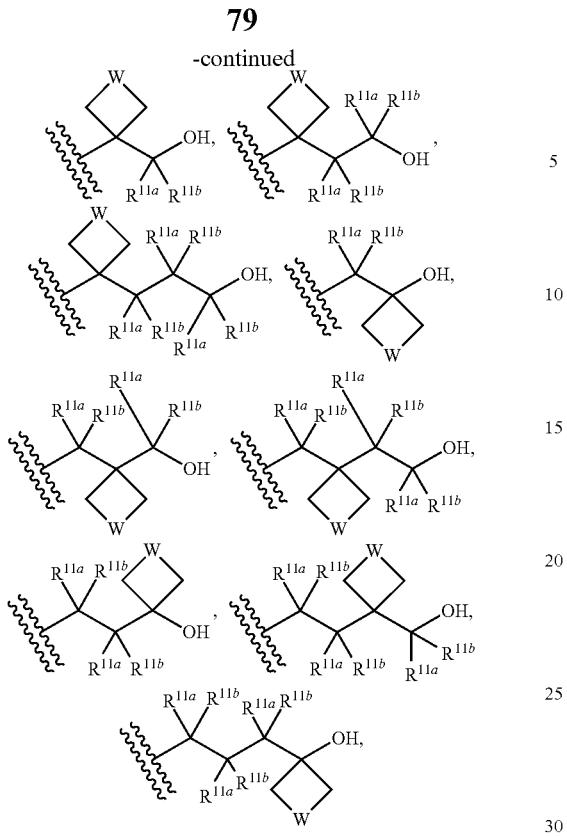

wherein m, $R^{11a}$ and $R^{11b}$ are as defined in the above (21);
v in an integer of 0 to 3 (e.g., 0 or 1, and e.g., 0);
—W— is —O—, —S— or —N($R^{17}$)— (e.g., —O—);
$R^{17}$ is a hydrogen atom, substituted or unsubstituted alkyl, substituted or unsubstituted alkenyl, substituted or unsubstituted alkynyl, substituted or unsubstituted acyl and the like.

In general formula (VIII), general formula (IX), and general formula (VII), "$R^{14a}$ and $R^{14b}$ together with the carbon atom to which they are attached form a substituted or unsubstituted cycloalkane ring, a substituted or unsubstituted cycloalkene ring, or a substituted or unsubstituted non-aromatic heterocyclic ring" includes the followings:

[Chemical Formula 55]

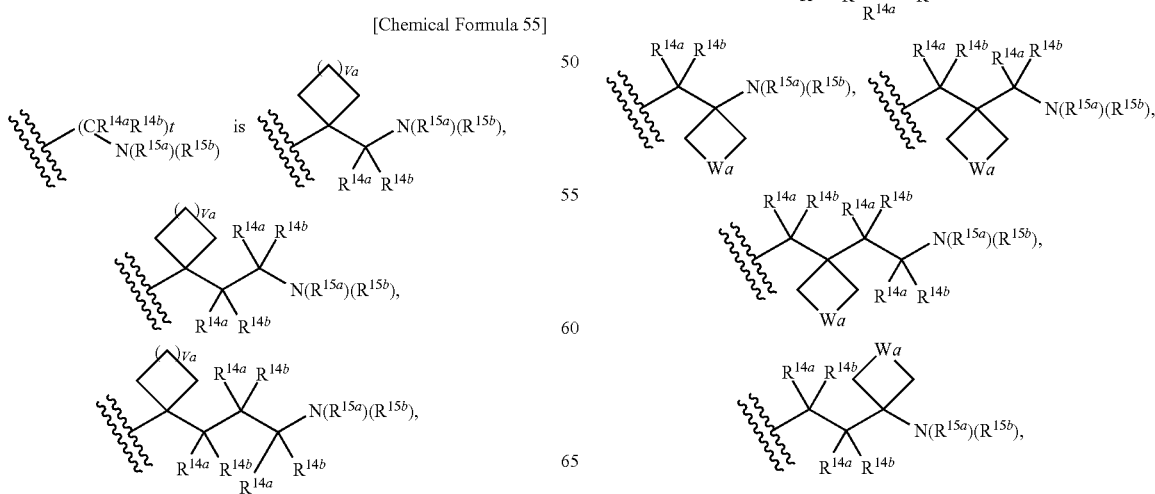

-continued

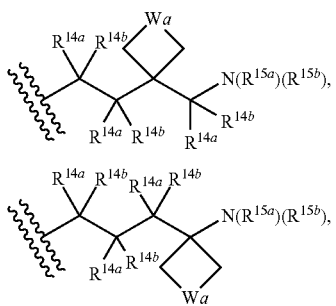

wherein t, $R^{14a}$ and $R^{14b}$ are as defined in the above (24);
va is an integer of 0 to 3 (e.g., 0 or 1, and e.g., 0);
—Wa— is —O—, —S— or —N($R^{17a}$)— (e.g., —O—);
$R^{17a}$ is a hydrogen atom, substituted or unsubstituted alkyl, substituted or unsubstituted alkenyl, substituted or unsubstituted alkynyl, substituted or unsubstituted acyl
and the like.

In general formula (VIII), general formula (IX), and general formula (VII), "$R^{14b}$ and $R^{14b'}$ together with the carbon atom to which they are attached form a substituted or unsubstituted cycloalkane ring, a substituted or unsubstituted cycloalkene ring, or a substituted or unsubstituted non-aromatic heterocyclic ring" includes the followings:

[Chemical Formula 56]

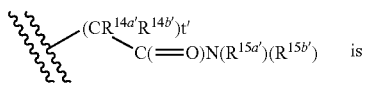 is

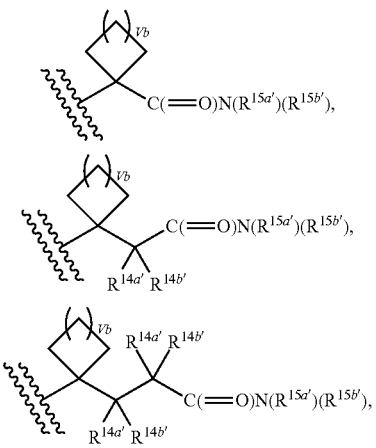

-continued

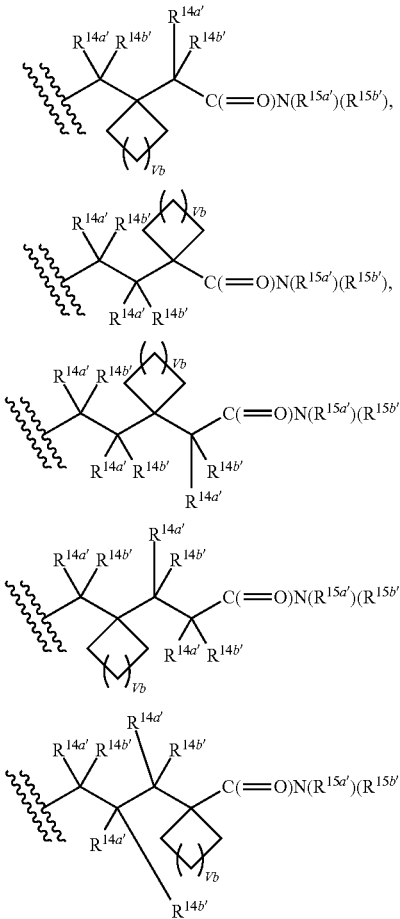

[Chemical Formula 57]

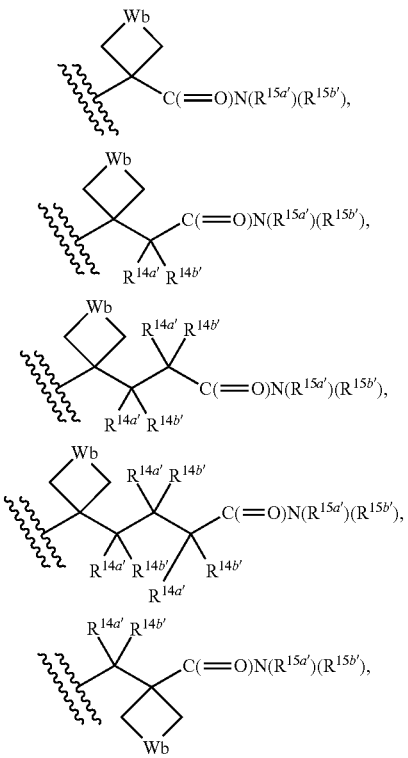

-continued

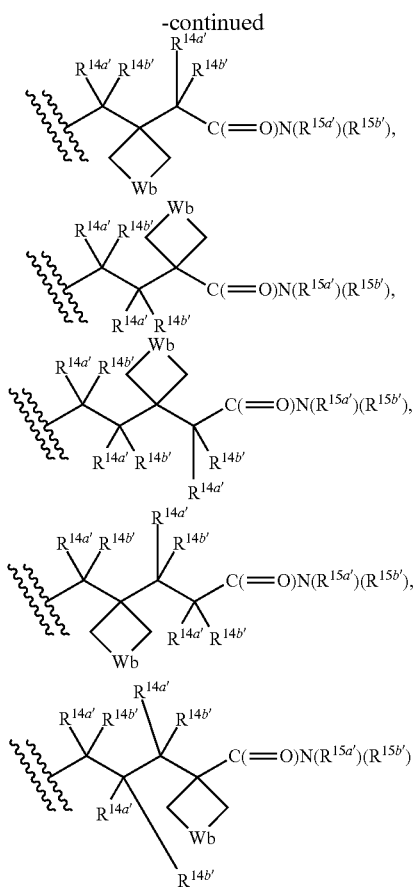

wherein t, $R^{14a}$ and $R^{14b}$ are as defined in the above (24);
va is an integer of 0 to 3 (e.g., 0 or 1, and e.g., 0);
—Wa— is —O—, —S— or —N($R^{17a}$)— (e.g., —O—);
$R^{17a}$ is a hydrogen atom, substituted or unsubstituted alkyl, substituted or unsubstituted alkenyl, substituted or unsubstituted alkynyl, substituted or unsubstituted acyl
and the like.

One embodiment of the compound of the present invention or the composition of the present invention is mentioned below.

The following (II"-A) to (II"-C) are embodiments of a pharmaceutical composition having an analgesic effect and/or an improving effect of urination disorder comprising the compound of the formula (II");

[Chemical Formula 58]

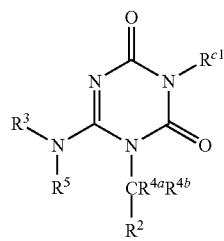

(II")

or its pharmaceutically acceptable salt or a solvate thereof as an active ingredient.

(II"-A)
A pharmaceutical composition having an analgesic effect and for an improving effect of urination disorder comprising the compound wherein $R^{c1}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group A, or alkynyl substituted with one or more substituents selected from Substituent Group A;
$R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl and alkylsilylalkynyl), heteroaryl optionally substituted with one or more substituents selected from Substituent Group C, or cycloalkyl optionally substituted with one or more substituents selected from Substituent Group C;
$R^3$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryloxyl optionally substituted with one or more substituents selected from Substituent Group D;
$R^{4a}$ and $R^{4b}$ are both hydrogen,
$R^5$ is hydrogen,
or its pharmaceutically acceptable salt or a solvate thereof as an active ingredient.
(II"-B)
A pharmaceutical composition having an analgesic and/or an improving effect of urination disorder comprising the compound wherein $R^{c1}$ is a group of the formula:

[Chemical Formula 59]

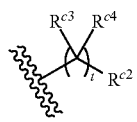

wherein t is an integer of 1 to 4;
$R^{c2}$ is halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxylcarbonyl, substituted or unsubstituted heteroaryloxylcarbonyl, substituted or unsubstituted carbamoyl, substituted or unsubstituted sulfamoyl, substituted or unsubstituted amino, substituted or unsubstituted imino, substituted or unsubstituted guanidyl, substituted or unsubstituted alkylthio, substituted or unsubstituted alkenylthio, substituted or unsubstituted alkynylthio, substituted or unsubstituted acyl, substituted or unsubstituted cycloalkyloxycarbonyl, substituted or unsubstituted cycloalkenyloxycarbonyl, substituted or unsubstituted non-aromatic heterocyclyloxycarbonyl, substituted or unsubstituted aryloxylcarbonyl, substituted or unsubstituted heteroaryloxylcarbonyl, or nitro;

$R^3$ and $R^4$ are each independently hydrogen, hydroxy, halogen, substituted or unsubstituted alkyl, substituted or unsubstituted alkenyl, or substituted or unsubstituted alkynyl, or (i) $R^{c3}$ and $R^{c4}$ are taken together to form oxo or thioxo, or, (ii) $R^{c3}$ and $R^{c4}$ attached to the same carbon atom, are taken together to form —$(CR^{c5}R^{c6})x$—;

$R^{c5}$ and $R^{c6}$ are each independently hydrogen, halogen, hydroxy, substituted or unaubatitutad alkyl, substituted or unsubstituted alkenyl, or substituted or unsubstituted alkynyl;

$R^2$ is substituied or unsubstituted aryl, substituted or unsubstituted heteroaryl, or heteroaryl optionally substituted with one or more substituents selected from Substituent Group C;

x is an integer of 1 to 4;

$R^3$ is aryl optionally substituted with one or more substituents selected from Substituent Group D, or heteroaryl optionally substituted with one or more substituents selected from Substituent Group D;

$R^{4a}$ and $R^{4b}$ are both hydrogen;

$R^5$ is hydrogen, its pharmaceutically acceptable salt or a solvate thereof as an active ingredient.

(II'-C)

A pharmaceutical composition having an analgesic effect and/or an improving effect of urination disorder comprising the compound of the above (II'-A) wherein $R^{c1}$ is alkyl substituted with one or more substituents selected from Substituent Group E (Substituent Group E: sulfo; substituted or unsubstituted sulfamoyl; substituted or unsubstituted imino; substituted or unsubstituted guanidyl; a substituted or unsubstituted non-aromatic heterocyclic group (provided that the heterocyclic group is morpholino, imidazolidine, tetrahydropyranyl, and piperizino) and substituted or unsubstituted heteroaryl (provided that the heteroaryl pyridino)), alkenyl optionally substituted with one or more substituents selected from Substituent Group E, or alkynyl substituted with one or more substituents selected from Substituent Group E, its pharmaceutically acceptable salt or a solvate thereof as an active ingredient.

One embodiment of the compound of the present invention or the composition of the present invention is mentioned below.

The following (III"-A) to (III"-C) are embodiments of a pharmaceutical composition having an analgesic effect and/ or an improving effect of urination disorder comprising the compound of the formula (III"):

[Chemical Formula 60]

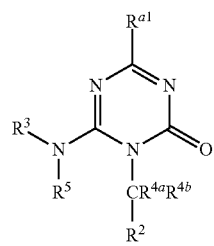

(III")

its pharmaceutically acceptable salt or a solvate thereof as an active ingredient.

A pharmaceutical composition having an analgesic effect and/or an improving effect of urination disorder comprising the compound wherein $R^{a1}$ is alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), alkenyl substituted with one or more substituents selected from Substituent Group A, alkynyl substituted with one or more substituents selected from Substituent Group A, alkyloxy substituted with one or more substituents selected from Substituent Group A, alkenyloxy substituted with one or more substituents selected from Substituent Group A, alkenyloxy substituted with one or more substituents selected from Substituent Group A, alkylthio substituted with one or more substituents selected from Substituent Group A, alkenylthio substituted with one or more substituents selected from Substituent Group A, alkynylthio substituted with one or more substituents selected from Substituent Group A, alkylamino substituted with one or more substituents selected from Substituent Group A, alkenylamino substituted with one or more substituents selected from Substituent Group A or alkynylamino substituted with one or more substituents selected from Substituent Group A, $R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl and alkylsilylalkynyl) or heteroaryl optionally substituted with one or more substituents selected from Substituent Group C;

$R^3$ is aryl optionally substituted with one or more substituents selected from Substituent Group D (Substituent Group D: halogen; hydroxy; alkyl optionally substituted with halogen, hydroxy, cyano, alkyloxylmino, dialkylamino, alkyloxy, cycloalkyl, or heteroaryl; alkenyl optionally substituted with cycloalkyl; alkynyl optionally substituted with cycloalkyl; alkyloxy optionally substituted with halogen, alkyloxy, cycloalkyl, aryl or a non-aromatic heterocyclic group optionally substituted with alkyl; alkylthio; cycloalkyl; cycloalkenyl; cycloalkyloxy; aryloxy; heteroaryloxy optionally substituted with alkyl; a non-aromatic heterocyclic group; and alkylamino), or heteroaryl optionally substituted with one or more substituents selected from Substituent Group D;
$R^{4a}$ and $R^{4b}$ are both hydrogen;
$R^5$ is hydrogen,
or its pharmaceutically acceptable salt or a solvate thereof as an active ingredient.
(III'-B)
A pharmaceutical composition having an analgesic effect and/or an improving effect of urination disorder comprising the compound wherein $R^{a1}$ is

[Chemical Formula 61]

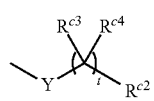

wherein —Y— is —O—, —S— or —$NR^Y$—;
$R^Y$ is hydrogen, substituted or unsubstituted alkyl or substituted or unsubstituted acyl;
and other symbols are as defined in the above II'-B;
$R^{c5}$ and $R^{c6}$ are each independently, hydrogen, halogen, hydroxy, substituted or unsubstituted alkyl, substituted or unsubstituted alkenyl, or substituted or unsubstituted alkynyl;
$R^2$ is substituted or unsubstituted aryl, or substituted or unsubstituted heteroaryl;
x is an integer of 1 to 4;
$R^3$ is aryl optionally substituted with one or more substituents selected from Substituent Group D, or heteroaryl optionally substituted with one or more substituents selected from Substituent Group D;
$R^{4a}$ and $R^{4b}$ are both hydrogen;
$R^5$ is hydrogen,
or its pharmaceutically acceptable salt or a solvate thereof as an active ingredient.
One embodiment of the compound of the present invention is mentioned below. A compound of the formula (VII'):

[Chemical Formula 62]

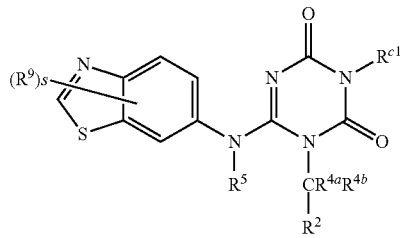

wherein
$R^{c1}$ is unsubstituted alkyl, alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), unsubstituted alkenyl, alkenyl substituted with one or more substituents selected from Substituent Group A, unsubstituted alkynyl or alkynyl substituted with one or more substituents selected from Substituent Group A;
$R^{4a}$ and $R^{4b}$ are both hydrogen;
$R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl and alkylsilylalkynyl) or heteroaryl optionally substituted with one or more substituents selected from Substituent Group C, or cycloalkyl optionally substituted with one or more substituents selected from Substituent Group C;
$R^5$ is hydrogen;
$R^9$ is halogen, hydroxy, carboxy, cyano, alkyloxy, unsubstituted alkyl, alkyl optionally substituted with one or more substituents selected from Substituent Group F (Substituent Group F: halogen, hydroxy, carboxy, cyano, alkyloxyimino, dialkylamino, alkyloxy, cycloalkyl, and heteroaryl), unsubstituted alkenyl, alkenyl optionally substituted with one or more substituents selected from Substituent Group F, unsubstituted alkynyl, or alkynyl optionally substituted with one or more substituents selected from Substituent Group F;
and s is an integer of 0 to 2,
its pharmaceutically acceptable salt or a solvate thereof.
One embodiment of the compound of the present invention is mentioned below. A compound of the formula (VIII');

[Chemical Formula 63]

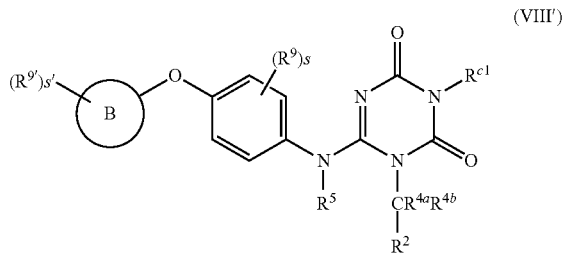

wherein
$R^{c1}$ is unsubstituted alkyl, alkyl substituted with one or more substituents selected from Substituent Group A (Substituent Group A: halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, and substituted or unsubstituted guanidyl), unsubstituted alkenyl, alkenyl substituted with one or more substituents selected from Substituent Group A, unsubstituted alkynyl or alkynyl substituted with one or more substituents selected from Substituent Group A;

$R^{4a}$ and $R^{4b}$ are both hydrogen;
$R^2$ is aryl optionally substituted with one or more substituents selected from Substituent Group C (Substituent Group C: halogen, alkyl, alkenyl, alkynyl, alkyloxy, alkenyloxy, alkynyloxy, cycloalkyl, cycloalkenyl, cycloalkynyl and alkylsilylalkynyl) or heteroaryl optionally substituted with one or more substituents selected from Substituent Group C, or cycloalkyl optionally substituted with one or more substituents selected from Substituent Group C;
$R^5$ is hydrogen;
$R^9$ is halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsulystituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl;
s is an integer of 0 to 2,
ring B is thiazole, oxazole, isoxazole, pyrazole, imidazole, triazole, furan, thiophen, oxadiazole, thiadiazole, pyridine, pyrimidine, pyridazine triazine or benzoxazole;
$R^{9'}$ is halogen, hydroxy, carboxy, cyano, nitro, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkyloxycarbonyl, substituted or unsubstituted alkenyloxycarbonyl, substituted or unsubstituted alkynyloxy carbonyl, substituted or unsubstituted carbamoyl, substituted or unsulystituted amino, substituted or unsubstituted sulfamoyl, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl;
s' is an integer of 0 to 2,
or its pharmaceutically acceptable salt or a solvate thereof.

The following embodiments are examples of the compound (VIII) of the present invention.

A compound of the formula (VIII-a):

[Chemical Formula 64]

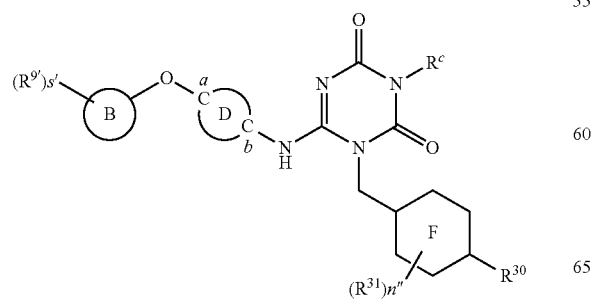

(VIII-a)

wherein
$R^c$ is selected from the following (a1) to (a32):

[Chemical Formula 65]

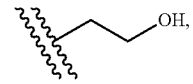 (a1)

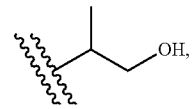 (a2)

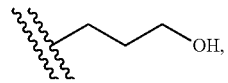 (a3)

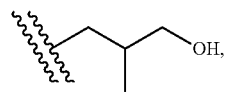 (a4)

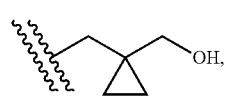 (a5)

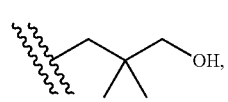 (a6)

 (a7)

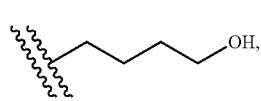 (a8)

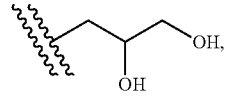 (a9)

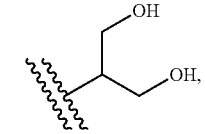 (a10)

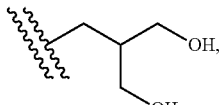 (a11)

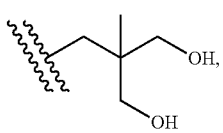 (a12)

-continued

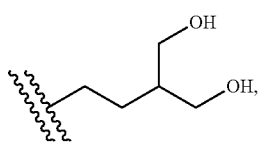

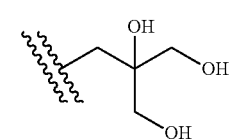

[Chemical Formula 66]

(a13) 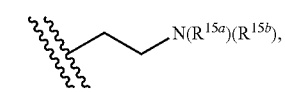

(a14) 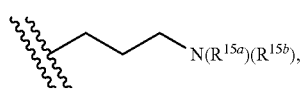

(a15) 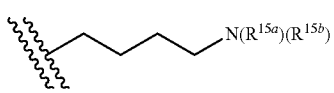

(a16) 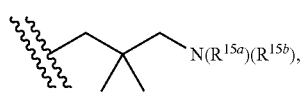

(a17) 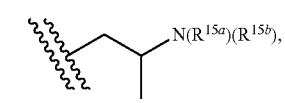

(a18) 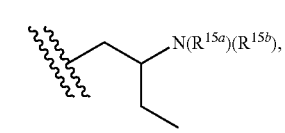

(a19) 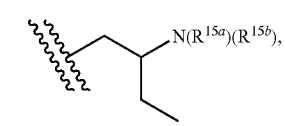

(a20) 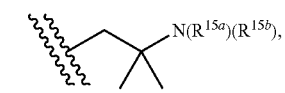

(a21) 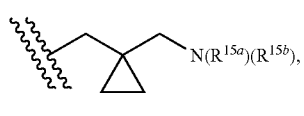

(a22) 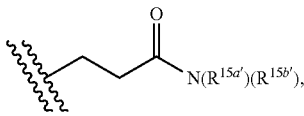

(a23) 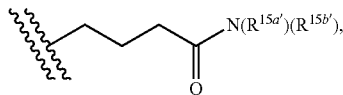

-continued (a24) 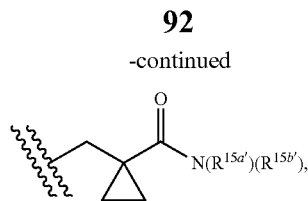

(a25)

(a26) 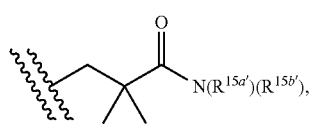

(a27) 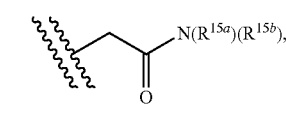

(a28) 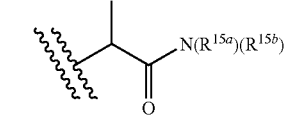

(a29) 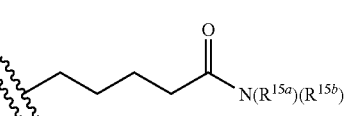

(a30)

wherein $R^{15a}$, $R^{15b}$, $R^{15a'}$ and $R^{15b'}$ are each independently selected from the following (b1) and (b2):
(b1) hydrogen atom, cyano, substituted or unsubstituted alkyl, substituted or unsubstituted alkenyl, substituted or unsubstituted alkynyl, substituted or unsubstituted carbamoyl, substituted or unsubstituted sulfamoyl, substituted or unsubstituted acyl, substituted sulfonyl or substituted sulfinyl, and
(b2) a hydrogen atom, methyl, ethyl, acetyl or trifluoroacetyl,
(a31) ethyl; and.
(a32) methyl;
ring F is selected from the following (c1) to (c3)
(c1) a benzene ring;
(c2) a pyridine ring; and
(c3) a cyclohexane ring;
$R^{30}$ is selected from the following (d1) and (d2);
(d1) substituted or unsubstituted alkyl, substituted or unsubstituted alkenyl or substituted or unsubstituted alkynyl; and
(d2) fluoro, chloro, methyl, monofluoromethyl, difluoromethyl, trifluoromethyl or ethyl;
$R^{31}$ is halogen, substituted or unsubstituted alkyl, substituted or unsubstituted alkenyl or substituted or unsubstituted alkynyl;
n" is 0 or 1;
ring D is selected from the following (e1) and (e2);
(e1) a benzene ring; and
(e2) a pyridine ring;
relationship of carbon atom a and carbon atom b on the ring D are selected from the following (f1) and (f2):
(f1) 1,4 relationship; and
(f2) 1,3 relationship;
ring B as selected from the following (g1) to (g12);
(g1) a thiazole ring;
(g2) an isothiazole ring;
(g3) an oxazole ring;
(g4) an isoxazole ring;
(g5) a thiadiazole ring;
(g6) an oxadiazole ring;

(g7) a pyridine ring;
(g8) a pyrimidine ring;
(g9) a pyrazine ring;
(g10) a pyridazine ring;
(g11) a triazine ring; and
(g12) pyrazole ring;
s' is selected from the following (h1) and (h2):
(h1) 0; and
(h2) 1;
when s' is 1, then $R^{9'}$ is selected from the following (i1) to (i14);
(i1) hydroxy;
(i2) carboxy;
(i3) cyano;
(i4) alkyl substituted with hydroxy, carboxy, cyano, carbamoyl, amino, sulfamoyl, methanesulfonyl or methanesulfinyl;
(i5) substituted or unsubstituted carbamoyl;
(i6) alkylcarbamoyl or alkenylcarbamoyl;
(i7) substituted or unsubstituted amino;
(i8) amino substituted with carbamoyl, alkylcarbamoyl, alkylcarbamoylalkyl, carbamoylalkyl or carboxyalkyl;
(i9) substituted or unsubstituted sulfamoyl;
(i10) alkylsulfamoyl or alkenylsulfamoyl;
(i11) substituted sulfonyl;
(i12) substituted sulfinyl;
(i13) unsubstituted alkyl, or alkyl substituted with halogen, haloalkyloxy, cycloalkyl, cycloalkenyl, alkyloxy or alkenyloxy; and
(i11) unsubstituted alkyl.

The compound of the formula (VIII-a) of the present invention includes the compounds comprising the combination of some or all of options of the above (a1) to (a32), (b1) and (b2), (c1) to (c3), (d1) and (d2), (e1) and (e2), (f1) and (f2), (g1) to (g12), (h1) and (h2), and (i1) to (i14).

The following embodiments are examples of the compound (VIII) of the present invention.

A compound of the formula (VIII-b):

[Chemical Formula 67]

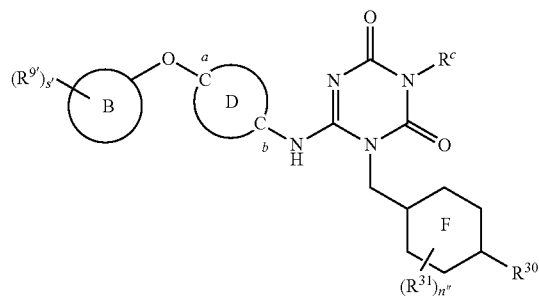

(VIII-b)

wherein
$R^c$ is a group selected from the following (ba1) to (ba16):
(ba1) a group of the formula: —$(CR^{11a}R^{11b})$m—OH
wherein $R^{11a}$ and $R^{11b}$ are each independently, a hydrogen atom, substituted or unsubstituted alkyl, substituted or unsubstituted alkenyl, or substituted or unsubstituted alkynyl, or $R^{11a}$ and $R^{11b}$ together with the carbon atom to which they are attached form a substituted or unsubstituted cyclopropane ring, a substituted or unsubstituted cyclopropene ring; a substituted or unsubstituted oxetane ring, a substituted or unsubstituted thietane ring, or a substituted or unsubstituted azetizine ring; m is an integer of 2 to 4;

(ba2) a group of the formula: —$(CR^{11a}R^{11b})$m—OH
wherein $R^{11a}$ is a hydrogen atom, substituted or unsubstituted alkyl, substituted or unsubstituted alkenyl, or substituted or unsubstituted alkynyl;
$R^{11b}$ is a group of the formula: —$(CR^{12a}R^{12b})$u—OH
wherein $R^{12a}$ and $R^{12b}$ are each independently a hydrogen atom, substituted or unsubstituted alkyl, substituted or unsubstituted alkenyl, or substituted or unsubstituted alkynyl; u is an integer of 0 to 2;
m is an integer of 2 to 4;
(ba3) a group of the formula:

[Chemical Formula 68]

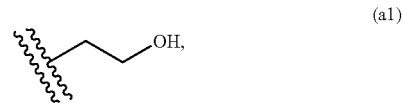 (a1)

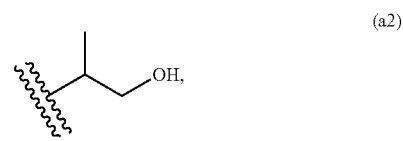 (a2)

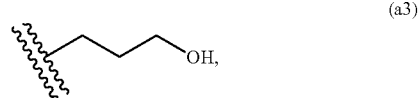 (a3)

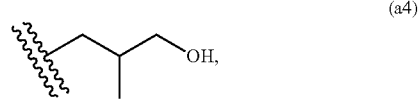 (a4)

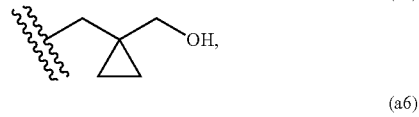 (a5)

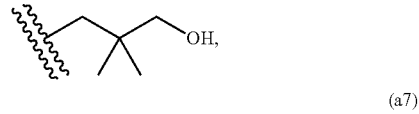 (a6)

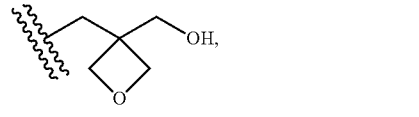 (a7)

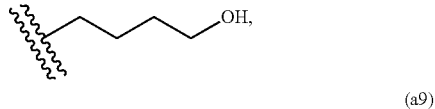 (a8)

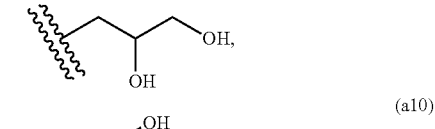 (a9)

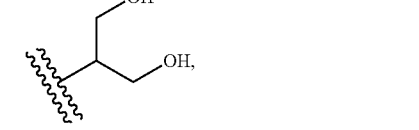 (a10)

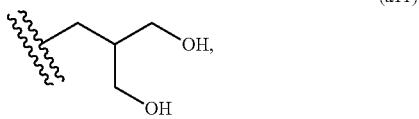 (a11)

(ba4) a group of the formula:

[Chemical Formula 69]

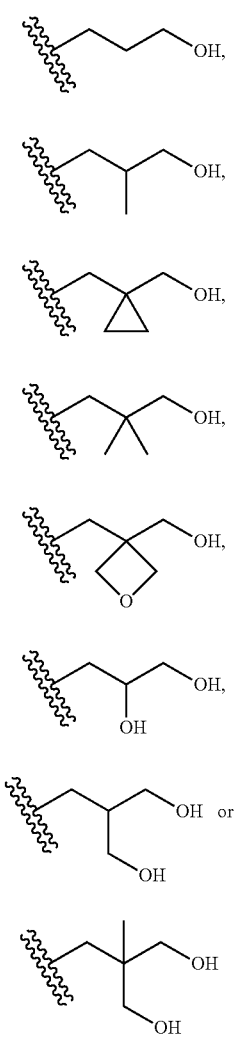

(a3)

(a4)

(a5)

(a6)

(a7)

(a9)

(a11)

(a12)

(a13)

(a14)

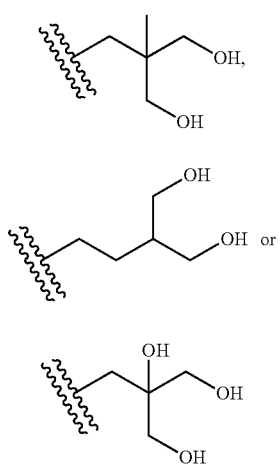

(ba5) a group of the formula:

[Chemical Formula 70]

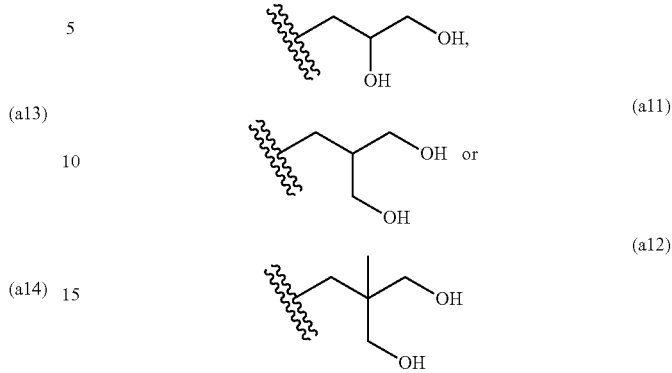

(a9)

(a11)

(a12)

(ba6) a group of the formula: —(CR$^{14a}$R$^{14b}$)t—N(R$^{15a}$)(R$^{15b}$)

wherein R$^{14a}$ and R$^{14b}$ are each independently hydrogen atom, substituted or unsubstituted alkyl, substituted or unsubstituted alkenyl, or substituted or unsubstituted alkynyl, or R$^{14a}$ and R$^{14b}$ together with the carbon atom to which they are attached form a substituted or unsubstituted cyclopropane ring, a substituted or unsubstituted cyclopropene ring, a substituted or unsubstituted oxetane ring, a substituted or unsubstituted thietane ring, or a substituted or unsubstituted azetizine ring; t is an integer of 2 to 4; R$^{15a}$ and R$^{15b}$ are each independently a hydrogen atom, substituted or unsubstituted alkyl, substituted or unsubstituted alkenyl, substituted or unsubstituted alkynyl, substituted or unsubstituted carbamoyl, substituted or unsubstituted sulfamoyl, substituted or unsubstituted acyl, substituted sulfonyl or substituted sulfinyl;

(ba7) a group of the formula:

[Chemical Formula 71]

(a15)

(a16)

(a17)

(a18)

(a19)

(a20)

-continued

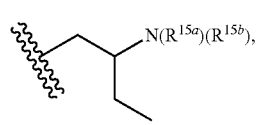 (a21)

 (a22)

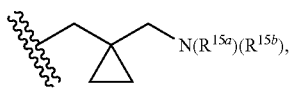 (a23)

wherein $R^{15a}$ and $R^{15b}$ are as defined in the above (ba6);
(ba8) a group of the formula:

[Chemical Formula 72]

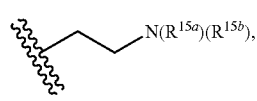 (a15)

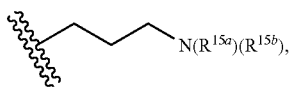 (a16)

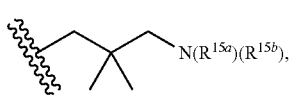 (a18)

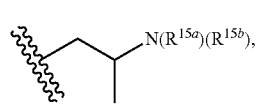 (a19)

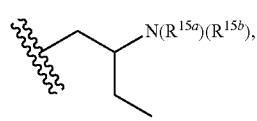 (a20)

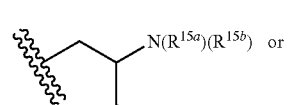 (a21)

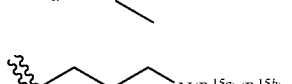 (a23)

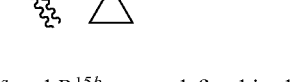

wherein $R^{15a}$ and $R^{15b}$ are as defined in the above (ba6);
(ba9) a group of the formula: $-(CR^{14a'}R^{14b'})_{t'}-C(=O)N(R^{15a'})(R^{15b'})$
wherein $R^{15a'}$ and $R^{15b'}$ are each independently a hydrogen atom, substituted or unsubstituted alkyl, substituted or unsubstituted alkenyl, or substituted or unsubstituted alkynyl, or $R^{15a'}$ and $R^{15b'}$ together with the carbon atom to which they are attached form a substituted or unsubstituted cyclopropane ring, a substituted or unsubstituted cyclopropene ring, a substituted or unsubstituted oxetane ring, a substituted or unsubstituted thietane ring, or a substituted or unsubstituted azetizine ring; t' is an integer of 1 to 4; $R^{15a'}$ and $R^{15b'}$ are each independently a hydrogen atom, cyano, substituted or unsubstituted alkyl, substituted or unsubstituted alkenyl, substituted or unsubstituted alkynyl, substituted or unsubstituted carbamoyl, substituted or unsubstituted sulfamoyl, substituted or unsubstituted acyl, substituted sulfonyl or substituted sulfinyl;

(ba10) a group of the formula:

[Chemical Formula 73]

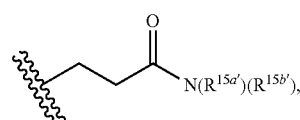 (a24)

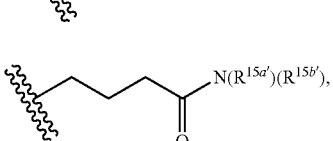 (a25)

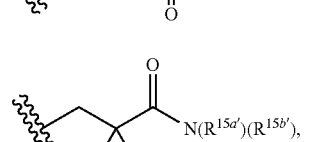 (a26)

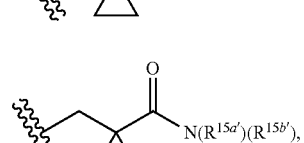 (a27)

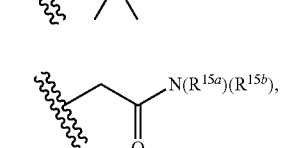 (a28)

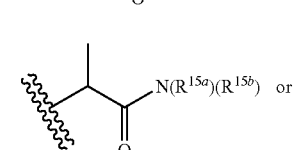 (a29)

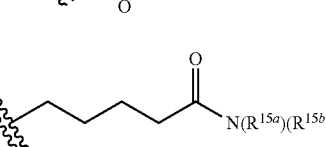 (a30)

wherein $R^{15a'}$ and $R^{15b'}$ are as defined in the above (ba9);
(ba11) a group of the formula:

[Chemical Formula 74]

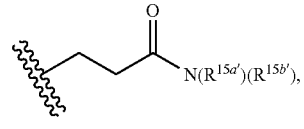 (a24)

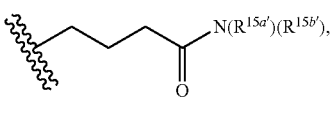 (a25)

-continued

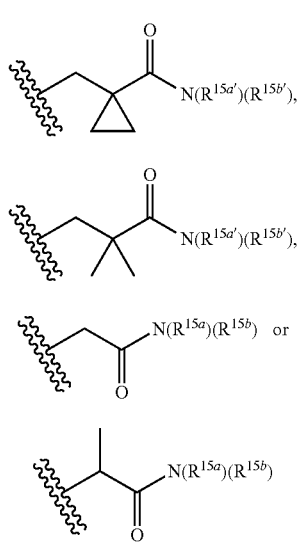

(a26)

(a27)

(a28)

(a29)

wherein $R^{15a'}$ and $R^{15b'}$ are as defined in the above (b9);
(ba12) a group of the formula:

[Chemical Formula 75]

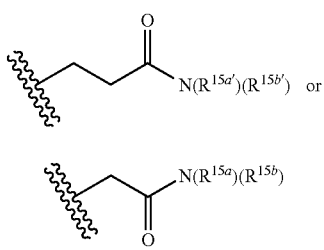

(a24)

(a28)

wherein $R^{15a'}$ and $R^{15b'}$ are as defined in the above (ba9);
(ba13) unsubstituted alkyl; or alkyl substituted with halogen, haloalkyloxy, cycloalkyl, cycloalkenyl, alkyloxy or alkenyloxy;
(ba14) unsubstituted alkyl;
(ba15) methyl; ethyl; methyl substituted with halogen, haloalkyloxy, cycloalkyl, cycloalkenyl, alkyloxy or alkenyloxy; or ethyl substituted with halogen, haloalkyloxy, cycloalkyl, cycloalkenyl, alkyloxy or alkenyloxy; and
(ba16) methyl or ethyl;
ring F is a group selected from the following (bc1) and (bc2):
(bc1) a benzene ring, a pyridine ring or a cyclohexane ring; and
(bc2) a benzene ring;
$R^{30}$ is a group selected from the following (bd1) and (bd2);
(bd1) halogen, substituted or unsubstituted alkyl, substituted or unsubstituted alkenyl or substituted or unsubstituted alkynyl;
(bd2) fluoro, chloro, methyl, monofluoromethyl, difluoromethyl, trifluoromethyl or ethyl;
$R^{31}$ halogen, substituted or unsubstituted alkyl, substituted or unsubstituted alkenyl or substituted or unsubstituted alkynyl;
n" is 0 or 1;

ring D is a group selected from the following (be1) to (be4):
(be1) a benzene ring, a pyridine ring, a pyrimidine ring, a pyrazine ring or a pyridazine ring;
(be2) a benzene ring or a pyridine ring;
(be3) a benzene ring; and
(be4) a pyridine ring;
relationship of carbon atom a and carbon atom b or ring D is selected from the following (bf1) to (bf3):
(bf1) 1,4 relationship, or 1,3 relationship;
(bf2) 1,4 relationship;
(bf3) 1,3 relationship;
ring B is a group selected from the following (bg1) and (bg9);
(bg1) an aromatic heterocyclic ring;
(bg2) a five- or six-membered aromatic heterocyclic ring;
(bg3) a thiazole ring, an isothiazole ring, an oxazole ring, an isoxazole ring, a thiadiazole ring, an oxadiazole ring, a pyridine ring, a pyrimidine ring, a pyrazine ring, a pyridazine ring, a triazine ring, or a pyrazole ring;
(bg4) a thiazole ring, an isoxazole ring, a thiadiazole ring, a pyridine ring, a pyrimidine ring, a pyrazine ring or a pyridazine ring;
(bg5) a six-membered heterocyclic ring;
(bg6) a pyridine ring, a pyrimidine ring, a pyrazine ring, a pyridazine ring or a triazine ring;
(bg 7) a five-membered aromatic heterocyclic ring;
(bg 8) a thiazole ring, an isothiazole ring, an oxazole ring, an isoxazole ring, a thiadiazole ring, an oxadiazole ring or a pyrazole ring; or
(bg 9) a thiazole ring, an isoxazole ring or a thiadiazole ring;
s' is a group selected from the following (bh1) to (bh3);
(bh1) 0 or 1;
(bh2) 0; and
(bh3) 1;
when s' is 1, then $R^{9'}$ is a group selected from the following (bi1) to (bi7):
(bi1) hydroxy; carboxy; cyano; alkyl substituted with hydroxy, carboxy, cyano, carbamoyl, amino, sulfamoyl, methanesulfonyl or methanesulfinyl; substituted or unsubstituted carbamoyl; substituted or unsubstituted amino; substituted or unsubstituted sulfamoyl; substituted sulfonyl; or substituted sulfinyl;
(bi2) hydroxy; carboxy; cyano; alkyl substituted with hydroxy, carboxy, cyano, carbamoyl, amino, sulfamoyl, methanesulfonyl or methanesulfinyl; carbamoyl; alkylcarbamoyl; amino substituted with alkyl, haloalkyl, hydroxy alkyl, alkyloxy, haloalkyloxy, carbamoyl, alkylcarbamoyl, alkylcarbamoylalkyl, carbamoylalkyl or carboxylalkyl; sulfamoyl; alkylsulfamoyl; alkylsulfonyl; or alkylsulfinyl;
(bi3) carboxy; carbamoyl; alkylcarbamoyl; sulfamoyl; alkylsulfamoyl or alkylsulfonyl;
(bi4) alkyl substituted with halogen, haloalkyloxy, cycloalkyl, cycloalkenyl, alkyloxy or alkenyloxy; or unsubstituted alkyl;
(bi5) unsubstituted alkyl;
(bi6) methyl; ethyl; methyl substituted with halogen, haloalkyloxy, cycloalkyl, cycloalkenyl, alkyloxy or alkenyloxy; or ethyl substituted with halogen, haloalkyloxy, cycloalkyl, cycloalkenyl, alkyloxy or alkenyloxy; and
(bi7) methyl or ethyl,
or its pharmaceutically acceptable salt or a solvate thereof.

The compound of the formula (VIII-b) of the present invention includes the compounds comprising the combination of some or all of options of the above (ba1) to (ba16), (bc1) and (bc2), (bd1) andd (bd2), (be1) to (be4), (bf1) to (bf3), (bg1) to (bg9), (bh1) to (bh3) and (bi1) to (bi7).

The following embodiments are examples of the compound (IX) of the present invention.

A compound of the formula (IX-a):

[Chemical Formula 76]

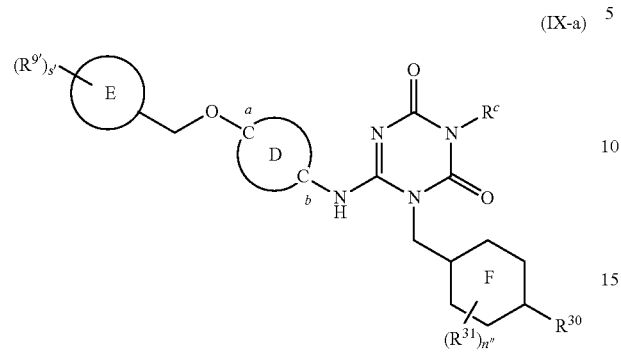
(IX-a)

wherein
$R^c$ is a group selected from the following (ca1) to (ca5):
(ca1) a group of the formula: —$(CR^{11a}R^{11b})_m$—OH
wherein $R^{11a}$ and $R^{11b}$ are each independently, a hydrogen atom, substituted or unsubstituted alkyl, substituted or unsubstituted alkenyl, or substituted or unsubstituted alkynyl, or $R^{11a}$ and $R^{11b}$ together with the carbon atom to which they are attached form a substituted or unsubstituted cyclopropane ring, a substituted or unsubstituted cyclopropene ring; a substituted or unsubstituted oxetane ring, a substituted or unsubstituted thietane ring, or a substituted or unsubstituted azetizine ring; m is an integer of 2 to 4;
(ca2) a group of the formula: —$(CR^{11a}R^{11b})_m$—OH
wherein $R^{11a}$ is a hydrogen atom, substituted or unsubstituted alkyl, substituted or unsubstituted alkenyl, or substituted or unsubstituted alkynyl;
$R^{11b}$ is a group of the formula: —$(CR^{12a}R^{12b})_u$—OH
wherein $R^{12a}$ and $R^{12b}$ are each independently a hydrogen atom, substituted or unsubstituted alkyl, substituted or unsubstituted alkenyl, or substituted or unsubstituted alkynyl; u is an integer of 0 to 2; m is an integer of 2 to 4:
(ca3) a group or the formula:

[Chemical Formula 77]

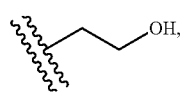 (a1)

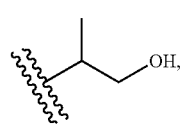 (a2)

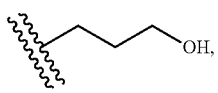 (a3)

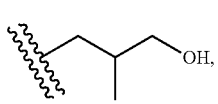 (a4)

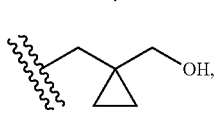 (a5)

 (a6)

 (a7)

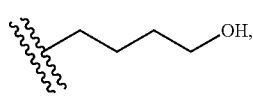 (a8)

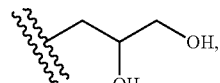 (a9)

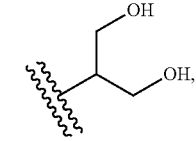 (a10)

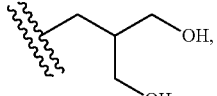 (a11)

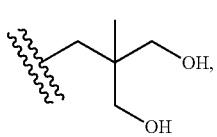 (a12)

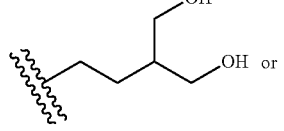 (a13)

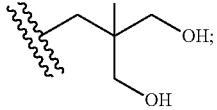 (a14)

(c4) a group of the formula:

[Chemical Formula 78]

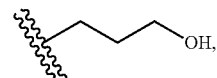 (a3)

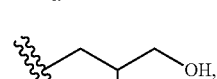 (a4)

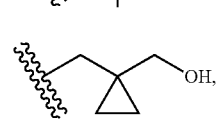 (a5)

-continued

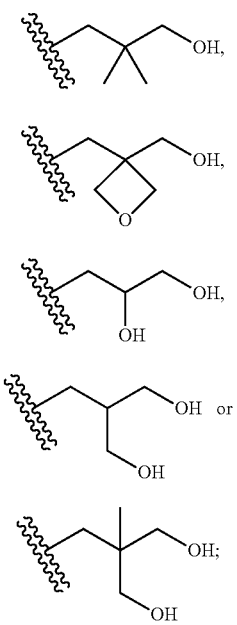

(a6)

(a7)

(a9)

(a11)

(a12)

and
(c5) a group of the formula:

[Chemical Formula 79]

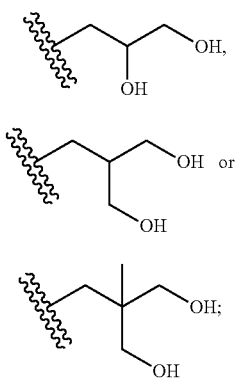

(a9)

(a11)

(a12)

ring F is a group selected from the following (cc1) and (cc2);
(cc1) a benzene ring, a pyridine ring or a cyclohexane ring; and
(cc2) a benzene ring;
$R^{30}$ is a group selected from the following (cd1) and (cd2);
(cd1) halogen, substituted or unsubstituted alkyl, substituted or unsubstituted alkenyl or substituted or unsubstituted alkynyl;
n" is 0 or 1;
ring D is a group selected from the following (ce1) to (ce4):
(ce1) a benzene ring, a pyridine ring, a pyrimidine ring, a pyrazine ring or a pyridazine ring;
(ce2) a benzene ring or a pyridine ring;
(ce3) a benzene ring; and
(ce4) a pyridine ring;
relationship of carbon atom a and carbon atom b or ring D is selected from the following (cf1) to (cf3):

(cf1) 1,4 relationship, or 1,3 relationship;
(cf2) 1,4 relationship;
(cf3) 1,3 relationship;
ring E is a group selected from the following (cg1) and (cg3);
(cg1) a cycloalkane ring or a cycloalkene ring;
(cg2) a cycloalkane ring; and
(cg3) a cyclopropane ring;
s' is
(ch1) 0 or 1;
(ch2) 0; and
(ch3) 1;
when s' is 1, then $R^{9'}$ is a group selected from the following (ci1) to (ci4):
(ci1) alkyl substituted with halogen, haloalkyloxy, cycloalkyl, cycloalkenyl, alkyloxy, or alkenyloxy; or unsubstituted alkyl;
(ci2) unsubstituted alkyl;
(ci3) methyl; ethyl; methyl substituted with halogen, haloalkyloxy, cycloalkyl, cycloalkenyl, alkyloxy or alkenyloxy; or ethyl substituted with halogen, haloalkyloxy, cycloalkyl, cycloalkenyl, alkyloxy or alkenyloxy; and
(ci4) methyl or ethyl,
or its pharmaceutically acceptable salt or a solvate thereof.

The compound of the formula (VIII-b) of the present invention includes the compounds comprising the combination of some or all of options of the above (ca1) to (ca5), (cc1) and (cc2), (cd1) and (cd2), (ce1) and (ce4), (cf1) and (cf3), (cg1) and (cg3), (ch1) and (ch3) and (ci1) and (ci4).

The following embodiments are examples of the compound (VIII) of the present invention.

A compound of the formula (VIII-c):

[Chemical Formula 80]

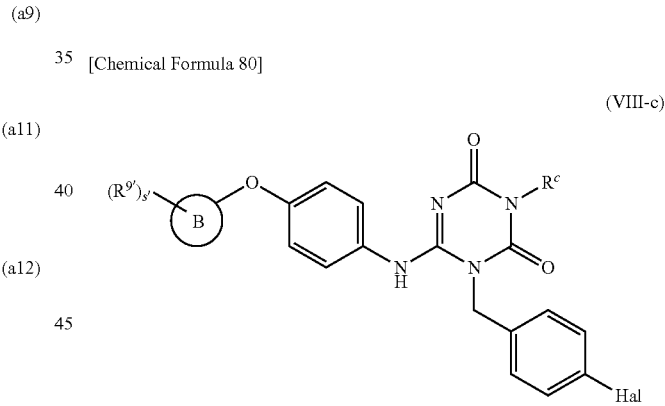

(VIII-c)

wherein
Hal is halogen:
$R^c$ is
(da1) a group of the formula:

[Chemical Formula 81]

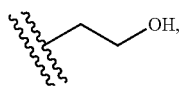

(a1)

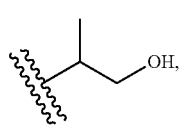

(a2)

-continued
(a3) 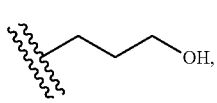
(a4) 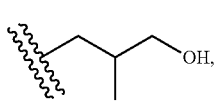
(a5) 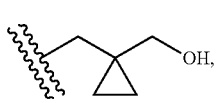
(a6) 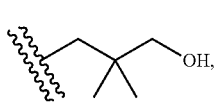
(a7) 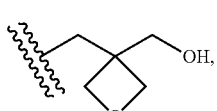
(a8) 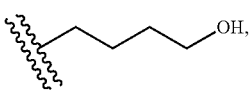
(a9) 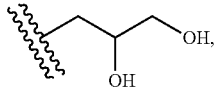
(a10) 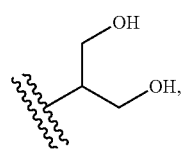
(a11) 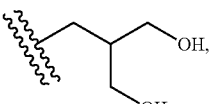
(a12) 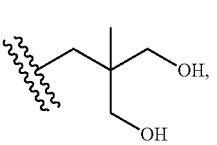
(a13) 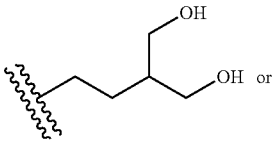
(a14) 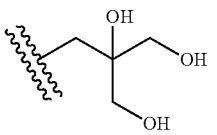
(da2) a group of the formula:
[Chemical Formula 82]
(a3) 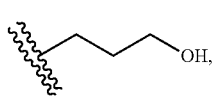
(a4) 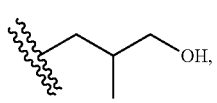
(a5) 
(a6) 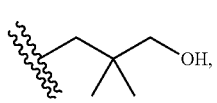
(a7) 
(a9) 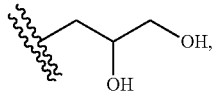
(a11) 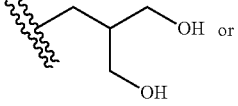
(a12) 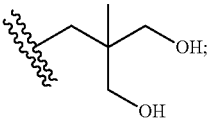
or
(da3) a group of the formula:
[Chemical Formula 83]
(a9) 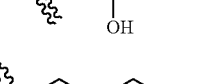
(a11) 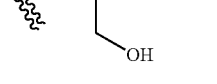
(a12) 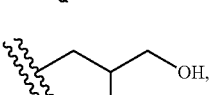
ring B is:
(dg1) an aromatic heterocyclic ring;
(dg2) a five- or six-membered aromatic heterocyclic ring;
(dg3) a thiazole ring, an isothiazole ring, an oxazole ring, an isoxazole ring, a thiadiazole ring, an oxadiazole ring, a pyridine ring, a pyrimidine ring, a pyrazine ring, a pyridazine ring, a triazine ring, or a pyrazole ring;
(dg4) a thiazole ring, an isoxazole ring, a thiadiazole ring, a pyridine ring, a pyrimidine ring, a pyrazine ring or a pyridazine ring;
(dg5) a six-membered heterocyclic ring;
(dg6) a pyridine ring, a pyrimidine ring, a pyrazine ring, a pyridazine ring or a triazine ring;
(dg 7) a five-membered aromatic heterocyclic ring;
(dg 8) a thiazole ring, an isothiazole ring, an oxazole ring, an isoxazole ring, a thiadiazole ring, an oxadiazole ring, or a pyrazole ring; or
(dg 9) a thiazole ring, an isoxazole ring or a thiadiazole ring; a group of the formula $(R^9)s'$— is;
(dj1) s' is 0;
(dj2) s' is 1, and $R^{9'}$ is hydroxy; carboxy; cyano; alkyl substituted with hydroxy, carboxy, cyano, carbamoyl, amino, sulfamoyl, methansulfonyl or methansulfinyl; substituted or unsubstituted carbamoyl; substituted or unsubstituted amino; substituted or unsubstituted sulfamoyl; substituted sulfonyl; or substituted sulfinyl;
(dj3) s' is 1, and $R^{9'}$ is hydroxy; carboxy; cyano; alkyl substituted with hydroxy, carboxy, cyano, carbamoyl, amino, sulfamoyl, methansulfonyl or methansulfinyl; carbamoyl; alkylcarbamoyl; amino substituted with alkyl, haloalkyl, hydroxyalkyl, alkyloxy, haloalkyloxy, carbamoyl, alkylcarbamoyl, alkylcarbamoylalkyl, carbamoylalkyl or carboxyalkyl; sulfamoyl; alkylsulfamoyl; alkylsulfonyl; or alkylsulfinyl;
(dj4) s' is 1, and $R^{9'}$ is carboxy; carbamoyl; alkylcarbamoyl; sulfamoyl; alkylsulfamoyl or alkylsulfonyl;
(dj5) s' is 1, and $R^{9'}$ is alkyl substituted with halogen, haloalkyloxy, cycloalkyl, cycloalkenyl, alkyloxy or alkenyloxy; or unsubstituted alkyl;
(bj6) s' is 1, and $R^{9'}$ is unsubstituted alkyl;
(dj7) s' is 1, and $R^{9'}$ is methyl; ethyl; methyl substituted with halogen, haloalkyloxy, cycloalkyl, cycloalkenyl, alkyloxy or alkenyloxy; or ethyl substituted with halogen, haloalkyloxy, cycloalkyl, cycloalkenyl, alkyloxy or alkenyloxy; and
(dj8) s' is 1, and $R^{9'}$ is methyl or ethyl,
or its pharmaceutically acceptable salt or a solvate thereof. The compound of the formula (VIII-c) of the present invention includes the compounds comprising the combination of some or all of options of the above. Specifically, the following combinations are included,
(da1, dg3, di3), (da1, dg3, di4), (da1, dg3, di5), (da1, dg3, di6), (da1, dg3, di7), (da1, dg3, di8), (da1, dg4, di1), (da1, dg4, di2), (da1, dg4, di3), (da1, dg4, di4), (da1, dg4, di5), (da1, dg4, di6), (da1, dg4, di7), (da1, dg4, di8), (da1, dg5, di1), (da1, dg5, di2), (da1, dg5, di3), (da1, dg5, di4), (da1, dg5, di5), (da1, dg5, di6), (da1, dg5, di7), (da1, dg5, di8), (da1, dg6, di1), (da1, dg6, di2), (da1, dg6, di3), (da1, dg6, di4), (da1, dg6, di5), (da1, dg6, di6), (da1, dg6, di7), (da1, dg6, di8), (da1, dg7, di1), (da1, dg7, di2), (da1, dg7, di3), (da1, dg7, di4), (da1, dg7, di5), (da1, dg7, di6), (da1, dg7, di7), (da1, dg7, di8), (da1, dg8, di1), (da1, dg8, di2), (da1, dg8, di3), (da1, dg8, di4), (da1, dg8, di5), (da1, dg8, di6), (da1, dg8, di7), (da1, dg8, di8), (da1, dg9, di1), (da1, dg9, di2), (da1, dg9, di3), (da1, dg9, di4), (da1, dg9, di5), (da1, dg9, di6), (da1, dg9, di7), (da1, dg9, di8), (da2, dg1, di1), (da2, dg1, di2), (da2, dg1, di3), (da2, dg1, di4), (da2, dg1, di5), (da2, dg1, di6), (da2, dg1, di7), (da2, dg1, di8), (da2, dg2, di1), (da2, dg2, di2), (da2, dg2, di3), (da2, dg2, di4), (da2, dg2, di5), (da2, dg2, di6), (da2, dg2, di7), (da2, dg2, di8), (da2, dg3, di1), (da2, dg3, di2), (da2, dg3, di3), (da2, dg3, di4), (da2, dg3, di5), (da2, dg3, di6), (da2, dg3, di7), (da2, dg3, di8), (da2, dg4, di1), (da2, dg4, di2), (da2, dg4, di3), (da2, dg4, di4), (da2, dg4, di5), (da2, dg4, di6), (da2, dg4, di7), (da2, dg4, di8), (da2, dg5, di1), (da2, dg5, di2), (da2, dg5, di3), (da2, dg5, di4), (da2, dg5, di5), (da2, dg5, di6), (da2, dg5, di7), (da2, dg5, di8), (da2, dg6, di1), (da2, dg6, di2), (da2, dg6, di3), (da2, dg6, di4), (da2, dg6, di5), (da2, dg6, di6), (da2, dg6, di7), (da2, dg6, di8), (da2, dg7, di1), (da2, dg7, di2), (da2, dg7, di3), (da2, dg7, di4), (da2, dg7, di5), (da2, dg7, di6), (da2, dg7, di7), (da2, dg7, di8), (da2, dg8, di1), (da2, dg8, di2), (da2, dg8, di3), (da2, dg8, di4), (da2, dg8, di5), (da2, dg8, di6), (da2, dg8, di7), (da2, dg8, di8), (da2, dg9, di1), (da2, dg9, di2), (da2, dg9, di3), (da2, dg9, di4), (da2, dg9, di5), (da2, dg9, di6), (da2, dg9, di7), (da2, dg9, di8), (da3, dg1, di1), (da3, dg1, di2), (da3, dg1, di3), (da3, dg1, di4), (da3, dg1, di5), (da3, dg1, di6), (da3, dg1, di7), (da3, dg1, di8), (da3, dg2, di1), (da3, dg2, di2), (da3, dg2, di3), (da3, dg2, di4), (da3, dg2, di5), (da3, dg2, di6), (da3, dg2, di7), (da3, dg2, di8), (da3, dg3, di1), (da3, dg3, di2), (da3, dg3, di3), (da3, dg3, di4), (da3, dg3, di5), (da3, dg3, di6), (da3, dg3, di7), (da3, dg3, di8), (da3, dg4, di1), (da3, dg4, di2), (da3, dg4, di3), (da3, dg4, di4), (da3, dg4, di5), (da3, dg4, di6), (da3, dg4, di7), (da3, dg4, di8), (da3, dg5, di1), (da3, dg5, di2), (da3, dg5, di3), (da3, dg5, di4), (da3, dg5, di5), (da3, dg5, di6), (da3, dg5, di7), (da3, dg5, di8), (da3, dg6, di1), (da3, dg6, di2), (da3, dg6, di3), (da3, dg6, di4), (da3, dg6, di5), (da3, dg6, di6), (da3, dg6, di7), (da3, dg6, di8), (da3, dg7, di1), (da3, dg7, di2), (da3, dg7, di3), (da3, dg7, di4), (da3, dg7, di5), (da3, dg7, di6), (da3, dg7, di7), (da3, dg7, di8), (da3, dg8, di1), (da3, dg8, di2), (da3, dg8, di3), (da3, dg8, di4), (da3, dg8, di5), (da3, dg8, di6), (da3, dg8, di7), (da3, dg8, di8), (da3, dg9, di1), (da3, dg9, di2), (da3, dg9, di3), (da3, dg9, di4), (da3, dg9, di5), (da3, dg9, di6), (da3, dg9, di7), (da3, dg9, di8)

The following embodiments are examples of the compound (IX) of the present invention.

A compound of the formula (IX-b):

[Chemical Formula 84]

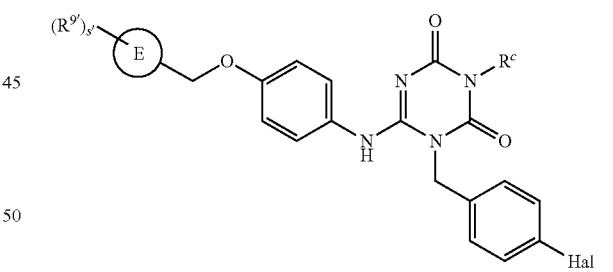

(IX-b)

wherein

Hal is halogen:

$R^c$ is (ea1) a group of the formula:

[Chemical Formula 85]

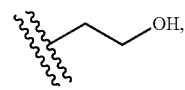

(a1)

-continued
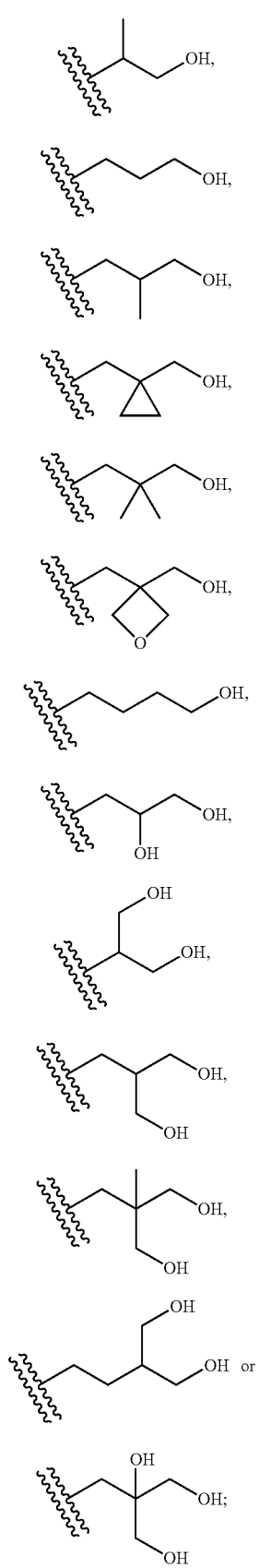
(ea2) a group of the formula:
[Chemical Formula 86]
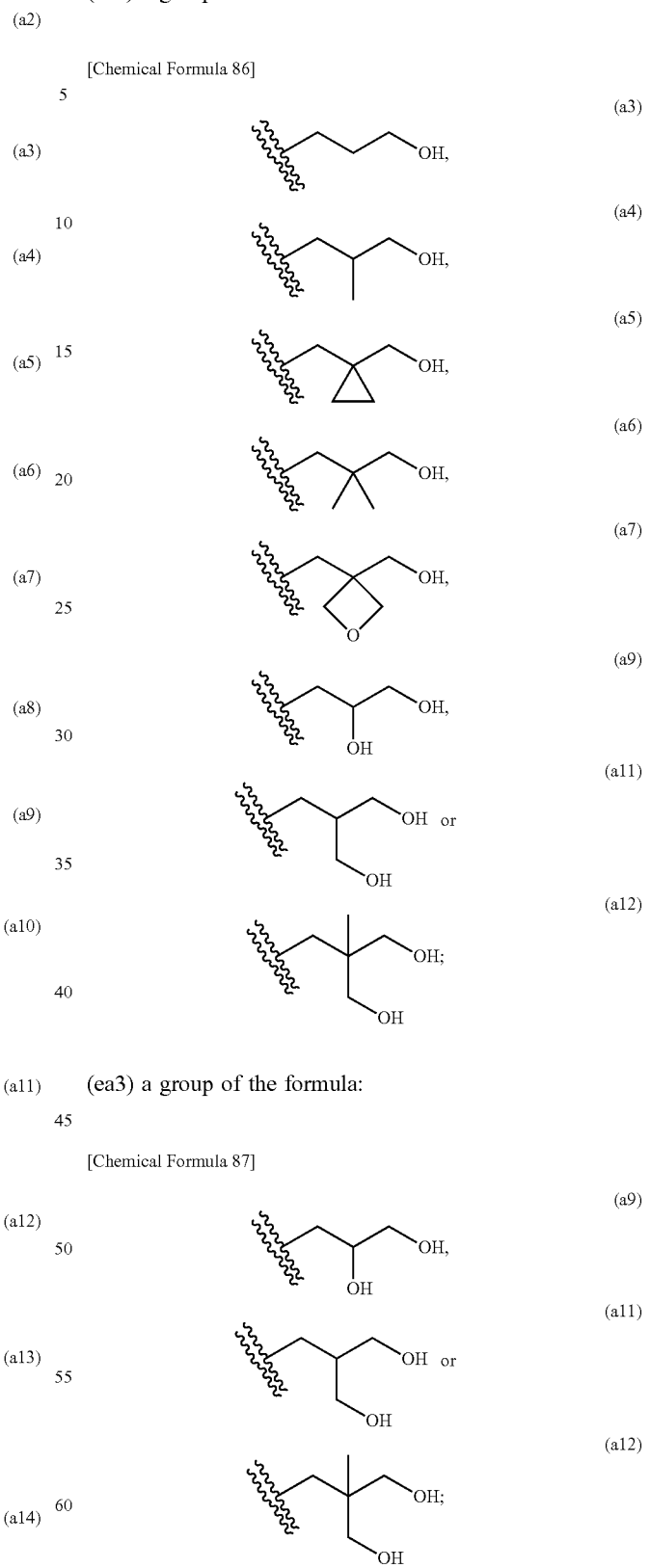
(ea3) a group of the formula:
[Chemical Formula 87]
ring E is
(cg1) a cycloalkane ring or a cycloalkene ring;
(cg2) a cycloalkane ring;

(cg3) a cyclopropane ring;

a group of the formula: $(R^{9'})s'—$ is;

(ej1) s' is 0;

(ej2) s' is 1, and $R^{9'}$ is alkyl substituted with halogen, haloalkyl, cycloalkyl, cycloalkenyl, alkyloxy or alkenyloxy; or unsubstituted alkyl;

(ej3) s' is 1, and $R^{9'}$ is unsubstituted alkyl;

(ej4) s' is 1, and $R^{9'}$ is methyl; ethyl; methyl substituted with halogen, haloalkyloxy, cycloalkyl, cycloalkenyl, alkyloxy or alkenyloxy; or ethyl substituted with halogen, haloalkyloxy, cycloalkyl, cycloalkenyl, alkyloxy or alkenyloxy; and (ej5) s' is 1, and $R^{9'}$ is methyl; ethyl;

or its pharmaceutically acceptable salt or a solvate thereof.

The compound of the formula (IX-b) of the present invention includes the compounds comprising the combination of some or all of options of the above. Specifically, the following combinations are included.

(ea1, eg1, ei1), (ea1, eg1, ei2), (ea1, eg1, ei3), (ea1, eg1, ei4), (ea1, eg1, ei5), (ea1, eg2, ei1), (ea1, eg2, ei2), (ea1, eg2, ei3), (ea1, eg2, ei4), (ea1, eg2, ei5), (ea1, eg3, ei1), (ea1, eg3, ei2), (ea1, eg3, ei3), (ea1, eg3, ei4), (ea1, eg3, ei5), (ea2, eg1, ei1), (ea2, eg1, ei2), (ea2, eg1, ei3), (ea2, eg1, ei4), (ea2, eg1, ei5), (ea2, eg2, ei1), (ea2, eg2, ei2), (ea2, eg2, ei3), (ea2, eg2, ei4), (ea2, eg2, ei5), (ea2, eg3, ei1), (ea2, eg3, ei2), (ea2, eg3, ei3), (ea2, eg3, ei4), (ea2, eg3, ei5), (ea3, eg1, ei1), (ea3, eg1, ei2), (ea3, eg1, ei3), (ea3, eg1, ei4), (ea3, eg1, ei5), (ea3, eg2, ei1), (ea3, eg2, ei2), (ea3, eg2, ei3), (ea3, eg2, ei4), (ea3, eg2, ei5), (ea3, eg3, ei1), (ea3, eg3, ei2), (ea3, eg3, ei3), (ea3, eg3, ei4), (ea3, eg3, ei5)

The following is a general method for synthesizing the compounds of this invention. The starting materials and reagents used for synthesizing these compounds are commercially available or can be manufactured in accordance with a widely known method in this field using commercially available compounds.

For example, the compounds of the general formula (I), general formula general formula (III), general formula (IV), general formula (VII), general formula (VIII) and general formula (IX) described in this invention can be manufactured by the following synthesis route:

[Method A]

[Chemical Formula 88]

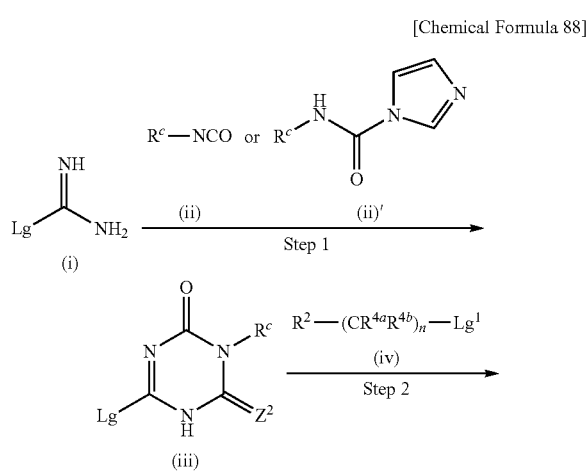

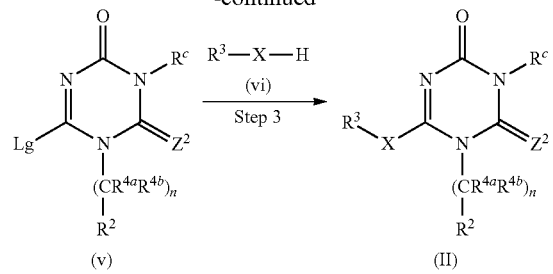

wherein, Lg is a leaving group of the formula:

[Chemical Formula 89]

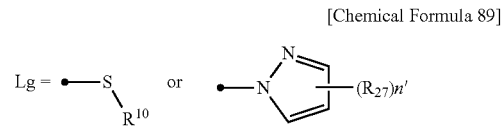

$R^{10}$ is alkyl, $R^{27}$ is alkyl, n' is an integer from 0 to 3, $Lg^1$ is a leaving group and other symbols are as defined above.

(Step 1)

The compound (i) or its hydrochloride or bromate is reacted with isocyanate (ii) or 1-carbamoyl imidazole (ii)' in a solvent, such as N,N-dimethylformamide, N,N-dimethylacetamide, N,N'-dimethylimidazolidinone and dimethylsulfoxide, in the presence of a base, such as DBU, triethylamine and pyridine (preferably DBU) at a temperature between −20 and 50° C., preferably at a temperature between −10° C. and below zero. After that, the compound (iii) can be manufactured by reacting the reactive mixture with a carbonylating or thiocarbonylating agent, such as 1,1'-carbonyldiimidazole, 1,1'-thiocarbonyldiimidazole, phosgene, thiophosgene and triphosgene, etc., and a base, such as DBU, triethylamine or pyridine (preferably DBU) at a temperature between −20 and 50° C., preferably at a temperature between −10° C. and below zero.

(Step 2)

The compound tel can be manufactured by reacting the compound with the compound (iv) in a solvent, such as acetonitrile, acetone, DMF and DMSO, in the presence of a base, such as potassium carbonate and sodium carbonate, at a temperature between 50° C. to reflux, preferably at reflux.

The examples of leaving group include halogen and $—OSO_2(C_tF_{2t+1})$ wherein t is an integer from 1 to 4. As halogen, chloro, iodo and bromo are preferred. As $—OSO_2(C_tF_{2t+1})$ group. —OTf group (trifluoromethanesulfonate) is preferred. This leaving group can also be used in the aforementioned (60').

The base and/or carbonylating agent or thiocarbonylating agent in (Step 1) and (Step 2) can also be used in the aforementioned (60').

The "carbonylating agent" and "thiocarbonylating agent" include a reagent that is used in a reaction where —C (=O) or —C (=S)— is inserted.

(Step 3)

The compound indicated by the general formula (II) can be manufactured by reacting the compound (v) with the compound (vii) in a solvent, such as NMP, DMF and DMSO, or under solvent-free conditions under microwave irradiation at a temperature between 150° C. and 250° C., preferably at a temperature between 200° C. and 230° C., or in a solvent, such as t-butanol, in the presence of an acid, such as acetic acid, at a temperature between 60° C. and 150° C., preferably at a temperature between 80° C. and 120° C.

Using optically active isocyanate (ii) enables to synthesize optically active compound (II).

[Method B]

[Chemical Formula 90]

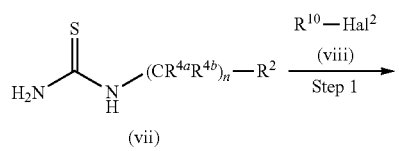

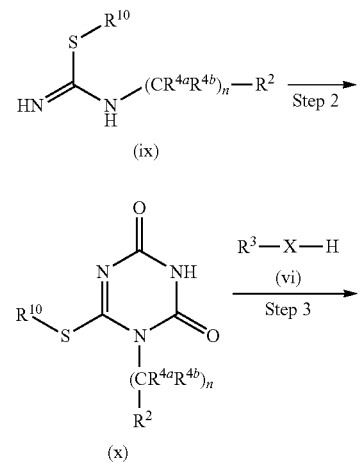

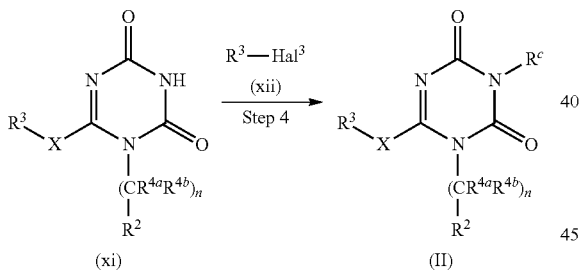

wherein $Hal^2$ and $Hal^3$ are halogen and other symbols are as defined above.

(Step 1)

The compound (ix) can be manufactured by reacting the compound (vii) with alkylating agent (viii), such as methyl iodide and ethyl iodide, in a solvent, such as methanol and ethanol, at a temperature between −40 and 30° C., preferably below zero.

(Step 2)

The compound (x) can be manufactured by reacting the compound (ix) with isocyanate, such as N-(chlorocarbonyl) isocyanate, in a solvent, such as dichloromethane, chloroform, 1,2-dichloroethane, in the presence of a base, such as triethylamine and N,N-diisopropylethylamine, at a temperature between −20 and 30° C., preferably below zero.

(Step 3)

The compound (xi) can be manufactured by reacting the compound (x) with the compound (vi) in a solvent, such as t-butanol, isopropanol, ethanol and acetonitrile, in the presence of an acid, such as acetic acid, formic acid and methanesulfonic acid, at reflux.

(Step 4)

The compound indicated by the general formula (II) can be manufactured by reacting the compound (xi) with the compound (xii) in a solvent, such as DMF and NMP, in the presence of a base, such as potassium t-butoxide and sodium hydride, at a temperature between 40 and 100° C., preferably at a temperature between 50 and 70° C.

Using optically-active compound (xii) enables to synthesise optically-active compound (II).

[Method C]

[Chemical Formula 91]

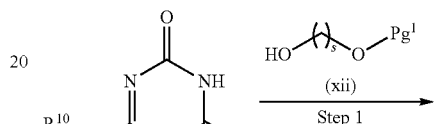

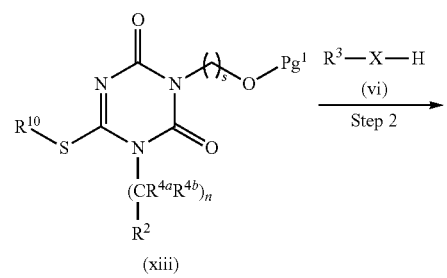

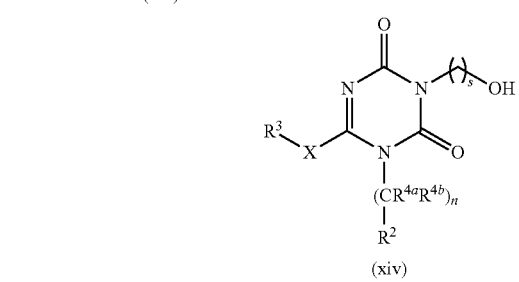

wherein $Pg^2$ is an appropriate hydroxy protecting group, s is an integer from 1 to 4 and other symbols are as defined above.

(Step 1)

The compound (xiii) can be manufactured by reacting a mixture of the compound (x) obtained by the method B, the alcohol (xii) whose one hydroxyl group is protected, such as 2-(tetrahydro-2H-pyran-2-yloxy) ethanol and a solvent, such as THF and dioxane, etc., with triphenylphosphine, and diethyl azodicarboxylate, etc.

(Step 2)

The compound (xiv) can be manufactured by reacting the compound (xiii) with the compound (vi) in the presence of an acid, such as formic acid and acetic acid, etc., at reflux.

[Method D]

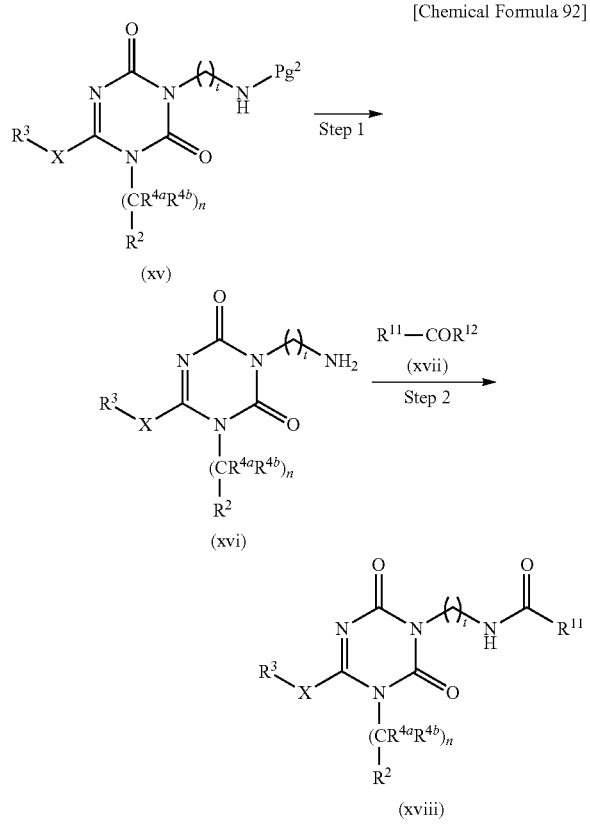

wherein Pg² is an appropriate amino protecting group, R¹¹ is substituted or unsubstituted alkyl, substituted or unsubstituted arylalkyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, substituted or unsubstituted acyl, a substituted or unsubstituted non-aromatic heterocyclic group, substituted or unsubstituted aryl or substituted or unsubstituted heteroaryl, R¹² is hydroxy or halogen, t is an integer from 1 to 4 and other symbols are as defined above.)

(Step 1)
The compound (xvi) can be manufactured by reacting the compound (xv) obtained by the method A or B with acid, such as hydrochloric acid-dioxane solution, hydrochloric acid-methanol, hydrochloric acid-ethyl acetate solution and trifluoroacetic acid, etc.

(Step 2)
The compound (xviii) can be manufactured by reacting the compound (xvi) with the acid halide (xvii) (R¹² is halogen) in a solvent, such as THF and dioxane, etc., in the presence of a base, such as triethylamine and diisopropylethylamine, etc. If necessary, dimethylaminopyridine, etc., can be added.

Alternatively, the compound (xviii) can be manufactured by reacting the compound (xvi) with the carboxylic acid (xvii, R¹² is hydroxy) in a solvent, such as THF and DMF, in the presence of a condensing agent, such as 1-hydroxybenzotriazole and 1-ethyl-3-(3-dimethylaminopropyl) carbodiimide hydrochloride, and a base, such as triethylamine and diisipropylethylamine, etc.

[Method E]

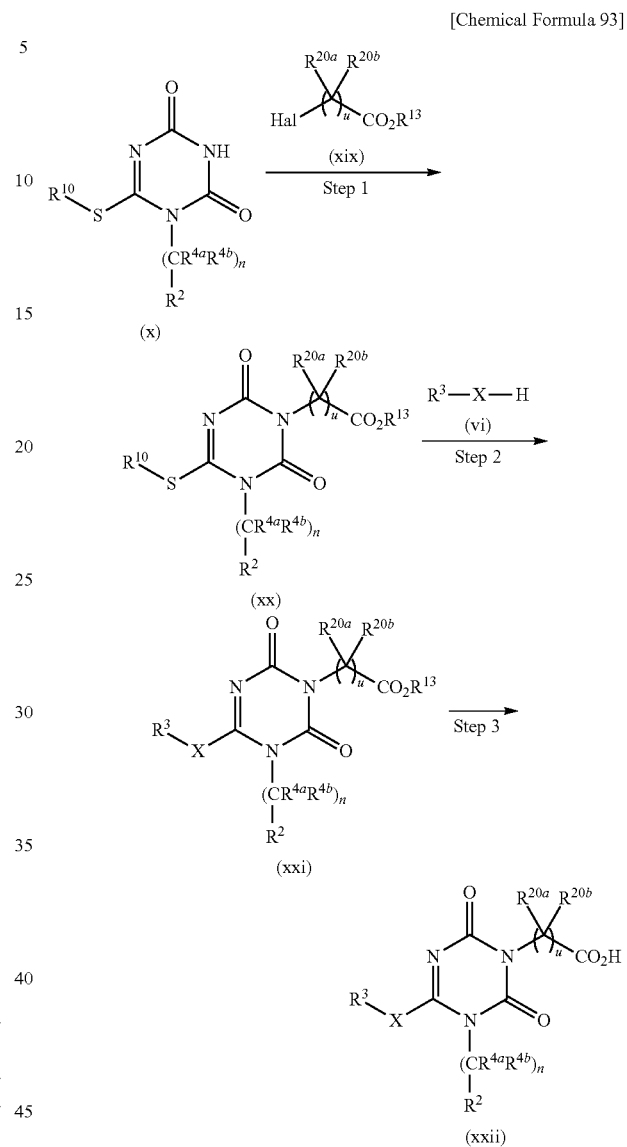

wherein R¹³ is substituted or unsubstituted alkyl, $R^{20a}$ and $R^{20b}$ are hydrogen, halogen, cyano, hydroxy, carboxy, sulfo, substituted or unsubstituted alkyloxy, substituted or unsubstituted alkenyloxy, substituted or unsubstituted alkynyloxy, substituted or unsubstituted cycloalkyl, substituted or unsubstituted cycloalkenyl, a substituted or unsubstituted non-aromatic heterocyclic group, substituted or unsubstituted aryl, substituted or unsubstituted heteroaryl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted amino, substituted or unsubstituted imino, substituted or unsubstituted guanidyl or $R^{20a}$ and $R^{20b}$ are taken together to form oxo or thioxo, u is an integer from 1 to 4, and other symbols are as defined above.

(Step 1)
The compound (xx) can be manufactured by reacting the compound (x) obtained by the method B with the compound (xix) in a solvent, such as DMF, NMP and THF, in the presence of a base, such as DBU, potassium t-butoxide and sodium hydride, at a temperature between 0 and 80 20 C., preferably at a temperature between 30 and 50° C.
(Step 2)
The compound (xxi) can be manufactured by reacting the compound (xx) with the compound (vi) in a solvent such as t-butanol, isopropanol, ethanol and acetonitrile in the presence of an acid such as formic acid, acetic acid and methanesulfonic acid, etc., at reflux.
(Step 3)
The compound (xxii) can be manufactured by reacting the compound (xxi) with a solution, such as lithium hydroxide aqueous solution, sodium hydroxide aqueous solution and potassium hydroxide aqueous solution, in a solvent, such as methanol and ethanol, or in a mixture of such solvent and a solvent, such as THF and dioxane, etc.

[Method F]

[Chemical Formula 94]

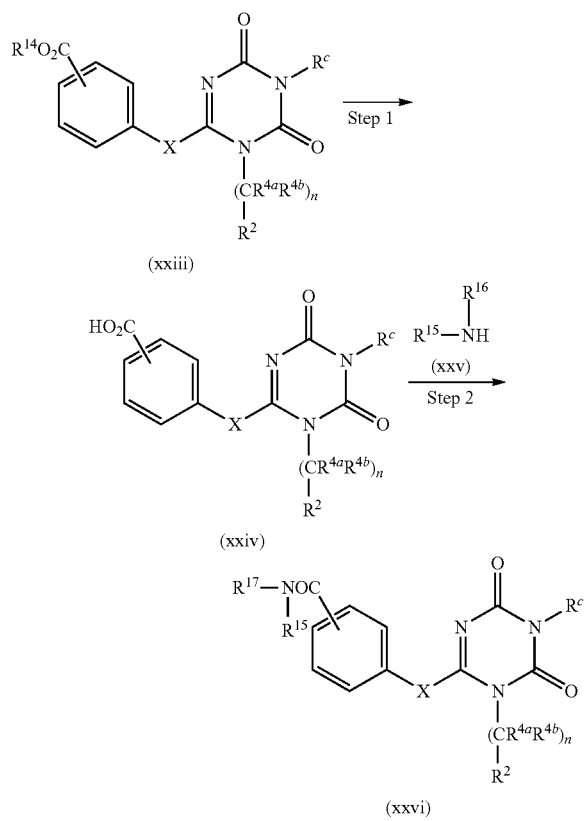

wherein $R^{14}$ is substituted or unsubstituted alkyl, $R^{15}$ and $R^{16}$ are each independently substituted or unsubstituted alkyl, substituted or unsubstituted arylalklyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, substituted or unsubstituted acyl, a substituted or unsubstituted non-aromatic heterocyclic group, substituted or unsubstituted aryl or substituted or unsubstituted heteroaryl, u is an integer from 1 to 4 and other symbols are as defined above.
(Step 1)
The compound (xxiv) can be manufactured reacting the compound (xxiii) obtained by the method A or B with a solution, such as lithium hydroxide aqueous solution, sodium hydroxide aqueous solution and potassium hydroxide aqueous solution, in a solvent, such as methanol and ethanol, or in a mixture of such solvent and a solvent, such as dioxane and THF, etc.
(Step 2)
The compound (xxvi) can be manufactured by reacting the compound (xxiv) with the compound (xxv) in a solvent, such THF, DMF and NMP, in the prosence of a condensing agent, such as 1-hydroxybenzotriazole, HOAt, 1-ethyl-3-(3-dimethylaminopropyl) carbodiimide hydrochloride, HATU and PyBOP, and a base, such as triethylamine and diisipropylethylamine, etc.

[Method G]

[Chemical Formula 95]

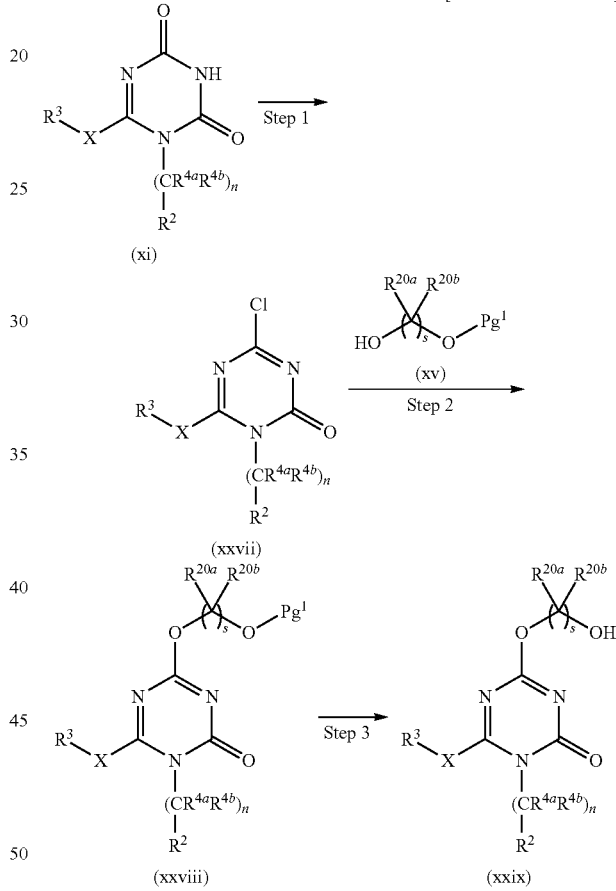

wherein $Pg^1$ is an appropriate hydroxy protecting group and other symbols are as defined above.
(Step 1)
The compound (xxvii) can be manufactured by reacting the compound (xi) obtained by the method B with a halogenating agent, swift as phosphorous oxychloride and phosphorous oxybromide, under solvent-free conditions or in a solvent, such as toluene and tetrahydrofuran, at a temperature between 0 and 100° C., preferably at a temperature between 40 and 60° C.
(Step 2)
The compound (xxviii) can be manufactured by reacting a mixture of the alcohol (xv) whose one hydroxyl group is protected, such as 2-(tetrahydro-2H-pyran-2-yloxy) ethanol, and a solvent, such as THF, dioxane and DMF, with the compound (xv) after adding a base, such as sodium hydride and potassium t-butoxide.

(Step 3)

The compound (xxix) can be manufactured by reacting the compound (xxviii) with an acid, such as hydrochloric acid, p-toluenesulfonic acid or its hydrate and pyridine p-toluenesulfonate, in a solvent, such as methanol, etc.

[Chemical Formula 96]

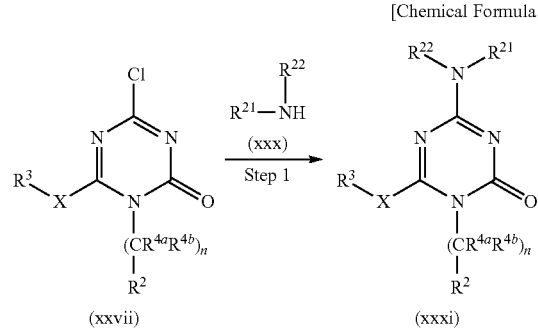

[Chemical Formula 96]

wherein $R^{21}$ is substituted or unsubstituted alkyl, substituted or unsubstituted arylalkyl, substituted or unsubstituted heteroarylalkyl, substituted or unsubstituted alkenyl, substituted or unsubstituted alkynyl, substituted or unsubstituted cycloalkyl, substituted or unsubstituted cycloalkenyl, substituted or unsubstituted acyl, a substituted or unsubstituted non-aromatic heterocyclic group, substituted or unsubstituted aryl or substituted or unsubstituted heteroaryl, $R^{22}$ is hydrogen, substituted or unsubstituted alkyl or substituted or unsubstituted acyl, and other symbols are as defined above.

(Step 1)

The compound (xxxi) can be manufactured by reacting the compound (xxvii) obtained by the method G with the compound (xxx) in a solvent, such as THF and dioxane, etc.

[Method 1]

[Chemical Formula 97]

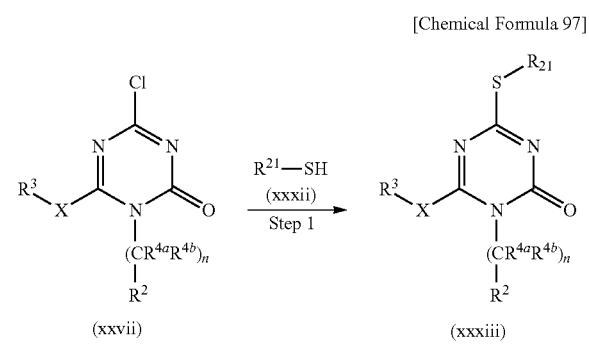

wherein the symbols in the formula are as defined above.

(Step 1)

The compound (xxxiii) can be manufactured by reacting the compound (xxvii) obtainod by the method G with the compound (xxxii) in a solvent, such as THF and dioxane after adding a base, such as sodium hydride, etc.

[Method J]

[Chemical Formula 98]

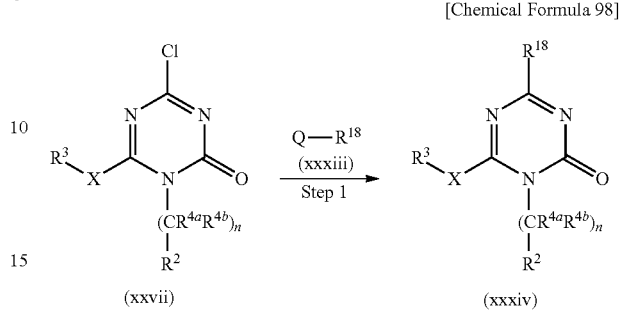

wherein $R^{18}$ is substituted or unsubstituted alkyl, substituted or unsubstituted alkenyl or substituted or unsubstituted alkynyl, Q is dihydroxyboran, dialkoxyboran or dialkylboran,

[Chemical Formula 99]

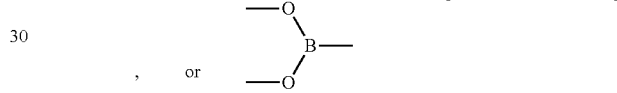

and other symbols are as defined above.

The compound (xxxiv) can be manufactured by reacting compound (xxvii) obtained by the method G with the compound (xxxiii) in a solvent, such as THF and dioxane, in the presence of a palladium catalyst, and a solution, such as potassium carbonate, cesium carbonate and sodium carbonate aqueous solution, etc., at a temperature between 50° C. and reflux, preferably at reflux, or under microwave irradiation at a temperature of 120 and 200° C., preferably at a temperature between 30 and 150° C.

[Method K]

[Chemical Formula 100]

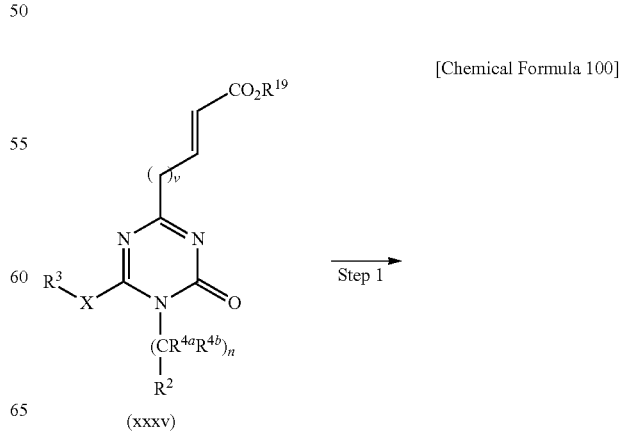

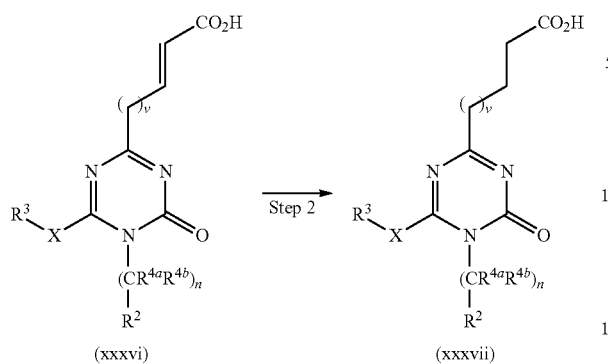

wherein $R^{15}$ is substituted or unsubstituted alkyl, v is an integer from 0 to 4 and other symbols are as defined above.

The compound (xxxvi) can be manufactured by hydrolyzing the compound (xxxv) using a mixture of an ethers solvent, such as dioxane, THF and DME, etc., an alcohols solvent, such as ethanol and methanol, or a solvent, such as DMF, DMA, DMSO and NMP, and water, as well as using a base, such as sodium hydroxide and lithium hydroxide. Although the preferable reaction temperature is room temperature, it can be increased if the reaction proceeds slowly.

(Step 2)

The compound (xxxvii) can be obtained by dissolving the compound (xxxvi) in an alcohols solvent, such as methanol and ethanol, and performing catalytic reduction using a hydrogenation reactor (such as H-Cube [10% Pt-C, H2=1 atm]) or a metallic catalyst, such as palladium-carbon, platinum oxide and chlorotris (triphenylphosphine) rodiumu (I), etc.

[Method L]

[Chemical Formula 101]

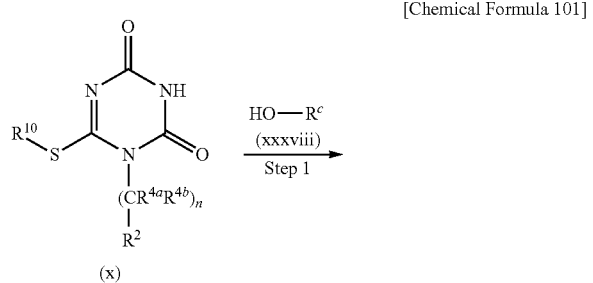

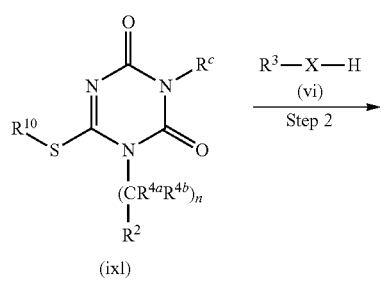

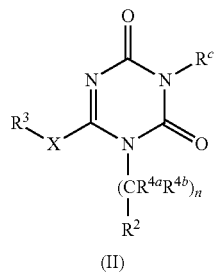

wherein the symbols in the formula are as defined above.

(Step 1)

The compound (ix1) can be manufactured by reacting a mixture of the compound (x) obtained by the method B, the alcohol (xxxviii) and a solvent, such as THF and dioxane, with triphenylphosphine, etc., and diethyl azodicarboxylate, etc.

(Step 2)

The compound (II) can be manufactured by reacting the compound (ix1) the compound (vi) in the presence of an acid, such as formic acid and acetic acid, at reflux.

Using the optically-active alcohol (xxxviii) enables to synthesize the optically-active compound (II).

The alcohol used as an intermediate (xxxviii) is commercially available or can be manufactured according to a method specified in the following documents:

Tetrahedron (1993), 49(11), 2325-44.

Chemical Communications (2008), (47), 6408-6410.

Tetrahedron (1990), 40(24), 8207-28.

Synlett (1994), (3), 199-200.

Bulletin of the Chemical Society of Japan (1994), 67(8), 2244-7

Canadian Journal of Chemistry (1996), 74, 1731-1737

Chemistry—A European Journal (2010), 16(2), 577-587

Bioorganic & Medicinal Chemistry Letters (2009), 19(21), 6196-6199

Chemische Berichte (1985), 118(10), 3966-79.

Tetrahedron: Asymmetry (1992), 3(4), 515-16.

Organic Letters (1999), 1(6), 957-959.

Chimia (1986), 40(5), 172-3.

[Method M]

[Chemical Formula 102]

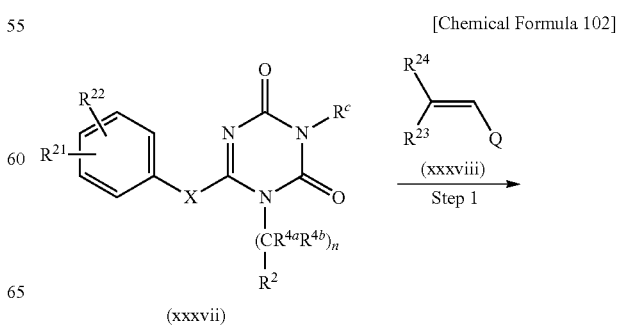

-continued

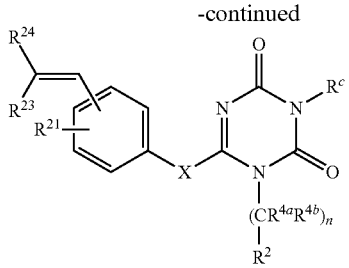

(xxxix)

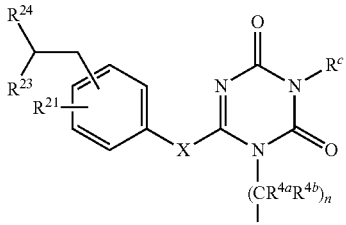

(Xl)

wherein $R^{21}$ is hydrogen, substituted or unsubstituted alkyl or substituted or unsubstituted alkoxy, etc., $R^{22}$ is bromo or iodo, $R^{23}$ and $R^{24}$ are each independently substituted or unsubstituted alkyl, substituted or unsubstituted arylalkyl, substituted or unsubstituted heteroarylalkyl, substituted or unsubstituted cycloalkyl, a substituted or unsubstituted non-aromatic heterocyclic group, substituted or unsubstituted aryl or substituted or unsubstituted heteroaryl, and other symbols are as defined above.

(Step 1)

The compound (xxxix) can be manufactured by reacting the compound (xxxvii) obtained by the method from A to F or L with the compound (xxxviii) in a solvent, such as THF and dioxane, in the presence of a palladium catalyst and a solution, such as potassium carbonate, cesium carbonate and sodium carbonate aqueous solution, etc., at a temperature between 50° C. and reflux, preferably at reflux, or under microwave irradiation at a temperature between 120 and 200° C., preferably at a temperature between 130 and 150° C.

(Step 2)

The compound (xl) can be obtained by dissolving the compound (xxxix) in an alcohols solvent, such as methanol and ethanol, and performing catalytic reduction using a hydrogenation reactor (such as H-Cube (10% Pt-C, H2=1 atm)) or a metallic catalyst, such as palladium-carbon, platinum oxide, chlorotris (triphenylphosphine) rhodium (I), etc.

[Method N]

[Chemical Formula 103]

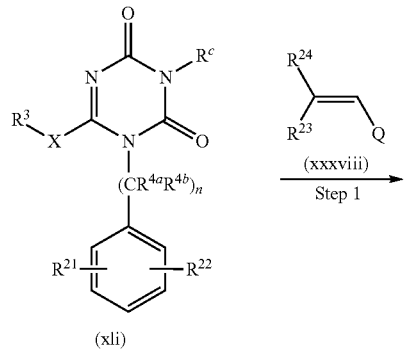

-continued

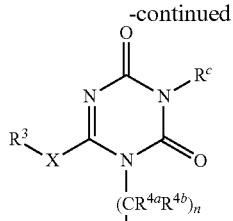

(xlii)

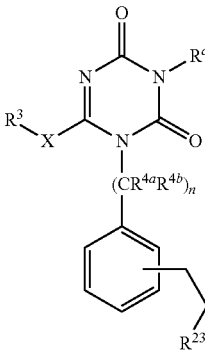

(xliii)

wherein the symbols in the formula are as defined above.

(Step 1)

The compound (xlii) can be manufactured by reacting the compound (xli) obtained by the method from A to F or L with the compound (xxxviii) in a solvent, such as THF and dioxane, in the presence of a palladium catalyst and a solution, such as potassium carbonate, cesium carbonate and sodium carbonate aqueous solution, etc., at a temperature between 50° C. and reflux, preferably at reflux, or under microwave irradiation at a temperature between 120 and 200° C., preferably at a temperature between 130 and 150° C.

(Step 2)

The compound (xliii) can be obtained by dissolving the compound (xlii) in an alcohols solvent, such as methanol and ethanol, and performing catalytic reduction using a hydrogenation reactor (such as H-Cube (10% Pt-C, H2=1 atm)) or a metallic catalyst, such as palladium-carbon, platinum oxide, chlorotris (triphenylphosphine) rhodium (I), etc.

[Method O]

[Chemical Formula 104]

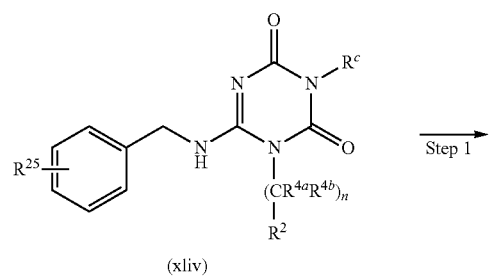

(xliv)

-continued

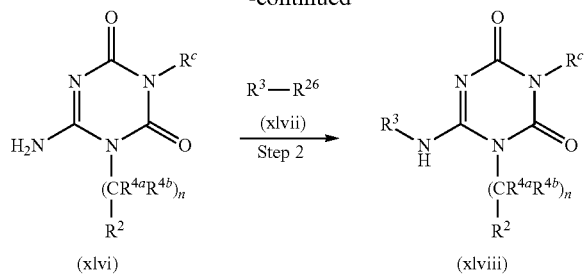

wherein $R^{25}$ is substituted or unsubstituted alkyl or substituted or unsubstituted alkoxy, $R^{26}$ is bromo or iodo, and other symbols are as defined above.

(Step 1)

The compound (xlvi) can be obtained from the compound (xlvi) in the presence of Lewis acid or trifluoroacetic acid, etc., under solvent-free conditions or in an appropriate solvent at a temperature between 0° C. and reflux.

(Step 2)

The compound (xlviii) can be manufactured by reacting the compound (xlvi) with the compound (xlvii) in a solvent, such as THF and dioxane, in the presence of a palladium catalyst and a solution, such as potassium carbonate, cesium carbonate and sodium carbonate aqueous solution, etc., at a temperature between 50° C. and reflux, preferably at reflux, or under microwave irradiation at a temperature of 120 and 200° C., preferably at a temperature between 130 and 150° C.

[Method P]

[Chemical Formula 105]

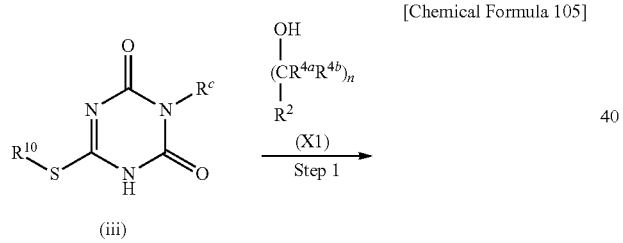

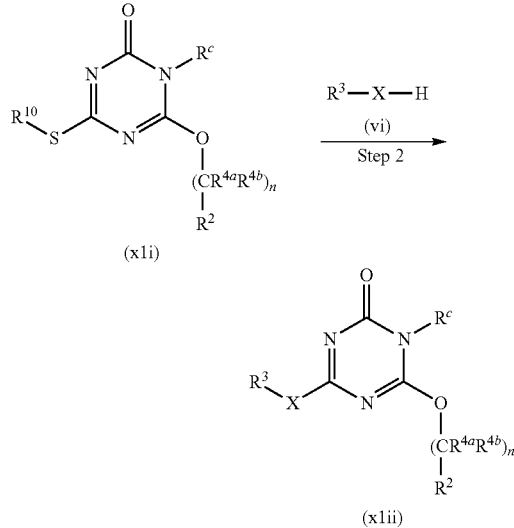

wherein the symbols in the formula are as defined above.

(Step 1)

The compound (xli) can be manufactured by reacting a mixture of the compound (iii) obtained by the method A, the alcohol (x1) and a solvent, such as THF and dioxane, with triphenylphospine, etc., and diethyl azodicarboxylate, etc.

(Step 2)

The compound (xli) can be manufactured by reacting be compound (xli) with the compound (vi) in the presence of formic acid and acetic acid, etc., at reflux.

[Method Q]

[Chemical formula 106]

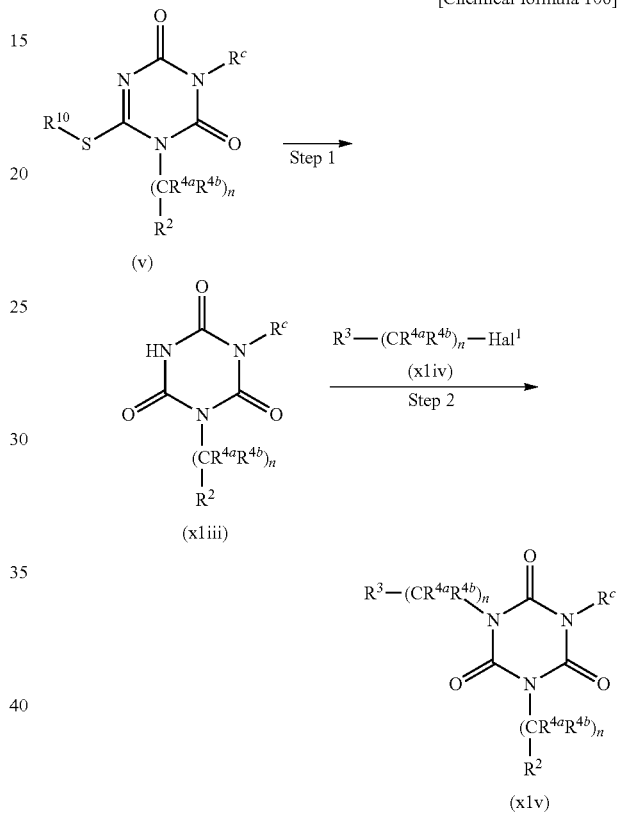

wherein the symbols in the formula are as defined above.

(Step 1)

The compound (xliii) can be manufactured by reacting the compound (v) obtained by the method A in a solvent, such as water, acetic acid and methanol, in the presence of an oxidation agent, such as hydrogen peroxide water and MCPBA, at a temperature between −20 and 100° C., preferably at room temperature.

(Step 2)

The compound (xlv) can be manufactured by reacting the compound (xliii) with the compound (xliv) in a solvent, such as acetonitrile, acetone, DMF and DMSO, in the presence of a base, such as potassium carbonate and sodium carbonate, at a temperature between 50° C. and reflux, preferably at reflux.

The compounds of this invention (I) are not limited to a specific isomer but include all possible isomers and racemates. For example, they include a tautomer as shown below. The compounds indicated by the formula (VIII), formula (IX) and formula (VII), etc., also include similar tautomers.

[Chemical Formula 107]

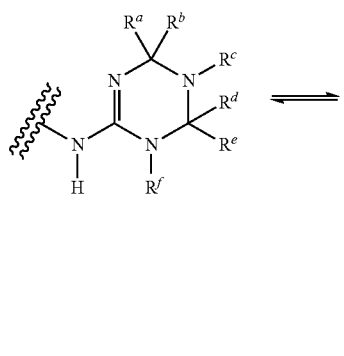

In addition, one or more hydrogen atoms, carbon atoms or other atoms of the compound of the formula (I), formula (VIII), formula (IX), formula (VII) and the like can be replaced by an isotope of the hydrogen atom, carbon atom or other atoms. Compounds of the formula (I), formula (VIII), formula (IX), formula (VII) and the like include all radiolabeled forms of compounds of the formula (I), formula (VIII), formula (IX), formula (VII) and the like. The "radiolabeled," "radiolabeled form" and the like of the compound of the formula (I), formula (VIII), formula (IX), formula (VII) and the like are encompassed by the present invention and useful as a research and/or diagnostic tool in metabolism pharmacokinetic studies and in binding assays. It is also useful for a medicament.

Examples of isotopes that can be incorporated into the compound of the formula (I), formula (VIII), formula (IX), formula (VII) and the like of the invention include isotopes of hydrogen, carbon, nitrogen, oxygen, phosphorous, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$, respectively. Radiolabeled compounds of the present invention can be prepared by methods known the art. For example, tritiated compounds of formula (I) can be prepared by introducing tritium into the particular compound of formula (I), for example, by catalytic dehalogenation with tritium. This method may include reacting a suitably halogen-substituted precursor of a compound of formula (I), formula (VIII), formula (IX), formula (VII) and the like with tritium gas in the presence of a suitable catalyst such as Pd/C, in the presence or absence of a base. Other suitable methods for preparing tritiated compounds can be found in *Isotopes in the Physical and Biomedical Sciences, Vol. 1, Labeled Compounds (Part A)* Chapter 6, (1987). $^{14}C$-labeled compounds can be prepared by employing starting materials having a $^{14}C$ carbon.

The compounds of the above formula (I), formula (VIII), formula (IX), formula (VII) and the like or its salt can be converted into hydrate or solvate thereof by known methods. Examples of suitable solvates are solvate with acetone, 2-butanol, 2-propanol, ethanol, ethyl acetate, tetrahydrofuran, diethyl ether or the like. For example, it includes a non-toxic and water-soluble hydrate or solvate such as a solvate with ethanol.

As pharmaceutically acceptable salt of the compound of the formula (I), formula (VIII), formula (IX), formula (VII) and the like, examples include salts with alkaline metals (e.g. lithium, sodium and potassium), alkaline earth metals (e.g., calcium and barium), magnesium, transition metal (e.g., zinc and iron), ammonia, organic bases (e.g. trimethylamine, triethylamine, dicyclohexylamine, ethanolamine, diethanolamine, triethanolamine, megulmine, diethanolamine, ethylenediamine, pyridine, picoline, quinoline), and amino acids, and salts with inorganic acids (e.g. hydrochloric acid, sulfuric acid, nitric acid, carbonic acid, hydrobromic acid, phosphoric acid and hydroidic acid) and organic acids (e.g. formic acid, acetic acid, propionic trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid and ethanesulfonic acid). Especially preferable are salts with hydrochloric acid, sulfuric acid, phosphoric acid, tartaric acid, or methanesulfonic acid. These salts may be formed by usual methods.

The compound of the formula (I), formula (VIII), formula (IX), formula (VII) and the like or its pharmaceutically acceptable salt may form solvate such as hydrate, and/or crystalline polymorphism, and the present invention also includes such various kinds of solvate and crystalline polymorphism. The "solvate" includes a compound of the formula (I), formula (VIII), formula (IX), formula (VII) and the like which coordinate arbitrary number of solvent molecules such as water molecules. The compound of the formula (I), formula (VIII), formula (IX), formula (VII) and the like or its pharmaceutically acceptable salt can adhere water or form hydrate by absorbing water molecules after leaving in the atmosphere. Moreover, the compound of the formula (I), formula (VIII), formula (IX), formula (VII) and the like or its pharmaceutically acceptable salt can form the crystalline polymorphism by recrystallization.

The compound of the formula (I), formula (VIII), formula (IX), formula (VII) and the like of the present invention or its pharmaceutically acceptable salt may form prodrug, and the present invention also includes such various kinds of prodrug. Prodrug is a derivative of the compound of the present invention having a group which can be chemically or metabolically decomposed and the one which becomes a pharmaceutically active compound of the present invention by solvolysis or physiological conditions in vivo. Prodrug includes a compound which converts into the compound of the formula (I), formula (VIII), formula (IX), formula (VII) and the like by enzymatical oxidation, reduction, hydrolysis or the like under physiological conditions in a living body, and a compound which converts into the compound of the formula (I), formula (VIII), formula (IX), formula (VII) and the like by hydrolyzing by stomach acid or the like. The method of selecting suitable prodrug derivatives and the method of manufacturing them are disclosed in Design of Prodrugs, Elsevier, and Amsterdam 1985. Prodrug itself may possess the activity.

When the compound of the formula (I), formula (VIII), formula (IIX), formula (VII) and the like or its pharmaceutically acceptable salt has a hydroxy group, examples of the prodrug includes acyloxy derivatives and sulfonyloxy derivatives which can be manufactured by reacting a compound having a hydroxy group with a suitable acid halide, suitable acid anhydride, suitable sulfonyl chloride, suitable sulfonylanhydride and mixed anhydride. For example, $CH_3COO-$, $C_2H_5COO-$, t—$BuCOO-$, $C_{18}H_{31}COO-$, $PhCOO-$, (m—$NaOOCPh$)$COO-$, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p—$CH_3$—O—$PhSO_3-$, $PhSO_3-$, and p—$CH_3PhSO_3-$ are exemplified.

The compound of the general formula (I), formula (VIII), formula (IX), formula (VII) and the like has an antagonistic effect on P2X$_3$ and/or P2X$_{2/3}$ receptor, and therefore, is useful as a therapeutic agent for diseases associated with a P2X$_3$ and/or P2X$_{2/3}$ receptor. Since P2X$_3$ and/or P2X$_{2/3}$ receptor is believed to associate with pain and diseases in urinary system (Nature 407, 26, 1011-1015 (2000), Nature, Vol. 407, No. 26, 1015-1017 (2000), Non-Patent Document 1, Non-Patent Document 2, etc.), the compound of the invention is useful in the treatment, alleviation of symptoms or prevention of diseases, such as for example, pain associated with rheumatoid arthritis, pain associated with osteoarthritis, headache, migraine, orofacial pain, toothache, glossagra, pain associated with temporomandibular arthrosis, trigeminal neuralgia, shoulder pain, pain associated with hernia of intervertebral disk, pain associated with cervical spondylosis deformans, pain associated with spinal canal stenosis, pain associated with thoracic outlet syndrome, pain associated with traumatic brachial plexus injury syndrome, pain associated with shoulder-hand syndrome, pain associated with whiplash injury, chest pain, abdominal pain, colic pain, pain associated with cholelithiasis, pain associated with pancreatitis, pain associated with urinary calculosis, pain associated with irritable bowel syndrome, lumbar backache, sciatica, pain associated with bone fracture, pain associated with osteoporosis, joint pain, pain associated with gout, pain associated with cauda equina syndrome, pain associated with ankylosing spondylitis, sore muscle, pain associated with painful spasm, pain associated with myofascial pain syndrome, pain associated with fibromyalgia syndrome, complex regional pain syndrome, pain associated with arteriosclerosis obliterans, pain associated with Buerger's disease, pain associated with Raynaud's phenomenon, pain associated with zoster, causalgic pain, pain associated with entrapment neuropathy, pain associated with carpal canal syndrome, pain associated with diabetes, pain associated with Guillain-Barre syndrome, pain associated with Hansen's disease, pain associated with drug therapy, pain associated with radiation therapy, pain associated with cord injury, pain associated with syringomyelia, pain associated with stroke, thalamic pain, pain associated with deafferentation, sympathetically-maintained pain, ABC syndrome, multiple sclerosis, pain associated with skin disease, cancer pain, postoperative pain, pain associated with injury, pain associated with gangrene, pain associated with somatoform disorder, pain associated with somatization disorder, pain associated with depression, pain associated with Parkinson's disease, knee joint pain, pain associated with arthritis, neuropathic pain such as menstrual pain, intermenstrual pain, labor pain, etc., inflammatory pain, nociceptive pain, psychogenic pain, pain of bladder such as overactive bladder, blader inflammation etc., incontinence, pollakiuria, urinary urgency, cystatrophia, prostatic hypertrophy, prostatitis, prostate pain, detrusor hyperreflesxia, urination disorder, nervous pollakiuria, chronic prostatitis, chronic cystitis, etc.

"A pharmaceutical composition having an improving effect of urination disorder" includes "a pharmaceutical composition for treating overactive bladder", "a pharmaceutical composition for treating interstitial bladder cystitis" and the like.

The compound of the present invention or the pharmaceutical composition of the present invention can be a drug with reduced side-effect such as effect on motor function because it has a high affinity for ATP receptor, especially P2X$_3$ receptor, and also has high subtype selectivity and high selectivity for other receptors. Also, the compound encompassed by the present invention or the pharmaceutical composition encompassed by the present invention is advantageous because of its high P2X3 receptor inhibitor activity in the presence of RSA, high metabolic stability, high oral absorption, good bioavailability low clearance, long half-life, prolonged duration of action, low activity of hepatic enzyme inhibition, high unbound fraction in serum and/or high safety etc.

In another embodiment, the present invention provides a pharmaceutical composition comprising an effective amount of the compound of the present invention, in combination with a pharmaceutically acceptable carrier.

For use of the compound of the present invention as a medicament, a pharmaceutical composition can be prepared according to conventional methods, using pharmaceutically acceptable carriers well-known in the art, such as excipients, binders, disintegrants, lubricants, colourants, flavors, surfactants, etc.

For the pharmaceutical composition of the present invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage form can be formulated according to methods well-known in the art.

The amount of the present compound in a formulation can vary depending on its dosage form, route for administration, dosing regimen, etc.

Means for administration of the present pharmaceutical composition may be selected depending on dosage form, patient's age, sex, body weight, severity of the disease, and other factors, etc., and route for administration can be selected from various routes such as oral, subcutaneous, transdermal, rectal, intranasal, buccal, etc.

Dose of the present compound in the present pharmaceutical composition can be determined depending on the choice of route for administration, patient's age, sex, body weight, severity of the disease, the compound to be administered, and other factors, etc., and can be generally from 0.05 to 1000 mg/kg/day, preferably from 0.1 to 10 mg/kg/day, for oral administration to adults. For parenteral administration, dose can vary widely depending on its route but generally from 0.005 to 100 mg/kg/day, preferably from 0.01 to 1 mg/kg/day. Such pharmaceutical composition of the present invention may be administered once a day or in several times at a divided dosage in a day.

In some embodiments of the present compounds, there is provided compounds of the following general formula (V) and the general formula (VI) having the following groups are provided:

[Chemical Formula 108]

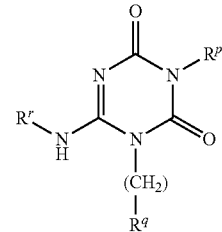

(V)

-continued

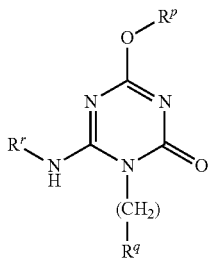

(VI)

wherein $R^p$, $R^q$, and $R^r$ are selected from the following Tables 1 to 3.

TABLE 1

| | Rp |
|---|---|
| Rp1 | HO(CH2)2 |
| Rp2 | HO(CH2)3 |
| Rp3 | (HOCH2)2CHCH2 |
| Rp4 | (HOCH2)2C(Me)CH2 |
| Rp5 | HOCH2CH(OH)CH2 |
| Rp6 | HOCO(CH2)2 |
| Rp7 | HOCOC(Me)2CH2 |
| Rp8 | HOCOC(—CH2CH2—)CH2 |
| Rp9 | HOCOCH(Me)CH2 |
| Rp10 | HOCOCH(Me)CH(Me) |
| Rp11 | HOCOC(CH2)3 |

TABLE 2

| | Rq |
|---|---|
| Rq1 | 4-Me—Ph |
| Rq2 | 4-Et—Ph |
| Rq3 | 4-Cl—Ph |
| Rq4 | 4-Br—Ph |
| Rq5 | cyclohexyl |

TABLE 3

| | Rr | | Rr |
|---|---|---|---|
| Rr1 | 2-Me-benzothiazol-6-yl | Rr20 | 2-Piperidine-5-pyridyl |
| Rr2 | 2-Me-benzothiazol-5-yl | Rr21 | 5-c-PrCH2O-2-pyridyl |
| Rr3 | 2-Me-benzimidazol-6-yl | Rr22 | 5-c-BuO-2-pyridyl |
| Rr4 | 2-Me-benthoiphen-5-yl | Rr23 | 5-PhO-2-pyridyl |
| Rr5 | 3-Me-benzisoxazol-6-yl | Rr24 | 5-Piperidino-2-pyridyl |
| Rr6 | 3-Me-2H-1,4-benzoxazin-7-yl | Rr25 | 2-c-BuO-3-Cl-5-pyridyl |
| Rr7 | 7-Me-1,8-naphthyridin-3-yl | Rr26 | 2-c-BuO-3-Me-5-pyridyl |
| Rr8 | 7-Me-quinolin-3-yl | Rr27 | 2-c-PentylO-3-Cl-5-pyridyl |
| Rr9 | 2-Me-quinazolin-6-yl | Rr28 | 2-c-PentylO-3-Me-5-pyridyl |
| Rr10 | 4-c-PrO—Ph | Rr29 | 2-PhO-3-Cl-5-pyridyl |
| Rr11 | 3-Me-4-c-PrO—Ph | Rr30 | 3-Me-4-i-PrCONH—Ph |
| Rr12 | 3-Cl-4-c-PrO—Ph | Rr31 | 3-Cl-4-i-PrCONH—Ph |
| Rr13 | 4-c-PrCH2—Ph | Rr32 | 3-Me-4-i-PrNHCO—Ph |
| Rr14 | 3-Me-4-c-PrCH2—Ph | Rr33 | 3-Cl-4-i-PrNHCO—Ph |
| Rr15 | 3-Cl-4-c-PrCH2—Ph | Rr34 | 3-Me-4-i-PrSO2NH—Ph |
| Rr16 | 4-c-BuCH2—Ph | Rr35 | 3-Cl-4-i-PrSO2NH—Ph |
| Rr17 | 3-MeO-4-c-BuCH2—Ph | Rr36 | 3-Me-4-i-PrNHSO2—Ph |
| Rr18 | 2-c-PrCH2O-5-pyridyl | Rr37 | 3-Cl-4-i-PrNHSO2—Ph |
| Rr19 | 2-PhO-5-pyridyl | | |

The combination of Rp, Rq and Rr, i.e., (Rp, Rq, Rr), is any one of the following combinations:
(Rp, Rq, Rr)=
(Rp1,Rq1,Rr1),(Rp1,Rq1,Rr2),(Rp1,Rq1,Rr3),(Rp1, Rq1,Rr4),(Rp1,Rq1,Rr5),(Rp1,Rq1,Rr6), (Rp1,Rq1,Rr7),(Rp1, Rq1,Rr8),(Rp1,Rq1,Rr9),(Rp1,Rq1,Rr10),(Rp1,Rq1,Rr11), (Rp1,Rq1,Rr12), (Rp1,Rq1,Rr13),(Rp1,Rq1,Rr14),(Rp1, Rq1,Rr15),(Rp1,Rq1,Rr16),(Rp1,Rq1,Rr17),(Rp1,Rq1, Rr18),(Rp1,Rq1,Rr19),(Rp1,Rq1,Rr20),(Rp1,Rq1,Rr21), (Rp1,Rq1,Rr22),(Rp1,Rq1,Rr23),(Rp1,Rq1,Rr24),(Rp1, Rq1,Rr25),(Rp1,Rq1,Rr26),(Rp1,Rq1,Rr27),(Rp1,Rq1, Rr28),(Rp1,Rq1,Rr29),(Rp1,Rq1,Rr30),(Rp1,Rq1,Rr31), (Rp1,Rq1,Rr32),(Rp1,Rq1,Rr33),(Rp1,Rq1,Rr34), (Rp1, Rq1,Rr35),(Rp1,Rq1,Rr36),(Rp1,Rq1,Rr37),(Rp1,Rq2, Rr1),(Rp1,Rq2,Rr2),(Rp1,Rq2,Rr3),(Rp1,Rq2,Rr4),(Rp1, Rq2,Rr5),(Rp1,Rq2,Rr6),(Rp1,Rq2,Rr7),(Rp1,Rq2,Rr8), (Rp1,Rq2,Rr9),(Rp1,Rq2,Rr10),(Rp1,Rq2,Rr11),(Rp1,Rq2, Rr12),(Rp1,Rq2,Rr13),(Rp1,Rq2,Rr14),(Rp1,Rq2,Rr15), (Rp1,Rq2,Rr16),(Rp1,Rq2,Rr17),(Rp1,Rq2,Rr18),(Rp1, Rq2,Rr19),(Rp1,Rq2,Rr20), (Rp1,Rq2,Rr21),(Rp1,Rq2, Rr22),(Rp1,Rq2,Rr23),(Rp1,Rq2,Rr24),(Rp1,Rq2,Rr25), (Rp1,Rq2,Rr26),(Rp1,Rq2,Rr27),(Rp1,Rq2,Rr28),(Rp1, Rq2,Rr29),(Rp1,Rq2,Rr30),(Rp1,Rq2,Rr31),(Rp1,Rq2, Rr32),(Rp1,Rq2,Rr33),(Rp1,Rq2,Rr34),(Rp1,Rq2,Rr35), (Rp1,Rq2,Rr36),(Rp1,Rq2,Rr37),(Rp1,Rq3,Rr1),(Rp1,Rq3, Rr2),(Rp1,Rq3,Rr3),(Rp1,Rq3,Rr4),(Rp1,Rq3,Rr5),(Rp1, Rq3,Rr6),(Rp1,Rq3,Rr7),(Rp1,Rq3,Rr8),(Rp1,Rq3,Rr9), (Rp1,Rq3,Rr10),(Rp1,Rq3,Rr11),(Rp1,Rq3,Rr12), (Rp1, Rq3,Rr13),(Rp1,Rq3,Rr14),(Rp1,Rq3,Rr15),(Rp1,Rq3, Rr16),(Rp1,Rq3,Rr17), (Rp1,Rq3,Rr18),(Rp1,Rq3,Rr19), (Rp1,Rq3,Rr20),(Rp1,Rq3,Rr21),(Rp1,Rq3,Rr22),(Rp1, Rq3,Rr23),(Rp1,Rq3,Rr24),(Rp1,Rq3,Rr25),(Rp1,Rq3, Rr26),(Rp1,Rq3,Rr27),(Rp1,Rq3,Rr28),(Rp1,Rq3,Rr29), (Rp1,Rq3,Rr30),(Rp1,Rq3,Rr31),(Rp1,Rq3,Rr32),(Rp1, Rq3,Rr33),(Rp1,Rq3,Rr34),(Rp1,Rq3,Rr35),(Rp1,Rq3, Rr36),(Rp1,Rq3,Rr37),(Rp1,Rq4,Rr1),(Rp1,Rq4,Rr2), (Rp1,Rq1,Rr3),(Rp1,Rq4,Rr4),(Rp1,Rq4,Rr5),(Rp1,Rq4, Rr6),(Rp1,Rq4,Rr7),(Rp1,Rq4,Rr8),(Rp1,Rq4,Rr9),(Rp1, Rq4,Rr10),(Rp1,Rq4,Rr11),(Rp1,Rq4,Rr12), (Rp1,Rq4, Rr13),(Rp1,Rq4,Rr14), (Rp1,Rq4,Rr15),(Rp1,Rq4,Rr16), (Rp1,Rq4,Rr17),(Rp1,Rq4,Rr18),(Rp1,Rq4,Rr19),(Rp1, Rq4,Rr20),(Rp1,Rq4,Rr21),(Rp1,Rq4,Rr22),(Rp1,Rq4, Rr23),(Rp1,Rq4,Rr24),(Rp1,Rq4,Rr25),(Rp1,Rq4,Rr26), (Rp1,Rq4,Rr27),(Rp1,Rq4,Rr28),(Rp1,Rq4,Rr29),(Rp1, Rq4,Rr30),(Rp1,Rq4,Rr31),(Rp1,Rq4,Rr32),(Rp1,Rq4, Rr33),(Rp1,Rq4,Rr34),(Rp1,Rq4,Rr35),(Rp1,Rq4,Rr36), (Rp1,Rq4,Rr37),(Rp1,Rq5,Rr1),(Rp1,Rq5,Rr2),(Rp1,Rq5, Rr3),(Rp1,Rq5,Rr4),(Rp1,Rq5,Rr5),(Rp1,Rq5,Rr6),(Rp1, Rq5,Rr7),(Rp1,Rq5,Rr8),(Rp1,Rq5,Rr9),(Rp1,Rq5,Rr10), (Rp1,Rq5,Rr11),(Rp1,Rq5,Rr12), (Rp1,Rq5,Rr13),(Rp1, Rq5,Rr14),(Rp1,Rq5,Rr15),(Rp1,Rq5,Rr16),(Rp1,Rq5, Rr17),(Rp1,Rq5,Rr18),(Rp1,Rq5,Rr19),(Rp1,Rq5,Rr20), (Rp1,Rq5,Rr21),(Rp1,Rq5,Rr22),(Rp1,Rq5,Rr23),(Rp1, Rq5,Rr24),(Rp1,Rq5,Rr25),(Rp1,Rq5,Rr26),(Rp1,Rq5, Rr27),(Rp1,Rq5,Rr28),(Rp1,Rq5,Rr29),(Rp1,Rq5,Rr30), (Rp1,Rq5,Rr31),(Rp1,Rq5,Rr32),(Rp1,Rq5,Rr33),(Rp1, Rq5,Rr34),(Rp1,Rq5,Rr35),(Rp1,Rq5,Rr36),(Rp1,Rq5, Rr37),(Rp2,Rq1,Rr1),(Rp2,Rq1,Rr2), (Rp2,Rq1,Rr3),(Rp2, Rq1,Rr4),(Rp2,Rq1,Rr5),(Rp2,Rq1,Rr6),(Rp2,Rq1,Rr7), (Rp2,Rq1,Rr8), (Rp2,Rq1,Rr9),(Rp2,Rq1,Rr10),(Rp2,Rq1, Rr11),(Rp2,Rq1,Rr12), (Rp2,Rq1,Rr13),(Rp2,Rq1,Rr14), (Rp2,Rq1,Rr15),(Rp2,Rq1,Rr16),(Rp2,Rq1,Rr17),(Rp2, Rq1,Rr18),(Rp2,Rq1,Rr19),(Rp2,Rq1,Rr20),(Rp2,Rq1, Rr21),(Rp2,Rq1,Rr22),(Rp2,Rq1,Rr23),(Rp2,Rq1,Rr24), (Rp2,Rq1,Rr25),(Rp2,Rq1,Rr26),(Rp2,Rq1,Rr27),(Rp2, Rq1,Rr28),(Rp2,Rq1,Rr29),(Rp2,Rq1,Rr30),(Rp2,Rq1, Rr31),(Rp2,Rq1,Rr32),(Rp2,Rq1,Rr33),(Rp2,Rq1,Rr34), (Rp2,Rq1,Rr35),(Rp2,Rq1,Rr36),(Rp2,Rq1,Rr37),(Rp2, Rq2,Rr1),(Rp2,Rq2,Rr2),(Rp2,Rq2,Rr3),(Rp2,Rq2,Rr4), (Rp2,Rq2,Rr5),(Rp2,Rq2,Rr6),(Rp2,Rq2,Rr7),(Rp2,Rq2, Rr8),(Rp2,Rq2,Rr9),(Rp2,Rq2,Rr10),(Rp2,Rq2,Rr11), (Rp2,Rq2,Rr12),(Rp2,Rq2,Rr13),(Rp2,Rq2,Rr14),(Rp2, Rq2,Rr15),(Rp2,Rq2,Rr16),(Rp2,Rq2,Rr17),(Rp2,Rq2, Rr18),(Rp2,Rq2,Rr19),(Rp2,Rq2,Rr20),(Rp2,Rq2,Rr21), (Rp2,Rq2,Rr22),(Rp2,Rq2,Rr23),(Rp2,Rq2,Rr24),(Rp2,Rq2,Rr25),(Rp2,Rq2,Rr26),(Rp2,Rq2,Rr27),(Rp2,Rq2,Rr28),(Rp2,Rq2,Rr29),(Rp2,Rq2,Rr30),(Rp2,Rq2,Rr31),(Rp1,Rq2,Rr32),(Rp2,Rq2,Rr33),(Rp2,Rq2,Rr34),(Rp2,Rq2,Rr35),(Rp2,Rq2,Rr36),(Rp2,Rq2,Rr37),(Rp2,Rq3,Rr1),(Rp2,Rq3,Rr2),(Rp2,Rq3,Rr3),(Rp2,Rq3,Rr4),(Rp2,Rq3,Rr5),(Rp2,Rq3,Rr6),(Rp2,Rq3,Rr7),(Rp2,Rq3,Rr8),(Rp2,Rq3,Rr9),(Rp2,Rq3,Rr10),(Rp2,Rq3,Rr11),(Rp2,Rq3,Rr12), (Rp2,Rq3,Rr13),(Rp2,Rq3,Rr14),(Rp2,Rq3,Rr15),(Rp2,Rq3,Rr16),(Rp2,Rq3,Rr17),(Rp2,Rq3,Rr18),(Rp2,Rq3,Rr19),(Rp2,Rq3,Rr20),(Rp2,Rq3,Rr21),(Rp2,Rq3,Rr22),(Rp2,Rq3,Rr23),(Rp2,Rq3,Rr24),(Rp2,Rq3,Rr25),(Rp2,Rq3,Rr26),(Rp2,Rq3,Rr27),(Rp2,Rq3,Rr28),(Rp1,Rq3,Rr29),(Rp2,Rq3,Rr30),(Rp2,Rq3,Rr31),(Rp2,Rq3,Rr32),(Rp2,Rq3,Rr33),(Rp2,Rq3,Rr34),(Rp2,Rq3,Rr35),(Rp2,Rq3,Rr36),(Rp2,Rq3,Rr37),(Rp2,Rq4,Rr1),(Rp2,Rq4,Rr2),(Rp2,Rq1,Rr3),(Rp2,Rq4,Rr4),(Rp2,Rq4,Rr5),(Rp2,Rq4,Rr6),(Rp2,Rq4,Rr7),(Rp2,Rq4,Rr8),(Rp2,Rq4,Rr9),(Rp2,Rq4,Rr10),(Rp2,Rq4,Rr11),(Rp2,Rq4,Rr12), (Rp2,Rq4,Rr13),(Rp2,Rq4,Rr14),(Rp2,Rq4,Rr15),(Rp2,Rq4,Rr16),(Rp2,Rq4,Rr17),(Rp2,Rq4,Rr18),(Rp2,Rq4,Rr19),(Rp2,Rq4,Rr20),(Rp2,Rq4,Rr21),(Rp2,Rq4,Rr22),(Rp2,Rq4,Rr23),(Rp2,Rq4,Rr24),(Rp2,Rq4,Rr25),(Rp1,Rq4,Rr26),(Rp2,Rq4,Rr27),(Rp2,Rq4,Rr28),(Rp2,Rq4,Rr29),(Rp2,Rq4,Rr30),(Rp2,Rq4,Rr31),(Rp2,Rq4,Rr32),(Rp2,Rq4,Rr33),(Rp2,Rq4,Rr34),(Rp2,Rq4,Rr35),(Rp2,Rq4,Rr36),(Rp2,Rq4,Rr37),(Rp2,Rq5,Rr1),(Rp2,Rq5,Rr2),(Rp2,Rq5,Rr3),(Rp2,Rq5,Rr4),(Rp2,Rq5,Rr5),(Rp1,Rq5,Rr6),(Rp2,Rq5,Rr7),(Rp2,Rq5,Rr8),(Rp2,Rq5,Rr9),(Rp2,Rq5,Rr10),(Rp2,Rq5,Rr11),(Rp2,Rq5,Rr12), (Rp2,Rq5,Rr13),(Rp2,Rq5,Rr14),(Rp2,Rq5,Rr15),(Rp2,Rq5,Rr16),(Rp2,Rq5,Rr17),(Rp2,Rq5,Rr18),(Rp2,Rq5,Rr19),(Rp2,Rq5,Rr20),(Rp2,Rq5,Rr21),(Rp2,Rq5,Rr22),(Rp1,Rq5,Rr23),(Rp2,Rq5,Rr24), (Rp2,Rq5,Rr25),(Rp2,Rq5,Rr26),(Rp2,Rq5,Rr27),(Rp2,Rq5,Rr28),(Rp2,Rq5,Rr29),(Rp2,Rq5,Rr30),(Rp2,Rq5,Rr31),(Rp2,Rq5,Rr32),(Rp2,Rq5,Rr33),(Rp2,Rq5,Rr34),(Rp2,Rq5,Rr35),(Rp2,Rq5,Rr36),(Rp2,Rq5,Rr37),(Rp3,Rq1,Rr1),(Rp3,Rq1,Rr2),(Rp3,Rq1,Rr3),(Rp3,Rq1,Rr4), (Rp3,Rq1,Rr5),(Rp3,Rq1,Rr6),(Rp3,Rq1,Rr7),(Rp3,Rq1,Rr8),(Rp3,Rq1,Rr9),(Rp3,Rq1,Rr10), (Rp3,Rq1,Rr11),(Rp3,Rq1,Rr12), (Rp3,Rq1,Rr13),(Rp3,Rq1,Rr14),(Rp3,Rq1,Rr15),(Rp3,Rq 1,Rr16),(Rp3,Rq1,Rr17),(Rp3,Rq1,Rr18),(Rp3,Rq1,Rr19),(Rp3,Rq1,Rr20),(Rp3,Rq1,Rr21),(Rp3,Rq1,Rr22),(Rp3,Rq1,Rr23),(Rp3,Rq1,Rr24),(Rp3,Rq1,Rr25),(Rp3,Rq1,Rr26),(Rp3,Rq1,Rr27),(Rp3,Rq1,Rr28),(Rp3,Rq1,Rr29),(Rp3,Rq1,Rr30),(Rp3,Rq1,Rr31),(Rp3,Rq1,Rr32),(Rp3,Rq1,Rr33),(Rp3,Rq1,Rr34),(Rp3,Rq1,Rr35),(Rp3,Rq1,Rr36),(Rp3,Rq1,Rr37),(Rp3,Rq2,Rr1),(Rp3,Rq2,Rr2),(Rp3,Rq2,Rr3),(Rp3,Rq2,Rr4),(Rp3,Rq2,Rr5),(Rp3,Rq2,Rr6),(Rp3,Rq2,Rr7),(Rp3,Rq2,Rr8),(Rp3,Rq2,Rr9),(Rp3,Rq2,Rr10),(Rp3,Rq2,Rr11),(Rp3,Rq2,Rr12),(Rp3,Rq 2,Rr13),(Rp3,Rq2,Rr14),(Rp3,Rq2,Rr15),(Rp3,Rq2,Rr16),(Rp3,Rq2,Rr17),(Rp3,Rq2,Rr18), (Rp3,Rq2,Rr19),(Rp3,Rq2,Rr20),(Rp3,Rq2,Rr21),(Rp3,Rq2,Rr22),(Rp3,Rq2,Rr23),(Rp3,Rq2,Rr24),(Rp3,Rq2,Rr25),(Rp3,Rq2,Rr26),(Rp3,Rq2,Rr27),(Rp3,Rq2,Rr28),(Rp3,Rq2,Rr29),(Rp3,Rq2,Rr30),(Rp3,Rq2,Rr31),(Rp1,Rq2,Rr32),(Rp3,Rq2,Rr33),(Rp3,Rq2,Rr34),(Rp3,Rq2,Rr35),(Rp3,Rq2,Rr36),(Rp3,Rq2,Rr37),(Rp3,Rq3,Rr1),(Rp3,Rq3,Rr2),(Rp3,Rq3,Rr3),(Rp3,Rq 3,Rr4),(Rp3,Rq3,Rr5),(Rp3,Rq3,Rr6),(Rp3,Rq3,Rr7),(Rp3,Rq3,Rr8),(Rp3,Rq3,Rr9),(Rp3,Rq 3,Rr10),(Rp3,Rq3,Rr11),(Rp3,Rq3,Rr12), (Rp3,Rq3,Rr13),(Rp3,Rq3,Rr14),(Rp3,Rq3,Rr15),(Rp3,Rq3,Rr16),(Rp3,Rq3,Rr17),(Rp3,Rq3,Rr18),(Rp3,Rq3,Rr19),(Rp3,Rq3,Rr20),(Rp3,Rq3,Rr21),(Rp3,Rq3,Rr22),(Rp3,Rq3,Rr23),(Rp3,Rq3,Rr24),(Rp3,Rq3,Rr25),(Rp3,Rq3,Rr26),(Rp3,Rq3,Rr27),(Rp3,Rq3,Rr28),(Rp1,Rq3,Rr29),(Rp3,Rq3,Rr30),(Rp3,Rq3,Rr31),(Rp3,Rq3,Rr32),(Rp3,Rq3,Rr33),(Rp3,Rq3,Rr34),(Rp3,Rq3,Rr35),(Rp3,Rq3,Rr36),(Rp3,Rq3,Rr37),(Rp3,Rq4,Rr1),(Rp3,Rq4,Rr2),(Rp3,Rq1,Rr3),(Rp3,Rq4,Rr4),(Rp3,Rq4,Rr5),(Rp3,Rq4,Rr6),(Rp3,Rq4,Rr7),(Rp3,Rq4,Rr8),(Rp3,Rq4,Rr9),(Rp3,Rq4,Rr10),(Rp3,Rq4,Rr11),(Rp3,Rq4,Rr12), (Rp3,Rq4,Rr13),(Rp3,Rq4,Rr14),(Rp3,Rq4,Rr15),(Rp3,Rq4,Rr16),(Rp3,Rq4,Rr17),(Rp3,Rq4,Rr18),(Rp3,Rq4,Rr19),(Rp3,Rq4,Rr20),(Rp3,Rq4,Rr21),(Rp3,Rq4,Rr22),(Rp3,Rq4,Rr23),(Rp3,Rq4,Rr24),(Rp3,Rq4,Rr25),(Rp1,Rq4,Rr26),(Rp3,Rq4,Rr27),(Rp3,Rq4,Rr28),(Rp3,Rq4,Rr29),(Rp3,Rq4,Rr30),(Rp3,Rq4,Rr31),(Rp3,Rq4,Rr32),(Rp3,Rq4,Rr33),(Rp3,Rq4,Rr34),(Rp3,Rq4,Rr35),(Rp3,Rq4,Rr36),(Rp3,Rq4,Rr37),(Rp3,Rq5,Rr1),(Rp3,Rq5,Rr2),(Rp3,Rq5,Rr3),(Rp3,Rq5,Rr4),(Rp3,Rq5,Rr5),(Rp1,Rq5,Rr6),(Rp3,Rq5,Rr7),(Rp3,Rq5,Rr8),(Rp3,Rq5,Rr9),(Rp3,Rq5,Rr10),(Rp3,Rq5,Rr11),(Rp3,Rq5,Rr12), (Rp3,Rq5,Rr13),(Rp3,Rq5,Rr14),(Rp3,Rq5,Rr15),(Rp3,Rq5,Rr16),(Rp3,Rq5,Rr17),(Rp3,Rq5,Rr18),(Rp3,Rq5,Rr19),(Rp3,Rq5,Rr20),(Rp3,Rq5,Rr21),(Rp3,Rq5,Rr22),(Rp1,Rq5,Rr23),(Rp3,Rq5,Rr24),(Rp3,Rq5,Rr25),(Rp3,Rq5,Rr26),(Rp3,Rq5,Rr27),(Rp3,Rq5,Rr28),(Rp3,Rq5,Rr29),(Rp3,Rq5,Rr30),(Rp3,Rq5,Rr31),(Rp3,Rq5,Rr32),(Rp3,Rq5,Rr33),(Rp3,Rq5,Rr34),(Rp3,Rq5,Rr35),(Rp3,Rq5,Rr36),(Rp3,Rq5,Rr37),(Rp4,Rq1,Rr1),(Rp4,Rq1,Rr2),(Rp4,Rq1,Rr3),(Rp4,Rq1,Rr4),(Rp4,Rq1,Rr5),(Rp4,Rq1,Rr6),(Rp4,Rq1,Rr7),(Rp4,Rq1,Rr8),(Rp4,Rq1,Rr9),(Rp4,Rq1,Rr10),(Rp4,Rq1,Rr11),(Rp4,Rq1,Rr12), (Rp4,Rq1,Rr13),(Rp4,Rq1,Rr14),(Rp4,Rq1,Rr15),(Rp4,Rq1,Rr16),(Rp4,Rq1,Rr17),(Rp2,Rq1,Rr18),(Rp4,Rq1,Rr19),(Rp4,Rq1,Rr20),(Rp4,Rq1,Rr21),(Rp4,Rq1,Rr22),(Rp4,Rq1,Rr23),(Rp4,Rq1,Rr24),(Rp4,Rq1,Rr25),(Rp4,Rq1,Rr26),(Rp4,Rq1,Rr27),(Rp4,Rq1,Rr28),(Rp4,Rq1,Rr29),(Rp4,Rq1,Rr30),(Rp4,Rq1,Rr31),(Rp4,Rq1,Rr32),(Rp4,Rq1,Rr33),(Rp4,Rq1,Rr34),(Rp4,Rq1,Rr35),(Rp4,Rq1,Rr36),(Rp4,Rq1,Rr37),(Rp4,Rq2,Rr1),(Rp4,Rq2,Rr2),(Rp4,Rq2,Rr3),(Rp4,Rq2,Rr4),(Rp4,Rq2,Rr5),(Rp4,Rq2,Rr6),(Rp4,Rq2,Rr7),(Rp4,Rq2,Rr8),(Rp4,Rq2,Rr9),(Rp4,Rq2,Rr10),(Rp4,Rq2,Rr11),(Rp4,Rq2,Rr12),(Rp4,Rq2,Rr13),(Rp4,Rq2,Rr14),(Rp4,Rq2,Rr15),(Rp4,Rq2,Rr16),(Rp4,Rq2,Rr17),(Rp4,Rq2,Rr18),(Rp4,Rq2,Rr19),(Rp4,Rq2,Rr 20),(Rp4,Rq2,Rr21),(Rp4,Rq2,Rr22),(Rp4,Rq2,Rr23),(Rp4,Rq2,Rr24),(Rp4,Rq2,Rr25),(Rp4,Rq2,Rr26),(Rp4,Rq2,Rr27),(Rp4,Rq2,Rr28),(Rp4,Rq2,Rr29),(Rp4,Rq2,Rr30),(Rp4,Rq2,Rr31),(Rp3,Rq2,Rr32),(Rp4,Rq2,Rr33),(Rp4,Rq2,Rr34),(Rp4,Rq2,Rr35),(Rp4,Rq2,Rr36),(Rp4,Rq2,Rr37),(Rp4,Rq3,Rr1),(Rp4,Rq3,Rr2),(Rp4,Rq3,Rr3),(Rp4,Rq3,Rr4),(Rp4,Rq3,Rr5),(Rp4,Rq3,Rr6),(Rp4,Rq3,Rr7),(Rp4,Rq3,Rr8),(Rp4,Rq3,Rr9),(Rp4,Rq3,Rr10),(Rp4,Rq3,Rr11),(Rp4,Rq3,Rr12), (Rp4,Rq3,Rr13),(Rp4,Rq3,Rr14),(Rp4,Rq3,Rr15),(Rp4,Rq3,Rr16),(Rp4,Rq3,Rr17), (Rp4,Rq3,Rr18),(Rp4,Rq3,Rr19),(Rp4,Rq3,Rr20),(Rp4,Rq3,Rr21),(Rp4,Rq3,Rr22),(Rp4,Rq3,Rr23),(Rp4,Rq3,Rr24),(Rp4,Rq3,Rr25),(Rp4,Rq3,Rr26),(Rp4,Rq3,Rr27),(Rp4,Rq3,Rr28), (Rp3,Rq3,Rr29),(Rp4,Rq3,Rr30),(Rp4,Rq3,Rr31),(Rp4,Rq3,Rr32),(Rp4,Rq3,Rr33),(Rp4,Rq3,Rr34),(Rp4,Rq3,Rr35),(Rp4,Rq3,Rr36),(Rp4,Rq3,Rr37),(Rp4,Rq4,Rr1),(Rp4,Rq4,Rr2),(Rp4,Rq1,Rr3),(Rp4,Rq4,Rr4),(Rp4,Rq4,Rr5),(Rp4,Rq4,Rr6),(Rp4,Rq4,Rr7),(Rp4,Rq4,Rr8),(Rp4,Rq4,Rr9),(Rp4,Rq4,Rr10),(Rp4,Rq4,Rr11),(Rp4,Rq4,Rr12), (Rp4,Rq4,Rr13),(Rp4,Rq4,Rr14), (Rp4,Rq4,Rr15),(Rp4,Rq4,Rr16),(Rp4,Rq4,Rr17),(Rp4,Rq4,Rr18),(Rp4,Rq4,Rr19),(Rp4,Rq4,Rr20),(Rp4,Rq4,Rr21),(Rp4,Rq4,Rr22),(Rp4,Rq4,Rr23),(Rp4,Rq4,Rr24),(Rp4,Rq4,Rr25), (Rp4,Rq4,Rr26),(Rp4,Rq4,Rr27),(Rp4,Rq4,Rr28),(Rp4,Rq4,Rr29),(Rp4,Rq4,Rr30),(Rp4,Rq4,Rr31),(Rp4,Rq4,Rr32),(Rp4,Rq4,Rr33),(Rp4,Rq4,Rr34),(Rp4, Rq4,Rr35),(Rp4,Rq4,Rr36),(Rp4,Rq4,Rr37),(Rp4,Rq5, Rr1),(Rp4,Rq5,Rr2),(Rp4,Rq5,Rr3),(Rp4,Rq5,Rr4),(Rp4, Rq5,Rr5), (Rp4,Rq5,Rr6),(Rp4,Rq5,Rr7),(Rp4,Rq5,Rr8), (Rp4,Rq5,Rr9),(Rp4,Rq5,Rr10),(Rp4,Rq5,Rr11),(Rp4,Rq5, Rr12), (Rp4,Rq5,Rr13),(Rp4,Rq5,Rr14),(Rp4,Rq5,Rr15), (Rp4,Rq5,Rr16),(Rp4,Rq5,Rr17),(Rp4,Rq5,Rr18),(Rp4, Rq5,Rr19),(Rp4,Rq5,Rr20),(Rp4,Rq5,Rr21),(Rp4,Rq5, Rr22), (Rp4,Rq5,Rr23),(Rp4,Rq5,Rr24),(Rp4,Rq5,Rr25), (Rp4,Rq5,Rr26),(Rp4,Rq5,Rr27),(Rp4,Rq5,Rr28),(Rp4, Rq5,Rr29),(Rp4,Rq5,Rr30),(Rp4,Rq5,Rr31),(Rp4,Rq5, Rr32),(Rp4,Rq5,Rr33), (Rp4,Rq5,Rr34),(Rp4,Rq5,Rr35), (Rp4,Rq5,Rr36),(Rp4,Rq5,Rr37),(Rp5,Rq1,Rr1),(Rp5,Rq1, Rr2),(Rp5,Rq1,Rr3),(Rp5,Rq1,Rr4),(Rp5,Rq1,Rr5),(Rp5, Rq1,Rr6),(Rp5,Rq1,Rr7),(Rp5,Rq1,Rr8),(Rp5,Rq1,Rr9), (Rp5,Rq1,Rr10),(Rp5,Rq1,Rr11),(Rp5,Rq1,Rr12), (Rp5, Rq1,Rr13),(Rp5,Rq1,Rr14),(Rp5,Rq1,Rr15),(Rp5,Rq1, Rr16),(Rp5,Rq1,Rr17),(Rp5,Rq1,Rr18),(Rp5,Rq1,Rr19), (Rp5,Rq1,Rr20),(Rp5,Rq1,Rr21),(Rp3,Rq1,Rr22),(Rp5, Rq1,Rr23),(Rp5,Rq1,Rr24),(Rp5,Rq1,Rr25),(Rp5,Rq1, Rr26),(Rp5,Rq1,Rr27),(Rp5,Rq1,Rr28),(Rp5,Rq1,Rr29), (Rp5,Rq1,Rr30), (Rp5,Rq1,Rr31),(Rp5,Rq1,Rr32),(Rp3, Rq1,Rr33),(Rp5,Rq1,Rr34),(Rp5,Rq1,Rr35),(Rp5,Rq1, Rr36),(Rp5,Rq1,Rr37),(Rp5,Rq2,Rr1),(Rp5,Rq2,Rr2), (Rp5,Rq2,Rr3),(Rp5,Rq2,Rr4),(Rp5,Rq2,Rr5),(Rp5,Rq2, Rr6),(Rp5,Rq2,Rr7),(Rp5,Rq2,Rr8),(Rp5,Rq2,Rr9),(Rp5, Rq2,Rr10),(Rp5,Rq2,Rr11),(Rp5,Rq2,Rr12),(Rp5,Rq2, Rr13),(Rp5,Rq2,Rr14),(Rp5,Rq2,Rr15),(Rp5,Rq2,Rr16), (Rp5,Rq2,Rr17),(Rp5,Rq2,Rr18),(Rp5,Rq2,Rr19),(Rp5, Rq2,Rr20),(Rp5,Rq2,Rr21),(Rp5,Rq2,Rr22),(Rp5,Rq2, Rr23),(Rp5,Rq2,Rr24),(Rp5,Rq2,Rr25),(Rp5,Rq2,Rr26), (Rp5,Rq2,Rr27), (Rp5,Rq2,Rr28),(Rp5,Rq2,Rr29),(Rp3, Rq2,Rr30),(Rp5,Rq2,Rr31),(Rp5,Rq2,Rr32),(Rp5,Rq2, Rr33),(Rp5,Rq2,Rr34),(Rp5,Rq2,Rr35),(Rp5,Rq2,Rr36), (Rp5,Rq2,Rr37),(Rp5,Rq3,Rr1),(Rp5,Rq3,Rr2),(Rp5,Rq3, Rr3),(Rp5,Rq3,Rr4),(Rp5,Rq3,Rr5),(Rp5,Rq3,Rr6),(Rp5, Rq3,Rr7),(Rp5,Rq3,Rr8),(Rp5,Rq3,Rr9),(Rp5,Rq3,Rr10), (Rp5,Rq3,Rr11),(Rp5,Rq3,Rr12), (Rp5,Rq3,Rr13), (Rp5, Rq3,Rr14),(Rp5,Rq3,Rr15),(Rp3,Rq3,Rr16),(Rp5,Rq3, Rr17),(Rp5,Rq3,Rr18),(Rp5,Rq3,Rr19),(Rp5,Rq3,Rr20), (Rp5,Rq3,Rr21),(Rp5,Rq3,Rr22),(Rp5,Rq3,Rr23),(Rp5, Rq3,Rr24), (Rp5,Rq3,Rr25),(Rp5,Rq3,Rr26),(Rp3,Rq3, Rr27),(Rp5,Rq3,Rr28),(Rp5,Rq3,Rr29),(Rp5,Rq3,Rr30), (Rp5,Rq3,Rr31),(Rp5,Rq3,Rr32),(Rp5,Rq3,Rr33),(Rp5, Rq3,Rr34),(Rp5,Rq3,Rr35),(Rp5,Rq3,Rr36),(Rp5,Rq3, Rr37),(Rp5,Rq4,Rr1),(Rp5,Rq4,Rr2),(Rp5,Rq1,Rr3),(Rp5, Rq4,Rr4), (Rp5,Rq4,Rr5),(Rp5,Rq4,Rr6),(Rp5,Rq4,Rr7), (Rp5,Rq4,Rr8),(Rp5,Rq4,Rr9),(Rp5,Rq4,Rr10), (Rp5,Rq4, Rr11),(Rp5,Rq4,Rr12),(Rp5,Rq4,Rr13),(Rp5,Rq4,Rr14), (Rp5,Rq4,Rr15),(Rp5,Rq4,Rr16),(Rp5,Rq4,Rr17),(Rp5, Rq4,Rr18),(Rp5,Rq4,Rr19),(Rp5,Rq4,Rr20),(Rp5,Rq4, Rr21), (Rp5,Rq4,Rr22),(Rp5,Rq4,Rr23),(Rp5,Rq4,Rr24), (Rp5,Rq4,Rr25),(Rp5,Rq4,Rr26),(Rp5,Rq4,Rr27),(Rp5, Rq4,Rr28),(Rp5,Rq4,Rr29),(Rp5,Rq4,Rr30),(Rp5,Rq4, Rr31),(Rp5,Rq4,Rr32),(Rp5,Rq4,Rr33),(Rp5,Rq4,Rr34), (Rp5,Rq4,Rr35),(Rp5,Rq4,Rr36),(Rp5,Rq4,Rr37),(Rp5, Rq5,Rr1), (Rp5,Rq5,Rr2),(Rp5,Rq5,Rr3),(Rp5,Rq5,Rr4), (Rp5,Rq5,Rr5),(Rp5,Rq5,Rr6),(Rp5,Rq5,Rr7), (Rp5,Rq5, Rr8),(Rp5,Rq5,Rr9),(Rp3,Rq5,Rr10),(Rp5,Rq5,Rr11), (Rp5,Rq5,Rr12), (Rp5,Rq5,Rr13),(Rp5,Rq5,Rr14),(Rp5, Rq5,Rr15),(Rp5,Rq5,Rr16),(Rp5,Rq5,Rr17),(Rp5,Rq5, Rr18), (Rp5,Rq5,Rr19),(Rp5,Rq5,Rr20),(Rp3,Rq5,Rr21), (Rp5,Rq5,Rr22),(Rp5,Rq5,Rr23),(Rp5,Rq5,Rr24),(Rp5, Rq5,Rr25),(Rp5,Rq5,Rr26),(Rp5,Rq5,Rr27),(Rp5,Rq5, Rr28),(Rp5,Rq5,Rr29),(Rp5,Rq5,Rr30),(Rp5,Rq5,Rr31), (Rp5,Rq5,Rr32),(Rp5,Rq5,Rr33),(Rp5,Rq5,Rr34),(Rp5, Rq5,Rr35), (Rp5,Rq5,Rr36),(Rp5,Rq5,Rr37),(Rp6,Rq1, Rr1),(Rp6,Rq1,Rr2),(Rp6,Rq1,Rr3),(Rp6,Rq1,Rr4),(Rp6, Rq1,Rr5),(Rp6,Rq1,Rr6),(Rp6,Rq1,Rr7),(Rp6,Rq1,Rr8), (Rp6,Rq1,Rr9),(Rp6,Rq1,Rr10),(Rp6,Rq1,Rr11),(Rp6,Rq1, Rr12), (Rp6,Rq1,Rr13),(Rp6,Rq1,Rr14),(Rp6,Rq1,Rr15), (Rp6,Rq1,Rr16),(Rp6,Rq1,Rr17),(Rp4,Rq1,Rr18),(Rp6, Rq1,Rr19),(Rp6,Rq1,Rr20),(Rp6,Rq1,Rr21),(Rp6,Rq1, Rr22),(Rp6,Rq1,Rr23),(Rp6,Rq1,Rr24),(Rp6,Rq1,Rr25), (Rp6,Rq1,Rr26),(Rp6,Rq1,Rr27),(Rp6,Rq1,Rr28),(Rp6, Rq1,Rr29),(Rp6,Rq1,Rr30),(Rp6,Rq1,Rr31),(Rp6,Rq1, Rr32), (Rp6,Rq1,Rr33),(Rp6,Rq1,Rr34),(Rp6,Rq1,Rr35), (Rp6,Rq1,Rr36),(Rp6,Rq1,Rr37),(Rp6,Rq2,Rr1),(Rp6,Rq2, Rr2),(Rp6,Rq2,Rr3),(Rp6,Rq2,Rr4),(Rp6,Rq2,Rr5),(Rp6, Rq2,Rr6),(Rp6,Rq2,Rr7),(Rp6,Rq2,Rr8),(Rp6,Rq2,Rr9), (Rp6,Rq2,Rr10),(Rp6,Rq2,Rr11),(Rp6,Rq2,Rr12), (Rp6, Rq2,Rr13),(Rp6,Rq2,Rr14),(Rp4,Rq2,Rr15),(Rp6,Rq2, Rr16),(Rp6,Rq2,Rr17),(Rp6,Rq2,Rr18),(Rp6,Rq2,Rr19), (Rp6,Rq2,Rr20),(Rp6,Rq2,Rr21),(Rp6,Rq2,Rr22),(Rp6, Rq2,Rr23),(Rp6,Rq2,Rr24),(Rp6,Rq2,Rr25),(Rp6,Rq2, Rr26),(Rp6,Rq2,Rr27),(Rp6,Rq2,Rr28),(Rp6,Rq2,Rr29), (Rp6,Rq2,Rr30),(Rp6,Rq2,Rr31),(Rp3,Rq2,Rr32),(Rp6, Rq2,Rr33),(Rp6,Rq2,Rr34),(Rp6,Rq2,Rr35),(Rp6,Rq2, Rr36),(Rp6,Rq2,Rr37),(Rp6,Rq3,Rr1),(Rp6,Rq3,Rr2), (Rp6,Rq3,Rr3),(Rp6,Rq3,Rr4),(Rp6,Rq3,Rr5),(Rp6,Rq3, Rr6),(Rp6,Rq3,Rr7),(Rp6,Rq3,Rr8),(Rp6,Rq3,Rr9),(Rp6, Rq3,Rr10),(Rp6,Rq3,Rr11),(Rp6,Rq3,Rr12), (Rp6,Rq3, Rr13),(Rp6,Rq3,Rr14),(Rp6,Rq3,Rr15),(Rp6,Rq3,Rr16), (Rp6,Rq3,Rr17),(Rp6,Rq3,Rr18),(Rp6,Rq3,Rr19),(Rp6, Rq3,Rr20),(Rp6,Rq3,Rr21),(Rp6,Rq3,Rr22),(Rp6,Rq3, Rr23),(Rp6,Rq3,Rr24),(Rp6,Rq3,Rr25),(Rp6,Rq3,Rr26), (Rp6,Rq3,Rr27),(Rp6,Rq3,Rr28),(Rp3,Rq3,Rr29),(Rp6, Rq3,Rr30),(Rp6,Rq3,Rr31),(Rp6,Rq3,Rr32),(Rp6,Rq3, Rr33),(Rp6,Rq3,Rr34),(Rp6,Rq3,Rr35),(Rp6,Rq3,Rr36), (Rp6,Rq3,Rr37), (Rp6,Rq4,Rr1),(Rp6,Rq4,Rr2),(Rp6,Rq1, Rr3),(Rp6,Rq4,Rr4),(Rp6,Rq4,Rr5),(Rp6,Rq4,Rr6), (Rp6, Rq4,Rr7),(Rp6,Rq4,Rr8),(Rp6,Rq4,Rr9),(Rp6,Rq4,Rr10), (Rp6,Rq4,Rr11),(Rp6,Rq4,Rr12), (Rp6,Rq4,Rr13),(Rp6, Rq4,Rr14),(Rp6,Rq4,Rr15),(Rp6,Rq4,Rr16),(Rp6,Rq4, Rr17),(Rp6,Rq4,Rr18),(Rp6,Rq4,Rr19),(Rp6,Rq4,Rr20), (Rp6,Rq4,Rr21),(Rp6,Rq4,Rr22),(Rp6,Rq4,Rr23), (Rp6, Rq4,Rr24),(Rp6,Rq4,Rr25),(Rp6,Rq4,Rr26),(Rp6,Rq4, Rr27),(Rp6,Rq4,Rr28),(Rp6,Rq4,Rr29),(Rp6,Rq4,Rr30), (Rp6,Rq4,Rr31),(Rp6,Rq4,Rr32),(Rp6,Rq4,Rr33),(Rp6, Rq4,Rr34), (Rp6,Rq4,Rr35),(Rp6,Rq4,Rr36),(Rp4,Rq4, Rr37),(Rp6,Rq5,Rr1),(Rp6,Rq5,Rr2),(Rp6,Rq5,Rr3), (Rp6, Rq5,Rr4),(Rp6,Rq5,Rr5),(Rp6,Rq5,Rr6),(Rp6,Rq5,Rr7), (Rp6,Rq5,Rr8),(Rp6,Rq5,Rr9), (Rp6,Rq5,Rr10),(Rp6,Rq5, Rr11),(Rp6,Rq5,Rr12), (Rp6,Rq5,Rr13),(Rp6,Rq5,Rr14), (Rp6,Rq5,Rr15),(Rp6,Rq5,Rr16),(Rp6,Rq5,Rr17),(Rp6, Rq5,Rr18),(Rp6,Rq5,Rr19),(Rp6,Rq5,Rr20), (Rp6,Rq5, Rr21),(Rp6,Rq5,Rr22),(Rp6,Rq5,Rr23),(Rp6,Rq5,Rr24), (Rp6,Rq5,Rr25),(Rp6,Rq5,Rr26),(Rp6,Rq5,Rr27),(Rp6, Rq5,Rr28),(Rp6,Rq5,Rr29),(Rp6,Rq5,Rr30),(Rp6,Rq5, Rr31), (Rp6,Rq5,Rr32),(Rp6,Rq5,Rr33),(Rp6,Rq5,Rr34), (Rp6,Rq5,Rr35),(Rp6,Rq5,Rr36),(Rp6,Rq5,Rr37),(Rp7, Rq1,Rr1),(Rp7,Rq1,Rr2),(Rp7,Rq1,Rr3),(Rp7,Rq1,Rr4), (Rp7,Rq1,Rr5),(Rp7,Rq1,Rr6),(Rp7,Rq1,Rr7),(Rp7,Rq1, Rr8),(Rp7,Rq1,Rr9),(Rp7,Rq1,Rr10),(Rp7,Rq1,Rr11), (Rp7,Rq1,Rr12), (Rp7,Rq1,Rr13),(Rp7,Rq1,Rr14),(Rp7, Rq1,Rr15),(Rp7,Rq1,Rr16),(Rp7,Rq1,Rr17), (Rp7,Rq1, Rr18),(Rp7,Rq1,Rr19),(Rp7,Rq1,Rr20),(Rp7,Rq1,Rr21), (Rp3,Rq1,Rr22),(Rp7,Rq1,Rr23),(Rp7,Rq1,Rr24),(Rp7, Rq1,Rr25),(Rp7,Rq1,Rr26),(Rp7,Rq1,Rr27),(Rp7,Rq1, Rr28), (Rp7,Rq1,Rr29),(Rp7,Rq1,Rr30),(Rp7,Rq1,Rr31), (Rp7,Rq1,Rr32),(Rp3,Rq1,Rr33),(Rp7,Rq1,Rr34),(Rp7, Rq1,Rr35),(Rp7,Rq1,Rr36),(Rp7,Rq1,Rr37),(Rp7,Rq2, Rr1),(Rp7,Rq2,Rr2),(Rp7,Rq2,Rr3),(Rp7,Rq2,Rr4),(Rp7, Rq2,Rr5),(Rp7,Rq2,Rr6),(Rp7,Rq2,Rr7),(Rp7,Rq2,Rr8), (Rp7,Rq2,Rr9),(Rp7,Rq2,Rr10),(Rp7,Rq2,Rr11),(Rp7,Rq2, Rr12),(Rp7,Rq2,Rr13),(Rp7,Rq2,Rr14), (Rp7,Rq2,Rr15), (Rp7,Rq2,Rr16),(Rp7,Rq2,Rr17),(Rp7,Rq2,Rr18),(Rp7, Rq2,Rr19),(Rp7,Rq2,Rr20),(Rp7,Rq2,Rr21),(Rp7,Rq2, Rr22),(Rp7,Rq2,Rr23),(Rp7,Rq2,Rr24),(Rp7,Rq2,Rr25), (Rp7,Rq2,Rr26),(Rp7,Rq2,Rr27),(Rp7,Rq2,Rr28),(Rp7, Rq2,Rr29),(Rp3,Rq2,Rr30),(Rp7,Rq2,Rr31),(Rp7,Rq2, Rr32),(Rp7,Rq2,Rr33),(Rp7,Rq2,Rr34),(Rp7,Rq2,Rr35), (Rp7,Rq2,Rr36),(Rp7,Rq2,Rr37),(Rp7,Rq3,Rr1),(Rp7,Rq3, Rr2),(Rp7,Rq3,Rr3),(Rp7,Rq3,Rr4),(Rp7,Rq3,Rr5), (Rp7, Rq3,Rr6),(Rp7,Rq3,Rr7),(Rp7,Rq3,Rr8),(Rp7,Rq3,Rr9), (Rp7,Rq3,Rr10),(Rp7,Rq3,Rr11), (Rp7,Rq3,Rr12), (Rp7, Rq3,Rr13),(Rp7,Rq3,Rr14),(Rp7,Rq3,Rr15),(Rp3,Rq3, Rr16),(Rp7,Rq3,Rr17),(Rp7,Rq3,Rr18),(Rp7,Rq3,Rr19), (Rp7,Rq3,Rr20),(Rp7,Rq3,Rr21),(Rp7,Rq3,Rr22), (Rp7, Rq3,Rr23),(Rp7,Rq3,Rr24),(Rp7,Rq3,Rr25),(Rp7,Rq3, Rr26),(Rp3,Rq3,Rr27),(Rp7,Rq3,Rr28),(Rp7,Rq3,Rr29), (Rp7,Rq3,Rr30),(Rp7,Rq3,Rr31),(Rp7,Rq3,Rr32),(Rp7, Rq3,Rr33),(Rp7,Rq3,Rr34),(Rp7,Rq3,Rr35),(Rp7,Rq3, Rr36),(Rp7,Rq3,Rr37),(Rp7,Rq4,Rr1),(Rp7,Rq4,Rr2), (Rp7,Rq4,Rr3),(Rp7,Rq1,Rr3),(Rp7,Rq4,Rr4),(Rp7,Rq4,Rr5),(Rp7,Rq4, Rr6),(Rp7,Rq4,Rr7),(Rp7,Rq4,Rr8), (Rp7,Rq4,Rr9),(Rp7, Rq4,Rr10),(Rp7,Rq4,Rr11),(Rp7,Rq4,Rr12),(Rp7,Rq4, Rr13),(Rp7,Rq4,Rr14),(Rp7,Rq4,Rr15),(Rp7,Rq4,Rr16), (Rp7,Rq4,Rr17),(Rp7,Rq4,Rr18),(Rp7,Rq4,Rr19), (Rp7, Rq4,Rr20),(Rp7,Rq4,Rr21),(Rp7,Rq4,Rr22),(Rp7,Rq4, Rr23),(Rp7,Rq4,Rr24),(Rp7,Rq4,Rr25),(Rp7,Rq4,Rr26), (Rp7,Rq4,Rr27),(Rp7,Rq4,Rr28),(Rp7,Rq4,Rr29),(Rp7, Rq4,Rr30),(Rp7,Rq4,Rr31),(Rp7,Rq4,Rr32),(Rp7,Rq4, Rr33),(Rp7,Rq4,Rr34),(Rp7,Rq4,Rr35),(Rp7,Rq4,Rr36), (Rp7,Rq4,Rr37),(Rp7,Rq5,Rr1),(Rp7,Rq5,Rr2),(Rp7,Rq5, Rr3),(Rp7,Rq5,Rr4),(Rp7,Rq5,Rr5),(Rp7,Rq5,Rr6),(Rp7, Rq5,Rr7),(Rp7,Rq5,Rr8),(Rp7,Rq5,Rr9),(Rp3,Rq5,Rr10), (Rp7,Rq5,Rr11),(Rp7,Rq5,Rr12), (Rp7,Rq5,Rr13),(Rp7, Rq5,Rr14),(Rp7,Rq5,Rr15),(Rp7,Rq5,Rr16), (Rp7,Rq5, Rr17),(Rp7,Rq5,Rr18),(Rp7,Rq5,Rr19),(Rp7,Rq5,Rr20), (Rp3,Rq5,Rr21),(Rp7,Rq5,Rr22),(Rp7,Rq5,Rr23),(Rp7, Rq5,Rr24),(Rp7,Rq5,Rr25),(Rp7,Rq5,Rr26),(Rp7,Rq5, Rr27),(Rp7,Rq5,Rr28),(Rp7,Rq5,Rr29),(Rp7,Rq5,Rr30), (Rp7,Rq5,Rr31),(Rp7,Rq5,Rr32),(Rp7,Rq5,Rr33), (Rp7, Rq5,Rr34),(Rp7,Rq5,Rr35),(Rp7,Rq5,Rr36),(Rp7,Rq5, Rr37),(Rp8,Rq1,Rr1),(Rp8,Rq1,Rr2),(Rp8,Rq1,Rr3),(Rp8, Rq1,Rr4),(Rp8,Rq1,Rr5),(Rp8,Rq1,Rr6),(Rp8,Rq1,Rr7), (Rp8,Rq1,Rr8),(Rp8,Rq1,Rr9),(Rp8,Rq1,Rr10),(Rp8,Rq1, Rr11),(Rp8,Rq1,Rr12), (Rp8,Rq1,Rr13), (Rp8,Rq1,Rr14), (Rp8,Rq1,Rr15),(Rp8,Rq1,Rr16),(Rp8,Rq1,Rr17),(Rp4, Rq1,Rr18),(Rp8,Rq1,Rr19),(Rp8,Rq1,Rr20),(Rp8,Rq1, Rr21),(Rp8,Rq1,Rr22),(Rp8,Rq1,Rr23),(Rp8,Rq1,Rr24), (Rp8,Rq1,Rr25),(Rp8,Rq1,Rr26),(Rp8,Rq1,Rr27),(Rp8, Rq1,Rr28),(Rp8,Rq1,Rr29),(Rp8,Rq1,Rr30), (Rp8,Rq1, Rr31),(Rp8,Rq1,Rr32),(Rp8,Rq1,Rr33),(Rp8,Rq1,Rr34), (Rp8,Rq1,Rr35),(Rp8,Rq1,Rr36),(Rp8,Rq1,Rr37),(Rp8, Rq2,Rr1),(Rp8,Rq2,Rr2),(Rp8,Rq2,Rr3),(Rp8,Rq2,Rr4), (Rp8,Rq2,Rr5),(Rp8,Rq2,Rr6),(Rp8,Rq2,Rr7),(Rp8,Rq2, Rr8),(Rp8,Rq2,Rr9),(Rp8,Rq2,Rr10), (Rp8,Rq2,Rr11), (Rp8,Rq2,Rr12),(Rp8,Rq2,Rr13),(Rp8,Rq2,Rr14),(Rp4, Rq2,Rr15),(Rp8,Rq2,Rr16),(Rp8,Rq2,Rr17),(Rp8,Rq2, Rr18),(Rp8,Rq2,Rr19),(Rp8,Rq2,Rr20),(Rp8,Rq2,Rr21), (Rp8,Rq2,Rr22),(Rp8,Rq2,Rr23),(Rp8,Rq2,Rr24),(Rp8, Rq2,Rr25),(Rp8,Rq2,Rr26),(Rp8,Rq2,Rr27), (Rp8,Rq2, Rr28),(Rp8,Rq2,Rr29),(Rp8,Rq2,Rr30),(Rp8,Rq2,Rr31), (Rp3,Rq2,Rr32),(Rp8,Rq2,Rr33),(Rp8,Rq2,Rr34),(Rp8, Rq2,Rr35),(Rp8,Rq2,Rr36),(Rp8,Rq2,Rr37),(Rp8,Rq3, Rr1), (Rp8,Rq3,Rr2),(Rp8,Rq3,Rr3),(Rp8,Rq3,Rr4),(Rp8, Rq3,Rr5),(Rp8,Rq3,Rr6),(Rp8,Rq3,Rr7), (Rp8,Rq3,Rr8), (Rp8,Rq3,Rr9),(Rp8,Rq3,Rr10),(Rp8,Rq3,Rr11),(Rp8,Rq3, Rr12), (Rp8,Rq3, Rr13), (Rp8,Rq3,Rr14),(Rp8,Rq3,Rr15), (Rp8,Rq3,Rr16),(Rp8,Rq3,Rr17),(Rp8,Rq3,Rr18),(Rp8, Rq3,Rr19),(Rp8,Rq3,Rr20),(Rp8,Rq3,Rr21),(Rp8,Rq3, Rr22),(Rp8,Rq3,Rr23),(Rp8,Rq3,Rr24), (Rp8,Rq3,Rr25), (Rp8,Rq3,Rr26),(Rp8,Rq3,Rr27),(Rp8,Rq3,Rr28),(Rp3, Rq3,Rr29),(Rp8,Rq3,Rr30),(Rp8,Rq3,Rr31),(Rp8,Rq3, Rr32),(Rp8,Rq3,Rr33),(Rp8,Rq3,Rr34),(Rp8,Rq3,Rr35), (Rp8,Rq3,Rr36),(Rp8,Rq3,Rr37),(Rp8,Rq4,Rr1),(Rp8,Rq4, Rr2),(Rp8,Rq1,Rr3),(Rp8,Rq4,Rr4), (Rp8,Rq4,Rr5),(Rp8, Rq4,Rr6),(Rp8,Rq4,Rr7),(Rp8,Rq4,Rr8),(Rp8,Rq4,Rr9), (Rp8,Rq4,Rr10), (Rp8,Rq4,Rr11),(Rp8,Rq4,Rr12), (Rp8, Rq4,Rr13),(Rp8,Rq4,Rr14),(Rp8,Rq4,Rr15),(Rp8,Rq4, Rr16),(Rp8,Rq4,Rr17),(Rp8,Rq4,Rr18),(Rp8,Rq4,Rr19), (Rp8,Rq4,Rr20),(Rp8,Rq4,Rr21), (Rp8,Rq4,Rr22),(Rp8, Rq4,Rr23),(Rp8,Rq4,Rr24),(Rp8,Rq4,Rr25),(Rp8,Rq4, Rr26),(Rp8,Rq4,Rr27),(Rp8,Rq4,Rr28),(Rp8,Rq4,Rr29), (Rp8,Rq4,Rr30),(Rp8,Rq4,Rr31),(Rp8,Rq4,Rr32), (Rp8, Rq4,Rr33),(Rp8,Rq4,Rr34),(Rp8,Rq4,Rr35),(Rp8,Rq4, Rr36),(Rp4,Rq4,Rr37),(Rp8,Rq5,Rr1),(Rp8,Rq5,Rr2), (Rp8,Rq5,Rr3),(Rp8,Rq5,Rr4),(Rp8,Rq5,Rr5),(Rp8,Rq5, Rr6),(Rp8,Rq5,Rr7),(Rp8,Rq5,Rr8),(Rp8,Rq5,Rr9),(Rp8, Rq5,Rr10),(Rp8,Rq5,Rr11),(Rp8,Rq5,Rr12), (Rp8,Rq5, Rr13),(Rp8,Rq5,Rr14),(Rp8,Rq5,Rr15),(Rp8,Rq5,Rr16), (Rp8,Rq5,Rr17),(Rp8,Rq5,Rr18), (Rp8,Rq5,Rr19),(Rp8, Rq5,Rr20),(Rp8,Rq5,Rr21),(Rp8,Rq5,Rr22),(Rp8,Rq5, Rr23),(Rp8,Rq5,Rr24),(Rp8,Rq5,Rr25),(Rp8,Rq5,Rr26), (Rp8,Rq5,Rr27),(Rp8,Rq5,Rr28),(Rp8,Rq5,Rr29), (Rp8, Rq5,Rr30),(Rp8,Rq5,Rr31),(Rp8,Rq5,Rr32),(Rp8,Rq5, Rr33),(Rp8,Rq5,Rr34),(Rp8,Rq5,Rr35),(Rp8,Rq5,Rr36), (Rp8,Rq5,Rr37),(Rp9,Rq1,Rr1),(Rp9,Rq1,Rr2),(Rp9,Rq1, Rr3),(Rp9,Rq1,Rr4),(Rp9,Rq1,Rr5),(Rp9,Rq1,Rr6),(Rp9, Rq1,Rr7),(Rp9,Rq1,Rr8),(Rp9,Rq1,Rr9),(Rp9,Rq1,Rr10), (Rp9,Rq1,Rr11),(Rp9,Rq1,Rr12), (Rp9,Rq1,Rr13),(Rp9, Rq1,Rr14),(Rp9,Rq1,Rr15), (Rp9,Rq1,Rr16),(Rp9,Rq1, Rr17),(Rp9,Rq1,Rr18),(Rp9,Rq1,Rr19),(Rp9,Rq1,Rr20), (Rp9,Rq1,Rr21),(Rp9,Rq1,Rr22),(Rp9,Rq1,Rr23),(Rp9, Rq1,Rr24),(Rp9,Rq1,Rr25),(Rp9,Rq1,Rr26), (Rp9,Rq1, Rr27),(Rp9,Rq1,Rr28),(Rp9,Rq1,Rr29),(Rp9,Rq1,Rr30), (Rp9,Rq1,Rr31),(Rp9,Rq1,Rr32),(Rp9,Rq1,Rr33),(Rp9, Rq1,Rr34),(Rp9,Rq1,Rr35),(Rp9,Rq1,Rr36),(Rp9,Rq1, Rr37), (Rp9,Rq2,Rr1),(Rp9,Rq2,Rr2),(Rp9,Rq2,Rr3),(Rp9, Rq2,Rr4),(Rp9,Rq2,Rr5),(Rp9,Rq2,Rr6),(Rp9,Rq2,Rr7), (Rp9,Rq2,Rr8),(Rp9,Rq2,Rr9),(Rp9,Rq2,Rr10),(Rp9,Rq2, Rr11),(Rp9,Rq2,Rr12), (Rp9,Rq2,Rr13),(Rp9,Rq2,Rr14), (Rp9,Rq2,Rr15),(Rp9,Rq2,Rr16),(Rp9,Rq2,Rr17),(Rp9, Rq2,Rr18),(Rp9,Rq2,Rr19),(Rp9,Rq2,Rr20),(Rp9,Rq2, Rr21),(Rp9,Rq2,Rr22),(Rp9,Rq2,Rr23), (Rp9,Rq2,Rr24), (Rp9,Rq2,Rr25),(Rp9,Rq2,Rr26),(Rp9,Rq2,Rr27),(Rp9, Rq2,Rr28),(Rp9,Rq2,Rr29),(Rp9,Rq2,Rr30),(Rp9,Rq2, Rr31),(Rp9,Rq2,Rr32),(Rp9,Rq2,Rr33),(Rp9,Rq2,Rr34), (Rp9,Rq2,Rr35),(Rp9,Rq2,Rr36),(Rp9,Rq2,Rr37),(Rp9, Rq3,Rr1),(Rp9,Rq3,Rr2),(Rp9,Rq3,Rr3), (Rp9,Rq3,Rr4), (Rp9,Rq3,Rr5),(Rp9,Rq3,Rr6),(Rp9,Rq3,Rr7),(Rp9,Rq3, Rr8),(Rp9,Rq3,Rr9), (Rp9,Rq3,Rr10),(Rp9,Rq3,Rr11), (Rp9,Rq3,Rr12), (Rp9,Rq3,Rr13),(Rp9,Rq3,Rr14),(Rp9, Rq3,Rr15),(Rp9,Rq3,Rr16),(Rp9,Rq3,Rr17),(Rp9,Rq3, Rr18),(Rp9,Rq3,Rr19),(Rp9,Rq3,Rr20), (Rp9,Rq3,Rr21), (Rp9,Rq3,Rr22),(Rp9,Rq3,Rr23),(Rp9,Rq3,Rr24),(Rp9, Rq3,Rr25),(Rp9,Rq3,Rr26),(Rp9,Rq3,Rr27),(Rp9,Rq3, Rr28),(Rp9,Rq3,Rr29),(Rp9,Rq3,Rr30),(Rp9,Rq3,Rr31), (Rp9,Rq3,Rr32),(Rp9,Rq3,Rr33),(Rp9,Rq3,Rr34),(Rp9, Rq3,Rr35),(Rp9,Rq3,Rr36),(Rp9,Rq3,Rr37), (Rp9,Rq4, Rr1),(Rp9,Rq4,Rr2),(Rp9,Rq1,Rr3),(Rp9,Rq4,Rr4),(Rp9, Rq4,Rr5),(Rp9,Rq4,Rr6),(Rp9,Rq4,Rr7),(Rp9,Rq4,Rr8), (Rp9,Rq4,Rr9),(Rp9,Rq4,Rr10),(Rp9,Rq4,Rr11),(Rp9,Rq4, Rr12),(Rp9,Rq4,Rr13),(Rp9,Rq4,Rr14),(Rp9,Rq4,Rr15), (Rp9,Rq4,Rr16),(Rp9,Rq4,Rr17), (Rp9,Rq4,Rr18),(Rp9, Rq4,Rr19),(Rp9,Rq4,Rr20),(Rp9,Rq4,Rr21),(Rp9,Rq4, Rr22),(Rp9,Rq4,Rr23),(Rp9,Rq4,Rr24),(Rp9,Rq4,Rr25), (Rp9,Rq4,Rr26),(Rp9,Rq4,Rr27),(Rp9,Rq4,Rr28), (Rp9, Rq4,Rr29),(Rp9,Rq4,Rr30),(Rp9,Rq4,Rr31),(Rp9,Rq4, Rr32),(Rp9,Rq4,Rr33),(Rp9,Rq4,Rr34), (Rp9,Rq4,Rr35), (Rp9,Rq4,Rr36),(Rp9,Rq4,Rr37),(Rp9,Rq5,Rr1),(Rp9,Rq5, Rr2),(Rp9,Rq5,Rr3),(Rp9,Rq5,Rr4),(Rp9,Rq5,Rr5),(Rp9, Rq5,Rr6),(Rp9,Rq5,Rr7),(Rp9,Rq5,Rr8),(Rp9,Rq5,Rr9), (Rp9,Rq5,Rr10),(Rp9,Rq5,Rr11),(Rp9,Rq5,Rr12), (Rp9, Rq5,Rr13),(Rp9,Rq5,Rr14), (Rp9,Rq5,Rr15),(Rp9,Rq5, Rr16),(Rp9,Rq5,Rr17),(Rp9,Rq5,Rr18),(Rp9,Rq5,Rr19), (Rp9,Rq5,Rr20),(Rp9,Rq5,Rr21),(Rp9,Rq5,Rr22),(Rp9, Rq5,Rr23),(Rp9,Rq5,Rr24),(Rp9,Rq5,Rr25),(Rp9,Rq5, Rr26),(Rp9,Rq5,Rr27),(Rp9,Rq5,Rr28),(Rp9,Rq5,Rr29), (Rp9,Rq5,Rr30),(Rp9,Rq5,Rr31), (Rp9,Rq5,Rr32),(Rp9, Rq5,Rr33),(Rp9,Rq5,Rr34),(Rp9,Rq5,Rr35),(Rp9,Rq5, Rr36),(Rp9,Rq5,Rr37),(Rp10,Rq1,Rr1),(Rp10,Rq1,Rr2), (Rp10,Rq1,Rr3),(Rp10,Rq1,Rr4),(Rp10,Rq1,Rr5), (Rp10, Rq1,Rr6),(Rp10,Rq1,Rr7),(Rp10,Rq1,Rr8),(Rp10,Rq1, Rr9),(Rp10,Rq1,Rr10),(Rp10,Rq1,Rr11),(Rp10,Rq1,Rr12), (Rp10,Rq1,Rr13),(Rp10,Rq1,Rr14),(Rp10,Rq1,Rr15), (Rp10,Rq1,Rr16),(Rp10,Rq1,Rr17),(Rp4,Rq1,Rr18),(Rp10, Rq1,Rr19),(Rp10,Rq1,Rr20),(Rp10,Rq1,Rr21),(Rp10,Rq1, Rr22),(Rp10,Rq1,Rr23),(Rp10,Rq1,Rr24),(Rp10,Rq1, Rr25),(Rp10,Rq1,Rr26), (Rp10,Rq1,Rr27),(Rp10,Rq1, Rr28),(Rp10,Rq1,Rr29),(Rp10,Rq1,Rr30),(Rp10,Rq1, Rr31), (Rp10,Rq1,Rr32),(Rp10,Rq1,Rr33),(Rp10,Rq1, Rr34),(Rp10,Rq1,Rr35),(Rp10,Rq1,Rr36), (Rp10,Rq1, Rr37),(Rp10,Rq2,Rr1),(Rp10,Rq2,Rr2),(Rp10,Rq2,Rr3), (Rp10,Rq2,Rr4),(Rp10,Rq2,Rr5),(Rp10,Rq2,Rr6),(Rp10, Rq2,Rr7),(Rp10,Rq2,Rr8),(Rp10,Rq2,Rr9),(Rp10,Rq2, Rr10), (Rp10,Rq2,Rr11),(Rp10,Rq2,Rr12),(Rp10,Rq2, Rr13),(Rp10,Rq2,Rr14),(Rp4,Rq2,Rr15),(Rp10,Rq2,Rr16), (Rp10,Rq2,Rr17),(Rp10,Rq2,Rr18),(Rp10,Rq2,Rr19), (Rp10,Rq2,Rr20),(Rp10,Rq2,Rr21),(Rp10,Rq2,Rr22), (Rp10,Rq2,Rr23),(Rp10,Rq2,Rr24),(Rp10,Rq2,Rr25), (Rp10,Rq2,Rr26),(Rp10,Rq2,Rr27), (Rp10,Rq2,Rr28), (Rp10,Rq2,Rr29),(Rp10,Rq2,Rr30),(Rp10,Rq2,Rr31), (Rp10,Rq2,Rr32),(Rp10,Rq2,Rr33),(Rp10,Rq2,Rr34), (Rp10,Rq2,Rr35),(Rp10,Rq2,Rr36),(Rp10,Rq2,Rr37), (Rp10,Rq3,Rr1), (Rp10,Rq3,Rr2),(Rp10,Rq3,Rr3),(Rp10, Rq3,Rr4),(Rp10,Rq3,Rr5),(Rp10,Rq3,Rr6),(Rp10,Rq3, Rr7), (Rp10,Rq3,Rr8),(Rp10,Rq3,Rr9),(Rp10,Rq3,Rr10), (Rp10,Rq3,Rr11),(Rp10,Rq3,Rr12), (Rp10,Rq3,Rr13), (Rp10,Rq3,Rr14),(Rp10,Rq3,Rr15),(Rp10,Rq3,Rr16), (Rp10,Rq3,Rr17),(Rp10,Rq3,Rr18),(Rp10,Rq3,Rr19), (Rp10,Rq3,Rr20),(Rp10,Rq3,Rr21),(Rp10,Rq3,Rr22), (Rp10,Rq3,Rr23),(Rp10,Rq3,Rr24), (Rp10,Rq3,Rr25), (Rp10,Rq3,Rr26),(Rp10,Rq3,Rr27),(Rp10,Rq3,Rr28), (Rp10,Rq3,Rr29),(Rp10,Rq3,Rr30),(Rp10,Rq3,Rr31), (Rp10,Rq3,Rr32),(Rp10,Rq3,Rr33),(Rp10,Rq3,Rr34), (Rp10,Rq3,Rr35), (Rp10,Rq3,Rr36),(Rp10,Rq3,Rr37), (Rp10,Rq4,Rr1),(Rp10,Rq4,Rr2),(Rp10,Rq1,Rr3),(Rp10, Rq4,Rr4), (Rp10,Rq4,Rr5),(Rp10,Rq4,Rr6),(Rp10,Rq4, Rr7),(Rp10,Rq4,Rr8),(Rp10,Rq4,Rr9),(Rp10,Rq4,Rr10), (Rp10,Rq4,Rr11),(Rp10,Rq4,Rr12), (Rp10,Rq4,Rr13), (Rp10,Rq4,Rr14),(Rp10,Rq4,Rr15),(Rp10,Rq4,Rr16), (Rp10,Rq4,Rr17),(Rp10,Rq4,Rr18),(Rp10,Rq4,Rr19), (Rp10,Rq4,Rr20),(Rp10,Rq4,Rr21), (Rp10,Rq4,Rr22), (Rp10,Rq4,Rr23),(Rp10,Rq4,Rr24),(Rp10,Rq4,Rr25), (Rp10,Rq4,Rr26),(Rp10,Rq4,Rr27),(Rp10,Rq4,Rr28), (Rp10,Rq4,Rr29),(Rp10,Rq4,Rr30),(Rp10,Rq4,Rr31), (Rp10,Rq4,Rr32), (Rp10,Rq4,Rr33),(Rp10,Rq4,Rr34), (Rp10,Rq4,Rr35),(Rp10,Rq4,Rr36),(Rp4,Rq4,Rr37),(Rp10, Rq5,Rr1),(Rp10,Rq5,Rr2),(Rp10,Rq5,Rr3),(Rp10,Rq5, Rr4),(Rp10,Rq5,Rr5),(Rp10,Rq5,Rr6),(Rp10,Rq5,Rr7), (Rp10,Rq5,Rr8),(Rp10,Rq5,Rr9),(Rp10,Rq5,Rr10),(Rp10, Rq5,Rr11),(Rp10,Rq5,Rr12), (Rp10,Rq5,Rr13),(Rp10,Rq5, Rr14),(Rp10,Rq5,Rr15),(Rp10,Rq5,Rr16),(Rp10,Rq5, Rr17),(Rp10,Rq5,Rr18), (Rp10,Rq5,Rr19),(Rp10,Rq5, Rr20),(Rp10,Rq5,Rr21),(Rp10,Rq5,Rr22),(Rp10,Rq5, Rr23),(Rp10,Rq5,Rr24),(Rp10,Rq5,Rr25),(Rp10,Rq5, Rr26),(Rp10,Rq5,Rr27),(Rp10,Rq5,Rr28),(Rp10,Rq5, Rr29), (Rp10,Rq5,Rr30),(Rp10,Rq5,Rr31),(Rp10,Rq5, Rr32),(Rp10,Rq5,Rr33),(Rp10,Rq5,Rr34),(Rp10,Rq5, Rr35),(Rp10,Rq5,Rr36),(Rp10,Rq5,Rr37),(Rp11,Rq1,Rr1), (Rp11,Rq1,Rr2),(Rp11,Rq1,Rr3),(Rp11,Rq1,Rr4),(Rp11, Rq1,Rr5),(Rp11,Rq1,Rr6),(Rp11,Rq1,Rr7),(Rp11,Rq1, Rr8),(Rp11,Rq1,Rr9),(Rp11,Rq1,Rr10),(Rp11,Rq1,Rr11), (Rp11,Rq1,Rr12), (Rp11,Rq1,Rr13),(Rp11,Rq1,Rr14), (Rp11,Rq1,Rr15), (Rp11,Rq1,Rr16),(Rp11,Rq1,Rr17), (Rp11,Rq1,Rr18),(Rp11,Rq1,Rr19),(Rp11,Rq1,Rr20), (Rp11,Rq1,Rr21),(Rp11,Rq1,Rr22),(Rp11,Rq1,Rr23), (Rp11,Rq1,Rr24),(Rp11,Rq1,Rr25),(Rp11,Rq1,Rr26), (Rp11,Rq1,Rr27),(Rp11,Rq1,Rr28),(Rp11,Rq1,Rr29), (Rp11,Rq1,Rr30),(Rp11,Rq1,Rr31),(Rp11,Rq1,Rr32), (Rp11,Rq1,Rr33),(Rp11,Rq1,Rr34),(Rp11,Rq1,Rr35), (Rp11,Rq1,Rr36),(Rp11,Rq1,Rr37), (Rp11,Rq2,Rr1), (Rp11,Rq2,Rr2),(Rp11,Rq2,Rr3),(Rp11,Rq2,Rr4),(Rp11, Rq2,Rr5),(Rp11,Rq2,Rr6),(Rp11,Rq2,Rr7),(Rp11,Rq2, Rr8),(Rp11,Rq2,Rr9),(Rp11,Rq2,Rr10),(Rp11,Rq2,Rr11), (Rp11,Rq2,Rr12), (Rp11,Rq2,Rr13),(Rp11,Rq2,Rr14), (Rp11,Rq2,Rr15),(Rp11,Rq2,Rr16),(Rp11,Rq2,Rr17), (Rp11,Rq2,Rr18),(Rp11,Rq2,Rr19),(Rp11,Rq2,Rr20), (Rp11,Rq2,Rr21),(Rp11,Rq2,Rr22),(Rp11,Rq2,Rr23), (Rp11,Rq2,Rr24),(Rp11,Rq2,Rr25),(Rp11,Rq2,Rr26), (Rp11,Rq2,Rr27),(Rp11,Rq2,Rr28),(Rp11,Rq2,Rr29), (Rp11,Rq2,Rr30),(Rp11,Rq2,Rr31),(Rp11,Rq2,Rr32), (Rp11,Rq2,Rr33),(Rp11,Rq2,Rr34),(Rp11,Rq2,Rr35), (Rp11,Rq2,Rr36),(Rp11,Rq2,Rr37),(Rp11,Rq3,Rr1),(Rp11, Rq3,Rr2),(Rp11,Rq3,Rr3), (Rp11,Rq3,Rr4),(Rp11,Rq3, Rr5),(Rp11,Rq3,Rr6),(Rp11,Rq3,Rr7),(Rp11,Rq3,Rr8), (Rp11,Rq3,Rr9), (Rp11,Rq3,Rr10),(Rp11,Rq3,Rr11), (Rp11,Rq3,Rr12), (Rp11,Rq3,Rr13),(Rp11,Rq3,Rr14), (Rp11,Rq3,Rr15),(Rp11,Rq3,Rr16),(Rp11,Rq3,Rr17), (Rp11,Rq3,Rr18),(Rp11,Rq3,Rr19),(Rp11,Rq3,Rr20), (Rp11,Rq3,Rr21),(Rp11,Rq3,Rr22),(Rp11,Rq3,Rr23), (Rp11,Rq3,Rr24),(Rp11,Rq3,Rr25),(Rp11,Rq3,Rr26), (Rp11,Rq3,Rr27),(Rp11,Rq3,Rr28),(Rp11,Rq3,Rr29), (Rp11,Rq3,Rr30),(Rp11,Rq3,Rr31),(Rp11,Rq3,Rr32), (Rp11,Rq3,Rr33),(Rp11,Rq3,Rr34),(Rp11,Rq3,Rr35), (Rp11,Rq3,Rr36),(Rp11,Rq3,Rr37), (Rp11,Rq4,Rr1), (Rp11,Rq4,Rr2),(Rp11,Rq1,Rr3),(Rp11,Rq4,Rr4),(Rp11, Rq4,Rr5),(Rp11,Rq4,Rr6),(Rp11,Rq4,Rr7),(Rp11,Rq4, Rr8),(Rp11,Rq4,Rr9),(Rp11,Rq4,Rr10),(Rp11,Rq4,Rr11), (Rp11,Rq4,Rr12),(Rp11,Rq4,Rr13),(Rp11,Rq4,Rr14), (Rp11,Rq4,Rr15),(Rp11,Rq4,Rr16),(Rp11,Rq4,Rr17), (Rp11,Rq4,Rr18),(Rp11,Rq4,Rr19),(Rp11,Rq4,Rr20), (Rp11,Rq4,Rr21),(Rp11,Rq4,Rr22),(Rp11,Rq4,Rr23), (Rp11,Rq4,Rr24),(Rp11,Rq4,Rr25),(Rp11,Rq4,Rr26), (Rp11,Rq4,Rr27),(Rp11,Rq4,Rr28), (Rp11,Rq4,Rr29), (Rp11,Rq4,Rr30),(Rp11,Rq4,Rr31),(Rp11,Rq4,Rr32), (Rp11,Rq4,Rr33),(Rp11,Rq4,Rr34), (Rp11,Rq4,Rr35), (Rp11,Rq4,Rr36),(Rp11,Rq4,Rr37),(Rp11,Rq5,Rr1),(Rp11, Rq5,Rr2),(Rp11,Rq5,Rr3),(Rp11,Rq5,Rr4),(Rp11,Rq5, Rr5),(Rp11,Rq5,Rr6),(Rp11,Rq5,Rr7),(Rp11,Rq5,Rr8), (Rp11,Rq5,Rr9),(Rp11,Rq5,Rr10),(Rp11,Rq5,Rr11),(Rp11, Rq5,Rr12), (Rp11,Rq5,Rr13),(Rp11,Rq5,Rr14), (Rp11,Rq5, Rr15),(Rp11,Rq5,Rr16),(Rp11,Rq5,Rr17),(Rp11,Rq5, Rr18),(Rp11,Rq5,Rr19),(Rp11,Rq5,Rr20),(Rp11,Rq5, Rr21),(Rp11,Rq5,Rr22),(Rp11,Rq5,Rr23),(Rp11,Rq5, Rr24),(Rp11,Rq5,Rr25),(Rp11,Rq5,Rr26),(Rp11,Rq5, Rr27),(Rp11,Rq5,Rr28),(Rp11,Rq5,Rr29),(Rp11,Rq5, Rr30),(Rp11,Rq5,Rr31), (Rp11,Rq5,Rr32),(Rp11,Rq5, Rr33),(Rp11,Rq5,Rr34),(Rp11,Rq5,Rr35),(Rp11,Rq5, Rr36),(Rp11,Rq5,Rr37).

Following examples illustrate the present invention in more detail, but the present invention is not limited by these examples. The meaning of each abbreviation is as follows:
Me: methyl
Et: ethyl
Bu: butyl
Ac: acetyl
TMS: tetramethylsilane
TMS-Cl: trimethylsilyl chloride
DMSO: dimethyl sulfoxide
DMF: dimethylformamide
THF: tetrahydrafuran
1,8-diazabicyclo [5.4.0]undeca-7-ene
NMP: N-methyl-2-pyrrolidone
HOAt: 1-hydroxy-7-azabenzotriazole
HATU: 2-(7-azabenzotriazole-1-yl)-1,1,3,3-tetramethyluronium hexafluorophosphate
PyBOP: benzotriazole-1-yl-oxytrispyrrolidinophosphonium hexafluorophosphate
rt: room temperature
M: mol/L

EXAMPLE 1

Preparation of 6-(ethylthio)-(4-fluorbenzyl)-3-isopropyl-1,3,5-triazine-2,4(1H, 3H)-dion

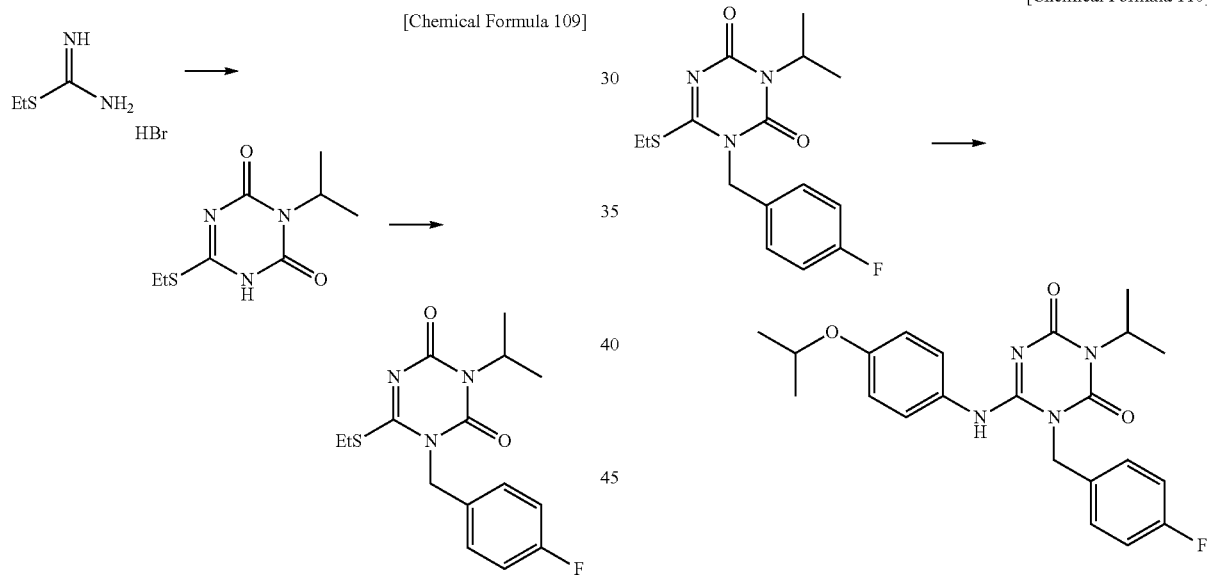

[Chemical Formula 109]

To a mixture of S-ethylisothiourea hydrobromide (14.8 g, 80 mmol) and DMF (75 mL) were added isopropyl isocyanate (8.2 mL, 84 mmol) and DBU (12.6 mL, 84 mmol) under ice-cooling, and the resulting mixture was stirred for 6 hours under ice-cooling. To the reaction mixture were added 1,1'-carbonyldiiimdazole (15.57 g, 96 mmol) and DBU (18.0 mL, 120 mmol) under ice-cooling, and the resulting mixture was stirred for additional 2 hours. To the reaction mixture was added 2 mol/L, hydrochloric acid (240 mL) under ice-cooling over 50 minutes, and the precipitated solid was filtered off. The resulting solid was dissolved in ethyl acetate, and the mixture was dried over anhydrous magnesium sulfate and concentrated in vacuo to give 6-(ethylthio)-3-isopropyl-1,3,5-triazine-2,4(1H, 3H)-dion (12.29 g, Yield.: 71%) as pale brown solid.
1H -NMR (δ ppm TMS/DMSO-d6): 1.27 (6H, t, J=7.2 Hz)), 1.33 (6H, d, J=6.9 Hz), 3.05 (2H, q, J=7.2 Hz), 4.81 (1H, sept, J=6.9 Hz).

To a mixture of 6-(ethylthio)-3-isopropyl-1,3,5-triazine-2,4 (1H, 3H)-dion (4.09 g, 19 mmol), potassium carbonate (7.88 g, 57 mmol) and acetonitrile (80 mL), 4-fluorbenzyl bromide (3.55 mL, 28.5 mmol) was added, and the resulting mixture was heated under reflux for 1.5 hours. To the mixture was added iced water (200 mL), and the mixture was extracted with ethyl acetate (100 mL). The extract was dried over anhydrous sodium sulphate, and concentrated in vacuo. The resulting residue was purified by silica gel column chromatography (ethyl acetate/hexane). The obtained residue was precipitated by ethyl acetate and hexane to give 6-(ethylthio)-1-(4-fluorbenzyl)-3-isopropyl-1,3,5-triazine-2,4(1H, 3H) dion (5.96 g, Yield: 97%) as colorless solid.
1H -NMR (δ ppm TMS/CDCl3): 1.37 (3H, t, J=7.5 Hz)), 1.47 (6H, d, J=6.9 Hz), 3.21 (2H, q, J=7.5 Hz), 5.02 (1H, sept, J=6.9 Hz), 5.06 (2H, s), 7.01-7.07 (2H, m), 7.31-7.36 (2H, m).

EXAMPLE 2

Preparation of 1-(4-fluorobenzyl)-6-(4-isopropoxyphenylamino)-3-isopropyl-1,3,5-triazine-2,4(1H,3H)-dion (I-0133)

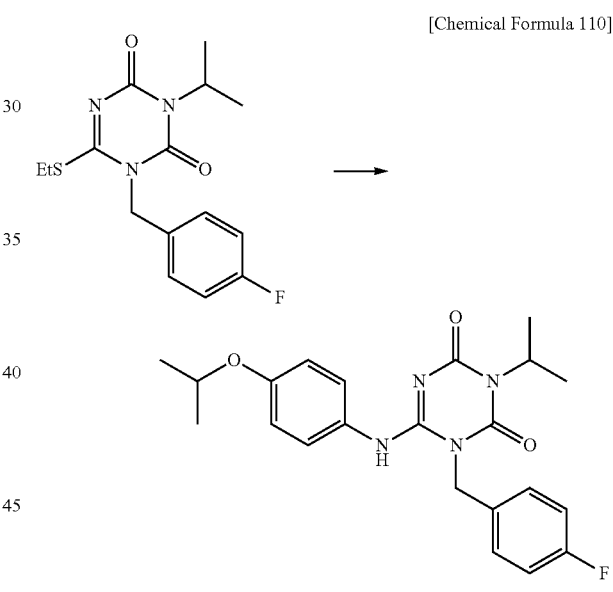

[Chemical Formula 110]

A mixture of 6-(ethylthio)-1-(4-fluorobenzyl)-3-isopropyl-1,3,5-triazine-2,4(1H, 3H)-dion (0.323 g, 1 mmol), 4-isopropoxyaniline (0.907 g, 6 mmol) and 1-methyl-2-pyrrolidone (1 mL) was stirred at 230° C. for 30 minutes under microwave irradiation. To the mixture was added water (100 mL), and time resulting mixture was extracted with ethyl acetate (100 mL). The extract was dried over anhydrous sodium sulphate, and concentrated in vacuo. The resulting residue was purified by silica gel column chromatography (ethyl acetate/hexane). The obtained residue was precipitated by ethyl acetate and hexane to give 1-(4-fluorobenzyl)-6-(4-isopropoxyphenylamino)-3-isopropyl-1,3,5-triazine-2,4(1H,3H)-dion (0.21 g, Yield: 51%) as colorless solid.
Melting point: 176-177° C.
1H -NMR (δ ppm TMS/CDCl3): 1.34 (6H, d, J=6.0 Hz)), 1.44 (6H, d, J=6.9 Hz), 4.49 (1H, sept, J=6.0 Hz), 4.96 (1H, sept, J=6.9 Hz), 5.18 (2H, s), 6.75-7.06 (6H, m), 7.53-7.57 (2H, m).

EXAMPLE 3

Preparation of 6-(3-chloro-4-isopropoxyphenylamino)-1-(4-chlorobenzyl)-3-isopropyl-1,3,5-triazine-2,4(1H, 3H)-dion (I-0228)

[Chemical Formula 111]

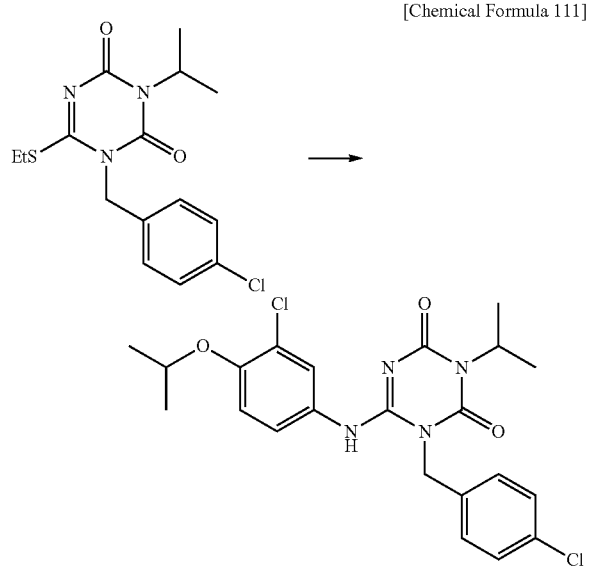

A mixture of 1-(4-chlorobenzyl)-6-(ethylthio)-3-isopropyl-1,3,5-triazine-2,4(1H, 3H)-dion (0.60 g, 1.78 mmol), 3-chloro-4-isopropoxyaniline (0.99 g, 5.3 mmol) and acetic acid (10 mL) was stirred at 90° C. for 6 hours. The reaction mixture was poured into saturated aqueous sodium bicarbonate (100 mL), and extracted with ethyl acetate (100 mL). The extract was washed by saturated aqueous sodium bicarbonate (100 mL) and brine (100 mL), dried over anhydrous sodium sulphate, and concentrated in vacuo. The resulting residue was purified by gel column chromatography (ethyl acetate/hexane). The obtained residue was precipitated by diethyl ether and hexane to give 6-(3-chloro-4-isopropoxyphenylamino)-1-(4-chlorobenzyl)-3-isopropyl-1,3,5-triazine-2,4(1H, 3H)-dion (0.605 g, Yield: 73%) as colorless solid.

Melting point: 167° C.

1H-NMR (δ ppm TMS/DMSO-d6): 1.28 (6H, d, J=6.0 Hz), 1.34 (6H, d, J=6.9 Hz), 4.62 (1H, d, J=8.7 Hz), 9.23 (1H, brs).

EXAMPLE 4

Preparation of 1-(4-chlorobenzyl)-6-(methylthio)-1,3,5-triazine-2,4(1H,3H)-dion

[Chemical Formula 112]

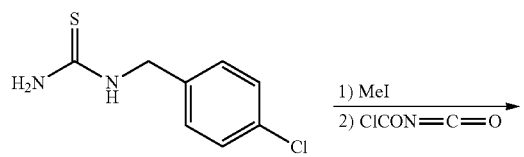

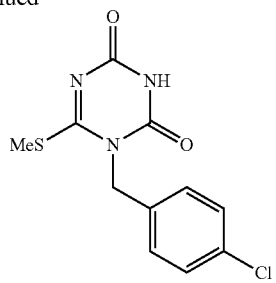

To a mixture of 1-(4-chlorobenzyl)thiourea (11.19 g, 55.8 mmol) and methanol (50 mL) was added methyl iodide (4.18 ml, 66.9 mmol) under ice-cooling, and the resulting mixture was stirred at room temperature for 5 hours. The mixture was concentrated in vacuo. To the resulting residue were added dichloromethane (60 ml) and N,N-diisopropylethylamine (29.2 ml, 167 mmol), and then a solution of N-chlorocarbonyl isocyanate (4.94 ml, 61.4 mmol) in dichloromethane (20 ml) was added gradually under ice-cooling. The resulting mixture was stirred at room temperature for 1 hour. The precipitated solid was filtered off and the resulting solid was washed by small amount on dichloromethane. The mixture was dried under reduced pressure to give 1-(4-chlorobenzyl)-6-(methylthio)-1,3,5-triazine-2,4(1H, 3H)-dion (9.19 g, Yield: 58%) as colorless solid.

1H-NMR (δ ppm TMS/DMSO-d6): 2.46 (3H, s), 5.04 (2H, s), 7.31-7.43 (4H, m), 11.60 (1H, brs).

EXAMPLE 5

Preparation of 1-(4-chlorobenzyl)-6-(3-fluoro-4-isopropoxyphenylamino)-1,3,5-triazine-2,4(1H,3H)-dion (I-0269)

[Chemical Formula 113]

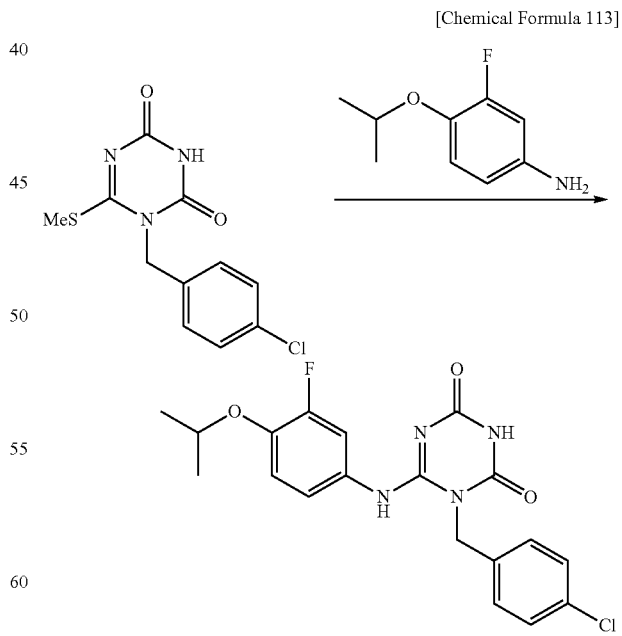

A mixture of 1-(4-chlorobenzyl)-6-(methylthio)-1,3,5-triazine-2,4(1H,3H)-dion (4.21 g, 14.8 mmol), 3-fluoro-4-isopropoxyaniline (3.77 g, 22.3 mmol), t-butanol (84 ml) and acetic acid (17 mL) was heated under reflux for 8 hours. The reaction mixture was poured into saturated aqueous sodium bicarbonate (300 mL), and the resulting mixture was extracted with ethyl acetate (100 mL). The extract was washed by saturated aqueous sodium bicarbonate (100 mL) and brine (100 mL), dried over anhydrous sodium sulphate, and concentrated in vacuo. The resulting residue was purified by silica gel column chromatography (ethyl acetate/hexane). The obtained residue is precipitated by diisopropyl ether to give: 1-(4-chlorobenzyl)-6-(3-fluoro-4-isopropoxyphenylamino)-1,3,5-triazine-2,4(1H, 3H)-dion (4.54 g, Yield: 76%) as colorless solid.

1H -NMR (δ ppm TMS/CDCl3): 1.36 (6H, d, J=6.1 Hz), 4.49 (1H, sept, J=6.1 Hz), 5.14 (2H, s), 6.47 (1, m), 6.59 (1H, m), 6.97 (1H, m), 7.30 (2H, d, J=8.5 Hz), 7.47 (2H, d, J=8.5 Hz), 8.06 (1H, brs).

EXAMPLE 6

Preparation of 1-(4-chlorobenzyl)-6-(3-fluoro-4-isopropoxyphenylamino)-3-(2-pyridylmethyl)-1,3,5-triazine-2,4(1H, 3H)-dion (I-300)

EXAMPLE 7

Preparation of 1-(4-chlorobenzyl)-6-(3-fluoro-4-isopropoxyphenylamino)-3-(2-hydroxyethyl)-1,3,5-triazine-2,4(1H, 3H)-dion (I-0273)

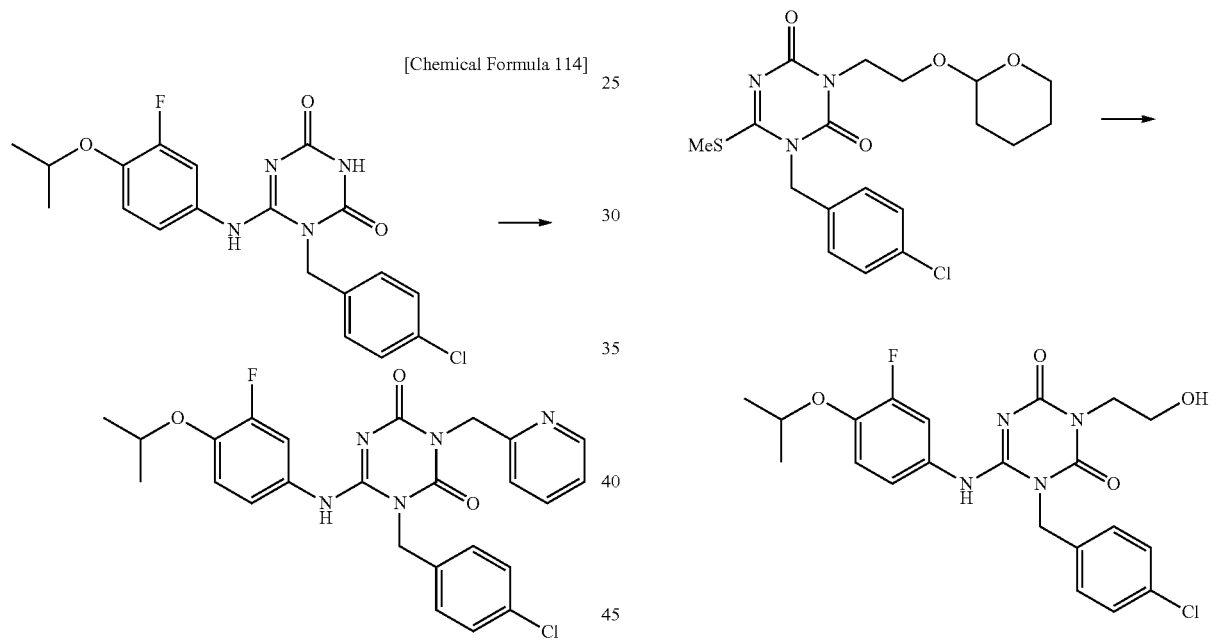

To a mixture of 1-(4-chlorobenzyl)-6-(3-fluoro-4-isopropoxyphenylamino)-1,3,5-triazine-2,4(1H,3H)-dion (0.15 g, 0.37 mmol) and DMF (3 mL) was added potassium tert-butoxide (0.09 mg, 0.82 mmol) at room temperature and stirred for 5 minutes. To the mixture was added 2-(bromomethyl)pyridine hydrobromide (0.103 g, 0.41 mmol) and the resulting mixture was stirred at (60° C. for 2 hours. To the reaction mixture was added water (20 mL), and the mixture was extracted with ethyl acetate (20 mL×2). The extract was washed by brine (20 mL×2), dried over anhydrous sodium sulphate, and concentrated in vacuo. The resulting residue was purified by silica gel column chromatography (ethyl acetate/hexane). The obtained residue was precipitated by hexane to give 1-(4-chlorobenzyl)-6-(3-fluoro-4-isopropoxyphenylamino)-3-(2-pyridylmethyl)-1,3,5-triazine-2,4(1H,3H)-dion (0.069 g, Yield: 37%) as colorless solid.

1H -NMR (δ ppm TMS/CDCl3): 1.36 (2H, d, J=6.2 Hz), 4.47 (1H, sept, J=6.2 Hz), 5.15 (2H, s), 5.19 (2, s), 6.51 (1H, m), 6.62 (1H, m), 6.97 (1H, m), 7.17-7.48 (7H, m), 7.65 (1H, m), 8.53 (1H, m).

To a mixture of 1-(4-chlorobenzyl)-6-(methylthio)-1,3,5-triazine-2,4(1H, 3H)-dion (0.28 g, 1 mmol), 2-(tetrahydro-2H-pyrane-2-yloxy)ethanol (0.15 g, 1.000 mmol), triphenylphosphine (0.53 g, 2 mmol) and THF (5 mL) was gradually added diisopropyl azodicarboxylate (0.23 ml, 1.2 mmol) under ice-cooling, and then the mixture was stirred at room temperature for 3 hours. To the reaction mixture was added water (20 mL), and the resulting mixture was extracted with ethyl acetate (20 mL×2). The extract was washed by brine (20 mL), dried over anhydrous sodium sulphate, and concentrated in vacuo. The resulting residue was purified by silica gel column chromatography (ethyl acetate/hexane) to give 1-(4-chlorobenzyl)-6-(methylthio)-3-[2-(tetrahydro-2H-pyrane-2-yloxy)ethyl]-1,3,5-triazine-2,4(1H, 3H)-dion (0.32 g, Yield: 78%) as colorless amorphous.

1H -NMR (δ ppm TMS/CDCl3): 1.42-1.83 (6H, m), 2.58 (3H, s), 3.47 (1H, m), 3.74-4.32 (5H, m), 4.63 (1H, m), 5.10 (2H, s), 7.28-7.33 (4H, m).

A mixture of 1-(4-chlorobenzyl)-6-(methylthio)-3-[2-(tetrahydro-2H-pyrane-2-yloxy)ethyl]-1,3,5-triazine-2,4(1H,3H)-dion (0.32 g, 0.78 mmol), 3-fluoro-4-isopropoxyaniline (0.40 g, 2.4 mmol) and acetic acid(3 mL) was stirred at 100° C. for 3 hours. The reaction mixture was poured into saturated aqueous sodium bicarbonate (100 mL), and extracted with chloroform (100 mL×2). The extract was dried over anhydrous sodium sulphate and concentrated in vacuo. The resulting residue was purified by silica gel column chromatography (methanol/chloroform), and The obtained residue was precipitated by diisopropyl ether and hexane to give 1-(4-chlorobenzyl)-6-(3-fluoro-4-isopropoxyphenylamino)-3-(2-hydroxyethyl)-1,3,5-triazine-2,4(1H, 3H)-dion (0.12 g, Yield: 33%) as colorless solid.

1H -NMR (δ ppm TMS/CDCl3): 1.37 (6H, d, J=5.9 Hz), 1.96 (1H, t, J=5.9 Hz), 3.83 (2H, m), 4.05 (2, m), 4.47 (1H, sept, J=5.9 Hz), 5.17 (2H, s), 6.48 (1H, m), 6.58 (1H, m), 6.97 (1H, m), 7.30 (2H, d, J=8.5 Hz), 7.47 (2H, d, J=8.5 Hz), 7.56 (1H, brs).

EXAMPLE 8

Preparation of 3-(2-aminoethyl)-1-(4-chlorobenzyl)-6-(3-fluoro-4-isopropoxyphenylamino)-1,3,5-triazine-2,4(1H, 3H)-dion hydrochloride (I-0290)

[Chemical Formula 116]

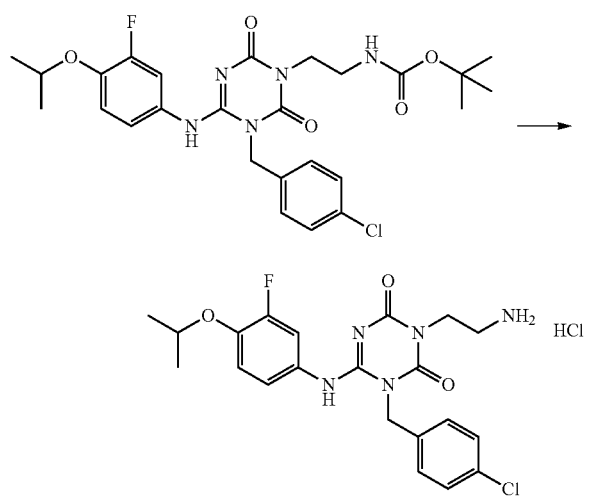

To 3-(2-butoxycarbonylaminoethyl)-1-(4-chlorobenzyl)-6-(3-fluoro-4-isopropoxyphenylamino)-1,3,5-triazine-2,4(1H, 3H)-dion (0.44 g, 0.8 mmol) was added 4 mol/L hydrogen chloride in dioxane (5 mL) under ice-cooling, and the mixture was stirred at room temperature for 1 hour. The resulting precipitated solid was filtered off. The resulting solid was washed by diethyl ether and dried under reduced pressure to give 3-(2-aminoethyl)-1-(4-chlorobenzyl)-6-(3-fluoro-4-isopropoxyphenylamino)-1,3,5-triazine-2,4(1H, 3H)-dion hydrochloride (0.31 g, Yield: 81%) as colorless solid.

1H -NMR (δ ppm TMS/DMSO-d6): 1.27 (6H, d, J=5.9 Hz), 3.01 (2H, m), 3.98 (2H, m), 4.57 (1H, sept, J=5.9 Hz), 5.27 (2H, brs), 6.98-7.17 (3H, s), 7.87 (2H, brs).

EXAMPLE 9

Preparation of 3-(2-acetylaminoethyl)-1-(4-chlorobenzyl)-6-(3-fluoro-4-isopropoxyphenylamino)-1,3,5-triazine-2,4(1H,3H)-dion (I-0292)

[Chemical Formula 117]

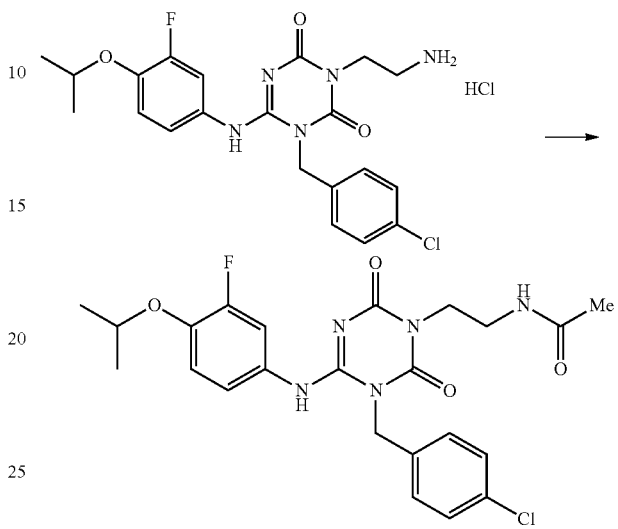

To a mixture of 3-(2-aminoethyl)-1-(4-chlorobenzyl)-6-(3-fluoro-4-isopropoxyphenylamino)-1,3,5-triazine-2,4(1H, 3H)-dion hydrochloride (0.104 g, 0.22 mmol), triethylamine (0.074 mL, 0.54 mmol), dimethylaminopyridine (0.026 g, 0.22 mmol) and THF (2 mL) was added dropwise acetyl chloride (0.023 mL, 0.32 mmol) under ice-cooling, and the resulting mixture was stirred at room temperature for 30 minutes. To the reaction mixture was added water (20 mL), and the mixture was extracted with ethyl acetate (10 mL×2). The extract was washed by brine (10 mL), dried over anhydrous sodium sulphate, and concentrated in vacuo. The resulting residue was purified by silica gel column chromatography (ethyl acetate/hexane). The obtained residue was precipitated by diisopropyl ether and hexane to give 3-(2-acetylaminoethyl)-1-(4-chlorobenzyl)-6-(3-fluoro-4-isopropoxyphenylamino)-1,3,5-triazine-2,4(1H,3H)-dion (0.104 g, Yield: 99%) as colorless solid.

1H -NMR (δ ppm TMS/CDCl3): 1.37 (6H, d, J=6.1 Hz), 1.86 (3H, s), 3.51 (2H, m), 4.00 (2H, m), 4.47 (1H, sept, J=6.1 Hz), 5.16 (2H, s), 5.83 (1H, m), 6.51 (1H, m), 6.60 (1H, m), 6.97 (1H, m), 7.27-7.51 (5H, m).

EXAMPLE 10

Preparation of 1-(4-chlorobenzyl)-6-(3-fluoro-4-isopropoxyphenylamino)-3-(methoxycarbonylmethyl)-1,3,5-triazine-2,4(1H, 3H)-dion (I-0338)

[Chemical Formula 118]

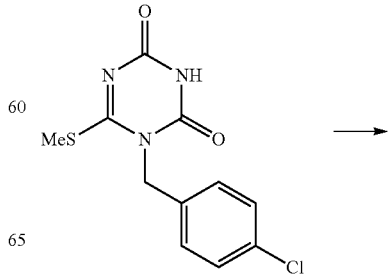

-continued

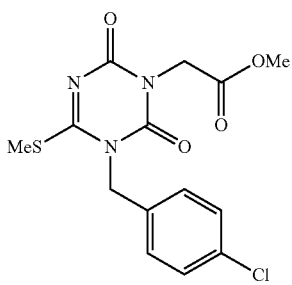

To a mixture of 1-(4-chlorobenzyl)-6-(methylthio)-1,3,5-triazine-2,4(1H, 3H)-dion (0.28 g, 1 mmol) and THF (3 mL) was added DBU (0.166 mL, 1.1 mmol), and the mixture was stirred at room temperature for 5 minutes. Further, methyl bromoacetate (0.104 mL, 1.1 mmol) was added to the mixture, and the resulting mixture was stirred at room temperature for 3 hours. To the reaction mixture was added water (20 mL). The precipitated solid was filtered off, dried, and purified by silica gel column chromatography (ethyl acetate/hexane) to give 1-(4-chlorobenzyl)-3-(methoxycarbonylmethyl)-6-(methylthio)-1,3,5-triazine-2,4(1H, 3H)-dion (0.25 g, Yield: 69%) as colorless solid.

1H -NMR (δ ppm TMS/CDCl3): 2.59 (3H, s), 3.78 (3H, s), 4.69 (2H, s), 5.13 (2H,m), 7.27-7.35 (4H, m).

A mixture of 1-(4-chlorobenzyl)-3-(methoxycarbonylmethyl)-6-(methylthio)-1,3,5-triazine-2,4(1H, 3H)-dion (0.24 g, 0.68 mmol), 3-fluoro-4-isopropoxyaniline (0.17 mg, 1.03 mmol), t-butanol (4.8 mL) and acetic acid (0.4 mL) was heated at reflux for 32 hours. The reaction mixture was poured into saturated aqueous sodium bicarbonate (20 mL), and the resulting mixture was extracted with ethyl acetate (10 mL). The extract was washed by brine (10 mL), dried over anhydrous sodium sulphate, and concentrated in vacuo. The resulting residue was purified by silica gel column chromatography (ethyl acetate/hexane), and The obtained residue was precipitated by diisopropyl ether to give 1-(4-chlorobenzyl)-6-(3-fluoro-4-isopropoxyphenylamino)-3-(methoxycarbonylmethyl)-1,3,5-triazine-2,4(1H, 3H)-dion (0.31 g, Yield: 95%) as colorless amorphous.

1H -NMR (δ ppm TMS/CDCl3): 1.37 (6H, d, J=5.9 Hz), 3.78 (3H, s), 4.47 (1H, sept, J=5.9 Hz), 4.58 (2H, s), 5.17 (2H, s), 6.50 (1H, m), 6.60 (1H, m), 6.97 (1H, m), 7.28-7.47 (5H, m).

EXAMPLE 11

Preparation of 1-(4-chlorobenzyl)-6-(3-fluoro-4-isopropoxyphenylamino)-3-(methoxycarbonylmethyl)-1,3,5-triazine-2,4(1H, 3H)-dion (I-0284)

[Chemical Formula 119]

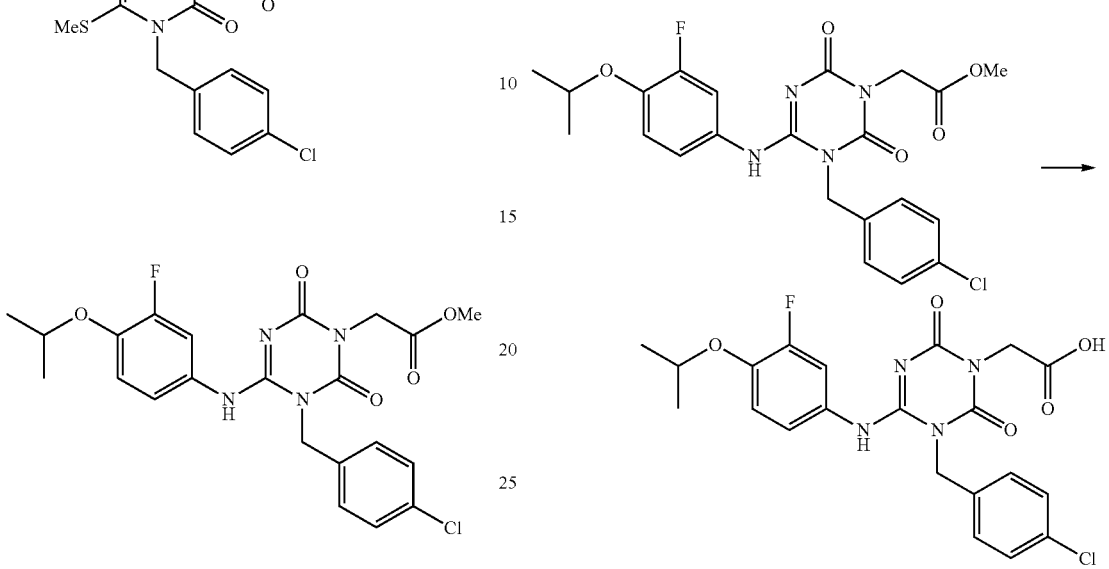

To a mixture of 1-(4-chlorobenzyl)-6-(3-fluoro-4-isopropoxyphenylamino)-3-(methoxycarbonylmethyl)-1,3,5-triazine-2,4(1H, 3H)-dion (0.30 g, 0.63 mmol), methanol (3 mL) was added 1 mol/L lithium hydroxide (3.8 mL) under ice-cooling, and the mixture was stirred at room temperature for 1hour. The pH of the mixture was adjusted with 2 mol/L hydrochloric and to a pH of less than 2. To the mixture was added brine (20 mL), and the resulting mixture was extracted by chloroform (10 mL×3). The extract was dried over anhydrous sodium sulphate and and concentrated in vacuo. The obtained residue was precipitated by diethyl ether and hexane to give 1-(4-chlorobenzyl)-6-(3-fluoro-4-isopropoxyphenylamino)-3-(methoxycarbonylmethyl)-1,3,5-triazine-2,4(1H, 3H)-dion (0.28 g, Yield: 97% as colorless solid.

1H -NMR (δ ppm TMS/CDCl3): 1.36 (6H, d, J=6.1 Hz), 4.47 (1H, sept, J=6.1 Hz), 4.62 (2H, m), 5.18 (2H, s), 6.51 (1H, m), 6.00 (1H, m), 6.96 (1H, m), 7.30 (2H, d, J=8.7 Hz), 7.45 (2H, d, J=8.7 Hz), 7.64 (1H, brs).

EXAMPLE 12

Preparation of 1-(4-chlorobenzyl)-6-(3-fluoro-4-isopropoxyphenylamino)-3-(methoxycarbonylmethyl)-1,3,5-triazine-2,4(1H, 3H)-dion (I-0294)

[Chemical Formula 120]

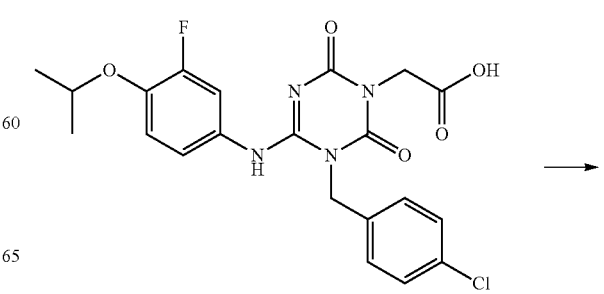

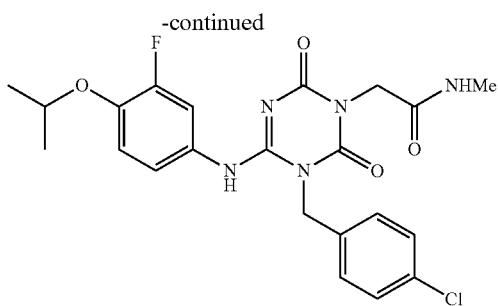

To a mixture of 1-(4-chlorobenzyl)-6-(3-fluoro-4-isopropoxyphenylamino)-3-(hydroxycarbonylmethyl)-1,3,5-triazine-2,4(1H, 3H)-dion (0.083 g, 0.19 mmol) and DMF (2 mL) were added methylamine hydrochloride (0.015 g, 0.21 mmol), 1-hydroxybenzotriazole hydrate (0.03 g, 0.2 mmol), 4-dimethylaminopyridine (0.002 g, 0.02 mmol), 1-(3-dimethylaminopropyl)-3-ethylcarbodiimide hydrochloride (0.038 g, 0.2 mmol) and triethylamine (0.03 mL, 0.21 mmol), and the resulting mixture was stirred at 60° C. for 4 hours. The reaction mixture was poured into water (20 mL), and extracted with ethyl acetate (20 mL). The extract was washed by brine (10 mL), dried over anhydrous sodium sulphate, and concentrated in vacuo. The resulting residue was purified by silica gel column chromatography (ethyl acetate hexane). The obtained residue was precipitated by diisopropyl ether to give 1-(4-chlorobenzyl)-6-(3-fluoro-4-isopropoxyphenylamino)-3-(methoxycarbamoylmethyl)-1,3,5-triazine-2,4(1H, 3H)-dion (0.076 g, Yield: 89%) as colorless solid.

1H -NMR (δ ppm TMS/CDCl3): 1.37 (6H, d, J=6.1 Hz), 2.85 (3H, d, J=4.9 Hz), 4.37 (2H, s), 4.46 (1H, sept, J=6.1 Hz), 5.15 (2H, s), 5.78 (1H, d, J=4.7 Hz), 6.46 (1H, m), 6.57 (1H, m), 6.95 (1H, m), 7.27-7.46 (4H, m), 7.99 (1H, ms).

EXAMPLE 13

Preparation of 4-chloro-1-(4-chlorobenzyl)-6-(3-fluoro-4-isopropoxyphenylamino)-1,3,5-triazine-2(1H)-one

[Chemical Formula 121]

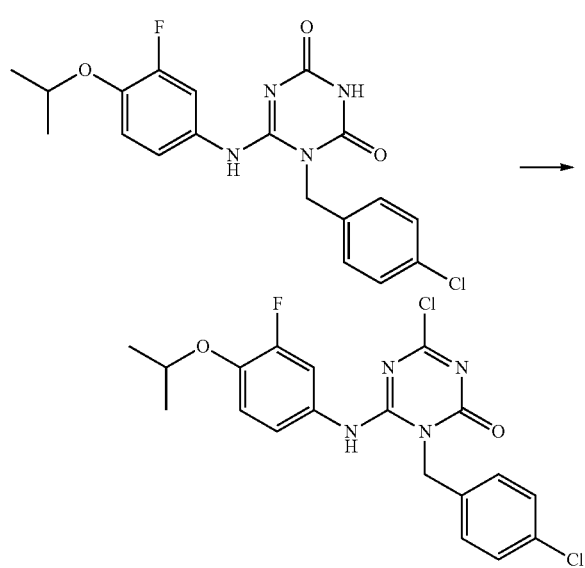

Phosphorus oxychloride (2.24 mL, 24 mmol) was added to 1-(4-chlorobenzyl)-6-(3-fluoro-4-isopropoxyphenylamino)-1,3,5-triazine-2,4(1H, 3H)-dion 0.486 g, 1.2 mmol), and the mixture was stirred at 50° C. for 2 hours. The resulting mixture was concentrated in vacuo. The resulting residue was dissolved in ethyl acetate (30 mL), and the mixture was washed by saturated aqueous sodium bicarbonate (10 mL) and brine (10 mL). The extract was dried ever anhydrous sodium sulphate and concentrated in vacuo to give 4-chloro-1-(4-chlorobenzyl)-6-(3-fluoro-4-isopropoxyphenylamino)-1,3,5-triazine-2(1H)-one (0.57 g) as crude product.

1H -NMR (δ ppm TMS/CDCl3): 1.35 (6H, d, J=6.3 Hz), 4.51 (1H, sept, J=6.3 Hz), 5.28 (2H, s), 6.72 (1H, brs), 6.80 (1H, m), 6.91 (1H, m), 7.08 (1H, m), 7.30 (2H, d, J=8.4 Hz), 7.44 (2H, d, J=8.4 Hz).

EXAMPLE 14

Preparation of 1-(4-chlorobenzyl)-6-(3-fluoro-4-isopropoxyphenylamino)-4-(2-hydroxyethoxy)-1,3,5-triazine-2(1H)-one (I-0434)

[Chemical Formula 122]

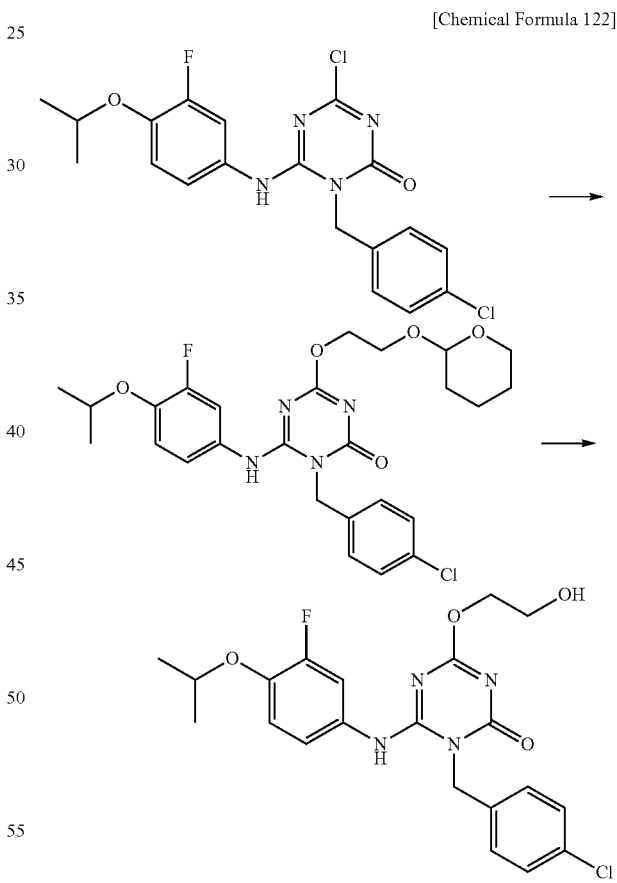

To a mixture of 2(tetrahydro-2H-pyrane-2-yloxy)ethanol (0.17 mL, corresponding to 1.25 mmol) and THF (5.6 mL) was added 60% sodium hydride (0.05 g, 1.25 mmol), and the mixture was stirred at room temperature for 10 minutes. To the mixture was added a solution of crude 4-chloro-1-(4-chlorobenzyl)-6-(3-fluoro-4-isopropoxyphenylamino)-1,3,5-triazine-2(1H)-one (0.224 g, corresponding to 0.5 mmol) in THF (2 mL) under ice-cooling, and the resulting mixture was stirred at room temperature for 5 hours. To the reaction mixture was added half-saturated aqueous ammonium chloride (50 mL), and the mixture was extracted with ethyl acetate (50 mL). The extract was washed by brine (10 mL), dried over anhydrous sodium sulphate, and concentrated in vacuo. The resulting residue was purified by silica gel column chromatography (ethyl acetate/hexane). The obtained residue was precipitated by hexane to give 1-(4-chlorobenzyl)-6-(3-fluoro-4-isopropoxyphenylamino)-4-(2-(tetrahydro-2H-pyrane-2-yloxy)ethoxy)-1,3,5-triazine-2(1H)-one (0.166 g, Yield: 62%) as colorless as oil.

To a mixture of 1-(4-chlorobenzyl)-6-(3-fluoro-4-isopropoxyphenylamino)-4-(2-(tetrahydro-2H-pyrane-2-yloxy)ethoxy)-1,3,5-triazine-2(1H)-one (0.15 g, 0.28 mmol) and methanol (1.5 mL) was added p-toluenesulfonic acid hydrate (0.08 g, 0.1 mmol), and the resulting mixture was stirred at room temperature for 2 hours. The reaction mixture was poured to half-saturated aqueous sodium bicarbonate (10 mL), and the mixture was extracted with ethyl acetate (20 mL). The extract was washed by brine (10 mL), dried over anhydrous sodium sulphate, and concentrated in vacuo. The resulting residue was purified by silica gel column chromatography (methanol/chloroform). The obtained residue was precipitated by hexane to give. 1-(4-chlorobenzyl)-6-(3-fluoro-4-isopropoxyphenylamino)-4-(2-(hydroxyethoxy)-1,3,5-triazine-2(1H)-one (0.104 g, Yield: 83%) as colorless solid.
1H -NMR (δ ppm TMS/CDCl3): 1.34 (6H, d, J=6.1 Hz), 2.53 (1H, brs), 3.91 (2H, brs), 4.44-4.52 (3H, m), 5.30 (2H, s), 6.60 (1H, brs), 6.75-7.10 (3H, m), 7.27-7.43 (4H, m).

EXAMPLE 15

Preparation of 4-benzylamino-1-(4-chlorobenzyl)-6-(3-fluoro-4-isopropoxyphenylamino)-1,3,5-triazine-2(1H)-one (I-0435)

[Chemical Formula 123]

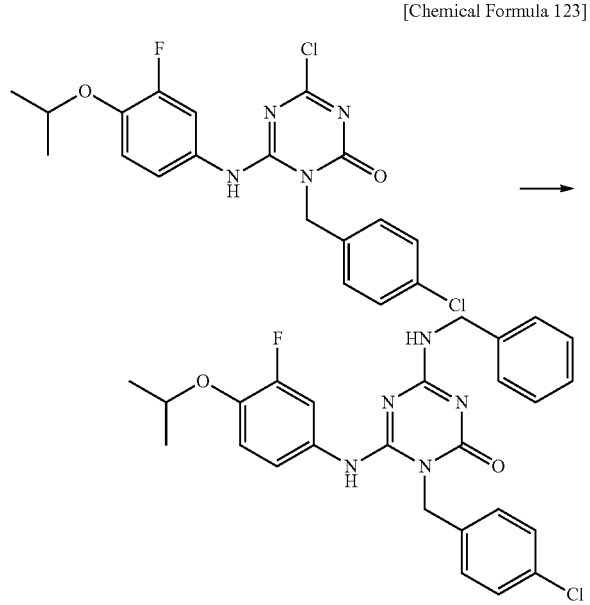

To a mixture of crude 4-chloro-1-(4-chlorobenzyl)-6-(3-fluoro-4-isopropoxyphenylamino)-1,3,5-triazine-2(1H)-one (0.19 g, corresponding to 0.4 mmol) and THF (4.7 mL) was added benzylamine (0.108 mL, 1 mmol), and the mixture was stirred at room temperature for 6 hours. To the reaction mixture were added water (10 mL) and ethyl acetate (10 mL), and the precipitated solid was filtered off. The resulting solid was washed by ethyl acetate, dried under reduced pressure to give 4-benzylamino-1-(4-chlorobenzyl)-6-(3-fluoro-4-isopropoxyphenylamino)-1,3,5-triazine-2(1H)-one (0.102 g, Yield: 52%) as colorless solid.
1H -NMR (δ ppm TMS/CDCl3): 1.25 (6H, d, J=5.7 Hz), 4.28 (1H, m), 4.41 (1H, m), 4.54 (1H, sept, J=5.7 Hz), 5.22 (2H, m), 7.08-7.52 (8H, m), 7.90 (1H, brs), 8.94 (1H, brs).

EXAMPLE 16

Preparation of 1-(4-chlorobenzyl)-4-(dodecylthio)-6-(3-fluoro-4-isopropoxyphenylamino)-1,3,5-triazine-2(1H)-one (I-0436)

[Chemical Formula 124]

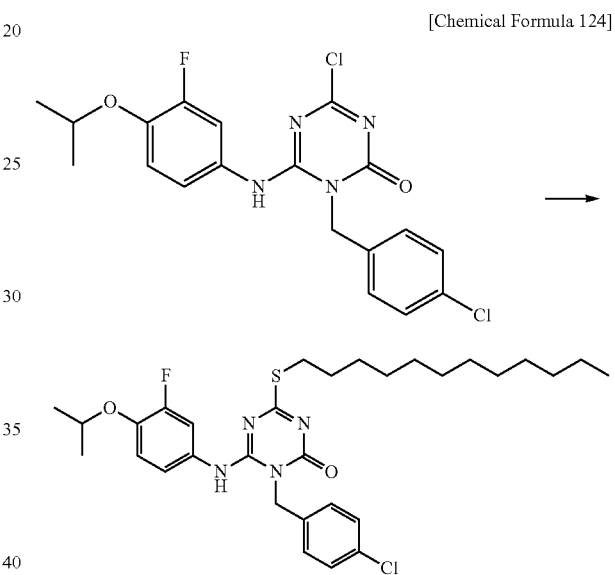

To a mixture of 1-dodecanthiol (0.24 mL, 1.0 mmol) and THF (4.8 mL) was added 60% sodium hydride (0.045 g, 1.0 mmol), and the mixture was stirred at room temperature for 10 minutes. To the resulting mixture was added a solution of crude 4-chloro-1-(4-chlorobenzyl)-6-(3-fluoro-4-isopropoxyphenylamino)-1,3,5-triazine-2(1H)-one (0.19 g, corresponding to 0.4 mmol) and THF (2 mL) under ice-cooling, and the mixture was stirred at 50° C. for 5 hours. To the reaction mixture was added half-saturated aqueous ammonium chloride (50 mL), and the mixture was extracted with ethyl acetate (50 mL). The extract was washed by brine (10 mL), dried over anhydrous sodium sulphate, and concentrated in vacuo. The resulting residue was purified by silica gel column chromatography (ethyl acetate/hexane). The obtained residue was precipitated by hexane to give 1-(4-chlorobenzyl)-4-(dodecylthio)-6-(3-fluoro-4-isopropoxyphenylamino)-1,3,5-triazine-2(1H)-one (0.092 g, Yield: 39%) as colorless oil.
1H -NMR (δ ppm TMS/CDCl3): 0.89 (3H, t, J=6.9 Hz), 1.27 (14H, s), 1.34(6H, d, J=6 Hz), 1.50-1.70 (6H, m), 3.02 (2H, t, J=7.5 Hz), 4.48 (1H, sept, J=6 Hz), 5.26 (2H, s), 6.52 (1H, brs), 6.75 (1H, m), 6.88 (1H, m), 7.10 (1H, m), 7.28-7.50 (4H, m).

EXAMPLE 17

Preparation of 1-(4-chlorobenzyl)-6-(4-hydroxycarbonylphenylamino)-3-isopropopyl-1,3,5-triazine-2,4(1H, 3H)-dion (I-0252)

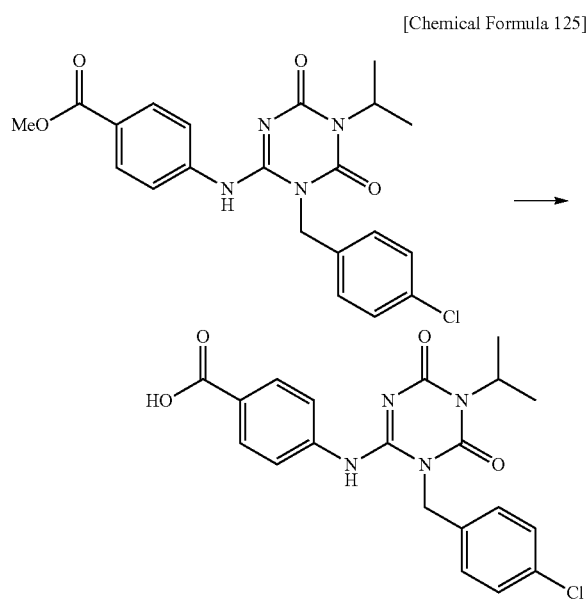

[Chemical Formula 125]

To a mixture of 1-(4-chlorobenzyl)-6-(4-methoxycarbonylphenylamino)-3-isopropyl-1,3,5-triazine-2,4(1H, 3H)-dion (0.70 g, 1.63 mmol), methanol (4 mL) and THF (4 mL) was added 2 mol/L lithium hydroxide (4.9 mL) under ice-cooling, and the mixture was stirred at room temperature for 8 hours. The reaction mixture was poured into water (50 mL), adjusted with 2 mol/L hydrochloric acid to a pH of less than 3, and extracted with ethyl acetate (50 mL×2). The extract was washed by brine (50 mL), dried over anhydrous sodium sulphate, and concentrated in vacuo. The resulting solid was washed by diethyl ether to give 1-(4-chlorobenzyl)-6-(4-hydroxycarbonylphenylamino)-3-isopropopyl-1,3,5-triazine-2,4(1H, 3H)-dion (0.60 g, Yield: 89%) as colorless solid.

1H -NMR (δ ppm TMS/CDCl3): 1.46 (6H, d, J=6.9 Hz), 4.98 (1H, sept, J=6.9 Hz), 5.19 (2H, s), 6.90 (2H, d, J=8.1 Hz), 7.31 (2H, d, J=8.7 Hz), 7.50 (2H, d, J=8.7 Hz), 7.90 (2H, d, J=8.1 Hz).

EXAMPLE 18

Preparation of 1-(4-chlorobenzyl)-6-[4-N-benzylcarbamoyl)phenylamino]-3-isopropyl-1,3,5-triazine-2,4(1H,3H)-dion (I-0259)

[Chemical Formula 126]

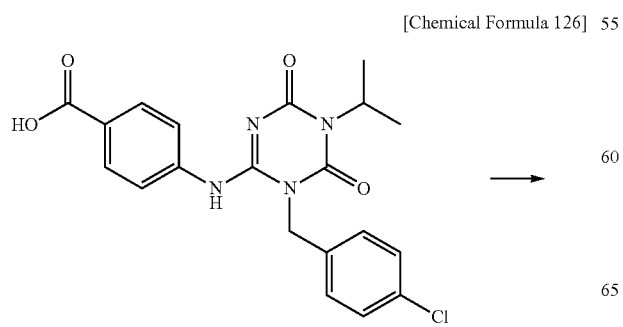

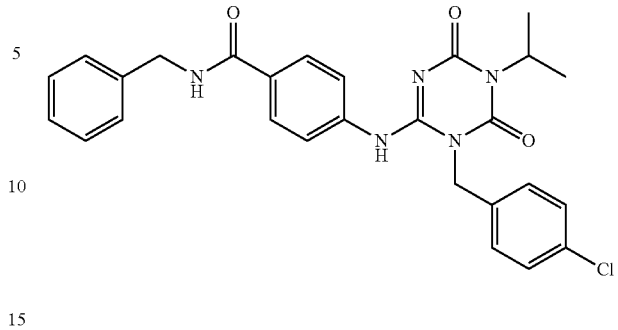

To a mixture of 1-(4-chlorobenzyl)-6-[4-N-benzylcarbamoyl)phenylamino]-3-isopropyl-1,3,5-triazine-2,4(1H, 3H)-dion (0.08 g, 0.19 mmol) and THF (2 mL) were added benzylamine (0.023 mL, 0.21 mmol), 1-hydroxybenzotriazole (0.03 g, 0.21 mmol), 1-(3-dimethylaminopropyl)-3-ethylcarbodiimide hydrochloride (0.041 g, 0.2 mmol) and triethylamine (0.03 mL, 0.21 mmol) under ice-cooling, and the resulting mixture was stirred at room temperature 4 hours. The reaction mixture was poured into water (30 mL), and the mixture was extracted with ethyl acetate (30 mL). The extract was washed by brine (30 mL), dried over anhydrous sodium sulphate, concentration in vacuo. The resulting residue was purified by silica gel column chromatography (ethyl acetate/hexane). The obtained residue was precipitated by diethyl ether to give 1-(4-chlorobenzyl)-6-[4-N-benzylcarbamoyl)phenylamino]-3-isopropyl-1,3,5-triazine-2,4(1H,3H)-dion (0.07 g, Yield: 72%) as colorless solid.

1H -NMR (δ ppm TMS/CDCl3): 1.43 (6H, d, J=6.9 Hz), 4.67 (2H, d, J=4.0 Hz), 4.96 (1H, sept, J=6.9 Hz), 5.18 (2H, s), 6.34 (1H, m), 6.88 (2H, d, J=8.4 Hz), 7.17 (1H, brs), 7.29-7.34 (6H, m), 7.50 (2H, d, J=8.4 Hz), 7.80 (2H, d, J=8.4 Hz).

EXAMPLE 19

Preparation of 1-(4-chlorobenzyl)-6-(3-chloro-4-isopropoxyphenylamino)-4-hydroxycarbonylethyl1,3,5-triazine-2(1H)-one (I-0579)

[Chemical Formula 127]

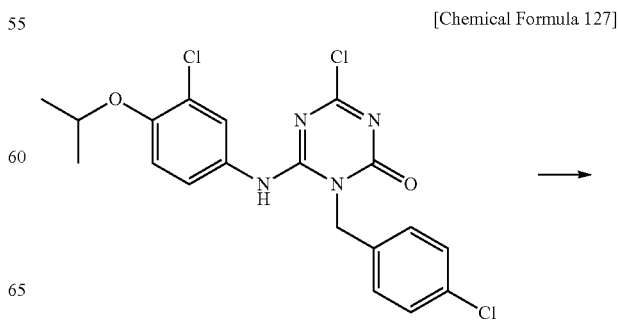

-continued

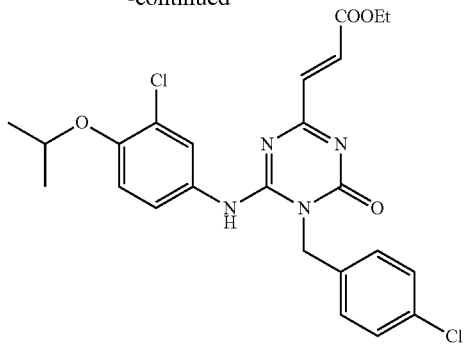

To a mixture of 4-chloro-1-(4-chlorobenzyl)-6-(3-fluoro-4-isopropoxyphenylamino)-1,3,5-triazine-2(1H)-one (0.15 g, 0.34 mmol), [1,1'-bis(di-tert-butylphosphino)ferrocene]dichloropalladium (II) (22.23 mg, 0.34 mmol) and THF (3 mL) were added (E)-ethyl-3-(4,4,5,5-tetramethyl-1,3,2-dioxaborolane-2-yl)acrylate (0.063 g, 0.49 mmol) and 2 mol/L potassium carbonate (0.682 ml, 1.364 mmol) under nitrogen atmosphere, and the resulting mixture was heated at reflux for 7 hours. To the mixture was added water (30 mL), and the resulting mixture was extracted with chloroform (30 mL). The extract was dried over anhydrous sodium sulphate and concentrated in vacuo. The resulting residue was purified by high speed liquid chromatography (0.3% $HCO_2H$ $H_2O$/MeCN 50-80%) to give 1-(4-chlorobenzyl)6-(3-chloro-4-isopropoxyphenylamino)-ethoxycarbonylethenyl1,3,5-triazine-2(1H)-one (0.05 g, Yield: 30%) as pale orange oil.

1H -NMR (δ ppm TMS/DMSO-d6): 1.20-1.28 (9H, m), 4.17-4.22 (2H, m), 4.54 (1H, brs), 5.10 (2H, brs), 7.40 (8H, brs), 8.14 (1H, s), 9.77 (1H, s).

-continued

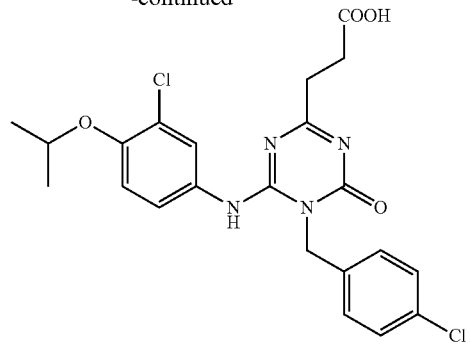

To a mixture of 1-(4-chlorobenzyl)-6-(3-chloro-4-isopropoxyphenylamino)-4-ethoxycarbonylethyl1,3,5-triazine-2(1H)-one (0.05 g, 0.1 mmol), THF (1 ml), EtOH (1 ml) and water (0.3 ml) was added lithium hydroxide hydrate (12.5 mg, 0.3 mmol), and the resulting mixture was stirred at room temperature for 3 days. The reaction mixture was purified by high speed liquid chromatography (0.3% $HCO_2H$ $H_2O$/MeCN 40-70%) to give 1-(4-chlorobenzyl)6-(3-chloro-4-isopropoxyphenylamino)-4-hydroxycarbonylethenyl1,3,5-triazine-2(1H)-one (27 mg, Yield: 57%) as pale orange oil. The obtained intermediate was dissolved in methanol (3 mL) and conducted by catalytic reduction by using H-Cube (10% Pt-C, H2=1 atm). Then, the mixture was purified by high speed liquid chromatography (0.3% $HCO_2H$ $H_2O$/MeCN 50-80%) to give 1-(4-chlorobenzyl)6-(3-chloro-4-isopropoxyphenylamino)-4-hydroxycarbonylethyl1,3,5-triazine-2(1H)-one (2.3 mg, Yield: 8.5%) as colorless oil.

1H -NMR (δ ppm TMS/CDCl3): 1.36 (6H, d, J=5.7 Hz), 2.22 (1H, t, J=7.8 Hz), 2.74 (3H, brs), 4.48 (1H, sept, J=5.7 Hz), 5.18 (2H, s), 6.88 (2H, s), 7.13 (1H, s), 7.30 (2H, d, J=8.4 Hz), 7.45 (2H, d, J=8.4 Hz).

EXAMPLE 20

Preparation of (R)-1-(4-chlorobenzyl)6-(3-chloro-4-isopropoxyphenylamino)-3-(2-methoxycarbonylpropyl)-1,3,5-triazine-2,4-dion (I-0461)

[Chemical Formula 128]

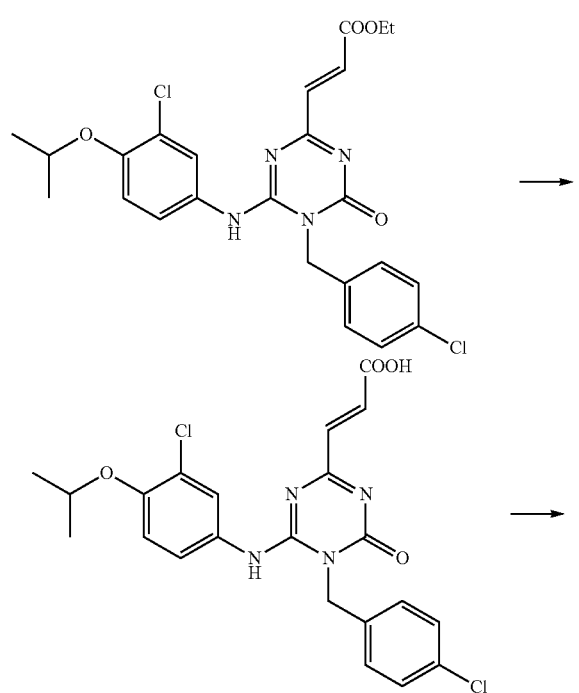

[Chemical Formula 129]

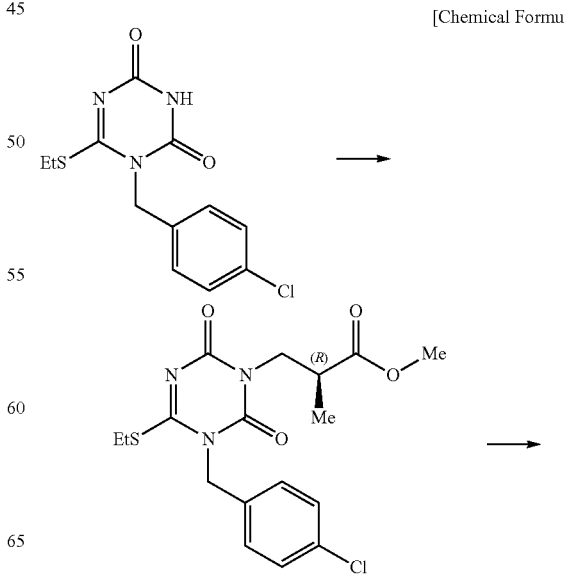

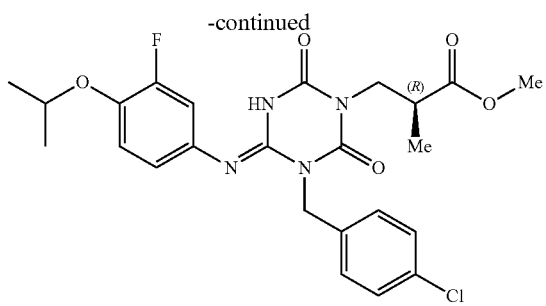

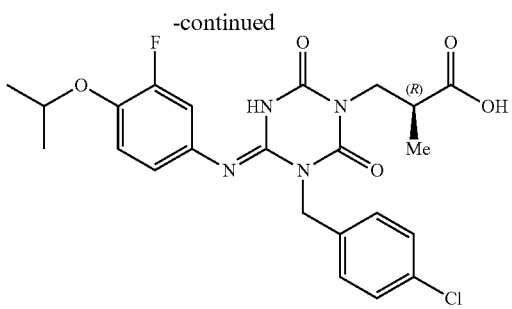

To a mixture of 1-(4-chlorobenzyl)-6-(ethylthio)-1,3,5-triazine-2,4-dion (1.00 g, 3.4 mmol), di-2-methoxyethylazodicarboxylate (1.02 g, 4.4 mmol), triphenylphosphine (1.15 g, 4.4 mmol) and dioxane (8 mL) was gradually added (R)-(-) 3-methyl 2-hydroxyisobutyrate (0.52 g, 4.4 mmol), and the mixture was stirred at room temperature for 1 hour. To the reaction mixture was added water (40 mL), and the resulting mixture was extracted with ethyl acetate (20 mL×2). The extract was washed by brine (20 mL), dried over anhydrous magnesium sulfate, and concentrated in vacuo. The resulting residue was purified hy silica gel column chromatography (ethyl acetate/hexane) to give (R)-1-(4-chlorobenzyl)6-(ethylthio)-3-(2-methoxycarbonylpropyl)-1,3,5-triazine-2,4(1H,3H)-dion (0.98 g, Yield: 74%) as colorless amorphous.
1H-NMR (δ ppm TMS/CDCl3): 1.19 (3H, d, J=5.7 Hz), 1.37 (3H, t, J=7.1 Hz), 2.96 (1H, m), 3.12 (2H, q, J=7.1 Hz), 3.60 (3H, s), 3.98 (1H, m), 4.21 (1H, m), 5.08 (2H, s), 7.29-7.34 (4H, m).
A mixture of (R)-1-(4-chlorobenzyl)6-(ethylthio)-(3-(2-methoxycarbonylpropyl)-1,3,5-triazine-2,4(1H,3H)-dion (0.32 g, 0.8 mmol), 3-fluoro-4-isopropoxyaniline (0.20 g, 1.2 mmol), acetic acid (0.72 g, 12 mmol ) and t-butanol (6) was heated at reflux over night. The reaction mixture was poured into saturated aqueous sodium bicarbonate (40 mL), and the mixture was extracted with ethyl acetate (40 mL×2). The extract was washed by 2 mol/L aqueous hydrochloric acid (20 mL×2), dried over anhydrous sodium sulphate, and concentrated in vacuo. The resulting residue was purified by silica gel column chromatography (ethyl acetate/hexane).

The obtained residue was precipitated by diethyl ether to give (R)-1-(4-chlorobenzyl)6-(3-fluoro-4-isopropoxyphenylamino)-3-(2-methoxycarbonylpropyl)-1,3,5-triazine-2,4(1H,3H)-dion (0.29 g, Yield: 71%) as pale purple powder.
1H -NMR (δ ppm TMS/CDCl3): 1.19 (3H, d, J=5.7 Hz), 1.37 (6H, d, J=5.7 Hz), 2.90 (1H, m), 3.60 (3H, s), 3.91 (1H, m), 4.10 (1H, m), 4.47 (1H, sept, J=5.7 Hz), 5.16 (2H, m), 6.49-6.62 (2H, m) 6.96 (1H, m), 7.29-7.47 (5H, m).

EXAMPLE 21

Preparation of (R)-1-(4-chlorobenzyl)6-(3-chloro-4-isopropoxyphenylamino)-3-(2-hydroxycarbonylpropyl)-1,3,5-triazine-2,4-dion (I-0464)

[Chemical Formula 130]

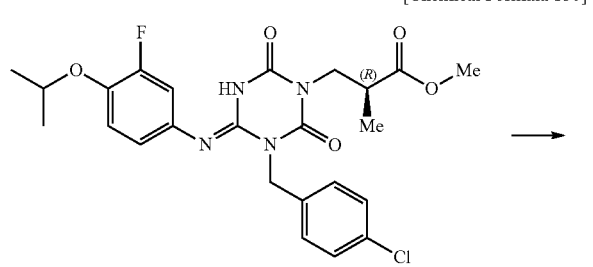

To a mixture of (R)-1-(4-chlorobenzyl)6-(3-fluoro-4-isopropoxyphenylamino)-3-(2-methoxycarbonylpropyl)-1,3,5-triazinane-2,4-dion (0.26 g, 0.5 mmol) and dioxane (4 mL) was added 1 mol/L lithium hydroxide (1.6 mL), and the mixture was stirred at 50° C. for 6 hours. To the mixture was added water (50 mL), adjusted with 2 mol/L hydrochloric acid to a pH of about 3, and the precipitated solid was filtered off. The solid was dried 40° C. to give (R)-1-(4-chlorobenzyl)6-(3-fluoro-4-isopropoxyphenylamino)-3-(2-hydroxycarbonylpropyl)-1,3,5-triazine-2,4(1H,3H)-dion (0.21 g, Yield: 84%) as colorless solid.
1H -NMR (δ ppm TMS/CDCl3): 1.19 (3H, d, J=5.7 Hz), 1.34 (6H, d, J=5.7 Hz), 2.91 (1H, m) 3.89 (1H, m), 4.11 (1H, m), 4.44 (1H, sept, J=5.7 Hz), 5.16 (2H, s), 6.47-6.60 (2H, m), 6.93 (1H, m), 7.28-7.44 (4H, m), 7.94 (1H, brs).

EXAMPLE 22

Preparation of 1-(4-chlorobenzyl)6-(3-chloro-4-isopropoxyphenylamino)-3-[2,2-di(hydroxymethyl)propyl]-1,3,5-triazine-2,4(1H,3H)-dion (I-0274)

[Chemical Formula 131]

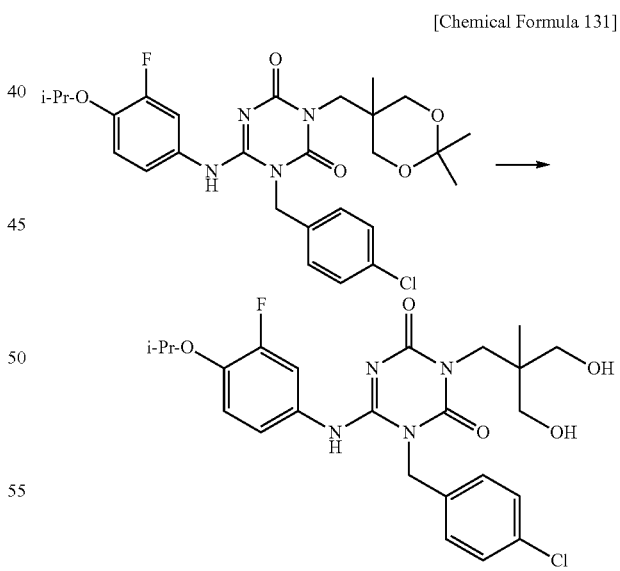

To a mixture of 1-(4-chlorobenzyl)6-(3-fluoro-4-isopropoxyphenylamino)-3-(2,2,5-trimethyl-1,3-dioxane5-yl) methyl-1,3,5-triazine-2,4(1H,3H)-dion (7.9 g, 14.44 mmol) and methanol (160 mL) was added p-toluenesulfonic acid monohydrate (5.49 g, 28.9 mmol) and the mixture was stirred at room temperature for 1 hour. The reaction mixture was poured into saturated aqueous sodium bicarbonate (200 mL), and extracted with ethyl acetate (300 mL×2). The extract was washed by brine (300 mL), dried over anhydrous sodium sulphate, and concentrated in vacuo. The resulting residue was purified by silica gel column chromatography (ethyl acetate/hexane). The obtained residue was precipitated by water and the filtered off.

The residue was dried at 70° C. for 6 hours to give. 1-(4-chlorobenzyl)6-(3-chloro-4-isopropoxyphenylamino)-3-[2,2-di(hydroxymethyl)propyl]-1,3,5-triazine-2,4(1H,3H)-dion (5.12 g, Yield: 70%) as a white powder.

1H-NMR (δ ppm TMS/CDCl3): 1.37 (6H, d, J=6.0 Hz), 3.26-3.46 (6H, m), 3.99 (2H, s), 4.48 (1H, sept, J=6.0 Hz), 5.19 (2H, s), 6.49-6.64 (2H, m), 6.99 (1H, m), 7.30-7.51 (5H, m).

Elementary analysis

Calculated value $C_{24}H_{28}ClFN_4O_5 \cdot 1/3\ H_2O$,
 C: 56.19, H: 5.63, Cl: 6.91, F: 3.70, N: 10.92
 water: 1.18%
Measured value C: 56.33, H: 5.60, Cl: 6.79, F: 3.58, N: 11.06
 Karl Fischer water determination: 1.02%

EXAMPLE 23

Preparation of 1-(4-chlorobenzyl)6-(Ethylthio)-1,3,5-triazine-2,4(1H,3H)-dion

[Chemical Formula 132]

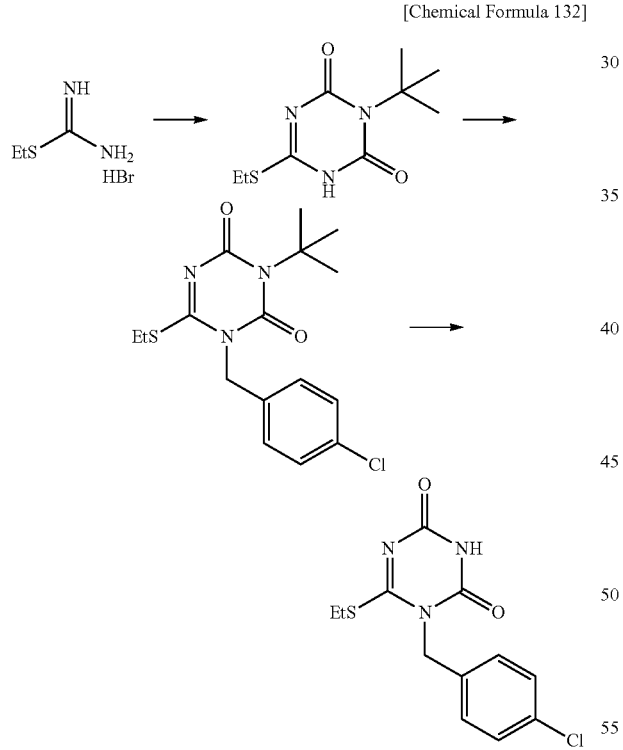

To a mixture of S-ethylisothiourea hydrobromide (1.85 g, 10 mmol) and DMF (9.3 mL) were added t-butylisocyanide (1.2 mL, 10.5 mmol) and DBU (1.9 mL, 12.8 mmol) under ice-cooling, and the mixture was stirred under ice-cooling for 6 hours. To the reaction mixture were added 1,1'-carbonyldiimidazole (1.95 g, 12 mmol) and DBU (1.9 mL, 12.8 mmol) under ice-cooling, and the resulting mixture was stirred for additional 2 hours. To the mixture was added 2 mol/L hydrochloric acid (80 mL) under ice-cooling over about 50 minutes, and the precipitated solid was filtered off. The resulting solid was dissolved in ethyl acetate, and the mixture was dried over anhydrous magnesium sulfate and concentrated in vacuo to give 6-(ethylthio)-3-t-butyl-1,3,5-triazine-2,4(1H,3H)-dion (1.15 g, Yield: 50%) as pale brown solid.

1H-NMR (δ ppm TMS/DMSO-d6): 1.27 (3H, t, J=7.3 Hz), 1.55 (9H, s), 3.03 (2H, q, J=7.3), 12.30 (1H, brs)

To a mixture of 6-(ethylthio)-3-t-butyl-1,3,5-triazine-2,4(1H,3H)-dion (22.93 g, 100 mmol), 4-chlorobenzylbromido (22.60 g, 110 mmol) and acetonitrile (200 mL) was added potassium carbonate (17.97 g, 180 mmol), and the mixture was heated at reflux for 3 hours. The reaction mixture was filtered to remove the insoluble. The filtrate was concentrated in vacuo to give 39.9 g of crude 3-t-butyl-1-(4-chlorobenzyl)-6-(ethylthio)-1,3,5-triazine-2,4(1H,3H)-dion as pale brown oil. To the obtained crude product was added trifluoroacetic acid (100 mL) under ice-cooling, and the mixture was stirred at room temperature for 17 hours. The reaction mixture was concentrated in vacuo to give crude residue. The residue was precipitated to give 1-(4-chlorobenzyl)-6-(ethylthio)-1,3,5-triazine-2,4(1H,3H)-dion (29.03 g, Yield: 97%) as pale brown solid.

1H-NMR (δ ppm TMS/d6-DMSO): 1.25 (3H, t, J=7.3 Hz), 3.08 (2H, q, J=7.3 Hz), 5.02 (2H, s), 7.30-7.33 (2H, m), 7.39-7.42 (2H, m), 11.61 (1H, s).

EXAMPLE 24

Preparation of 1-(4-chlorobenzyl)-6-(3-fluoro-4-isopropoxyphenylimino-3-(2-sulfoethyl)-1,3,5-triazinane-2,4-dion (I-0654)

[Chemical Formula 133]

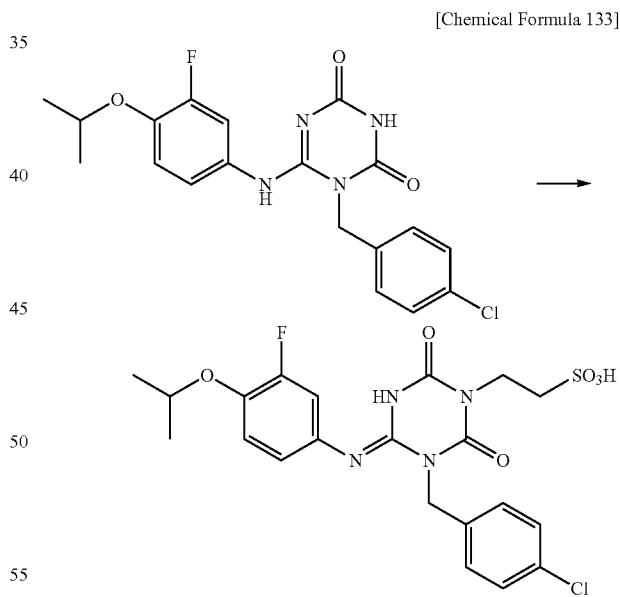

To a mixture of 1-(4-chlorobenzyl)-6-(3-fluoro-4-isopropoxyphenylimino)-3-(2-sulfoethyl)-1,3,5-triazinane-2,4-dion (100 mg, 0.247 mmol) and DMF (2 mL) was added cesium carbonate (105 mg, 0.321 mmol), and the mixture was stirred at room temperature for 5 minutes. Further, 2-bromoethanesulfonic acid sodium (62.5 mg, 0.296 mmol) was added to the mixture, and the resulting mixture was stirred at 120° C. for 1 hour. To the reaction mixture was added 1 mol/L aqueous hydrochloric acid to be acidic. The resulting mixture was extracted with chloroform. The extract was dried over anhydrous magnesium sulfate and concentrated in vacuo. The resulting residue was purified by high speed liquid chromatography (0.3% HCO$_2$H H$_2$O/MeCN 40-70%) to give 1-(4-chlorobenzyl)-6-(3-fluoro-4-isopropoxyphenylimino-3-(2-sulfoethyl)-1,3,5-triazinane-2,4-dion (22 mg, Yield: 17%) as pale brown solid.

1H-NMR (δ ppm TMS/d6-DMSO): 1.26 (6H, d, J=6.1 Hz), 2.62-2.67 (2H, m), 3.93-3.99 (2H, m), 4.54 (1H, sept, J=6.1 Hz), 5.17 (2H, s), 6.90 (1H, m), 7.07-7.12 (2H, m), 7.35-7.42 (4H, m).

EXAMPLE 25

Preparation of 1-(4-chlorobenzyl)-6-(3-fluoro-4-isopropoxyphenylimino-3-(3-sulfopropyl)-1,3,5-triazinane-2,4-dion (I-0645)

[Chemical Formula 134]

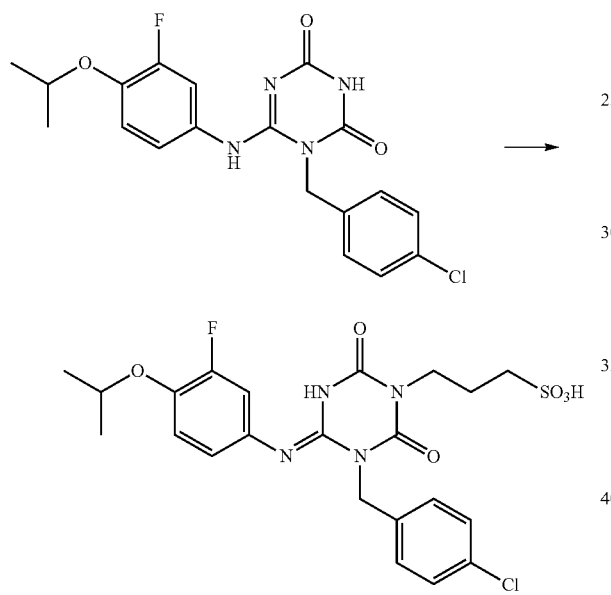

To a mixture of 1-(4-chlorobenzyl)-6-(3-fluoro-4-isopropoxyphenylimino-1,3,5-triazine-(1H,3H)-2,4-dion (200 mg, 0.494 mmol) and DMF (4 mL) was added potassium tert-butoxide (83 mg, 0.741 mmol), and the mixture wan stirred at room temperature for 10 minutes. Further, 1,3-propanesultone (91 mg, 0.741 mmol) was added and the resulting mixture was stirred at 90° C. for 2 hours. To the reaction mixture was added 4 mol/L hydrogen chloride in dioxane (20 mL) to be acidic. The mixture was concentrated in vacuo and the resulting residue was purified by high speed liquid chromatography (0.3% HCO$_2$H H$_2$O/MeCN 40-70%). The resulting residue was precipitated by ethyl acetate to give 1-(4-chlorobenzyl)-6-(3-fluoro-4-isopropoxyphenylimino-3-(3-sulfopropyl)-1,3,5-triazinane-2,4-dion (96 mg, Yield: 37%) as colorless solid.

1H-NMR (δ ppm TMS/DMSO-d6): 1.26 (6H, d, J=6.1 Hz), 1.81 (2H, m), 2.35-2.40 (2H, m), 3.70-3.74 (2H, m), 4.54 (1H, sept, J=6.1 Hz), 5.19 (2H, s), 6.90 (1H, m), 7.07-7.13 (2H, m), 7.34-7.42 (4H, m).

EXAMPLE 26

Preparation of 1-(4-chlorobenzyl)-6-(3-fluoro-4-isopropoxyphenylimino-3-(5-tetrazolylmethyl)-1,3,5-triazinane-2,4-dion (I-1297)

[Chemical Formula 135]

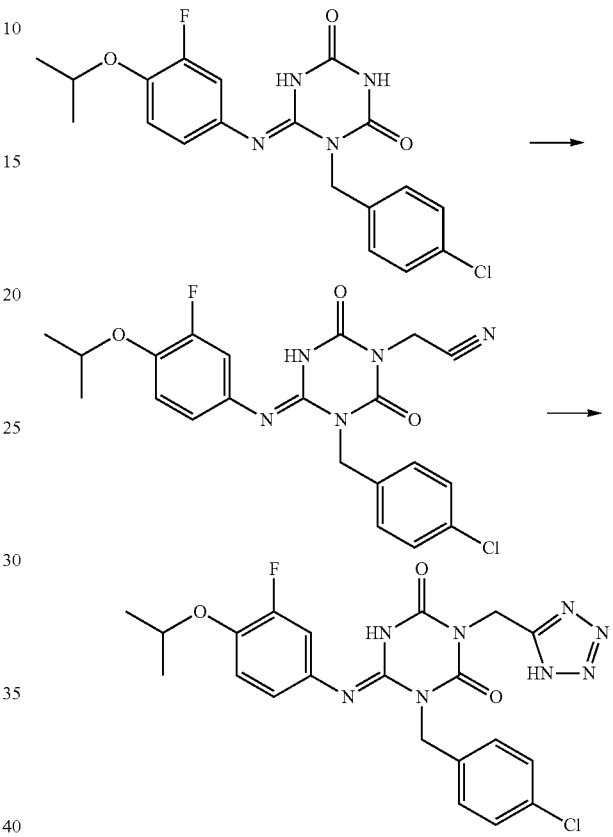

To a mixture of 1-(4-chlorobenzyl)-6-(3-fluoro-4-isopropoxyphenylimino-1,3,5-triazine-(1H,3H)-2,4-dion (1.214 g, 3 mmol), 2-bromoacetonitrile (0.4 g, 3.3 mmol) and DMF (6 mL) was added potassium carbonate (0.54 g, 3.9 mmol), and the mixture was stirred at 60° C. for 1 hour. To the reaction mixture was added water (150 mL), and the mixture was extracted with ethyl acetate (150 mL) The extract was washed by brine (150 mL), dried over anhydrous magnesium sulfate, and concentrated in vacuo. The resulting residue was purified by silica gel column chromatography (ethyl acelate/hexane). The obtained residue was precipitated by ethyl acetate and hexane to give 1-(4-chlorobenzyl)-6-(3-fluoro-4-isopropoxyphenylimino-3-cyanomethyl)-1,3,5-triazinane-2,4-dion (0.78 g, Yield: 59%) as colorless solid.
1H-NMR (δ ppm TMS/CDCl$_3$): 1.37 (6H, d, J=6.1 Hz), 4.47 (1H, sept, J=6.1 Hz), 4.69 (2H, s), 5.18 (2H, s), 6.49 (1H, m), 6.99 (1H, m), 7.32 (2H, d, J=6.6 Hz), 7.49 (2H, d), J=6.6 Hz), 7.74 (1H, s).
To a mixture of 1-(4-chlorobenzyl)-6-(3-fluoro-4-isopropoxyphenylimino-3-cyanomethyl)-1,3,5-triazinane-2,4-dion (0.10 g, 0.23 mmol), ammonium chloride (84 mg, 1.58 mmol) and DMF (2 mL) was added sodium azide (73.2 mg, 1.13 mmol), and the mixture was stirred at 95° C. for 2 hours. To the reaction mixture was added water (150 mL), and the mixture was extracted with ethyl acetate (150 mL).

The extract was washed by brine (150 mL), dried over anhydrous magnesium sulfate, and concentrated in vacuo. The resulting residue was purified by HPLC and the obtained residue was precipitated by ethyl ether to give 1-(4-chlorobenzyl)-6-(3-fluoro-4-isopropoxyphenylimino-3-(5-tetrazolylmethyl)-1,3,5-triazinane-2,4-dion (60 mg, Yield: 55%) as colorless powder.

1H-NMR (δ ppm TMS/DMSO-d6): 1.27 (6H, d, J=5.9 Hz), 4.59 (1H, m), 5.15-5.27 (4H, m), 6.60 (1H, brs), 7.00-7.45 (7H, m), 9.44 (1H, mbrs).

EXAMPLE 27

Preparation of 1-(4-chlorobenzyl)-6-(3-fluoro-4-isopropoxyphenylimino-3-(2-amino-2-hydroxyiminoethyl)-1,3,5-triazinane-2,4-dion (I-0599)

[Chemical Formula 136]

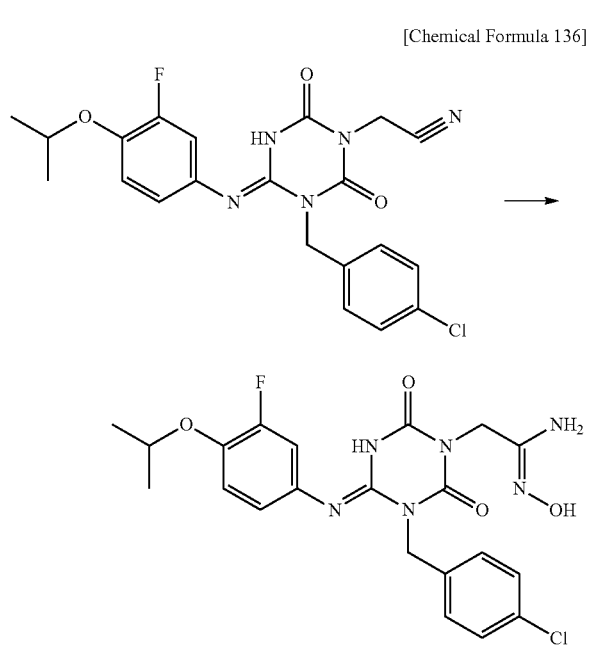

To a mixture of sodium methoxide (34.1 mg, 0.03 mmol) and methanol (2 mL) was added hydroxylamine hydrochloride (43.8 mg, 0.631 mmol) under ice-cooling. After the mixture was neutralized, 1-(4-chlorobenzyl)-6-(3-fluoro-4-isopropoxyphenylimino-3-cyanomethyl)-1,3,5-triazinane-2,4-dion (0.14 g, 0.315 mmol) was added and the resulting mixture was heated at reflux for 2 hours. To the mixture was added water (150 mL) and the mixture was extracted with ethyl acetate (150 mL). The extract was washed by brine (150 mL), dried over anhydrous magnesium sulfate, and concentrated vacuo. The resulting residue was precipitated by ethyl ether to give 1-(4-chlorobenzyl)-6-(3-fluoro-4-isopropoxyphenylimino-3-(2-amino-2-hydroxyiminoethyl)-1,3,5-triazinane-2,4-dion (91 mg, Yield: 61%) as colorless solid.

1H-NMR (δ ppm TMS/DMSO-d6): 1.27 (6H, d, J=5.9 Hz), 4.34 (2H, brs), 4.58 (1H, m), 5.25 (2H, brs), 5.43 (2H, brs), 7.00-7.45 (7H, m), 8.99 (1H, brs), 9.28 (1H, brs).

EXAMPLE 28

Preparation of 1-(4-chlorobenzyl)-6-(3-fluoro-4-isopropoxyphenylimino-3-(5-oxo-4,5-dihyrdo-1,2,4-oxadiazol-3-ylmethyl)-1,3,5-triazinane-2,4-dion (I-0601)

[Chemical Formula 137]

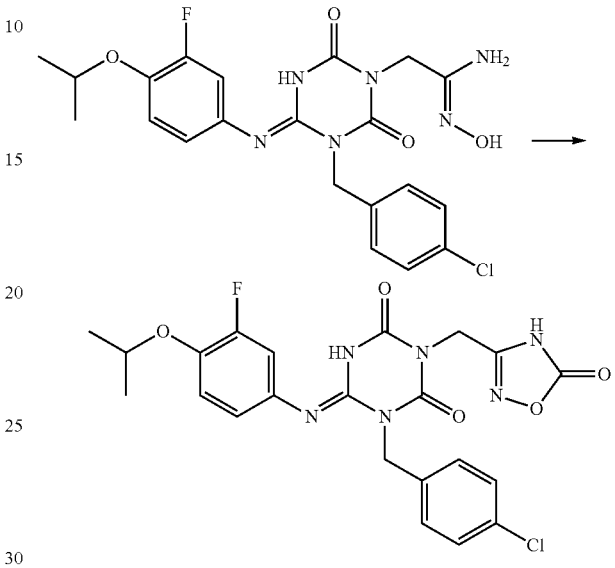

To a mixture of 1-(4-chlorobenzyl)-6-(3-fluoro-4-isopropoxyphenylimino-3-(2-amino-2-hydroxyiminoethyl)-1,3,5-triazinane-2,4-dion (80 mg, 0.17 mmol) and pyridine (2 mL) was added ethyl chlorocarbonate (20 mg, 0.19 in mmol), and the mixture was stirred at room temperature, overnight. Further, the reaction mixture was heated at reflux for 7 hours. The resulting reaction mixture was purified by high speed liquid chromatography (0.3% HCO₂H H₂O/MeCN 40-70%) to give 1-(4-chlorobenzyl)-6-(3-fluoro-4-isopropoxyphenylimino-3-(5-oxo-4,5-dihydro-1,2,4-oxadiazol-3-ylmethyl)-1,3,5-triazinane-2,4-dion (20 mg, Yield: 24%) as colorless amorphous.

1H-NMR (δ ppm TMS/DMSO-d6): 1.27 (6H, d, J=5.9 Hz), 4.60 (1H, sept, J=5.9 Hz), 4.86 (2H, s), 5.27 (2H, s), 7.00-7.50 (7H, m), 9.44 (1H, brs), 12.48 (1H, brs).

EXAMPLE 29

Preparation of (R)-1-(4-chlorobenzyl)6-(3-chloro-4-isopropoxyphenylamino)-3-(2,3-dihydroxypropyl)-1,3,5-triazinane-2,4-dion (I-0638)

[Chemical Formula 138]

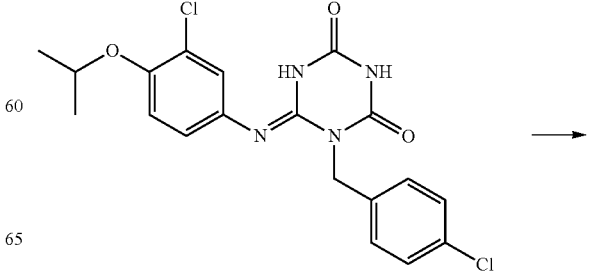

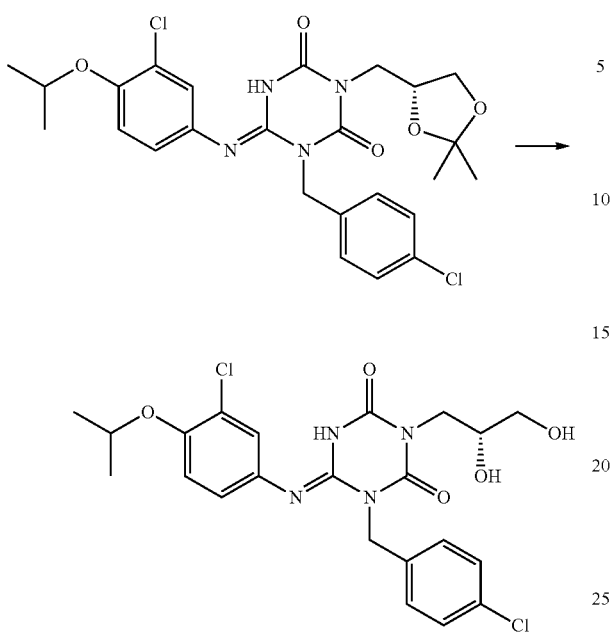

A mixture of 1-(4-chlorobenzyl)6-(3-chloro-4-isopropoxyphenylamino)-1,3,5-triazinane-2,4-dion (300 mg, 0.712 mmol), (S)-4-(bromomethyl)-2,2-dimethyl-1,3-dioxolane (222 mg, 1.14 mmol), potassium tert-butoxide (176 mg, 1.57 mmol) and DMF (6 mL) was stirred at 60° C. for 16 hours. To the reaction mixture was added water, and the mixture was extracted with ethyl acetate. The extract was washed by water, dried over anhydrous sodium sulphate, and concentrated in vacuo. The resulting residue was purified by silica gel column chromatography (ethyl acetate/hexane) to give (R)-1-(4-chlorobenzyl)6-(3-chloro-4-isopropoxyphenylamino)-3-[2,2-dimethyl-1,3-dioxolane4-yl)methyl]-1,3,5-triazinane-2,4-dion (116 mg, Yield: 30%) as colorless solid.

1H-NMR (δ ppm TMS/DMSO-d6): 1.23-1.32 (12H, m), 3.73-3.76 (2H, m), 3.94-3.98 (2H, m), 4.24-4.26 (1H, m), 4.64 (1H, brs), 5.25 (2H, s), 7.16-7.25 (2H, m), 7.88-7.47 (5H, m), 9.30 (1H, s).

To a solution of (R)-1-(4-chlorobenzyl)6-(3-chloro-4-isopropoxyphenylamino)-3-[2,2-dimethyl-1,3-dioxolane4-yl)methyl]-1,3,5-triazinane-2,4-dion (110 mg, 0.205 mmol) in methanol (4 mL) was added p-toluenesulfonic acid monohydrate (59 mg, 0.31 mmol), and the mixture was stirred at. room temperature for 5 hours. The reaction mixture was concentrated, and the residue was extracted with ethyl acetate. The extract was washed by water, dried over anhydrous sodium sulphate, and concentrated in vacuo. The resulting residue was precipitated by dichloromethane and hexane to give (R)-1-(4-chlorobenzyl)6-(3-chloro-4-isopropoxyphenylamino)-3-(2,3-dihydroxypropyl)-1,3,5-triazinane-2,4-dion (88 mg, Yield: 86%) as colorless solid.

1H-NMR (δ ppm TMS/DMSO-d6): 1.28 (6H, d, J=5.6 Hz), 3.68-3.84 (4H, m), 4.54 (1H, brs), 4.73 (1H, brs), 5.25 (2H, s), 7.16-7.25 (2H, m), 7.38-7.46 (5H, m), 9.23 (1H, s).

EXAMPLE 30

Preparation of 6-(3-chloro-4-isopropoxyphenylamino)-3-(2,3-ethoxycarbonylethyl)-1-(4-methylbenzyl)-1,3,5-triazinane-2,4-dion (I-0866)

[Chemical Formula 139]

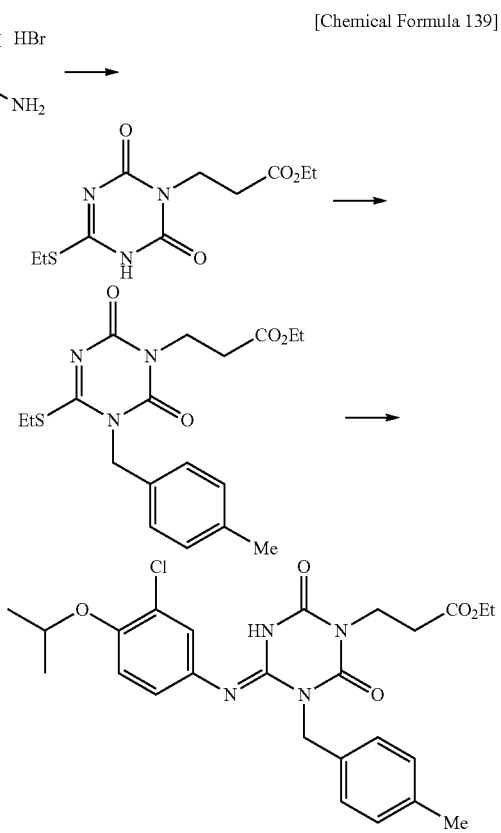

To a mixture of S-ethylisothiourea hydrobromide (6.00 g, 32.4 mmol) and DMF (30 mL) were added ethyl 6-isocyanatocaproate (4.48 mL, 34.0 mmol) and DBU (5.13 mL, 34.0 mmol) under ice-cooling, and the mixture was stirred under ice-cooling for 5 hours. To the reaction mixture were added 1,1'-carbonyldiimidazole (6.31 g, 38.9 in mmol) and DBU (7.33 mL, 49.0 mmol) under ice-cooling, and the mixture was stirred at room temperature for 1 hour. To the reaction mixture was added 2 mol/L hydrochloric acid (96 mL) under ice-cooling over 15 minutes, and the mixture was enacted with ethyl acetate. The extract was washed by water and brine, dried over anhydrous sodium sulphate. The extract was concentrated in vacuo to give 6-(ethylthio)-3-(2-ethoxycarbonylethyl)-1,3,5-triazine-2,4(1H,3H)-dion (7.86 g, Yield: 89%) as colorless solid.

1H-NMR (δ ppm TMS/CDCl3): 1.22 (3H, t, J=7.1 Hz), 1.33 (3H, t, J=7.3 Hz), 2.67 (2H, t, J=7.2 Hz), 3.16 (2H, q, J=7.3 Hz), 4.07-4.17 (4H, m).

To the mixture of 6-(ethylthio)-3-(2-ethoxycarbonylethyl)-1,3,5-triazine-2,4(1H,3H)-dion (4.00 g, 14.6 mmol), 4-methylbenzylbromide (3.25 g, 17.6 mmol) and acetonitrile (80 mL) was added potassium carbonate (3.03 g, 22.0 mmol), and the mixture was heated at reflux for 2 hours. The reaction mixture was filtered off to remove insoluble, and concentrated in vacuo. The resulting residue was purified by silica gel column chromatography (ethyl acetate/hexane) to give 6-(ethylthio)-3-(2-ethoxycarbonylethyl)-1-(4-methylbenzyl)-1,3,5-triazine-2,4(1H,3H)-dion (5.10 g, Yield: 92%) as pale yellow solid.

1H-NMR (δ ppm TMS/CDCl3): 1.25 (3H, t, J=7.1 Hz), 1.37 (3H, t, J=7.4 Hz), 2.35 (3H, s), 2.71 (2H, t, J=7.3 Hz), 3.21 (2H, q, J=7.4 Hz), 4.12 (2H, q, J=7.1 Hz), 4.24 (2H, t, J=7.3 Hz), 5.09 (2H, s), 7.36 (4H, d, J=8.2 Hz), 7.28 (4H, d, J=8.2 Hz).

A mixture of 6-(ethylthio)-3-(2-ethoxycarbonylethyl)-1,3,5-triazine-2,4(1H,3H)-dion (398 mg, 1.05 mmol), 3-chloro-4-isopropoxyaniline (294 mg, 1.58 mmol), acetic acid (0.905 mL) and t-butanol (4 mL) was heated at reflux for 5 hours. To the reaction mixture was added saturated aqueous sodium bicarbonate, and the mixture was extracted with ethyl acetate. The extract was washed by brine, dried over anhydrous sodium sulphate, and concentrated in vacuo. The resulting residue was purified by silica gel column chromatography (ethyl acetate/hexane) to give 6-(3-chloro-4-isopropoxyphenylimino)-3-(2-ethoxycarbonylethyl)-1-(4-methylbenzyl)-1,3,5-triazinane-2,4-dion (393 mg, Yield: 74%) as pale pink solid.

1H-NMR (δ ppm TMS/DMSO-d6): 1.13-1.20 (3H, m), 1.28 (6H, d, J=6.1 Hz), 2.28 (3H, s), 2.55 (2H, t, J=6.9 Hz), 3.33-3.39 (2H, m), 3.98-4.06 (2H, m), 4.60-4.62 (1H, m), 5.21 (2H, s), 7.12-7.23 (6H, m), 7.41-7.46 (1H, m), 9.26 (1H, brs).

EXAMPLE 31

Preparation of 6-(3-chloro-4-isopropoxyphenylimino)-3-(2-hydroxycarbonylethyl)-1-(4-methylbenzyl)-1,3,5-triazinane-2,4-dion (I-0896)

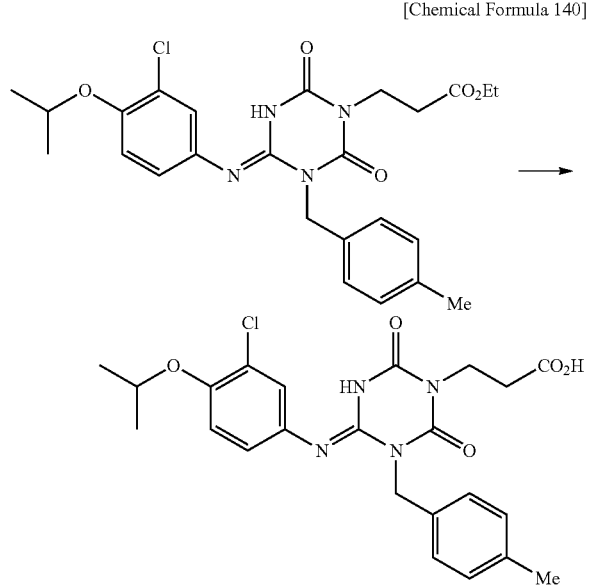

To a mixture of 6-(3-chloro-4-isopropoxyphenylimino)-3-(2-ethoxycarbonylethyl)-1-(4-methylbenzyl)-1,3,5-triazinane-2,4-dion (371 mg, 0.741 mmol), methanol (2 mL) and THF (2 mL) was added 1 mol/L lithium hydroxide (2.4 mL, and the mixture was stirred at room temperature for 15 hours. The reaction mixture was concentrated. To the reaction mixture was added 2 mol/L hydrochloric acid (1.3 mL). The precipitated crystalline was filtered off, and the residue was precipitated by ethyl acetate/hexane to give 6-(3-chloro-4-isopropoxyphenylimino)-3-(2-hydroxycarbonylethyl)-1-(4-methylbenzyl)-1,3,5-triazinane-2,4-dion (247 mg, Yield: 71%) as colorless solid.

1H-NMR (δ ppm TMS/DMSO-d6): 1.28 (6H, d, J=5.8 Hz), 2.28 (3H, s), 2.49-2.52 (2H, m), 3.93-3.96 (2H, m), 4.59-4.62 (1H, m), 5.19 (2H, s), 7.12-7.23 (7H, m).

EXAMPLE 32

Preparation of 1-(4-chlorobenzyl)-6-(3-fluoro-4-isopropoxyphenylimino)-3-(2-hydrazinecarbonylethyl)-1,3,5-triazinane-2,4-dion (I0644)

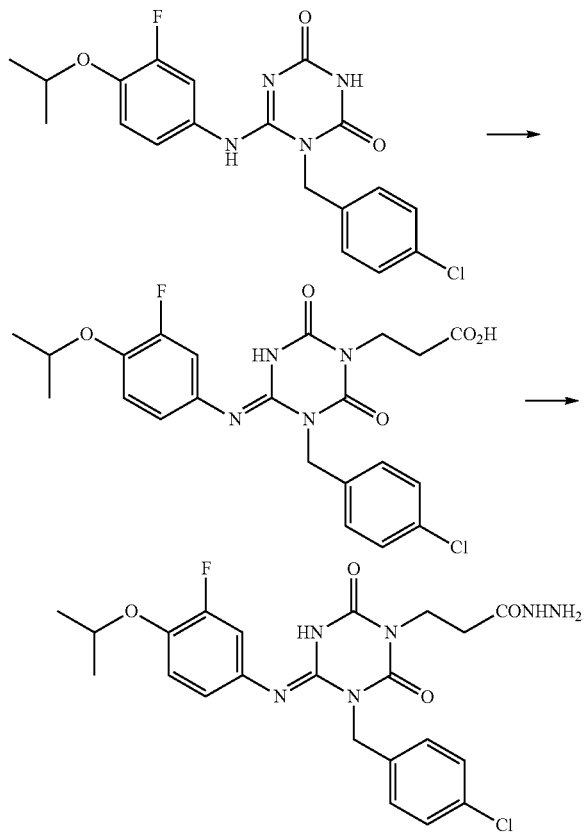

To a mixture of 1-(4-chlorobenzyl)-6-(3-fluoro-4isopropoxyphenylimino)-1,3,5-triazine-2,4(1H,3H)-dion (2g, 4.94 mmol) and DMF (30 mL) was added potassium tert-butoxide (1.331 g, 11.86 mmol) at room temperature and the resulting mixture was stirred for 5 minutes. Further, to tho reaction mixture was added methylacrylate (1.074 mL, 11.86 mmol), and the resulting mixture was stirred at 60° C. for 1.5 hours. To the reaction mixture were added potassium tert-butoxide (0.554 g, 4.94 mmol) and methylacrylate (0.448 mL, 4.94 mmol), and the resulting mixture was stirred at 60° C. for 2 hours. Water (0.5 mL) was added to the mixture and the resulting mixture was stirred at 80° C. for 2 hours. The reaction mixture was concentrated in vacuo and 2 mol/L aqueous hydrochloric acid (80 mL) was added to the resulting residue. The mixture was extracted with ethyl acetate (50 mL×3). The extract was washed hy brine (100 mL), dried over anhydrous sodium sulphate, and concentrated in vacuo. The resulting residue was purified by silica gel column chromatography (methanol/chloroform). The resulting residue was precipitated by ethyl acetate and hexane to give 1-(4-chlorobenzyl)-6-(3-fluoro-4-isopropoxyphenylimino)-3-(2-hydroxycarbonylethyl)-1,3,5-triazinane-2,4-dion (1.64 g, Yield: 70%) as colorless solid.
1H-NMR (δ ppm TMS/CDCl$_3$): 1.37 (6H, d, J=6.1 Hz), 2.71 (2H, t, J=7.2 Hz), 4.16 (2H, t, J=7.2 Hz), 1.47 (1H, sept, J=6.1 Hz), 5.17 (2H, s), 6.50 (1H, br. d, J=8.8 Hz), 6.60 (1H, br. d, 11.1 Hz), 6.97 (1H, t, J=8.8 Hz), 7.31 (2H, d, J=8.2 Hz), 7.48 (2H, d, J=8.2 Hz), 7.57 (1H, br. s).

To a mixture of 1-(4-chlorobenzyl)-6-(3-fluoro-4-isopropoxyphenylimino)-3-(2-hydroxycarbonylethyl)-1,3,5triazinane-2,4-dion (300 mg, 0.629 mmol), O-(7-azabenzotriazol1-yl)-N,N,N',N'-tetramethyluronium hexafluorophosphate (287 mg, 0.755 mmol), triethylamine (0.13 mL, 0.94 mmol) and DMF (6 mL) was added hydrazine monohydrate (0.015 g, 0.21 mmol), and the mixture was stirred at room temperature overnight. The mixture wee added to water (200 mL), and the resulting mixture was extracted with ethyl acetate (300 mL). The extract was washed by brine (200 mL), dried over anhydrous magnesium sulfate, and concentrated in vacuo. The resulting residue was purified by high speed liquid chromatography (0.3% HCO$_2$H H$_2$O/MeCN 40-70%). The resulting residue was precipitated by ethyl acetate and hexane to give 1-(4-methylbenzyl)-6-(3-fluoro-4-isopropoxyphenylimino)-3-(2-hydrazinecarbonylethyl)-1,3,5-triazinane-2,4-dion (184 mg, Yield: 60%) as colorless solid.
1H-NMR (δ ppm TMS/CDCl$_3$): 1.31 (6H, m), 2.55 (4H, m), 4.08 (2H, m), 4.42 (1H, m), 5.16 (1H, m), 6.48 (2H, m), 6.90 (2H, m), 7.28 (2H, m), 7.40 (1H, m).

EXAMPLE 33

Preparation of 1-(4-methylbenzyl)-6-(3-fluoro-4-isopropoxyphenylimino)-3-(5-oxo-4,5-dihyrdo-1,3,4-oxadiazol-2-yl)methyl)-1,3,5-triazinane-2,4-dion (I-0646)

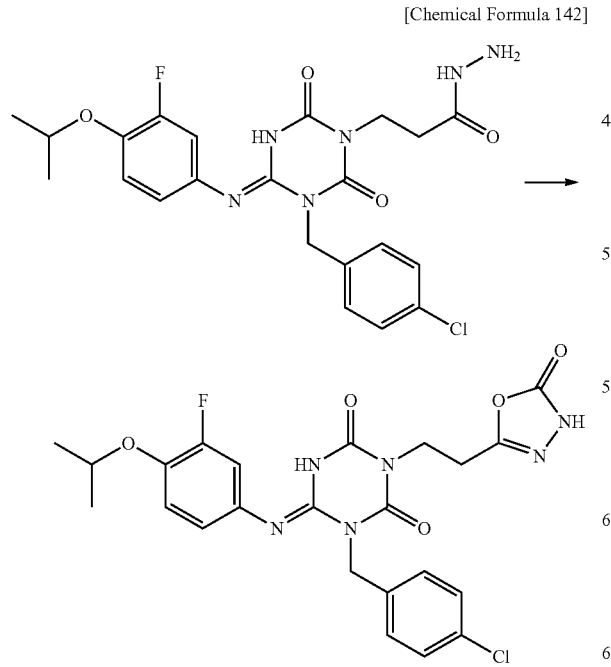

[Chemical Formula 142]

To a mixture of 1-(4-chlorobenzyl)-6-(3-fluoro-4-isopropoxyphenylimino)-3-(2-hydrazinecarbonylethyl)-1,3,5-triazinane-2,4-dion (134.6 mg, 0.274 mmol) and DMF (2 mL) was added 1,1'-carbonyldiimidazole (53.3 mg, 0.329 mmol), and the mixture was stirred at room temperature overnight. The mixture was added to water (200 mL), and extracted with ethyl acetate (300 mL). The extract was washed by brine (200 mL), dried over anhydrous magnesium sulfate, and concentrated in vacuo. The resulting residue was precipitated by hexane to give 1-(4-chlorobenzyl)-6-(3-fluoro-4-isopropoxyphenylimino)-3-(5-oxo-4,5-dihyrdo-1,3,4-oxadiazol-2-yl)methyl)-1,3,5-triazinane-2,4-dion (113 mg, Yield: 80%) as colorless powder.
1H-NMR (δ ppm TMS/CDCl$_3$): 1.37 (6H, d, J=6.1 Hz), 2.89 (2H, m), 4.16 (2H, m), 4.48 (1H, sept, J=6.0 Hz), 5.16 (2H, s), 6.49-6.62 (2H, m), 6.98 (1H, t, J=9.0 Hz), 7.31-7.48 (4H, m), 8.00-8.40 (1H, m).

EXAMPLE 34

Preparation of 1-(4-chlorobenzyl)-6-(3-fluoro-4-isopropoxyphenylimino)-3-[2-(1,2,4-triazol-5-yl)ethyl]-1,3,5-triazinane-2,4-dion (I-0672)

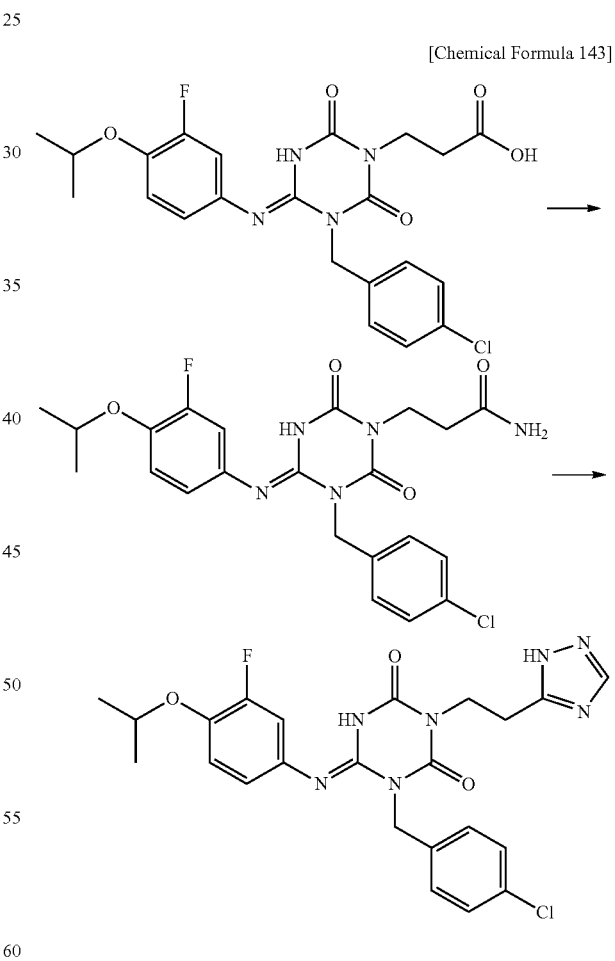

[Chemical Formula 143]

To a mixture of 1-(4-chlorobenzyl)-6-(3-fluoro-4-isopropoxyphenylimino)-3-(2-hydroxycarbonylethyl)-1,3,5-triazinane-2,4-dion (2.86 g, 6 mmol) and DMF (20 mL) were added ammonium chloride (0.385 g, 7.20 mmol), 1-hydroxybenzotriazole hydrate (1.011 g, 6.60 mmol), 4-dimethylaminopyridine (0.073 g, 0.600 mmol), 1-(3-dimethylaminopropyl)-3-ethylcarbodiimide hydrochloride (1.265 g, 6.60 mmol) and triethylamine (0.998 mL, 7.20 mmol), and the mixture was stirred at room temperature for 3 hours. The reaction mixture was poured into water (200 mL), and the mixture was extracted with ethyl acetate (200 mL). The extract was washed by saturated aqueous sodium bicarbonate (200 mL) and brine (200 mL), dried over anhydrous sodium sulphate, and concentrated in vacuo. The resulting residue was precipitated by ethyl acetate and hexane to give 1-(4-chlorobenzyl)-6-(3-fluoro-4-isopropoxyphenylimino)-3-(2-carbamoylethyl)-1,3,5-triazinane-2,4-dion (2.29 g, 84%) as colorless solid.
1H-NMR (δ ppm TMS/DMSO-d6): 1.28 (6H, d, J=6.1 Hz), 2.34 (2H, t, J=7.6 Hz), 3.90 (2H, t, J=7.6 Hz), 4.55 (1H, m), 5.22 (2H, brs), 6.50 (1H, brs), 6.84 (brs), 7.00-7.40 (7H, m), 9.25 (1H, brs).
A mixture of 1-(4-chlorobenzyl)-6-(3-fluoro-4-isopropoxyphenylimino)-3-(2-carbamoylethyl)-1,3,5-triazinane-2,4-dion (150 mg, 0.315 mmol) and N,N-dimethylformamide dimethyl acetal (2 mL) was stirred at: 80° C. for 1.5 hours. The reaction mixture was concentrated in vacuo. To the residue were added acetic acid (1 mL) and hydrazine monohydrate (0.046 mL, 0.944 mmol), and the mixture was stirred at 90° C. for 0.5 hour. The reaction mixture was poured into water (200 mL), and the resulting mixture was extracted with chloroform (200 mL×2). The extract was dried over anhydrous sodium sulphate, and concentrated in vacuo. The resulting residue was precipitated by ethyl acetatate and hexane to give 1-(4-chlorobenzyl)-6-(3-fluoro-4-isopropoxyphenylimino)-3-[2-(1,2,4-triazol-5-yl)ethyl]-1,3,5-triazinane-2,4-dion (75.3 mg, Yield: 48%) as colorless powder.
1H-NMR (δ ppm TMS/CDCl₃): 1.37 (6H, d, J=6.3 Hz), 3.20 (2H, t, J=6.3 Hz), 4.24 (2H, t, J=6.4 Hz), 4.47 (1H, sept, J=5.9 Hz), 5.14 (2H, s), 6.48-6.52 (1H, m), 6.59 (1H, dd, J=11.7, 2.6 Hz), 6.97 (1H, t, 8.5 Hz), 7.30 (2H, d, J=8.2 Hz), 7.46 (2H, d, J=8.2 Hz), 7.78-7.89 (1H, m), 11.2 (1H, brs).

EXAMPLE 35

Preparation of 1-(4-chlorobenzyl)-6-(3-fluoro-4-isopropoxyphenylimino)-3-[2-(cyanocarbamoyl)ethyl]-1,3,5-triazinane-2,4-dion (I-0758)

[Chemical Formula 144]

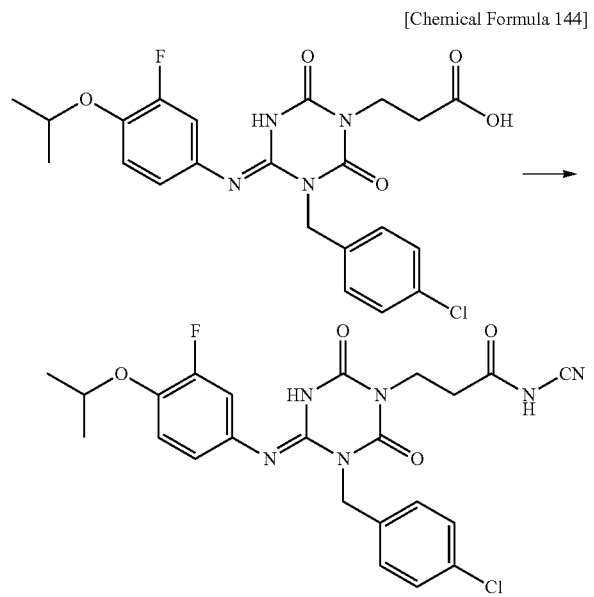

To a mixture of 1-(4-chlorobenzyl)-6-(3-fluoro-4-isopropoxyphenylimino)-3-[2-(cyanocarbamoyl)ethyl]-1,3,5-triazinane-2,4-dion (300 mg, 0.629 mmol), triethylamine (0.105 mL, 0.755 mmol) and DMF (3 mL), methyl chlorocarbonate (0.063 mL, 0.755 mmol) was added under ice-cooling, and the resulting mixture was stirred at 0° C. for 2 hours. To the mixture were added cyanamide monosodium salt (121 mg, 1.89 mmol) and 4-methylaminopyridine (23 mg, 0.19 mmol), and the resulting mixture was stirred at room temperature for 3 hours. The reaction mixture was poured into water (200 mL), and the resulting mixture was extracted with ethyl acetate (200 mL). The extract was washed by brine (200 mL), dried over anhydrous sodium sulphate, and concentrated in vacuo. The resulting residue was purified by high speed liquid chromatography (0.3% HCO₂H H₂O/MeCN 40-70%) to give 1-(4-chlorobenzyl)-6-(3-fluoro-4-isopropoxyphenylimino)-3-[2-(cyanocarbamoyl)ethyl]-1,3,5-triazinane-2,4-dion (20 mg, Yield: 6%) as colorless solid.
1H-NMR (δ ppm TMS/DMSO-d6): 1.26 (6H, d, J=5.8 Hz), 2.50 (2H, m), 3.93-3.97 (2H, m), 4.42-4.64 (1H, m), 5.06, 5.22 (2H, s), 6.43-6.60 (1H, m), 7.01-7.10 (2H, m), 7.28-7.43 (4H, m), 9.26 (1H, s).

EXAMPLE 36

Preparation of 1-(4-chlorobenzyl)-6-(3-methyl-4-isopropoxyphenylimino)-3-(4-methoxycarbonyl-2-oxazolyl)-1,3,5-triazinane-2,4-dion (I-0780)

[Chemical Formula 145]

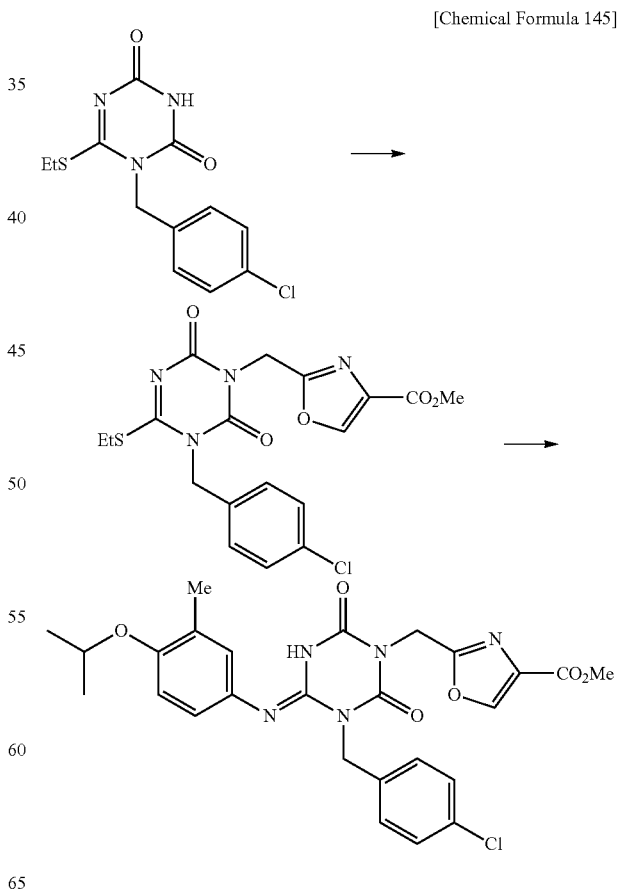

To a mixture of 1-(4-chlorobenzyl)-6-(ethylthio)-1,3,5-triazine-2,4(1H,3H)-dion (300 mg, 1.01 mmol) and DMF (3 mL) were added potassium carbonate (167 mg, 1.21 mmol) and methyl 2-(chloromethyl)-1,3-oxazole-4-carboxylate (212 mg, 1.21 mmol), and the resulting mixture was stirred at 70° C. for 2 hours. The reaction mixture was poured into water (200 mL), and the resulting mixture was extracted with ethyl acetate (200 mL). The extract was washed by brine (200 mL), dried over anhydrous magnesium sulfate, and concentrated in vacuo to give 1-(4-chlorobenzyl)-6-(ethylthio)-3-(4-methoxycarbonyl-2-oxazolyl)-1,3,5-triazinane-2,4-dion (520 mg) as crude product as yellow amorphous.

To the obtained crude 1-(4-chlorobenzyl)-6-(ethylthio)-3-(4-methoxycarbonyl-2-oxazolyl)-1,3,5-triazinane-2,4-dion were added 3-methyl-4-isopropoxyaniline (248 mg, 1.5 mmol), t-butyl alcohol (8 mL) and acetic acid (0.86 mL), and the resulting mixture was heated under reflux for 5 hours. The reaction mixture was poured into saturated aqueous sodium bicarbonate (100 mL ), and extracted with ethyl acetate (100 mL). The extract was washed by saturated aqueous sodium bicarbonate (100 mL) and brine (100 mL), dried aver anhydrous magnesium sulfate, and concentrated in vacuo. The resulting residue was purified by silica gel column chromatography (ethyl acetate/hexane) to give 1-(4-chlorobenzyl)-6-(3-methyl-4-isopropoxyphenylimino)-3-(4-methoxycarbonyl-2-oxazolyl)-1,3,5-triazinane-2,4-dion (535 mg, Yield: 99%) as colorless amorphous.

1H-NMR (δ ppm TMS/CDCl$_3$): 1.31, 1.35 (6H, d, J=6.1 Hz), 2.15, 2.20 (3H, s), 3.91 (3H, s), 4.47 (1H, sept, J=6.1 Hz), 5.17, 5.19, 5.23, 5.32 (4H, m), 6.57-6.63 (2H, m), 6.82-6.88 (1H, m), 7.28-7.34 (2H, m), 7.45-7.53 (2H, m), 8.17 (1H, s).

EXAMPLE 37

Preparation of 1-(4-chlorobenzyl)-6-(3-methyl-4-isopropoxyphenylimino)-3-(4-hydroxycarbonyl-2-oxazolyl)-1,3,5-triazinane-2,4-dion (I-0800)

[Chemical Formula 146]

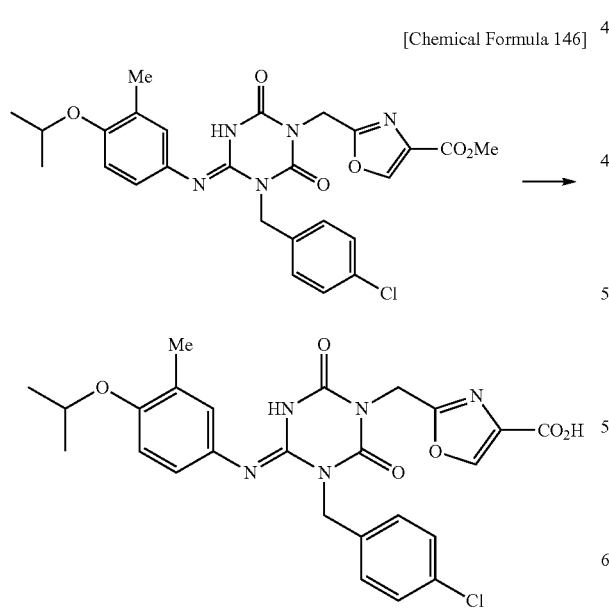

To a mixture of 1-(4-chlorobenzyl)-6-(3-mehyl-(4-isopropoxyphenylimino-3-(4-methoxycarbonyl-2-oxazolyl)-1,3,5-triazinane-2,4-dion (520 mg, 0.963 mmol), methanol (5 mL), and water (2.5 mL) was added 4 mol/L lithium hydroxide (0.722 mL), and the resulting mixture was stirred at room temperature for 2 hours. To the mixture were added water (100 mL) and 2 mol/L hydrochloric acid (10 mL), and the resulting mixture was extracted with ethyl acetate (300 mL). The extract was washed by brine (100 mL), dried over anhydrous magnesium sulfate, and concentrated in vacuo. The resulting residue was precipitated by ethyl acetate and hexane to give 1-(4-chlorobenzyl)-6-(3-mehyl-(4-isopropoxyphenylimino-3-(4-hydroxycarbonyl-2-oxazolyl)-1,3,5-triazinane-2,4-dion (370 mg, Yield: 73%) as colorless solid.

1H-NMR (δ ppm TMS/CDCl$_3$): 1.35 (6H, d, J=5.9 Hz), 2.19 (3H, s), 4.47 (1H, sept, J=5.9 Hz), 5.20 (2H, s), 5.20 (2H, s), 6.64-6.81 (3H, m), 7.31-7.59 (4H, m), 8.26 (1H, s).

EXAMPLE 38

Preparation of 1-(4-chlorobenzyl)-6-(3-fluoro-4-isopropoxyphenylimino)-3-(4-cyanoimino-4-phenoxy-3-isobutyl)-1,3,5-triazinane-2,4-dion (I-0652)

[Chemical Formula 147]

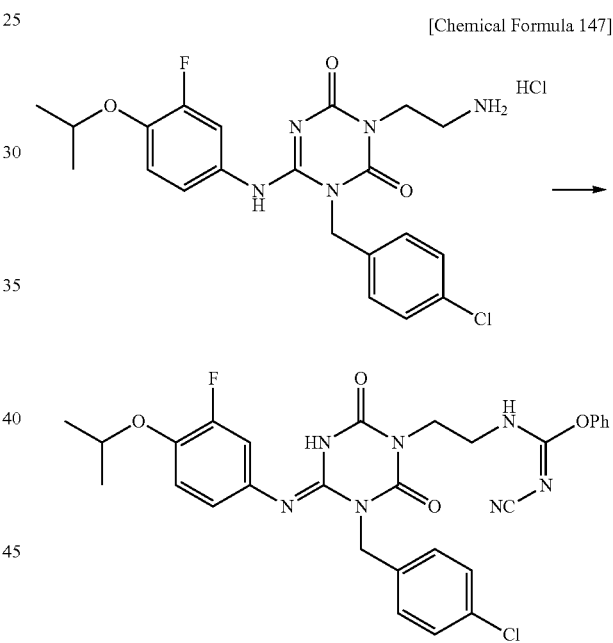

To a mixture of 3 -(2-aminoethyl)-1-chlorobenzyl)-6-(3-fluoro-4-isopropoxyphenylimino)-1,3,5-triazinane-2,4-dion hydrochloride (200 mg, 0.413 mmol) and ethyl ether (8 mL) were added triethylamine (0.126 mL, 0.908 mmol) and diphenyl-N-cyanocarbonimidate (216 mg, 0.908 mmol) , and the resulting mixture was stirred at room temperature for 1 hour. The reaction mixture was concentrated in vacuo. The resulting residue was purified by silica gel column chromatography (ethyl acetate/hexane) to give 1-(4-chlorobenzyl)-6-(3-fluoro-4-isopropoxyphenylimino)-3-(4-cyanoimino-4-phenoxy-3-azabutyl)-1,3,5-triazinane-2,4-dion (170 mg, Yield: 70%) as colorless solid.

1H-NMR (δ ppm TMS/CDCl$_3$): 1.40 (6H, d, J=6.0 Hz), 3.70 (2H, m), 4.07 (2H, m), 4.49 (1H, sept, J=6.0 Hz), 5.17 (2H, s), 6.47-6.61 (1H, m), 6.94 (1H, t, J=8.7 Hz), 7.16-7.20 (4H, m), 7.30-7.46 (4H, m), 7.79 (1H, m) 8.25 (1H, s).

EXAMPLE 39

Preparation of 1-(4-chlorobenzyl)-6-(3-fluoro-4-isopropoxyphenylimino)-3-(4-cyanoimino-4-methylamino-3-azabutyl)-1,3,5-triazinane-2,4-dion (I-0653)

[Chemical Formula 148]

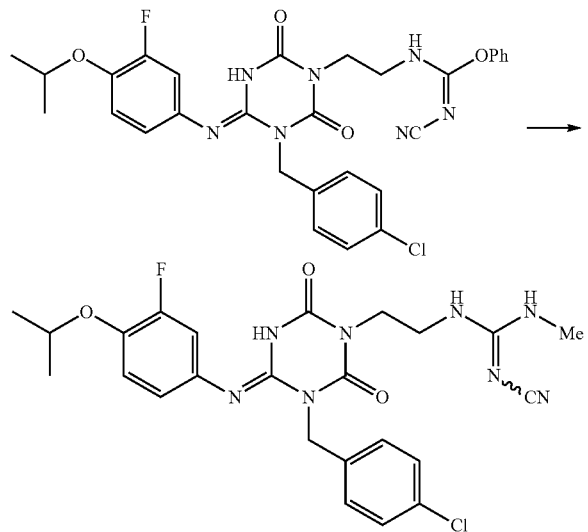

To a mixture of 1-(4-chlorobenzyl)-6-(3-fluoro-4-isopropoxyphenylimino)-3-(4-cyanoimino-4-phenoxy-3-azabutyl)-1,3,5-triazinane-2,4-dion (155 mg, 0.262 mmol), 2-propanol (2 mL) and ethyl acetate (1 mL) was added 2 mol/L methylamine in THF (1.964 mL, 3.93 mmol), and the resulting mixture was stirred at room temperature overnight. The reaction mixture was concentrated in vacuo. The resulting residue was purified by silica gel column chromatography (ethyl acetate/hexane). The resulting residue was precipitated by ethyl acetate and hexane to give 1-(4-chlorobenzyl)-6-(3-fluoro-4-isopropoxyphenylimino)-3-(4-cyanoimino-4-phenoxy-3-azabutyl)-1,3,5-triazinane-2,4-dion (135 mg, Yield: 98%) as colorless solid.

1H-NMR (δ ppm TMS/CDCl$_3$): 1.37 (6H, d, J=5.9 Hz), 2.71-2.84 (3H, m), 3.47-3.56 (2H, m), 4.01-4.16 (2H, m), 4.48 (1H, sept, J=5.9 Hz), 5.18-5.27 (2H, m), 5.40-5.46 (1H, m), 6.57-6.68 (1H, m), 6.80-7.02 (2H, m), 7.32 (2H, d, J=8.4 Hz), 7.49 (2H, d, J=8.4 Hz), 7.73 (1H, br. s).

EXAMPLE 40

Preparation of 1-(4-chlorobenzyl)-6-(3-fluoro-4-isopropoxyphenylimino)-3-(4-imino-4-amino-3-azabutyl)-1,3,5-triazinane-2,4-dion (I-0659)

[Chemical Formula 149]

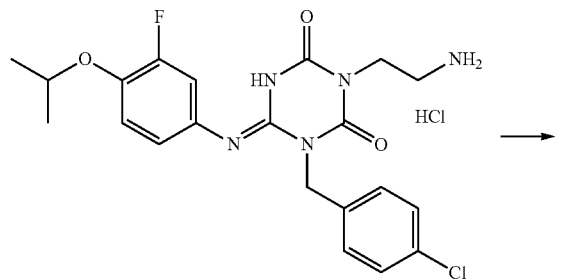

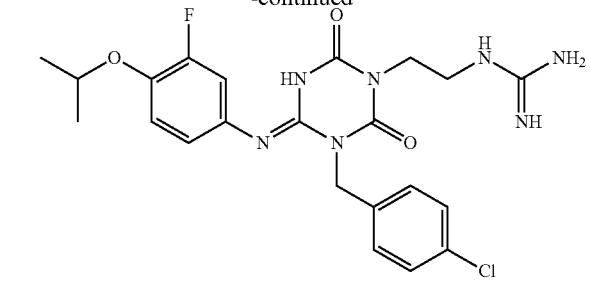

To a mixture of 3-(2-aminoethyl)-1-(4-chlorobenzyl)-6-(3-fluoro-4-isopropoxyphenylimino)-1,3,5-triazinane-2,4-dion hydrochloride (150 mg, 0.31 mmol) and DMF (3 mL) were added diisopropylethylamine(0.270 mL, 1.548 mmol) and 1H-pyrazole-1-carboxyimidate hydrochloride (136 mg, 0.929 mmol), and the resulting mixture was stirred at room temperature for 1 hour. The reaction mixture was poured into water (200 mL) and extracted with ethyl acetate (300 mL). The extract was washed by brine (200 mL), dried over anhydrous magnesium sulfate, and concentrated in vacuo. The resulting residue was purified by high speed liquid chromatography (0.3% HCO$_2$H H$_2$O/MeCN 40-70%).

The resulting residue was precipitated by ethyl acetate to give 1-(4-chlorobenzyl)-6-(3-fluoro-4-isopropoxyphenylimino)-3-(4-imino-4-amino-3-azabutyl)-1,3,5-triazinane-2,4-dion (96 mg, Yield: 63%) as flesh color solid.

1H-NMR (δ ppm TMS/DMSO-d6): 1.22 (6H, d, J=6.1 Hz), 3.19 (2H, m), 3.70 (2H, t, J=6.25 Hz), 4.35 (1H, sept, J=5.9 Hz), 5.09 (2H, s), 6.65-6.68 (1H, m), 6.84 (1H, t, J=9.0 Hz), 7.07 (1H, dd, J=14.3, 2.4 Hz), 7.17 (2H, brs), 7.30-7.38 (4H, m), 7.59 (1H, m).

EXAMPLE 41

Preparation of 1-(4-chlorobenzyl)-6-(3-fluoro-4-isopropoxyphenylimino)-3-(6-methoxy-3-pyridyl)methyl)-1,3,5-triazinane-2,4-dion (I-0641)

[Chemical Formula 150]

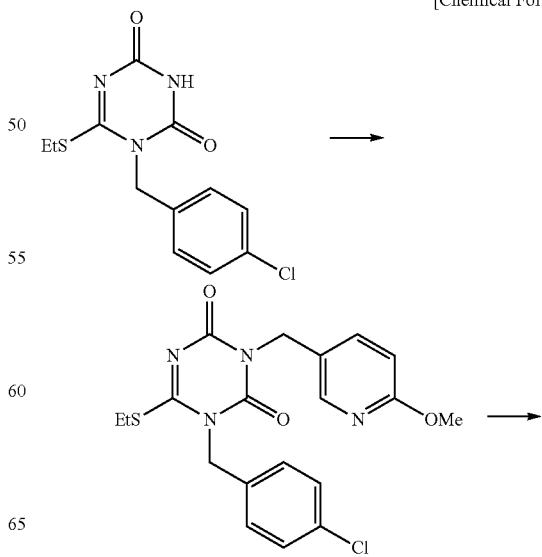

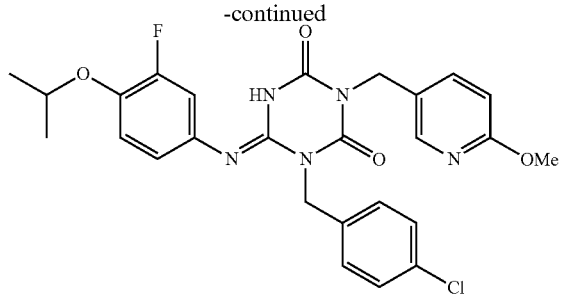

To a mixture of 1-(4-chlorobenzyl)-6-(Ethylthio)-1,3,5-triazine-2,4(1H,3H)-dion (0.5 g, 1.68 mmol), (6-methoxy-3-pyridyl)methanol (0.3 g, 2.18 mmol), triphenylphosphine (0.57 g, 2.18 mmol) and dioxane (10 mL) was gradually added di-2-methoxyethylazodicarboxylate (0.57 g, 2.18 mmol), and the mixture was stirred at room temperature overnight. To the reaction mixture was added water (200 mL), and the resulting mixture was extracted with ethyl acetate (200 mL). The extract was washed by brine (100 mL), dried over anhydrous magnesium sulfate, and concentrated in vacuo. The resulting residue was purified by silica gel column chromatography (ethyl acetate/hexane) to give 1(4-chlorobenzyl)-6-(ethylthio)-3-(6-methoxy-3-pyridyl)methyl-1,3,5-triazinane-2,4-dion (0.64 g, Yield: 91%) as colorless amorphous.
1H-NMR (δ ppm TMS/CDCl$_3$): 1.40 (3H, t, J=7.2 Hz), 3.25 (2H, q, J=7.4 Hz), 3.96 (3H, s), 5.06 (2H, s), 5.11 (2H, s), 6.73 (1H, d, J=8.66 Hz), 7.29-7.38 (4H, m) 7.82 (1H, dd, J=8.4, 2.4 Hz), 8.39 (1H, m).
The mixture of 1-(4-chlorobenzyl)-6-(ethylthio)-3-(6-methoxy-3-pyridyl)methyl-1,3,5-triazinane-2,4(1H,3H)-dion (0.32 g, 0.76 mmol), 3-fluoro-4-isopropoxyaniline (0.19 g, 1.15 mmol), t-butanol (6.4 mL) and acetic acid (0.66 mL) was heated at reflux for 24 hours. The reaction mixture was poured into saturated aqueous sodium bicarbonate (100 mL), and extracted with ethyl acetate (100 mL). The extract was washed by saturated aqueous sodium bicarbonate (100 mL) and brine (100 mL), dried over anhydrous magnesium sulfate. The extract was concentrated in vacuo. The resulting residue was purified by silica gel column chromatography (ethyl acetate/hexane). The resulting residue was precipitated by hexane to give 1-(4-chlorobenzyl)-6-(3-fluoro-4-isopropoxyphenylimino)-3-(6-methoxy-3-pyridyl)methyl)-1,3,5-triazinane-2,4-dion (0.33 g, Yield: 82%) as colorless powder.
1H-NMR (δ ppm TMS/CDCl$_3$): 1.37 (6H, d, J=6.1 Hz), 3.93 (3H, s), 4.74 (1H, sept, J=6.1 Hz), 4.93 (2H, s), 5.16 (2H, s), 6.47 (1H, m), 6.58 (1H, m), 6.70 (1H, d, J=8.8 Hz), 6.96 (1H, t, J=8.8 Hz), 7.29-7.49 (4H, m), 7.71 (1H, m), 8.30 (1H, m).

EXAMPLE 42

Preparation of 1-(4-chlorobenzyl)-6-(3-fluoro-4-isopropoxyphenylimino)-3-(6-oxo-1,6-dihydro-3-pyridyl)methyl)-1,3,5-triazinane-2,4-dion (I-0649)

[Chemical Formula 151]

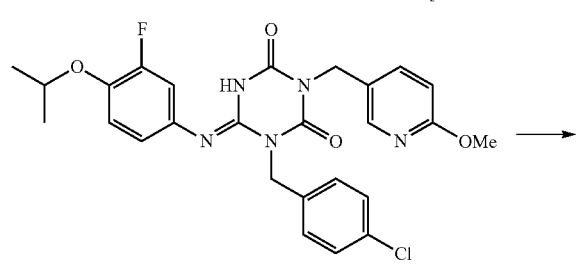

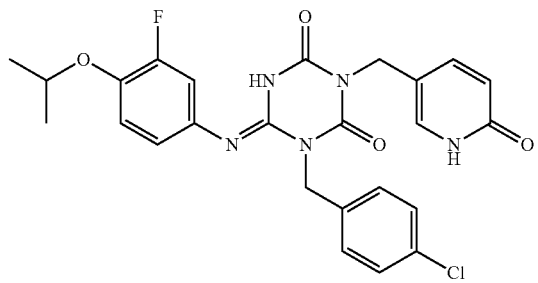

A mixture of 1-(4-chlorobenzyl)-6-(3-fluoro-4-isopropoxyphenylimino)-3-(6-methoxy-3-pyridyl)methyl)-1,3,5-triazinane-2,4-dion (245 mg, 0.466 mmol), sodium iodide (209 mg, 1.379 mmol), acetonitrile (5 mL) and chlorotrimethylsilane (0.179 mL, 1.379 mmol) was heated at reflux for 1 hour. The reaction mixture was poured into water (200 mL) and extracted with ethyl acetate (300 mL). The extract was washed by brine (200 mL), dried over anhydrous magnesium sulfate, and concentrated in vacuo. The resulting residue was precipitated by ethyl acetate to give 1-(4-chlorobenzyl)-6-(3-fluoro-4-isopropoxyphenylimino)-3-(6-oxo-1,6-dihydro-3-pyridyl)methyl)-1,3,5-triazinane-2,4-dion (237 mg, Yield: 99%) as colorless solid.
1H-NMR (δ ppm TMS/DMSO-d6): 1.26 (6H, d, J=6.0 Hz), 4.62 (3H, m), 5.22 (2H, m), 6.26 (1H, d, J=9.3 Hz), 7.05-7.15 (2H, m), 7.31-7.42 (5H, m), 9.31 (1H, m), 11.5 (1H, m).

EXAMPLE 43

Preparation of 1-(4-chlorobenzyl)-6-(3-fluoro-4-isopropoxyphenylimino)-3-(1-methyl-2-oxo-1,2-dihydro-3-pyridyl)methyl)-1,3,5-triazinane-2,4-dion (I-0689)

[Chemical Formula 152]

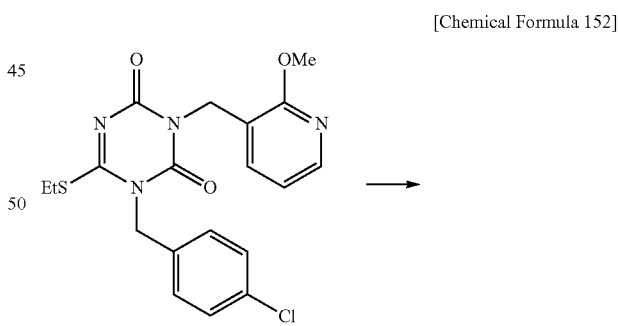

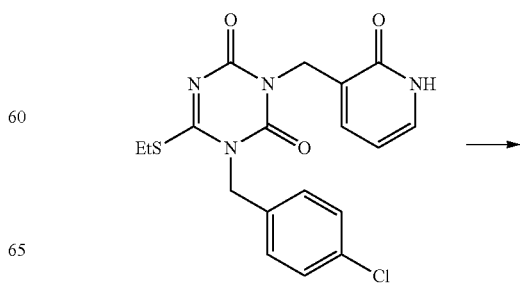

181

-continued

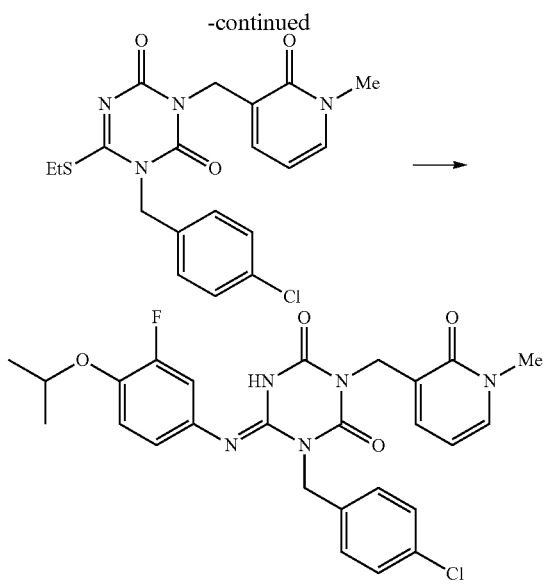

A mixture of 1-(4-chlorobenzyl)-6-(ethylthio)-3-(2-methyl-2-oxo-1,2-dihydro-3-pyridyl)methyl)-1,3,5-triazinane-2,4 (1H,3H)-dion (340 mg, 0.812 mmol), sodium iodide (365 mg, 2.44 mmol), chlorotrimethylsilane (0.311 mL, 2.44 mmol) and acetonitrile (14 mL) was stirred at 100° C. for 1 hour. To the reaction mixture was added 10% aqueous sodium hydrogensulfate, and the resulting mixture was extracted with ethyl acetate and THF. The extract was washed by water, dried over anhydrous sodium sulphate, and concentrated in vacuo. The resulting residue was precipitated by ethyl acetate and hexane to give 1-(4-chlorobenzyl)-6-(ethylthio)-3-(2-oxo-1,2-dihydro-3-pyridyl)methyl)-1,3,5-triazine-2,4(1H,3H)-dion (260 mg, Yield: 79%) as colorless solid.

1H-NMR (δ ppm TMS/DMSO-d6): 1.28 (3H, t, J=7.6 Hz), 3.13 (2H, q, J=7.6 Hz), 4.70 (2H, s), 5.09 (2H, s), 6.14 (1H, t, J=6.8 Hz), 7.20 (1H, d, J=6.0 Hz), 7.31 (1H, d, J=6.0 Hz), 7.37-7.43 (4H, m), 11.71 (1H, s).

A mixture of 1-(4-chlorobenzyl)-6-(ethylthio)-3-(2-oxo-1,2-dihydro-3-pyridyl)methyl)-1,3,5-triazine-2,4(1H,3H)-dion (150 mg, 0.370 mmol), 60% sodium hydride (21 mg, 0.52 mmol), trifluoromethanesulfonic acid methyl ester (0.049 mL, 0.45 mmol) and DMF (3 mL) was stirred at room temperature for 3 hours. To the mixture was added 10% aqueous citric acid and the resulting mixture was extracted with ethyl acetate. The extract was washed by water, dried over anhydrous sodium sulphate, and concentrated in vacuo. The resulting residue was purified by silica gel column chromatography (ethyl acetate/hexane) to give 1-(4-chlorobenzyl)-6-(ethylthio)-3-(1-methyl-2-oxo-1,2-dihydro-3-pyridyl)methyl)-1,3,5-triazine-2,4(1H,3H)-dion (130 mg, Yield: 84%) as colorless solid.

1H-NMR (δ ppm TMS/DMSO-d6): 1.28 (3H, t, J=7.6 Hz), 3.13 (2H, q, J=7.6 Hz), 3.46 (3H, s), 4.72 (2H, s), 5.09 (2H, s), 6.17 (1H, t, J=6.8 Hz), 7.20 (1H, d, J=6.0 Hz), 7.37-7.43 (4H, m), 7.63 (1H, d, J=6.0 Hz).

A mixture of 1-(4-chlorobenzyl)-6-(ethylthio)-3-(1-methyl-2-oxo-1,2-dihydro-3-pyridyl)methyl)-1,3,5-triazine-2,4(1H, 3H)-dion (125 mg, 0.298 mmol), 3-fluoro-4-isopropoxyaniline (76 mg, 0.45 mmol),acetic acid (0.256 mL) and t-butanol (2.4 mL) was heated at reflux for 9 hours. The reaction mixture was concentrated in vacuo. The resulting residue was purified by high speed liquid chromatography

182

(0.3% HCO₂H H₂O/MeCN 40-70%) to give 1-(4-chlorobenzyl)-6-(3-fluoro-4-isopropoxyphenylimino)-3-(1-methyl-2-oxo-1,2-dihydro-3-pyridyl)methyl)-1,3,5-triazine-2,4(1H, 3H)-dion (50 mg, Yield: 32%) as colorless solid.

1H-NMR (δ ppm TMS/DMSO-d6): 1.27 (6H, d, J=5.6 Hz), 3.45 (3H, s), 4.57 (1H, brs), 4.68 (2H, s), 5.24 (2H, brs), 5.09 (2H, s), 6.17 (1H, t, J=6.8 ), 7.11-7.14 (3H, m), 7.42 (4H, brs), 7.62 (1H, d, J=6.0 Hz).

EXAMPLE 44

Preparation of 1-(4-chlorobenzyl)-6-(3-fluoro-4-isopropoxyphenylimino)-3-(2-sulfamoylmethyl)-1,3,5-triazinane-2,4-dion (I-0693)

[Chemical Formula 153]

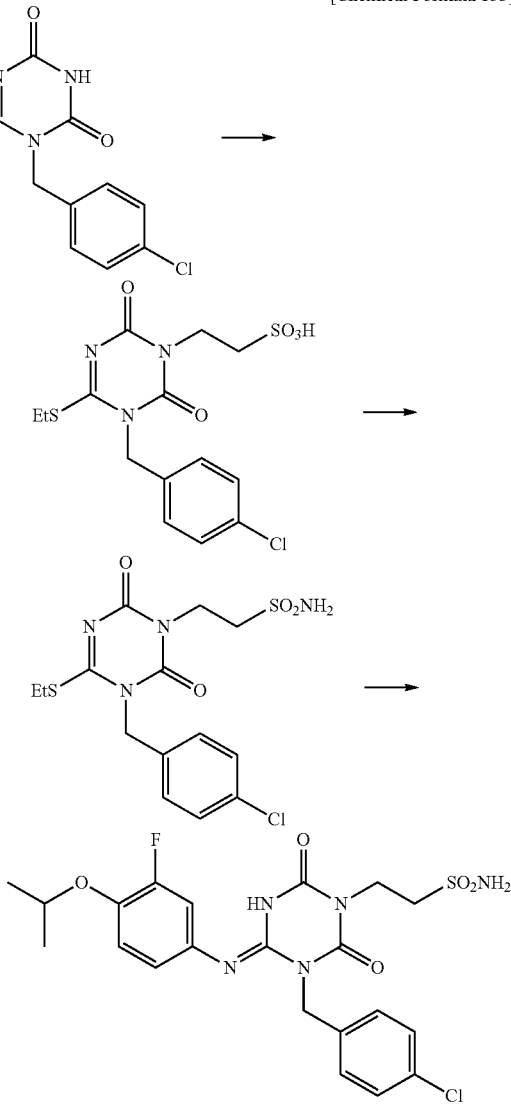

To a mixture of 1-(4-chlorobenzyl)-6-(ethylthio)-1,3,5-triazine-2,4(1H,3H)-dion (500 mg, 1.679 mmol) and N-methyl-2-pyrrolidone (2.5 mL) were added cesium carbonate (1094 mg, 3.36 mmol) and 2-bromoethanesulfonic acid sodium (709 mg, 3.36 mmol), and the resulting mixture was stirred at 140° C. under microwave irradiation for 1 hour. To the reaction mixture was added 2 mol/L aqueous hydrochloric acid (2.5 mL), and purified by high speed liquid chromatography (0.3% HCO₂H H₂O/MeCN 40-70%) to give 1-(4-chlorobenzyl)-6-(ethylthio)-3-(2-sulfoethyl)-1,3,5-triazine-2,4(1H,3H)-dion (120 mg, Yield: 18%) as pale yellow amorphous.

1H-NMR (δ ppm TMS/DMSO-d6): 1.04, 1.24 (3H, t, J=7.0 Hz), 2.63-2.72 (2H, m), 3.09, 3.42 (2H, q, J=7.0 Hz), 3.91-4.03 (2H, m), 4.83 (2H, s), 7.35-7.38 (4H, m), 11.7 (1H, s).

To 1-(4-chlorobenzyl)-6-(ethylthio)-3-(2-sulfoethyl)-1,3,5-triazine-2,4(1H,3H)-dion (120 mg, 0.296 mmol) was added phosphorus oxychloride (2.5 mL), and the mixture was heated at reflux for 2 hours. The reaction mixture was concentrated in vacuo and the resulting residue was dissolved in dioxane (5 mL). The dioxane solution of the residue was gradually added to 0.5 mol/L ammonia in dioxane (5.9 mL) under ice-cooling, and the resulting mixture was stirred at room temperature overnight. The precipitated insoluble were tillered off and the filtrate was concentrated in vacuo. The resulting residue was purified by HPLC to give 1-(4-chlorobenzyl)-6-(ethylthio)-3-(2-sulfoethyl)-1,3,5-triazine-2,4(1H,3H)-dion (7.4 mg, Yield: 6%) as colorless solid.

1H-NMR (δ ppm TMS/CDCl₃): 1.37 (3H, t, J=7.5 Hz), 3.22 (2H, q, J=7.5 Hz), 3.48-3.51 (2H, m), 4.43-4.49 (2H, m), 5.12 (1H, s), 5.20 (2H, s), 7.25-7.35 (4H, m).

A mixture of 1-(4-chlorobenzyl)-6-(ethylthio)-3-(2-sulfamoylethyl)-1,3,5-triazine-2,4(1H,3H)-dion (6.9 mg, 0.017 mmol), 3-fluoro-4-isopropoxyaniline (4.33 mg, 0.026 mmol), t-butanol (1 mL) and acetic acid (0.015 mL) was heated at reflux for 24 hours. The reaction was purified by high speed liquid chromatography (0.3% HCO₂H H₂O/MeCN 40-70%) to give 1-(4-chlorobenzyl)-6-(3-fluoro-4-isopropoxyphenylimino)-3-(2-sulfamoylethyl)-1,3,5-triazinane-2,4-dion (5 mg, Yield: 57%) as colorless solid.

1H-NMR (δ ppm TMS/DMSO-d6): 1.26 (6H, d, J=5.8 Hz), 3.19-3.26 (2H, m), 4.06-4.12 (2H, m), 4.50 (1H, sept, J=5.8 Hz), 5.17 (2H, s), 6.83-7.38 (9H, m).

EXAMPLE 45

Preparation of (S)-1-(4-chlorobenzyl)-3-(2-methoxycarbonylpropyl)-6-(4-phenoxy-phenylimino)-1,3,5-triazinane-2,4-dion (I-0989)

[Chemical Formula 154]

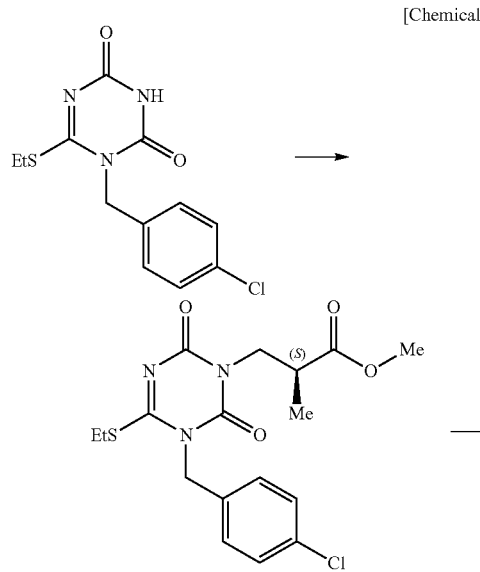

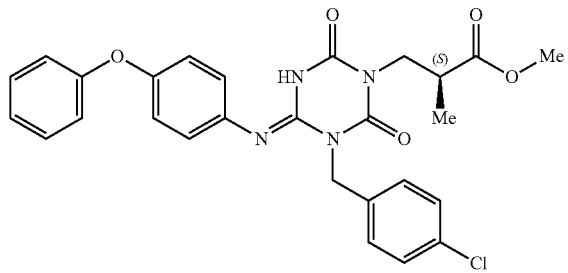

To a mixture of 1-(4-chlorobenzyl)-6-(ethylthio)-1,3,5-triazine-2,4(1H,3H)-dion (5.96 g, 20 mmol), triphenylphosphine (6.29 g, 24 mmol), (S)-3-methyl-2-hydroxyisobutyrate (2.84 g, 24 mmol) and dioxane (40 mL) was added di-2-methoxyethylazodicarboxylate (5.62 g, 24 mmol) over 10 minutes, and the resulting mixture was stirred at room temperature for 3 hours. Tho reaction mixture was poured into water (250 mL) and the resulting mixture was extracted with ethyl acetate (200 mL). The extract was washed by brine (250 mL), dried over anhydrous magnesium sulfate, and concentrated in vacuo. The resulting residue was purified by silica gel column chromatography (ethyl acetate/hexane). The resulting residue was precipitated by ethyl acetate and hexane to give (S)-1-(4-chlorobenzyl)-6-(ethylthio)-3-(2-methoxycarbonylpropyl)-1,3,5-triazine-2,4(1H,3H)-dion (6.0 g, Yield: 75%) as colorless solid.

1H-NMR (δ ppm TMS/CDCl₃): 1.19 (3H, d, J=5.7 Hz), 1.37 (3H, t, J=7.1 Hz), 2.96 (1H, m), 3.12 (2H, q, J=7.1 Hz), 3.60 (3H, s), 3.98 (1H, m), 4.21 (1H, m), 5.08 (2H, s), 7.29-7.34 (4H, m).

A mixture of (S)-1-(4-chlorobenzyl)-6-(ethylthio)-3-(2-methoxycarbonylpropyl)-1,3,5-triazine-2,4(1H,3H)-dion (0.279 g, 0.7 mmol), 4-phenoxyaniline (0.194 g, 1.05 mmol), acetic acid(0.6 mL) and t-butanol (6 mL) was heated at reflux for 5 hours. The reaction mixture was poured into saturated aqueous sodium bicarbonate (150 mL), and the resulting mixture was extracted with ethyl acetate (150 mL). The extract was washed by brine (150 mL), dried over anhydrous magnesium sulfate, and concentrated in vacuo. The resulting residue was purified by silica gel column chromatography (ethyl acetate/hexane) to give (S)-1-(4-chlorobenzyl)-3-(2-methoxycarbonylpropyl)-6-(4-phenoxy-phenylimino)-1,3,5-triazinane-2,4-dion (0.34 g, Yield: 93%) as pale brown amorphous.

1H-NMR (δ ppm TMS/CDCl₃): 1.19 (3H, d, J=7.1 Hz), 2.90 (1H, m), 3.61 (3H, s), 3.90 (1H, m), 4.12 (1H, m), 5.15 (1H, d, J=14.3 Hz), 5.23 (1H, d, J=14.3 Hz), 6.80 (2H, d, J=8.5 Hz), 7.01-7.40 (10H, m), 7.50 (2H, d, J=8.5 Hz ).

EXAMPLE 46

Preparation of (S)-1-(4-chlorobenzyl)-3-(2-methoxycarbonylpropyl)-6-(4-phenoxyphenylimino)-1,3,5-triazinane-2,4-dion (I-0991)

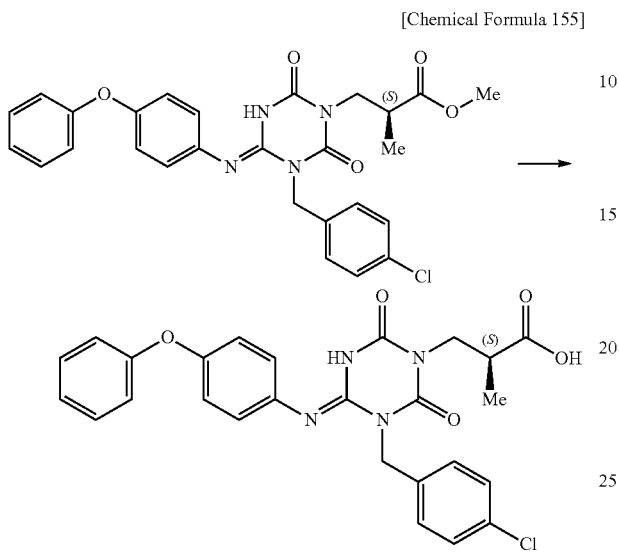

[Chemical Formula 155]

To a mixture of (S)-1-(4-chlorobenzyl)-3-(2-methoxycarbonylpropyl)-6-(4-phenoxyphenylimino)-1,3,5-triazinane-2,4-dion (0.313 g, 0.6 mmol), methanol (1 mL) and THF (1 mL) was added 4 mol/L lithium hydroxide (0.75 mL), and the resulting mixture was stirred at 60° C. for 1 hour. To the reaction mixture were added water (100 mL) and 2 mol/L hydrochloric acid (2 mL) and the resulting mixture was extracted with ethyl acetate (100 mL). The extract was washed by brine (100 mL), dried over anhydrous magnesium sulfate, and concentrated in vacuo. The resulting residue was precipitated by ethyl acetate and hexane to give (S)-1-(4-chlorobenzyl)-3-(2-hydroxycarbonylpropyl)-6-(4-phenoxyphenylimino)-1,3,5-triazinane-2,4-dion (0.29 g, Yield: 95%) as pale brown powder.

1H-NMR (δ ppm TMS/CDCl$_3$): 1.20 (3H, d, J=6.6 Hz) 2.95 (1H, m), 3.90 (1H, m), 4.10 (1H, m), 5.19 (2H, s), 6.79 (2H, d, J=8.5 Hz), 6.98-7.36 (9H, m), 7.47 (2H, d, J=8.0 Hz), 7.80 (1H, s).

EXAMPLE 47

Preparation of 1-(4-chlorobenzyl)-6-(3-fluoro-4-isopropoxyphenylimino)-3-(2-ethoxycarbonyl-2-methoxyiminoethyl)-1,3,5-triazinane-2,4-dion (I-0735)

[Chemical Formula 156]

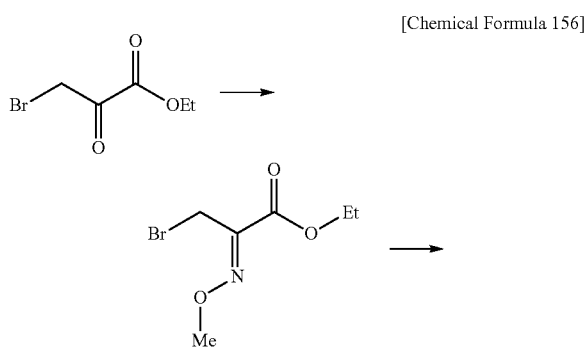

To a mixture of ethyl 3-bromo-2-oxo-propionate (5.85 g, 30 mmol) and ethanol (30 mL) was added O-methoxyamine hydrochloride (5.01 g, 60.0 mmol), and the resulting mixture was stirred at room temperature for 3 hours. To the reaction mixture was added water (200 mL), and the resulting mixture was extracted with ethyl acetate (200 mL). The extract was washed by brine (200 mL), dried over anhydrous magnesium sulfate, and concentrated in vacuo to give crude ethyl 3-bromo-2-methoxyiminopropionate 6.02 g as colorless oil.

To a mixture of 1-(4-chlorobenzyl)-6-(ethylthio)-1,3,5-triazinane-2,4(1H,3H)-dion (1.49 g, 5 mmol), ethyl 3-bromo-2-methoxyiminopropionate (1.34 g, 6.00 mmol), and DMF (10 mL) was added potassium carbonate (0.898 g, 6.50 mmol), and the resulting mixture was stirred at 60° C. for 2 hours. To the reaction mixture was added water (200 mL), and the resulting mixture was extracted with ethyl acetate (200 mL). The extract was washed by brine (200 mL), dried over anhydrous magnesium sulfate, and concentrated in vacuo. The resulting residue was purified by silica gel column chromatography (ethyl acetate/hexane) to give 1-(4-chlorobenzyl)-6-(ethylthio)-3-(2-ethoxycarbonyl-2-methoxyiminoethyl)-1,3,5-triazinane-2,4(1H,3H)-dion (2.10 g, 95%) as colorless oil.

1H-NMR (δ ppm TMS/CDCl$_3$): 1.28-1.38(6H, m), 3.21 (2H, q, J=7.4 Hz), 4.03 (3H, s), 4.28 (2H, q, J=7.1 Hz), 4.97 (2H, s), 5.11 (2H, s) 7.26-7.34 (4H, m).

A mixture of 1-(4-chlorobenzyl)-6-(ethylthio)-3-(2-ethoxycarbonyl-2-methoxyiminoethyl)-1,3,5-triazinane-2,4(1H,3H)-dion (0.35 g, 0.8 mmol), 3-fluoro-4-isopropoxyaniline (0.20 g, 1.2 mmol), acetic acid(0.72 g, 12 mmol) and t-butanol(7 mL) was heated at reflux overnight. The reaction mixture was poured into saturated aqueous sodium bicarbonate (100 mL), and the resulting mixture was extracted with ethyl acetate (200 mL). The extract was washed by brine (200 mL), dried over anhydrous magnesium sulfate, and concentrated in vacuo. The resulting residue was purified by silica gel column chromatography (ethyl acetate/ hexane) to give 1-(4-chlorobenzyl)-6-(3-fluoro-4-isopropoxyphenylimino)-3-(2-ethoxycarbonyl-2-methoxyiminoethyl)-1,3,5-triazinane-2,4-dion (0.31 g, Yield: 70%) as colorless amorphous.

1H-NMR (δ ppm TMS/CDCl₃): 1.30 (3H, t, J=7.3 Hz) 1.37 (6H, d, J=6.1 Hz), 4.04 (3H, s), 4.27 (2H, q, J=7.1 Hz), 4.48 (1H, sept, J=6.1 Hz), 4.89 (2H, s), 5.17 (2H, s), 6.48-6.52 (1H, m), 6.60 (1H, dd, J=11.7, 2.6 Hz), 6.97 (1H, t, J=8.5 Hz), 7.28-7.47 (5H, m).

EXAMPLE 48

Preparation of 1-(4-chlorobenzyl)-6-(3-fluoro-4-isopropoxyphenylimino)-3-(2-hydroxycarbonyl-2-methoxyiminoethyl)-1,3,5-triazinane-2,4-dion (I-0737)

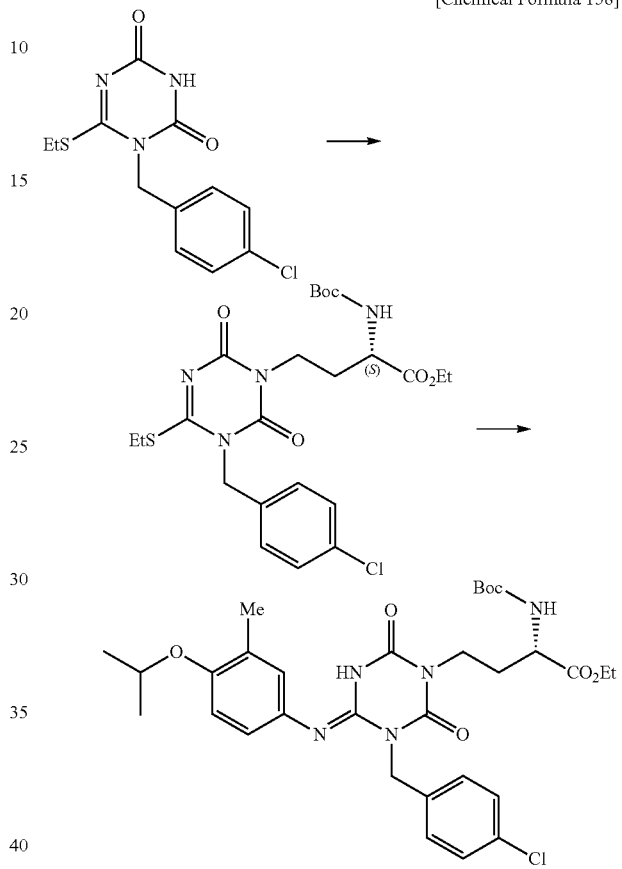

[Chemical Formula 157]

To a mixture 1-(4-chlorobenzyl)-6-(3-fluoro-4-isopropoxyphenylimino)-3-(2-hydroxycarbonyl-2-methoxyiminoethyl)-1,3,5-triazinane-2,4-dion (0.29 g, 0.53 mmol), methanol (3 mL) and water (1.5 mL) was added 4 mol/L lithium hydroxide (0.4 mL), and the resulting mixture was stirred at room temperature overnight. To the reaction mixture was added water (100 mL). The pH of the mixture was adjusted with 2 mol/L hydrochloric acid to a pH of about 3, and the resulting mixture was extracted with ethyl acetate (200 mL). The extract was washed by brine (200 mL), dried over anhydrous magnesium sulfate, and concentrated in vacuo. The resulting residue was precipitated by ethyl acetate and hexane to give 1-(4-chlorobenzyl)-6-(3-fluoro-4-isopropoxyphenylimino)-3-(2-hydroxycarbonyl-2-methoxyiminoethyl)-1,3,5-triazinane-2,4-dion (0.27 g, Yield: 99%) as colorless powder.

1H-NMR (δ ppm TMS/DMSO-d6): 1.28 (6H, d, J=6.0 Hz), 3.81 (3H, s), 4.53 (1H, sept, J=6.0 Hz), 4.68 (2H, s), 5.21 (2H, s), 7.05 (3H, m), 7.41 (4H, m).

EXAMPLE 49

Preparation of (S)-1-(4-chlorobenzyl)-3-(3-t-butoxycarbonylamino-3-ethoxycarbonyl-propyl)-6-(3-mehyl-4-isopropoxyphenylimino)-1,3,5-triazinane-2,4-dion (I-0717)

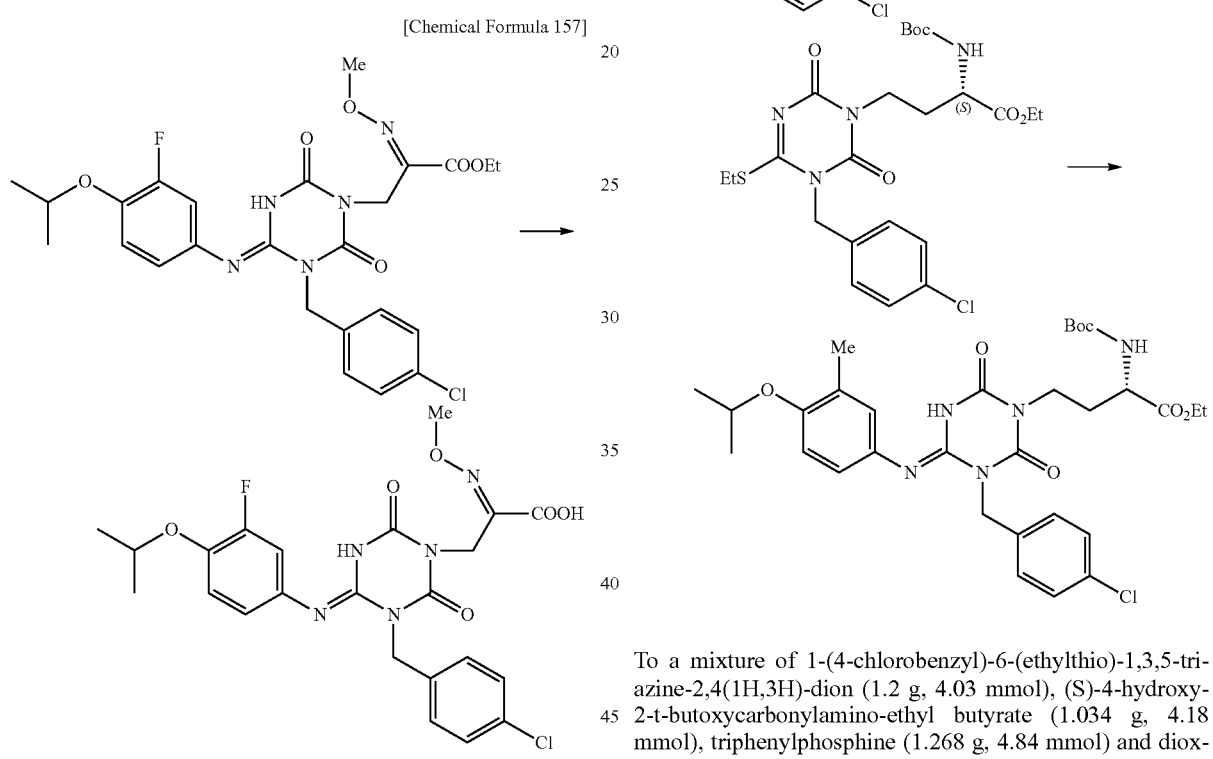

[Chemical Formula 158]

To a mixture of 1-(4-chlorobenzyl)-6-(ethylthio)-1,3,5-triazine-2,4(1H,3H)-dion (1.2 g, 4.03 mmol), (S)-4-hydroxy-2-t-butoxycarbonylamino-ethyl butyrate (1.034 g, 4.18 mmol), triphenylphosphine (1.268 g, 4.84 mmol) and dioxane (12 mL) was gradually added di-2-methoxyethylazodicarboxylate (1.133 g, 4.84 mmol), and the resulting mixture was stirred at room temperature for 1 hour. The reaction mixture was poured into water (200 mL), and the resulting mixture was extracted with ethyl acetate (300 mL). The extract was washed by brine (200 mL), dried over anhydrous magnesium sulfate, and concentrated in vacuo. The resulting residue was purified by silica gel column chromatography (ethyl acetate/hexane) to give (S)-1-(4-chlorobenzyl)-3-(3-t-butoxycarbonylamino-3-ethoxycarbonylpropyl)-6-(ethylthio)-1,3,5-triazine-2,4(1H,3H)-dion (2.15 g, Yield: 100%) as colorless amorphous.

1H-NMR (δ ppm TMS/CDCl₃): 1.23 (3H, t, J=7.1 Hz), 1.33 (3H, t, J=7.4 Hz), 1.42 (9H, s), 2.10-2.16 (2H, m), 3.17 (2H, q, J=7.4 Hz), 3.97-4.02 (2H, m), 4.05-4.14 (2H, m), 4.34 (1H, m), 5.06 (2H, m), 5.49 (1H, m), 7.28-7.35 (4H, m).

A mixture of (S)-1-(4-chlorobenzyl)-3-(3-t-butoxycarbonylamino-3-ethoxycarbonylpropyl)-6-(ethylthio)-1,3,5-triazine-2,4(1H,3H)-dion (500 mg, 0.949 mmol), 3-methyl-4-isopropoxyaniline (235 mg, 1.423 mmol), acetic acid(0.814 mL) and t-butanol (10 mL) was heated at reflux overnight.

The reaction mixture was added to saturated aqueous sodium bicarbonate (100 mL), and the resulting mixture was extracted with ethyl acetate (800 mL). The extract, was washed by brine (200 mL), dried over anhydrous sodium sulphate, and concentrated in vacuo. The resulting residue was purified by silica gel column chromatography (ethyl acetate/hexane). The resulting residue was precipitated by methanol to give (S)-1-(4-chlorobenzyl)-3-(3-t-butoxycarbonylamino-3-ethoxycarbonylpropyl)-6-(3-mehyl-4isopropoxyphenylimino)-1,3,5-triazine-2,4-dion (550 mg, Yield: 92%) as pale purple powder.

1H-NMR (δ ppm TMS/CDCl$_3$): 1.24-1.32 (3H, m), 1.35 (6H, d, J=6.1 Hz), 1.45 (9H, s), 2.05-2.14 (2H, m), 2.19 (3H, s), 3.94 (2H, t, J=7.2 Hz), 4.09-4.18 (2H, m), 4.33-4.40 (1H, m), 4.46 (1H, sept, J=6.1 Hz), 5.17 (2H, s), 5.31 (1H, m), 6.54-6.60 (2H, m), 6.82 (1H, d, J=8.4 Hz), 7.29-7.53 (5H, m).

EXAMPLE 50

Preparation of (S)-1-(4-chlorobenzyl)-3-(3-t-butoxycarbonylamino-3-hydroxycarbonylpropyl)-6-(3-mehyl-4-isopropoxyphenylimino)-1,3,5-triazinane-2,4-dion (I-0732)

[Chemical Formula 159]

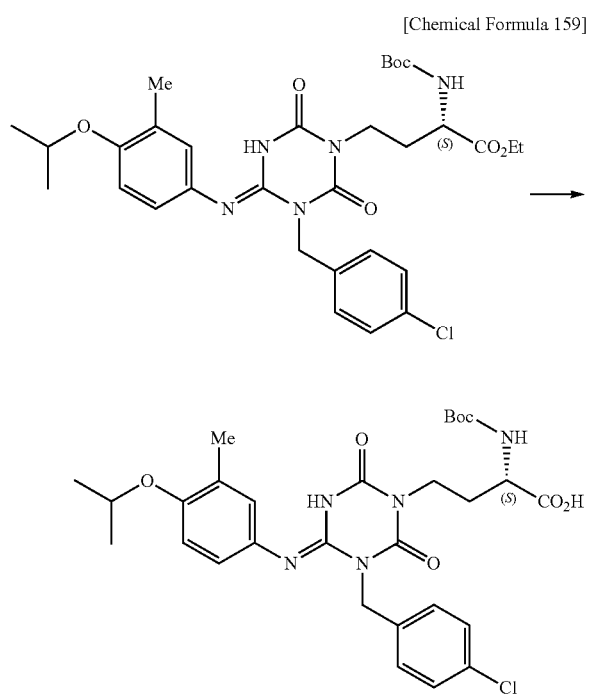

To a mixture of (S)-1-(4-chlorobenzyl)-3-(3-t-butoxycarbonylamino-3-ethoxycarbonylpropyl)-6-(3-mehyl-4-isopropoxyphenylimino)-1,3,5-triazinane-2,4-dion (530 mg, 0.841 mmol), methanol (5 mL) and water (2.5 mL) was added 4 mol/L lithium hydroxide (0.63 mL), and the resulting mixture was stirred at room temperature for 2 hours. To the reaction mixture were water 100 mL and saturated aqueous ammonium chloride (10 mL), and the resulting mixture was extracted with ethyl acetate (300 mL). The extract was dried over anhydrous magnesium sulfate and concentrated in vacuo to give (S)-1-(4-chlorobenzyl)-3-(3-t-butoxycarbonylamino-3-hydroxycarbonylpropyl)-6-(3-mehyl-4-isopropoxyphenylimino)-1,3,5-triazinane-2,4-dion (474 mg, Yield: 94%) as pale purple amorphous.

1H-NMR (δ ppm TMS/CDCl$_3$): 1.33 (6H, d, J=5.8 Hz), 1.44 (9H, s), 2.17 (5H, m), 3.97 (2H, m), 4.32 (1H, m), 4.45 (1H, sept, J=5.8 Hz), 5.17 (2H, s), 5.40 (1H, m), 6.60-6.81 (3H, m), 7.33-7.48 (4H, m).

EXAMPLE 51

Preparation of (S)-1-(4-chlorobenzyl)-3-(3-amino-3-hydroxycarbonylpropyl)-6-(3-mehyl-4-isopropoxyphenylimino)-1,3,5-triazinane-2,4-dion (I-0736)

[Chemical Formula 160]

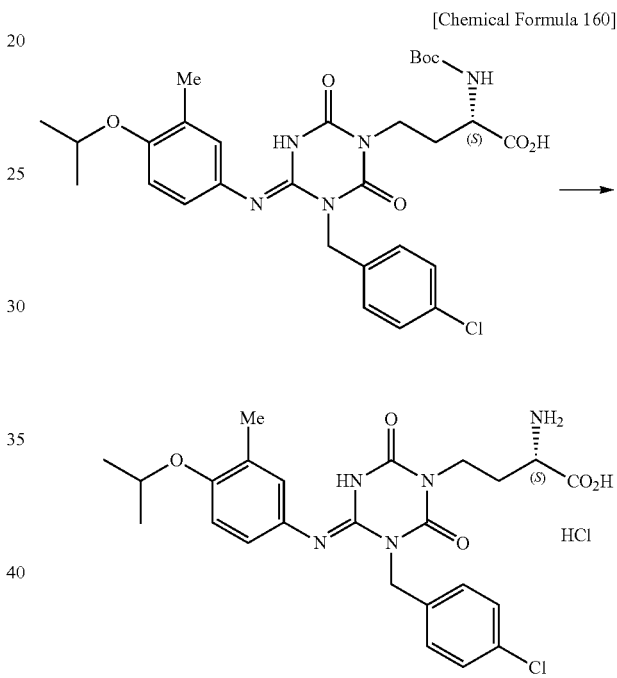

To a mixture of (S)-1-(4-chlorobenzyl)-3-(3-amino-3-hydroxycarbonylpropyl)-6-(3-mehyl-4-isopropoxyphenylimino)-1,3,5-triazinane-2,4-dion (460 mg, 0.764 mmol) and dioxane (2.3 mL) was added 4 mol/L hydrogen chloride in dioxane (3.82 mL) under ice-cooling, and the resulting mixture was stirred at room temperature for 2 hours. To the reaction mixture were added ethyl acetate (2 mL) and hexane (10 mL). The precipitated solid was filtered off and obtained solid was washed by hexane. The obtained solid was dried under reduced pressure to give (S)-1-(4-chlorobenzyl)-3-(3-amino-3-hydroxycarbonylpropyl)-6-(3-mehyl-4-isopropoxyphenylimino)-1,3,5-triazinane-2,4-dion hydrochloride (403 mg, Yield: 98%) as colorless solid.

1H-NMR (δ ppm TMS/DMSO-d6): 1.26 (6H, d, J=6.1 Hz), 1.94-2.14 (2H, m), 2.10 (3H, s), 3.86-3.96 (3H, m), 4.54 (1H, sept, J=6.1 Hz), 5.25 (2H, s), 6.90-7.03 (3H, m), 7.36 (2H, d, J=8.7 Hz), 7.43 (2H, J=8.7 Hz), 8.30 (3H, brs), 9.28 (1H, brs).

EXAMPLE 52

Preparation of (S)-1-(4-chlorobenzyl)-6-(3-mehyl-4-isopropoxyphenylimino)-3-(2-methoxycarbonyl-2-methoxyethyl)-1,3,5-triazinane-2,4-dion (I-0806)

[Chemical Formula 161]

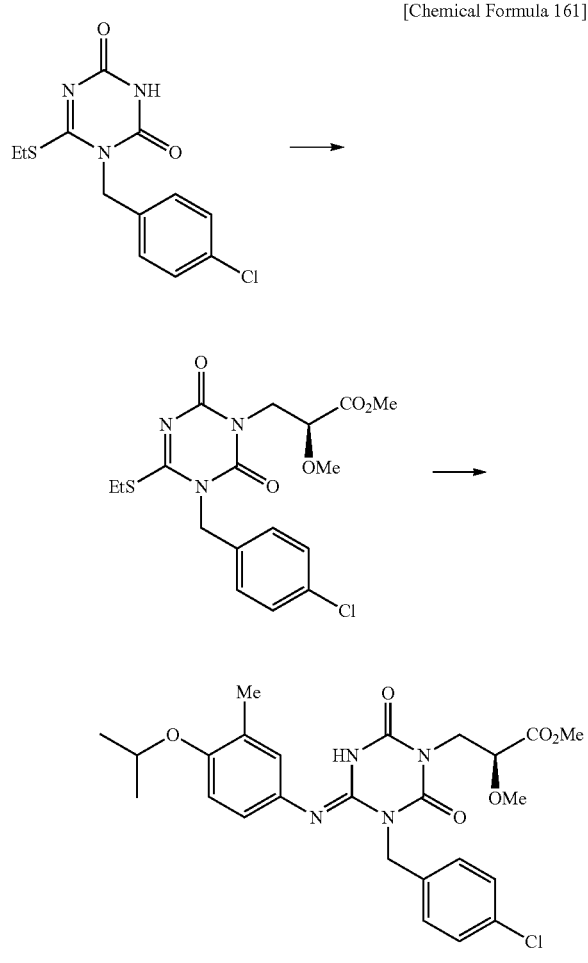

To a mixture of 1-(4-chlorobenzyl)-6-(ethylthio)-1,3,5-triazine-2,4(1H,3H)-dion (550 mg, 1.85 mmol), di-2-methoxyethylazodicarboxylate (606 mg, 2.59 mmol), triphenylphosphine (969 mg, 3.69 mmol) and dioxane (11 mL) was gradually added (S)-3-hydroxy-2-methoxy-methyl propionate (297 mg, 2.22 mmol), and the resulting mixture was stirred at room temperature for 1 hour. To the reaction mixture was added water, the resulting mixture was extracted with ethyl acetate. The extract was washed by brine, dried over anhydrous sodium sulphate, and concentrated in vacuo. The resulting residue was purified by silica gel column chromatography (ethyl acetale/hexane) to give (S)-1-(4-chlorobenzyl)-6-(ethylthio)-3-(2-methoxycarbonyl-2-methoxy-ethyl)-1,3,5-triazine-2,4(1H,3H)-dion (559 mg, Yield: 73%) as colorless oil.

1H-NMR (δ ppm TMS/DMSO-d6): 1.26 (3H, t, J=7.6 Hz), 3.12 (2H, q, J=7.6 Hz), 3.27 (3H, s), 3.61 (3H, s), 3.99-4.10 (3H, m), 5.08 (2H, s), 7.32 (2H, d, J=8.0 Hz), 7.44 (2H, d, J=8.0 Hz).

A mixture of (S)-1-(4-chlorobenzyl)-6-(ethylthio)-3-(2-methoxycarbonyl-2-methoxy-ethyl)-1,3,5-triazine-2,4(1H,3H)-dion (300 mg, 0.725 mmol), 3-methyl-4-isopropoxyaniline (180 mg, 1.09 mmol), acetic acid (0.622 mL) and t-butanol (6 mL) was heated at reflux for 8 hours. The reaction mixture was added to saturated aqueous sodium bicarbonate, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give (S)-1-(4-chlorobenzyl)-6-(3-mehyl-4-isopropoxyphenylimino)-3-(2-methoxycarbonyl-2-methoxyethyl)-1,3,5-triazinane-2,4(1H,3H)-dion (365 mg, Yield: 97%) as colorless solid.

1H-NMR (δ ppm TMS/DMSO-d6): 1.27 (6H, d, J=5.6 Hz), 2.11 (3H, s), 3.26 (3H, s), 3.57 (3H, s), 3.98-4.05 (3H, m), 4.56 (1H, sept, J=5.9 Hz), 5.26 (2H, s), 6.94 (1H, d, J=8.0 Hz), 7.04-7.07 (2H, m), 7.33 (2H, d, J=8.0 Hz), 7.46 (2H, d, J=8.0 Hz), 9.25 (1H, s).

EXAMPLE 53

Preparation of (S)-1-(4-chlorobenzyl)-6-(3-mehyl-4-isopropoxyphenylimino)-3-(2-hydroxycarbonyl-2-methoxyethyl)-1,3,5-triazinane-2,4-dion (I-0807)

[Chemical Formula 162]

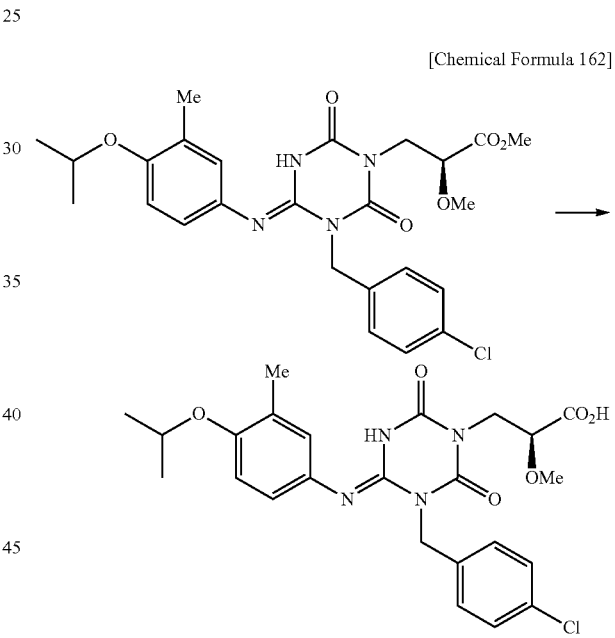

To a mixture of (S)-1-(4-chlorobenzyl)-6-(3-mehyl-4-isopropoxyphenylimino)-3-(2-methoxycarbonyl-2-methoxyethyl)-1,3,5-triazinane-2,4-dion (340 mg, 0.658 mmol), methanol (2 mL) and THF (2 mL) was added 1 mol/L lithium hydroxide (2 mL), and the resulting mixture was stirred at 60° C. for 30 minutes. To the reaction mixture was added 10% aqueous citric acid, extracted with ethyl acetate. The extract was washed, dried over anhydrous sodium sulphate, and concentrated in vacuo. The resulting residue was precipitated by dichloromethane and hexane to give (S)-1-(4-chlorobenzyl)-6-(3-mehyl-4-isopropoxyphenylimino)-3-(2-methoxycarbonyl-2-methoxyethyl)-1,3,5-triazinane-2,4-dion (243 mg, Yield: 74%) as colorless solid.

1H-NMR (δ ppm TMS/DMSO-d6): 1.26 (6H, d, J=5.6 Hz), 2.11 (3H, s), 3.25 (3H, s), 3.94-4.05 (3H, m), 4.55 (1H, sept, J=5.9 Hz), 5.27 (2H, s), 6.93 (1H, d, J=8.0 Hz), 7.04-7.07 (2H, m), 7.33 (2H, d, J=8.0 Hz), 7.45 (2H, d, J=8.0 Hz), 9.20 (1H, s), 12.89 (1H, brs).

EXAMPLE 54

Preparation of (S)-1-(4-chlorobenzyl)-6-(3-mehyl-4-isopropoxyphenylimino)-3-(2-hydroxycarbonyl-2-hydroxyethyl)-1,3,5-triazinane-2,4-dion (I-0852)

[Chemical Formula 163]

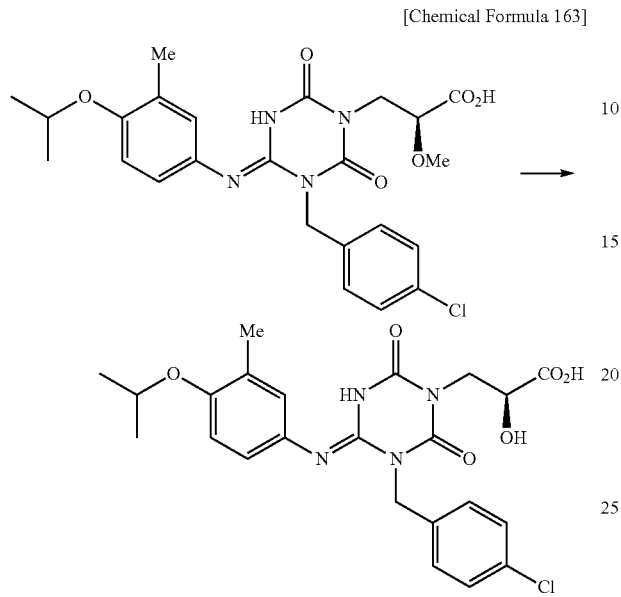

To a solution of sodium iodide (119 mg, 0.795 mmol) in acetonitrile (3.2 mL) were added chlorotrimethylsilane (0.102 mL, 0.795 mmol) and (S)-1-(4-chlorobenzyl)-6-(3-mehyl-4-isopropoxyphenylimino)-3-(2-hydroxycarbonyl-2-hydroxyethyl)-1,3,5-triazinane-2,4-dion (80 mg, 0.16 mmol), and the resulting mixture was heated at reflux for 4 hours. The reaction mixture was added to 10% aqueous sodium hydrogensulfate, and the resulting mixture was extracted with ethyl acetate. The extract was washed by brine, dried over anhydrous sodium sulphate, and concentrated in vacuo. The resulting residue was purified by high speed liquid chromatography (0.3% HCO$_2$H H$_2$O/MeCN 40-70%) to give (S)-1-(4-chlorobenzyl)-6-(3-mehyl-4-isopropoxyphenylimino)-3-(2-hydroxycarbonyl-2-hydroxyethyl)-1,3,5-triazinane-2,4-dion (23 mg, Yield: 30%) as colorless solid.

1H-NMR (δ ppm TMS/DMSO-d6): 1.26 (6H, d, J=5.6 Hz), 2.11 (3H, s), 3.93-3.95 (2H, m), 4.24-4.28 (1H, m), 4.55 (1H, sept, J=5.9 Hz), 5.27 (2H, s), 6.93 (1H, d, J=8.0 Hz), 7.04-7.07 (2H, m), 7.34 (2H, d, J=8.0 Hz), 7.45 (2H, d, J=8.0 Hz), 9.15 (1H, s), 12.57 (1H, brs).

EXAMPLE 55

Preparation of (S)-1-(4-chlorobenzyl)-6-(3-mehyl-4-isopropoxyphenylimino)-3-[2-methoxycarbonyl-2-(methoxymethyloxyethyl)ethyl]-1,3,5-triazinane-2,4-dion (I-0993)

[Chemical Formula 164]

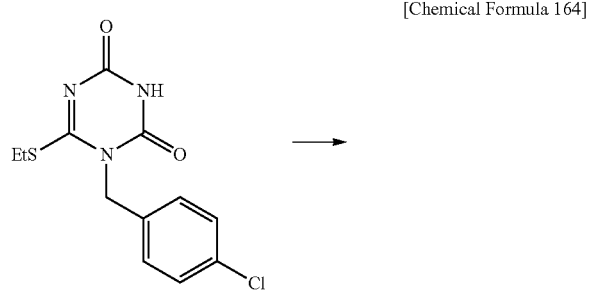

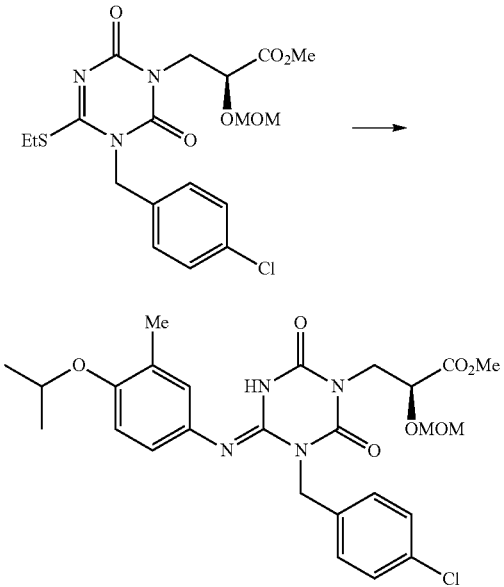

To a mixture of 1-(4-chlorobenzyl)-6-(ethylthio)-1,3,5-triazine-2,4-dion (440 mg, 1.48 mmol), di-2-methoxyethylazodicarboxylate (485 mg, 2.07 mmol), triphenylphosphine (775 mg, 2.96 mmol) and dioxane (9 mL) was gradually added (S)-3-hydroxy-2-methoxy-methyloxypropanoic acid methyl (291 mg, 1.77 mmol), and the resulting mixture was stirred at room temperature for 1 hour. To the reaction mixture was added water, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give (S)-1-(4-chlorobenzyl)-6-(ethylthio)-3-[2-methoxycarbonyl-2-(methoxy-methyloxyethyl)ethyl]-1,3,5-triazine-2,4(1H,3H)-dion (650 mg, Yield: 99%) as colorless oil.

1H-NMR (δ ppm TMS/DMSO-d6): 1.26 (3H, t, J=7.6 Hz), 3.07-3.15 (5H, m), 3.63 (3H, s), 4.01-4.21 (2H, m), 4.38-4.4.42 (1H, m), 4.58 (2H, s), 5.09 (2H, s), 7.33 (2H, d, J=8.0 Hz), 7.44 (2H, d, J=8.0 Hz).

A mixture of (S)-1-(4-chlorobenzyl)-6-(ethylthio)-3-[2-methoxycarbonyl-2-(methoxymethyloxy)ethyl]1,3,5-triazine-2,4-dion (650 mg, 1.46 mmol), 3-methyl-4-isopropoxyaniline (363 mg, 2.20 mmol), acetic acid(1.26 mL) and t-butanol (6.5 mL) was heated at reflux for 6 hours. The reaction mixture was added to saturated aqueous sodium bicarbonate, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give (S)-1-(4-chlorobenzyl)-6-(3-mehyl-4-isopropoxyphenylimino)-3-[2-methoxycarbonyl-2-(methoxymethyloxy)ethyl]1,3,5-triazinane-2,4-dion (590 mg, Yield: 74%) as colorless solid.

1H-NMR (δ ppm TMS/DMSO-d6): 1.27 (6H, d, J=5.6 Hz), 2.11 (3H, s), 3.17 (3H, s), 3.59 (3H, s), 3.97-4.12 (2H, m), 4.34-4.40 (1H, m), 4.56 (3H, s), 5.26 (2H, s), 6.95 (1H, d, J=8.0 Hz), 7.04 (2H, brs), 7.35 (2H, d, J=8.0 Hz), 7.46 (2H, d, J=8.0 Hz), 9.25 (1H, s).

EXAMPLE 56

Preparation of (S)-1-(4-chlorobenzyl)-6-(3-mehyl-4-isopropoxyphenylimino)-3-(2-methoxycarbonyl-2-hydroxyethyl)-1,3,5-triazinane-2,4-dion (I-0994)

[Chemical Formula 165]

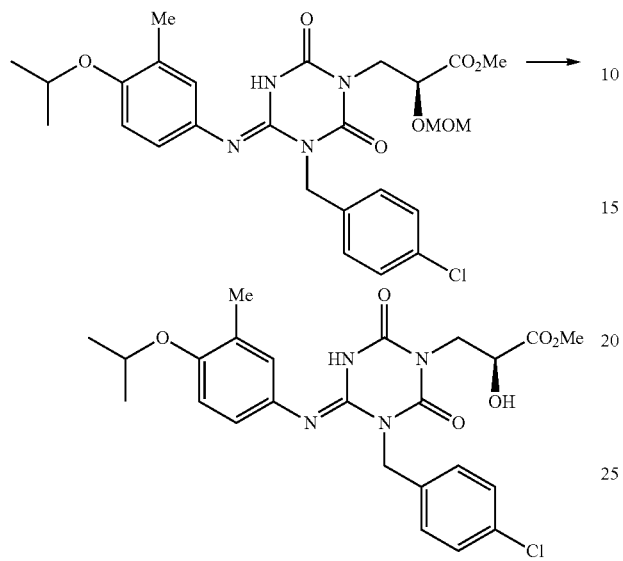

A mixture of (S)-1-(4-chlorobenzyl)-6-(3-mehyl-4-isopropoxyphenylimino)-3-[2-methoxycarbonyl-2-(methoxymethyloxy)ethyl]-1,3,5-triazinane-2,4-dion (585 mg, 1.07 mmol) and 4 mol/L hydrogen chloride in dioxane (6 mL), and the resulting mixture was stirred at room temperature for 15 minutes. The reaction mixture was added to saturated aqueous sodium bicarbonate, and the resulting mixture was extracted with ethyl acetate. The extract was washed by brine, dried over anhydrous sodium sulphate, and concentrated in vacuo to give (S)-1-(4-chlorobenzyl)-6-(3-mehyl-4-isopropoxyphenylimino)-3-(2-methoxycarbonyl-2-hydroxyethyl)-1,3,5-triazinane-2,4-dion (537 mg, Yield: 100%) as pale purple solid.

1H-NMR (δ ppm TMS/DMSO-d6): 1.27 (6H, d, J=5.6 Hz), 2.11 (3H, s), 3.53 (3H, s), 3.94-3.96 (2H, m), 4.27-4.30 (1H, m), 4.54-4.57 (1H, m), 5.26 (2H, s), 5.72-5.79 (1H, m), 6.94 (1H, d, J=8.0 Hz), 7.04-7.07 (2H, m), 7.35 (2H, d, J=8.0 Hz), 7.46 (2H, d, J=8.0 Hz), 9.20 (1H, s).

EXAMPLE 57

Preparation of 1-(4-chlorobenzyl)-6-(3-mehyl-4-isopropoxyphenylimino)-3-(2-methoxycarbonyl-2-oxoethyl)-1,3,5-triazinane-2,4-dion (I-0996)

[Chemical Formula 166]

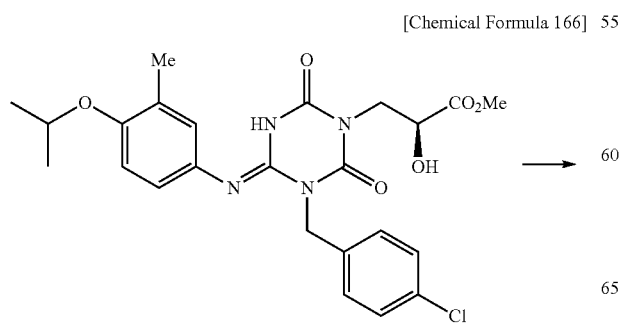

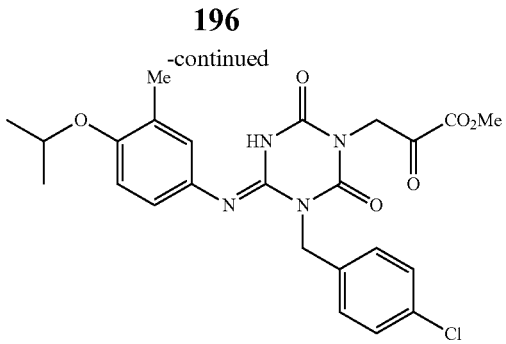

To a solution of (S)-1-(4-chlorobenzyl)-6-(3-mehyl-4-isopropoxyphenylimino)-3-(2-methoxycarbonyl-2-hydroxyethyl)-1,3,5-triazinane-2,4-dion (150 mg, 0.298 mmol) in dichloromethane (6 mL) was added 0.3 mol/L Dess-Martin reagent in dichloromethane (1.19 mL, 0.358 mmol) under ice-cooling, and the resulting mixture was stirred at room temperature for 1 hour. To the reaction mixture were added 10% aqueous sodium hydrogensulfate and saturated aqueous sodium bicarbonate, and the resulting mixture was extracted with ethyl acetate. The extract was washed by brine, dried over anhydrous sodium sulphate, and concentrated in vacuo. The resulting residue was purified by high speed liquid chromatography (0.3% HCO$_2$H H$_2$O/MeCN 50-80%) to give 1-(4-chlorobenzyl)-6-(3-mehyl-4-isopropoxyphenylimino)-3-(2-methoxycarbonyl-2-oxoethyl)-1,3,5-triazinane-2,4-dion (17 mg, Yield: 11%) as colorless solid.

1H-NMR (δ ppm TMS/DMSO-d6): 1.27 (6H, d, J=5.6 Hz), 2.12 (3H, s), 3.81 (3H, s), 4.54-4.57 (1H, m), 5.03 (2H, s), 5.28 (2H, s), 6.94 (1H, d, J=8.0 Hz), 7.05 (2H, brs), 7.35 (2H, d, J=8.0 Hz), 7.47 (2H, d, J=8.0 Hz), 9.37 (1H, s).

EXAMPLE 58

Preparation of 1-(4-chlorobenzyl)-6-(3-mehyl-4-isopropoxyphenylimino)-3-(2-methoxycarbonyl-2-oxoethyl)-1,3,5-triazinane-2,4-dion (I-1009)

[Chemical Formula 167]

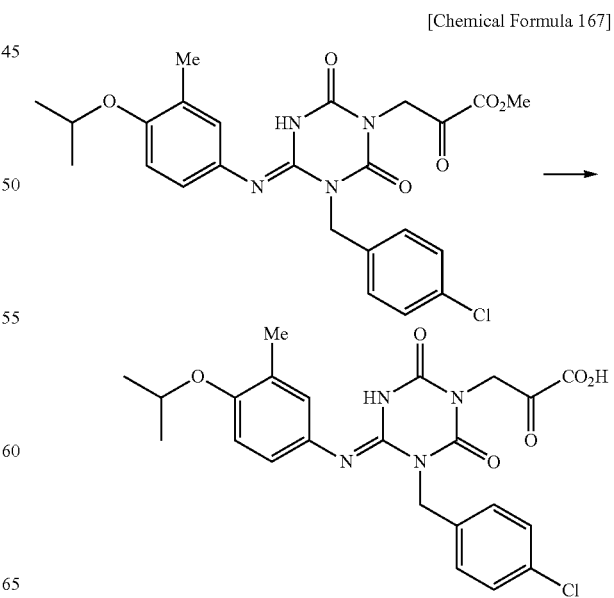

To a mixture of 1-(4-chlorobenzyl)-6-(3-mehyl-4-isopropoxyphenylimino)-3-(2-methoxycarbonyl-2-oxoethyl)-1,3,5-triazinane-2,4-dion (15 mg, 0.030 mmol), methanol (0.3 mL) and THF (0.3 mL) was added 1 mol/L lithium hydroxide (0.09 mL), and the resulting mixture was stirred at 50° C. for 3 hours. To the reaction mixture were added 10% aqueous citric acid, and the resulting mixture was extracted with ethyl acetate. The extract was washed by water, dried over anhydrous sodium sulphate, and concentrated in vacuo. The resulting residue was precipitated by dichloromethane and hexane to give 1-(4-chlorobenzyl)-6-(3-mehyl-4-isopropoxyphenylimino)-3-(2-methoxycarbonyl-2-oxoethyl)-1,3,5-triazinane-2,4-dion (5 mg, Yield: 34%) as colorless solid.

1H-NMR (δ ppm TMS/DMSO-d6): 1.27 (6H, d, J=5.6 Hz), 2.11 (3H, s), 4.53-4.57 (1H, m), 4.98 (2H, s), 5.28 (2H, s), 6.94 (1H, d, J=8.0 Hz), 7.05 (2H, brs), 7.35 (2H, d, J=8.0 Hz), 7.47 (2H, d, J=8.0 Hz), 9.35 (1H, s).

EXAMPLE 59

Preparation of (S)-1-(4-methylbenzyl)-6-(3-vinyl-4-isopropoxyphenylimino)-3-(2-methoxycarbonylpropyl)-1,3,5-triazinane-2,4-dion (I-0907)

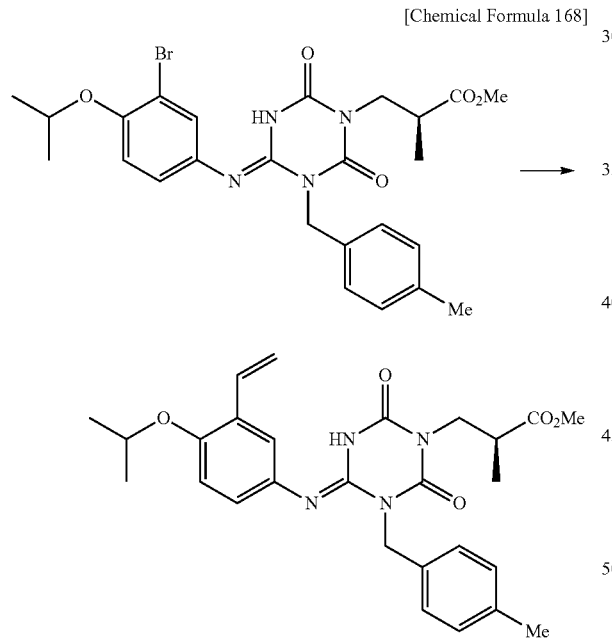

[Chemical Formula 168]

A mixture of (S)-1-(4-methylbenzyl)-6-(3-bromo-4-isopropoxyphenylimino)-3-(2-methoxycarbonylpropyl)-1,3,5-triazinane-2,4-dion (350 mg, 0.642 mmol), vinyl boronic acid pinacol ester (0.163 mL, 0.963 mmol), dichloro[1,1'-bis(di-tert-butylphosphino)ferrocene]palladium(II) (42 mg, 0.064 mmol), THF (7 mL), and 2 mol/L aqueous potassium carbonate 0.28 mL) was boated at reflux fur 10 minutes. To the reaction mixture was added water and the resulting mixture wae extracted with ethyl acetate. The extract was washed by brine, dried over anhydrous sodium sulphate, and concentrated in vacuo. The resulting residue was purified by silica gel column chromatography (ethyl acetate/hexane) to give (S)-1-(4-chlorobenzyl)-6-(3-vinyl-4-isopropoxyphenylimino)-3-(2-methoxycarbonylpropyl)-1,3,5-triazinane-2,4-dion (302 mg, Yield: 96%) as colorless solid.

1H-NMR (δ ppm TMS/DMSO-d6): 1.04-1.07 (3H, m), (6H, d, J=5.6 Hz), 2.28 (3H, s), 2.80-2.83 (1H, m), 3.49 (3H, s), 3.78-3.97 (2H, m), 4.58-4.61 (1H, m), 5.24-5.28 (3H, m), 5.70 (1H, d, J=16.0 Hz), 6.90-7.04 (2H, m), 7.20 (5H, s), 9.24 (1H, s).

EXAMPLE 60

Preparation of (S)-1-(4-methylbenzyl)-6-(3-vinyl-4-isopropoxyphenylimino)-3-(2-hydroxycarbonylpropyl)-1,3,5-triazinane-2,4-dion (I-0910)

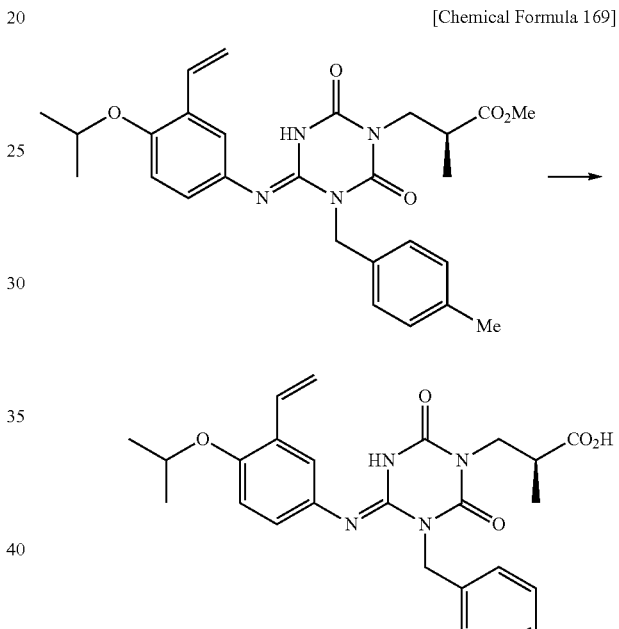

[Chemical Formula 169]

To a mixture of (S)-1-(4-methylbenzyl)-6-(3-vinyl-4-isopropoxyphenylimino)-3-(2-methoxycarbonylpropyl)-1,3,5-triazinane-2,4-dion (85 mg, 0.17 mmol), methanol (0.6 mL) and THF (0.6 mL) was added 1 mol/L lithium hydroxide (0.52 mL), and the resulting mixture was stirred at room temperature for 3 days. To the reaction mixture was added 10% aqueous citric acid, and the resulting mixture was extracted with ethyl acetate. The extract was washed by water, dried over anhydrous sodium sulphate, and concentrated in vacuo. The resulting residue was precipitated by ethyl acetate and hexane to give (S)-1-(4-methylbenzyl)-6-(3-vinyl-4-isopropoxyphenylimino)-3-(2-methoxycarbonylpropyl)-1,3,5-triazinane-2,4-dion (59 mg, Yield: 71%) colorless solid.

1H-NMR (δ ppm TMS/DMSO-d6): 1.04-1.07 (3H, m), 1.27 (6H, d, J=5.6 Hz), 2.28 (3H, s), 2.80-2.83 (1H, m), 3.78-3.97 (2H, m), 4.58-4.61 (1H, m), 5.24-5.28 (3H, m), 5.70 (1H, d, J=16.0 Hz), 6.90-7.04 (2H, m), 7.20-7.38 (5H, m), 7.47 (1H, s), 9.24 (1H, brs).

EXAMPLE 61

Preparation of (S)-1-(4-methylbenzyl)-6-(3-ethyl-4-isopropoxyphenylimino)-3-(2-methoxycarbonylpropyl)-1,3,5-triazinane-2,4-dion (I-0908)

[Chemical Formula 170]

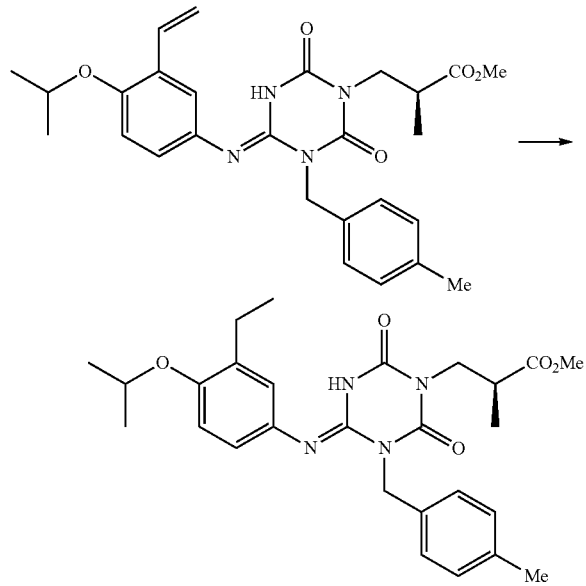

A solution of (S)-1-(4-methylbenzyl)-6-(3-vinyl-4-isopropoxyphenylimino)-3-(2-methoxycarbonylpropyl)-1,3,5-triazinane-2,4-dion (200 mg, 0.406 mmol) in methanol (20 mL) was hydrogenated under 5% Pt/C. The reaction mixture was concentrated in vacuo. The resulting residue was precipitated by ethyl acetate and hexane to give (S)-1-(4-methylbenzyl)-6-(3-ethyl-4-isopropoxyphenylimino)-3-(2-methoxycarbonylpropyl)-1,3,5-triazinane-2,4-dion (188 mg, Yield: 94%) as colorless solid.
1H-NMR (δ ppm TMS/DMSO-d6): 1.03-1.12 (6H, m), 1.27 (6H, d, J=5.6 Hz), 2.28 (3H, s), 2.50-2.53 (2H, m), 2.80-2.83 (1H, m), 3.56 (3H, s), 3.78-3.90 (2H, m), 4.56-4.58 (1H, m), 5.20 (2H, m), 6.93-7.11 (3H, m), 7.20 (4H, s), 9.16 (1H, s).

EXAMPLE 62

Preparation of (S)-1-(4-methylbenzyl)-6-(3-ethyl-4-isopropoxyphenylimino)-3-(2-hydroxycarbonylpropyl)-1,3,5-triazinane-2,4-dion (I-0911)

[Chemical Formula 171]

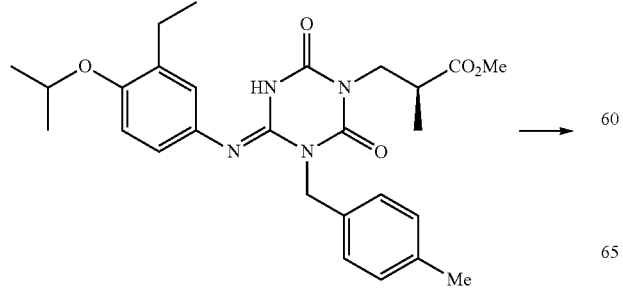

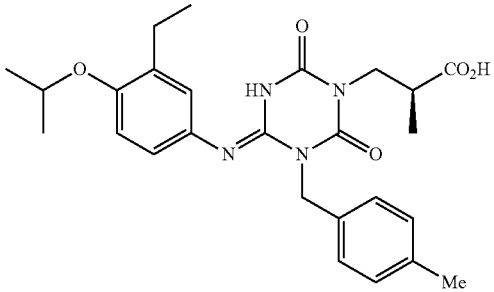

To a mixture of (S)-1-(4-methylbenzyl)-6-(3-ethyl-4-isopropoxyphenylimino)-3-(2-hydroxycarbonylpropyl)-1,3,5-triazinane-2,4-dion (160 mg, 0.324 mmol), methanol (1 mL) and THF (1 mL) was added 1 mol/L lithium hydroxide (1 mL), and the resulting mixture was stirred at 60° C. for 1 hour. To the reaction mixture was added 10% aqueous citric acid, and the resulting mixture was extracted with ethyl acetate. The extract was washed by water, dried over anhydrous sodium sulphate, and concentrated in vacuo. The resulting residue was precipitated by ethyl acetate and hexane to give (S)-1-(4-methylbenzyl)-6-(3-ethyl-4-isopropoxyphenylimino)-3-(2-hydroxycarbonylpropyl)-1,3,5-triazinane-2,4-dion (122 mg 79%) as colorless solid.
1H-NMR (δ ppm TMS/DMSO-d6): 1.01 (3H, d, J=6.8 Hz), 1.10 (3H, t, J=7.6 Hz), 1.27 (6H, d, J=5.6 Hz), 2.28 (3H, s), 2.50-2.53 (2H, m), 2.80-2.83 (1H, m), 3.78-3.96 (2H, m), 4.56-4.58 (1H, m), 5.24 (2H, m), 6.81-7.19 (3H, m), 7.28 (4H, s), 9.11 (1H, s), 12.30 (1H, brs).

EXAMPLE 63

Preparation of (S)-1-(4-vinylbenzyl)-6-(3-mehyl-4-isopropoxyphenylimino)-3-(2-methoxycarbonylpropyl)-1,3,5-triazinane-2,4-dion (I-0892)

[Chemical Formula 172]

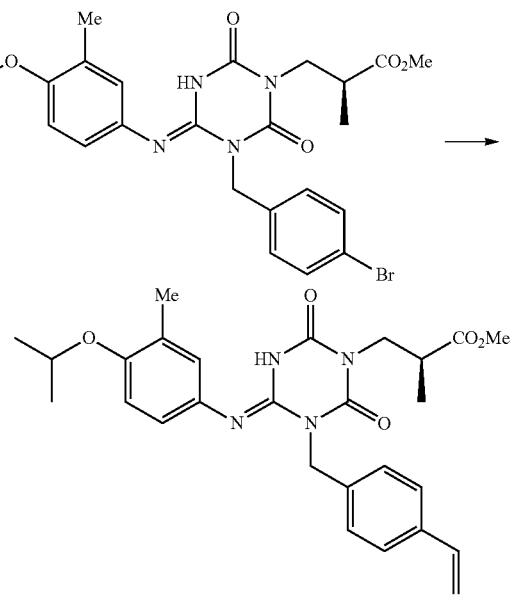

To a mixture of (S)-1-(4-bromobenzyl)-6-(3-mehyl-4-isopropoxyphenylimino)-3-(2-methoxycarbonylpropyl)-1,3,5- triazinane-2,4-dion (300 mg, 0.550 mmol), vinyl boronic acid pinacol ester (0.140 mL, 0.825 mmol). dichloro[1,1'-bis(di-tert-butylphosphino)ferrocene]palladium(II) (36 mg, 0.055 mmol), THF (6 mL) and 2 mol/L aqueous potassium carbonate (1.10 mL) was heated at reflux for 1 hour. To the reaction mixture was added water and the resulting mixture was extracted with ethyl acetate. The extract wan washed by brine, dried over anhydrous sodium sulphate, and concentrated in vacuo. The resulting residue was purified by silica gel column chromatography (ethyl acetate/hexane) to give (S)-1-(4-vinylbenzyl)-6-(3-mehyl-4-isopropoxyphenylimino)-3-(2-methoxycarbonylpropyl)-1,3,5-triazinane-2,4-dion (256 mg, Yield: 95%) as colorless solid.

1H-NMR (δ ppm TMS/DMSO-d6): 1.04 (3H, d, J=6.8 Hz), 1.27 (6H, d, J=5.6 Hz), 2.11 (3H, s), 2.80-2.83 (1H, m), 3.49 (3H, s), 3.79-3.06 (2H, m), 4.53-4.56 (1H, m), 5.24-5.27 (3H, m), 5.83 (1H, d, J=16.0 Hz), 6.69-6.76 (1H, m), 8.03 (1H, d, J=8.0 Hz), 7.05-7.07 (2H, m), 7.28 (2H, d, J=8.0 Hz), 7.49 (2H, d, J=8.0 Hz), 9.10 (1H, s).

EXAMPLE 64

Preparation of (S)-1-(4-vinylbenzyl)-6-(3-mehyl-4-isopropoxyphenylimino)-3-(2-hydroxycarbonylpropyl)-1,3,5-triazinane-2,4-dion (I-0897)

[Chemical Formula 173]

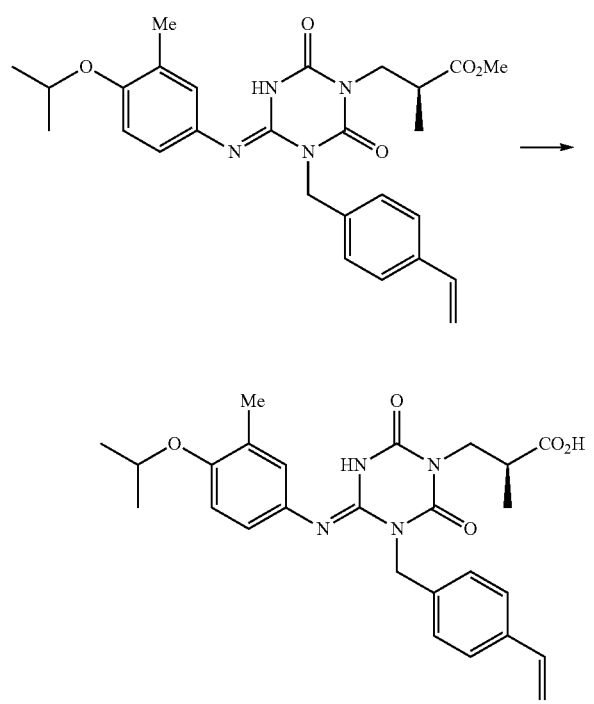

A mixture of (S)-1-(4-vinylbenzyl)-6-(3-mehyl-4-isopropoxyphenylimino)-3-(2-methoxycarbonylpropyl)-1,3,5-triazinane-2,4-dion (50 mg, 0.10 mmol), methanol (0.4 mL) and THF(0.4 mL) was added 1 mol/L lithium hydroxide (0.8 mL), and the resulting mixture was stirred at room temperature 6 hours. To the reaction mixture was added 10% aqueous citric acid, and the resulting mixture was extracted with ethyl acetate. The extract was washed by water, dried over anhydrous sodium sulphate, and concentrated in vacuo. The resulting residue was precipitated by ethyl acetate and hexane to give (S)-1-(4-vinylbenzyl)-6-(3-mehyl-4-isopropoxyphenylimino)-3-(2-hydroxycarbonylpropyl)-1,3,5-triazinane-2,4-dion (36 mg, Yield: 74%) as colorless solid.

1H-NMR (δ ppm TMS/DMSO-d6): 1.01 (3H, d, J=6.8 Hz), 1.26 (6H, d, J=5.6 Hz), 2.10 (3H, s), 2.76-2.80 (1H, m), 3.78-3.97 (2H, m), 4.50-4.55 (1H, m), 5.24-5.27 (3H, m), 5.83 (1H, d, J=16.0 Hz), 6.69-6.76 (1H, m), 6.93 (1H, d, J=8.0 Hz), 7.04-7.07 (2H, m), 7.28 (2H, d, J=8.0 Hz), 7.49 (2H, d, J=8.0 Hz), 9.14 (1H, s), 12.29 (1H, brs).

EXAMPLE 65

Preparation of (S)-1-(4-vinylbenzyl)-6-(3-mehyl-4-isopropoxyphenylimino)-3-(2-methoxycarbonylpropyl)-1,3,5-triazinane-2,4-dion (I-0894)

[Chemical Formula 174]

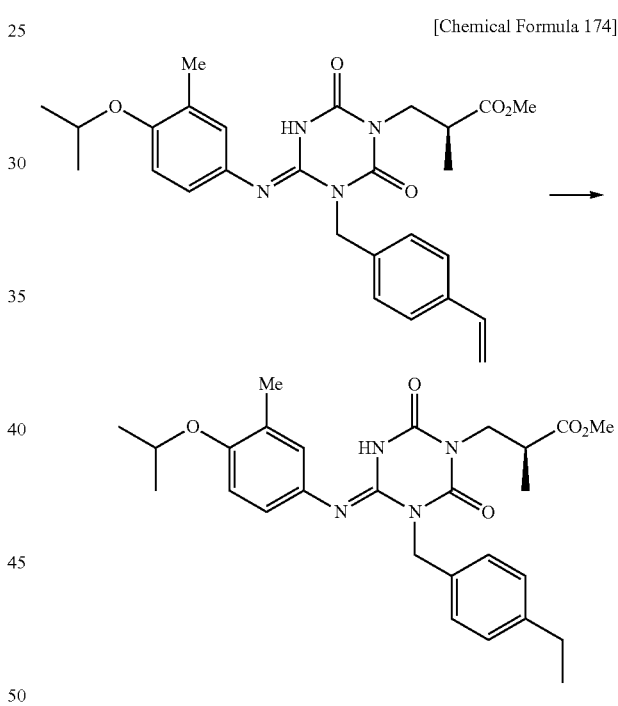

A solution of (S)-1-(4-vinylbenzyl)-6-(3-mehyl-4-isopropoxyphenylimino)-3-(2-hydroxycarbonylpropyl)-1,3,5-triazinane-2,4-dion (190 mg, 0.386 mmol) in methanol (19 mL) was hydrogenated under 5% Pt/C. The reaction mixture was concentrated vacuo. The resulting residue was purified by silica gel column chromatography (ethyl acetate/hexane) to give (S)-1-(4-vinylbenzyl)-6-(3-mehyl-4-isopropoxyphenylimino)-3-(2-methoxycarbonylpropyl)-1,3,5-triazinane-2,4-dion (99 mg, Yield: 52%) as colorless solid.

1H-NMR (δ ppm TMS/DMSO-d6): 1.04 (3H, d, J=6.8 Hz), 1.15 (3H, t, J=7.6 Hz), 1.27 (6H, d, J=5.6 Hz), 2.11 (3H, s), 2.58 (2H, q, J=7.6 Hz), 2.79-2.84 (1H, m), 3.47 (3H, s), 3.78-3.96 (2H, m), 4.53-4.57 (1H, m), 5.23 (2H, s), 6.93 (1H, d, J=8.0 Hz), 7.05-7.08 (2H, m), 7.22 (4H, s), 9.18 (1H, s).

EXAMPLE 66

Preparation of (S)-1-(4-ethylbenzyl)-6-(3-mehyl-4-isopropoxyphenylimino)-3-(2-hydroxycarbonylpropyl)-1,3,5-triazinane-2,4-dion (I-0898)

[Chemical Formula 175]

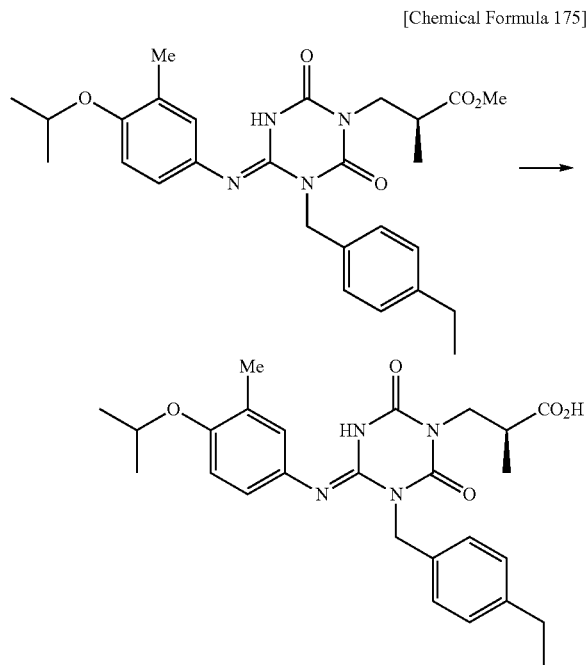

To a mixture of (S)-1-(4-ethylbenzyl)-6-(3-mehyl-4-isopropoxyphenylimino)-3-(2-methoxycarbonylpropyl)-1,3,5-triazinane-2,4-dion (94 mg, 0.19 mmol), methanol (1 mL) and THF(1 mL) was added 1 mol/L lithium hydroxide (0.57 mL), and the resulting mixture was stirred at 60° C. for 3 hours. To the reaction mixture was added 10% aqueous citric acid, and the resulting mixture was extracted with ethyl acetate. The extract was washed by water, dried over anhydrous sodium sulphate, and concentrated in vacuo. The resulting residue was precipitated by ethyl acetate and hexane to give (S)-1-(4-ethylbenzyl)-6-(3-mehyl-4-isopropoxyphenylimino)-3-(2-methoxycarbonylpropyl)-1,3,5-triazinane-2,4-dion (78 mg, Yield: 85%) as colorless solid. 1H-NMR (δ ppm TMS/DMSO-d6): 1.01 (3H, d, J=6.8 Hz), 1.16 (3H, t, J=7.6 Hz), 1.26 (6H, d, J=5.6 Hz), 2.10 (3H, s), 2.58 (2H, d, J=7.6 Hz), 2.79-2.84 (1H, m), 3.74-3.97 (2H, m), 4.53-4.57 (1H, m), 5.24 (2H, s), 6.92 (1H, d, J=8.0 Hz), 7.05-7.08 (2H, m), 7.22 (4H, s), Hz), 9.12 (1H, s), 12.31 (1H, brs).

EXAMPLE 67

Preparation of 1-(4-chlorobenzyl)-6-(3-chloro-4-isopropoxyphenylimino)-3-(1-hydroxymethyl)-3-oxacyclobutyl)methyl-1,3,5-triazinane-2,4-dion (I-1010)

[Chemical Formula 176]

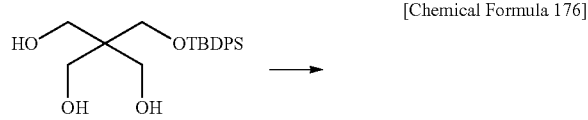

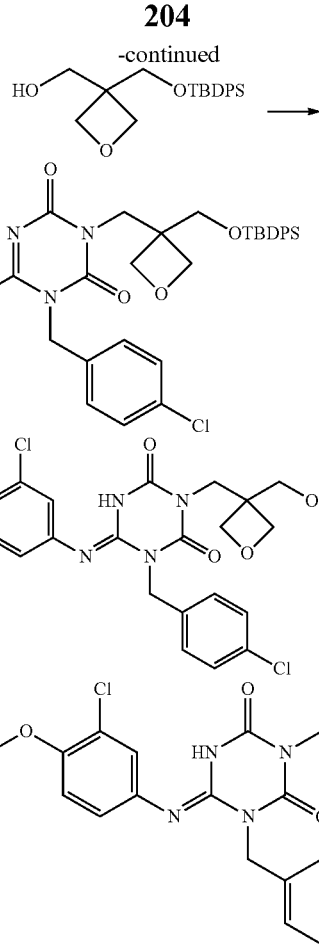

To a solution of 2-(t-butyl-diphenylsilyloxymethyl)-2-hydroxymethyl-propane-1,3-diol (441 mg, 1.18 mmol) in THF (9 mL) were added 1.67 mol/L, n-butyllithium/n-hexane solution (1.55 mL, 2.59 mmol) and p-toluenesulfonyl chloride (247 mg. 1.30 mmol) under ice-cooling, and the resulting mixture was stirred at room temperature for 20 hours. To the reaction mixture was added water, and the resulting mixture was extracted with diethyl ether. The extract was washed by water, dried over anhydrous sodium sulphate, and concentrated in vacuo. The resulting residue was purified by silica gel column chromatography (ethyl acetate/hexane) to give 1-(t-butyl-diphenylsilyloxymethyl)-1-hydroxymethyl-3-oxacyclobutane (148 mg, Yield: 35%) as colorless oil. 1H-NMR (δ ppm TMS/DMSO-d6): 1.01 (9H, s), 3.67 (2H, d, J=4.8 Hz), 3.80 (2H, s), 4.33-4.36 (4H, m), 4.90-4.93 (1H, m), 7.42-7.47 (6H, m), 7.63 (4H, d, J=6.8 Hz).

To a mixture of 1-(4-chlorobenzyl)-6-(ethylthio)-1,3,5-triazine-2,4(1H,3H)-dion (150 mg, 0.504 mmol), 1-(t-butyl-diphenylsilylocxymethyl)-1-hydroxymethyl-3-oxacyclobutane (198 mg, 0.554 mmol), triphenylphosphine (198 mg, 0.756 mmol) and dioxane (2 mL) was added di-2-methoxyethylazodicarboxylate (165 mg, 0.705 mmol), and the resulting mixture was stirred at room temperature for 1 hour. To the reaction mixture was added water, extracted with ethyl acetate. The extract was washed by brine, dried over anhydrous sodium sulphate, and concentrated in vacuo. The resulting residue was purified by silica gel column chromatography (ethyl acetate/hexane) to give 1-(4-chlorobenzyl)-6-(ethylthio)-(3-[1-(t-butyly-diphenylsilyloxymethyl)-3-oxacyclobutyl]methyl-1,3,5-triazine-2,4-dion (273 mg, Yield: 85%) as colorless solid.

1H-NMR (δ ppm TMS/DMSO-d6): 0.99 (9.0H, s), 1.26 (3.0H, t, J=7.2 Hz), 3.11 (2.0H, q, J=7.2 Hz), 3.86 (2.0H, s), 4.11 (2.0H, s), 4.20 (2.0H, d, J=6.1 Hz), 4.47 (2.0H, d, 6.1 Hz), 5.06 (2.0H, s), 7.32-7.37 (4.0H, m), 7.41-7.47 (6.0H, m), 7.61 (4.0H, d, J=7.3 Hz).

A mixture of 1-(4-chlorobenzyl)-6-(ethylthio)-(3-[1-(t-butyl-diphenylsilyloxymethyl)-3-oxacyclobutyl]methyl-1,3,5-triazine-2,4(1H,3H)-dion (273 mg, 0.429 mmol), 3-chloro-4-isopropoxyaniline (119 mg, 0.644 mmol), acetic acid (0.368 mL) and t-butanol (3 mL) was heated at reflux for 7 hours. The reaction mixture was added to saturated aqueous sodium bicarbonate, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give 1-(4-chlorobenzyl)-6-(3-chloro-4-isopropoxyphenylimino)-3-[1-(t-butyl-diphenylsilyloxymethyl)-3-oxacyclobutyl]methyl-1,3,5-triazine-2,4-dion (248 mg, Yield: 76%) as colorless solid.

1H-NMR (δ ppm TMS/DMSO-d6): 1.00 (9H, s), 1.29 (6H, d, J=5.8 Hz), 3.83 (2H, s), 4.05 (2H, s), 4.19 (2H, d, J=6.1 Hz), 4.44 (2H, d, J=6.1 Hz), 4.57-4.66 (1H, m), 5.22 (2H, s), 7.10-7.50 (13H, m), 7.61 (4H, d, J=7.1 Hz), 9.35 (1H, brs).

To a solution of 1-(4-chlorobenzyl)-6-(3-chloro-4-isopropoxyphenylimino)-3-[1-(t-butyl-diphenylsilyloxymethyl)-3-oxacyclobutyl]methyl-1,3,5-triazine-2,4-dion (240 mg, 0.316 mmol) in THF (3 mL) wax added a solution of 1 mol/L tetra-n-butylammonium fluoride in THF (0.88 mL, 0.88 mmol), and the resulting mixture was stirred at 45° C. for 3 hours. The reaction mixture was added to aqueous ammonium chloride, and the resulting mixture was extracted with ethyl acetate. The extract was washed by brine, dried over anhydrous sodium sulphate, and concentrated in vacuo. The resulting residue was purified by silica gel column chromatography (ethyl acetate/hexane) to give 1-(4-chlorobenzyl)-6-(3-chloro-4-isopropoxyphenylimino)-3-(1-hydroxymethyl-3-oxacyclobutyl)methyl-1,3,5-triazine-2,4-dion (120 mg, Yield: 73%) as colorless solid.

1H-NMR (δ ppm TMS/DMSO-d6): 1.29 (6H, d, J=5.8 Hz), 3.61 (2H, d, J=4.5 Hz), 3.95 (2H, s), 4.18 (2H, d, J=6.1 Hz), 4.40 (2H, d, J=6.1 Hz), 4.60-4.62 (1H, m), 4.93-4.95 (1H, m), 5.22 (2H, s), 7.12-7.41 (7H, m).

EXAMPLE 68

Preparation of 1-(4-chlorobenzyl)-6-(3-chloro-4-isopropoxyphenylimino)-3-(1-hydroxymethyl-3-oxacyclobutyl)methyl-1,3,5-triazinane-2,4-dion (I-1011)

[Chemical Formula 177]

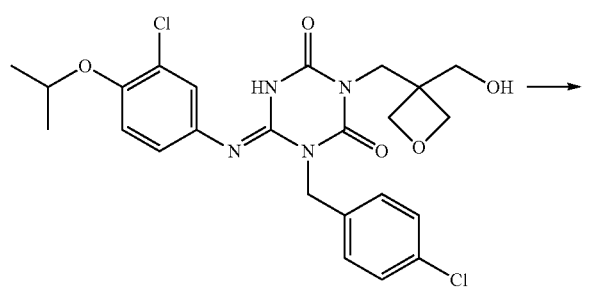

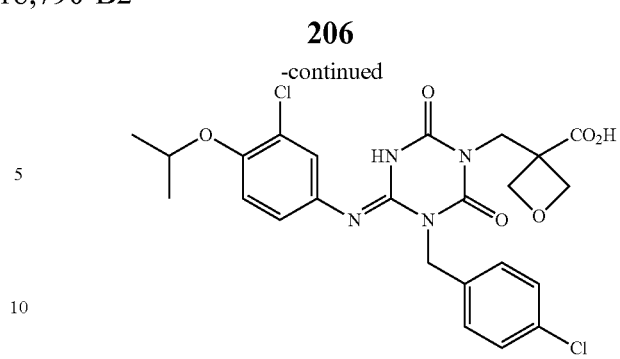

To a solution of 1-(4-chlorobenzyl)-6-(3-chloro-4-isopropoxyphenylimino)-3-(1-hydroxymethyl-3-oxacyclobutyl)methyl-1,3,5-triazinane-2,4-dion (50 mg, 0.096 mmol)in acetone (0.8 mL) was added 2.67 mol/L Jones reagent (0.079 mL, 0.21 mmol), and the resulting mixture was stirred at room temperature for 1 hour. To the reaction mixture were added isopropanol and water, and the resulting mixture was extracted with ethyl acetate. The extract was washed by brine, dried over anhydrous sodium sulphate, and concentrated in vacuo. The resulting residue was purified in high speed liquid chromatography (0.3% $HCO_2H$ $H_2O$/MeCN 40-70%) to give 1-(4-chlorobenzyl)-6-(3-chloro-4-isopropoxyphenylimino)-3-(1-hydroxycarbonyl)-3-oxacyclobutyl)methyl-1,3,5-triazinane-2,4-dion (8 mg, Yield: 16%) as colorless solid.

1H-NMR (δ ppm TMS/DMSO-d6): 1.36 (6H, d, J=6.0 Hz), 4.43 (2H, s), 4.44-4.52 (1H, m), 4.67 (2H, d, J=6.7 Hz), 4.76 (2H, d, J=6.7 Hz), 5.16 (2H, s), 6.65-6.67 (1H, m), 6.86-6.90 (2H, m), 7.31 (2H, d, J=8.4 Hz), 7.41 (2H, d, J=8.4 Hz).

EXAMPLE 69

Preparation of (S)-1-(4-chlorobenzyl)-6-(3-mehyl-4-cyclopropylethynylphenylimino)-3-(2-methoxycarbonylpropyl)-1,3,5-triazinane-2,4-dion (I-1041)

[Chemical Formula 178]

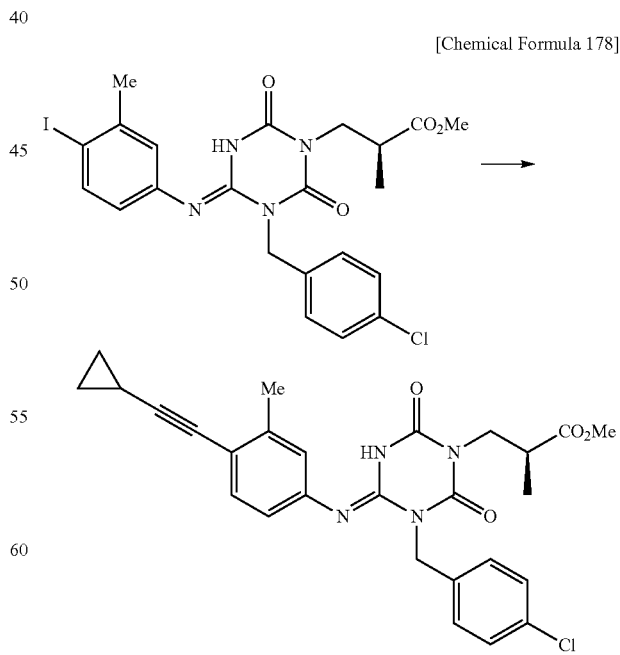

A mixture of (S)-1-(4-chlorobenzyl)-6-(4-iodo-3-methylphenylimino)-3-(2-methoxycarbonylpropyl)-1,3,5-triazinane-2,4-dion (268 mg, 0.471 mmol), ethynylcyclopropane (0.080 mL, 0.94 mmol), bis(triphenylphosphine)palladium (II) dichloride (8.3 mg, 0.942 mmol), cuprous iodide (I) (4.5 mg, 0.024 mmol), triethylamine (0.131 mL, 0.942 mmol) and DMF (3 mL) was stirred at 60° C. for 2 hours. To the reaction mixture was added 5% aqueous citric acid, and the resulting mixture was extracted with ethyl acetate. The extract was washed by saturated aqueous sodium bicarbonate and brine, dried over anhydrous sodium sulphate, and concentrated in vacuo. The resulting residue was purified by silica gel column chromatography (ethyl acetate/hexane) to give (S)-1-(4-chlorobenzyl)-6-(3-mehyl-4-cyclopropylethynylphenylimino)-3-(2-methoxycarbonylpropyl)-1,3,5-triazinane-2,4-dion (200 mg, Yield: 84%) as brown solid.

1H-NMR (δ ppm TMS/CDCl3): 0.75-0.95 (4H, m), 1.18 (3H, d, J=6.9 Hz), 1.49 (1H, m), 2.37 (3H, s), 2.89 (1H, m), 3.60 (3H, s), 3.87 (1H, dd, J=6.0, 13.8 Hz), 4.09 (1H, m), 5.10-5.24 (2H, m), 6.57 (1H, m), 6.63 (1H, m), 7.26-7.30 (4H, m), 7.48 (2H, d, J=8.4 Hz).

EXAMPLE 70

Preparation of (S)-1-(4-chlorobenzyl)-6-(3-mehyl-4-cyclopropylethynylphenylimino)-3-(2-methoxycarbonylpropyl)-1,3,5-triazinane-2,4-dion (I-1041)

[Chemical Formula 179]

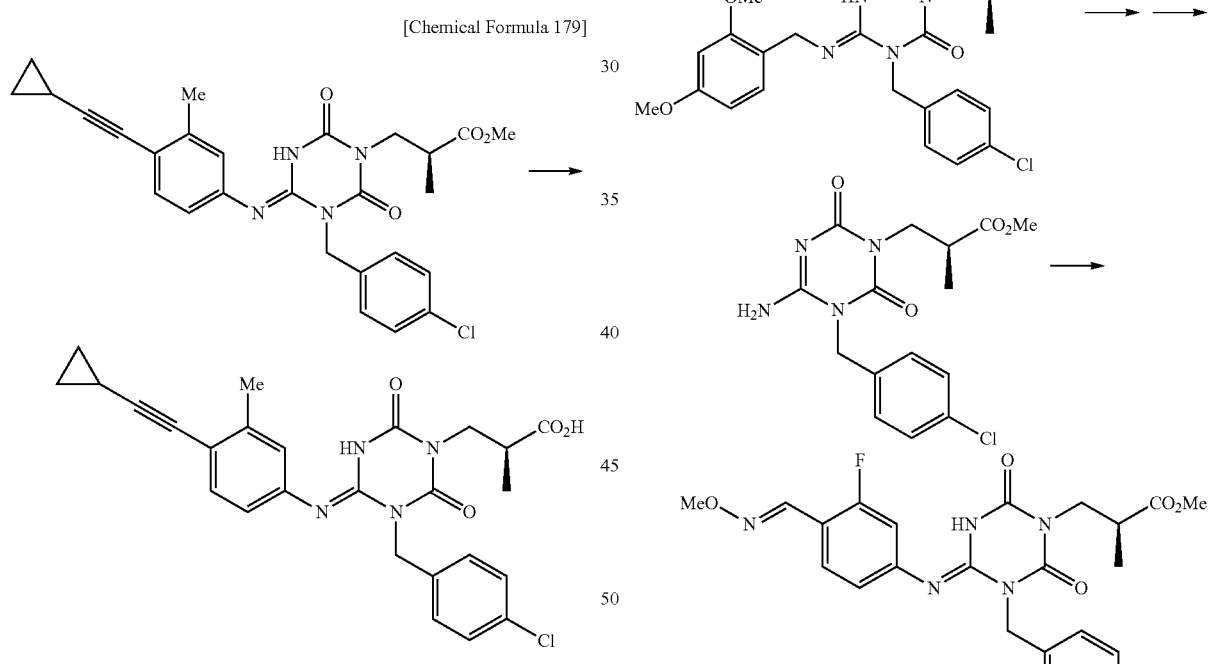

To a mixture of (S)-1-(4-chlorobenzyl)-6-(3-mehyl-4-cyclopropylethynylphenylimino)-3-(2-methoxycarbonylpropyl)-1,3,5-triazinane-2,4-dion (180 mg, 0.355 mmol), methanol (1 mL) and THF (1 mL) was added 1 mol/L sodium hydroxide (1.1 mL), and the resulting mixture was stirred at room temperature for 2.5 hours. To the reaction mixture was added 2 mol/L hydrochloric acid, and the resulting mixture was extracted with ethyl acetate. The, extract was washed by water, dried over anhydrous sodium sulphate, and concentrated in vacuo. The resulting residue was precipitated by ethyl acetate and hexane to give (S)-1-(4-chlorobenzyl)-6-(3-mehyl-4-cyclopropylethynylphenylimino)-3-(2-hydroxycarbonylpropyl)-1,3,5-triazinane-2,4-dion (78 mg, Yield: 85%) as pale brown solid.

1H-NMR (δ ppm TMS/CDCl3): 0.75-0.95 (4H, m), 1.19 (3H, d, J=6.9 Hz), 1.48 (1H, m), 2.35 (3H, s), 2.92 (1H, m), 3.87 (1H, dd, J=6.3, 13.5 Hz), 4.10 (1H, dd, J=7.2, 13.2 Hz), 5.16 (2H, s), 6.55 (1H, m), 6.61 (1H, s), 7.24-7.64 (3H, m), 7.44 (2H, d, J=8.4 Hz), 7.66 (1H, s).

EXAMPLE 71

Preparation of (S)-1-(4-chlorobenzyl)-6-(3-fluoro-4-methoxyiminomethylphenylimino)-3-(2-methoxycarbonylpropyl)-1,3,5-triazinane-2,4-dion (I-0881)

[Chemical Formula 180]

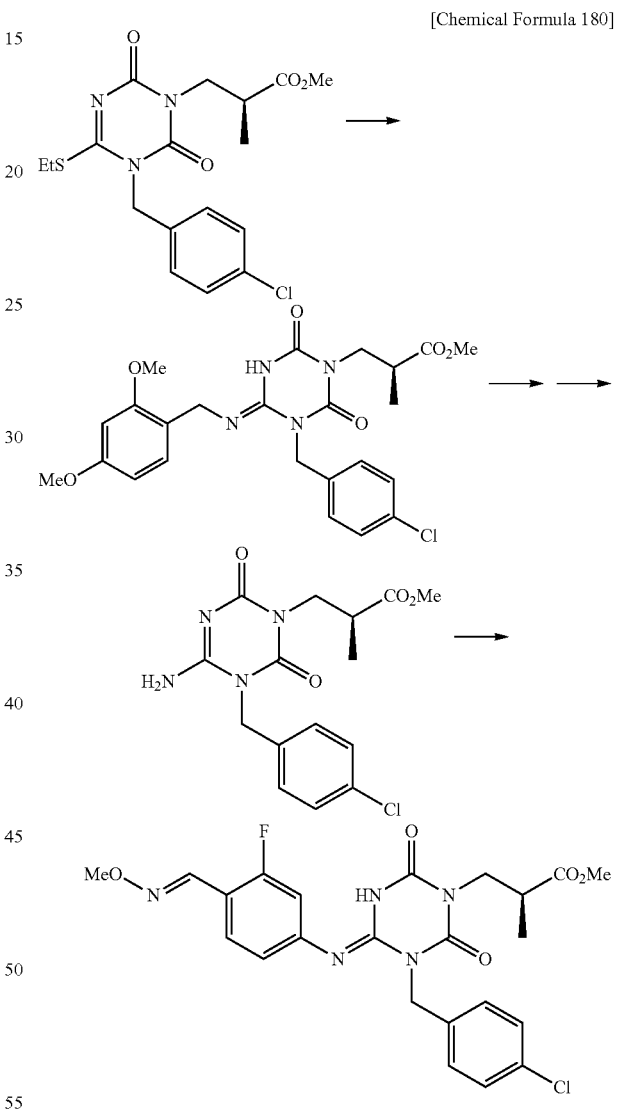

A mixture of (S)-1-(4-chlorobenzyl)-6-(ethylthio)-3-(2-methoxycarbonylpropyl)methyl-1,3,5-triazine-2,4(1H,3H)-dion (1.00 g, 2.51 mmol), 2,4-dimethoxybenzylamine (630 mg, 3.77 mmol), acetic acid (2.16 mL) and t-butanol (20 mL) was heated at reflux for 15 hours. The reaction mixture was added to saturated aqueous sodium bicarbonate, and the resulting mixture was extracted with ethyl acetate. The extract was washed by 2 mol/L hydrochloric acid and brine, dried over anhydrous sodium sulphate, and concentrated in vacuo. The resulting residue was purified by silica gel column chromatography (ethyl acetate/hexane) to give (S)-

1-(4-chlorobenzyl)-6-(2,4-dimethoxybenzylimino)-3-(2-methoxycarbonylpropyl)methyl-1,3,5-triazine-2,4(1H,3H)-dion (1.19 g, Yield: 94%) as colorless solid.

1H-NMR (δ ppm TMS/DMSO-d6): 1.04 (3H, d, J=6.8 Hz), 2.82 (1H, q, J=6.8 Hz), 3.48 (3H, s), 3.72 (6H, s), 3.77-3.82 (1H, m), 3.90-3.95 (1H, m), 4.37 (2H, s), 5.15 (2H, s), 6.35 (1H, d J=8.4 Hz), 6.51 (1H, s), 6.73 (1H, d, J=8.4 Hz), 7.27 (2H, d, J=7.6 Hz), 7.44 (2H, d, J=7.6 Hz), 7.94 (1H, brs).

A solution of (S)-1-(4-chlorobenzyl)-6-(2,4-dimethoxybenzylimino)-3-(2-methoxycarbonylpropyl)methyl-1,3,5-triazine-2,4(1H,3H)-dion (1.15 g, 2.29 mmol) in trifluoro acetic acid (11 mL) was stirred at room temperature for 1 hour. The reaction mixture was concentrated in vacuo, and the residue was extracted with chloroform. The extract was washed by saturated aqueous sodium bicarbonate and brine, dried over anhydrous sodium sulphate, and concentrated in vacuo. The resulting residue was precipitated by ethyl acetate and hexane to give (S)-6-amino-1-(4-chlorobenzyl)-3-(2-methoxycarbonylpropyl)methyl-1,3,5-triazine-2,4(1H,3H)-dion (0.80 g, Yield:99%) as colorless solid.

1H-NMR (δ ppm TMS/DMSO-d6): 1.04 (3H, d, J=6.8 Hz), 2.81 (1H, q, J=6.8 Hz), 3.49 (3H, s), 3.74-3.81 (1H, m), 3.89-3.94 (1H, m), 5.03 (2H, s), 7.27 (2H, d, J=7.6 Hz), 7.43 (2H, d J=7.6 Hz), 7.86 (2H, brs).

A mixture of (S)-6-amino-1-(4-chlorobenzyl)-3-(2-methoxycarbonylpropyl)methyl-1,3,5-triazine-2,4(1H,3H)-dion (80 mg 0.35 mmol), 3-fluoro-4-methoxyiminomethylaniline (146 mg, 0.414 mmol), acetic acid palladium (7.7 mg, 0.034 mmol), 4,5-bis(diphenylphosphino)-9,9-dimethylxanthene (30 mg, 0.052 mmol), cesium carbonate (157 mg, 0.483 mmol) and dioxane (2.4 mL) was heated at reflux for 24 hours. To the reaction mixture was added water, and the resulting mixture was extracted with ethyl acetate and THF. The extract was washed by brine, dried over anhydrous sodium sulphate, and concentrated in vacuo. The resulting residue was purified by silica gel column chromatography (ethyl acetate/hexane) to give (S)-1-(4-chlorobenzyl)-6-(3-fluoro-4-methoxyiminomethylphenylimino)-3-(2-methoxycarbonylpropyl)methyl-1,3,5-triazine-2,4(1H,3H)-dion (53 mg, Yield: 31%) as colorless solid.

1H-NMR (δ ppm TMS/DMSO-d6): 1.07 (3H, d, J=6.8 Hz), 2.81 (1H, q, J=6.8 Hz), 3.50 (3H, s), 3.83 (1H, brs), 3.90 (4H, brs), 5.09 (2H, s), 6.65-6.69 (1H, m), 7.41 (5H, brs), 7.63 (1H, brs), 8.25 (1H, s), 10.97 (1H, brs).

EXAMPLE 72

Preparation of (S)-1-(4-chlorobenzyl)-6-(3-fluoro-4-methoxyiminomethylphenylimino)-3-(2-hydroxycarbonylpropyl)methyl-1,3,5-triazinane-2,4-dion (I-0893)

[Chemical Formula 181]

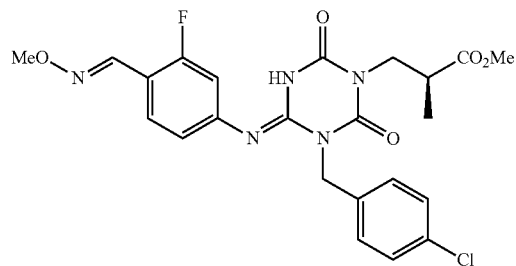

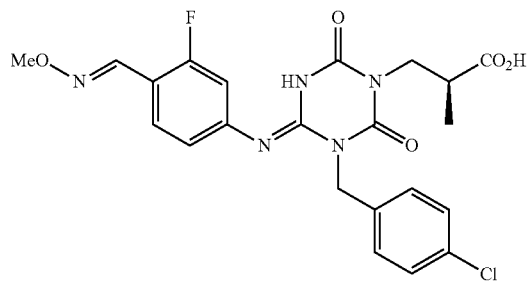

To a mixture of (S)-1-(4-chlorobenzyl)-6-(3-fluoro-4-methoxyiminomethylphenylimino)-3-(2-hydroxycarbonylpropyl)methyl-1,3,5-triazinane-2,4-dion (50 mg, 0.099 mmol), methanol (1 mL) and THF (1 mL) was added 1 mol/L lithium hydroxide (0.3 mL), and the resulting mixture was stirred at 60° C. for 2 hours. To the reaction mixture was added 10% aqueous citric acid, and the resulting mixture was extracted with ethyl acetate. The extract was washed by water, dried over anhydrous sodium sulphate, and concentrated in vacuo. The resulting residue was precipitated by ethyl acetate and hexane to give (S)-1-(4-chlorobenzyl)-6-(3-fluoro-4-methoxyiminomethylphenylimino)-3-(2-hydroxycarbonylpropyl)methyl-1,3,5-triazinane-2,4-dion (44 mg, Yield: 91)%) as colorless solid.

1H-NMR (δ ppm TMS/DMSO-d6): 1.04 (3H, d, J=6.8 Hz), 2.76 (1H, q, J=6.8 Hz), 3.81 (1H, brs), 3.90 (4H, brs), 5.12 (2H, s), 6.67 (1H, brs), 7.40 (5H, s), 7.65 (1H, brs), 8.24 (1H, s), 10.92 (1H, brs), 12.36 (1H, brs).

EXAMPLE 73

Preparation of (S)-6-(3-chloro-4-isopropoxyphenylimino)-1-(4-methoxybenzyl)-3-(2-methoxycarbonylpropyl)methyl-1,3,5-triazinane-2,4-dion (I-1143)

[Chemical Formula 182]

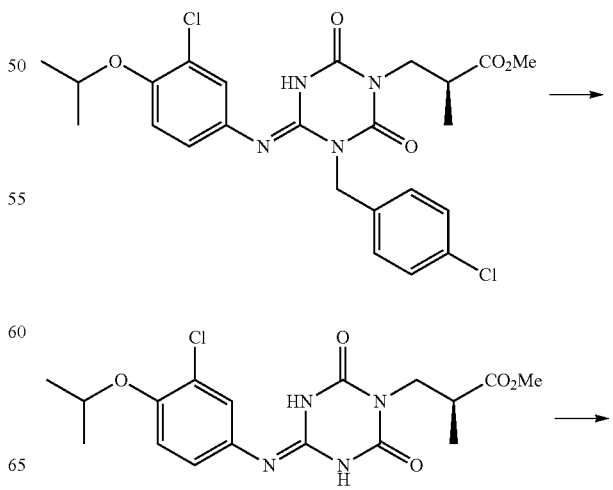

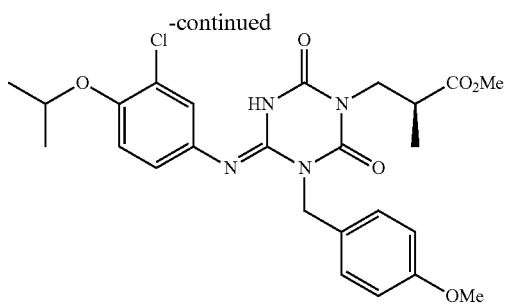

A mixture of (S)-6-(3-chloro-4-isopropoxyphenylimino)-1-(4-chlorobenzyl)-3-(2-methoxycarbonylpropyl)methyl-1,3,5-triazinane-2,4-dion (800 mg, 1.53 mmol) in methanol (75 mL) and DMF (5 mL) was hydrogenated under 10% Pd/C. The reaction mixture was concentrated in vacuo. The resulting residue was purified by high speed liquid chromatography (0.3% $HCO_2H$ $H_2O$/MeCN 40-70%) to give (S)-6-(3-chloro-4-isopropoxyphenylimino)-3-(2-methoxycarbonylpropyl)methyl-1,3,5-triazinane-2,4-dion (498 mg, Yield: 82%) as colorless solid.

1H-NMR (δ ppm TMS/DMSO-d6): 1.05 (3H, d, J=6.8 Hz), 1.29 (6H, d, J=5.6 Hz), 2.81 (1H, q, J=6.8 Hz), 3.56 (3H, s), 3.77-3.82 (1H, m), 3.87-3.92 (1H, m), 4.62 (1H, sept, J=5.6 Hz), 7.16 (1H, d, J=8.4 Hz), 7.34 (1H, d, J=8.4 Hz), 7.69 (1H, s), 8.14 (1H, s).

To a mixture of (S)-6-(3-chloro-4-isopropoxyphenylimino)-3-(2-methoxycarbonylpropyl)methyl-1,3,5-triazinane-2,4-dion (480 mg, 1.21 mmol), 4-methoxybenzyl chloride (341 mg, 2.18 mmol) and DMF (10 mL) was added potassium carbonate (301 mg, 2.18 mmol), and the resulting mixture was stirred at room temperature 12 hours. To the reaction mixture was added water, extracted with ethyl acetate. The extract was washed by water, dried over anhydrous sodium sulphate, and concentrated in vacuo. The resulting residue was purified by silica gel column chromatography (ethyl acetate/hexane) to give (S)-6-(3-chloro-4-isopropoxyphenylimino)-1-(4-methoxybenzyl)-3-(2-methoxycarbonylpropyl)methyl-1,3,5-triazinane-2,4-dion (190 mg, Yield: 30%) as colorless solid.

1H-NMR (δ ppm TMS/DMSO-d6): 1.05 (3H, d, J=6.8 Hz), 1.29 (6H, d, J=5.6 Hz), 2.81 (1H, q, J=6.8 Hz), 3.49 (3H, s), 3.73 (3H, s), 3.77-3.82 (1H, m), 3.87-3.92 (1H, m), 4.64 (1H, sept, J=5.6 Hz), 5.20 (2H, s), 6.94 (2H, d, J=7.2 Hz), 7.16-7.28 (4H, m), 7.47 (1H, s), 9.28 (1H, s).

EXAMPLE 74

Preparation of (S)-6-(3-chloro-4-isopropoxyphenylimino)-1-(4-methoxybenzyl)-3-(2-methoxycarbonylpropyl)methyl-1,3,5-triazinane-2,4-dion (I-1159)

[Chemical Formula 183]

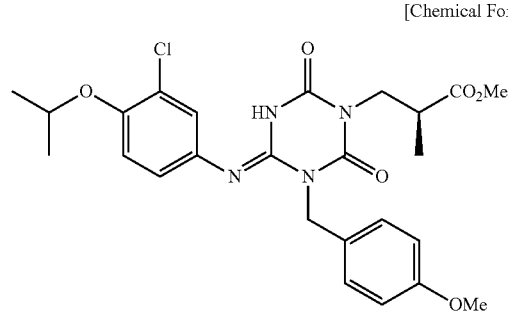

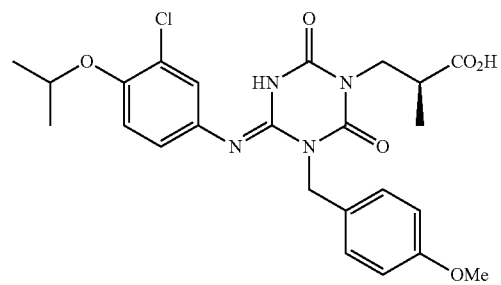

To a mixture of (S)-6-(3-chloro-4-isopropoxyphenylimino)-1-(4-methoxybenzyl)-3-(2-methoxycarbonylpropyl)methyl-1,3,5-triazine-2,4-dion (180 g, 0.348 mmol), methanol (2 mL) and THF (2 mL) was added 1 mol/L lithium hydroxide (1 mL), and the resulting mixture was stirred at 50° C. for 5 hours. To the reaction mixture was added 10% aqueous citric acid, and the resulting mixture was extracted with ethyl acetate. The extract was washed by water, dried over anhydrous sodium sulphate, and concentrated in vacuo. The resulting residue was precipitated by ethyl acetate and hexane to give (S)-6-(3-chloro-4-isopropoxyphenylimino)-1-(4-methoxybenzyl)-3-(2-hydroxycarbonylpropyl)methyl-1,3,5-triazine-2,4-dion (160 mg, Yield 91%) as colorless solid.

1H-NMR (δ ppm TMS/DMSO-d6): 1.02 (3H, d, J=6.8 Hz), 1.29 (6H, q, J=5.6 Hz), 2.76 (1H, q, J=6.8 Hz), 3.73 (3H, s), 3.77-3.82 (1H, m), 3.87-3.92 (1H, m), 4.63 (1H, sept, J=5.6 Hz), 5.21 (2H, s), 6.93 (2H, d, J=7.2 Hz), 7.15-7.28 (4H, m), 7.47 (1H, s), 9.23 (1H, s), 12.33 (1H, brs).

EXAMPLE 75

Preparation of 6-(4-chlorobenzyloxy)-4-ethylthio-(3-fluoro-4-isopropoxyphenylimino)-1-t-butyl-1,3,5-triazine-2(1H)-one (I-1296)

[Chemical Formula 184]

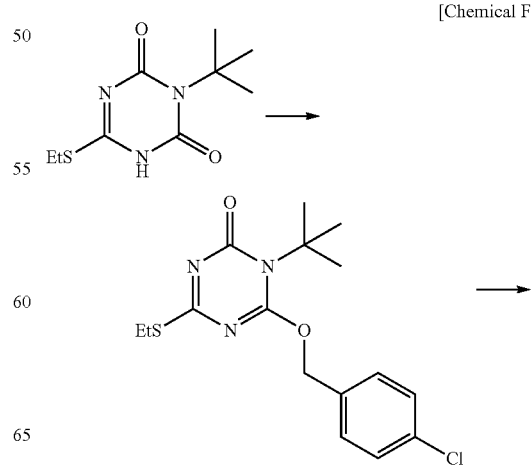

-continued

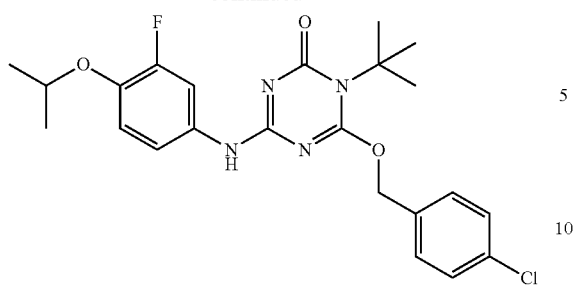

To a mixture of 6-(ethylthio)-3-t-butyl-1,3,5-triazine-2,4 (1H,3H)-dion (1.0 g, 4.4 mmol), 4-chlorobenzyl alcohol (1.02 g, 4.4 mmol), triphenylphosphine (1.49 g, 5.7 mmol) and THF (10 mL) was gradually added di-2-methoxyethyl-azodicarboxylate (1.33 g, 5.7 mmol) under ice-cooling, and the resulting mixture was stirred at room temperature for 1 hour. To the reaction mixture was water (200 mL), and the resulting mixture was extracted with ethyl acetate (200 mL). The extract was washed by brine (200 mL), dried over anhydrous magnesium sulfate, and concentrated in vacuo. The resulting residue was purified by silica gel column chromatography (ethyl acetate/hexane) to give crude 6-(4-chlorobenzyloxy)-4-ethylthio-1-t-butyl-1,3,5-triazine-2 (1H)-one. To the obtained crude product were added 3-fluoro-4-isopropoxyaniline (0.18 g, 1.09 mmol) and acetic acid (10 mL), and the resulting mixture was stirred at room temperature for 2.5 hours. To the reaction mixture was added saturated aqueous sodium bicarbonate (200 mL), and the resulting mixture was extracted with ethyl acetate (300 mL). The extract was washed by brine (200 mL), dried over anhydrous magnesium sulfate, and concentrated in vacuo. The resulting residue was purified by silica gel column chromatography (ethyl acetate/hexane). The resulting residue was precipitated by ethyl acetate and hexane to give 6-(4-chlorobenzyloxy)-4-(3-fluoro-4-isopropoxyphenylimino)-1-t-butyl-1,3,5-triazine-2(1H)-one (0.12 g, Yield: 6%) as a white powder.

1H-NMR (δ ppm TMS/CDCl$_3$): 1.35 (6H, d, J=6.1 Hz), 1.66 (9H, s), 4.48 (1H, sept, J=6.1 Hz), 5.37 (2H, s), 6.93 (1H, m), 7.26-7.43 (7H, m).

EXAMPLE 76

Preparation of 1-(4-chlorobenzyl)-3-isopropyl-5-(4-trifluoromethylbenzyl)-1,3,5-triazinane-2,4,6-trione (I-1289)

[Chemical Formula 185]

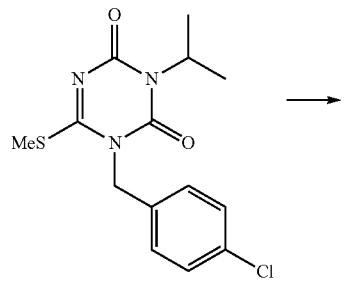

-continued

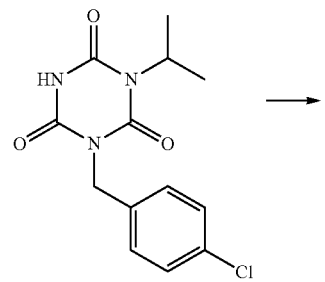

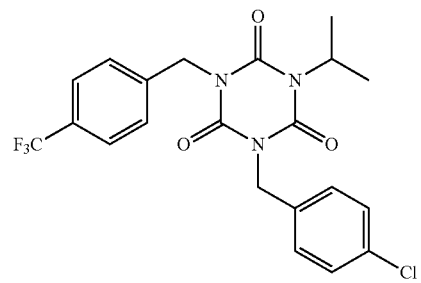

To a mixture of 1-(4-chlorobenzyl)-6-(methylthio)-3-isopropyl-1,3,5-triazine-2,4(1H,3H)-dion (0.2 g, 0.6 mmol) and acetic acid (10 mL) was added 30% hydrogen peroxide solution (0.7 g, 6 mmol) under ice-cooling, and the resulting mixture was stirred at room temperature for 18 hours. To the reaction mixture was added brine (30 mL), and the resulting mixture was extracted with dichloromethane (30 ml×2). The extract was washed by brine (30 mL), dried over anhydrous sodium sulphate, and concentrated in vacuo. The resulting residue was precipitated by hexane to give 1-(4-chlorobenzyl)-3-isopropyl-1,3,5-triazine-2,4,6-trione (0.2 g) as a white powder.

1H-NMR (δ ppm TMS/DMSO-d6): 1.35 (6H, d, J=6.9 Hz), 4.81 (1H, q, J=6.9 Hz), 4.84 (2H, s), 7.36 (4H, d, J=8.7 Hz), 11.66 (1H, s).

To a mixture of 1-(4-chlorobenzyl)-3-isopropyl-1,3,5-triazine-2,4,6-trione (80 mg, 0.27 mmol), 4-trifluorbenzyl alcohol (52.4 mg, 0.3 mmol), triphenylphosphine (92 mg, 0.35 mmol) and THF (2 mL) was gradually added di-2-methoxyethylazodicarboxylate (82 mg, 0.35 mmol) under ice-cooling, and the resulting mixture was stirred at room temperature for 2 hours. The reaction mixture was concentrated in vacuo. The resulting residue was purified by silica gel column chromatography (ethyl acetate/hexane). The resulting residue was precipitated by hexane to give 1-(4-chlorobenzyl)-3-isopropyl-5-(4-trifluoromethylbenzyl)-1,3,5-triazine-2,4,6-trione (65 mg, Yield: 53%) as a white powder.

1H-NMR (δ ppm TMS/CDCl$_3$): 1.45 (6H, d, J=6.9 Hz), 4.96 (m, 1H), 4.98 (2H, s), 5.05 (2H, s), 7.26-7.32 (2H, m), 7.36-7.44 (2H, m), 7.52-7.62 (4H, m).

EXAMPLE 77

Preparation of 1-(4-chlorobenzyl)-3-isopropyl-6-(4-isopropoxyphenylimino)-2-thioxo-1,3,5-triazinane-4-one (I-2253)

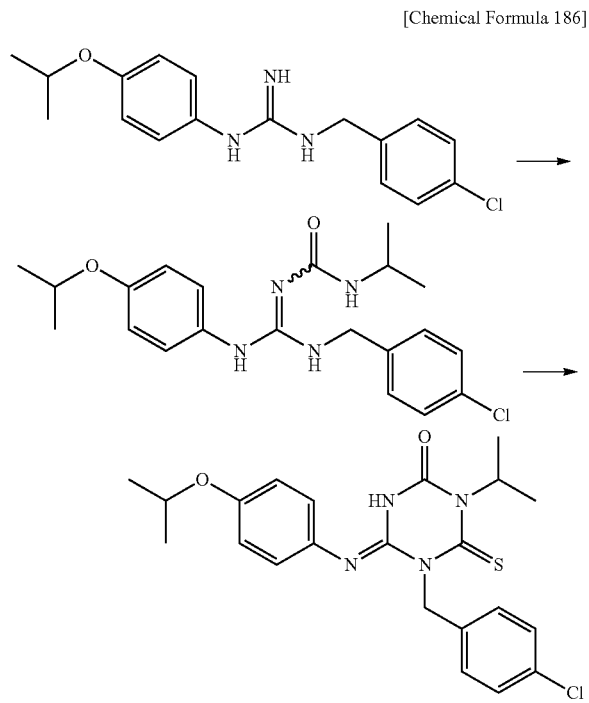

[Chemical Formula 186]

To a suspension of 1-(4-chlorobenzyl)-3-(4-isopropoxyphenyl)guanidine (500 mg, 1.57 mmol) in toluene (5.0 mL) was added 2-isocyanatepropane (0.187 mL, 1.89 mmol) under ice-cooling, and the resulting mixture was stirred at room temperature for 17 hours. The resulting pale yellow solution was concentrated in vacuo, and the residue was purified by silica gel column chromatography (ethyl acetate/hexane) to give 1-((4-chlorobenzylamino)(4-isopropoxyphenylamino)methylene)-3-isopropylurea (629 mg, Yield: 99%) as colorless gum.

The isopropylurea derivative (201 mg, 0.500 mmol) was dissolved in THF (2.2 mL). To the mixture was added thiophosgene (0.042 mL, 0.550 mmol), and the resulting mixture was heated at reflux for 16 hours. Further, potassium carbonate (152 mg, 1.10 mmol) was added to the mixture, and the resulting mixture was heated at reflux for 2.5 hours. To the resulting solution was added ethyl acetate (50 mL), and the resulting mixture was washed by water (20 mL×2) and brine (10 mL). The organic layer was dried over anhydrous sodium sulphate, and concentrated in vacuo. The resulting residue was purified by reversed-phase HPLC (0.1% formic acid in acetonitrile/water) and silica gel column chromatography (ethyl acetate/hexane) to give 1-(4-chlorobenzyl)-3-isopropyl-6-(4-isopropoxyphenylimino)-2-thioxo-1,3,5-triazinane-4-one (0.32 mg, Yield: 0.1%) as colorless oil.

1H-NMR (δ ppm TMS/CDCl3): 1.34 & 1.37 (d×2, 6H), 1.53 (d, 6H), 4.52-4.64 (m, 1H), 5.17 (s, 2H), 5.86-5.97 (m,1H), 6.85 & 7.39 (s×2, 1H), 6.98 (d, 2H), 7.08 (d, 2H), 7.28 (d, 2H), 7.45 (d, 2H).

EXAMPLE 78

Preparation of 1-(4-chlorobenzyl)-3-isopropyl-6-(4-isopropoxyphenylimino)-4-thioxo-1,3,5-triazinane-2-one (I-2254)

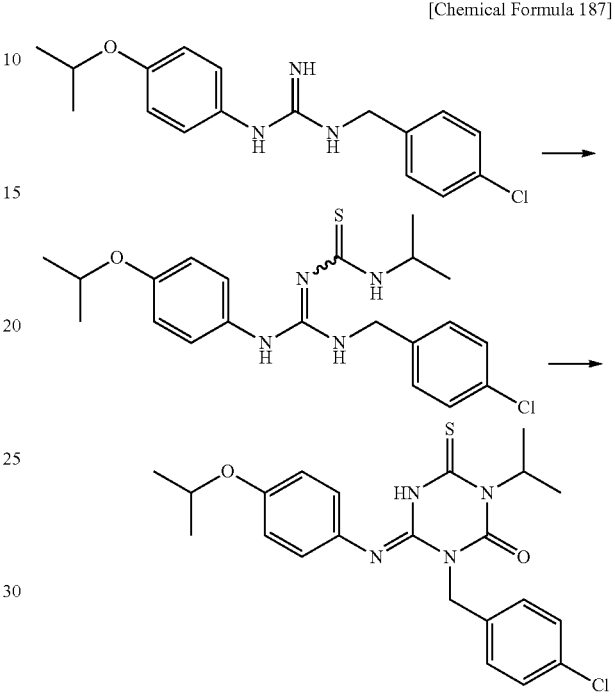

[Chemical Formula 187]

To a suspension of 1-(4-chlorobenzyl)-3-(4-isopropoxyphenyl)guanidine (654 mg, 2.06 mmol) in toluene (6.5 mL) was added isopropyl isocyanate (0.307 mL, 2.88 mmol) under ice-cooling, and the resulting mixture was stirred at room temperature for 18 hours, 60° C. for 2 hours, and 70° C. for 2.5 hours. The resulting mixture was concentrated in vacuo, and the residue was purified by silica gel column chromatography (ethyl acetate/hexane) to give 1-((4-chlorobenzylamino)(4-isopropoxyphenylamino)methylene-3-isopropylthiourea (619 mg, Yield: 72%) as white solid.

The thiourea derivative (200 mg, 0.477 mmol) was dissolved in THF (2.0 mL), and carbonyldiimidazole (77 mg, 0.477 mmol) was added to the solution under ice-cooling. The resulting mixture was heated at reflux for 22 hours under nitrogen atmosphere. Further, carbonyldiimidazole (77 mg, 0.477 mmol) and triethylamine (0.066 mL, 0.477 mmol) were added to the mixture, and the resulting mixture was heated at reflux for 3.5 hours. To the mixture was added ethyl acetate (50 mL), and the resulting mixture was washed by water (20 mL×2) and brine (10 mL). The organic layer was dried over anhydrous sodium sulphate and concentrated in vacuo. The resulting residue was purified by silica gel column chromatography (ethyl acetate/hexane), and the resulting residue was precipitated by ethyl acetate/hexane to give aimed 1-(4-chlorobenzyl)-3-isopropyl-6-(4-isopropoxyphenylimino)-4-thioxo-1,3,5-triazinane-2-one (8.3 mg, Yield: 3.9%) as a white powder.

1H-NMR (δ ppm TMS/CDCl$_3$): 1.35 (d, 6H), 1.49 (d, 6H), 4.45-4.55 (m, 1H), 5.14 (s, 2H), 5.65-5.80 (m,1H), 6.74 (d, 2H), 6.89 (d, 2H), 7.30 (d, 2H), 7.48 (d, 2H), 8.48 (br, s, 1H).

EXAMPLE 79

Preparation of 1-(4-chlorobenzyl)-3-isopropyl-6-(4-isopropoxyphenylimino)-1,3,5-triazinane-2,4-dithione (I-2256)

[Chemical Formula 188]

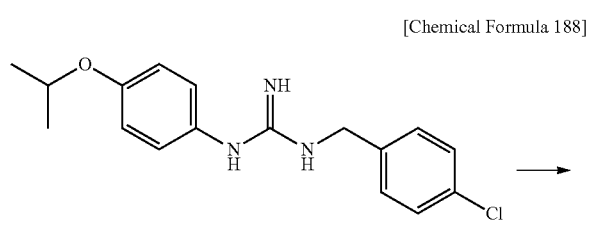

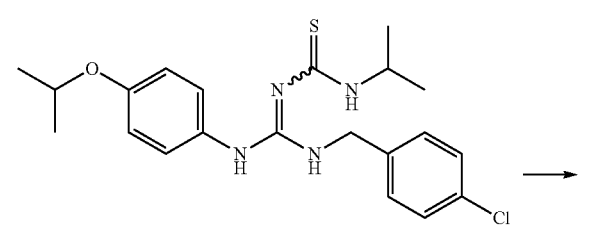

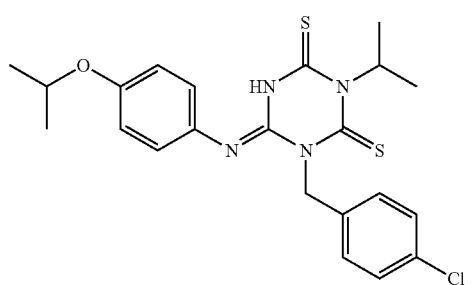

In the similar manner as described the above, 1-((4-chlorobenzylamino)(4-isopropoxyphenylamino)methylene-3-isopropylthiourea was synthesized. The thiourea derivative (199 mg, 0.475 mmol) was dissolved in THF (2.0 mL). To the colorless solution was added thiophosgene (0.040 mL, 0.522 mmol) under ice-cooling, and the resulting mixture was stirred for 2 hours in an ice-bath. To the resulting yellow solution was added ethyl acetate (50 mL), and washed by saturated aqueous sodium bicarbonate (20 ml×2), 5% aqueous citric acid (20 mL×2), and brine (10 mL). The organic layer was dried over anhydrous sodium sulphate and concentrated in vacuo. The resulting residue was purified by silica gel column chromatography (ethyl acetate/hexane). The resulting residue was crystallized by ethyl acetate/hexane to give 1-(4-chlorobenzyl)-3-isopropyl-6-(4-isopropoxyphenylimino)-1,3,5-triazinane-2,4-dithione (14.8 mg; Yield 6.8%) as yellow crystalline.

1H-NMR (δ ppm TMS/CDCl3): 1.16 (d, 6H), 1.32 (d, 6H), 4.00 & 4.61 (br, s×2, 1H), 4.44-4.54 (m,1H), 6.08 (d, 2H), 6.82 (d, 2H), 6.99 (d, 2H), 7.26 (d, 2H), 7.46 (d, 2H).

EXAMPLE 80

Preparation of 1-(4-chlorobenzyl)-3-isopropyl-6-(3-chloro-4-isopropoxyphenylimino)-4-thioxo-1,3,5-triazinane-2-one (I-2257)

[Chemical Formula 189]

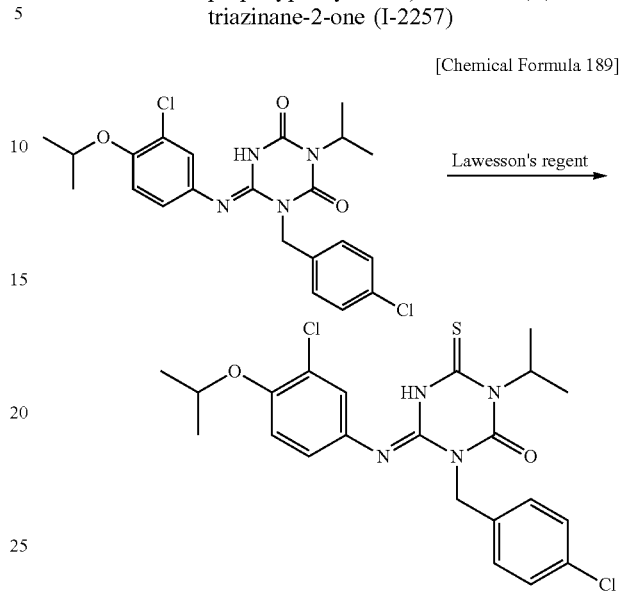

To a suspension of 6-(3-chloro-4-isopropoxyphenylamino)-1-(4-chlorobenzyl)-3-1,3,5-triazine-2,4-dion (95.4 mg, 0.206 mmol) in toluene (2.0 mL) was added Lawesson's reagent (666 mg, 1.65 mmol). The resulting mixture was heated at reflux for 10 hours. To the resulting yellow suspension was added ethyl acetate, and the insoluble are filtered off by using Celite. The filtrate (about 100 mL) was washed by saturated aqueous sodium bicarbonate (30 mL×2) and brine (15 mL), dried over anhydrous sodium sulphate, and concentrated in vacuo. The resulting residue was purified by silica gel column chromatography (ethyl acetate/hexane). The residue was crystallized by hot hexane to give 1-(4-chlorobenzyl)-3-isopropyl-6-(3-chloro-4-isopropoxyphenylimino)-4-thioxo-1,3,5-triazinane-2-one (73.7 mg, Yield: 75%) as white solid.

1H-NMR (δ ppm TMS/CDCl3): 1.39 (d, 6H), 1.50 (d, 6H), 4.43-4.57 (m, 1H), 5.12 (s, 2H), 5.65-5.81 (m,1H), 6.66 (dd, 1H), 6.89 (d, 1H), 6.95 (d, 1H), 7.31 (d, 1H), 7.47 (d, 1H), 8.41 (br, s, 1H).

EXAMPLE 81

Preparation of 1-(4-chlorobenzyl)-3-isopropyl-6-(3-chloro-4-isopropoxyphenylimino)-4-methylimino-1,3,5-triazinane-2-one (I-2259)

[Chemical Formula 190]

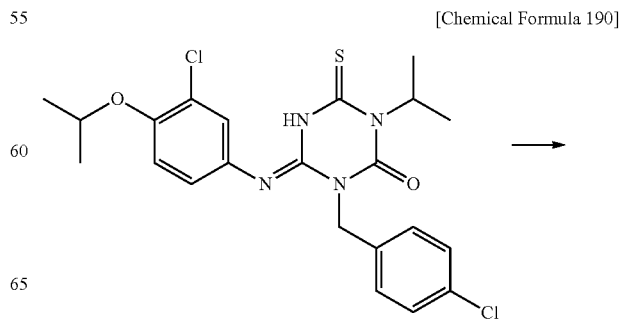

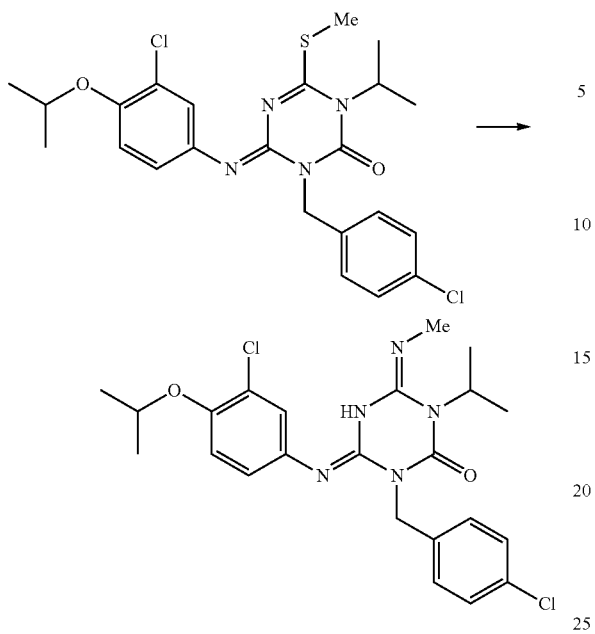

To a solution of 4-thiocarbonyl derivative (37.5 mg, 0.078 mmol) in acetone (0.8 mL) was added methyl iodide (0.0073 mL, 0.117 mmol), and resulting mixture was heated at reflux for 15 hours. Methyl iodide and solvate were removed under reduced pressure, and methanol (0.36 and 40% methylaminemethanol solution (0.04 mL, 0.391 mmol) were added to the residue. The resulting mixture was heated at reflux fo 8.5 hours, and concentrated in vacuo. The residue was purified by silica gel column chromatography (ethyl acetate/hexane) to give aimed 1-(4-chlorobenzyl)-3-isopropyl-6-(3-chloro-4-isopropoxyphenylimino)-4-methylimino-1,3,5-triazinane-2-one (23.6 mg, Yield: 63%) as pale yellow oil.

1H-NMR (δ ppm TMS/CDCl$_3$): 1.35 (d, 6H), 1.47 (d, 6H), 2.90 (d, 3H), 4.45 (sept. 1H), 4.70 (br, s, 1H), 4.82 (sept. 1H), 5.20 (s, 2H), 6.88 (d, 1H), 7.00 (dd, 1H), 7.26 (d, 2H), 7.40 (d, 1H), 7.50 (d, 2H).

EXAMPLE 82

Preparation of 1-(4-chlorobenzyl)-3-ethyl-6-[4-(5-methoxycarbonyl-3-pyridyloxy)phenylimino]-4-thioxo-1,3,5-triazinane-2-one (I-2262)

[Chemical Formula 191]

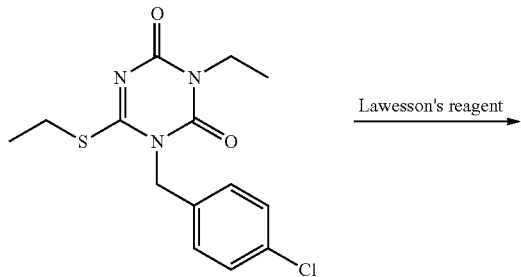

Lawesson's reagent →

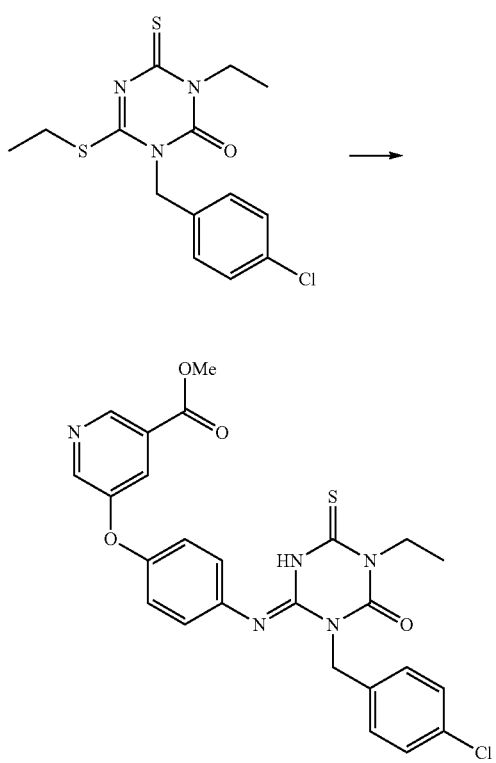

To a solution of 1-(4-chlorobenzyl)-3-ethyl-6-(ethylthio)-1,3,5-triazine-2,4-(1H, 3H)-dion (1.02 g, 3.13 mmol) in toluene (10 mL) was added Lawesson's reagent (2.53 g, 6.26 mmol), and the resulting mixture was stirred at reflux for 3 hours. To the resulting yellow suspension was added ethyl acetate(200 mL), and the resulting mixture was washed by water (100 mL) and brine(50 mL). The organic layer was dried over anhydrous sodium sulphate, and concentrated in vacuo. The resulting residue was purified by silica gel column chromatography (ethyl acetate/hexane) to give 1-(4-chlorobenzyl)-3-ethyl-6-(ethylthio)-4-thioxo-3,4-dihydro-1,3,5-triazine-2 (1H)-one (939 mg, Yield: 88%) as yellow solid.

4-Thioxo derivative (257 mg, 0.752 mmol) and 5-(-4-aminophenoxy)nicotinic acid methyl ester (257 mg, 1.05 mmol) were suspended in t-butanol (2.5 mL), and the suspension was heated at reflux for 5 hours. To the resulting reaction mixture was added ethyl acetate (60 mL), and the mixture was washed by saturated aqueous sodium bicarbonate (25 mL×2) and brine (15 mL). The organic layer was dried over anhydrous sodium sulphate, and concentrated in vacuo. The resulting residue was purified by silica gel column chromatography (ethyl acetate/hexane) to give 1-(4-chlorobenzyl)-3-ethyl-6-[4-(5-methoxycarbonyl-3-pyridyloxy)phenylimino]-4-thioxo-1,3,5-triazinane-2-one (258 mg, Yield: 66%) as white solid.

1H-NMR (δ ppm TMS/CDCl$_3$): 1.30 (t, 3H), 3.94 (s, 3H), 4.35 (q, 3H), 5.19 (s, 2H), 6.87 (dt, 2H), 7.07 (dt, 2H), 7.32 (dt, 2H), 7.51 (dt, 2H), 7.85 (dd, 1H), 8.40 (br, s, 1H), 8.60 (d, 1H), 8.96 (d, 1H).

EXAMPLE 83

Preparation of 1-(4-chlorobenzyl)-3-ethyl-4-methylthio-6-[4-(5-methoxycarbonyl-3-pyridyloxy)phenylimino]-1,3,5-triazine-2-(1H)-one (I-2264)

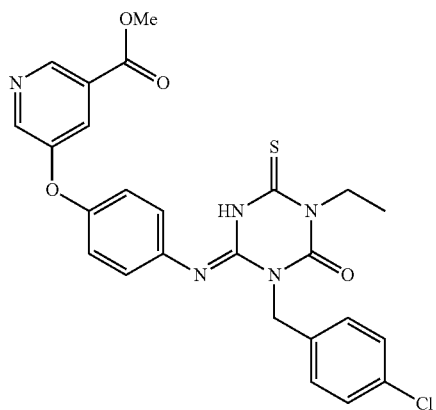

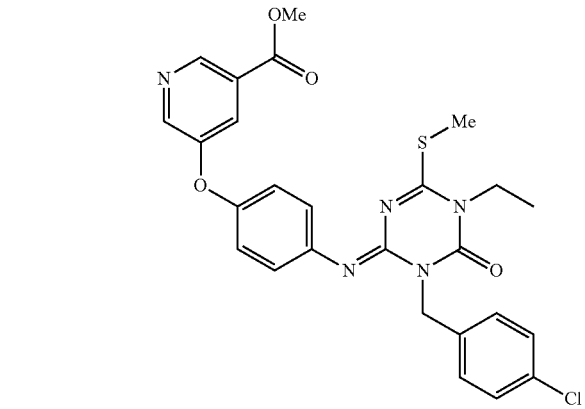

Thiocarbonyl derivative (50 mg, 0.095 mmol) was suspended in acetone (1.0 mL), and methyl iodide (0.009 mL, 0.143 mmol) was added to the suspension. The mixture was stirred at room temperature for 15 hours and at 40° C. for 15 hours. To the reaction mixture was added ethyl acetate (30 mL). The organic layer was washed by saturated aqueous sodium bicarbonate (10 mL×2) and brine (10 mL), dried over anhydrous sodium sulphate, and concentrated in vacuo. The resulting residue was purified by silica gel column chromatography (ethyl acetate/hexane), 1-(4-chlorobenzyl)-3-ethyl-4-methylthio-6-[4-(5-3methoxycarbonyl-3-pyridyloxy)phenylimino]-1,3,5-triazine-2-(1H)-one (40.5 mg, Yield: 79%) as white solid.

1H-NMR (δ ppm TMS/CDCl₃): 1.30 (t, 3H), 2.32 (s, 3H), 3.92 (s, 3H), 3.93 (q, 2H), 5.22 (s, 2H), 6.97 (d, 2H), 7.08 (d, 2H), 7.29 (d, 2H), 7.54 (d, 2H), 7.73-7.79 (m, 1H), 8.54 (d, 1H), 8.89 (s, 1H).

EXAMPLE 84

Preparation of (E)-3-(4-chlorobenzyl)-4-(4-isopropoxyphenylimino)-1-isopropyl-3,4-dihydro-1,3,5-triazine-2(1H)-one (I-2276)

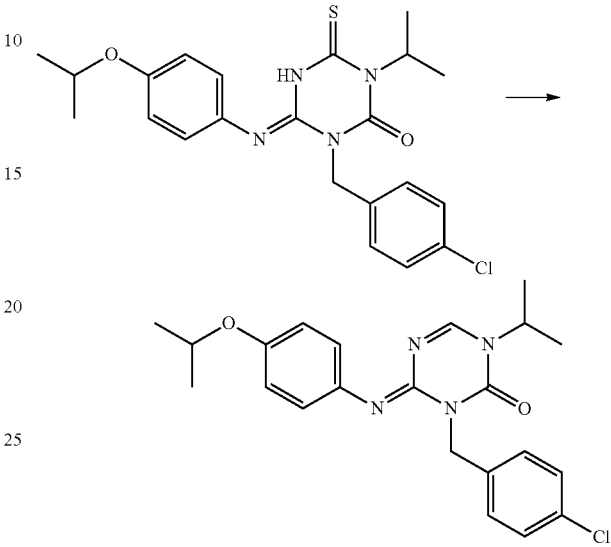

(Reference: Tetrahedron Lett. 2004, 45, 7197-7199.)

To a solution of thiocarbonyl derivative (49.3 mg, 0111 mmol) in methanol (1.0 mL) was added hydrogen peroxide urea (52.1 mg, 0.554 mmol), and the resulting mixture was stirred at room temperature for 5.5 hours. To the reaction mixture was added ethyl acetate (30 mL), and the mixture was washed by 5% aqueous citric acid (15 mL×2), saturated aqueous sodium bicarbonate (15 mL×2) and brine (10 mL). The organic layer was dried over anhydrous sodium sulphate, and concentrated in vacuo. The resulting residue was purified by silica gel column chromatography (ethyl acetate/hexane) to give (E)-3-(4-chlorobenzyl)-4-(4-isopropoxyphenylimino)-1-isopropyl-3,4-dihydro-1,3,5-triazine-2(1H)-one (31.6 mg, Yield: 69%) as brown solid.

1H-NMR (δ ppm TMS/CDCl₃): 1.32 (d, 6H, J=6.1 Hz), 1.37 (d, 6H, J=6.6 Hz), 4.44-4.50 (m, 1H), 4.66-4.72 (m, 1H), 5.21 (s, 2H), 6.84 (d, 2H, J=11.7 Hz), 6.91 (d, 2H, J=6.6 Hz), 7.28 (d, 2H, J=8.1 Hz), 7.55 (d, 2H, J=8.1 Hz), 7.61 (s, 1H).

EXAMPLE 85

Preparation of 2-methyl-6-(1-pyrazolyl)-1,3,5-triazine-2,4(1H,3H)-dion

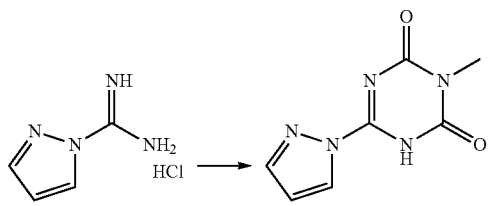

To a mixture of methylamine hydrochloride (276 g, 4.09 mol) and DMA (2 L) was added DBU (679 mL, 4.50 mol) at 10° C. over 4 minutes. Then, 1,1'-carbonyldiimidazole (730 g, 4.50 mol) was added to the mixture at 20° C., and the resulting mixture was stirred at 0° C. for 2 hours. To the reaction mixture was added 1-amidinopyrazole-hydrochloride (500 g, 3.41 mol) at −5° C. over 3 minutes. Then, DBU (540 mL, 3.58 mol) was added to the mixture at 10° C. over 25 minutes, and the resulting mixture was stirred at 45° C. for 7.5 hours. Further, to the reaction mixture was added 1,1'-carbonyldiimidazole (830 g, 5.11 mol), and DBU (771 mL, 5.11 mol) was added to the mixture at 6° C. over 2 hours. The resulting mixture was stirred at 0° C. for 40 minutes. To the reaction mixture was added 2.8 mol/L, hydrochloric acid (10 L) at 20° C. over 1 hour. The precipitated solid was filtered off to give 2-methyl-6-(1-pyrazolyl)-1,3,5-triazine-2,4(1H,3H)-dion (421 g, Yield: 64%) as pale brown powder.

1H-NMR (δ ppm TMS/DMSO-d6): 3.16 (3H, s), 6.71 (1H, dd, J=3.0, 1.5 Hz), 8.04 (1H, d, J=1.0 Hz), 8.57 (1H, d, =3.0 Hz).

EXAMPLE 86

Preparation of 2-ethyl-6-(1-pyrazolyl-1,3,5-triazine-2,4(1H,3H)-dion

[Chemical Formula 195]

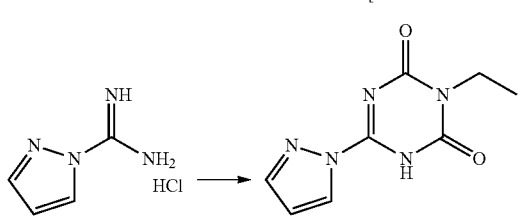

To the mixture of 1-amidinopyrazole-hydrochloride (58.6 g, 400 mmol), ethyl isocyanate (33.2 mL, 420 mmol) and DMA (240 mL) was added DBU (63.3 mL, 420 mmol) dropwise at −10° C. over 15 minutes, and the resulting mixture was stirred under ice-cooling for 30 minutes. To the reaction mixture was added 1,1'-carbonyldiimidazole (30 g, 600 mmol) under ice-cooling, and DBU (93 mL, 620 mmol) was added −5° C. over 30 minutes to the mixture. The resulting mixture was stirred under ice-cooling for 1 hour. Further, the mixture was stirred at room temperature for 1 hour. To the mixture was added 2 mol/L hydrochloric acid (1.16 L) at 20° C. over 1 hour. The precipitated solid was filtered off to give 2-ethyl-6-(1-pyrazolyl)1,3,5-triazine-2,4 (1H,3H)-dion (73.0 g, Yield: 88%) as pale brown powder.

1H-NMR (δ ppm TMS/CDCl3): 1.30 (6H, t, J=7.0 Hz), 4.02 (2H, q, J=7.0 Hz), 6.59 (1H, m), 7.34 (1H, m), 8.48 (1H, m), 9.79 (1H, brs).

EXAMPLE 87

Preparation of 1-(4-chlorobenzyl)-2-ethyl-6-(1-pyrazolyl)-1,3,5-triazine-2,4(1H,3H)-dion (II-3)

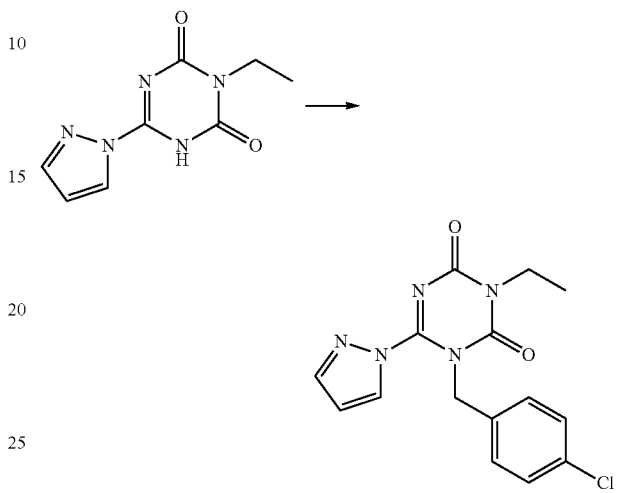

To a mixture of 2-ethyl-6-(1-pyrazolyl)-1,3,5-triazine-2,4(1H,3H)-dion (89 g, 480 mmol), 4-chlorobenzylbromide (108 g, 528 mmol) and DMA (400 mL) was added diisopropyletlylamine (92 mL, 528 mmol) dropwise at room temperature over 10 minutes, and the mixture was stirred at 60° C. for 2 hours. To the reaction mixture was added water (800 mL) dropwise under ice-cooling for 40 minutes, and hexane (200 mL) was added to the mixture. The precipitated solid was filtered off to give 1-(4-chlorobenzyl)-2-ethyl-6-(1-pyrazolyl)-1,3,5-triazine-2,4(1H,3H)-dion (11-3.156 g, Yield: 97.6%) as pale brown powder. 1H-NMR (δ ppm TMS/CDCl₃): 1.30 (3H, t, J=7.1 Hz), 4.04 (2H, q, J=7.1 Hz), 5.86 (2H, s), 6.48 (1H, m), 7.02 (2H, d, J=8.6 Hz), 7.20-7.25 (2H, m), 7.84 (1H, m), 8.33 (1H, m).

EXAMPLE 88

Preparation of 1-(4-chlorobenzyl)-6-[4-(3-cyanophenoxy)phenylimino]-3-ethyl-1,3,5-triazinane-2,4-dion (I-2305)

[Chemical Formula 196]

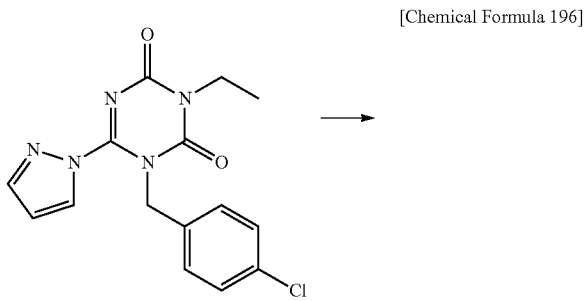

-continued

A mixture of 1-(4-chlorobenzyl)-2-ethyl-6-(1-pyrazolyl-1,3,5-triazine-2,4(1H,3H)-dion (0.30 g, 0.9 mmol), 4-(3-cyanophenoxy)aniline (0.209 g, 1 mmol) and t-butanol (6 mL) was stirred at 90° C. for 15 hours. To the reaction mixture was added 50% ethyl acetate/hexane (6 mL), and the precipitated solid was filtered off to give 1-(4-chlorobenzyl)-6-[4-(3H-cyanophenoxy)phenylimino]-3-ethyl-1,3,5-triazinane-2,4-dion (I-2305, 0.385 g, Yield: 89.8%) as pale brown powder.

1H-NMR (δ ppm TMS/CDCl$_3$): 1.24 (3H, J=7.2 Hz), 3.91 (2H, q, J=7.2 Hz), 5.20 (2H, s), 6.84 (2H, d, J=8.7 Hz), 7.04 (2H, d, J=8.4 Hz), 7.2-7.46 (6H, m), 7.51 (2H, d, J=8.4 Hz).

The following compound of the invention and intermediate thereof were synthesized in a manner similar to those described in the above general procedures for the synthesis of the compound of the invention and Examples. The chemical structure of the compounds and the physical properties of them are described below.

(Method of Identification for the Compound)

LC/MS data of compound of the present invention were measured under any one of the following 2 conditions (Method 1 and 2), and a retention time and [M+H]$^+$ are shown.

(Method 1)
  Column: Luna C18(2) (5 μm, i.d.4.6×50 mm) (Phenomenex)
  Flow rate: 3 mL/min
  UV detection wavelength: 254 nm
  Mobile phase: [A] is 0.1% formic acid-containing aqueous solution, and [B] is 0.1% formic acid-containing acetonitrile solution
  Gradient: Linear gradient of 10% to 100% solvent [B] for 3 minutes was performed, and 100% solvent [B] was maintained for 1 minute.

(Method 2)
  Column: Xbridge C18 (5 μm, i.d.4.6×50 mm) (Waters)
  Flow rate: 3 mL/min
  UV detection wavelength: 254 nm
  Mobile phase: [A] is 0.1% formic acid-containing aqueous solution, and [B] is 0.1% formic acid-containing acetonitrile solution
  Gradient: Linear gradient of 10% to 100% solvent [B] for 3 minutes was performed, and 100% solvent, [B] was maintained for 1 minute.

(Method 3)
  Column: Shim-pack XR-ODS (2.2 μm, i.d.50×3.0 mm) (Shimadzu)
  Flow rate:1.6 mL/min
  UV detection wavelength: 254 nm
  Mobile phase: [A] is 0.1% formic acid-containing aqueous solution, and [B] is 0.1% formic acid-containing acetonitrile solution
  Gradient: Linear gradient of 10% to 100% solvent [B] for 3 minutes was performed, and 100% solvent [B] was maintained for 1 minute.

(Method 4)
  Column: Develo sil RPAq, (50×4.6 mm)
  Flow rate: 1.5 mL/min
  UV detection wavelength: 254 nm
  Mobile phase: [A] is a formic acid-containing aqueous solution, and [B] is 0.1% form in acid-containing acetonitrile solution
  Gradient: 60% solvent [B] was maintained for 0.5 minute, linear gradient of 60% to and 100% solvent [B] for 4.5 minutes was performed, and 100% solvent [B] was maintained for 10 minutes.

(Method 5)
  Column: ACQUITY UPLC (registered trademark) BEH C18 (1.7 μm, i.d.2.1×3.0 mm)
  Flow rate: 0.8 ml/min
  UV detection wavelength: 254 nm
  Mobile phase: [A] is 0.1% formic acid-containing aqueous solution, and [B] is 0.1% formic acid-containing acetonitrile solution
  Gradient: Linear gradient of 10% to 100% solvent [B] for 3.5 minutes was performed, and 100% solvent [B] was maintained for 0.5 minute.

TABLE 4

| Structure | Compound No. | Retention Time (min) | [M + H] | Method |
|---|---|---|---|---|
| 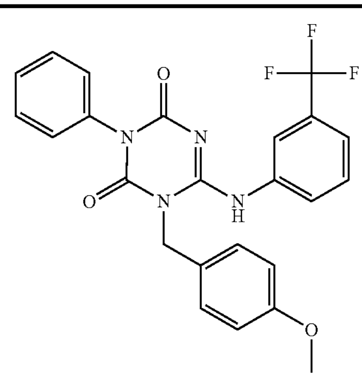 | I-0001 | 2.46 | 469 | 3 |

TABLE 4-continued

| Structure | Compound No. | Retention Time (min) | [M + H] | Method |
|---|---|---|---|---|
| 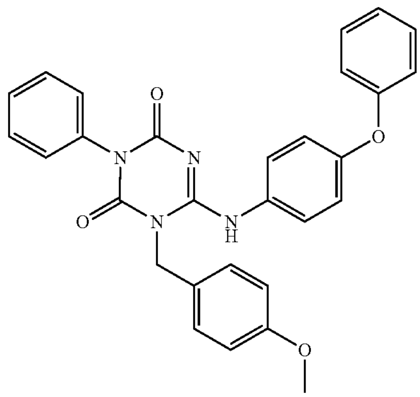 [SMILES: COc1ccc(Cn2c(Nc3ccc(Oc4ccccc4)cc3)nc(=O)n(-c3ccccc3)c2=O)cc1] | I-0002 | 2.49 | 493 | 3 |
| 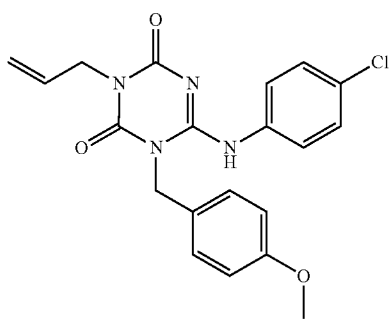 [SMILES: C=CCn1c(=O)nc(Nc2ccc(Cl)cc2)n(Cc2ccc(OC)cc2)c1=O] | I-0003 | 2.31 | 399 | 3 |
| 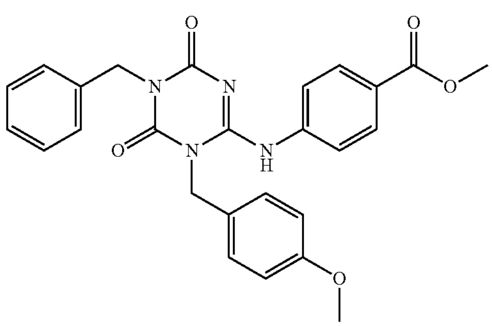 [SMILES: COC(=O)c1ccc(Nc2nc(=O)n(Cc3ccccc3)c(=O)n2Cc2ccc(OC)cc2)cc1] | I-0004 | 2.47 | 473 | 3 |
| 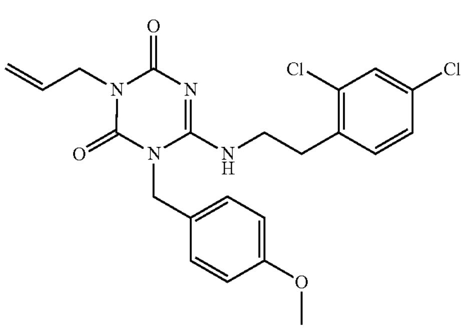 [SMILES: C=CCn1c(=O)nc(NCCc2ccc(Cl)cc2Cl)n(Cc2ccc(OC)cc2)c1=O] | I-0005 | 2.37 | 461 | 3 |

TABLE 5

| Structure | Compound No. | Retention Time (min) | [M + H] | Method |
|---|---|---|---|---|
| 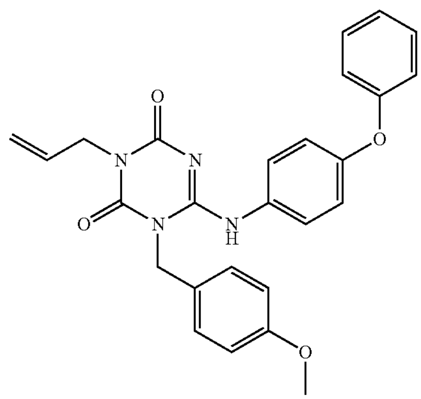 [SMILES: C=CCn1c(=O)nc(Nc2ccc(Oc3ccccc3)cc2)n(Cc2ccc(OC)cc2)c1=O] | I-0006 | 2.48 | 457 | 3 |
| 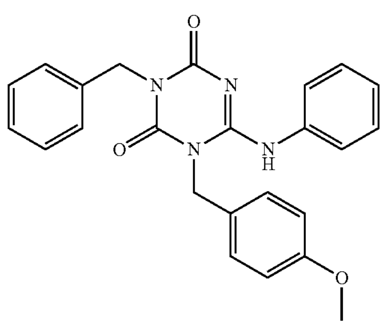 [SMILES: COc1ccc(Cn2c(Nc3ccccc3)nc(=O)n(Cc3ccccc3)c2=O)cc1] | I-0007 | 2.34 | 415 | 3 |
| 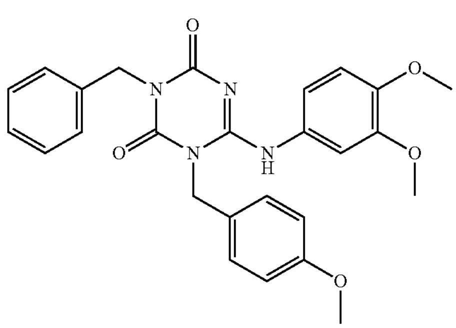 [SMILES: COc1ccc(Cn2c(Nc3ccc(OC)c(OC)c3)nc(=O)n(Cc3ccccc3)c2=O)cc1] | I-0008 | 2.22 | 475 | 3 |
| 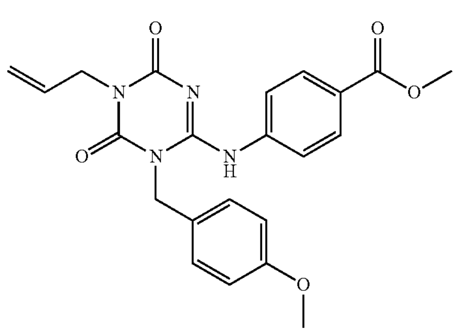 [SMILES: C=CCn1c(=O)nc(Nc2ccc(C(=O)OC)cc2)n(Cc2ccc(OC)cc2)c1=O] | I-0009 | 2.23 | 423 | 3 |

TABLE 5-continued

| Structure | Compound No. | Retention Time (min) | [M + H] | Method |
|---|---|---|---|---|
| 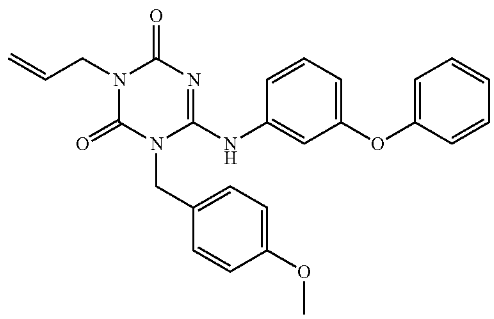 [SMILES: C=CCn1c(=O)nc(Nc2cccc(Oc3ccccc3)c2)n(Cc2ccc(OC)cc2)c1=O] | I-0010 | 2.48 | 457 | 3 |

TABLE 6

| Structure | Compound No. | Retention Time (min) | [M + H] | Method |
|---|---|---|---|---|
| 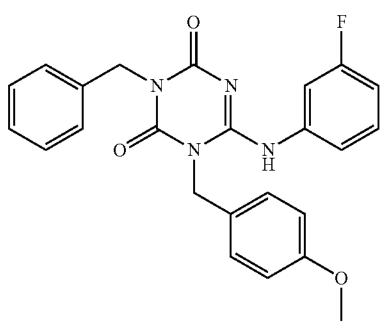 [SMILES: COc1ccc(Cn2c(Nc3cccc(F)c3)nc(=O)n(Cc3ccccc3)c2=O)cc1] | I-0011 | 2.47 | 433 | 3 |
| 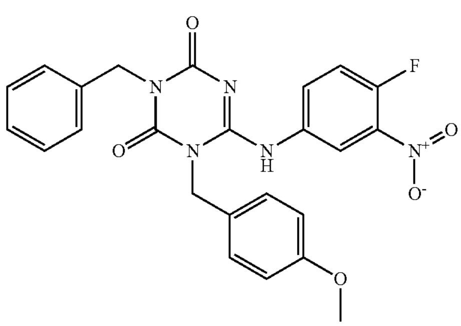 [SMILES: COc1ccc(Cn2c(Nc3ccc(F)c([N+](=O)[O-])c3)nc(=O)n(Cc3ccccc3)c2=O)cc1] | I-0012 | 2.51 | 478 | 3 |
| 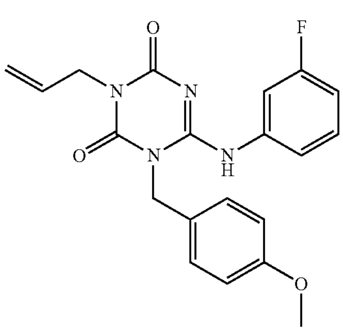 [SMILES: C=CCn1c(=O)nc(Nc2cccc(F)c2)n(Cc2ccc(OC)cc2)c1=O] | I-0013 | 2.23 | 383 | 3 |

TABLE 6-continued

| Structure | Compound No. | Retention Time (min) | [M + H] | Method |
|---|---|---|---|---|
| 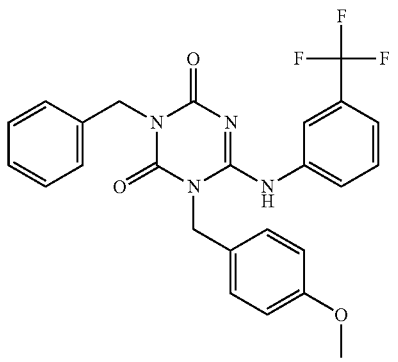 [SMILES: COc1ccc(Cn2c(Nc3cccc(C(F)(F)F)c3)nc(=O)n(Cc3ccccc3)c2=O)cc1] | I-0014 | 2.65 | 483 | 3 |
| 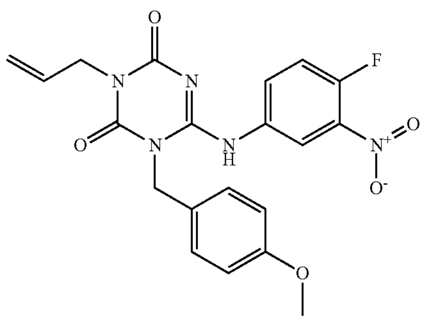 [SMILES: C=CCn1c(=O)nc(Nc2ccc(F)c([N+](=O)[O-])c2)n(Cc2ccc(OC)cc2)c1=O] | I-0015 | 2.29 | 428 | 3 |

TABLE 7

| Structure | Compound No. | Retention Time (min) | [M + H] | Method |
|---|---|---|---|---|
| 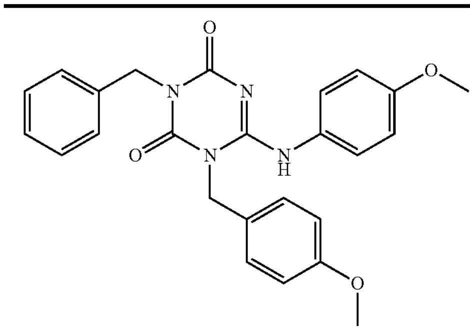 | I-0016 | 2.29 | 445 | 3 |
| 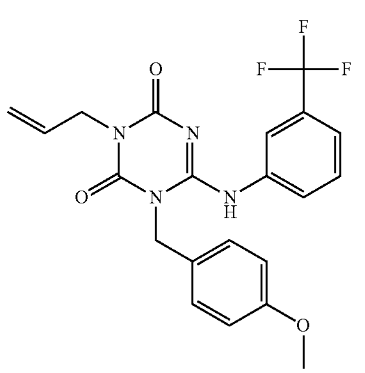 [SMILES: C=CCn1c(=O)nc(Nc2cccc(C(F)(F)F)c2)n(Cc2ccc(OC)cc2)c1=O] | I-0017 | 2.45 | 433 | 3 |

TABLE 7-continued
| Structure | Compound No. | Retention Time (min) | [M + H] | Method |
|---|---|---|---|---|
| 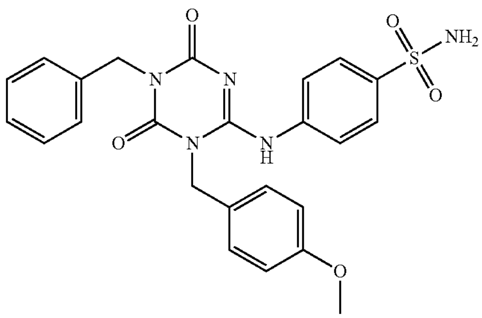 [SMILES: COc1ccc(Cn2c(Nc3ccc(S(N)(=O)=O)cc3)nc(=O)n(Cc3ccccc3)c2=O)cc1] | I-0018 | 2.09 | 494 | 3 |
| 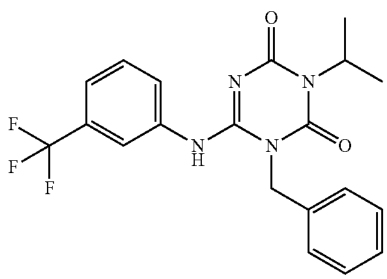 [SMILES: CC(C)n1c(=O)nc(Nc2cccc(C(F)(F)F)c2)n(Cc2ccccc2)c1=O] | I-0019 | 2.16 | 405 | 4 |
| 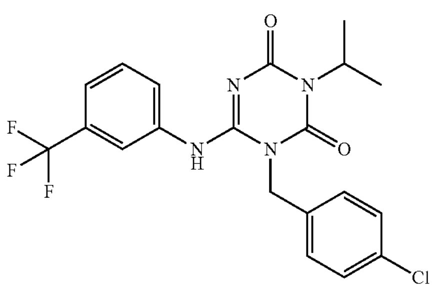 [SMILES: CC(C)n1c(=O)nc(Nc2cccc(C(F)(F)F)c2)n(Cc2ccc(Cl)cc2)c1=O] | I-0020 | 3.88 | 439 | 4 |
TABLE 8
| Structure | Compound No. | Retention Time (min) | [M + H] | Method |
|---|---|---|---|---|
| 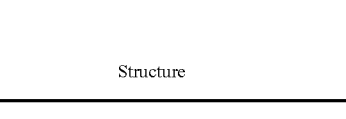 | I-0021 | 3.63 | 419 | 4 |

TABLE 8-continued

| Structure | Compound No. | Retention Time (min) | [M + H] | Method |
|---|---|---|---|---|
| 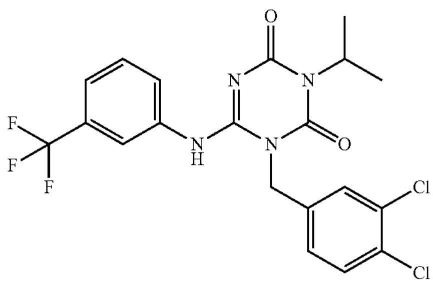 [SMILES: CC(C)n1c(=O)nc(Nc2cccc(C(F)(F)F)c2)n(Cc2ccc(Cl)c(Cl)c2)c1=O] | I-0022 | 4.43 | 474 | 4 |
| 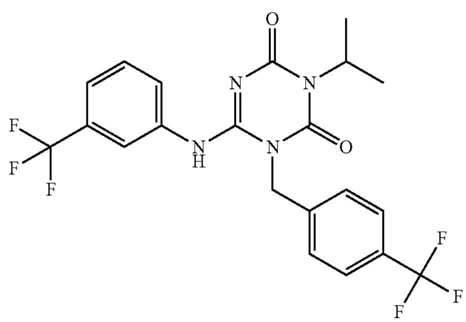 [SMILES: CC(C)n1c(=O)nc(Nc2cccc(C(F)(F)F)c2)n(Cc2ccc(C(F)(F)F)cc2)c1=O] | I-0023 | 3.91 | 473 | 4 |
| 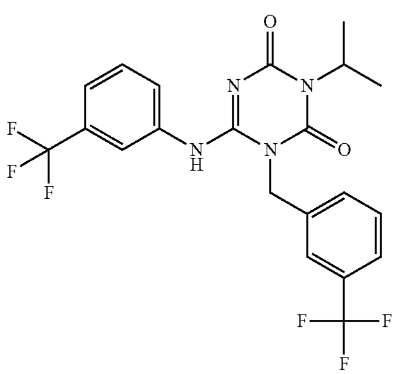 [SMILES: CC(C)n1c(=O)nc(Nc2cccc(C(F)(F)F)c2)n(Cc2cccc(C(F)(F)F)c2)c1=O] | I-0024 | 3.93 | 473 | 4 |
| 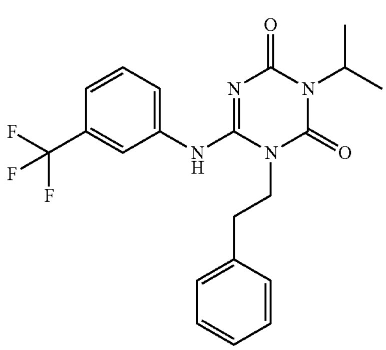 [SMILES: CC(C)n1c(=O)nc(Nc2cccc(C(F)(F)F)c2)n(CCc2ccccc2)c1=O] | I-0025 | 3.33 | 419 | 4 |

TABLE 9

| Structure | Compound No. | Retention Time (min) | [M + H] | Method |
|---|---|---|---|---|
| (structure) | I-0026 | 3.16 | 449 | 4 |
| (structure) | I-0027 | 2.46 | 419 | 4 |
| (structure) | I-0028 | 3.27 | 453 | 4 |
| (structure) | I-0029 | 2.95 | 433 | 4 |
| (structure) | I-0030 | 3.94 | 488 | 4 |

TABLE 10
| Structure | Compound No. | Retention Time (min) | [M + H] | Method |
|---|---|---|---|---|
| 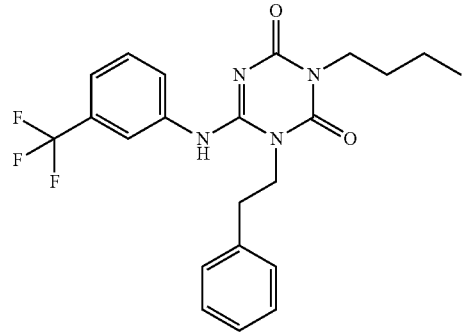 [SMILES: CCCCn1c(=O)nc(Nc2cccc(C(F)(F)F)c2)n(CCc2ccccc2)c1=O] | I-0031 | 2.61 | 433 | 4 |
| 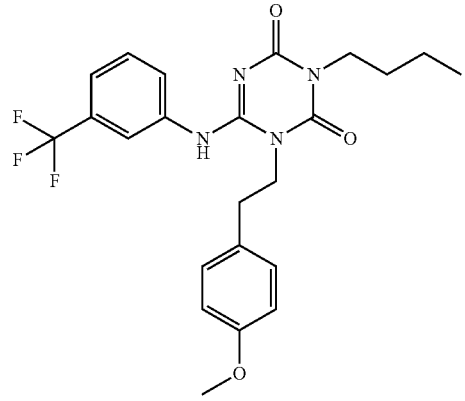 [SMILES: CCCCn1c(=O)nc(Nc2cccc(C(F)(F)F)c2)n(CCc2ccc(OC)cc2)c1=O] | I-0032 | 2.39 | 463 | 4 |
| 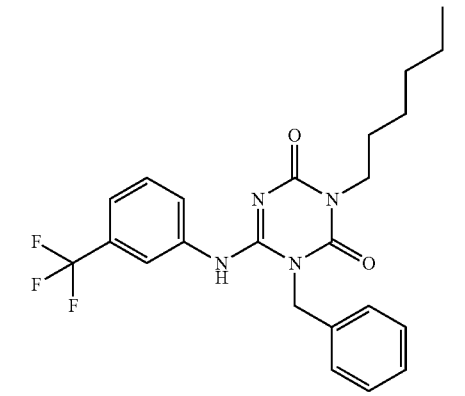 [SMILES: CCCCCCn1c(=O)nc(Nc2cccc(C(F)(F)F)c2)n(Cc2ccccc2)c1=O] | I-0033 | 4.31 | 447 | 4 |
| 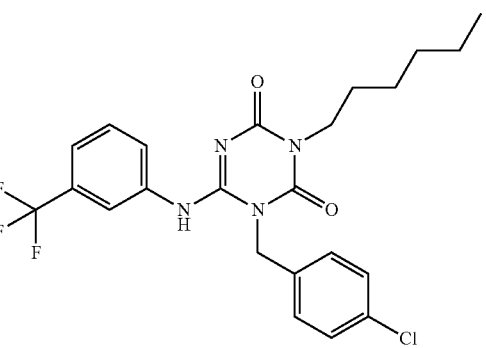 | I-0034 | 4.86 | 481 | 4 |

TABLE 10-continued
| Structure | Compound No. | Retention Time (min) | [M + H] | Method |
|---|---|---|---|---|
| 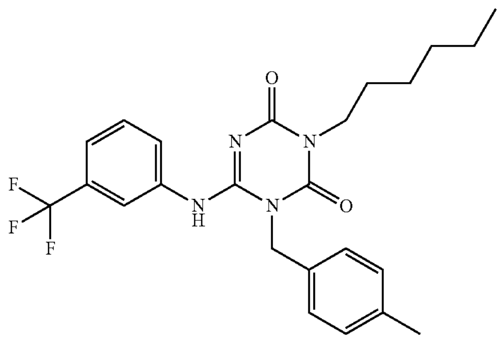 [SMILES: CCCCCCn1c(=O)nc(Nc2cccc(C(F)(F)F)c2)n(Cc2ccc(C)cc2)c1=O] | I-0035 | 4.68 | 461 | 4 |
TABLE 11
| Structure | Compound No. | Retention Time (min) | [M + H] | Method |
|---|---|---|---|---|
| 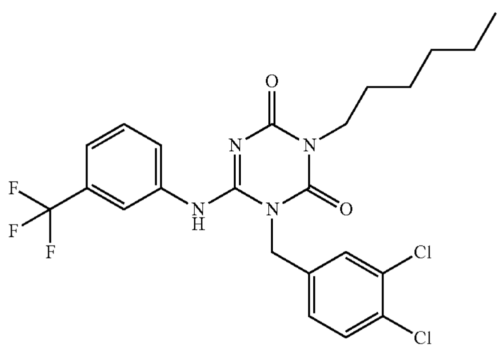 [SMILES: CCCCCCn1c(=O)nc(Nc2cccc(C(F)(F)F)c2)n(Cc2ccc(Cl)c(Cl)c2)c1=O] | I-0036 | 3.73 | 516 | 4 |
| 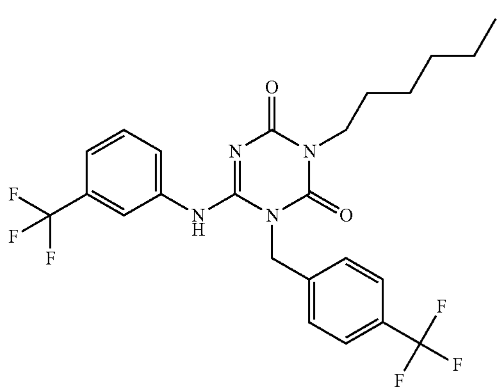 [SMILES: CCCCCCn1c(=O)nc(Nc2cccc(C(F)(F)F)c2)n(Cc2ccc(C(F)(F)F)cc2)c1=O] | I-0037 | 4.80 | 515 | 4 |
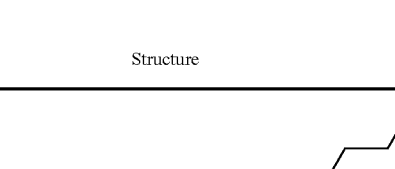

TABLE 11-continued

| Structure | Compound No. | Retention Time (min) | [M + H] | Method |
|---|---|---|---|---|
| 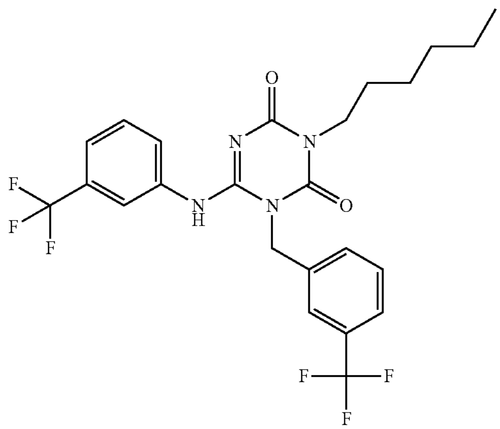 [SMILES: CCCCCCn1c(=O)nc(Nc2cccc(C(F)(F)F)c2)n(Cc2cccc(C(F)(F)F)c2)c1=O] | I-0038 | 4.83 | 515 | 4 |
| 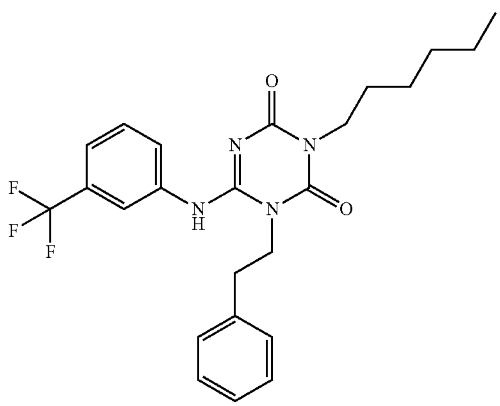 [SMILES: CCCCCCn1c(=O)nc(Nc2cccc(C(F)(F)F)c2)n(CCc2ccccc2)c1=O] | I-0039 | 3.67 | 461 | 4 |
| 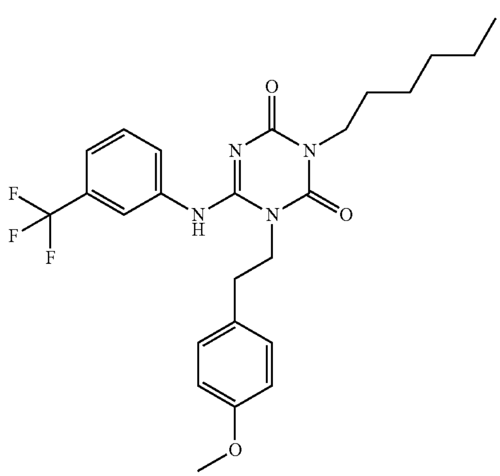 [SMILES: CCCCCCn1c(=O)nc(Nc2cccc(C(F)(F)F)c2)n(CCc2ccc(OC)cc2)c1=O] | I-0040 | 3.47 | 491 | 4 |

TABLE 12

| Structure | Compound No. | Retention Time (min) | [M + H] | Method |
|---|---|---|---|---|
| 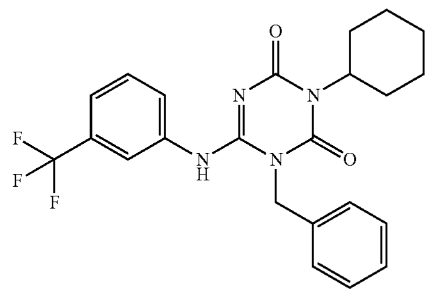 [SMILES: O=c1nc(Nc2cccc(C(F)(F)F)c2)n(Cc2ccccc2)c(=O)n1C1CCCCC1] | I-0041 | 4.09 | 445 | 4 |
| 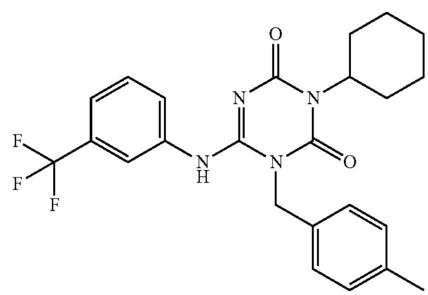 [SMILES: Cc1ccc(Cn2c(Nc3cccc(C(F)(F)F)c3)nc(=O)n(C3CCCCC3)c2=O)cc1] | I-0042 | 4.45 | 459 | 4 |
| 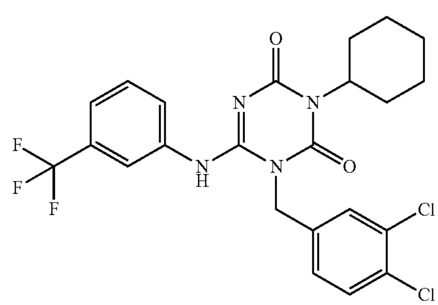 [SMILES: O=c1nc(Nc2cccc(C(F)(F)F)c2)n(Cc2ccc(Cl)c(Cl)c2)c(=O)n1C1CCCCC1] | I-0043 | 3.51 | 514 | 4 |
| 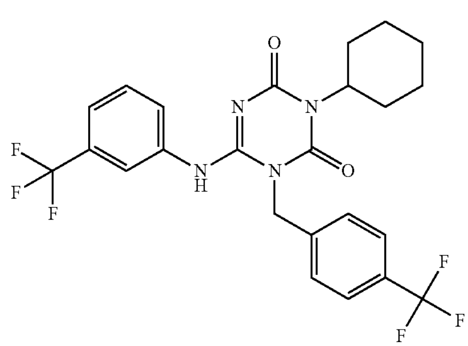 [SMILES: O=c1nc(Nc2cccc(C(F)(F)F)c2)n(Cc2ccc(C(F)(F)F)cc2)c(=O)n1C1CCCCC1] | I-0044 | 4.62 | 513 | 4 |

TABLE 12-continued

| Structure | Compound No. | Retention Time (min) | [M + H] | Method |
|---|---|---|---|---|
| (structure of I-0045) | I-0045 | 4.65 | 513 | 4 |

TABLE 13

| Structure | Compound No. | Retention Time (min) | [M + H] | Method |
|---|---|---|---|---|
| (structure of I-0046) | I-0046 | 3.17 | 489 | 4 |
| (structure of I-0047) | I-0047 | 3.46 | 453 | 4 |

TABLE 13-continued

| Structure | Compound No. | Retention Time (min) | [M + H] | Method |
|---|---|---|---|---|
| 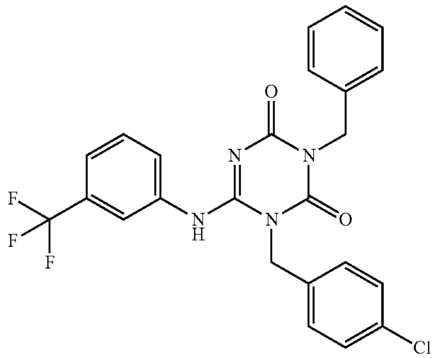 [SMILES: O=c1nc(Nc2cccc(C(F)(F)F)c2)n(Cc2ccc(Cl)cc2)c(=O)n1Cc1ccccc1] | I-0048 | 4.09 | 487 | 4 |
| 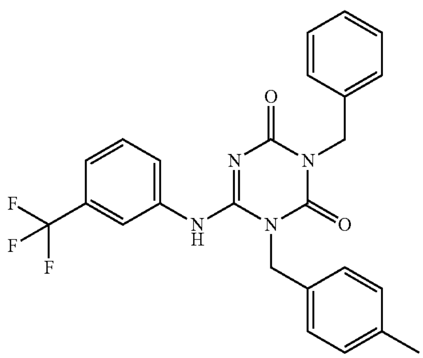 [SMILES: Cc1ccc(Cn2c(Nc3cccc(C(F)(F)F)c3)nc(=O)n(Cc3ccccc3)c2=O)cc1] | I-0049 | 3.83 | 467 | 4 |
| 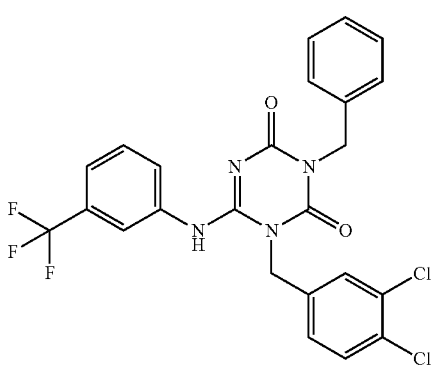 [SMILES: O=c1nc(Nc2cccc(C(F)(F)F)c2)n(Cc2ccc(Cl)c(Cl)c2)c(=O)n1Cc1ccccc1] | I-0050 | 4.56 | 522 | 4 |

TABLE 14
| Structure | Compound No. | Retention Time (min) | [M + H] | Method |
|---|---|---|---|---|
| 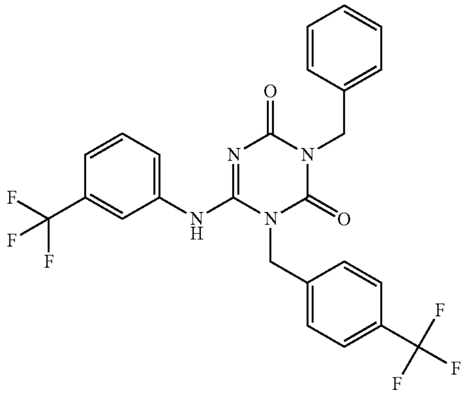 [SMILES: O=c1nc(Nc2cccc(C(F)(F)F)c2)n(Cc2ccc(C(F)(F)F)cc2)c(=O)n1Cc1ccccc1] | I-0051 | 4.09 | 521 | 4 |
| 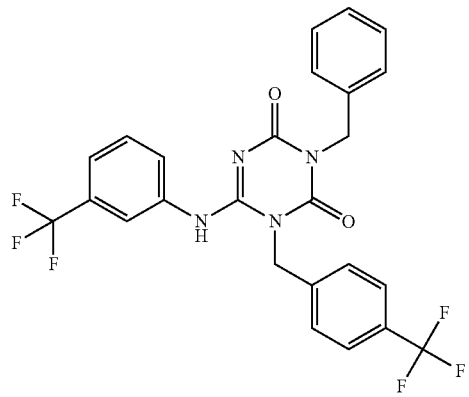 | I-0052 | 4.12 | 521 | 4 |
| 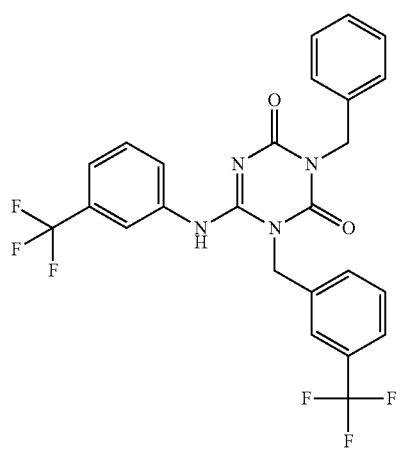 [SMILES: O=c1nc(Nc2cccc(C(F)(F)F)c2)n(Cc2cccc(C(F)(F)F)c2)c(=O)n1Cc1ccccc1] | I-0053 | 3.57 | 467 | 4 |

TABLE 14-continued

| Structure | Compound No. | Retention Time (min) | [M + H] | Method |
|---|---|---|---|---|
| 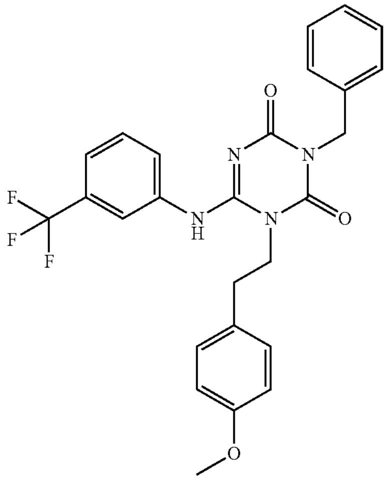 [SMILES: COc1ccc(CCn2c(Nc3cccc(C(F)(F)F)c3)nc(=O)n(Cc3ccccc3)c2=O)cc1] | I-0054 | 3.42 | 497 | 4 |
| 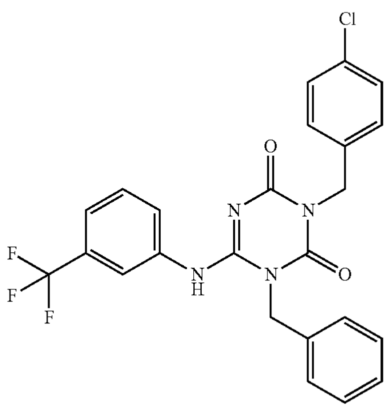 [SMILES: O=c1nc(Nc2cccc(C(F)(F)F)c2)n(Cc2ccccc2)c(=O)n1Cc1ccc(Cl)cc1] | I-0055 | 3.90 | 487 | 4 |

TABLE 15

| Structure | Compound No. | Retention Time (min) | [M + H] | Method |
|---|---|---|---|---|
| 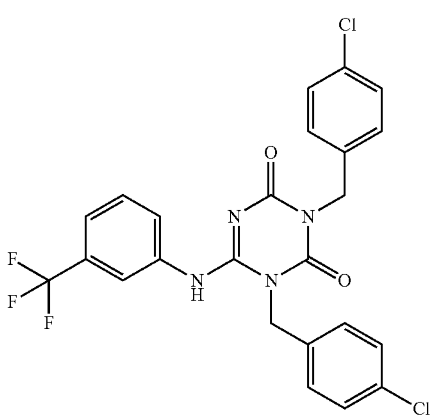 [SMILES: O=c1nc(Nc2cccc(C(F)(F)F)c2)n(Cc2ccc(Cl)cc2)c(=O)n1Cc1ccc(Cl)cc1] | I-0056 | 4.49 | 522 | 4 |

TABLE 15-continued
| Structure | Compound No. | Retention Time (min) | [M + H] | Method |
|---|---|---|---|---|
| 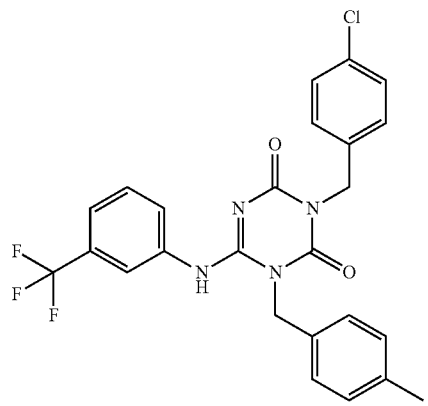 [SMILES: Cc1ccc(Cn2c(Nc3cccc(C(F)(F)F)c3)nc(=O)n(Cc3ccc(Cl)cc3)c2=O)cc1] | I-0057 | 4.26 | 501 | 4 |
| 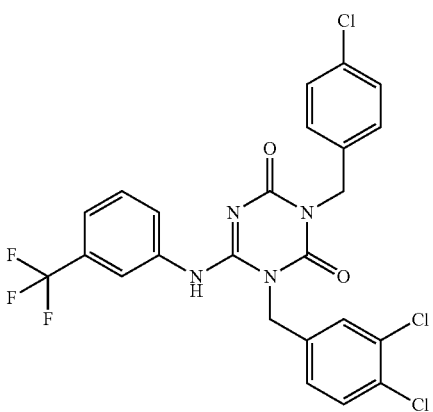 [SMILES: O=c1nc(Nc2cccc(C(F)(F)F)c2)n(Cc2ccc(Cl)c(Cl)c2)c(=O)n1Cc1ccc(Cl)cc1] | I-0058 | 4.94 | 556 | 4 |
| 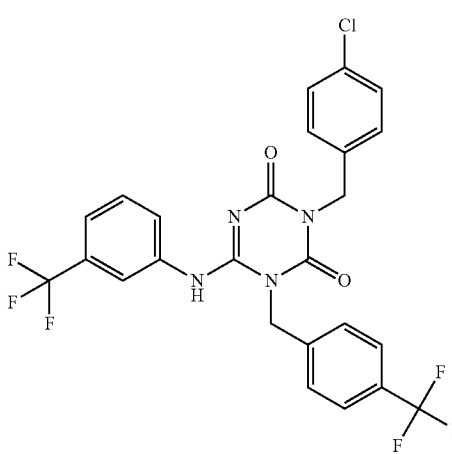 | I-0059 | 4.45 | 555 | 4 |

TABLE 15-continued

| Structure | Compound No. | Retention Time (min) | [M + H] | Method |
|---|---|---|---|---|
| 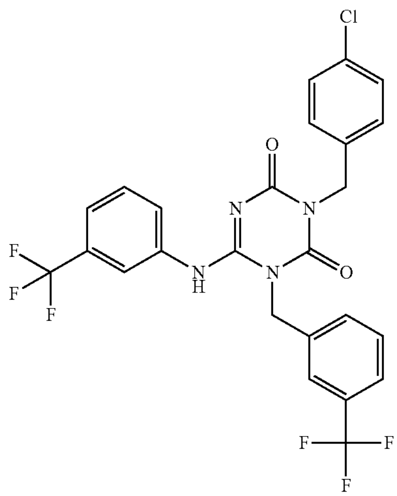 [SMILES: O=c1nc(Nc2cccc(C(F)(F)F)c2)n(Cc2cccc(C(F)(F)F)c2)c(=O)n1Cc1ccc(Cl)cc1] | I-0060 | 4.50 | 555 | 4 |

TABLE 16

| Structure | Compound No. | Retention Time (min) | [M + H] | Method |
|---|---|---|---|---|
| 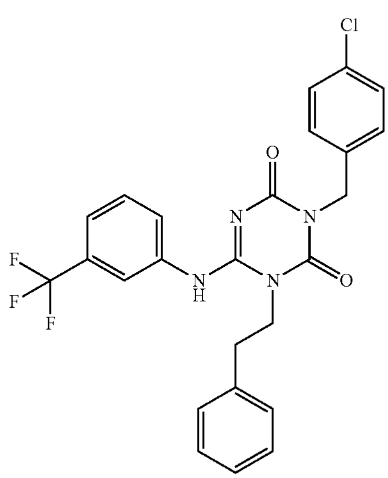 [SMILES: O=c1nc(Nc2cccc(C(F)(F)F)c2)n(CCc2ccccc2)c(=O)n1Cc1ccc(Cl)cc1] | I-0061 | 3.99 | 501 | 4 |

TABLE 16-continued
| Structure | Compound No. | Retention Time (min) | [M + H] | Method |
|---|---|---|---|---|
| 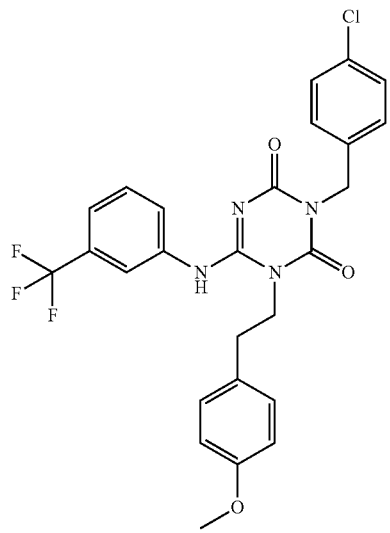 [SMILES: COc1ccc(CCn2c(Nc3cccc(C(F)(F)F)c3)nc(=O)n(Cc3ccc(Cl)cc3)c2=O)cc1] | I-0062 | 3.86 | 531 | 4 |
| 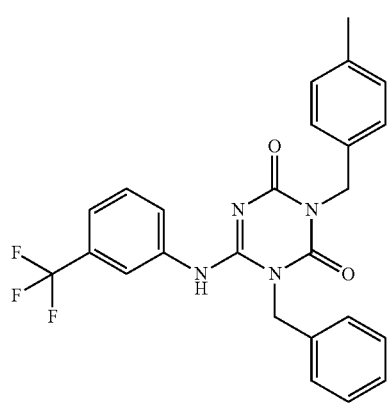 [SMILES: Cc1ccc(Cn2c(=O)nc(Nc3cccc(C(F)(F)F)c3)n(Cc3ccccc3)c2=O)cc1] | I-0063 | 2.81 | 467 | 4 |
| 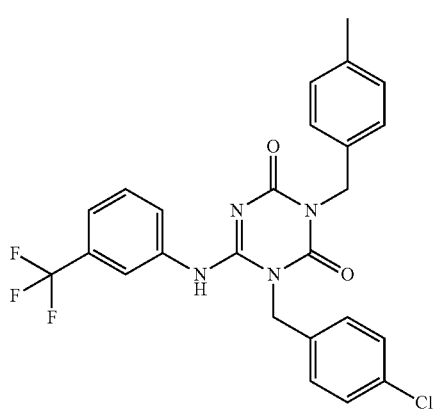 [SMILES: Cc1ccc(Cn2c(=O)nc(Nc3cccc(C(F)(F)F)c3)n(Cc3ccc(Cl)cc3)c2=O)cc1] | I-0064 | 2.40 | 501 | 4 |

TABLE 16-continued

| Structure | Compound No. | Retention Time (min) | [M + H] | Method |
|---|---|---|---|---|
| 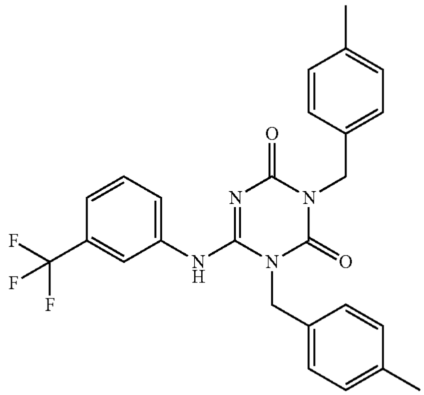 [SMILES: Cc1ccc(Cn2c(Nc3cccc(C(F)(F)F)c3)nc(=O)n(Cc3ccc(C)cc3)c2=O)cc1] | I-0065 | 3.32 | 481 | 4 |

TABLE 17

| Structure | Compound No. | Retention Time (min) | [M + H] | Method |
|---|---|---|---|---|
| 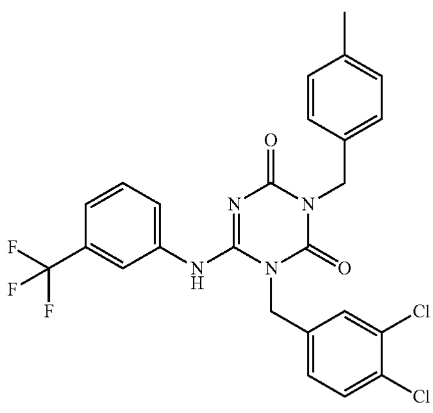 [SMILES: Cc1ccc(Cn2c(=O)nc(Nc3cccc(C(F)(F)F)c3)n(Cc3ccc(Cl)c(Cl)c3)c2=O)cc1] | I-0066 | 4.30 | 534 | 4 |
| 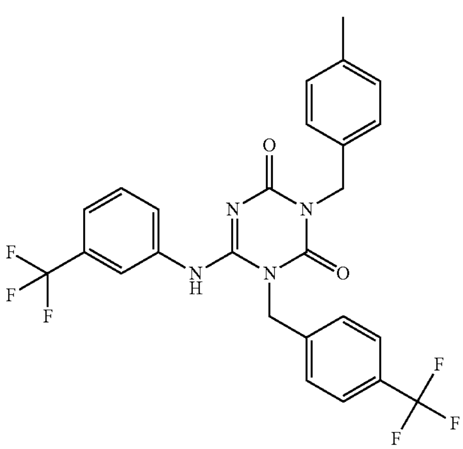 [SMILES: Cc1ccc(Cn2c(=O)nc(Nc3cccc(C(F)(F)F)c3)n(Cc3ccc(C(F)(F)F)cc3)c2=O)cc1] | I-0067 | 3.60 | 535 | 4 |

TABLE 17-continued

| Structure | Compound No. | Retention Time (min) | [M + H] | Method |
|---|---|---|---|---|
| 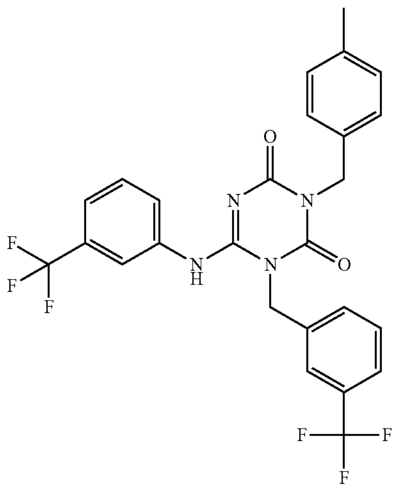 [SMILES: Cc1ccc(Cn2c(=O)nc(Nc3cccc(C(F)(F)F)c3)n(Cc3cccc(C(F)(F)F)c3)c2=O)cc1] | I-0068 | 3.60 | 535 | 4 |
| 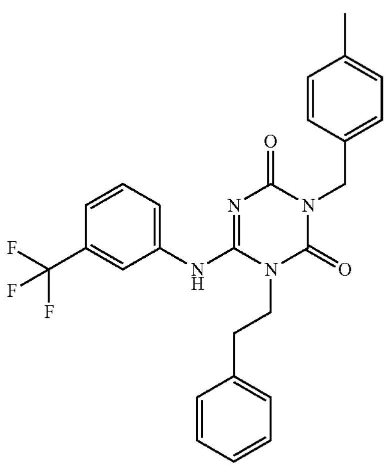 [SMILES: Cc1ccc(Cn2c(=O)nc(Nc3cccc(C(F)(F)F)c3)n(CCc3ccccc3)c2=O)cc1] | I-0069 | 3.91 | 481 | 4 |
| 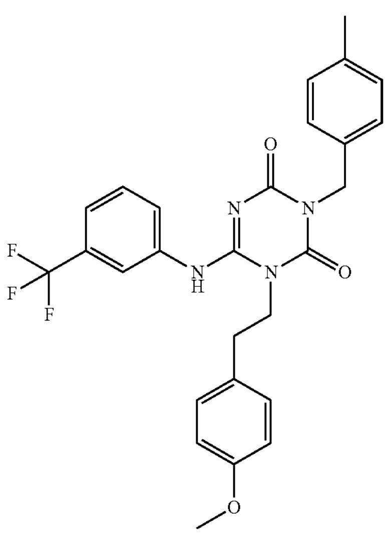 [SMILES: COc1ccc(CCn2c(Nc3cccc(C(F)(F)F)c3)nc(=O)n(Cc3ccc(C)cc3)c2=O)cc1] | I-0070 | 2.76 | 511 | 4 |

TABLE 18

| Structure | Compound No. | Retention Time (min) | [M + H] | Method |
|---|---|---|---|---|
| 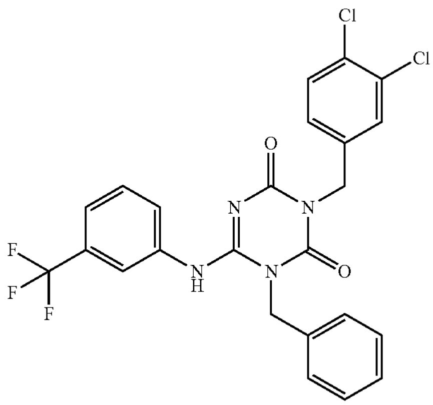 [SMILES: O=c1nc(Nc2cccc(C(F)(F)F)c2)n(Cc2ccccc2)c(=O)n1Cc1ccc(Cl)c(Cl)c1] | I-0071 | 3.43 | 522 | 4 |
| 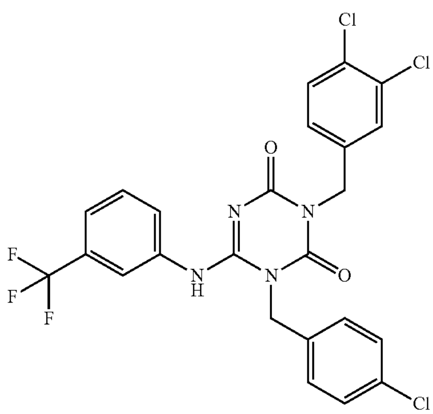 [SMILES: O=c1nc(Nc2cccc(C(F)(F)F)c2)n(Cc2ccc(Cl)cc2)c(=O)n1Cc1ccc(Cl)c(Cl)c1] | I-0072 | 4.12 | 556 | 4 |
| 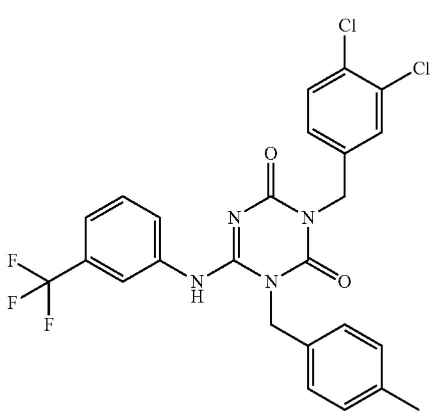 [SMILES: Cc1ccc(Cn2c(Nc3cccc(C(F)(F)F)c3)nc(=O)n(Cc3ccc(Cl)c(Cl)c3)c2=O)cc1] | I-0073 | 3.86 | 536 | 4 |

TABLE 18-continued

| Structure | Compound No. | Retention Time (min) | [M + H] | Method |
|---|---|---|---|---|
| 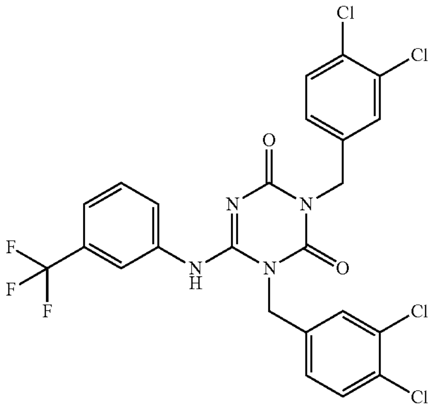 [SMILES: O=c1nc(Nc2cccc(C(F)(F)F)c2)n(Cc2ccc(Cl)c(Cl)c2)c(=O)n1Cc1ccc(Cl)c(Cl)c1] | I-0074 | 4.68 | 591 | 4 |
| 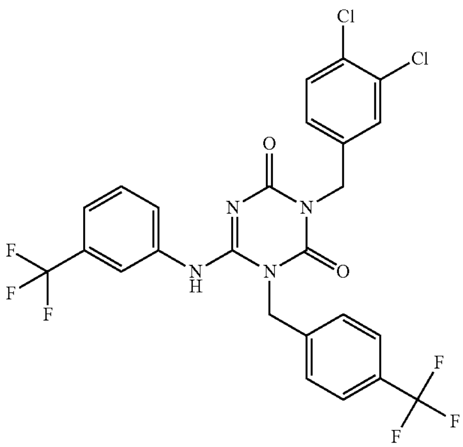 [SMILES: O=c1nc(Nc2cccc(C(F)(F)F)c2)n(Cc2ccc(C(F)(F)F)cc2)c(=O)n1Cc1ccc(Cl)c(Cl)c1] | I-0075 | 4.07 | 590 | 4 |

TABLE 19

| Structure | Compound No. | Retention Time (min) | [M + H] | Method |
|---|---|---|---|---|
| 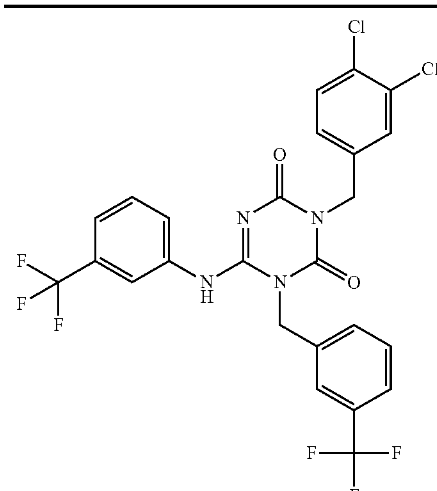 | I-0076 | 4.11 | 590 | 4 |

TABLE 19-continued
| Structure | Compound No. | Retention Time (min) | [M + H] | Method |
|---|---|---|---|---|
| 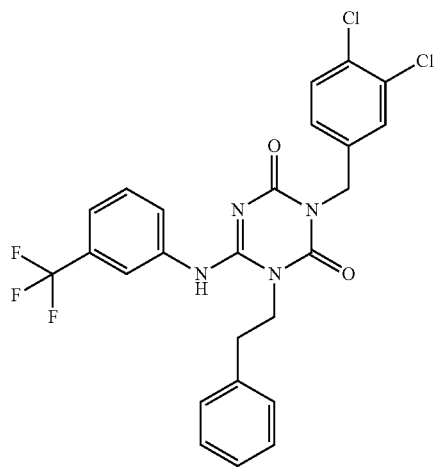 [SMILES: O=c1nc(Nc2cccc(C(F)(F)F)c2)n(CCc2ccccc2)c(=O)n1Cc1ccc(Cl)c(Cl)c1] | I-0077 | 3.55 | 536 | 4 |
| 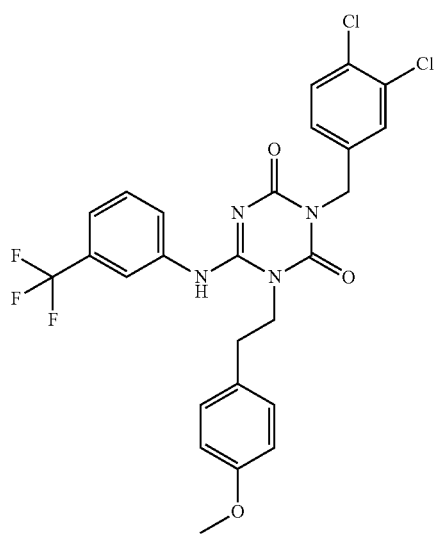 [SMILES: COc1ccc(CCn2c(Nc3cccc(C(F)(F)F)c3)nc(=O)n(Cc3ccc(Cl)c(Cl)c3)c2=O)cc1] | I-0078 | 3.49 | 566 | 4 |
| 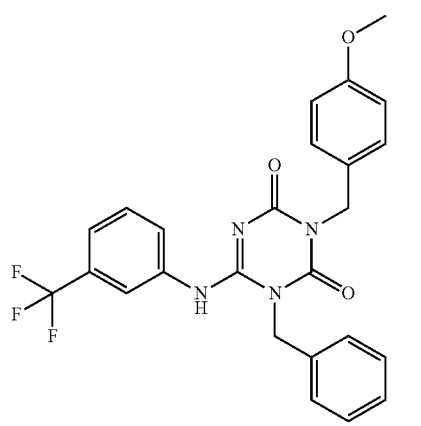 [SMILES: COc1ccc(Cn2c(=O)nc(Nc3cccc(C(F)(F)F)c3)n(Cc3ccccc3)c2=O)cc1] | I-0079 | 2.38 | 483 | 4 |

TABLE 19-continued

| Structure | Compound No. | Retention Time (min) | [M + H] | Method |
|---|---|---|---|---|
| 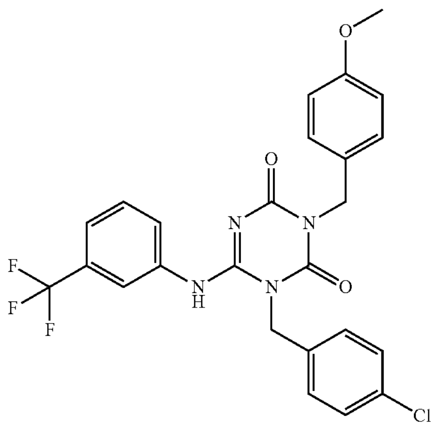 [SMILES: COc1ccc(Cn2c(=O)nc(Nc3cccc(C(F)(F)F)c3)n(Cc3ccc(Cl)cc3)c2=O)cc1] | I-0080 | 3.21 | 517 | 4 |

TABLE 20

| Structure | Compound No. | Retention Time (min) | [M + H] | Method |
|---|---|---|---|---|
| 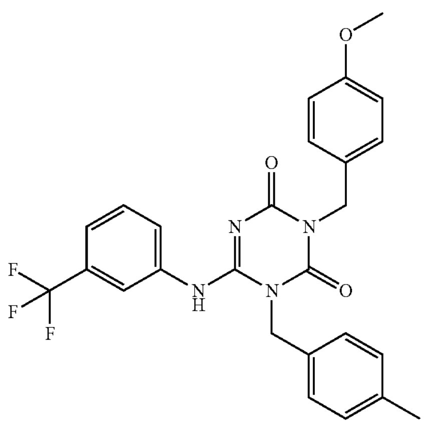 [SMILES: COc1ccc(Cn2c(=O)nc(Nc3cccc(C(F)(F)F)c3)n(Cc3ccc(C)cc3)c2=O)cc1] | I-0081 | 2.85 | 497 | 4 |
| 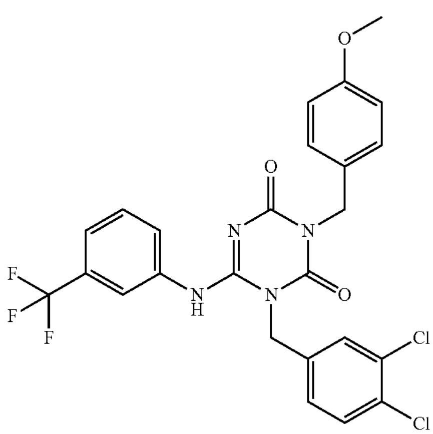 [SMILES: COc1ccc(Cn2c(=O)nc(Nc3cccc(C(F)(F)F)c3)n(Cc3ccc(Cl)c(Cl)c3)c2=O)cc1] | I-0082 | 3.85 | 552 | 4 |

TABLE 20-continued

| Structure | Compound No. | Retention Time (min) | [M + H] | Method |
|---|---|---|---|---|
| 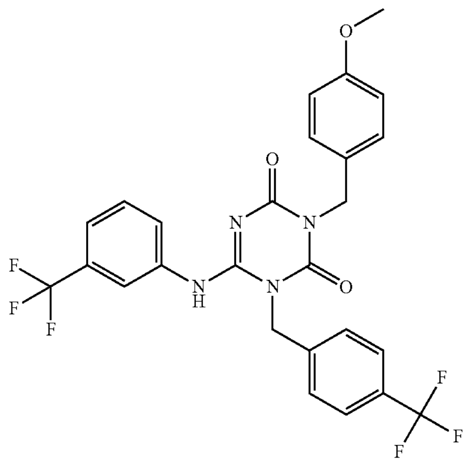 [SMILES: COc1ccc(Cn2c(=O)nc(Nc3cccc(C(F)(F)F)c3)n(Cc3ccc(C(F)(F)F)cc3)c2=O)cc1] | I-0083 | 3.22 | 551 | 4 |
| 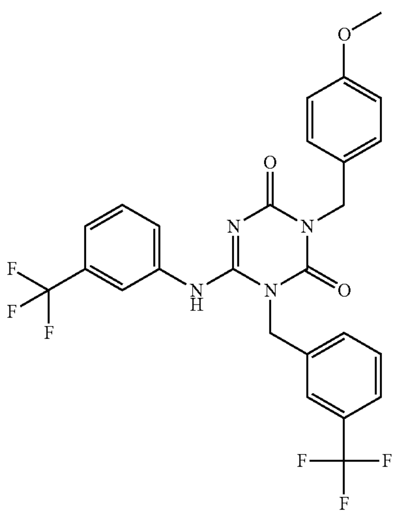 [SMILES: COc1ccc(Cn2c(=O)nc(Nc3cccc(C(F)(F)F)c3)n(Cc3cccc(C(F)(F)F)c3)c2=O)cc1] | I-0084 | 3.23 | 551 | 4 |
| 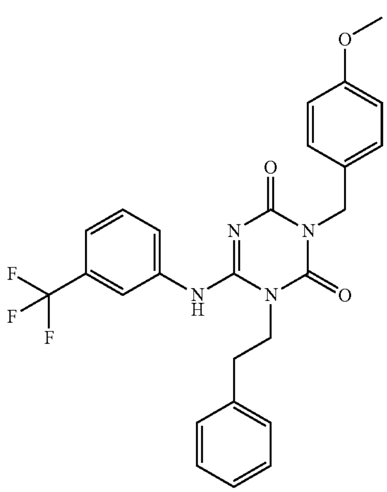 [SMILES: COc1ccc(Cn2c(=O)nc(Nc3cccc(C(F)(F)F)c3)n(CCc3ccccc3)c2=O)cc1] | I-0085 | 2.48 | 497 | 4 |

TABLE 21
| Structure | Compound No. | Retention Time (min) | [M + H] | Method |
|---|---|---|---|---|
| 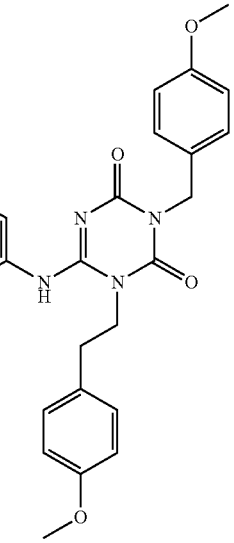 | I-0086 | 2.29 | 527 | 4 |
| 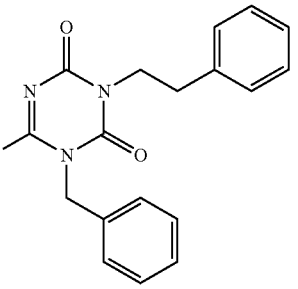 | I-0087 | 2.75 | 467 | 4 |
| 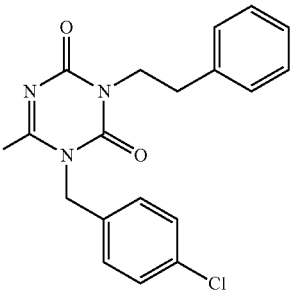 | I-0088 | 3.54 | 501 | 4 |
| 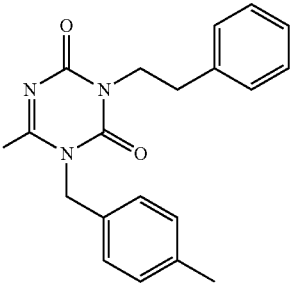 | I-0089 | 3.19 | 481 | 4 |

TABLE 21-continued

| Structure | Compound No. | Retention Time (min) | [M + H] | Method |
|---|---|---|---|---|
| 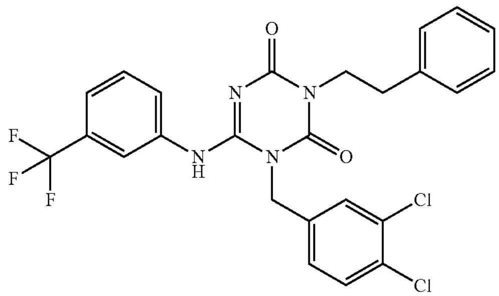 [SMILES: O=c1nc(Nc2cccc(C(F)(F)F)c2)n(Cc2ccc(Cl)c(Cl)c2)c(=O)n1CCc1ccccc1] | I-0090 | 4.15 | 636 | 4 |

TABLE 22

| Structure | Compound No. | Retention Time (min) | [M + H] | Method |
|---|---|---|---|---|
| 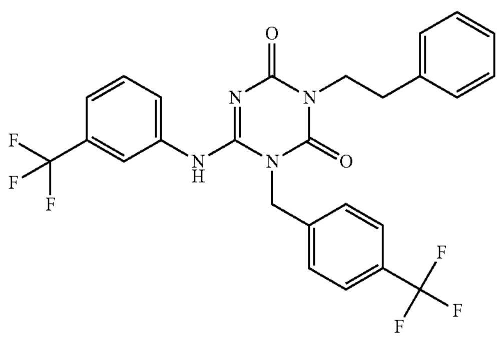 [SMILES: O=c1nc(Nc2cccc(C(F)(F)F)c2)n(Cc2ccc(C(F)(F)F)cc2)c(=O)n1CCc1ccccc1] | I-0091 | 3.49 | 535 | 4 |
| 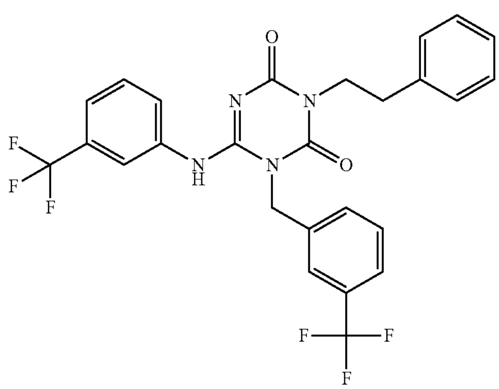 [SMILES: O=c1nc(Nc2cccc(C(F)(F)F)c2)n(Cc2cccc(C(F)(F)F)c2)c(=O)n1CCc1ccccc1] | I-0092 | 3.57 | 535 | 4 |
| 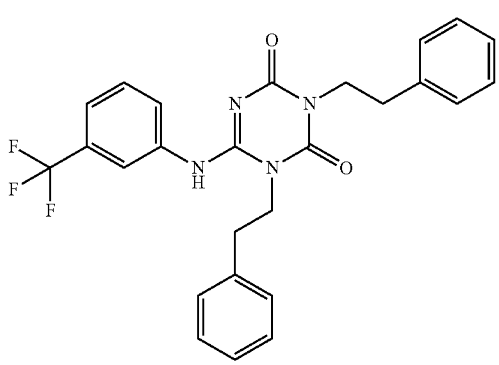 [SMILES: O=c1nc(Nc2cccc(C(F)(F)F)c2)n(CCc2ccccc2)c(=O)n1CCc1ccccc1] | I-0093 | 3.03 | 481 | 4 |

TABLE 22-continued

| Structure | Compound No. | Retention Time (min) | [M + H] | Method |
|---|---|---|---|---|
| 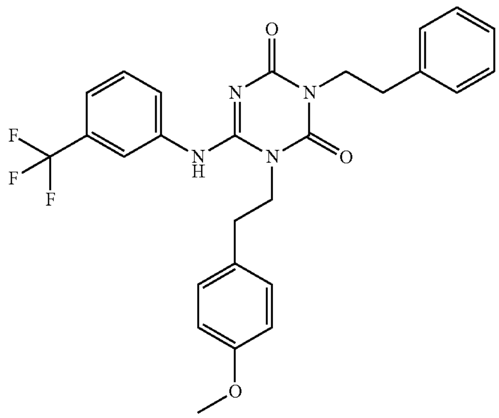 [SMILES: COc1ccc(CCn2c(Nc3cccc(C(F)(F)F)c3)nc(=O)n(CCc3ccccc3)c2=O)cc1] | I-0094 | 2.79 | 511 | 4 |
| 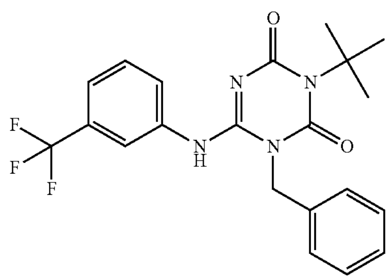 [SMILES: CC(C)(C)n1c(=O)nc(Nc2cccc(C(F)(F)F)c2)n(Cc2ccccc2)c1=O] | I-0095 | 3.58 | 419 | 4 |

TABLE 23

| Structure | Compound No. | Retention Time (min) | [M + H] | Method |
|---|---|---|---|---|
| 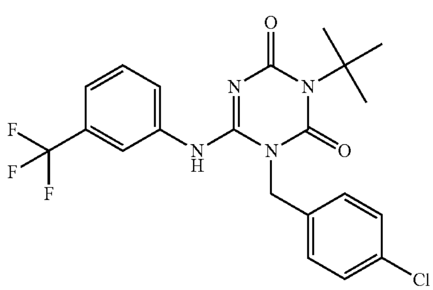 [SMILES: CC(C)(C)n1c(=O)nc(Nc2cccc(C(F)(F)F)c2)n(Cc2ccc(Cl)cc2)c1=O] | I-0096 | 4.22 | 453 | 4 |
| 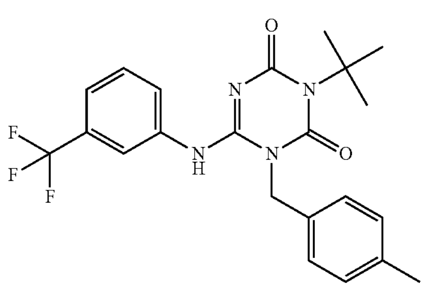 [SMILES: Cc1ccc(Cn2c(Nc3cccc(C(F)(F)F)c3)nc(=O)n(C(C)(C)C)c2=O)cc1] | I-0097 | 4.21 | 433 | 4 |

TABLE 23-continued

| Structure | Compound No. | Retention Time (min) | [M + H] | Method |
|---|---|---|---|---|
| 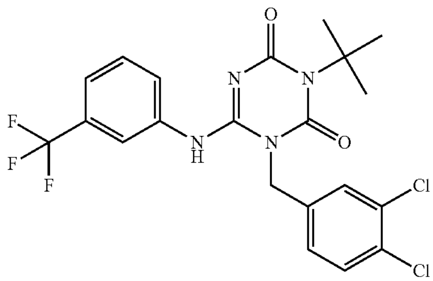 [SMILES: CC(C)(C)n1c(=O)nc(Nc2cccc(C(F)(F)F)c2)n(Cc2ccc(Cl)c(Cl)c2)c1=O] | I-0098 | 4.03 | 488 | 4 |
| 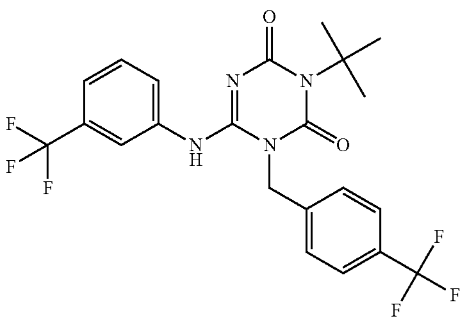 [SMILES: CC(C)(C)n1c(=O)nc(Nc2cccc(C(F)(F)F)c2)n(Cc2ccc(C(F)(F)F)cc2)c1=O] | I-0099 | 3.38 | 487 | 4 |
| 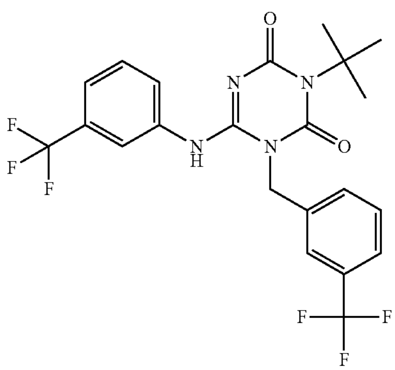 [SMILES: CC(C)(C)n1c(=O)nc(Nc2cccc(C(F)(F)F)c2)n(Cc2cccc(C(F)(F)F)c2)c1=O] | I-0100 | 4.24 | 487 | 4 |

TABLE 24

| Structure | Compound No. | Retention Time (min) | [M + H] | Method |
|---|---|---|---|---|
| 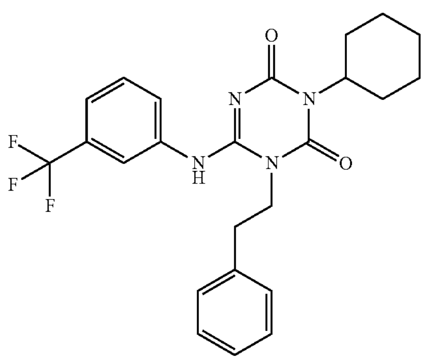 [SMILES: O=c1nc(Nc2cccc(C(F)(F)F)c2)n(CCc2ccccc2)c(=O)n1C1CCCCC1] | I-0101 | 3.38 | 459 | 4 |

TABLE 24-continued

| Structure | Compound No. | Retention Time (min) | [M + H] | Method |
|---|---|---|---|---|
| 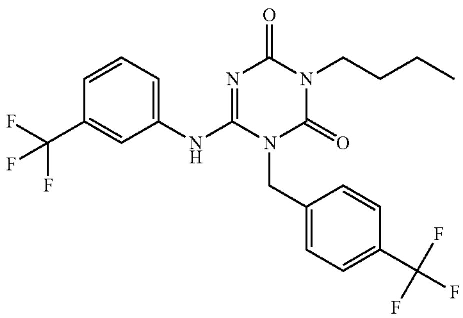 [SMILES: CCCCn1c(=O)nc(Nc2cccc(C(F)(F)F)c2)n(Cc2ccc(C(F)(F)F)cc2)c1=O] | I-0102 | 4.16 | 487 | 4 |
| 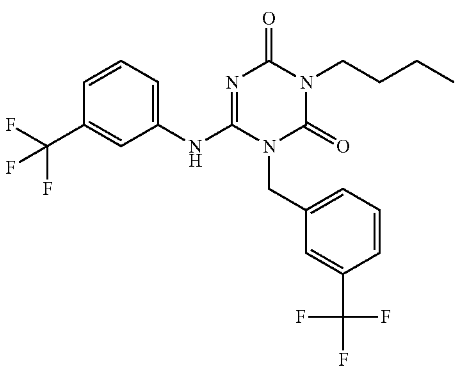 [SMILES: CCCCn1c(=O)nc(Nc2cccc(C(F)(F)F)c2)n(Cc2cccc(C(F)(F)F)c2)c1=O] | I-0103 | 4.18 | 487 | 4 |
| 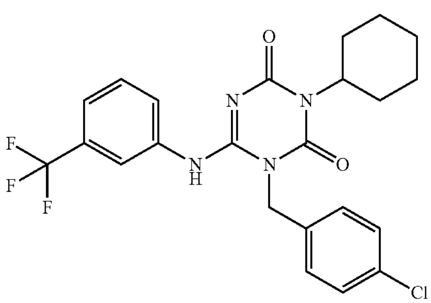 [SMILES: O=c1nc(Nc2cccc(C(F)(F)F)c2)n(Cc2ccc(Cl)cc2)c(=O)n1C1CCCCC1] | I-0104 | 4.69 | 479 | 4 |
| 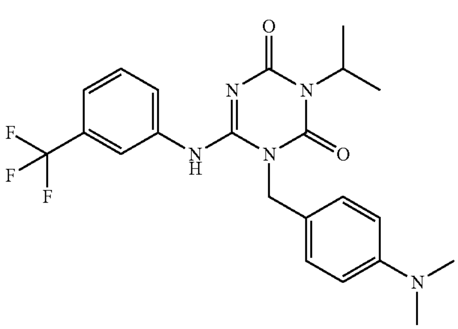 [SMILES: CC(C)n1c(=O)nc(Nc2cccc(C(F)(F)F)c2)n(Cc2ccc(N(C)C)cc2)c1=O] | I-0105 | 3.38 | 448 | 4 |

TABLE 25

| Structure | Compound No. | Retention Time (min) | [M + H] | Method |
|---|---|---|---|---|
| 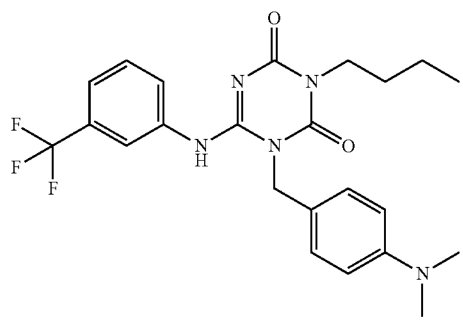 [SMILES: CCCCn1c(=O)nc(Nc2cccc(C(F)(F)F)c2)n(Cc2ccc(N(C)C)cc2)c1=O] | I-0106 | 3.59 | 462 | 4 |
| 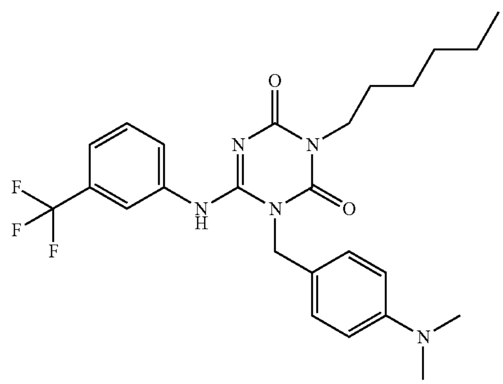 [SMILES: CCCCCCn1c(=O)nc(Nc2cccc(C(F)(F)F)c2)n(Cc2ccc(N(C)C)cc2)c1=O] | I-0107 | 4.05 | 490 | 4 |
| 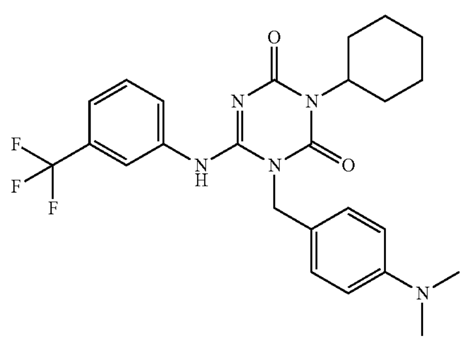 [SMILES: CN(C)c1ccc(Cn2c(Nc3cccc(C(F)(F)F)c3)nc(=O)n(C3CCCCC3)c2=O)cc1] | I-0108 | 385 | 488 | 4 |
| 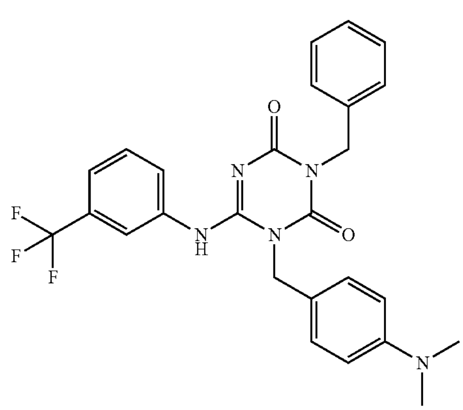 [SMILES: CN(C)c1ccc(Cn2c(Nc3cccc(C(F)(F)F)c3)nc(=O)n(Cc3ccccc3)c2=O)cc1] | I-0109 | 3.66 | 496 | 4 |

TABLE 25-continued

| Structure | Compound No. | Retention Time (min) | [M + H] | Method |
|---|---|---|---|---|
| 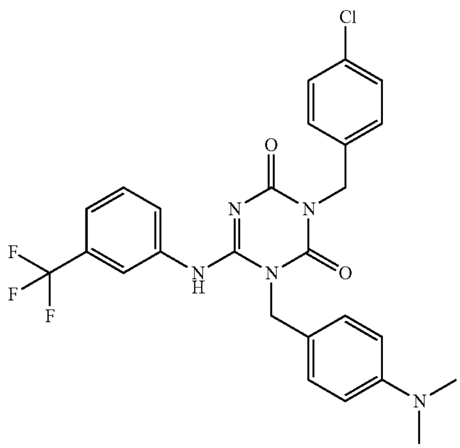 [SMILES: CN(C)c1ccc(Cn2c(Nc3cccc(C(F)(F)F)c3)nc(=O)n(Cc3ccc(Cl)cc3)c2=O)cc1] | I-0110 | 3.97 | 530 | 4 |

TABLE 26

| Structure | Compound No. | Retention Time (min) | [M + H] | Method |
|---|---|---|---|---|
| 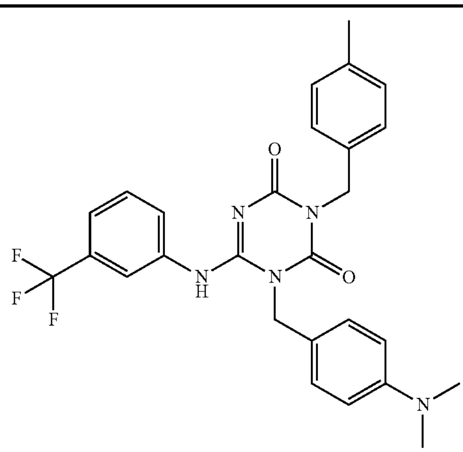 | I-0111 | 3.84 | 510 | 4 |
| 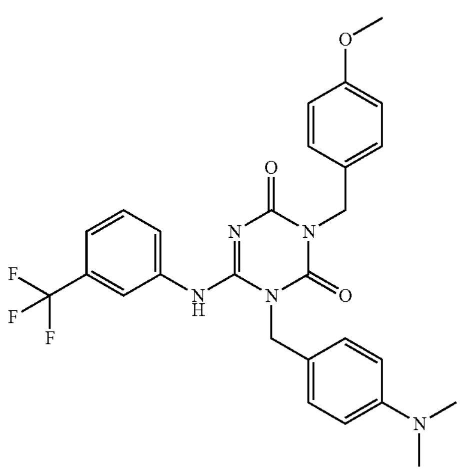 [SMILES: COc1ccc(Cn2c(=O)nc(Nc3cccc(C(F)(F)F)c3)n(Cc3ccc(N(C)C)cc3)c2=O)cc1] | I-0112 | 3.67 | 526 | 4 |

TABLE 26-continued
| Structure | Compound No. | Retention Time (min) | [M + H] | Method |
|---|---|---|---|---|
| 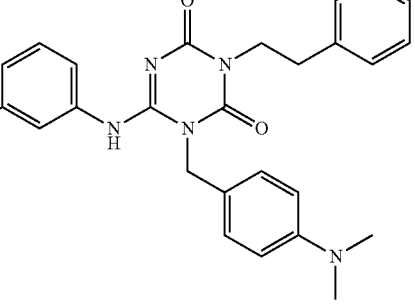 | I-0113 | 3.77 | 510 | 4 |
| 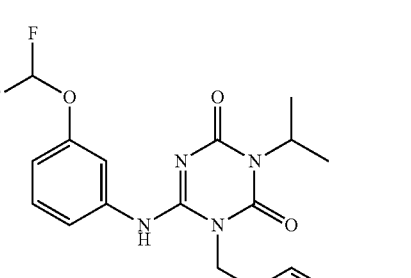 | I-0114 | 2.44 | 417 | 1 |
| 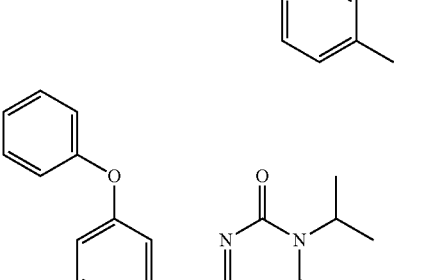 | I-0115 | 2.67 | 443 | 1 |
TABLE 27
| Structure | Compound No. | Retention Time (min) | [M + H] | Method |
|---|---|---|---|---|
| 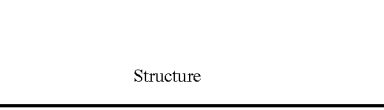 | I-0116 | 2.59 | 443 | |

TABLE 27-continued

| Structure | Compound No. | Retention Time (min) | [M + H] | Method |
|---|---|---|---|---|
| 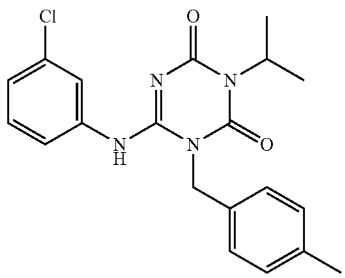 [SMILES: Cc1ccc(Cn2c(Nc3cccc(Cl)c3)nc(=O)n(C(C)C)c2=O)cc1] | I-0117 | 2.52 | 385 | 1 |
| 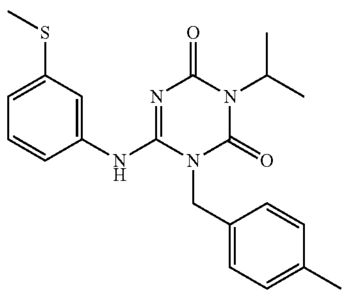 [SMILES: CSc1cccc(Nc2nc(=O)n(C(C)C)c(=O)n2Cc2ccc(C)cc2)c1] | I-0118 | 2.44 | 397 | 1 |
| 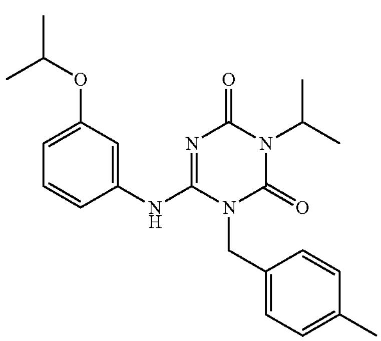 [SMILES: Cc1ccc(Cn2c(Nc3cccc(OC(C)C)c3)nc(=O)n(C(C)C)c2=O)cc1] | I-0119 | 2.52 | 409 | 1 |
| 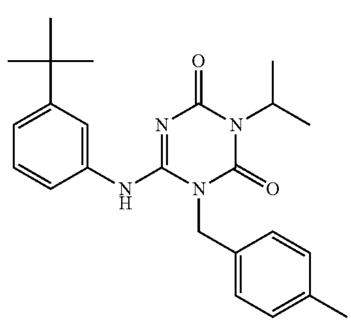 [SMILES: Cc1ccc(Cn2c(Nc3cccc(C(C)(C)C)c3)nc(=O)n(C(C)C)c2=O)cc1] | I-0120 | 2.70 | 407 | 1 |

TABLE 28

| Structure | Compound No. | Retention Time (min) | [M + H] | Method |
|---|---|---|---|---|
| 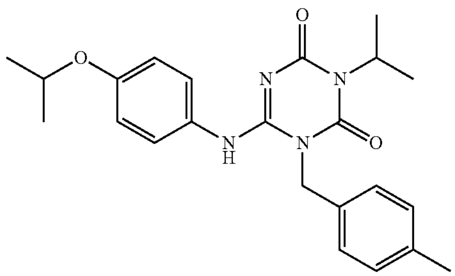 [SMILES: Cc1ccc(Cn2c(Nc3ccc(OC(C)C)cc3)nc(=O)n(C(C)C)c2=O)cc1] | I-0121 | 2.40 | 409 | 1 |
| 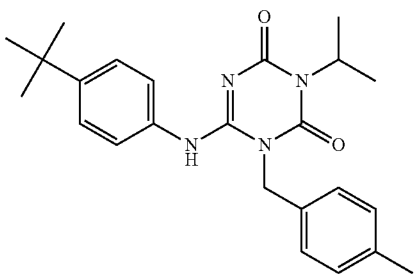 [SMILES: Cc1ccc(Cn2c(Nc3ccc(C(C)(C)C)cc3)nc(=O)n(C(C)C)c2=O)cc1] | I-0122 | 2.68 | 407 | 1 |
| 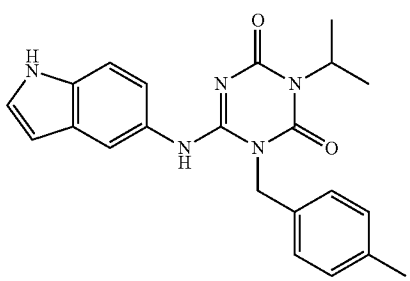 [SMILES: Cc1ccc(Cn2c(Nc3ccc4[nH]ccc4c3)nc(=O)n(C(C)C)c2=O)cc1] | I-0123 | 2.05 | 390 | 1 |
| 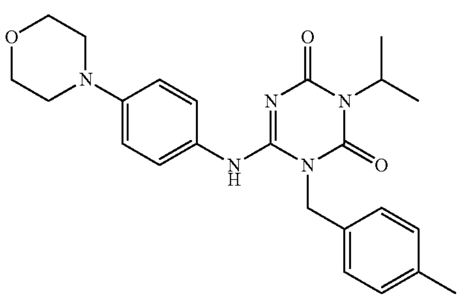 [SMILES: Cc1ccc(Cn2c(Nc3ccc(N4CCOCC4)cc3)nc(=O)n(C(C)C)c2=O)cc1] | I-0124 | 2.04 | 436 | 1 |
| 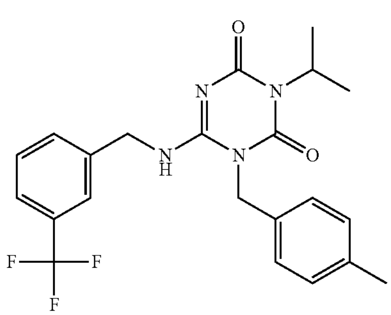 [SMILES: Cc1ccc(Cn2c(NCc3cccc(C(F)(F)F)c3)nc(=O)n(C(C)C)c2=O)cc1] | I-0125 | 2.31 | 423 | 1 |

TABLE 29

| Structure | Compound No. | Retention Time (min) | [M + H] | Method |
|---|---|---|---|---|
| (structure) | I-0126 | 2.51 | 423 | 1 |
| (structure) | I-0127 | 2.60 | 447 | 1 |
| (structure) | I-0128 | 2.52 | 447 | 1 |
| (structure) | I-0129 | 2.44 | 389 | 1 |

TABLE 29-continued

| Structure | Compound No. | Retention Time (min) | [M + H] | Method |
|---|---|---|---|---|
| 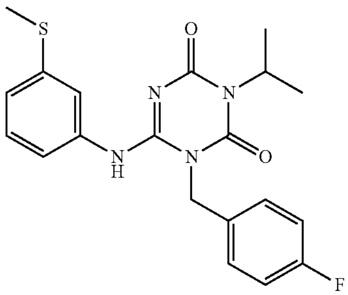 [SMILES: CSc1cccc(Nc2nc(=O)n(C(C)C)c(=O)n2Cc2ccc(F)cc2)c1] | I-0130 | 2.36 | 401 | 1 |

TABLE 30

| Structure | Compound No. | Retention Time (min) | [M + H] | Method |
|---|---|---|---|---|
| 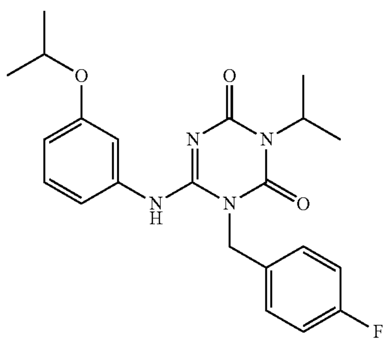 [SMILES: CC(C)Oc1cccc(Nc2nc(=O)n(C(C)C)c(=O)n2Cc2ccc(F)cc2)c1] | I-0131 | 2.44 | 413 | 1 |
| 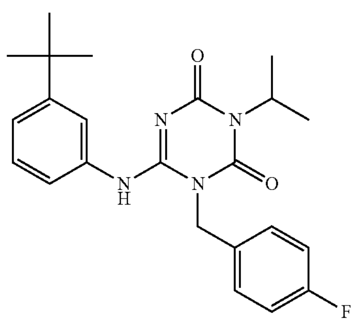 [SMILES: CC(C)n1c(=O)nc(Nc2cccc(C(C)(C)C)c2)n(Cc2ccc(F)cc2)c1=O] | I-0132 | 2.60 | 411 | 1 |
| 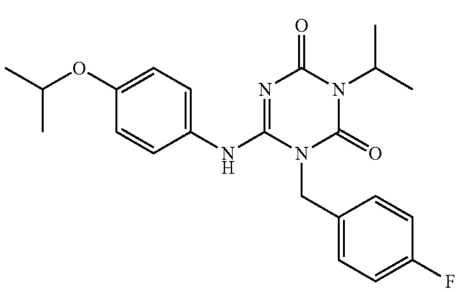 [SMILES: CC(C)Oc1ccc(Nc2nc(=O)n(C(C)C)c(=O)n2Cc2ccc(F)cc2)cc1] | I-0133 | 2.31 | 413 | 1 |

TABLE 30-continued

| Structure | Compound No. | Retention Time (min) | [M + H] | Method |
|---|---|---|---|---|
| (4-tert-butylphenyl)amino / isopropyl / 4-fluorobenzyl triazinedione | I-0134 | 2.58 | 411 | 1 |
| (1H-indol-5-yl)amino / isopropyl / 4-fluorobenzyl triazinedione | I-0135 | 1.96 | 394 | 1 |

TABLE 31

| Structure | Compound No. | Retention Time (min) | [M + H] | Method |
|---|---|---|---|---|
| (4-morpholinophenyl)amino / isopropyl / 4-fluorobenzyl triazinedione | I-0136 | 1.93 | 440 | 1 |
| (3-(trifluoromethyl)benzyl)amino / isopropyl / 4-fluorobenzyl triazinedione | I-0137 | 2.18 | 437 | 1 |

TABLE 31-continued
| Structure | Compound No. | Retention Time (min) | [M + H] | Method |
|---|---|---|---|---|
| 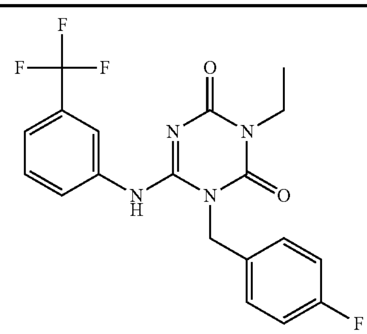 | I-0138 | 2.35 | 409 | 1 |
| 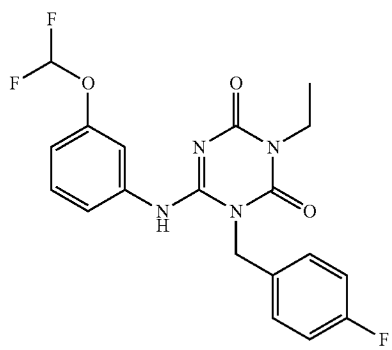 [SMILES: CCn1c(=O)nc(Nc2cccc(OC(F)F)c2)n(Cc2ccc(F)cc2)c1=O] | I-0139 | 2.18 | 407 | 1 |
| 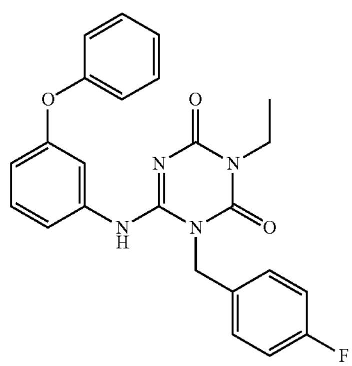 [SMILES: CCn1c(=O)nc(Nc2cccc(Oc3ccccc3)c2)n(Cc2ccc(F)cc2)c1=O] | I-0140 | 2.44 | 433 | 1 |
TABLE 32
| Structure | Compound No. | Retention Time (min) | [M + H] | Method |
|---|---|---|---|---|
| 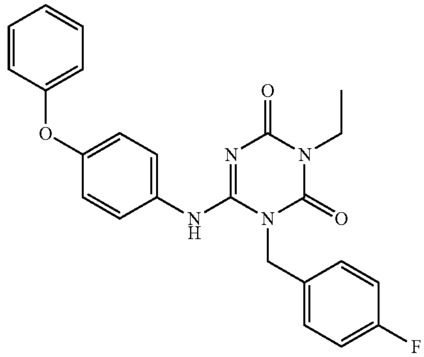 [SMILES: CCn1c(=O)nc(Nc2ccc(Oc3ccccc3)cc2)n(Cc2ccc(F)cc2)c1=O] | I-0141 | 2.37 | 433 | 1 |
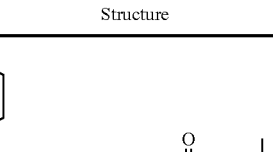

TABLE 32-continued

| Structure | Compound No. | Retention Time (min) | [M + H] | Method |
|---|---|---|---|---|
| (3-chlorophenyl-NH / 3-ethyl-1-(4-fluorobenzyl)triazine-2,4-dione) | I-0142 | 2.26 | 374 | 1 |
| (3-methylthiophenyl-NH / 3-ethyl-1-(4-fluorobenzyl)triazine-2,4-dione) | I-0143 | 2.17 | 387 | 1 |
| (3-isopropoxyphenyl-NH / 3-ethyl-1-(4-fluorobenzyl)triazine-2,4-dione) | I-0144 | 2.27 | 399 | 1 |
| (3-tert-butylphenyl-NH / 3-ethyl-1-(4-fluorobenzyl)triazine-2,4-dione) | I-0145 | 2.45 | 397 | 1 |

TABLE 33

| Structure | Compound No. | Retention Time (min) | [M + H] | Method |
|---|---|---|---|---|
| 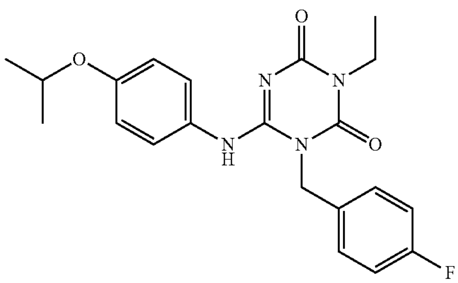 [SMILES: CCn1c(=O)nc(Nc2ccc(OC(C)C)cc2)n(Cc2ccc(F)cc2)c1=O] | I-0146 | 2.13 | 399 | 1 |
| 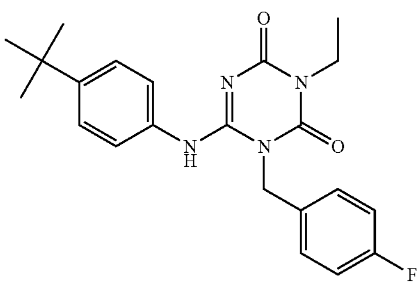 [SMILES: CCn1c(=O)nc(Nc2ccc(C(C)(C)C)cc2)n(Cc2ccc(F)cc2)c1=O] | I-0147 | 2.42 | 397 | 1 |
| 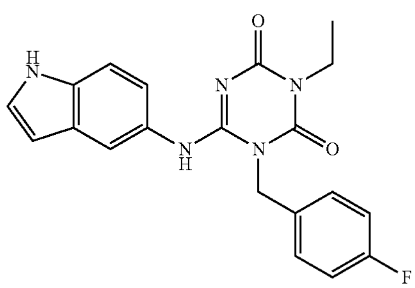 [SMILES: CCn1c(=O)nc(Nc2ccc3[nH]ccc3c2)n(Cc2ccc(F)cc2)c1=O] | I-0148 | 1.78 | 380 | 1 |
| 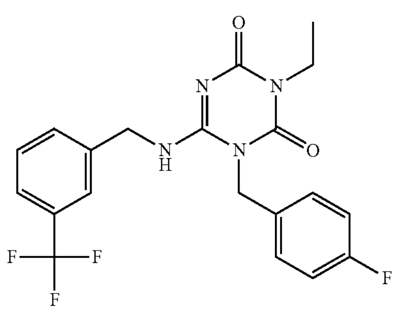 [SMILES: CCn1c(=O)nc(NCc2cccc(C(F)(F)F)c2)n(Cc2ccc(F)cc2)c1=O] | I-0149 | 2.04 | 423 | 1 |
| 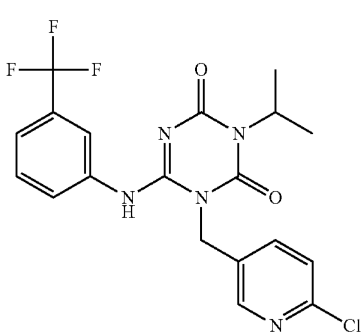 [SMILES: CC(C)n1c(=O)nc(Nc2cccc(C(F)(F)F)c2)n(Cc2ccc(Cl)nc2)c1=O] | I-0150 | 2.40 | 440 | 1 |

TABLE 34
| Structure | Compound No. | Retention Time (min) | [M + H] | Method |
|---|---|---|---|---|
| 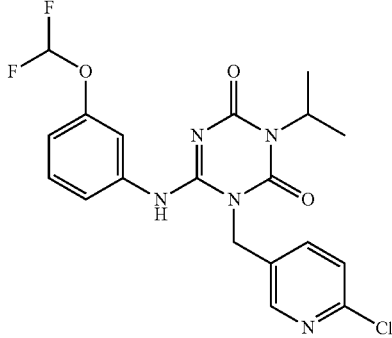 [SMILES: CC(C)n1c(=O)nc(Nc2cccc(OC(F)F)c2)n(Cc2ccc(Cl)nc2)c1=O] | I-0151 | 2.24 | 438 | 1 |
| 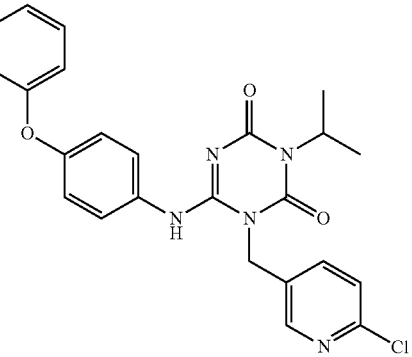 | I-0152 | 2.44 | 464 | 1 |
| 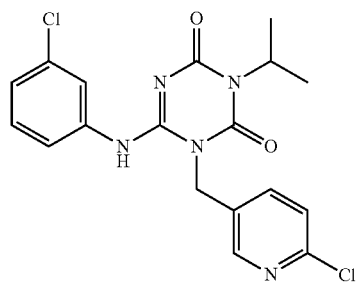 [SMILES: CC(C)n1c(=O)nc(Nc2cccc(Cl)c2)n(Cc2ccc(Cl)nc2)c1=O] | I-0153 | 2.30 | 407 | 1 |
| 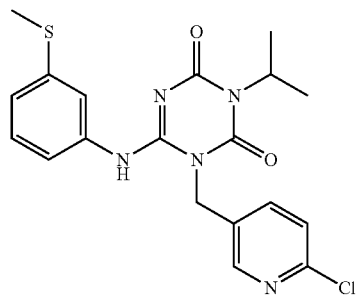 [SMILES: CSc1cccc(Nc2nc(=O)n(C(C)C)c(=O)n2Cc2ccc(Cl)nc2)c1] | I-0154 | 2.25 | 418 | 1 |

TABLE 34-continued

| Structure | Compound No. | Retention Time (min) | [M + H] | Method |
|---|---|---|---|---|
| 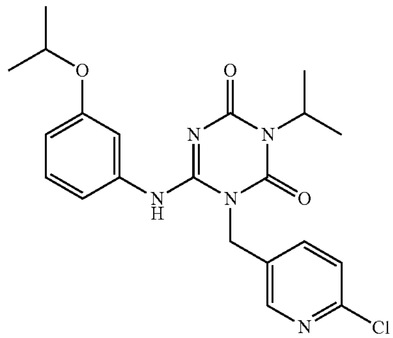 [SMILES: CC(C)Oc1cccc(Nc2nc(=O)n(C(C)C)c(=O)n2Cc2ccc(Cl)nc2)c1] | I-0155 | 2.34 | 430 | 1 |

TABLE 35

| Structure | Compound No. | Retention Time (min) | [M + H] | Method |
|---|---|---|---|---|
| 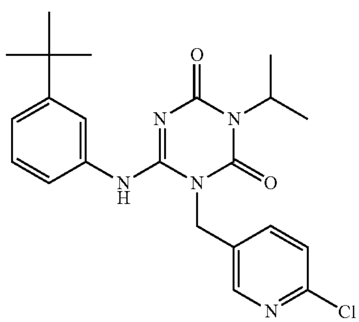 [SMILES: CC(C)n1c(=O)nc(Nc2cccc(C(C)(C)C)c2)n(Cc2ccc(Cl)nc2)c1=O] | I-0156 | 2.53 | 428 | 1 |
| 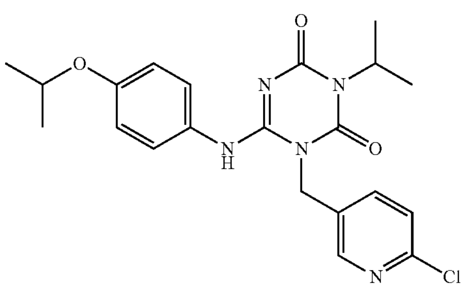 [SMILES: CC(C)Oc1ccc(Nc2nc(=O)n(C(C)C)c(=O)n2Cc2ccc(Cl)nc2)cc1] | I-0157 | 2.21 | 430 | 1 |
| 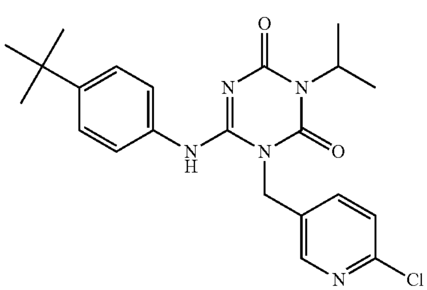 [SMILES: CC(C)n1c(=O)nc(Nc2ccc(C(C)(C)C)cc2)n(Cc2ccc(Cl)nc2)c1=O] | I-0158 | 2.51 | 428 | 1 |

TABLE 35-continued
| Structure | Compound No. | Retention Time (min) | [M + H] | Method |
|---|---|---|---|---|
| 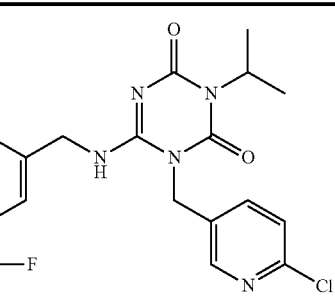 | I-0159 | 1.83 | 411 | 1 |
| 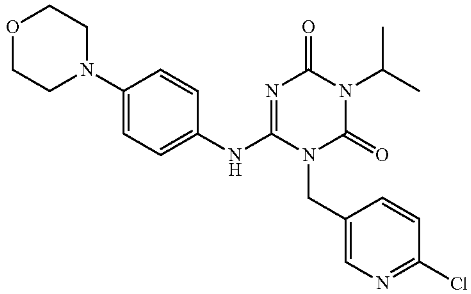 [SMILES: CC(C)n1c(=O)nc(Nc2ccc(N3CCOCC3)cc2)n(Cc2ccc(Cl)nc2)c1=O] | I-0160 | 1.77 | 457 | 1 |
TABLE 36
| Structure | Compound No. | Retention Time (min) | [M + H] | Method |
|---|---|---|---|---|
| 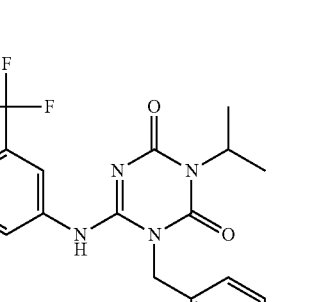 | I-0161 | 2.04 | 454 | 1 |
| 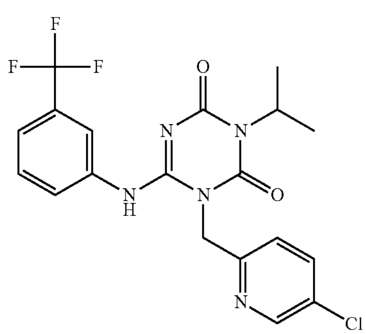 [SMILES: CC(C)n1c(=O)nc(Nc2cccc(C(F)(F)F)c2)n(Cc2ccc(Cl)cn2)c1=O] | I-0162 | 2.40 | 440 | 1 |

TABLE 36-continued

| Structure | Compound No. | Retention Time (min) | [M + H] | Method |
|---|---|---|---|---|
| 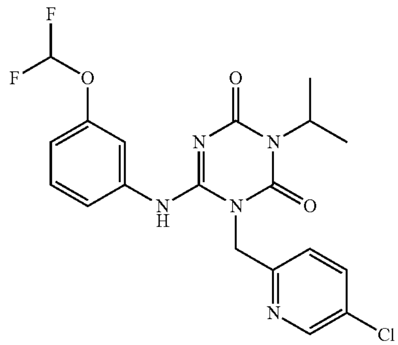 [SMILES: CC(C)n1c(=O)nc(Nc2cccc(OC(F)F)c2)n(Cc2ccc(Cl)cn2)c1=O] | I-0163 | 2.24 | 438 | 1 |
| 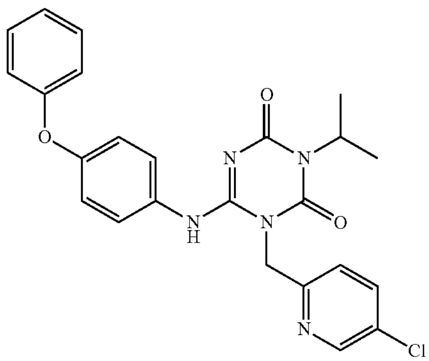 [SMILES: CC(C)n1c(=O)nc(Nc2ccc(Oc3ccccc3)cc2)n(Cc2ccc(Cl)cn2)c1=O] | I-0164 | 2.48 | 464 | 1 |
| 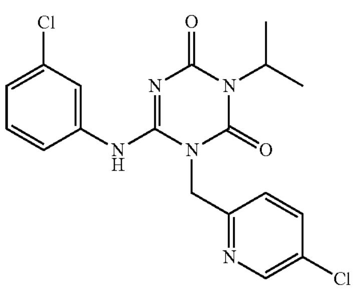 [SMILES: CC(C)n1c(=O)nc(Nc2cccc(Cl)c2)n(Cc2ccc(Cl)cn2)c1=O] | I-0165 | 2.31 | 407 | 1 |

TABLE 37

| Structure | Compound No. | Retention Time (min) | [M + H] | Method |
|---|---|---|---|---|
| 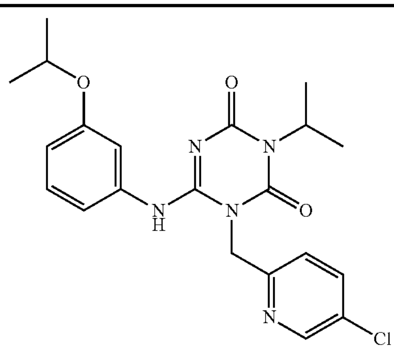 | I-0166 | 2.38 | 430 | 1 |

TABLE 37-continued

| Structure | Compound No. | Retention Time (min) | [M + H] | Method |
|---|---|---|---|---|
| 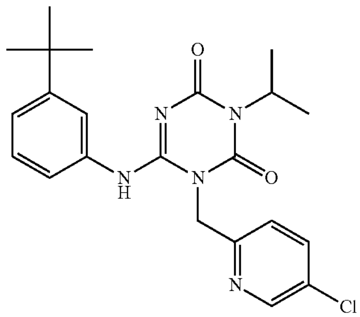 [SMILES: CC(C)n1c(=O)nc(Nc2cccc(C(C)(C)C)c2)n(Cc2ccc(Cl)cn2)c1=O] | I-0167 | 2.58 | 428 | 1 |
| 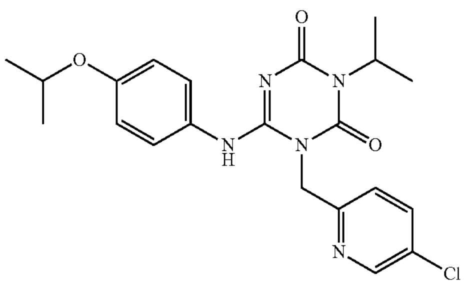 | I-0168 | 2.31 | 430 | 1 |
| 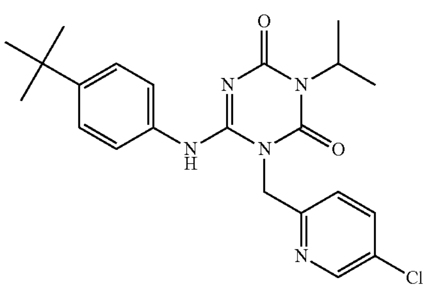 [SMILES: CC(C)n1c(=O)nc(Nc2ccc(C(C)(C)C)cc2)n(Cc2ccc(Cl)cn2)c1=O] | I-0169 | 2.60 | 430 | 1 |
| 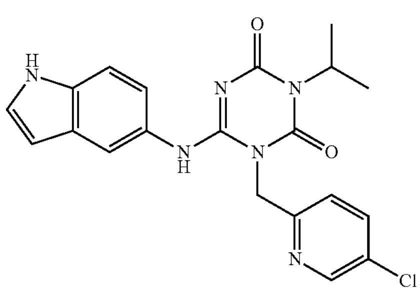 [SMILES: CC(C)n1c(=O)nc(Nc2ccc3[nH]ccc3c2)n(Cc2ccc(Cl)cn2)c1=O] | I-0170 | 1.94 | 411 | 1 |

TABLE 38

| Structure | Compound No. | Retention Time (min) | [M + H] | Method |
|---|---|---|---|---|
| 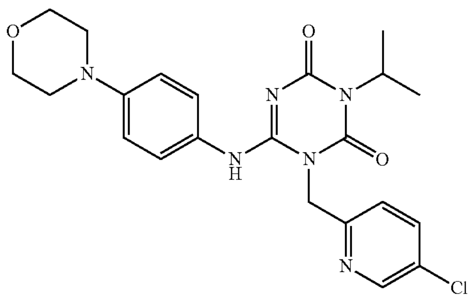 [SMILES: CC(C)n1c(=O)nc(Nc2ccc(N3CCOCC3)cc2)n(Cc2ccc(Cl)cn2)c1=O] | I-0171 | 1.92 | 457 | 1 |
| 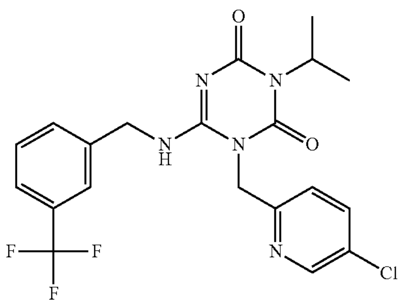 [SMILES: CC(C)n1c(=O)nc(NCc2cccc(C(F)(F)F)c2)n(Cc2ccc(Cl)cn2)c1=O] | I-0172 | 2.20 | 454 | 1 |
| 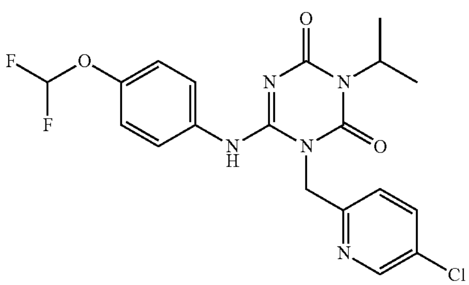 [SMILES: CC(C)n1c(=O)nc(Nc2ccc(OC(F)F)cc2)n(Cc2ccc(Cl)cn2)c1=O] | I-0173 | 2.30 | 438 | 3 |
| 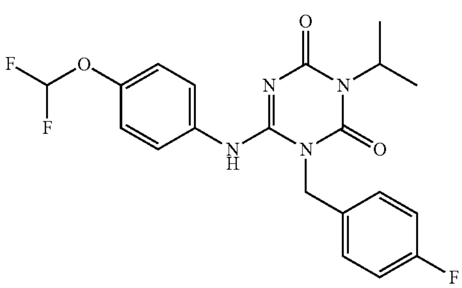 [SMILES: CC(C)n1c(=O)nc(Nc2ccc(OC(F)F)cc2)n(Cc2ccc(F)cc2)c1=O] | I-0174 | 2.38 | 421 | 3 |
| 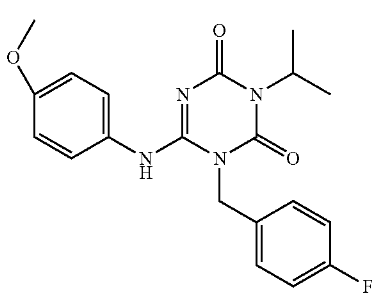 [SMILES: COc1ccc(Nc2nc(=O)n(C(C)C)c(=O)n2Cc2ccc(F)cc2)cc1] | I-0175 | 2.20 | 385 | 3 |

TABLE 39

| Structure | Compound No. | Retention Time (min) | [M + H] | Method |
|---|---|---|---|---|
| 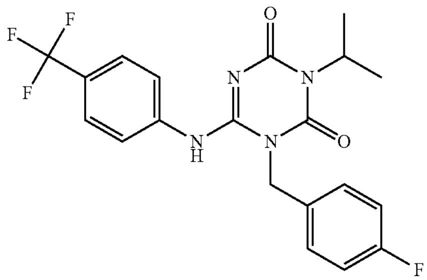 [SMILES: CC(C)n1c(=O)nc(Nc2ccc(C(F)(F)F)cc2)n(Cc2ccc(F)cc2)c1=O] | I-0176 | 2.70 | 423 | 3 |
| 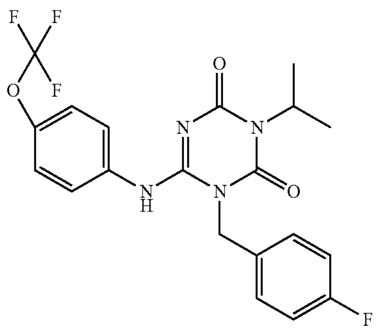 [SMILES: CC(C)n1c(=O)nc(Nc2ccc(OC(F)(F)F)cc2)n(Cc2ccc(F)cc2)c1=O] | I-0177 | 2.70 | 439 | 3 |
| 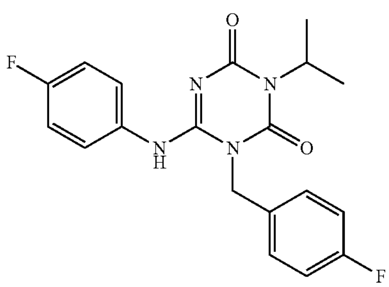 [SMILES: CC(C)n1c(=O)nc(Nc2ccc(F)cc2)n(Cc2ccc(F)cc2)c1=O] | I-0178 | 2.30 | 373 | 3 |
| 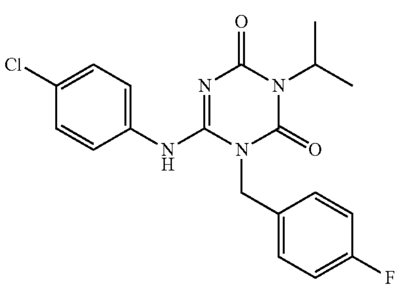 [SMILES: CC(C)n1c(=O)nc(Nc2ccc(Cl)cc2)n(Cc2ccc(F)cc2)c1=O] | I-0179 | 2.50 | 389 | 3 |
| 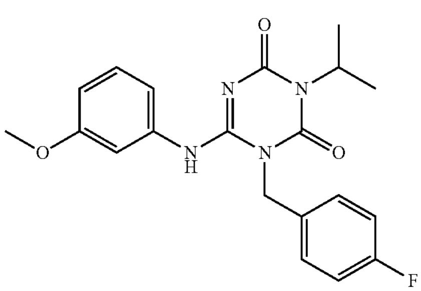 [SMILES: COc1cccc(Nc2nc(=O)n(C(C)C)c(=O)n2Cc2ccc(F)cc2)c1] | I-0180 | 2.40 | 385 | 3 |

TABLE 40

| Structure | Compound No. | Retention Time (min) | [M + H] | Method |
|---|---|---|---|---|
| 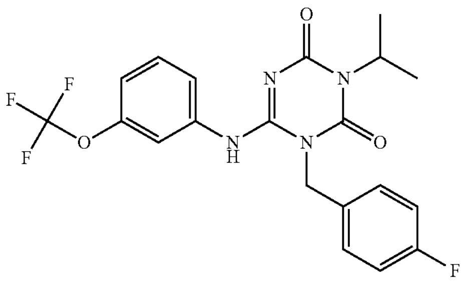 [SMILES: CC(C)n1c(=O)nc(Nc2cccc(OC(F)(F)F)c2)n(Cc2ccc(F)cc2)c1=O] | I-0181 | 2.70 | 439 | 3 |
| 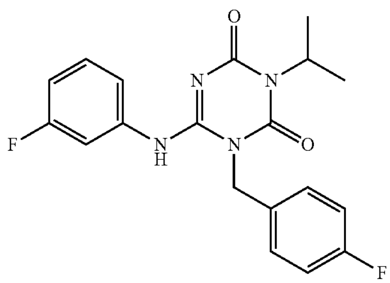 [SMILES: CC(C)n1c(=O)nc(Nc2cccc(F)c2)n(Cc2ccc(F)cc2)c1=O] | I-0182 | 2.40 | 373 | 3 |
| 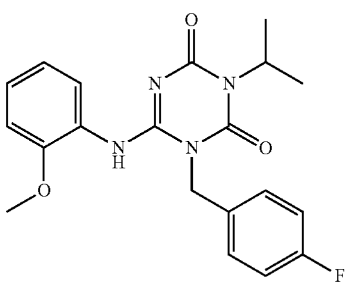 [SMILES: COc1ccccc1Nc1nc(=O)n(C(C)C)c(=O)n1Cc1ccc(F)cc1] | I-0183 | 2.30 | 385 | 3 |
| 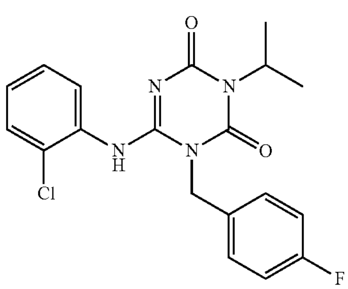 | I-0184 | 2.60 | 389 | 3 |
| 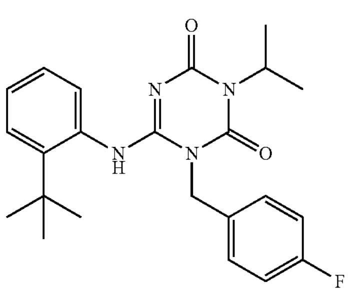 [SMILES: CC(C)n1c(=O)nc(Nc2ccccc2C(C)(C)C)n(Cc2ccc(F)cc2)c1=O] | I-0185 | 2.90 | 411 | 3 |

TABLE 41

| Structure | Compound No. | Retention Time (min) | [M + H] | Method |
|---|---|---|---|---|
| 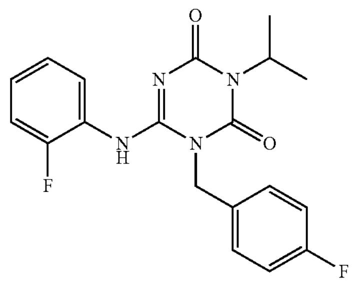 [SMILES: CC(C)n1c(=O)nc(Nc2ccccc2F)n(Cc2ccc(F)cc2)c1=O] | I-0186 | 2.40 | 373 | 3 |
| 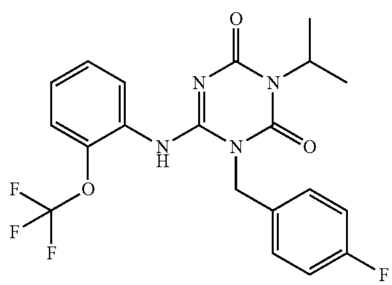 [SMILES: CC(C)n1c(=O)nc(Nc2ccccc2OC(F)(F)F)n(Cc2ccc(F)cc2)c1=O] | I-0187 | 2.70 | 439 | 3 |
| 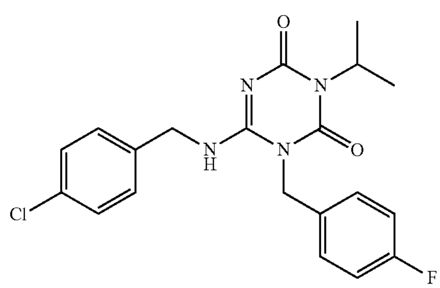 [SMILES: CC(C)n1c(=O)nc(NCc2ccc(Cl)cc2)n(Cc2ccc(F)cc2)c1=O] | I-0188 | 1.20 | 403 | 3 |
| 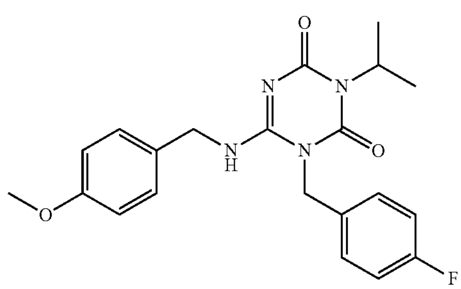 [SMILES: COc1ccc(CNc2nc(=O)n(C(C)C)c(=O)n2Cc2ccc(F)cc2)cc1] | I-0189 | 1.20 | 399 | 3 |
| 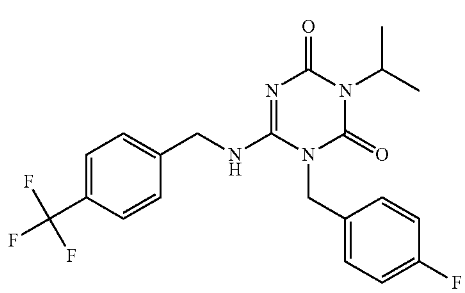 [SMILES: CC(C)n1c(=O)nc(NCc2ccc(C(F)(F)F)cc2)n(Cc2ccc(F)cc2)c1=O] | I-0190 | 2.10 | 437 | 3 |

TABLE 42

| Structure | Compound No. | Retention Time (min) | [M + H] | Method |
|---|---|---|---|---|
| (3-methoxybenzyl) structure | I-0191 | 1.90 | 399 | 3 |
| (2-methoxybenzyl) structure | I-0192 | 1.90 | 399 | 3 |
| (3-chlorobenzyl) structure | I-0193 | 2.20 | 403 | 3 |
| (2-chlorobenzyl) structure | I-0194 | 2.20 | 403 | 3 |
| (2-trifluoromethylbenzyl) structure | I-0195 | 2.30 | 437 | 3 |

TABLE 43

| Structure | Compound No. | Retention Time (min) | [M + H] | Method |
|---|---|---|---|---|
| (structure) | I-0196 | 1.70 | 337 | 3 |
| (structure) | I-0197 | 2.80 | 424 | 3 |
| (structure) | I-0198 | 2.80 | 457 | 3 |
| (structure) | I-0199 | 1.40 | 452 | 3 |
| (structure) | I-0200 | 2.60 | 429 | 3 |

TABLE 44

| Structure | Compound No. | Retention Time (min) | [M + H] | Method |
|---|---|---|---|---|
| 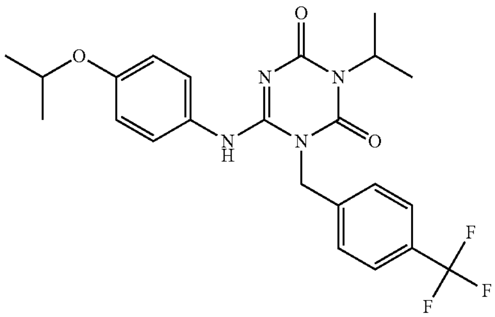 [SMILES: CC(C)Oc1ccc(Nc2nc(=O)n(C(C)C)c(=O)n2Cc2ccc(C(F)(F)F)cc2)cc1] | I-0201 | 2.70 | 463 | 3 |
| 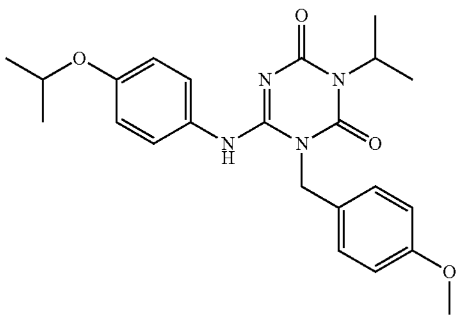 [SMILES: COc1ccc(Cn2c(Nc3ccc(OC(C)C)cc3)nc(=O)n(C(C)C)c2=O)cc1] | I-0202 | 2.40 | 425 | 3 |
| 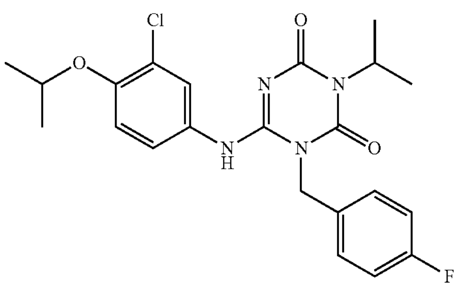 [SMILES: CC(C)Oc1ccc(Nc2nc(=O)n(C(C)C)c(=O)n2Cc2ccc(F)cc2)cc1Cl] | I-0203 | 2.70 | 447 | 3 |
| 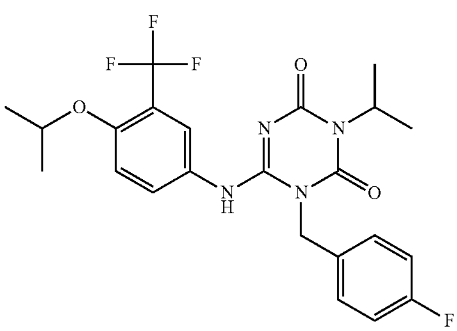 [SMILES: CC(C)Oc1ccc(Nc2nc(=O)n(C(C)C)c(=O)n2Cc2ccc(F)cc2)cc1C(F)(F)F] | I-0204 | 2.80 | 481 | 3 |
| 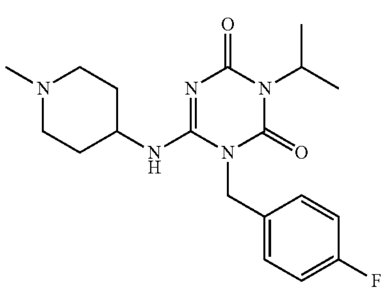 [SMILES: CC(C)n1c(=O)nc(NC2CCN(C)CC2)n(Cc2ccc(F)cc2)c1=O] | I-0205 | 1.20 | 376 | 3 |

TABLE 45

| Structure | Compound No. | Retention Time (min) | [M + H] | Method |
|---|---|---|---|---|
| 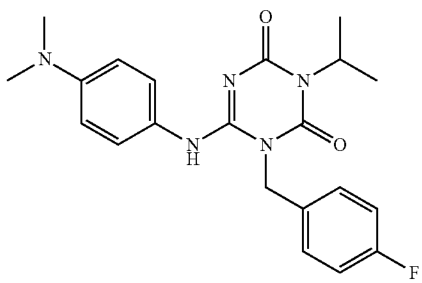 [SMILES: CC(C)n1c(=O)nc(Nc2ccc(N(C)C)cc2)n(Cc2ccc(F)cc2)c1=O] | I-0206 | 1.80 | 398 | 3 |
| 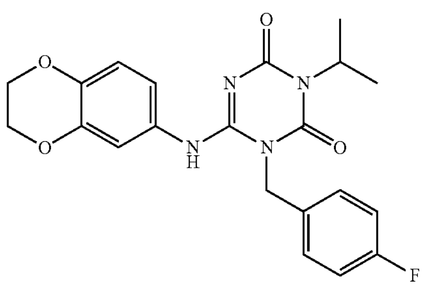 [SMILES: CC(C)n1c(=O)nc(Nc2ccc3c(c2)OCCO3)n(Cc2ccc(F)cc2)c1=O] | I-0207 | 2.20 | 413 | 3 |
| 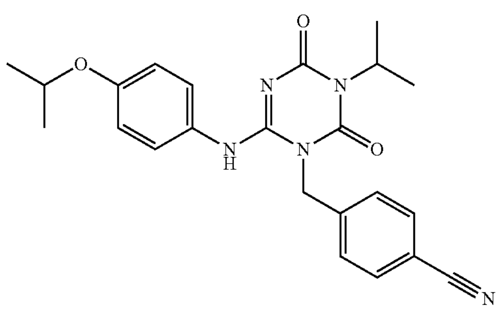 [SMILES: CC(C)Oc1ccc(Nc2nc(=O)n(C(C)C)c(=O)n2Cc2ccc(C#N)cc2)cc1] | I-0208 | 2.30 | 420 | 3 |
| 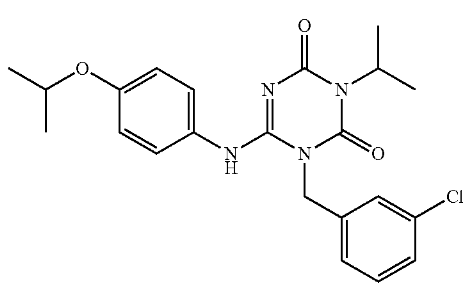 [SMILES: CC(C)Oc1ccc(Nc2nc(=O)n(C(C)C)c(=O)n2Cc2cccc(Cl)c2)cc1] | I-0209 | 2.60 | 429 | 3 |
| 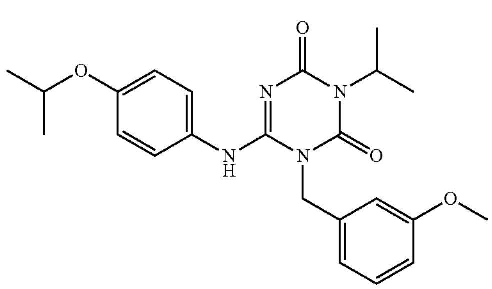 [SMILES: COc1cccc(Cn2c(Nc3ccc(OC(C)C)cc3)nc(=O)n(C(C)C)c2=O)c1] | I-0210 | 2.40 | 425 | 3 |

TABLE 46

| Structure | Compound No. | Retention Time (min) | [M + H] | Method |
|---|---|---|---|---|
| 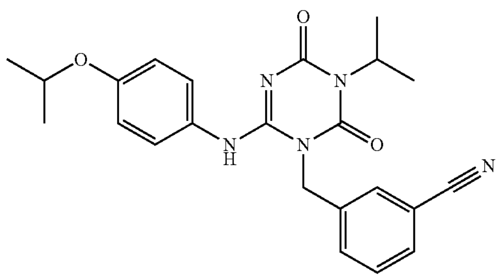 [SMILES: CC(C)Oc1ccc(Nc2nc(=O)n(C(C)C)c(=O)n2Cc2cccc(C#N)c2)cc1] | I-0211 | 2.40 | 420 | 3 |
| 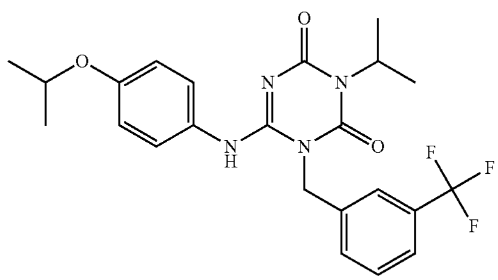 [SMILES: CC(C)Oc1ccc(Nc2nc(=O)n(C(C)C)c(=O)n2Cc2cccc(C(F)(F)F)c2)cc1] | I-0212 | 2.70 | 463 | 3 |
| 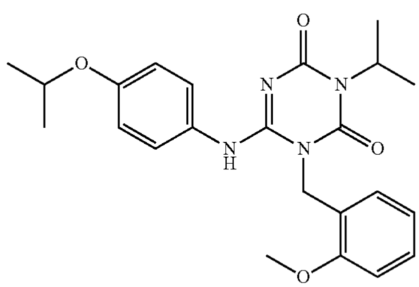 [SMILES: COc1ccccc1Cn1c(Nc2ccc(OC(C)C)cc2)nc(=O)n(C(C)C)c1=O] | I-0213 | 2.40 | 425 | 3 |
| 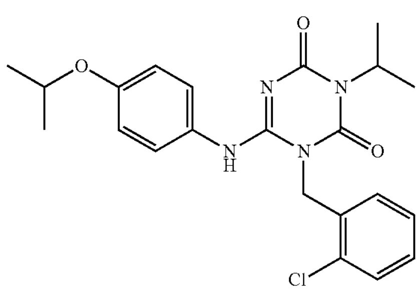 [SMILES: CC(C)Oc1ccc(Nc2nc(=O)n(C(C)C)c(=O)n2Cc2ccccc2Cl)cc1] | I-0214 | 2.60 | 429 | 3 |
| 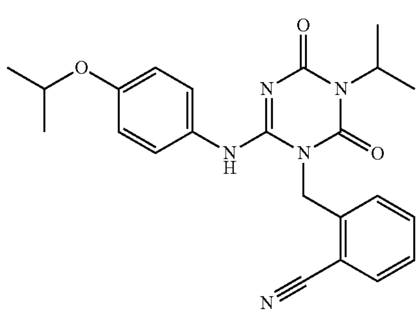 [SMILES: CC(C)Oc1ccc(Nc2nc(=O)n(C(C)C)c(=O)n2Cc2ccccc2C#N)cc1] | I-0215 | 2.40 | 420 | 3 |

TABLE 47

| Structure | Compound No. | Retention Time (min) | [M + H] | Method |
|---|---|---|---|---|
| 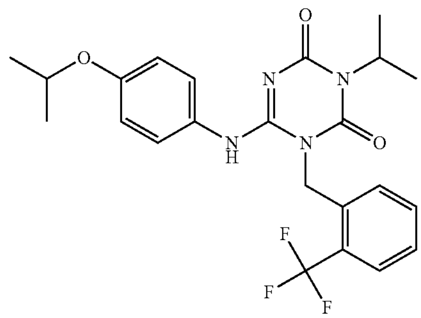 [SMILES: CC(C)Oc1ccc(Nc2nc(=O)n(C(C)C)c(=O)n2Cc2ccccc2C(F)(F)F)cc1] | I-0216 | 2.70 | 463 | 3 |
| 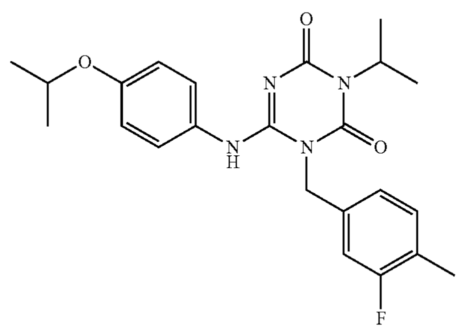 [SMILES: Cc1ccc(Cn2c(Nc3ccc(OC(C)C)cc3)nc(=O)n(C(C)C)c2=O)cc1F] | I-0217 | 2.60 | 427 | 3 |
| 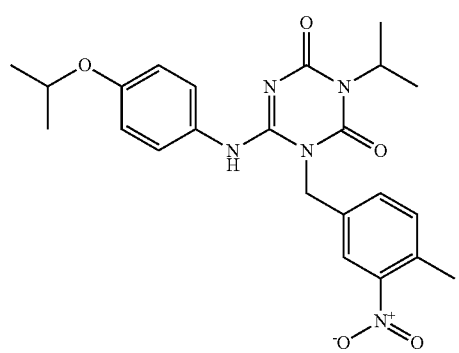 | I-0218 | 2.50 | 454 | 3 |
| 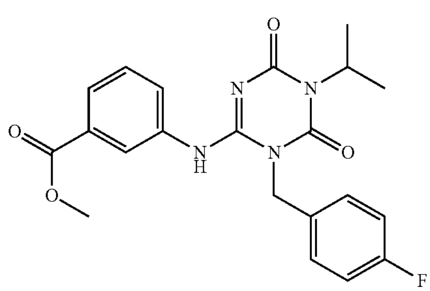 [SMILES: COC(=O)c1cccc(Nc2nc(=O)n(C(C)C)c(=O)n2Cc2ccc(F)cc2)c1] | I-0219 | 2.40 | 413 | 3 |

TABLE 47-continued

| Structure | Compound No. | Retention Time (min) | [M + H] | Method |
|---|---|---|---|---|
| (structure) | I-0220 | 2.90 | 451 | 3 |

TABLE 48

| Structure | Compound No. | Retention Time (min) | [M + H] | Method |
|---|---|---|---|---|
| (structure) | I-0221 | 2.40 | 413 | 3 |
| (structure) | I-0222 | 2.40 | 427 | 3 |
| (structure) | I-0223 | 2.40 | 417 | 3 |

TABLE 48-continued

| Structure | Compound No. | Retention Time (min) | [M + H] | Method |
|---|---|---|---|---|
| 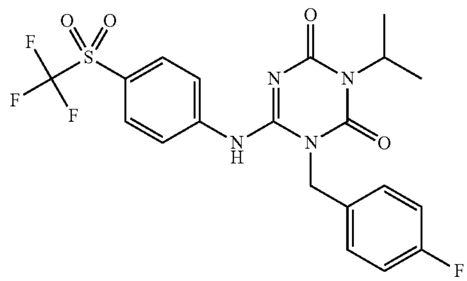 [SMILES: CC(C)n1c(=O)nc(Nc2ccc(S(=O)(=O)C(F)(F)F)cc2)n(Cc2ccc(F)cc2)c1=O] | I-0224 | 2.70 | 487 | 3 |
| 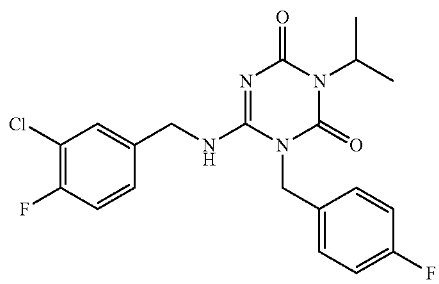 [SMILES: CC(C)n1c(=O)nc(NCc2ccc(F)c(Cl)c2)n(Cc2ccc(F)cc2)c1=O] | I-0225 | 2.30 | 421 | 3 |

TABLE 49

| Structure | Compound No. | Retention Time (min) | [M + H] | Method |
|---|---|---|---|---|
| 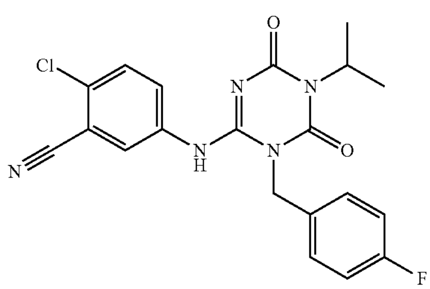 [SMILES: CC(C)n1c(=O)nc(Nc2ccc(Cl)c(C#N)c2)n(Cc2ccc(F)cc2)c1=O] | I-0226 | 2.60 | 414 | 3 |
| 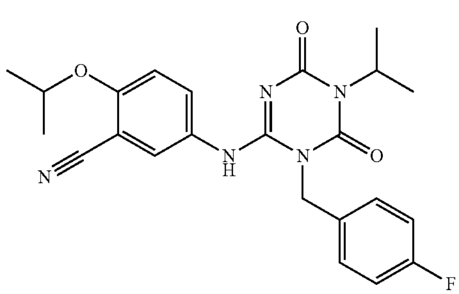 [SMILES: CC(C)Oc1ccc(Nc2nc(=O)n(C(C)C)c(=O)n2Cc2ccc(F)cc2)cc1C#N] | I-0227 | 2.50 | 438 | 3 |

TABLE 49-continued

| Structure | Compound No. | Retention Time (min) | [M + H] | Method |
|---|---|---|---|---|
| (structure) | I-0228 | 2.90 | 463 | 3 |
| (structure) | I-0229 | 2.40 | 437 | 3 |
| (structure) | I-0230 | 2.60 | 475 | 3 |

TABLE 50

| Structure | Compound No. | Retention Time (min) | [M + H] | Method |
|---|---|---|---|---|
| (structure) | I-0231 | 2.40 | 417 | 3 |

TABLE 50-continued

| Structure | Compound No. | Retention Time (min) | [M + H] | Method |
|---|---|---|---|---|
| 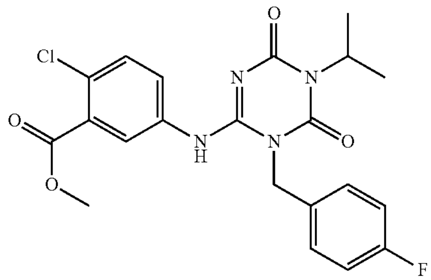 [SMILES: COC(=O)c1cc(Nc2nc(=O)n(C(C)C)c(=O)n2Cc2ccc(F)cc2)ccc1Cl] | I-0232 | 2.40 | 447 | 3 |
| 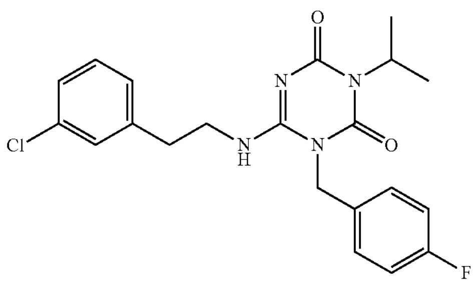 [SMILES: CC(C)n1c(=O)nc(NCCc2cccc(Cl)c2)n(Cc2ccc(F)cc2)c1=O] | I-0233 | 2.40 | 417 | 3 |
| 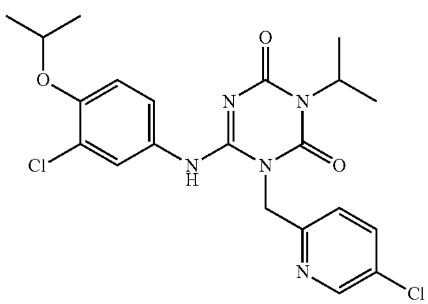 [SMILES: CC(C)Oc1ccc(Nc2nc(=O)n(C(C)C)c(=O)n2Cc2ccc(Cl)cn2)cc1Cl] | I-0234 | 2.60 | 465 | 3 |
| 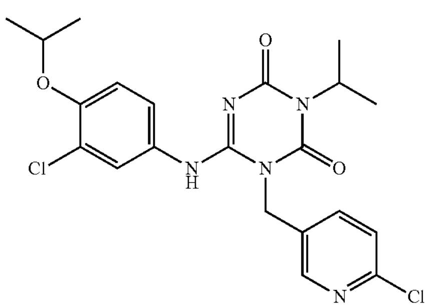 [SMILES: CC(C)Oc1ccc(Nc2nc(=O)n(C(C)C)c(=O)n2Cc2ccc(Cl)nc2)cc1Cl] | I-0235 | 1.20 | 464 | 3 |

TABLE 51

| Structure | Compound No. | Retention Time (min) | [M + H] | Method |
|---|---|---|---|---|
| (structure) | I-0236 | 2.40 | 417 | 3 |
| (structure) | I-0237 | 2.60 | 479 | 3 |
| (structure) | I-0238 | 2.70 | 447 | 3 |
| (structure) | I-0239 | 2.70 | 505 | 3 |
| (structure) | I-0240 | 3.10 | 497 | 3 |

TABLE 52

| Structure | Compound No. | Retention Time (min) | [M + H] | Method |
|---|---|---|---|---|
| 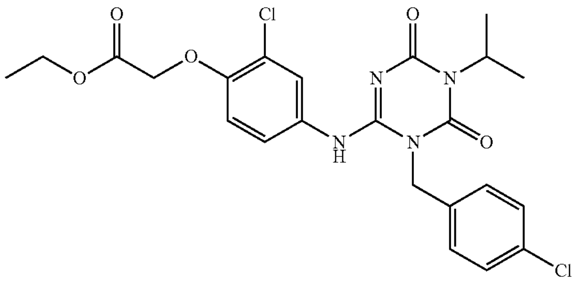 [SMILES: CCOC(=O)COc1ccc(Nc2nc(=O)n(C(C)C)c(=O)n2Cc2ccc(Cl)cc2)cc1Cl] | I-0241 | 2.70 | 507 | 3 |
| 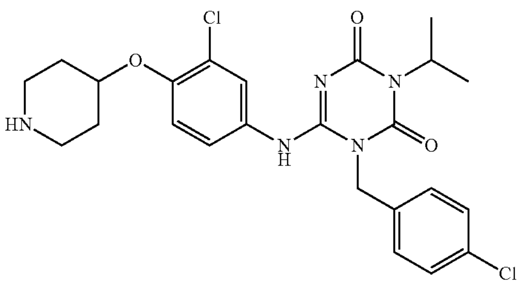 [SMILES: CC(C)n1c(=O)nc(Nc2ccc(OC3CCNCC3)c(Cl)c2)n(Cc2ccc(Cl)cc2)c1=O] | I-0242 | 1.60 | 505 | 3 |
| 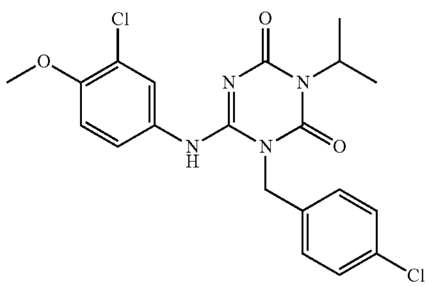 [SMILES: COc1ccc(Nc2nc(=O)n(C(C)C)c(=O)n2Cc2ccc(Cl)cc2)cc1Cl] | I-0243 | 2.60 | 435 | 3 |
| 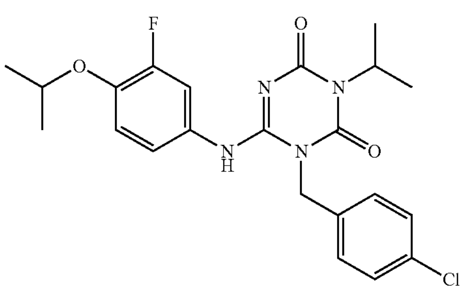 [SMILES: CC(C)Oc1ccc(Nc2nc(=O)n(C(C)C)c(=O)n2Cc2ccc(Cl)cc2)cc1F] | I-0244 | 2.80 | 447 | 3 |
| 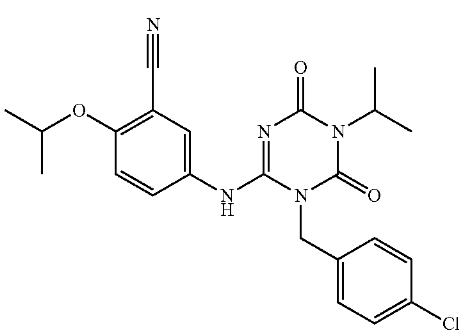 [SMILES: CC(C)Oc1ccc(Nc2nc(=O)n(C(C)C)c(=O)n2Cc2ccc(Cl)cc2)cc1C#N] | I-0245 | 2.70 | 454 | 3 |

TABLE 53

| Structure | Compound No. | Retention Time (min) | [M + H] | Method |
|---|---|---|---|---|
| 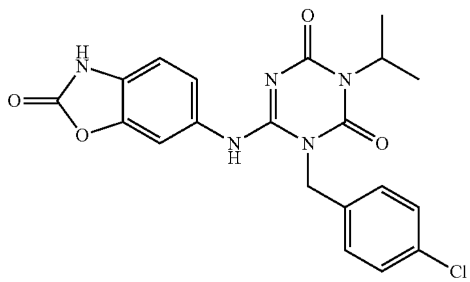 [SMILES: CC(C)n1c(=O)nc(Nc2ccc3[nH]c(=O)oc3c2)n(Cc2ccc(Cl)cc2)c1=O] | I-0246 | 2.20 | 428 | 3 |
| 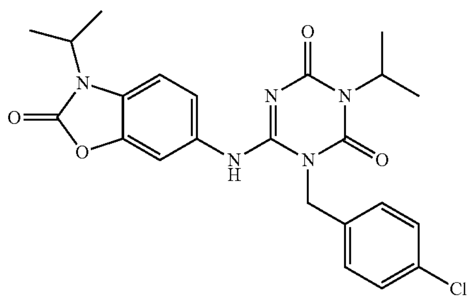 [SMILES: CC(C)n1c(=O)nc(Nc2ccc3c(c2)oc(=O)n3C(C)C)n(Cc2ccc(Cl)cc2)c1=O] | I-0247 | 2.50 | 470 | 3 |
| 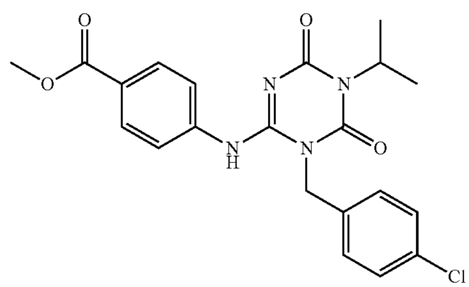 [SMILES: COC(=O)c1ccc(Nc2nc(=O)n(C(C)C)c(=O)n2Cc2ccc(Cl)cc2)cc1] | I-0248 | 2.60 | 429 | 3 |
| 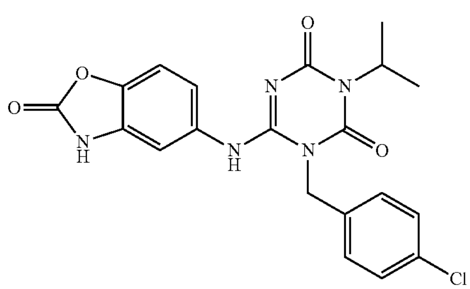 [SMILES: CC(C)n1c(=O)nc(Nc2ccc3oc(=O)[nH]c3c2)n(Cc2ccc(Cl)cc2)c1=O] | I-0249 | 2.20 | 428 | 3 |
| 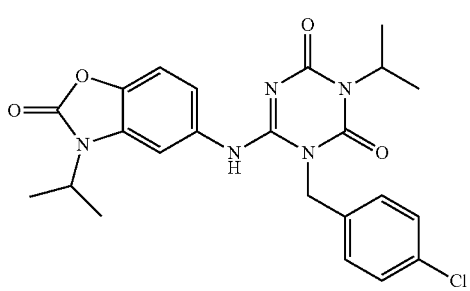 [SMILES: CC(C)n1c(=O)nc(Nc2ccc3oc(=O)n(C(C)C)c3c2)n(Cc2ccc(Cl)cc2)c1=O] | I-0250 | 2.60 | 470 | 3 |

TABLE 54

| Structure | Compound No. | Retention Time (min) | [M + H] | Method |
|---|---|---|---|---|
| 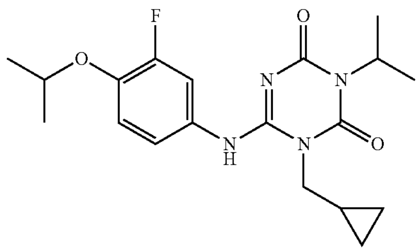 [SMILES: CC(C)Oc1ccc(Nc2nc(=O)n(C(C)C)c(=O)n2CC2CC2)cc1F] | I-0251 | 2.40 | 377 | 3 |
| 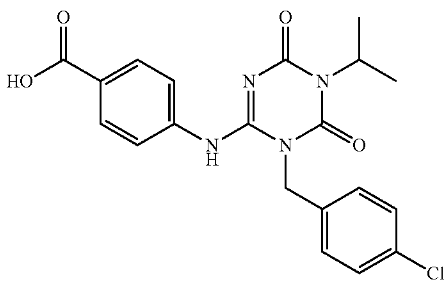 [SMILES: CC(C)n1c(=O)nc(Nc2ccc(C(=O)O)cc2)n(Cc2ccc(Cl)cc2)c1=O] | I-0252 | 2.30 | 415 | 3 |
| 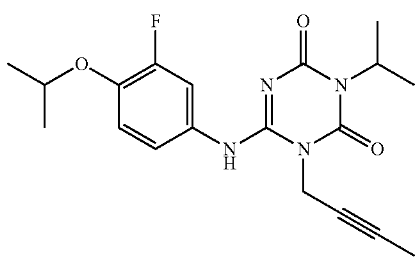 [SMILES: CC#CCn1c(Nc2ccc(OC(C)C)c(F)c2)nc(=O)n(C(C)C)c1=O] | I-0253 | 2.30 | 375 | 3 |
| 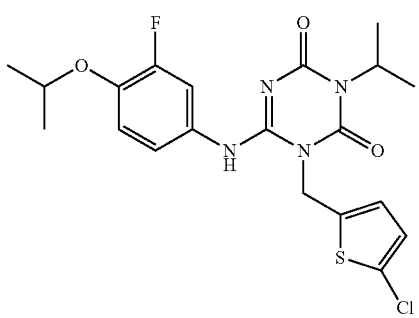 [SMILES: CC(C)Oc1ccc(Nc2nc(=O)n(C(C)C)c(=O)n2Cc2ccc(Cl)s2)cc1F] | I-0254 | 2.90 | 453 | 3 |
| 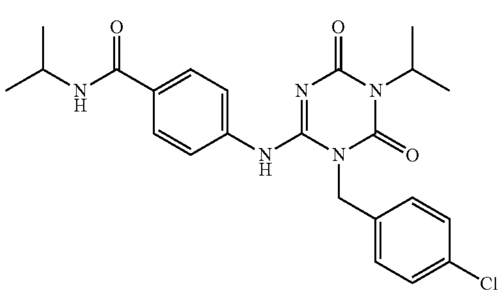 [SMILES: CC(C)NC(=O)c1ccc(Nc2nc(=O)n(C(C)C)c(=O)n2Cc2ccc(Cl)cc2)cc1] | I-0255 | 2.40 | 456 | 3 |

TABLE 55

| Structure | Compound No. | Retention Time (min) | [M + H] | Method |
|---|---|---|---|---|
| 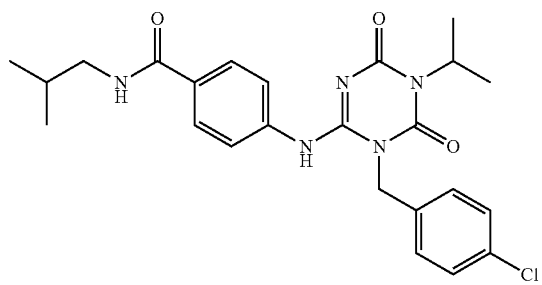 [SMILES: CC(C)CNC(=O)c1ccc(Nc2nc(=O)n(C(C)C)c(=O)n2Cc2ccc(Cl)cc2)cc1] | I-0256 | 2.50 | 470 | 3 |
| 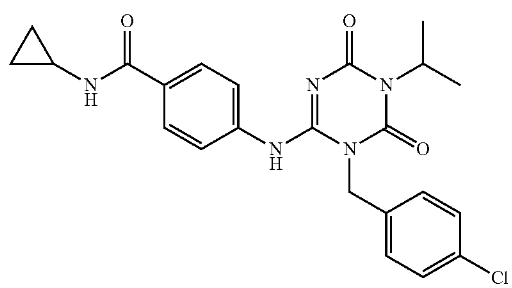 [SMILES: CC(C)n1c(=O)nc(Nc2ccc(C(=O)NC3CC3)cc2)n(Cc2ccc(Cl)cc2)c1=O] | I-0257 | 2.20 | 454 | 3 |
| 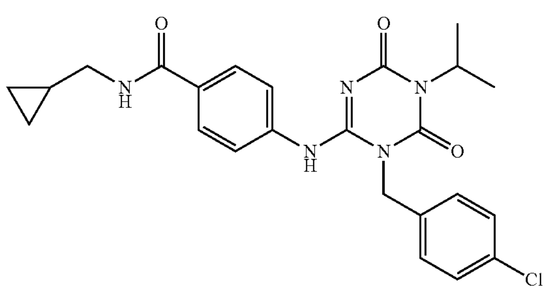 [SMILES: CC(C)n1c(=O)nc(Nc2ccc(C(=O)NCC3CC3)cc2)n(Cc2ccc(Cl)cc2)c1=O] | I-0258 | 2.40 | 468 | 3 |
| 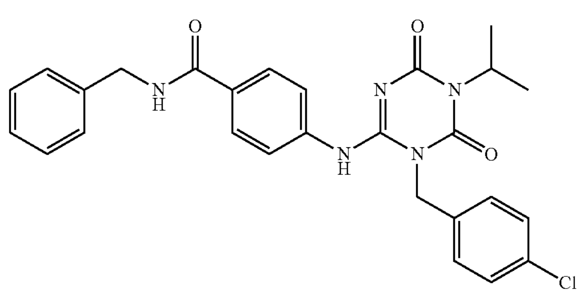 [SMILES: CC(C)n1c(=O)nc(Nc2ccc(C(=O)NCc3ccccc3)cc2)n(Cc2ccc(Cl)cc2)c1=O] | I-0259 | 2.50 | 504 | 3 |
| 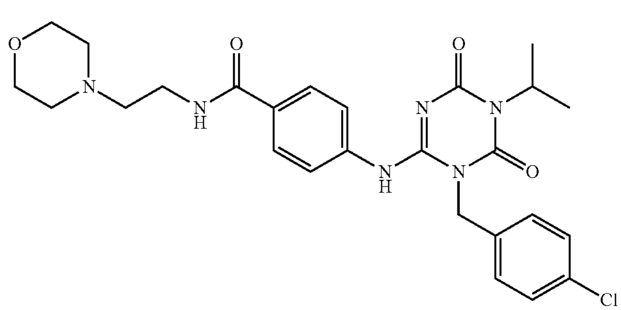 [SMILES: CC(C)n1c(=O)nc(Nc2ccc(C(=O)NCCN3CCOCC3)cc2)n(Cc2ccc(Cl)cc2)c1=O] | I-0260 | 1.50 | 528 | 3 |

TABLE 56

| Structure | Compound No. | Retention Time (min) | [M + H] | Method |
|---|---|---|---|---|
| (structure) | I-0261 | 2.60 | 482 | 3 |
| (structure) | I-0262 | 2.20 | 484 | 3 |
| (structure) | I-0263 | 2.10 | 428 | 3 |
| (structure) | I-0264 | 2.50 | 482 | 3 |
| (structure) | I-0265 | 2.30 | 442 | 3 |

TABLE 57

| Structure | Compound No. | Retention Time (min) | [M + H] | Method |
|---|---|---|---|---|
| (structure) | I-0266 | 2.60 | 490 | 3 |
| (structure) | I-0267 | 2.00 | 458 | 3 |
| (structure) | I-0268 | 2.60 | 484 | 3 |
| (structure) | I-0269 | 2.03 | 405 | 1 |
| (structure) | I-0270 | 2.42 | 477 | 1 |

TABLE 58

| Structure | Compound No. | Retention Time (min) | [M + H] | Method |
|---|---|---|---|---|
| 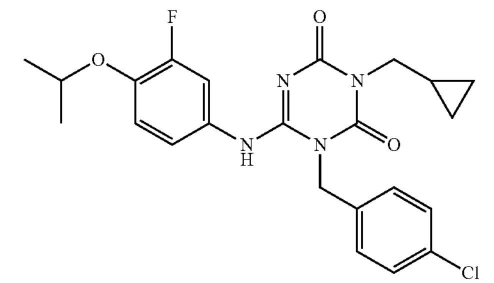 [SMILES: CC(C)Oc1ccc(Nc2nc(=O)n(CC3CC3)c(=O)n2Cc2ccc(Cl)cc2)cc1F] | I-0271 | 2.49 | 459 | 1 |
| 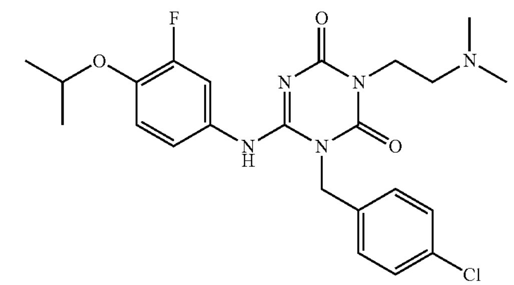 [SMILES: CC(C)Oc1ccc(Nc2nc(=O)n(CCN(C)C)c(=O)n2Cc2ccc(Cl)cc2)cc1F] | I-0272 | 1.44 | 476 | 1 |
| 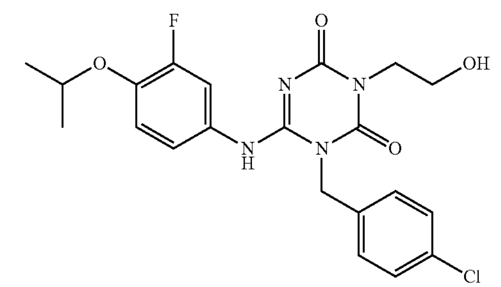 [SMILES: CC(C)Oc1ccc(Nc2nc(=O)n(CCO)c(=O)n2Cc2ccc(Cl)cc2)cc1F] | I-0273 | 1.96 | 449 | 1 |
| 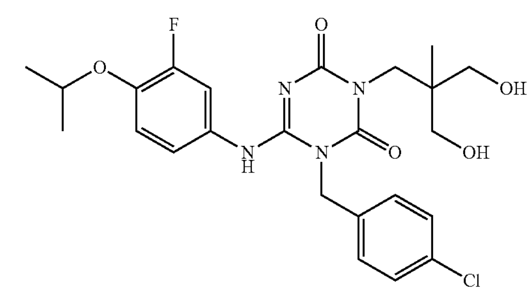 [SMILES: CC(C)Oc1ccc(Nc2nc(=O)n(CC(C)(CO)CO)c(=O)n2Cc2ccc(Cl)cc2)cc1F] | I-0274 | 1.98 | 507 | 1 |
| 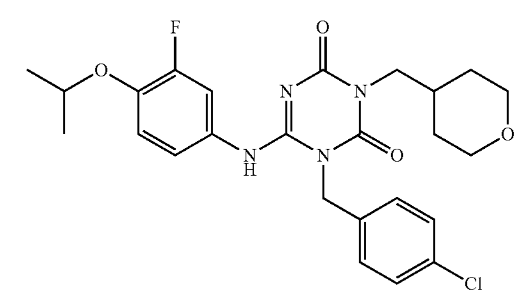 [SMILES: CC(C)Oc1ccc(Nc2nc(=O)n(CC3CCOCC3)c(=O)n2Cc2ccc(Cl)cc2)cc1F] | I-0275 | 2.27 | 503 | 1 |

TABLE 59

| Structure | Compound No. | Retention Time (min) | [M + H] | Method |
|---|---|---|---|---|
| 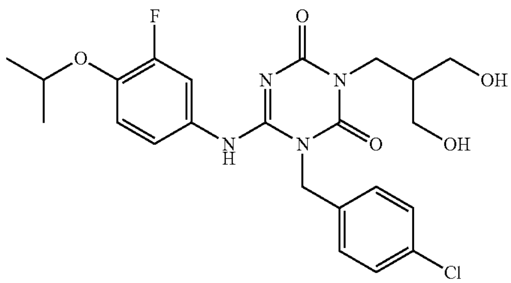 [SMILES: CC(C)Oc1ccc(Nc2nc(=O)n(CC(CO)CO)c(=O)n2Cc2ccc(Cl)cc2)cc1F] | I-0276 | 1.85 | 493 | 1 |
| 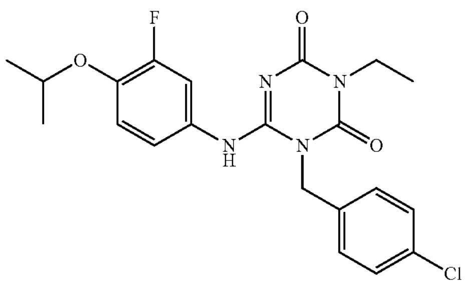 [SMILES: CCn1c(=O)nc(Nc2ccc(OC(C)C)c(F)c2)n(Cc2ccc(Cl)cc2)c1=O] | I-0277 | 2.34 | 433 | 1 |
| 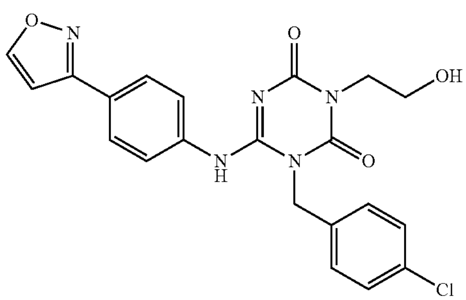 [SMILES: O=c1nc(Nc2ccc(-c3ccon3)cc2)n(Cc2ccc(Cl)cc2)c(=O)n1CCO] | I-0278 | 1.70 | 440 | 1 |
| 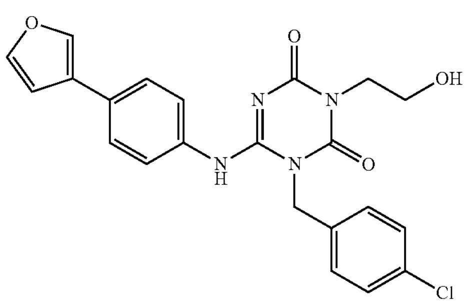 [SMILES: O=c1nc(Nc2ccc(-c3ccoc3)cc2)n(Cc2ccc(Cl)cc2)c(=O)n1CCO] | I-0279 | 1.90 | 439 | 1 |
| 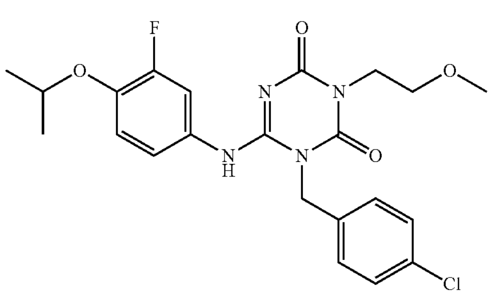 [SMILES: COCCn1c(=O)nc(Nc2ccc(OC(C)C)c(F)c2)n(Cc2ccc(Cl)cc2)c1=O] | I-0280 | 2.21 | 463 | 1 |

TABLE 60

| Structure | Compound No. | Retention Time (min) | [M + H] | Method |
|---|---|---|---|---|
| 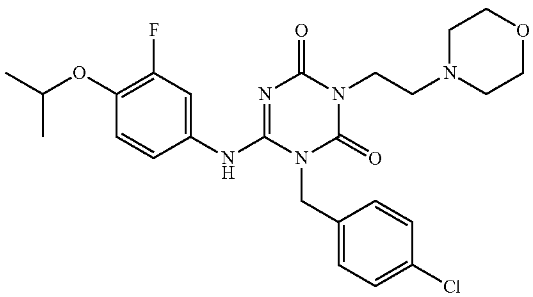 [SMILES: CC(C)Oc1ccc(Nc2nc(=O)n(CCN3CCOCC3)c(=O)n2Cc2ccc(Cl)cc2)cc1F] | I-0281 | 1.47 | 518 | 1 |
| 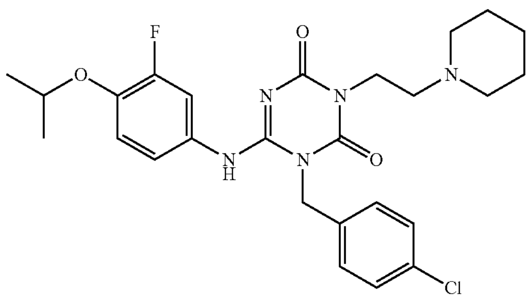 [SMILES: CC(C)Oc1ccc(Nc2nc(=O)n(CCN3CCCCC3)c(=O)n2Cc2ccc(Cl)cc2)cc1F] | I-0282 | 1.50 | 516 | 1 |
| 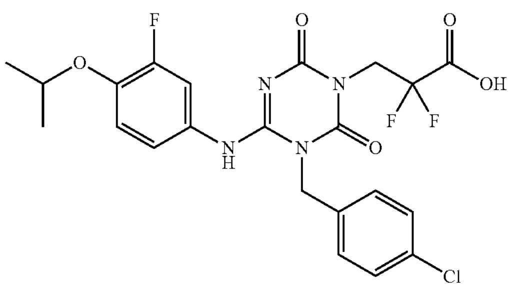 | I-0283 | 1.82 | 513 | 1 |
| 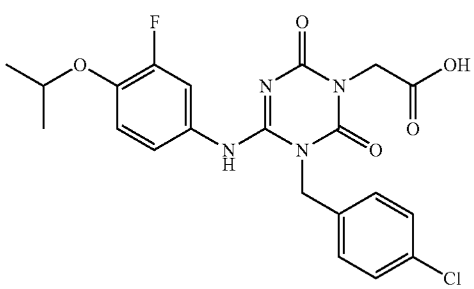 [SMILES: CC(C)Oc1ccc(Nc2nc(=O)n(CC(=O)O)c(=O)n2Cc2ccc(Cl)cc2)cc1F] | I-0284 | 1.96 | 463 | 1 |
| 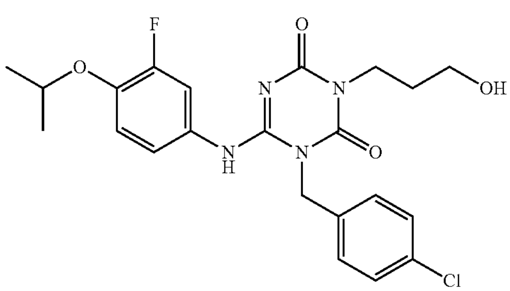 | I-0285 | 2.00 | 463 | 1 |

TABLE 61

| Structure | Compound No. | Retention Time (min) | [M + H] | Method |
|---|---|---|---|---|
| (structure) | I-0286 | 1.80 | 479 | 1 |
| (structure) | I-0287 | 1.30 | 509 | 1 |
| (structure) | I-0288 | 2.15 | 444 | 1 |
| (structure) | I-0289 | 2.00 | 477 | 1 |
| (structure) | I-0290 | 1.40 | 448 | 1 |

TABLE 62

| Structure | Compound No. | Retention Time (min) | [M + H] | Method |
|---|---|---|---|---|
| 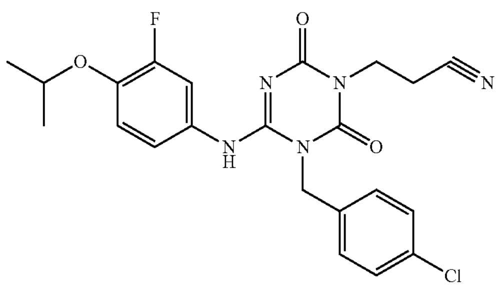 [SMILES: CC(C)Oc1ccc(Nc2nc(=O)n(CCC#N)c(=O)n2Cc2ccc(Cl)cc2)cc1F] | I-0291 | 2.15 | 458 | 1 |
| 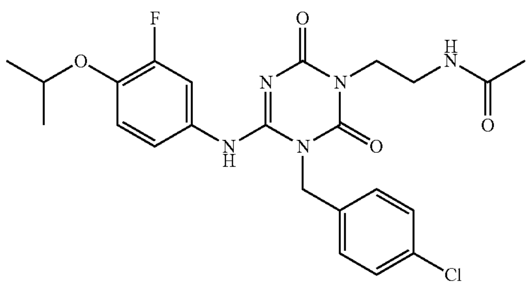 [SMILES: CC(=O)NCCn1c(=O)nc(Nc2ccc(OC(C)C)c(F)c2)n(Cc2ccc(Cl)cc2)c1=O] | I-0292 | 1.90 | 489 | 1 |
| 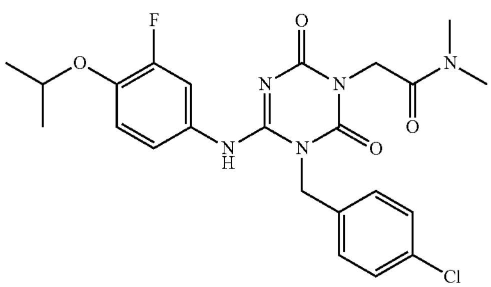 [SMILES: CC(C)Oc1ccc(Nc2nc(=O)n(CC(=O)N(C)C)c(=O)n2Cc2ccc(Cl)cc2)cc1F] | I-0293 | 2.00 | 490 | 1 |
| 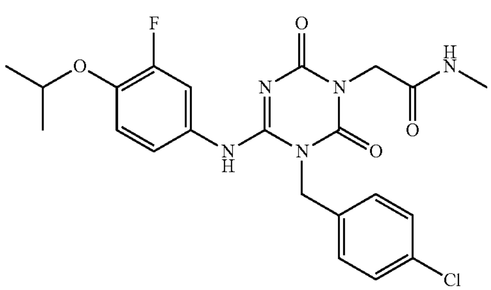 [SMILES: CNC(=O)Cn1c(=O)nc(Nc2ccc(OC(C)C)c(F)c2)n(Cc2ccc(Cl)cc2)c1=O] | I-0294 | 1.91 | 476 | 1 |
| 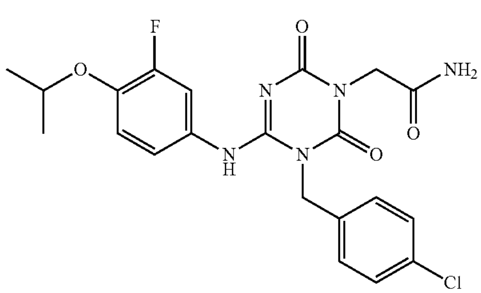 [SMILES: CC(C)Oc1ccc(Nc2nc(=O)n(CC(N)=O)c(=O)n2Cc2ccc(Cl)cc2)cc1F] | I-0295 | 1.85 | 462 | 1 |

TABLE 63

| Structure | Compound No. | Retention Time (min) | [M + H] | Method |
|---|---|---|---|---|
| 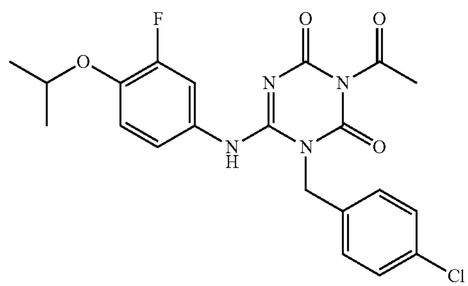 [SMILES: CC(=O)n1c(=O)nc(Nc2ccc(OC(C)C)c(F)c2)n(Cc2ccc(Cl)cc2)c1=O] | I-0296 | 2.18 | 447 | 1 |
| 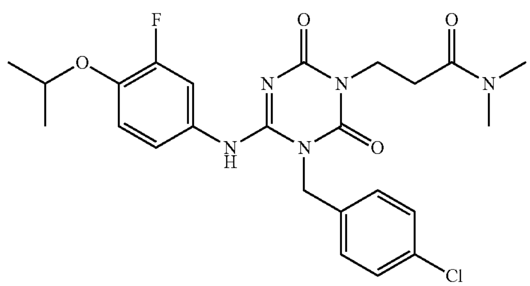 [SMILES: CC(C)Oc1ccc(Nc2nc(=O)n(CCC(=O)N(C)C)c(=O)n2Cc2ccc(Cl)cc2)cc1F] | I-0297 | 2.04 | 504 | 1 |
| 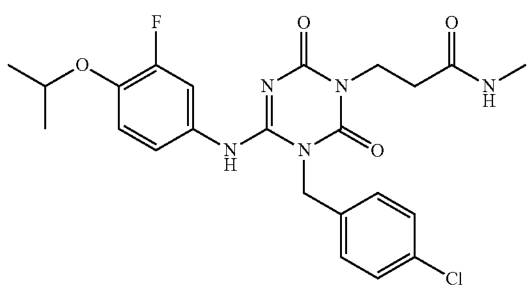 [SMILES: CNC(=O)CCn1c(=O)nc(Nc2ccc(OC(C)C)c(F)c2)n(Cc2ccc(Cl)cc2)c1=O] | I-0298 | 1.90 | 490 | 1 |
| 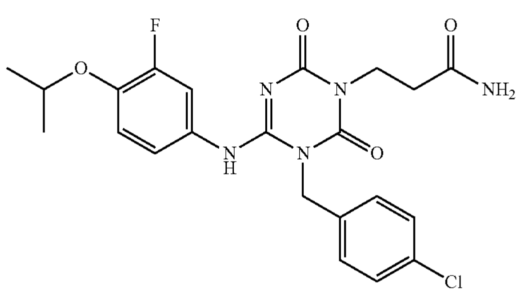 [SMILES: CC(C)Oc1ccc(Nc2nc(=O)n(CCC(N)=O)c(=O)n2Cc2ccc(Cl)cc2)cc1F] | I-0299 | 1.86 | 476 | 1 |
| 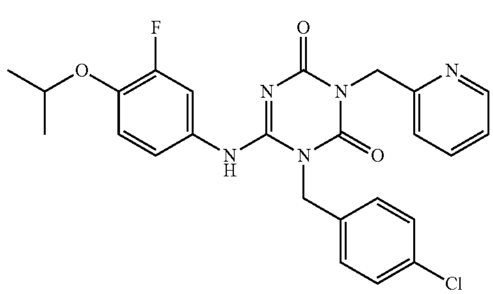 [SMILES: CC(C)Oc1ccc(Nc2nc(=O)n(Cc3ccccn3)c(=O)n2Cc2ccc(Cl)cc2)cc1F] | I-0300 | 2.06 | 496 | 1 |

TABLE 64

| Structure | Compound No. | Retention Time (min) | [M + H] | Method |
|---|---|---|---|---|
| 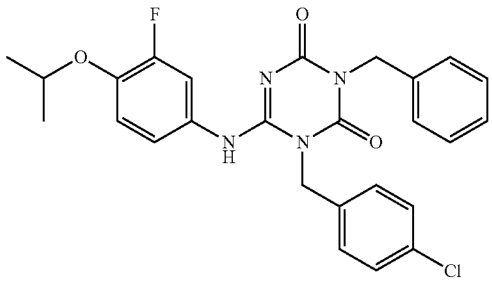 [SMILES: CC(C)Oc1ccc(Nc2nc(=O)n(Cc3ccccc3)c(=O)n2Cc2ccc(Cl)cc2)cc1F] | I-0301 | 2.53 | 495 | 1 |
| 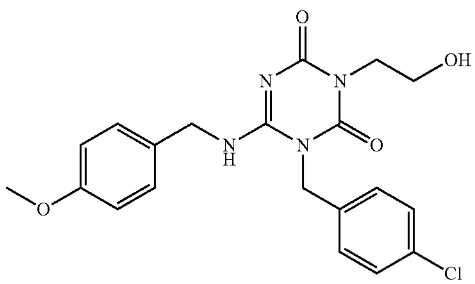 [SMILES: COc1ccc(CNc2nc(=O)n(CCO)c(=O)n2Cc2ccc(Cl)cc2)cc1] | I-0302 | 1.50 | 417 | 1 |
| 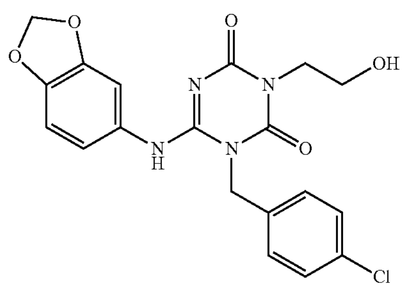 [SMILES: O=c1nc(Nc2ccc3c(c2)OCO3)n(Cc2ccc(Cl)cc2)c(=O)n1CCO] | I-0303 | 1.60 | 417 | 1 |
| 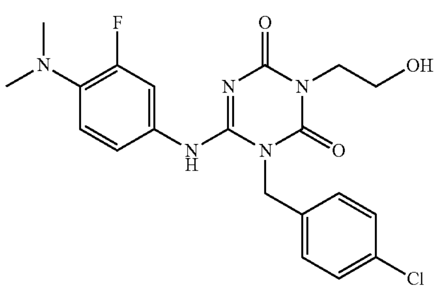 [SMILES: CN(C)c1ccc(Nc2nc(=O)n(CCO)c(=O)n2Cc2ccc(Cl)cc2)cc1F] | I-0304 | 1.50 | 434 | 1 |
| 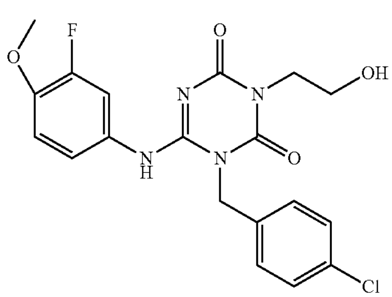 [SMILES: COc1ccc(Nc2nc(=O)n(CCO)c(=O)n2Cc2ccc(Cl)cc2)cc1F] | I-0305 | 1.69 | 421 | 1 |

TABLE 65

| Structure | Compound No. | Retention Time (min) | [M + H] | Method |
|---|---|---|---|---|
| (structure) | I-0306 | 1.11 | 444 | 1 |
| (structure) | I-0307 | 1.72 | 417 | 1 |
| (structure) | I-0308 | 1.80 | 391 | 1 |
| (structure) | I-0309 | 2.09 | 457 | 1 |
| (structure) | I-0310 | 2.21 | 455 | 1 |

TABLE 66

| Structure | Compound No. | Retention Time (min) | [M + H] | Method |
|---|---|---|---|---|
| 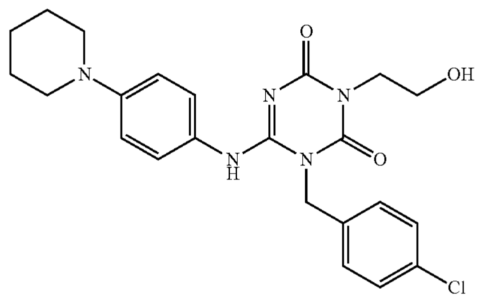 [SMILES: O=c1nc(Nc2ccc(N3CCCCC3)cc2)n(Cc2ccc(Cl)cc2)c(=O)n1CCO] | I-0311 | 1.14 | 456 | 1 |
| 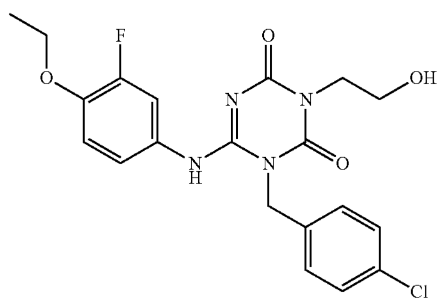 [SMILES: CCOc1ccc(Nc2nc(=O)n(CCO)c(=O)n2Cc2ccc(Cl)cc2)cc1F] | I-0312 | 1.83 | 435 | 1 |
| 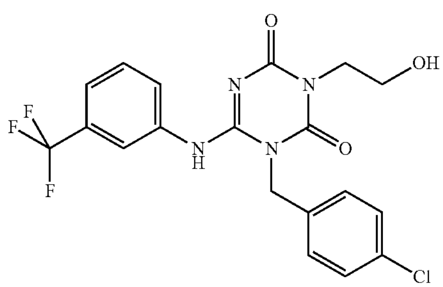 [SMILES: O=c1nc(Nc2cccc(C(F)(F)F)c2)n(Cc2ccc(Cl)cc2)c(=O)n1CCO] | I-0313 | 2.00 | 441 | 2 |
| 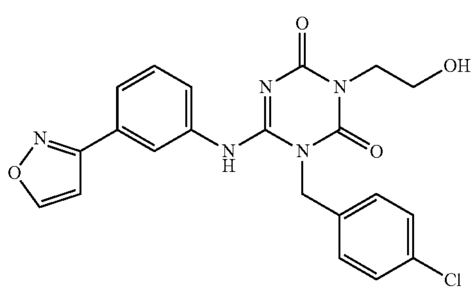 [SMILES: O=c1nc(Nc2cccc(-c3ccon3)c2)n(Cc2ccc(Cl)cc2)c(=O)n1CCO] | I-0314 | 1.70 | 440 | 2 |
| 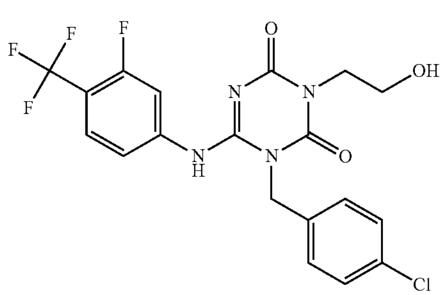 [SMILES: O=c1nc(Nc2ccc(C(F)(F)F)c(F)c2)n(Cc2ccc(Cl)cc2)c(=O)n1CCO] | I-0315 | 2.09 | 459 | 2 |

TABLE 67

| Structure | Compound No. | Retention Time (min) | [M + H] | Method |
|---|---|---|---|---|
| 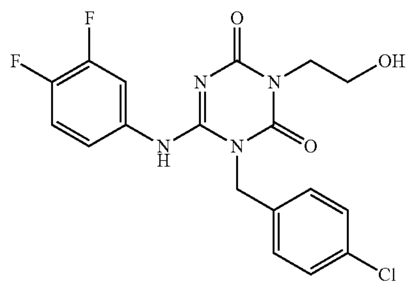 [SMILES: O=c1nc(Nc2ccc(F)c(F)c2)n(Cc2ccc(Cl)cc2)c(=O)n1CCO] | I-0316 | 1.84 | 409 | 2 |
| 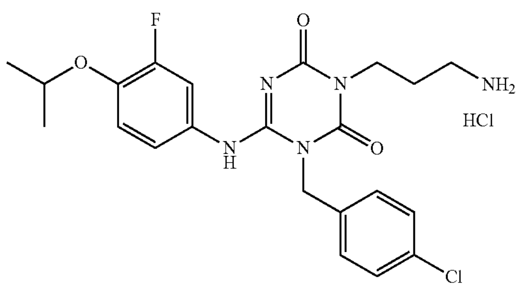 [SMILES: CC(C)Oc1ccc(Nc2nc(=O)n(CCCN)c(=O)n2Cc2ccc(Cl)cc2)cc1F ; Cl] | I-0317 | 1.40 | 462 | 2 |
| 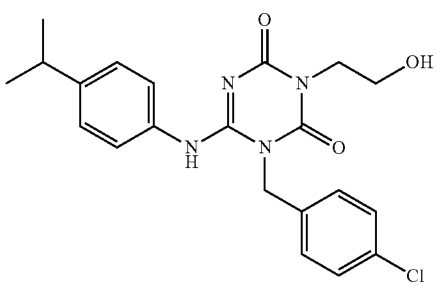 [SMILES: CC(C)c1ccc(Nc2nc(=O)n(CCO)c(=O)n2Cc2ccc(Cl)cc2)cc1] | I-0318 | 2.01 | 415 | 2 |
| 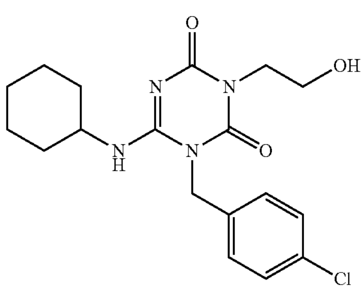 [SMILES: O=c1nc(NC2CCCCC2)n(Cc2ccc(Cl)cc2)c(=O)n1CCO] | I-0319 | 1.68 | 379 | 2 |
| 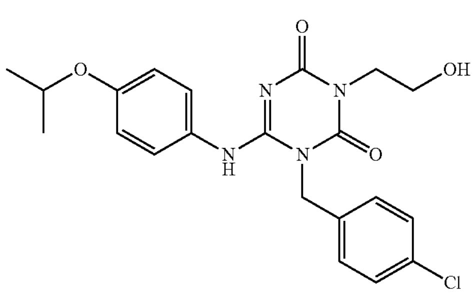 | I-0320 | 1.83 | 431 | 2 |

TABLE 68

| Structure | Compound No. | Retention Time (min) | [M + H] | Method |
|---|---|---|---|---|
| 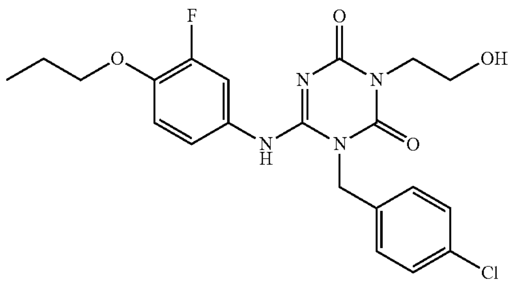 [SMILES: CCCOc1ccc(Nc2nc(=O)n(CCO)c(=O)n2Cc2ccc(Cl)cc2)cc1F] | I-0321 | 1.99 | 449 | 2 |
| 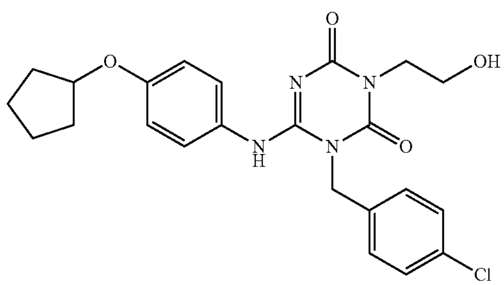 [SMILES: O=c1nc(Nc2ccc(OC3CCCC3)cc2)n(Cc2ccc(Cl)cc2)c(=O)n1CCO] | I-0322 | 2.03 | 457 | 2 |
| 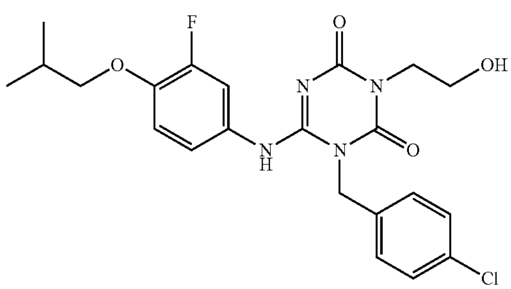 [SMILES: CC(C)COc1ccc(Nc2nc(=O)n(CCO)c(=O)n2Cc2ccc(Cl)cc2)cc1F] | I-0323 | 2.16 | 463 | 2 |
| 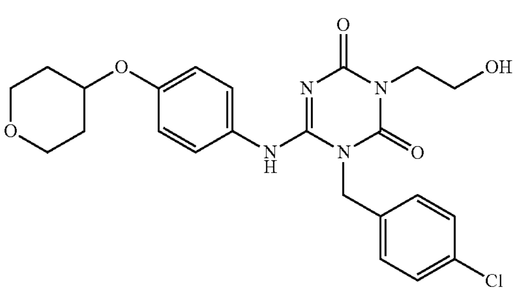 [SMILES: O=c1nc(Nc2ccc(OC3CCOCC3)cc2)n(Cc2ccc(Cl)cc2)c(=O)n1CCO] | I-0324 | 1.61 | 473 | 2 |
| 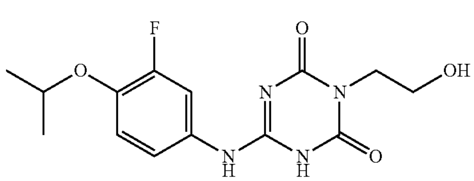 [SMILES: CC(C)Oc1ccc(Nc2nc(=O)n(CCO)c(=O)[nH]2)cc1F] | I-0325 | 1.10 | 325 | 2 |

TABLE 69

| Structure | Compound No. | Retention Time (min) | [M + H] | Method |
|---|---|---|---|---|
| 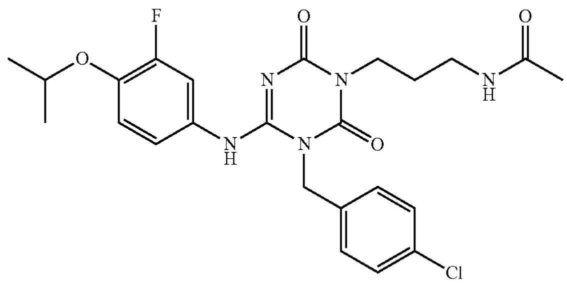 [SMILES: CC(=O)NCCCn1c(=O)nc(Nc2ccc(OC(C)C)c(F)c2)n(Cc2ccc(Cl)cc2)c1=O] | I-0326 | 1.93 | 504 | 2 |
| 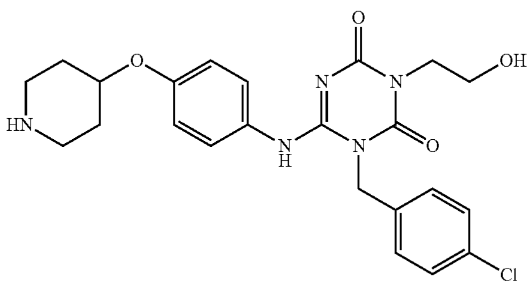 [SMILES: O=c1nc(Nc2ccc(OC3CCNCC3)cc2)n(Cc2ccc(Cl)cc2)c(=O)n1CCO] | I-0327 | 1.03 | 472 | 2 |
| 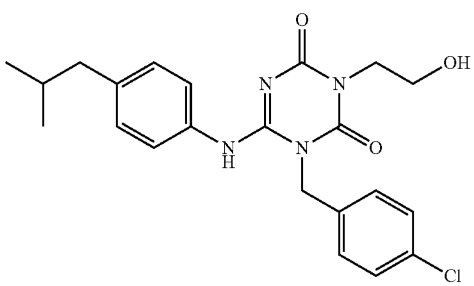 [SMILES: CC(C)Cc1ccc(Nc2nc(=O)n(CCO)c(=O)n2Cc2ccc(Cl)cc2)cc1] | I-0328 | 2.15 | 429 | 2 |
| 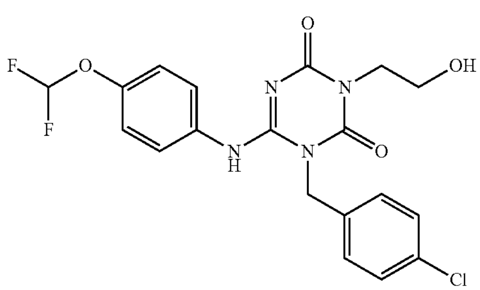 [SMILES: O=c1nc(Nc2ccc(OC(F)F)cc2)n(Cc2ccc(Cl)cc2)c(=O)n1CCO] | I-0329 | 1.80 | 439 | 2 |
| 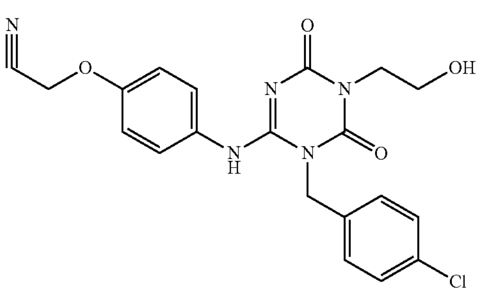 [SMILES: N#CCOc1ccc(Nc2nc(=O)n(CCO)c(=O)n2Cc2ccc(Cl)cc2)cc1] | I-0330 | 1.56 | 428 | 2 |

TABLE 70

| Structure | Compound No. | Retention Time (min) | [M + H] | Method |
|---|---|---|---|---|
| (structure with F, isopropoxy, 4-Cl-benzyl, gem-dimethyl-CH2NH2·HCl) | I-0331 | 1.49 | 490 | 2 |
| (structure with F, isopropoxy, 4-Cl-benzyl, gem-dimethyl-CH2OH) | I-0332 | 2.26 | 491 | 2 |
| (structure with F, isopropoxy, 4-F-benzyl, CH2CH2OH) | I-0333 | 1.80 | 433 | 2 |
| (structure with phenoxy, 4-Cl-benzyl, CH2CH2OH) | I-0334 | 2.35 | 465 | 3 |
| (structure with F, isopropoxy, 4-Cl-benzyl, cyclopropyl-CH2OH) | I-0335 | 2.19 | 489 | 2 |

TABLE 71

| Structure | Compound No. | Retention Time (min) | [M + H] | Method |
|---|---|---|---|---|
| 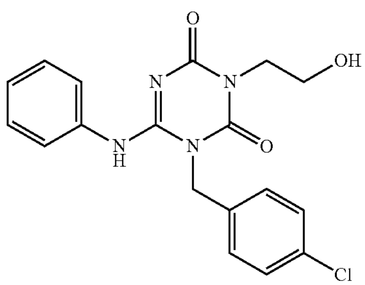 [SMILES: O=c1nc(Nc2ccccc2)n(Cc2ccc(Cl)cc2)c(=O)n1CCO] | I-0336 | 1.61 | 373 | 2 |
| 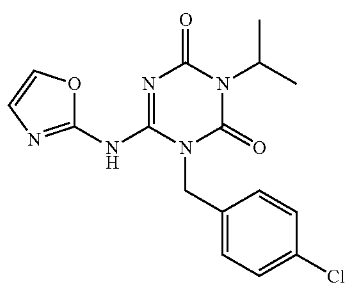 [SMILES: CC(C)n1c(=O)nc(Nc2ncco2)n(Cc2ccc(Cl)cc2)c1=O] | I-0337 | 2.39 | 362 | 2 |
| 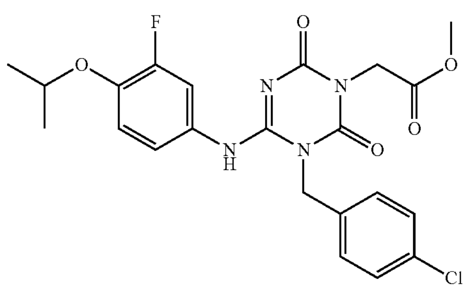 [SMILES: COC(=O)Cn1c(=O)nc(Nc2ccc(OC(C)C)c(F)c2)n(Cc2ccc(Cl)cc2)c1=O] | I-0338 | 2.45 | 477 | 3 |
| 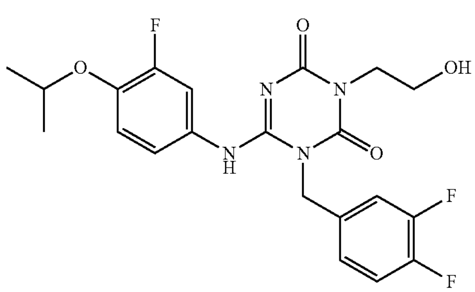 [SMILES: CC(C)Oc1ccc(Nc2nc(=O)n(CCO)c(=O)n2Cc2ccc(F)c(F)c2)cc1F] | I-0339 | 1.88 | 451 | 2 |
| 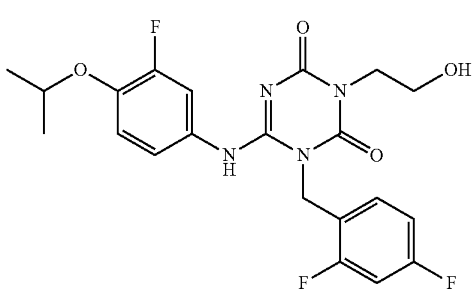 [SMILES: CC(C)Oc1ccc(Nc2nc(=O)n(CCO)c(=O)n2Cc2ccc(F)cc2F)cc1F] | I-0340 | 1.84 | 451 | 2 |

TABLE 72

| Structure | Compound No. | Retention Time (min) | [M + H] | Method |
|---|---|---|---|---|
| 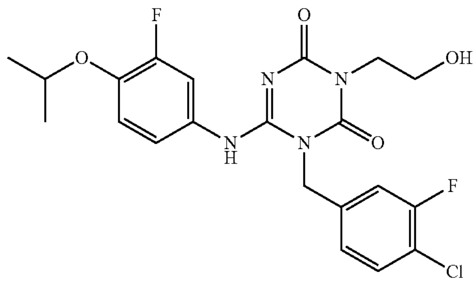 [SMILES: CC(C)Oc1ccc(Nc2nc(=O)n(CCO)c(=O)n2Cc2ccc(Cl)c(F)c2)cc1F] | I-0341 | 2.01 | 467 | 2 |
| 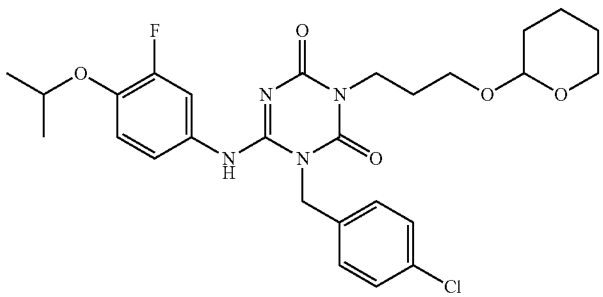 [SMILES: CC(C)Oc1ccc(Nc2nc(=O)n(CCCOC3CCCCO3)c(=O)n2Cc2ccc(Cl)cc2)cc1F] | I-0342 | 2.81 | 548 | 3 |
| 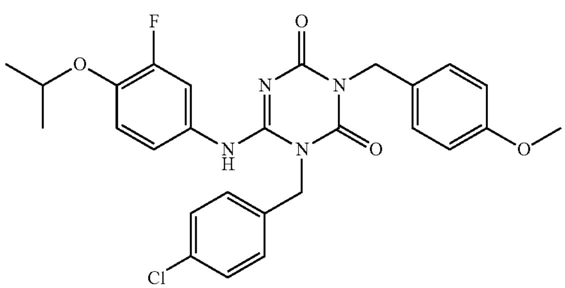 [SMILES: COc1ccc(Cn2c(=O)nc(Nc3ccc(OC(C)C)c(F)c3)n(Cc3ccc(Cl)cc3)c2=O)cc1] | I-0343 | 2.50 | 525 | 2 |
| 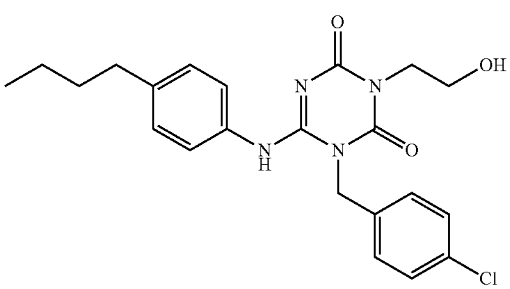 | I-0344 | 2.48 | 429 | 3 |
| 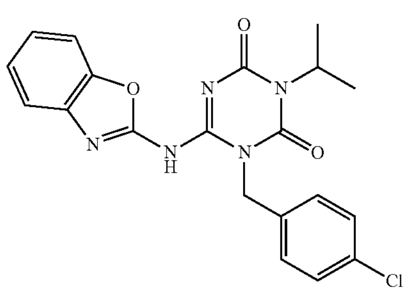 [SMILES: CC(C)n1c(=O)nc(Nc2nc3ccccc3o2)n(Cc2ccc(Cl)cc2)c1=O] | I-0345 | 2.74 | 412 | 2 |

TABLE 73

| Structure | Compound No. | Retention Time (min) | [M + H] | Method |
|---|---|---|---|---|
| 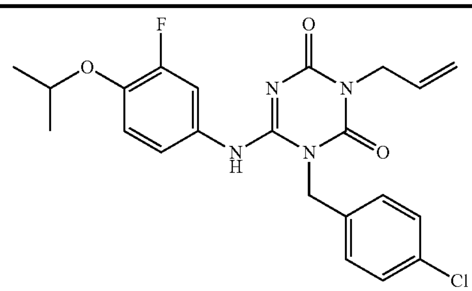 | I-0346 | 2.34 | 445 | 2 |
| 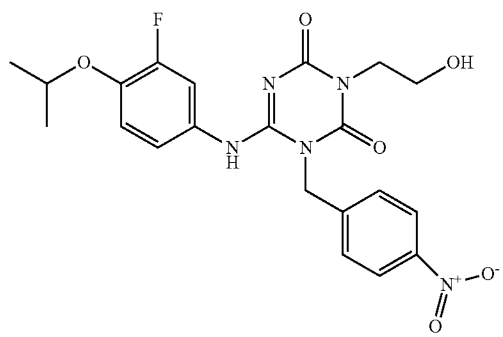 [SMILES: CC(C)Oc1ccc(Nc2nc(=O)n(CCO)c(=O)n2Cc2ccc([N+](=O)[O-])cc2)cc1F] | I-0347 | 1.78 | 460 | 2 |
| 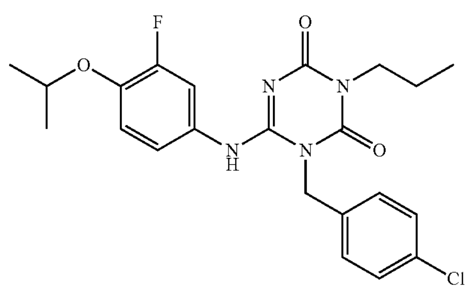 [SMILES: CCCn1c(=O)nc(Nc2ccc(OC(C)C)c(F)c2)n(Cc2ccc(Cl)cc2)c1=O] | I-0348 | 2.45 | 447 | 2 |
| 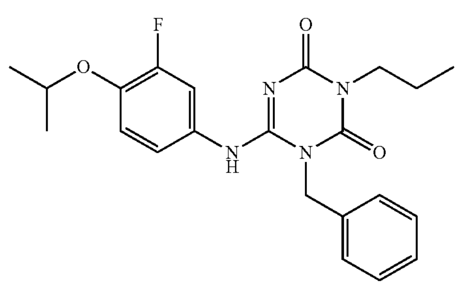 [SMILES: CCCn1c(=O)nc(Nc2ccc(OC(C)C)c(F)c2)n(Cc2ccccc2)c1=O] | I-0349 | 2.20 | 413 | 2 |
| 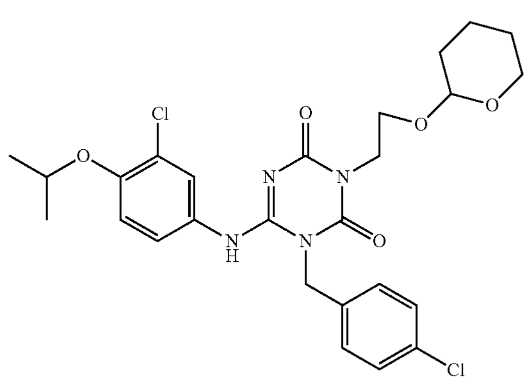 [SMILES: CC(C)Oc1ccc(Nc2nc(=O)n(CCOC3CCCCO3)c(=O)n2Cc2ccc(Cl)cc2)cc1Cl] | I-0350 | 2.55 | 549 | 2 |

TABLE 74

| Structure | Compound No. | Retention Time (min) | [M + H] | Method |
|---|---|---|---|---|
| 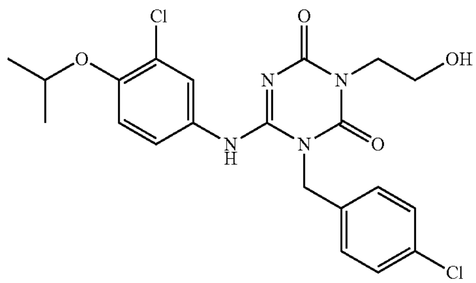 [SMILES: CC(C)Oc1ccc(Nc2nc(=O)n(CCO)c(=O)n2Cc2ccc(Cl)cc2)cc1Cl] | I-0351 | 2.06 | 465 | 2 |
| 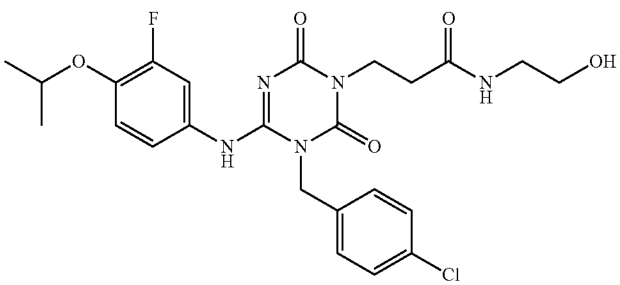 [SMILES: CC(C)Oc1ccc(Nc2nc(=O)n(CCC(=O)NCCO)c(=O)n2Cc2ccc(Cl)cc2)cc1F] | I-0352 | 1.78 | 520 | 2 |
| 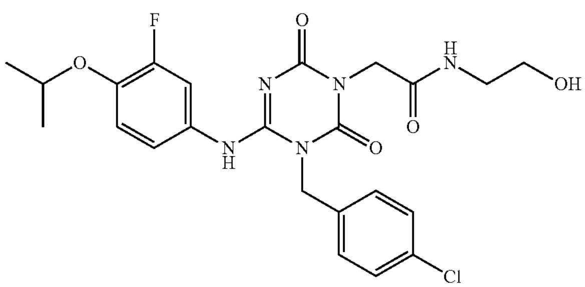 [SMILES: CC(C)Oc1ccc(Nc2nc(=O)n(CC(=O)NCCO)c(=O)n2Cc2ccc(Cl)cc2)cc1F] | I-0353 | 1.77 | 506 | 2 |
| 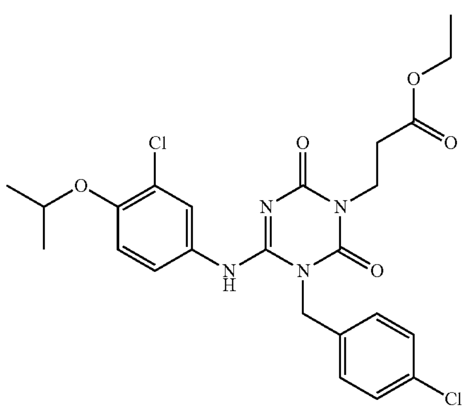 [SMILES: CCOC(=O)CCn1c(=O)nc(Nc2ccc(OC(C)C)c(Cl)c2)n(Cc2ccc(Cl)cc2)c1=O] | I-0354 | 2.47 | 521 | 2 |
| 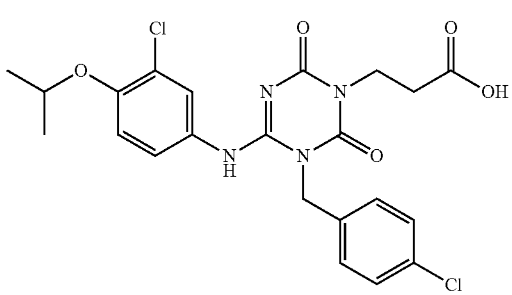 [SMILES: CC(C)Oc1ccc(Nc2nc(=O)n(CCC(=O)O)c(=O)n2Cc2ccc(Cl)cc2)cc1Cl] | I-0355 | 2.10 | 493 | 2 |

TABLE 75

| Structure | Compound No. | Retention Time (min) | [M + H] | Method |
|---|---|---|---|---|
| 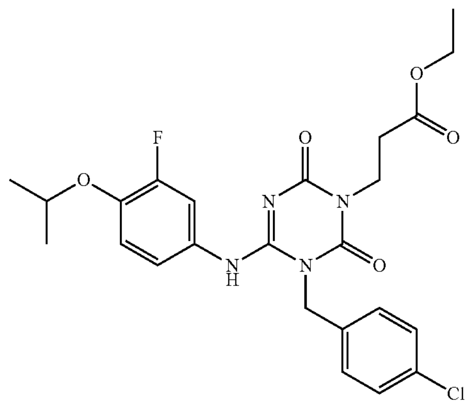 [SMILES: CCOC(=O)CCn1c(=O)nc(Nc2ccc(OC(C)C)c(F)c2)n(Cc2ccc(Cl)cc2)c1=O] | I-0356 | 2.33 | 505 | 2 |
| 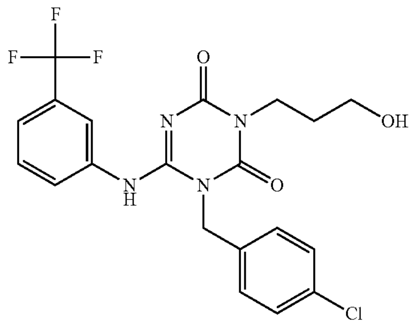 [SMILES: O=c1nc(Nc2cccc(C(F)(F)F)c2)n(Cc2ccc(Cl)cc2)c(=O)n1CCCO] | I-0357 | 2.07 | 455 | 2 |
| 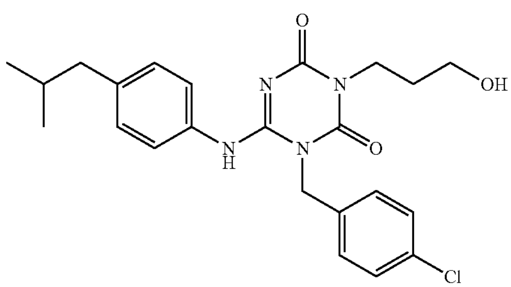 [SMILES: CC(C)Cc1ccc(Nc2nc(=O)n(CCCO)c(=O)n2Cc2ccc(Cl)cc2)cc1] | I-0358 | 2.23 | 442 | 2 |
| 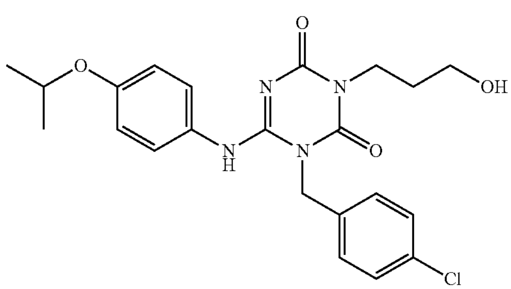 [SMILES: CC(C)Oc1ccc(Nc2nc(=O)n(CCCO)c(=O)n2Cc2ccc(Cl)cc2)cc1] | I-0359 | 1.85 | 445 | 2 |
| 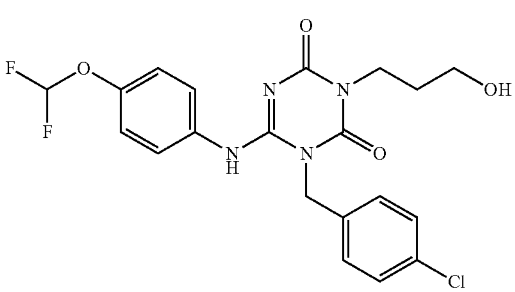 | I-0360 | 1.84 | 453 | 2 |

TABLE 76

| Structure | Compound No. | Retention Time (min) | [M + H] | Method |
|---|---|---|---|---|
| 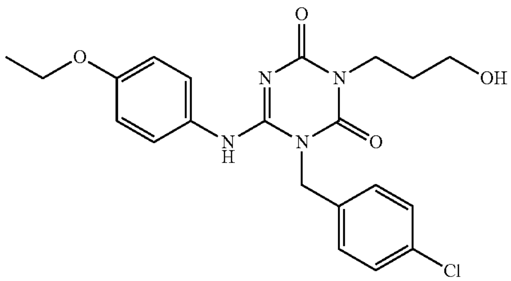 [SMILES: CCOc1ccc(Nc2nc(=O)n(CCCO)c(=O)n2Cc2ccc(Cl)cc2)cc1] | I-0361 | 1.77 | 431 | 2 |
| 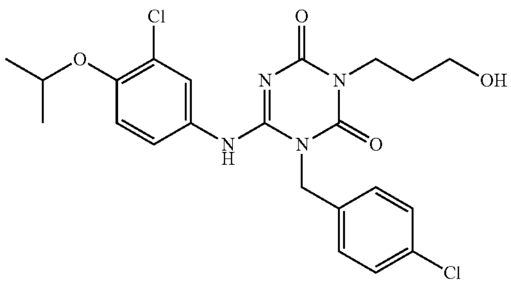 [SMILES: CC(C)Oc1ccc(Nc2nc(=O)n(CCCO)c(=O)n2Cc2ccc(Cl)cc2)cc1Cl] | I-0362 | 2.12 | 479 | 2 |
| 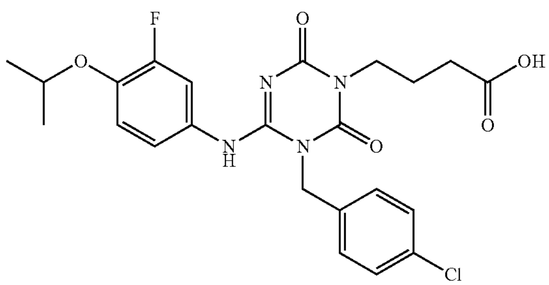 [SMILES: CC(C)Oc1ccc(Nc2nc(=O)n(CCCC(=O)O)c(=O)n2Cc2ccc(Cl)cc2)cc1F] | I-0363 | 2.05 | 491 | 2 |
| 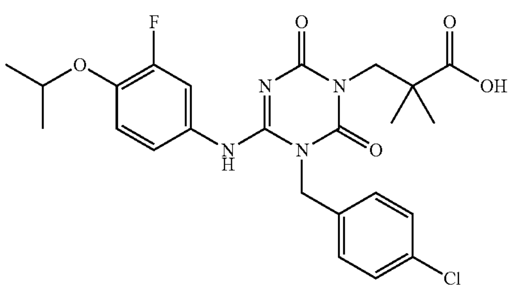 [SMILES: CC(C)Oc1ccc(Nc2nc(=O)n(CC(C)(C)C(=O)O)c(=O)n2Cc2ccc(Cl)cc2)cc1F] | I-0364 | 2.12 | 505 | 2 |
| 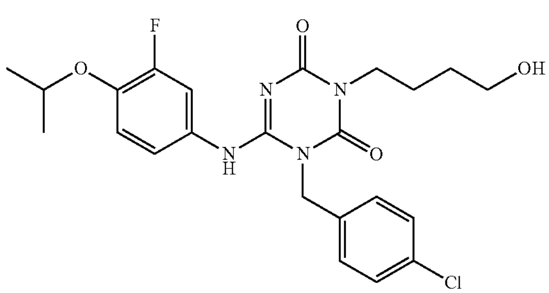 [SMILES: CC(C)Oc1ccc(Nc2nc(=O)n(CCCCO)c(=O)n2Cc2ccc(Cl)cc2)cc1F] | I-0365 | 2.03 | 477 | 2 |

TABLE 77

| Structure | Compound No. | Retention Time (min) | [M + H] | Method |
|---|---|---|---|---|
| 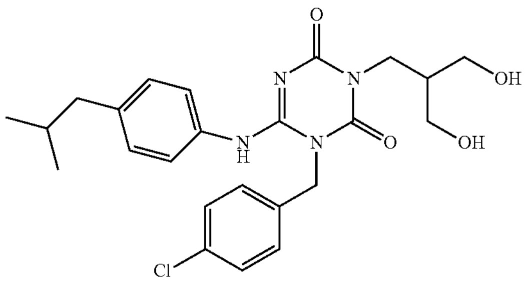 [SMILES: CC(C)Cc1ccc(Nc2nc(=O)n(CC(CO)CO)c(=O)n2Cc2ccc(Cl)cc2)cc1] | I-0366 | 2.33 | 473 | 3 |
| 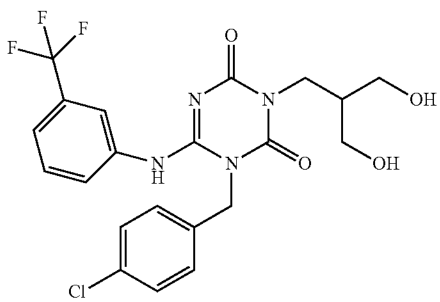 [SMILES: O=c1nc(Nc2cccc(C(F)(F)F)c2)n(Cc2ccc(Cl)cc2)c(=O)n1CC(CO)CO] | I-0367 | 2.17 | 485 | 3 |
| 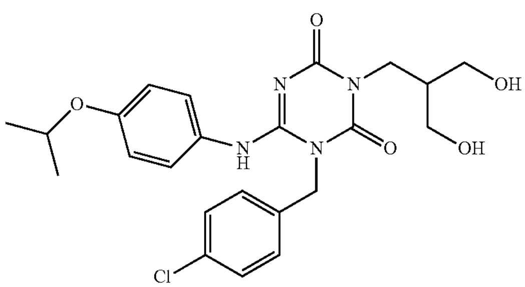 [SMILES: CC(C)Oc1ccc(Nc2nc(=O)n(CC(CO)CO)c(=O)n2Cc2ccc(Cl)cc2)cc1] | I-0368 | 2.00 | 475 | 3 |
| 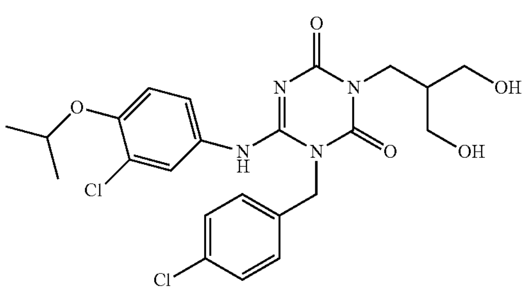 [SMILES: CC(C)Oc1ccc(Nc2nc(=O)n(CC(CO)CO)c(=O)n2Cc2ccc(Cl)cc2)cc1Cl] | I-0369 | 2.24 | 510 | 3 |
| 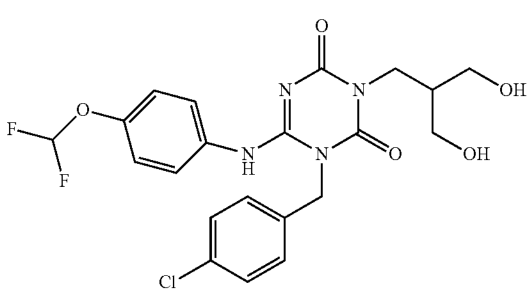 [SMILES: O=c1nc(Nc2ccc(OC(F)F)cc2)n(Cc2ccc(Cl)cc2)c(=O)n1CC(CO)CO] | I-0370 | 1.98 | 483 | 3 |

TABLE 78

| Structure | Compound No. | Retention Time (min) | [M + H] | Method |
|---|---|---|---|---|
| 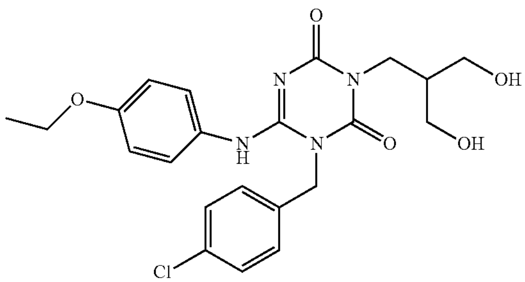 [SMILES: CCOc1ccc(Nc2nc(=O)n(CC(CO)CO)c(=O)n2Cc2ccc(Cl)cc2)cc1] | I-0371 | 1.88 | 461 | 3 |
| 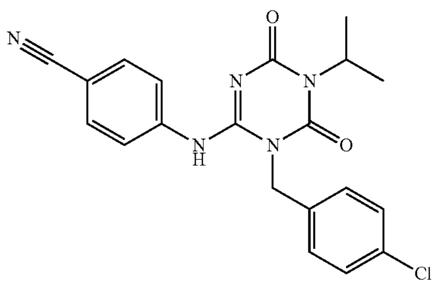 [SMILES: CC(C)n1c(=O)nc(Nc2ccc(C#N)cc2)n(Cc2ccc(Cl)cc2)c1=O] | I-0372 | 2.27 | 396 | 2 |
| 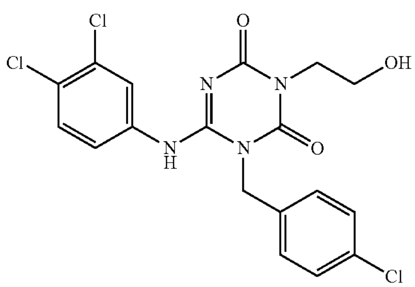 [SMILES: O=c1nc(Nc2ccc(Cl)c(Cl)c2)n(Cc2ccc(Cl)cc2)c(=O)n1CCO] | I-0373 | 2.17 | 443 | 2 |
| 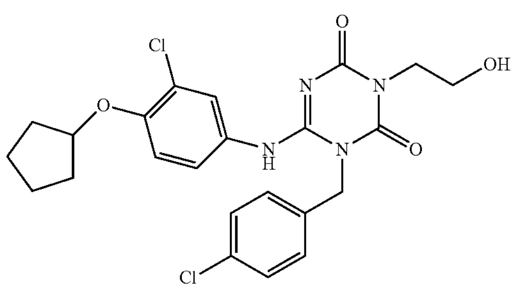 [SMILES: O=c1nc(Nc2ccc(OC3CCCC3)c(Cl)c2)n(Cc2ccc(Cl)cc2)c(=O)n1CCO] | I-0374 | 2.28 | 491 | 2 |
| 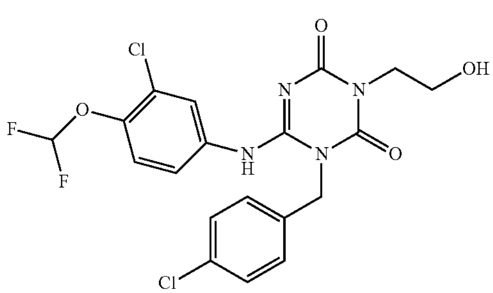 [SMILES: O=c1nc(Nc2ccc(OC(F)F)c(Cl)c2)n(Cc2ccc(Cl)cc2)c(=O)n1CCO] | I-0375 | 2.32 | 473 | 3 |

TABLE 79

| Structure | Compound No. | Retention Time (min) | [M + H] | Method |
|---|---|---|---|---|
| 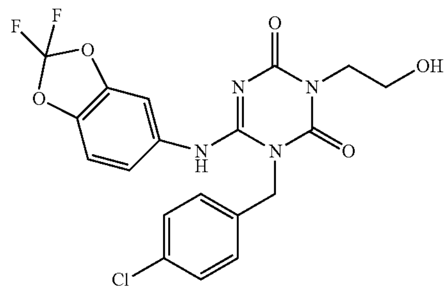 [SMILES: O=c1nc(Nc2ccc3c(c2)OC(F)(F)O3)n(Cc2ccc(Cl)cc2)c(=O)n1CCO] | I-0376 | 2.30 | 453 | 3 |
| 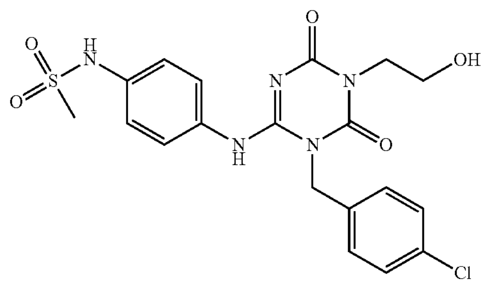 [SMILES: CS(=O)(=O)Nc1ccc(Nc2nc(=O)n(CCO)c(=O)n2Cc2ccc(Cl)cc2)cc1] | I-0377 | 1.41 | 446 | 2 |
| 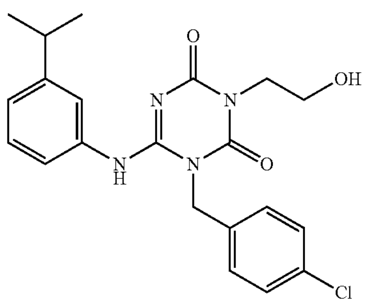 [SMILES: CC(C)c1cccc(Nc2nc(=O)n(CCO)c(=O)n2Cc2ccc(Cl)cc2)c1] | I-0378 | 2.02 | 415 | 2 |
| 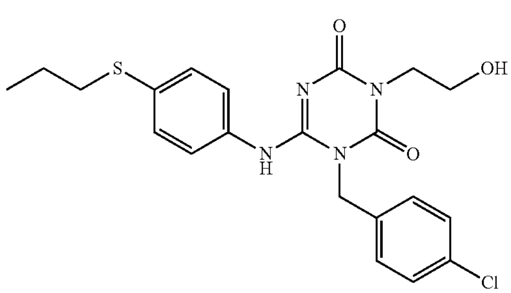 [SMILES: CCCSc1ccc(Nc2nc(=O)n(CCO)c(=O)n2Cc2ccc(Cl)cc2)cc1] | I-0379 | 2.11 | 447 | 2 |
| 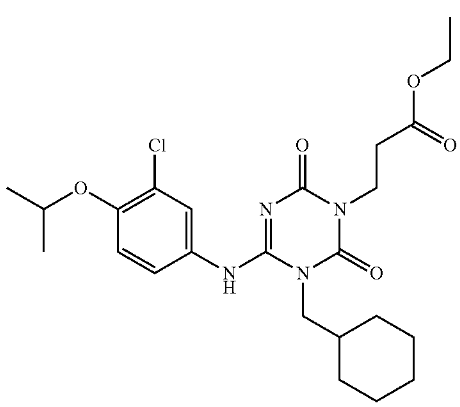 [SMILES: CCOC(=O)CCn1c(=O)nc(Nc2ccc(OC(C)C)c(Cl)c2)n(CC2CCCCC2)c1=O] | I-0380 | 2.49 | 493 | 2 |

TABLE 80
| Structure | Compound No. | Retention Time (min) | [M + H] | Method |
|---|---|---|---|---|
| 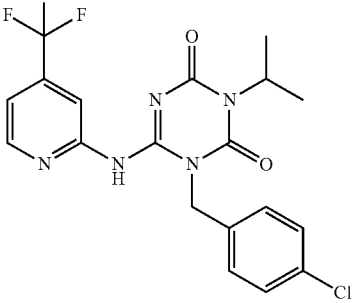 | I-0381 | 3.04 | 440 | 3 |
| 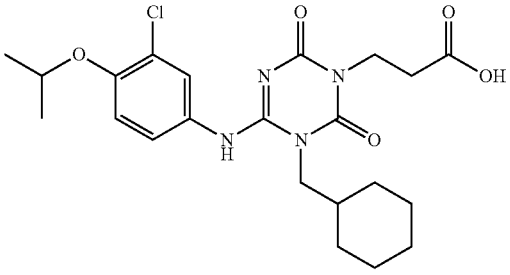 [SMILES: CC(C)Oc1ccc(Nc2nc(=O)n(CCC(=O)O)c(=O)n2CC2CCCCC2)cc1Cl] | I-0382 | 2.09 | 465 | 2 |
| 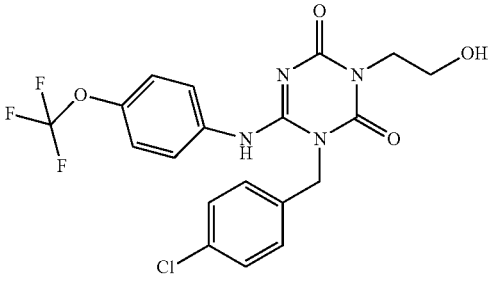 [SMILES: O=c1nc(Nc2ccc(OC(F)(F)F)cc2)n(Cc2ccc(Cl)cc2)c(=O)n1CCO] | I-0383 | 2.32 | 457 | 3 |
| 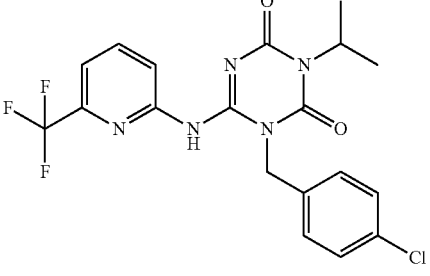 | I-0384 | 2.77 | 440 | 2 |
| 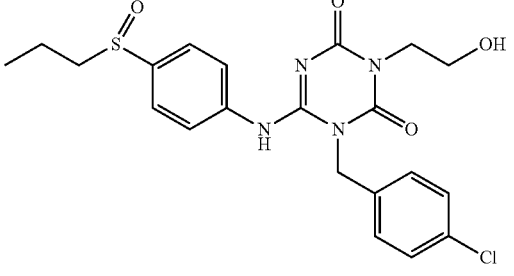 | I-0385 | 1.56 | 463 | 2 |

TABLE 81

| Structure | Compound No. | Retention Time (min) | [M + H] | Method |
|---|---|---|---|---|
| 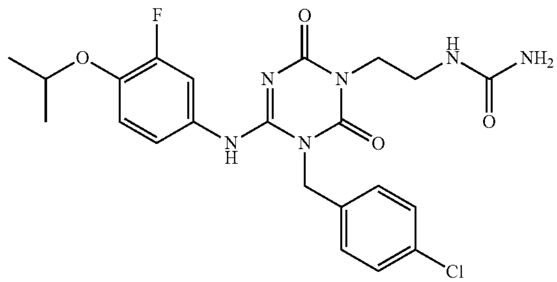 [SMILES: CC(C)Oc1ccc(Nc2nc(=O)n(CCNC(N)=O)c(=O)n2Cc2ccc(Cl)cc2)cc1F] | I-0386 | 1.81 | 491 | 2 |
| 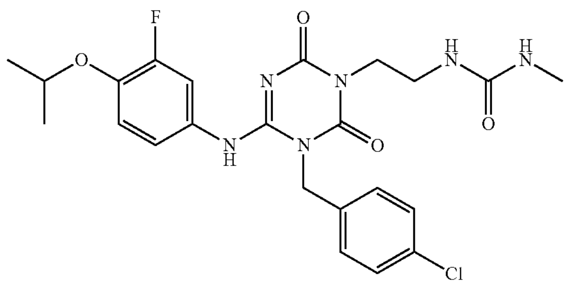 [SMILES: CNC(=O)NCCn1c(=O)nc(Nc2ccc(OC(C)C)c(F)c2)n(Cc2ccc(Cl)cc2)c1=O] | I-0387 | 1.86 | 505 | 2 |
| 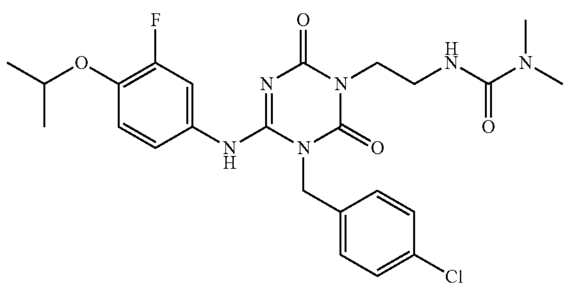 [SMILES: CC(C)Oc1ccc(Nc2nc(=O)n(CCNC(=O)N(C)C)c(=O)n2Cc2ccc(Cl)cc2)cc1F] | I-0388 | 1.98 | 519 | 2 |
| 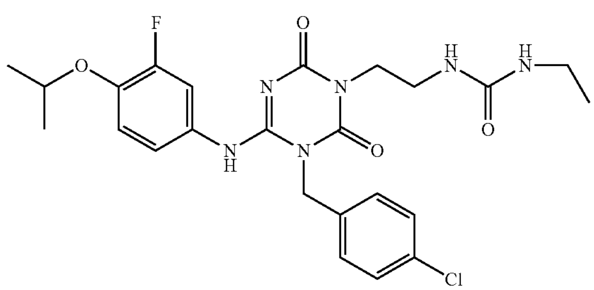 [SMILES: CCNC(=O)NCCn1c(=O)nc(Nc2ccc(OC(C)C)c(F)c2)n(Cc2ccc(Cl)cc2)c1=O] | I-0389 | 1.94 | 519 | 2 |
| 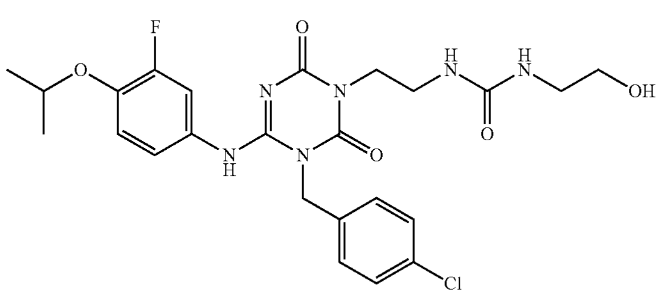 [SMILES: CC(C)Oc1ccc(Nc2nc(=O)n(CCNC(=O)NCCO)c(=O)n2Cc2ccc(Cl)cc2)cc1F] | I-0390 | 1.77 | 535 | 2 |

TABLE 82

| Structure | Compound No. | Retention Time (min) | [M + H] | Method |
|---|---|---|---|---|
| 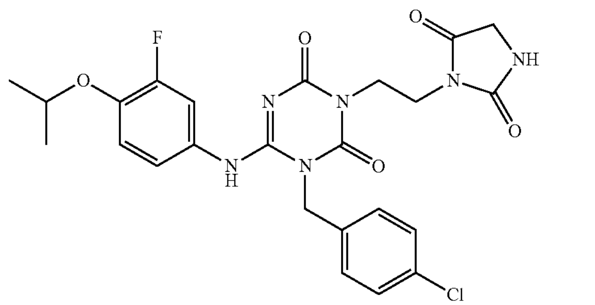 [SMILES: CC(C)Oc1ccc(Nc2nc(=O)n(CCN3C(=O)CNC3=O)c(=O)n2Cc2ccc(Cl)cc2)cc1F] | I-0391 | 1.89 | 531 | 2 |
| 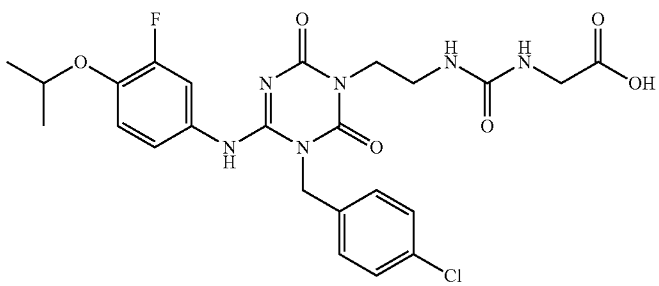 [SMILES: CC(C)Oc1ccc(Nc2nc(=O)n(CCNC(=O)NCC(=O)O)c(=O)n2Cc2ccc(Cl)cc2)cc1F] | I-0392 | 1.77 | 549 | 2 |
| 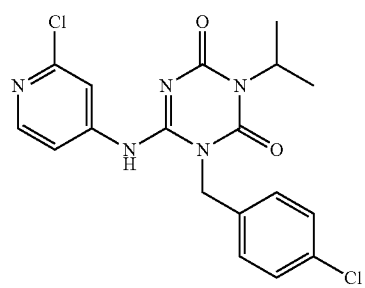 [SMILES: CC(C)n1c(=O)nc(Nc2ccnc(Cl)c2)n(Cc2ccc(Cl)cc2)c1=O] | I-0393 | 2.28 | 406 | 2 |
| 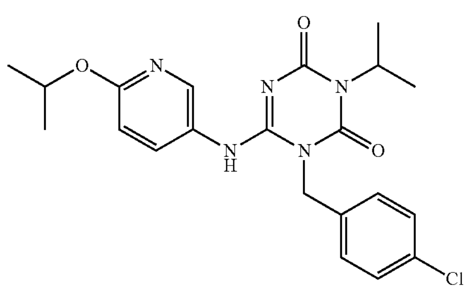 [SMILES: CC(C)Oc1ccc(Nc2nc(=O)n(C(C)C)c(=O)n2Cc2ccc(Cl)cc2)cn1] | I-0394 | 2.30 | 430 | 2 |
| 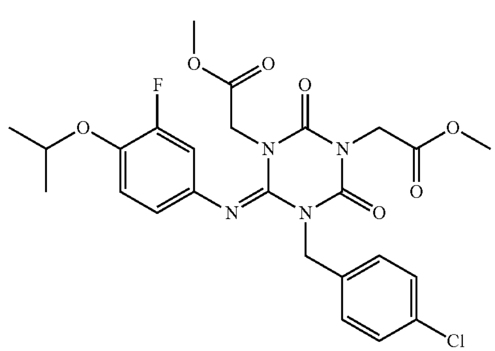 [SMILES: COC(=O)Cn1c(=O)n(CC(=O)OC)/c(=N\c2ccc(OC(C)C)c(F)c2)n(Cc2ccc(Cl)cc2)c1=O] | I-0395 | 2.77 | 549 | 3 |

TABLE 83

| Structure | Compound No. | Retention Time (min) | [M + H] | Method |
|---|---|---|---|---|
| 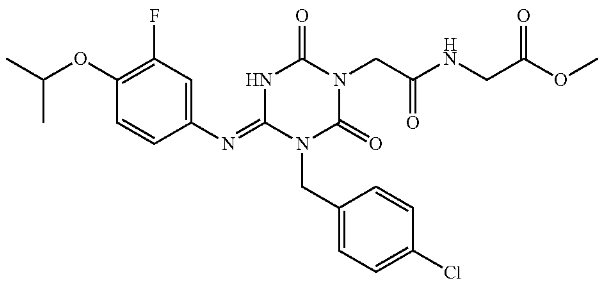 [SMILES: COC(=O)CNC(=O)Cn1c(=O)[nH]/c(=N\c2ccc(OC(C)C)c(F)c2)n(Cc2ccc(Cl)cc2)c1=O] | I-0396 | 1.94 | 534 | 2 |
| 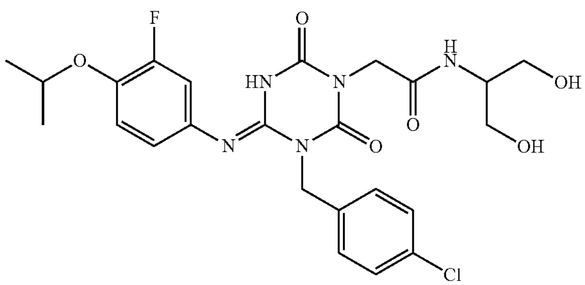 | I-0397 | 1.69 | 536 | 2 |
| 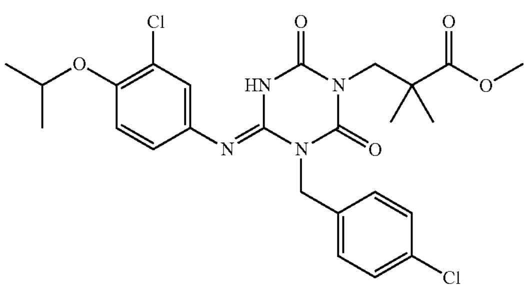 | I-0398 | 2.51 | 535 | 2 |
| 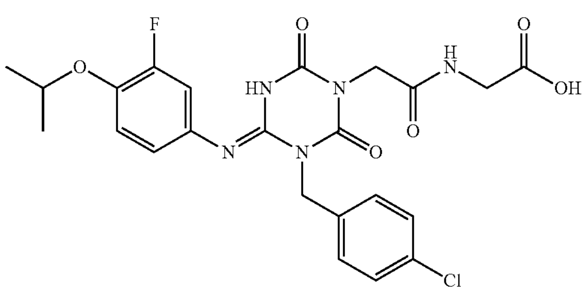 [SMILES: CC(C)Oc1ccc(/N=c2\[nH]c(=O)n(CC(=O)NCC(=O)O)c(=O)n2Cc2ccc(Cl)cc2)cc1F] | I-0399 | 1.81 | 520 | 2 |
| 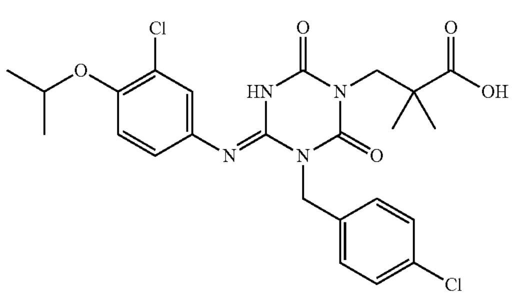 [SMILES: CC(C)Oc1ccc(/N=c2\[nH]c(=O)n(CC(C)(C)C(=O)O)c(=O)n2Cc2ccc(Cl)cc2)cc1Cl] | I-0400 | 2.24 | 521 | 2 |

TABLE 84

| Structure | Compound No. | Retention Time (min) | [M + H] | Method |
|---|---|---|---|---|
| 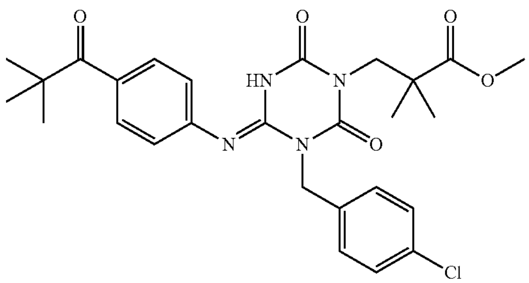 [SMILES: COC(=O)C(C)(C)Cn1c(=O)[nH]/c(=N\c2ccc(C(=O)C(C)(C)C)cc2)n(Cc2ccc(Cl)cc2)c1=O] | I-0401 | 2.49 | 527 | 2 |
| 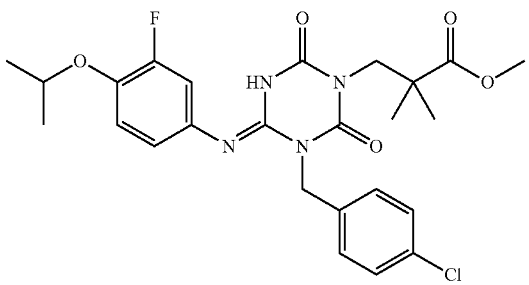 [SMILES: COC(=O)C(C)(C)Cn1c(=O)[nH]/c(=N\c2ccc(OC(C)C)c(F)c2)n(Cc2ccc(Cl)cc2)c1=O] | I-0402 | 2.40 | 519 | 2 |
| 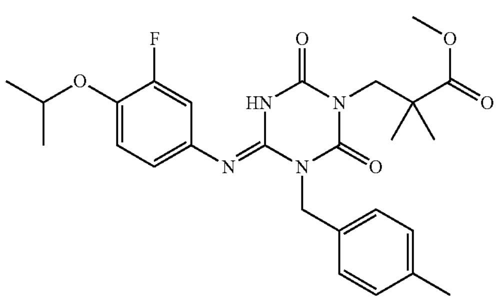 [SMILES: COC(=O)C(C)(C)Cn1c(=O)[nH]/c(=N\c2ccc(OC(C)C)c(F)c2)n(Cc2ccc(C)cc2)c1=O] | I-0403 | 2.32 | 499 | 2 |
| 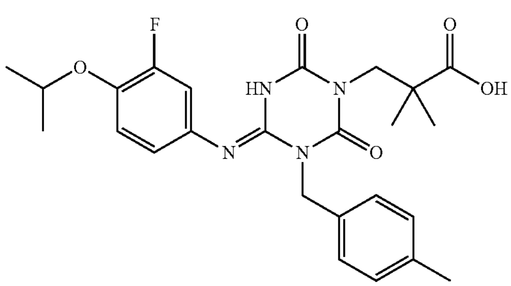 [SMILES: Cc1ccc(Cn2c(=O)n(CC(C)(C)C(=O)O)c(=O)[nH]/c2=N\c2ccc(OC(C)C)c(F)c2)cc1] | I-0404 | 2.04 | 485 | 2 |
| 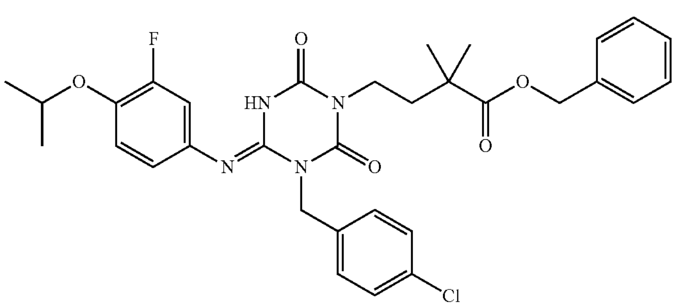 [SMILES: CC(C)Oc1ccc(/N=c2\[nH]c(=O)n(CCC(C)(C)C(=O)OCc3ccccc3)c(=O)n2Cc2ccc(Cl)cc2)cc1F] | I-0405 | 2.74 | 609 | 2 |

TABLE 85

| Structure | Compound No. | Retention Time (min) | [M + H] | Method |
|---|---|---|---|---|
| 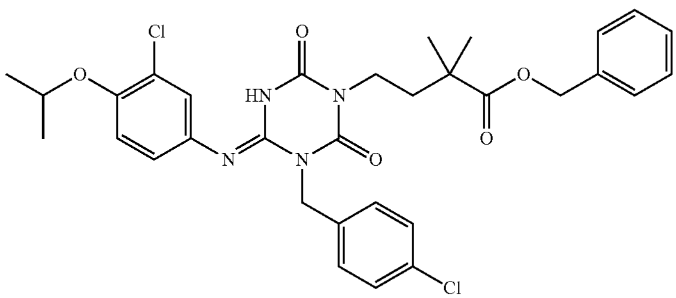 | I-0406 | 2.84 | 625 | 2 |
| 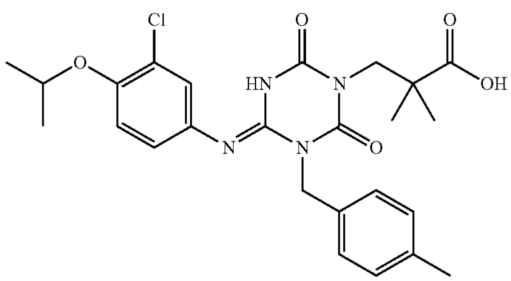 | I-0407 | 2.16 | 501 | 2 |
| 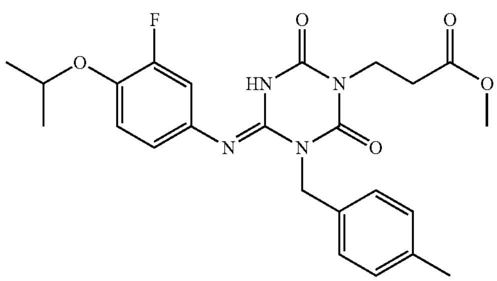 [SMILES: COC(=O)CCn1c(=O)[nH]/c(=N\c2ccc(OC(C)C)c(F)c2)n(Cc2ccc(C)cc2)c1=O] | I-0408 | 2.13 | 471 | 2 |
| 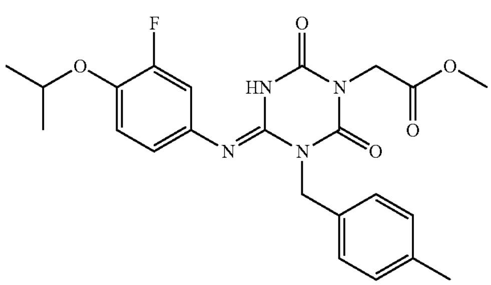 [SMILES: COC(=O)Cn1c(=O)[nH]/c(=N\c2ccc(OC(C)C)c(F)c2)n(Cc2ccc(C)cc2)c1=O] | I-0409 | 2.09 | 457 | 2 |
| 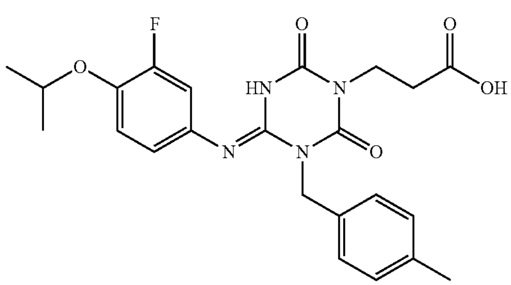 [SMILES: Cc1ccc(Cn2c(=O)n(CCC(=O)O)c(=O)[nH]/c2=N\c2ccc(OC(C)C)c(F)c2)cc1] | I-0410 | 1.92 | 457 | 2 |

TABLE 86

| Structure | Compound No. | Retention Time (min) | [M + H] | Method |
|---|---|---|---|---|
| 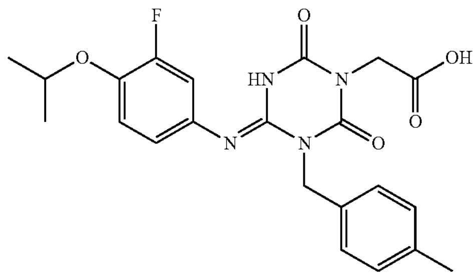 [SMILES: Cc1ccc(Cn2c(=O)n(CC(=O)O)c(=O)[nH]/c2=N\c2ccc(OC(C)C)c(F)c2)cc1] | I-0411 | 1.87 | 443 | 2 |
| 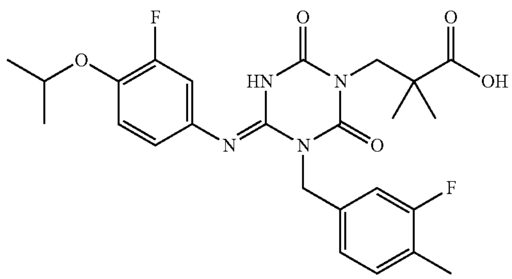 [SMILES: Cc1ccc(Cn2c(=O)n(CC(C)(C)C(=O)O)c(=O)[nH]/c2=N\c2ccc(OC(C)C)c(F)c2)cc1F] | I-0412 | 2.10 | 503 | 2 |
| 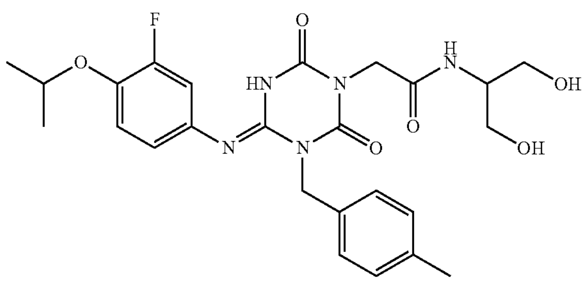 [SMILES: Cc1ccc(Cn2c(=O)n(CC(=O)NC(CO)CO)c(=O)[nH]/c2=N\c2ccc(OC(C)C)c(F)c2)cc1] | I-0413 | 1.63 | 516 | 2 |
| 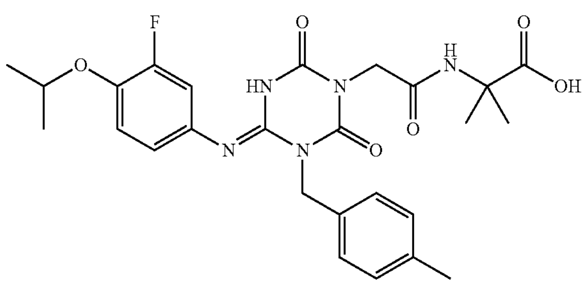 [SMILES: Cc1ccc(Cn2c(=O)n(CC(=O)NC(C)(C)C(=O)O)c(=O)[nH]/c2=N\c2ccc(OC(C)C)c(F)c2)cc1] | I-0414 | 1.84 | 528 | 2 |
| 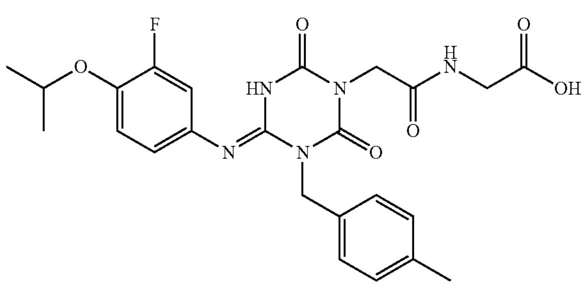 [SMILES: Cc1ccc(Cn2c(=O)n(CC(=O)NCC(=O)O)c(=O)[nH]/c2=N\c2ccc(OC(C)C)c(F)c2)cc1] | I-0415 | 1.74 | 500 | 2 |

TABLE 87

| Structure | Compound No. | Retention Time (min) | [M + H] | Method |
|---|---|---|---|---|
| 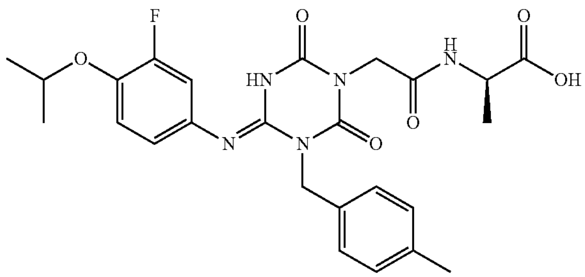 [SMILES: Cc1ccc(Cn2c(=O)n(CC(=O)N[C@H](C)C(=O)O)c(=O)[nH]/c2=N\c2ccc(OC(C)C)c(F)c2)cc1] | I-0416 | 1.78 | 514 | 2 |
| 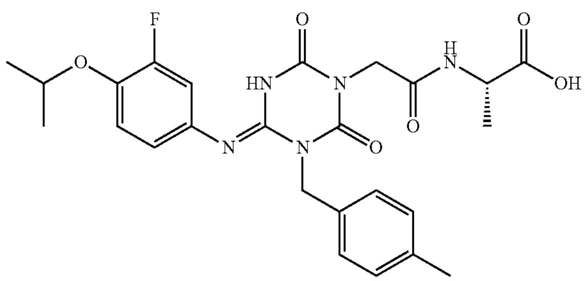 [SMILES: Cc1ccc(Cn2c(=O)n(CC(=O)N[C@@H](C)C(=O)O)c(=O)[nH]/c2=N\c2ccc(OC(C)C)c(F)c2)cc1] | I-0417 | 1.79 | 514 | 2 |
| 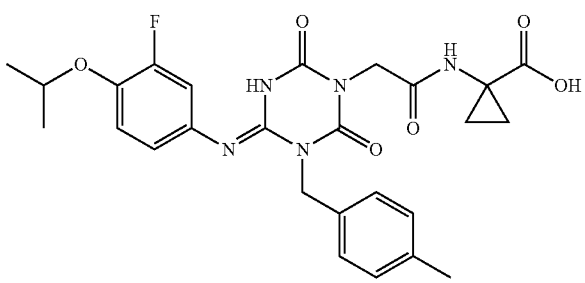 [SMILES: Cc1ccc(Cn2c(=O)n(CC(=O)NC3(C(=O)O)CC3)c(=O)[nH]/c2=N\c2ccc(OC(C)C)c(F)c2)cc1] | I-0418 | 1.78 | 526 | 2 |
| 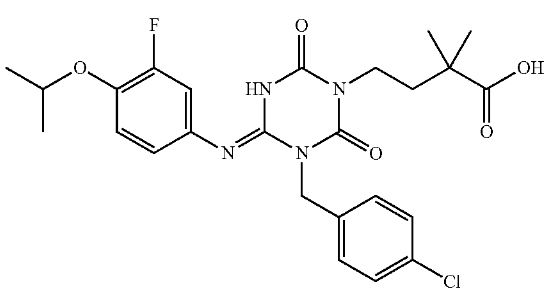 [SMILES: CC(C)Oc1ccc(/N=c2\[nH]c(=O)n(CCC(C)(C)C(=O)O)c(=O)n2Cc2ccc(Cl)cc2)cc1F] | I-0419 | 2.21 | 519 | 2 |
| 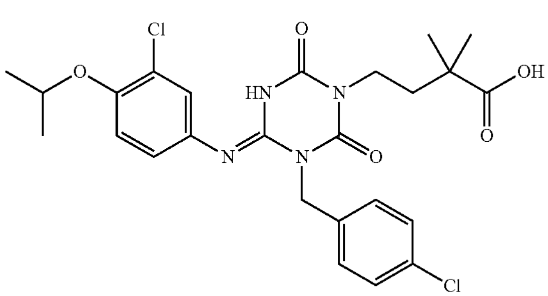 | I-0420 | 2.32 | 535 | 2 |

TABLE 88

| Structure | Compound No. | Retention Time (min) | [M + H] | Method |
|---|---|---|---|---|
| 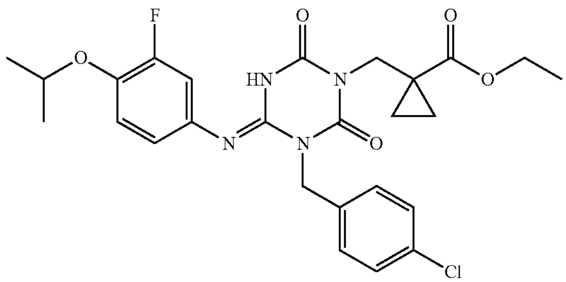 | I-0421 | 2.45 | 531 | 2 |
| 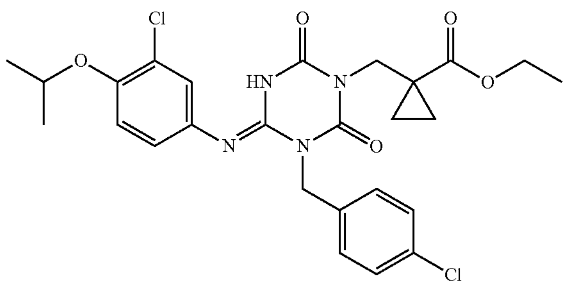 | I-0422 | 2.53 | 547 | 2 |
| 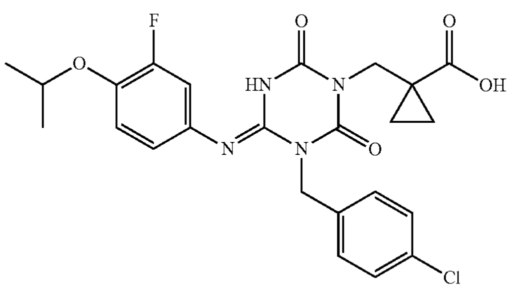 | I-0423 | 2.09 | 503 | 2 |
| 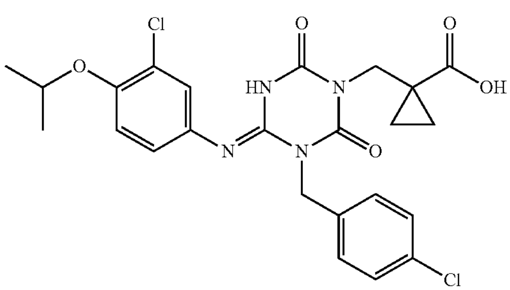 [SMILES: CC(C)Oc1ccc(/N=c2\[nH]c(=O)n(CC3(C(=O)O)CC3)c(=O)n2Cc2ccc(Cl)cc2)cc1Cl] | I-0424 | 2.20 | 519 | 2 |
| 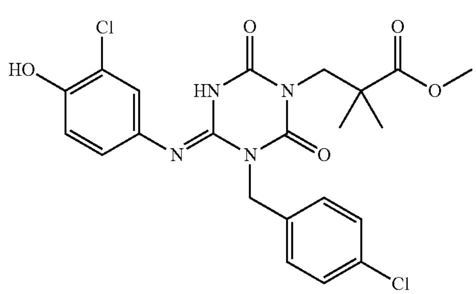 [SMILES: COC(=O)C(C)(C)Cn1c(=O)[nH]/c(=N\c2ccc(O)c(Cl)c2)n(Cc2ccc(Cl)cc2)c1=O] | I-0425 | 1.99 | 493 | 2 |

TABLE 89

| Structure | Compound No. | Retention Time (min) | [M + H] | Method |
|---|---|---|---|---|
| 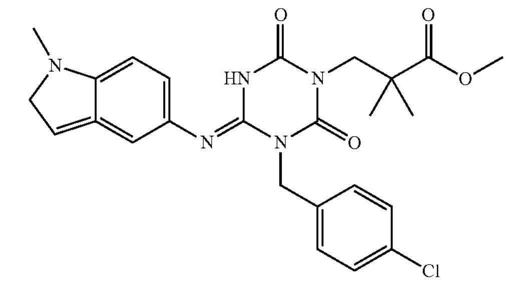 | I-0426 | 2.12 | 496 | 2 |
| 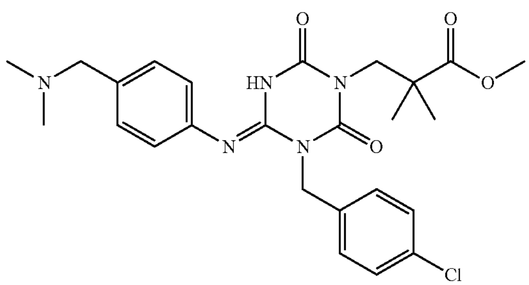 | I-0427 | 1.25 | 500 | 2 |
| 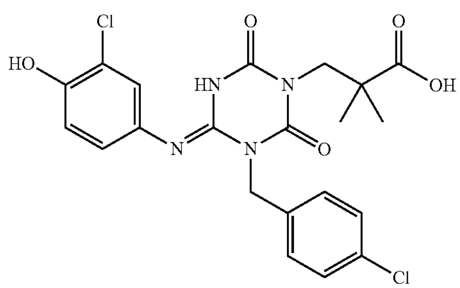 [SMILES: CC(C)(Cn1c(=O)[nH]/c(=N\c2ccc(O)c(Cl)c2)n(Cc2ccc(Cl)cc2)c1=O)C(=O)O] | I-0428 | 1.72 | 479 | 2 |
| 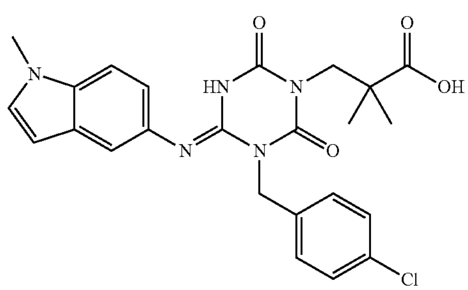 [SMILES: Cn1ccc2cc(/N=c3\[nH]c(=O)n(CC(C)(C)C(=O)O)c(=O)n3Cc3ccc(Cl)cc3)ccc21] | I-0429 | 1.85 | 482 | 2 |
| 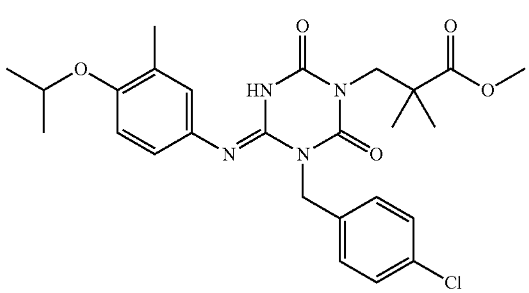 | I-0430 | 2.44 | 515 | 2 |

TABLE 90

| Structure | Compound No. | Retention Time (min) | [M + H] | Method |
|---|---|---|---|---|
| (structure) | I-0431 | 2.15 | 501 | 2 |
| (structure) | I-0432 | 2.10 | 435 | 1 |
| (structure) | I-0433 | 1.79 | 462 | 1 |
| (structure) | I-0434 | 1.80 | 449 | 1 |
| (structure) | I-0435 | 1.90 | 494 | 1 |

TABLE 91

| Structure | Compound No. | Retention Time (min) | [M + H] | Method |
|---|---|---|---|---|
| (structure) | I-0436 | 3.40 | 590 | 1 |
| (structure) | I-0437 | 1.50 | 448 | 2 |
| (structure) | I-0438 | 1.80 | 464 | 2 |
| (structure) | I-0439 | 1.50 | 462 | 2 |
| (structure) | I-0440 | 1.70 | 493 | 2 |

TABLE 92

| Structure | Compound No. | Retention Time (min) | [M + H] | Method |
|---|---|---|---|---|
| 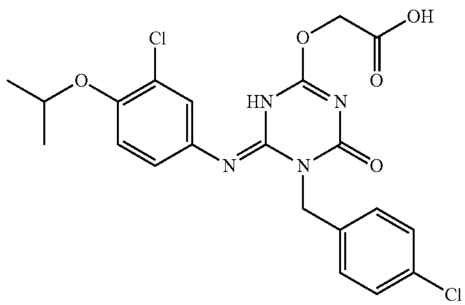 | I-0441 | 1.88 | 479 | 1 |
| 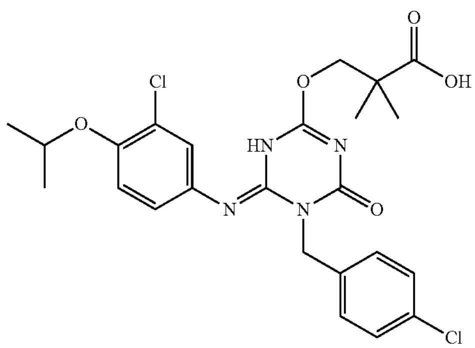 [SMILES: CC(C)Oc1ccc(/N=c2\[nH]c(OCC(C)(C)C(=O)O)nc(=O)n2Cc2ccc(Cl)cc2)cc1Cl] | I-0442 | 2.09 | 521 | 1 |
| 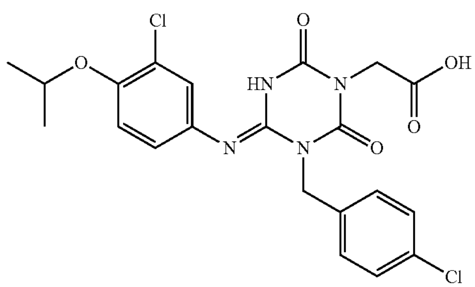 [SMILES: CC(C)Oc1ccc(/N=c2\[nH]c(=O)n(CC(=O)O)c(=O)n2Cc2ccc(Cl)cc2)cc1Cl] | I-0443 | 2.06 | 479 | 2 |
| 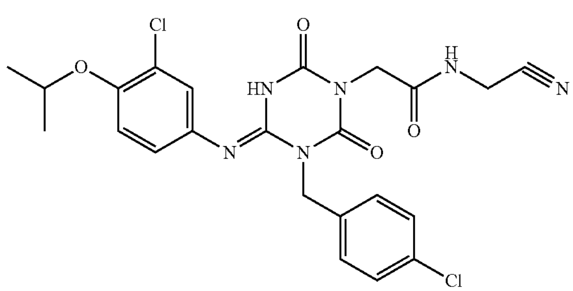 [SMILES: CC(C)Oc1ccc(/N=c2\[nH]c(=O)n(CC(=O)NCC#N)c(=O)n2Cc2ccc(Cl)cc2)cc1Cl] | I-0444 | 2.21 | 517 | 3 |
| 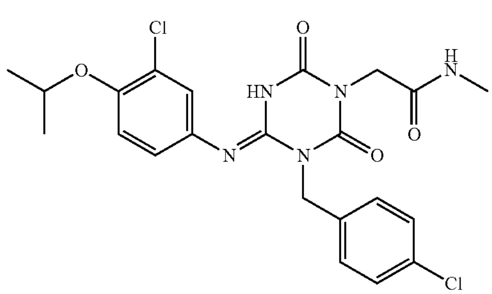 [SMILES: CNC(=O)Cn1c(=O)[nH]/c(=N\c2ccc(OC(C)C)c(Cl)c2)n(Cc2ccc(Cl)cc2)c1=O] | I-0445 | 2.16 | 492 | 3 |

TABLE 93

| Structure | Compound No. | Retention Time (min) | [M + H] | Method |
|---|---|---|---|---|
| 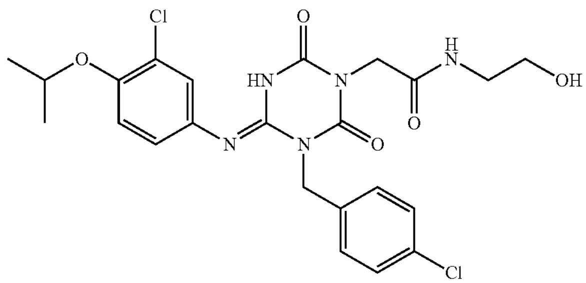 [SMILES: CC(C)Oc1ccc(/N=c2\[nH]c(=O)n(CC(=O)NCCO)c(=O)n2Cc2ccc(Cl)cc2)cc1Cl] | I-0446 | 2.03 | 522 | 3 |
| 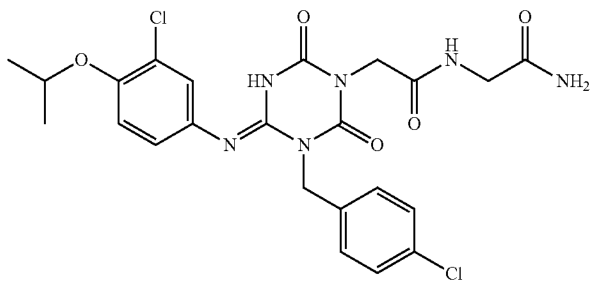 [SMILES: CC(C)Oc1ccc(/N=c2\[nH]c(=O)n(CC(=O)NCC(N)=O)c(=O)n2Cc2ccc(Cl)cc2)cc1Cl] | I-0447 | 1.98 | 535 | 3 |
| 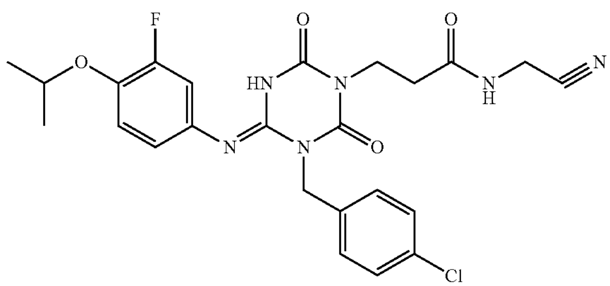 [SMILES: CC(C)Oc1ccc(/N=c2\[nH]c(=O)n(CCC(=O)NCC#N)c(=O)n2Cc2ccc(Cl)cc2)cc1F] | I-0448 | 2.11 | 515 | 3 |
| 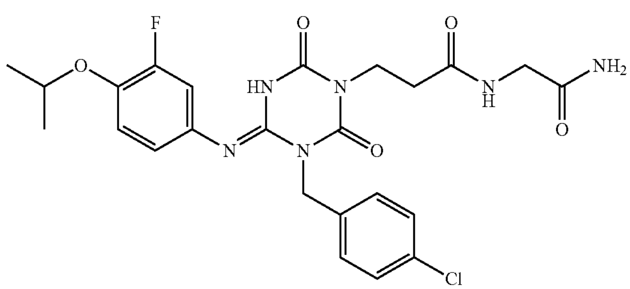 [SMILES: CC(C)Oc1ccc(/N=c2\[nH]c(=O)n(CCC(=O)NCC(N)=O)c(=O)n2Cc2ccc(Cl)cc2)cc1F] | I-0449 | 1.87 | 533 | 3 |
| 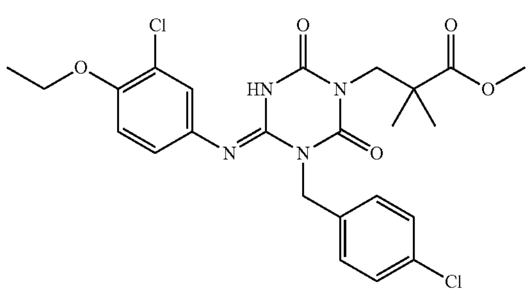 | I-0450 | 2.43 | 521 | 2 |

TABLE 94

| Structure | Compound No. | Retention Time (min) | [M + H] | Method |
|---|---|---|---|---|
| 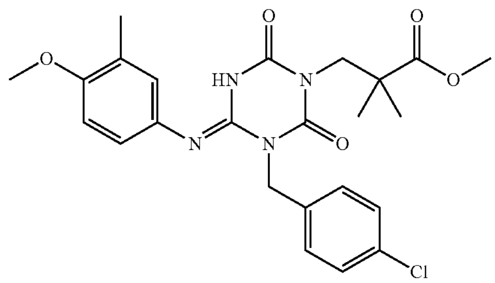 | I-0451 | 2.23 | 487 | 2 |
| 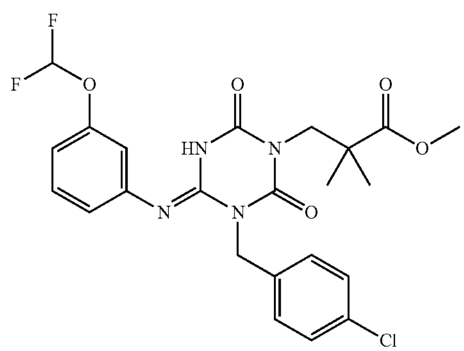 [SMILES: COC(=O)C(C)(C)Cn1c(=O)[nH]/c(=N\c2cccc(OC(F)F)c2)n(Cc2ccc(Cl)cc2)c1=O] | I-0452 | 2.50 | 509 | 3 |
| 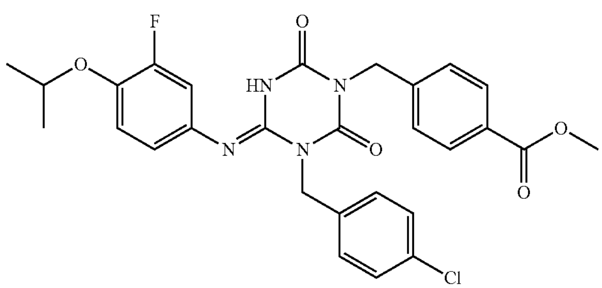 [SMILES: COC(=O)c1ccc(Cn2c(=O)[nH]/c(=N\c3ccc(OC(C)C)c(F)c3)n(Cc3ccc(Cl)cc3)c2=O)cc1] | I-0453 | 2.61 | 553 | 3 |
| 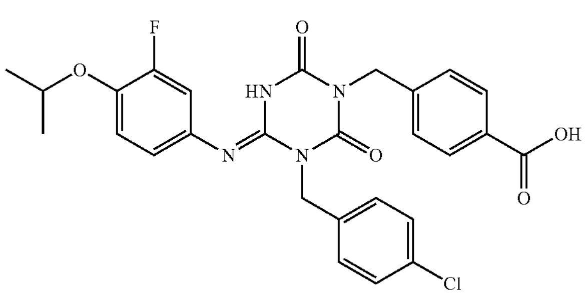 [SMILES: CC(C)Oc1ccc(/N=c2\[nH]c(=O)n(Cc3ccc(C(=O)O)cc3)c(=O)n2Cc2ccc(Cl)cc2)cc1F] | I-0454 | 2.33 | 539 | 3 |
| 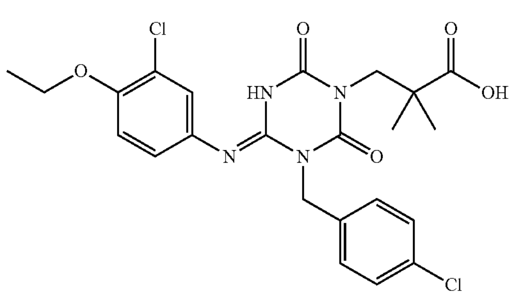 [SMILES: CCOc1ccc(/N=c2\[nH]c(=O)n(CC(C)(C)C(=O)O)c(=O)n2Cc2ccc(Cl)cc2)cc1Cl] | I-0455 | 2.31 | 507 | 2 |

TABLE 95

| Structure | Compound No. | Retention Time (min) | [M + H] | Method |
|---|---|---|---|---|
| 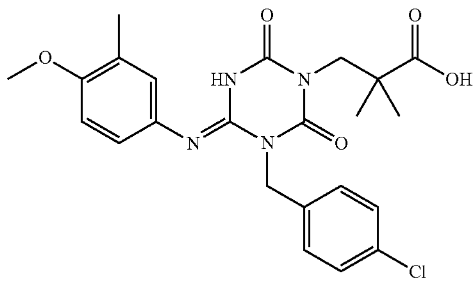 [SMILES: COc1ccc(/N=c2\[nH]c(=O)n(CC(C)(C)C(=O)O)c(=O)n2Cc2ccc(Cl)cc2)cc1C] | I-0456 | 2.10 | 473 | 2 |
| 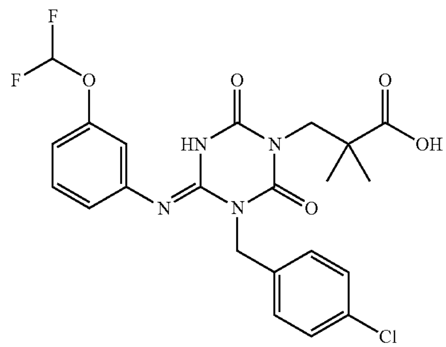 [SMILES: CC(C)(Cn1c(=O)[nH]/c(=N\c2cccc(OC(F)F)c2)n(Cc2ccc(Cl)cc2)c1=O)C(=O)O] | I-0457 | 2.22 | 495 | 2 |
| 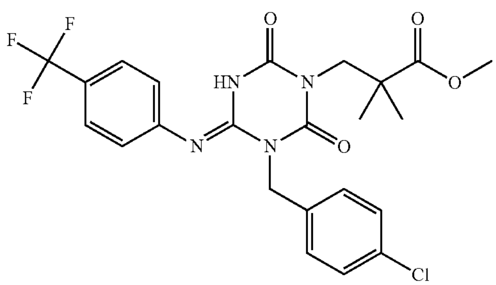 [SMILES: COC(=O)C(C)(C)Cn1c(=O)[nH]/c(=N\c2ccc(C(F)(F)F)cc2)n(Cc2ccc(Cl)cc2)c1=O] | I-0458 | 2.67 | 511 | 2 |
| 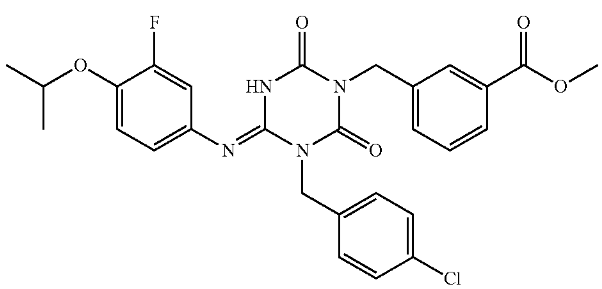 [SMILES: COC(=O)c1cccc(Cn2c(=O)[nH]/c(=N\c3ccc(OC(C)C)c(F)c3)n(Cc3ccc(Cl)cc3)c2=O)c1] | I-0459 | 2.63 | 553 | 3 |
| 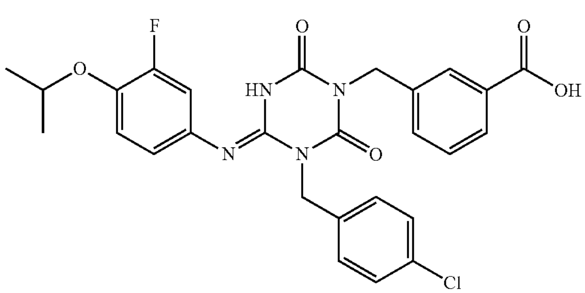 [SMILES: CC(C)Oc1ccc(/N=c2\[nH]c(=O)n(Cc3cccc(C(=O)O)c3)c(=O)n2Cc2ccc(Cl)cc2)cc1F] | I-0460 | 2.36 | 539 | 3 |

TABLE 96

| Structure | Compound No. | Retention Time (min) | [M + H] | Method |
|---|---|---|---|---|
| 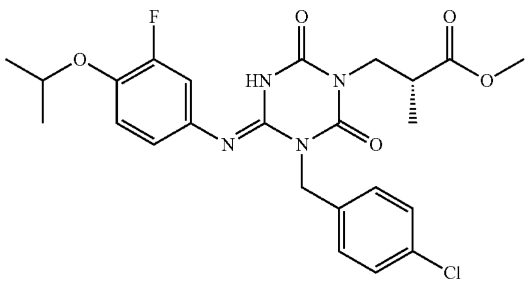 | I-0461 | 2.29 | 505 | 2 |
| 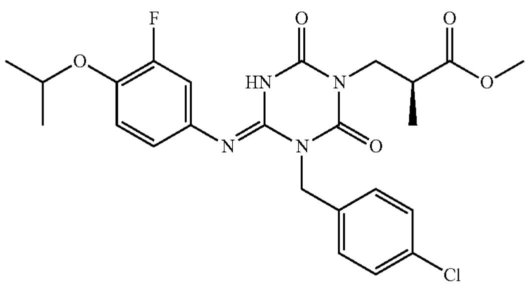 | I-0462 | 2.30 | 505 | 2 |
| 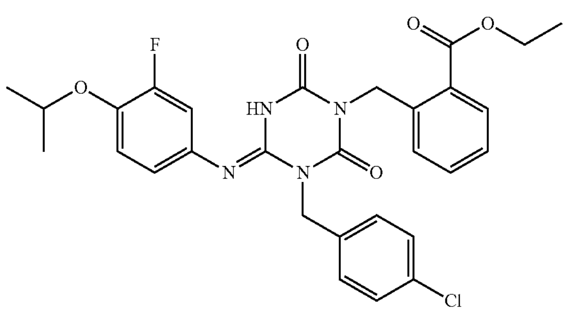 [SMILES: CCOC(=O)c1ccccc1Cn1c(=O)[nH]/c(=N\c2ccc(OC(C)C)c(F)c2)n(Cc2ccc(Cl)cc2)c1=O] | I-0463 | 2.74 | 567 | 3 |
| 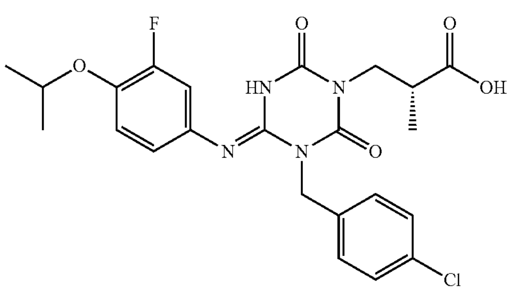 [SMILES: CC(C)Oc1ccc(/N=c2\[nH]c(=O)n(C[C@@H](C)C(=O)O)c(=O)n2Cc2ccc(Cl)cc2)cc1F] | I-0464 | 2.22 | 491 | 3 |
| 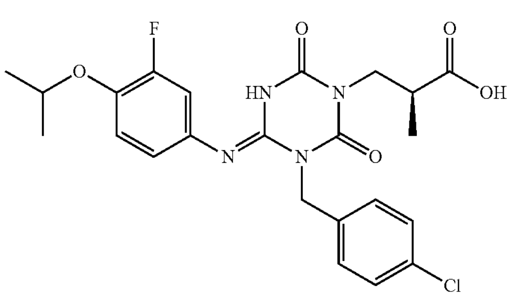 [SMILES: CC(C)Oc1ccc(/N=c2\[nH]c(=O)n(C[C@H](C)C(=O)O)c(=O)n2Cc2ccc(Cl)cc2)cc1F] | I-0465 | 2.22 | 491 | 3 |

TABLE 97

| Structure | Compound No. | Retention Time (min) | [M + H] | Method |
|---|---|---|---|---|
| 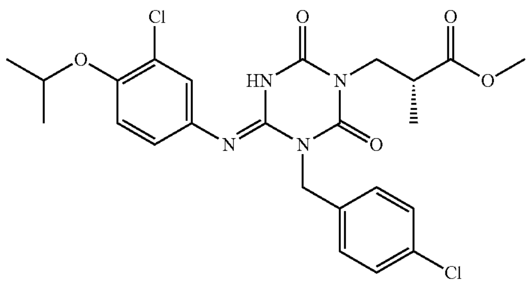 | I-0466 | 2.41 | 521 | 2 |
| 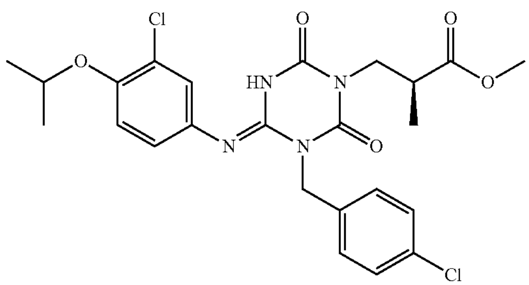 | I-0467 | 2.41 | 521 | 2 |
| 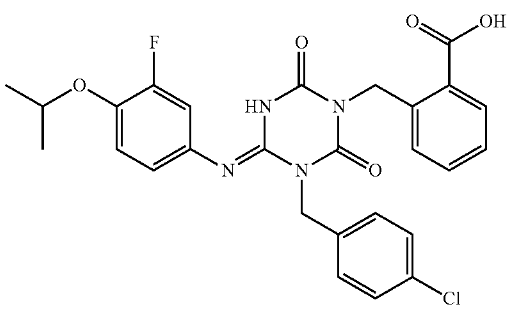 [SMILES: CC(C)Oc1ccc(/N=c2\[nH]c(=O)n(Cc3ccccc3C(=O)O)c(=O)n2Cc2ccc(Cl)cc2)cc1F] | I-0468 | 2.38 | 539 | 3 |
| 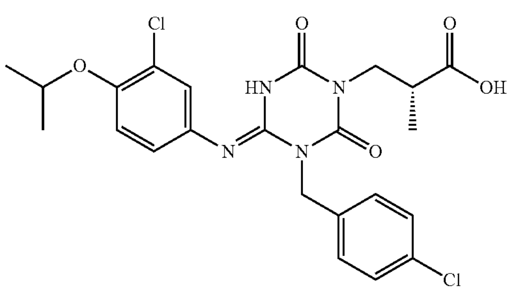 [SMILES: CC(C)Oc1ccc(/N=c2\[nH]c(=O)n(C[C@@H](C)C(=O)O)c(=O)n2Cc2ccc(Cl)cc2)cc1Cl] | I-0469 | 2.34 | 507 | 3 |
| 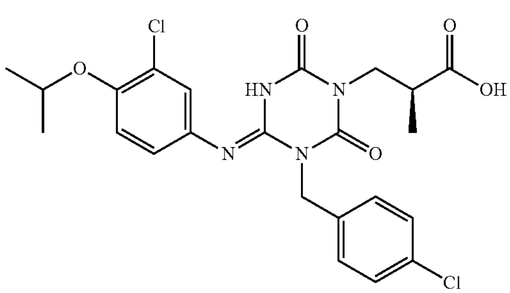 [SMILES: CC(C)Oc1ccc(/N=c2\[nH]c(=O)n(C[C@H](C)C(=O)O)c(=O)n2Cc2ccc(Cl)cc2)cc1Cl] | I-0470 | 2.33 | 507 | 3 |

TABLE 98

| Structure | Compound No. | Retention Time (min) | [M + H] | Method |
|---|---|---|---|---|
| (4-ethoxy-3-methylphenyl)imino triazinedione with 4-chlorobenzyl and methyl 2,2-dimethylpropanoate | I-0471 | 2.33 | 501 | 2 |
| (3,4-dimethylphenyl)imino triazinedione with 4-chlorobenzyl and methyl 2,2-dimethylpropanoate | I-0472 | 2.31 | 471 | 2 |
| (3,4-dimethylphenyl)imino triazinedione with 4-chlorobenzyl and 2,2-dimethylpropanoic acid | I-0473 | 2.02 | 457 | 2 |
| (4-ethoxy-3-methylphenyl)imino triazinedione with 4-chlorobenzyl and 2,2-dimethylpropanoic acid | I-0474 | 2.06 | 487 | 2 |
| (3-chlorophenyl)imino triazinedione with 4-chlorobenzyl and methyl 2,2-dimethylpropanoate | I-0475 | 2.41 | 477 | 2 |

TABLE 99

| Structure | Compound No. | Retention Time (min) | [M + H] | Method |
|---|---|---|---|---|
| 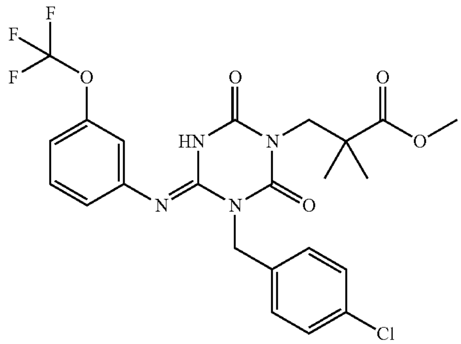 [SMILES: COC(=O)C(C)(C)Cn1c(=O)[nH]/c(=N\c2cccc(OC(F)(F)F)c2)n(Cc2ccc(Cl)cc2)c1=O] | I-0476 | 2.50 | 527 | 2 |
| 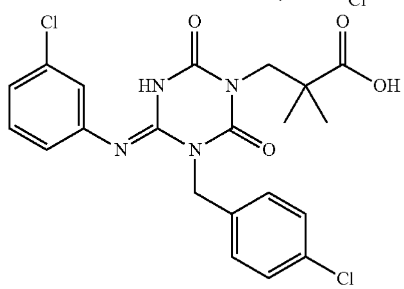 | I-0477 | 2.29 | 463 | 3 |
| 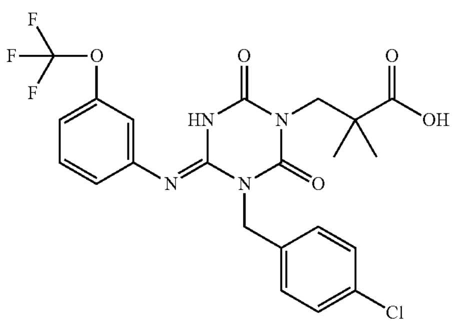 [SMILES: CC(C)(Cn1c(=O)[nH]/c(=N\c2cccc(OC(F)(F)F)c2)n(Cc2ccc(Cl)cc2)c1=O)C(=O)O] | I-0478 | 2.41 | 513 | 3 |
| 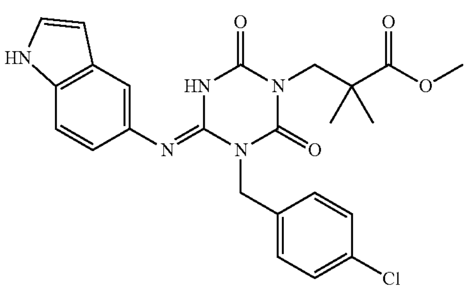 [SMILES: COC(=O)C(C)(C)Cn1c(=O)[nH]/c(=N\c2ccc3[nH]ccc3c2)n(Cc2ccc(Cl)cc2)c1=O] | I-0479 | 2.15 | 482 | 3 |
| 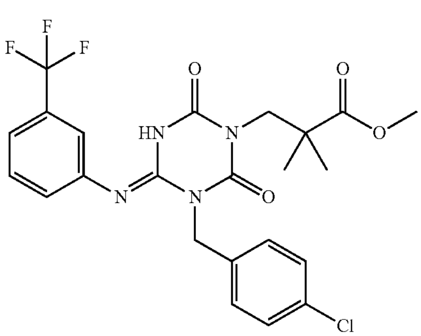 [SMILES: COC(=O)C(C)(C)Cn1c(=O)[nH]/c(=N\c2cccc(C(F)(F)F)c2)n(Cc2ccc(Cl)cc2)c1=O] | I-0480 | 2.63 | 511 | 3 |

TABLE 100

| Structure | Compound No. | Retention Time (min) | [M + H] | Method |
|---|---|---|---|---|
| 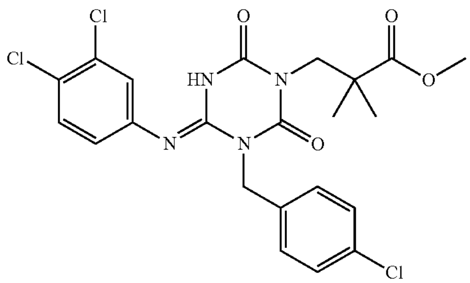 [SMILES: COC(=O)C(C)(C)Cn1c(=O)[nH]/c(=N\c2ccc(Cl)c(Cl)c2)n(Cc2ccc(Cl)cc2)c1=O] | I-0481 | 2.75 | 512 | 3 |
| 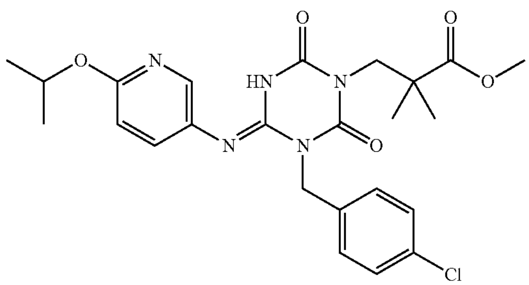 [SMILES: COC(=O)C(C)(C)Cn1c(=O)[nH]/c(=N\c2ccc(OC(C)C)nc2)n(Cc2ccc(Cl)cc2)c1=O] | I-0482 | 1.78 | 502 | 2 |
| 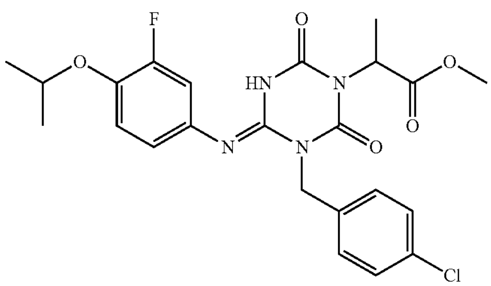 [SMILES: COC(=O)C(C)n1c(=O)[nH]/c(=N\c2ccc(OC(C)C)c(F)c2)n(Cc2ccc(Cl)cc2)c1=O] | I-0483 | 2.42 | 491 | 3 |
| 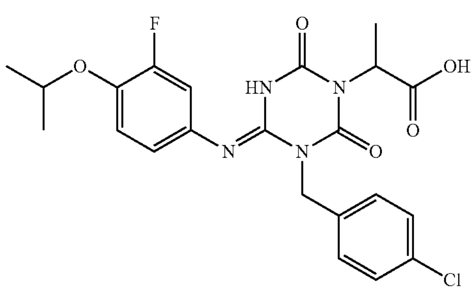 [SMILES: CC(C)Oc1ccc(/N=c2\[nH]c(=O)n(C(C)C(=O)O)c(=O)n2Cc2ccc(Cl)cc2)cc1F] | I-0484 | 2.18 | 477 | 3 |
| 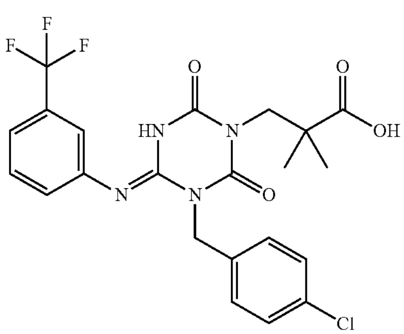 [SMILES: CC(C)(Cn1c(=O)[nH]/c(=N\c2cccc(C(F)(F)F)c2)n(Cc2ccc(Cl)cc2)c1=O)C(=O)O] | I-0485 | 2.20 | 497 | 2 |

TABLE 101

| Structure | Compound No. | Retention Time (min) | [M + H] | Method |
|---|---|---|---|---|
| 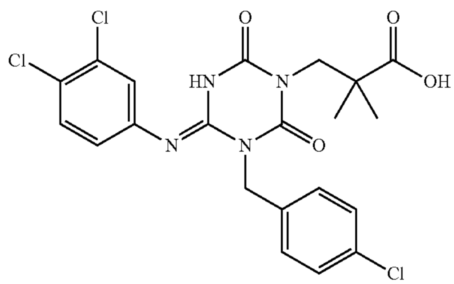 [SMILES: CC(C)(Cn1c(=O)[nH]/c(=N\c2ccc(Cl)c(Cl)c2)n(Cc2ccc(Cl)cc2)c1=O)C(=O)O] | I-0486 | 2.31 | 499 | 2 |
| 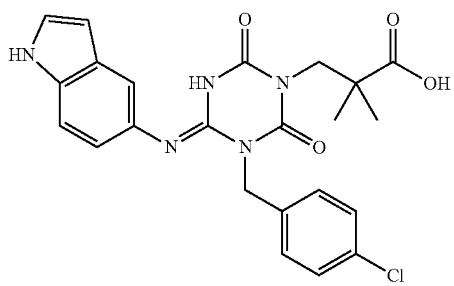 [SMILES: CC(C)(Cn1c(=O)[nH]/c(=N\c2ccc3[nH]ccc3c2)n(Cc2ccc(Cl)cc2)c1=O)C(=O)O] | I-0487 | 1.71 | 468 | 2 |
| 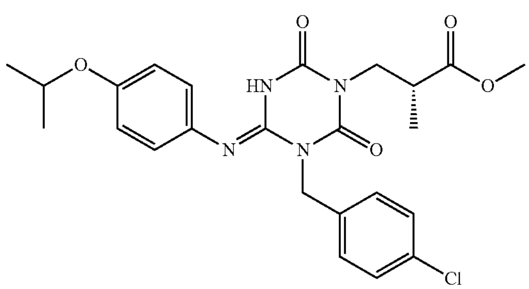 | I-0488 | 2.17 | 487 | 2 |
| 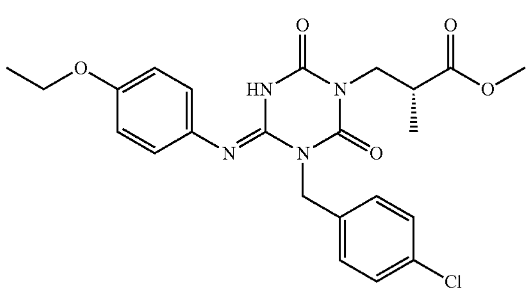 [SMILES: CCOc1ccc(/N=c2\[nH]c(=O)n(C[C@@H](C)C(=O)OC)c(=O)n2Cc2ccc(Cl)cc2)cc1] | I-0489 | 2.06 | 473 | 2 |
| 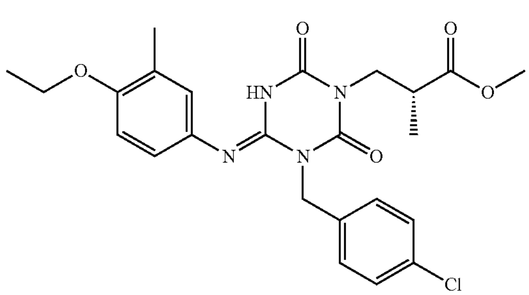 [SMILES: CCOc1ccc(/N=c2\[nH]c(=O)n(C[C@@H](C)C(=O)OC)c(=O)n2Cc2ccc(Cl)cc2)cc1C] | I-0490 | 2.22 | 487 | 2 |

TABLE 102

| Structure | Compound No. | Retention Time (min) | [M + H] | Method |
|---|---|---|---|---|
| 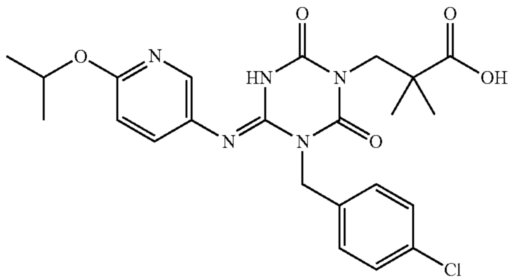 [SMILES: CC(C)Oc1ccc(/N=c2\[nH]c(=O)n(CC(C)(C)C(=O)O)c(=O)n2Cc2ccc(Cl)cc2)cn1] | I-0491 | 1.53 | 488 | 2 |
| 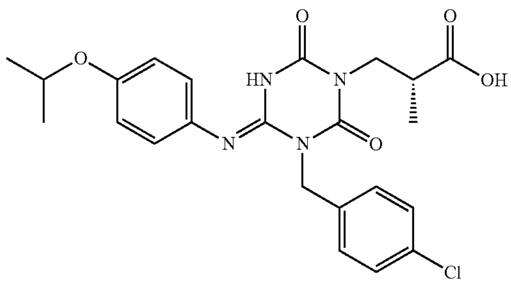 [SMILES: CC(C)Oc1ccc(/N=c2\[nH]c(=O)n(C[C@@H](C)C(=O)O)c(=O)n2Cc2ccc(Cl)cc2)cc1] | I-0492 | 1.93 | 473 | 2 |
| 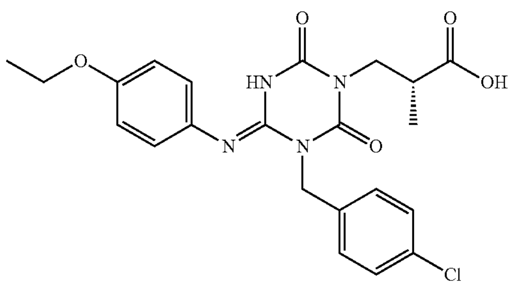 [SMILES: CCOc1ccc(/N=c2\[nH]c(=O)n(C[C@@H](C)C(=O)O)c(=O)n2Cc2ccc(Cl)cc2)cc1] | I-0493 | 1.82 | 459 | 2 |
| 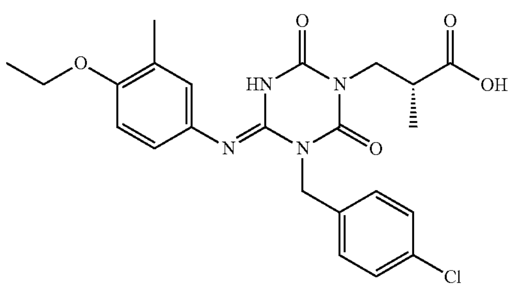 [SMILES: CCOc1ccc(/N=c2\[nH]c(=O)n(C[C@@H](C)C(=O)O)c(=O)n2Cc2ccc(Cl)cc2)cc1C] | I-0494 | 1.98 | 473 | 2 |
| 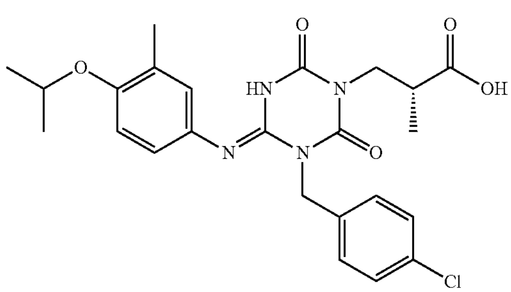 [SMILES: Cc1cc(/N=c2\[nH]c(=O)n(C[C@@H](C)C(=O)O)c(=O)n2Cc2ccc(Cl)cc2)ccc1OC(C)C] | I-0495 | 2.08 | 487 | 2 |

TABLE 103

| Structure | Compound No. | Retention Time (min) | [M + H] | Method |
|---|---|---|---|---|
| 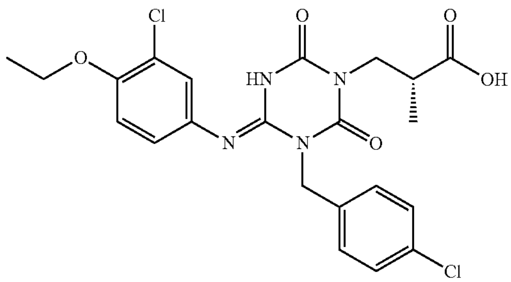 [SMILES: CCOc1ccc(/N=c2\[nH]c(=O)n(C[C@@H](C)C(=O)O)c(=O)n2Cc2ccc(Cl)cc2)cc1Cl] | I-0496 | 2.03 | 493 | 2 |
| 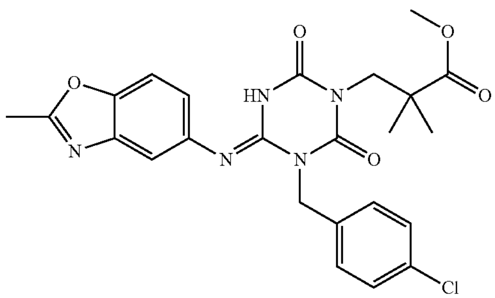 [SMILES: COC(=O)C(C)(C)Cn1c(=O)[nH]/c(=N\c2ccc3oc(C)nc3c2)n(Cc2ccc(Cl)cc2)c1=O] | I-0497 | 1.98 | 498 | 2 |
| 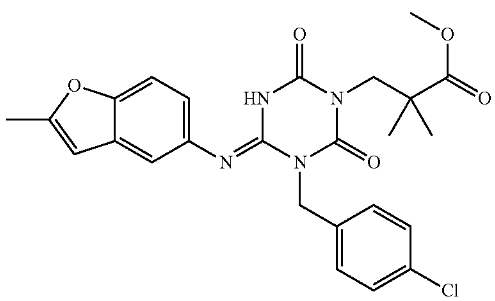 [SMILES: COC(=O)C(C)(C)Cn1c(=O)[nH]/c(=N\c2ccc3oc(C)cc3c2)n(Cc2ccc(Cl)cc2)c1=O] | I-0498 | 2.28 | 497 | 2 |
| 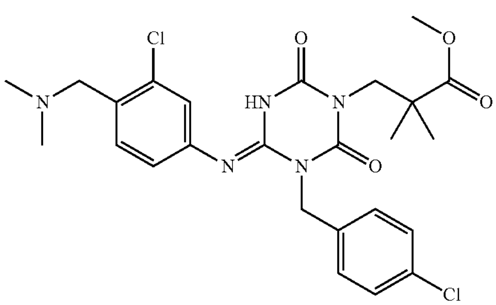 [SMILES: COC(=O)C(C)(C)Cn1c(=O)[nH]/c(=N\c2ccc(CN(C)C)c(Cl)c2)n(Cc2ccc(Cl)cc2)c1=O] | I-0499 | 1.62 | 534 | 2 |
| 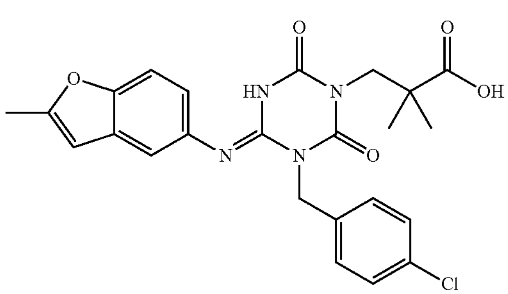 | I-0500 | 2.00 | 483 | 2 |

TABLE 104

| Structure | Compound No. | Retention Time (min) | [M + H] | Method |
|---|---|---|---|---|
| 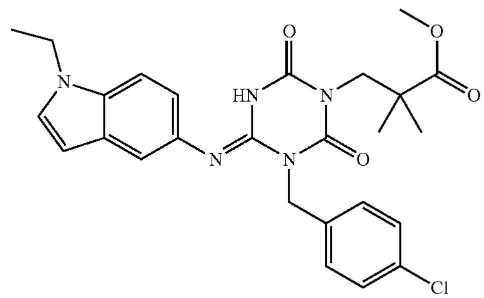 [SMILES: CCn1ccc2cc(/N=c3\[nH]c(=O)n(CC(C)(C)C(=O)OC)c(=O)n3Cc3ccc(Cl)cc3)ccc21] | I-0501 | 2.23 | 510 | 2 |
| 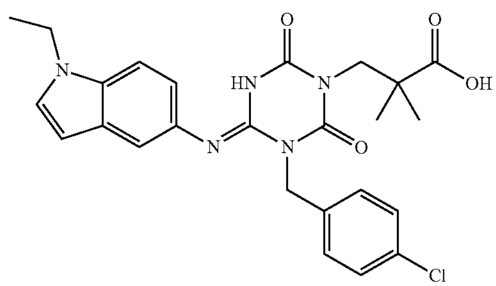 [SMILES: CCn1ccc2cc(/N=c3\[nH]c(=O)n(CC(C)(C)C(=O)O)c(=O)n3Cc3ccc(Cl)cc3)ccc21] | I-0502 | 1.96 | 496 | 2 |
| 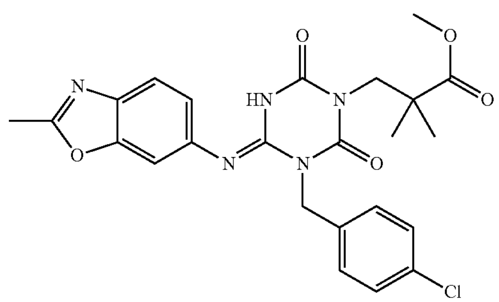 [SMILES: COC(=O)C(C)(C)Cn1c(=O)[nH]/c(=N\c2ccc3nc(C)oc3c2)n(Cc2ccc(Cl)cc2)c1=O] | I-0503 | 2.04 | 498 | 2 |
| 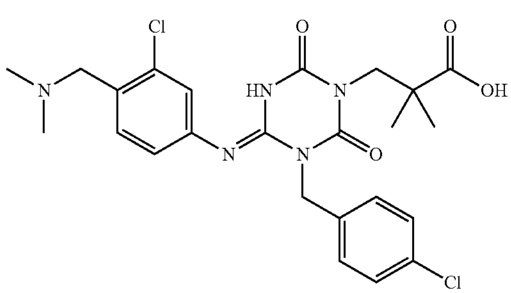 [SMILES: CN(C)Cc1ccc(/N=c2\[nH]c(=O)n(CC(C)(C)C(=O)O)c(=O)n2Cc2ccc(Cl)cc2)cc1Cl] | I-0504 | 1.43 | 520 | 2 |
| 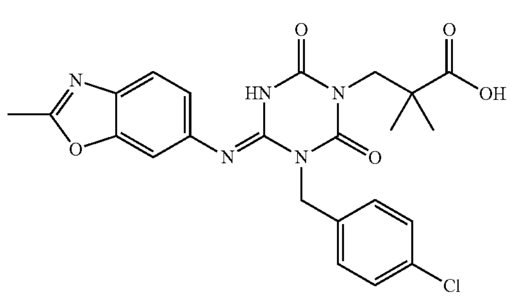 | I-0505 | 1.75 | 484 | 2 |

TABLE 105
| Structure | Compound No. | Retention Time (min) | [M + H] | Method |
|---|---|---|---|---|
| 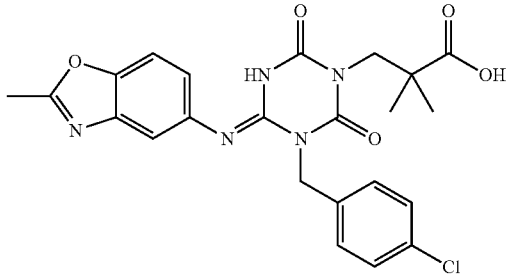 [SMILES: Cc1nc2cc(/N=c3\[nH]c(=O)n(CC(C)(C)C(=O)O)c(=O)n3Cc3ccc(Cl)cc3)ccc2o1] | I-0506 | 1.74 | 484 | 2 |
| 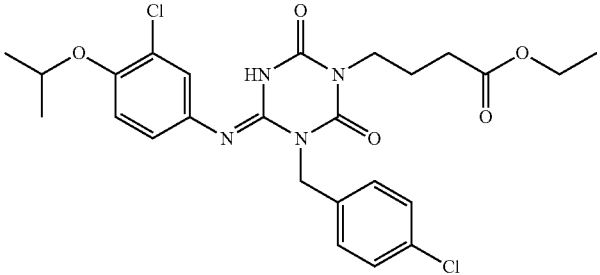 | I-0507 | 2.50 | 535 | 2 |
| 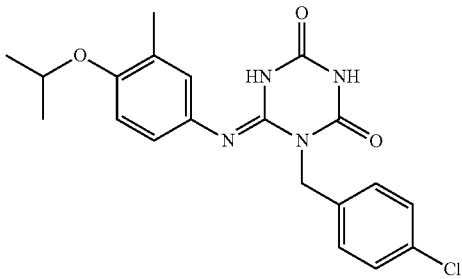 | I-0508 | 2.03 | 401 | 2 |
| 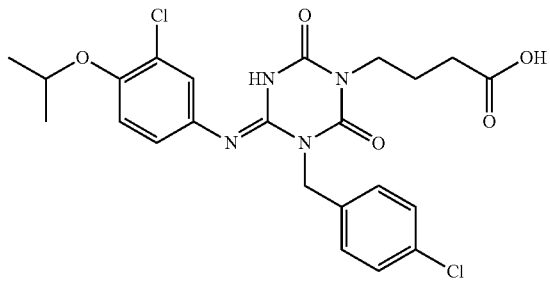 | I-0509 | 2.13 | 507 | 2 |
| 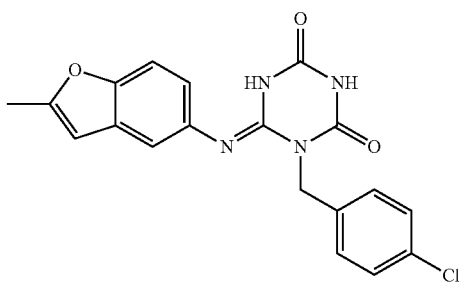 [SMILES: Cc1cc2cc(/N=c3\[nH]c(=O)[nH]c(=O)n3Cc3ccc(Cl)cc3)ccc2o1] | I-0510 | 1.85 | 383 | 2 |

TABLE 106

| Structure | Compound No. | Retention Time (min) | [M + H] | Method |
|---|---|---|---|---|
| 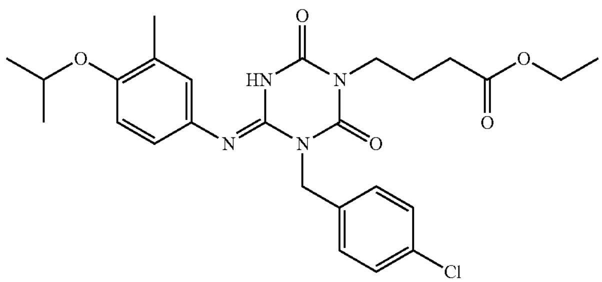 [SMILES: CCOC(=O)CCCn1c(=O)[nH]/c(=N\c2ccc(OC(C)C)c(C)c2)n(Cc2ccc(Cl)cc2)c1=O] | I-0511 | 2.41 | 515 | 2 |
| 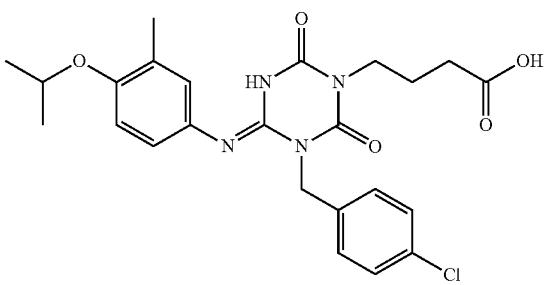 [SMILES: Cc1cc(/N=c2\[nH]c(=O)n(CCCC(=O)O)c(=O)n2Cc2ccc(Cl)cc2)ccc1OC(C)C] | I-0512 | 2.06 | 487 | 2 |
| 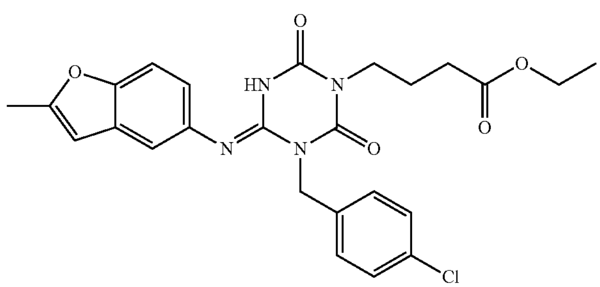 [SMILES: CCOC(=O)CCCn1c(=O)[nH]/c(=N\c2ccc3oc(C)cc3c2)n(Cc2ccc(Cl)cc2)c1=O] | I-0513 | 2.25 | 497 | 2 |
| 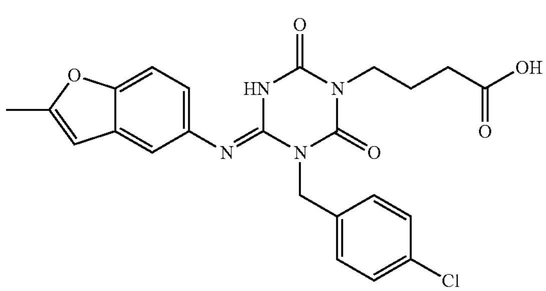 [SMILES: Cc1cc2cc(/N=c3\[nH]c(=O)n(CCCC(=O)O)c(=O)n3Cc3ccc(Cl)cc3)ccc2o1] | I-0514 | 1.89 | 469 | 2 |
| 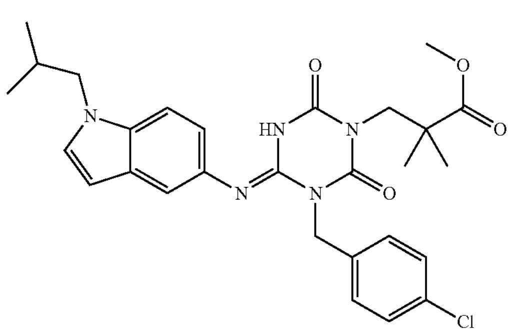 [SMILES: COC(=O)C(C)(C)Cn1c(=O)[nH]/c(=N\c2ccc3c(ccn3CC(C)C)c2)n(Cc2ccc(Cl)cc2)c1=O] | I-0515 | 2.44 | 538 | 2 |

TABLE 107

| Structure | Compound No. | Retention Time (min) | [M + H] | Method |
|---|---|---|---|---|
| 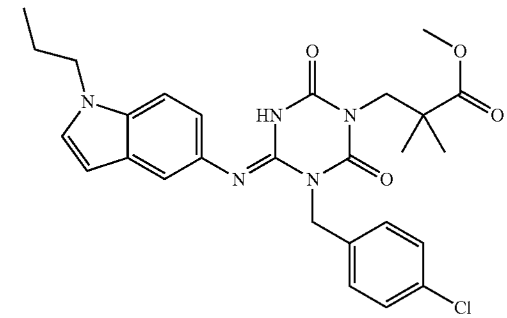 [SMILES: CCCn1ccc2cc(/N=c3\[nH]c(=O)n(CC(C)(C)C(=O)OC)c(=O)n3Cc3ccc(Cl)cc3)ccc21] | I-0516 | 2.34 | 524 | 2 |
| 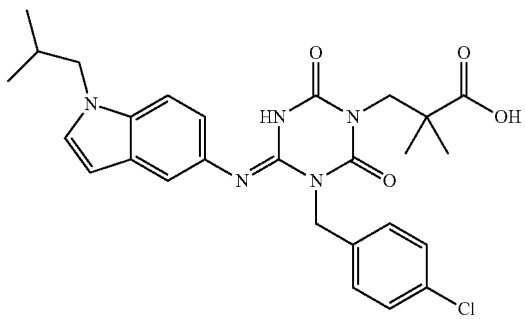 [SMILES: CC(C)Cn1ccc2cc(/N=c3\[nH]c(=O)n(CC(C)(C)C(=O)O)c(=O)n3Cc3ccc(Cl)cc3)ccc21] | I-0517 | 2.17 | 524 | 2 |
| 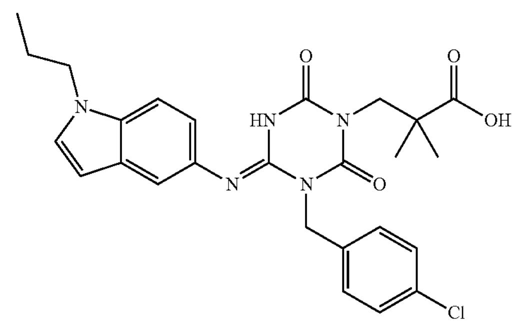 [SMILES: CCCn1ccc2cc(/N=c3\[nH]c(=O)n(CC(C)(C)C(=O)O)c(=O)n3Cc3ccc(Cl)cc3)ccc21] | I-0518 | 2.07 | 510 | 2 |
| 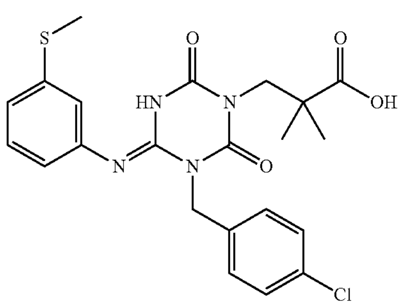 [SMILES: CSc1cccc(/N=c2\[nH]c(=O)n(CC(C)(C)C(=O)O)c(=O)n2Cc2ccc(Cl)cc2)c1] | I-0519 | 2.23 | 475 | 3 |
| 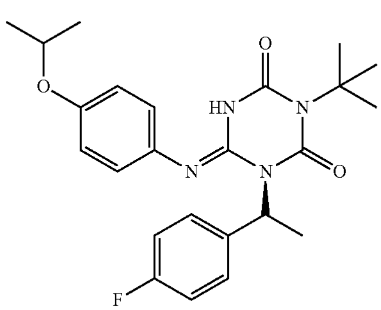 | I-0520 | 2.67 | 441 | 3 |

TABLE 108

| Structure | Compound No. | Retention Time (min) | [M + H] | Method |
|---|---|---|---|---|
| 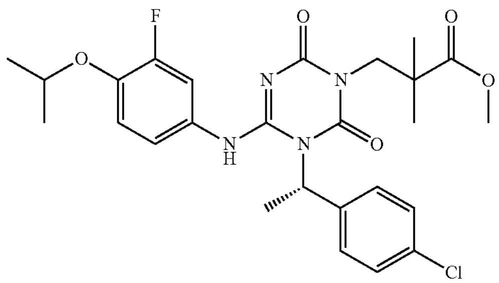 [SMILES: COC(=O)C(C)(C)Cn1c(=O)nc(Nc2ccc(OC(C)C)c(F)c2)n([C@@H](C)c2ccc(Cl)cc2)c1=O] | I-0521 | 2.75 | 533 | 3 |
| 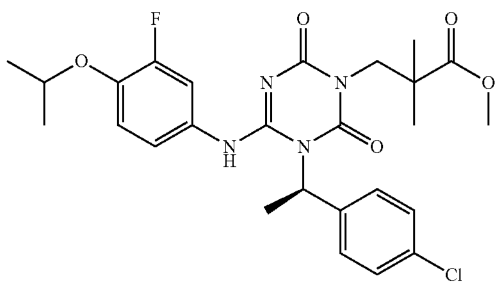 [SMILES: COC(=O)C(C)(C)Cn1c(=O)nc(Nc2ccc(OC(C)C)c(F)c2)n([C@H](C)c2ccc(Cl)cc2)c1=O] | I-0522 | 2.75 | 533 | 3 |
| 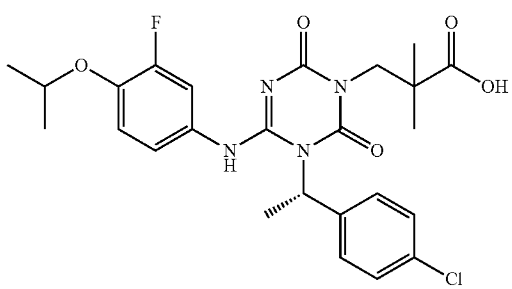 [SMILES: CC(C)Oc1ccc(Nc2nc(=O)n(CC(C)(C)C(=O)O)c(=O)n2[C@@H](C)c2ccc(Cl)cc2)cc1F] | I-0523 | 2.50 | 519 | 3 |
| 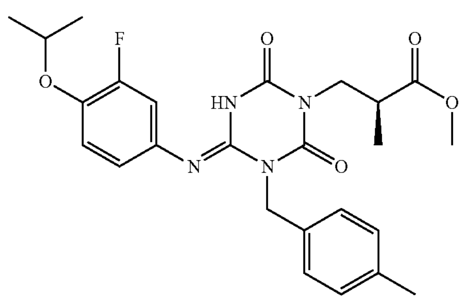 [SMILES: COC(=O)[C@@H](C)Cn1c(=O)[nH]/c(=N\c2ccc(OC(C)C)c(F)c2)n(Cc2ccc(C)cc2)c1=O] | I-0524 | 2.40 | 485 | 3 |
| 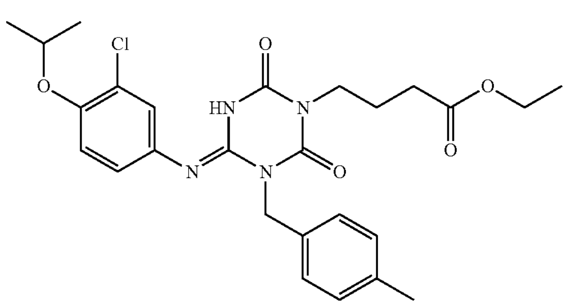 [SMILES: CCOC(=O)CCCn1c(=O)[nH]/c(=N\c2ccc(OC(C)C)c(Cl)c2)n(Cc2ccc(C)cc2)c1=O] | I-0525 | 2.62 | 516 | 3 |

TABLE 109

| Structure | Compound No. | Retention Time (min) | [M + H] | Method |
|---|---|---|---|---|
| 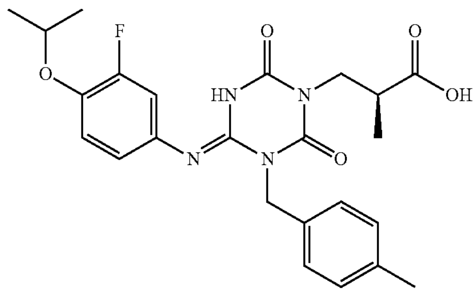 [SMILES: Cc1ccc(Cn2c(=O)n(C[C@H](C)C(=O)O)c(=O)[nH]/c2=N\c2ccc(OC(C)C)c(F)c2)cc1] | I-0526 | 2.18 | 471 | 3 |
| 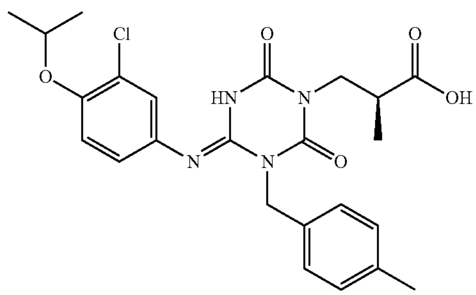 [SMILES: Cc1ccc(Cn2c(=O)n(C[C@H](C)C(=O)O)c(=O)[nH]/c2=N\c2ccc(OC(C)C)c(Cl)c2)cc1] | I-0527 | 2.28 | 487 | 3 |
| 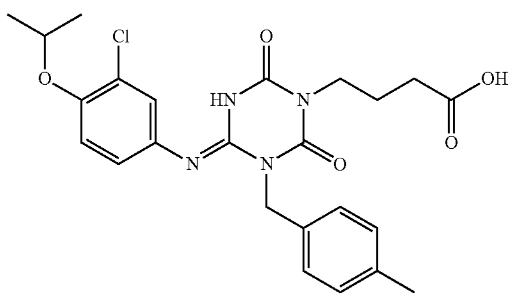 [SMILES: Cc1ccc(Cn2c(=O)n(CCCC(=O)O)c(=O)[nH]/c2=N\c2ccc(OC(C)C)c(Cl)c2)cc1] | I-0528 | 2.25 | 487 | 3 |
| 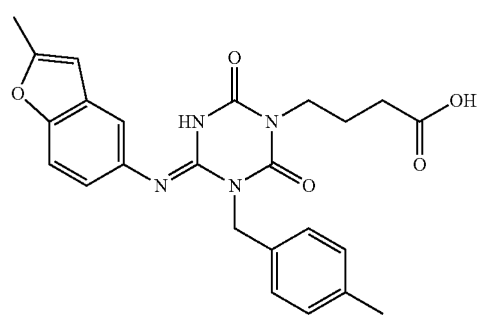 [SMILES: Cc1ccc(Cn2c(=O)n(CCCC(=O)O)c(=O)[nH]/c2=N\c2ccc3oc(C)cc3c2)cc1] | I-0529 | 2.00 | 449 | 3 |
| 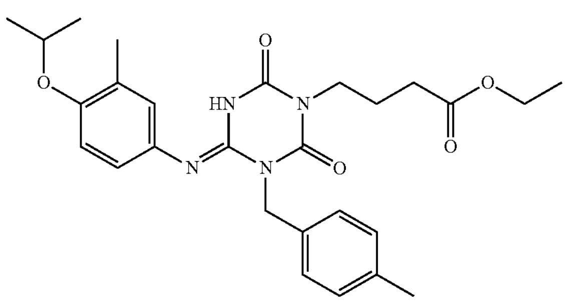 [SMILES: CCOC(=O)CCCn1c(=O)[nH]/c(=N\c2ccc(OC(C)C)c(C)c2)n(Cc2ccc(C)cc2)c1=O] | I-0530 | 2.55 | 495 | 3 |

TABLE 110

| Structure | Compound No. | Retention Time (min) | [M + H] | Method |
|---|---|---|---|---|
| 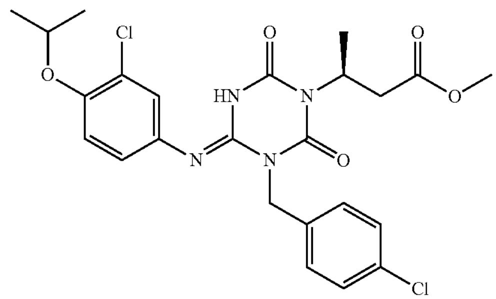 [SMILES: COC(=O)C[C@H](C)n1c(=O)[nH]/c(=N\c2ccc(OC(C)C)c(Cl)c2)n(Cc2ccc(Cl)cc2)c1=O] | I-0531 | 2.64 | 521 | 3 |
| 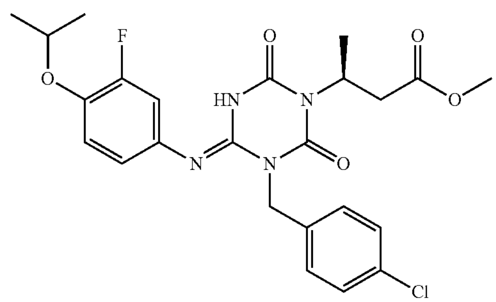 | I-0532 | 2.53 | 505 | 3 |
| 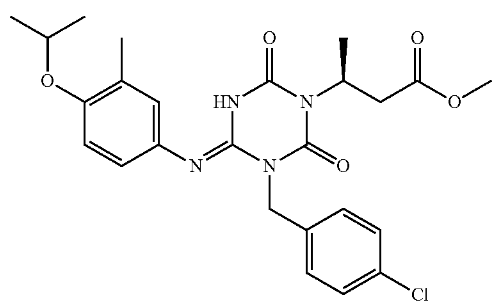 | I-0533 | 2.57 | 501 | 3 |
| 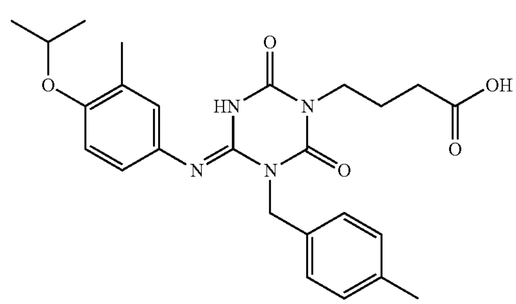 | I-0534 | 2.20 | 467 | 3 |
| 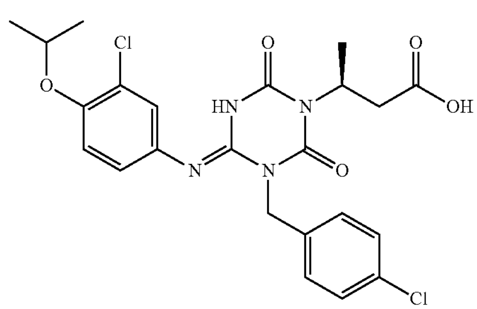 [SMILES: CC(C)Oc1ccc(/N=c2\[nH]c(=O)n([C@@H](C)CC(=O)O)c(=O)n2Cc2ccc(Cl)cc2)cc1Cl] | I-0535 | 2.38 | 507 | 3 |

TABLE 111

| Structure | Compound No. | Retention Time (min) | [M + H] | Method |
|---|---|---|---|---|
| (structure) | I-0536 | 2.26 | 491 | 3 |
| (structure) | I-0537 | 2.30 | 487 | 3 |
| (structure) | I-0538 | 2.18 | 487 | 2 |
| (structure) | I-0539 | 2.07 | 473 | 2 |
| (structure) | I-0540 | 2.33 | 501 | 2 |

TABLE 112

| Structure | Compound No. | Retention Time (min) | [M + H] | Method |
|---|---|---|---|---|
| 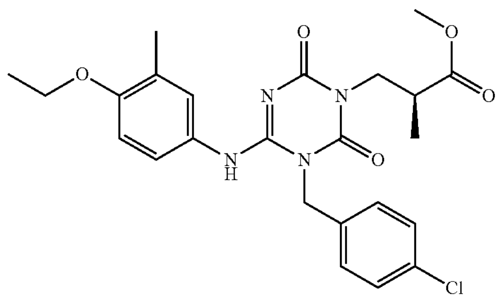 [SMILES: CCOc1ccc(Nc2nc(=O)n(C[C@H](C)C(=O)OC)c(=O)n2Cc2ccc(Cl)cc2)cc1C] | I-0541 | 2.23 | 487 | 2 |
| 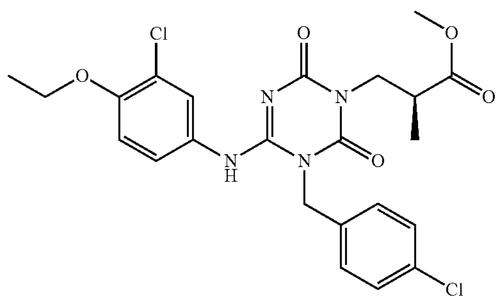 | I-0542 | 2.29 | 507 | 2 |
| 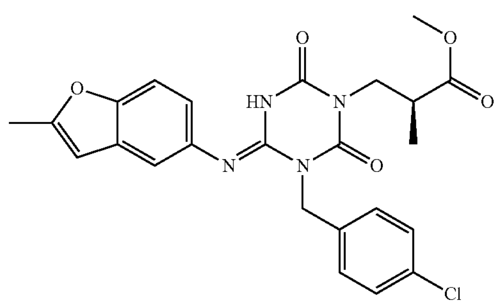 [SMILES: COC(=O)[C@@H](C)Cn1c(=O)[nH]/c(=N\c2ccc3oc(C)cc3c2)n(Cc2ccc(Cl)cc2)c1=O] | I-0543 | 2.16 | 483 | 2 |
| 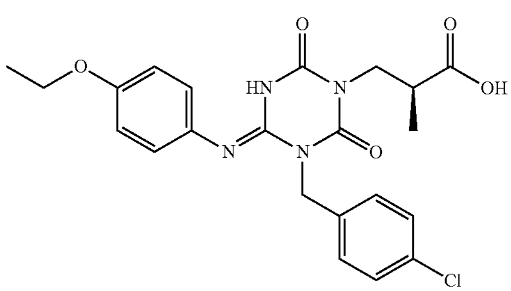 | I-0544 | 1.82 | 459 | 2 |
| 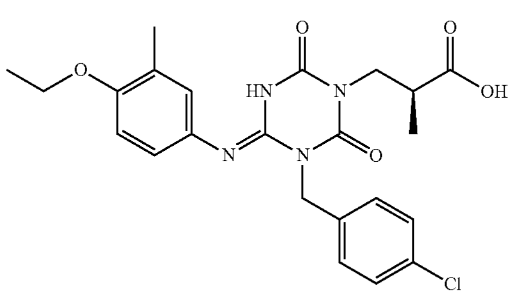 | I-0545 | 1.98 | 473 | 2 |

TABLE 113

| Structure | Compound No. | Retention Time (min) | [M + H] | Method |
|---|---|---|---|---|
| (4-isopropoxyphenyl)imino-triazinedione with 4-chlorobenzyl and (S)-propanoic acid | I-0546 | 1.91 | 473 | 2 |
| (4-isopropoxy-3-methylphenyl)imino-triazinedione with 4-chlorobenzyl and (S)-propanoic acid | I-0547 | 2.09 | 487 | 2 |
| (3-chloro-4-ethoxyphenyl)imino-triazinedione with 4-chlorobenzyl and (S)-propanoic acid | I-0548 | 2.03 | 493 | 2 |
| (2-methylbenzofuran-5-yl)imino-triazinedione with 4-chlorobenzyl and (S)-propanoic acid | I-0549 | 1.91 | 469 | 2 |
| (4-isopropoxyphenyl)imino-triazinedione with 4-chlorobenzyl and 2,2-dimethylpropanoic acid | I-0550 | 1.99 | 487 | 2 |

TABLE 114

| Structure | Compound No. | Retention Time (min) | [M + H] | Method |
|---|---|---|---|---|
| (structure) | I-0551 | 1.90 | 473 | 2 |
| (structure) | I-0552 | 1.97 | 495 | 2 |
| (structure) | I-0553 | 1.99 | 475 | 2 |
| (structure) | I-0554 | 2.41 | 533 | 2 |
| (structure) | I-0555 | 2.76 | 547 | 2 |

TABLE 115

| Structure | Compound No. | Retention Time (min) | [M + H] | Method |
|---|---|---|---|---|
| 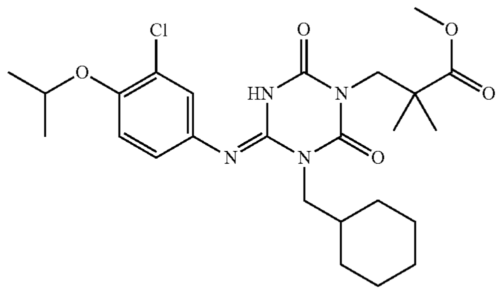 [SMILES: COC(=O)C(C)(C)Cn1c(=O)[nH]/c(=N\c2ccc(OC(C)C)c(Cl)c2)n(CC2CCCCC2)c1=O] | I-0556 | 2.53 | 507 | 2 |
| 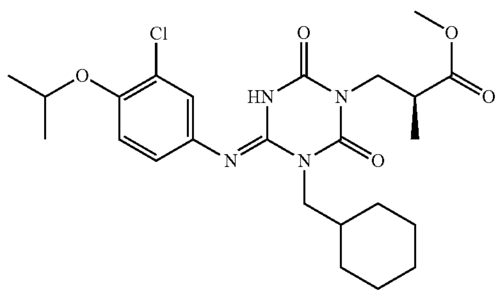 | I-0557 | 2.42 | 493 | 2 |
| 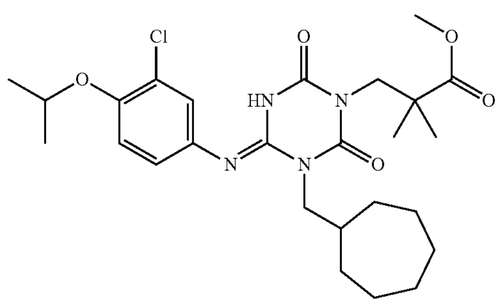 [SMILES: COC(=O)C(C)(C)Cn1c(=O)[nH]/c(=N\c2ccc(OC(C)C)c(Cl)c2)n(CC2CCCCCC2)c1=O] | I-0558 | 2.65 | 521 | 2 |
| 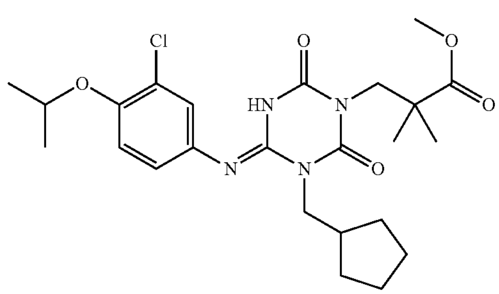 [SMILES: COC(=O)C(C)(C)Cn1c(=O)[nH]/c(=N\c2ccc(OC(C)C)c(Cl)c2)n(CC2CCCC2)c1=O] | I-0559 | 2.43 | 493 | 2 |
| 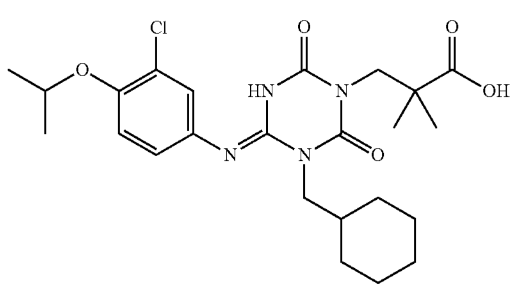 [SMILES: CC(C)Oc1ccc(/N=c2\[nH]c(=O)n(CC(C)(C)C(=O)O)c(=O)n2CC2CCCCC2)cc1Cl] | I-0560 | 2.23 | 493 | 2 |

TABLE 116

| Structure | Compound No. | Retention Time (min) | [M + H] | Method |
|---|---|---|---|---|
| 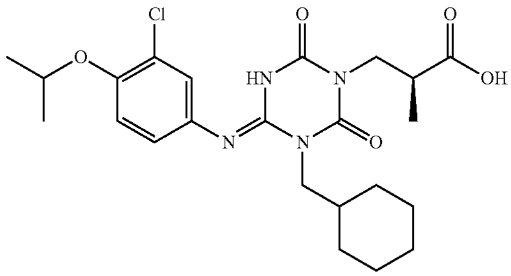 [SMILES: CC(C)Oc1ccc(/N=c2\[nH]c(=O)n(C[C@H](C)C(=O)O)c(=O)n2CC2CCCCC2)cc1Cl] | I-0561 | 2.16 | 479 | 2 |
| 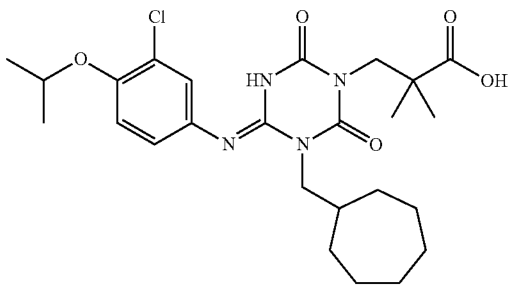 [SMILES: CC(C)Oc1ccc(/N=c2\[nH]c(=O)n(CC(C)(C)C(=O)O)c(=O)n2CC2CCCCCC2)cc1Cl] | I-0562 | 2.35 | 507 | 2 |
| 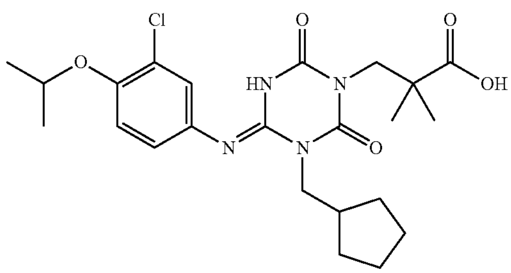 [SMILES: CC(C)Oc1ccc(/N=c2\[nH]c(=O)n(CC(C)(C)C(=O)O)c(=O)n2CC2CCCC2)cc1Cl] | I-0563 | 2.12 | 479 | 2 |
| 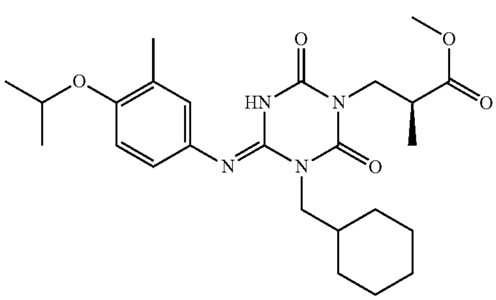 [SMILES: COC(=O)[C@@H](C)Cn1c(=O)[nH]/c(=N\c2ccc(OC(C)C)c(C)c2)n(CC2CCCCC2)c1=O] | I-0564 | 2.37 | 473 | 2 |
| 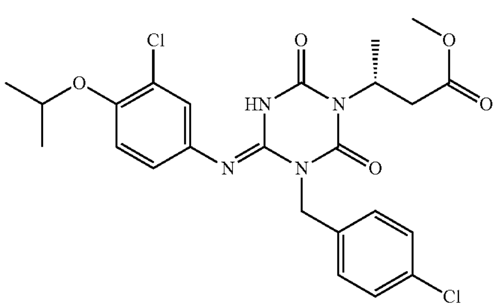 [SMILES: COC(=O)C[C@@H](C)n1c(=O)[nH]/c(=N\c2ccc(OC(C)C)c(Cl)c2)n(Cc2ccc(Cl)cc2)c1=O] | I-0565 | 2.44 | 521 | 2 |

TABLE 117

| Structure | Compound No. | Retention Time (min) | [M + H] | Method |
|---|---|---|---|---|
| 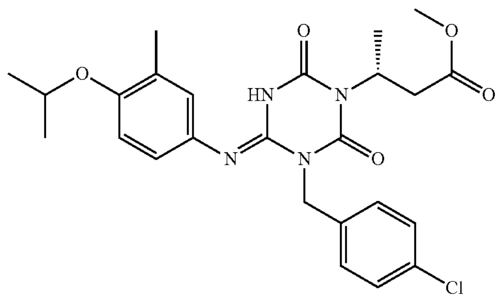 [SMILES: COC(=O)C[C@@H](C)n1c(=O)[nH]/c(=N\c2ccc(OC(C)C)c(C)c2)n(Cc2ccc(Cl)cc2)c1=O] | I-0566 | 2.37 | 501 | 2 |
| 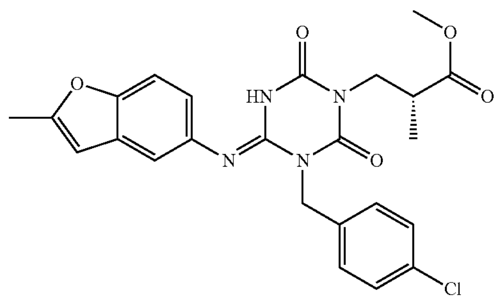 [SMILES: COC(=O)[C@H](C)Cn1c(=O)[nH]/c(=N\c2ccc3oc(C)cc3c2)n(Cc2ccc(Cl)cc2)c1=O] | I-0567 | 2.16 | 483 | 2 |
| 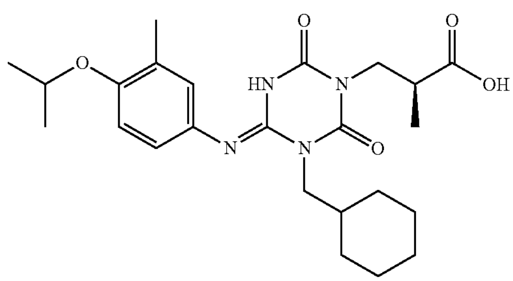 [SMILES: Cc1cc(/N=c2\[nH]c(=O)n(C[C@H](C)C(=O)O)c(=O)n2CC2CCCCC2)ccc1OC(C)C] | I-0568 | 2.09 | 459 | 2 |
| 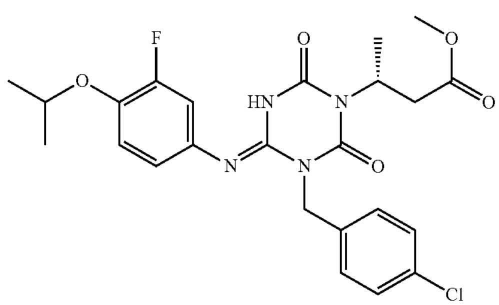 [SMILES: COC(=O)C[C@@H](C)n1c(=O)[nH]/c(=N\c2ccc(OC(C)C)c(F)c2)n(Cc2ccc(Cl)cc2)c1=O] | I-0569 | 2.34 | 505 | 2 |
| 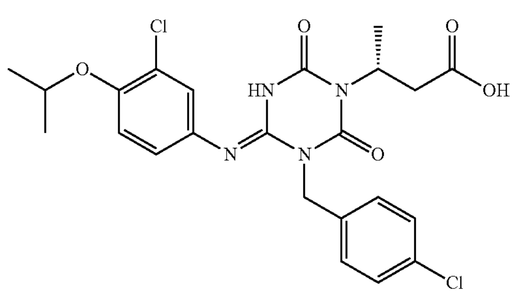 | I-0570 | 2.18 | 507 | 2 |

TABLE 118

| Structure | Compound No. | Retention Time (min) | [M + H] | Method |
|---|---|---|---|---|
| 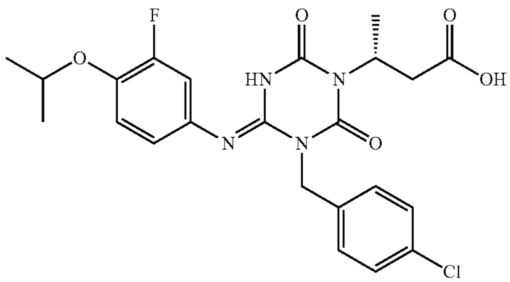 [SMILES: CC(C)Oc1ccc(/N=c2\[nH]c(=O)n([C@H](C)CC(=O)O)c(=O)n2Cc2ccc(Cl)cc2)cc1Cl] | I-0571 | 2.28 | 491 | 3 |
| 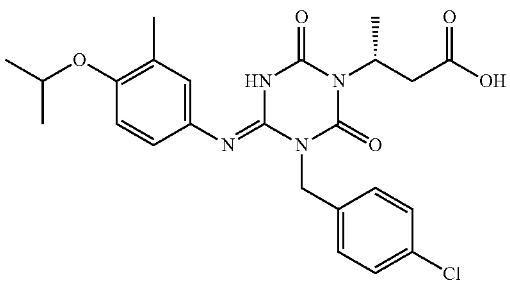 [SMILES: Cc1cc(/N=c2\[nH]c(=O)n([C@H](C)CC(=O)O)c(=O)n2Cc2ccc(Cl)cc2)ccc1OC(C)C] | I-0572 | 2.32 | 487 | 3 |
| 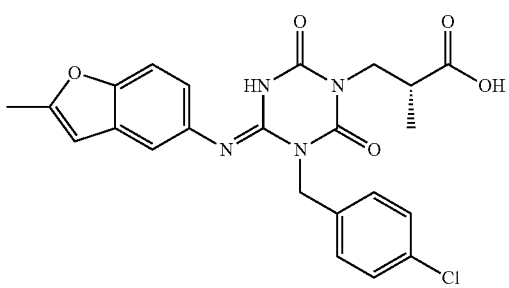 [SMILES: Cc1cc2cc(/N=c3\[nH]c(=O)n(C[C@@H](C)C(=O)O)c(=O)n3Cc3ccc(Cl)cc3)ccc2o1] | I-0573 | 2.11 | 469 | 3 |
| 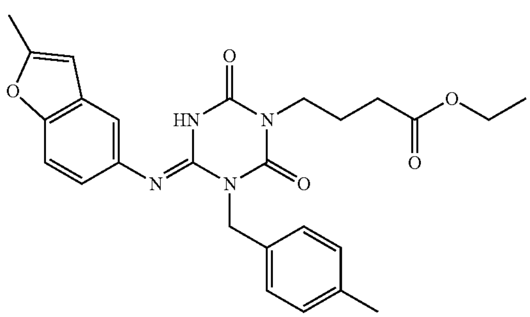 [SMILES: CCOC(=O)CCCn1c(=O)[nH]/c(=N\c2ccc3oc(C)cc3c2)n(Cc2ccc(C)cc2)c1=O] | I-0574 | 2.41 | 477 | 3 |
| 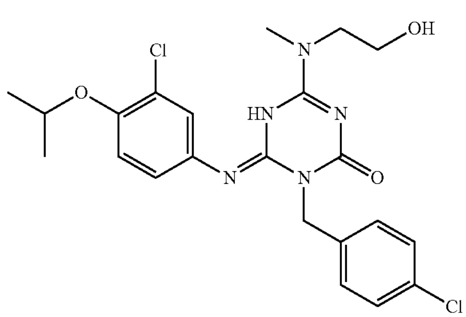 [SMILES: CC(C)Oc1ccc(/N=c2\[nH]c(N(C)CCO)nc(=O)n2Cc2ccc(Cl)cc2)cc1Cl] | I-0575 | 1.74 | 478 | 2 |

TABLE 119

| Structure | Compound No. | Retention Time (min) | [M + H] | Method |
|---|---|---|---|---|
| 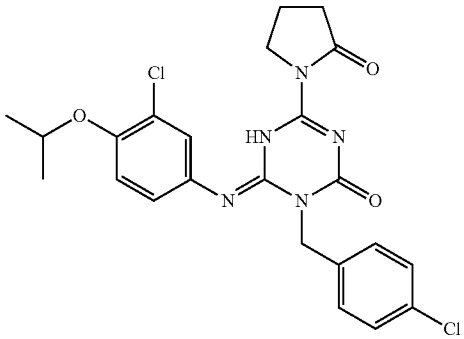 [SMILES: CC(C)Oc1ccc(/N=c2\[nH]c(N3CCCC3=O)nc(=O)n2Cc2ccc(Cl)cc2)cc1Cl] | I-0576 | 2.44 | 488 | 2 |
| 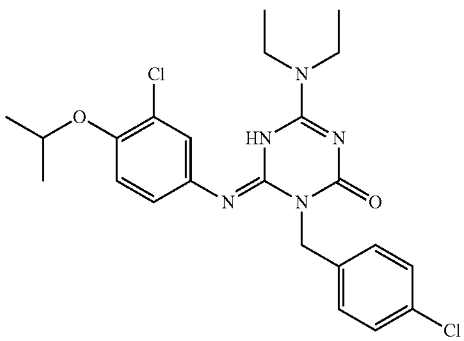 [SMILES: CCN(CC)c1nc(=O)n(Cc2ccc(Cl)cc2)/c(=N/c2ccc(OC(C)C)c(Cl)c2)[nH]1] | I-0577 | 2.04 | 476 | 2 |
| 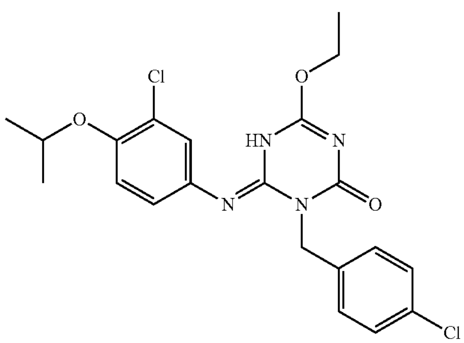 [SMILES: CCOc1nc(=O)n(Cc2ccc(Cl)cc2)/c(=N/c2ccc(OC(C)C)c(Cl)c2)[nH]1] | I-0578 | 2.21 | 449 | 2 |
| 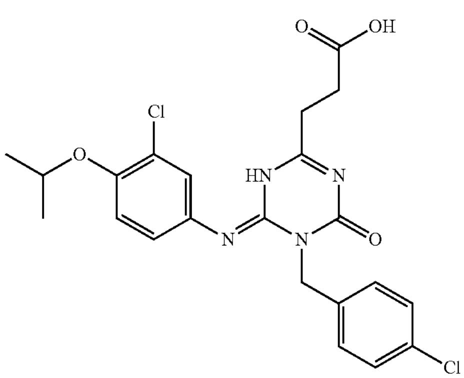 [SMILES: CC(C)Oc1ccc(/N=c2\[nH]c(CCC(=O)O)nc(=O)n2Cc2ccc(Cl)cc2)cc1Cl] | I-0579 | 2.07 | 477 | 2 |

TABLE 119-continued

| Structure | Compound No. | Retention Time (min) | [M + H] | Method |
|---|---|---|---|---|
| (structure) | I-0580 | 2.28 | 419 | 2 |

TABLE 120

| Structure | Compound No. | Retention Time (min) | [M + H] | Method |
|---|---|---|---|---|
| (structure) | I-0581 | 1.78 | 463 | 2 |
| (structure) | I-0582 | 1.62 | 506 | 2 |
| (structure) | I-0583 | 1.72 | 505 | 2 |

TABLE 120-continued

| Structure | Compound No. | Retention Time (min) | [M + H] | Method |
|---|---|---|---|---|
| 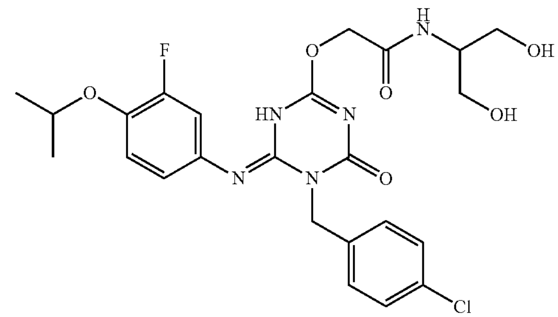 [SMILES: CC(C)Oc1ccc(/N=c2\[nH]c(OCC(=O)NC(CO)CO)nc(=O)n2Cc2ccc(Cl)cc2)cc1F] | I-0584 | 1.56 | 536 | 2 |
| 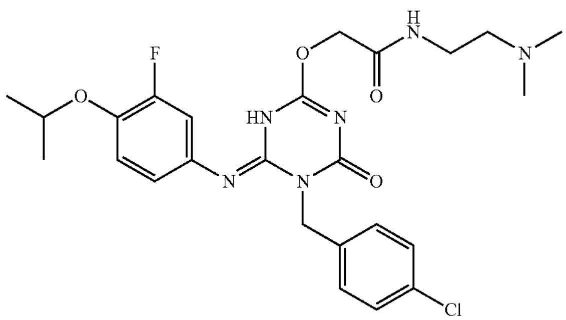 [SMILES: CC(C)Oc1ccc(/N=c2\[nH]c(OCC(=O)NCCN(C)C)nc(=O)n2Cc2ccc(Cl)cc2)cc1F] | I-0585 | 1.40 | 533 | 2 |

TABLE 121

| Structure | Compound No. | Retention Time (min) | [M + H] | Method |
|---|---|---|---|---|
| 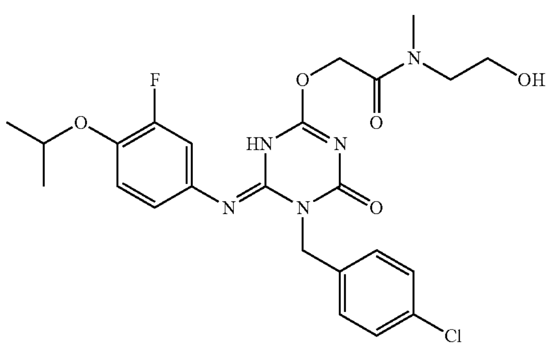 [SMILES: CC(C)Oc1ccc(/N=c2\[nH]c(OCC(=O)N(C)CCO)nc(=O)n2Cc2ccc(Cl)cc2)cc1F] | I-0586 | 1.65 | 520 | 2 |
| 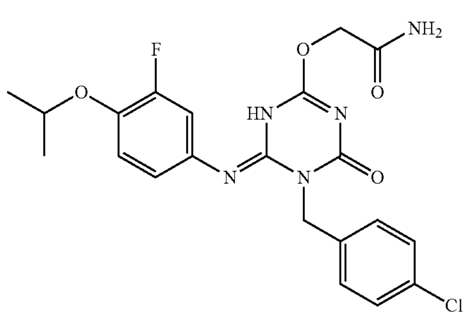 [SMILES: CC(C)Oc1ccc(/N=c2\[nH]c(OCC(N)=O)nc(=O)n2Cc2ccc(Cl)cc2)cc1F] | I-0587 | 1.66 | 462 | 2 |

TABLE 121-continued
| Structure | Compound No. | Retention Time (min) | [M + H] | Method |
|---|---|---|---|---|
| 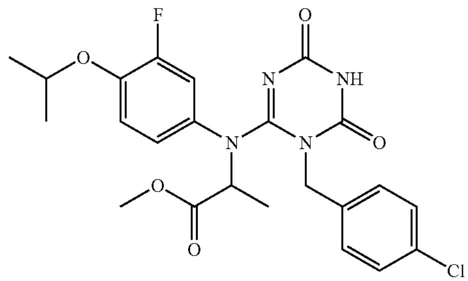 [SMILES: COC(=O)C(C)N(c1ccc(OC(C)C)c(F)c1)c1nc(=O)[nH]c(=O)n1Cc1ccc(Cl)cc1] | I-0588 | 2.24 | 491 | 3 |
| 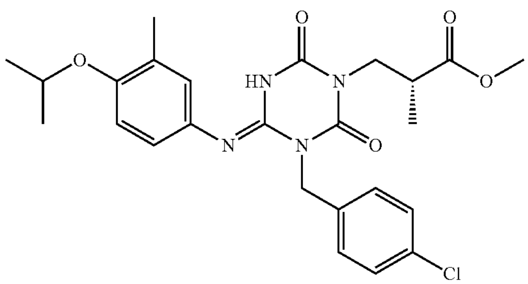 [SMILES: COC(=O)[C@H](C)Cn1c(=O)[nH]/c(=N\c2ccc(OC(C)C)c(C)c2)n(Cc2ccc(Cl)cc2)c1=O] | I-0589 | 2.53 | 501 | 3 |
| 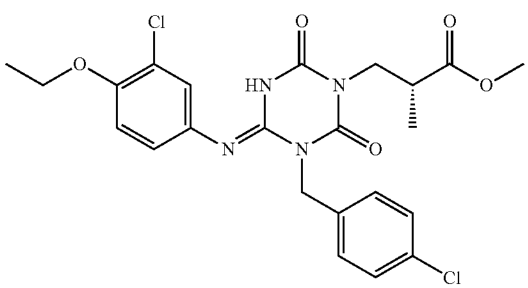 [SMILES: CCOc1ccc(/N=c2\[nH]c(=O)n(C[C@@H](C)C(=O)OC)c(=O)n2Cc2ccc(Cl)cc2)cc1Cl] | I-0590 | 2.50 | 507 | 3 |
TABLE 122
| Structure | Compound No. | Retention Time (min) | [M + H] | Method |
|---|---|---|---|---|
| 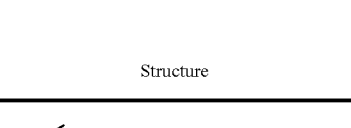 | I-0591 | 2.67 | 441 | 3 |

TABLE 122-continued

| Structure | Compound No. | Retention Time (min) | [M + H] | Method |
|---|---|---|---|---|
| 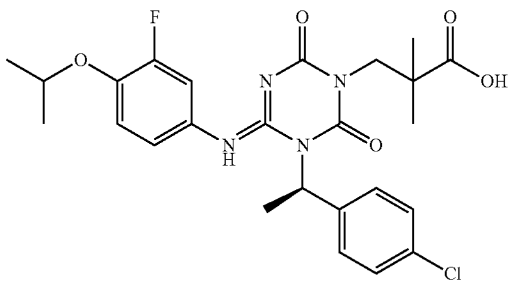 | I-0592 | 2.50 | 519 | 3 |
| 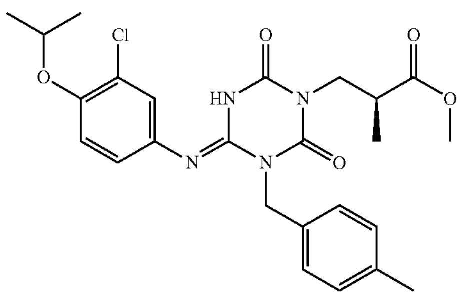 | I-0593 | 2.56 | 501 | 3 |
| 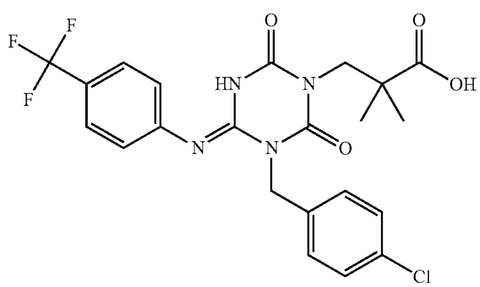 [SMILES: CC(C)(Cn1c(=O)[nH]/c(=N\c2ccc(C(F)(F)F)cc2)n(Cc2ccc(Cl)cc2)c1=O)C(=O)O] | I-0594 | 2.40 | 497 | 2 |
| 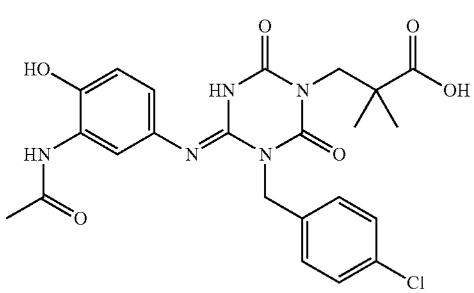 [SMILES: CC(=O)Nc1cc(/N=c2\[nH]c(=O)n(CC(C)(C)C(=O)O)c(=O)n2Cc2ccc(Cl)cc2)ccc1O] | I-0595 | 1.49 | 502 | 3 |

TABLE 123

| Structure | Compound No. | Retention Time (min) | [M + H] | Method |
|---|---|---|---|---|
| 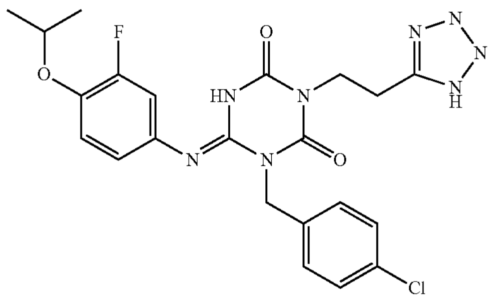 [SMILES: CC(C)Oc1ccc(/N=c2\[nH]c(=O)n(CCC3=NNNN3)c(=O)n2Cc2ccc(Cl)cc2)cc1F] | I-0596 | 2.08 | 501 | 3 |
| 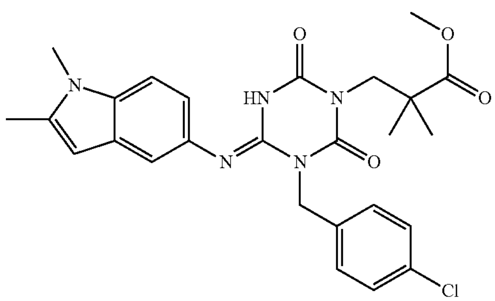 [SMILES: COC(=O)C(C)(C)Cn1c(=O)[nH]/c(=N\c2ccc3c(c2)cc(C)n3C)n(Cc2ccc(Cl)cc2)c1=O] | I-0597 | 2.19 | 510 | 2 |
| 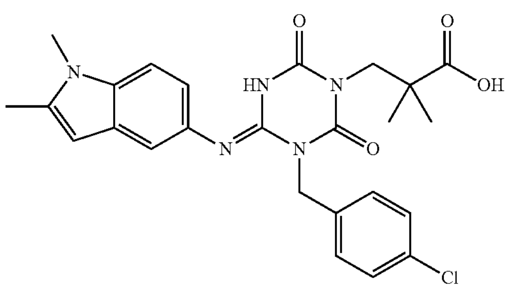 [SMILES: Cc1cc2cc(/N=c3\[nH]c(=O)n(CC(C)(C)C(=O)O)c(=O)n3Cc3ccc(Cl)cc3)ccc2n1C] | I-0598 | 1.93 | 496 | 2 |
| 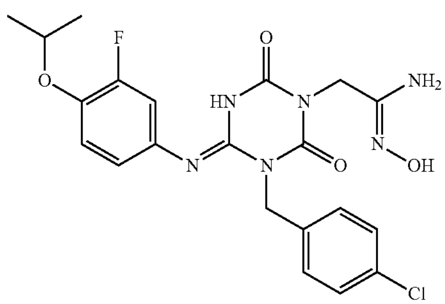 [SMILES: CC(C)Oc1ccc(/N=c2\[nH]c(=O)n(C/C(N)=N/O)c(=O)n2Cc2ccc(Cl)cc2)cc1F] | I-0599 | 1.69 | 477 | 3 |
| 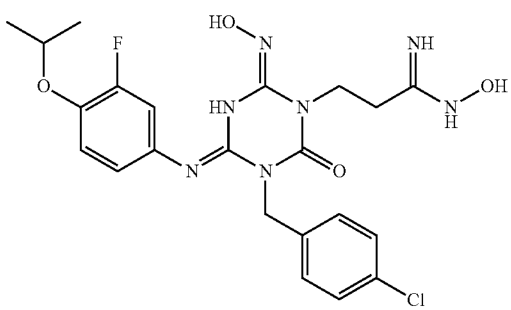 [SMILES: CC(C)Oc1ccc(/N=c2\[nH]/c(=N\O)n(CCC(=N)NO)c(=O)n2Cc2ccc(Cl)cc2)cc1F] | I-0600 | 1.67 | 507 | 3 |

TABLE 124

| Structure | Compound No. | Retention Time (min) | [M + H] | Method |
|---|---|---|---|---|
| 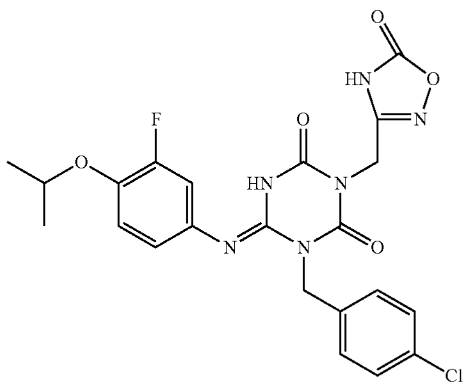 [SMILES: CC(C)Oc1ccc(/N=c2\[nH]c(=O)n(Cc3noc(=O)[nH]3)c(=O)n2Cc2ccc(Cl)cc2)cc1F] | I-0601 | 2.14 | 503 | 3 |
| 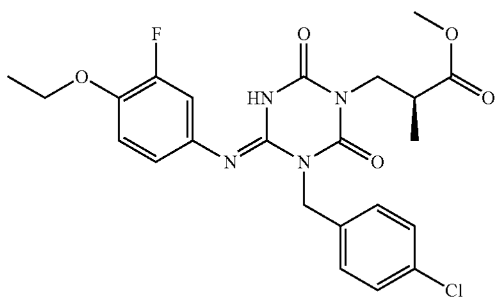 [SMILES: CCOc1ccc(/N=c2\[nH]c(=O)n(C[C@H](C)C(=O)OC)c(=O)n2Cc2ccc(Cl)cc2)cc1F] | I-0602 | 2.17 | 491 | 2 |
| 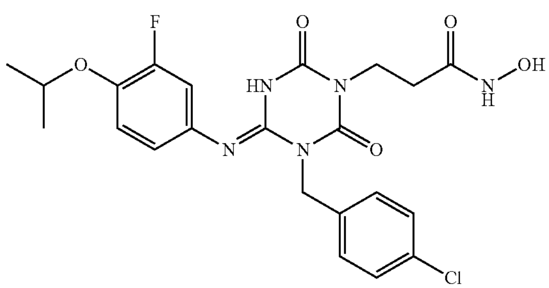 [SMILES: CC(C)Oc1ccc(/N=c2\[nH]c(=O)n(CCC(=O)NO)c(=O)n2Cc2ccc(Cl)cc2)cc1F] | I-0603 | 1.74 | 492 | 2 |
| 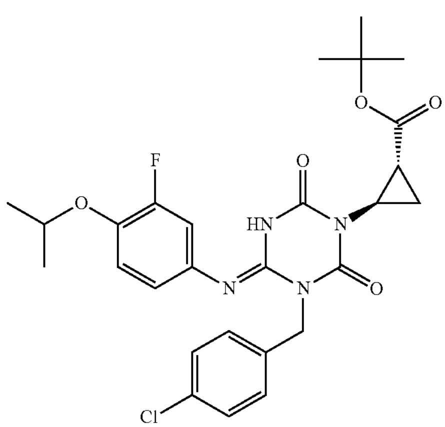 [SMILES: CC(C)Oc1ccc(/N=c2\[nH]c(=O)n([C@@H]3C[C@H]3C(=O)OC(C)(C)C)c(=O)n2Cc2ccc(Cl)cc2)cc1F] | I-0604 | 2.73 | 545 | 3 |

TABLE 124-continued

| Structure | Compound No. | Retention Time (min) | [M + H] | Method |
|---|---|---|---|---|
| 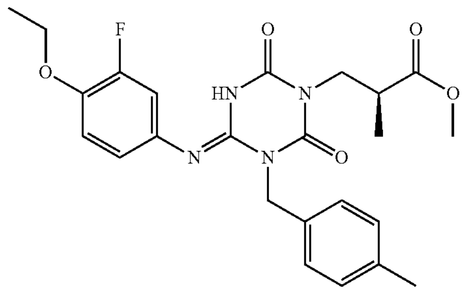 [SMILES: CCOc1ccc(/N=c2\[nH]c(=O)n(C[C@H](C)C(=O)OC)c(=O)n2Cc2ccc(C)cc2)cc1F] | I-0605 | 2.32 | 471 | 3 |

TABLE 125

| Structure | Compound No. | Retention Time (min) | [M + H] | Method |
|---|---|---|---|---|
| 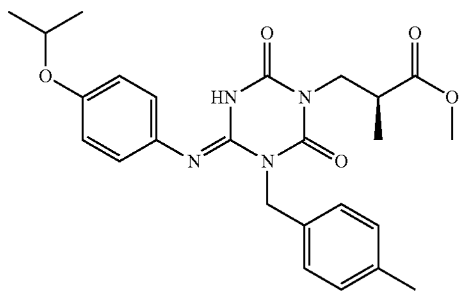 | I-0606 | 2.33 | 467 | 3 |
| 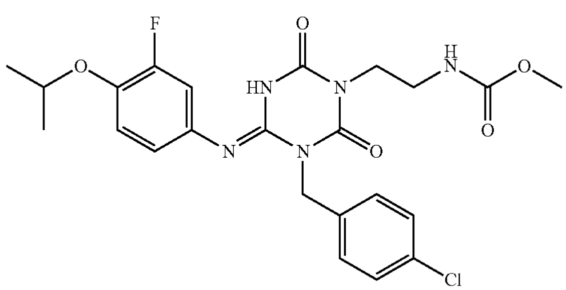 [SMILES: COC(=O)NCCn1c(=O)[nH]/c(=N\c2ccc(OC(C)C)c(F)c2)n(Cc2ccc(Cl)cc2)c1=O] | I-0607 | 2.05 | 506 | 2 |
| 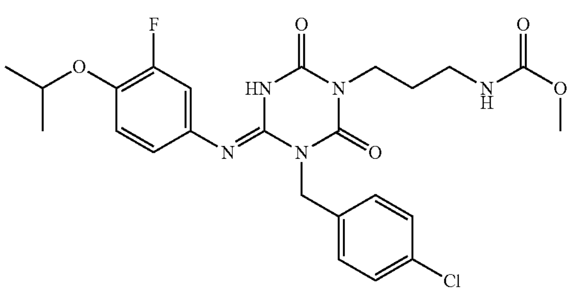 [SMILES: COC(=O)NCCCn1c(=O)[nH]/c(=N\c2ccc(OC(C)C)c(F)c2)n(Cc2ccc(Cl)cc2)c1=O] | I-0608 | 2.11 | 520 | 2 |

TABLE 125-continued

| Structure | Compound No. | Retention Time (min) | [M + H] | Method |
|---|---|---|---|---|
| (structure) | I-0609 | 1.92 | 477 | 2 |
| (structure) | I-0610 | 1.84 | 457 | 2 |

TABLE 126

| Structure | Compound No. | Retention Time (min) | [M + H] | Method |
|---|---|---|---|---|
| (structure) | I-0611 | 1.86 | 454 | 2 |
| (structure) | I-0612 | 1.96 | 489 | 2 |

TABLE 126-continued
| Structure | Compound No. | Retention Time (min) | [M + H] | Method |
|---|---|---|---|---|
| 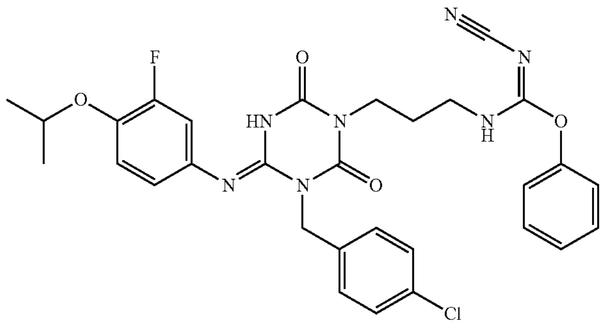 [SMILES: CC(C)Oc1ccc(/N=c2\[nH]c(=O)n(CCCN/C(=N\C#N)Oc3ccccc3)c(=O)n2Cc2ccc(Cl)cc2)cc1F] | I-0613 | 2.30 | 606 | 2 |
| 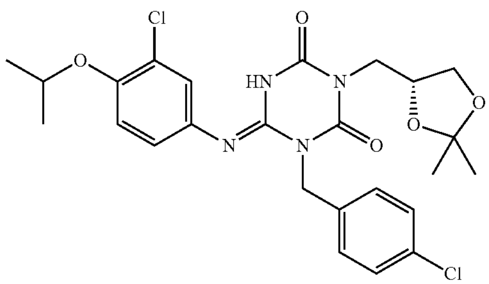 [SMILES: CC(C)Oc1ccc(/N=c2\[nH]c(=O)n(C[C@@H]3COC(C)(C)O3)c(=O)n2Cc2ccc(Cl)cc2)cc1Cl] | I-0614 | 2.43 | 535 | 2 |
| 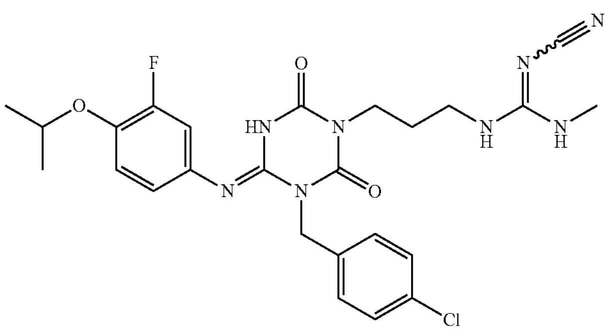 [SMILES: CNC(=NC#N)NCCCn1c(=O)[nH]/c(=N\c2ccc(OC(C)C)c(F)c2)n(Cc2ccc(Cl)cc2)c1=O] | I-0615 | 1.96 | 543 | 2 |
TABLE 127
| Structure | Compound No. | Retention Time (min) | [M + H] | Method |
|---|---|---|---|---|
| 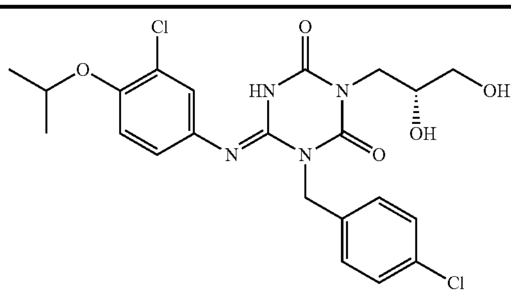 | I-0616 | 1.91 | 495 | 2 |

TABLE 127-continued

| Structure | Compound No. | Retention Time (min) | [M + H] | Method |
|---|---|---|---|---|
| 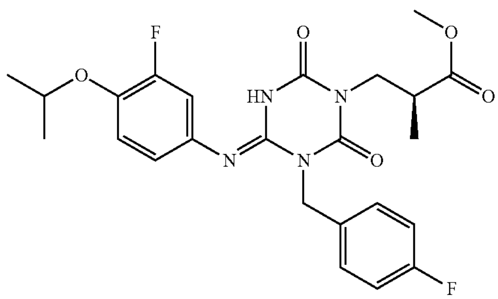 [SMILES: COC(=O)[C@@H](C)Cn1c(=O)[nH]/c(=N\c2ccc(OC(C)C)c(F)c2)n(Cc2ccc(F)cc2)c1=O] | I-0617 | 2.14 | 489 | 2 |
| 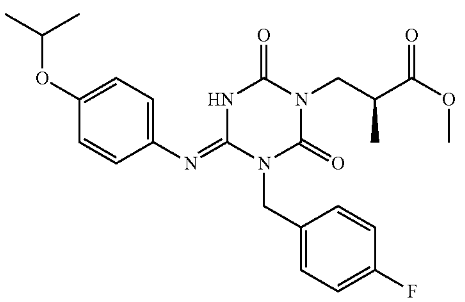 [SMILES: COC(=O)[C@@H](C)Cn1c(=O)[nH]/c(=N\c2ccc(OC(C)C)cc2)n(Cc2ccc(F)cc2)c1=O] | I-0618 | 2.26 | 471 | 3 |
| 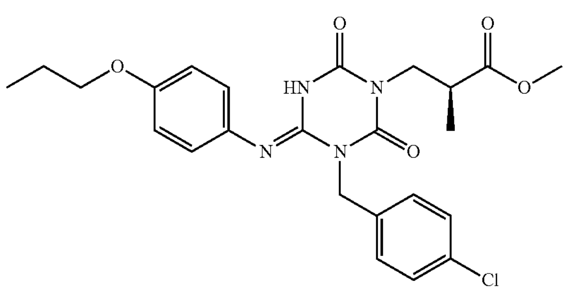 | I-0619 | 2.43 | 487 | 3 |
| 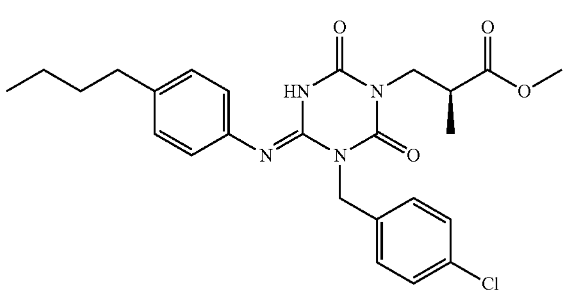 [SMILES: CCCCc1ccc(/N=c2\[nH]c(=O)n(C[C@H](C)C(=O)OC)c(=O)n2Cc2ccc(Cl)cc2)cc1] | I-0620 | 2.71 | 485 | 3 |

TABLE 128

| Structure | Compound No. | Retention Time (min) | [M + H] | Method |
|---|---|---|---|---|
| 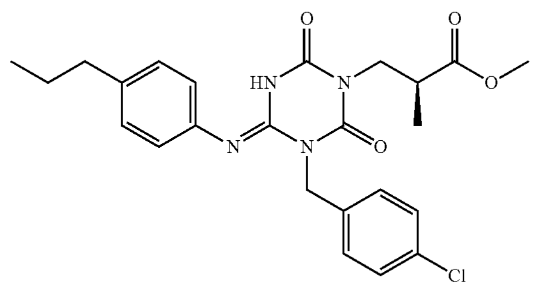 [SMILES: CCCc1ccc(/N=c2\[nH]c(=O)n(C[C@H](C)C(=O)OC)c(=O)n2Cc2ccc(Cl)cc2)cc1] | I-0621 | 2.57 | 471 | 3 |
| 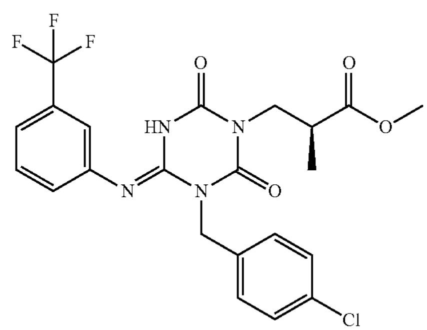 [SMILES: COC(=O)[C@@H](C)Cn1c(=O)[nH]/c(=N\c2cccc(C(F)(F)F)c2)n(Cc2ccc(Cl)cc2)c1=O] | I-0622 | 2.56 | 497 | 3 |
| 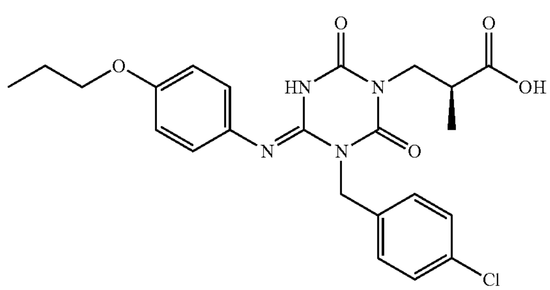 [SMILES: CCCOc1ccc(/N=c2\[nH]c(=O)n(C[C@H](C)C(=O)O)c(=O)n2Cc2ccc(Cl)cc2)cc1] | I-0623 | 2.16 | 473 | 3 |
| 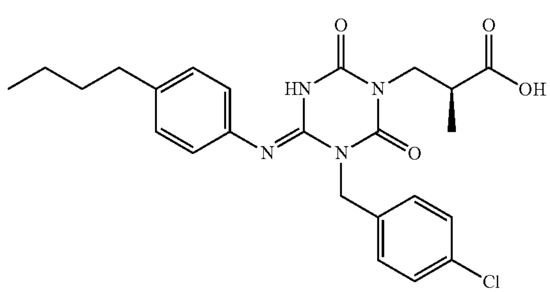 [SMILES: CCCCc1ccc(/N=c2\[nH]c(=O)n(C[C@H](C)C(=O)O)c(=O)n2Cc2ccc(Cl)cc2)cc1] | I-0624 | 2.54 | 471 | 3 |
| 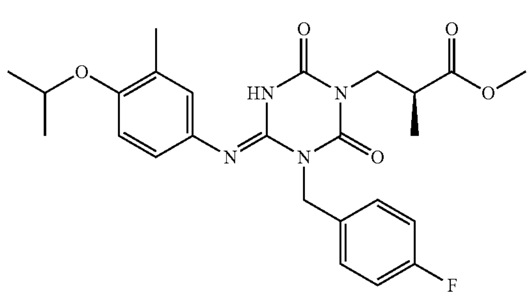 [SMILES: COC(=O)[C@@H](C)Cn1c(=O)[nH]/c(=N\c2ccc(OC(C)C)c(C)c2)n(Cc2ccc(F)cc2)c1=O] | I-0625 | 2.40 | 485 | 3 |

TABLE 129
| Structure | Compound No. | Retention Time (min) | [M + H] | Method |
|---|---|---|---|---|
| 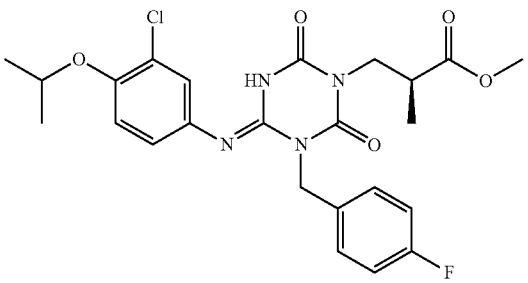 [SMILES: COC(=O)[C@@H](C)Cn1c(=O)[nH]/c(=N\c2ccc(OC(C)C)c(Cl)c2)n(Cc2ccc(F)cc2)c1=O] | I-0626 | 2.46 | 505 | 3 |
| 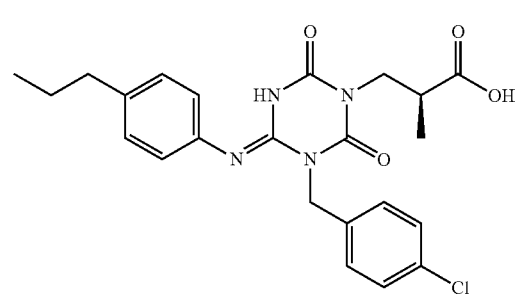 [SMILES: CCCc1ccc(/N=c2\[nH]c(=O)n(C[C@H](C)C(=O)O)c(=O)n2Cc2ccc(Cl)cc2)cc1] | I-0627 | 2.31 | 457 | 3 |
| 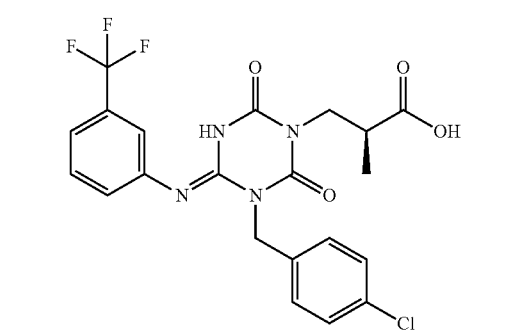 [SMILES: C[C@@H](Cn1c(=O)[nH]/c(=N\c2cccc(C(F)(F)F)c2)n(Cc2ccc(Cl)cc2)c1=O)C(=O)O] | I-0628 | 2.29 | 483 | 3 |
| 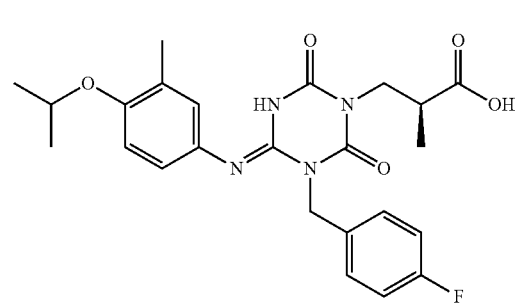 | I-0629 | 2.14 | 471 | 3 |
| 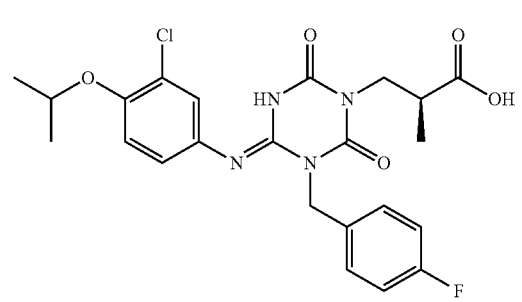 [SMILES: CC(C)Oc1ccc(/N=c2\[nH]c(=O)n(C[C@H](C)C(=O)O)c(=O)n2Cc2ccc(F)cc2)cc1Cl] | I-0630 | 2.21 | 491 | 3 |

TABLE 130

| Structure | Compound No. | Retention Time (min) | [M + H] | Method |
|---|---|---|---|---|
| (structure) | I-0631 | 2.36 | 473 | 2 |
| (structure) | I-0632 | 2.29 | 479 | 2 |
| (structure) | I-0633 | 2.43 | 535 | 2 |
| (structure) | I-0634 | 1.60 | 504 | 2 |
| (structure) | I-0635 | 1.70 | 477 | 2 |

TABLE 131

| Structure | Compound No. | Retention Time (min) | [M + H] | Method |
|---|---|---|---|---|
| 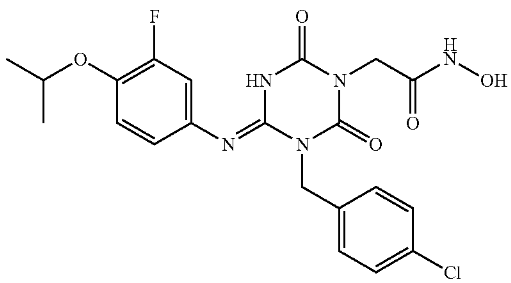 [SMILES: CC(C)Oc1ccc(/N=c2\[nH]c(=O)n(CC(=O)NO)c(=O)n2Cc2ccc(Cl)cc2)cc1F] | I-0636 | 1.75 | 478 | 2 |
| 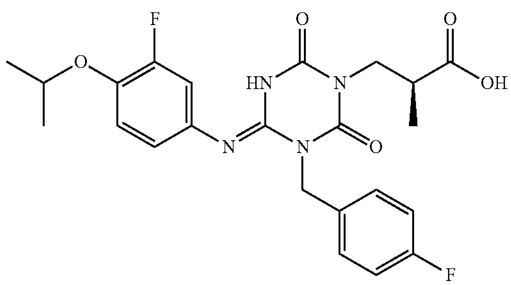 | I-0637 | 1.90 | 475 | 2 |
| 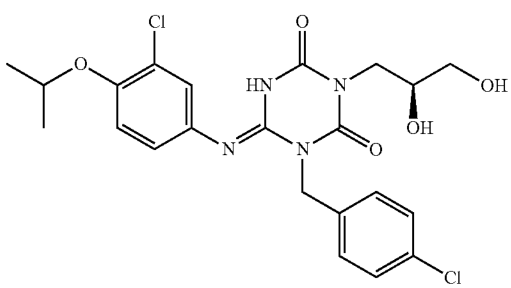 [SMILES: CC(C)Oc1ccc(/N=c2\[nH]c(=O)n(C[C@H](O)CO)c(=O)n2Cc2ccc(Cl)cc2)cc1Cl] | I-0638 | 1.91 | 495 | 2 |
| 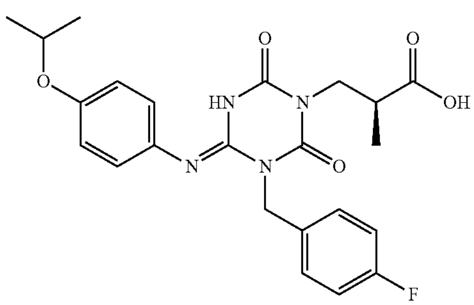 [SMILES: CC(C)Oc1ccc(/N=c2\[nH]c(=O)n(C[C@H](C)C(=O)O)c(=O)n2Cc2ccc(F)cc2)cc1] | I-0639 | 2.00 | 457 | 3 |
| 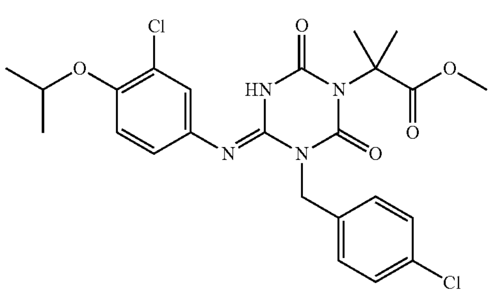 [SMILES: COC(=O)C(C)(C)n1c(=O)[nH]/c(=N\c2ccc(OC(C)C)c(Cl)c2)n(Cc2ccc(Cl)cc2)c1=O] | I-0640 | 2.43 | 521 | 2 |

TABLE 132

| Structure | Compound No. | Retention Time (min) | [M + H] | Method |
|---|---|---|---|---|
| 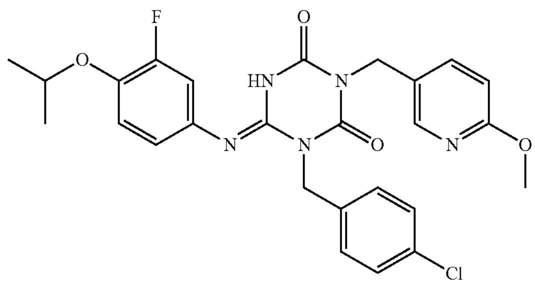 [SMILES: COc1ccc(Cn2c(=O)[nH]/c(=N\c3ccc(OC(C)C)c(F)c3)n(Cc3ccc(Cl)cc3)c2=O)cn1] | I-0641 | 2.34 | 526 | 2 |
| 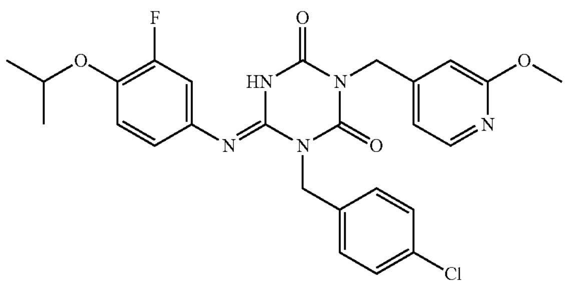 [SMILES: COc1cc(Cn2c(=O)[nH]/c(=N\c3ccc(OC(C)C)c(F)c3)n(Cc3ccc(Cl)cc3)c2=O)ccn1] | I-0642 | 2.29 | 526 | 2 |
| 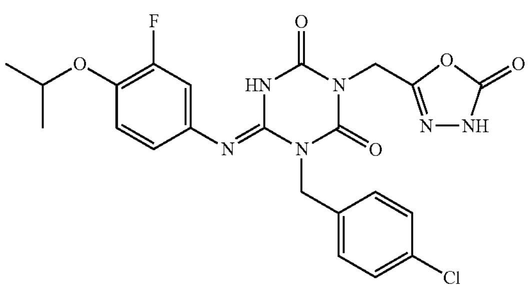 [SMILES: CC(C)Oc1ccc(/N=c2\[nH]c(=O)n(Cc3n[nH]c(=O)o3)c(=O)n2Cc2ccc(Cl)cc2)cc1F] | I-0643 | 1.94 | 503 | 2 |
| 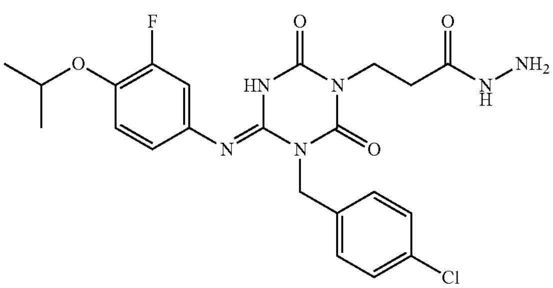 [SMILES: CC(C)Oc1ccc(/N=c2\[nH]c(=O)n(CCC(=O)NN)c(=O)n2Cc2ccc(Cl)cc2)cc1F] | I-0644 | 1.69 | 491 | 2 |
| 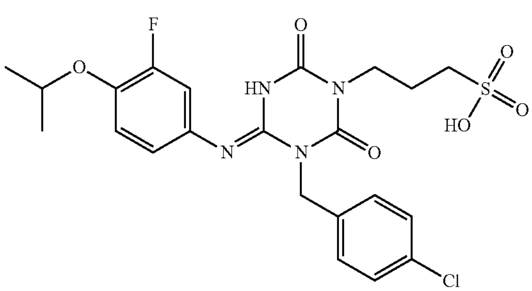 [SMILES: CC(C)Oc1ccc(/N=c2\[nH]c(=O)n(CCCS(=O)(=O)O)c(=O)n2Cc2ccc(Cl)cc2)cc1F] | I-0645 | 1.72 | 527 | 2 |

TABLE 133

| Structure | Compound No. | Retention Time (min) | [M + H] | Method |
|---|---|---|---|---|
| 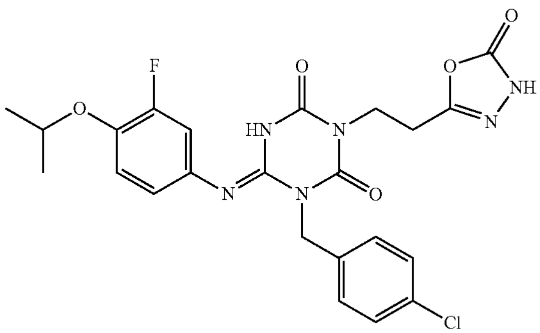 [SMILES: CC(C)Oc1ccc(/N=c2\[nH]c(=O)n(CCc3n[nH]c(=O)o3)c(=O)n2Cc2ccc(Cl)cc2)cc1F] | I-0646 | 1.97 | 517 | 2 |
| 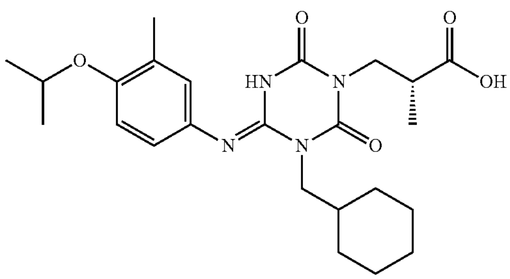 [SMILES: Cc1cc(/N=c2\[nH]c(=O)n(C[C@@H](C)C(=O)O)c(=O)n2CC2CCCCC2)ccc1OC(C)C] | I-0647 | 2.09 | 459 | 2 |
| 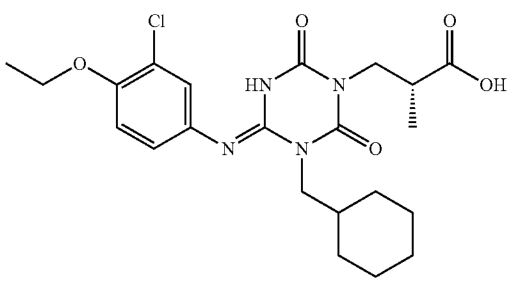 [SMILES: CCOc1ccc(/N=c2\[nH]c(=O)n(C[C@@H](C)C(=O)O)c(=O)n2CC2CCCCC2)cc1Cl] | I-0648 | 2.01 | 465 | 2 |
| 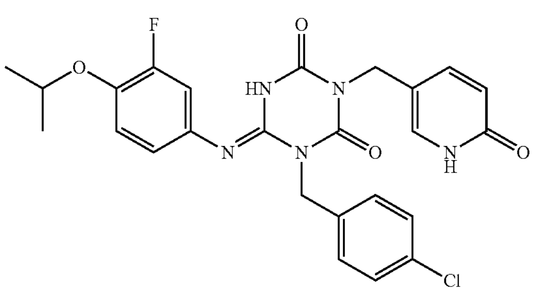 [SMILES: CC(C)Oc1ccc(/N=c2\[nH]c(=O)n(Cc3ccc(=O)[nH]c3)c(=O)n2Cc2ccc(Cl)cc2)cc1F] | I-0649 | 1.85 | 512 | 2 |
| 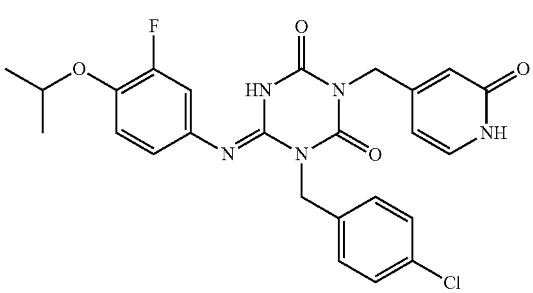 [SMILES: CC(C)Oc1ccc(/N=c2\[nH]c(=O)n(Cc3cc[nH]c(=O)c3)c(=O)n2Cc2ccc(Cl)cc2)cc1F] | I-0650 | 1.83 | 512 | 2 |

TABLE 134

| Structure | Compound No. | Retention Time (min) | [M + H] | Method |
|---|---|---|---|---|
| (structure) | I-0651 | 2.14 | 507 | 2 |
| (structure) | I-0652 | 2.24 | 592 | 2 |
| (structure) | I-0653 | 1.90 | 529 | 2 |
| (structure) | I-0654 | 1.64 | 513 | 2 |
| (structure) | I-0655 | 2.47 | 513 | 3 |

TABLE 135

| Structure | Compound No. | Retention Time (min) | [M + H] | Method |
|---|---|---|---|---|
| 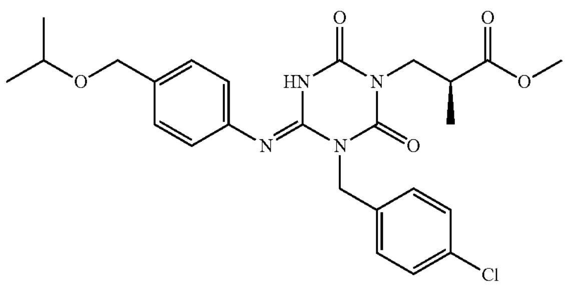 [SMILES: COC(=O)[C@@H](C)Cn1c(=O)[nH]/c(=N\c2ccc(COC(C)C)cc2)n(Cc2ccc(Cl)cc2)c1=O] | I-0656 | 2.44 | 501 | 3 |
| 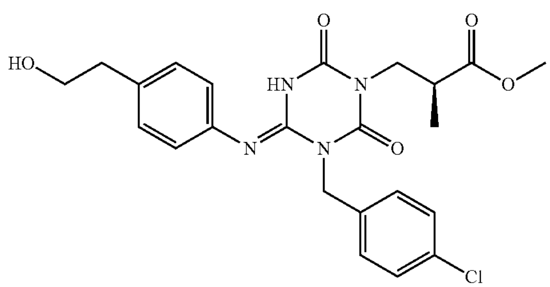 [SMILES: COC(=O)[C@@H](C)Cn1c(=O)[nH]/c(=N\c2ccc(CCO)cc2)n(Cc2ccc(Cl)cc2)c1=O] | I-0657 | 1.93 | 473 | 3 |
| 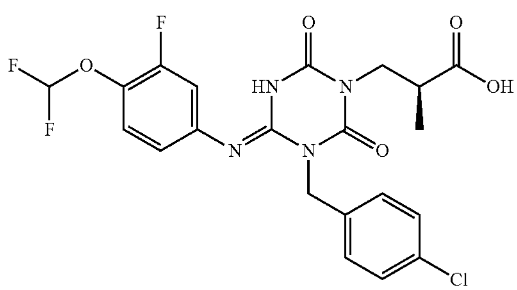 | I-0658 | 2.21 | 499 | 3 |
| 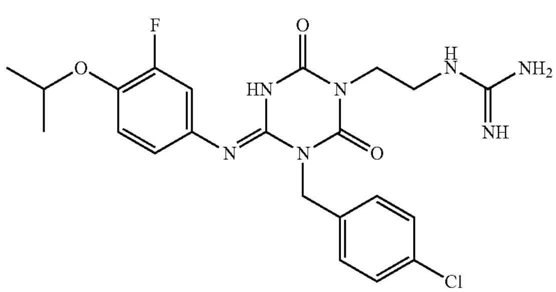 [SMILES: CC(C)Oc1ccc(/N=c2\[nH]c(=O)n(CCNC(=N)N)c(=O)n2Cc2ccc(Cl)cc2)cc1F] | I-0659 | 1.49 | 490 | 2 |
| 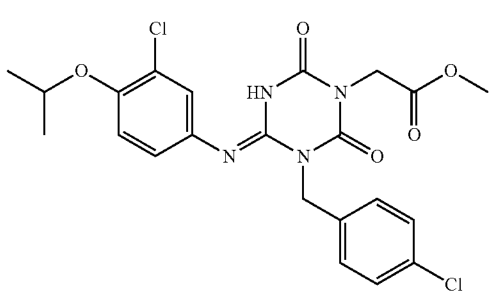 [SMILES: COC(=O)Cn1c(=O)[nH]/c(=N\c2ccc(OC(C)C)c(Cl)c2)n(Cc2ccc(Cl)cc2)c1=O] | I-0660 | 2.28 | 493 | 2 |

TABLE 136

| Structure | Compound No. | Retention Time (min) | [M + H] | Method |
|---|---|---|---|---|
| 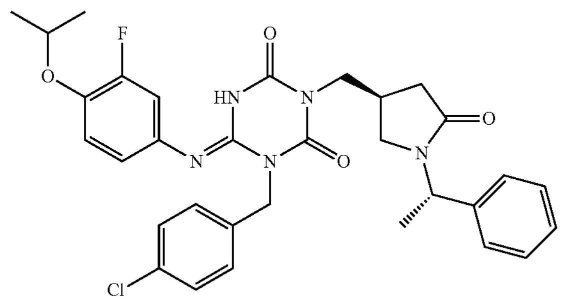 [SMILES: CC(C)Oc1ccc(/N=c2\[nH]c(=O)n(C[C@H]3CC(=O)N([C@@H](C)c4ccccc4)C3)c(=O)n2Cc2ccc(Cl)cc2)cc1F] | I-0661 | 2.35 | 606 | 2 |
| 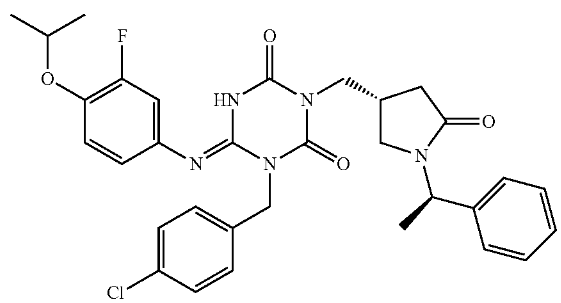 [SMILES: CC(C)Oc1ccc(/N=c2\[nH]c(=O)n(C[C@@H]3CC(=O)N([C@H](C)c4ccccc4)C3)c(=O)n2Cc2ccc(Cl)cc2)cc1F] | I-0662 | 2.35 | 606 | 2 |
| 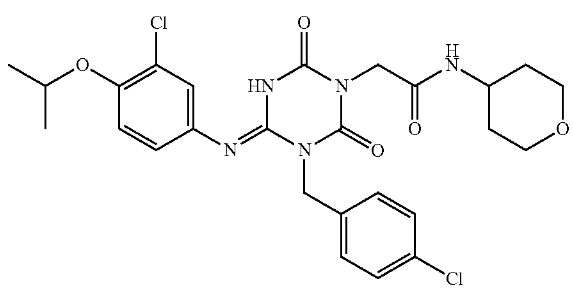 [SMILES: CC(C)Oc1ccc(/N=c2\[nH]c(=O)n(CC(=O)NC3CCOCC3)c(=O)n2Cc2ccc(Cl)cc2)cc1Cl] | I-0663 | 2.04 | 562 | 2 |
| 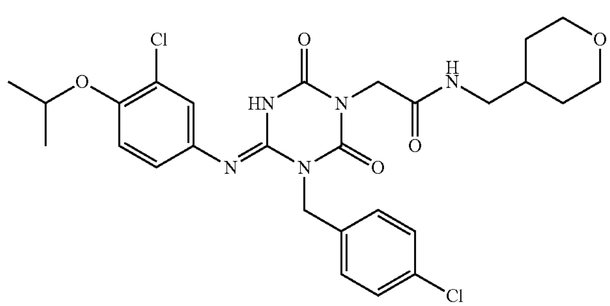 [SMILES: CC(C)Oc1ccc(/N=c2\[nH]c(=O)n(CC(=O)NCC3CCOCC3)c(=O)n2Cc2ccc(Cl)cc2)cc1Cl] | I-0664 | 2.06 | 576 | 2 |
| 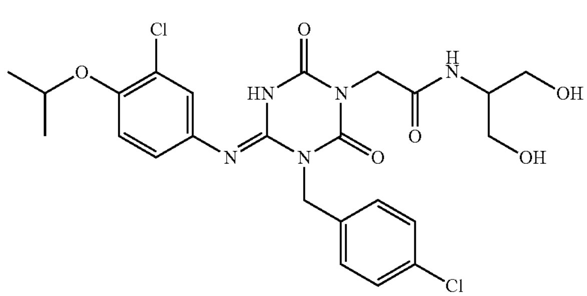 [SMILES: CC(C)Oc1ccc(/N=c2\[nH]c(=O)n(CC(=O)NC(CO)CO)c(=O)n2Cc2ccc(Cl)cc2)cc1Cl] | I-0665 | 1.79 | 552 | 2 |

TABLE 137
| Structure | Compound No. | Retention Time (min) | [M + H] | Method |
|---|---|---|---|---|
| 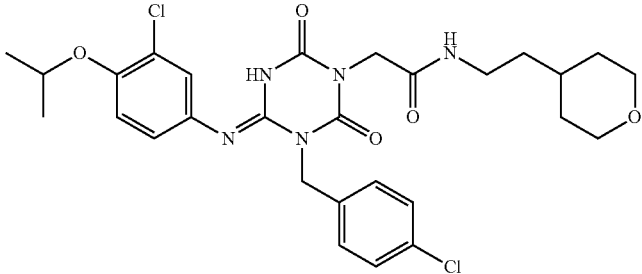 [SMILES: CC(C)Oc1ccc(/N=c2\[nH]c(=O)n(CC(=O)NCCC3CCOCC3)c(=O)n2Cc2ccc(Cl)cc2)cc1Cl] | I-0666 | 2.13 | 590 | 2 |
| 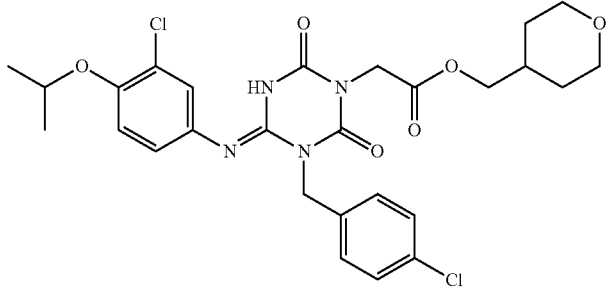 [SMILES: CC(C)Oc1ccc(/N=c2\[nH]c(=O)n(CC(=O)OCC3CCOCC3)c(=O)n2Cc2ccc(Cl)cc2)cc1Cl] | I-0667 | 2.34 | 577 | 2 |
| 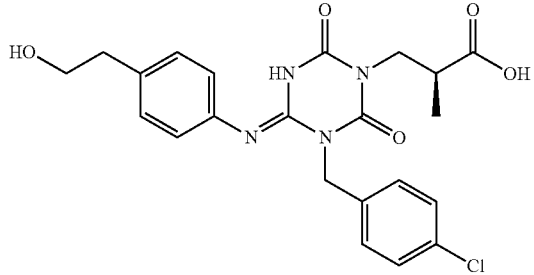 [SMILES: C[C@@H](Cn1c(=O)[nH]/c(=N\c2ccc(CCO)cc2)n(Cc2ccc(Cl)cc2)c1=O)C(=O)O] | I-0668 | 1.67 | 459 | 3 |
| 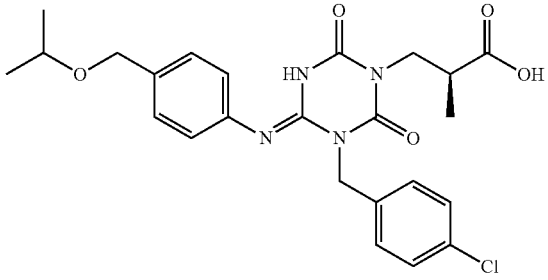 | I-0669 | 1.98 | 487 | 2 |
| 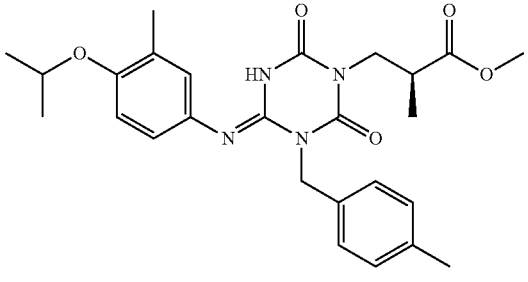 | I-0670 | 2.28 | 481 | 2 |

TABLE 138
| Structure | Compound No. | Retention Time (min) | [M + H] | Method |
|---|---|---|---|---|
| 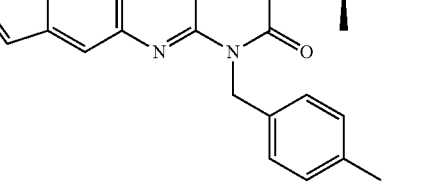 | I-0671 | 2.09 | 463 | 2 |
| 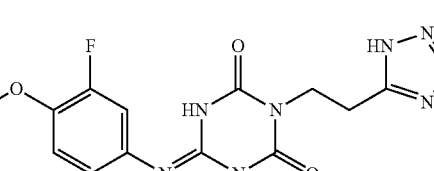 | I-0672 | 1.81 | 500 | 2 |
| 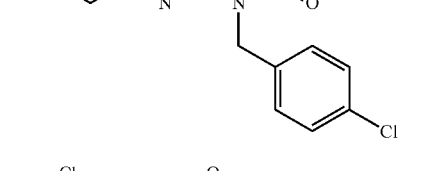 | I-0673 | 2.29 | 563 | 2 |
| 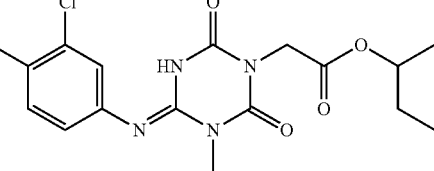 | I-0674 | 1.96 | 489 | 2 |
| 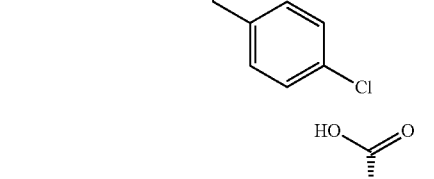 | I-0675 | 1.96 | 489 | 2 |

TABLE 139
| Structure | Compound No. | Retention Time (min) | [M + H] | Method |
|---|---|---|---|---|
| 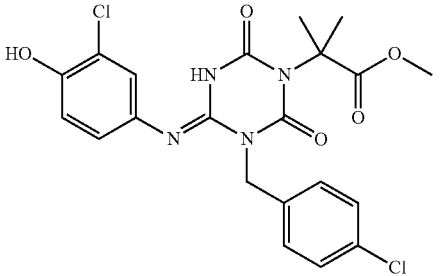 [SMILES: COC(=O)C(C)(C)n1c(=O)[nH]/c(=N\c2ccc(O)c(Cl)c2)n(Cc2ccc(Cl)cc2)c1=O] | I-0676 | 1.94 | 479 | 2 |
| 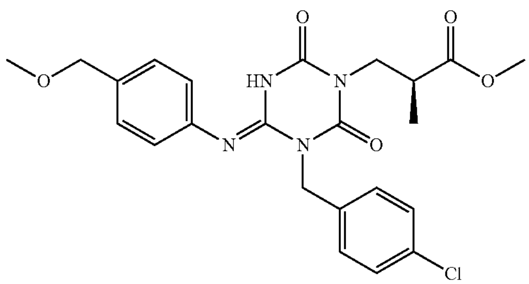 | I-0677 | 2.19 | 472 | 3 |
| 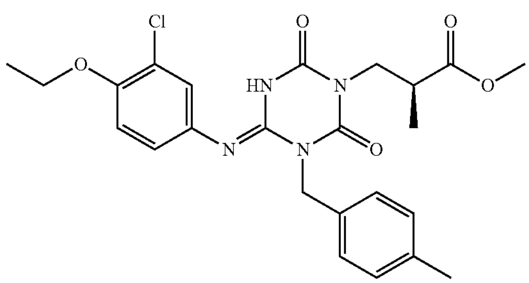 | I-0678 | 2.23 | 487 | 2 |
| 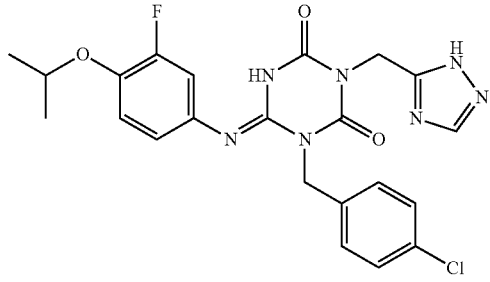 [SMILES: CC(C)Oc1ccc(/N=c2\[nH]c(=O)n(Cc3ncn[nH]3)c(=O)n2Cc2ccc(Cl)cc2)cc1F] | I-0679 | 1.81 | 486 | 2 |
| 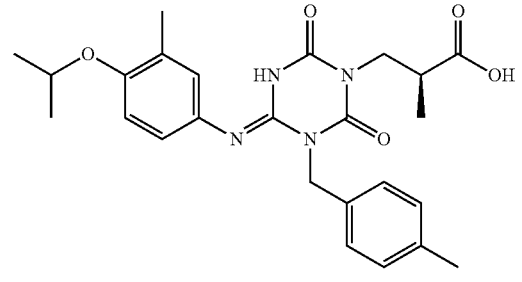 [SMILES: Cc1ccc(Cn2c(=O)n(C[C@H](C)C(=O)O)c(=O)[nH]/c2=N\c2ccc(OC(C)C)c(C)c2)cc1] | I-0680 | 2.04 | 467 | 2 |

TABLE 140

| Structure | Compound No. | Retention Time (min) | [M + H] | Method |
|---|---|---|---|---|
| 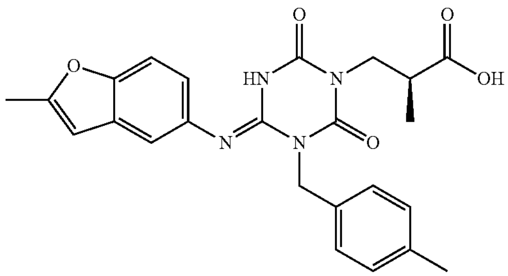 [SMILES: Cc1ccc(Cn2c(=O)n(C[C@H](C)C(=O)O)c(=O)[nH]/c2=N\c2ccc3oc(C)cc3c2)cc1] | I-0681 | 1.87 | 449 | 2 |
| 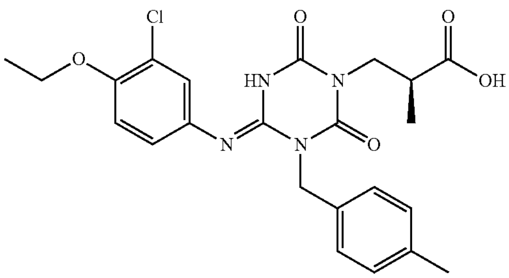 | I-0682 | 1.99 | 473 | 2 |
| 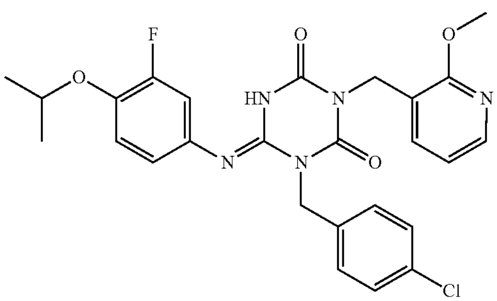 [SMILES: COc1ncccc1Cn1c(=O)[nH]/c(=N\c2ccc(OC(C)C)c(F)c2)n(Cc2ccc(Cl)cc2)c1=O] | I-0683 | 2.35 | 526 | 2 |
| 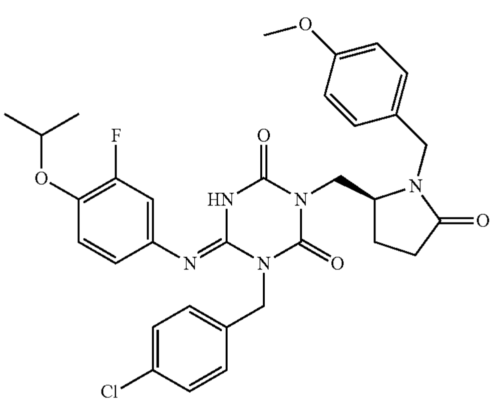 [SMILES: COc1ccc(CN2C(=O)CC[C@H]2Cn2c(=O)[nH]/c(=N\c3ccc(OC(C)C)c(F)c3)n(Cc3ccc(Cl)cc3)c2=O)cc1] | I-0684 | 2.51 | 622 | 3 |
| 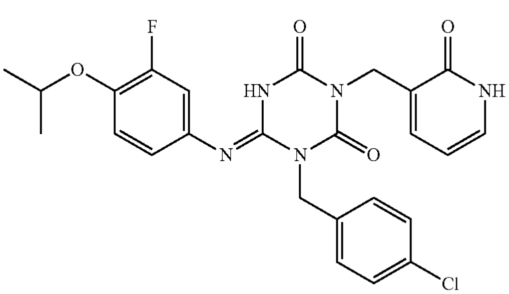 [SMILES: CC(C)Oc1ccc(/N=c2\[nH]c(=O)n(Cc3ccc[nH]c3=O)c(=O)n2Cc2ccc(Cl)cc2)cc1F] | I-0685 | 1.90 | 512 | 2 |

TABLE 141

| Structure | Compound No. | Retention Time (min) | [M + H] | Method |
|---|---|---|---|---|
| 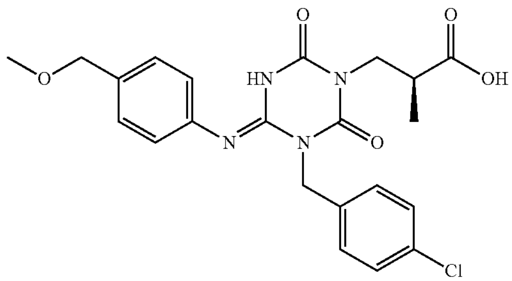 | I-0686 | 1.91 | 459 | 3 |
| 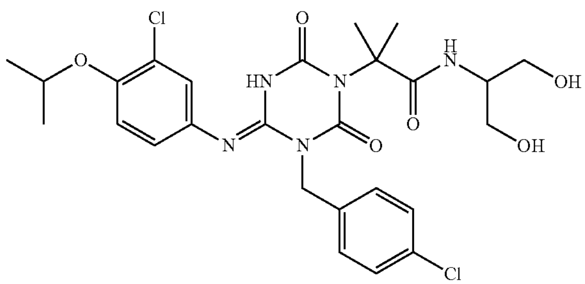 [SMILES: CC(C)Oc1ccc(/N=c2\[nH]c(=O)n(C(C)(C)C(=O)NC(CO)CO)c(=O)n2Cc2ccc(Cl)cc2)cc1Cl] | I-0687 | 1.86 | 580 | 2 |
| 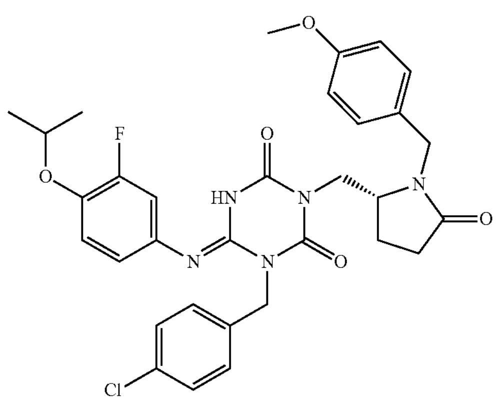 [SMILES: COc1ccc(CN2C(=O)CC[C@@H]2Cn2c(=O)[nH]/c(=N\c3ccc(OC(C)C)c(F)c3)n(Cc3ccc(Cl)cc3)c2=O)cc1] | I-0688 | 2.51 | 622 | 3 |
| 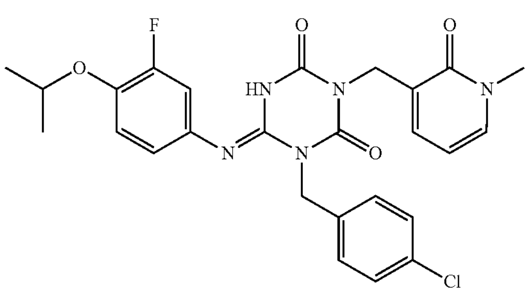 [SMILES: CC(C)Oc1ccc(/N=c2\[nH]c(=O)n(Cc3cccn(C)c3=O)c(=O)n2Cc2ccc(Cl)cc2)cc1F] | I-0689 | 1.97 | 526 | 2 |

TABLE 141-continued

| Structure | Compound No. | Retention Time (min) | [M + H] | Method |
|---|---|---|---|---|
| (structure) | I-0690 | 2.31 | 487 | 2 |

TABLE 142

| Structure | Compound No. | Retention Time (min) | [M + H] | Method |
|---|---|---|---|---|
| (structure) | I-0691 | 2.39 | 477 | 2 |
| (structure) | I-0692 | 1.96 | 482 | 2 |
| (structure) | I-0693 | 1.92 | 512 | 2 |

TABLE 142-continued

| Structure | Compound No. | Retention Time (min) | [M + H] | Method |
|---|---|---|---|---|
| 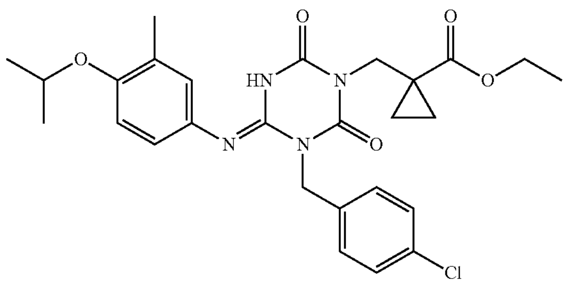 [SMILES: CCOC(=O)C1(Cn2c(=O)[nH]/c(=N\c3ccc(OC(C)C)c(C)c3)n(Cc3ccc(Cl)cc3)c2=O)CC1] | I-0694 | 2.48 | 527 | 2 |
| 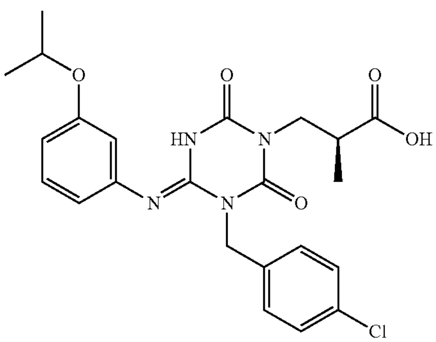 [SMILES: CC(C)Oc1cccc(/N=c2\[nH]c(=O)n(C[C@H](C)C(=O)O)c(=O)n2Cc2ccc(Cl)cc2)c1] | I-0695 | 2.05 | 473 | 2 |

TABLE 143

| Structure | Compound No. | Retention Time (min) | [M + H] | Method |
|---|---|---|---|---|
| 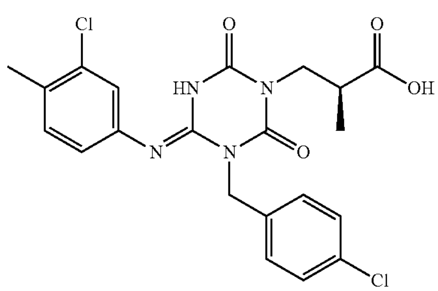 [SMILES: Cc1ccc(/N=c2\[nH]c(=O)n(C[C@H](C)C(=O)O)c(=O)n2Cc2ccc(Cl)cc2)cc1Cl] | I-0696 | 2.12 | 463 | 2 |
| 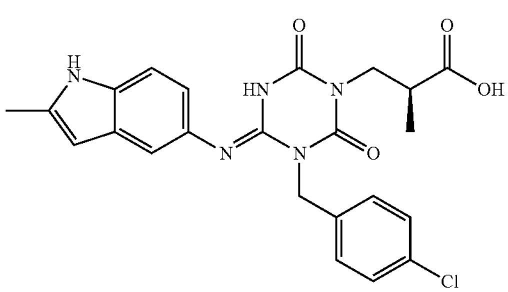 [SMILES: Cc1cc2cc(/N=c3\[nH]c(=O)n(C[C@H](C)C(=O)O)c(=O)n3Cc3ccc(Cl)cc3)ccc2[nH]1] | I-0697 | 1.73 | 468 | 2 |

TABLE 143-continued
| Structure | Compound No. | Retention Time (min) | [M + H] | Method |
|---|---|---|---|---|
| (structure) | I-0698 | 2.12 | 499 | 2 |
| (structure) | I-0699 | 2.51 | 628 | 2 |
| (structure) | I-0700 | 2.34 | 539 | 2 |
TABLE 144
| Structure | Compound No. | Retention Time (min) | [M + H] | Method |
|---|---|---|---|---|
| (structure) | I-0701 | 2.94 | 557 | 3 |
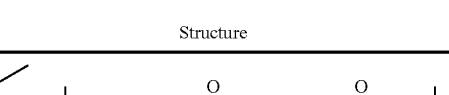

TABLE 144-continued

| Structure | Compound No. | Retention Time (min) | [M + H] | Method |
|---|---|---|---|---|
| 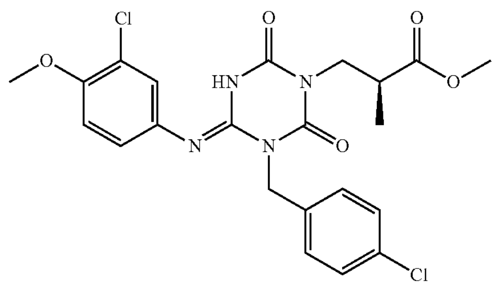 | I-0702 | 2.16 | 493 | 2 |
| 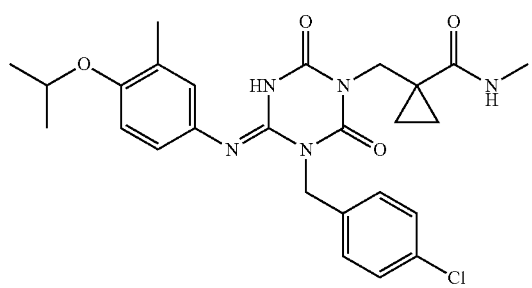 [SMILES: CNC(=O)C1(Cn2c(=O)[nH]/c(=N\c3ccc(OC(C)C)c(C)c3)n(Cc3ccc(Cl)cc3)c2=O)CC1] | I-0703 | 2.10 | 512 | 2 |
| 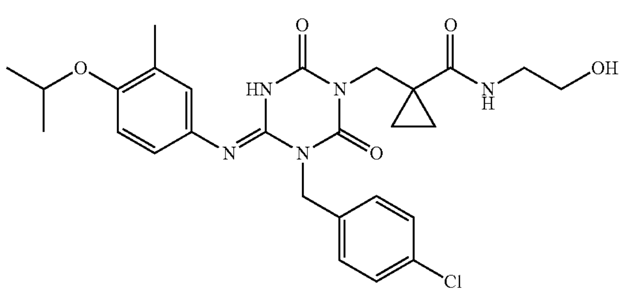 [SMILES: Cc1cc(/N=c2\[nH]c(=O)n(CC3(C(=O)NCCO)CC3)c(=O)n2Cc2ccc(Cl)cc2)ccc1OC(C)C] | I-0704 | 1.94 | 542 | 2 |
| 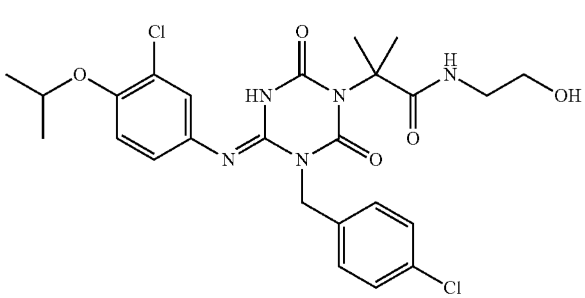 [SMILES: CC(C)Oc1ccc(/N=c2\[nH]c(=O)n(C(C)(C)C(=O)NCCO)c(=O)n2Cc2ccc(Cl)cc2)cc1Cl] | I-0705 | 1.94 | 550 | 2 |

TABLE 145

| Structure | Compound No. | Retention Time (min) | [M + H] | Method |
|---|---|---|---|---|
| 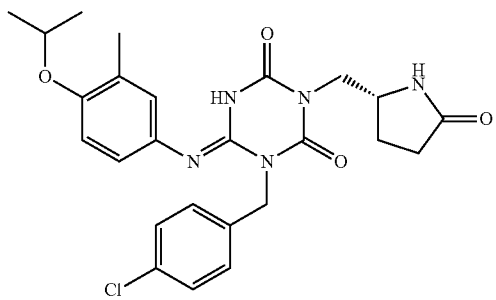 [SMILES: Cc1cc(/N=c2\[nH]c(=O)n(C[C@H]3CCC(=O)N3)c(=O)n2Cc2ccc(Cl)cc2)ccc1OC(C)C] | I-0706 | 2.16 | 499 | 3 |
| 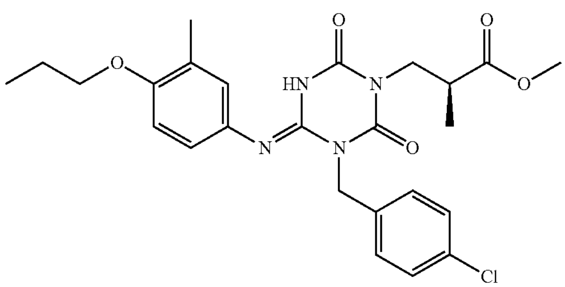 [SMILES: CCCOc1ccc(/N=c2\[nH]c(=O)n(C[C@H](C)C(=O)OC)c(=O)n2Cc2ccc(Cl)cc2)cc1C] | I-0707 | 2.59 | 501 | 3 |
| 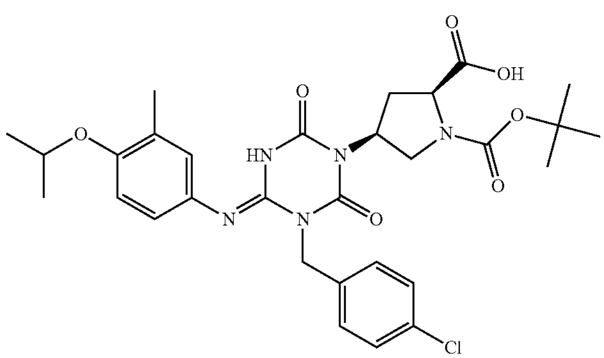 [SMILES: Cc1cc(/N=c2\[nH]c(=O)n([C@H]3C[C@@H](C(=O)O)N(C(=O)OC(C)(C)C)C3)c(=O)n2Cc2ccc(Cl)cc2)ccc1OC(C)C] | I-0708 | 2.28 | 614 | 2 |
| 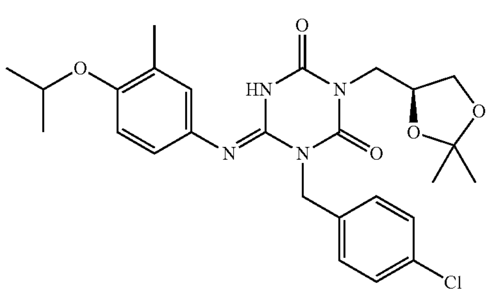 [SMILES: Cc1cc(/N=c2\[nH]c(=O)n(C[C@H]3COC(C)(C)O3)c(=O)n2Cc2ccc(Cl)cc2)ccc1OC(C)C] | I-0709 | 2.37 | 515 | 2 |
| 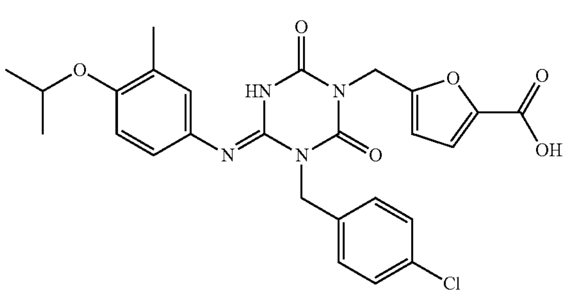 | I-0710 | 2.09 | 525 | 2 |

TABLE 146

| Structure | Compound No. | Retention Time (min) | [M + H] | Method |
|---|---|---|---|---|
| (structure) | I-0711 | 2.34 | 487 | 3 |
| (structure) | I-0712 | 2.28 | 636 | 2 |
| (structure) | I-0713 | 1.93 | 552 | 2 |
| (structure) | I-0714 | 2.56 | 636 | 2 |
| (structure) | I-0715 | 2.16 | 552 | 2 |

TABLE 147
| Structure | Compound No. | Retention Time (min) | [M + H] | Method |
|---|---|---|---|---|
| 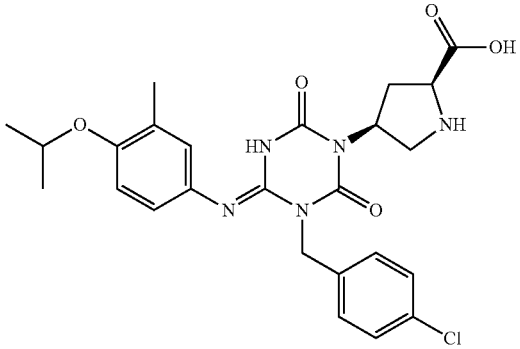 [SMILES: Cc1cc(/N=c2\[nH]c(=O)n([C@@H]3CN[C@H](C(=O)O)C3)c(=O)n2Cc2ccc(Cl)cc2)ccc1OC(C)C] | I-0716 | 1.58 | 514 | 2 |
| 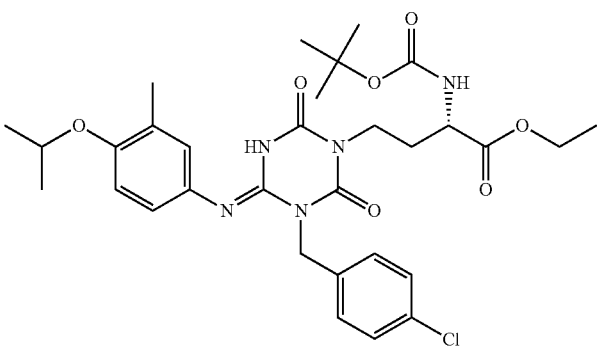 [SMILES: CCOC(=O)[C@H](CCn1c(=O)[nH]/c(=N\c2ccc(OC(C)C)c(C)c2)n(Cc2ccc(Cl)cc2)c1=O)NC(=O)OC(C)(C)C] | I-0717 | 2.56 | 630 | 2 |
| 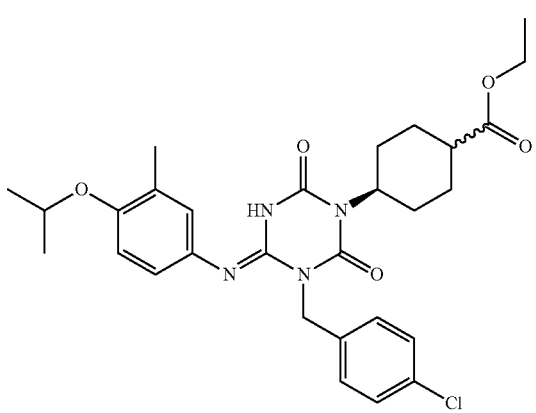 | I-0718 | 2.64 | 555 | 2 |
| 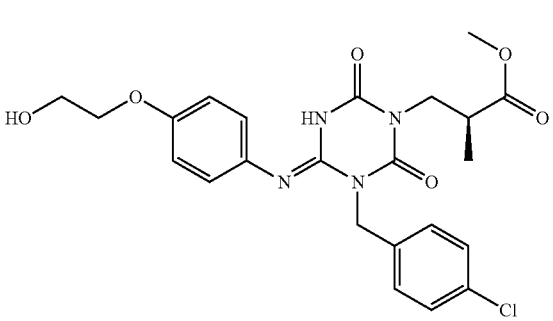 [SMILES: COC(=O)[C@@H](C)Cn1c(=O)[nH]/c(=N\c2ccc(OCCO)cc2)n(Cc2ccc(Cl)cc2)c1=O] | I-0719 | 1.68 | 489 | 2 |

TABLE 147-continued

| Structure | Compound No. | Retention Time (min) | [M + H] | Method |
|---|---|---|---|---|
| 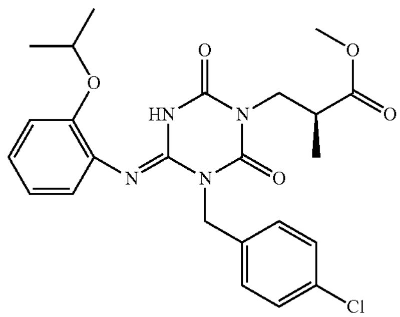 [SMILES: COC(=O)[C@@H](C)Cn1c(=O)[nH]/c(=N\c2ccccc2OC(C)C)n(Cc2ccc(Cl)cc2)c1=O] | I-0720 | 2.24 | 487 | 2 |

TABLE 148

| Structure | Compound No. | Retention Time (min) | [M + H] | Method |
|---|---|---|---|---|
| 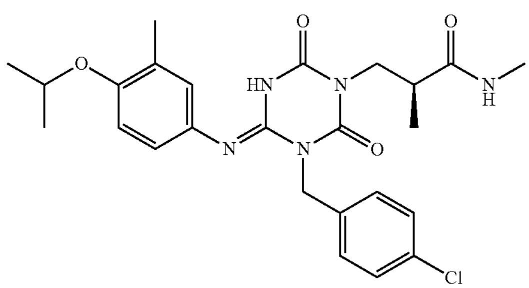 [SMILES: CNC(=O)[C@@H](C)Cn1c(=O)[nH]/c(=N\c2ccc(OC(C)C)c(C)c2)n(Cc2ccc(Cl)cc2)c1=O] | I-0721 | 1.98 | 500 | 2 |
| 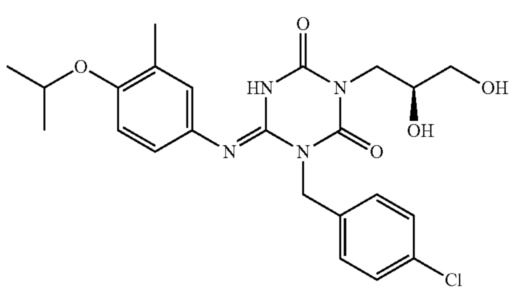 [SMILES: Cc1cc(/N=c2\[nH]c(=O)n(C[C@H](O)CO)c(=O)n2Cc2ccc(Cl)cc2)ccc1OC(C)C] | I-0722 | 1.86 | 475 | 2 |
| 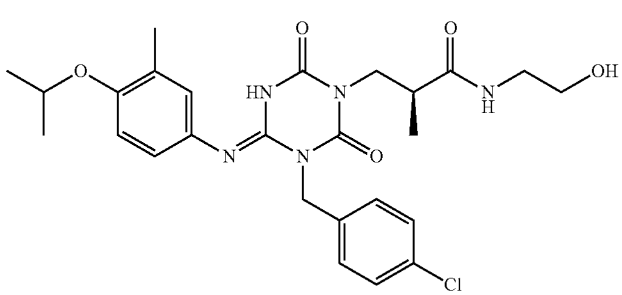 [SMILES: Cc1cc(/N=c2\[nH]c(=O)n(C[C@H](C)C(=O)NCCO)c(=O)n2Cc2ccc(Cl)cc2)ccc1OC(C)C] | I-0723 | 1.86 | 530 | 2 |

TABLE 148-continued

| Structure | Compound No. | Retention Time (min) | [M + H] | Method |
|---|---|---|---|---|
| 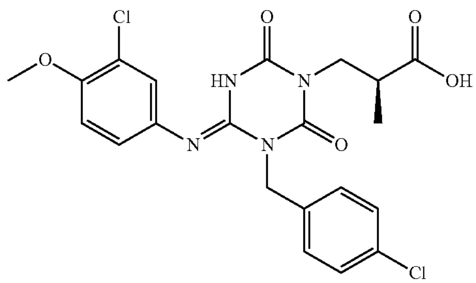 [SMILES: COc1ccc(/N=c2\[nH]c(=O)n(C[C@H](C)C(=O)O)c(=O)n2Cc2ccc(Cl)cc2)cc1Cl] | I-0724 | 1.91 | 479 | 2 |
| 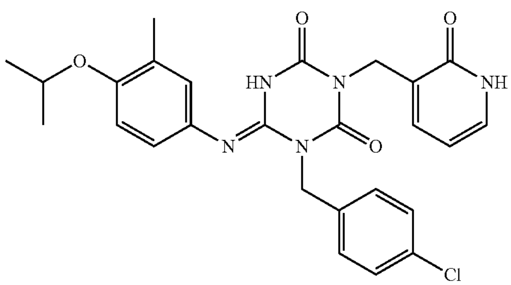 [SMILES: Cc1cc(/N=c2\[nH]c(=O)n(Cc3ccc[nH]c3=O)c(=O)n2Cc2ccc(Cl)cc2)ccc1OC(C)C] | I-0725 | 1.98 | 508 | 2 |

TABLE 149

| Structure | Compound No. | Retention Time (min) | [M + H] | Method |
|---|---|---|---|---|
| 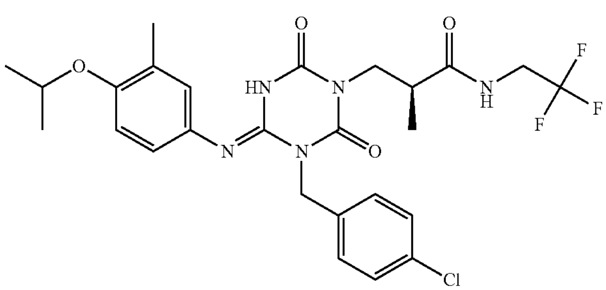 [SMILES: Cc1cc(/N=c2\[nH]c(=O)n(C[C@H](C)C(=O)NCC(F)(F)F)c(=O)n2Cc2ccc(Cl)cc2)ccc1OC(C)C] | I-0726 | 2.24 | 568 | 2 |
| 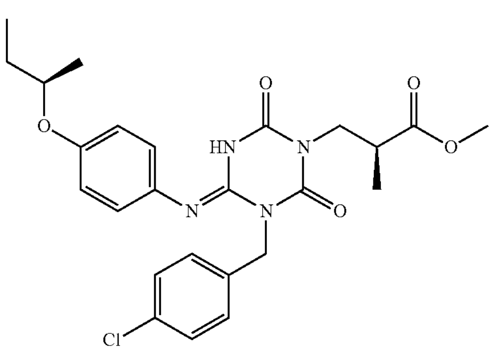 [SMILES: CC[C@@H](C)Oc1ccc(/N=c2\[nH]c(=O)n(C[C@H](C)C(=O)OC)c(=O)n2Cc2ccc(Cl)cc2)cc1] | I-0727 | 2.53 | 501 | 3 |

TABLE 149-continued

| Structure | Compound No. | Retention Time (min) | [M + H] | Method |
|---|---|---|---|---|
| 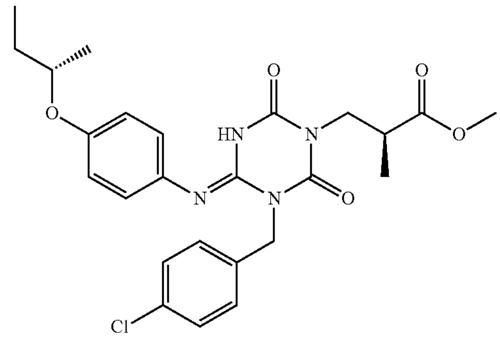 [SMILES: CC[C@H](C)Oc1ccc(/N=c2\[nH]c(=O)n(C[C@H](C)C(=O)OC)c(=O)n2Cc2ccc(Cl)cc2)cc1] | I-0728 | 2.53 | 501 | 3 |
| 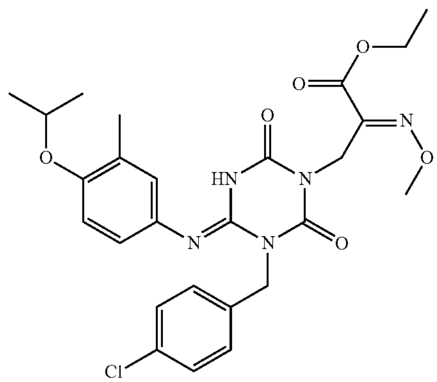 [SMILES: CCOC(=O)/C(Cn1c(=O)[nH]/c(=N\c2ccc(OC(C)C)c(C)c2)n(Cc2ccc(Cl)cc2)c1=O)=N/OC] | I-0729 | 2.57 | 545 | 3 |
| 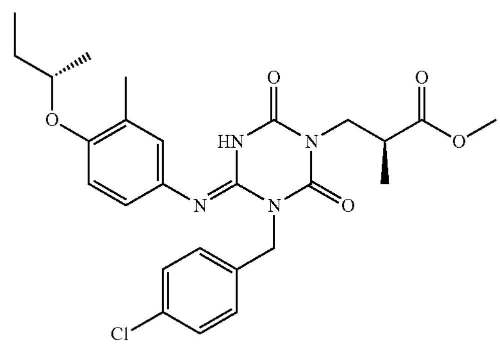 [SMILES: CC[C@H](C)Oc1ccc(/N=c2\[nH]c(=O)n(C[C@H](C)C(=O)OC)c(=O)n2Cc2ccc(Cl)cc2)cc1C] | I-0730 | 2.69 | 516 | 3 |

TABLE 150

| Structure | Compound No. | Retention Time (min) | [M + H] | Method |
|---|---|---|---|---|
| 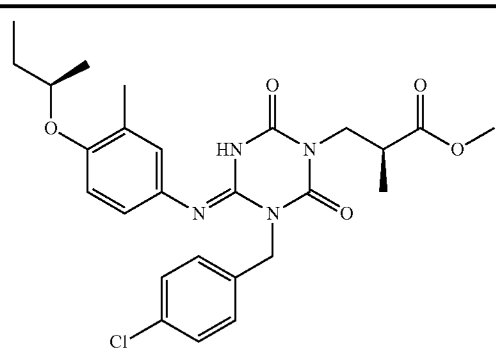 | I-0731 | 2.68 | 516 | 3 |

TABLE 150-continued

| Structure | Compound No. | Retention Time (min) | [M + H] | Method |
|---|---|---|---|---|
| 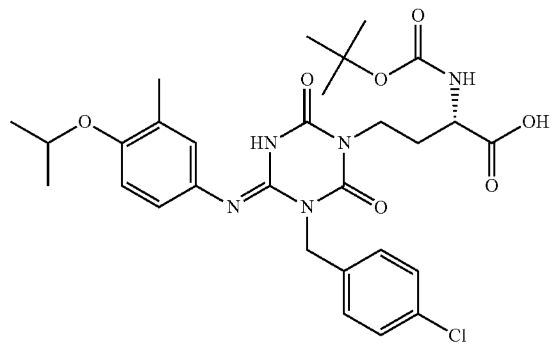 [SMILES: Cc1cc(/N=c2\[nH]c(=O)n(CC[C@H](NC(=O)OC(C)(C)C)C(=O)O)c(=O)n2Cc2ccc(Cl)cc2)ccc1OC(C)C] | I-0732 | 2.26 | 602 | 2 |
| 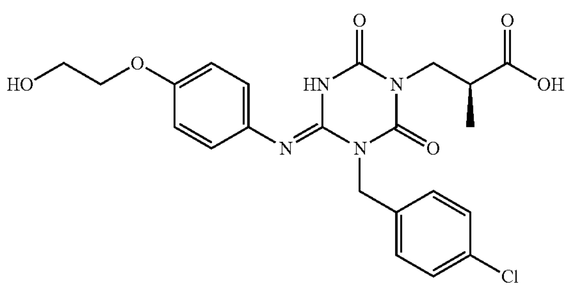 [SMILES: C[C@@H](Cn1c(=O)[nH]/c(=N\c2ccc(OCCO)cc2)n(Cc2ccc(Cl)cc2)c1=O)C(=O)O] | I-0733 | 1.45 | 475 | 2 |
| 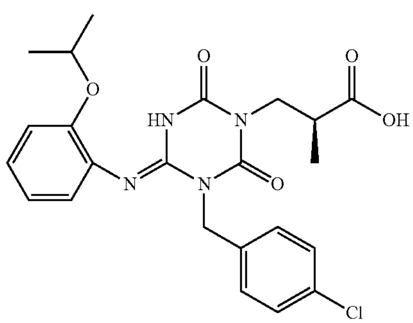 [SMILES: CC(C)Oc1ccccc1/N=c1\[nH]c(=O)n(C[C@H](C)C(=O)O)c(=O)n1Cc1ccc(Cl)cc1] | I-0734 | 1.95 | 473 | 2 |
| 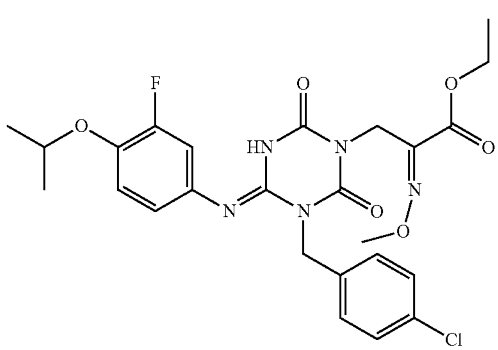 [SMILES: CCOC(=O)/C(Cn1c(=O)[nH]/c(=N\c2ccc(OC(C)C)c(F)c2)n(Cc2ccc(Cl)cc2)c1=O)=N/OC] | I-0735 | 2.30 | 548 | 2 |

TABLE 151

| Structure | Compound No. | Retention Time (min) | [M + H] | Method |
|---|---|---|---|---|
| 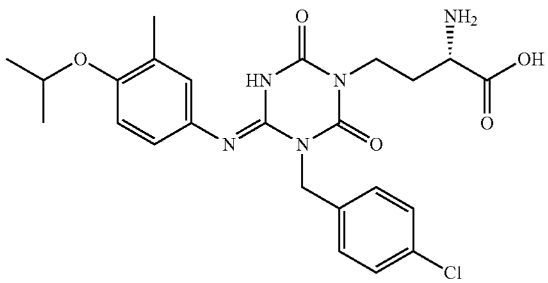 [SMILES: Cc1cc(/N=c2\[nH]c(=O)n(CC[C@H](N)C(=O)O)c(=O)n2Cc2ccc(Cl)cc2)ccc1OC(C)C] | I-0736 | 1.56 | 502 | 2 |
| 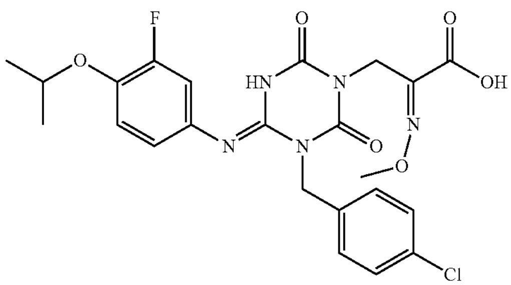 [SMILES: CO/N=C(\Cn1c(=O)[nH]/c(=N\c2ccc(OC(C)C)c(F)c2)n(Cc2ccc(Cl)cc2)c1=O)C(=O)O] | I-0737 | 1.97 | 520 | 2 |
| 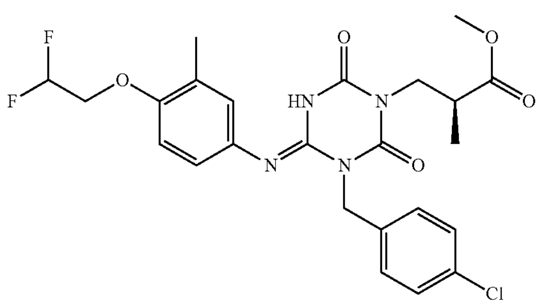 [SMILES: COC(=O)[C@@H](C)Cn1c(=O)[nH]/c(=N\c2ccc(OCC(F)F)c(C)c2)n(Cc2ccc(Cl)cc2)c1=O] | I-0738 | 2.19 | 523 | 2 |
| 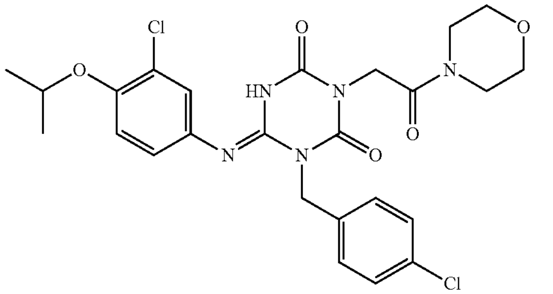 [SMILES: CC(C)Oc1ccc(/N=c2\[nH]c(=O)n(CC(=O)N3CCOCC3)c(=O)n2Cc2ccc(Cl)cc2)cc1Cl] | I-0739 | 2.07 | 548 | 2 |
| 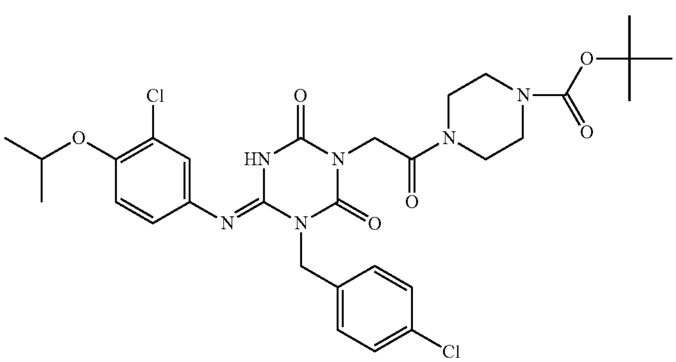 [SMILES: CC(C)Oc1ccc(/N=c2\[nH]c(=O)n(CC(=O)N3CCN(C(=O)OC(C)(C)C)CC3)c(=O)n2Cc2ccc(Cl)cc2)cc1Cl] | I-0740 | 2.39 | 647 | 2 |

TABLE 152

| Structure | Compound No. | Retention Time (min) | [M + H] | Method |
|---|---|---|---|---|
| 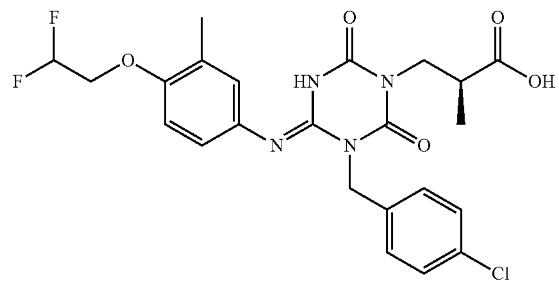 [SMILES: Cc1cc(/N=c2\[nH]c(=O)n(C[C@H](C)C(=O)O)c(=O)n2Cc2ccc(Cl)cc2)ccc1OCC(F)F] | I-0741 | 1.95 | 509 | 2 |
| 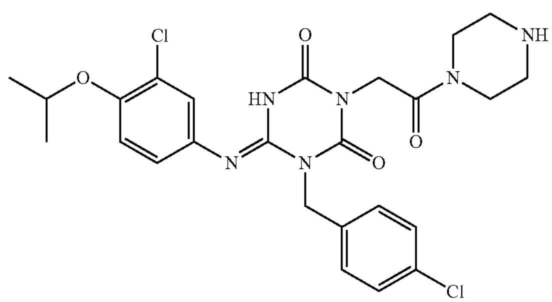 [SMILES: CC(C)Oc1ccc(/N=c2\[nH]c(=O)n(CC(=O)N3CCNCC3)c(=O)n2Cc2ccc(Cl)cc2)cc1Cl] | I-0742 | 1.56 | 547 | 2 |
| 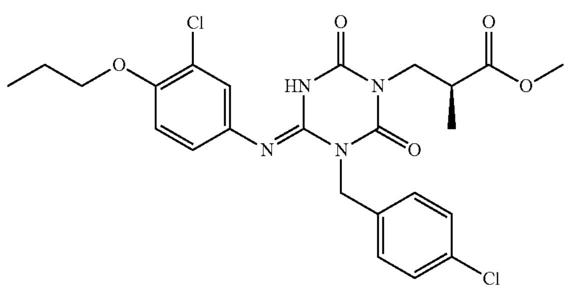 [SMILES: CCCOc1ccc(/N=c2\[nH]c(=O)n(C[C@H](C)C(=O)OC)c(=O)n2Cc2ccc(Cl)cc2)cc1Cl] | I-0743 | 2.66 | 521 | 3 |
| 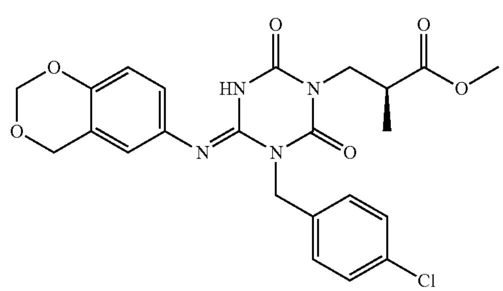 [SMILES: COC(=O)[C@@H](C)Cn1c(=O)[nH]/c(=N\c2ccc3c(c2)COCO3)n(Cc2ccc(Cl)cc2)c1=O] | I-0744 | 2.13 | 487 | 3 |
| 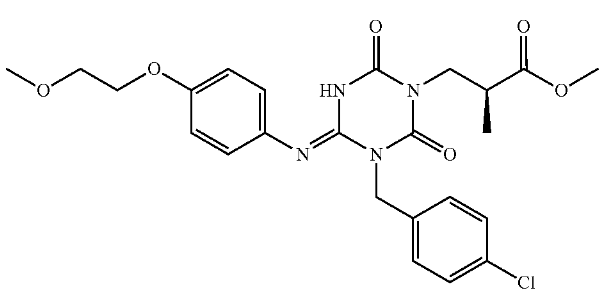 | I-0745 | 2.13 | 503 | 3 |

TABLE 153

| Structure | Compound No. | Retention Time (min) | [M + H] | Method |
|---|---|---|---|---|
| 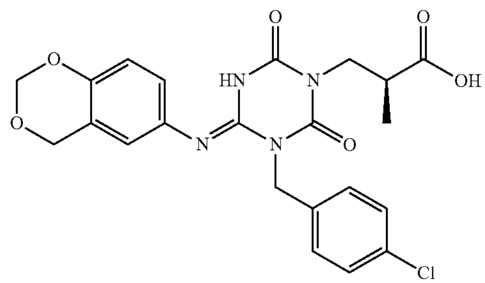 [SMILES: C[C@@H](Cn1c(=O)[nH]/c(=N\c2ccc3c(c2)COCO3)n(Cc2ccc(Cl)cc2)c1=O)C(=O)O] | I-0746 | 1.86 | 473 | 3 |
| 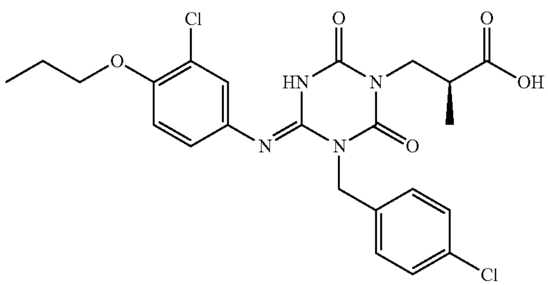 [SMILES: CCCOc1ccc(/N=c2\[nH]c(=O)n(C[C@H](C)C(=O)O)c(=O)n2Cc2ccc(Cl)cc2)cc1Cl] | I-0747 | 2.40 | 507 | 3 |
| 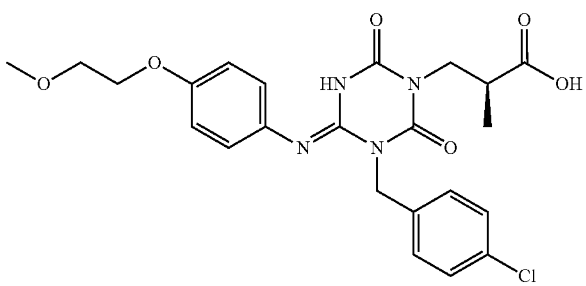 [SMILES: COCCOc1ccc(/N=c2\[nH]c(=O)n(C[C@H](C)C(=O)O)c(=O)n2Cc2ccc(Cl)cc2)cc1] | I-0748 | 1.86 | 489 | 3 |
| 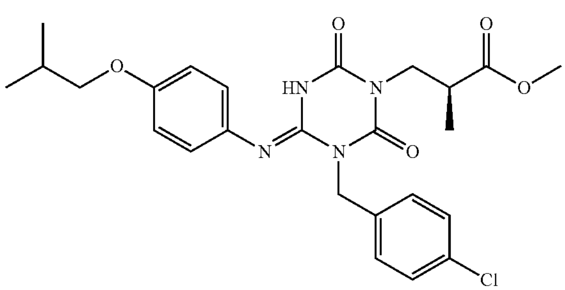 [SMILES: COC(=O)[C@@H](C)Cn1c(=O)[nH]/c(=N\c2ccc(OCC(C)C)cc2)n(Cc2ccc(Cl)cc2)c1=O] | I-0749 | 2.57 | 501 | 3 |
| 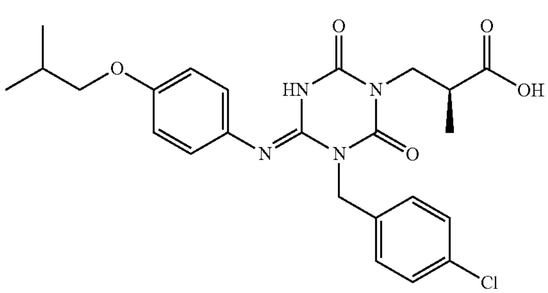 [SMILES: CC(C)COc1ccc(/N=c2\[nH]c(=O)n(C[C@H](C)C(=O)O)c(=O)n2Cc2ccc(Cl)cc2)cc1] | I-0750 | 2.32 | 487 | 3 |

TABLE 154

| Structure | Compound No. | Retention Time (min) | [M + H] | Method |
|---|---|---|---|---|
| 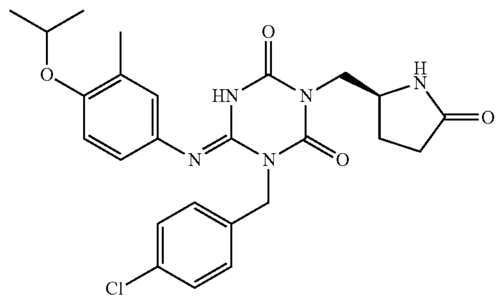 [SMILES: Cc1cc(/N=c2\[nH]c(=O)n(C[C@@H]3CCC(=O)N3)c(=O)n2Cc2ccc(Cl)cc2)ccc1OC(C)C] | I-0751 | 2.17 | 499 | 3 |
| 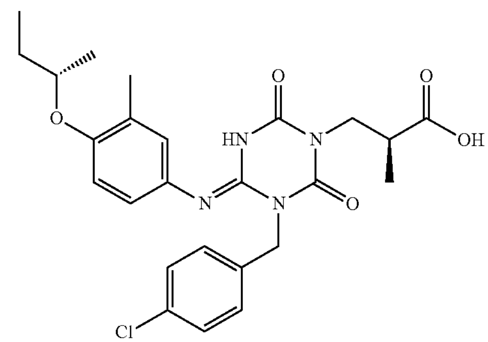 [SMILES: CC[C@H](C)Oc1ccc(/N=c2\[nH]c(=O)n(C[C@H](C)C(=O)O)c(=O)n2Cc2ccc(Cl)cc2)cc1C] | I-0752 | 2.43 | 502 | 3 |
| 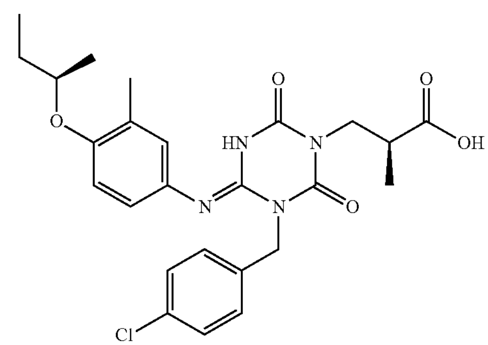 [SMILES: CC[C@@H](C)Oc1ccc(/N=c2\[nH]c(=O)n(C[C@H](C)C(=O)O)c(=O)n2Cc2ccc(Cl)cc2)cc1C] | I-0753 | 2.43 | 502 | 3 |
| 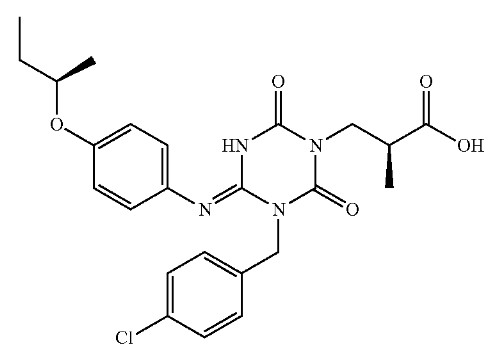 [SMILES: CC[C@@H](C)Oc1ccc(/N=c2\[nH]c(=O)n(C[C@H](C)C(=O)O)c(=O)n2Cc2ccc(Cl)cc2)cc1] | I-0754 | 2.07 | 487 | 2 |

TABLE 154-continued
| Structure | Compound No. | Retention Time (min) | [M + H] | Method |
|---|---|---|---|---|
| 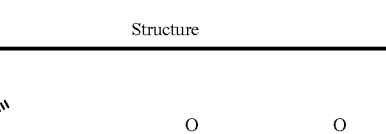 | I-0755 | 2.07 | 487 | 2 |
TABLE 155
| Structure | Compound No. | Retention Time (min) | [M + H] | Method |
|---|---|---|---|---|
| 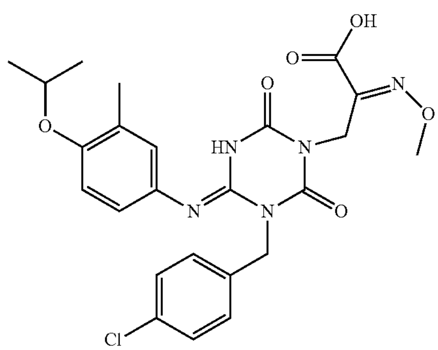 [SMILES: CO/N=C(\Cn1c(=O)[nH]/c(=N\c2ccc(OC(C)C)c(C)c2)n(Cc2ccc(Cl)cc2)c1=O)C(=O)O] | I-0756 | 2.03 | 516 | 2 |
| 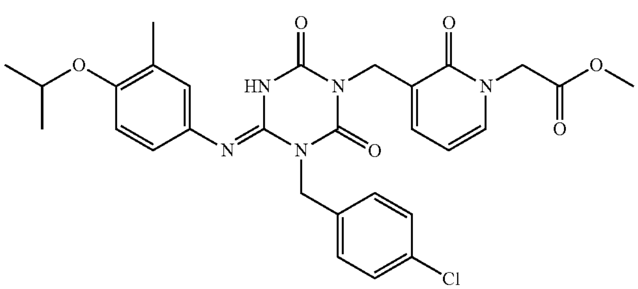 [SMILES: COC(=O)Cn1cccc(Cn2c(=O)[nH]/c(=N\c3ccc(OC(C)C)c(C)c3)n(Cc3ccc(Cl)cc3)c2=O)c1=O] | I-0757 | 2.09 | 580 | 2 |
| 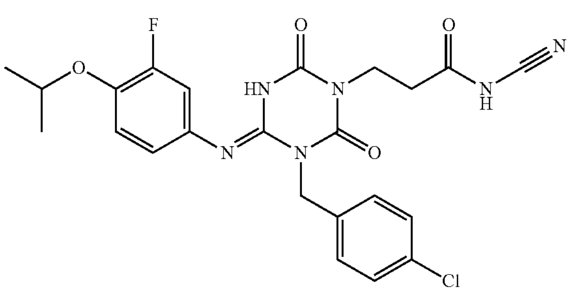 [SMILES: CC(C)Oc1ccc(/N=c2\[nH]c(=O)n(CCC(=O)NC#N)c(=O)n2Cc2ccc(Cl)cc2)cc1F] | I-0758 | 2.00 | 501 | 2 |

TABLE 155-continued

| Structure | Compound No. | Retention Time (min) | [M + H] | Method |
|---|---|---|---|---|
| 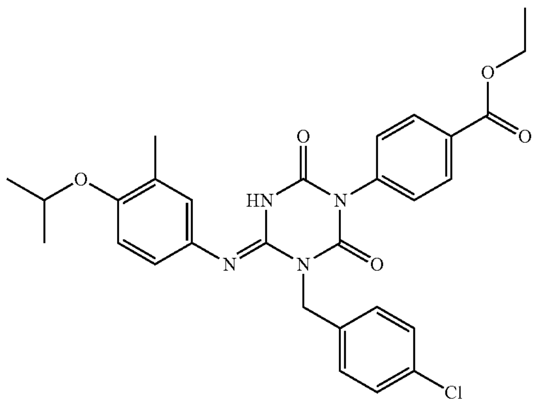 [SMILES: CCOC(=O)c1ccc(-n2c(=O)[nH]/c(=N\c3ccc(OC(C)C)c(C)c3)n(Cc3ccc(Cl)cc3)c2=O)cc1] | I-0759 | 2.45 | 549 | 2 |
| 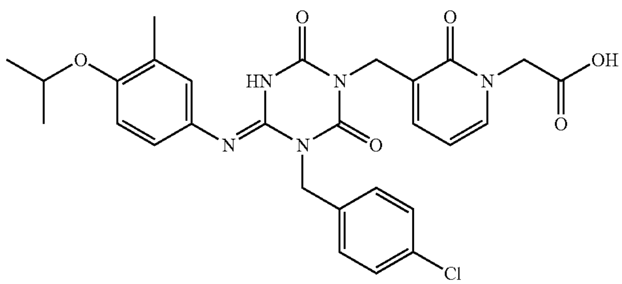 [SMILES: Cc1cc(/N=c2\[nH]c(=O)n(Cc3cccn(CC(=O)O)c3=O)c(=O)n2Cc2ccc(Cl)cc2)ccc1OC(C)C] | I-0760 | 1.96 | 566 | 2 |

TABLE 156

| Structure | Compound No. | Retention Time (min) | [M + H] | Method |
|---|---|---|---|---|
| 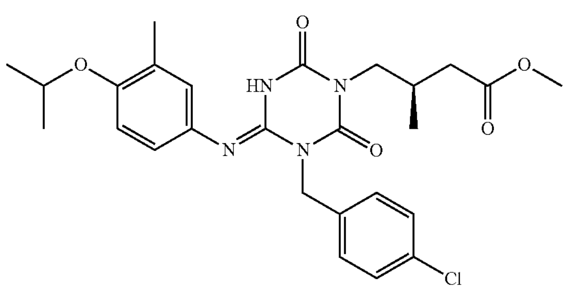 [SMILES: COC(=O)C[C@@H](C)Cn1c(=O)[nH]/c(=N\c2ccc(OC(C)C)c(C)c2)n(Cc2ccc(Cl)cc2)c1=O] | I-0761 | 2.40 | 515 | 2 |
| 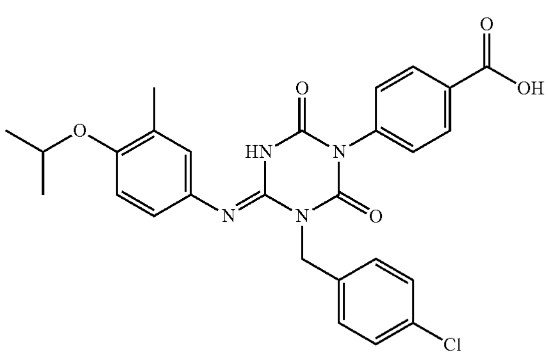 [SMILES: Cc1cc(/N=c2\[nH]c(=O)n(-c3ccc(C(=O)O)cc3)c(=O)n2Cc2ccc(Cl)cc2)ccc1OC(C)C] | I-0762 | 2.12 | 521 | 2 |

TABLE 156-continued

| Structure | Compound No. | Retention Time (min) | [M + H] | Method |
|---|---|---|---|---|
| (structure) | I-0763 | 2.23 | 487 | 2 |
| (structure) | I-0764 | 2.13 | 467 | 2 |
| (structure) | I-0765 | 2.13 | 501 | 2 |

TABLE 157

| Structure | Compound No. | Retention Time (min) | [M + H] | Method |
|---|---|---|---|---|
| (structure) | I-0766 | 2.39 | 502 | 3 |

TABLE 157-continued

| Structure | Compound No. | Retention Time (min) | [M + H] | Method |
|---|---|---|---|---|
| 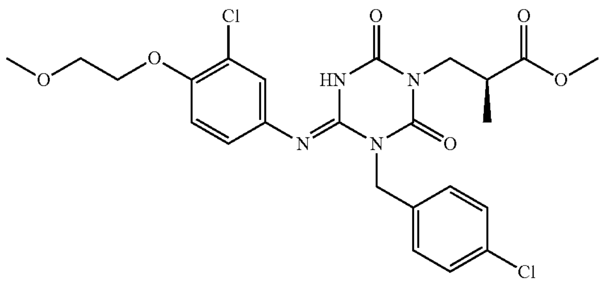 | I-0767 | 2.38 | 537 | 3 |
| 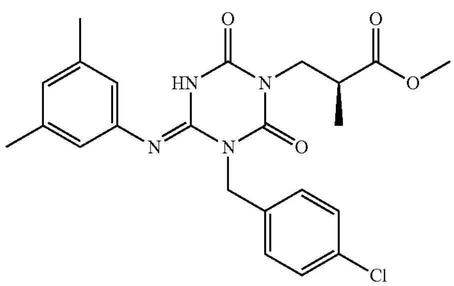 | I-0768 | 2.49 | 457 | 3 |
| 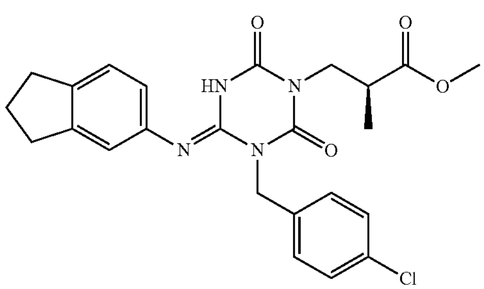 | I-0769 | 2.48 | 469 | 3 |
| 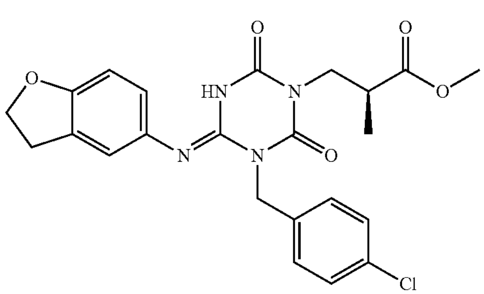 [SMILES: COC(=O)[C@@H](C)Cn1c(=O)[nH]/c(=N\c2ccc3c(c2)CCC3)n(Cc2ccc(Cl)cc2)c1=O] | I-0770 | 2.13 | 471 | 3 |

TABLE 158
| Structure | Compound No. | Retention Time (min) | [M + H] | Method |
|---|---|---|---|---|
| 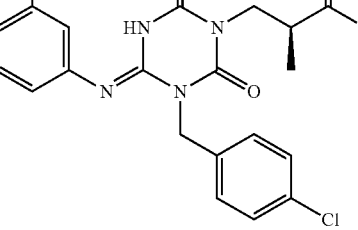 | I-0771 | 2.20 | 443 | 3 |
| 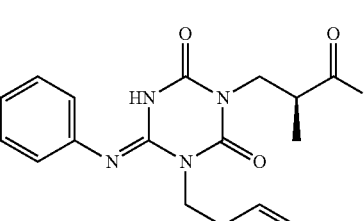 | I-0772 | 2.20 | 455 | 3 |
| 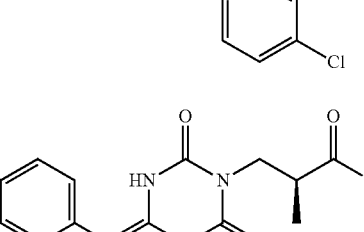 | I-0773 | 1.86 | 457 | 3 |
| 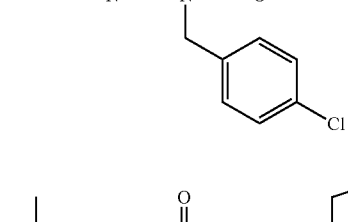 | I-0774 | 2.02 | 513 | 2 |
| 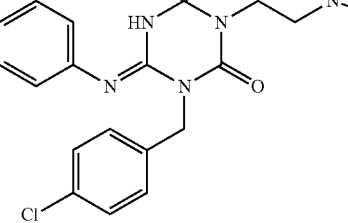 | I-0775 | 2.14 | 485 | 2 |

TABLE 159

| Structure | Compound No. | Retention Time (min) | [M + H] | Method |
|---|---|---|---|---|
| 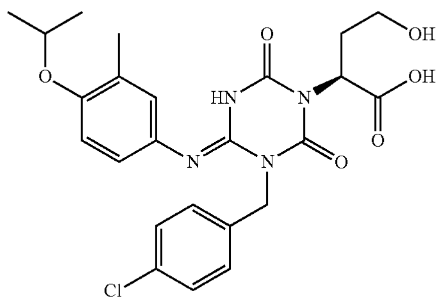 [SMILES: Cc1cc(/N=c2\[nH]c(=O)n([C@@H](CCO)C(=O)O)c(=O)n2Cc2ccc(Cl)cc2)ccc1OC(C)C] | I-0776 | 1.84 | 503 | 2 |
| 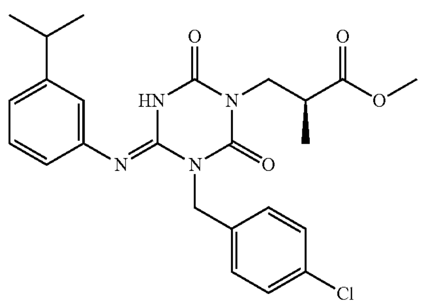 [SMILES: COC(=O)[C@@H](C)Cn1c(=O)[nH]/c(=N\c2cccc(C(C)C)c2)n(Cc2ccc(Cl)cc2)c1=O] | I-0777 | 2.56 | 471 | 3 |
| 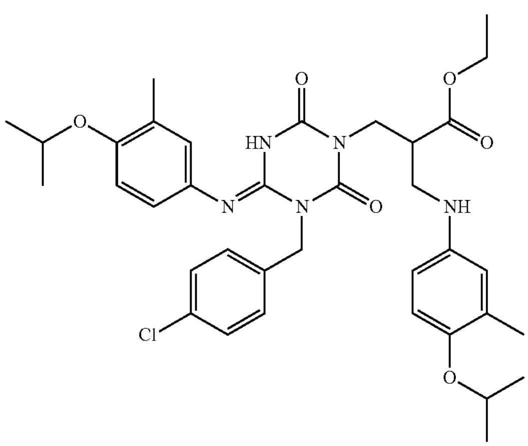 [SMILES: CCOC(=O)C(CNc1ccc(OC(C)C)c(C)c1)Cn1c(=O)[nH]/c(=N\c2ccc(OC(C)C)c(C)c2)n(Cc2ccc(Cl)cc2)c1=O] | I-0778 | 2.75 | 678 | 2 |
| 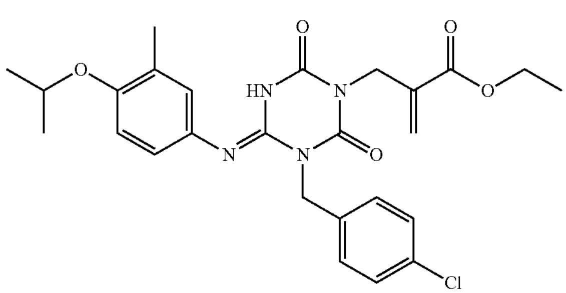 [SMILES: C=C(Cn1c(=O)[nH]/c(=N\c2ccc(OC(C)C)c(C)c2)n(Cc2ccc(Cl)cc2)c1=O)C(=O)OCC] | I-0779 | 2.42 | 513 | 2 |

TABLE 159-continued

| Structure | Compound No. | Retention Time (min) | [M + H] | Method |
|---|---|---|---|---|
| 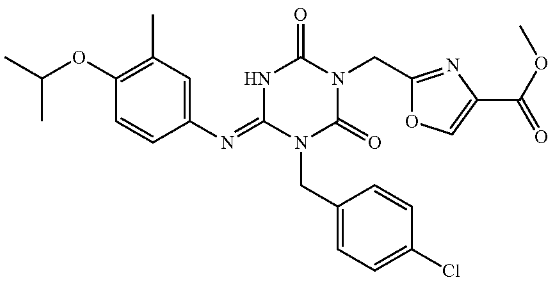 [SMILES: COC(=O)c1coc(Cn2c(=O)[nH]/c(=N\c3ccc(OC(C)C)c(C)c3)n(Cc3ccc(Cl)cc3)c2=O)n1] | I-0780 | 2.18 | 540 | 2 |

TABLE 160

| Structure | Compound No. | Retention Time (min) | [M + H] | Method |
|---|---|---|---|---|
| 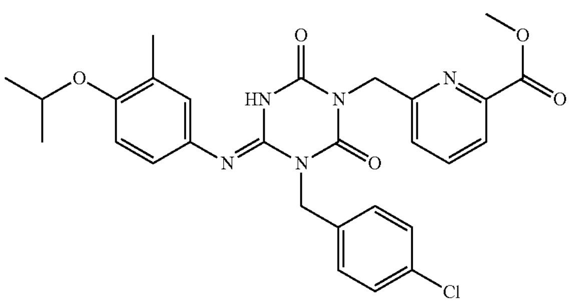 [SMILES: COC(=O)c1cccc(Cn2c(=O)[nH]/c(=N\c3ccc(OC(C)C)c(C)c3)n(Cc3ccc(Cl)cc3)c2=O)n1] | I-0781 | 2.24 | 550 | 2 |
| 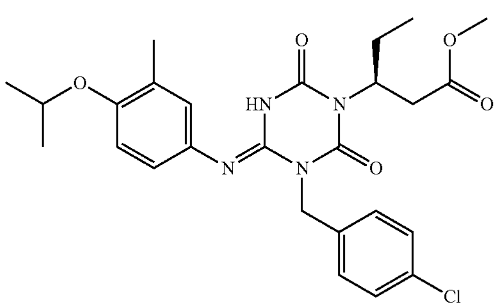 [SMILES: CC[C@@H](CC(=O)OC)n1c(=O)[nH]/c(=N\c2ccc(OC(C)C)c(C)c2)n(Cc2ccc(Cl)cc2)c1=O] | I-0782 | 2.45 | 515 | 2 |
| 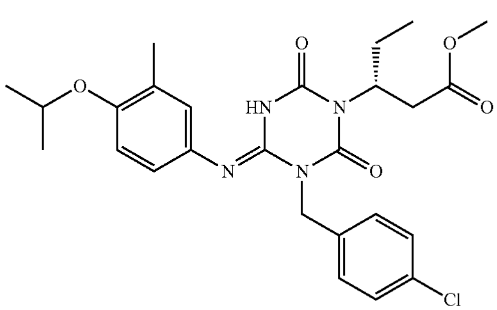 [SMILES: CC[C@H](CC(=O)OC)n1c(=O)[nH]/c(=N\c2ccc(OC(C)C)c(C)c2)n(Cc2ccc(Cl)cc2)c1=O] | I-0783 | 2.45 | 515 | 2 |

TABLE 160-continued

| Structure | Compound No. | Retention Time (min) | [M + H] | Method |
|---|---|---|---|---|
| 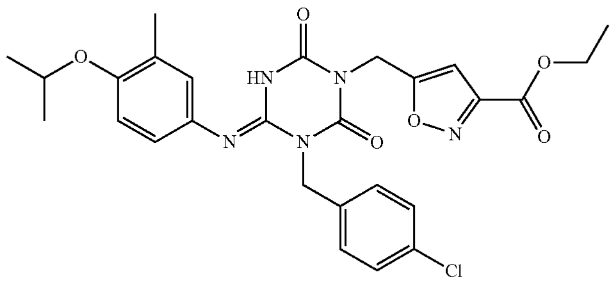 [SMILES: CCOC(=O)c1cc(Cn2c(=O)[nH]/c(=N\c3ccc(OC(C)C)c(C)c3)n(Cc3ccc(Cl)cc3)c2=O)on1] | I-0784 | 2.38 | 554 | 2 |
| 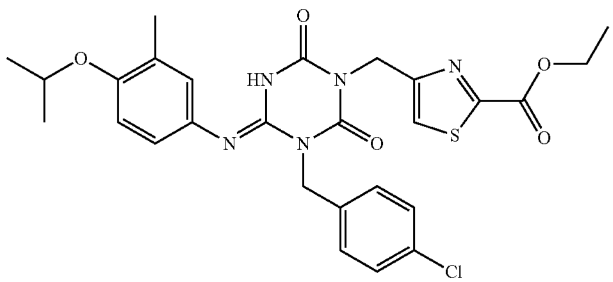 [SMILES: CCOC(=O)c1nc(Cn2c(=O)[nH]/c(=N\c3ccc(OC(C)C)c(C)c3)n(Cc3ccc(Cl)cc3)c2=O)cs1] | I-0785 | 2.37 | 570 | 2 |

TABLE 161

| Structure | Compound No. | Retention Time (min) | [M + H] | Method |
|---|---|---|---|---|
| 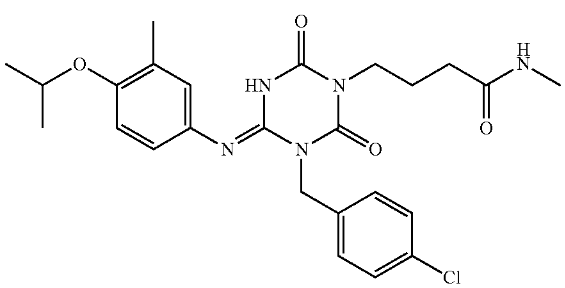 [SMILES: CNC(=O)CCCn1c(=O)[nH]/c(=N\c2ccc(OC(C)C)c(C)c2)n(Cc2ccc(Cl)cc2)c1=O] | I-0786 | 1.99 | 500 | 2 |
| 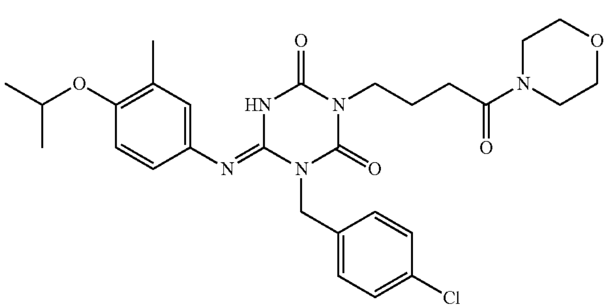 [SMILES: Cc1cc(/N=c2\[nH]c(=O)n(CCCC(=O)N3CCOCC3)c(=O)n2Cc2ccc(Cl)cc2)ccc1OC(C)C] | I-0787 | 2.05 | 556 | 2 |

TABLE 161-continued

| Structure | Compound No. | Retention Time (min) | [M + H] | Method |
|---|---|---|---|---|
| 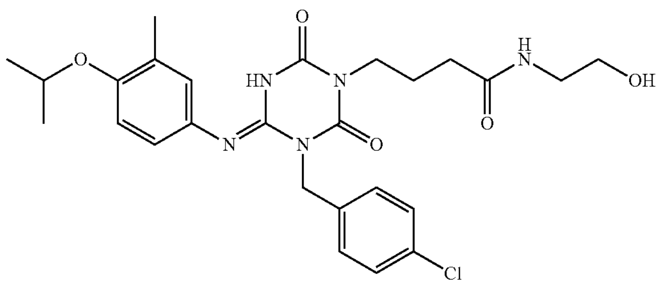 [SMILES: Cc1cc(/N=c2\[nH]c(=O)n(CCCC(=O)NCCO)c(=O)n2Cc2ccc(Cl)cc2)ccc1OC(C)C] | I-0788 | 1.86 | 530 | 2 |
| 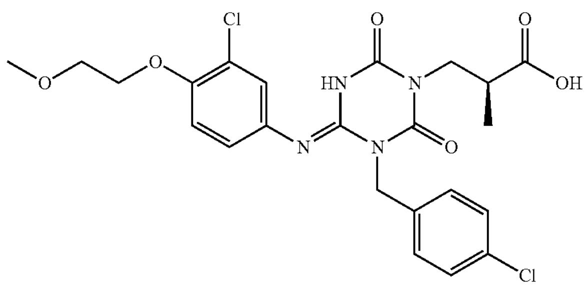 | I-0789 | 2.11 | 523 | 3 |
| 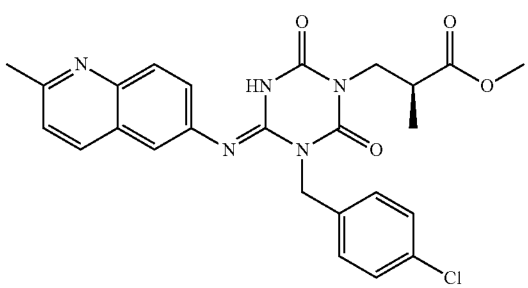 | I-0790 | 1.53 | 494 | 3 |

TABLE 162

| Structure | Compound No. | Retention Time (min) | [M + H] | Method |
|---|---|---|---|---|
| 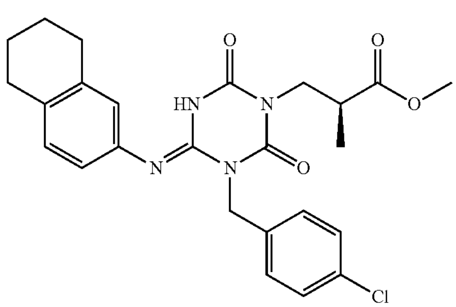 [SMILES: COC(=O)[C@@H](C)Cn1c(=O)[nH]/c(=N\c2ccc3c(c2)CCCC3)n(Cc2ccc(Cl)cc2)c1=O] | I-0791 | 2.57 | 483 | 3 |

TABLE 162-continued

| Structure | Compound No. | Retention Time (min) | [M + H] | Method |
|---|---|---|---|---|
| 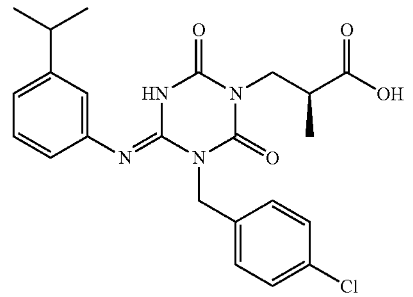 [SMILES: CC(C)c1cccc(/N=c2\[nH]c(=O)n(C[C@H](C)C(=O)O)c(=O)n2Cc2ccc(Cl)cc2)c1] | I-0792 | 2.31 | 457 | 3 |
| 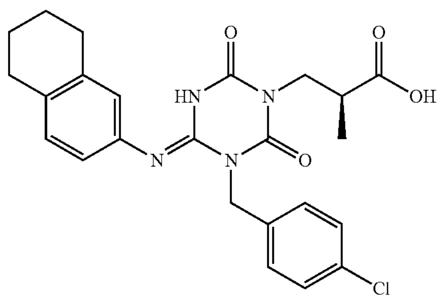 [SMILES: C[C@@H](Cn1c(=O)[nH]/c(=N\c2ccc3c(c2)CCCC3)n(Cc2ccc(Cl)cc2)c1=O)C(=O)O] | I-0793 | 2.30 | 469 | 3 |
| 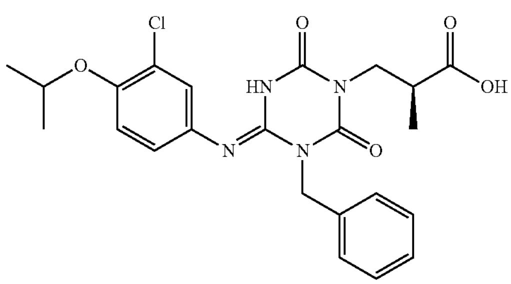 | I-0794 | 1.97 | 473 | 2 |
| 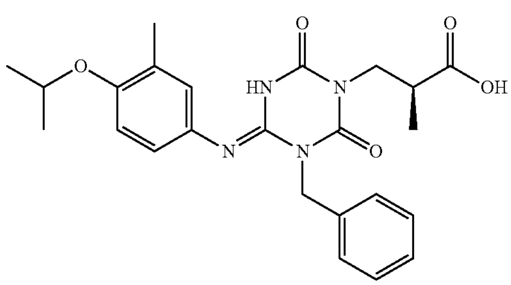 [SMILES: Cc1cc(/N=c2\[nH]c(=O)n(C[C@H](C)C(=O)O)c(=O)n2Cc2ccccc2)ccc1OC(C)C] | I-0795 | 1.92 | 453 | 2 |

TABLE 163
| Structure | Compound No. | Retention Time (min) | [M + H] | Method |
|---|---|---|---|---|
| 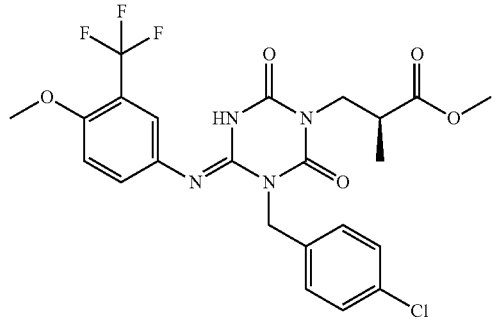 | I-0796 | 2.28 | 527 | 2 |
| 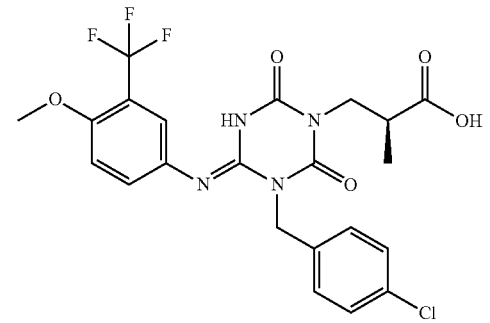 [SMILES: COc1ccc(/N=c2\[nH]c(=O)n(C[C@H](C)C(=O)O)c(=O)n2Cc2ccc(Cl)cc2)cc1C(F)(F)F] | I-0797 | 2.04 | 513 | 2 |
| 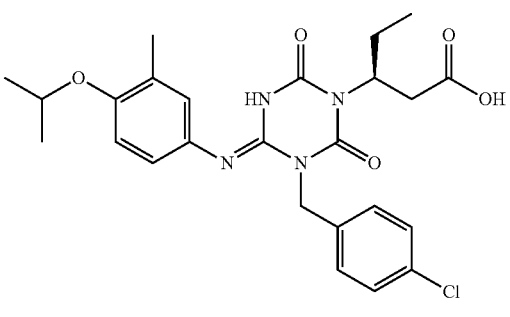 [SMILES: CC[C@@H](CC(=O)O)n1c(=O)[nH]/c(=N\c2ccc(OC(C)C)c(C)c2)n(Cc2ccc(Cl)cc2)c1=O] | I-0798 | 2.19 | 501 | 2 |
| 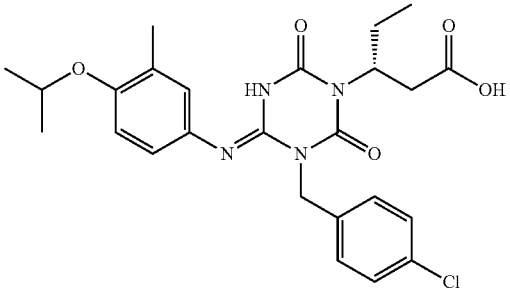 [SMILES: CC[C@H](CC(=O)O)n1c(=O)[nH]/c(=N\c2ccc(OC(C)C)c(C)c2)n(Cc2ccc(Cl)cc2)c1=O] | I-0799 | 2.19 | 501 | 2 |
| 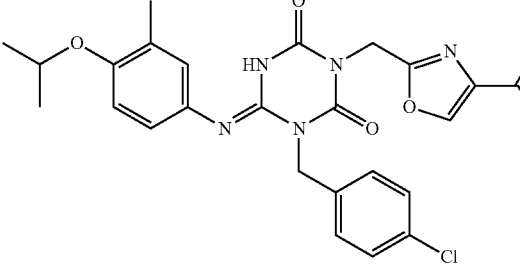 | I-0800 | 1.98 | 526 | 2 |

TABLE 164

| Structure | Compound No. | Retention Time (min) | [M + H] | Method |
|---|---|---|---|---|
| 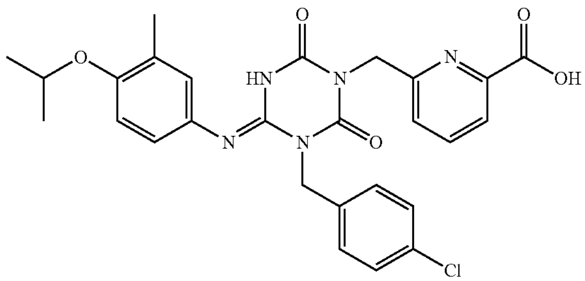 [SMILES: Cc1cc(/N=c2\[nH]c(=O)n(Cc3cccc(C(=O)O)n3)c(=O)n2Cc2ccc(Cl)cc2)ccc1OC(C)C] | I-0801 | 2.04 | 536 | 2 |
| 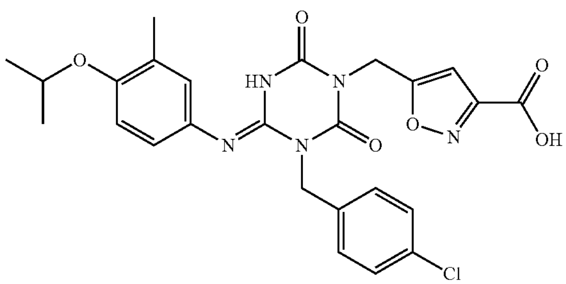 [SMILES: Cc1cc(/N=c2\[nH]c(=O)n(Cc3cc(C(=O)O)no3)c(=O)n2Cc2ccc(Cl)cc2)ccc1OC(C)C] | I-0802 | 2.03 | 526 | 2 |
| 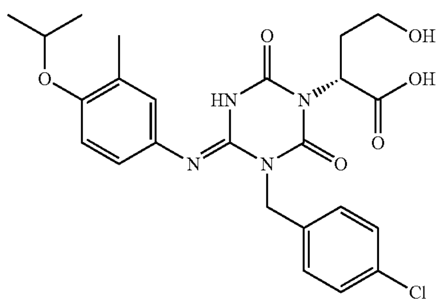 [SMILES: Cc1cc(/N=c2\[nH]c(=O)n([C@H](CCO)C(=O)O)c(=O)n2Cc2ccc(Cl)cc2)ccc1OC(C)C] | I-0803 | 2.04 | 503 | 3 |
| 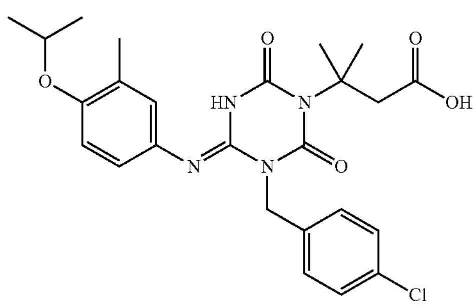 [SMILES: Cc1cc(/N=c2\[nH]c(=O)n(C(C)(C)CC(=O)O)c(=O)n2Cc2ccc(Cl)cc2)ccc1OC(C)C] | I-0804 | 2.17 | 501 | 2 |
| 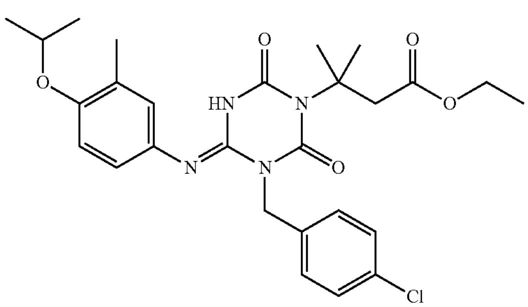 [SMILES: CCOC(=O)CC(C)(C)n1c(=O)[nH]/c(=N\c2ccc(OC(C)C)c(C)c2)n(Cc2ccc(Cl)cc2)c1=O] | I-0805 | 2.54 | 529 | 2 |

TABLE 165

| Structure | Compound No. | Retention Time (min) | [M + H] | Method |
|---|---|---|---|---|
| 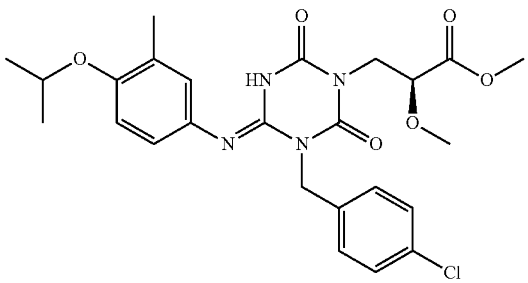 [SMILES: COC(=O)[C@H](Cn1c(=O)[nH]/c(=N\c2ccc(OC(C)C)c(C)c2)n(Cc2ccc(Cl)cc2)c1=O)OC] | I-0806 | 2.22 | 517 | 2 |
| 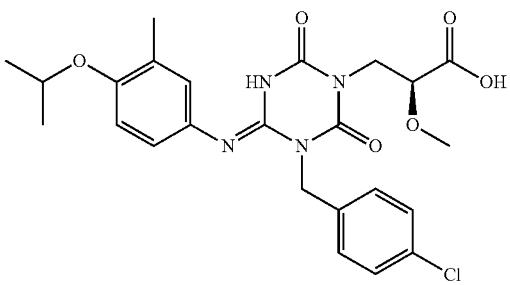 [SMILES: CO[C@@H](Cn1c(=O)[nH]/c(=N\c2ccc(OC(C)C)c(C)c2)n(Cc2ccc(Cl)cc2)c1=O)C(=O)O] | I-0807 | 2.00 | 503 | 2 |
| 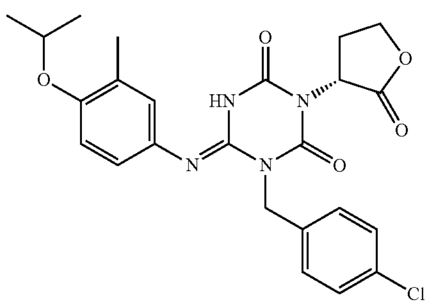 [SMILES: Cc1cc(/N=c2\[nH]c(=O)n([C@@H]3CCOC3=O)c(=O)n2Cc2ccc(Cl)cc2)ccc1OC(C)C] | I-0808 | 2.33 | 485 | 3 |
| 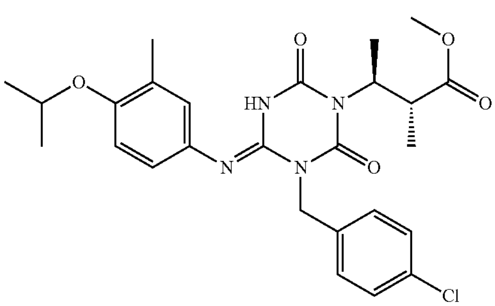 [SMILES: COC(=O)[C@H](C)[C@H](C)n1c(=O)[nH]/c(=N\c2ccc(OC(C)C)c(C)c2)n(Cc2ccc(Cl)cc2)c1=O] | I-0809 | 2.47 | 515 | 2 |
| 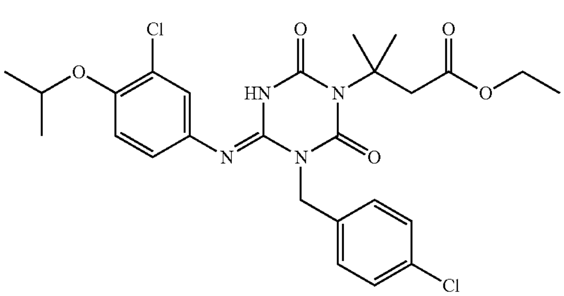 [SMILES: CCOC(=O)CC(C)(C)n1c(=O)[nH]/c(=N\c2ccc(OC(C)C)c(Cl)c2)n(Cc2ccc(Cl)cc2)c1=O] | I-0810 | 2.85 | 549 | 3 |

TABLE 166

| Structure | Compound No. | Retention Time (min) | [M + H] | Method |
|---|---|---|---|---|
| 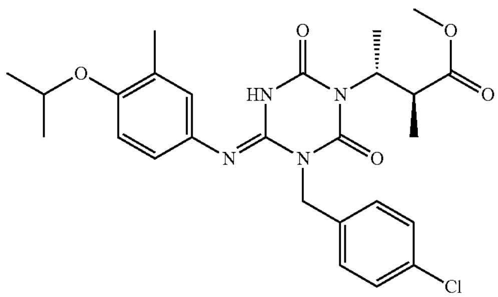 [SMILES: COC(=O)[C@@H](C)[C@@H](C)n1c(=O)[nH]/c(=N\c2ccc(OC(C)C)c(C)c2)n(Cc2ccc(Cl)cc2)c1=O] | I-0811 | 2.69 | 515 | 3 |
| 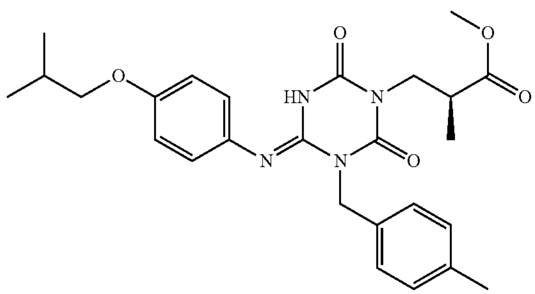 [SMILES: COC(=O)[C@@H](C)Cn1c(=O)[nH]/c(=N\c2ccc(OCC(C)C)cc2)n(Cc2ccc(C)cc2)c1=O] | I-0812 | 2.53 | 481 | 3 |
| 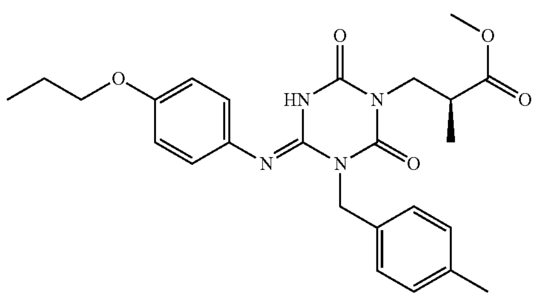 [SMILES: CCCOc1ccc(/N=c2\[nH]c(=O)n(C[C@H](C)C(=O)OC)c(=O)n2Cc2ccc(C)cc2)cc1] | I-0813 | 2.38 | 467 | 3 |
| 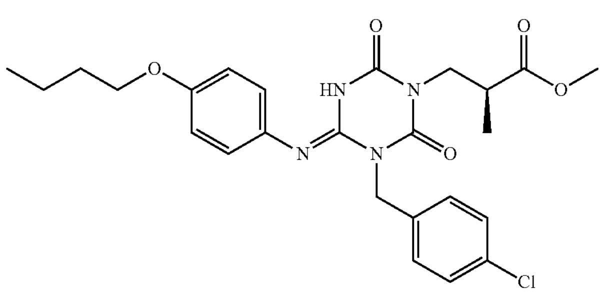 [SMILES: CCCCOc1ccc(/N=c2\[nH]c(=O)n(C[C@H](C)C(=O)OC)c(=O)n2Cc2ccc(Cl)cc2)cc1] | I-0814 | 2.58 | 501 | 3 |
| 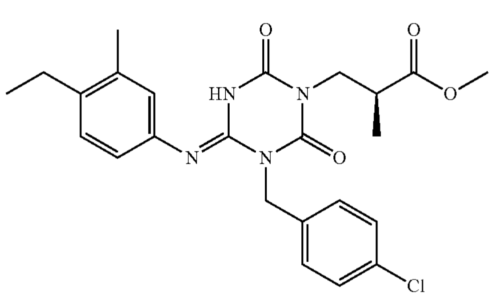 [SMILES: CCc1ccc(/N=c2\[nH]c(=O)n(C[C@H](C)C(=O)OC)c(=O)n2Cc2ccc(Cl)cc2)cc1C] | I-0815 | 2.55 | 471 | 3 |

TABLE 167

| Structure | Compound No. | Retention Time (min) | [M + H] | Method |
|---|---|---|---|---|
| 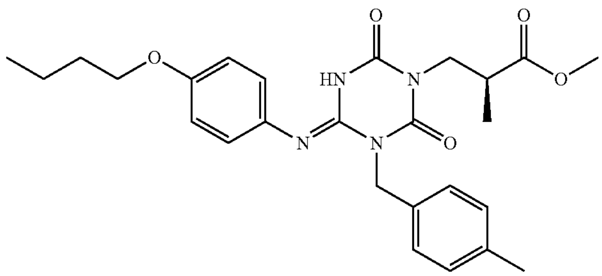 | I-0816 | 2.52 | 481 | 3 |
| 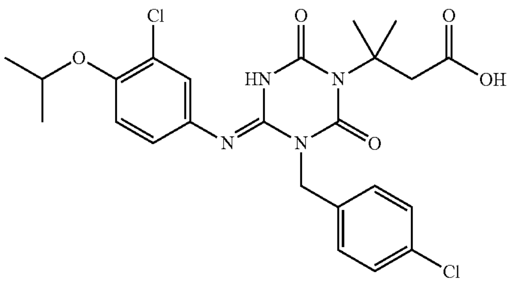 | I-0817 | 2.45 | 521 | 3 |
| 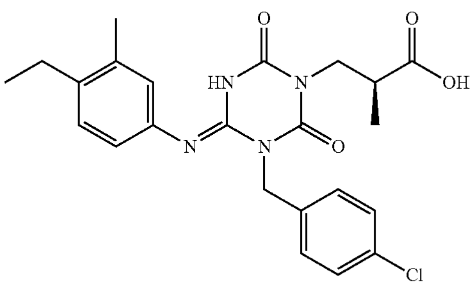 [SMILES: CCc1ccc(/N=c2\[nH]c(=O)n(C[C@H](C)C(=O)O)c(=O)n2Cc2ccc(Cl)cc2)cc1C] | I-0818 | 2.27 | 457 | 3 |
| 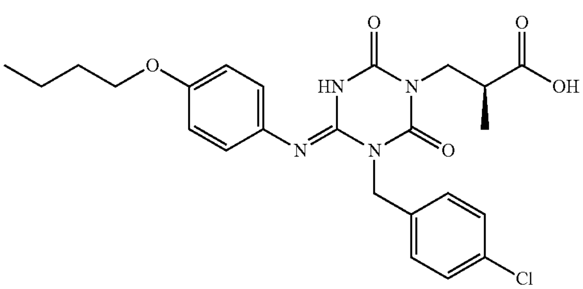 [SMILES: CCCCOc1ccc(/N=c2\[nH]c(=O)n(C[C@H](C)C(=O)O)c(=O)n2Cc2ccc(Cl)cc2)cc1] | I-0819 | 2.32 | 487 | 3 |
| 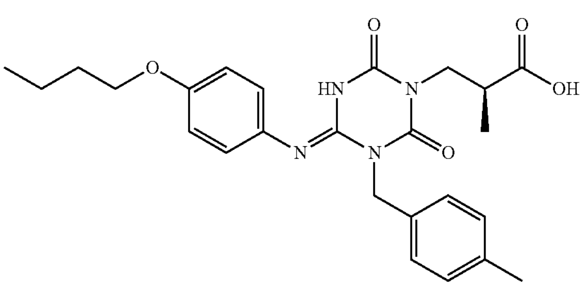 [SMILES: CCCCOc1ccc(/N=c2\[nH]c(=O)n(C[C@H](C)C(=O)O)c(=O)n2Cc2ccc(C)cc2)cc1] | I-0820 | 2.27 | 467 | 3 |

TABLE 168

| Structure | Compound No. | Retention Time (min) | [M + H] | Method |
|---|---|---|---|---|
| 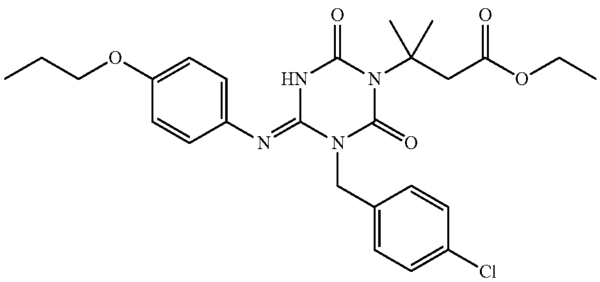 [SMILES: CCCOc1ccc(/N=c2\[nH]c(=O)n(C(C)(C)CC(=O)OCC)c(=O)n2Cc2ccc(Cl)cc2)cc1] | I-0821 | 2.69 | 515 | 3 |
| 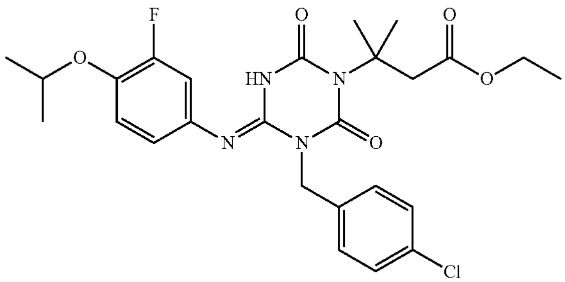 | I-0822 | 2.75 | 533 | 3 |
| 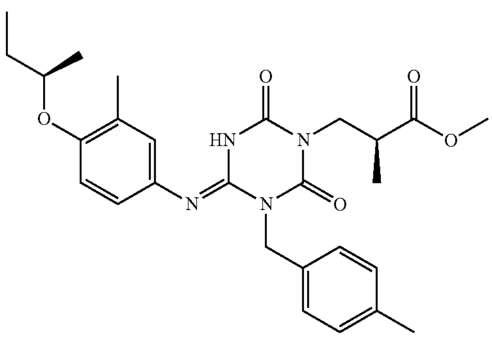 [SMILES: CC[C@@H](C)Oc1ccc(/N=c2\[nH]c(=O)n(C[C@H](C)C(=O)OC)c(=O)n2Cc2ccc(C)cc2)cc1C] | I-0823 | 2.61 | 495 | 3 |
| 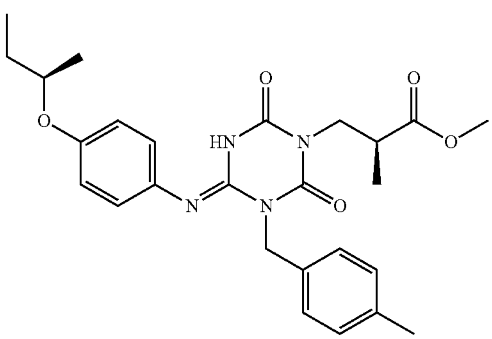 [SMILES: CC[C@@H](C)Oc1ccc(/N=c2\[nH]c(=O)n(C[C@H](C)C(=O)OC)c(=O)n2Cc2ccc(C)cc2)cc1] | I-0824 | 2.47 | 481 | 3 |
| 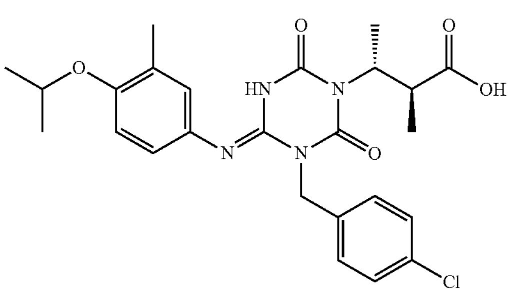 [SMILES: Cc1cc(/N=c2\[nH]c(=O)n([C@H](C)[C@H](C)C(=O)O)c(=O)n2Cc2ccc(Cl)cc2)ccc1OC(C)C] | I-0825 | 2.20 | 501 | 2 |

TABLE 169
| Structure | Compound No. | Retention Time (min) | [M + H] | Method |
|---|---|---|---|---|
| 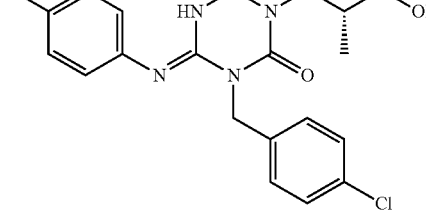 | I-0826 | 2.19 | 501 | 2 |
| 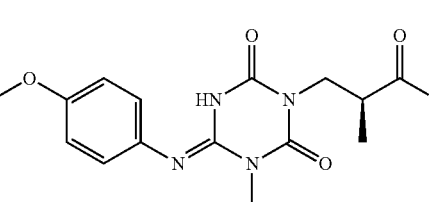 | I-0827 | 2.07 | 467 | 2 |
| 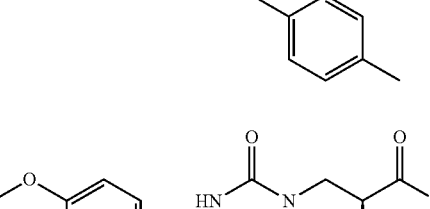 | I-0828 | 1.92 | 453 | 2 |
| 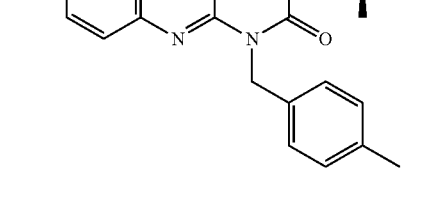 | I-0829 | 2.29 | 487 | 3 |
| 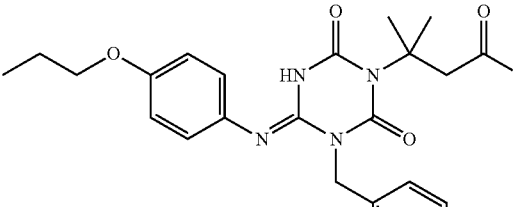 | I-0830 | 2.35 | 505 | 3 |

TABLE 170

| Structure | Compound No. | Retention Time (min) | [M + H] | Method |
|---|---|---|---|---|
| 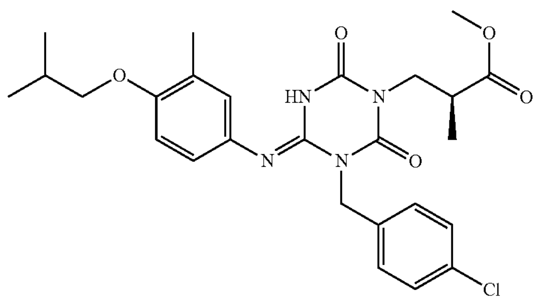 [SMILES: COC(=O)[C@@H](C)Cn1c(=O)[nH]/c(=N\c2ccc(OCC(C)C)c(C)c2)n(Cc2ccc(Cl)cc2)c1=O] | I-0831 | 2.51 | 515 | 2 |
| 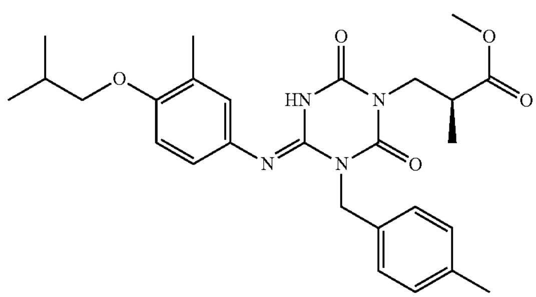 [SMILES: COC(=O)[C@@H](C)Cn1c(=O)[nH]/c(=N\c2ccc(OCC(C)C)c(C)c2)n(Cc2ccc(C)cc2)c1=O] | I-0832 | 2.45 | 495 | 2 |
| 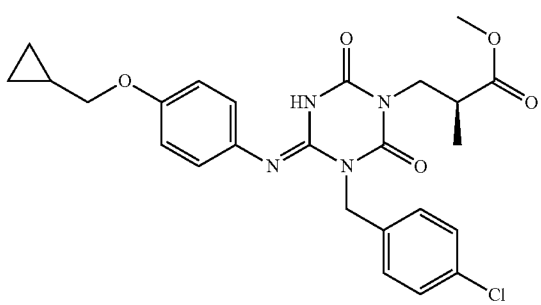 [SMILES: COC(=O)[C@@H](C)Cn1c(=O)[nH]/c(=N\c2ccc(OCC3CC3)cc2)n(Cc2ccc(Cl)cc2)c1=O] | I-0833 | 2.17 | 499 | 2 |
| 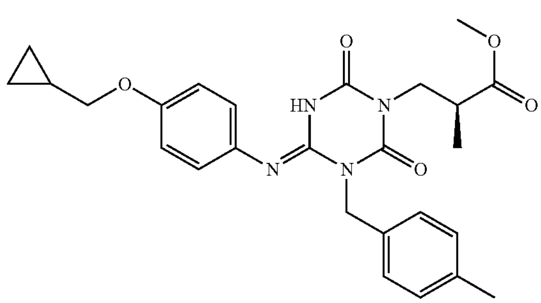 [SMILES: COC(=O)[C@@H](C)Cn1c(=O)[nH]/c(=N\c2ccc(OCC3CC3)cc2)n(Cc2ccc(C)cc2)c1=O] | I-0834 | 2.12 | 479 | 2 |
| 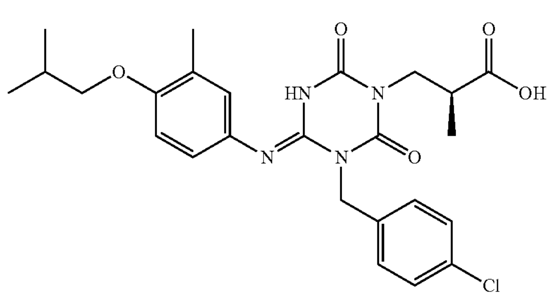 [SMILES: Cc1cc(/N=c2\[nH]c(=O)n(C[C@H](C)C(=O)O)c(=O)n2Cc2ccc(Cl)cc2)ccc1OCC(C)C] | I-0835 | 2.28 | 501 | 2 |

TABLE 171

| Structure | Compound No. | Retention Time (min) | [M + H] | Method |
|---|---|---|---|---|
| 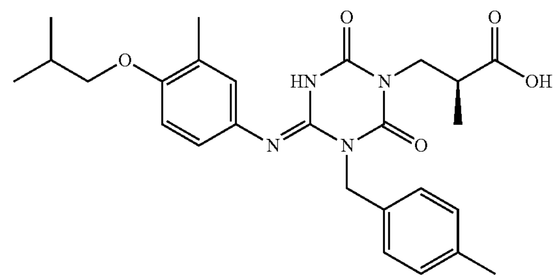 [SMILES: Cc1ccc(Cn2c(=O)n(C[C@H](C)C(=O)O)c(=O)[nH]/c2=N\c2ccc(OCC(C)C)c(C)c2)cc1] | I-0836 | 2.22 | 481 | 2 |
| 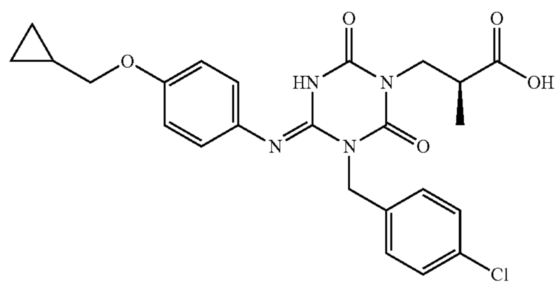 [SMILES: C[C@@H](Cn1c(=O)[nH]/c(=N\c2ccc(OCC3CC3)cc2)n(Cc2ccc(Cl)cc2)c1=O)C(=O)O] | I-0837 | 1.94 | 485 | 2 |
| 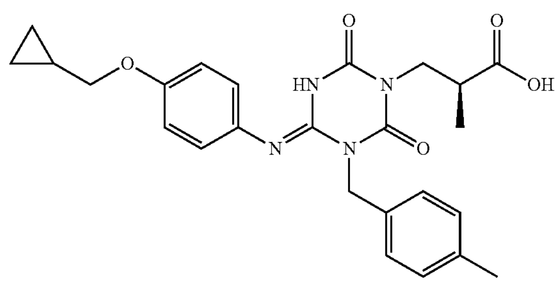 | I-0838 | 1.89 | 465 | 2 |
| 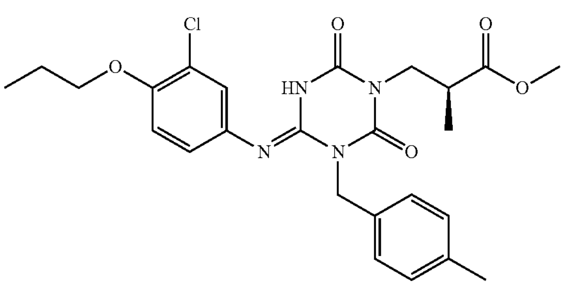 [SMILES: CCCOc1ccc(/N=c2\[nH]c(=O)n(C[C@H](C)C(=O)OC)c(=O)n2Cc2ccc(C)cc2)cc1Cl] | I-0839 | 2.56 | 501 | 3 |
| 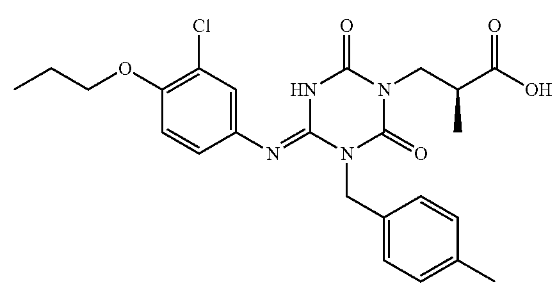 | I-0840 | 2.33 | 487 | 3 |

TABLE 172

| Structure | Compound No. | Retention Time (min) | [M + H] | Method |
|---|---|---|---|---|
| (structure) | I-0841 | 2.44 | 511 | 2 |
| (structure) | I-0842 | 1.96 | 485 | 3 |
| (structure) | I-0843 | 2.20 | 497 | 3 |
| (structure) | I-0844 | 1.70 | 471 | 3 |
| (structure) | I-0845 | 2.39 | 519 | 3 |

TABLE 173

| Structure | Compound No. | Retention Time (min) | [M + H] | Method |
|---|---|---|---|---|
| 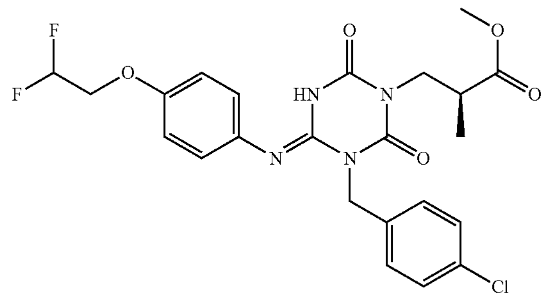 [SMILES: COC(=O)[C@@H](C)Cn1c(=O)[nH]/c(=N\c2ccc(OCC(F)F)cc2)n(Cc2ccc(Cl)cc2)c1=O] | I-0846 | 2.28 | 509 | 3 |
| 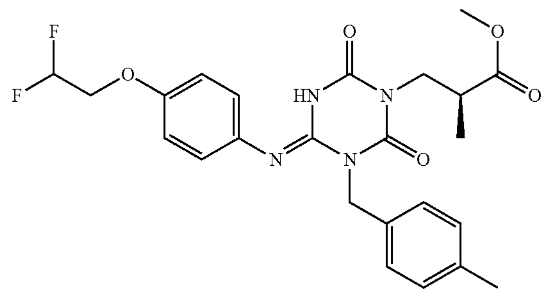 [SMILES: COC(=O)[C@@H](C)Cn1c(=O)[nH]/c(=N\c2ccc(OCC(F)F)cc2)n(Cc2ccc(C)cc2)c1=O] | I-0847 | 2.20 | 489 | 3 |
| 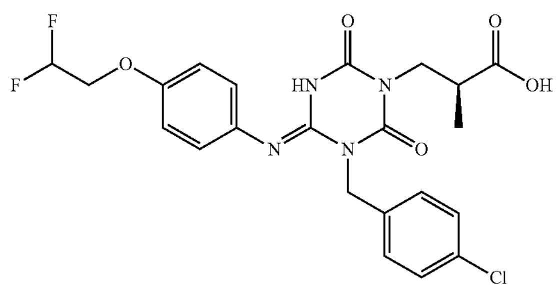 [SMILES: C[C@@H](Cn1c(=O)[nH]/c(=N\c2ccc(OCC(F)F)cc2)n(Cc2ccc(Cl)cc2)c1=O)C(=O)O] | I-0848 | 1.83 | 495 | 2 |
| 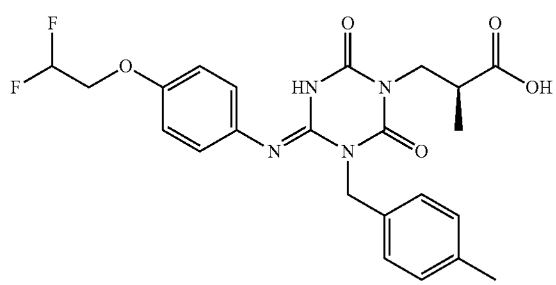 [SMILES: Cc1ccc(Cn2c(=O)n(C[C@H](C)C(=O)O)c(=O)[nH]/c2=N\c2ccc(OCC(F)F)cc2)cc1] | I-0849 | 1.77 | 475 | 2 |
| 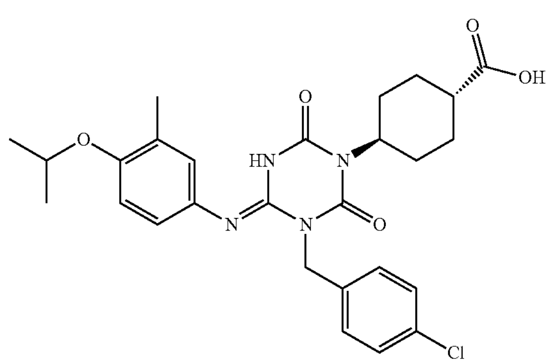 [SMILES: Cc1cc(/N=c2\[nH]c(=O)n([C@H]3CC[C@H](C(=O)O)CC3)c(=O)n2Cc2ccc(Cl)cc2)ccc1OC(C)C] | I-0850 | 2.24 | 527 | 2 |

TABLE 174
| Structure | Compound No. | Retention Time (min) | [M + H] | Method |
|---|---|---|---|---|
| 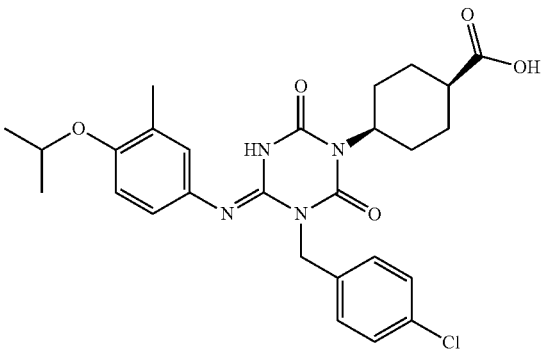 [SMILES: Cc1cc(/N=c2\[nH]c(=O)n([C@H]3CC[C@@H](C(=O)O)CC3)c(=O)n2Cc2ccc(Cl)cc2)ccc1OC(C)C] | I-0851 | 2.25 | 527 | 2 |
| 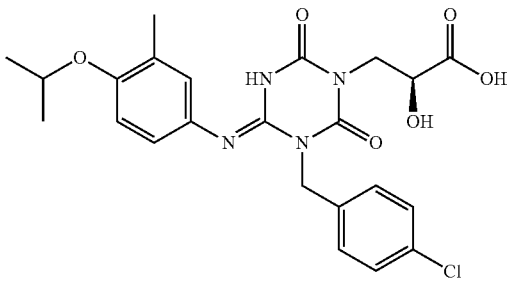 [SMILES: Cc1cc(/N=c2\[nH]c(=O)n(C[C@H](O)C(=O)O)c(=O)n2Cc2ccc(Cl)cc2)ccc1OC(C)C] | I-0852 | 1.87 | 489 | 2 |
| 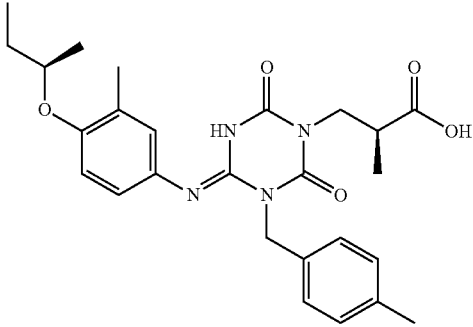 | I-0853 | 2.37 | 481 | 3 |
| 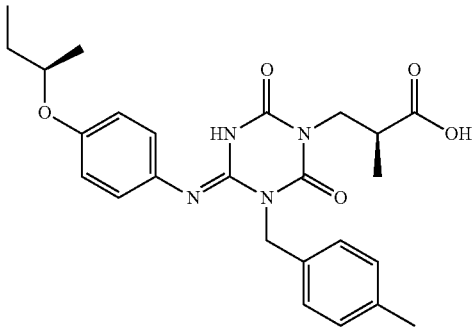 [SMILES: CC[C@@H](C)Oc1ccc(/N=c2\[nH]c(=O)n(C[C@H](C)C(=O)O)c(=O)n2Cc2ccc(C)cc2)cc1] | I-0854 | 2.21 | 467 | 3 |

TABLE 174-continued

| Structure | Compound No. | Retention Time (min) | [M + H] | Method |
|---|---|---|---|---|
| 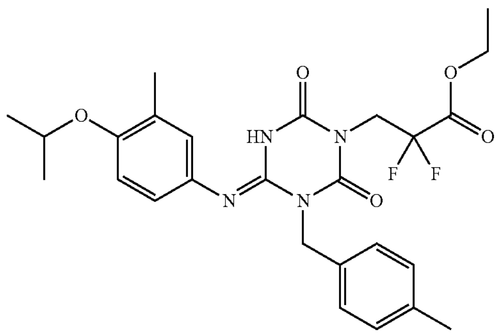 [SMILES: CCOC(=O)C(F)(F)Cn1c(=O)[nH]/c(=N\c2ccc(OC(C)C)c(C)c2)n(Cc2ccc(C)cc2)c1=O] | I-0855 | 2.39 | 517 | 2 |

TABLE 175

| Structure | Compound No. | Retention Time (min) | [M + H] | Method |
|---|---|---|---|---|
| 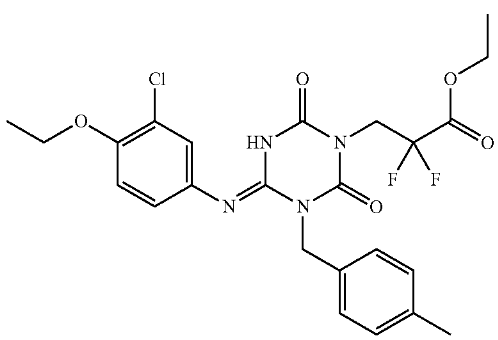 [SMILES: CCOC(=O)C(F)(F)Cn1c(=O)[nH]/c(=N\c2ccc(OCC)c(Cl)c2)n(Cc2ccc(C)cc2)c1=O] | I-0856 | 2.32 | 523 | 2 |
| 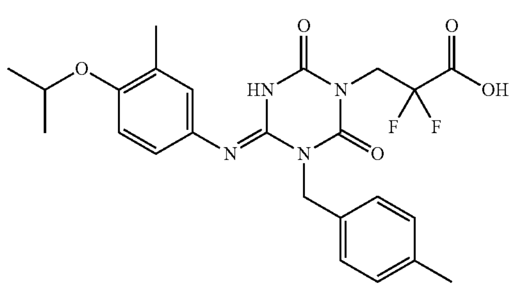 [SMILES: Cc1ccc(Cn2c(=O)n(CC(F)(F)C(=O)O)c(=O)[nH]/c2=N\c2ccc(OC(C)C)c(C)c2)cc1] | I-0857 | 1.84 | 489 | 2 |
| 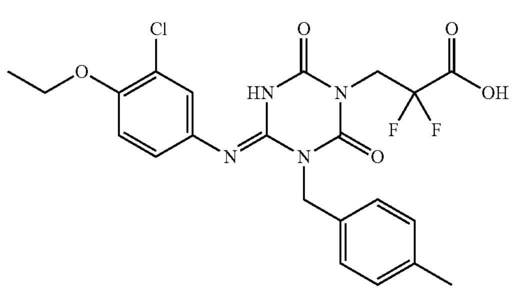 [SMILES: CCOc1ccc(/N=c2\[nH]c(=O)n(CC(F)(F)C(=O)O)c(=O)n2Cc2ccc(C)cc2)cc1Cl] | I-0858 | 1.70 | 495 | 2 |

TABLE 175-continued

| Structure | Compound No. | Retention Time (min) | [M + H] | Method |
|---|---|---|---|---|
| 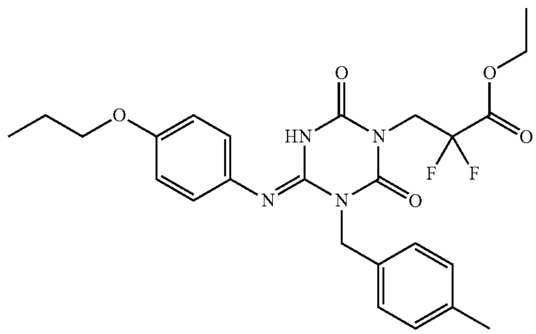 [SMILES: CCCOc1ccc(/N=c2\[nH]c(=O)n(CC(F)(F)C(=O)OCC)c(=O)n2Cc2ccc(C)cc2)cc1] | I-0859 | 2.30 | 503 | 2 |
| 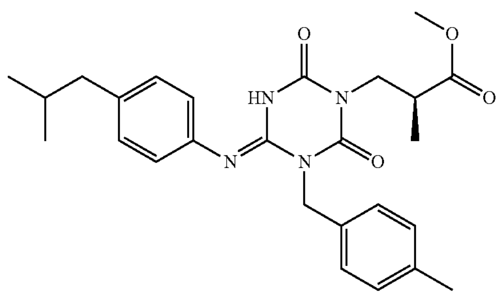 [SMILES: COC(=O)[C@@H](C)Cn1c(=O)[nH]/c(=N\c2ccc(CC(C)C)cc2)n(Cc2ccc(C)cc2)c1=O] | I-0860 | 2.42 | 465 | 2 |

TABLE 176

| Structure | Compound No. | Retention Time (min) | [M + H] | Method |
|---|---|---|---|---|
| 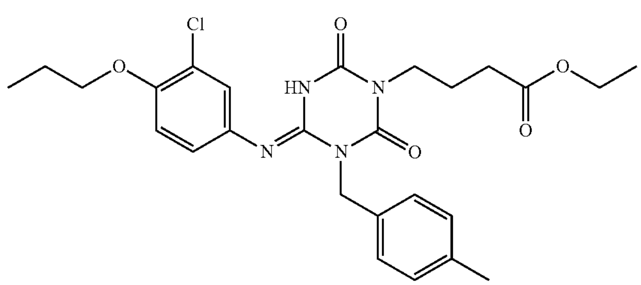 [SMILES: CCCOc1ccc(/N=c2\[nH]c(=O)n(CCCC(=O)OCC)c(=O)n2Cc2ccc(C)cc2)cc1Cl] | I-0861 | 2.44 | 515 | 2 |
| 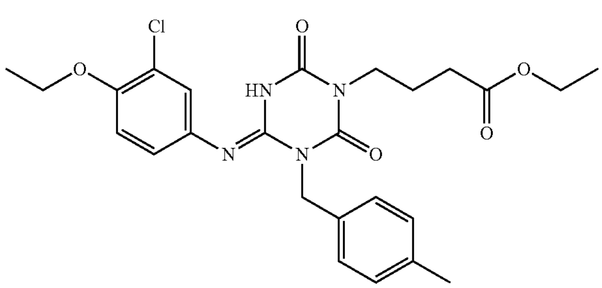 [SMILES: CCOC(=O)CCCn1c(=O)[nH]/c(=N\c2ccc(OCC)c(Cl)c2)n(Cc2ccc(C)cc2)c1=O] | I-0862 | 2.29 | 501 | 2 |

TABLE 176-continued

| Structure | Compound No. | Retention Time (min) | [M + H] | Method |
|---|---|---|---|---|
| (structure) | I-0863 | 1.95 | 503 | 2 |
| (structure) | I-0864 | 1.35 | 480 | 3 |
| (structure) | I-0865 | 2.37 | 545 | 2 |

TABLE 177

| Structure | Compound No. | Retention Time (min) | [M + H] | Method |
|---|---|---|---|---|
| (structure) | I-0866 | 2.35 | 501 | 2 |
| (structure) | I-0867 | 2.22 | 487 | 2 |

TABLE 177-continued

| Structure | Compound No. | Retention Time (min) | [M + H] | Method |
|---|---|---|---|---|
| 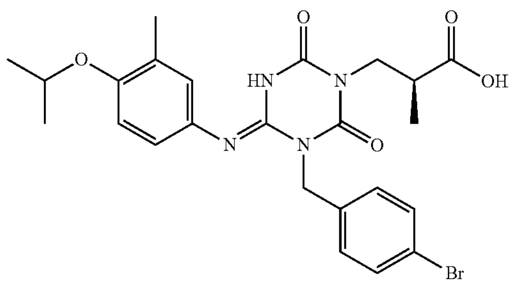 | I-0868 | 2.11 | 531 | 2 |
| 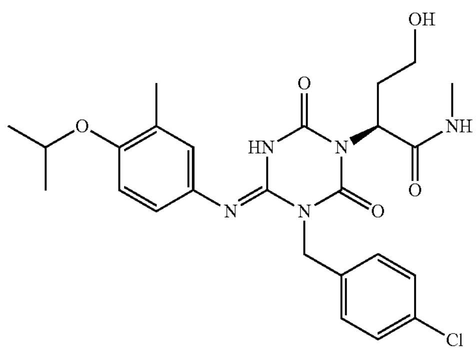 [SMILES: CNC(=O)[C@H](CCO)n1c(=O)[nH]/c(=N\c2ccc(OC(C)C)c(C)c2)n(Cc2ccc(Cl)cc2)c1=O] | I-0869 | 1.83 | 516 | 2 |
| 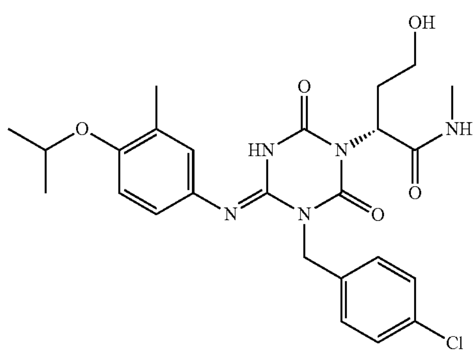 [SMILES: CNC(=O)[C@@H](CCO)n1c(=O)[nH]/c(=N\c2ccc(OC(C)C)c(C)c2)n(Cc2ccc(Cl)cc2)c1=O] | I-0870 | 1.83 | 516 | 2 |

TABLE 178

| Structure | Compound No. | Retention Time (min) | [M + H] | Method |
|---|---|---|---|---|
| 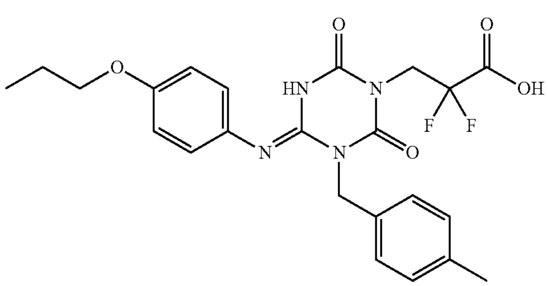 [SMILES: CCCOc1ccc(/N=c2\[nH]c(=O)n(CC(F)(F)C(=O)O)c(=O)n2Cc2ccc(C)cc2)cc1] | I-0871 | 1.73 | 475 | 2 |

TABLE 178-continued

| Structure | Compound No. | Retention Time (min) | [M + H] | Method |
|---|---|---|---|---|
| 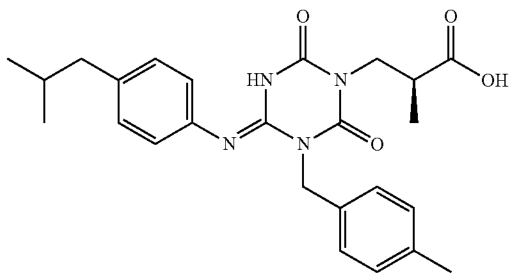 [SMILES: Cc1ccc(Cn2c(=O)n(C[C@H](C)C(=O)O)c(=O)[nH]/c2=N\c2ccc(CC(C)C)cc2)cc1] | I-0872 | 2.17 | 451 | 2 |
| 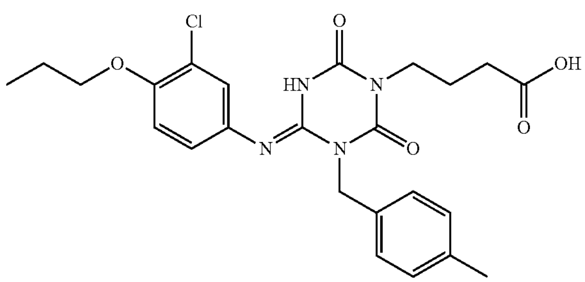 [SMILES: CCCOc1ccc(/N=c2\[nH]c(=O)n(CCCC(=O)O)c(=O)n2Cc2ccc(C)cc2)cc1Cl] | I-0873 | 2.09 | 487 | 2 |
| 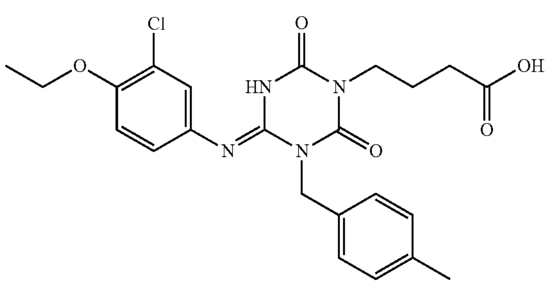 [SMILES: CCOc1ccc(/N=c2\[nH]c(=O)n(CCCC(=O)O)c(=O)n2Cc2ccc(C)cc2)cc1Cl] | I-0874 | 2.14 | 473 | 3 |
| 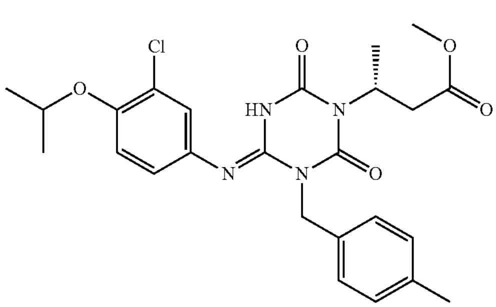 [SMILES: COC(=O)C[C@@H](C)n1c(=O)[nH]/c(=N\c2ccc(OC(C)C)c(Cl)c2)n(Cc2ccc(C)cc2)c1=O] | I-0875 | 2.36 | 501 | 2 |

TABLE 179

| Structure | Compound No. | Retention Time (min) | [M + H] | Method |
|---|---|---|---|---|
| (structure) | I-0878 | 2.24 | 487 | 2 |
| (structure) | I-0877 | 2.39 | 501 | 2 |
| (structure) | I-0878 | 2.32 | 487 | 3 |
| (structure) | I-0879 | 2.20 | 473 | 3 |
| (structure) | I-0880 | 2.15 | 487 | 2 |

TABLE 180

| Structure | Compound No. | Retention Time (min) | [M + H] | Method |
|---|---|---|---|---|
| (structure) | I-0881 | 2.37 | 504 | 2 |
| (structure) | I-0882 | 1.89 | 459 | 2 |
| (structure) | I-0883 | 2.27 | 481 | 2 |
| (structure) | I-0884 | 2.37 | 495 | 2 |
| (structure) | I-0885 | 1.99 | 467 | 2 |

TABLE 181

| Structure | Compound No. | Retention Time (min) | [M + H] | Method |
|---|---|---|---|---|
| (structure) | I-0886 | 2.10 | 481 | 2 |
| (structure) | I-0887 | 2.64 | 515 | 3 |
| (structure) | I-0888 | 2.53 | 501 | 3 |
| (structure) | I-0889 | 2.36 | 501 | 3 |
| (structure) | I-0890 | 2.25 | 487 | 3 |

TABLE 182

| Structure | Compound No. | Retention Time (min) | [M + H] | Method |
|---|---|---|---|---|
| (structure) | I-0891 | 2.61 | 501 | 3 |
| (structure) | I-0892 | 2.31 | 493 | 2 |
| (structure) | I-0893 | 2.11 | 490 | 2 |
| (structure) | I-0894 | 2.39 | 495 | 2 |
| (structure) | I-0895 | 2.27 | 473 | 3 |

TABLE 183

| Structure | Compound No. | Retention Time (min) | [M + H] | Method |
|---|---|---|---|---|
| 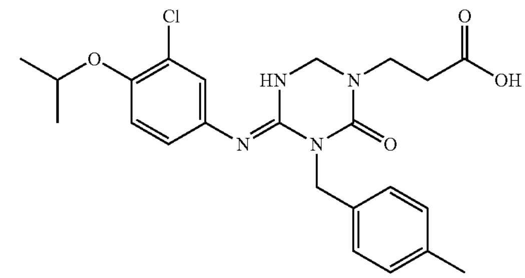 [SMILES: Cc1ccc(CN2C(=O)N(CCC(=O)O)CN/C2=N\c2ccc(OC(C)C)c(Cl)c2)cc1] | I-0896 | 2.02 | 473 | 2 |
| 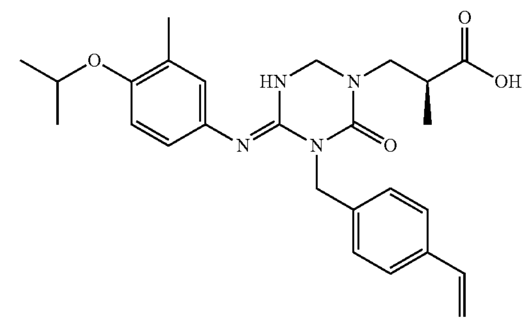 [SMILES: C=Cc1ccc(CN2C(=O)N(C[C@H](C)C(=O)O)CN/C2=N\c2ccc(OC(C)C)c(C)c2)cc1] | I-0897 | 2.07 | 479 | 2 |
| 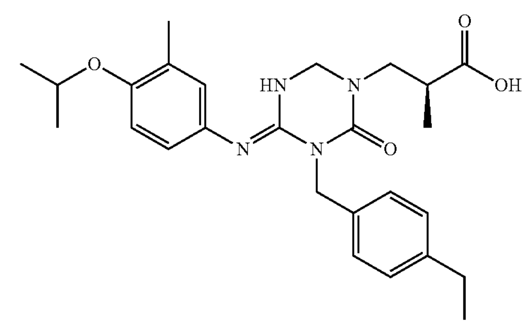 [SMILES: CCc1ccc(CN2C(=O)N(C[C@H](C)C(=O)O)CN/C2=N\c2ccc(OC(C)C)c(C)c2)cc1] | I-0898 | 2.14 | 481 | 2 |
| 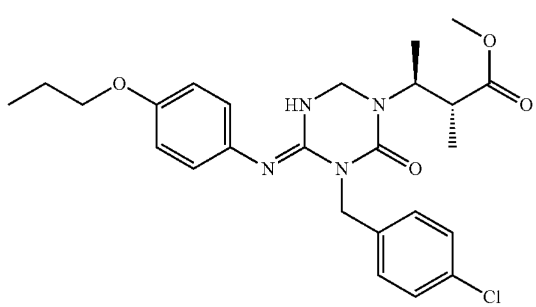 [SMILES: CCCOc1ccc(/N=C2\NCN([C@@H](C)[C@@H](C)C(=O)OC)C(=O)N2Cc2ccc(Cl)cc2)cc1] | I-0899 | 2.36 | 501 | 2 |
| 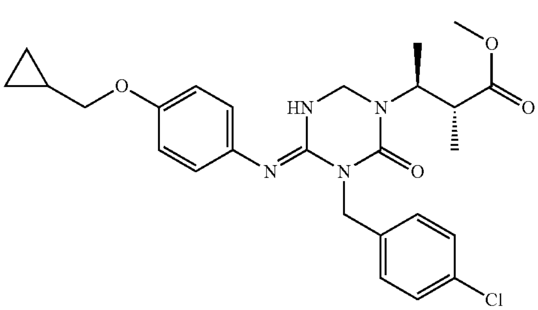 [SMILES: COC(=O)[C@H](C)[C@H](C)N1CN/C(=N\c2ccc(OCC3CC3)cc2)N(Cc2ccc(Cl)cc2)C1=O] | I-0900 | 2.33 | 513 | 2 |

TABLE 184

| Structure | Compound No. | Retention Time (min) | [M + H] | Method |
|---|---|---|---|---|
| (structure) | I-0901 | 2.37 | 545 | 2 |
| (structure) | I-0902 | 2.48 | 527 | 2 |
| (structure) | I-0903 | 2.38 | 513 | 2 |
| (structure) | I-0904 | 2.34 | 499 | 3 |
| (structure) | I-0905 | 2.22 | 485 | 3 |

TABLE 185

| Structure | Compound No. | Retention Time (min) | [M + H] | Method |
|---|---|---|---|---|
| 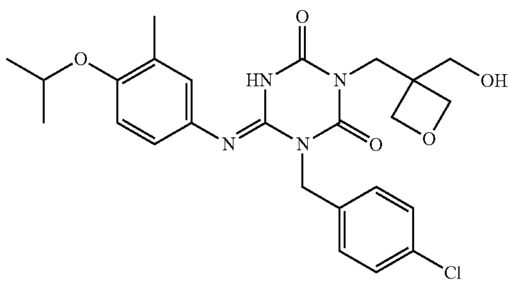 [SMILES: Cc1cc(/N=c2\[nH]c(=O)n(CC3(CO)COC3)c(=O)n2Cc2ccc(Cl)cc2)ccc1OC(C)C] | I-0906 | 1.99 | 501 | 2 |
| 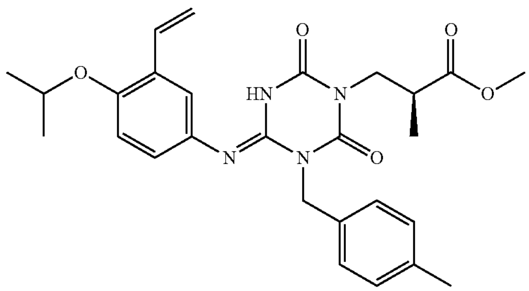 [SMILES: C=Cc1cc(/N=c2\[nH]c(=O)n(C[C@H](C)C(=O)OC)c(=O)n2Cc2ccc(C)cc2)ccc1OC(C)C] | I-0907 | 2.33 | 493 | 2 |
| 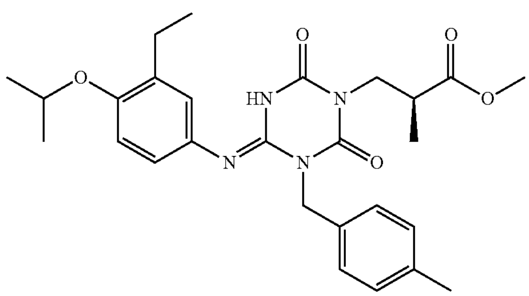 [SMILES: CCc1cc(/N=c2\[nH]c(=O)n(C[C@H](C)C(=O)OC)c(=O)n2Cc2ccc(C)cc2)ccc1OC(C)C] | I-0908 | 2.39 | 495 | 2 |
| 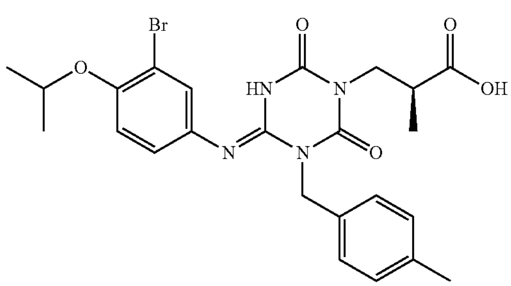 [SMILES: Cc1ccc(Cn2c(=O)n(C[C@H](C)C(=O)O)c(=O)[nH]/c2=N\c2ccc(OC(C)C)c(Br)c2)cc1] | I-0909 | 2.11 | 531 | 2 |
| 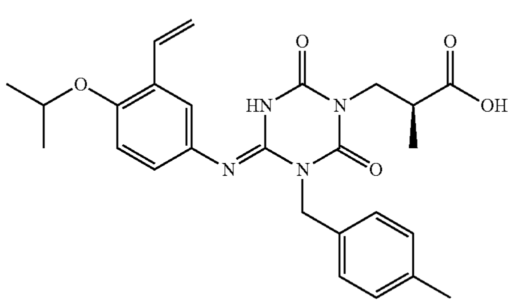 | I-0910 | 2.09 | 479 | 2 |

TABLE 186

| Structure | Compound No. | Retention Time (min) | [M + H] | Method |
|---|---|---|---|---|
| 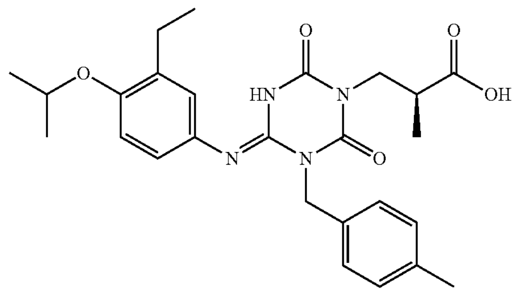 [SMILES: CCc1cc(/N=c2\[nH]c(=O)n(C[C@H](C)C(=O)O)c(=O)n2Cc2ccc(C)cc2)ccc1OC(C)C] | I-0911 | 2.15 | 481 | 2 |
| 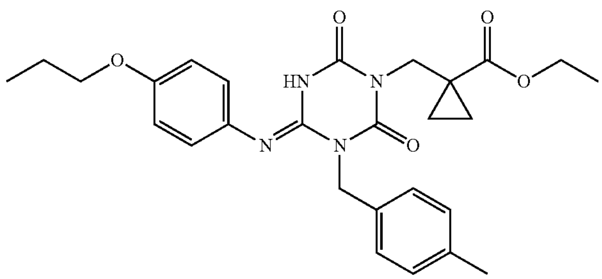 [SMILES: CCCOc1ccc(/N=c2\[nH]c(=O)n(CC3(C(=O)OCC)CC3)c(=O)n2Cc2ccc(C)cc2)cc1] | I-0912 | 2.52 | 493 | 3 |
| 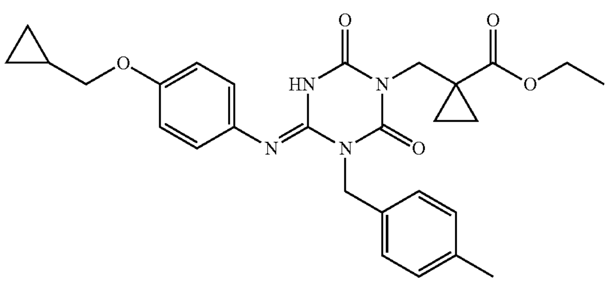 [SMILES: CCOC(=O)C1(Cn2c(=O)[nH]/c(=N\c3ccc(OCC4CC4)cc3)n(Cc3ccc(C)cc3)c2=O)CC1] | I-0913 | 2.49 | 505 | 3 |
| 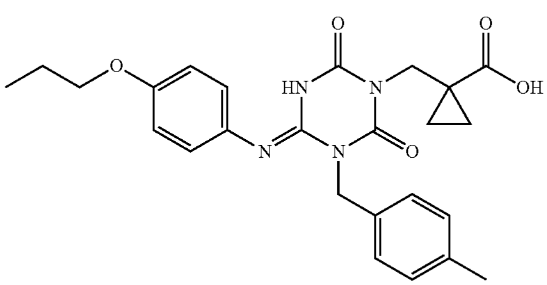 [SMILES: CCCOc1ccc(/N=c2\[nH]c(=O)n(CC3(C(=O)O)CC3)c(=O)n2Cc2ccc(C)cc2)cc1] | I-0914 | 2.16 | 265 | 3 |
| 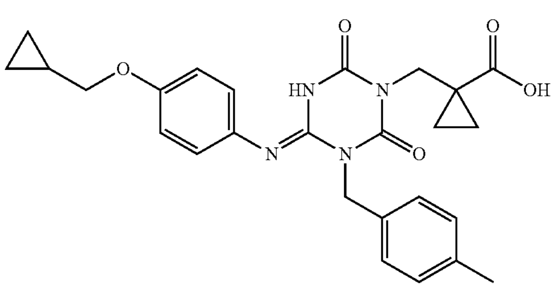 [SMILES: Cc1ccc(Cn2c(=O)n(CC3(C(=O)O)CC3)c(=O)[nH]/c2=N\c2ccc(OCC3CC3)cc2)cc1] | I-0915 | 2.13 | 477 | 3 |

TABLE 187

| Structure | Compound No. | Retention Time (min) | [M + H] | Method |
|---|---|---|---|---|
| 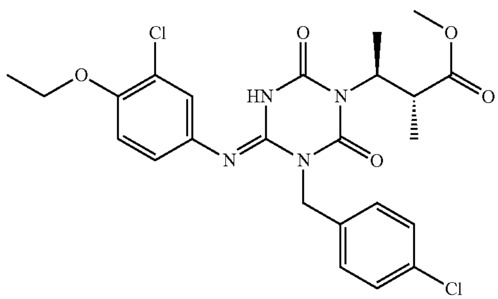 [SMILES: CCOc1ccc(/N=c2\[nH]c(=O)n([C@@H](C)[C@@H](C)C(=O)OC)c(=O)n2Cc2ccc(Cl)cc2)cc1Cl] | I-0916 | 2.43 | 521 | 2 |
| 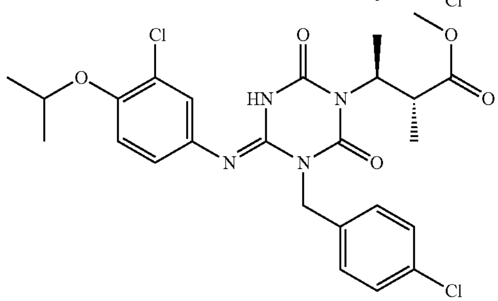 | I-0917 | 2.54 | 535 | 2 |
| 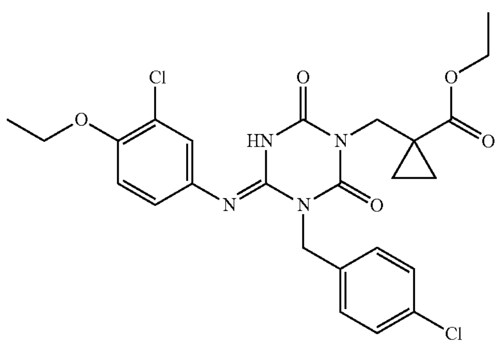 [SMILES: CCOC(=O)C1(Cn2c(=O)[nH]/c(=N\c3ccc(OCC)c(Cl)c3)n(Cc3ccc(Cl)cc3)c2=O)CC1] | I-0918 | 2.44 | 533 | 2 |
| 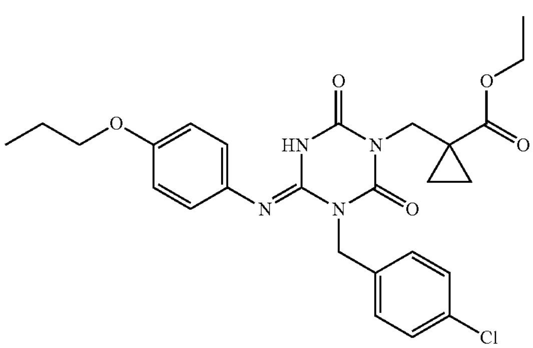 [SMILES: CCCOc1ccc(/N=c2\[nH]c(=O)n(CC3(C(=O)OCC)CC3)c(=O)n2Cc2ccc(Cl)cc2)cc1] | I-0919 | 2.37 | 513 | 2 |
| 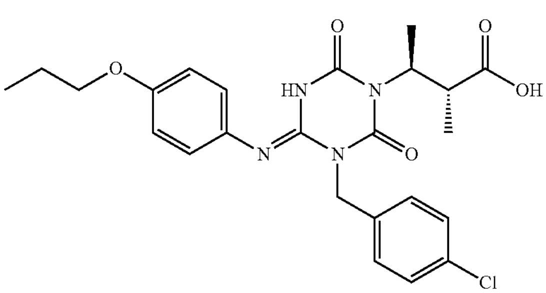 [SMILES: CCCOc1ccc(/N=c2\[nH]c(=O)n([C@@H](C)[C@@H](C)C(=O)O)c(=O)n2Cc2ccc(Cl)cc2)cc1] | I-0920 | 2.09 | 487 | 2 |

TABLE 188

| Structure | Compound No. | Retention Time (min) | [M + H] | Method |
|---|---|---|---|---|
| 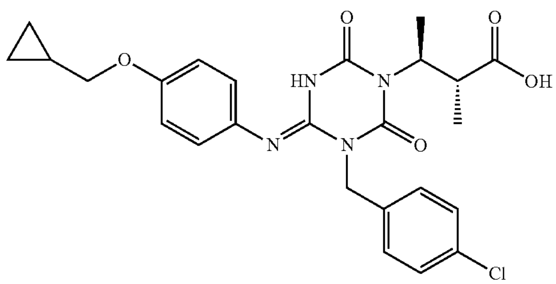 [SMILES: C[C@@H](C(=O)O)[C@H](C)n1c(=O)[nH]/c(=N\c2ccc(OCC3CC3)cc2)n(Cc2ccc(Cl)cc2)c1=O] | I-0921 | 2.06 | 499 | 2 |
| 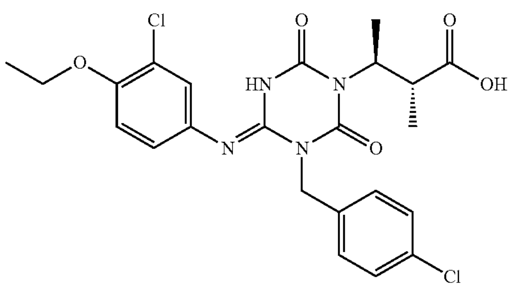 [SMILES: CCOc1ccc(/N=c2\[nH]c(=O)n([C@@H](C)[C@@H](C)C(=O)O)c(=O)n2Cc2ccc(Cl)cc2)cc1Cl] | I-0922 | 2.15 | 507 | 2 |
| 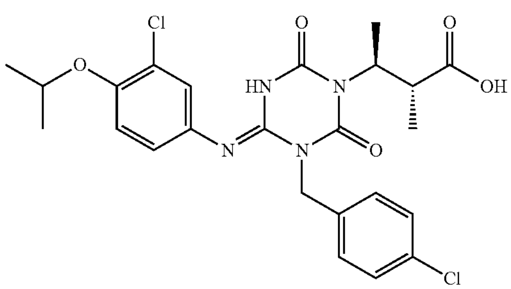 [SMILES: CC(C)Oc1ccc(/N=c2\[nH]c(=O)n([C@@H](C)[C@@H](C)C(=O)O)c(=O)n2Cc2ccc(Cl)cc2)cc1Cl] | I-0923 | 2.26 | 521 | 2 |
| 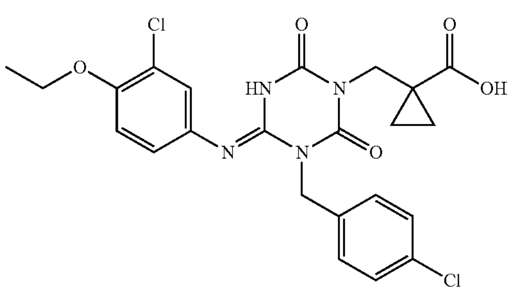 [SMILES: CCOc1ccc(/N=c2\[nH]c(=O)n(CC3(C(=O)O)CC3)c(=O)n2Cc2ccc(Cl)cc2)cc1Cl] | I-0924 | 2.07 | 505 | 2 |
| 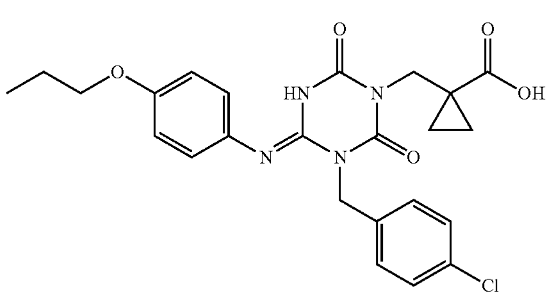 [SMILES: CCCOc1ccc(/N=c2\[nH]c(=O)n(CC3(C(=O)O)CC3)c(=O)n2Cc2ccc(Cl)cc2)cc1] | I-0925 | 2.01 | 485 | 2 |

TABLE 189

| Structure | Compound No. | Retention Time (min) | [M + H] | Method |
|---|---|---|---|---|
| 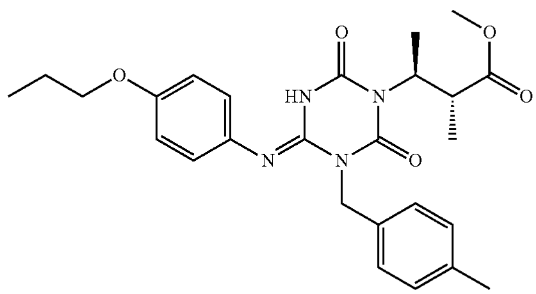 [SMILES: CCCOc1ccc(/N=c2\[nH]c(=O)n([C@@H](C)[C@@H](C)C(=O)OC)c(=O)n2Cc2ccc(C)cc2)cc1] | I-0926 | 2.29 | 481 | 2 |
| 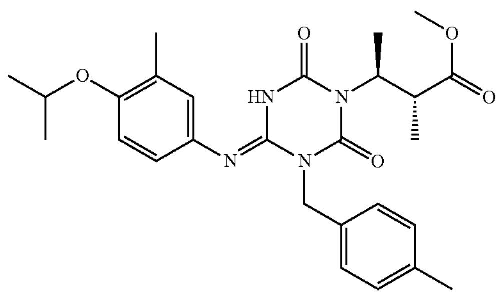 [SMILES: COC(=O)[C@H](C)[C@H](C)n1c(=O)[nH]/c(=N\c2ccc(OC(C)C)c(C)c2)n(Cc2ccc(C)cc2)c1=O] | I-0927 | 2.40 | 495 | 2 |
| 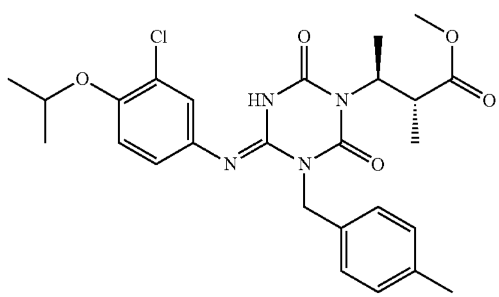 [SMILES: COC(=O)[C@H](C)[C@H](C)n1c(=O)[nH]/c(=N\c2ccc(OC(C)C)c(Cl)c2)n(Cc2ccc(C)cc2)c1=O] | I-0928 | 2.46 | 515 | 2 |
| 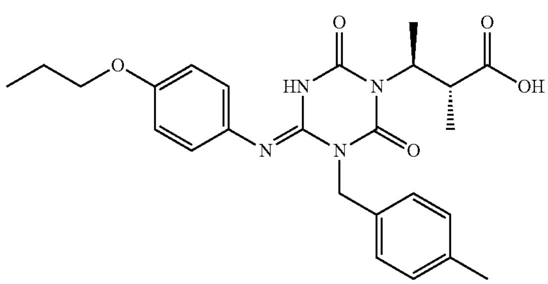 [SMILES: CCCOc1ccc(/N=c2\[nH]c(=O)n([C@@H](C)[C@@H](C)C(=O)O)c(=O)n2Cc2ccc(C)cc2)cc1] | I-0929 | 2.24 | 467 | 3 |
| 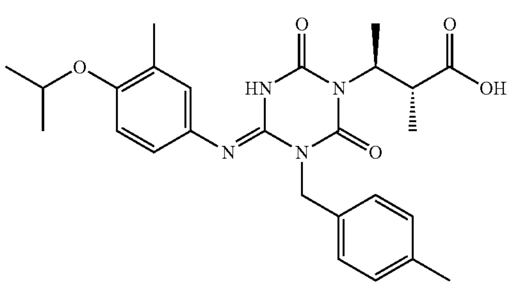 [SMILES: Cc1ccc(Cn2c(=O)n([C@@H](C)[C@@H](C)C(=O)O)c(=O)[nH]/c2=N\c2ccc(OC(C)C)c(C)c2)cc1] | I-0930 | 2.34 | 481 | 3 |

TABLE 190

| Structure | Compound No. | Retention Time (min) | [M + H] | Method |
|---|---|---|---|---|
| (structure) | I-0931 | 2.41 | 501 | 3 |
| (structure) | I-0932 | 2.05 | 527 | 2 |
| (structure) | I-0933 | 2.05 | 527 | 2 |
| (structure) | I-0934 | 1.97 | 497 | 2 |

TABLE 190-continued
| Structure | Compound No. | Retention Time (min) | [M + H] | Method |
|---|---|---|---|---|
| 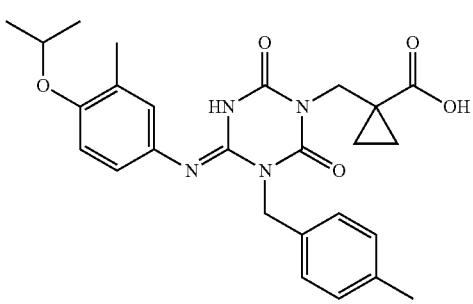 [SMILES: Cc1ccc(Cn2c(=O)n(CC3(C(=O)O)CC3)c(=O)[nH]/c2=N\c2ccc(OC(C)C)c(C)c2)cc1] | I-0935 | 2.08 | 479 | 2 |
TABLE 191
| Structure | Compound No. | Retention Time (min) | [M + H] | Method |
|---|---|---|---|---|
| 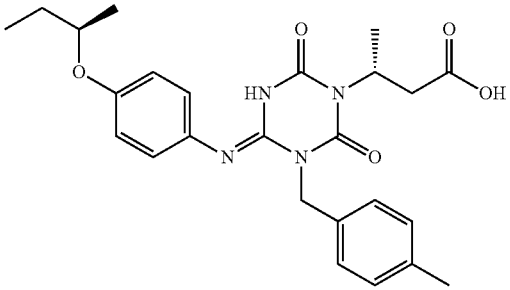 [SMILES: CC[C@@H](C)Oc1ccc(/N=c2\[nH]c(=O)n([C@H](C)CC(=O)O)c(=O)n2Cc2ccc(C)cc2)cc1] | I-0936 | 2.23 | 467 | 3 |
| 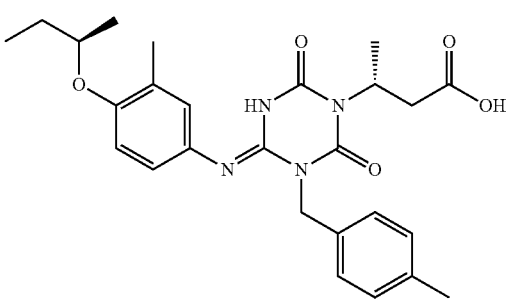 | I-0937 | 2.42 | 481 | 3 |
| 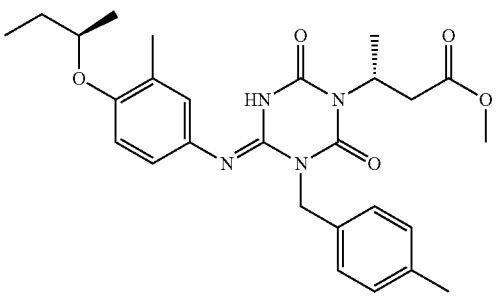 [SMILES: CC[C@@H](C)Oc1ccc(/N=c2\[nH]c(=O)n([C@H](C)CC(=O)OC)c(=O)n2Cc2ccc(C)cc2)cc1C] | I-0938 | 2.66 | 495 | 3 |

TABLE 191-continued

| Structure | Compound No. | Retention Time (min) | [M + H] | Method |
|---|---|---|---|---|
| 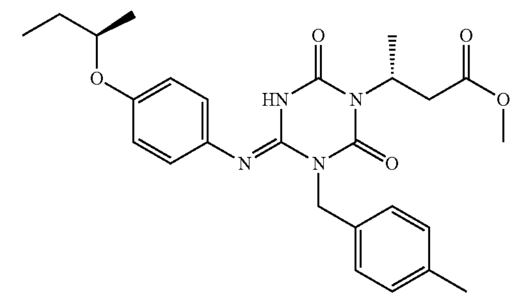 [SMILES: CC[C@@H](C)Oc1ccc(/N=c2\[nH]c(=O)n([C@H](C)CC(=O)OC)c(=O)n2Cc2ccc(C)cc2)cc1] | I-0939 | 2.51 | 481 | 3 |
| 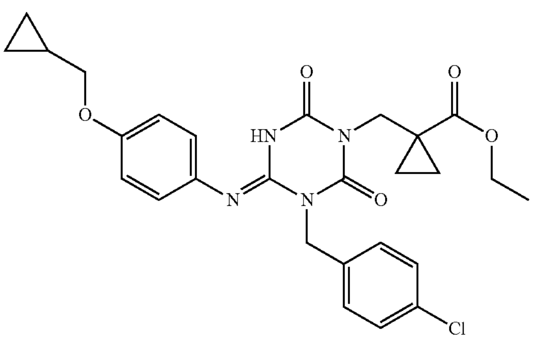 [SMILES: CCOC(=O)C1(Cn2c(=O)[nH]/c(=N\c3ccc(OCC4CC4)cc3)n(Cc3ccc(Cl)cc3)c2=O)CC1] | I-0940 | 2.56 | 525 | 3 |

TABLE 192

| Structure | Compound No. | Retention Time (min) | [M + H] | Method |
|---|---|---|---|---|
| 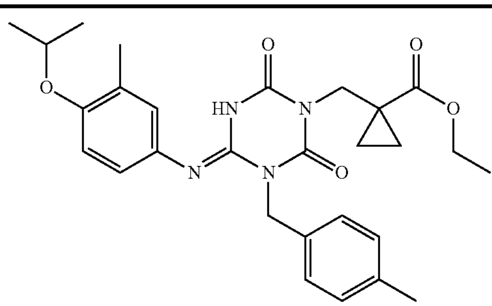 | I-0941 | 2.64 | 507 | 3 |
| 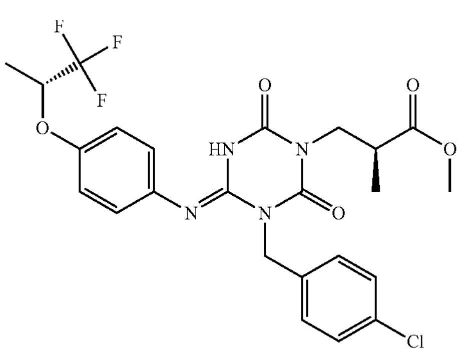 [SMILES: COC(=O)[C@@H](C)Cn1c(=O)[nH]/c(=N\c2ccc(O[C@H](C)C(F)(F)F)cc2)n(Cc2ccc(Cl)cc2)c1=O] | I-0942 | 2.30 | 541 | 2 |

TABLE 192-continued
| Structure | Compound No. | Retention Time (min) | [M + H] | Method |
|---|---|---|---|---|
| 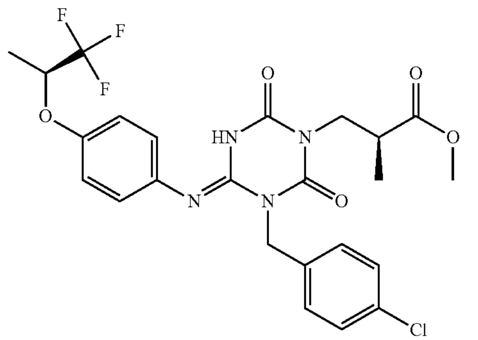 [SMILES: COC(=O)[C@@H](C)Cn1c(=O)[nH]/c(=N\c2ccc(O[C@@H](C)C(F)(F)F)cc2)n(Cc2ccc(Cl)cc2)c1=O] | I-0943 | 2.29 | 541 | 2 |
| 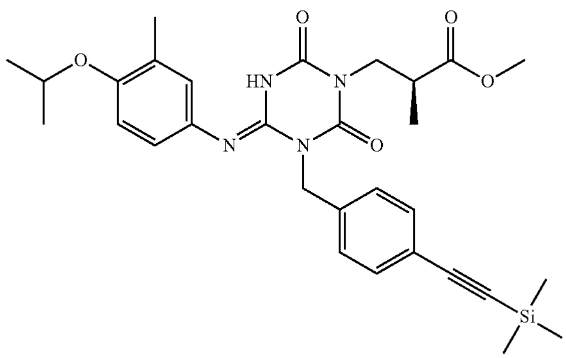 [SMILES: COC(=O)[C@@H](C)Cn1c(=O)[nH]/c(=N\c2ccc(OC(C)C)c(C)c2)n(Cc2ccc(C#C[Si](C)(C)C)cc2)c1=O] | I-0944 | 2.75 | 563 | 2 |
| 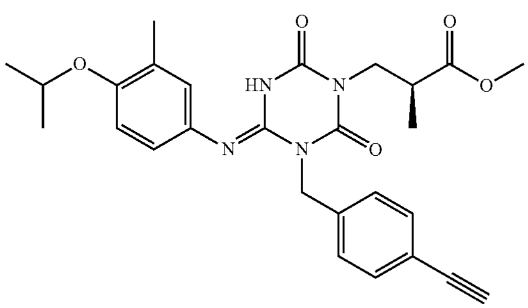 [SMILES: C#Cc1ccc(Cn2c(=O)n(C[C@H](C)C(=O)OC)c(=O)[nH]/c2=N\c2ccc(OC(C)C)c(C)c2)cc1] | I-0945 | 2.19 | 491 | 2 |
TABLE 193
| Structure | Compound No. | Retention Time (min) | [M + H] | Method |
|---|---|---|---|---|
| 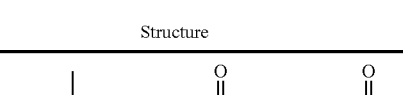 | I-0946 | 1.97 | 477 | 2 |

TABLE 193-continued

| Structure | Compound No. | Retention Time (min) | [M + H] | Method |
|---|---|---|---|---|
| 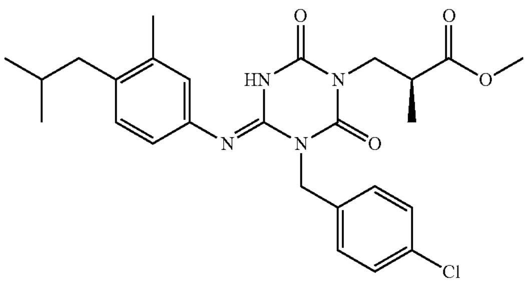 | I-0947 | 2.78 | 499 | 3 |
| 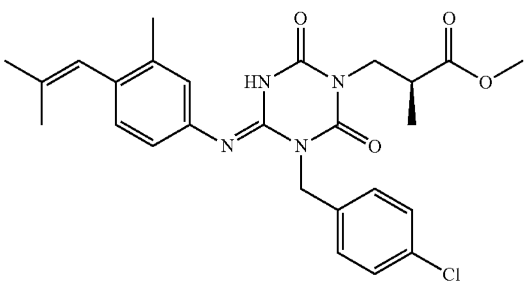 [SMILES: COC(=O)[C@@H](C)Cn1c(=O)[nH]/c(=N\c2ccc(C=C(C)C)c(C)c2)n(Cc2ccc(Cl)cc2)c1=O] | I-0948 | 2.74 | 497 | 3 |
| 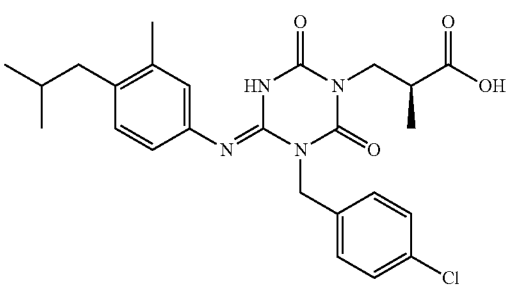 | I-0949 | 2.54 | 485 | 3 |
| 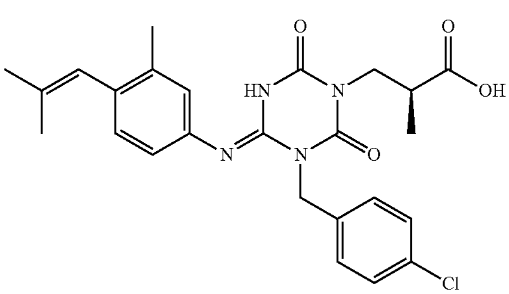 [SMILES: CC(C)=Cc1ccc(/N=c2\[nH]c(=O)n(C[C@H](C)C(=O)O)c(=O)n2Cc2ccc(Cl)cc2)cc1C] | I-0950 | 2.50 | 483 | 3 |

TABLE 194

| Structure | Compound No. | Retention Time (min) | [M + H] | Method |
|---|---|---|---|---|
| (structure) | I-0951 | 2.13 | 492 | 2 |
| (structure) | I-0952 | 1.49 | 514 | 2 |
| (structure) | I-0953 | 2.21 | 512 | 2 |
| (structure) | I-0954 | 1.52 | 512 | 2 |
| (structure) | I-0955 | 2.86 | 517 | 3 |

TABLE 195

| Structure | Compound No. | Retention Time (min) | [M + H] | Method |
|---|---|---|---|---|
| 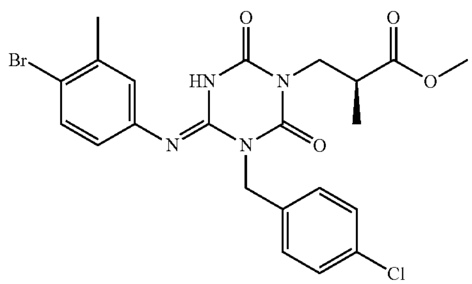 [SMILES: COC(=O)[C@@H](C)Cn1c(=O)[nH]/c(=N\c2ccc(Br)c(C)c2)n(Cc2ccc(Cl)cc2)c1=O] | I-0956 | 2.63 | 522 | 3 |
| 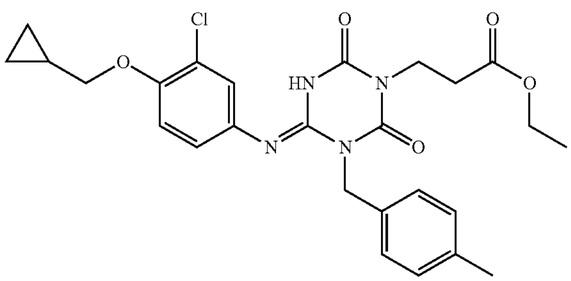 [SMILES: CCOC(=O)CCn1c(=O)[nH]/c(=N\c2ccc(OCC3CC3)c(Cl)c2)n(Cc2ccc(C)cc2)c1=O] | I-0957 | 2.57 | 513 | 3 |
| 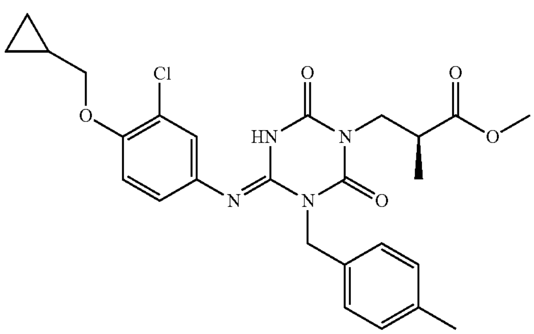 [SMILES: COC(=O)[C@@H](C)Cn1c(=O)[nH]/c(=N\c2ccc(OCC3CC3)c(Cl)c2)n(Cc2ccc(C)cc2)c1=O] | I-0958 | 2.55 | 513 | 3 |
| 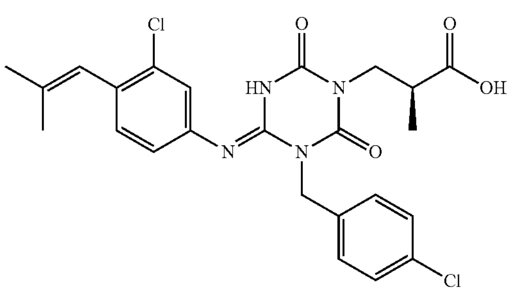 | I-0959 | 2.62 | 503 | 3 |
| 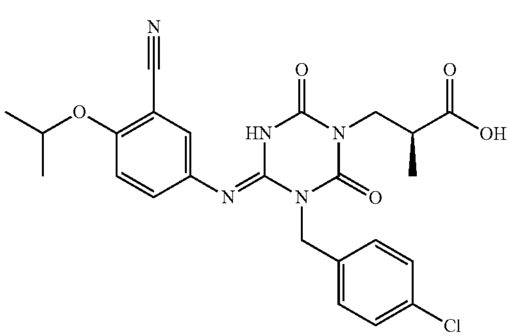 [SMILES: CC(C)Oc1ccc(/N=c2\[nH]c(=O)n(C[C@H](C)C(=O)O)c(=O)n2Cc2ccc(Cl)cc2)cc1C#N] | I-0960 | 1.98 | 498 | 2 |

TABLE 196

| Structure | Compound No. | Retention Time (min) | [M + H] | Method |
|---|---|---|---|---|
| 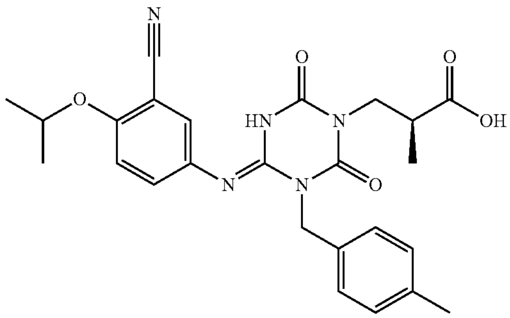 [SMILES: Cc1ccc(Cn2c(=O)n(C[C@H](C)C(=O)O)c(=O)[nH]/c2=N\c2ccc(OC(C)C)c(C#N)c2)cc1] | I-0961 | 1.90 | 478 | 2 |
| 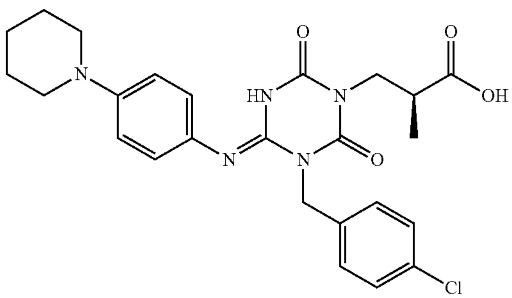 [SMILES: C[C@@H](Cn1c(=O)[nH]/c(=N\c2ccc(N3CCCCC3)cc2)n(Cc2ccc(Cl)cc2)c1=O)C(=O)O] | I-0962 | 1.34 | 498 | 2 |
| 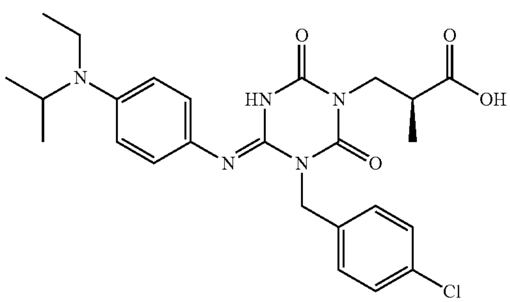 [SMILES: CCN(c1ccc(/N=c2\[nH]c(=O)n(C[C@H](C)C(=O)O)c(=O)n2Cc2ccc(Cl)cc2)cc1)C(C)C] | I-0963 | 1.34 | 500 | 2 |
| 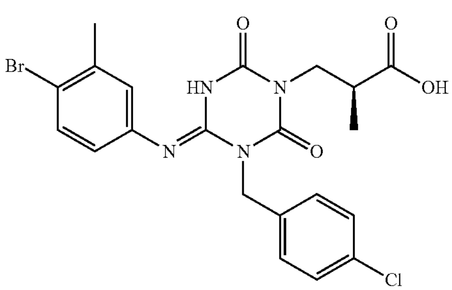 [SMILES: Cc1cc(/N=c2\[nH]c(=O)n(C[C@H](C)C(=O)O)c(=O)n2Cc2ccc(Cl)cc2)ccc1Br] | I-0964 | 2.36 | 508 | 3 |
| 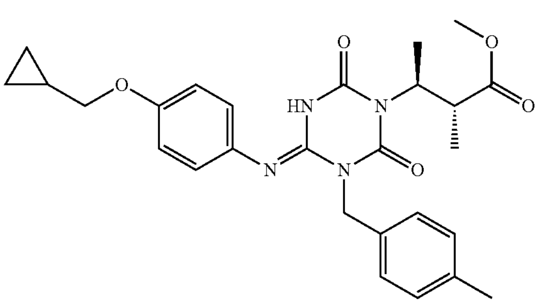 [SMILES: COC(=O)[C@H](C)[C@H](C)n1c(=O)[nH]/c(=N\c2ccc(OCC3CC3)cc2)n(Cc2ccc(C)cc2)c1=O] | I-0965 | 2.27 | 493 | 2 |

TABLE 197

| Structure | Compound No. | Retention Time (min) | [M + H] | Method |
|---|---|---|---|---|
| 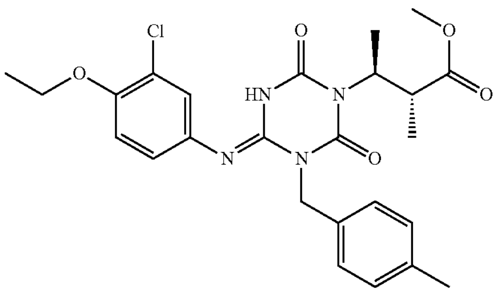 [SMILES: CCOc1ccc(/N=c2\[nH]c(=O)n([C@@H](C)[C@@H](C)C(=O)OC)c(=O)n2Cc2ccc(C)cc2)cc1Cl] | I-0966 | 2.35 | 501 | 2 |
| 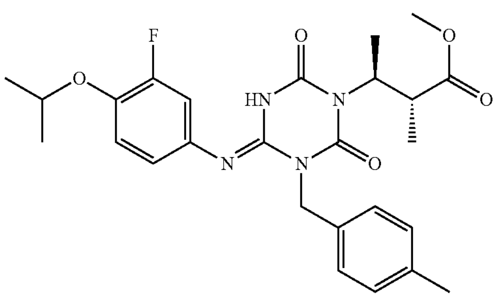 [SMILES: COC(=O)[C@H](C)[C@H](C)n1c(=O)[nH]/c(=N\c2ccc(OC(C)C)c(F)c2)n(Cc2ccc(C)cc2)c1=O] | I-0967 | 2.35 | 499 | 2 |
| 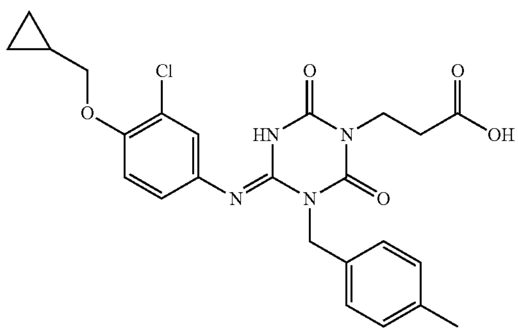 [SMILES: Cc1ccc(Cn2c(=O)n(CCC(=O)O)c(=O)[nH]/c2=N\c2ccc(OCC3CC3)c(Cl)c2)cc1] | I-0968 | 2.23 | 485 | 3 |
| 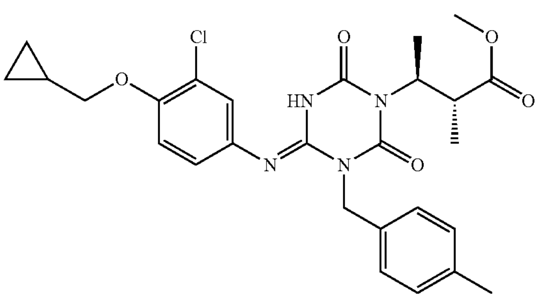 [SMILES: COC(=O)[C@H](C)[C@H](C)n1c(=O)[nH]/c(=N\c2ccc(OCC3CC3)c(Cl)c2)n(Cc2ccc(C)cc2)c1=O] | I-0969 | 2.45 | 527 | 2 |
| 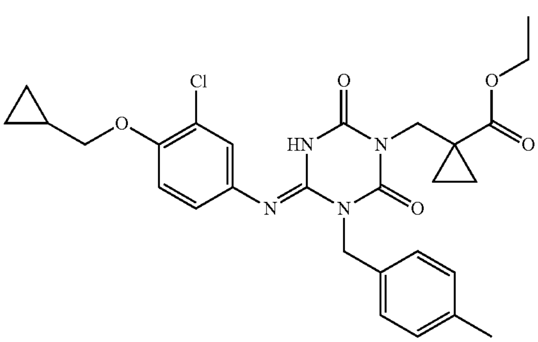 [SMILES: CCOC(=O)C1(Cn2c(=O)[nH]/c(=N\c3ccc(OCC4CC4)c(Cl)c3)n(Cc3ccc(C)cc3)c2=O)CC1] | I-0970 | 2.47 | 539 | 2 |

TABLE 198

| Structure | Compound No. | Retention Time (min) | [M + H] | Method |
|---|---|---|---|---|
| 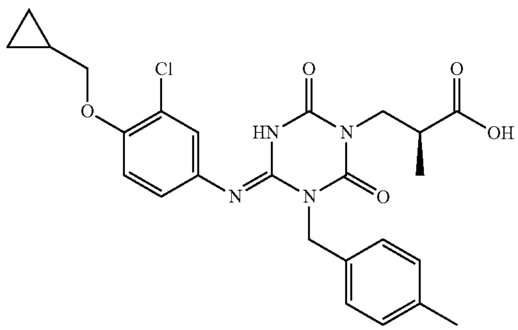 [SMILES: Cc1ccc(Cn2c(=O)n(C[C@H](C)C(=O)O)c(=O)[nH]/c2=N\c2ccc(OCC3CC3)c(Cl)c2)cc1] | I-0971 | 2.30 | 499 | 3 |
| 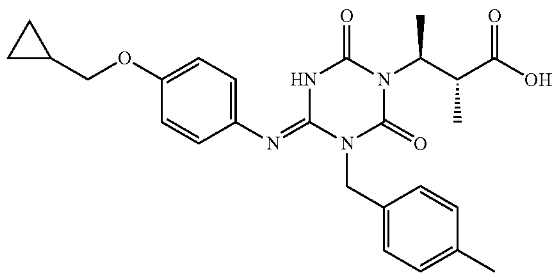 [SMILES: Cc1ccc(Cn2c(=O)n([C@@H](C)[C@@H](C)C(=O)O)c(=O)[nH]/c2=N\c2ccc(OCC3CC3)cc2)cc1] | I-0972 | 2.19 | 479 | 3 |
| 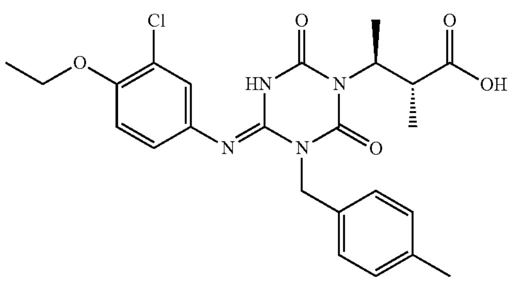 [SMILES: CCOc1ccc(/N=c2\[nH]c(=O)n([C@@H](C)[C@@H](C)C(=O)O)c(=O)n2Cc2ccc(C)cc2)cc1Cl] | I-0973 | 2.27 | 487 | 3 |
| 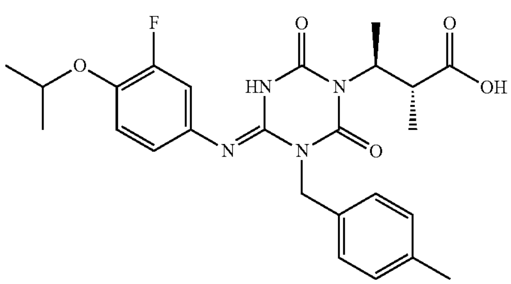 [SMILES: Cc1ccc(Cn2c(=O)n([C@@H](C)[C@@H](C)C(=O)O)c(=O)[nH]/c2=N\c2ccc(OC(C)C)c(F)c2)cc1] | I-0974 | 2.28 | 485 | 3 |
| 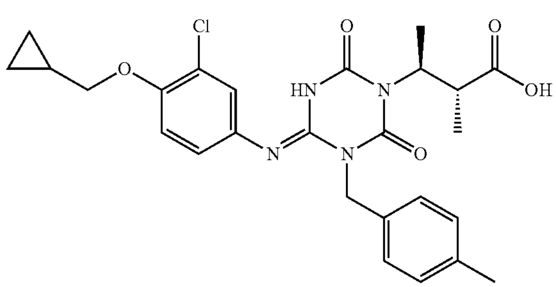 [SMILES: Cc1ccc(Cn2c(=O)n([C@@H](C)[C@@H](C)C(=O)O)c(=O)[nH]/c2=N\c2ccc(OCC3CC3)c(Cl)c2)cc1] | I-0975 | 2.40 | 513 | 3 |

TABLE 199

| Structure | Compound No. | Retention Time (min) | [M + H] | Method |
|---|---|---|---|---|
| (structure) | I-0976 | 2.34 | 511 | 3 |
| (structure) | I-0977 | 2.52 | 547 | 2 |
| (structure) | I-0978 | 2.43 | 527 | 2 |
| (structure) | I-0979 | 2.43 | 527 | 2 |
| (structure) | I-0980 | 2.37 | 507 | 2 |

TABLE 200

| Structure | Compound No. | Retention Time (min) | [M + H] | Method |
|---|---|---|---|---|
| 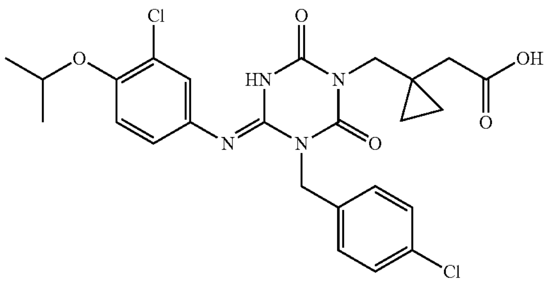 [SMILES: CC(C)Oc1ccc(/N=c2\[nH]c(=O)n(CC3(CC(=O)O)CC3)c(=O)n2Cc2ccc(Cl)cc2)cc1Cl] | I-0981 | 2.25 | 533 | 2 |
| 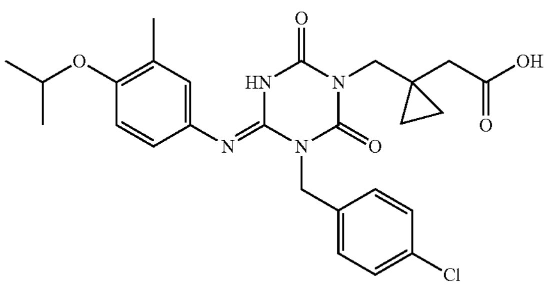 | I-0982 | 2.17 | 513 | 2 |
| 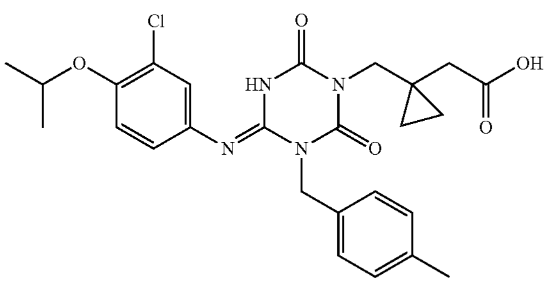 [SMILES: Cc1ccc(Cn2c(=O)n(CC3(CC(=O)O)CC3)c(=O)[nH]/c2=N\c2ccc(OC(C)C)c(Cl)c2)cc1] | I-0983 | 2.17 | 513 | 2 |
| 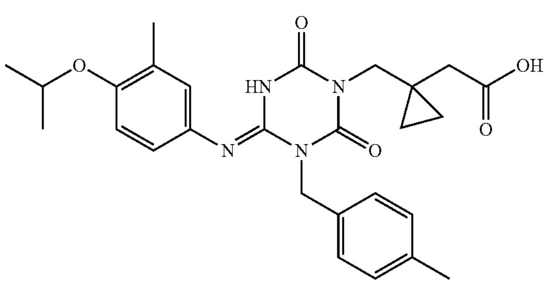 [SMILES: Cc1ccc(Cn2c(=O)n(CC3(CC(=O)O)CC3)c(=O)[nH]/c2=N\c2ccc(OC(C)C)c(C)c2)cc1] | I-0984 | 2.11 | 493 | 2 |
| 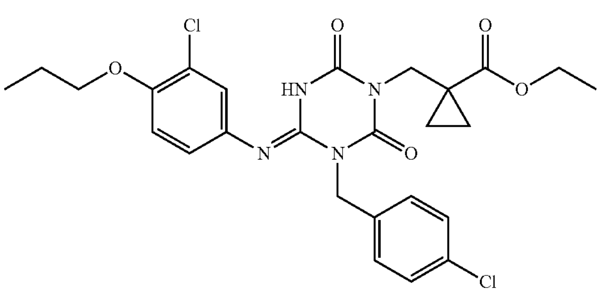 [SMILES: CCCOc1ccc(/N=c2\[nH]c(=O)n(CC3(C(=O)OCC)CC3)c(=O)n2Cc2ccc(Cl)cc2)cc1Cl] | I-0985 | 2.81 | 548 | 3 |

TABLE 201
| Structure | Compound No. | Retention Time (min) | [M + H] | Method |
|---|---|---|---|---|
| 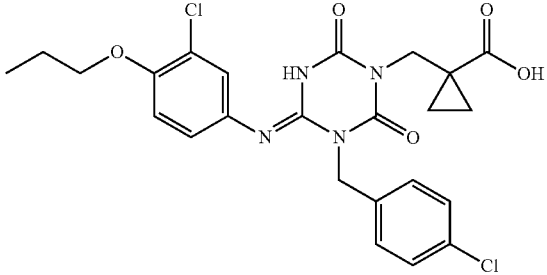 | I-0986 | 2.45 | 519 | 3 |
| 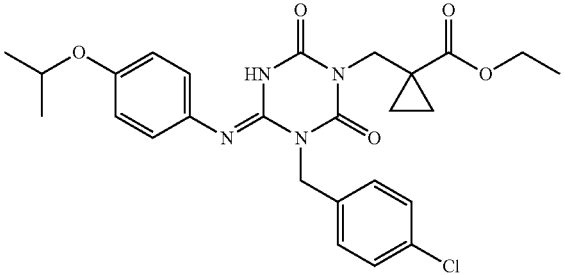 [SMILES: CCOC(=O)C1(Cn2c(=O)[nH]/c(=N\c3ccc(OC(C)C)cc3)n(Cc3ccc(Cl)cc3)c2=O)CC1] | I-0987 | 2.56 | 5 | 3 |
| 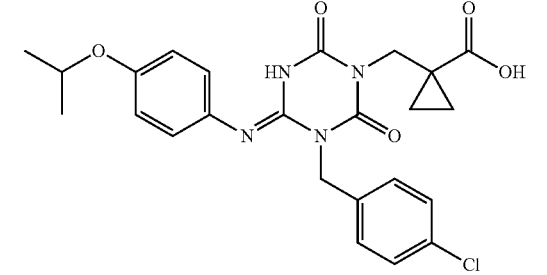 [SMILES: CC(C)Oc1ccc(/N=c2\[nH]c(=O)n(CC3(C(=O)O)CC3)c(=O)n2Cc2ccc(Cl)cc2)cc1] | I-0988 | 2.18 | 5 | 3 |
| 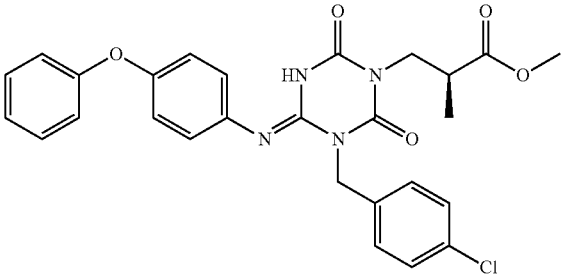 [SMILES: COC(=O)[C@@H](C)Cn1c(=O)[nH]/c(=N\c2ccc(Oc3ccccc3)cc2)n(Cc2ccc(Cl)cc2)c1=O] | I-0989 | 2.56 | 521 | 3 |
| 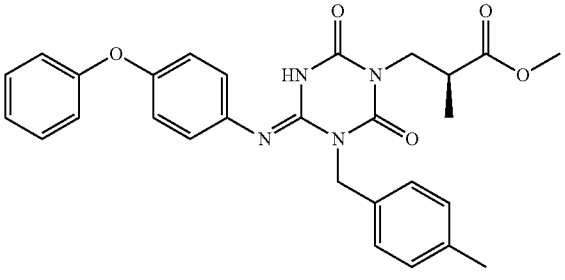 [SMILES: COC(=O)[C@@H](C)Cn1c(=O)[nH]/c(=N\c2ccc(Oc3ccccc3)cc2)n(Cc2ccc(C)cc2)c1=O] | I-0990 | 2.50 | 501 | 3 |

TABLE 202

| Structure | Compound No. | Retention Time (min) | [M + H] | Method |
|---|---|---|---|---|
| 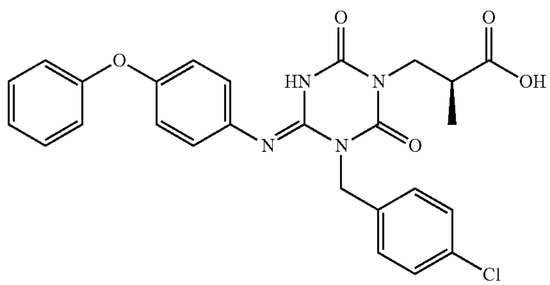 [SMILES: C[C@@H](Cn1c(=O)[nH]/c(=N\c2ccc(Oc3ccccc3)cc2)n(Cc2ccc(Cl)cc2)c1=O)C(=O)O] | I-0991 | 2.32 | 507 | 3 |
| 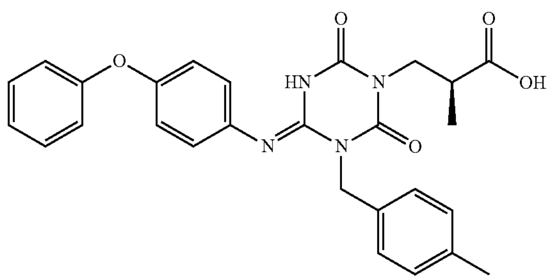 | I-0992 | 2.25 | 487 | 3 |
| 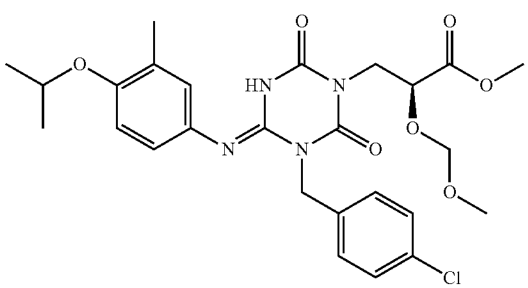 [SMILES: COCO[C@@H](Cn1c(=O)[nH]/c(=N\c2ccc(OC(C)C)c(C)c2)n(Cc2ccc(Cl)cc2)c1=O)C(=O)OC] | I-0993 | 2.25 | 547 | 2 |
| 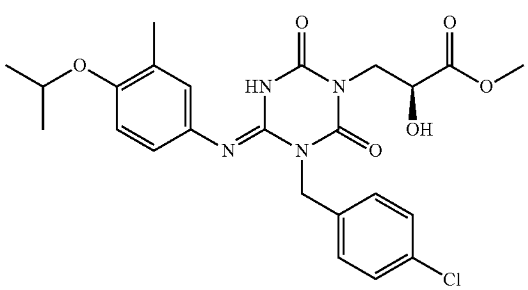 | I-0994 | 2.03 | 503 | 2 |
| 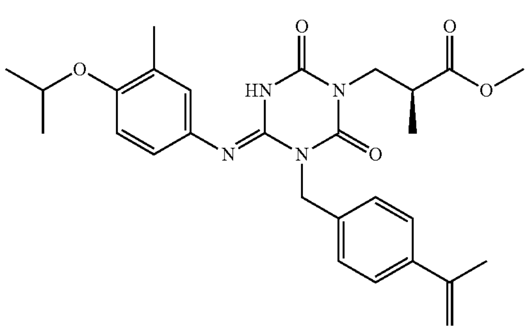 [SMILES: C=C(C)c1ccc(Cn2c(=O)n(C[C@H](C)C(=O)OC)c(=O)[nH]/c2=N\c2ccc(OC(C)C)c(C)c2)cc1] | I-0995 | 2.41 | 507 | 2 |

TABLE 203

| Structure | Compound No. | Retention Time (min) | [M + H] | Method |
|---|---|---|---|---|
| (structure) | I-0996 | 2.21 | 501 | 2 |
| (structure) | I-0997 | 2.49 | 509 | 2 |
| (structure) | I-0998 | 2.39 | 477 | 2 |
| (structure) | I-0999 | 2.29 | 493 | 2 |
| (structure) | I-1000 | 2.47 | 511 | 2 |

TABLE 204

| Structure | Compound No. | Retention Time (min) | [M + H] | Method |
|---|---|---|---|---|
| (structure) | I-1001 | 2.17 | 493 | 2 |
| (structure) | I-1002 | 2.03 | 479 | 2 |
| (structure) | I-1003 | 2.23 | 497 | 2 |
| (structure) | I-1004 | 2.15 | 463 | 2 |
| (structure) | I-1005 | 2.72 | 527 | 3 |

TABLE 205

| Structure | Compound No. | Retention Time (min) | [M + H] | Method |
|---|---|---|---|---|
| 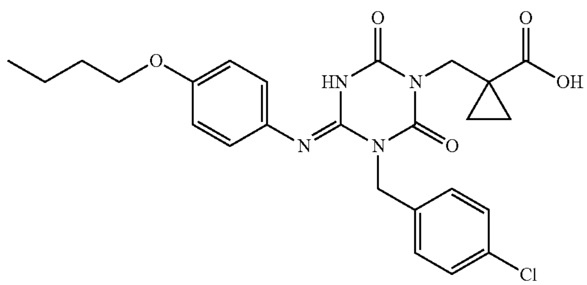 [SMILES: CCCCOc1ccc(/N=c2\[nH]c(=O)n(CC3(C(=O)O)CC3)c(=O)n2Cc2ccc(Cl)cc2)cc1] | I-1006 | 2.37 | 498 | 3 |
| 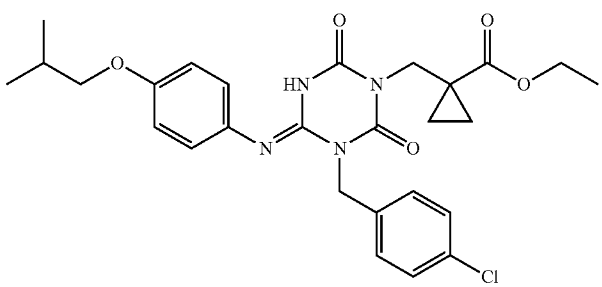 [SMILES: CCOC(=O)C1(Cn2c(=O)[nH]/c(=N\c3ccc(OCC(C)C)cc3)n(Cc3ccc(Cl)cc3)c2=O)CC1] | I-1007 | 2.73 | 527 | 3 |
| 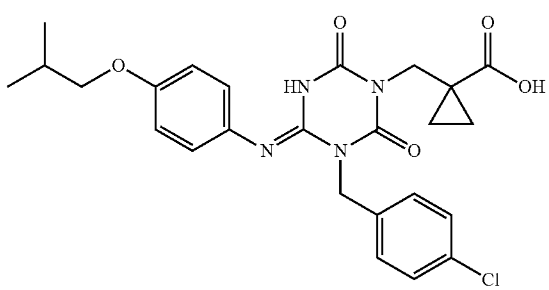 [SMILES: CC(C)COc1ccc(/N=c2\[nH]c(=O)n(CC3(C(=O)O)CC3)c(=O)n2Cc2ccc(Cl)cc2)cc1] | I-1008 | 2.38 | 498 | 3 |
| 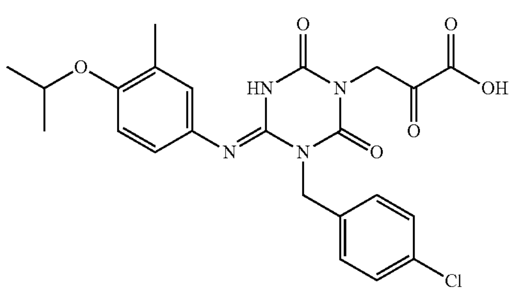 [SMILES: Cc1cc(/N=c2\[nH]c(=O)n(CC(=O)C(=O)O)c(=O)n2Cc2ccc(Cl)cc2)ccc1OC(C)C] | I-1009 | 1.89 | 487 | 2 |
| 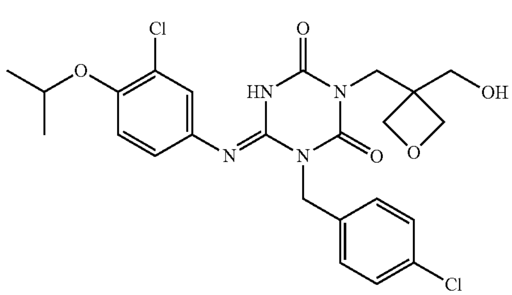 [SMILES: CC(C)Oc1ccc(/N=c2\[nH]c(=O)n(CC3(CO)COC3)c(=O)n2Cc2ccc(Cl)cc2)cc1Cl] | I-1010 | 2.05 | 521 | 2 |

TABLE 206

| Structure | Compound No. | Retention Time (min) | [M + H] | Method |
|---|---|---|---|---|
| 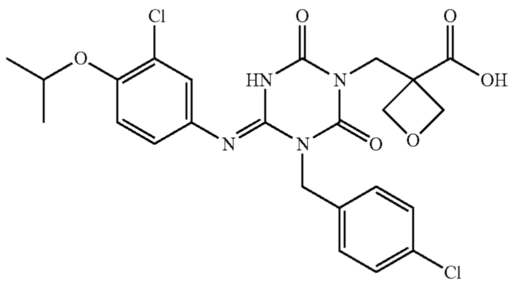 | I-1011 | 2.01 | 535 | 2 |
| 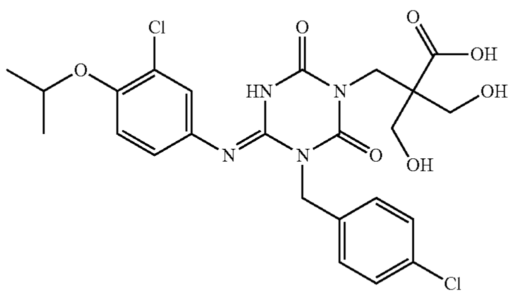 [SMILES: CC(C)Oc1ccc(/N=c2\[nH]c(=O)n(CC(CO)(CO)C(=O)O)c(=O)n2Cc2ccc(Cl)cc2)cc1Cl] | I-1012 | 1.90 | 553 | 2 |
| 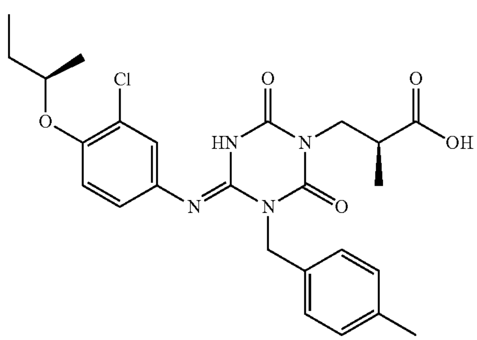 [SMILES: CC[C@@H](C)Oc1ccc(/N=c2\[nH]c(=O)n(C[C@H](C)C(=O)O)c(=O)n2Cc2ccc(C)cc2)cc1Cl] | I-1013 | 2.20 | 501 | 2 |
| 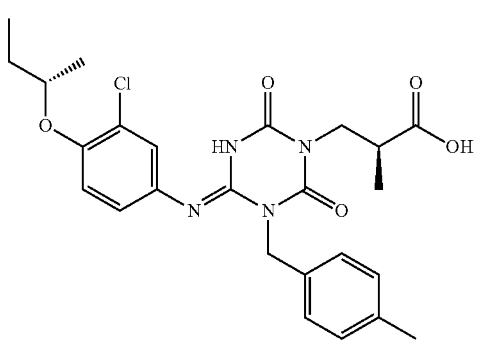 [SMILES: CC[C@H](C)Oc1ccc(/N=c2\[nH]c(=O)n(C[C@H](C)C(=O)O)c(=O)n2Cc2ccc(C)cc2)cc1Cl] | I-1014 | 2 | 501 | 2 |

TABLE 206-continued

| Structure | Compound No. | Retention Time (min) | [M + H] | Method |
|---|---|---|---|---|
| 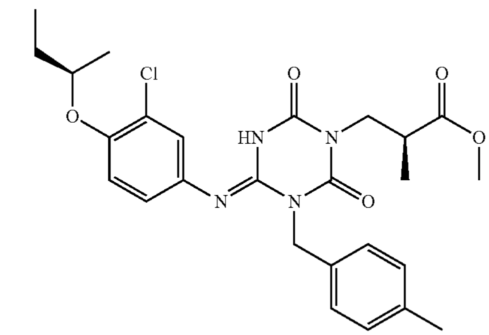 [SMILES: CC[C@@H](C)Oc1ccc(/N=c2\[nH]c(=O)n(C[C@H](C)C(=O)OC)c(=O)n2Cc2ccc(C)cc2)cc1Cl] | I-1015 | 2.44 | 515 | 2 |

TABLE 207

| Structure | Compound No. | Retention Time (min) | [M + H] | Method |
|---|---|---|---|---|
| 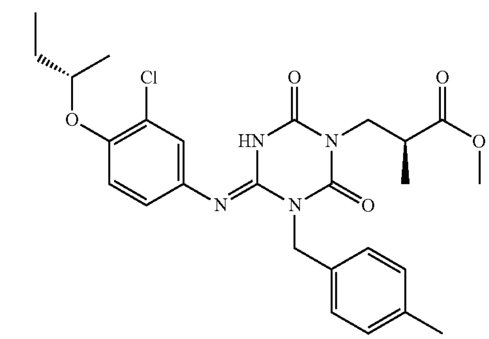 [SMILES: CC[C@H](C)Oc1ccc(/N=c2\[nH]c(=O)n(C[C@H](C)C(=O)OC)c(=O)n2Cc2ccc(C)cc2)cc1Cl] | I-1016 | 2.45 | 515 | 2 |
| 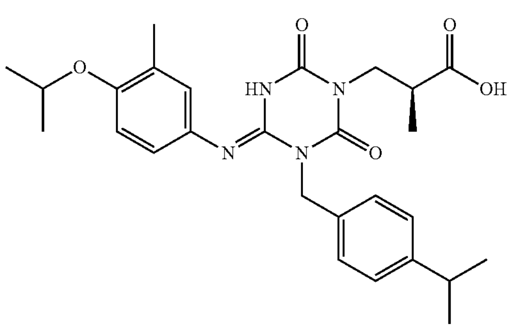 [SMILES: Cc1cc(/N=c2\[nH]c(=O)n(C[C@H](C)C(=O)O)c(=O)n2Cc2ccc(C(C)C)cc2)ccc1OC(C)C] | I-1017 | 2.24 | 495 | 2 |
| 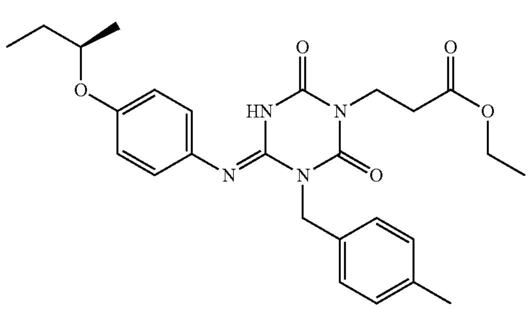 [SMILES: CCOC(=O)CCn1c(=O)[nH]/c(=N\c2ccc(O[C@H](C)CC)cc2)n(Cc2ccc(C)cc2)c1=O] | I-1018 | 2.51 | 481 | 3 |

TABLE 207-continued

| Structure | Compound No. | Retention Time (min) | [M + H] | Method |
|---|---|---|---|---|
| 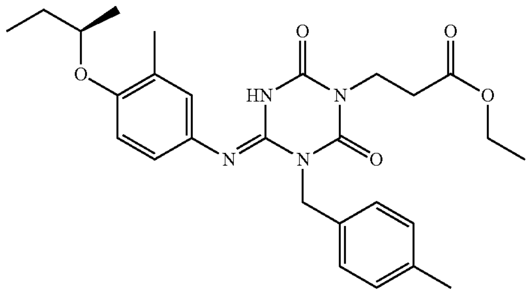 [SMILES: CCOC(=O)CCn1c(=O)[nH]/c(=N\c2ccc(O[C@H](C)CC)c(C)c2)n(Cc2ccc(C)cc2)c1=O] | I-1019 | 2.65 | 495 | 3 |
| 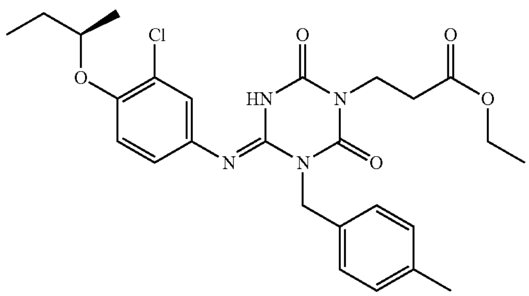 | I-1020 | 2.70 | 515 | 3 |

TABLE 208

| Structure | Compound No. | Retention Time (min) | [M + H] | Method |
|---|---|---|---|---|
| 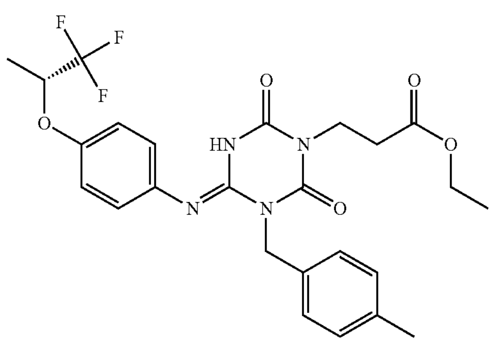 [SMILES: CCOC(=O)CCn1c(=O)[nH]/c(=N\c2ccc(O[C@H](C)C(F)(F)F)cc2)n(Cc2ccc(C)cc2)c1=O] | I-1021 | 2.24 | 521 | 2 |
| 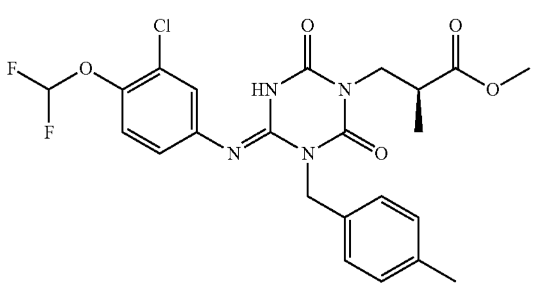 [SMILES: COC(=O)[C@@H](C)Cn1c(=O)[nH]/c(=N\c2ccc(OC(F)F)c(Cl)c2)n(Cc2ccc(C)cc2)c1=O] | I-1022 | 2.27 | 509 | 2 |

TABLE 208-continued
| Structure | Compound No. | Retention Time (min) | [M + H] | Method |
|---|---|---|---|---|
| 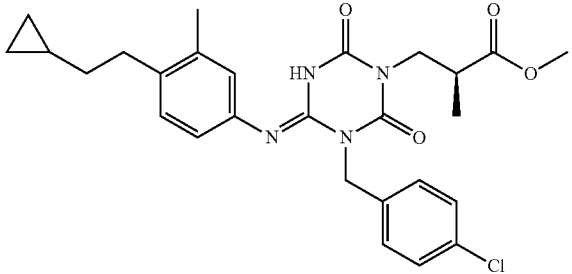 [SMILES: COC(=O)[C@@H](C)Cn1c(=O)[nH]/c(=N\c2ccc(CCC3CC3)c(C)c2)n(Cc2ccc(Cl)cc2)c1=O] | I-1023 | 2.80 | 511 | 3 |
| 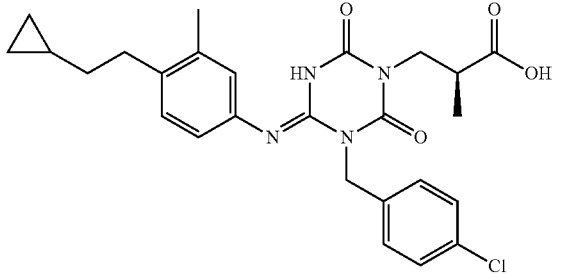 [SMILES: Cc1cc(/N=c2\[nH]c(=O)n(C[C@H](C)C(=O)O)c(=O)n2Cc2ccc(Cl)cc2)ccc1CCC1CC1] | I-1024 | 2.56 | 497 | 3 |
| 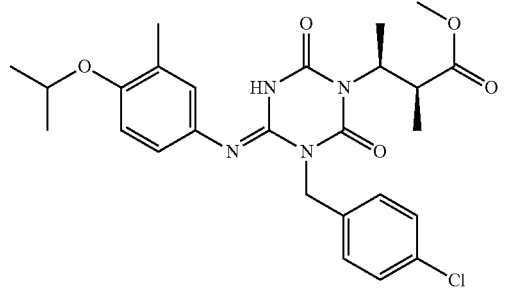 | I-1025 | 2.40 | 515 | 2 |
TABLE 209
| Structure | Compound No. | Retention Time (min) | [M + H] | Method |
|---|---|---|---|---|
| 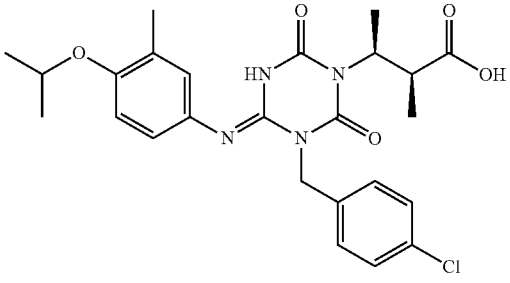 [SMILES: Cc1cc(/N=c2\[nH]c(=O)n([C@@H](C)[C@H](C)C(=O)O)c(=O)n2Cc2ccc(Cl)cc2)ccc1OC(C)C] | I-1026 | 2.13 | 501 | 2 |

TABLE 209-continued

| Structure | Compound No. | Retention Time (min) | [M + H] | Method |
|---|---|---|---|---|
| 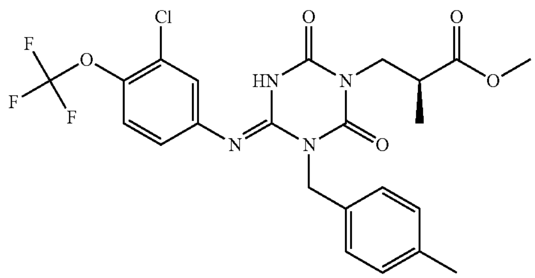 [SMILES: COC(=O)[C@@H](C)Cn1c(=O)[nH]/c(=N\c2ccc(OC(F)(F)F)c(Cl)c2)n(Cc2ccc(C)cc2)c1=O] | I-1027 | 2.52 | 527 | 2 |
| 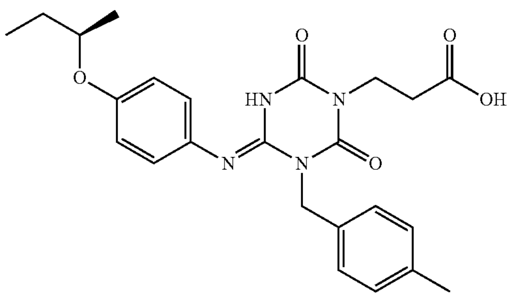 [SMILES: CC[C@@H](C)Oc1ccc(/N=c2\[nH]c(=O)n(CCC(=O)O)c(=O)n2Cc2ccc(C)cc2)cc1] | I-1028 | 2.17 | 453 | 3 |
| 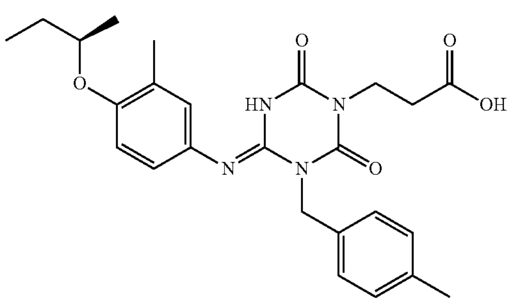 [SMILES: CC[C@@H](C)Oc1ccc(/N=c2\[nH]c(=O)n(CCC(=O)O)c(=O)n2Cc2ccc(C)cc2)cc1C] | I-1029 | 2.32 | 467 | 3 |
| 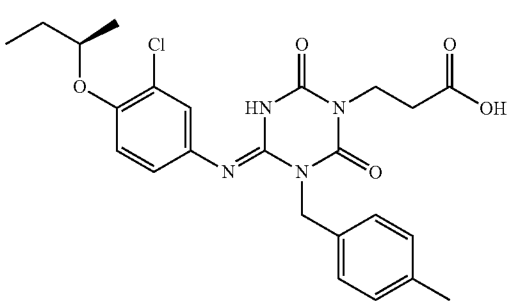 [SMILES: CC[C@@H](C)Oc1ccc(/N=c2\[nH]c(=O)n(CCC(=O)O)c(=O)n2Cc2ccc(C)cc2)cc1Cl] | I-1030 | 2.37 | 487 | 3 |

TABLE 210

| Structure | Compound No. | Retention Time (min) | [M + H] | Method |
|---|---|---|---|---|
| 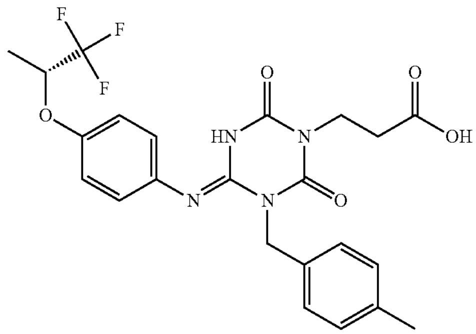 [SMILES: Cc1ccc(Cn2c(=O)n(CCC(=O)O)c(=O)[nH]/c2=N\c2ccc(O[C@H](C)C(F)(F)F)cc2)cc1] | I-1031 | 1.93 | 493 | 2 |
| 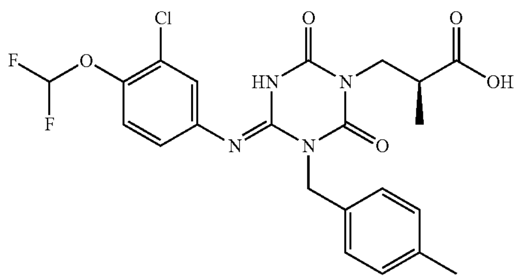 | I-1032 | 2.04 | 495 | 2 |
| 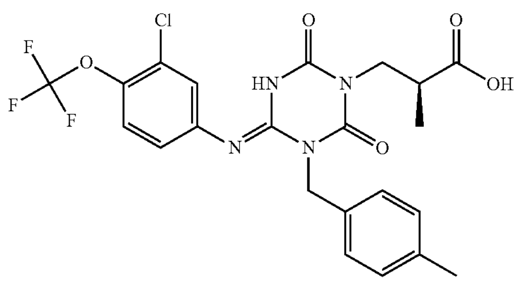 | I-1033 | 2.29 | 513 | 2 |
| 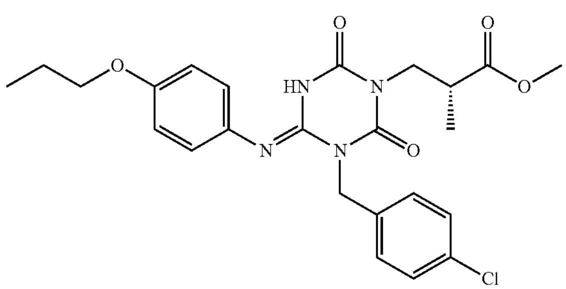 [SMILES: CCCOc1ccc(/N=c2\[nH]c(=O)n(C[C@@H](C)C(=O)OC)c(=O)n2Cc2ccc(Cl)cc2)cc1] | I-1034 | 2.45 | 487 | 3 |
| 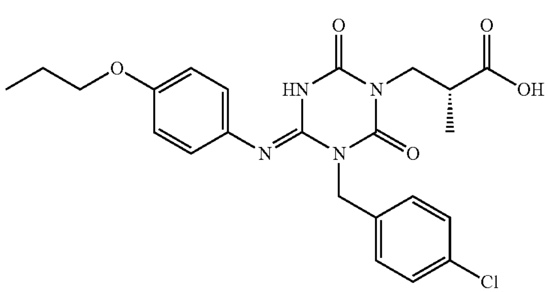 [SMILES: CCCOc1ccc(/N=c2\[nH]c(=O)n(C[C@@H](C)C(=O)O)c(=O)n2Cc2ccc(Cl)cc2)cc1] | I-1035 | 2.19 | 473 | 3 |

TABLE 211

| Structure | Compound No. | Retention Time (min) | [M + H] | Method |
|---|---|---|---|---|
| 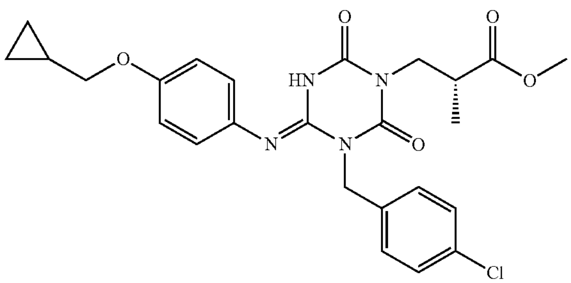 [SMILES: COC(=O)[C@H](C)Cn1c(=O)[nH]/c(=N\c2ccc(OCC3CC3)cc2)n(Cc2ccc(Cl)cc2)c1=O] | I-1036 | 2.42 | 499 | 3 |
| 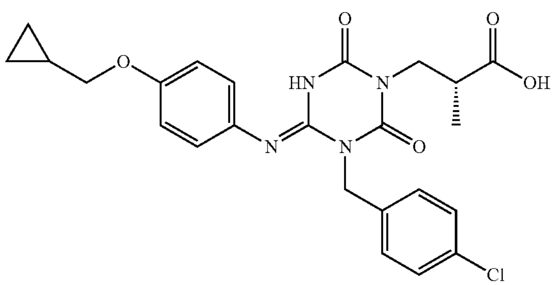 [SMILES: C[C@H](Cn1c(=O)[nH]/c(=N\c2ccc(OCC3CC3)cc2)n(Cc2ccc(Cl)cc2)c1=O)C(=O)O] | I-1037 | 2.16 | 485 | 3 |
| 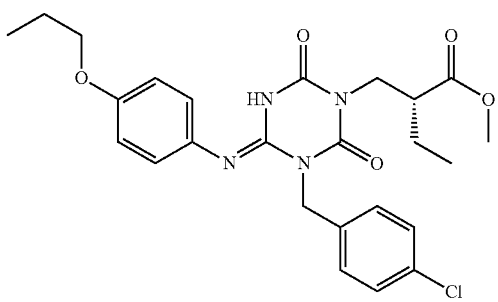 [SMILES: CCCOc1ccc(/N=c2\[nH]c(=O)n(C[C@@H](CC)C(=O)OC)c(=O)n2Cc2ccc(Cl)cc2)cc1] | I-1038 | 2.55 | 501 | 3 |
| 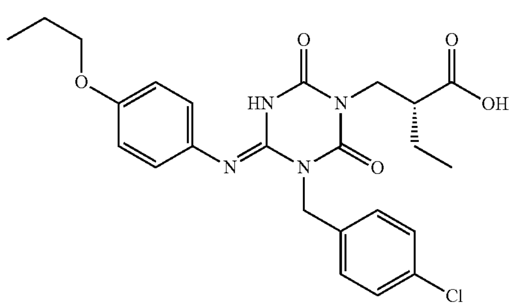 [SMILES: CCCOc1ccc(/N=c2\[nH]c(=O)n(C[C@@H](CC)C(=O)O)c(=O)n2Cc2ccc(Cl)cc2)cc1] | I-1039 | 2.27 | 487 | 3 |
| 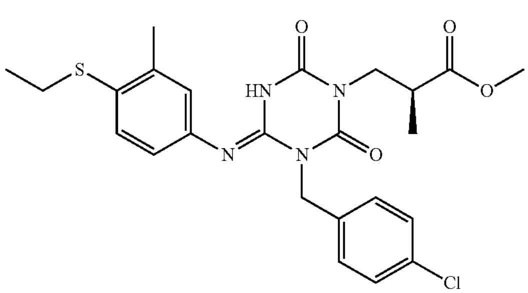 [SMILES: CCSc1ccc(/N=c2\[nH]c(=O)n(C[C@H](C)C(=O)OC)c(=O)n2Cc2ccc(Cl)cc2)cc1C] | I-1040 | 2.64 | 503 | 3 |

TABLE 212
| Structure | Compound No. | Retention Time (min) | [M + H] | Method |
|---|---|---|---|---|
| 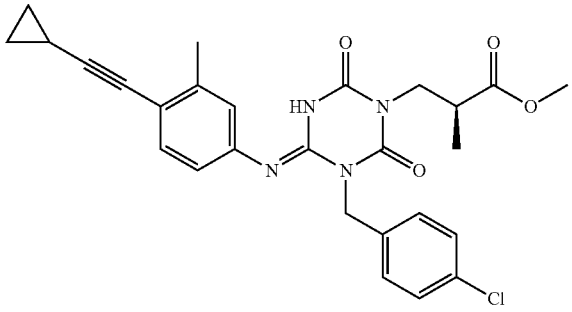 [SMILES: COC(=O)[C@@H](C)Cn1c(=O)[nH]/c(=N\c2ccc(C#CC3CC3)c(C)c2)n(Cc2ccc(Cl)cc2)c1=O] | I-1041 | 2.74 | 507 | 3 |
| 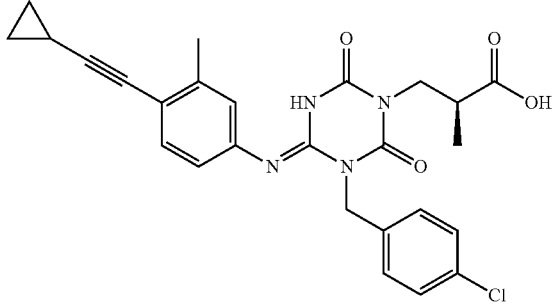 [SMILES: Cc1cc(/N=c2\[nH]c(=O)n(C[C@H](C)C(=O)O)c(=O)n2Cc2ccc(Cl)cc2)ccc1C#CC1CC1] | I-1042 | 2.49 | 493 | 3 |
| 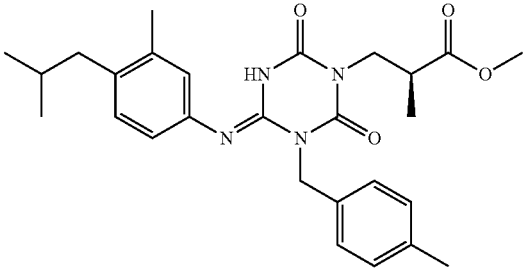 [SMILES: COC(=O)[C@@H](C)Cn1c(=O)[nH]/c(=N\c2ccc(CC(C)C)c(C)c2)n(Cc2ccc(C)cc2)c1=O] | I-1043 | 2.79 | 479 | 3 |
| 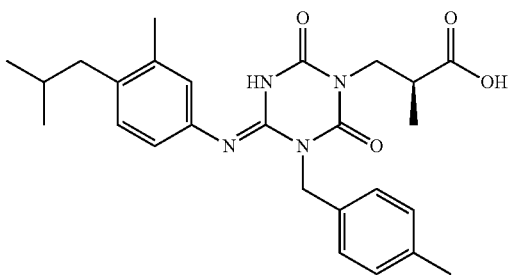 | I-1044 | 2.48 | 465 | 3 |
| 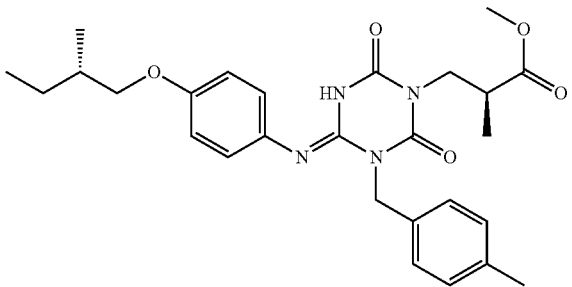 [SMILES: CC[C@H](C)COc1ccc(/N=c2\[nH]c(=O)n(C[C@H](C)C(=O)OC)c(=O)n2Cc2ccc(C)cc2)cc1] | I-1045 | 2.41 | 495 | 2 |

TABLE 213

| Structure | Compound No. | Retention Time (min) | [M + H] | Method |
|---|---|---|---|---|
| 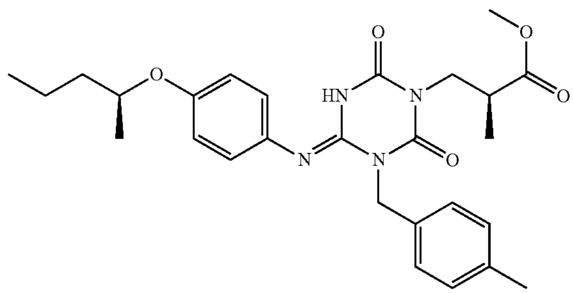 [SMILES: CCC[C@H](C)Oc1ccc(/N=c2\[nH]c(=O)n(C[C@H](C)C(=O)OC)c(=O)n2Cc2ccc(C)cc2)cc1] | I-1046 | 2.38 | 495 | 2 |
| 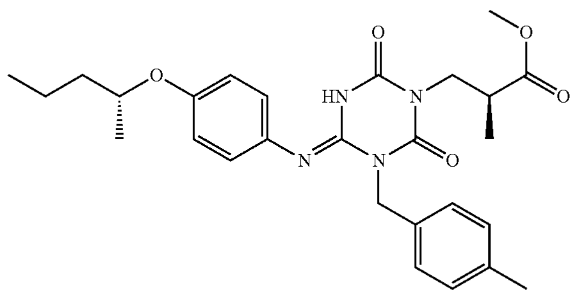 [SMILES: CCC[C@@H](C)Oc1ccc(/N=c2\[nH]c(=O)n(C[C@H](C)C(=O)OC)c(=O)n2Cc2ccc(C)cc2)cc1] | I-1047 | 2.37 | 495 | 2 |
| 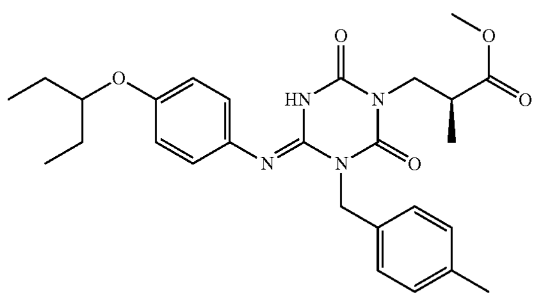 [SMILES: CCC(CC)Oc1ccc(/N=c2\[nH]c(=O)n(C[C@H](C)C(=O)OC)c(=O)n2Cc2ccc(C)cc2)cc1] | I-1048 | 2.38 | 495 | 2 |
| 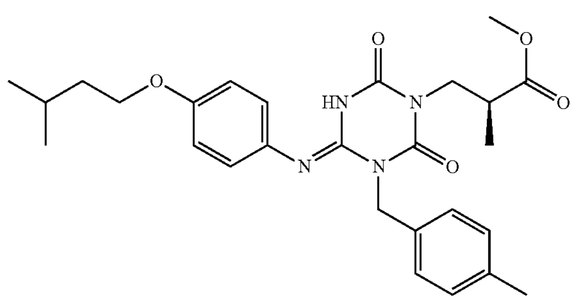 [SMILES: COC(=O)[C@@H](C)Cn1c(=O)[nH]/c(=N\c2ccc(OCCC(C)C)cc2)n(Cc2ccc(C)cc2)c1=O] | I-1049 | 2.40 | 495 | 2 |
| 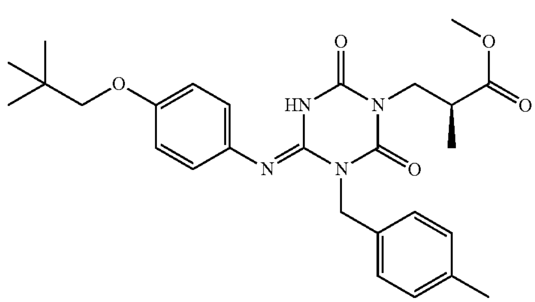 [SMILES: COC(=O)[C@@H](C)Cn1c(=O)[nH]/c(=N\c2ccc(OCC(C)(C)C)cc2)n(Cc2ccc(C)cc2)c1=O] | I-1050 | 2.43 | 495 | 2 |

TABLE 214

| Structure | Compound No. | Retention Time (min) | [M + H] | Method |
|---|---|---|---|---|
| 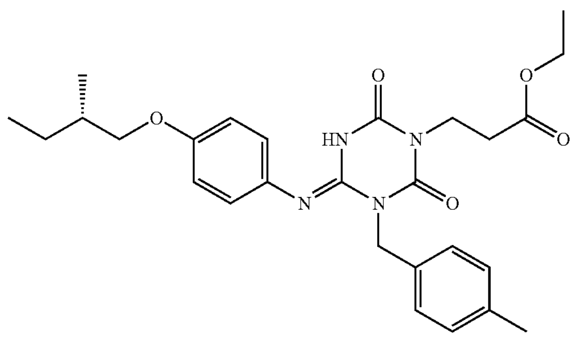 [SMILES: CCOC(=O)CCn1c(=O)[nH]/c(=N\c2ccc(OC[C@@H](C)CC)cc2)n(Cc2ccc(C)cc2)c1=O] | I-1051 | 2.45 | 495 | 2 |
| 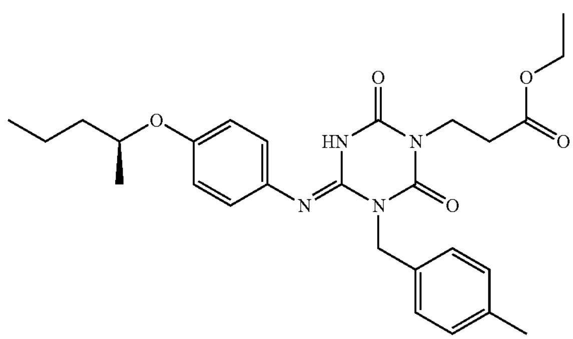 [SMILES: CCC[C@H](C)Oc1ccc(/N=c2\[nH]c(=O)n(CCC(=O)OCC)c(=O)n2Cc2ccc(C)cc2)cc1] | I-1052 | 2.39 | 495 | 2 |
| 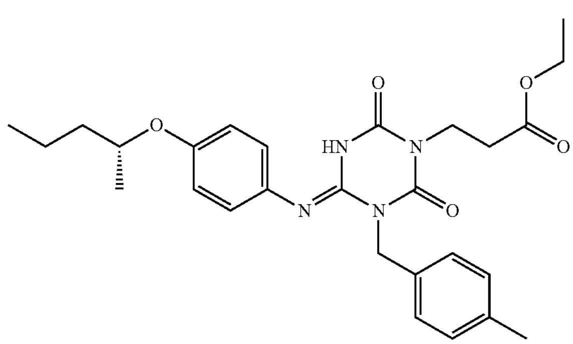 [SMILES: CCC[C@@H](C)Oc1ccc(/N=c2\[nH]c(=O)n(CCC(=O)OCC)c(=O)n2Cc2ccc(C)cc2)cc1] | I-1053 | 2.40 | 495 | 2 |
| 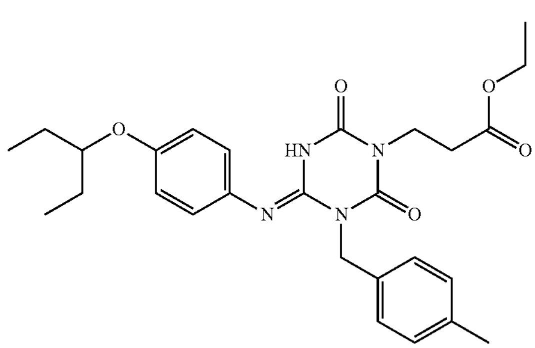 [SMILES: CCOC(=O)CCn1c(=O)[nH]/c(=N\c2ccc(OC(CC)CC)cc2)n(Cc2ccc(C)cc2)c1=O] | I-1054 | 2.38 | 495 | 2 |

TABLE 214-continued

| Structure | Compound No. | Retention Time (min) | [M + H] | Method |
|---|---|---|---|---|
| 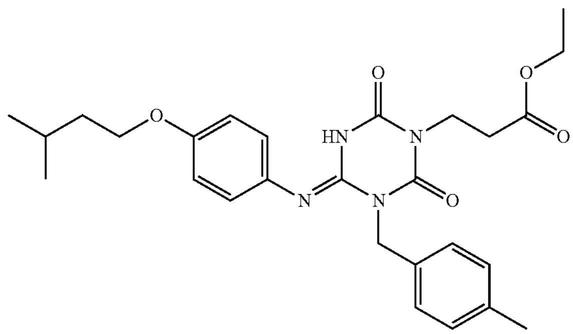 [SMILES: CCOC(=O)CCn1c(=O)[nH]/c(=N\c2ccc(OCCC(C)C)cc2)n(Cc2ccc(C)cc2)c1=O] | I-1055 | 2.43 | 495 | 2 |

TABLE 215

| Structure | Compound No. | Retention Time (min) | [M + H] | Method |
|---|---|---|---|---|
| 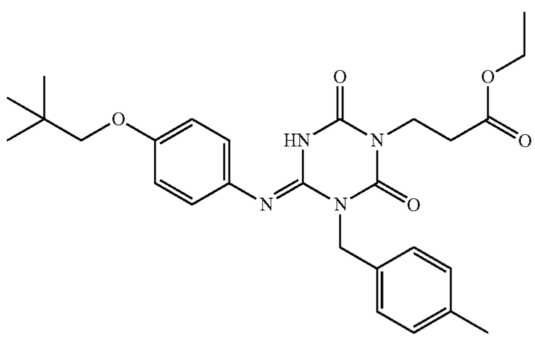 [SMILES: CCOC(=O)CCn1c(=O)[nH]/c(=N\c2ccc(OCC(C)(C)C)cc2)n(Cc2ccc(C)cc2)c1=O] | I-1056 | 2.46 | 495 | 2 |
| 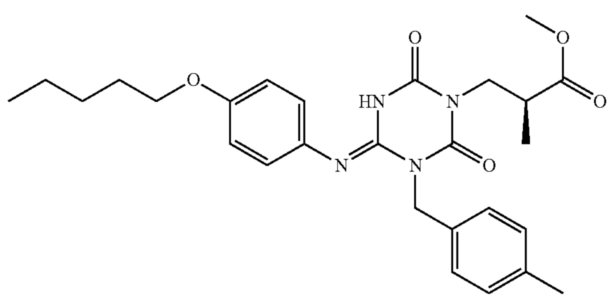 [SMILES: CCCCCOc1ccc(/N=c2\[nH]c(=O)n(C[C@H](C)C(=O)OC)c(=O)n2Cc2ccc(C)cc2)cc1] | I-1057 | 2.42 | 495 | 2 |
| 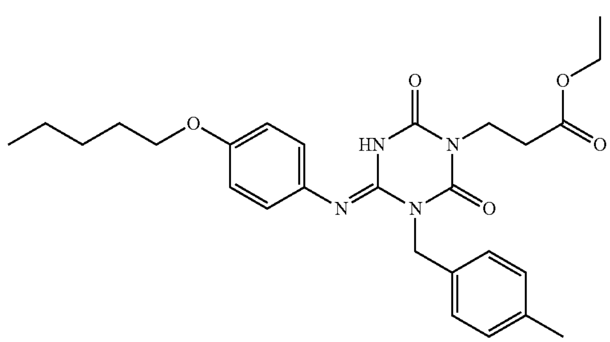 [SMILES: CCCCCOc1ccc(/N=c2\[nH]c(=O)n(CCC(=O)OCC)c(=O)n2Cc2ccc(C)cc2)cc1] | I-1058 | 2.45 | 495 | 2 |

TABLE 215-continued

| Structure | Compound No. | Retention Time (min) | [M + H] | Method |
|---|---|---|---|---|
| 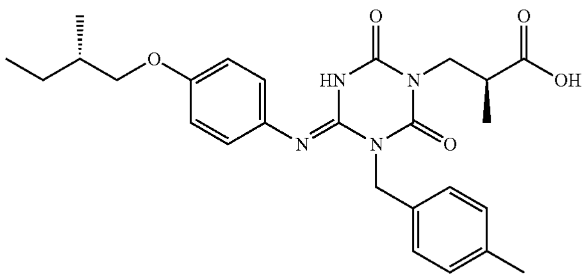 [SMILES: CC[C@H](C)COc1ccc(/N=c2\[nH]c(=O)n(C[C@H](C)C(=O)O)c(=O)n2Cc2ccc(C)cc2)cc1] | I-1059 | 2.19 | 481 | 2 |
| 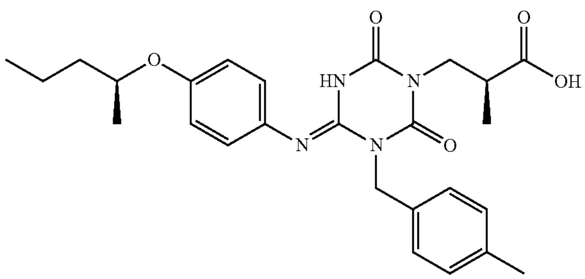 [SMILES: CCC[C@H](C)Oc1ccc(/N=c2\[nH]c(=O)n(C[C@H](C)C(=O)O)c(=O)n2Cc2ccc(C)cc2)cc1] | I-1060 | 2.15 | 481 | 2 |

TABLE 216

| Structure | Compound No. | Retention Time (min) | [M + H] | Method |
|---|---|---|---|---|
| 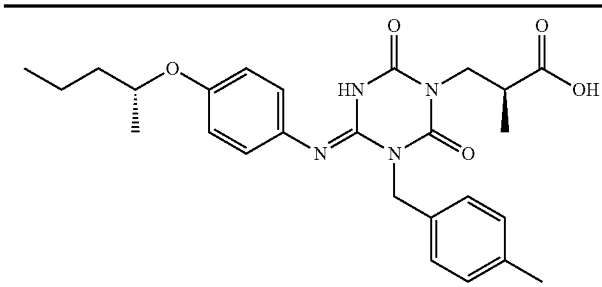 | I-1061 | 2.14 | 481 | 2 |
| 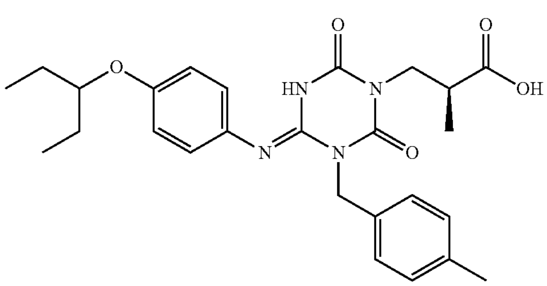 [SMILES: CCC(CC)Oc1ccc(/N=c2\[nH]c(=O)n(C[C@H](C)C(=O)O)c(=O)n2Cc2ccc(C)cc2)cc1] | I-1062 | 2.14 | 481 | 2 |
| 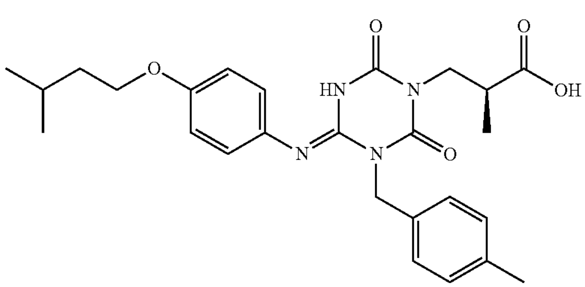 [SMILES: Cc1ccc(Cn2c(=O)n(C[C@H](C)C(=O)O)c(=O)[nH]/c2=N\c2ccc(OCCC(C)C)cc2)cc1] | I-1063 | 2.16 | 481 | 2 |

TABLE 216-continued
| Structure | Compound No. | Retention Time (min) | [M + H] | Method |
|---|---|---|---|---|
| 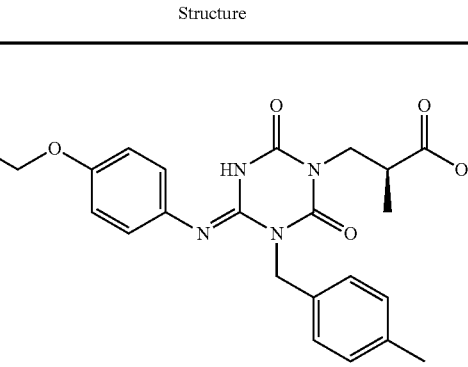 | I-1064 | 2.21 | 481 | 2 |
| 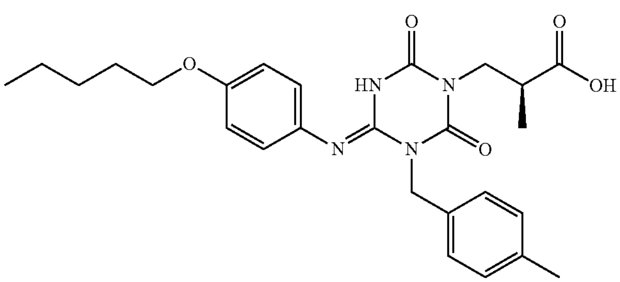 [SMILES: CCCCCOc1ccc(/N=c2\[nH]c(=O)n(C[C@H](C)C(=O)O)c(=O)n2Cc2ccc(C)cc2)cc1] | I-1065 | 2.19 | 481 | 2 |
TABLE 217
| Structure | Compound No. | Retention Time (min) | [M + H] | Method |
|---|---|---|---|---|
| 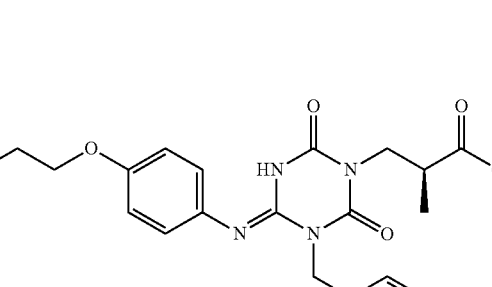 | I-1066 | 2.13 | 467 | 2 |
| 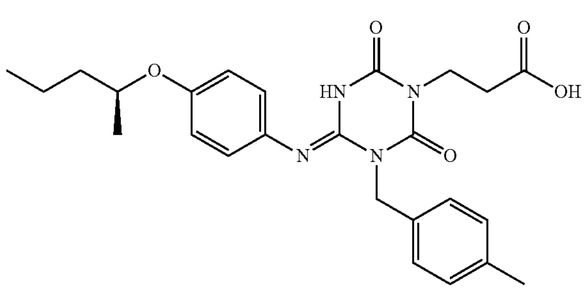 [SMILES: CCC[C@H](C)Oc1ccc(/N=c2\[nH]c(=O)n(CCC(=O)O)c(=O)n2Cc2ccc(C)cc2)cc1] | I-1067 | 2.08 | 467 | 2 |

TABLE 217-continued

| Structure | Compound No. | Retention Time (min) | [M + H] | Method |
|---|---|---|---|---|
| 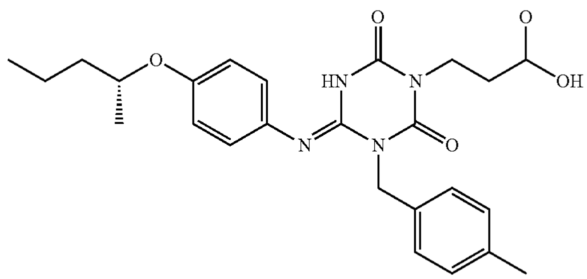 [SMILES: CCC[C@@H](C)Oc1ccc(/N=c2\[nH]c(=O)n(CCC(O)O)c(=O)n2Cc2ccc(C)cc2)cc1] | I-1068 | 2.09 | 467 | 2 |
| 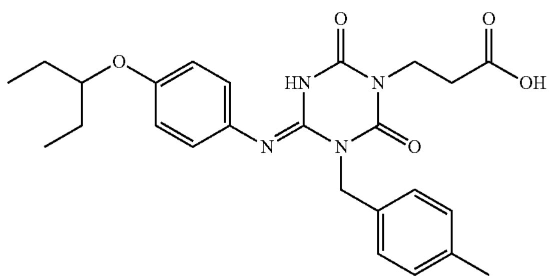 [SMILES: CCC(CC)Oc1ccc(/N=c2\[nH]c(=O)n(CCC(=O)O)c(=O)n2Cc2ccc(C)cc2)cc1] | I-1069 | 2.07 | 467 | 2 |
| 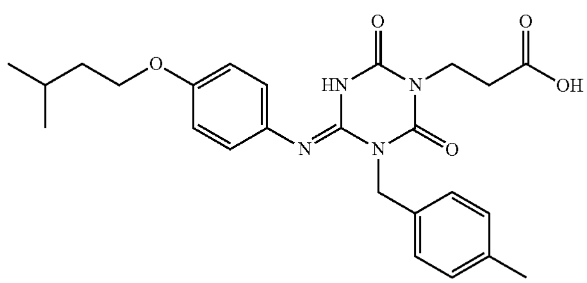 [SMILES: Cc1ccc(Cn2c(=O)n(CCC(=O)O)c(=O)[nH]/c2=N\c2ccc(OCCC(C)C)cc2)cc1] | I-1070 | 2.13 | 467 | 2 |

TABLE 218

| Structure | Compound No. | Retention Time (min) | [M + H] | Method |
|---|---|---|---|---|
| 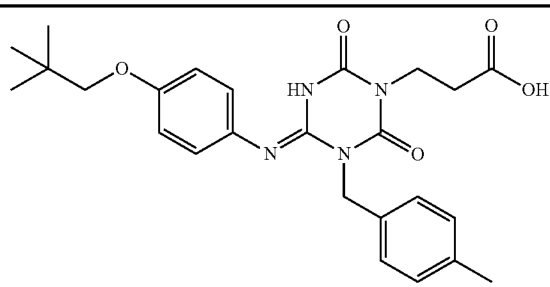 | I-1071 | 2.15 | 467 | 2 |
| 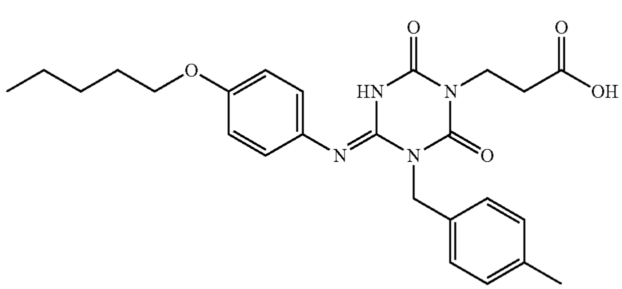 [SMILES: CCCCCOc1ccc(/N=c2\[nH]c(=O)n(CCC(=O)O)c(=O)n2Cc2ccc(C)cc2)cc1] | I-1072 | 2.15 | 467 | 2 |

TABLE 218-continued

| Structure | Compound No. | Retention Time (min) | [M + H] | Method |
|---|---|---|---|---|
| 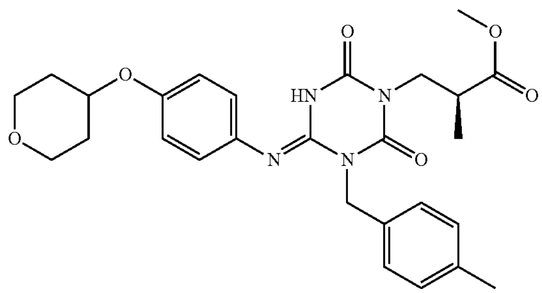 [SMILES: COC(=O)[C@@H](C)Cn1c(=O)[nH]/c(=N\c2ccc(OC3CCOCC3)cc2)n(Cc2ccc(C)cc2)c1=O] | I-1073 | 1.90 | 509 | 2 |
| 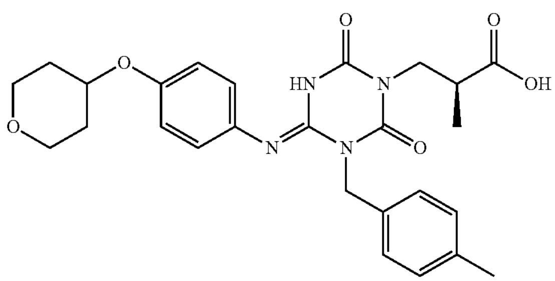 [SMILES: Cc1ccc(Cn2c(=O)n(C[C@H](C)C(=O)O)c(=O)[nH]/c2=N\c2ccc(OC3CCOCC3)cc2)cc1] | I-1074 | 1.65 | 495 | 2 |
| 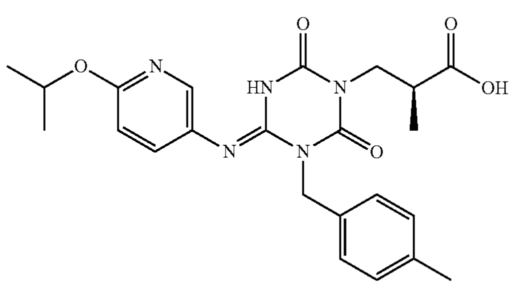 [SMILES: Cc1ccc(Cn2c(=O)n(C[C@H](C)C(=O)O)c(=O)[nH]/c2=N\c2ccc(OC(C)C)nc2)cc1] | I-1075 | 1.36 | 454 | 2 |

TABLE 219

| Structure | Compound No. | Retention Time (min) | [M + H] | Method |
|---|---|---|---|---|
| 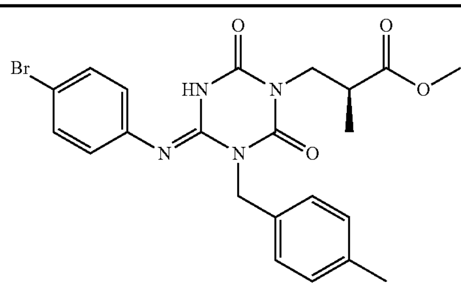 | I-1076 | 2.18 | 487 | 2 |

TABLE 219-continued

| Structure | Compound No. | Retention Time (min) | [M + H] | Method |
|---|---|---|---|---|
| (3-bromophenyl / 4-methylbenzyl triazine structure) | I-1077 | 2.23 | 487 | 2 |
| (4-cyclohexenylphenyl / 4-methylbenzyl triazine structure) | I-1078 | 2.49 | 489 | 2 |
| (3-cyclohexenylphenyl / 4-methylbenzyl triazine structure) | I-1079 | 2.49 | 489 | 2 |
| (4-isopropoxyphenyl / 4-iodobenzyl triazine structure) | I-1080 | 2.26 | 579 | 2 |

TABLE 220

| Structure | Compound No. | Retention Time (min) | [M + H] | Method |
|---|---|---|---|---|
| 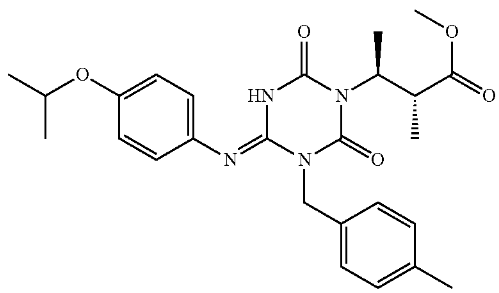 [SMILES: COC(=O)[C@H](C)[C@H](C)n1c(=O)[nH]/c(=N\c2ccc(OC(C)C)cc2)n(Cc2ccc(C)cc2)c1=O] | I-1081 | 2.23 | 481 | 2 |
| 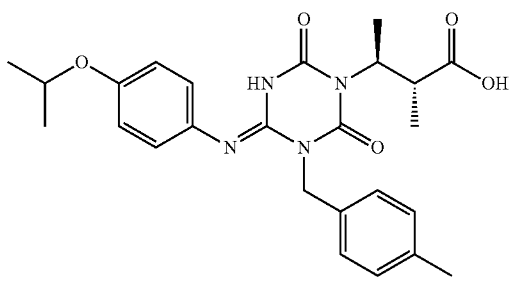 [SMILES: Cc1ccc(Cn2c(=O)n([C@@H](C)[C@@H](C)C(=O)O)c(=O)[nH]/c2=N\c2ccc(OC(C)C)cc2)cc1] | I-1082 | 1.97 | 467 | 2 |
| 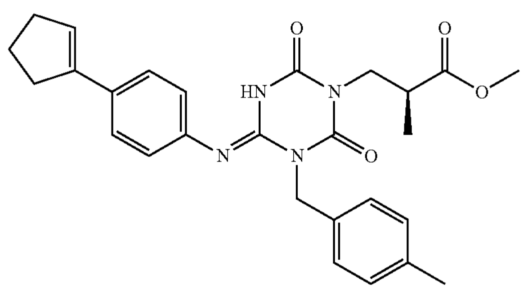 [SMILES: COC(=O)[C@@H](C)Cn1c(=O)[nH]/c(=N\c2ccc(C3=CCCC3)cc2)n(Cc2ccc(C)cc2)c1=O] | I-1083 | 2.42 | 475 | 2 |
| 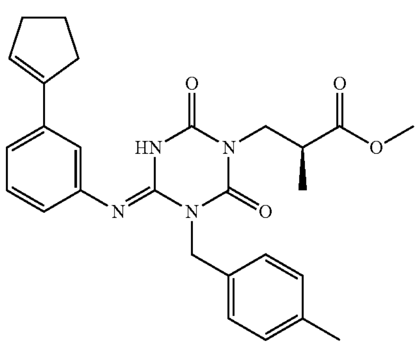 [SMILES: COC(=O)[C@@H](C)Cn1c(=O)[nH]/c(=N\c2cccc(C3=CCCC3)c2)n(Cc2ccc(C)cc2)c1=O] | I-1084 | 2.39 | 475 | 2 |
| 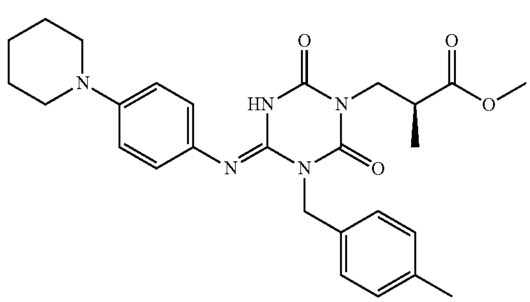 [SMILES: COC(=O)[C@@H](C)Cn1c(=O)[nH]/c(=N\c2ccc(N3CCCCC3)cc2)n(Cc2ccc(C)cc2)c1=O] | I-1085 | 1.79 | 492 | 2 |

TABLE 221

| Structure | Compound No. | Retention Time (min) | [M + H] | Method |
|---|---|---|---|---|
| 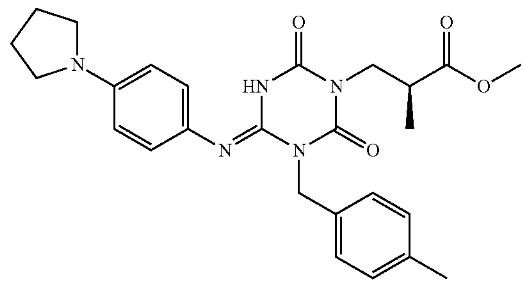 [SMILES: COC(=O)[C@@H](C)Cn1c(=O)[nH]/c(=N\c2ccc(N3CCCC3)cc2)n(Cc2ccc(C)cc2)c1=O] | I-1086 | 2.06 | 478 | 2 |
| 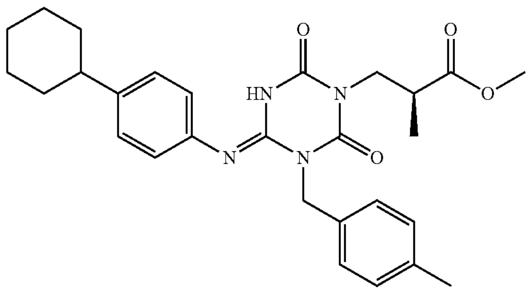 [SMILES: COC(=O)[C@@H](C)Cn1c(=O)[nH]/c(=N\c2ccc(C3CCCCC3)cc2)n(Cc2ccc(C)cc2)c1=O] | I-1087 | 2.56 | 491 | 2 |
| 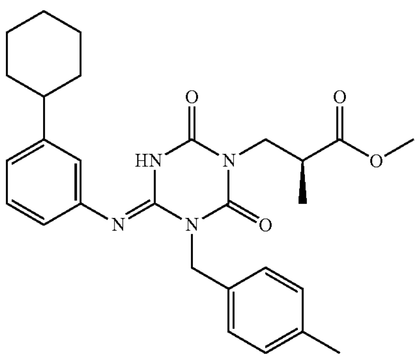 [SMILES: COC(=O)[C@@H](C)Cn1c(=O)[nH]/c(=N\c2cccc(C3CCCCC3)c2)n(Cc2ccc(C)cc2)c1=O] | I-1088 | 2.55 | 491 | 2 |
| 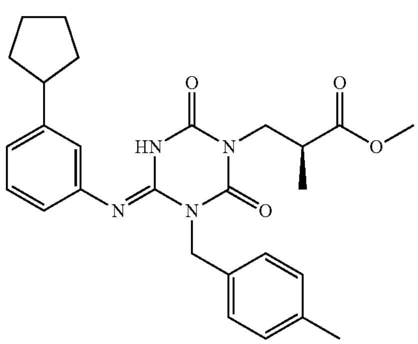 [SMILES: COC(=O)[C@@H](C)Cn1c(=O)[nH]/c(=N\c2cccc(C3CCCC3)c2)n(Cc2ccc(C)cc2)c1=O] | I-1089 | 2.45 | 477 | 2 |
| 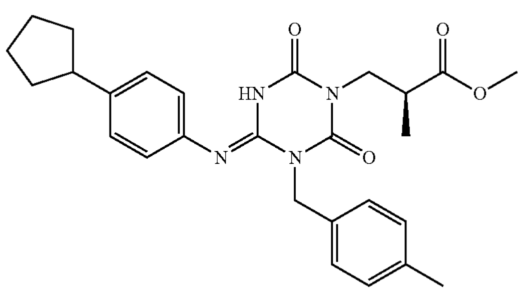 | I-1090 | 2.44 | 477 | 2 |

TABLE 222

| Structure | Compound No. | Retention Time (min) | [M + H] | Method |
|---|---|---|---|---|
| (structure) | I-1091 | 1.79 | 464 | 2 |
| (structure) | I-1092 | 2.01 | 565 | 2 |
| (structure) | I-1093 | 1.47 | 478 | 2 |
| (structure) | I-1094 | 2.74 | 489 | 3 |
| (structure) | I-1095 | 2.72 | 479 | 3 |

TABLE 223

| Structure | Compound No. | Retention Time (min) | [M + H] | Method |
|---|---|---|---|---|
| 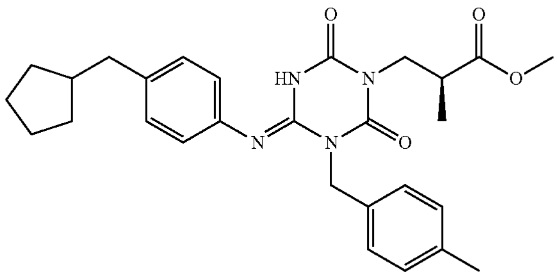 [SMILES: COC(=O)[C@@H](C)Cn1c(=O)[nH]/c(=N\c2ccc(CC3CCCC3)cc2)n(Cc2ccc(C)cc2)c1=O] | I-1096 | 2.80 | 491 | 3 |
| 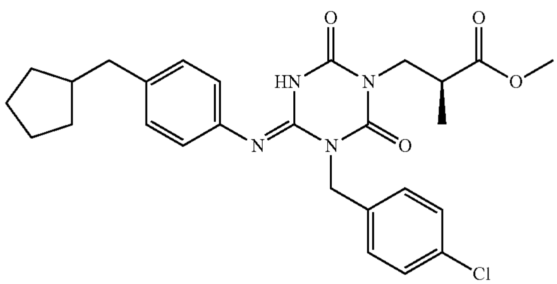 [SMILES: COC(=O)[C@@H](C)Cn1c(=O)[nH]/c(=N\c2ccc(CC3CCCC3)cc2)n(Cc2ccc(Cl)cc2)c1=O] | I-1097 | 2.87 | 511 | 3 |
| 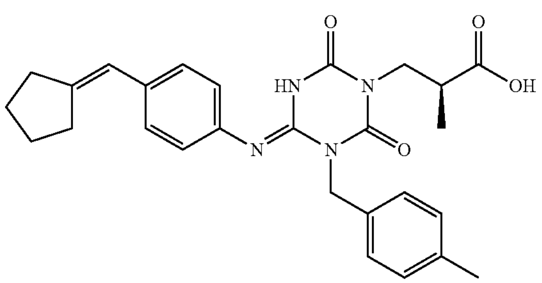 [SMILES: Cc1ccc(Cn2c(=O)n(C[C@H](C)C(=O)O)c(=O)[nH]/c2=N\c2ccc(C=C3CCCC3)cc2)cc1] | I-1098 | 2.49 | 475 | 3 |
| 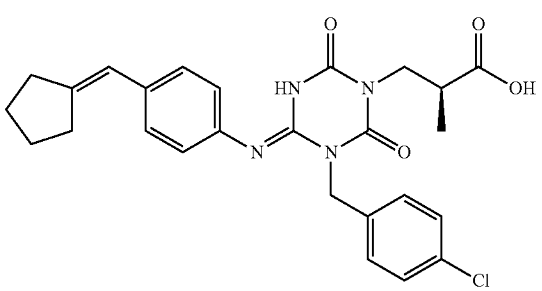 [SMILES: C[C@@H](Cn1c(=O)[nH]/c(=N\c2ccc(C=C3CCCC3)cc2)n(Cc2ccc(Cl)cc2)c1=O)C(=O)O] | I-1099 | 2.56 | 495 | 3 |
| 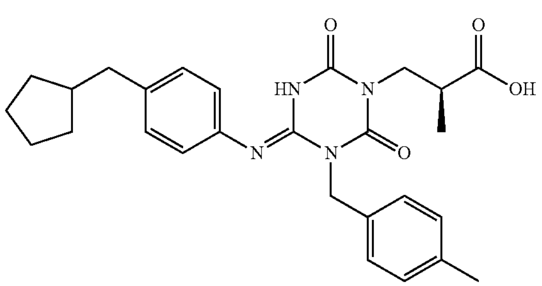 | I-1100 | 2.56 | 477 | 3 |

TABLE 224

| Structure | Compound No. | Retention Time (min) | [M + H] | Method |
|---|---|---|---|---|
| 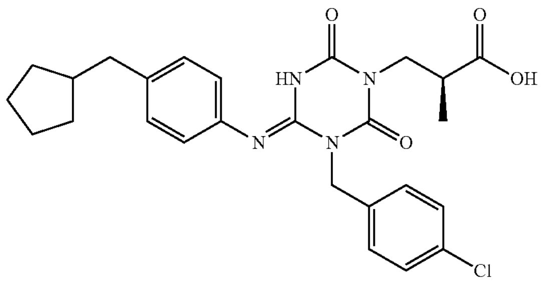 [SMILES: C[C@@H](Cn1c(=O)[nH]/c(=N\c2ccc(CC3CCCC3)cc2)n(Cc2ccc(Cl)cc2)c1=O)C(=O)O] | I-1101 | 2.62 | 497 | 3 |
| 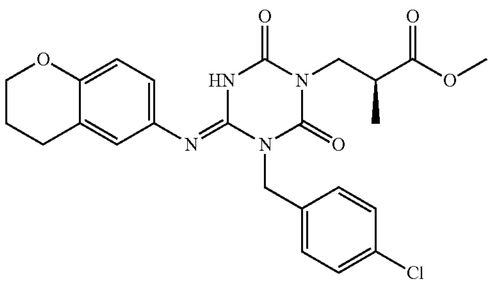 [SMILES: COC(=O)[C@@H](C)Cn1c(=O)[nH]/c(=N\c2ccc3c(c2)CCCO3)n(Cc2ccc(Cl)cc2)c1=O] | I-1102 | 2.24 | 485 | 3 |
| 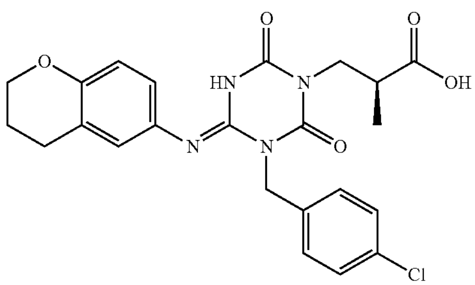 [SMILES: C[C@@H](Cn1c(=O)[nH]/c(=N\c2ccc3c(c2)CCCO3)n(Cc2ccc(Cl)cc2)c1=O)C(=O)O] | I-1103 | 1.96 | 471 | 3 |
| 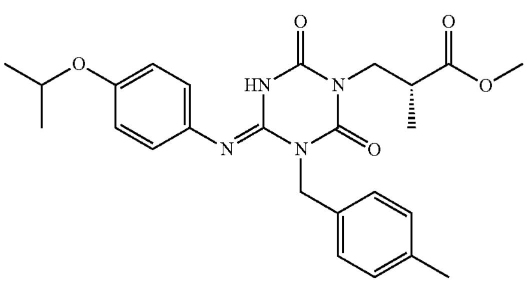 [SMILES: COC(=O)[C@H](C)Cn1c(=O)[nH]/c(=N\c2ccc(OC(C)C)cc2)n(Cc2ccc(C)cc2)c1=O] | I-1104 | 2.33 | 467 | 3 |
| 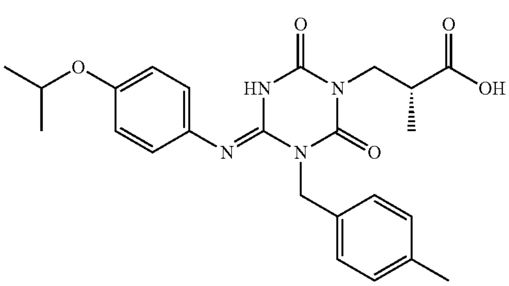 [SMILES: Cc1ccc(Cn2c(=O)n(C[C@@H](C)C(=O)O)c(=O)[nH]/c2=N\c2ccc(OC(C)C)cc2)cc1] | I-1105 | 2.07 | 453 | 3 |

TABLE 225
| Structure | Compound No. | Retention Time (min) | [M + H] | Method |
|---|---|---|---|---|
| 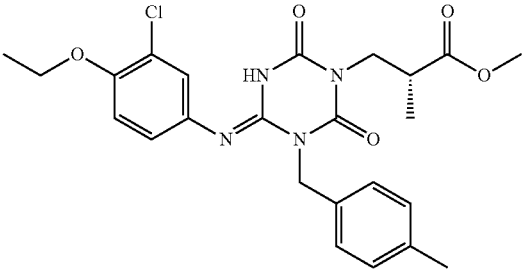 [SMILES: CCOc1ccc(/N=c2\[nH]c(=O)n(C[C@@H](C)C(=O)OC)c(=O)n2Cc2ccc(C)cc2)cc1Cl] | I-1106 | 2.43 | 487 | 3 |
| 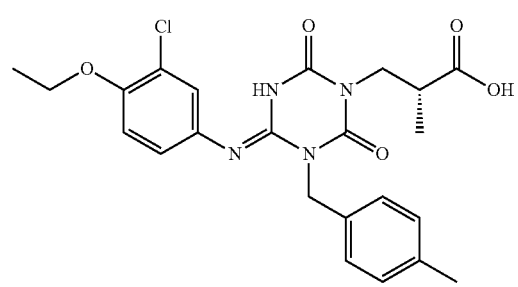 [SMILES: CCOc1ccc(/N=c2\[nH]c(=O)n(C[C@@H](C)C(=O)O)c(=O)n2Cc2ccc(C)cc2)cc1Cl] | I-1107 | 2.15 | 473 | 3 |
| 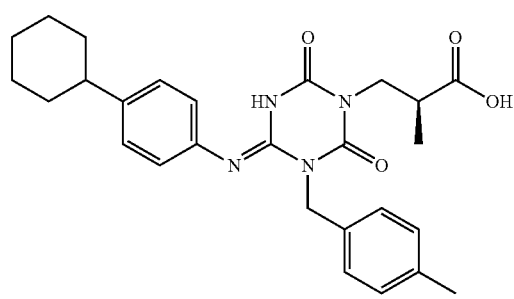 | I-1108 | 2.31 | 477 | 2 |
| 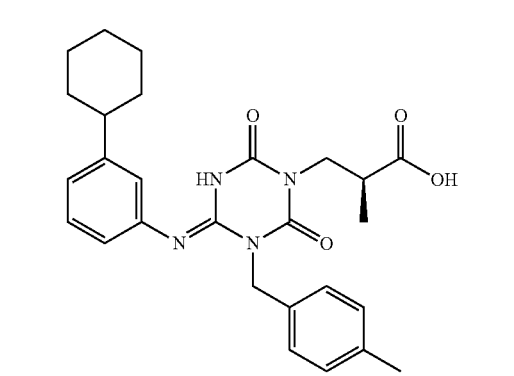 [SMILES: Cc1ccc(Cn2c(=O)n(C[C@H](C)C(=O)O)c(=O)[nH]/c2=N\c2cccc(C3CCCCC3)c2)cc1] | I-1109 | 2.32 | 477 | 2 |
| 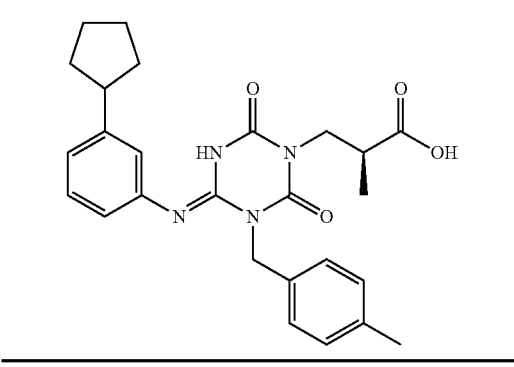 | I-1110 | 2.20 | 463 | 2 |

TABLE 226

| Structure | Compound No. | Retention Time (min) | [M + H] | Method |
|---|---|---|---|---|
| 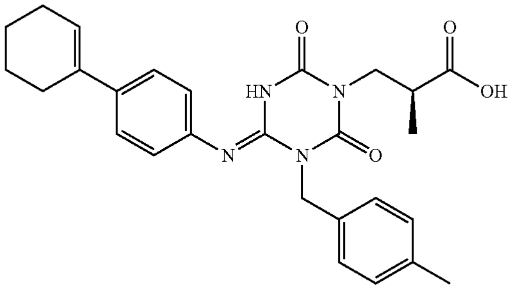 [SMILES: Cc1ccc(Cn2c(=O)n(C[C@H](C)C(=O)O)c(=O)[nH]/c2=N\c2ccc(C3=CCCCC3)cc2)cc1] | I-1111 | 2.25 | 475 | 2 |
| 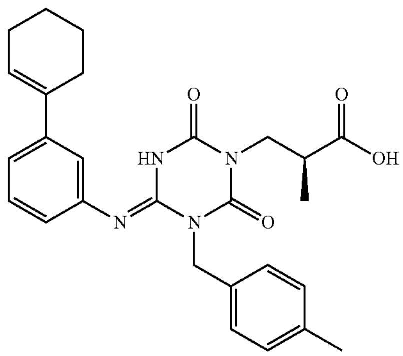 [SMILES: Cc1ccc(Cn2c(=O)n(C[C@H](C)C(=O)O)c(=O)[nH]/c2=N\c2cccc(C3=CCCCC3)c2)cc1] | I-1112 | 2.25 | 475 | 2 |
| | I-1113 | 2.21 | 463 | 2 |
| 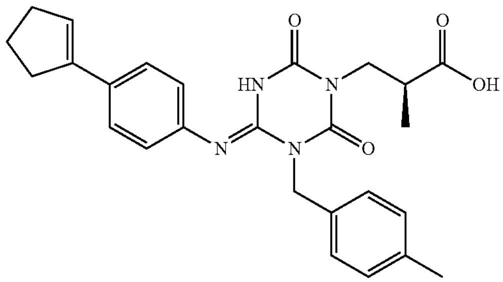 [SMILES: Cc1ccc(Cn2c(=O)n(C[C@H](C)C(=O)O)c(=O)[nH]/c2=N\c2ccc(C3CCCC3)cc2)cc1] | I-1114 | 2.15 | 461 | 2 |
| 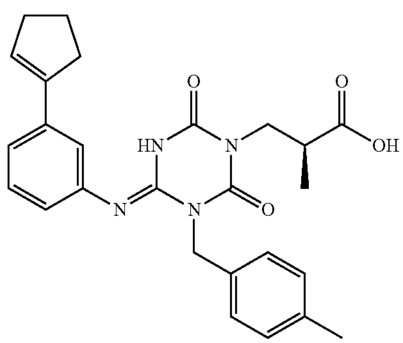 [SMILES: Cc1ccc(Cn2c(=O)n(C[C@H](C)C(=O)O)c(=O)[nH]/c2=N\c2cccc(C3=CCCC3)c2)cc1] | I-1115 | 2.15 | 461 | 2 |

TABLE 227

| Structure | Compound No. | Retention Time (min) | [M + H] | Method |
|---|---|---|---|---|
| 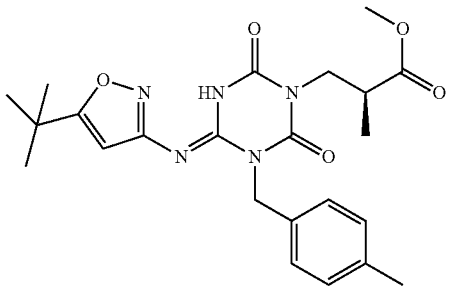 [SMILES: COC(=O)[C@@H](C)Cn1c(=O)[nH]/c(=N\c2cc(C(C)(C)C)on2)n(Cc2ccc(C)cc2)c1=O] | I-1116 | 2.64 | 456 | 2 |
| 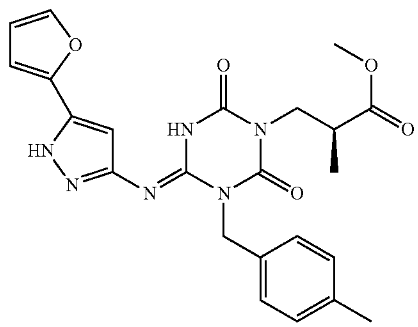 [SMILES: COC(=O)[C@@H](C)Cn1c(=O)[nH]/c(=N\c2cc(-c3ccco3)[nH]n2)n(Cc2ccc(C)cc2)c1=O] | I-1117 | 2.24 | 465 | 2 |
| 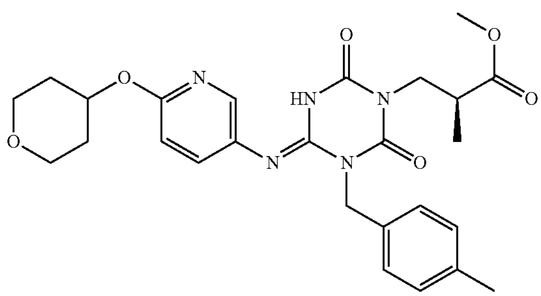 | I-1118 | 1.84 | 510 | 2 |
| 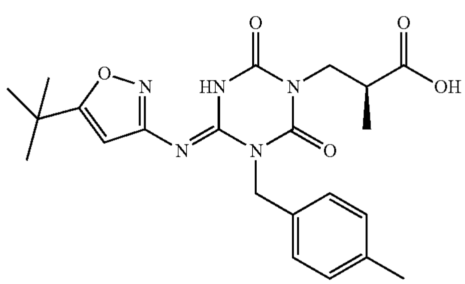 [SMILES: Cc1ccc(Cn2c(=O)n(C[C@H](C)C(=O)O)c(=O)[nH]/c2=N\c2cc(C(C)(C)C)on2)cc1] | I-1119 | 2.34 | 442 | 2 |
| 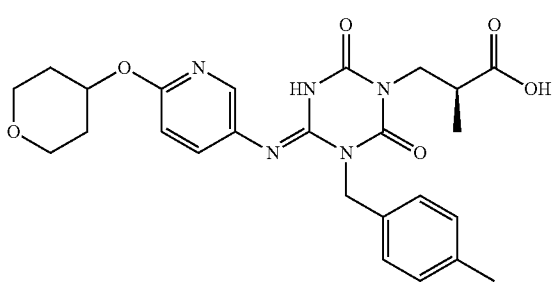 [SMILES: Cc1ccc(Cn2c(=O)n(C[C@H](C)C(=O)O)c(=O)[nH]/c2=N\c2ccc(OC3CCOCC3)nc2)cc1] | I-1120 | 1.59 | 496 | 2 |

TABLE 228

| Structure | Compound No. | Retention Time (min) | [M + H] | Method |
|---|---|---|---|---|
| 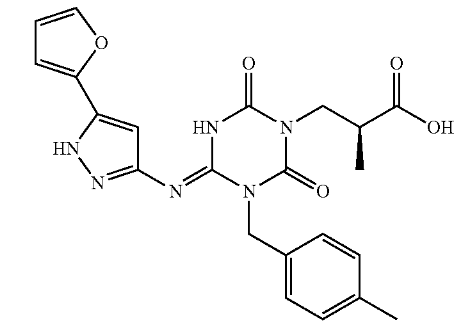 [SMILES: Cc1ccc(Cn2c(=O)n(C[C@H](C)C(=O)O)c(=O)[nH]/c2=N\c2cc(-c3ccco3)[nH]n2)cc1] | I-1121 | 1.98 | 451 | 2 |
| 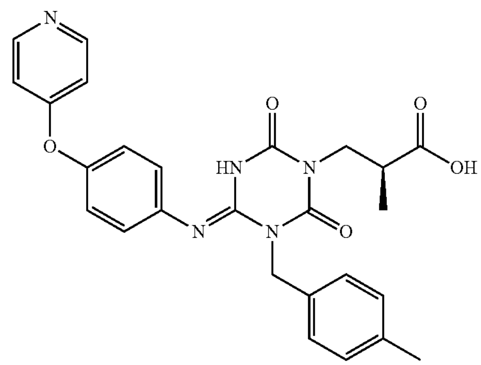 | I-1122 | 1.26 | 488 | 2 |
| 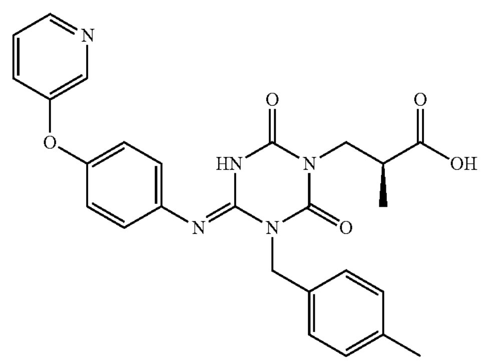 [SMILES: Cc1ccc(Cn2c(=O)n(C[C@H](C)C(=O)O)c(=O)[nH]/c2=N\c2ccc(Oc3cccnc3)cc2)cc1] | I-1123 | 1.52 | 488 | 2 |
| 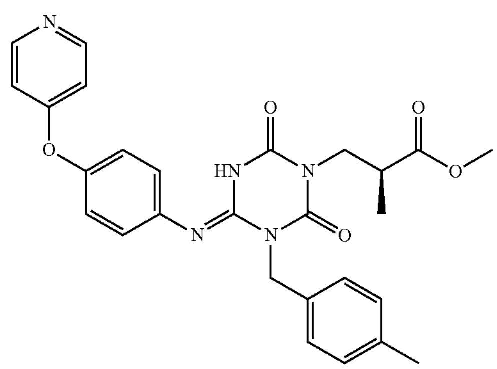 [SMILES: COC(=O)[C@@H](C)Cn1c(=O)[nH]/c(=N\c2ccc(Oc3ccncc3)cc2)n(Cc2ccc(C)cc2)c1=O] | I-1125 | 1.73 | 502 | 2 |

TABLE 229

| Structure | Compound No. | Retention Time (min) | [M + H] | Method |
|---|---|---|---|---|
| 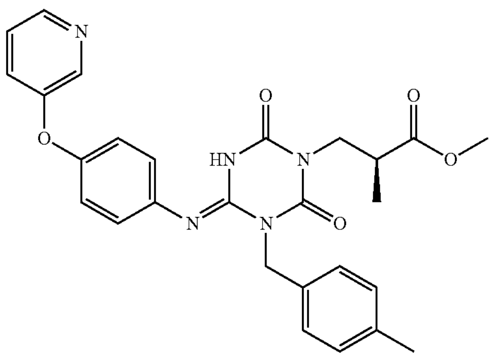 [SMILES: COC(=O)[C@@H](C)Cn1c(=O)[nH]/c(=N\c2ccc(Oc3cccnc3)cc2)n(Cc2ccc(C)cc2)c1=O] | I-1126 | 1.72 | 502 | 2 |
| 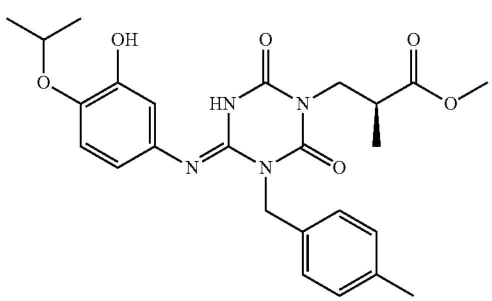 [SMILES: COC(=O)[C@@H](C)Cn1c(=O)[nH]/c(=N\c2ccc(OC(C)C)c(O)c2)n(Cc2ccc(C)cc2)c1=O] | I-1128 | 2.13 | 483 | 3 |
| 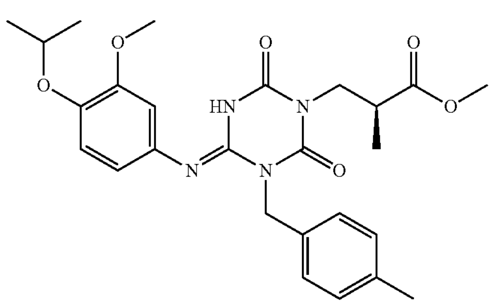 [SMILES: COC(=O)[C@@H](C)Cn1c(=O)[nH]/c(=N\c2ccc(OC(C)C)c(OC)c2)n(Cc2ccc(C)cc2)c1=O] | I-1129 | 2.02 | 497 | 2 |
| 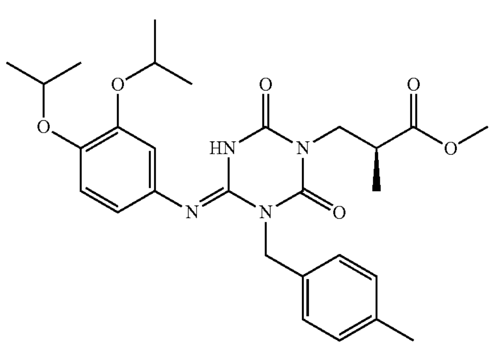 [SMILES: COC(=O)[C@@H](C)Cn1c(=O)[nH]/c(=N\c2ccc(OC(C)C)c(OC(C)C)c2)n(Cc2ccc(C)cc2)c1=O] | I-1130 | 2.27 | 525 | 3 |

TABLE 230

| Structure | Compound No. | Retention Time (min) | [M + H] | Method |
|---|---|---|---|---|
| 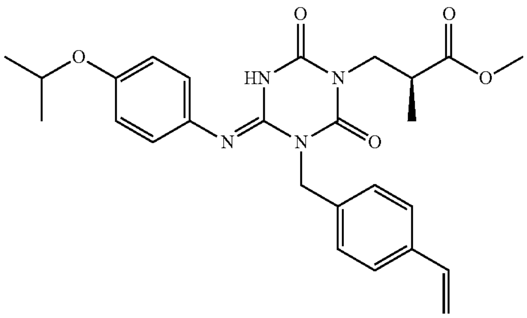 [SMILES: C=Cc1ccc(Cn2c(=O)n(C[C@H](C)C(=O)OC)c(=O)[nH]/c2=N\c2ccc(OC(C)C)cc2)cc1] | I-1131 | 2.13 | 479 | 2 |
| 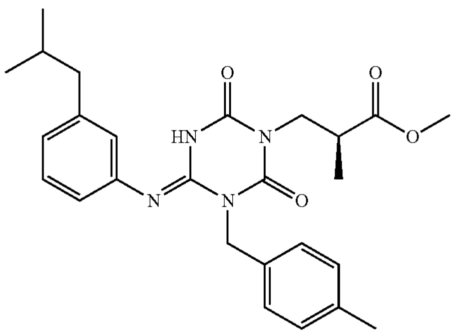 [SMILES: COC(=O)[C@@H](C)Cn1c(=O)[nH]/c(=N\c2cccc(CC(C)C)c2)n(Cc2ccc(C)cc2)c1=O] | I-1132 | 2.42 | 465 | 2 |
| 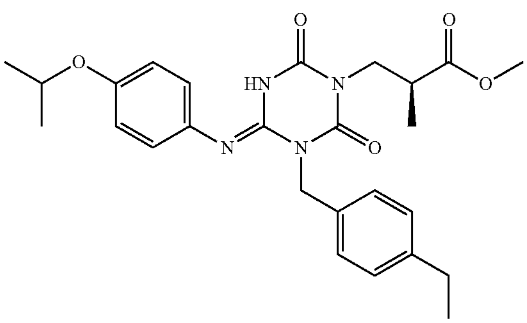 [SMILES: CCc1ccc(Cn2c(=O)n(C[C@H](C)C(=O)OC)c(=O)[nH]/c2=N\c2ccc(OC(C)C)cc2)cc1] | I-1133 | 2.23 | 481 | 2 |
| 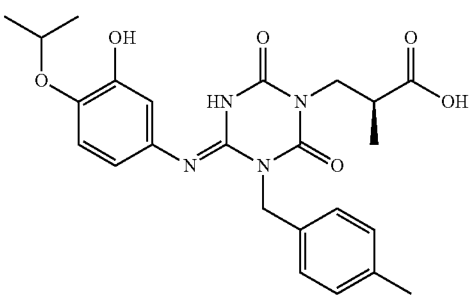 [SMILES: Cc1ccc(Cn2c(=O)n(C[C@H](C)C(=O)O)c(=O)[nH]/c2=N\c2ccc(OC(C)C)c(O)c2)cc1] | I-1134 | 1.68 | 469 | 2 |
| 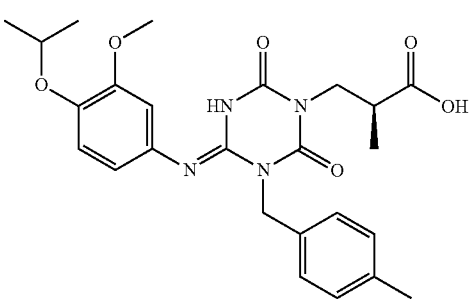 [SMILES: COc1cc(/N=c2\[nH]c(=O)n(C[C@H](C)C(=O)O)c(=O)n2Cc2ccc(C)cc2)ccc1OC(C)C] | I-1135 | 1.78 | 483 | 2 |

TABLE 231

| Structure | Compound No. | Retention Time (min) | [M + H] | Method |
|---|---|---|---|---|
| 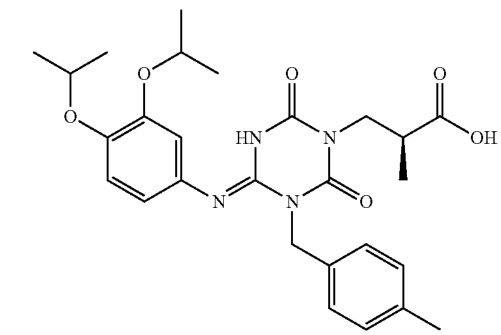 [SMILES: Cc1ccc(Cn2c(=O)n(C[C@H](C)C(=O)O)c(=O)[nH]/c2=N\c2ccc(OC(C)C)c(OC(C)C)c2)cc1] | I-1136 | 2.06 | 511 | 2 |
| 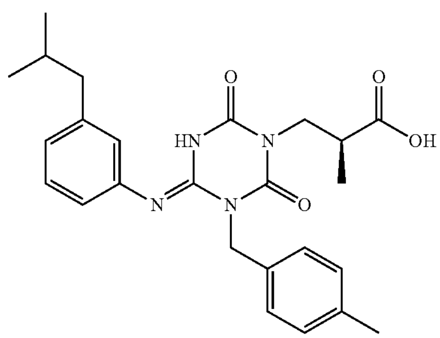 [SMILES: Cc1ccc(Cn2c(=O)n(C[C@H](C)C(=O)O)c(=O)[nH]/c2=N\c2cccc(CC(C)C)c2)cc1] | I-1137 | 2.18 | 451 | 2 |
| 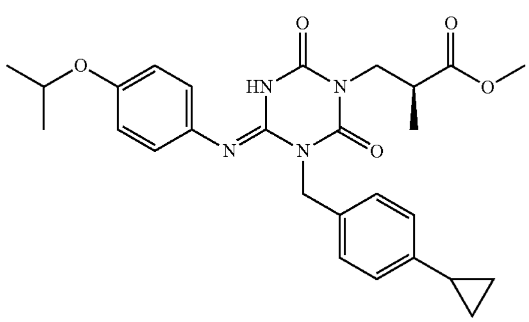 [SMILES: COC(=O)[C@@H](C)Cn1c(=O)[nH]/c(=N\c2ccc(OC(C)C)cc2)n(Cc2ccc(C3CC3)cc2)c1=O] | I-1138 | 2.20 | 493 | 2 |
| 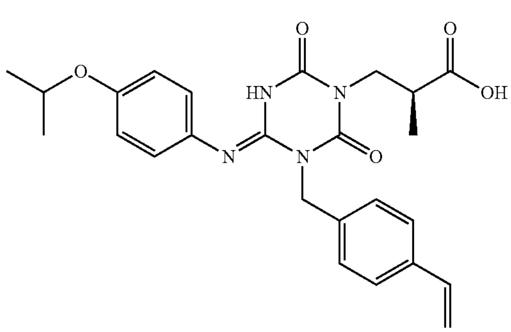 [SMILES: C=Cc1ccc(Cn2c(=O)n(C[C@H](C)C(=O)O)c(=O)[nH]/c2=N\c2ccc(OC(C)C)cc2)cc1] | I-1139 | 1.92 | 465 | 2 |

TABLE 231-continued

| Structure | Compound No. | Retention Time (min) | [M + H] | Method |
|---|---|---|---|---|
| 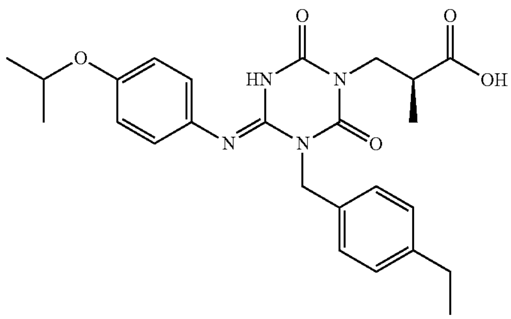 [SMILES: CCc1ccc(Cn2c(=O)n(C[C@H](C)C(=O)O)c(=O)[nH]/c2=N\c2ccc(OC(C)C)cc2)cc1] | I-1140 | 1.99 | 467 | 2 |

TABLE 232

| Structure | Compound No. | Retention Time (min) | [M + H] | Method |
|---|---|---|---|---|
| 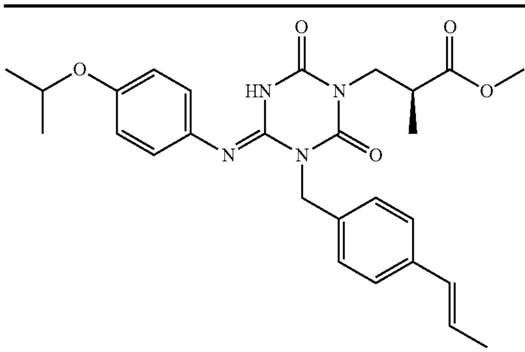 | I-1141 | 2.25 | 493 | 2 |
| 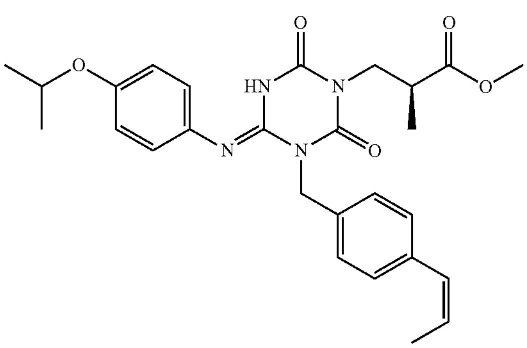 [SMILES: C/C=C\c1ccc(Cn2c(=O)n(C[C@H](C)C(=O)OC)c(=O)[nH]/c2=N\c2ccc(OC(C)C)cc2)cc1] | I-1142 | 2.26 | 493 | 2 |
| 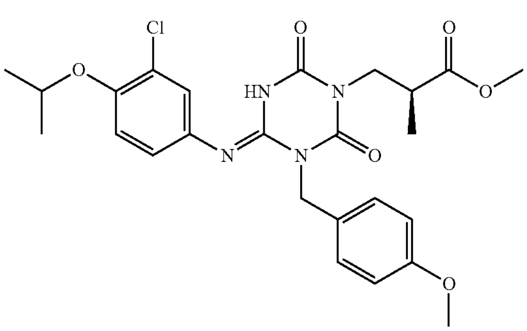 [SMILES: COC(=O)[C@@H](C)Cn1c(=O)[nH]/c(=N\c2ccc(OC(C)C)c(Cl)c2)n(Cc2ccc(OC)cc2)c1=O] | I-1143 | 2.16 | 517 | 2 |

TABLE 232-continued

| Structure | Compound No. | Retention Time (min) | [M + H] | Method |
|---|---|---|---|---|
| (structure of I-1144) | I-1144 | 2.36 | 495 | 2 |
| (structure of I-1145) | I-1145 | 1.98 | 479 | 2 |

TABLE 233

| Structure | Compound No. | Retention Time (min) | [M + H] | Method |
|---|---|---|---|---|
| (structure of I-1146) | I-1146 | 2.37 | 479 | 3 |
| (structure of I-1147) | I-1147 | 2.43 | 499 | 3 |

TABLE 233-continued

| Structure | Compound No. | Retention Time (min) | [M + H] | Method |
|---|---|---|---|---|
| 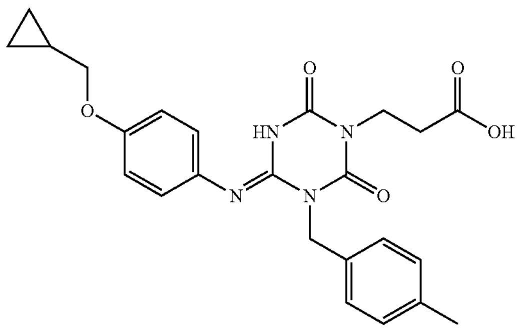 [SMILES: Cc1ccc(Cn2c(=O)n(CCC(=O)O)c(=O)[nH]/c2=N\c2ccc(OCC3CC3)cc2)cc1] | I-1148 | 2.30 | 451 | 3 |
| 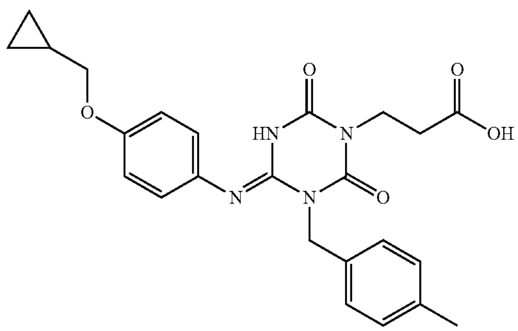 [SMILES: Cc1ccc(Cn2c(=O)n(CCC(=O)O)c(=O)[nH]/c2=N\c2ccc(OCC3CC3)cc2)cc1] | I-1149 | 2.08 | 471 | 3 |
| 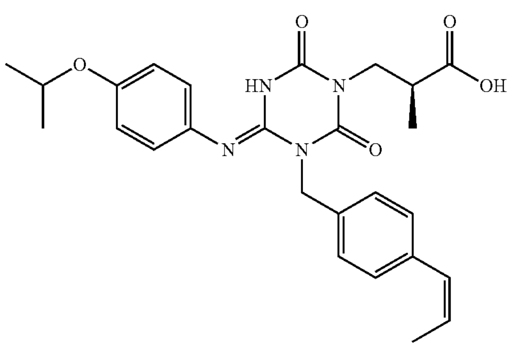 [SMILES: C/C=C\c1ccc(Cn2c(=O)n(C[C@H](C)C(=O)O)c(=O)[nH]/c2=N\c2ccc(OC(C)C)cc2)cc1] | I-1150 | 2.03 | 479 | 2 |

TABLE 234

| Structure | Compound No. | Retention Time (min) | [M + H] | Method |
|---|---|---|---|---|
| 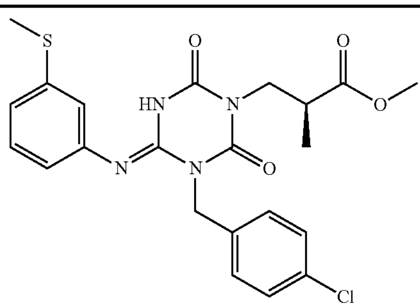 | I-1151 | 2.19 | 475 | 2 |

TABLE 234-continued

| Structure | Compound No. | Retention Time (min) | [M + H] | Method |
|---|---|---|---|---|
| 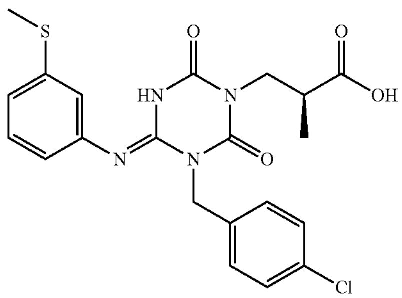 [SMILES: CSc1cccc(/N=c2\[nH]c(=O)n(C[C@H](C)C(=O)O)c(=O)n2Cc2ccc(Cl)cc2)c1] | I-1152 | 2.15 | 461 | 3 |
| 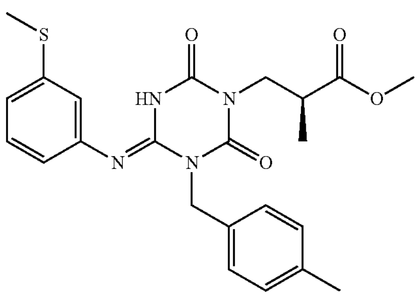 [SMILES: COC(=O)[C@@H](C)Cn1c(=O)[nH]/c(=N\c2cccc(SC)c2)n(Cc2ccc(C)cc2)c1=O] | I-1153 | 2.11 | 455 | 2 |
| 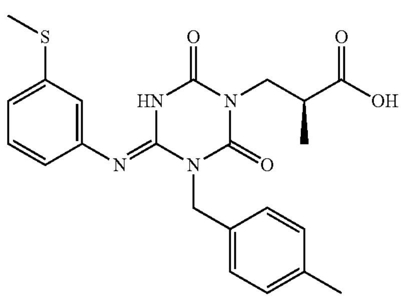 [SMILES: CSc1cccc(/N=c2\[nH]c(=O)n(C[C@H](C)C(=O)O)c(=O)n2Cc2ccc(C)cc2)c1] | I-1154 | 2.07 | 441 | 3 |
| 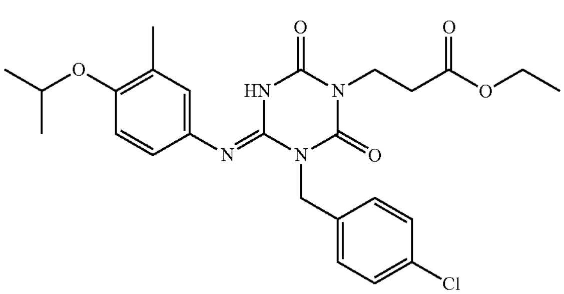 [SMILES: CCOC(=O)CCn1c(=O)[nH]/c(=N\c2ccc(OC(C)C)c(C)c2)n(Cc2ccc(Cl)cc2)c1=O] | I-1155 | 2.55 | 501 | 3 |

TABLE 235

| Structure | Compound No. | Retention Time (min) | [M + H] | Method |
|---|---|---|---|---|
| 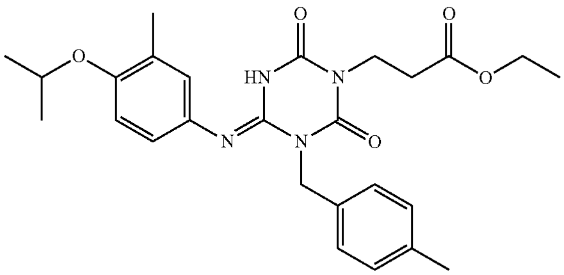 | I-1156 | 2.49 | 481 | 3 |
| 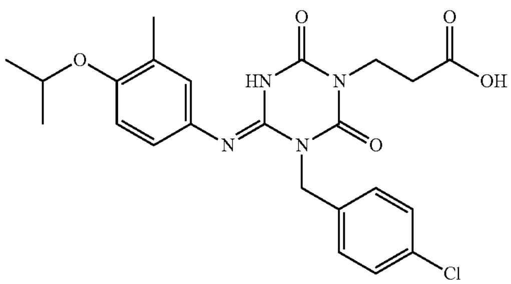 | I-1157 | 2.22 | 473 | 3 |
| 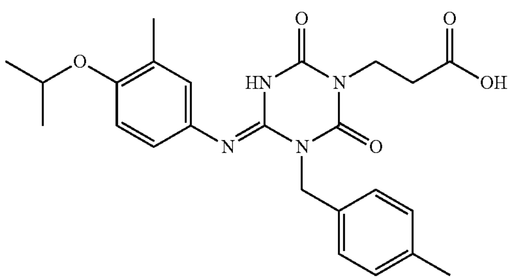 [SMILES: Cc1ccc(Cn2c(=O)n(CCC(=O)O)c(=O)[nH]/c2=N\c2ccc(OC(C)C)c(C)c2)cc1] | I-1158 | 2.14 | 453 | 3 |
| 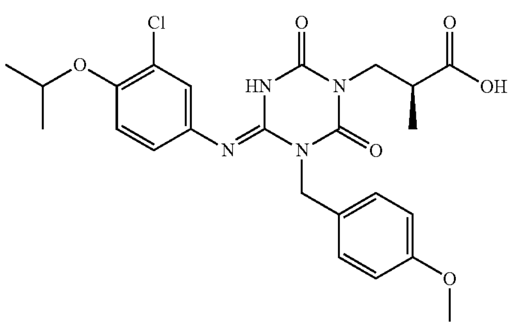 [SMILES: COc1ccc(Cn2c(=O)n(C[C@H](C)C(=O)O)c(=O)[nH]/c2=N\c2ccc(OC(C)C)c(Cl)c2)cc1] | I-1159 | 1.92 | 503 | 2 |
| 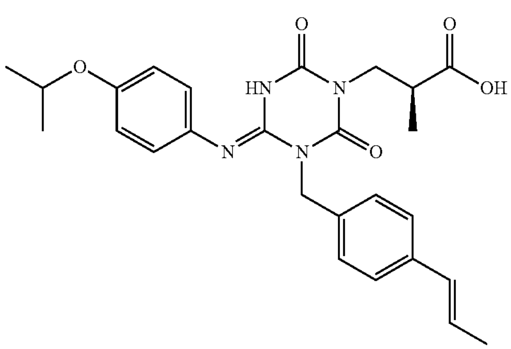 | I-1160 | 2.03 | 479 | 2 |

TABLE 236

| Structure | Compound No. | Retention Time (min) | [M + H] | Method |
|---|---|---|---|---|
| 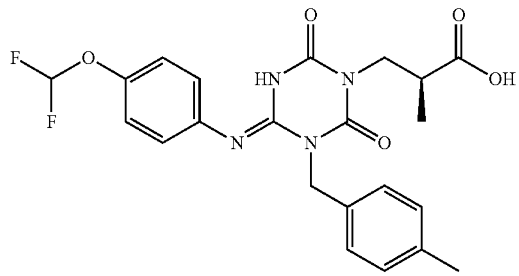 [SMILES: Cc1ccc(Cn2c(=O)n(C[C@H](C)C(=O)O)c(=O)[nH]/c2=N\c2ccc(OC(F)F)cc2)cc1] | I-1161 | 1.82 | 461 | 2 |
| 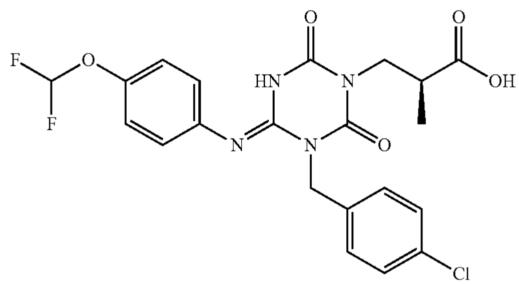 [SMILES: C[C@@H](Cn1c(=O)[nH]/c(=N\c2ccc(OC(F)F)cc2)n(Cc2ccc(Cl)cc2)c1=O)C(=O)O] | I-1162 | 1.89 | 481 | 2 |
| 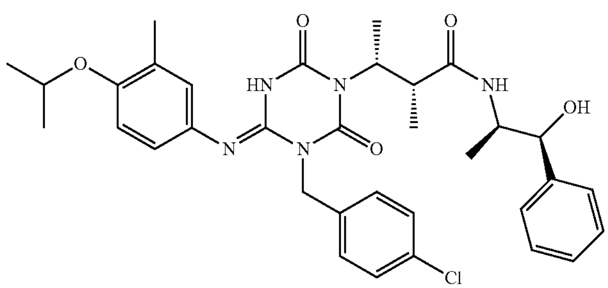 [SMILES: Cc1cc(/N=c2\[nH]c(=O)n([C@H](C)[C@@H](C)C(=O)N[C@H](C)[C@@H](O)c3ccccc3)c(=O)n2Cc2ccc(Cl)cc2)ccc1OC(C)C] | I-1163 | 2.36 | 634 | 2 |
| 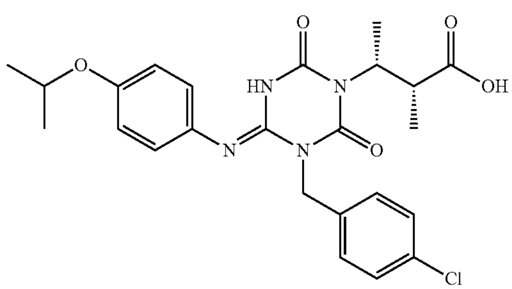 [SMILES: CC(C)Oc1ccc(/N=c2\[nH]c(=O)n([C@H](C)[C@@H](C)C(=O)O)c(=O)n2Cc2ccc(Cl)cc2)cc1] | I-1164 | 2.13 | 501 | 2 |
| 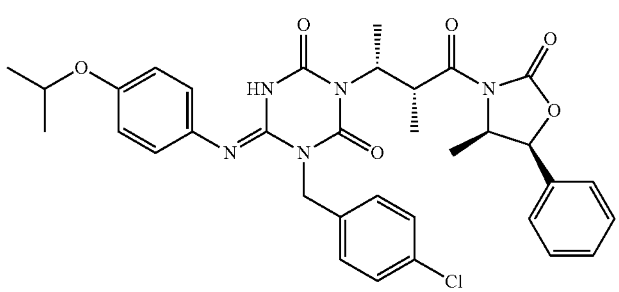 [SMILES: CC(C)Oc1ccc(/N=c2\[nH]c(=O)n([C@H](C)[C@@H](C)C(=O)N3C(=O)O[C@@H](c4ccccc4)[C@H]3C)c(=O)n2Cc2ccc(Cl)cc2)cc1] | I-1165 | 2.66 | 660 | 2 |

TABLE 237

| Structure | Compound No. | Retention Time (min) | [M + H] | Method |
|---|---|---|---|---|
| 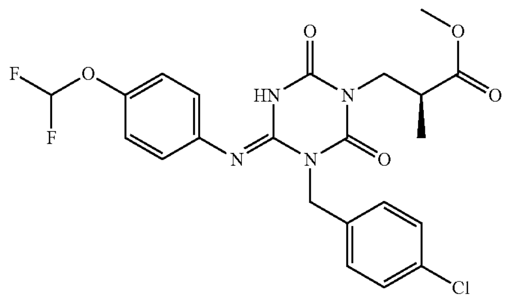 [SMILES: COC(=O)[C@@H](C)Cn1c(=O)[nH]/c(=N\c2ccc(OC(F)F)cc2)n(Cc2ccc(Cl)cc2)c1=O] | I-1166 | 2.14 | 495 | 2 |
| 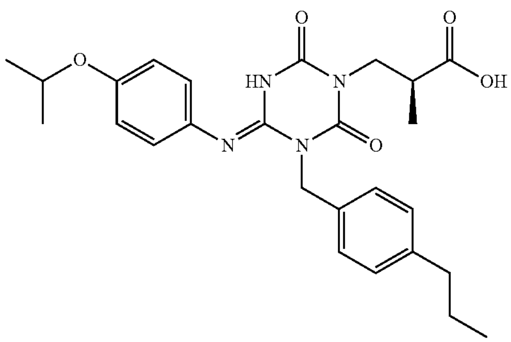 [SMILES: CCCc1ccc(Cn2c(=O)n(C[C@H](C)C(=O)O)c(=O)[nH]/c2=N\c2ccc(OC(C)C)cc2)cc1] | I-1167 | 2.13 | 481 | 2 |
| 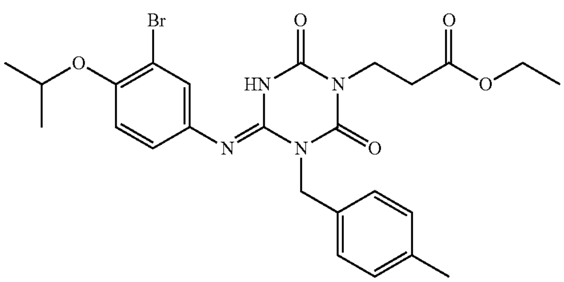 [SMILES: CCOC(=O)CCn1c(=O)[nH]/c(=N\c2ccc(OC(C)C)c(Br)c2)n(Cc2ccc(C)cc2)c1=O] | I-1168 | 2.37 | 545 | 2 |
| 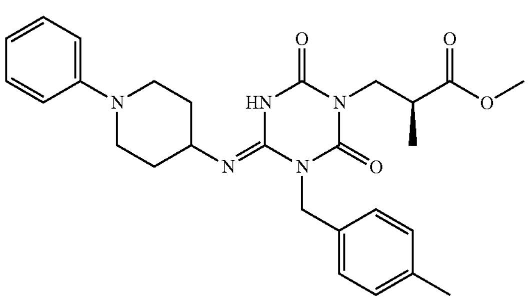 [SMILES: COC(=O)[C@@H](C)Cn1c(=O)[nH]/c(=N\C2CCN(c3ccccc3)CC2)n(Cc2ccc(C)cc2)c1=O] | I-1169 | 1.91 | 492 | 2 |
| 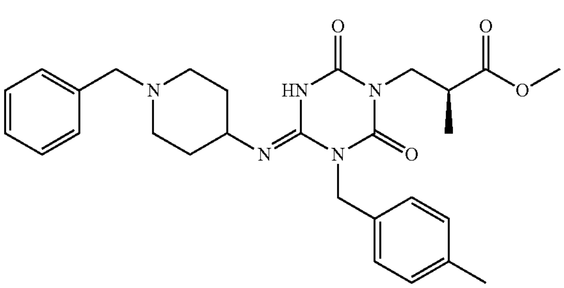 [SMILES: COC(=O)[C@@H](C)Cn1c(=O)[nH]/c(=N\C2CCN(Cc3ccccc3)CC2)n(Cc2ccc(C)cc2)c1=O] | I-1170 | 1.53 | 506 | 2 |

TABLE 238

| Structure | Compound No. | Retention Time (min) | [M + H] | Method |
|---|---|---|---|---|
| (structure) | I-1171 | 2.68 | 481 | 3 |
| (structure) | I-1172 | 1.63 | 500 | 2 |
| (structure) | I-1173 | 2.23 | 531 | 2 |
| (structure) | I-1174 | 2.42 | 467 | 3 |

TABLE 239

| Structure | Compound No. | Retention Time (min) | [M + H] | Method |
|---|---|---|---|---|
| (structure) | I-1177 | 1.40 | 486 | 2 |

TABLE 239-continued

| Structure | Compound No. | Retention Time (min) | [M + H] | Method |
|---|---|---|---|---|
| 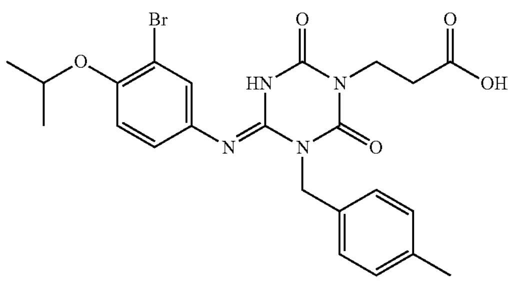 | I-1178 | 2.04 | 517 | 2 |
| 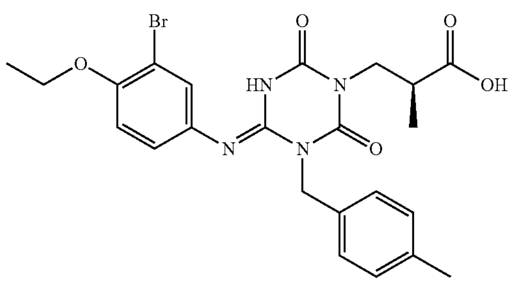 | I-1179 | 1.98 | 517 | 2 |
| 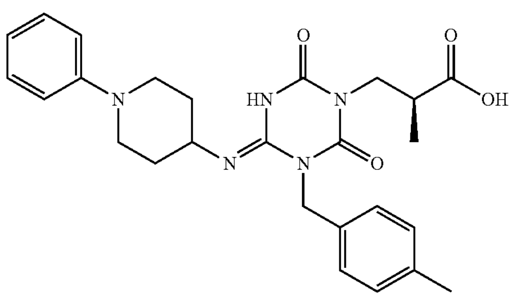 [SMILES: Cc1ccc(Cn2c(=O)n(C[C@H](C)C(=O)O)c(=O)[nH]/c2=N\C2CCN(c3ccccc3)CC2)cc1] | I-1180 | 1.58 | 478 | 2 |

TABLE 240

| Structure | Compound No. | Retention Time (min) | [M + H] | Method |
|---|---|---|---|---|
| 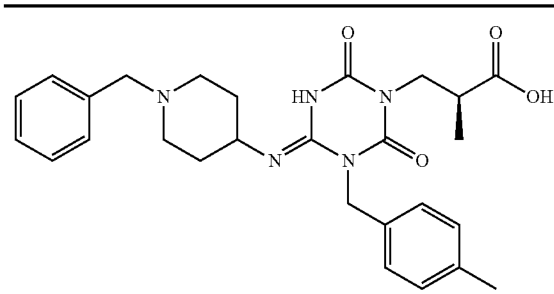 | I-1181 | 1.43 | 492 | 2 |

TABLE 240-continued

| Structure | Compound No. | Retention Time (min) | [M + H] | Method |
|---|---|---|---|---|
| 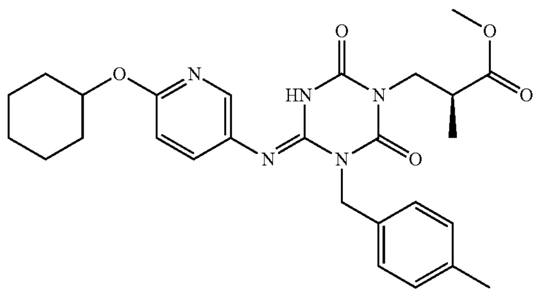 [SMILES: COC(=O)[C@@H](C)Cn1c(=O)[nH]/c(=N\c2ccc(OC3CCCCC3)nc2)n(Cc2ccc(C)cc2)c1=O] | I-1184 | 2.34 | 508 | 2 |
| 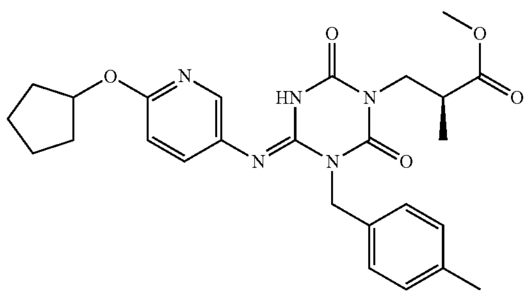 [SMILES: COC(=O)[C@@H](C)Cn1c(=O)[nH]/c(=N\c2ccc(OC3CCCC3)nc2)n(Cc2ccc(C)cc2)c1=O] | I-1185 | 2.19 | 494 | 2 |

TABLE 241

| Structure | Compound No. | Retention Time (min) | [M + H] | Method |
|---|---|---|---|---|
| 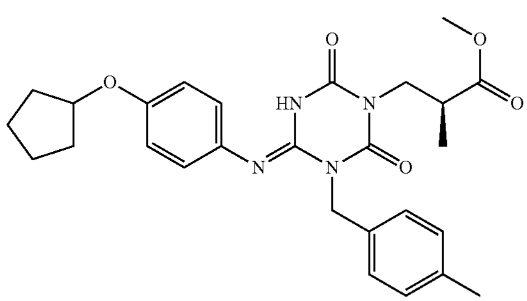 [SMILES: COC(=O)[C@@H](C)Cn1c(=O)[nH]/c(=N\c2ccc(OC3CCCC3)cc2)n(Cc2ccc(C)cc2)c1=O] | I-1186 | 2.28 | 493 | 2 |
| 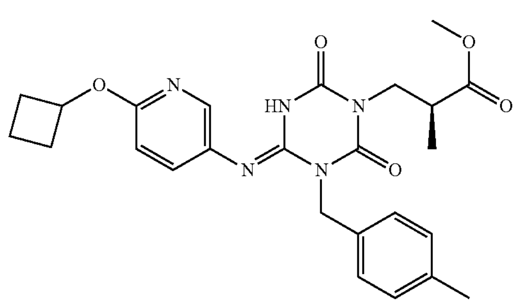 [SMILES: COC(=O)[C@@H](C)Cn1c(=O)[nH]/c(=N\c2ccc(OC3CCC3)nc2)n(Cc2ccc(C)cc2)c1=O] | I-1187 | 2.32 | 480 | 3 |

TABLE 241-continued

| Structure | Compound No. | Retention Time (min) | [M + H] | Method |
|---|---|---|---|---|
| 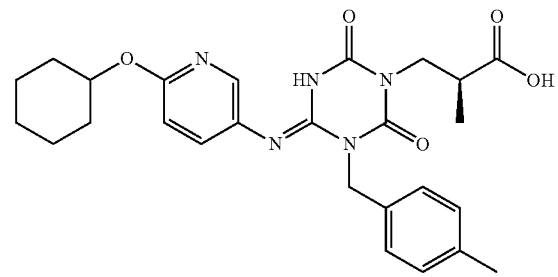 [SMILES: Cc1ccc(Cn2c(=O)n(C[C@H](C)C(=O)O)c(=O)[nH]/c2=N\c2ccc(OC3CCCCC3)nc2)cc1] | I-1188 | 2.09 | 494 | 2 |
| 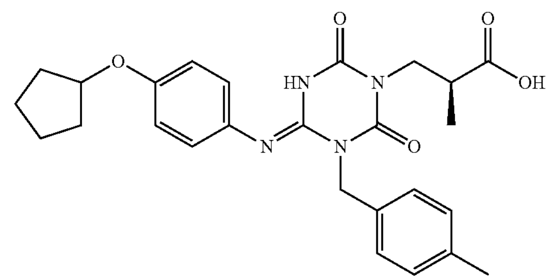 [SMILES: Cc1ccc(Cn2c(=O)n(C[C@H](C)C(=O)O)c(=O)[nH]/c2=N\c2ccc(OC3CCCC3)cc2)cc1] | I-1189 | 2.05 | 479 | 2 |
| 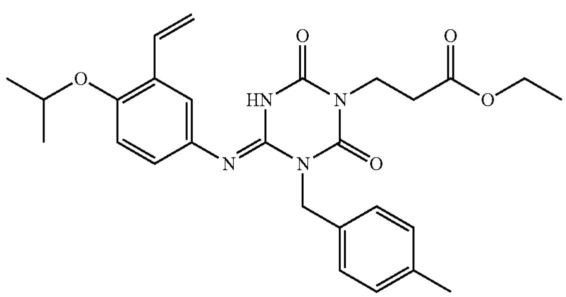 [SMILES: C=Cc1cc(/N=c2\[nH]c(=O)n(CCC(=O)OCC)c(=O)n2Cc2ccc(C)cc2)ccc1OC(C)C] | I-1190 | 2.34 | 493 | 2 |

TABLE 242

| Structure | Compound No. | Retention Time (min) | [M + H] | Method |
|---|---|---|---|---|
| 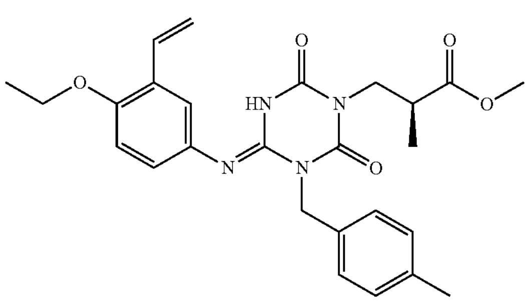 [SMILES: C=Cc1cc(/N=c2\[nH]c(=O)n(C[C@H](C)C(=O)OC)c(=O)n2Cc2ccc(C)cc2)ccc1OCC] | I-1191 | 2.21 | 479 | 2 |

TABLE 242-continued

| Structure | Compound No. | Retention Time (min) | [M + H] | Method |
|---|---|---|---|---|
| 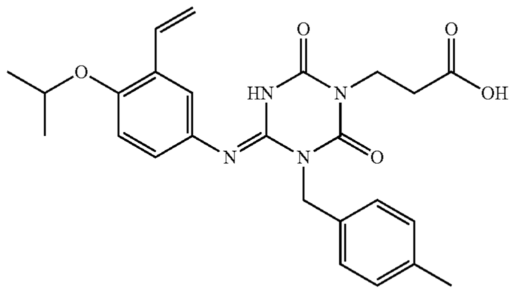 [SMILES: C=Cc1cc(/N=c2\[nH]c(=O)n(CCC(=O)O)c(=O)n2Cc2ccc(C)cc2)ccc1OC(C)C] | I-1192 | 2.02 | 465 | 2 |
| 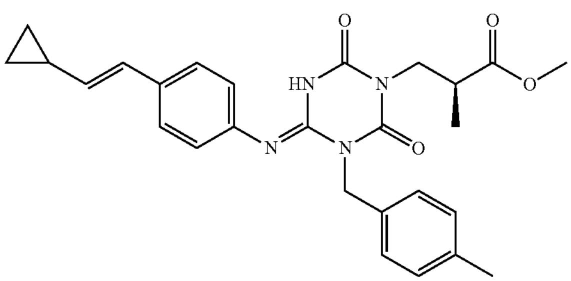 [SMILES: COC(=O)[C@@H](C)Cn1c(=O)[nH]/c(=N\c2ccc(/C=C/C3CC3)cc2)n(Cc2ccc(C)cc2)c1=O] | I-1193 | 2.32 | 475 | 2 |
| 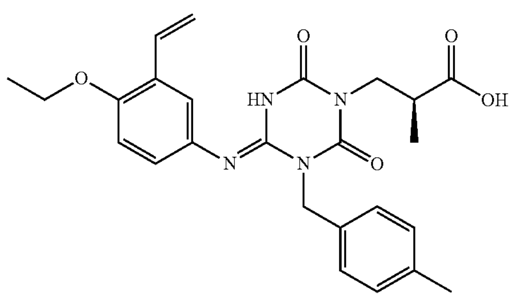 [SMILES: C=Cc1cc(/N=c2\[nH]c(=O)n(C[C@H](C)C(=O)O)c(=O)n2Cc2ccc(C)cc2)ccc1OCC] | I-1194 | 1.98 | 465 | 2 |
| 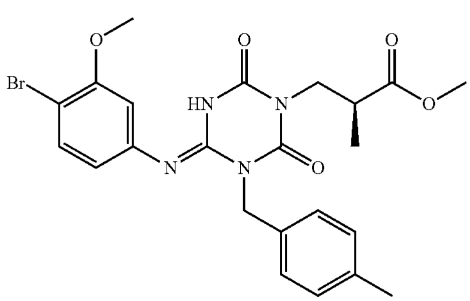 [SMILES: COC(=O)[C@@H](C)Cn1c(=O)[nH]/c(=N\c2ccc(Br)c(OC)c2)n(Cc2ccc(C)cc2)c1=O] | I-1195 | 2.22 | 517 | 2 |

TABLE 243

| Structure | Compound No. | Retention Time (min) | [M + H] | Method |
|---|---|---|---|---|
| 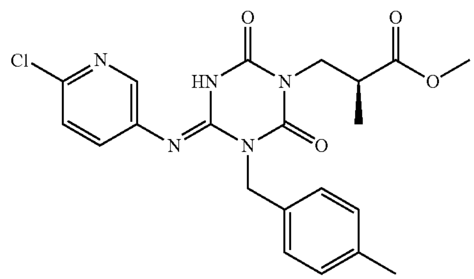 [SMILES: COC(=O)[C@@H](C)Cn1c(=O)[nH]/c(=N\c2ccc(Cl)nc2)n(Cc2ccc(C)cc2)c1=O] | I-1196 | 1.97 | 444 | 2 |
| 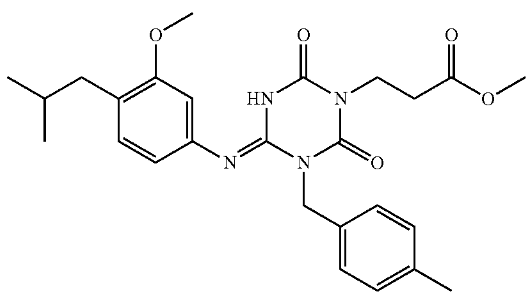 [SMILES: COC(=O)CCn1c(=O)[nH]/c(=N\c2ccc(CC(C)C)c(OC)c2)n(Cc2ccc(C)cc2)c1=O] | I-1197 | 2.44 | 495 | 2 |
| 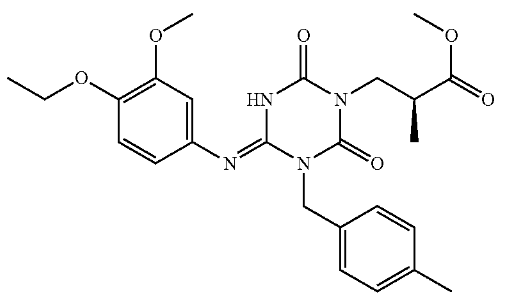 [SMILES: CCOc1ccc(/N=c2\[nH]c(=O)n(C[C@H](C)C(=O)OC)c(=O)n2Cc2ccc(C)cc2)cc1OC] | I-1198 | 2.30 | 481 | 2 |
| 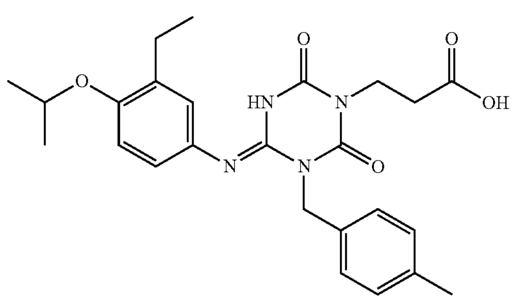 [SMILES: CCc1cc(/N=c2\[nH]c(=O)n(CCC(=O)O)c(=O)n2Cc2ccc(C)cc2)ccc1OC(C)C] | I-1199 | 2.11 | 467 | 2 |
| 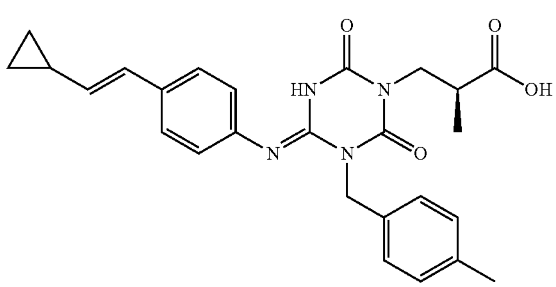 [SMILES: Cc1ccc(Cn2c(=O)n(C[C@H](C)C(=O)O)c(=O)[nH]/c2=N\c2ccc(/C=C/C3CC3)cc2)cc1] | I-1200 | 2.12 | 461 | 2 |

TABLE 244

| Structure | Compound No. | Retention Time (min) | [M + H] | Method |
|---|---|---|---|---|
| 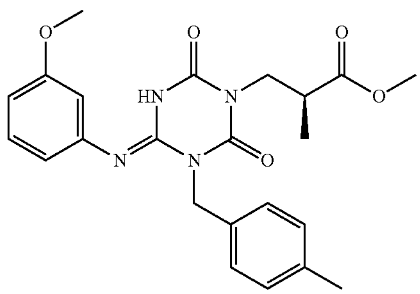 [SMILES: COC(=O)[C@@H](C)Cn1c(=O)[nH]/c(=N\c2cccc(OC)c2)n(Cc2ccc(C)cc2)c1=O] | I-1201 | 1.99 | 439 | 2 |
| 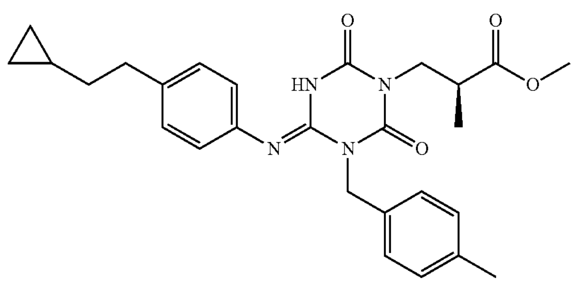 [SMILES: COC(=O)[C@@H](C)Cn1c(=O)[nH]/c(=N\c2ccc(CCC3CC3)cc2)n(Cc2ccc(C)cc2)c1=O] | I-1202 | 2.44 | 477 | 2 |
| 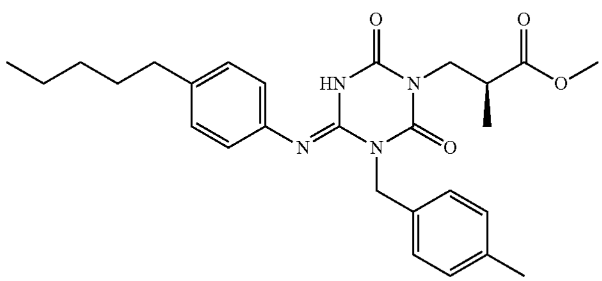 [SMILES: CCCCCc1ccc(/N=c2\[nH]c(=O)n(C[C@H](C)C(=O)OC)c(=O)n2Cc2ccc(C)cc2)cc1] | I-1203 | 2.59 | 479 | 2 |
| 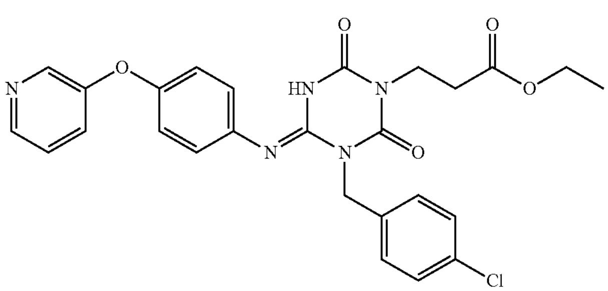 [SMILES: CCOC(=O)CCn1c(=O)[nH]/c(=N\c2ccc(Oc3cccnc3)cc2)n(Cc2ccc(Cl)cc2)c1=O] | I-1204 | 2.04 | 522 | 3 |
| 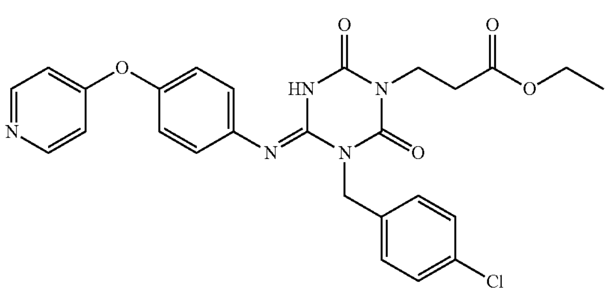 [SMILES: CCOC(=O)CCn1c(=O)[nH]/c(=N\c2ccc(Oc3ccncc3)cc2)n(Cc2ccc(Cl)cc2)c1=O] | I-1205 | 1.50 | 522 | 3 |

TABLE 245

| Structure | Compound No. | Retention Time (min) | [M + H] | Method |
|---|---|---|---|---|
| 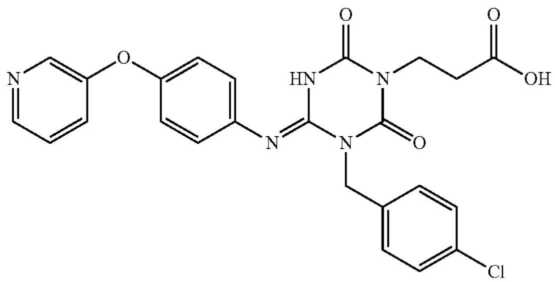 [SMILES: O=C(O)CCn1c(=O)[nH]/c(=N\c2ccc(Oc3cccnc3)cc2)n(Cc2ccc(Cl)cc2)c1=O] | I-1206 | 1.67 | 494 | 3 |
| 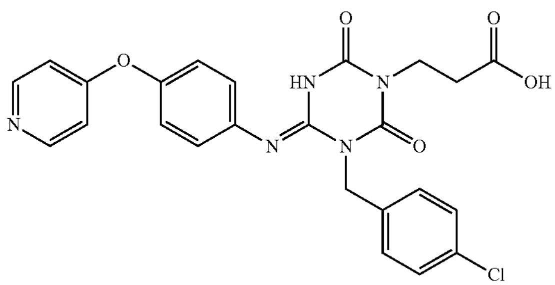 [SMILES: O=C(O)CCn1c(=O)[nH]/c(=N\c2ccc(Oc3ccncc3)cc2)n(Cc2ccc(Cl)cc2)c1=O] | I-1207 | 1.22 | 494 | 3 |
| 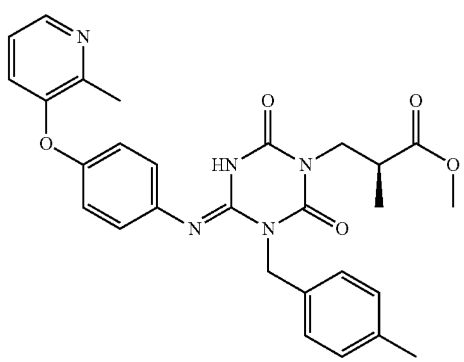 [SMILES: COC(=O)[C@@H](C)Cn1c(=O)[nH]/c(=N\c2ccc(Oc3cccnc3C)cc2)n(Cc2ccc(C)cc2)c1=O] | I-1208 | 1.75 | 516 | 3 |
| 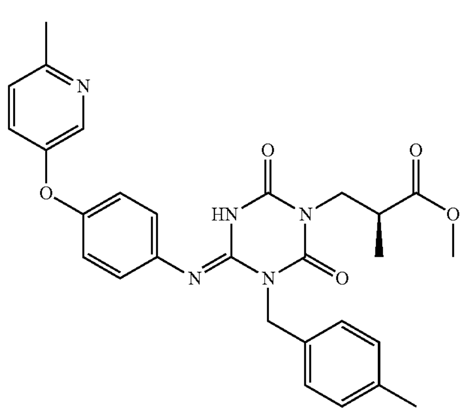 [SMILES: COC(=O)[C@@H](C)Cn1c(=O)[nH]/c(=N\c2ccc(Oc3ccc(C)nc3)cc2)n(Cc2ccc(C)cc2)c1=O] | I-1209 | 1.80 | 516 | 3 |

TABLE 245-continued

| Structure | Compound No. | Retention Time (min) | [M + H] | Method |
|---|---|---|---|---|
| (structure) | I-1210 | 2.61 | 465 | 3 |

TABLE 246

| Structure | Compound No. | Retention Time (min) | [M + H] | Method |
|---|---|---|---|---|
| (structure) | I-1211 | 2.67 | 485 | 3 |
| (structure) | I-1212 | 2.35 | 451 | 3 |
| (structure) | I-1213 | 2.42 | 471 | 3 |

TABLE 246-continued

| Structure | Compound No. | Retention Time (min) | [M + H] | Method |
|---|---|---|---|---|
| 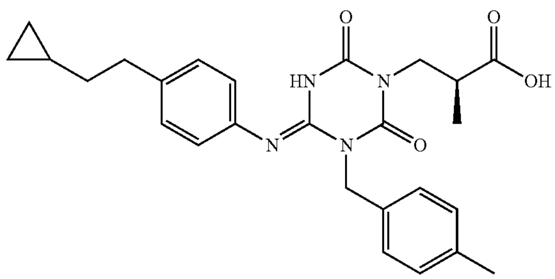 | I-1214 | 2.20 | 463 | 2 |
| 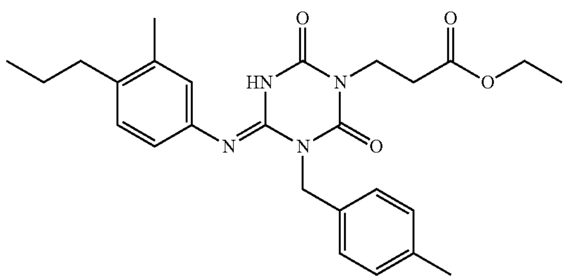 [SMILES: CCCc1ccc(/N=c2\[nH]c(=O)n(CCC(=O)OCC)c(=O)n2Cc2ccc(C)cc2)cc1C] | I-1215 | 2.63 | 465 | 3 |

TABLE 247

| Structure | Compound No. | Retention Time (min) | [M + H] | Method |
|---|---|---|---|---|
| 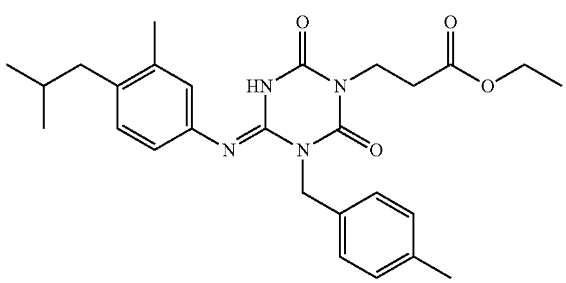 [SMILES: CCOC(=O)CCn1c(=O)[nH]/c(=N\c2ccc(CC(C)C)c(C)c2)n(Cc2ccc(C)cc2)c1=O] | I-1216 | 2.74 | 479 | 3 |
| 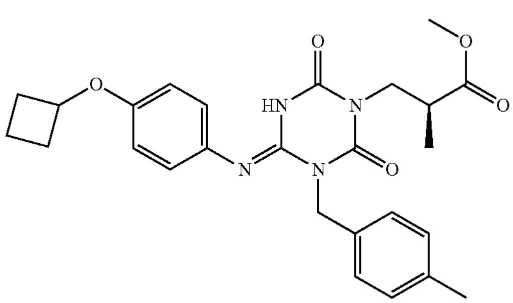 [SMILES: COC(=O)[C@@H](C)Cn1c(=O)[nH]/c(=N\c2ccc(OC3CCC3)cc2)n(Cc2ccc(C)cc2)c1=O] | I-1217 | 2.41 | 479 | 3 |

TABLE 247-continued

| Structure | Compound No. | Retention Time (min) | [M + H] | Method |
|---|---|---|---|---|
| 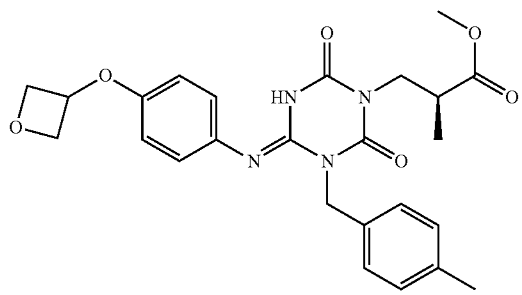 [SMILES: COC(=O)[C@@H](C)Cn1c(=O)[nH]/c(=N\c2ccc(OC3COC3)cc2)n(Cc2ccc(C)cc2)c1=O] | I-1218 | 1.77 | 481 | 2 |
| 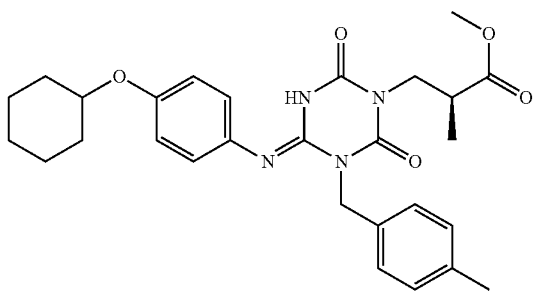 [SMILES: COC(=O)[C@@H](C)Cn1c(=O)[nH]/c(=N\c2ccc(OC3CCCCC3)cc2)n(Cc2ccc(C)cc2)c1=O] | I-1219 | 2.63 | 507 | 3 |
| 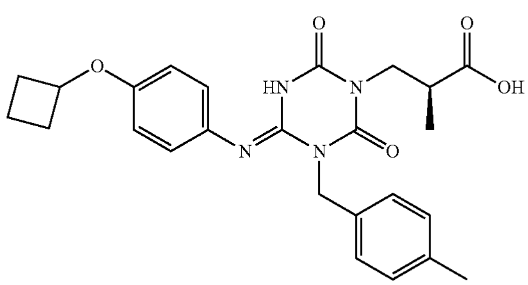 [SMILES: Cc1ccc(Cn2c(=O)n(C[C@H](C)C(=O)O)c(=O)[nH]/c2=N\c2ccc(OC3CCC3)cc2)cc1] | I-1220 | 1.96 | 465 | 2 |

TABLE 248

| Structure | Compound No. | Retention Time (min) | [M + H] | Method |
|---|---|---|---|---|
| 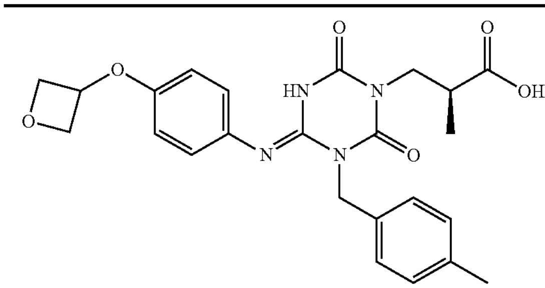 | I-1221 | 1.54 | 467 | 2 |

TABLE 248-continued

| Structure | Compound No. | Retention Time (min) | [M + H] | Method |
|---|---|---|---|---|
| 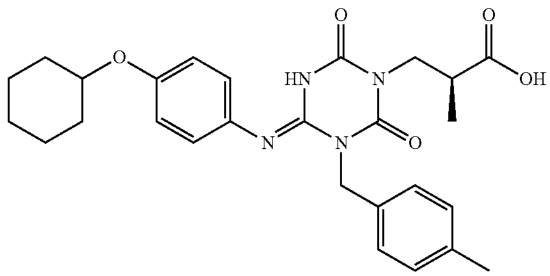 | I-1222 | 2.17 | 493 | 2 |
| 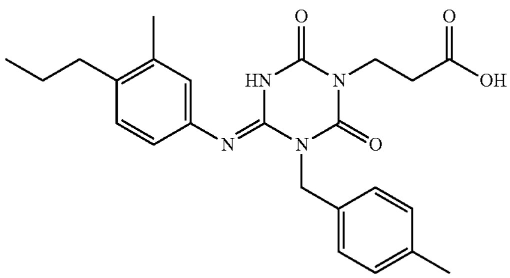 [SMILES: CCCc1ccc(/N=c2\[nH]c(=O)n(CCC(=O)O)c(=O)n2Cc2ccc(C)cc2)cc1C] | I-1223 | 2.28 | 437 | 3 |
| 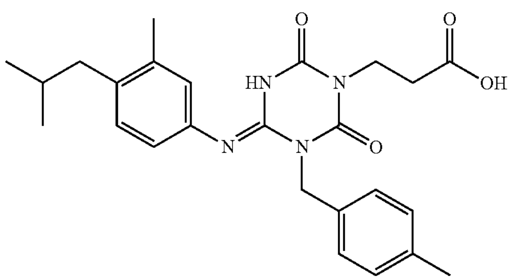 [SMILES: Cc1ccc(Cn2c(=O)n(CCC(=O)O)c(=O)[nH]/c2=N\c2ccc(CC(C)C)c(C)c2)cc1] | I-1224 | 2.41 | 451 | 3 |
| 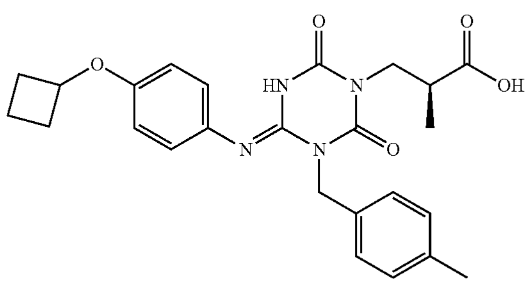 [SMILES: Cc1ccc(Cn2c(=O)n(C[C@H](C)C(=O)O)c(=O)[nH]/c2=N\c2ccc(OC3CCC3)cc2)cc1] | I-1225 | 1.86 | 466 | 2 |

TABLE 249

| Structure | Compound No. | Retention Time (min) | [M + H] | Method |
|---|---|---|---|---|
| 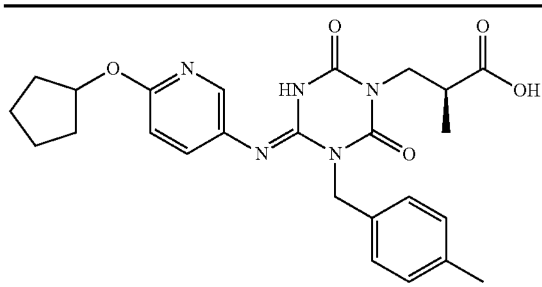 | I-1226 | 1.96 | 480 | 2 |

TABLE 249-continued

| Structure | Compound No. | Retention Time (min) | [M + H] | Method |
|---|---|---|---|---|
| 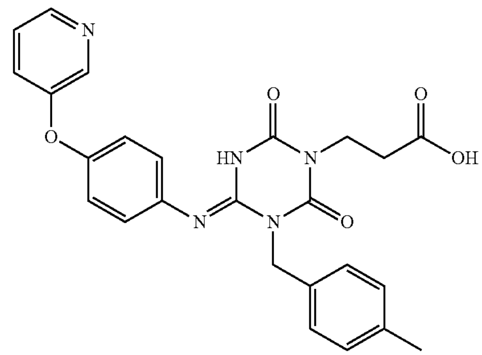 [SMILES: Cc1ccc(Cn2c(=O)n(CCC(=O)O)c(=O)[nH]/c2=N\c2ccc(Oc3cccnc3)cc2)cc1] | I-1227 | 1.40 | 474 | 2 |
| 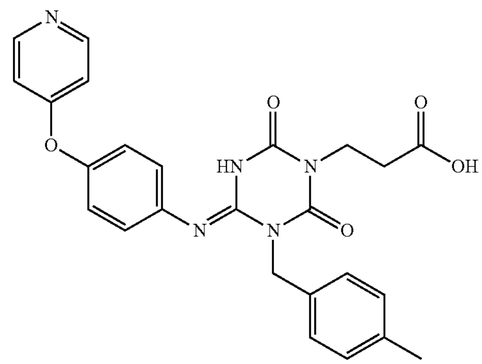 [SMILES: Cc1ccc(Cn2c(=O)n(CCC(=O)O)c(=O)[nH]/c2=N\c2ccc(Oc3ccncc3)cc2)cc1] | I-1228 | 1.17 | 474 | 2 |
| 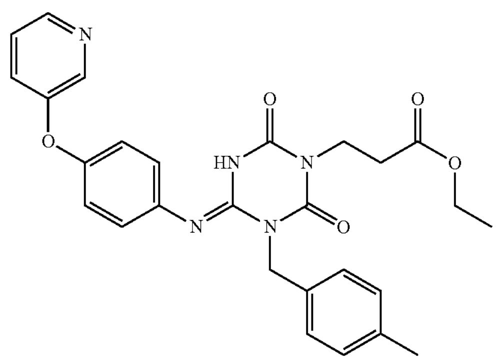 [SMILES: CCOC(=O)CCn1c(=O)[nH]/c(=N\c2ccc(Oc3cccnc3)cc2)n(Cc2ccc(C)cc2)c1=O] | I-1229 | 1.76 | 502 | 2 |
| 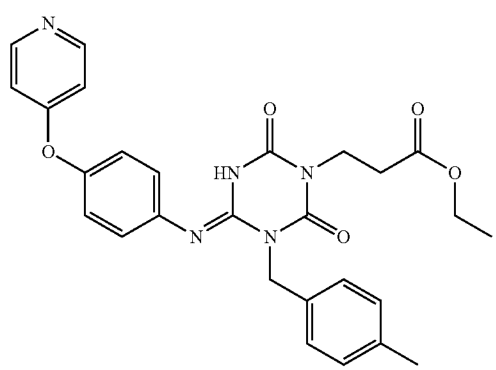 [SMILES: CCOC(=O)CCn1c(=O)[nH]/c(=N\c2ccc(Oc3ccncc3)cc2)n(Cc2ccc(C)cc2)c1=O] | I-1230 | 1.35 | 502 | 2 |

TABLE 250

| Structure | Compound No. | Retention Time (min) | [M + H] | Method |
|---|---|---|---|---|
| 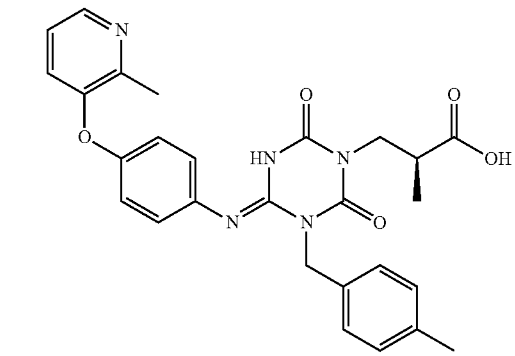 [SMILES: Cc1ccc(Cn2c(=O)n(C[C@H](C)C(=O)O)c(=O)[nH]/c2=N\c2ccc(Oc3cccnc3C)cc2)cc1] | I-1231 | 1.34 | 502 | 2 |
| 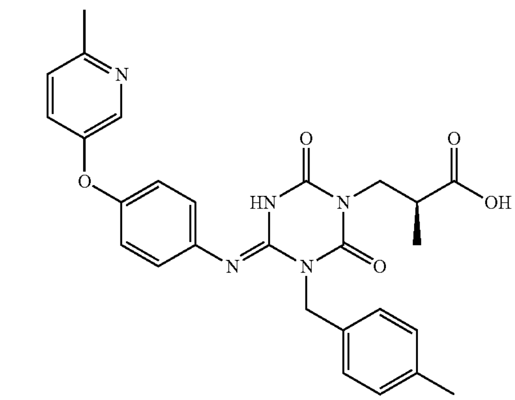 [SMILES: Cc1ccc(Cn2c(=O)n(C[C@H](C)C(=O)O)c(=O)[nH]/c2=N\c2ccc(Oc3ccc(C)nc3)cc2)cc1] | I-1232 | 1.37 | 502 | 2 |
| 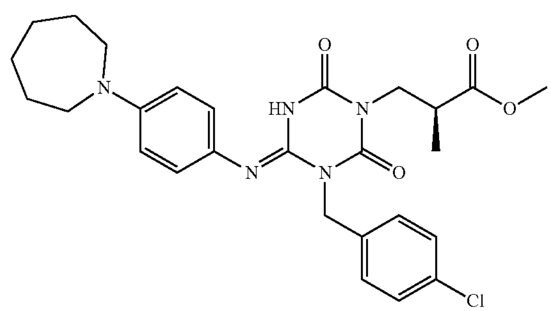 [SMILES: COC(=O)[C@@H](C)Cn1c(=O)[nH]/c(=N\c2ccc(N3CCCCCC3)cc2)n(Cc2ccc(Cl)cc2)c1=O] | I-1233 | 2.29 | 526 | 2 |
| 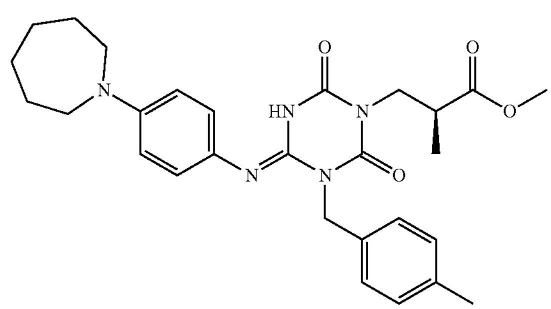 [SMILES: COC(=O)[C@@H](C)Cn1c(=O)[nH]/c(=N\c2ccc(N3CCCCCC3)cc2)n(Cc2ccc(C)cc2)c1=O] | I-1234 | 2.25 | 506 | 2 |

TABLE 250-continued
| Structure | Compound No. | Retention Time (min) | [M + H] | Method |
|---|---|---|---|---|
| 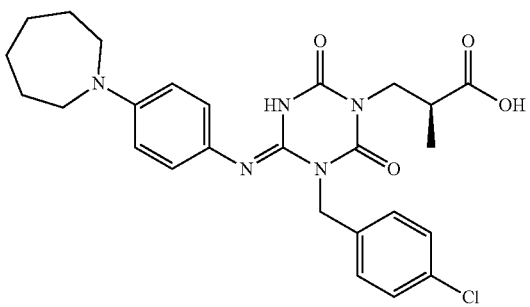 [SMILES: C[C@@H](Cn1c(=O)[nH]/c(=N\c2ccc(N3CCCCCC3)cc2)n(Cc2ccc(Cl)cc2)c1=O)C(=O)O] | I-1235 | 2.02 | 512 | 2 |
TABLE 251
| Structure | Compound No. | Retention Time (min) | [M + H] | Method |
|---|---|---|---|---|
| 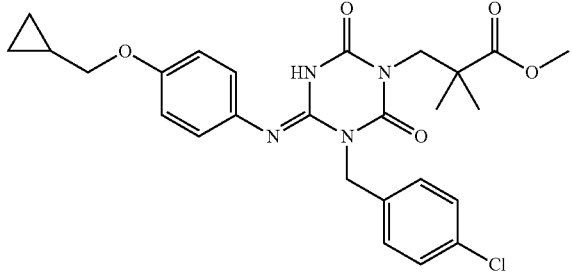 [SMILES: COC(=O)C(C)(C)Cn1c(=O)[nH]/c(=N\c2ccc(OCC3CC3)cc2)n(Cc2ccc(Cl)cc2)c1=O] | I-1236 | 2.30 | 513 | 2 |
| 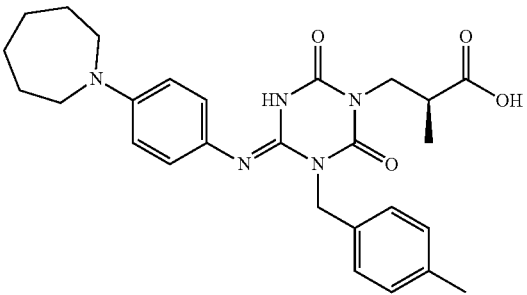 [SMILES: Cc1ccc(Cn2c(=O)n(C[C@H](C)C(=O)O)c(=O)[nH]/c2=N\c2ccc(N3CCCCCC3)cc2)cc1] | I-1237 | 1.98 | 492 | 2 |
| 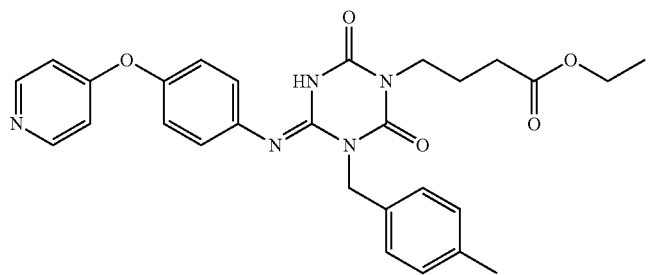 [SMILES: CCOC(=O)CCCn1c(=O)[nH]/c(=N\c2ccc(Oc3ccncc3)cc2)n(Cc2ccc(C)cc2)c1=O] | I-1238 | 1.50 | 516 | 2 |

TABLE 251-continued

| Structure | Compound No. | Retention Time (min) | [M + H] | Method |
|---|---|---|---|---|
| 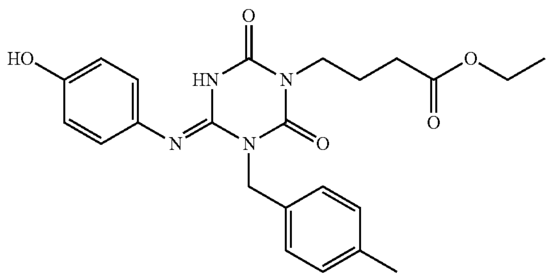 [SMILES: CCOC(=O)CCCn1c(=O)[nH]/c(=N\c2ccc(O)cc2)n(Cc2ccc(C)cc2)c1=O] | I-1239 | 1.72 | 439 | 2 |
| 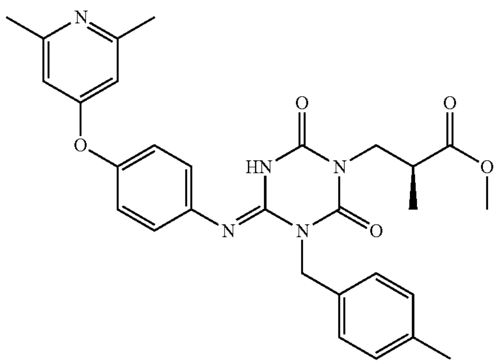 | I-1240 | 1.35 | 530 | 2 |

TABLE 252

| Structure | Compound No. | Retention Time (min) | [M + H] | Method |
|---|---|---|---|---|
| 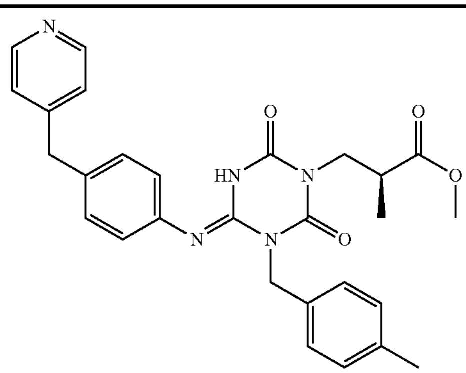 | I-1241 | 1.29 | 500 | 2 |
| 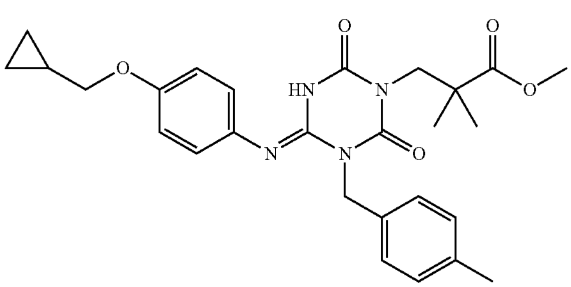 [SMILES: COC(=O)C(C)(C)Cn1c(=O)[nH]/c(=N\c2ccc(OCC3CC3)cc2)n(Cc2ccc(C)cc2)c1=O] | I-1242 | 2.24 | 493 | 2 |

TABLE 252-continued

| Structure | Compound No. | Retention Time (min) | [M + H] | Method |
|---|---|---|---|---|
| 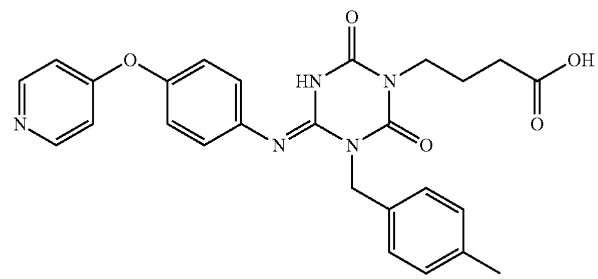 [SMILES: Cc1ccc(Cn2c(=O)n(CCCC(=O)O)c(=O)[nH]/c2=N\c2ccc(Oc3ccncc3)cc2)cc1] | I-1243 | 1.23 | 488 | 2 |
| 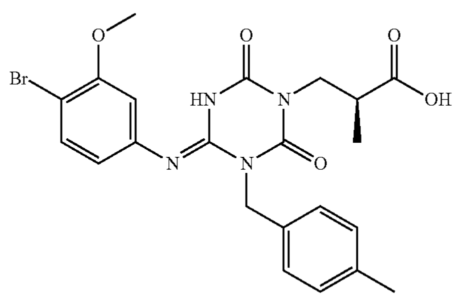 [SMILES: COc1cc(/N=c2\[nH]c(=O)n(C[C@H](C)C(=O)O)c(=O)n2Cc2ccc(C)cc2)ccc1Br] | I-1244 | 1.98 | 503 | 2 |
| 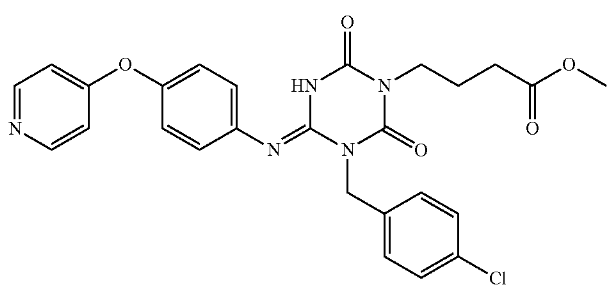 [SMILES: COC(=O)CCCn1c(=O)[nH]/c(=N\c2ccc(Oc3ccncc3)cc2)n(Cc2ccc(Cl)cc2)c1=O] | I-1245 | 1.47 | 522 | 2 |

TABLE 253

| Structure | Compound No. | Retention Time (min) | [M + H] | Method |
|---|---|---|---|---|
| 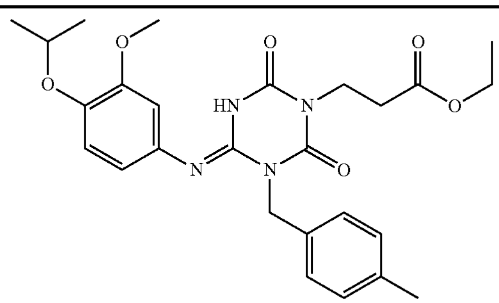 | I-1246 | 2.30 | 497 | 3 |

TABLE 253-continued

| Structure | Compound No. | Retention Time (min) | [M + H] | Method |
|---|---|---|---|---|
| 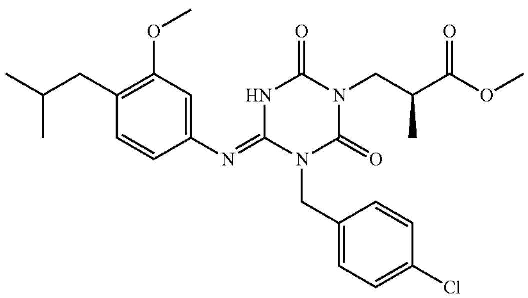 [SMILES: COC(=O)[C@@H](C)Cn1c(=O)[nH]/c(=N\c2ccc(CC(C)C)c(OC)c2)n(Cc2ccc(Cl)cc2)c1=O] | I-1247 | 2.58 | 515 | 2 |
| 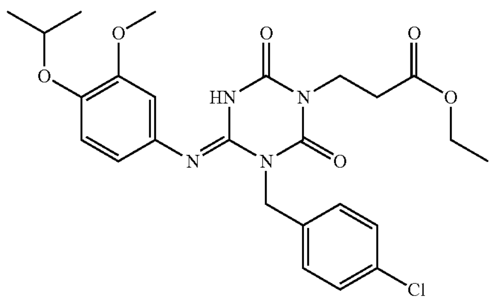 [SMILES: CCOC(=O)CCn1c(=O)[nH]/c(=N\c2ccc(OC(C)C)c(OC)c2)n(Cc2ccc(Cl)cc2)c1=O] | I-1248 | 2.37 | 517 | 3 |
| 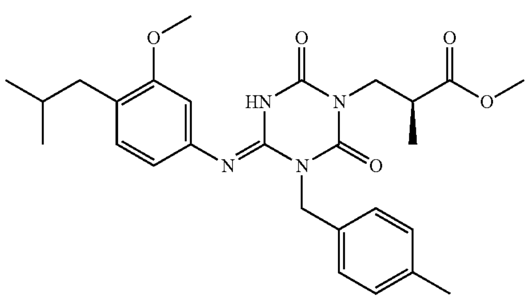 [SMILES: COC(=O)[C@@H](C)Cn1c(=O)[nH]/c(=N\c2ccc(CC(C)C)c(OC)c2)n(Cc2ccc(C)cc2)c1=O] | I-1249 | 2.52 | 495 | 2 |
| 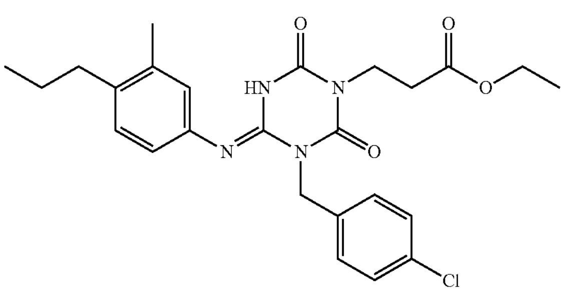 [SMILES: CCCc1ccc(/N=c2\[nH]c(=O)n(CCC(=O)OCC)c(=O)n2Cc2ccc(Cl)cc2)cc1C] | I-1250 | 2.69 | 485 | 3 |

TABLE 254

| Structure | Compound No. | Retention Time (min) | [M + H] | Method |
|---|---|---|---|---|
| 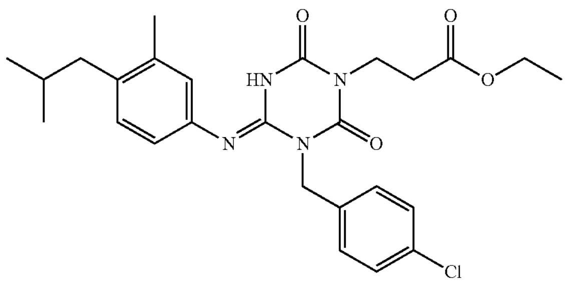 | I-1251 | 2.80 | 499 | 3 |
| 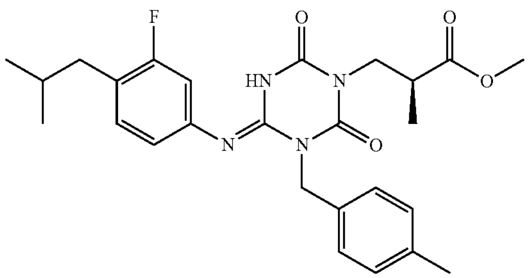 | I-1252 | 2.74 | 483 | 3 |
| 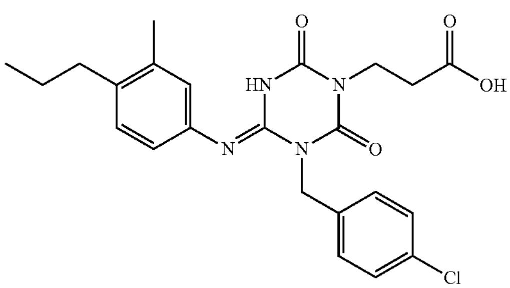 [SMILES: CCCc1ccc(/N=c2\[nH]c(=O)n(CCC(=O)O)c(=O)n2Cc2ccc(Cl)cc2)cc1C] | I-1253 | 2.35 | 457 | 3 |
| 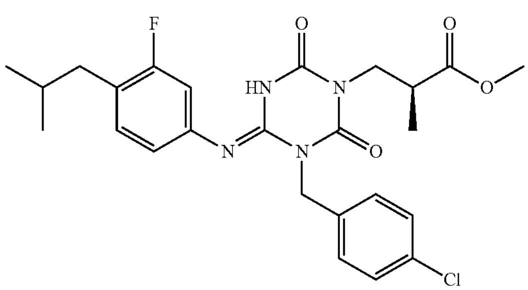 | I-1254 | 2.81 | 503 | 3 |
| 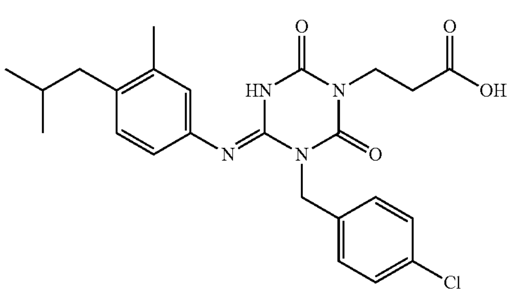 [SMILES: Cc1cc(/N=c2\[nH]c(=O)n(CCC(=O)O)c(=O)n2Cc2ccc(Cl)cc2)ccc1CC(C)C] | I-1255 | 2.47 | 471 | 3 |

TABLE 255

| Structure | Compound No. | Retention Time (min) | [M + H] | Method |
|---|---|---|---|---|
| 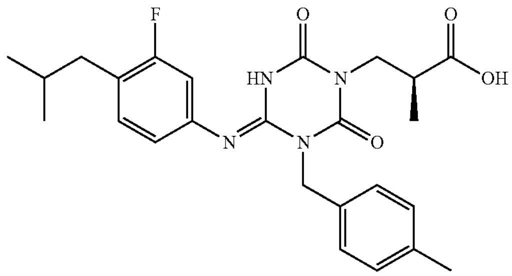 | I-1256 | 2.50 | 469 | 3 |
| 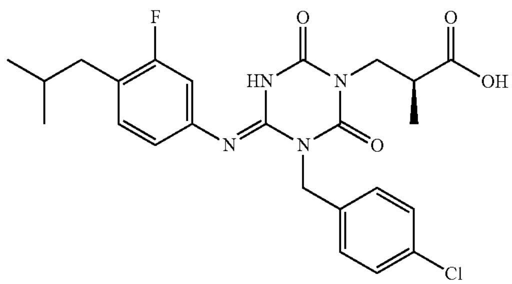 | I-1257 | 2.57 | 489 | 3 |
| 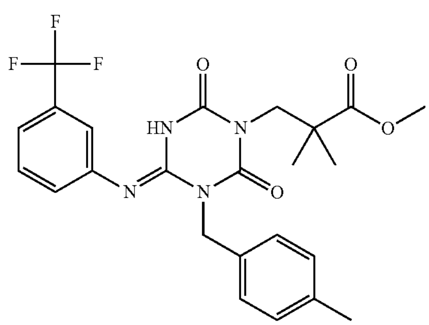 [SMILES: COC(=O)C(C)(C)Cn1c(=O)[nH]/c(=N\c2cccc(C(F)(F)F)c2)n(Cc2ccc(C)cc2)c1=O] | I-1258 | 2.40 | 491 | 2 |
| 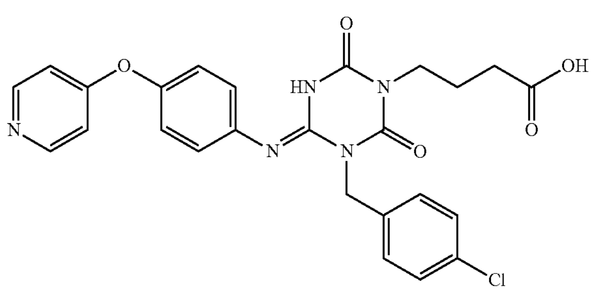 [SMILES: O=C(O)CCCn1c(=O)[nH]/c(=N\c2ccc(Oc3ccncc3)cc2)n(Cc2ccc(Cl)cc2)c1=O] | I-1259 | 1.28 | 508 | 2 |
| 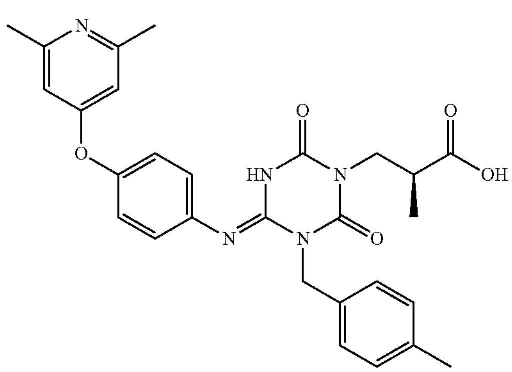 [SMILES: Cc1ccc(Cn2c(=O)n(C[C@H](C)C(=O)O)c(=O)[nH]/c2=N\c2ccc(Oc3cc(C)nc(C)c3)cc2)cc1] | I-1260 | 1.25 | 516 | 3 |

TABLE 256

| Structure | Compound No. | Retention Time (min) | [M + H] | Method |
|---|---|---|---|---|
| 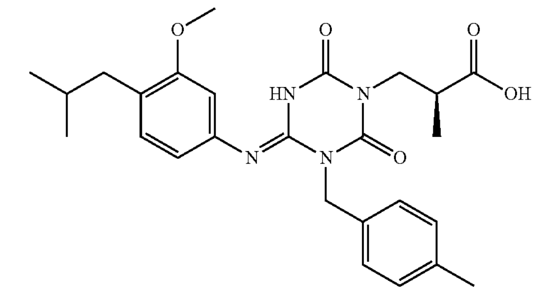 [SMILES: COc1cc(/N=c2\[nH]c(=O)n(C[C@H](C)C(=O)O)c(=O)n2Cc2ccc(C)cc2)ccc1CC(C)C] | I-1261 | 2.28 | 481 | 2 |
| 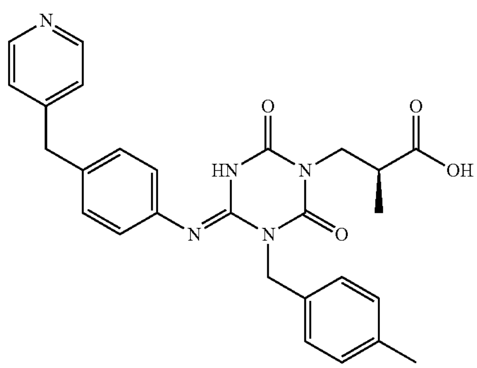 [SMILES: Cc1ccc(Cn2c(=O)n(C[C@H](C)C(=O)O)c(=O)[nH]/c2=N\c2ccc(Cc3ccncc3)cc2)cc1] | I-1262 | 1.23 | 486 | 3 |
| 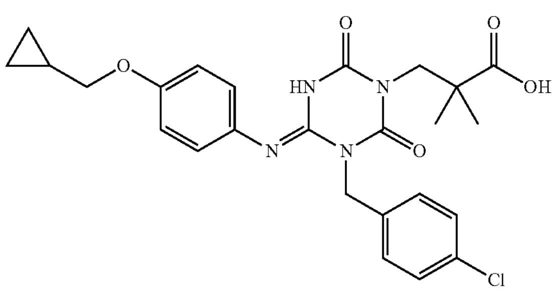 [SMILES: CC(C)(Cn1c(=O)[nH]/c(=N\c2ccc(OCC3CC3)cc2)n(Cc2ccc(Cl)cc2)c1=O)C(=O)O] | I-1263 | 2.02 | 499 | 2 |
| 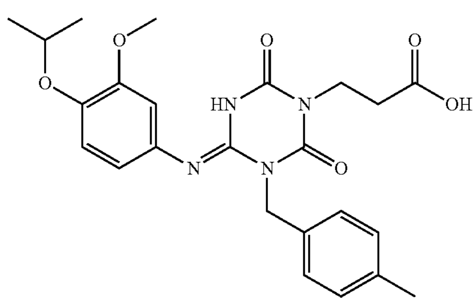 [SMILES: COc1cc(/N=c2\[nH]c(=O)n(CCC(=O)O)c(=O)n2Cc2ccc(C)cc2)ccc1OC(C)C] | I-1264 | 1.95 | 469 | 3 |
| 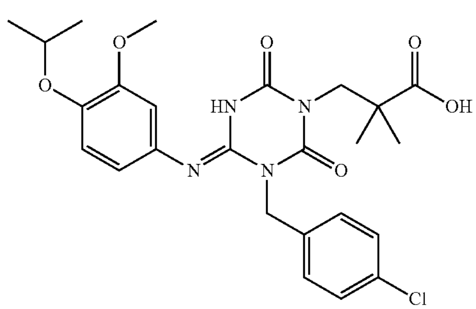 [SMILES: COc1cc(/N=c2\[nH]c(=O)n(CC(C)(C)C(=O)O)c(=O)n2Cc2ccc(Cl)cc2)ccc1OC(C)C] | I-1265 | 1.96 | 517 | 2 |

TABLE 257

| Structure | Compound No. | Retention Time (min) | [M + H] | Method |
|---|---|---|---|---|
| 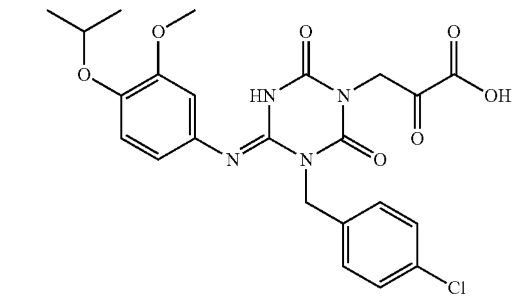 [SMILES: COc1cc(/N=c2\[nH]c(=O)n(CC(=O)C(=O)O)c(=O)n2Cc2ccc(Cl)cc2)ccc1OC(C)C] | I-1266 | 1.81 | 489 | 2 |
| 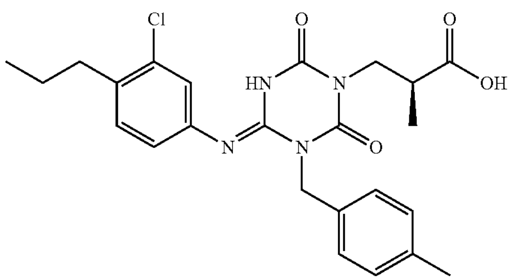 [SMILES: CCCc1ccc(/N=c2\[nH]c(=O)n(C[C@H](C)C(=O)O)c(=O)n2Cc2ccc(C)cc2)cc1Cl] | I-1267 | 2.52 | 471 | 3 |
| 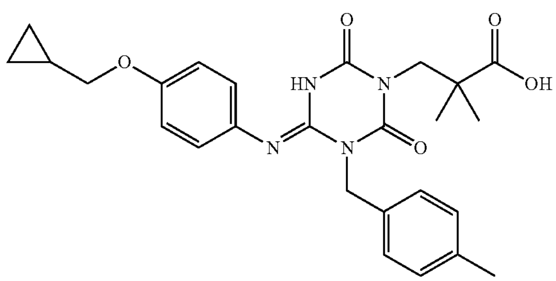 [SMILES: Cc1ccc(Cn2c(=O)n(CC(C)(C)C(=O)O)c(=O)[nH]/c2=N\c2ccc(OCC3CC3)cc2)cc1] | I-1268 | 1.97 | 479 | 2 |
| 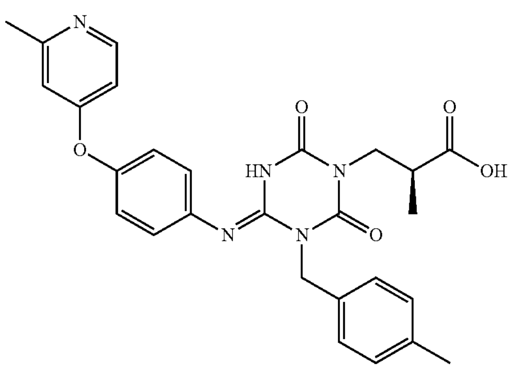 [SMILES: Cc1ccc(Cn2c(=O)n(C[C@H](C)C(=O)O)c(=O)[nH]/c2=N\c2ccc(Oc3ccnc(C)c3)cc2)cc1] | I-1269 | 1.22 | 502 | 3 |
| 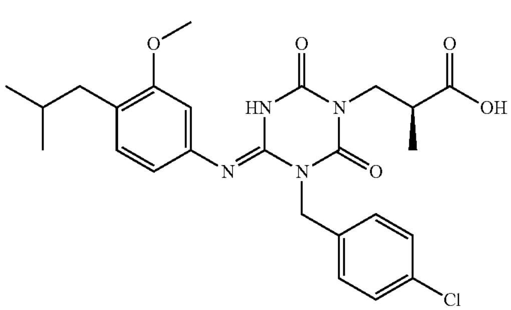 [SMILES: COc1cc(/N=c2\[nH]c(=O)n(C[C@H](C)C(=O)O)c(=O)n2Cc2ccc(Cl)cc2)ccc1CC(C)C] | I-1270 | 2.34 | 501 | 2 |

TABLE 258

| Structure | Compound No. | Retention Time (min) | [M + H] | Method |
|---|---|---|---|---|
| 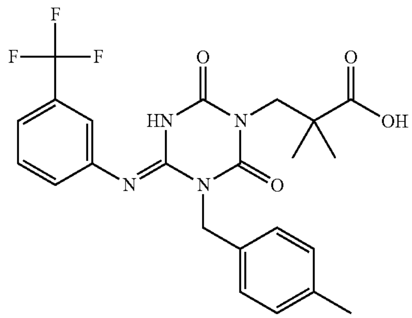 [SMILES: Cc1ccc(Cn2c(=O)n(CC(C)(C)C(=O)O)c(=O)[nH]/c2=N\c2cccc(C(F)(F)F)c2)cc1] | I-1271 | 2.13 | 477 | 2 |
| 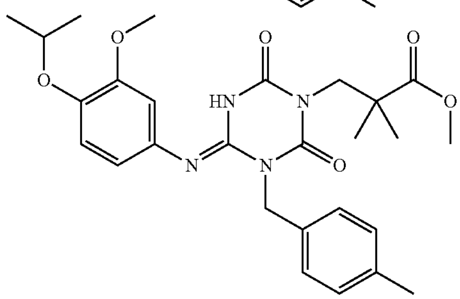 | I-1272 | 2.17 | 511 | 2 |
| 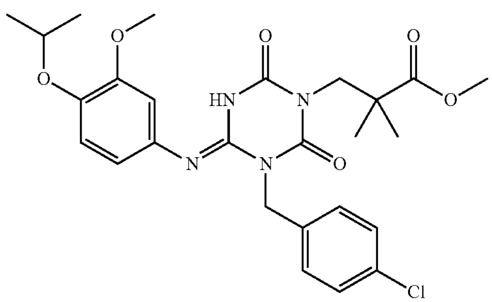 [SMILES: COC(=O)C(C)(C)Cn1c(=O)[nH]/c(=N\c2ccc(OC(C)C)c(OC)c2)n(Cc2ccc(Cl)cc2)c1=O] | I-1273 | 2.25 | 531 | 2 |
| 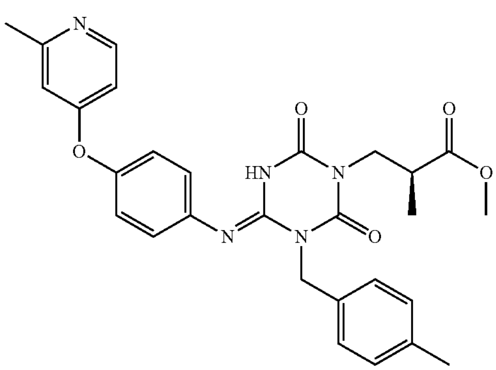 | I-1274 | 1.34 | 516 | 2 |
| 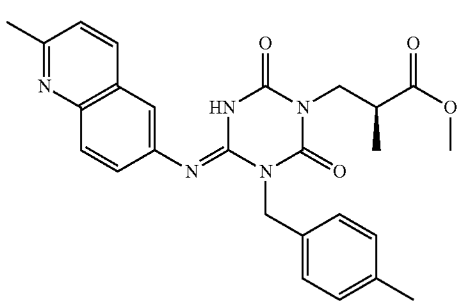 | I-1275 | 1.33 | 474 | 2 |

TABLE 259

| Structure | Compound No. | Retention Time (min) | [M + H] | Method |
|---|---|---|---|---|
| 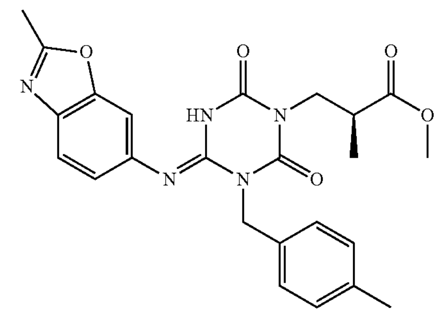 | I-1276 | 1.84 | 464 | 2 |
| 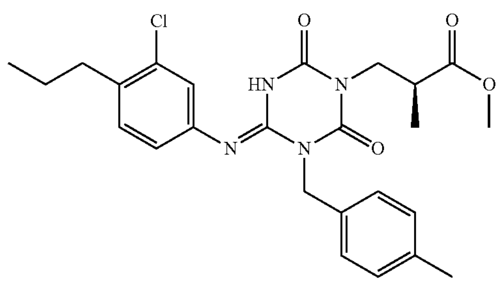 [SMILES: CCCc1ccc(/N=c2\[nH]c(=O)n(C[C@H](C)C(=O)OC)c(=O)n2Cc2ccc(C)cc2)cc1Cl] | I-1277 | 2.55 | 485 | 2 |
| 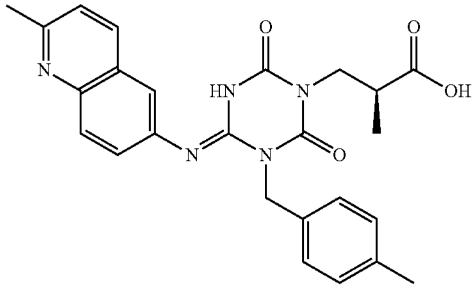 [SMILES: Cc1ccc(Cn2c(=O)n(C[C@H](C)C(=O)O)c(=O)[nH]/c2=N\c2ccc3nc(C)ccc3c2)cc1] | I-1278 | 1.19 | 460 | 2 |
| 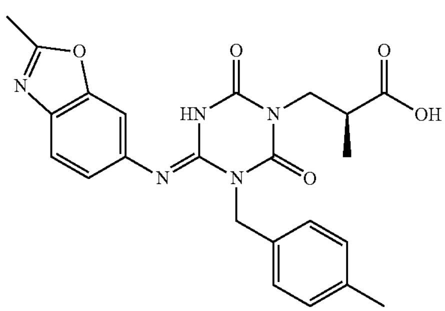 [SMILES: Cc1ccc(Cn2c(=O)n(C[C@H](C)C(=O)O)c(=O)[nH]/c2=N\c2ccc3nc(C)oc3c2)cc1] | I-1279 | 1.57 | 450 | 2 |
| 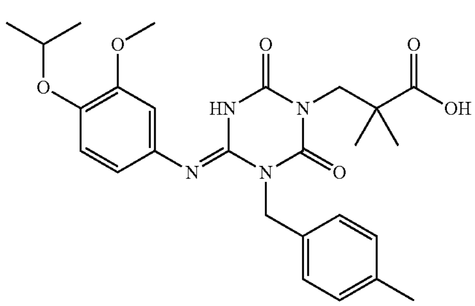 [SMILES: COc1cc(/N=c2\[nH]c(=O)n(CC(C)(C)C(=O)O)c(=O)n2Cc2ccc(C)cc2)ccc1OC(C)C] | I-1280 | 1.87 | 497 | 2 |

TABLE 260

| Structure | Compound No. | Retention Time (min) | [M + H] | Method |
|---|---|---|---|---|
| 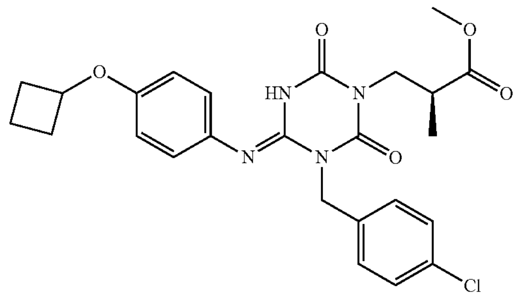 [SMILES: COC(=O)[C@@H](C)Cn1c(=O)[nH]/c(=N\c2ccc(OC3CCC3)cc2)n(Cc2ccc(Cl)cc2)c1=O] | I-1281 | 2.26 | 499 | 2 |
| 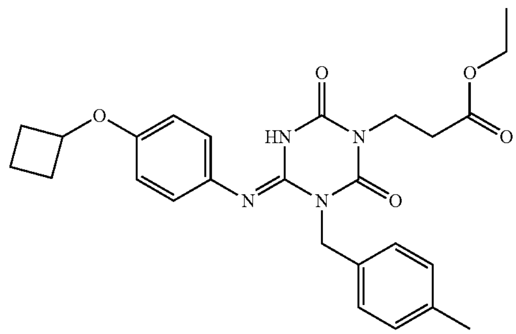 [SMILES: CCOC(=O)CCn1c(=O)[nH]/c(=N\c2ccc(OC3CCC3)cc2)n(Cc2ccc(C)cc2)c1=O] | I-1282 | 2.21 | 479 | 2 |
| 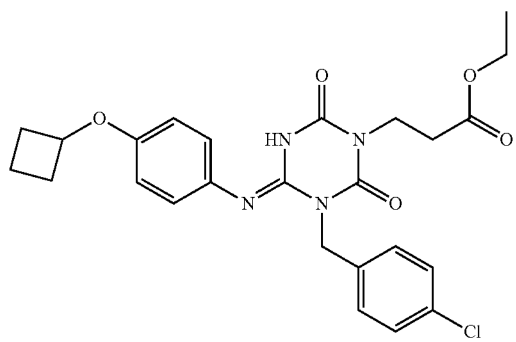 [SMILES: CCOC(=O)CCn1c(=O)[nH]/c(=N\c2ccc(OC3CCC3)cc2)n(Cc2ccc(Cl)cc2)c1=O] | I-1283 | 2.28 | 499 | 2 |
| 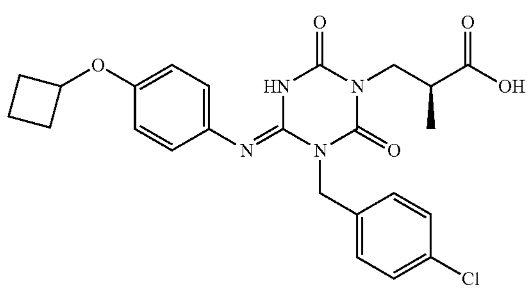 [SMILES: C[C@@H](Cn1c(=O)[nH]/c(=N\c2ccc(OC3CCC3)cc2)n(Cc2ccc(Cl)cc2)c1=O)C(=O)O] | I-1284 | 2.01 | 485 | 2 |
| 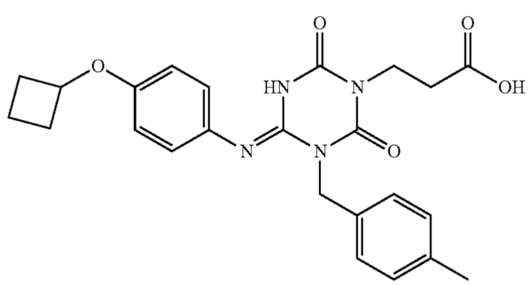 [SMILES: Cc1ccc(Cn2c(=O)n(CCC(=O)O)c(=O)[nH]/c2=N\c2ccc(OC3CCC3)cc2)cc1] | I-1285 | 1.89 | 451 | 2 |

TABLE 261

| Structure | Compound No. | Retention Time (min) | [M + H] | Method |
|---|---|---|---|---|
| 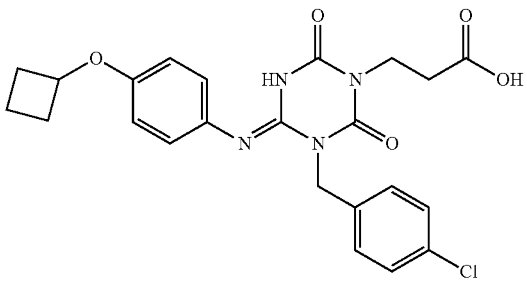 [SMILES: O=C(O)CCn1c(=O)[nH]/c(=N\c2ccc(OC3CCC3)cc2)n(Cc2ccc(Cl)cc2)c1=O] | I-1286 | 1.95 | 471 | 2 |
| 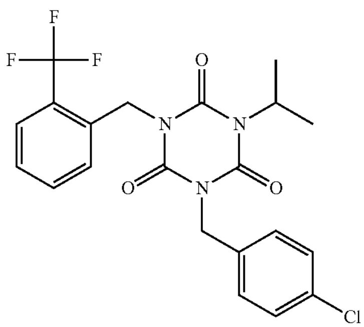 [SMILES: CC(C)n1c(=O)n(Cc2ccc(Cl)cc2)c(=O)n(Cc2ccccc2C(F)(F)F)c1=O] | I-1287 | 2.82 | 453 | 3 |
| 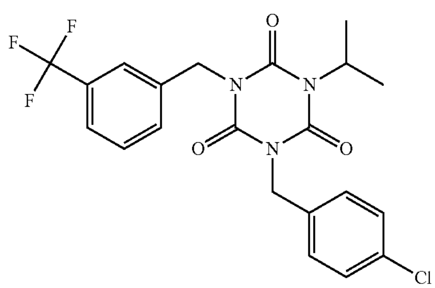 [SMILES: CC(C)n1c(=O)n(Cc2ccc(Cl)cc2)c(=O)n(Cc2cccc(C(F)(F)F)c2)c1=O] | I-1288 | 2.83 | 454 | 3 |
| 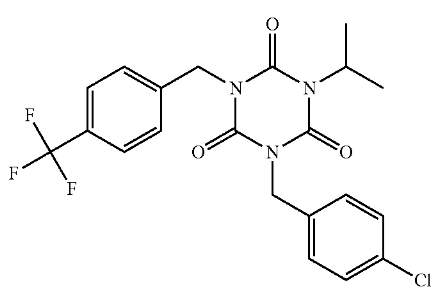 [SMILES: CC(C)n1c(=O)n(Cc2ccc(Cl)cc2)c(=O)n(Cc2ccc(C(F)(F)F)cc2)c1=O] | I-1289 | 2.85 | 454 | 3 |
| 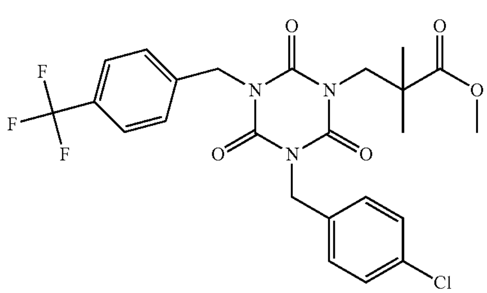 [SMILES: COC(=O)C(C)(C)Cn1c(=O)n(Cc2ccc(Cl)cc2)c(=O)n(Cc2ccc(C(F)(F)F)cc2)c1=O] | I-1290 | 2.67 | 526 | 2 |

TABLE 262

| Structure | Compound No. | Retention Time (min) | [M + H] | Method |
|---|---|---|---|---|
| 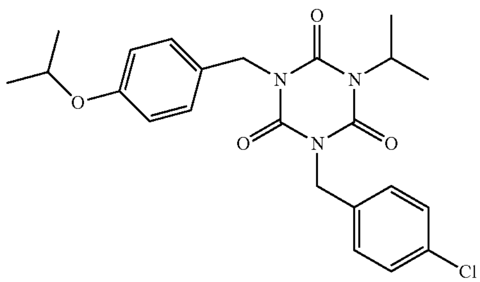 [SMILES: CC(C)Oc1ccc(Cn2c(=O)n(Cc3ccc(Cl)cc3)c(=O)n(C(C)C)c2=O)cc1] | I-1291 | 2.07 | 443 | 3 |
| 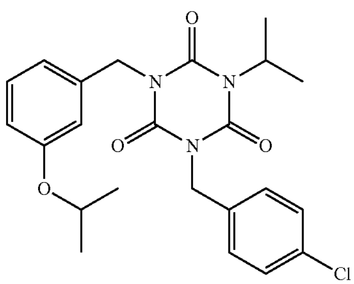 [SMILES: CC(C)Oc1cccc(Cn2c(=O)n(Cc3ccc(Cl)cc3)c(=O)n(C(C)C)c2=O)c1] | I-1292 | 2.05 | 444 | 3 |
| 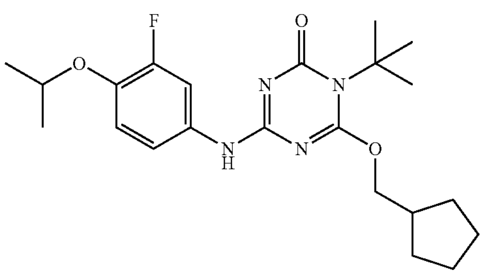 [SMILES: CC(C)Oc1ccc(Nc2nc(OCC3CCCC3)n(C(C)(C)C)c(=O)n2)cc1F] | I-1293 | 2.54 | 419 | 2 |
| 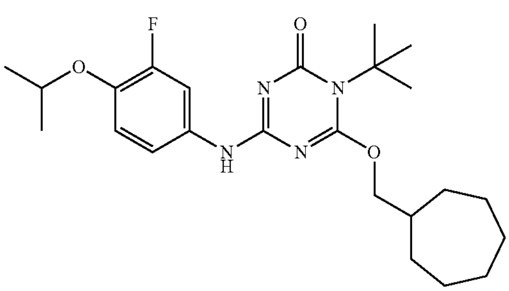 [SMILES: CC(C)Oc1ccc(Nc2nc(OCC3CCCCCC3)n(C(C)(C)C)c(=O)n2)cc1F] | I-1294 | 2.77 | 447 | 2 |
| 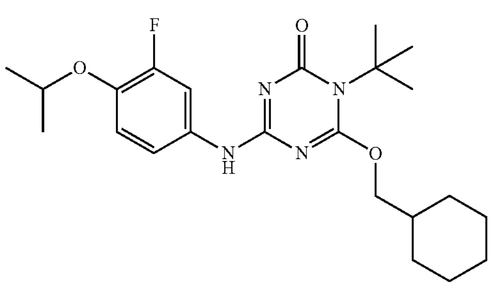 [SMILES: CC(C)Oc1ccc(Nc2nc(OCC3CCCCC3)n(C(C)(C)C)c(=O)n2)cc1F] | I-1295 | 2.65 | 433 | 2 |

TABLE 263

| Structure | Compound No. | Retention Time (min) | [M + H] | Method |
|---|---|---|---|---|
| 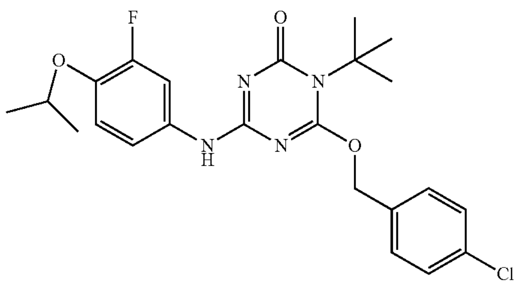 [SMILES: CC(C)Oc1ccc(Nc2nc(OCc3ccc(Cl)cc3)n(C(C)(C)C)c(=O)n2)cc1F] | I-1296 | 2.45 | 462 | 2 |
| 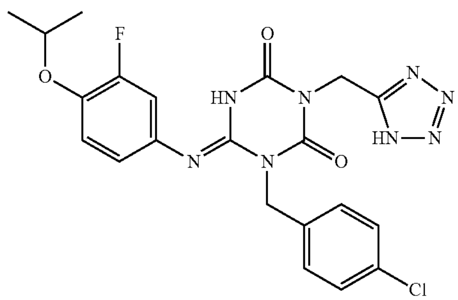 [SMILES: CC(C)Oc1ccc(/N=c2\[nH]c(=O)n(Cc3nnn[nH]3)c(=O)n2Cc2ccc(Cl)cc2)cc1F] | I-1297 | 1.89 | 487 | 2 |
| 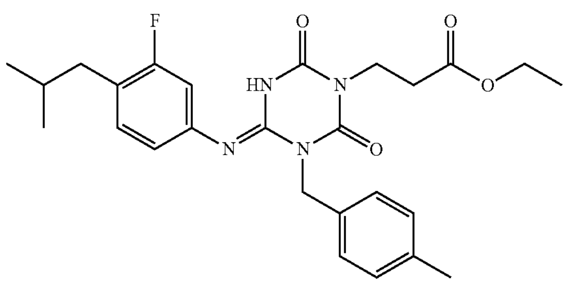 | I-1298 | 2.76 | 483 | 3 |
| 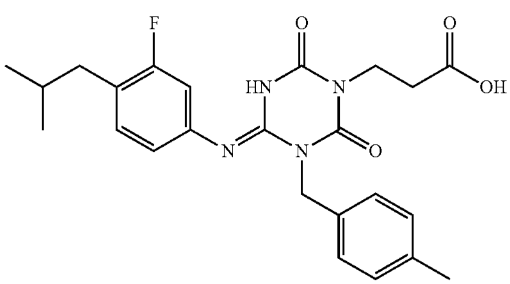 | I-1299 | 2.44 | 455 | 3 |
| 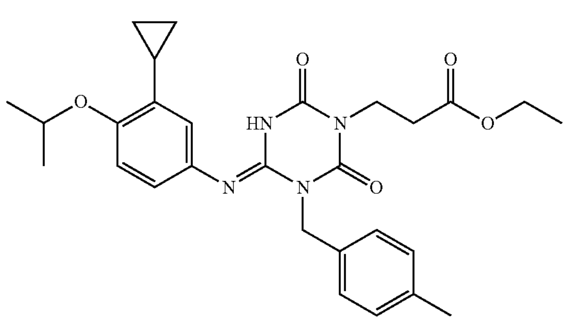 [SMILES: CCOC(=O)CCn1c(=O)[nH]/c(=N\c2ccc(OC(C)C)c(C3CC3)c2)n(Cc2ccc(C)cc2)c1=O] | I-1300 | 2.40 | 507 | 2 |

TABLE 264
| Structure | Compound No. | Retention Time (min) | [M + H] | Method |
|---|---|---|---|---|
| 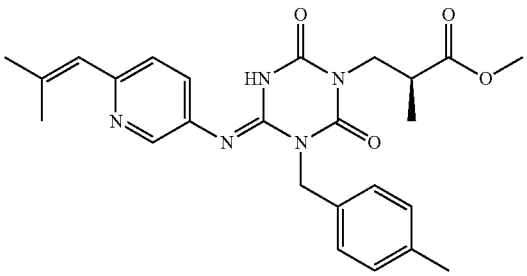 [SMILES: COC(=O)[C@@H](C)Cn1c(=O)[nH]/c(=N\c2ccc(C=C(C)C)nc2)n(Cc2ccc(C)cc2)c1=O] | I-1301 | 1.63 | 464 | 2 |
| 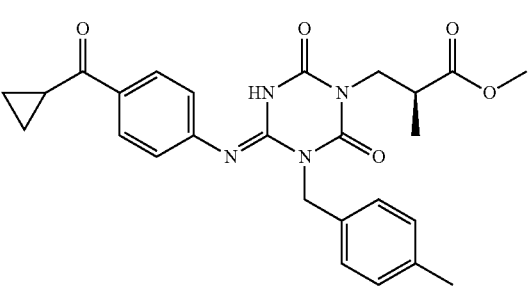 [SMILES: COC(=O)[C@@H](C)Cn1c(=O)[nH]/c(=N\c2ccc(C(=O)C3CC3)cc2)n(Cc2ccc(C)cc2)c1=O] | I-1302 | 2.10 | 477 | 2 |
| 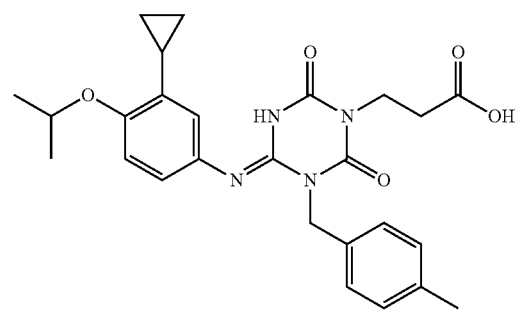 [SMILES: Cc1ccc(Cn2c(=O)n(CCC(=O)O)c(=O)[nH]/c2=N\c2ccc(OC(C)C)c(C3CC3)c2)cc1] | I-1303 | 2.08 | 479 | 2 |
| 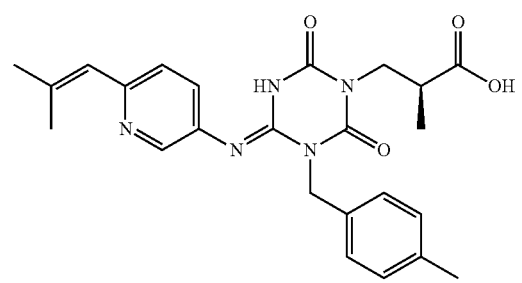 [SMILES: CC(C)=Cc1ccc(/N=c2\[nH]c(=O)n(C[C@H](C)C(=O)O)c(=O)n2Cc2ccc(C)cc2)cn1] | I-1304 | 1.43 | 450 | 2 |
| 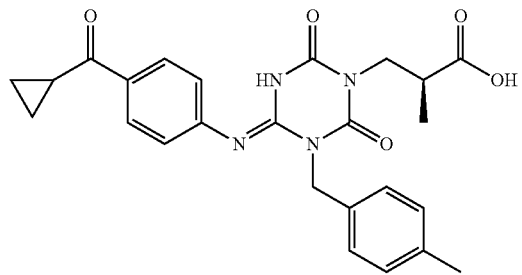 [SMILES: Cc1ccc(Cn2c(=O)n(C[C@H](C)C(=O)O)c(=O)[nH]/c2=N\c2ccc(C(=O)C3CC3)cc2)cc1] | I-1305 | 1.87 | 463 | 2 |

TABLE 265

| Structure | Compound No. | Retention Time (min) | [M + H] | Method |
|---|---|---|---|---|
| (structure) | I-1306 | 2.46 | 501 | 2 |
| (structure) | I-1307 | 2.52 | 561 | 2 |
| (structure) | I-1308 | 2.60 | 515 | 2 |
| (structure) | I-1309 | 2.44 | 491 | 2 |
| (structure) | I-1310 | 2.27 | 481 | 2 |

TABLE 266

| Structure | Compound No. | Retention Time (min) | [M + H] | Method |
|---|---|---|---|---|
| 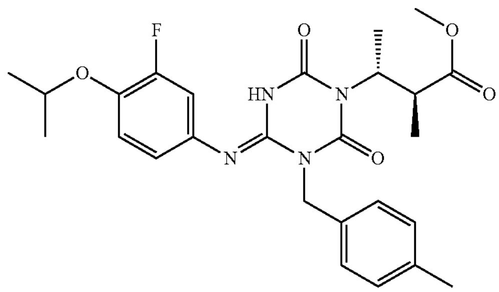 | I-1311 | 2.37 | 499 | 2 |
| 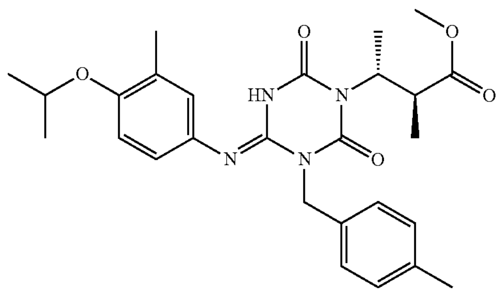 [SMILES: COC(=O)[C@@H](C)[C@@H](C)n1c(=O)[nH]/c(=N\c2ccc(OC(C)C)c(C)c2)n(Cc2ccc(C)cc2)c1=O] | I-1312 | 2.43 | 495 | 2 |
| 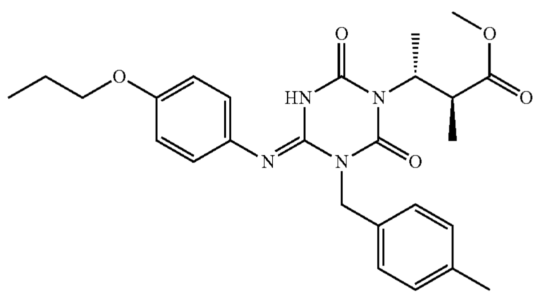 [SMILES: CCCOc1ccc(/N=c2\[nH]c(=O)n([C@H](C)[C@H](C)C(=O)OC)c(=O)n2Cc2ccc(C)cc2)cc1] | I-1313 | 2.32 | 481 | 2 |
| 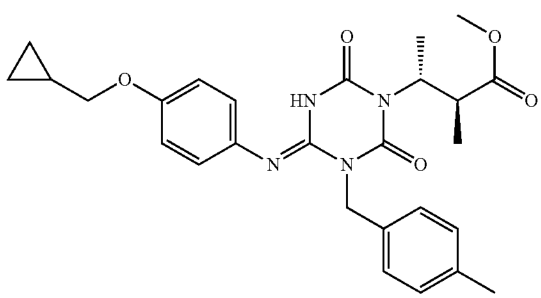 [SMILES: COC(=O)[C@@H](C)[C@@H](C)n1c(=O)[nH]/c(=N\c2ccc(OCC3CC3)cc2)n(Cc2ccc(C)cc2)c1=O] | I-1314 | 2.28 | 493 | 2 |
| 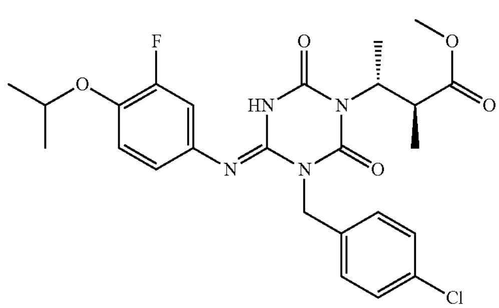 | I-1315 | 2.45 | 519 | 2 |

TABLE 267
| Structure | Compound No. | Retention Time (min) | [M + H] | Method |
|---|---|---|---|---|
| 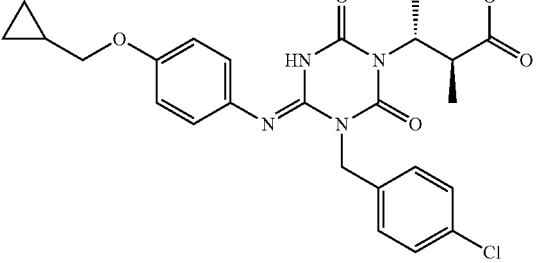 | I-1316 | 2.34 | 513 | 2 |
| 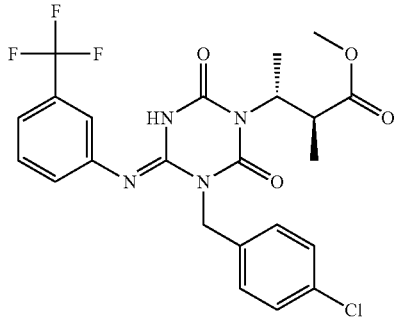 [SMILES: COC(=O)[C@@H](C)[C@@H](C)n1c(=O)[nH]/c(=N\c2cccc(C(F)(F)F)c2)n(Cc2ccc(Cl)cc2)c1=O] | I-1317 | 2.52 | 511 | 2 |
| 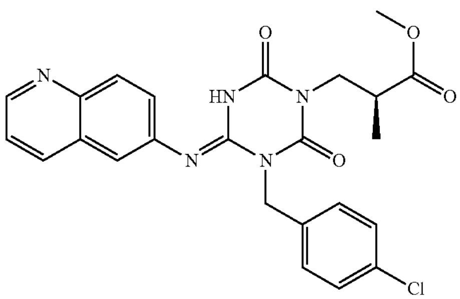 [SMILES: COC(=O)[C@@H](C)Cn1c(=O)[nH]/c(=N\c2ccc3ncccc3c2)n(Cc2ccc(Cl)cc2)c1=O] | I-1318 | 1.57 | 480 | 2 |
| 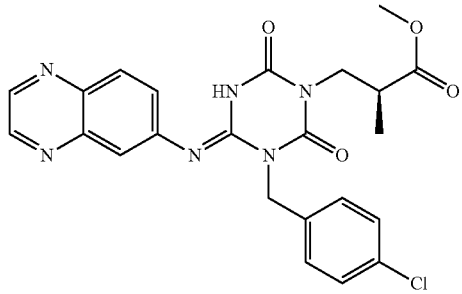 [SMILES: COC(=O)[C@@H](C)Cn1c(=O)[nH]/c(=N\c2ccc3nccnc3c2)n(Cc2ccc(Cl)cc2)c1=O] | I-1319 | 1.88 | 481 | 2 |
| 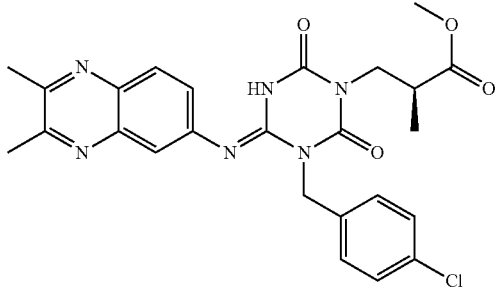 [SMILES: COC(=O)[C@@H](C)Cn1c(=O)[nH]/c(=N\c2ccc3nc(C)c(C)nc3c2)n(Cc2ccc(Cl)cc2)c1=O] | I-1320 | 1.95 | 509 | 2 |

TABLE 268

| Structure | Compound No. | Retention Time (min) | [M + H] | Method |
|---|---|---|---|---|
| 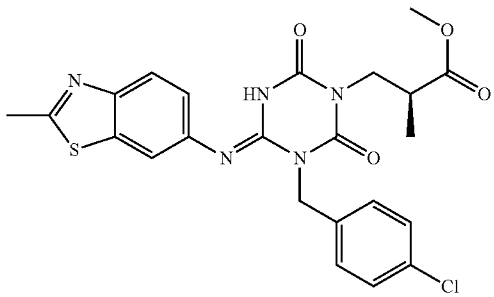 [SMILES: COC(=O)[C@@H](C)Cn1c(=O)[nH]/c(=N\c2ccc3nc(C)sc3c2)n(Cc2ccc(Cl)cc2)c1=O] | I-1321 | 2.02 | 500 | 2 |
| 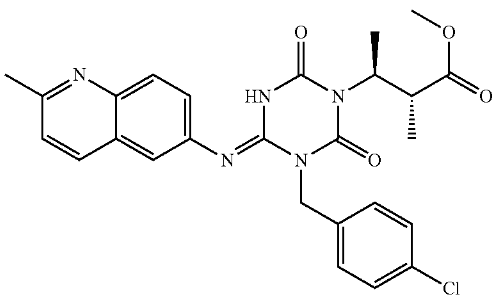 [SMILES: COC(=O)[C@H](C)[C@H](C)n1c(=O)[nH]/c(=N\c2ccc3nc(C)ccc3c2)n(Cc2ccc(Cl)cc2)c1=O] | I-1322 | 1.59 | 508 | 2 |
| 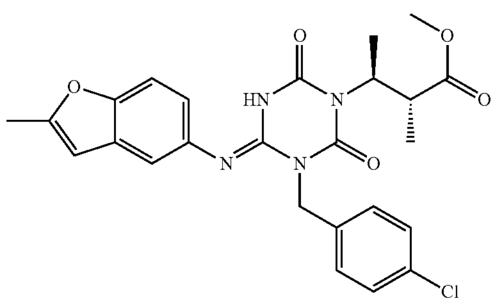 [SMILES: COC(=O)[C@H](C)[C@H](C)n1c(=O)[nH]/c(=N\c2ccc3oc(C)cc3c2)n(Cc2ccc(Cl)cc2)c1=O] | I-1323 | 2.33 | 497 | 2 |
| 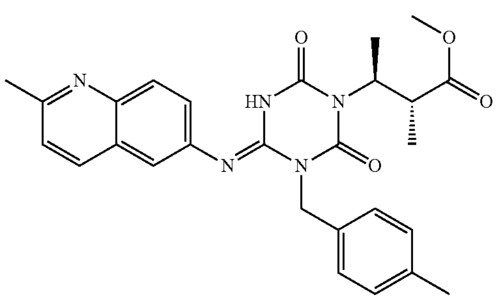 [SMILES: COC(=O)[C@H](C)[C@H](C)n1c(=O)[nH]/c(=N\c2ccc3nc(C)ccc3c2)n(Cc2ccc(C)cc2)c1=O] | I-1324 | 1.50 | 488 | 2 |
| 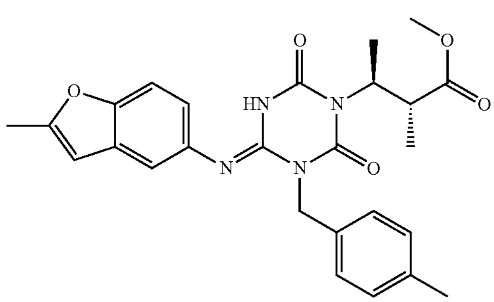 [SMILES: COC(=O)[C@H](C)[C@H](C)n1c(=O)[nH]/c(=N\c2ccc3oc(C)cc3c2)n(Cc2ccc(C)cc2)c1=O] | I-1325 | 2.25 | 477 | 2 |

TABLE 269

| Structure | Compound No. | Retention Time (min) | [M + H] | Method |
|---|---|---|---|---|
| 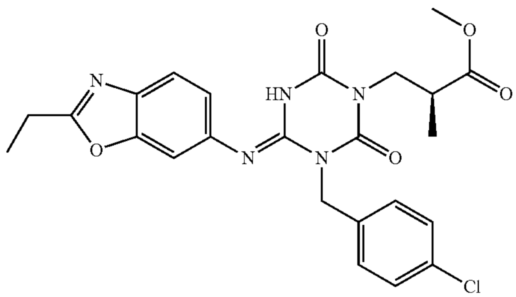 [SMILES: CCc1nc2ccc(/N=c3\[nH]c(=O)n(C[C@H](C)C(=O)OC)c(=O)n3Cc3ccc(Cl)cc3)cc2o1] | I-1326 | 2.01 | 498 | 2 |
| 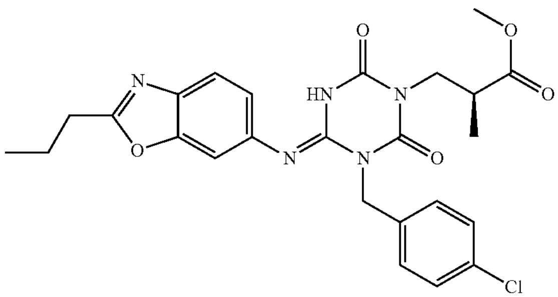 [SMILES: CCCc1nc2ccc(/N=c3\[nH]c(=O)n(C[C@H](C)C(=O)OC)c(=O)n3Cc3ccc(Cl)cc3)cc2o1] | I-1327 | 2.20 | 512 | 2 |
| 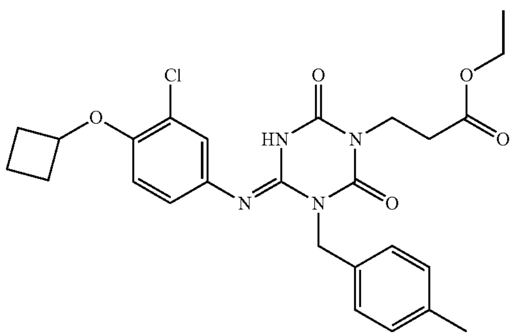 [SMILES: CCOC(=O)CCn1c(=O)[nH]/c(=N\c2ccc(OC3CCC3)c(Cl)c2)n(Cc2ccc(C)cc2)c1=O] | I-1328 | 2.42 | 513 | 2 |
| 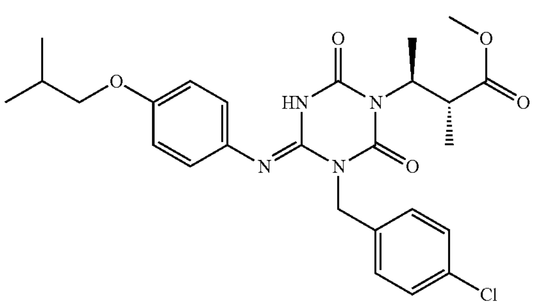 [SMILES: COC(=O)[C@H](C)[C@H](C)n1c(=O)[nH]/c(=N\c2ccc(OCC(C)C)cc2)n(Cc2ccc(Cl)cc2)c1=O] | I-1329 | 2.51 | 515 | 2 |
| 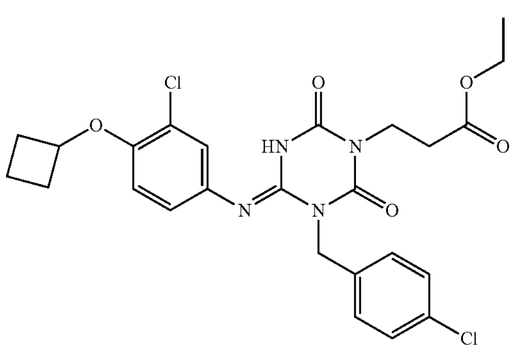 | I-1330 | 2.49 | 533 | 2 |

TABLE 270

| Structure | Compound | Retention Time (min) | [M + H] | Method |
|---|---|---|---|---|
| 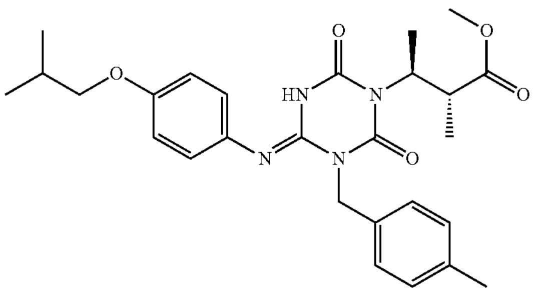 [SMILES: COC(=O)[C@H](C)[C@H](C)n1c(=O)[nH]/c(=N\c2ccc(OCC(C)C)cc2)n(Cc2ccc(C)cc2)c1=O] | I-1331 | 2.46 | 495 | 2 |
| 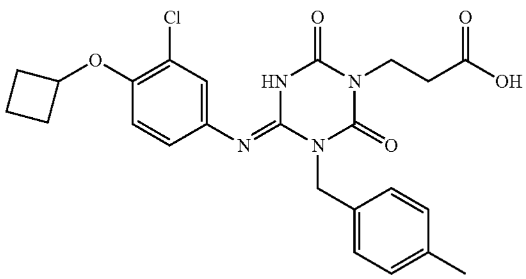 | I-1332 | 2.09 | 485 | 2 |
| 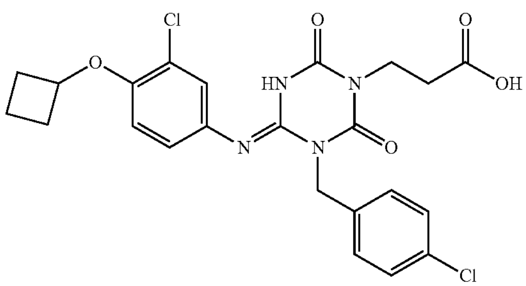 | I-1333 | 2.16 | 505 | 2 |
| 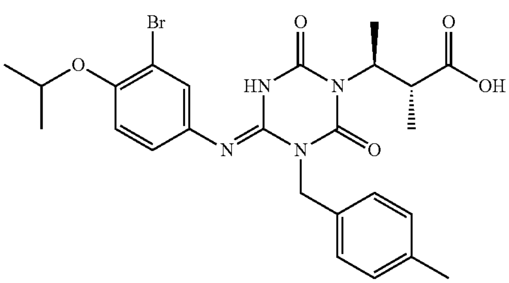 [SMILES: Cc1ccc(Cn2c(=O)n([C@@H](C)[C@@H](C)C(=O)O)c(=O)[nH]/c2=N\c2ccc(OC(C)C)c(Br)c2)cc1] | I-1334 | 2.23 | 547 | 2 |
| 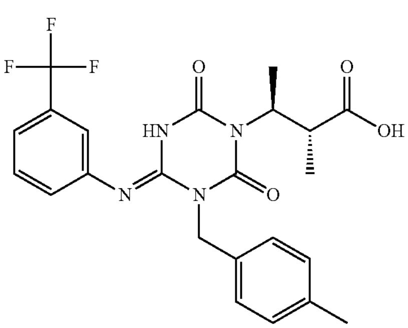 [SMILES: Cc1ccc(Cn2c(=O)n([C@@H](C)[C@@H](C)C(=O)O)c(=O)[nH]/c2=N\c2cccc(C(F)(F)F)c2)cc1] | I-1335 | 2.15 | 477 | 2 |

TABLE 271

| Structure | Compound No. | Retention Time (min) | [M + H] | Method |
|---|---|---|---|---|
| (I-1336 structure) | I-1336 | 1.98 | 467 | 2 |
| (I-1337 structure) | I-1337 | 2.20 | 501 | 2 |
| (I-1338 structure) | I-1338 | 2.08 | 485 | 2 |
| (I-1339 structure) | I-1339 | 2.13 | 481 | 2 |
| (I-1340 structure) | I-1340 | 2.03 | 467 | 2 |

TABLE 271

| Structure | Compound No. | Retention Time (min) | [M + H] | Method |
|---|---|---|---|---|
| 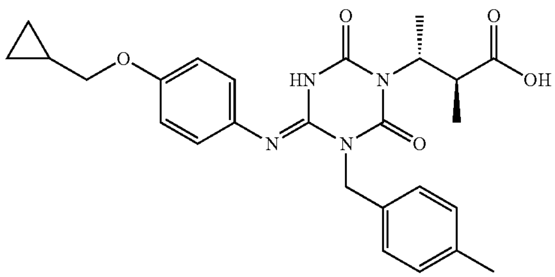 | I-1341 | 1.99 | 479 | 2 |
| 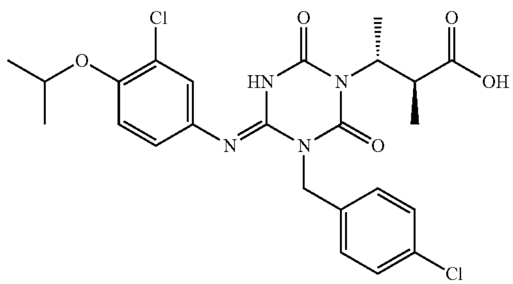 [SMILES: CC(C)Oc1ccc(/N=c2\[nH]c(=O)n([C@H](C)[C@H](C)C(=O)O)c(=O)n2Cc2ccc(Cl)cc2)cc1F] | I-1342 | 2.28 | 521 | 2 |
| 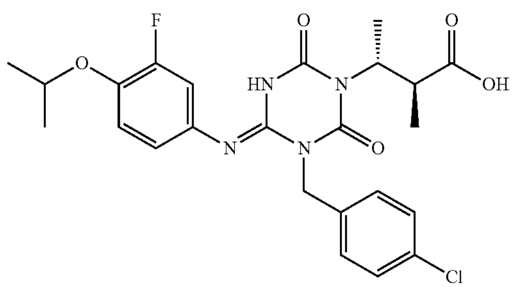 | I-1343 | 2.17 | 505 | 2 |
| 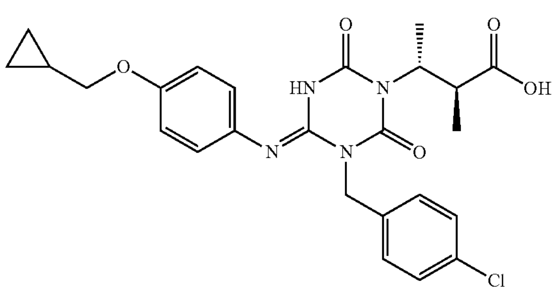 [SMILES: C[C@H](C(=O)O)[C@@H](C)n1c(=O)[nH]/c(=N\c2ccc(OCC3CC3)cc2)n(Cc2ccc(Cl)cc2)c1=O] | I-1344 | 2.06 | 499 | 2 |
| 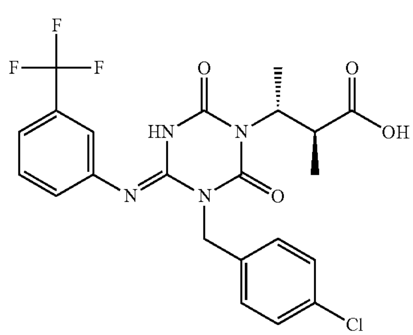 [SMILES: C[C@H](C(=O)O)[C@@H](C)n1c(=O)[nH]/c(=N\c2cccc(C(F)(F)F)c2)n(Cc2ccc(Cl)cc2)c1=O] | I-1345 | 2.25 | 497 | 2 |

TABLE 273

| Structure | Compound No. | Retention Time (min) | [M + H] | Method |
|---|---|---|---|---|
| 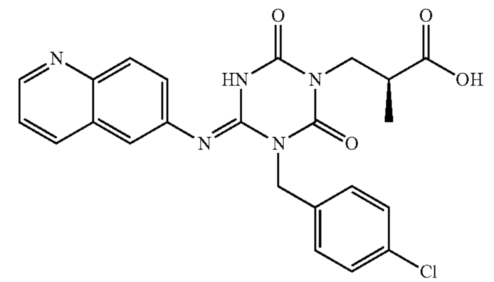 [SMILES: C[C@@H](Cn1c(=O)[nH]/c(=N\c2ccc3ncccc3c2)n(Cc2ccc(Cl)cc2)c1=O)C(=O)O] | I-1346 | 1.35 | 466 | 2 |
| 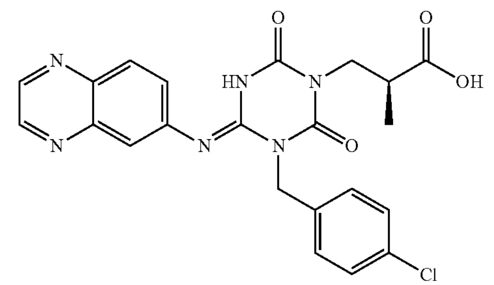 [SMILES: C[C@@H](Cn1c(=O)[nH]/c(=N\c2ccc3nccnc3c2)n(Cc2ccc(Cl)cc2)c1=O)C(=O)O] | I-1347 | 1.62 | 467 | 2 |
| 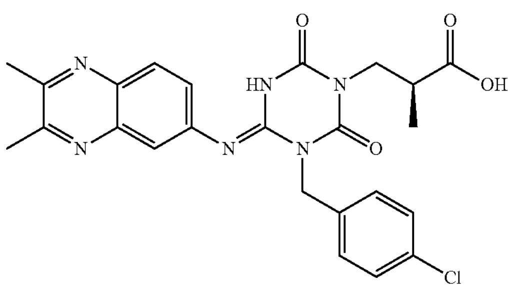 [SMILES: Cc1nc2ccc(/N=c3\[nH]c(=O)n(C[C@H](C)C(=O)O)c(=O)n3Cc3ccc(Cl)cc3)cc2nc1C] | I-1348 | 1.71 | 495 | 2 |
| 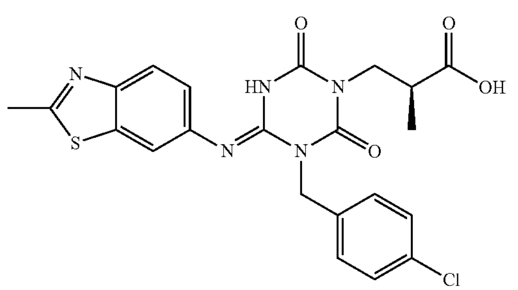 [SMILES: Cc1nc2ccc(/N=c3\[nH]c(=O)n(C[C@H](C)C(=O)O)c(=O)n3Cc3ccc(Cl)cc3)cc2s1] | I-1349 | 1.75 | 486 | 2 |
| 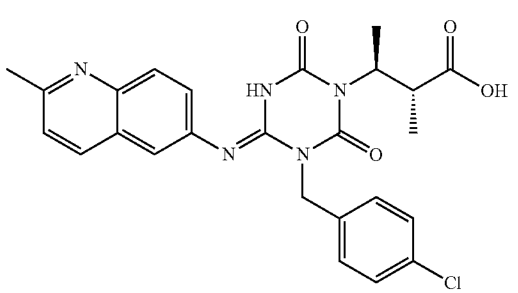 [SMILES: Cc1ccc2cc(/N=c3\[nH]c(=O)n([C@@H](C)[C@@H](C)C(=O)O)c(=O)n3Cc3ccc(Cl)cc3)ccc2n1] | I-1350 | 1.35 | 494 | 2 |

TABLE 274
| Structure | Compound No. | Retention Time (min) | [M + H] | Method |
|---|---|---|---|---|
| 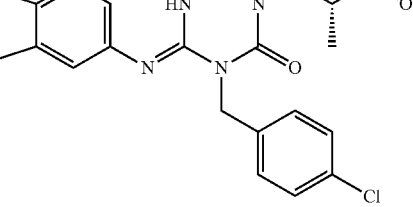 | I-1351 | 2.04 | 483 | 2 |
| 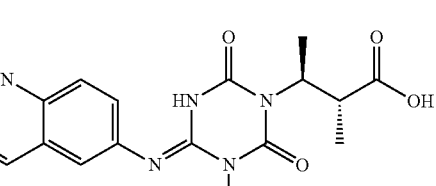 | I-1352 | 1.28 | 474 | 2 |
| 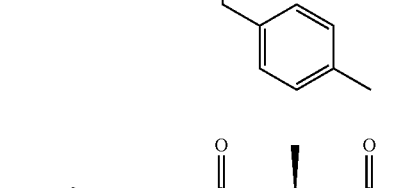 | I-1353 | 1.96 | 463 | 2 |
| 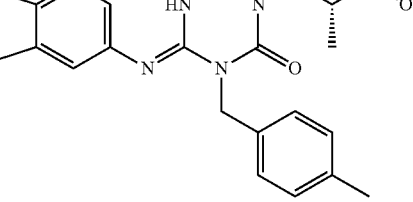 | I-1354 | 2.22 | 487 | 2 |
| 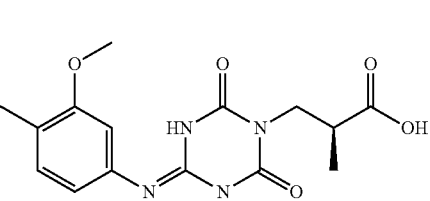 | I-1355 | 2.29 | 487 | 2 |

TABLE 275

| Structure | Compound No. | Retention Time (min) | [M +H] | Method |
|---|---|---|---|---|
| 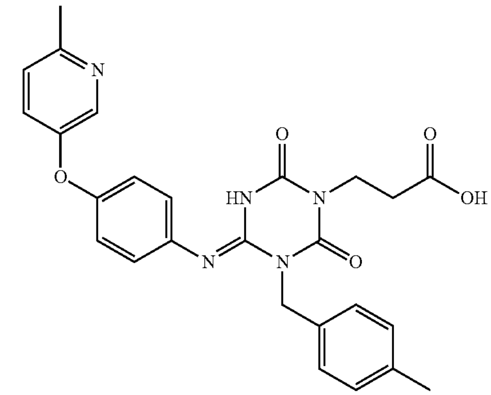 [SMILES: Cc1ccc(Cn2c(=O)n(CCC(=O)O)c(=O)[nH]/c2=N\c2ccc(Oc3ccc(C)nc3)cc2)cc1] | I-1356 | 1.43 | 488 | 3 |
| 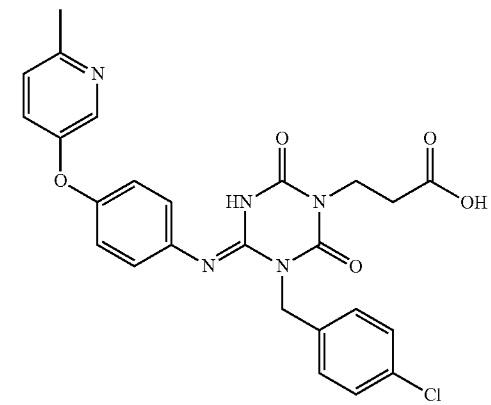 [SMILES: Cc1ccc(Oc2ccc(/N=c3\[nH]c(=O)n(CCC(=O)O)c(=O)n3Cc3ccc(Cl)cc3)cc2)cn1] | I-1357 | 1.52 | 508 | 3 |
| 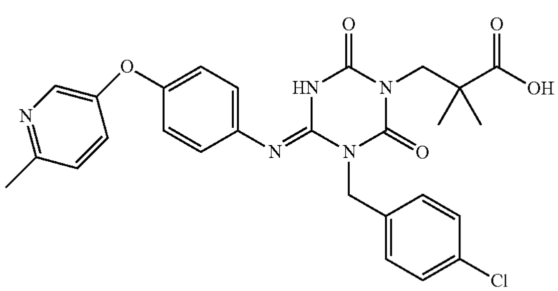 [SMILES: Cc1ccc(Oc2ccc(/N=c3\[nH]c(=O)n(CC(C)(C)C(=O)O)c(=O)n3Cc3ccc(Cl)cc3)cc2)cn1] | I-1358 | 1.70 | 536 | 3 |
| 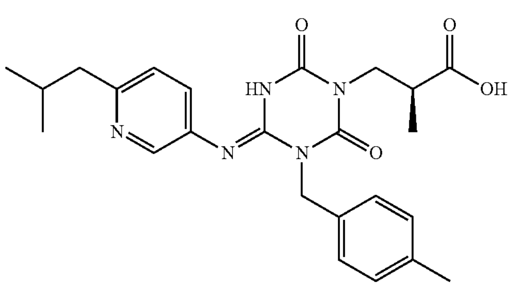 [SMILES: Cc1ccc(Cn2c(=O)n(C[C@H](C)C(=O)O)c(=O)[nH]/c2=N\c2ccc(CC(C)C)nc2)cc1] | I-1359 | 1.44 | 452 | 2 |

TABLE 275-continued

| Structure | Compound No. | Retention Time (min) | [M +H] | Method |
|---|---|---|---|---|
| 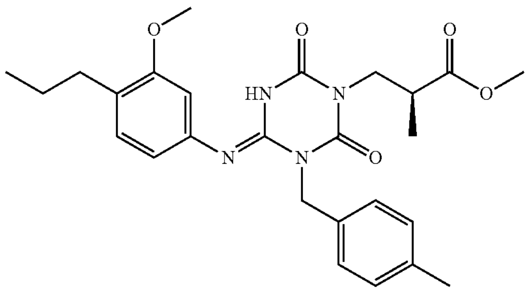 [SMILES: CCCc1ccc(/N=c2\[nH]c(=O)n(C[C@H](C)C(=O)OC)c(=O)n2Cc2ccc(C)cc2)cc1OC] | I-1360 | 2.39 | 481 | 2 |

TABLE 276

| Structure | Compound No. | Retention Time (min) | [M + H] | Method |
|---|---|---|---|---|
| 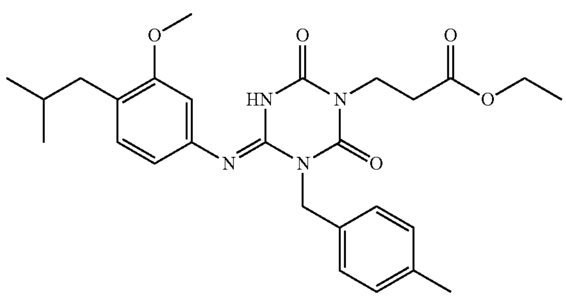 [SMILES: CCOC(=O)CCn1c(=O)[nH]/c(=N\c2ccc(CC(C)C)c(OC)c2)n(Cc2ccc(C)cc2)c1=O] | I-1361 | 2.53 | 495 | 2 |
| 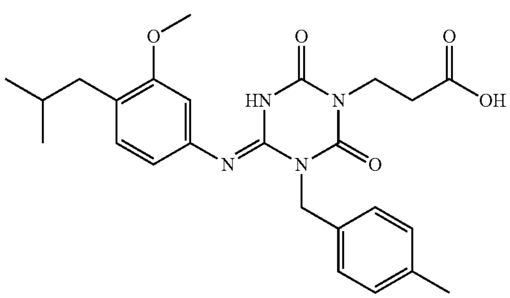 | I-1362 | 2.22 | 467 | 2 |
| 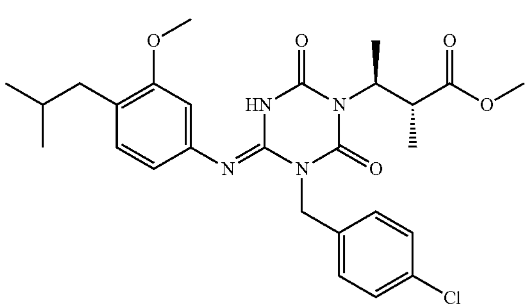 [SMILES: COC(=O)[C@H](C)[C@H](C)n1c(=O)[nH]/c(=N\c2ccc(CC(C)C)c(OC)c2)n(Cc2ccc(Cl)cc2)c1=O] | I-1363 | 2.71 | 529 | 2 |

TABLE 276-continued

| Structure | Compound No. | Retention Time (min) | [M + H] | Method |
|---|---|---|---|---|
| 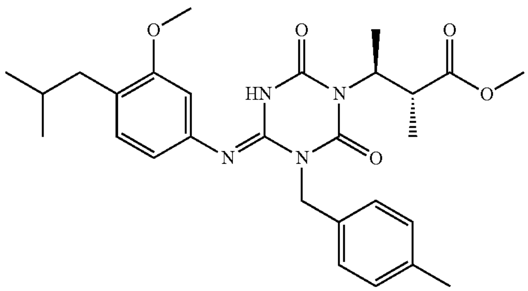 [SMILES: COC(=O)[C@H](C)[C@H](C)n1c(=O)[nH]/c(=N\c2ccc(CC(C)C)c(OC)c2)n(Cc2ccc(C)cc2)c1=O] | I-1364 | 2.65 | 509 | 2 |
| 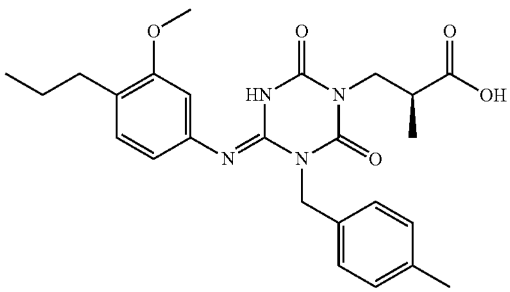 [SMILES: CCCc1ccc(/N=c2\[nH]c(=O)n(C[C@H](C)C(=O)O)c(=O)n2Cc2ccc(C)cc2)cc1OC] | I-1365 | 2.14 | 467 | 2 |

TABLE 277

| Structure | Compound No. | Retention Time (min) | [M + H] | Method |
|---|---|---|---|---|
| 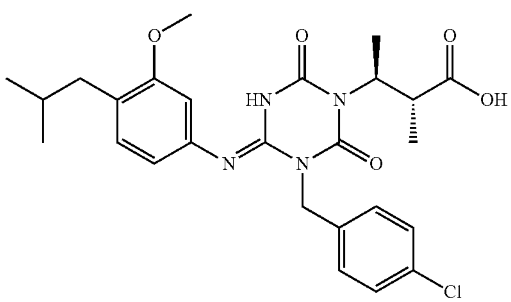 [SMILES: COc1cc(/N=c2\[nH]c(=O)n([C@@H](C)[C@@H](C)C(=O)O)c(=O)n2Cc2ccc(Cl)cc2)ccc1CC(C)C] | I-1366 | 2.46 | 515 | 2 |
| 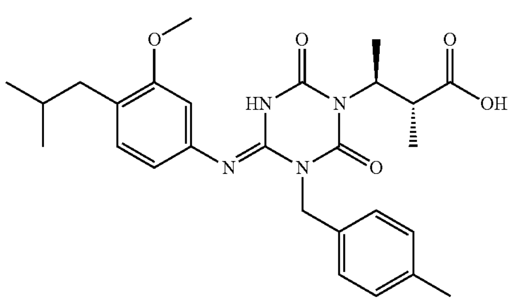 [SMILES: COc1cc(/N=c2\[nH]c(=O)n([C@@H](C)[C@@H](C)C(=O)O)c(=O)n2Cc2ccc(C)cc2)ccc1CC(C)C] | I-1367 | 2.40 | 495 | 2 |

TABLE 277-continued

| Structure | Compound No. | Retention Time (min) | [M + H] | Method |
|---|---|---|---|---|
| 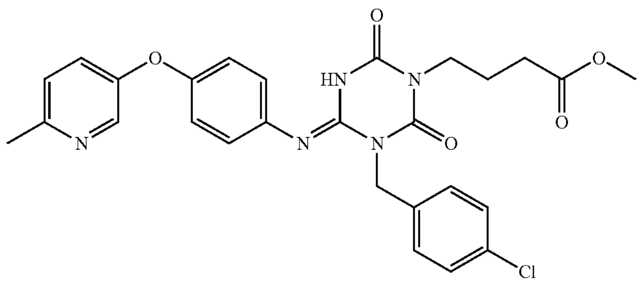 | I-1368 | 1.65 | 536 | 2 |
| 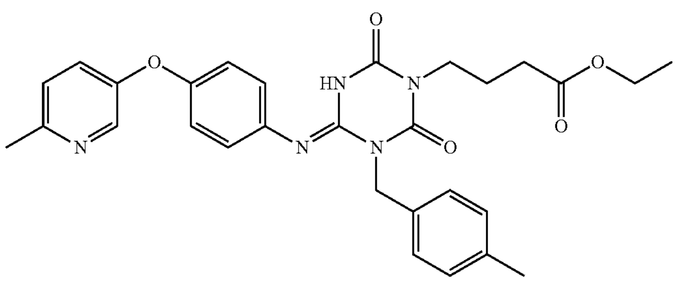 [SMILES: CCOC(=O)CCCn1c(=O)[nH]/c(=N\c2ccc(Oc3ccc(C)nc3)cc2)n(Cc2ccc(C)cc2)c1=O] | I-1369 | 1.69 | 530 | 2 |
| 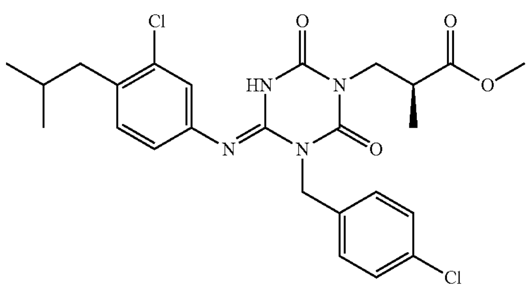 | I-1370 | 2.93 | 519 | 2 |

TABLE 278

| Structure | Compound No. | Retention Time (min) | [M + H] | Method |
|---|---|---|---|---|
| 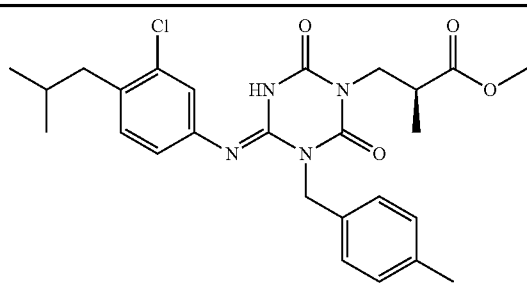 | I-1371 | 2.86 | 499 | 3 |
| 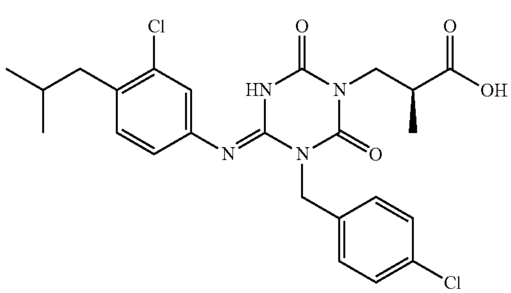 | I-1372 | 2.69 | 505 | 3 |

TABLE 278-continued
| Structure | Compound No. | Retention Time (min) | [M + H] | Method |
|---|---|---|---|---|
| 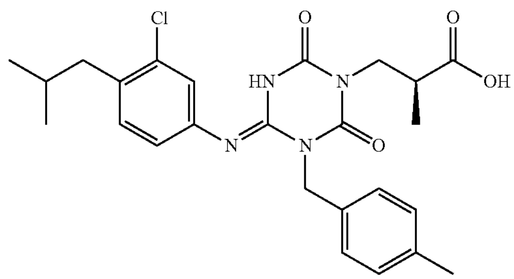 | I-1373 | 2.62 | 485 | 3 |
| 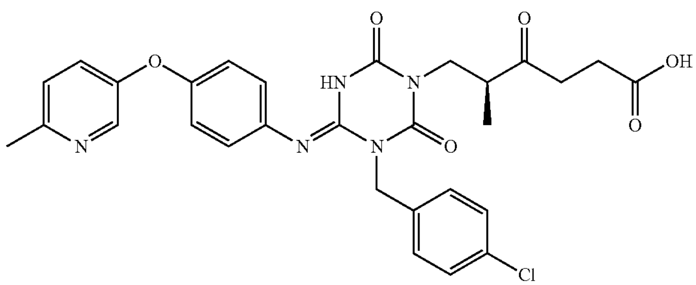 [SMILES: Cc1ccc(Oc2ccc(/N=c3\[nH]c(=O)n(C[C@H](C)C(=O)CCC(=O)O)c(=O)n3Cc3ccc(Cl)cc3)cc2)cn1] | I-1374 | 1.43 | 522 | 2 |
| 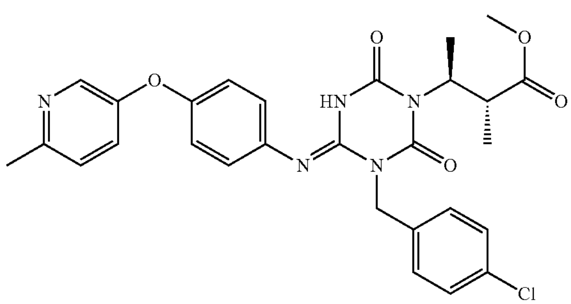 [SMILES: COC(=O)[C@H](C)[C@H](C)n1c(=O)[nH]/c(=N\c2ccc(Oc3ccc(C)nc3)cc2)n(Cc2ccc(Cl)cc2)c1=O] | I-1375 | 1.84 | 550 | 2 |
TABLE 279
| Structure | Compound No. | Retention Time (min) | [M + H] | Method |
|---|---|---|---|---|
| 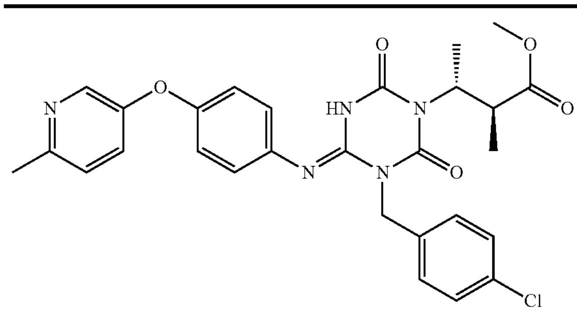 | I-1376 | 1.84 | 550 | 2 |
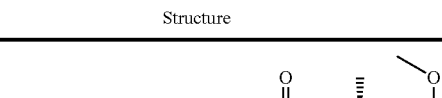

TABLE 279-continued

| Structure | Compound No. | Retention Time (min) | [M + H] | Method |
|---|---|---|---|---|
| 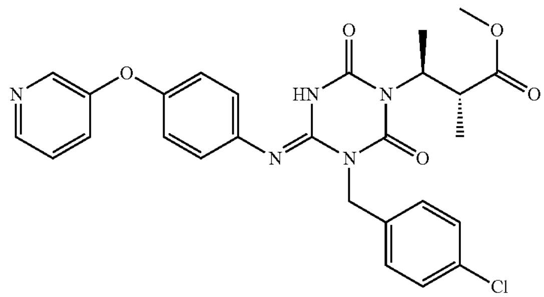 [SMILES: COC(=O)[C@H](C)[C@H](C)n1c(=O)[nH]/c(=N\c2ccc(Oc3cccnc3)cc2)n(Cc2ccc(Cl)cc2)c1=O] | I-1377 | 1.98 | 536 | 2 |
| 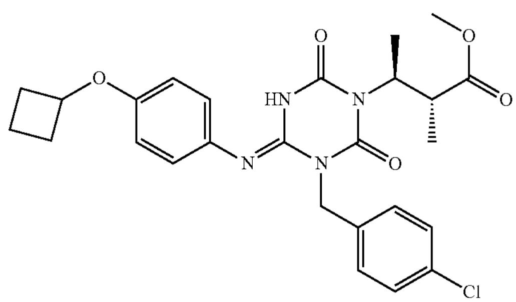 [SMILES: COC(=O)[C@H](C)[C@H](C)n1c(=O)[nH]/c(=N\c2ccc(OC3CCC3)cc2)n(Cc2ccc(Cl)cc2)c1=O] | I-1378 | 2.40 | 513 | 2 |
| 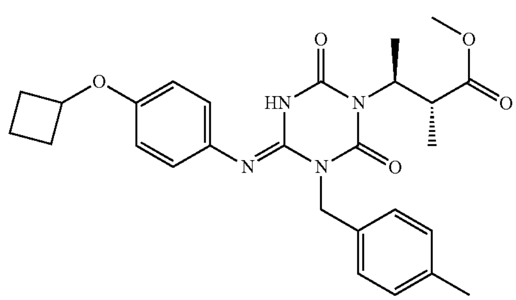 [SMILES: COC(=O)[C@H](C)[C@H](C)n1c(=O)[nH]/c(=N\c2ccc(OC3CCC3)cc2)n(Cc2ccc(C)cc2)c1=O] | I-1379 | 2.34 | 493 | 2 |
| 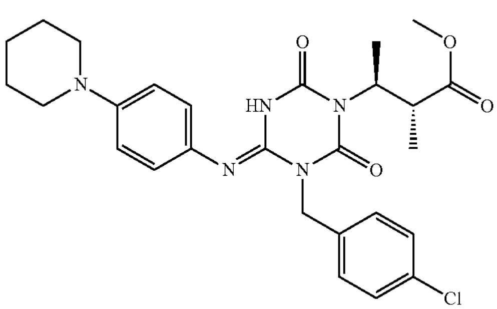 [SMILES: COC(=O)[C@H](C)[C@H](C)n1c(=O)[nH]/c(=N\c2ccc(N3CCCCC3)cc2)n(Cc2ccc(Cl)cc2)c1=O] | I-1380 | 1.65 | 526 | 2 |

TABLE 280

| Structure | Compound No. | Retention Time (min) | [M + H] | Method |
|---|---|---|---|---|
| 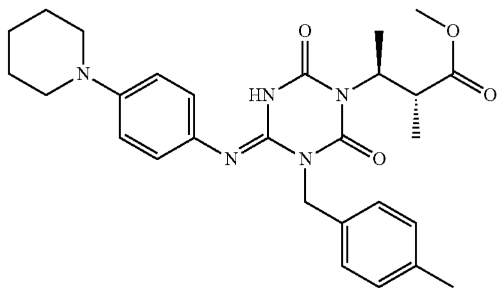 [SMILES: COC(=O)[C@H](C)[C@H](C)n1c(=O)[nH]/c(=N\c2ccc(N3CCCCC3)cc2)n(Cc2ccc(C)cc2)c1=O] | I-1381 | 1.58 | 506 | 2 |
| 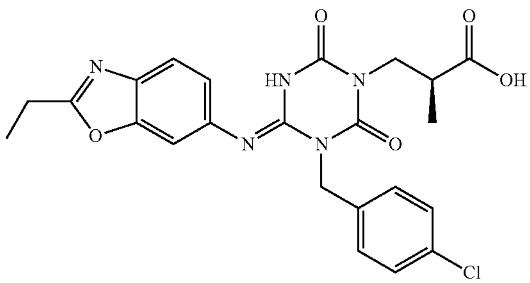 [SMILES: CCc1nc2ccc(/N=c3\[nH]c(=O)n(C[C@H](C)C(=O)O)c(=O)n3Cc3ccc(Cl)cc3)cc2o1] | I-1382 | 1.77 | 484 | 2 |
| 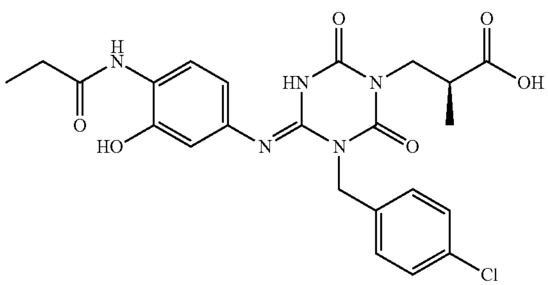 [SMILES: CCC(=O)Nc1ccc(/N=c2\[nH]c(=O)n(C[C@H](C)C(=O)O)c(=O)n2Cc2ccc(Cl)cc2)cc1O] | I-1383 | 1.51 | 502 | 2 |
| 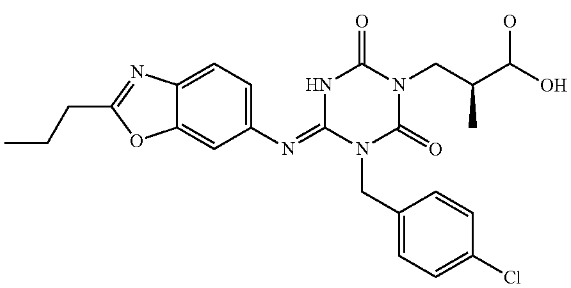 [SMILES: CCCc1nc2ccc(/N=c3\[nH]c(=O)n(C[C@H](C)C(O)O)c(=O)n3Cc3ccc(Cl)cc3)cc2o1] | I-1384 | 1.94 | 498 | 2 |
| 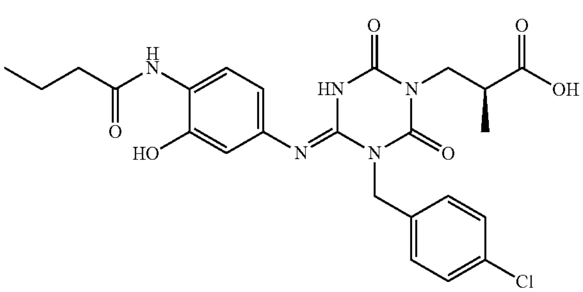 [SMILES: CCCC(=O)Nc1ccc(/N=c2\[nH]c(=O)n(C[C@H](C)C(=O)O)c(=O)n2Cc2ccc(Cl)cc2)cc1O] | I-1385 | 1.65 | 516 | 2 |

TABLE 281

| Structure | Compound No. | Retention Time (min) | [M + H] | Method |
|---|---|---|---|---|
| 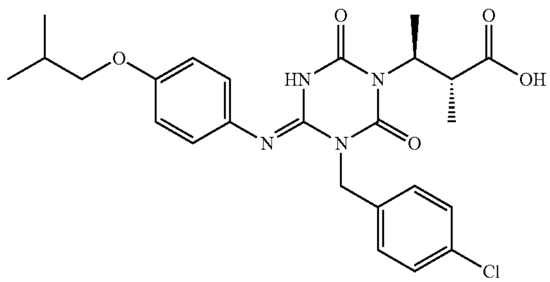 [SMILES: CC(C)COc1ccc(/N=c2\[nH]c(=O)n([C@@H](C)[C@@H](C)C(=O)O)c(=O)n2Cc2ccc(Cl)cc2)cc1] | I-1386 | 2.24 | 501 | 2 |
| 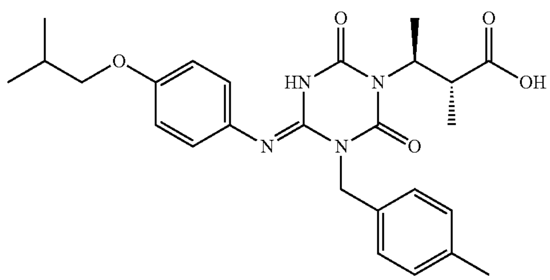 [SMILES: Cc1ccc(Cn2c(=O)n([C@@H](C)[C@@H](C)C(=O)O)c(=O)[nH]/c2=N\c2ccc(OCC(C)C)cc2)cc1] | I-1387 | 2.18 | 481 | 2 |
| 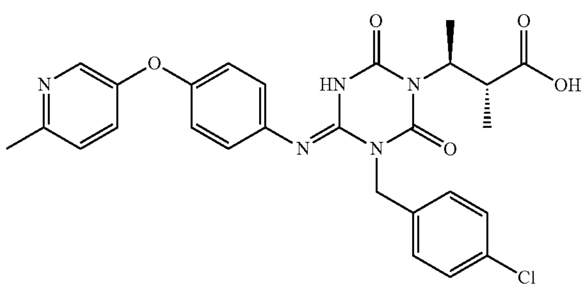 [SMILES: Cc1ccc(Oc2ccc(/N=c3\[nH]c(=O)n([C@@H](C)[C@@H](C)C(=O)O)c(=O)n3Cc3ccc(Cl)cc3)cc2)cn1] | I-1388 | 1.55 | 536 | 2 |
| 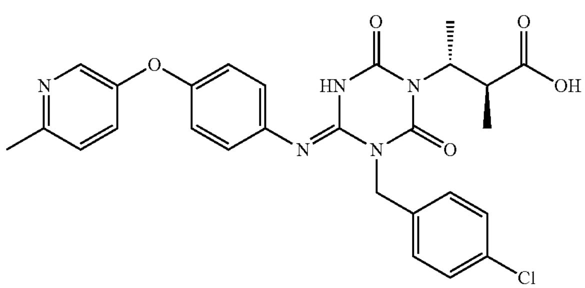 [SMILES: Cc1ccc(Oc2ccc(/N=c3\[nH]c(=O)n([C@H](C)[C@H](C)C(=O)O)c(=O)n3Cc3ccc(Cl)cc3)cc2)cn1] | I-1389 | 1.56 | 536 | 2 |
| 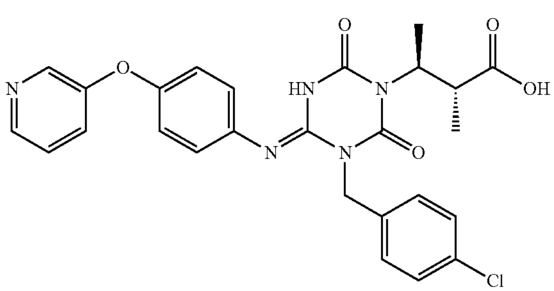 [SMILES: C[C@@H](C(=O)O)[C@H](C)n1c(=O)[nH]/c(=N\c2ccc(Oc3cccnc3)cc2)n(Cc2ccc(Cl)cc2)c1=O] | I-1390 | 1.67 | 522 | 2 |

TABLE 282

| Structure | Compound No. | Retention Time (min) | [M + H] | Method |
|---|---|---|---|---|
| (structure) | I-1391 | 2.12 | 499 | 2 |
| (structure) | I-1392 | 2.06 | 479 | 2 |
| (structure) | I-1393 | 1.40 | 512 | 2 |
| (structure) | I-1394 | 1.31 | 492 | 2 |
| (structure) | I-1395 | 1.34 | 502 | 2 |

TABLE 283

| Structure | Compound No. | Retention Time (min) | [M + H] | Method |
|---|---|---|---|---|
| (structure) | I-1396 | 1.51 | 536 | 2 |
| (structure) | I-1397 | 1.55 | 530 | 2 |
| (structure) | I-1398 | 2.46 | 514 | 2 |
| (structure) | I-1399 | 2.54 | 534 | 2 |
| (structure) | I-1400 | 2.58 | 493 | 3 |

TABLE 284

| Structure | Compound No. | Retention Time (min) | [M + H] | Method |
|---|---|---|---|---|
| 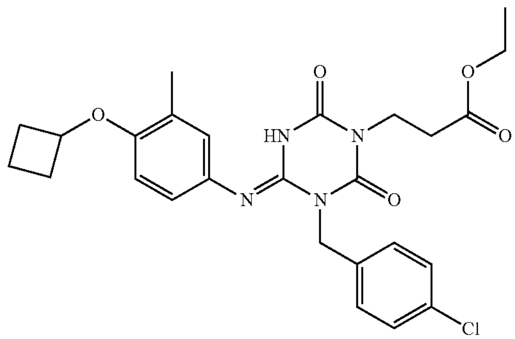 | I-1401 | 2.63 | 513 | 3 |
| 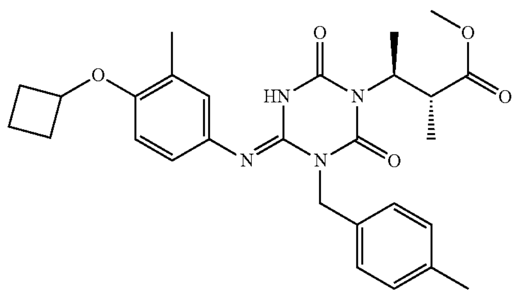 [SMILES: COC(=O)[C@H](C)[C@H](C)n1c(=O)[nH]/c(=N\c2ccc(OC3CCC3)c(C)c2)n(Cc2ccc(C)cc2)c1=O] | I-1402 | 2.69 | 507 | 3 |
| 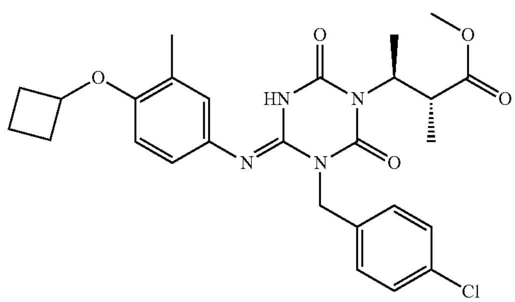 [SMILES: COC(=O)[C@H](C)[C@H](C)n1c(=O)[nH]/c(=N\c2ccc(OC3CCC3)c(C)c2)n(Cc2ccc(Cl)cc2)c1=O] | I-1403 | 2.74 | 527 | 3 |
| 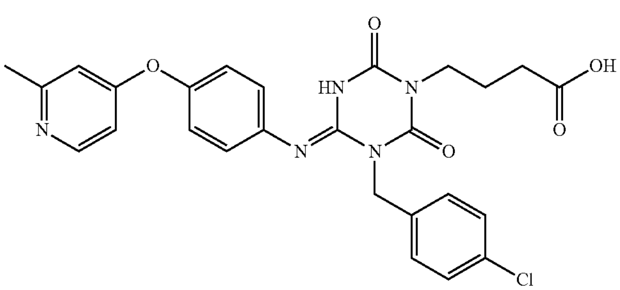 [SMILES: Cc1cc(Oc2ccc(/N=c3\[nH]c(=O)n(CCCC(=O)O)c(=O)n3Cc3ccc(Cl)cc3)cc2)ccn1] | I-1404 | 1.30 | 522 | 2 |
| 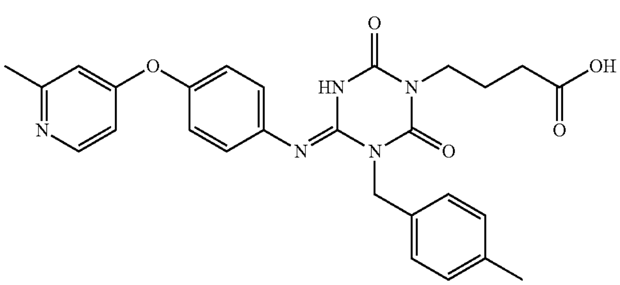 [SMILES: Cc1ccc(Cn2c(=O)n(CCCC(=O)O)c(=O)[nH]/c2=N\c2ccc(Oc3ccnc(C)c3)cc2)cc1] | I-1405 | 1.24 | 502 | 2 |

TABLE 285

| Structure | Compound No. | Retention Time (min) | [M + H] | Method |
|---|---|---|---|---|
| 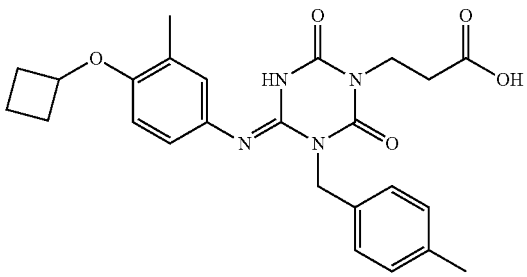 [SMILES: Cc1ccc(Cn2c(=O)n(CCC(=O)O)c(=O)[nH]/c2=N\c2ccc(OC3CCC3)c(C)c2)cc1] | I-1406 | 2.06 | 465 | 2 |
| 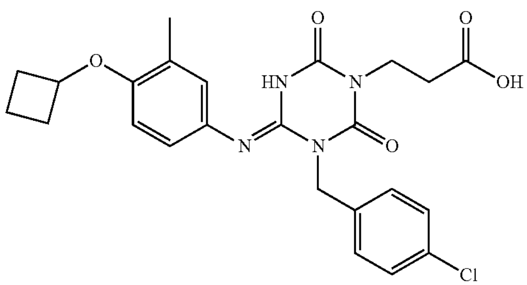 | I-1407 | 2.11 | 485 | 2 |
| 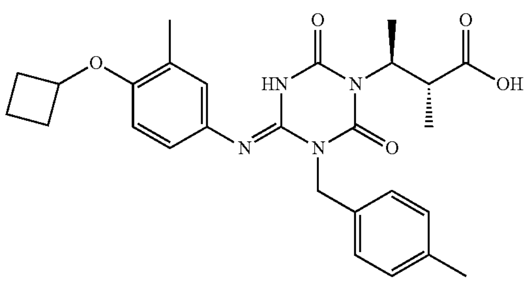 [SMILES: Cc1ccc(Cn2c(=O)n([C@@H](C)[C@@H](C)C(=O)O)c(=O)[nH]/c2=N\c2ccc(OC3CCC3)c(C)c2)cc1] | I-1408 | 2.22 | 493 | 2 |
| 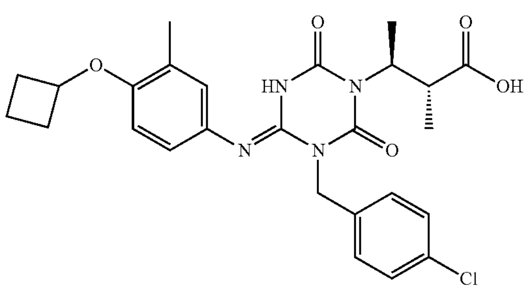 [SMILES: Cc1cc(/N=c2\[nH]c(=O)n([C@@H](C)[C@@H](C)C(=O)O)c(=O)n2Cc2ccc(Cl)cc2)ccc1OC1CCC1] | I-1409 | 2.28 | 513 | 2 |
| 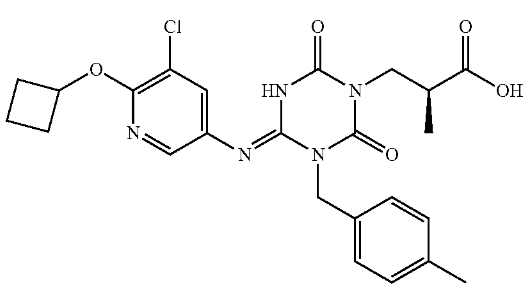 [SMILES: Cc1ccc(Cn2c(=O)n(C[C@H](C)C(=O)O)c(=O)[nH]/c2=N\c2cnc(OC3CCC3)c(Cl)c2)cc1] | I-1410 | 2.21 | 500 | 2 |

TABLE 286

| Structure | Compound No. | Retention Time (min) | [M + H] | Method |
|---|---|---|---|---|
| (structure) | I-1411 | 2.29 | 520 | 2 |
| (structure) | I-1412 | 1.82 | 512 | 2 |
| (structure) | I-1413 | 1.33 | 522 | 2 |
| (structure) | I-1414 | 2.01 | 534 | 3 |

TABLE 286-continued

| Structure | Compound No. | Retention Time (min) | [M + H] | Method |
|---|---|---|---|---|
| 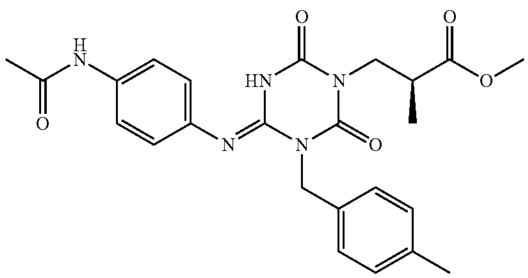 [SMILES: COC(=O)[C@@H](C)Cn1c(=O)[nH]/c(=N\c2ccc(NC(C)=O)cc2)n(Cc2ccc(C)cc2)c1=O] | I-1415 | 1.79 | 466 | 3 |

TABLE 287

| Structure | Compound No. | Retention Time (min) | [M + H] | Method |
|---|---|---|---|---|
| 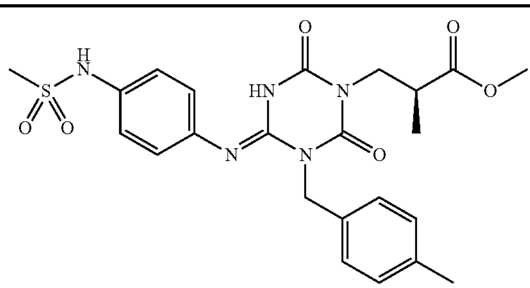 | I-1416 | 1.87 | 502 | 3 |
| 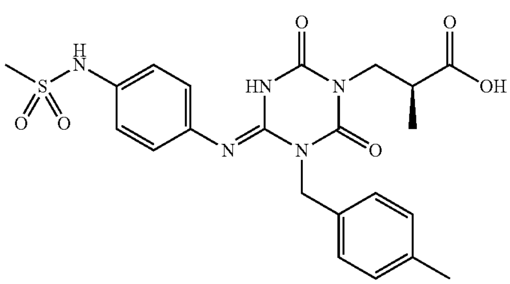 [SMILES: Cc1ccc(Cn2c(=O)n(C[C@H](C)C(=O)O)c(=O)[nH]/c2=N\c2ccc(NS(C)(=O)=O)cc2)cc1] | I-1417 | 1.63 | 488 | 3 |
| 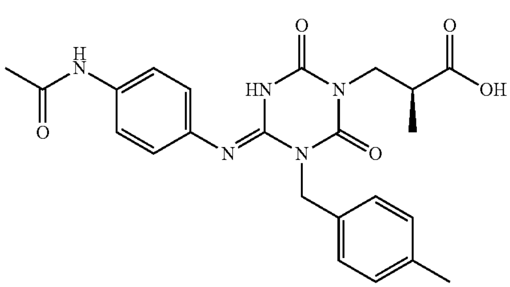 [SMILES: CC(=O)Nc1ccc(/N=c2\[nH]c(=O)n(C[C@H](C)C(=O)O)c(=O)n2Cc2ccc(C)cc2)cc1] | I-1418 | 1.55 | 452 | 3 |
| 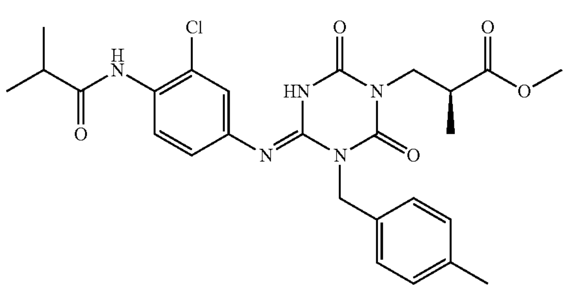 [SMILES: COC(=O)[C@@H](C)Cn1c(=O)[nH]/c(=N\c2ccc(NC(=O)C(C)C)c(Cl)c2)n(Cc2ccc(C)cc2)c1=O] | I-1419 | 2.26 | 528 | 3 |

TABLE 287-continued

| Structure | Compound No. | Retention Time (min) | [M + H] | Method |
|---|---|---|---|---|
| 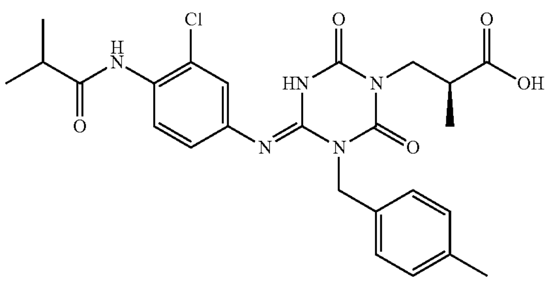 [SMILES: Cc1ccc(Cn2c(=O)n(C[C@H](C)C(=O)O)c(=O)[nH]/c2=N\c2ccc(NC(=O)C(C)C)c(Cl)c2)cc1] | I-1420 | 2.01 | 514 | 3 |

TABLE 288

| Structure | Compound No. | Retention Time (min) | [M + H] | Method |
|---|---|---|---|---|
| 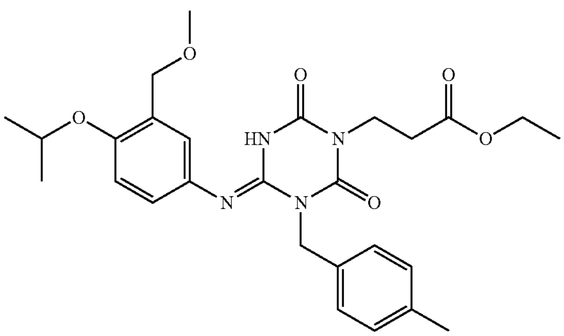 [SMILES: CCOC(=O)CCn1c(=O)[nH]/c(=N\c2ccc(OC(C)C)c(COC)c2)n(Cc2ccc(C)cc2)c1=O] | I-1421 | 2.19 | 511 | 2 |
| 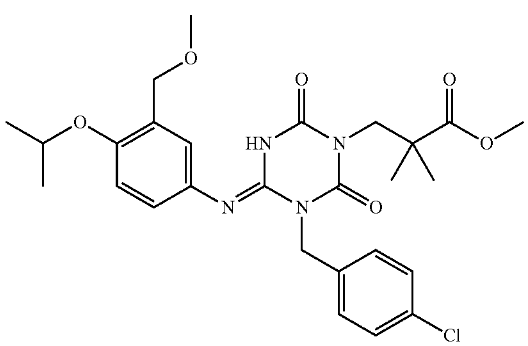 [SMILES: COCc1cc(/N=c2\[nH]c(=O)n(CC(C)(C)C(=O)OC)c(=O)n2Cc2ccc(Cl)cc2)ccc1OC(C)C] | I-1422 | 2.34 | 545 | 2 |
| 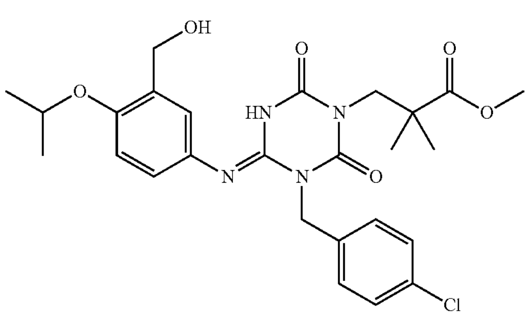 [SMILES: COC(=O)C(C)(C)Cn1c(=O)[nH]/c(=N\c2ccc(OC(C)C)c(CO)c2)n(Cc2ccc(Cl)cc2)c1=O] | I-1423 | 2.05 | 531 | 2 |

TABLE 288-continued

| Structure | Compound No. | Retention Time (min) | [M + H] | Method |
|---|---|---|---|---|
| (structure) | I-1424 | 1.91 | 497 | 3 |
| (structure) | I-1425 | 2.17 | 539 | 3 |

TABLE 289

| Structure | Compound No. | Retention Time (min) | [M + H] | Method |
|---|---|---|---|---|
| (structure) | I-1426 | 2.87 | 499 | 3 |
| (structure) | I-1427 | 2.55 | 471 | 3 |

TABLE 289-continued

| Structure | Compound No. | Retention Time (min) | [M + H] | Method |
|---|---|---|---|---|
| 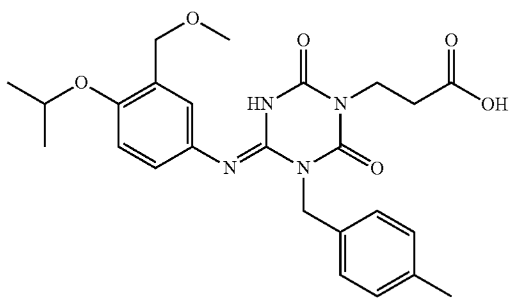 [SMILES: COCc1cc(/N=c2\[nH]c(=O)n(CCC(=O)O)c(=O)n2Cc2ccc(C)cc2)ccc1OC(C)C] | I-1428 | 1.86 | 483 | 2 |
| 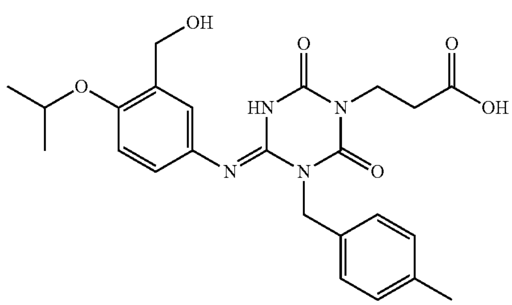 [SMILES: Cc1ccc(Cn2c(=O)n(CCC(=O)O)c(=O)[nH]/c2=N\c2ccc(OC(C)C)c(CO)c2)cc1] | I-1429 | 1.59 | 469 | 2 |
| 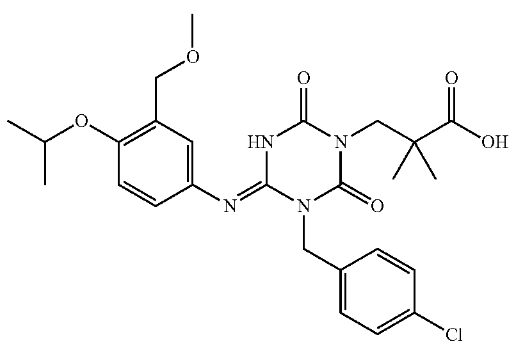 [SMILES: COCc1cc(/N=c2\[nH]c(=O)n(CC(C)(C)C(=O)O)c(=O)n2Cc2ccc(Cl)cc2)ccc1OC(C)C] | I-1430 | 2.06 | 531 | 2 |

TABLE 290

| Structure | Compound No. | Retention Time (min) | [M + H] | Method |
|---|---|---|---|---|
| 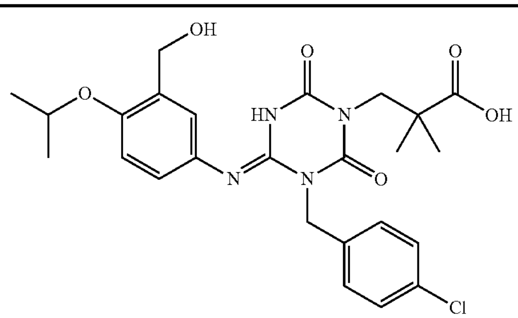 | I-1431 | 1.80 | 517 | 2 |

TABLE 290-continued

| Structure | Compound No. | Retention Time (min) | [M + H] | Method |
|---|---|---|---|---|
| 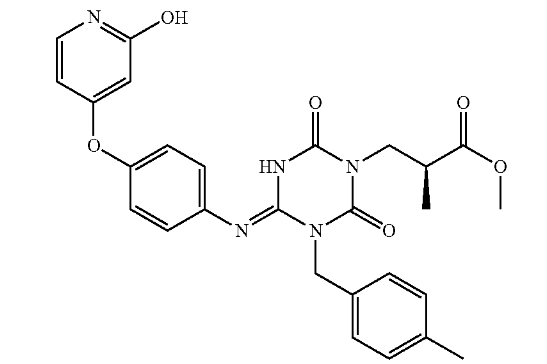 [SMILES: COC(=O)[C@@H](C)Cn1c(=O)[nH]/c(=N\c2ccc(Oc3ccnc(O)c3)cc2)n(Cc2ccc(C)cc2)c1=O] | I-1432 | 1.66 | 518 | 2 |
| 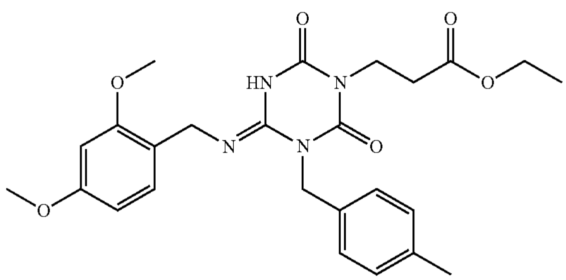 [SMILES: CCOC(=O)CCn1c(=O)[nH]/c(=N\Cc2ccc(OC)cc2OC)n(Cc2ccc(C)cc2)c1=O] | I-1433 | 1.94 | 483 | 2 |
| 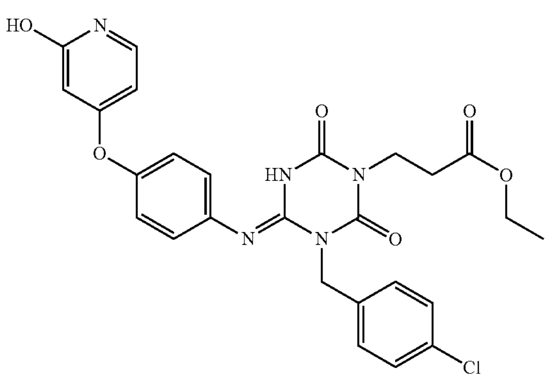 [SMILES: CCOC(=O)CCn1c(=O)[nH]/c(=N\c2ccc(Oc3ccnc(O)c3)cc2)n(Cc2ccc(Cl)cc2)c1=O] | I-1434 | 1.76 | 538 | 2 |
| 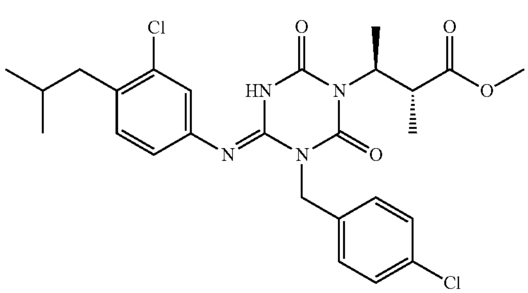 [SMILES: COC(=O)[C@H](C)[C@H](C)n1c(=O)[nH]/c(=N\c2ccc(CC(C)C)c(Cl)c2)n(Cc2ccc(Cl)cc2)c1=O] | I-1435 | 2.86 | 533 | 2 |

TABLE 291

| Structure | Compound No. | Retention Time (min) | [M + H] | Method |
|---|---|---|---|---|
| 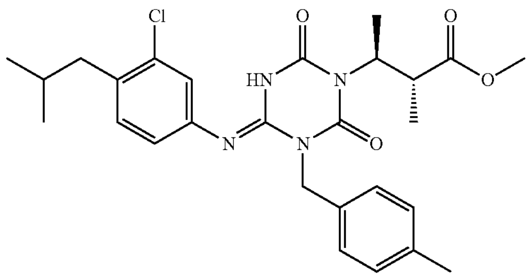 [SMILES: COC(=O)[C@H](C)[C@H](C)n1c(=O)[nH]/c(=N\c2ccc(CC(C)C)c(Cl)c2)n(Cc2ccc(C)cc2)c1=O] | I-1436 | 2.77 | 513 | 2 |
| 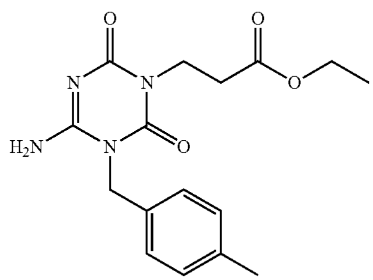 [SMILES: CCOC(=O)CCn1c(=O)nc(N)n(Cc2ccc(C)cc2)c1=O] | I-1437 | 1.39 | 333 | 2 |
| 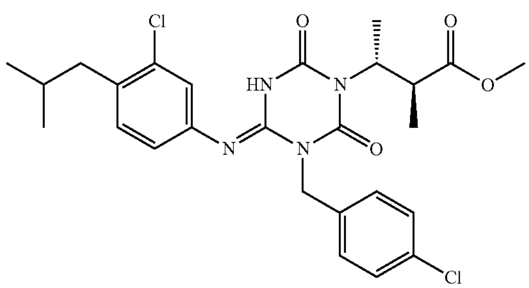 | I-1438 | 2.84 | 533 | 2 |
| 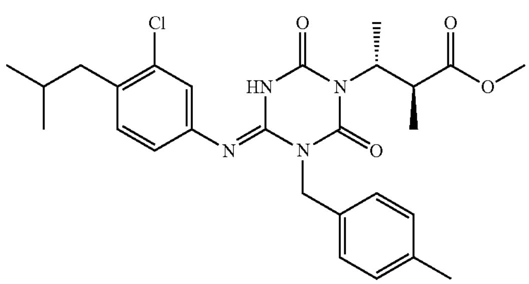 [SMILES: COC(=O)[C@@H](C)[C@@H](C)n1c(=O)[nH]/c(=N\c2ccc(CC(C)C)c(Cl)c2)n(Cc2ccc(C)cc2)c1=O] | I-1439 | 2.78 | 513 | 2 |
| 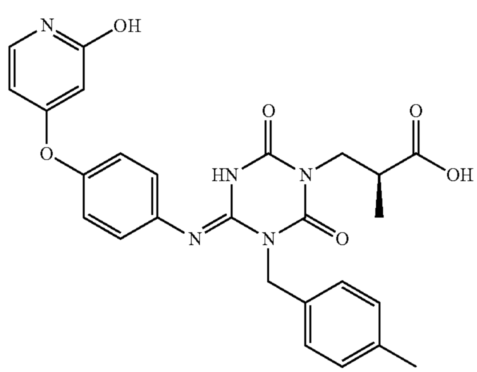 [SMILES: Cc1ccc(Cn2c(=O)n(C[C@H](C)C(=O)O)c(=O)[nH]/c2=N\c2ccc(Oc3ccnc(O)c3)cc2)cc1] | I-1440 | 1.47 | 504 | 2 |

TABLE 292

| Structure | Compound No. | Retention Time (min) | [M + H] | Method |
|---|---|---|---|---|
| (structure) | I-1441 | 1.45 | 510 | 2 |
| (structure) | I-1442 | 2.58 | 519 | 2 |
| (structure) | I-1443 | 2.51 | 499 | 2 |
| (structure) | I-1444 | 2.51 | 499 | 2 |
| (structure) | I-1445 | 2.62 | 519 | 2 |

TABLE 293

| Structure | Compound No. | Retention Time (min) | [M + H] | Method |
|---|---|---|---|---|
| (structure) | I-1446 | 2.23 | 382 | 2 |
| (structure) | I-1447 | 2.74 | 513 | 2 |
| (structure) | I-1448 | 2.75 | 525 | 2 |
| (structure) | I-1449 | 2.55 | 519 | 2 |
| (structure) | I-1450 | 2.64 | 658 | 2 |

TABLE 294

| Structure | Compound No. | Retention Time (min) | [M + H] | Method |
|---|---|---|---|---|
| 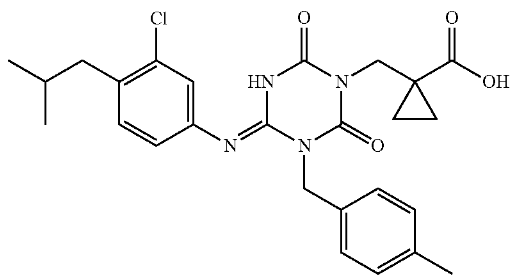 [SMILES: Cc1ccc(Cn2c(=O)n(CC3(C(=O)O)CC3)c(=O)[nH]/c2=N\c2ccc(CC(C)C)c(Cl)c2)cc1] | I-1451 | 2.45 | 497 | 2 |
| 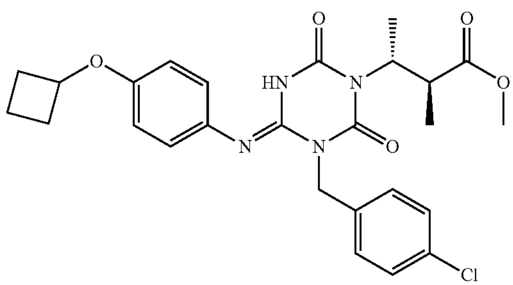 [SMILES: COC(=O)[C@@H](C)[C@@H](C)n1c(=O)[nH]/c(=N\c2ccc(OC3CCC3)cc2)n(Cc2ccc(Cl)cc2)c1=O] | I-1452 | 2.36 | 513 | 2 |
| 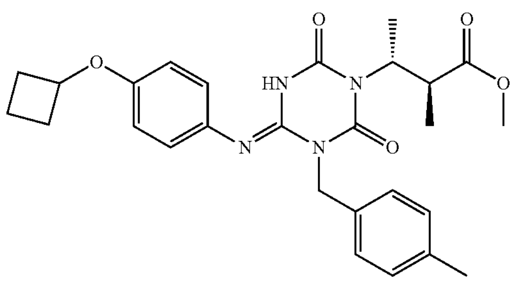 [SMILES: COC(=O)[C@@H](C)[C@@H](C)n1c(=O)[nH]/c(=N\c2ccc(OC3CCC3)cc2)n(Cc2ccc(C)cc2)c1=O] | I-1453 | 2.32 | 493 | 2 |
| 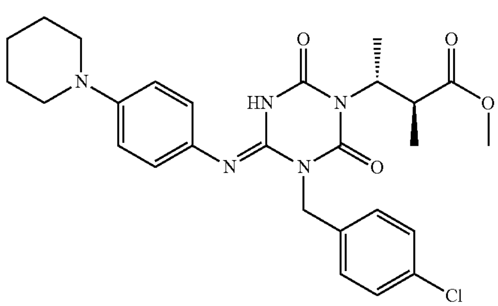 [SMILES: COC(=O)[C@@H](C)[C@@H](C)n1c(=O)[nH]/c(=N\c2ccc(N3CCCCC3)cc2)n(Cc2ccc(Cl)cc2)c1=O] | I-1454 | 1.66 | 526 | 2 |
| 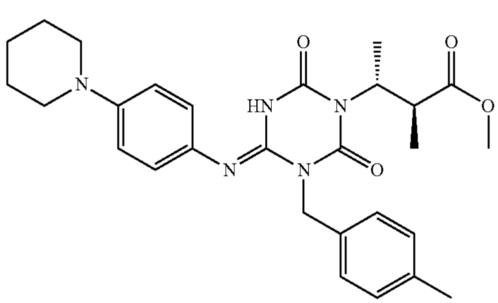 [SMILES: COC(=O)[C@@H](C)[C@@H](C)n1c(=O)[nH]/c(=N\c2ccc(N3CCCCC3)cc2)n(Cc2ccc(C)cc2)c1=O] | I-1455 | 1.58 | 506 | 2 |

TABLE 295

| Structure | Compound No. | Retention Time (min) | [M + H] | Method |
|---|---|---|---|---|
| 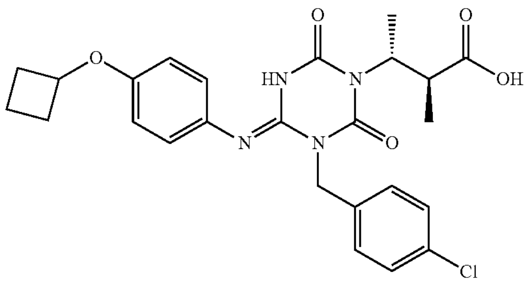 [SMILES: C[C@H](C(=O)O)[C@@H](C)n1c(=O)[nH]/c(=N\c2ccc(OC3CCC3)cc2)n(Cc2ccc(Cl)cc2)c1=O] | I-1456 | 2.11 | 499 | 2 |
| 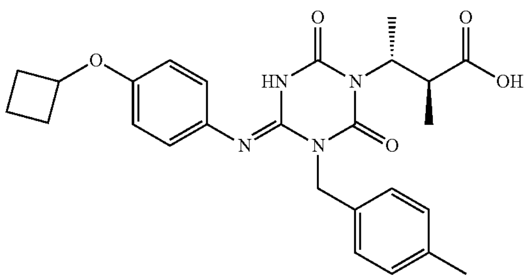 [SMILES: Cc1ccc(Cn2c(=O)n([C@H](C)[C@H](C)C(=O)O)c(=O)[nH]/c2=N\c2ccc(OC3CCC3)cc2)cc1] | I-1457 | 2.03 | 479 | 2 |
| 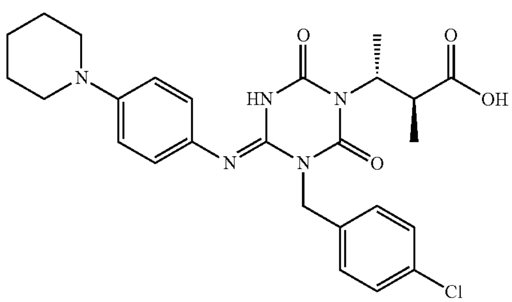 [SMILES: C[C@H](C(=O)O)[C@@H](C)n1c(=O)[nH]/c(=N\c2ccc(N3CCCCC3)cc2)n(Cc2ccc(Cl)cc2)c1=O] | I-1458 | 1.39 | 512 | 2 |
| 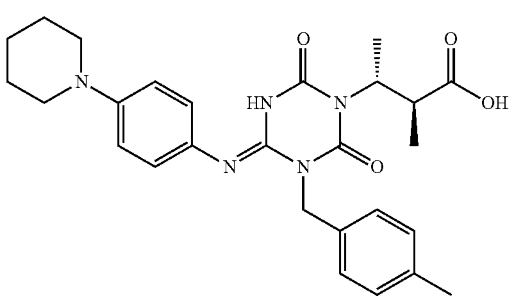 [SMILES: Cc1ccc(Cn2c(=O)n([C@H](C)[C@H](C)C(=O)O)c(=O)[nH]/c2=N\c2ccc(N3CCCCC3)cc2)cc1] | I-1459 | 1.32 | 492 | 2 |
| 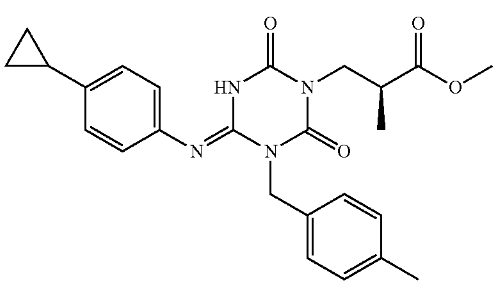 [SMILES: COC(=O)[C@@H](C)Cn1c(=O)[nH]/c(=N\c2ccc(C3CC3)cc2)n(Cc2ccc(C)cc2)c1=O] | I-1460 | 2.15 | 449 | 2 |

TABLE 296

| Structure | Compound No. | Retention Time (min) | [M + H] | Method |
|---|---|---|---|---|
| 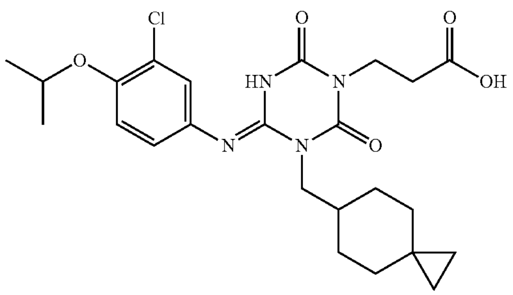 [SMILES: CC(C)Oc1ccc(/N=c2\[nH]c(=O)n(CCC(=O)O)c(=O)n2CC2CCC3(CC2)CC3)cc1Cl] | I-1461 | 2.18 | 491 | 2 |
| 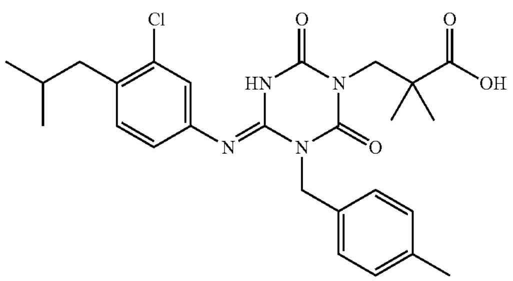 [SMILES: Cc1ccc(Cn2c(=O)n(CC(C)(C)C(=O)O)c(=O)[nH]/c2=N\c2ccc(CC(C)C)c(Cl)c2)cc1] | I-1462 | 2.48 | 499 | 2 |
| 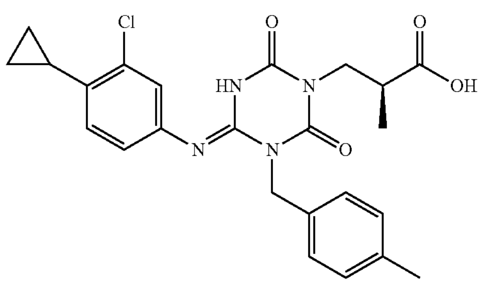 [SMILES: Cc1ccc(Cn2c(=O)n(C[C@H](C)C(=O)O)c(=O)[nH]/c2=N\c2ccc(C3CC3)c(Cl)c2)cc1] | I-1463 | 1.88 | 435 | 2 |
| 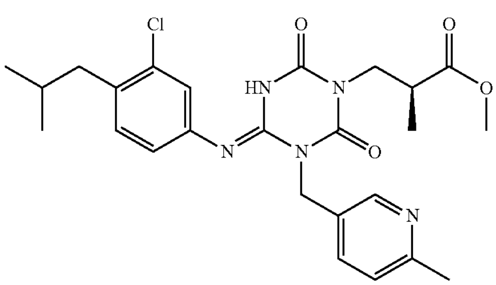 [SMILES: COC(=O)[C@@H](C)Cn1c(=O)[nH]/c(=N\c2ccc(CC(C)C)c(Cl)c2)n(Cc2ccc(C)nc2)c1=O] | I-1464 | 1.67 | 500 | 2 |
| 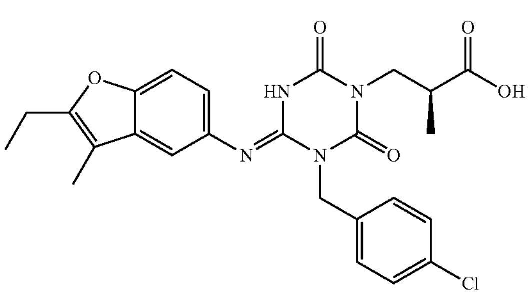 [SMILES: CCc1oc2ccc(/N=c3\[nH]c(=O)n(C[C@H](C)C(=O)O)c(=O)n3Cc3ccc(Cl)cc3)cc2c1C] | I-1465 | 2.15 | 497 | 2 |

TABLE 297

| Structure | Compound No. | Retention Time (min) | [M + H] | Method |
|---|---|---|---|---|
| (structure) | I-1466 | 1.76 | 471 | 2 |
| (structure) | I-1467 | 1.85 | 500 | 2 |
| (structure) | I-1468 | 1.76 | 480 | 2 |
| (structure) | I-1469 | 1.84 | 500 | 2 |
| (structure) | I-1470 | 1.75 | 480 | 2 |

TABLE 298

| Structure | Compound No. | Retention Time (min) | [M + H] | Method |
|---|---|---|---|---|
| 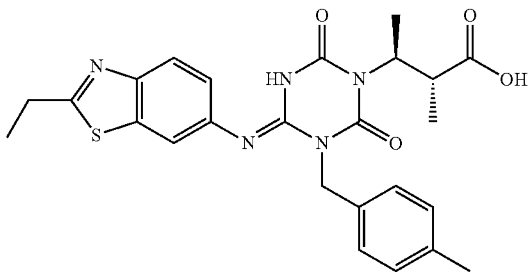 [SMILES: CCc1nc2ccc(/N=c3\[nH]c(=O)n([C@@H](C)[C@@H](C)C(=O)O)c(=O)n3Cc3ccc(C)cc3)cc2s1] | I-1471 | 1.99 | 514 | 2 |
| 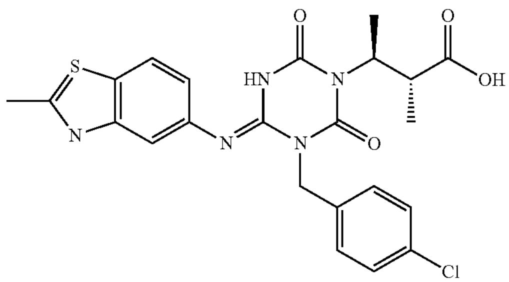 | I-1472 | 1.86 | 500 | 2 |
| 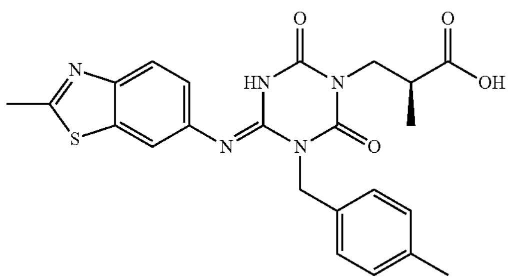 [SMILES: Cc1ccc(Cn2c(=O)n(C[C@H](C)C(=O)O)c(=O)[nH]/c2=N\c2ccc3nc(C)sc3c2)cc1] | I-1473 | 1.63 | 466 | 2 |
| 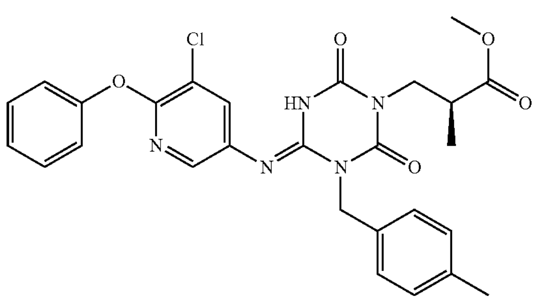 [SMILES: COC(=O)[C@@H](C)Cn1c(=O)[nH]/c(=N\c2cnc(Oc3ccccc3)c(Cl)c2)n(Cc2ccc(C)cc2)c1=O] | I-1474 | 2.39 | 536 | 2 |
| 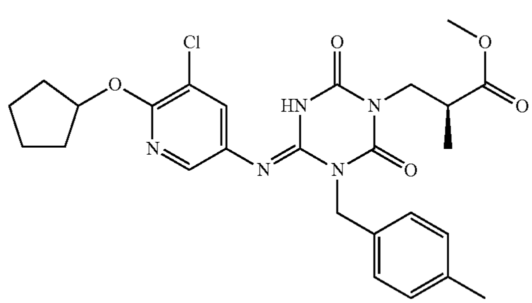 [SMILES: COC(=O)[C@@H](C)Cn1c(=O)[nH]/c(=N\c2cnc(OC3CCCC3)c(Cl)c2)n(Cc2ccc(C)cc2)c1=O] | I-1475 | 2.56 | 528 | 2 |

TABLE 299

| Structure | Compound No. | Retention Time (min) | [M + H] | Method |
|---|---|---|---|---|
| 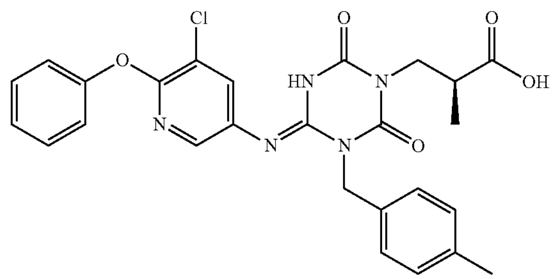 [SMILES: Cc1ccc(Cn2c(=O)n(C[C@H](C)C(=O)O)c(=O)[nH]/c2=N\c2cnc(Oc3ccccc3)c(Cl)c2)cc1] | I-1476 | 2.15 | 522 | 2 |
| 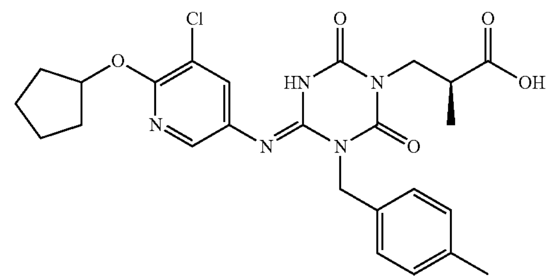 [SMILES: Cc1ccc(Cn2c(=O)n(C[C@H](C)C(=O)O)c(=O)[nH]/c2=N\c2cnc(OC3CCCC3)c(Cl)c2)cc1] | I-1477 | 2.31 | 514 | 2 |
| 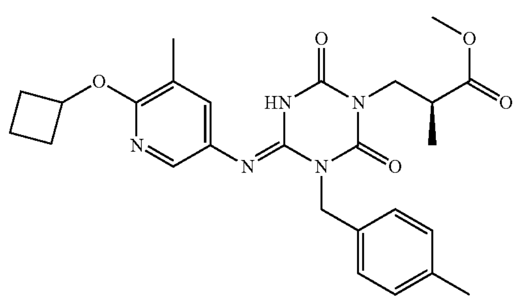 [SMILES: COC(=O)[C@@H](C)Cn1c(=O)[nH]/c(=N\c2cnc(OC3CCC3)c(C)c2)n(Cc2ccc(C)cc2)c1=O] | I-1478 | 2.28 | 494 | 2 |
| 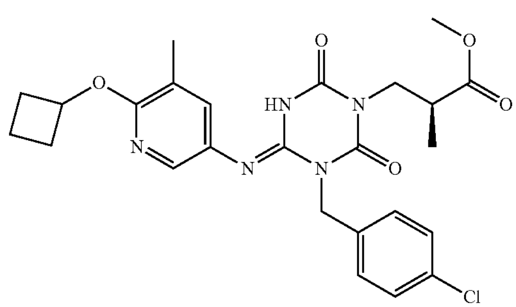 [SMILES: COC(=O)[C@@H](C)Cn1c(=O)[nH]/c(=N\c2cnc(OC3CCC3)c(C)c2)n(Cc2ccc(Cl)cc2)c1=O] | I-1479 | 2.33 | 514 | 2 |
| 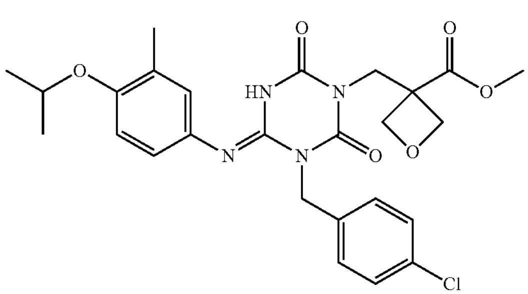 [SMILES: COC(=O)C1(Cn2c(=O)[nH]/c(=N\c3ccc(OC(C)C)c(C)c3)n(Cc3ccc(Cl)cc3)c2=O)COC1] | I-1480 | 2.18 | 529 | 2 |

TABLE 300

| Structure | Compound No. | Retention Time (min) | [M + H] | Method |
|---|---|---|---|---|
| 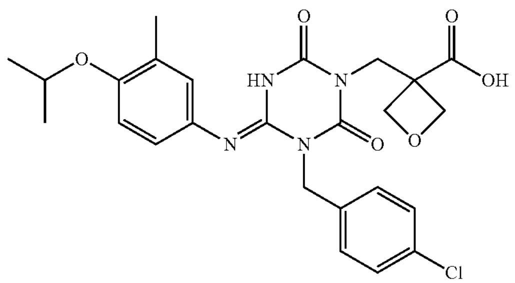 [SMILES: Cc1cc(/N=c2\[nH]c(=O)n(CC3(C(=O)O)COC3)c(=O)n2Cc2ccc(Cl)cc2)ccc1OC(C)C] | I-1481 | 1.94 | 515 | 2 |
| 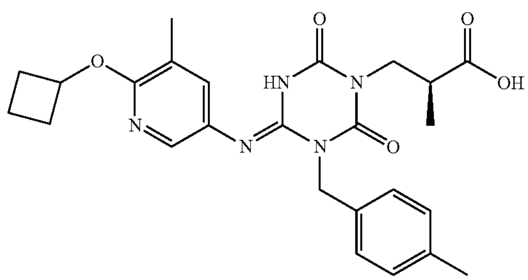 [SMILES: Cc1ccc(Cn2c(=O)n(C[C@H](C)C(=O)O)c(=O)[nH]/c2=N\c2cnc(OC3CCC3)c(C)c2)cc1] | I-1482 | 2.03 | 480 | 2 |
| 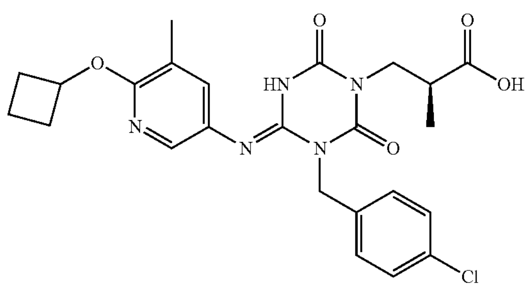 [SMILES: Cc1cc(/N=c2\[nH]c(=O)n(C[C@H](C)C(=O)O)c(=O)n2Cc2ccc(Cl)cc2)cnc1OC1CCC1] | I-1483 | 2.08 | 500 | 2 |
| 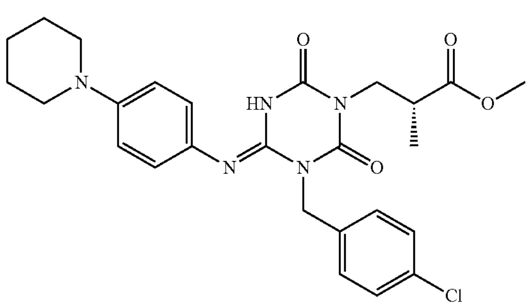 [SMILES: COC(=O)[C@H](C)Cn1c(=O)[nH]/c(=N\c2ccc(N3CCCCC3)cc2)n(Cc2ccc(Cl)cc2)c1=O] | I-1484 | 1.50 | 512 | 2 |
| 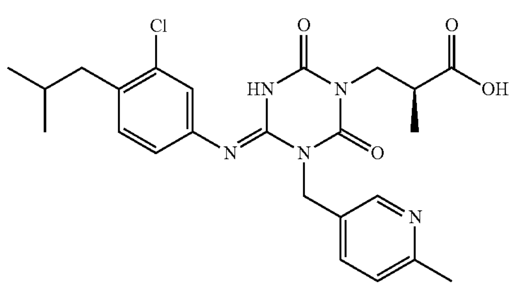 [SMILES: Cc1ccc(Cn2c(=O)n(C[C@H](C)C(=O)O)c(=O)[nH]/c2=N\c2ccc(CC(C)C)c(Cl)c2)cn1] | I-1485 | 1.49 | 486 | 2 |

TABLE 301

| Structure | Compound No. | Retention Time (min) | [M + H] | Method |
|---|---|---|---|---|
| 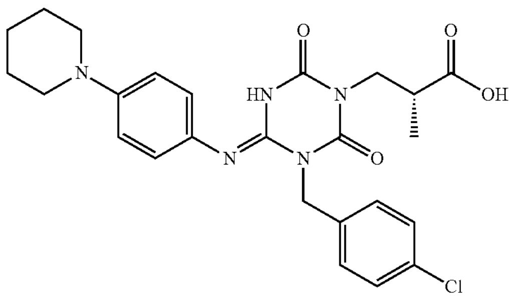 [SMILES: C[C@H](Cn1c(=O)[nH]/c(=N\c2ccc(N3CCCCC3)cc2)n(Cc2ccc(Cl)cc2)c1=O)C(=O)O] | I-1486 | 1.31 | 498 | 2 |
| 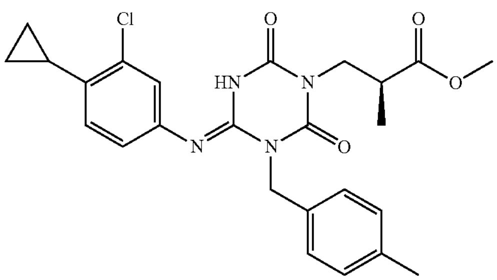 [SMILES: COC(=O)[C@@H](C)Cn1c(=O)[nH]/c(=N\c2ccc(C3CC3)c(Cl)c2)n(Cc2ccc(C)cc2)c1=O] | I-1487 | 2.40 | 483 | 2 |
| 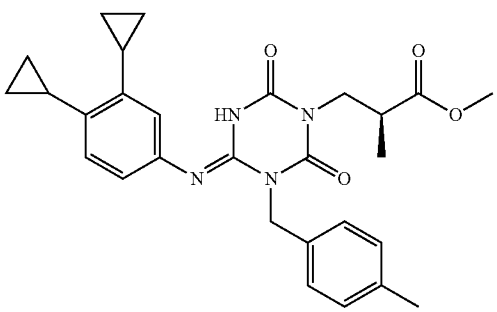 [SMILES: COC(=O)[C@@H](C)Cn1c(=O)[nH]/c(=N\c2ccc(C3CC3)c(C3CC3)c2)n(Cc2ccc(C)cc2)c1=O] | I-1488 | 2.36 | 489 | 2 |
| 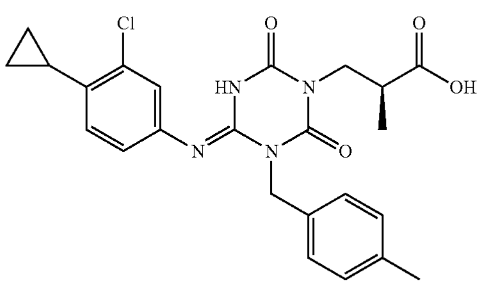 [SMILES: Cc1ccc(Cn2c(=O)n(C[C@H](C)C(=O)O)c(=O)[nH]/c2=N\c2ccc(C3CC3)c(Cl)c2)cc1] | I-1489 | 2.13 | 469 | 2 |
| 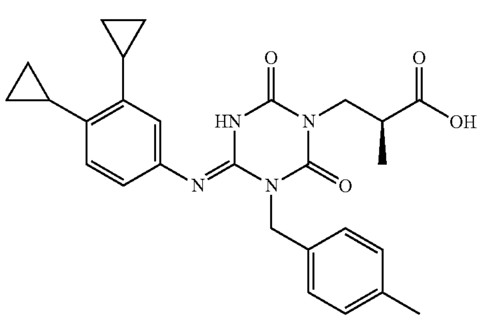 [SMILES: Cc1ccc(Cn2c(=O)n(C[C@H](C)C(=O)O)c(=O)[nH]/c2=N\c2ccc(C3CC3)c(C3CC3)c2)cc1] | I-1490 | 2.14 | 475 | 2 |

TABLE 302

| Structure | Compound No. | Retention Time (min) | [M + H] | Method |
|---|---|---|---|---|
| 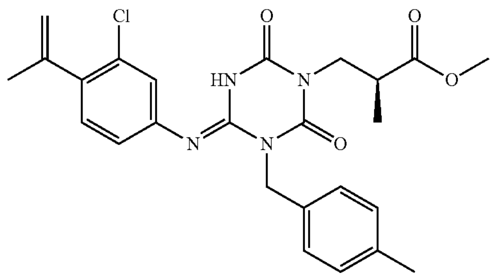 | I-1491 | 2.44 | 483 | 2 |
| 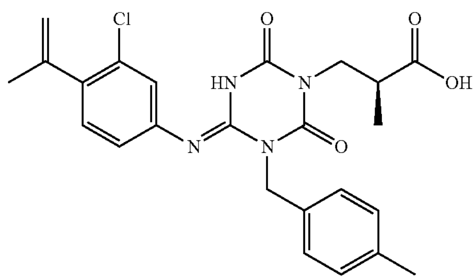 | I-1492 | 2.19 | 469 | 2 |
| 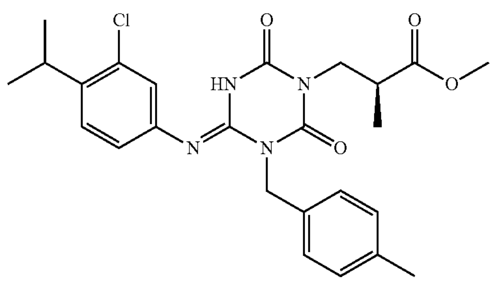 [SMILES: C=C(C)c1ccc(/N=c2\[nH]c(=O)n(C[C@H](C)C(=O)OC)c(=O)n2Cc2ccc(C)cc2)cc1Cl] | I-1493 | 2.48 | 485 | 2 |
| 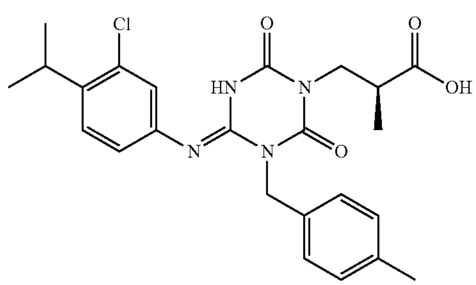 [SMILES: C=C(C)c1ccc(/N=c2\[nH]c(=O)n(C[C@H](C)C(=O)O)c(=O)n2Cc2ccc(C)cc2)cc1Cl] | I-1494 | 2.25 | 471 | 2 |
| 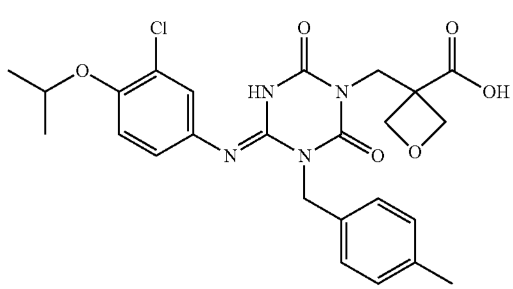 [SMILES: Cc1ccc(Cn2c(=O)n(CC3(C(=O)O)COC3)c(=O)[nH]/c2=N\c2ccc(OC(C)C)c(Cl)c2)cc1] | I-1495 | 1.91 | 515 | 2 |

TABLE 303

| Structure | Compound No. | Retention Time (min) | [M + H] | Method |
|---|---|---|---|---|
| 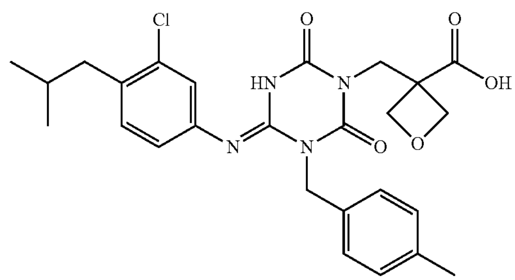 [SMILES: Cc1ccc(Cn2c(=O)n(CC3(C(=O)O)COC3)c(=O)[nH]/c2=N\c2ccc(CC(C)C)c(Cl)c2)cc1] | I-1496 | 2.26 | 513 | 2 |
| 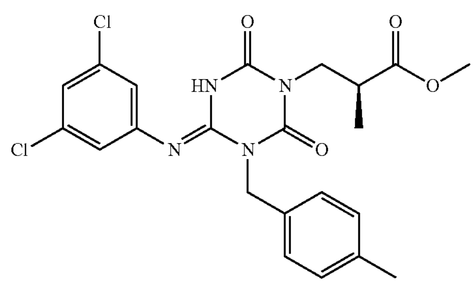 [SMILES: COC(=O)[C@@H](C)Cn1c(=O)[nH]/c(=N\c2cc(Cl)cc(Cl)c2)n(Cc2ccc(C)cc2)c1=O] | I-1497 | 2.50 | 477 | 2 |
| 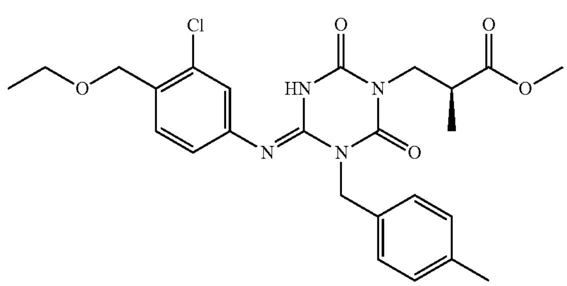 [SMILES: CCOCc1ccc(/N=c2\[nH]c(=O)n(C[C@H](C)C(=O)OC)c(=O)n2Cc2ccc(C)cc2)cc1Cl] | I-1498 | 2.28 | 501 | 2 |
| 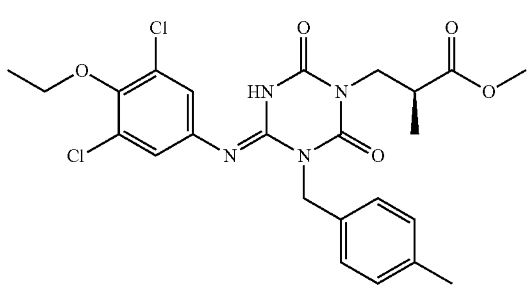 [SMILES: CCOc1c(Cl)cc(/N=c2\[nH]c(=O)n(C[C@H](C)C(=O)OC)c(=O)n2Cc2ccc(C)cc2)cc1Cl] | I-1499 | 2.51 | 521 | 2 |
| 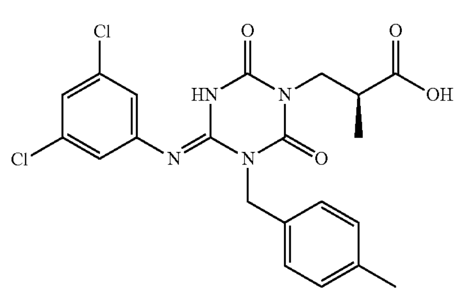 [SMILES: Cc1ccc(Cn2c(=O)n(C[C@H](C)C(=O)O)c(=O)[nH]/c2=N\c2cc(Cl)cc(Cl)c2)cc1] | I-1500 | 2.24 | 463 | 2 |

TABLE 304

| Structure | Compound No. | Retention Time (min) | [M + H] | Method |
|---|---|---|---|---|
| 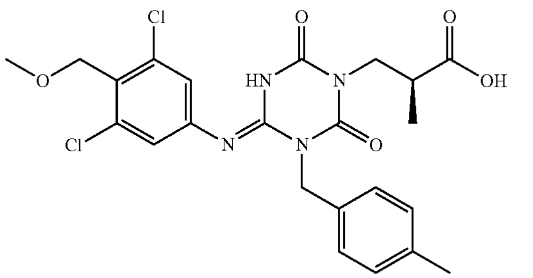 [SMILES: COCc1c(Cl)cc(/N=c2\[nH]c(=O)n(C[C@H](C)C(=O)O)c(=O)n2Cc2ccc(C)cc2)cc1Cl] | I-1501 | 2.29 | 507 | 2 |
| 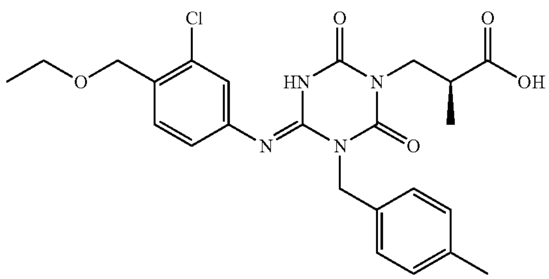 [SMILES: CCOCc1ccc(/N=c2\[nH]c(=O)n(C[C@H](C)C(=O)O)c(=O)n2Cc2ccc(C)cc2)cc1Cl] | I-1502 | 2.02 | 487 | 2 |
| 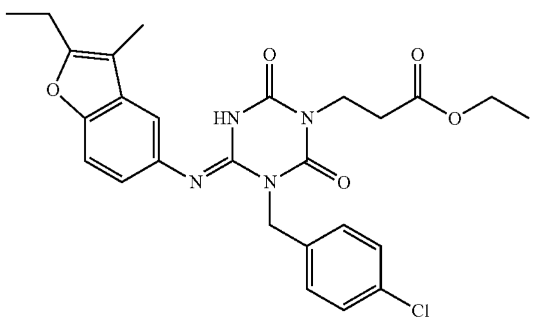 [SMILES: CCOC(=O)CCn1c(=O)[nH]/c(=N\c2ccc3oc(CC)c(C)c3c2)n(Cc2ccc(Cl)cc2)c1=O] | I-1503 | 2.63 | 511 | 3 |
| 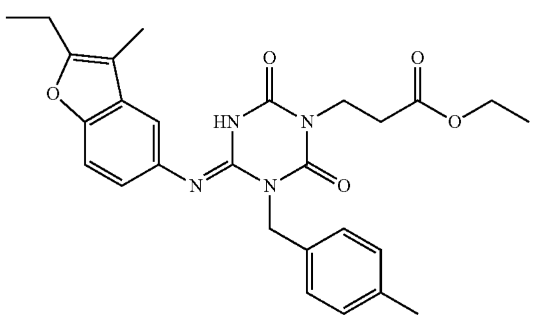 [SMILES: CCOC(=O)CCn1c(=O)[nH]/c(=N\c2ccc3oc(CC)c(C)c3c2)n(Cc2ccc(C)cc2)c1=O] | I-1504 | 2.56 | 491 | 3 |
| 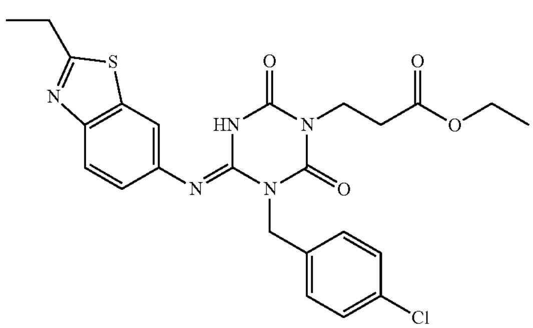 [SMILES: CCOC(=O)CCn1c(=O)[nH]/c(=N\c2ccc3nc(CC)sc3c2)n(Cc2ccc(Cl)cc2)c1=O] | I-1505 | 2.41 | 514 | 3 |

TABLE 305

| Structure | Compound No. | Retention Time (min) | [M + H] | Method |
|---|---|---|---|---|
| 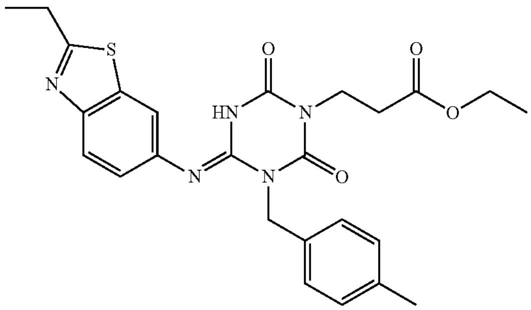 [SMILES: CCOC(=O)CCn1c(=O)[nH]/c(=N\c2ccc3nc(CC)sc3c2)n(Cc2ccc(C)cc2)c1=O] | I-1506 | 2.32 | 494 | 3 |
| 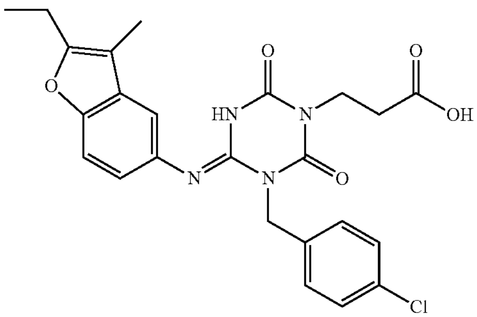 [SMILES: CCc1oc2ccc(/N=c3\[nH]c(=O)n(CCC(=O)O)c(=O)n3Cc3ccc(Cl)cc3)cc2c1C] | I-1507 | 2.30 | 483 | 3 |
| 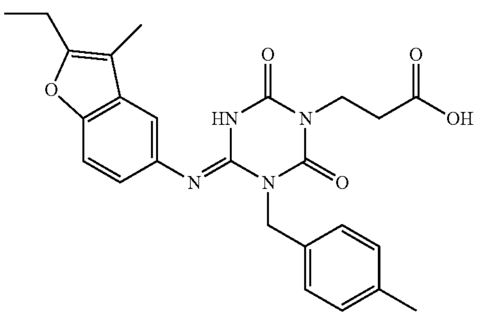 [SMILES: CCc1oc2ccc(/N=c3\[nH]c(=O)n(CCC(=O)O)c(=O)n3Cc3ccc(C)cc3)cc2c1C] | I-1508 | 2.22 | 463 | 3 |
| 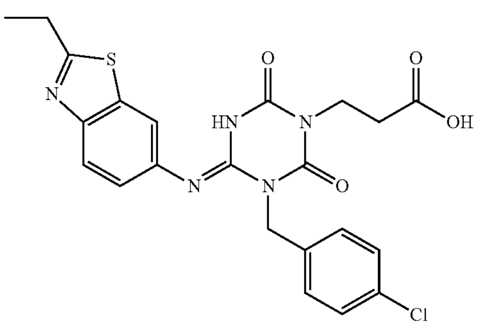 [SMILES: CCc1nc2ccc(/N=c3\[nH]c(=O)n(CCC(=O)O)c(=O)n3Cc3ccc(Cl)cc3)cc2s1] | I-1509 | 2.03 | 486 | 3 |
| 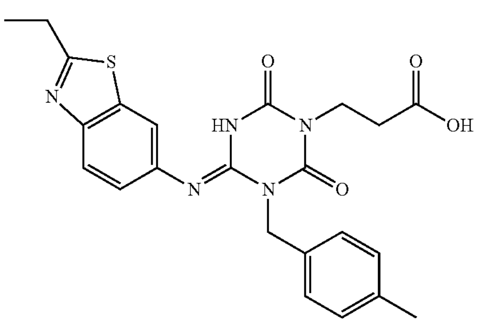 [SMILES: CCc1nc2ccc(/N=c3\[nH]c(=O)n(CCC(=O)O)c(=O)n3Cc3ccc(C)cc3)cc2s1] | I-1510 | 1.94 | 466 | 3 |

TABLE 306

| Structure | Compound No. | Retention Time (min) | [M + H] | Method |
|---|---|---|---|---|
| 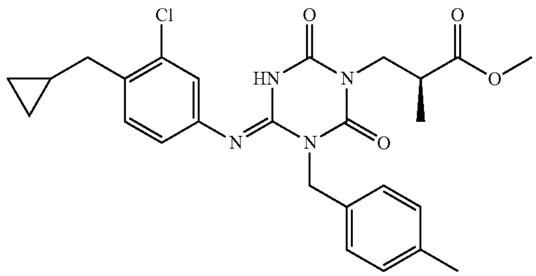 [SMILES: COC(=O)[C@@H](C)Cn1c(=O)[nH]/c(=N\c2ccc(CC3CC3)c(Cl)c2)n(Cc2ccc(C)cc2)c1=O] | I-1511 | 2.49 | 497 | 2 |
| 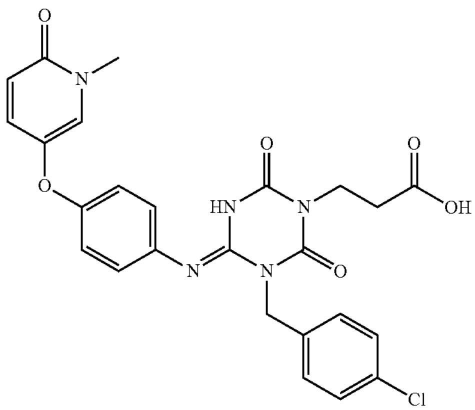 [SMILES: Cn1cc(Oc2ccc(/N=c3\[nH]c(=O)n(CCC(=O)O)c(=O)n3Cc3ccc(Cl)cc3)cc2)ccc1=O] | I-1512 | 1.78 | 524 | 2 |
| 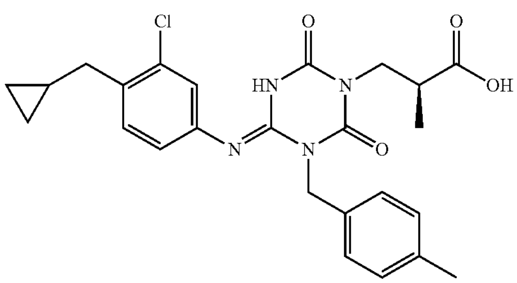 | I-1513 | 2.24 | 483 | 2 |
| 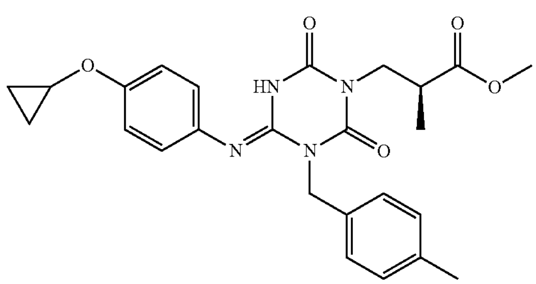 [SMILES: COC(=O)[C@@H](C)Cn1c(=O)[nH]/c(=N\c2ccc(OC3CC3)cc2)n(Cc2ccc(C)cc2)c1=O] | I-1514 | 2.00 | 465 | 2 |
| 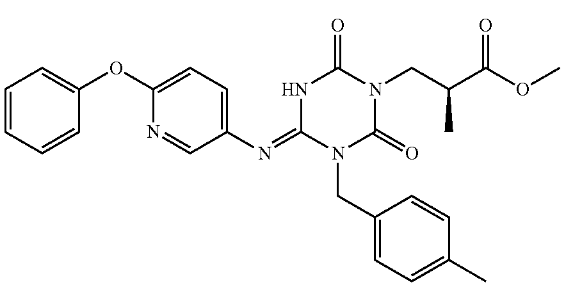 | I-1515 | 2.06 | 502 | 2 |

TABLE 307

| Structure | Compound No. | Retention Time (min) | [M + H] | Method |
|---|---|---|---|---|
| 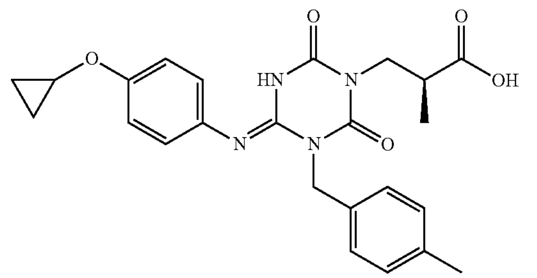 [SMILES: Cc1ccc(Cn2c(=O)n(C[C@H](C)C(=O)O)c(=O)[nH]/c2=N\c2ccc(OC3CC3)cc2)cc1] | I-1516 | 1.76 | 451 | 2 |
| 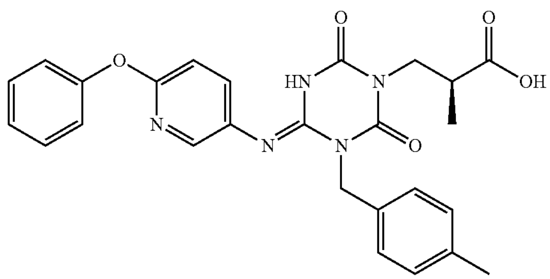 [SMILES: Cc1ccc(Cn2c(=O)n(C[C@H](C)C(=O)O)c(=O)[nH]/c2=N\c2ccc(Oc3ccccc3)nc2)cc1] | I-1517 | 1.84 | 488 | 2 |
| 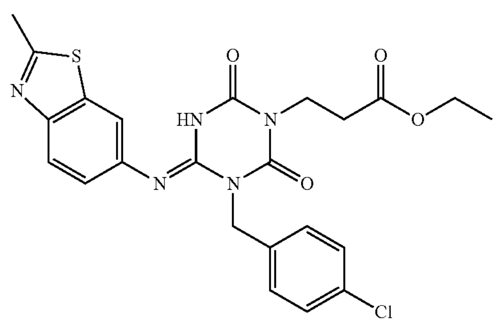 [SMILES: CCOC(=O)CCn1c(=O)[nH]/c(=N\c2ccc3nc(C)sc3c2)n(Cc2ccc(Cl)cc2)c1=O] | I-1518 | 2.27 | 500 | 3 |
| 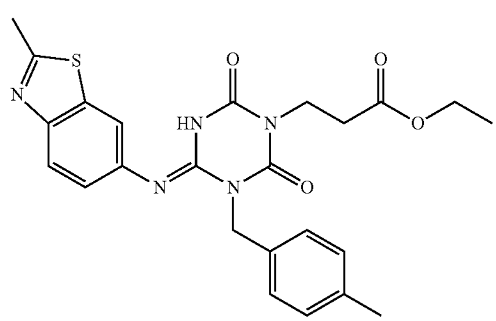 [SMILES: CCOC(=O)CCn1c(=O)[nH]/c(=N\c2ccc3nc(C)sc3c2)n(Cc2ccc(C)cc2)c1=O] | I-1519 | 2.17 | 480 | 3 |
| 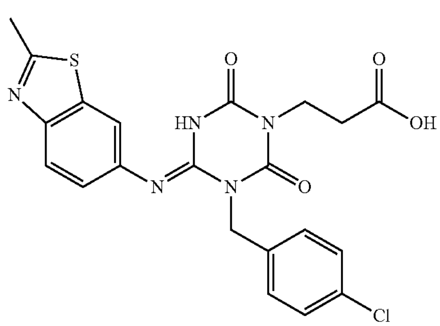 [SMILES: Cc1nc2ccc(/N=c3\[nH]c(=O)n(CCC(=O)O)c(=O)n3Cc3ccc(Cl)cc3)cc2s1] | I-1520 | 1.92 | 472 | 3 |

TABLE 308

| Structure | Compound No. | Retention Time (min) | [M + H] | Method |
|---|---|---|---|---|
| 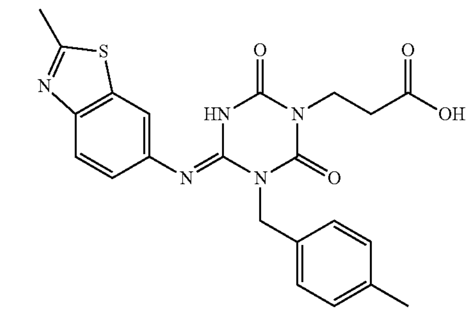 [SMILES: Cc1ccc(Cn2c(=O)n(CCC(=O)O)c(=O)[nH]/c2=N\c2ccc3nc(C)sc3c2)cc1] | I-1521 | 1.84 | 452 | 3 |
| 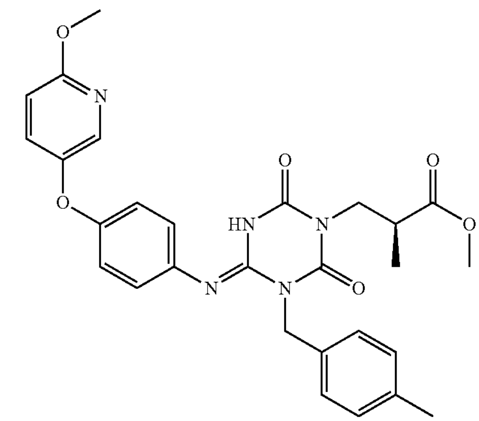 [SMILES: COC(=O)[C@@H](C)Cn1c(=O)[nH]/c(=N\c2ccc(Oc3ccc(OC)nc3)cc2)n(Cc2ccc(C)cc2)c1=O] | I-1522 | 2.42 | 532 | 3 |
| 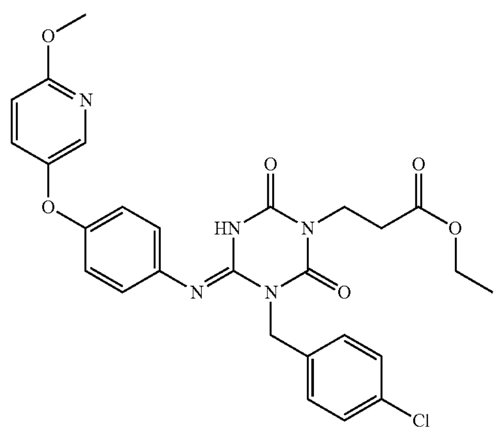 [SMILES: CCOC(=O)CCn1c(=O)[nH]/c(=N\c2ccc(Oc3ccc(OC)nc3)cc2)n(Cc2ccc(Cl)cc2)c1=O] | I-1523 | 2.51 | 552 | 3 |
| 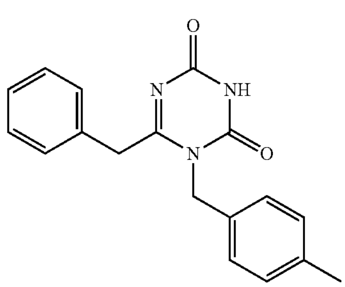 [SMILES: Cc1ccc(Cn2c(Cc3ccccc3)nc(=O)[nH]c2=O)cc1] | I-1524 | 1.67 | 308 | 2 |

TABLE 308-continued

| Structure | Compound No. | Retention Time (min) | [M + H] | Method |
|---|---|---|---|---|
| 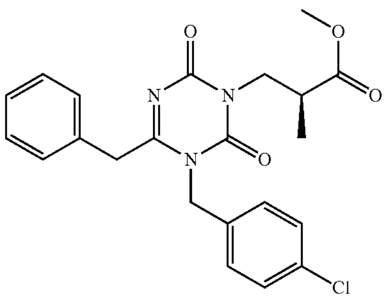 [SMILES: COC(=O)[C@@H](C)Cn1c(=O)nc(Cc2ccccc2)n(Cc2ccc(Cl)cc2)c1=O] | I-1525 | 2.05 | 428 | 2 |

TABLE 309

| Structure | Compound No. | Retention Time (min) | [M + H] | Method |
|---|---|---|---|---|
| 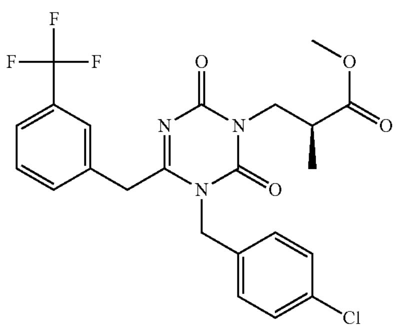 [SMILES: COC(=O)[C@@H](C)Cn1c(=O)nc(Cc2cccc(C(F)(F)F)c2)n(Cc2ccc(Cl)cc2)c1=O] | I-1526 | 2.20 | 496 | 2 |
| 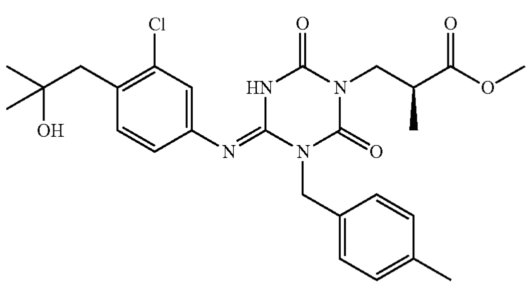 [SMILES: COC(=O)[C@@H](C)Cn1c(=O)[nH]/c(=N\c2ccc(CC(C)(C)O)c(Cl)c2)n(Cc2ccc(C)cc2)c1=O] | I-1527 | 2.32 | 515 | 3 |
| 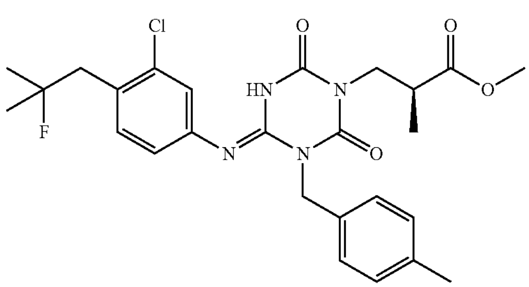 | I-1528 | 2.67 | 517 | 3 |

TABLE 309-continued
| Structure | Compound No. | Retention Time (min) | [M + H] | Method |
|---|---|---|---|---|
| 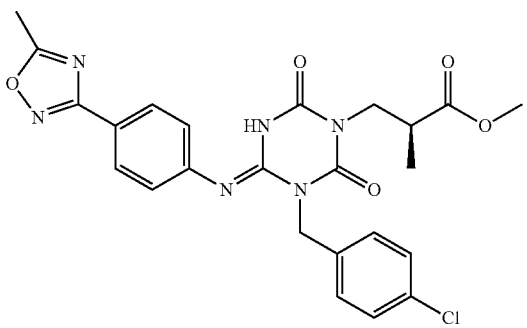 [SMILES: COC(=O)[C@@H](C)Cn1c(=O)[nH]/c(=N\c2ccc(-c3noc(C)n3)cc2)n(Cc2ccc(Cl)cc2)c1=O] | I-1529 | 2.35 | 511 | 3 |
| 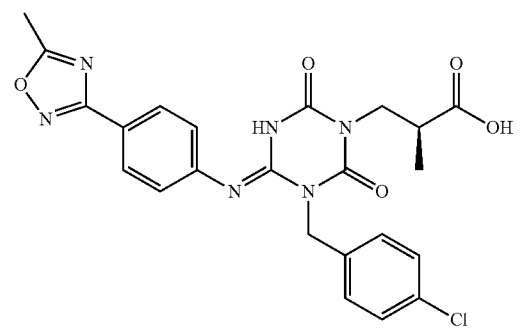 [SMILES: Cc1nc(-c2ccc(/N=c3\[nH]c(=O)n(C[C@H](C)C(=O)O)c(=O)n3Cc3ccc(Cl)cc3)cc2)no1] | I-1530 | 2.07 | 497 | 3 |
TABLE 310
| Structure | Compound No. | Retention Time (min) | [M + H] | Method |
|---|---|---|---|---|
| 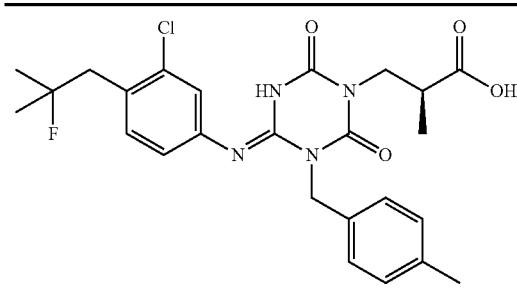 | I-1531 | 2.41 | 503 | 3 |
| 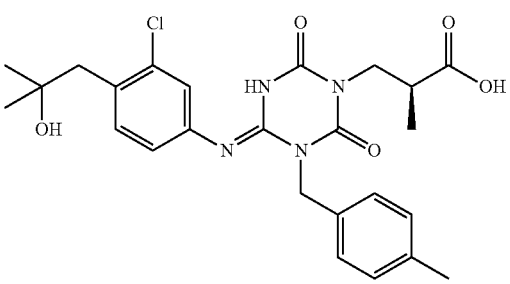 [SMILES: Cc1ccc(Cn2c(=O)n(C[C@H](C)C(=O)O)c(=O)[nH]/c2=N\c2ccc(CC(C)(C)O)c(Cl)c2)cc1] | I-1532 | 2.05 | 501 | 3 |

TABLE 310-continued

| Structure | Compound No. | Retention Time (min) | [M + H] | Method |
|---|---|---|---|---|
| (structure) | I-1533 | 1.84 | 524 | 2 |
| (structure) | I-1534 | 1.85 | 518 | 2 |
| (structure) | I-1535 | 1.38 | 510 | 2 |

TABLE 311

| Structure | Compound No. | Retention Time (min) | [M + H] | Method |
|---|---|---|---|---|
| (structure) | I-1536 | 1.36 | 504 | 3 |
| (structure) | I-1537 | 2.44 | 526 | 3 |
| (structure) | I-1538 | 2.78 | 537 | 3 |
| (structure) | I-1539 | 2.58 | 540 | 3 |
| (structure) | I-1540 | 2.11 | 506 | 2 |

TABLE 312

| Structure | Compound No. | Retention Time (min) | [M + H] | Method |
|---|---|---|---|---|
| 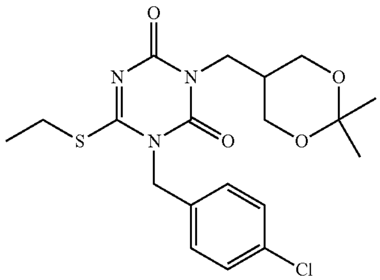 [SMILES: CCSc1nc(=O)n(CC2COC(C)(C)OC2)c(=O)n1Cc1ccc(Cl)cc1] | I-1541 | 1.84 | 426 | 2 |
| 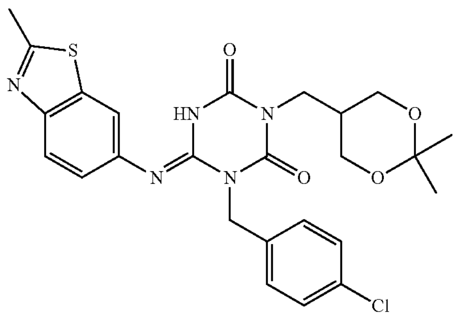 | I-1542 | 1.81 | 528 | 2 |
| 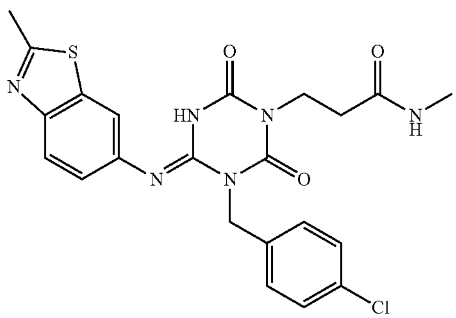 | I-1543 | 1.80 | 485 | 3 |
| 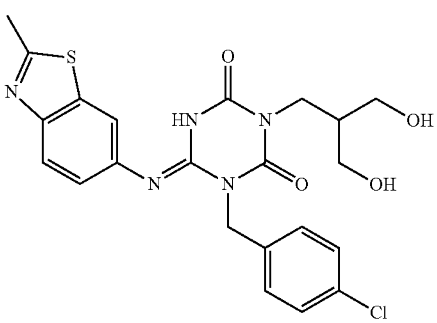 [SMILES: Cc1nc2ccc(/N=c3\[nH]c(=O)n(CC(CO)CO)c(=O)n3Cc3ccc(Cl)cc3)cc2s1] | I-1544 | 1.75 | 488 | 3 |
| 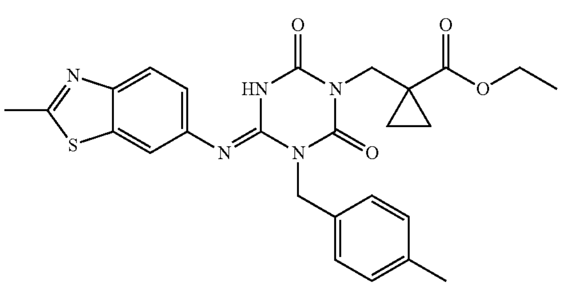 [SMILES: CCOC(=O)C1(Cn2c(=O)[nH]/c(=N\c3ccc4nc(C)sc4c3)n(Cc3ccc(C)cc3)c2=O)CC1] | I-1545 | 2.34 | 506 | 3 |

TABLE 313
| Structure | Compound No. | Retention Time (min) | [M + H] | Method |
|---|---|---|---|---|
| 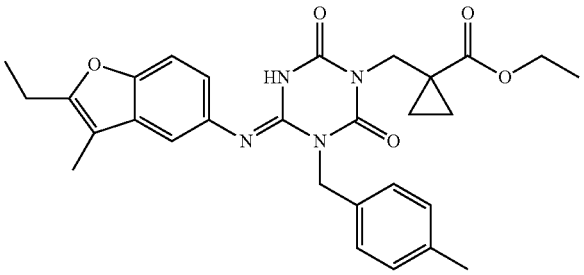 [SMILES: CCOC(=O)C1(Cn2c(=O)[nH]/c(=N\c3ccc4oc(CC)c(C)c4c3)n(Cc3ccc(C)cc3)c2=O)CC1] | I-1546 | 2.71 | 517 | 3 |
| 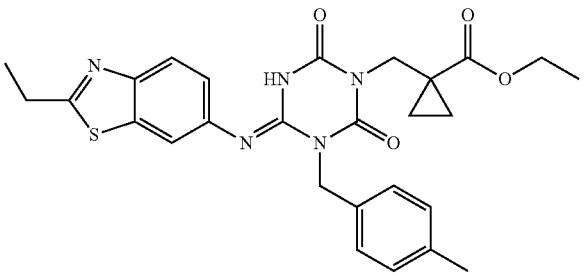 [SMILES: CCOC(=O)C1(Cn2c(=O)[nH]/c(=N\c3ccc4nc(CC)sc4c3)n(Cc3ccc(C)cc3)c2=O)CC1] | I-1547 | 2.49 | 520 | 3 |
| 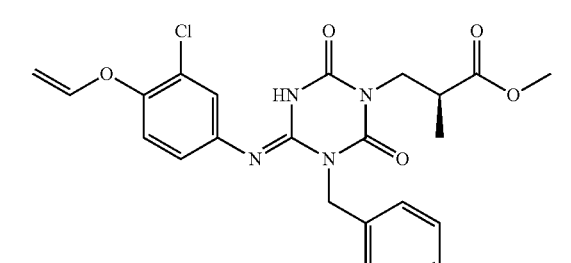 | I-1548 | 2.07 | 485 | 2 |
| 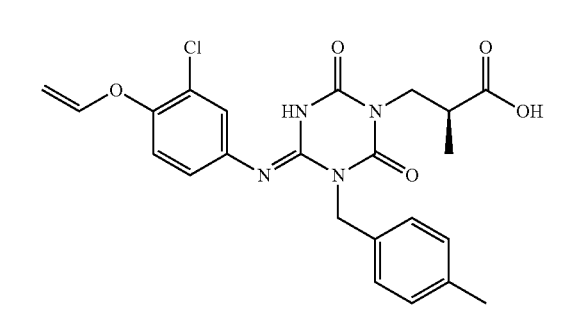 [SMILES: C=COc1ccc(/N=c2\[nH]c(=O)n(C[C@H](C)C(=O)O)c(=O)n2Cc2ccc(C)cc2)cc1Cl] | I-1549 | 1.86 | 471 | 2 |
| 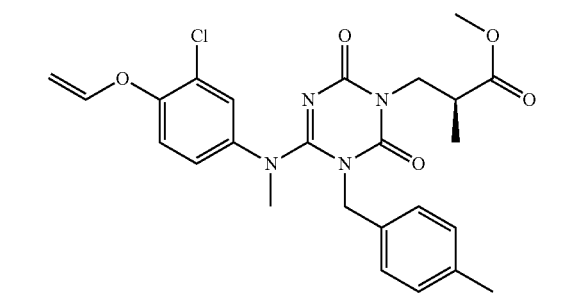 [SMILES: C=COc1ccc(N(C)c2nc(=O)n(C[C@H](C)C(=O)OC)c(=O)n2Cc2ccc(C)cc2)cc1Cl] | I-1550 | 2.02 | 499 | 2 |

TABLE 314
| Structure | Compound No. | Retention Time (min) | [M + H] | Method |
|---|---|---|---|---|
| 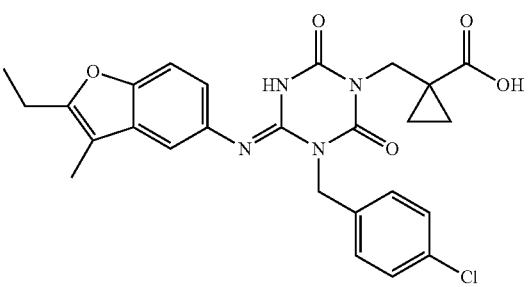 [SMILES: CCc1oc2ccc(/N=c3\[nH]c(=O)n(CC4(C(=O)O)CC4)c(=O)n3Cc3ccc(Cl)cc3)cc2c1C] | I-1551 | 1.99 | 509 | 2 |
| 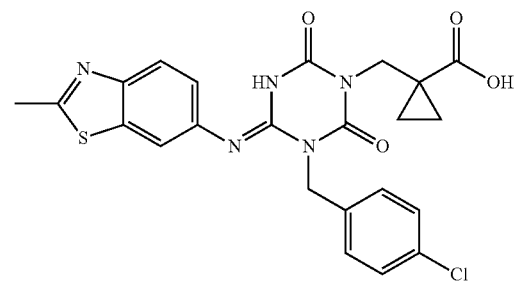 [SMILES: Cc1nc2ccc(/N=c3\[nH]c(=O)n(CC4(C(=O)O)CC4)c(=O)n3Cc3ccc(Cl)cc3)cc2s1] | I-1552 | 1.63 | 498 | 2 |
| 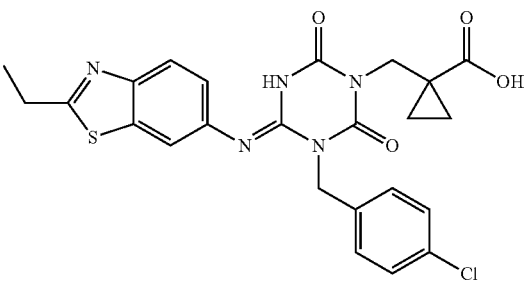 [SMILES: CCc1nc2ccc(/N=c3\[nH]c(=O)n(CC4(C(=O)O)CC4)c(=O)n3Cc3ccc(Cl)cc3)cc2s1] | I-1553 | 1.76 | 512 | 2 |
| 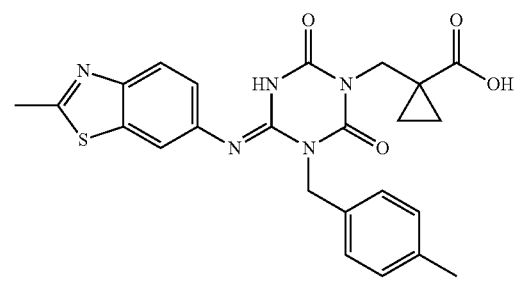 [SMILES: Cc1ccc(Cn2c(=O)n(CC3(C(=O)O)CC3)c(=O)[nH]/c2=N\c2ccc3nc(C)sc3c2)cc1] | I-1554 | 1.57 | 478 | 2 |
| 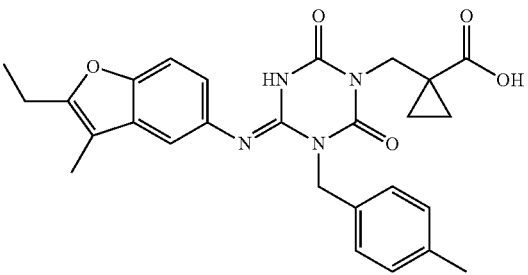 [SMILES: CCc1oc2ccc(/N=c3\[nH]c(=O)n(CC4(C(=O)O)CC4)c(=O)n3Cc3ccc(C)cc3)cc2c1C] | I-1555 | 1.92 | 489 | 2 |

TABLE 315

| Structure | Compound No. | Retention Time (min) | [M + H] | Method |
|---|---|---|---|---|
| 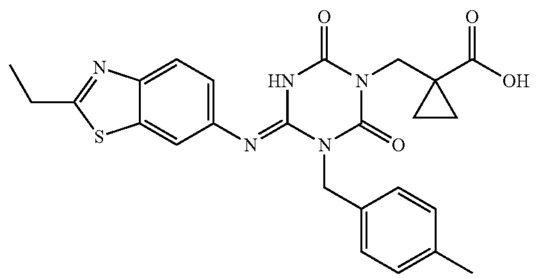 [SMILES: CCc1nc2ccc(/N=c3\[nH]c(=O)n(CC4(C(=O)O)CC4)c(=O)n3Cc3ccc(C)cc3)cc2s1] | I-1556 | 1.68 | 492 | 2 |
| 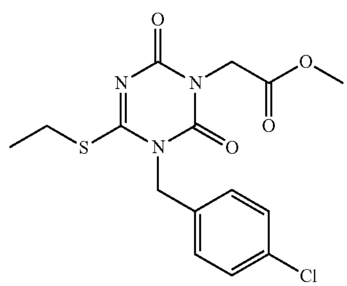 [SMILES: CCSc1nc(=O)n(CC(=O)OC)c(=O)n1Cc1ccc(Cl)cc1] | I-1557 | 2.14 | 370 | 3 |
| 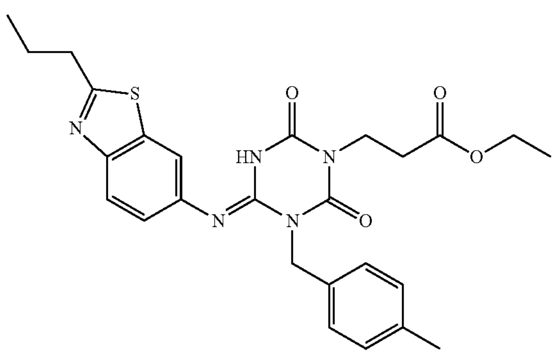 [SMILES: CCCc1nc2ccc(/N=c3\[nH]c(=O)n(CCC(=O)OCC)c(=O)n3Cc3ccc(C)cc3)cc2s1] | I-1558 | 2.42 | 508 | 3 |
| 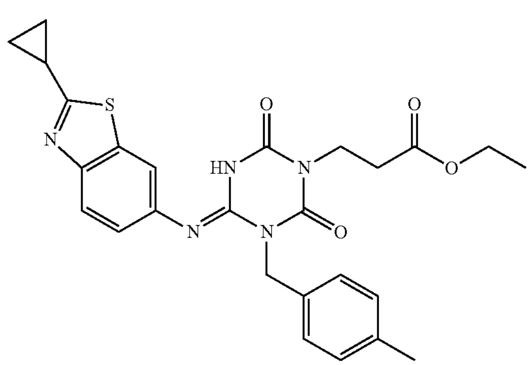 [SMILES: CCOC(=O)CCn1c(=O)[nH]/c(=N\c2ccc3nc(C4CC4)sc3c2)n(Cc2ccc(C)cc2)c1=O] | I-1559 | 2.38 | 506 | 3 |

TABLE 315-continued

| Structure | Compound No. | Retention Time (min) | [M + H] | Method |
|---|---|---|---|---|
| 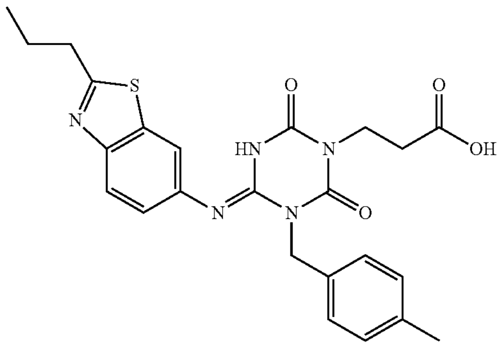 [SMILES: CCCc1nc2ccc(/N=c3\[nH]c(=O)n(CCC(=O)O)c(=O)n3Cc3ccc(C)cc3)cc2s1] | I-1560 | 2.10 | 480 | 3 |

TABLE 316

| Structure | Compound No. | Retention Time (min) | [M + H] | Method |
|---|---|---|---|---|
| 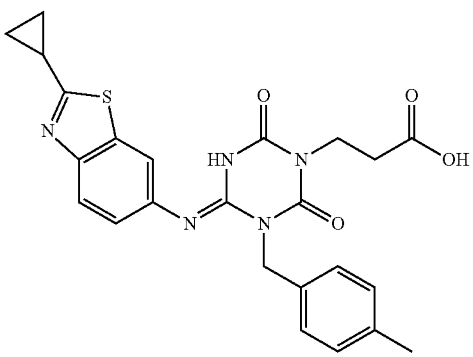 [SMILES: Cc1ccc(Cn2c(=O)n(CCC(=O)O)c(=O)[nH]/c2=N\c2ccc3nc(C4CC4)sc3c2)cc1] | I-1561 | 2.00 | 478 | 3 |
| 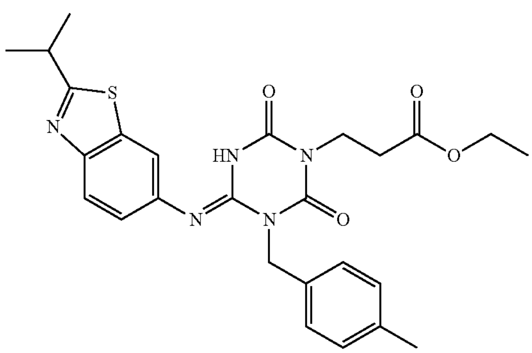 [SMILES: CCOC(=O)CCn1c(=O)[nH]/c(=N\c2ccc3nc(C(C)C)sc3c2)n(Cc2ccc(C)cc2)c1=O] | I-1562 | 2.49 | 508 | 3 |
| 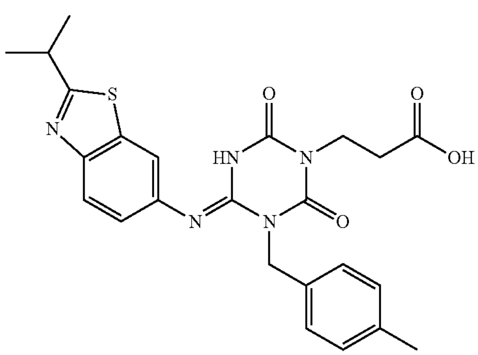 [SMILES: Cc1ccc(Cn2c(=O)n(CCC(=O)O)c(=O)[nH]/c2=N\c2ccc3nc(C(C)C)sc3c2)cc1] | I-1563 | 2.10 | 480 | 3 |

TABLE 316-continued
| Structure | Compound No. | Retention Time (min) | [M + H] | Method |
|---|---|---|---|---|
| 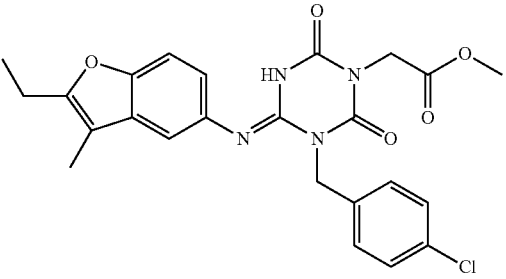 [SMILES: CCc1oc2ccc(/N=c3\[nH]c(=O)n(CC(=O)OC)c(=O)n3Cc3ccc(Cl)cc3)cc2c1C] | I-1564 | 2.49 | 483 | 3 |
| 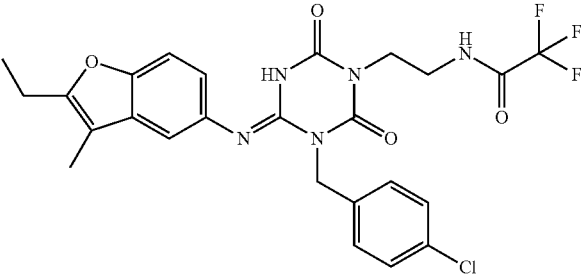 [SMILES: CCc1oc2ccc(/N=c3\[nH]c(=O)n(CCNC(=O)C(F)(F)F)c(=O)n3Cc3ccc(Cl)cc3)cc2c1C] | I-1565 | 2.54 | 550 | 3 |
TABLE 317
| Structure | Compound No. | Retention Time (min) | [M + H] | Method |
|---|---|---|---|---|
| 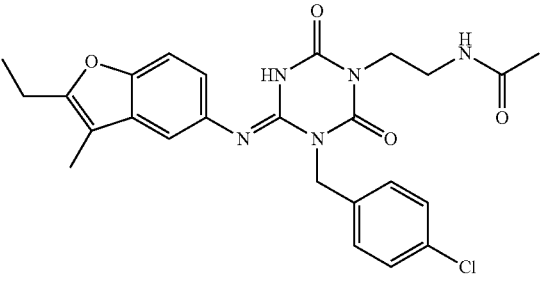 [SMILES: CCc1oc2ccc(/N=c3\[nH]c(=O)n(CCNC(C)=O)c(=O)n3Cc3ccc(Cl)cc3)cc2c1C] | I-1566 | 2.22 | 496 | 3 |
| 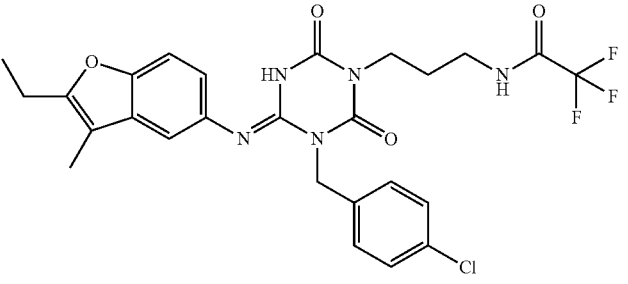 [SMILES: CCc1oc2ccc(/N=c3\[nH]c(=O)n(CCCNC(=O)C(F)(F)F)c(=O)n3Cc3ccc(Cl)cc3)cc2c1C] | I-1567 | 2.59 | 564 | 3 |

TABLE 317-continued

| Structure | Compound No. | Retention Time (min) | [M + H] | Method |
|---|---|---|---|---|
| 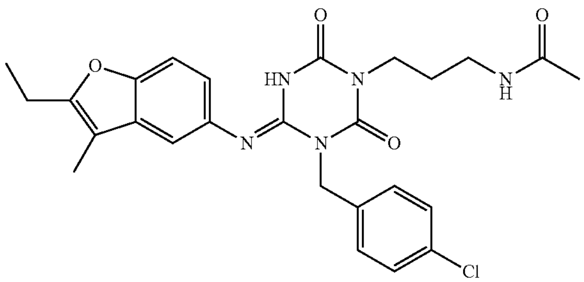 [SMILES: CCc1oc2ccc(/N=c3\[nH]c(=O)n(CCCNC(C)=O)c(=O)n3Cc3ccc(Cl)cc3)cc2c1C] | I-1568 | 2.25 | 510 | 3 |
| 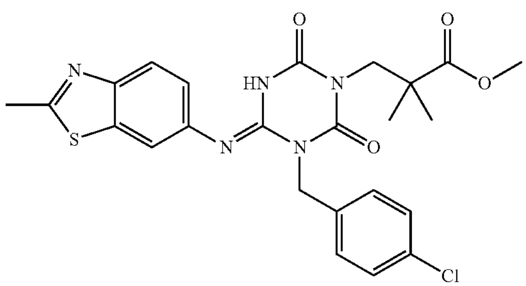 | I-1569 | 2.37 | 514 | 3 |
| 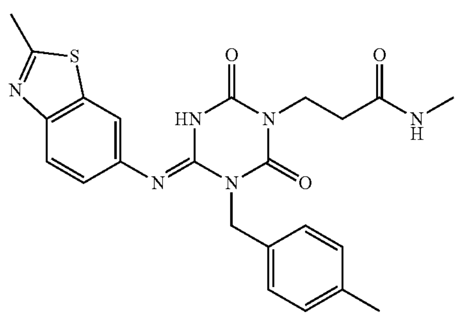 | I-1570 | 1.71 | 465 | 3 |

TABLE 318

| Structure | Compound No. | Retention Time (min) | [M + H] | Method |
|---|---|---|---|---|
| 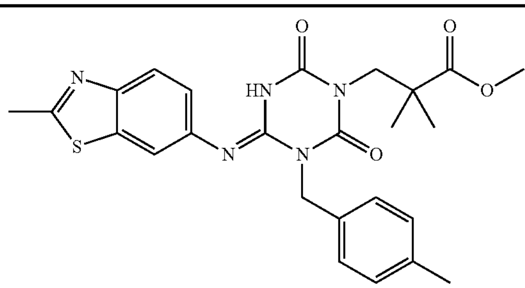 | I-1571 | 2.28 | 494 | 3 |

TABLE 318-continued

| Structure | Compound No. | Retention Time (min) | [M + H] | Method |
|---|---|---|---|---|
| (structure) | I-1572 | 2.52 | 528 | 3 |
| (structure) | I-1573 | 2.43 | 508 | 3 |
| (structure) | I-1574 | 2.73 | 525 | 3 |
| (structure) | I-1575 | 2.66 | 505 | 3 |

TABLE 319

| Structure | Compound No. | Retention Time (min) | [M + H] | Method |
|---|---|---|---|---|
| 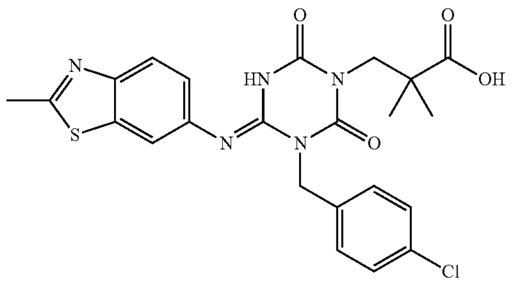 [SMILES: Cc1nc2ccc(/N=c3\[nH]c(=O)n(CC(C)(C)C(=O)O)c(=O)n3Cc3ccc(Cl)cc3)cc2s1] | I-1576 | 2.06 | 500 | 3 |
| 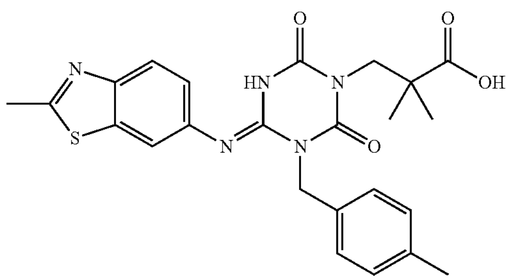 [SMILES: Cc1ccc(Cn2c(=O)n(CC(C)(C)C(=O)O)c(=O)[nH]/c2=N\c2ccc3nc(C)sc3c2)cc1] | I-1577 | 1.98 | 480 | 3 |
| 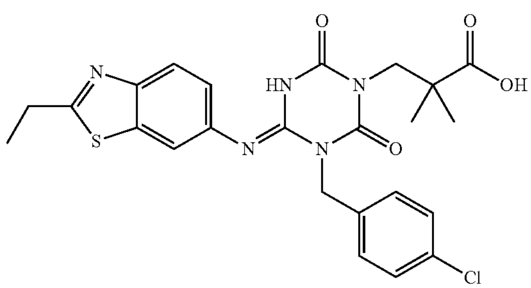 [SMILES: CCc1nc2ccc(/N=c3\[nH]c(=O)n(CC(C)(C)C(=O)O)c(=O)n3Cc3ccc(Cl)cc3)cc2s1] | I-1578 | 2.21 | 514 | 3 |
| 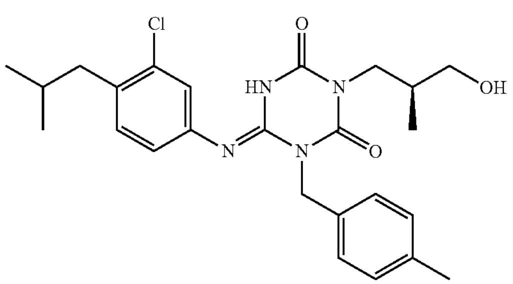 [SMILES: Cc1ccc(Cn2c(=O)n(C[C@H](C)CO)c(=O)[nH]/c2=N\c2ccc(CC(C)C)c(Cl)c2)cc1] | I-1579 | 2.70 | 471 | 3 |
| 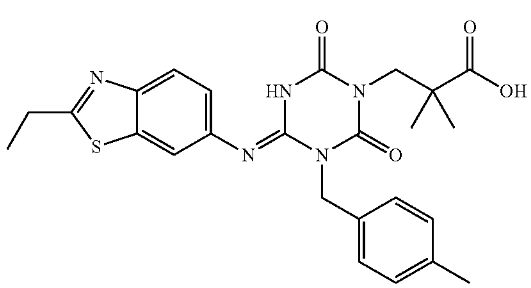 [SMILES: CCc1nc2ccc(/N=c3\[nH]c(=O)n(CC(C)(C)C(=O)O)c(=O)n3Cc3ccc(C)cc3)cc2s1] | I-1580 | 2.21 | 494 | 3 |

TABLE 320

| Structure | Compound No. | Retention Time (min) | [M + H] | Method |
|---|---|---|---|---|
| 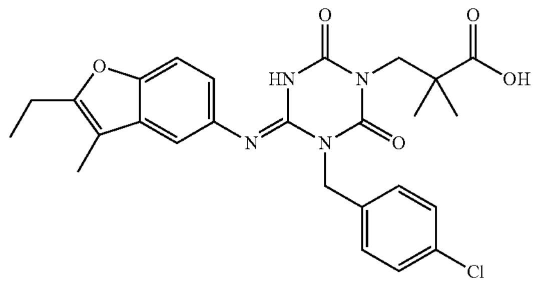 [SMILES: CCc1oc2ccc(/N=c3\[nH]c(=O)n(CC(C)(C)C(=O)O)c(=O)n3Cc3ccc(Cl)cc3)cc2c1C] | I-1581 | 2.45 | 511 | 3 |
| 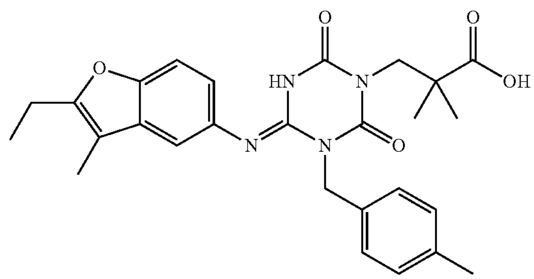 [SMILES: CCc1oc2ccc(/N=c3\[nH]c(=O)n(CC(C)(C)C(=O)O)c(=O)n3Cc3ccc(C)cc3)cc2c1C] | I-1582 | 2.38 | 491 | 3 |
| 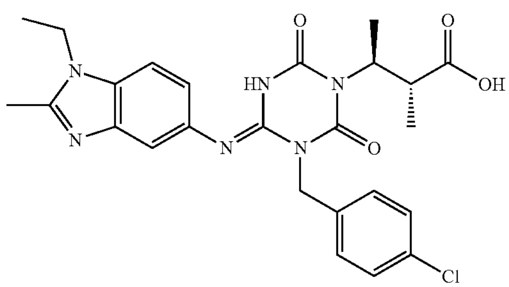 [SMILES: CCn1c(C)nc2cc(/N=c3\[nH]c(=O)n([C@@H](C)[C@@H](C)C(=O)O)c(=O)n3Cc3ccc(Cl)cc3)ccc21] | I-1583 | 1.24 | 511 | 2 |
| 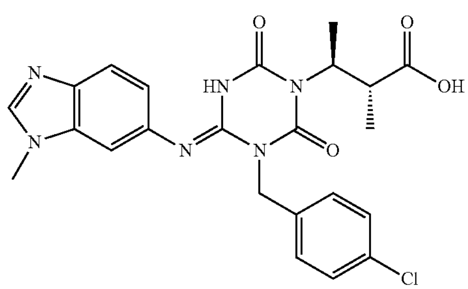 [SMILES: C[C@@H](C(=O)O)[C@H](C)n1c(=O)[nH]/c(=N\c2ccc3ncn(C)c3c2)n(Cc2ccc(Cl)cc2)c1=O] | I-1584 | 1.15 | 483 | 2 |
| 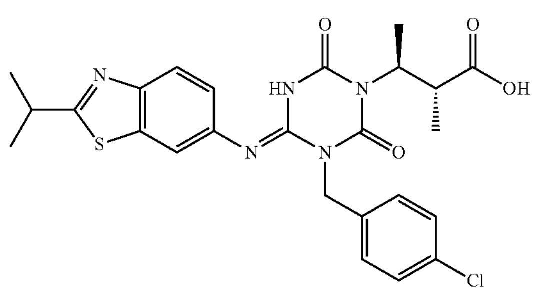 [SMILES: CC(C)c1nc2ccc(/N=c3\[nH]c(=O)n([C@@H](C)[C@@H](C)C(=O)O)c(=O)n3Cc3ccc(Cl)cc3)cc2s1] | I-1585 | 1.99 | 528 | 2 |

TABLE 321
| Structure | Compound No. | Retention Time (min) | [M + H] | Method |
|---|---|---|---|---|
| 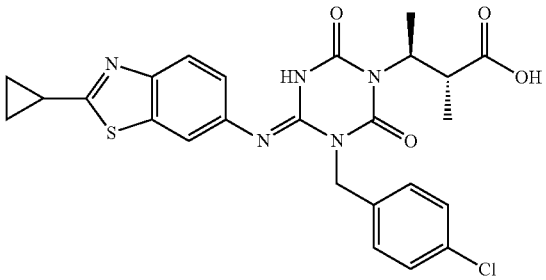 [SMILES: C[C@@H](C(=O)O)[C@H](C)n1c(=O)[nH]/c(=N\c2ccc3nc(C4CC4)sc3c2)n(Cc2ccc(Cl)cc2)c1=O] | I-1586 | 1.89 | 526 | 2 |
| 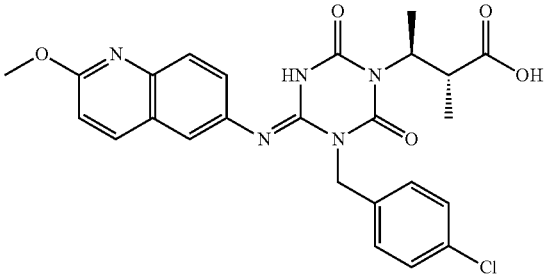 | I-1587 | 1.87 | 510 | 2 |
| 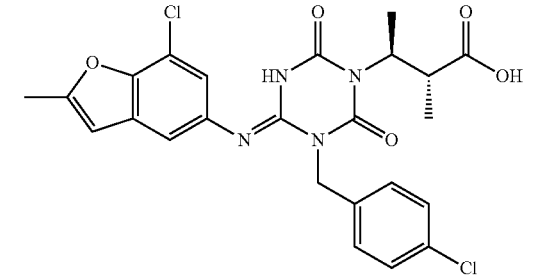 [SMILES: Cc1cc2cc(/N=c3\[nH]c(=O)n([C@@H](C)[C@@H](C)C(=O)O)c(=O)n3Cc3ccc(Cl)cc3)cc(Cl)c2o1] | I-1588 | 2.09 | 517 | 2 |
| 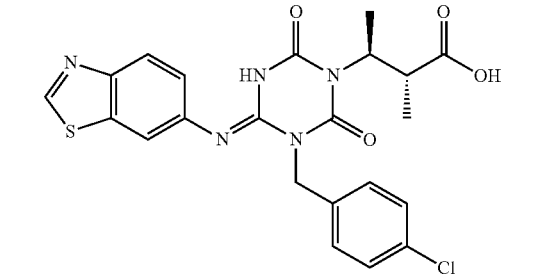 [SMILES: C[C@@H](C(=O)O)[C@H](C)n1c(=O)[nH]/c(=N\c2ccc3ncsc3c2)n(Cc2ccc(Cl)cc2)c1=O] | I-1589 | 1.66 | 486 | 2 |
| 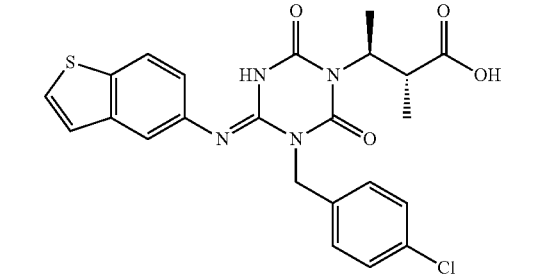 [SMILES: C[C@@H](C(=O)O)[C@H](C)n1c(=O)[nH]/c(=N\c2ccc3sccc3c2)n(Cc2ccc(Cl)cc2)c1=O] | I-1590 | 1.90 | 485 | 2 |

TABLE 322

| Structure | Compound No. | Retention Time (min) | [M + H] | Method |
|---|---|---|---|---|
| 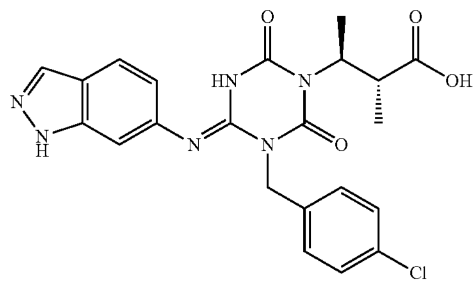 [SMILES: C[C@@H](C(=O)O)[C@H](C)n1c(=O)[nH]/c(=N\c2ccc3cn[nH]c3c2)n(Cc2ccc(Cl)cc2)c1=O] | I-1591 | 1.53 | 469 | 2 |
| 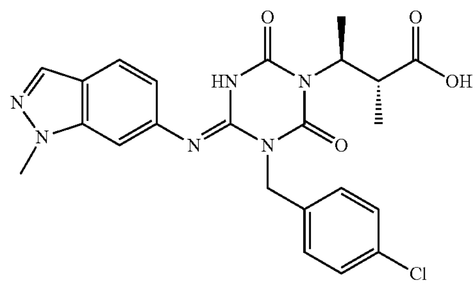 [SMILES: C[C@@H](C(=O)O)[C@H](C)n1c(=O)[nH]/c(=N\c2ccc3cnn(C)c3c2)n(Cc2ccc(Cl)cc2)c1=O] | I-1592 | 1.64 | 483 | 2 |
| 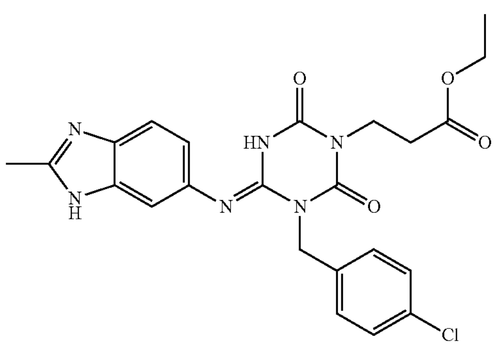 [SMILES: CCOC(=O)CCn1c(=O)[nH]/c(=N\c2ccc3nc(C)[nH]c3c2)n(Cc2ccc(Cl)cc2)c1=O] | I-1593 | 1.20 | 483 | 2 |
| 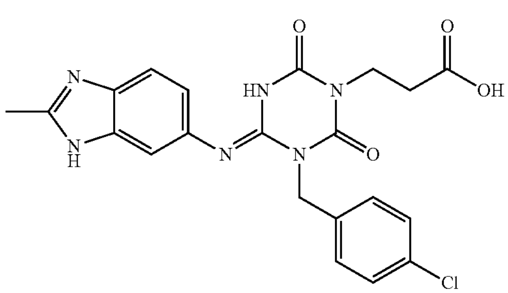 [SMILES: Cc1nc2ccc(/N=c3\[nH]c(=O)n(CCC(=O)O)c(=O)n3Cc3ccc(Cl)cc3)cc2[nH]1] | I-1594 | 0.99 | 455 | 2 |

TABLE 322-continued
| Structure | Compound No. | Retention Time (min) | [M + H] | Method |
|---|---|---|---|---|
| 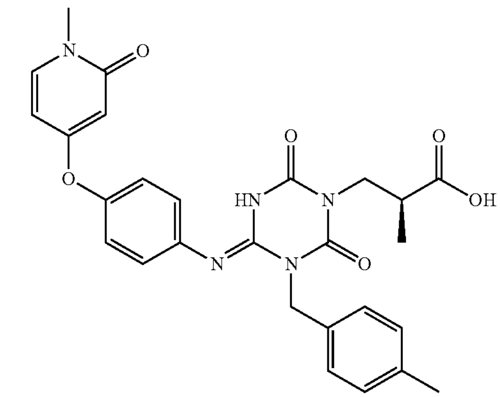 [SMILES: Cc1ccc(Cn2c(=O)n(C[C@H](C)C(=O)O)c(=O)[nH]/c2=N\c2ccc(Oc3ccn(C)c(=O)c3)cc2)cc1] | I-1595 | 2.02 | 518 | 3 |
TABLE 323
| Structure | Compound No. | Retention Time (min) | [M + H] | Method |
|---|---|---|---|---|
| 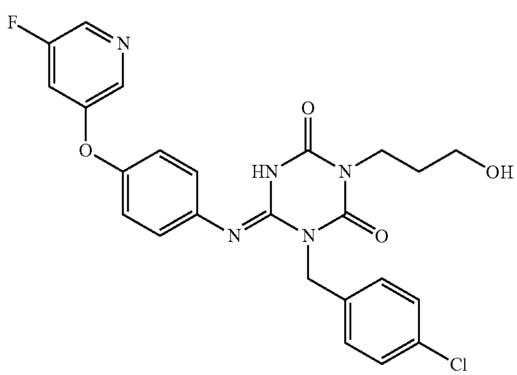 [SMILES: O=c1[nH]/c(=N\c2ccc(Oc3cncc(F)c3)cc2)n(Cc2ccc(Cl)cc2)c(=O)n1CCCO] | I-1596 | 2.04 | 498 | 3 |
| 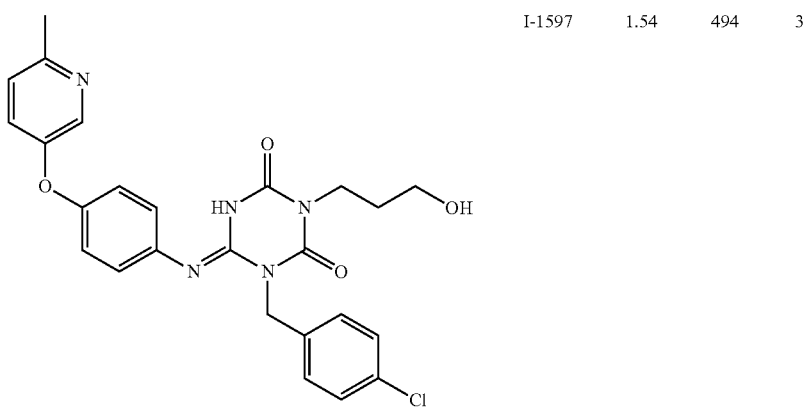 | I-1597 | 1.54 | 494 | 3 |

TABLE 323-continued
| Structure | Compound No. | Retention Time (min) | [M + H] | Method |
|---|---|---|---|---|
| 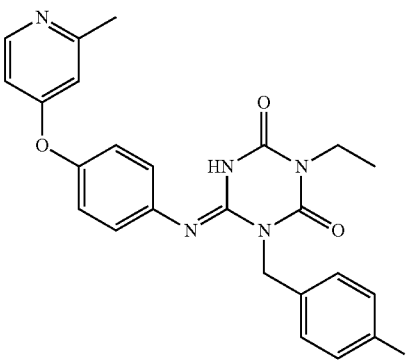 | I-1598 | 1.27 | 464 | 2 |
| 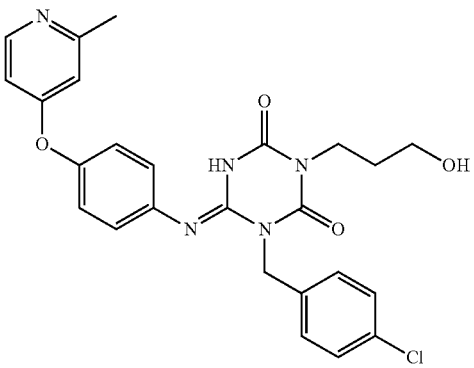 [SMILES: Cc1cc(Oc2ccc(/N=c3\[nH]c(=O)n(CCCO)c(=O)n3Cc3ccc(Cl)cc3)cc2)ccn1] | I-1599 | 1.16 | 494 | 2 |
| 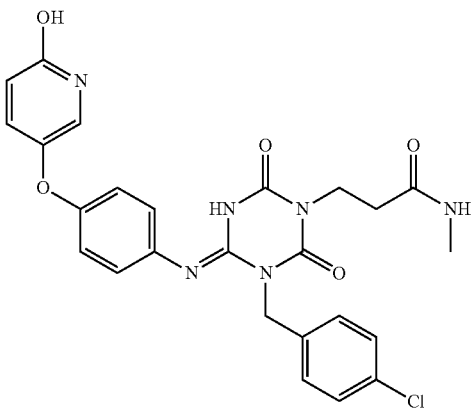 [SMILES: CNC(=O)CCn1c(=O)[nH]/c(=N\c2ccc(Oc3ccc(O)nc3)cc2)n(Cc2ccc(Cl)cc2)c1=O] | I-1600 | 1.49 | 523 | 3 |

TABLE 324

| Structure | Compound No. | Retention Time (min) | [M + H] | Method |
|---|---|---|---|---|
| 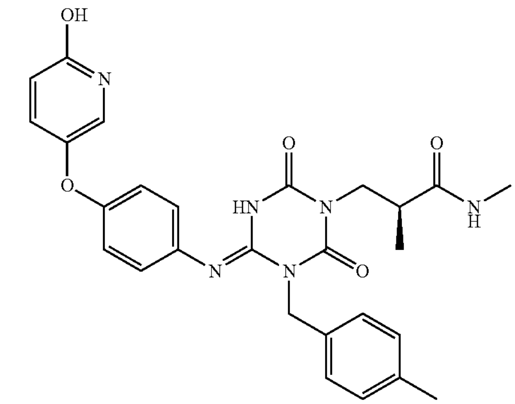 [SMILES: CNC(=O)[C@@H](C)Cn1c(=O)[nH]/c(=N\c2ccc(Oc3ccc(O)nc3)cc2)n(Cc2ccc(C)cc2)c1=O] | I-1601 | 1.48 | 517 | 3 |
| 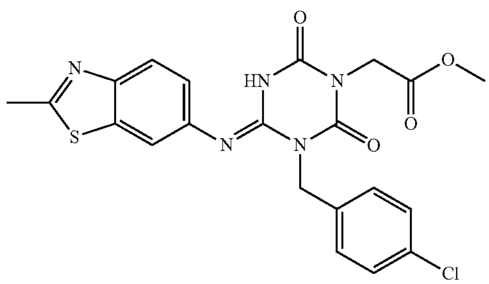 | I-1602 | 2.09 | 472 | 3 |
| 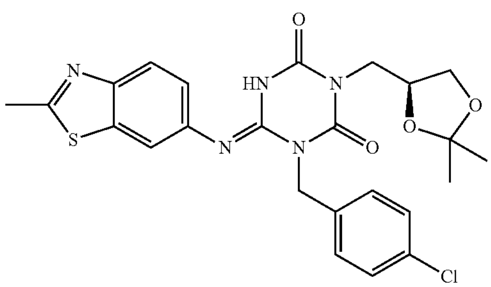 | I-1603 | 2.29 | 514 | 3 |
| 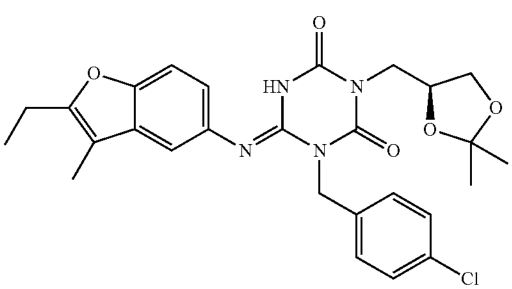 [SMILES: CCc1oc2ccc(/N=c3\[nH]c(=O)n(C[C@H]4COC(C)(C)O4)c(=O)n3Cc3ccc(Cl)cc3)cc2c1C] | I-1604 | 2.67 | 525 | 3 |
| 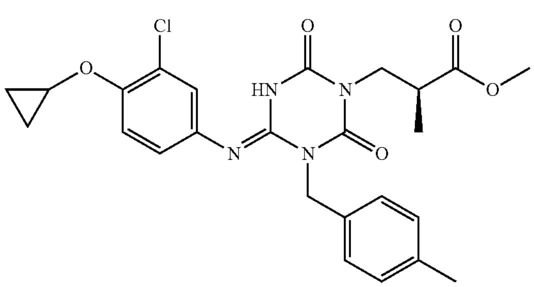 | I-1605 | 2.07 | 499 | 2 |

TABLE 325

| Structure | Compound No. | Retention Time (min) | [M + H] | Method |
|---|---|---|---|---|
| 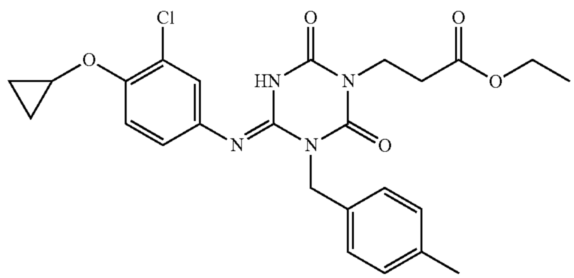 [SMILES: CCOC(=O)CCn1c(=O)[nH]/c(=N\c2ccc(OC3CC3)c(Cl)c2)n(Cc2ccc(C)cc2)c1=O] | I-1606 | 2.09 | 499 | 2 |
| 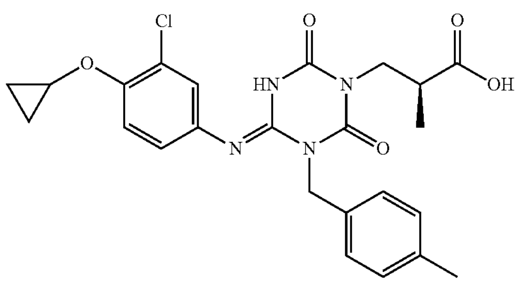 [SMILES: Cc1ccc(Cn2c(=O)n(C[C@H](C)C(=O)O)c(=O)[nH]/c2=N\c2ccc(OC3CC3)c(Cl)c2)cc1] | I-1607 | 1.85 | 485 | 2 |
| 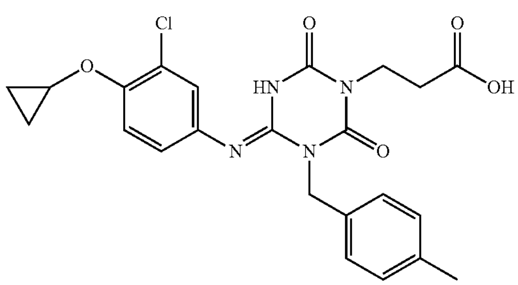 [SMILES: Cc1ccc(Cn2c(=O)n(CCC(=O)O)c(=O)[nH]/c2=N\c2ccc(OC3CC3)c(Cl)c2)cc1] | I-1608 | 1.80 | 471 | 2 |
| 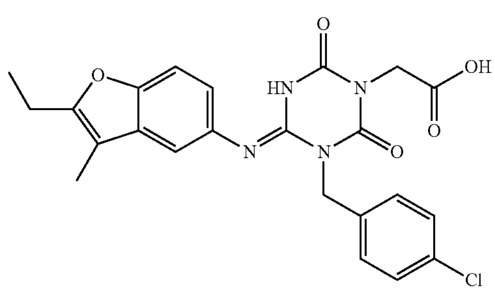 [SMILES: CCc1oc2ccc(/N=c3\[nH]c(=O)n(CC(=O)O)c(=O)n3Cc3ccc(Cl)cc3)cc2c1C] | I-1609 | 2.27 | 469 | 3 |
| 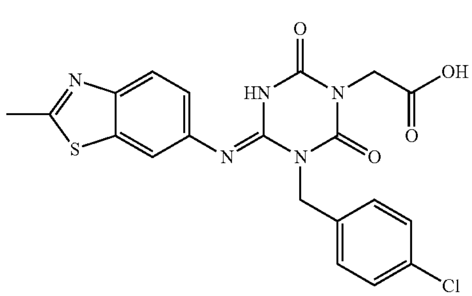 [SMILES: Cc1nc2ccc(/N=c3\[nH]c(=O)n(CC(=O)O)c(=O)n3Cc3ccc(Cl)cc3)cc2s1] | I-1610 | 1.84 | 458 | 3 |

TABLE 326

| Structure | Compound No. | Retention Time (min) | [M + H] | Method |
|---|---|---|---|---|
| 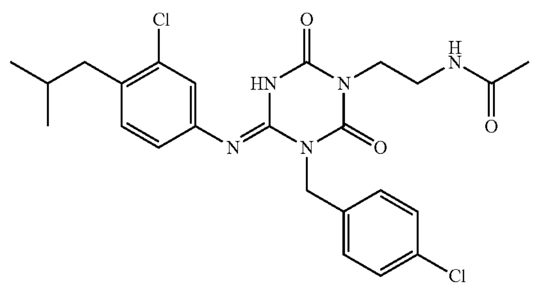 [SMILES: CC(=O)NCCn1c(=O)[nH]/c(=N\c2ccc(CC(C)C)c(Cl)c2)n(Cc2ccc(Cl)cc2)c1=O] | I-1611 | 2.56 | 504 | 3 |
| 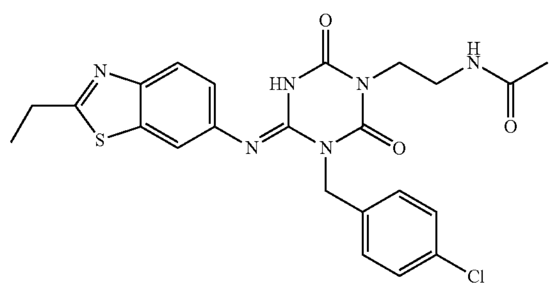 [SMILES: CCc1nc2ccc(/N=c3\[nH]c(=O)n(CCNC(C)=O)c(=O)n3Cc3ccc(Cl)cc3)cc2s1] | I-1612 | 1.94 | 499 | 3 |
| 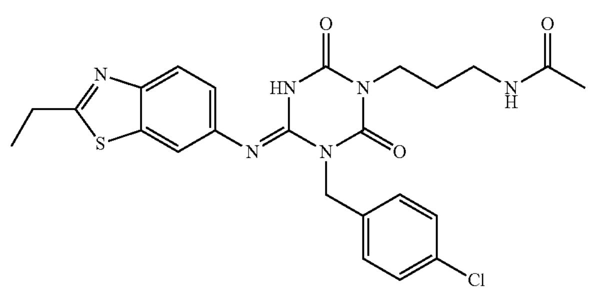 [SMILES: CCc1nc2ccc(/N=c3\[nH]c(=O)n(CCCNC(C)=O)c(=O)n3Cc3ccc(Cl)cc3)cc2s1] | I-1613 | 2.00 | 513 | 3 |
| 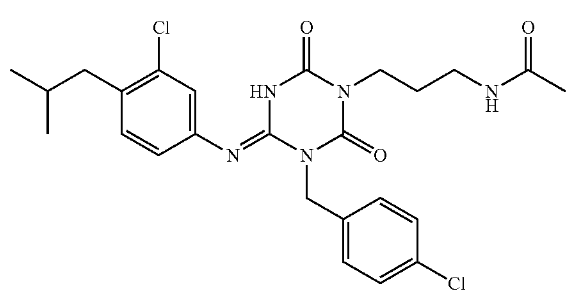 | I-1614 | 2.61 | 518 | 3 |
| 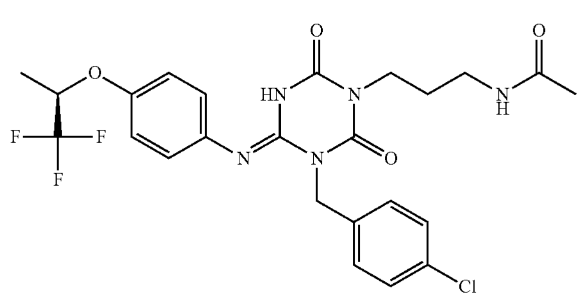 [SMILES: CC(=O)NCCCn1c(=O)[nH]/c(=N\c2ccc(O[C@H](C)C(F)(F)F)cc2)n(Cc2ccc(Cl)cc2)c1=O] | I-1615 | 2.15 | 540 | 3 |

TABLE 327

| Structure | Compound No. | Retention Time (min) | [M + H] | Method |
|---|---|---|---|---|
| 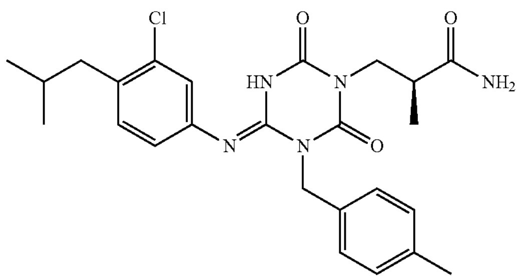 [SMILES: Cc1ccc(Cn2c(=O)n(C[C@H](C)C(N)=O)c(=O)[nH]/c2=N\c2ccc(CC(C)C)c(Cl)c2)cc1] | I-1616 | 2.47 | 484 | 3 |
| 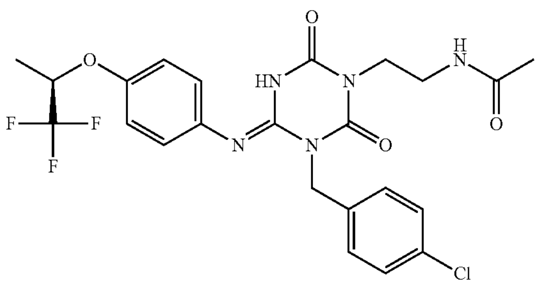 [SMILES: CC(=O)NCCn1c(=O)[nH]/c(=N\c2ccc(O[C@H](C)C(F)(F)F)cc2)n(Cc2ccc(Cl)cc2)c1=O] | I-1617 | 2.11 | 526 | 3 |
| 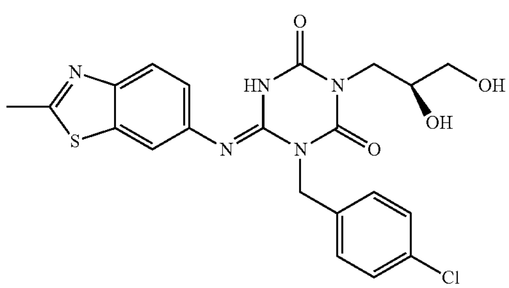 [SMILES: Cc1nc2ccc(/N=c3\[nH]c(=O)n(C[C@H](O)CO)c(=O)n3Cc3ccc(Cl)cc3)cc2s1] | I-1618 | 1.72 | 474 | 3 |
| 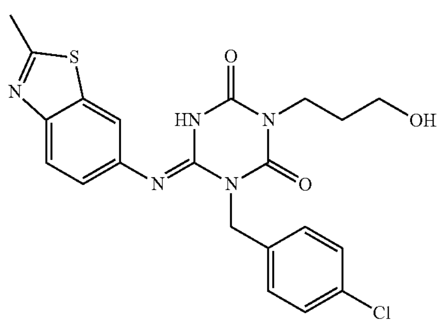 [SMILES: Cc1nc2ccc(/N=c3\[nH]c(=O)n(CCCO)c(=O)n3Cc3ccc(Cl)cc3)cc2s1] | I-1619 | 1.56 | 458 | 2 |
| 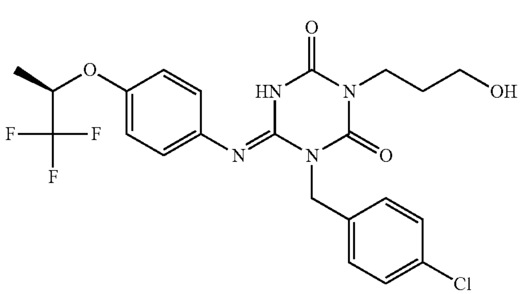 [SMILES: C[C@@H](Oc1ccc(/N=c2\[nH]c(=O)n(CCCO)c(=O)n2Cc2ccc(Cl)cc2)cc1)C(F)(F)F] | I-1620 | 1.83 | 499 | 2 |

TABLE 328
| Structure | Compound No. | Retention Time (min) | [M + H] | Method |
|---|---|---|---|---|
| 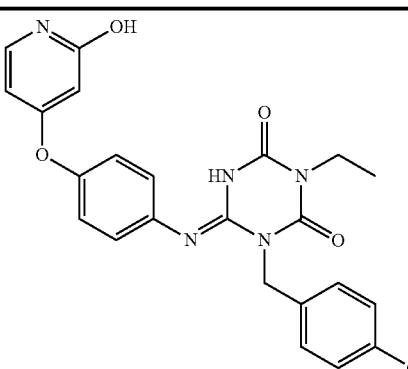 | I-1621 | 1.90 | 466 | 3 |
| 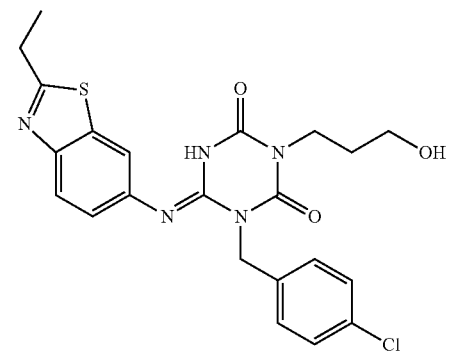 [SMILES: CCc1nc2ccc(/N=c3\[nH]c(=O)n(CCCO)c(=O)n3Cc3ccc(Cl)cc3)cc2s1] | I-1622 | 1.67 | 472 | 2 |
| 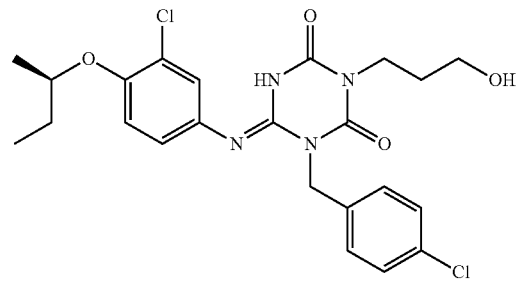 [SMILES: CC[C@@H](C)Oc1ccc(/N=c2\[nH]c(=O)n(CCCO)c(=O)n2Cc2ccc(Cl)cc2)cc1Cl] | I-1623 | 2.06 | 493 | 2 |
| 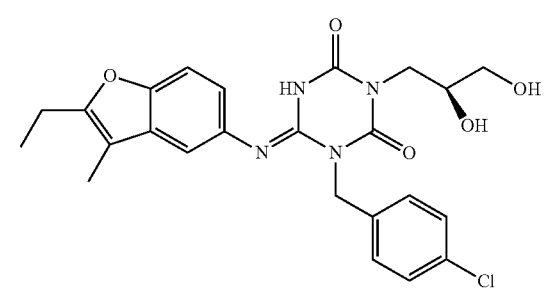 [SMILES: CCc1oc2ccc(/N=c3\[nH]c(=O)n(C[C@H](O)CO)c(=O)n3Cc3ccc(Cl)cc3)cc2c1C] | I-1624 | 2.15 | 485 | 3 |

TABLE 328-continued

| Structure | Compound No. | Retention Time (min) | [M + H] | Method |
|---|---|---|---|---|
| 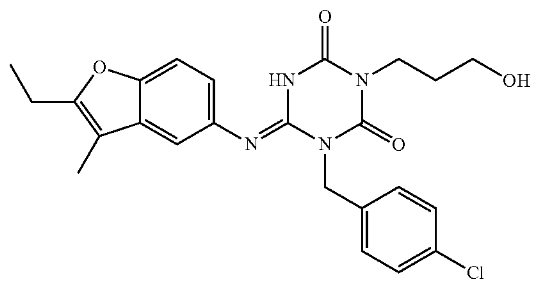 [SMILES: CCc1oc2ccc(/N=c3\[nH]c(=O)n(CCCO)c(=O)n3Cc3ccc(Cl)cc3)cc2c1C] | I-1625 | 1.91 | 469 | 2 |

TABLE 329

| Structure | Compound No. | Retention Time (min) | [M + H] | Method |
|---|---|---|---|---|
| 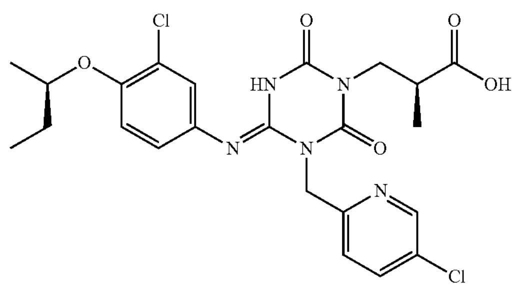 [SMILES: CC[C@@H](C)Oc1ccc(/N=c2\[nH]c(=O)n(C[C@H](C)C(=O)O)c(=O)n2Cc2ccc(Cl)cn2)cc1Cl] | I-1626 | 1.96 | 522 | 2 |
| 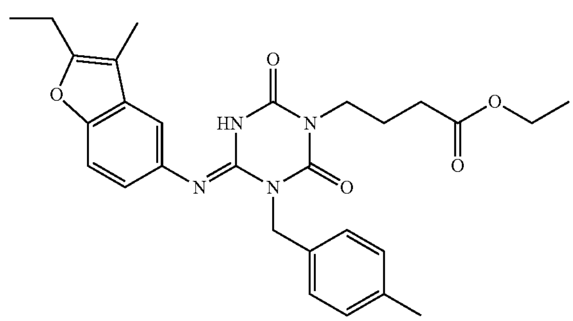 [SMILES: CCOC(=O)CCCn1c(=O)[nH]/c(=N\c2ccc3oc(CC)c(C)c3c2)n(Cc2ccc(C)cc2)c1=O] | I-1627 | 2.65 | 505 | 3 |
| 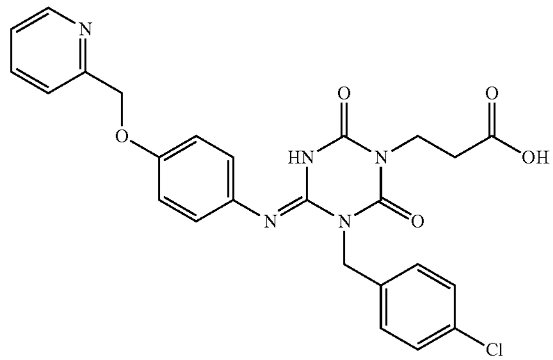 [SMILES: O=C(O)CCn1c(=O)[nH]/c(=N\c2ccc(OCc3ccccn3)cc2)n(Cc2ccc(Cl)cc2)c1=O] | I-1628 | 1.37 | 508 | 2 |

TABLE 329-continued
| Structure | Compound No. | Retention Time (min) | [M + H] | Method |
|---|---|---|---|---|
| 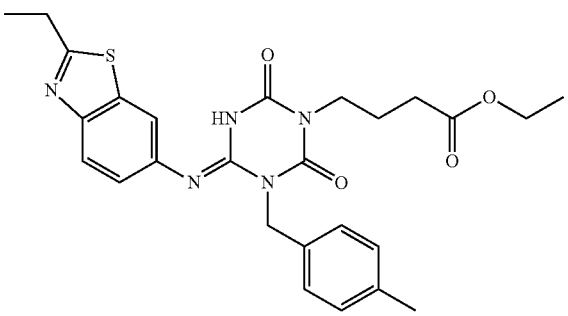 [SMILES: CCOC(=O)CCCn1c(=O)[nH]/c(=N\c2ccc3nc(CC)sc3c2)n(Cc2ccc(C)cc2)c1=O] | I-1629 | 2.42 | 508 | 3 |
| 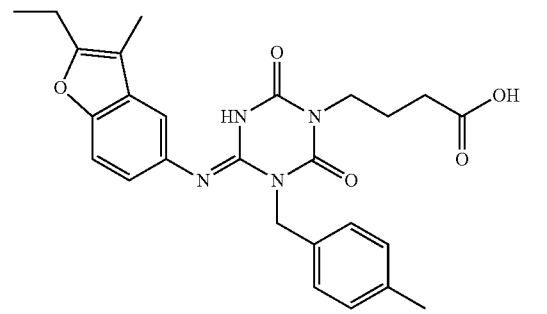 [SMILES: CCc1oc2ccc(/N=c3\[nH]c(=O)n(CCCC(=O)O)c(=O)n3Cc3ccc(C)cc3)cc2c1C] | I-1630 | 2.28 | 477 | 3 |
TABLE 330
| Structure | Compound No. | Retention Time (min) | [M + H] | Method |
|---|---|---|---|---|
| 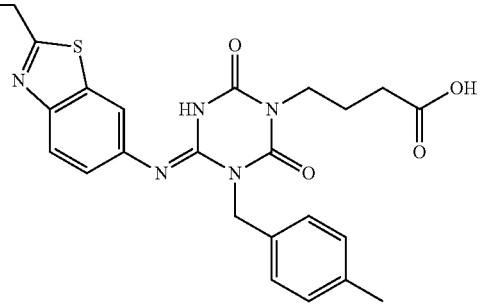 | I-1631 | 2.01 | 480 | 3 |
| 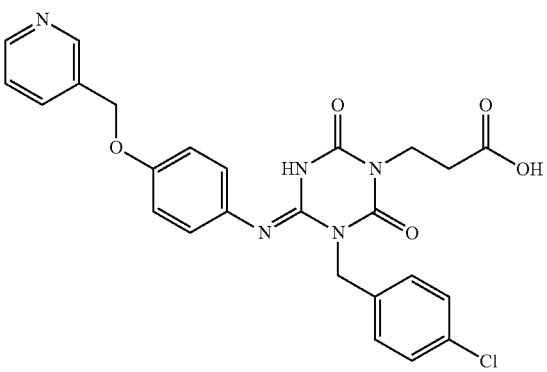 [SMILES: O=C(O)CCn1c(=O)[nH]/c(=N\c2ccc(OCc3cccnc3)cc2)n(Cc2ccc(Cl)cc2)c1=O] | I-1632 | 1.18 | 508 | 2 |

TABLE 330-continued

| Structure | Compound No. | Retention Time (min) | [M + H] | Method |
|---|---|---|---|---|
| 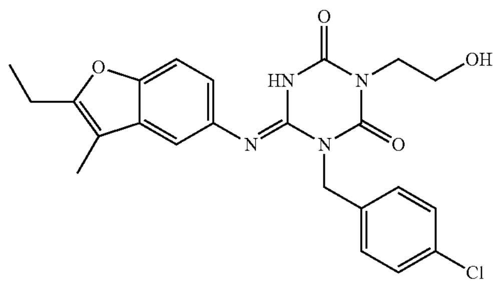 [SMILES: CCc1oc2ccc(/N=c3\[nH]c(=O)n(CCO)c(=O)n3Cc3ccc(Cl)cc3)cc2c1C] | I-1633 | 1.89 | 455 | 2 |
| 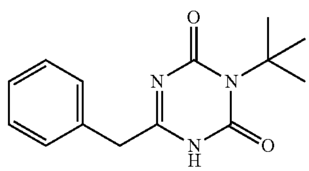 [SMILES: CC(C)(C)n1c(=O)nc(Cc2ccccc2)[nH]c1=O] | I-1634 | 1.34 | 260 | 2 |
| 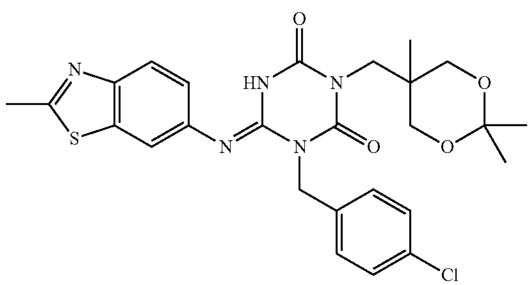 | I-1635 | 2.00 | 542 | 2 |

TABLE 331

| Structure | Compound No. | Retention Time (min) | [M + H] | Method |
|---|---|---|---|---|
| 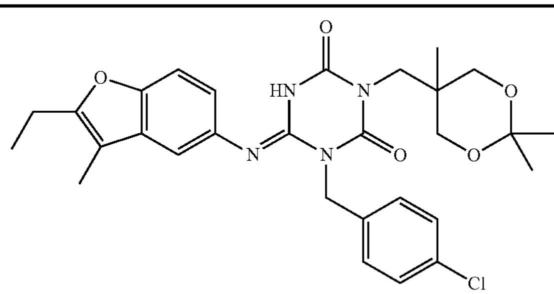 | I-1636 | 2.35 | 553 | 2 |
| 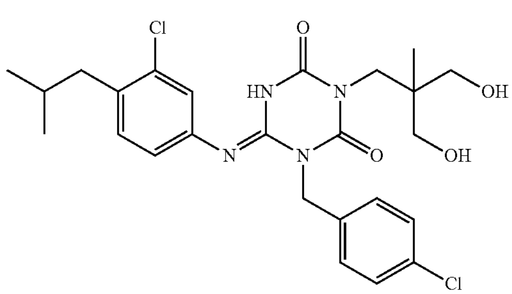 [SMILES: CC(C)Cc1ccc(/N=c2\[nH]c(=O)n(CC(C)(CO)CO)c(=O)n2Cc2ccc(Cl)cc2)cc1Cl] | I-1637 | 2.24 | 521 | 2 |

TABLE 331-continued

| Structure | Compound No. | Retention Time (min) | [M + H] | Method |
|---|---|---|---|---|
| (structure) | I-1638 | 1.51 | 570 | 2 |
| (structure) | I-1639 | 1.49 | 556 | 2 |
| (structure) | I-1640 | 2.35 | 570 | 2 |

TABLE 332

| Structure | Compound No. | Retention Time (min) | [M + H] | Method |
|---|---|---|---|---|
| (structure) | I-1641 | 2.33 | 556 | 2 |

TABLE 332-continued

| Structure | Compound No. | Retention Time (min) | [M + H] | Method |
|---|---|---|---|---|
| 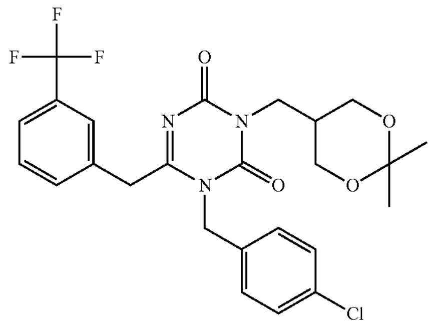 [SMILES: CC1(C)OCC(Cn2c(=O)nc(Cc3cccc(C(F)(F)F)c3)n(Cc3ccc(Cl)cc3)c2=O)CO1] | I-1642 | 2.10 | 524 | 2 |
| 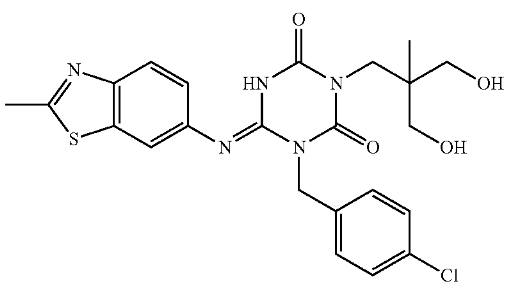 [SMILES: Cc1nc2ccc(/N=c3\[nH]c(=O)n(CC(C)(CO)CO)c(=O)n3Cc3ccc(Cl)cc3)cc2s1] | I-1643 | 1.56 | 502 | 2 |
| 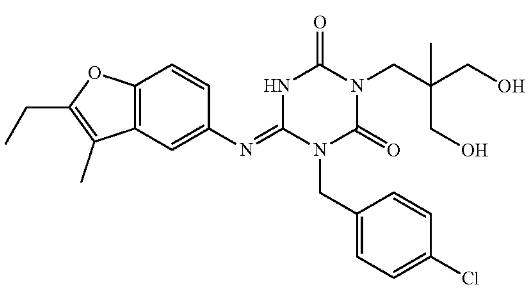 [SMILES: CCc1oc2ccc(/N=c3\[nH]c(=O)n(CC(C)(CO)CO)c(=O)n3Cc3ccc(Cl)cc3)cc2c1C] | I-1644 | 1.94 | 513 | 2 |
| 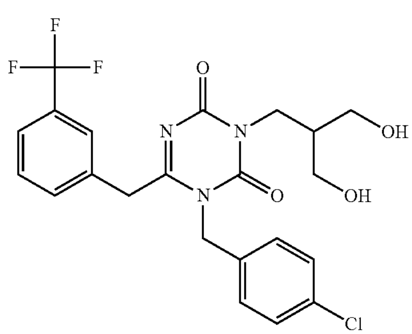 [SMILES: O=c1nc(Cc2cccc(C(F)(F)F)c2)n(Cc2ccc(Cl)cc2)c(=O)n1CC(CO)CO] | I-1645 | 1.68 | 484 | 2 |

TABLE 333

| Structure | Compound No. | Retention Time (min) | [M + H] | Method |
|---|---|---|---|---|
| 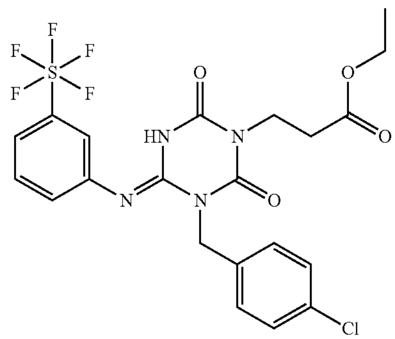 [SMILES: CCOC(=O)CCn1c(=O)[nH]/c(=N\c2cccc(S(F)(F)(F)(F)F)c2)n(Cc2ccc(Cl)cc2)c1=O] | I-1646 | 2.34 | 555 | 2 |
| 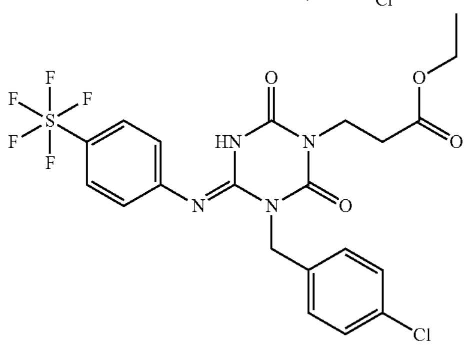 | I-1647 | 2.37 | 555 | 2 |
| 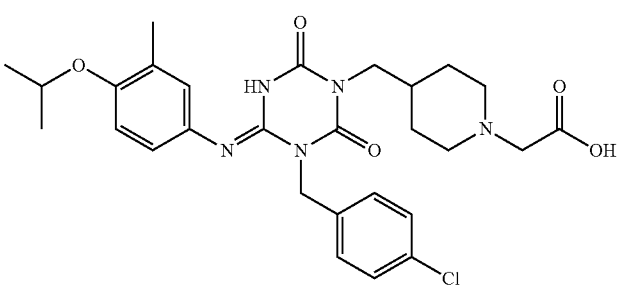 [SMILES: Cc1cc(/N=c2\[nH]c(=O)n(CC3CCN(CC(=O)O)CC3)c(=O)n2Cc2ccc(Cl)cc2)ccc1OC(C)C] | I-1648 | 1.57 | 556 | 2 |
| 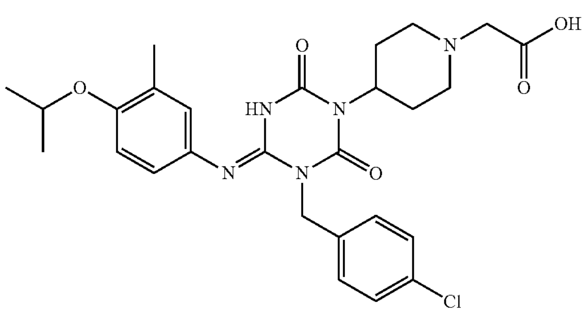 [SMILES: Cc1cc(/N=c2\[nH]c(=O)n(C3CCN(CC(=O)O)CC3)c(=O)n2Cc2ccc(Cl)cc2)ccc1OC(C)C] | I-1649 | 1.56 | 542 | 2 |
| 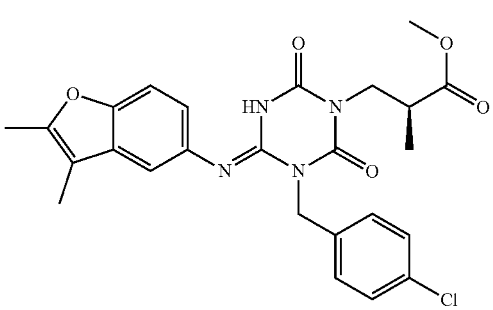 [SMILES: COC(=O)[C@@H](C)Cn1c(=O)[nH]/c(=N\c2ccc3oc(C)c(C)c3c2)n(Cc2ccc(Cl)cc2)c1=O] | I-1650 | 2.12 | 497 | 2 |

TABLE 334

| Structure | Compound No. | Retention Time (min) | [M + H] | Method |
|---|---|---|---|---|
| 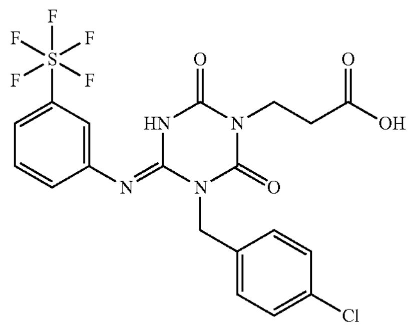 [SMILES: O=C(O)CCn1c(=O)[nH]/c(=N\c2cccc(S(F)(F)(F)(F)F)c2)n(Cc2ccc(Cl)cc2)c1=O] | I-1651 | 2.02 | 527 | 2 |
| 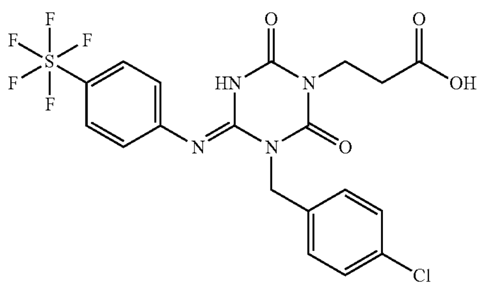 [SMILES: O=C(O)CCn1c(=O)[nH]/c(=N\c2ccc(S(F)(F)(F)(F)F)cc2)n(Cc2ccc(Cl)cc2)c1=O] | I-1652 | 2.07 | 527 | 2 |
| 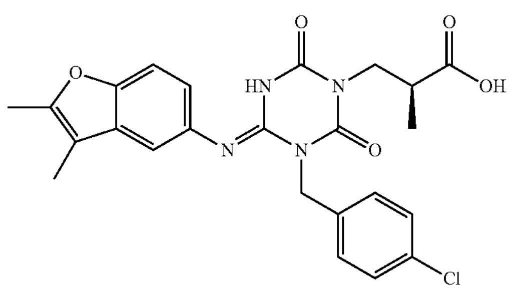 [SMILES: Cc1oc2ccc(/N=c3\[nH]c(=O)n(C[C@H](C)C(=O)O)c(=O)n3Cc3ccc(Cl)cc3)cc2c1C] | I-1653 | 1.90 | 483 | 2 |
| 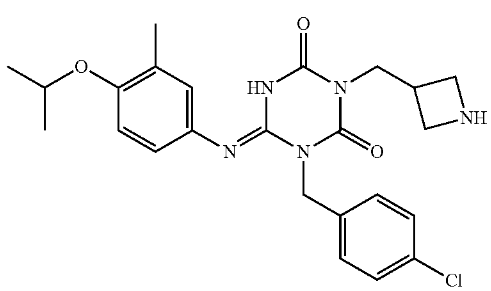 [SMILES: Cc1cc(/N=c2\[nH]c(=O)n(CC3CNC3)c(=O)n2Cc2ccc(Cl)cc2)ccc1OC(C)C] | I-1654 | 1.39 | 470 | 2 |
| 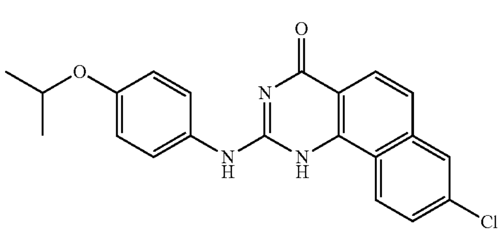 | I-1655 | 2.46 | 422 | 3 |

TABLE 335
| Structure | Compound No. | Retention Time (min) | [M + H] | Method |
|---|---|---|---|---|
| 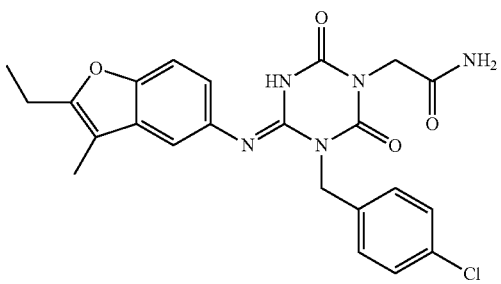 [SMILES: CCc1oc2ccc(/N=c3\[nH]c(=O)n(CC(N)=O)c(=O)n3Cc3ccc(Cl)cc3)cc2c1C] | I-1656 | 2.15 | 468 | 3 |
| 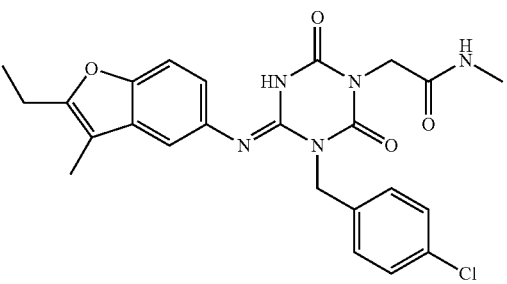 [SMILES: CCc1oc2ccc(/N=c3\[nH]c(=O)n(CC(=O)NC)c(=O)n3Cc3ccc(Cl)cc3)cc2c1C] | I-1657 | 2.22 | 482 | 3 |
| 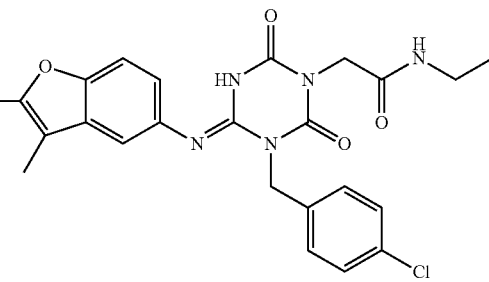 | I-1658 | 2.10 | 512 | 3 |
| 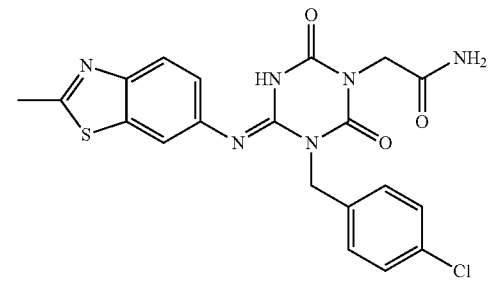 [SMILES: Cc1nc2ccc(/N=c3\[nH]c(=O)n(CC(N)=O)c(=O)n3Cc3ccc(Cl)cc3)cc2s1] | I-1659 | 1.72 | 457 | 3 |
| 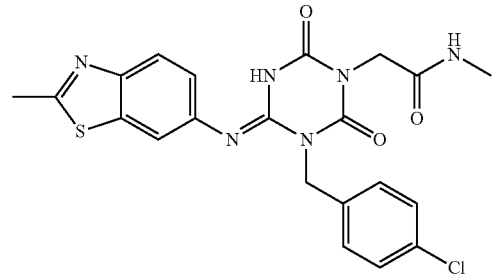 | I-1660 | 1.79 | 471 | 3 |

TABLE 336

| Structure | Compound No. | Retention Time (min) | [M + H] | Method |
|---|---|---|---|---|
| 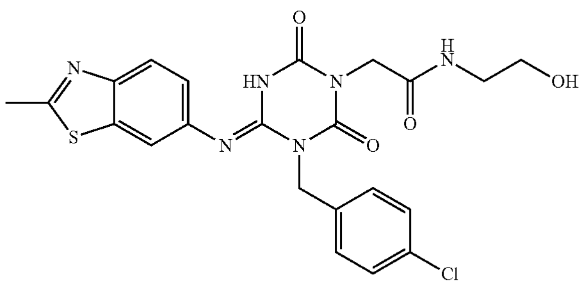 [SMILES: Cc1nc2ccc(/N=c3\[nH]c(=O)n(CC(=O)NCCO)c(=O)n3Cc3ccc(Cl)cc3)cc2s1] | I-1661 | 1.68 | 501 | 3 |
| 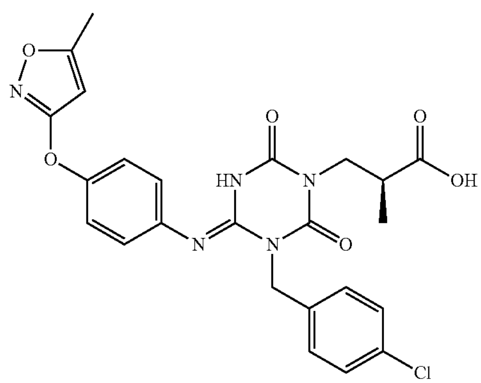 [SMILES: Cc1cc(Oc2ccc(/N=c3\[nH]c(=O)n(C[C@H](C)C(=O)O)c(=O)n3Cc3ccc(Cl)cc3)cc2)no1] | I-1662 | 2.10 | 512 | 3 |
| 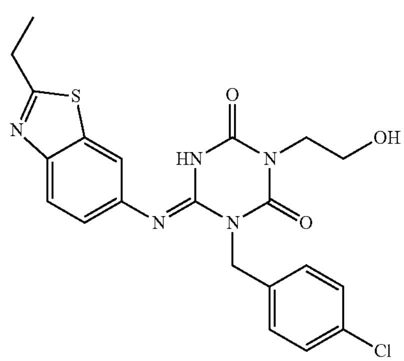 [SMILES: CCc1nc2ccc(/N=c3\[nH]c(=O)n(CCO)c(=O)n3Cc3ccc(Cl)cc3)cc2s1] | I-1663 | 1.63 | 458 | 2 |
| 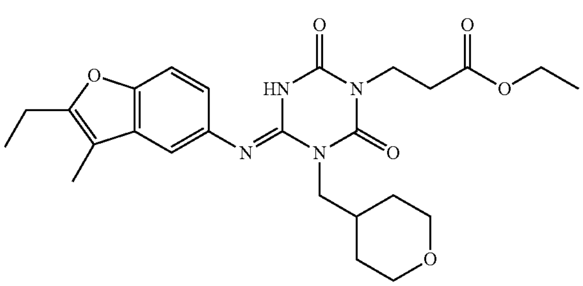 [SMILES: CCOC(=O)CCn1c(=O)[nH]/c(=N\c2ccc3oc(CC)c(C)c3c2)n(CC2CCOCC2)c1=O] | I-1664 | 2.13 | 485 | 3 |

TABLE 336-continued
| Structure | Compound No. | Retention Time (min) | [M + H] | Method |
|---|---|---|---|---|
| 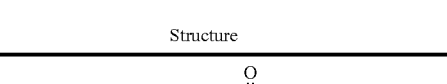 | I-1665 | 2.01 | 513 | 3 |
TABLE 337
| Structure | Compound No. | Retention Time (min) | [M + H] | Method |
|---|---|---|---|---|
| 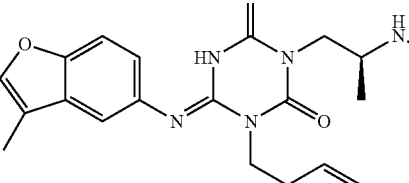 | I-1666 | 2.28 | 510 | 3 |
| 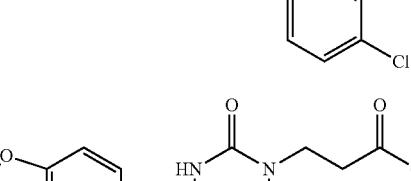 | I-1667 | 2.33 | 441 | 3 |
| 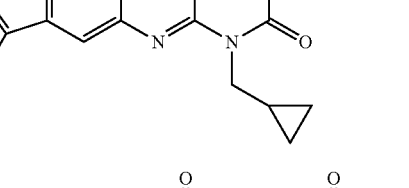 | I-1668 | 2.11 | 401 | 3 |
| 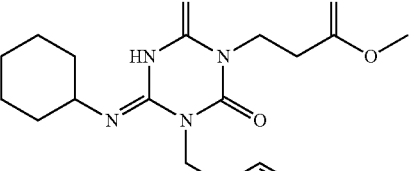 | I-1669 | 1.86 | 387 | 3 |

TABLE 337-continued

| Structure | Compound No. | Retention Time (min) | [M + H] | Method |
|---|---|---|---|---|
| 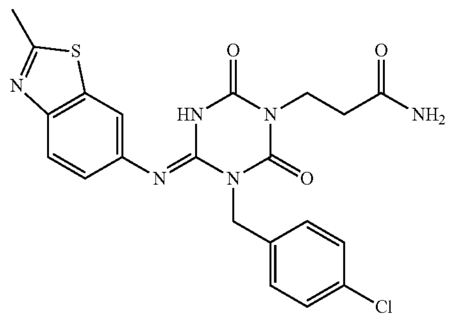 [SMILES: Cc1nc2ccc(/N=c3\[nH]c(=O)n(CCC(N)=O)c(=O)n3Cc3ccc(Cl)cc3)cc2s1] | I-1670 | 1.73 | 471 | 3 |

TABLE 338

| Structure | Compound No. | Retention Time (min) | [M + H] | Method |
|---|---|---|---|---|
| 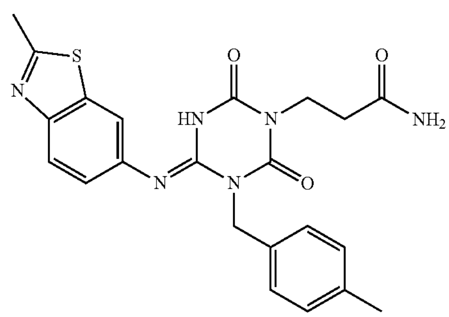 [SMILES: Cc1ccc(Cn2c(=O)n(CCC(N)=O)c(=O)[nH]/c2=N\c2ccc3nc(C)sc3c2)cc1] | I-1671 | 1.65 | 451 | 3 |
| 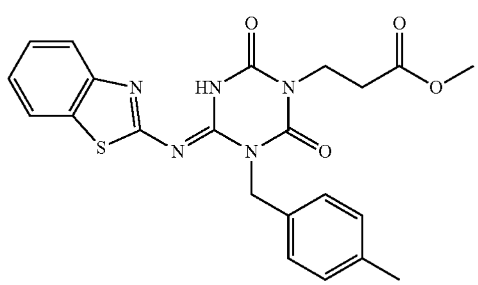 [SMILES: COC(=O)CCn1c(=O)[nH]/c(=N\c2nc3ccccc3s2)n(Cc2ccc(C)cc2)c1=O] | I-1672 | 2.36 | 452 | 3 |
| 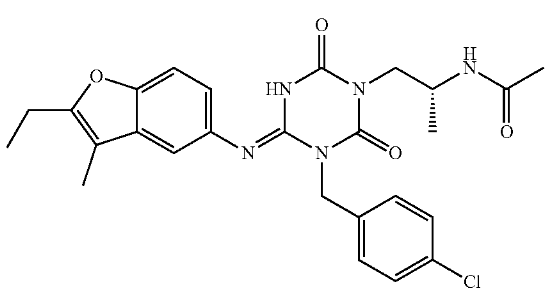 [SMILES: CCc1oc2ccc(/N=c3\[nH]c(=O)n(C[C@@H](C)NC(C)=O)c(=O)n3Cc3ccc(Cl)cc3)cc2c1C] | I-1673 | 2.28 | 510 | 3 |

TABLE 338-continued

| Structure | Compound No. | Retention Time (min) | [M + H] | Method |
|---|---|---|---|---|
| 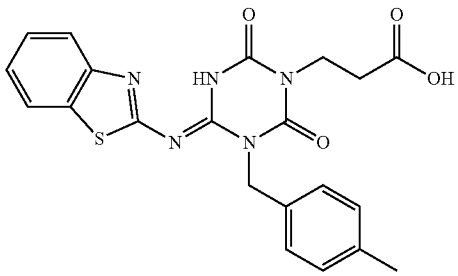 [SMILES: Cc1ccc(Cn2c(=O)n(CCC(=O)O)c(=O)[nH]/c2=N\c2nc3ccccc3s2)cc1] | I-1674 | 2.07 | 438 | 3 |
| 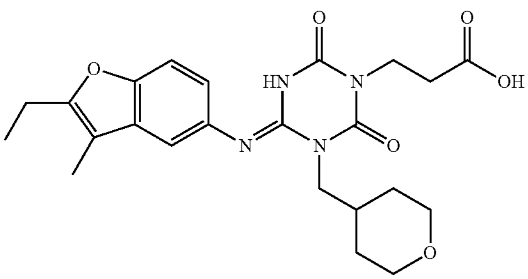 [SMILES: CCc1oc2ccc(/N=c3\[nH]c(=O)n(CCC(=O)O)c(=O)n3CC3CCOCC3)cc2c1C] | I-1675 | 2.31 | 488 | 2 |

TABLE 339

| Structure | Compound No. | Retention Time (min) | [M + H] | Method |
|---|---|---|---|---|
| 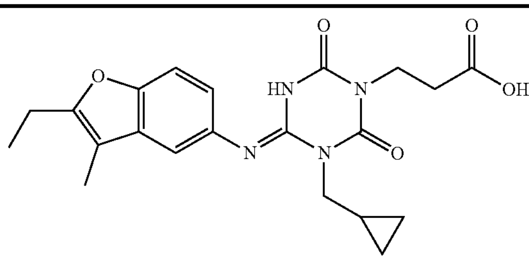 | I-1676 | 1.95 | 388 | 2 |
| 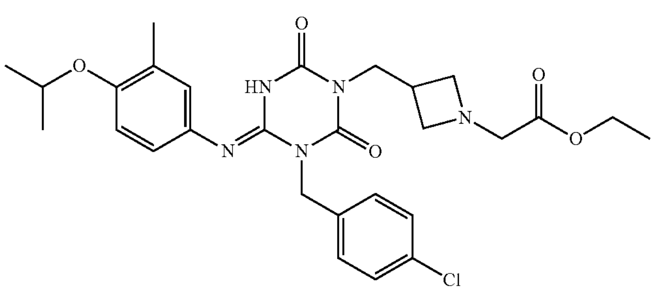 [SMILES: CCOC(=O)CN1CC(Cn2c(=O)[nH]/c(=N\c3ccc(OC(C)C)c(C)c3)n(Cc3ccc(Cl)cc3)c2=O)C1] | I-1677 | 1.78 | 457 | 3 |
| 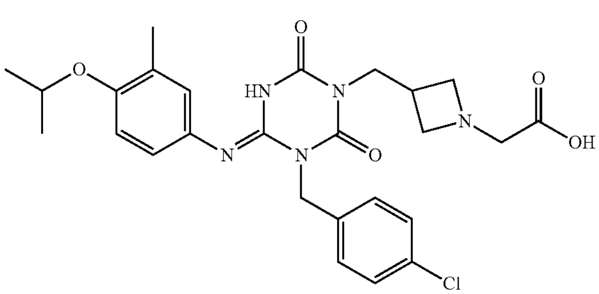 [SMILES: Cc1cc(/N=c2\[nH]c(=O)n(CC3CN(CC(=O)O)C3)c(=O)n2Cc2ccc(Cl)cc2)ccc1OC(C)C] | I-1678 | 1.95 | 413 | 3 |

TABLE 339-continued

| Structure | Compound No. | Retention Time (min) | [M + H] | Method |
|---|---|---|---|---|
| 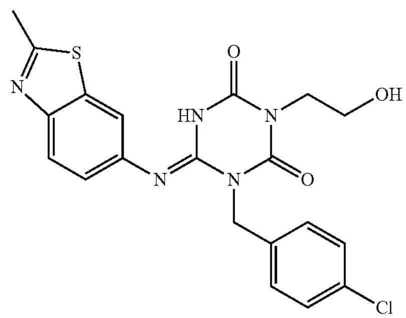 [SMILES: Cc1nc2ccc(/N=c3\[nH]c(=O)n(CCO)c(=O)n3Cc3ccc(Cl)cc3)cc2s1] | I-1679 | 1.61 | 386 | 2 |
| 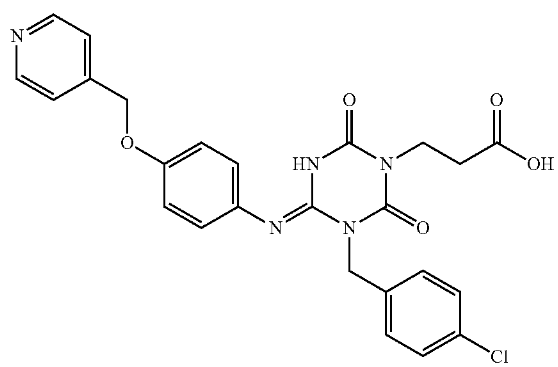 [SMILES: O=C(O)CCn1c(=O)[nH]/c(=N\c2ccc(OCc3ccncc3)cc2)n(Cc2ccc(Cl)cc2)c1=O] | I-1680 | 1.95 | 414 | 2 |

TABLE 340

| Structure | Compound No. | Retention Time (min) | [M + H] | Method |
|---|---|---|---|---|
| 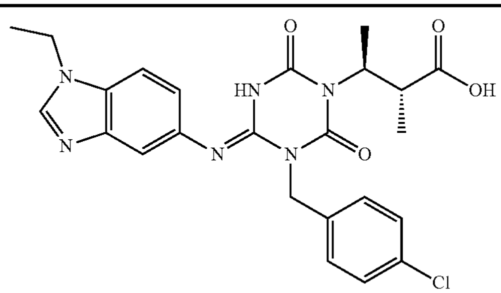 | I-1681 | 2.51 | 476 | 3 |
| 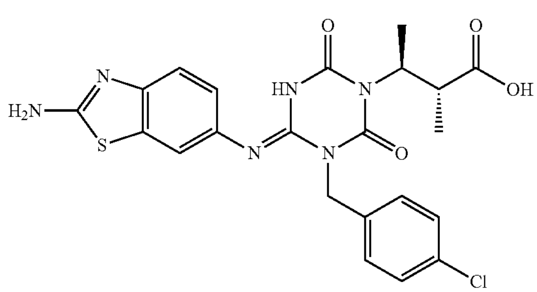 [SMILES: C[C@@H](C(=O)O)[C@H](C)n1c(=O)[nH]/c(=N\c2ccc3nc(N)sc3c2)n(Cc2ccc(Cl)cc2)c1=O] | I-1682 | 1.13 | 508 | 2 |

TABLE 340-continued
| Structure | Compound No. | Retention Time (min) | [M + H] | Method |
|---|---|---|---|---|
| 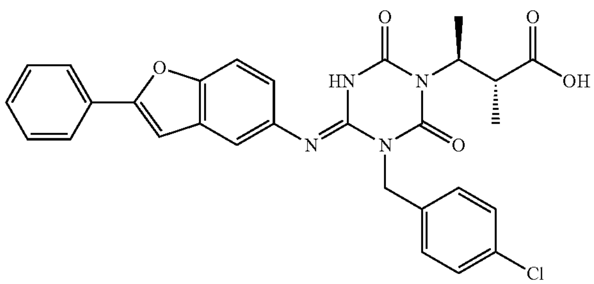 [SMILES: C[C@@H](C(=O)O)[C@H](C)n1c(=O)[nH]/c(=N\c2ccc3oc(-c4ccccc4)cc3c2)n(Cc2ccc(Cl)cc2)c1=O] | I-1683 | 1.46 | 497 | 5 |
| 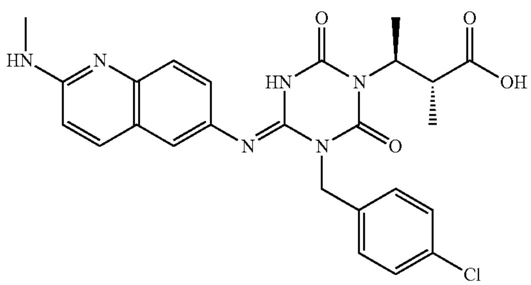 [SMILES: CNc1ccc2cc(/N=c3\[nH]c(=O)n([C@@H](C)[C@@H](C)C(=O)O)c(=O)n3Cc3ccc(Cl)cc3)ccc2n1] | I-1684 | 1.52 | 501 | 5 |
| 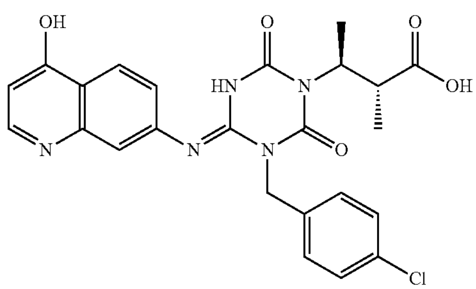 [SMILES: C[C@@H](C(=O)O)[C@H](C)n1c(=O)[nH]/c(=N\c2ccc3c(O)ccnc3c2)n(Cc2ccc(Cl)cc2)c1=O] | I-1685 | 2.63 | 545 | 5 |
TABLE 341
| Structure | Compound No. | Retention Time (min) | [M + H] | Method |
|---|---|---|---|---|
| 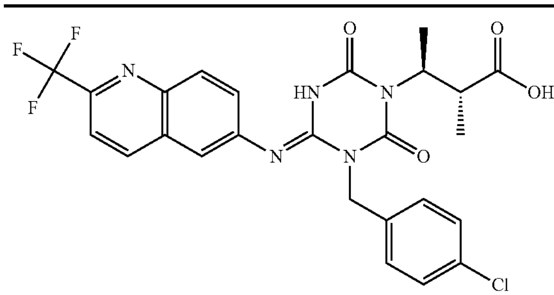 | I-1686 | 1.49 | 509 | 5 |
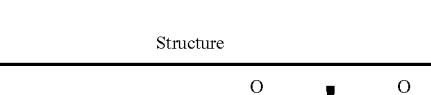

TABLE 341-continued

| Structure | Compound No. | Retention Time (min) | [M + H] | Method |
|---|---|---|---|---|
| 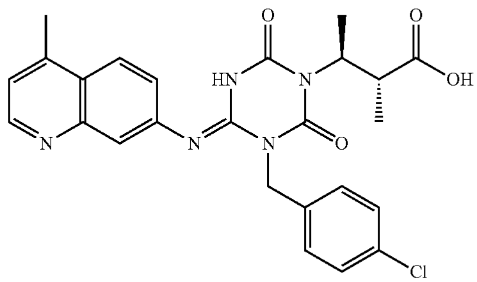 [SMILES: Cc1ccnc2cc(/N=c3\[nH]c(=O)n([C@@H](C)[C@@H](C)C(=O)O)c(=O)n3Cc3ccc(Cl)cc3)ccc12] | I-1687 | 1.56 | 496 | 5 |
| 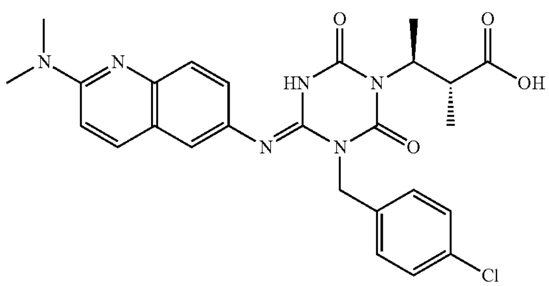 [SMILES: C[C@@H](C(=O)O)[C@H](C)n1c(=O)[nH]/c(=N\c2ccc3nc(N(C)C)ccc3c2)n(Cc2ccc(Cl)cc2)c1=O] | I-1688 | 2.46 | 548 | 5 |
| 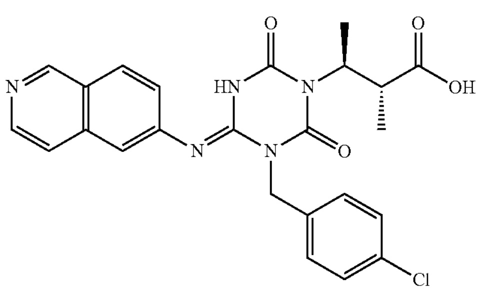 [SMILES: C[C@@H](C(=O)O)[C@H](C)n1c(=O)[nH]/c(=N\c2ccc3cnccc3c2)n(Cc2ccc(Cl)cc2)c1=O] | I-1689 | 1.57 | 494 | 5 |
| 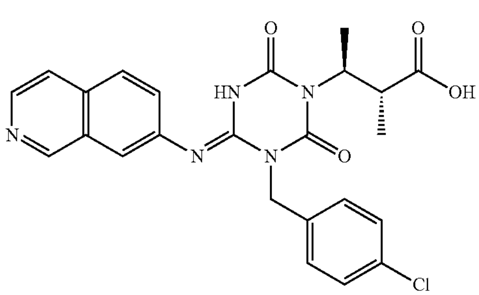 [SMILES: C[C@@H](C(=O)O)[C@H](C)n1c(=O)[nH]/c(=N\c2ccc3ccncc3c2)n(Cc2ccc(Cl)cc2)c1=O] | I-1690 | 1.43 | 523 | 5 |

TABLE 342

| Structure | Compound No. | Retention Time (min) | [M + H] | Method |
|---|---|---|---|---|
| 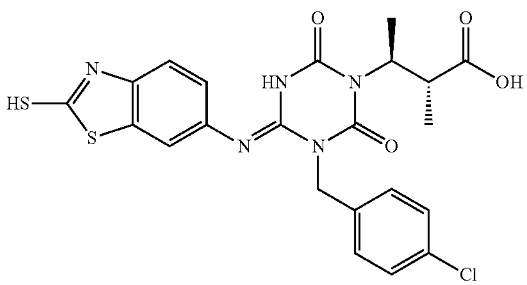 [SMILES: C[C@@H](C(=O)O)[C@H](C)n1c(=O)[nH]/c(=N\c2ccc3nc(S)sc3c2)n(Cc2ccc(Cl)cc2)c1=O] | I-1691 | 1.48 | 480 | 5 |
| 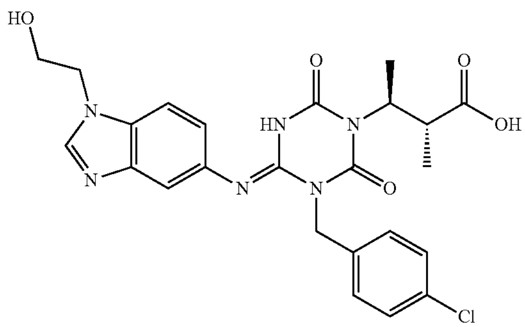 [SMILES: C[C@@H](C(=O)O)[C@H](C)n1c(=O)[nH]/c(=N\c2ccc3c(c2)ncn3CCO)n(Cc2ccc(Cl)cc2)c1=O] | I-1692 | 1.34 | 480 | 5 |
| 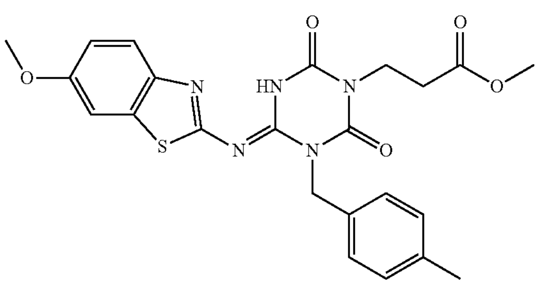 | I-1693 | 2.44 | 482 | 3 |
| 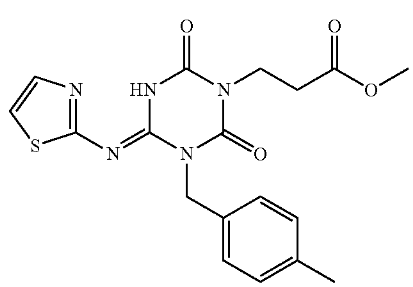 [SMILES: COC(=O)CCn1c(=O)[nH]/c(=N\c2nccs2)n(Cc2ccc(C)cc2)c1=O] | I-1694 | 1.93 | 402 | 3 |
| 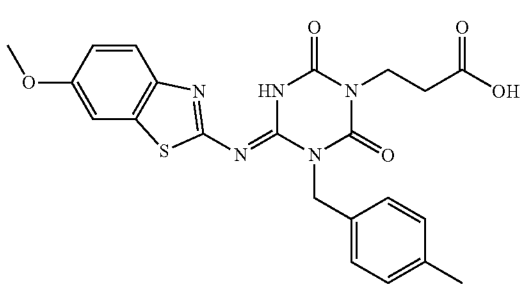 [SMILES: COc1ccc2nc(/N=c3\[nH]c(=O)n(CCC(=O)O)c(=O)n3Cc3ccc(C)cc3)sc2c1] | I-1695 | 2.14 | 468 | 3 |

TABLE 343

| Structure | Compound No. | Retention Time (min) | [M + H] | Method |
|---|---|---|---|---|
| 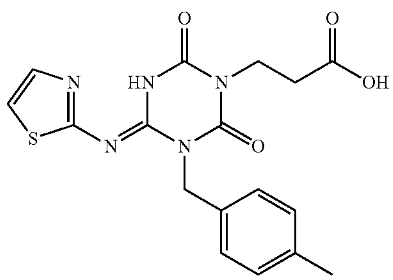 [SMILES: Cc1ccc(Cn2c(=O)n(CCC(=O)O)c(=O)[nH]/c2=N\c2nccs2)cc1] | I-1696 | 1.64 | 388 | 3 |
| 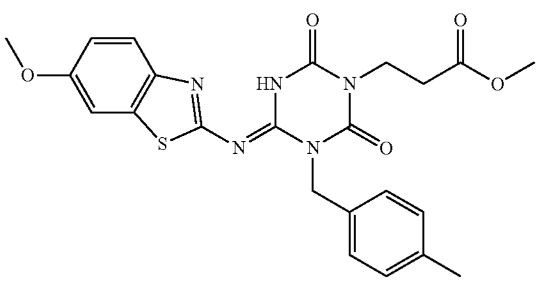 | I-1697 | 2.55 | 466 | 3 |
| 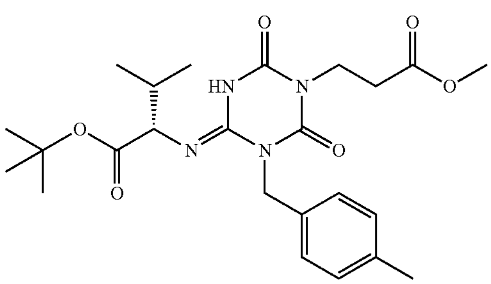 [SMILES: COC(=O)CCn1c(=O)[nH]/c(=N\[C@H](C(=O)OC(C)(C)C)C(C)C)n(Cc2ccc(C)cc2)c1=O] | I-1698 | 2.41 | 475 | 3 |
| 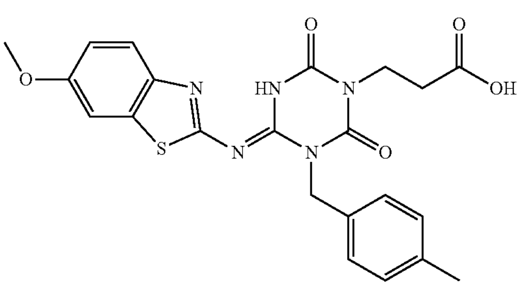 [SMILES: COc1ccc2nc(/N=c3\[nH]c(=O)n(CCC(=O)O)c(=O)n3Cc3ccc(C)cc3)sc2c1] | I-1699 | 2.26 | 452 | 3 |
| 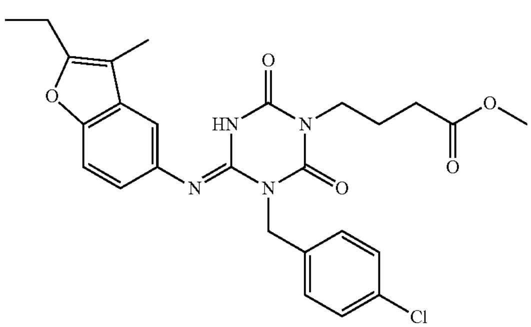 [SMILES: CCc1oc2ccc(/N=c3\[nH]c(=O)n(CCCC(=O)OC)c(=O)n3Cc3ccc(Cl)cc3)cc2c1C] | I-1700 | 2.62 | 511 | 3 |

TABLE 344

| Structure | Compound No. | Retention Time (min) | [M + H] | Method |
|---|---|---|---|---|
| 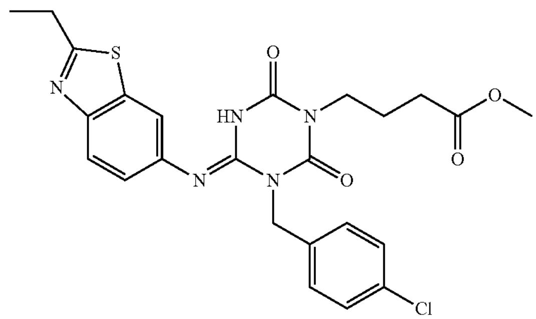 [SMILES: CCc1nc2ccc(/N=c3\[nH]c(=O)n(CCCC(=O)OC)c(=O)n3Cc3ccc(Cl)cc3)cc2s1] | I-1701 | 2.39 | 515 | 3 |
| 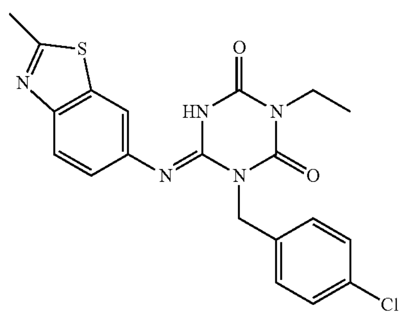 [SMILES: CCn1c(=O)[nH]/c(=N\c2ccc3nc(C)sc3c2)n(Cc2ccc(Cl)cc2)c1=O] | I-1702 | 2.25 | 428 | 3 |
| 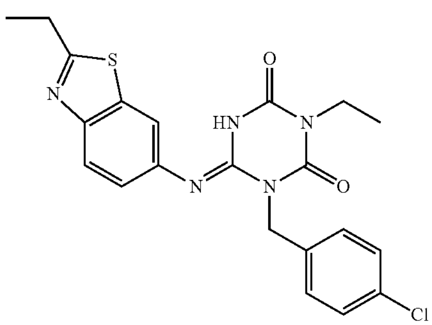 [SMILES: CCc1nc2ccc(/N=c3\[nH]c(=O)n(CC)c(=O)n3Cc3ccc(Cl)cc3)cc2s1] | I-1703 | 2.41 | 442 | 3 |
| 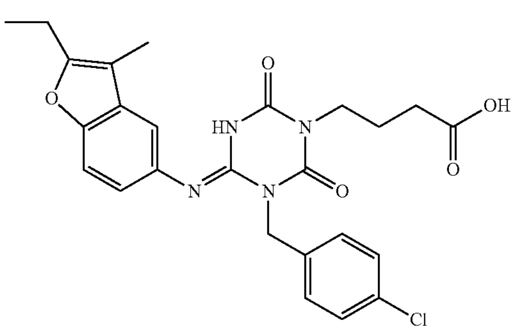 [SMILES: CCc1oc2ccc(/N=c3\[nH]c(=O)n(CCCC(=O)O)c(=O)n3Cc3ccc(Cl)cc3)cc2c1C] | I-1704 | 2.37 | 497 | 3 |

TABLE 344-continued

| Structure | Compound No. | Retention Time (min) | [M + H] | Method |
|---|---|---|---|---|
| 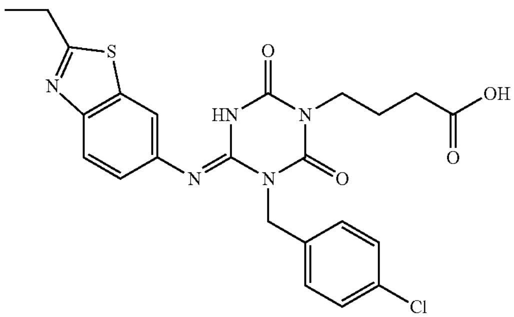 [SMILES: CCc1nc2ccc(/N=c3\[nH]c(=O)n(CCCC(=O)O)c(=O)n3Cc3ccc(Cl)cc3)cc2s1] | I-1705 | 2.12 | 500 | 3 |

TABLE 345

| Structure | Compound No. | Retention Time (min) | [M + H] | Method |
|---|---|---|---|---|
| 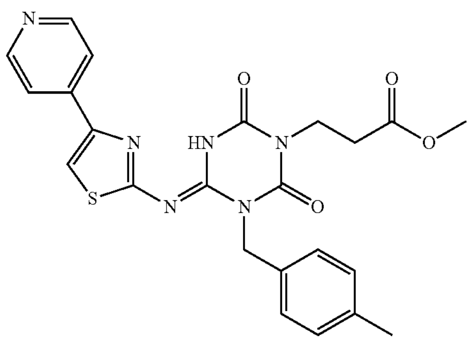 [SMILES: COC(=O)CCn1c(=O)[nH]/c(=N\c2nc(-c3ccncc3)cs2)n(Cc2ccc(C)cc2)c1=O] | I-1706 | 1.77 | 479 | 3 |
| 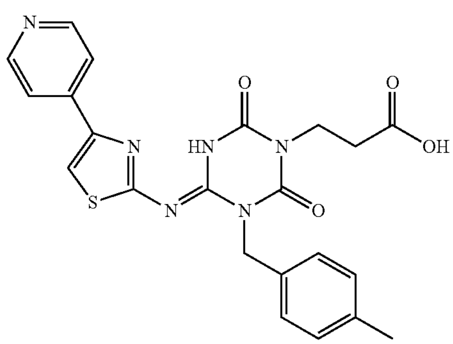 [SMILES: Cc1ccc(Cn2c(=O)n(CCC(=O)O)c(=O)[nH]/c2=N\c2nc(-c3ccncc3)cs2)cc1] | I-1707 | 1.55 | 465 | 3 |
| 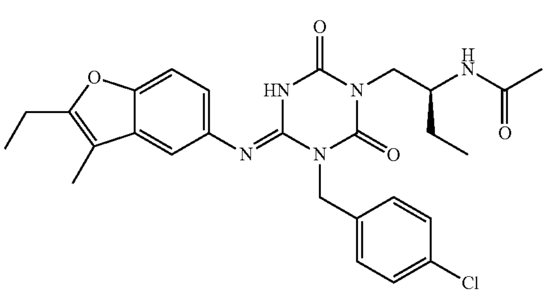 [SMILES: CCc1oc2ccc(/N=c3\[nH]c(=O)n(C[C@H](CC)NC(C)=O)c(=O)n3Cc3ccc(Cl)cc3)cc2c1C] | I-1708 | 2.37 | 524 | 3 |

TABLE 345-continued

| Structure | Compound No. | Retention Time (min) | [M + H] | Method |
|---|---|---|---|---|
| 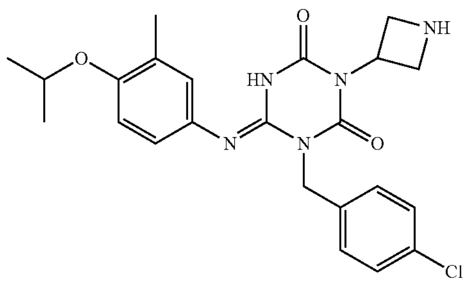 [SMILES: Cc1cc(/N=c2\[nH]c(=O)n(C3CNC3)c(=O)n2Cc2ccc(Cl)cc2)ccc1OC(C)C] | I-1709 | 1.51 | 456 | 2 |
| 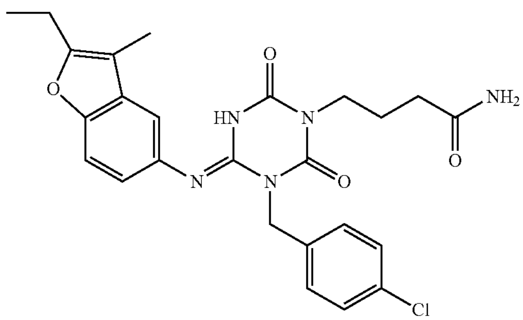 [SMILES: CCc1oc2ccc(/N=c3\[nH]c(=O)n(CCCC(N)=O)c(=O)n3Cc3ccc(Cl)cc3)cc2c1C] | I-1710 | 2.23 | 496 | 3 |

TABLE 346

| Structure | Compound No. | Retention Time (min) | [M + H] | Method |
|---|---|---|---|---|
| 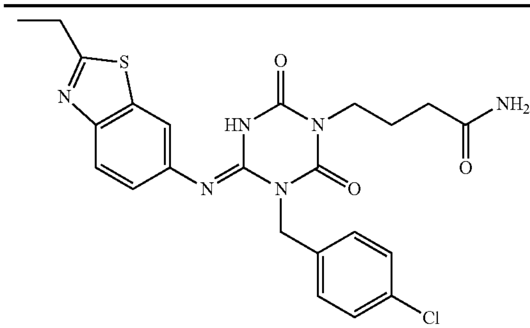 | I-1711 | 1.96 | 499 | 3 |
| 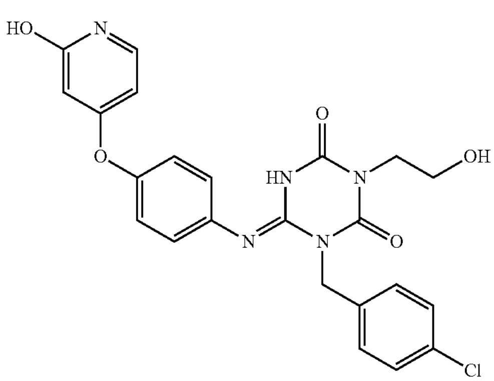 [SMILES: O=c1[nH]/c(=N\c2ccc(Oc3ccnc(O)c3)cc2)n(Cc2ccc(Cl)cc2)c(=O)n1CCO] | I-1712 | 1.62 | 482 | 3 |

TABLE 346-continued

| Structure | Compound No. | Retention Time (min) | [M + H] | Method |
|---|---|---|---|---|
| 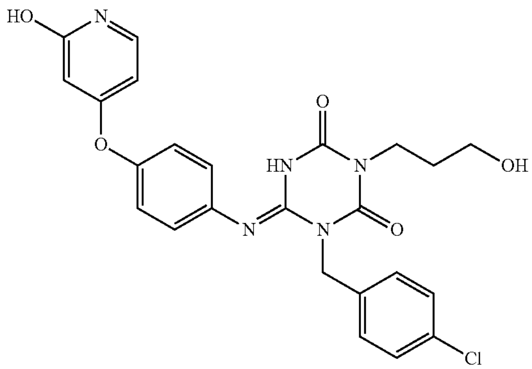 [SMILES: O=c1[nH]/c(=N\c2ccc(Oc3ccnc(O)c3)cc2)n(Cc2ccc(Cl)cc2)c(=O)n1CCCO] | I-1713 | 1.68 | 496 | 3 |
| 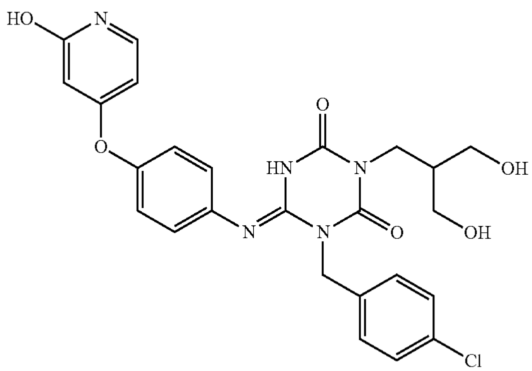 [SMILES: O=c1[nH]/c(=N\c2ccc(Oc3ccnc(O)c3)cc2)n(Cc2ccc(Cl)cc2)c(=O)n1CC(CO)CO] | I-1714 | 1.26 | 526 | 2 |
| 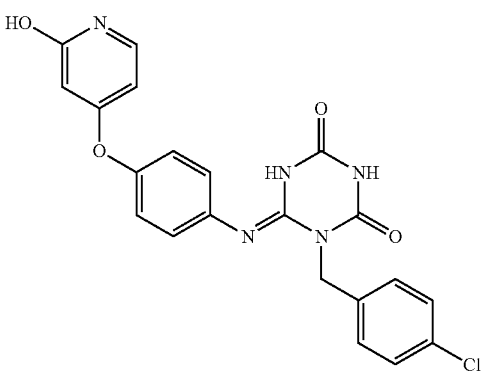 [SMILES: O=c1[nH]c(=O)n(Cc2ccc(Cl)cc2)/c(=N/c2ccc(Oc3ccnc(O)c3)cc2)[nH]1] | I-1715 | 1.34 | 437 | 2 |

TABLE 347

| Structure | Compound No. | Retention Time (min) | [M + H] | Method |
|---|---|---|---|---|
| 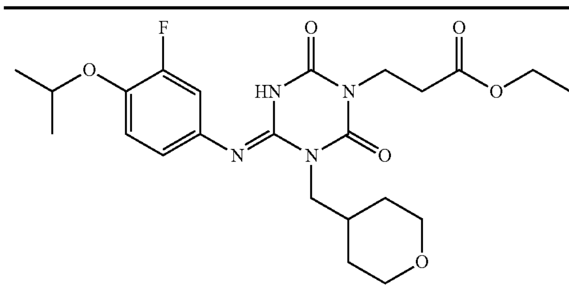 | I-1716 | 2.01 | 479 | 3 |

TABLE 347-continued

| Structure | Compound No. | Retention Time (min) | [M + H] | Method |
|---|---|---|---|---|
| 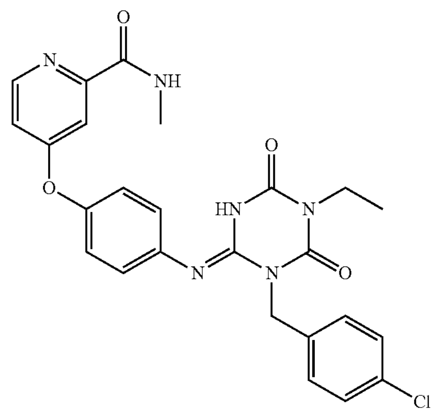 [SMILES: CCn1c(=O)[nH]/c(=N\c2ccc(Oc3ccnc(C(=O)NC)c3)cc2)n(Cc2ccc(Cl)cc2)c1=O] | I-1717 | 2.23 | 507 | 3 |
| 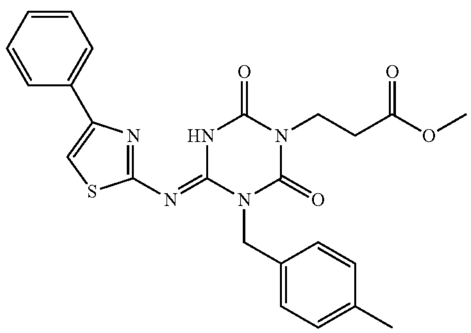 [SMILES: COC(=O)CCn1c(=O)[nH]/c(=N\c2nc(-c3ccccc3)cs2)n(Cc2ccc(C)cc2)c1=O] | I-1718 | 2.77 | 478 | 3 |
| 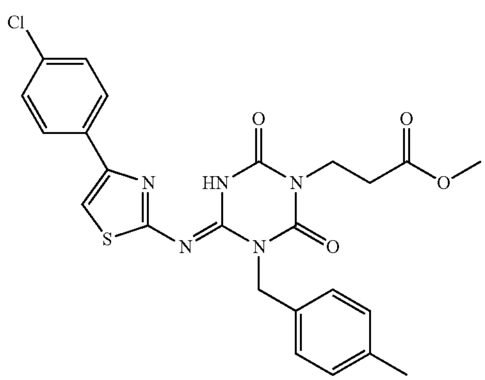 [SMILES: COC(=O)CCn1c(=O)[nH]/c(=N\c2nc(-c3ccc(Cl)cc3)cs2)n(Cc2ccc(C)cc2)c1=O] | I-1719 | 2.94 | 512 | 3 |
| 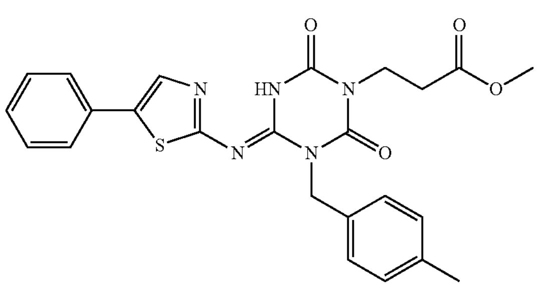 | I-1720 | 2.56 | 478 | 3 |

TABLE 348

| Structure | Compound No. | Retention Time (min) | [M + H] | Method |
|---|---|---|---|---|
| 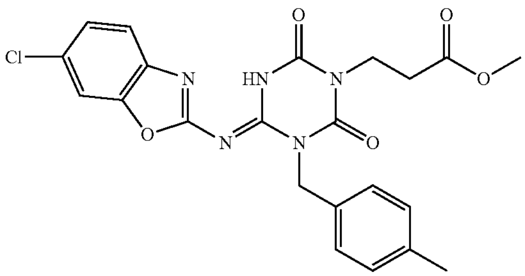 [SMILES: COC(=O)CCn1c(=O)[nH]/c(=N\c2nc3ccc(Cl)cc3o2)n(Cc2ccc(C)cc2)c1=O] | I-1721 | 2.83 | 470 | 3 |
| 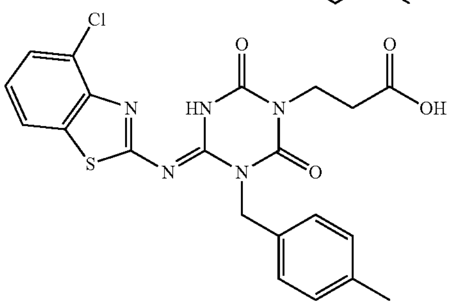 | I-1722 | 2.52 | 472 | 3 |
| 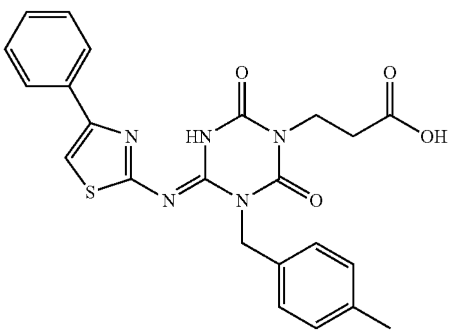 [SMILES: Cc1ccc(Cn2c(=O)n(CCC(=O)O)c(=O)[nH]/c2=N\c2nc(-c3ccccc3)cs2)cc1] | I-1723 | 2.47 | 464 | 3 |
| 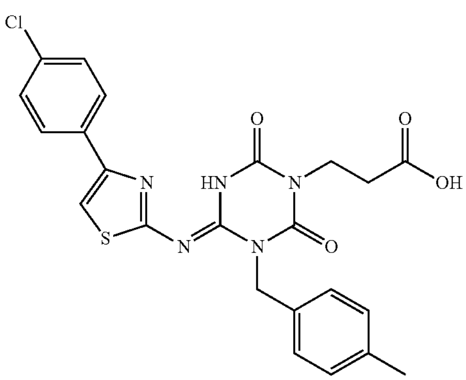 [SMILES: Cc1ccc(Cn2c(=O)n(CCC(=O)O)c(=O)[nH]/c2=N\c2nc(-c3ccc(Cl)cc3)cs2)cc1] | I-1724 | 2.67 | 498 | 3 |
| 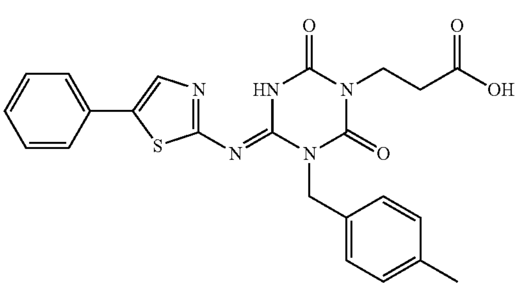 [SMILES: Cc1ccc(Cn2c(=O)n(CCC(=O)O)c(=O)[nH]/c2=N\c2ncc(-c3ccccc3)s2)cc1] | I-1725 | 2.27 | 464 | 3 |

TABLE 349

| Structure | Compound No. | Retention Time (min) | [M + H] | Method |
|---|---|---|---|---|
| 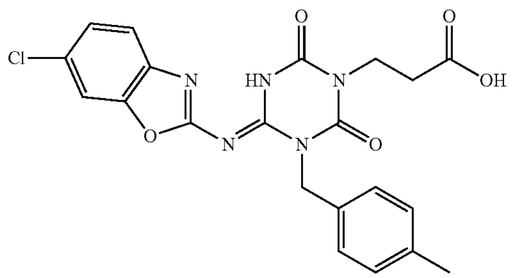 [SMILES: Cc1ccc(Cn2c(=O)n(CCC(=O)O)c(=O)[nH]/c2=N\c2nc3ccc(Cl)cc3o2)cc1] | I-1726 | 2.57 | 456 | 3 |
| 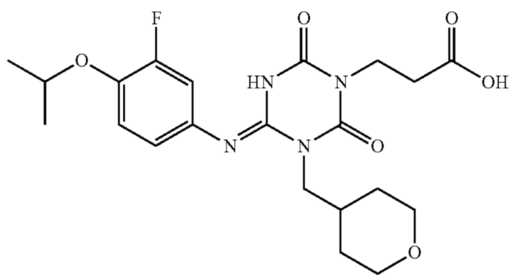 [SMILES: CC(C)Oc1ccc(/N=c2\[nH]c(=O)n(CCC(=O)O)c(=O)n2CC2CCOCC2)cc1F] | I-1727 | 1.66 | 451 | 3 |
| 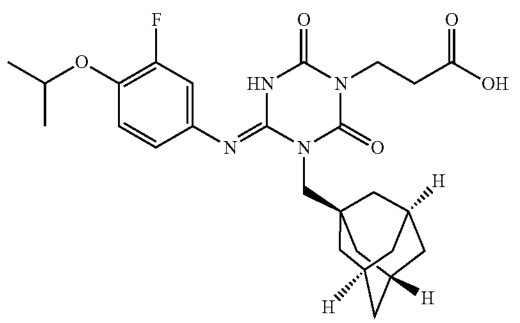 [SMILES: CC(C)Oc1ccc(/N=c2\[nH]c(=O)n(CCC(=O)O)c(=O)n2C[C@]23C[C@H]4C[C@H](C[C@H](C4)C2)C3)cc1F] | I-1728 | 2.48 | 501 | 3 |
| 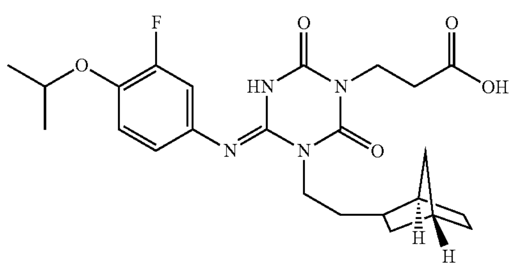 [SMILES: CC(C)Oc1ccc(/N=c2\[nH]c(=O)n(CCC(=O)O)c(=O)n2CCC2C[C@H]3CC[C@@H]2C3)cc1F] | I-1729 | 2.39 | 475 | 3 |
| 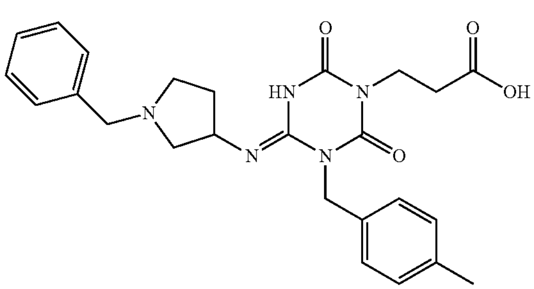 [SMILES: Cc1ccc(Cn2c(=O)n(CCC(=O)O)c(=O)[nH]/c2=N\C2CCN(Cc3ccccc3)C2)cc1] | I-1730 | 1.20 | 464 | 3 |

TABLE 350

| Structure | Compound No. | Retention Time (min) | [M + H] | Method |
|---|---|---|---|---|
| 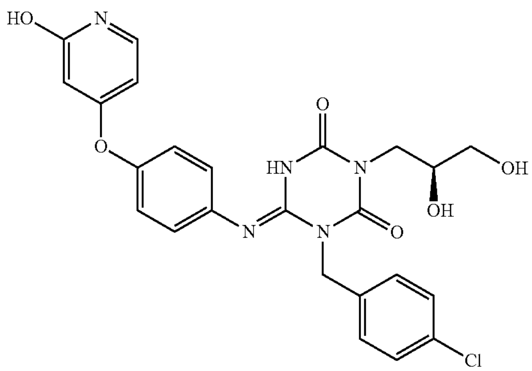 [SMILES: O=c1[nH]/c(=N\c2ccc(Oc3ccnc(O)c3)cc2)n(Cc2ccc(Cl)cc2)c(=O)n1C[C@H](O)CO] | I-1731 | 1.26 | 512 | 2 |
| 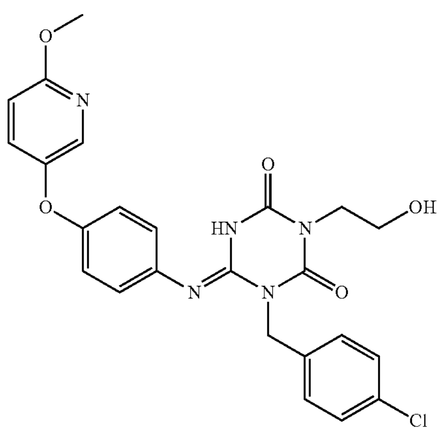 [SMILES: COc1ccc(Oc2ccc(/N=c3\[nH]c(=O)n(CCO)c(=O)n3Cc3ccc(Cl)cc3)cc2)cn1] | I-1732 | 1.86 | 496 | 2 |
| 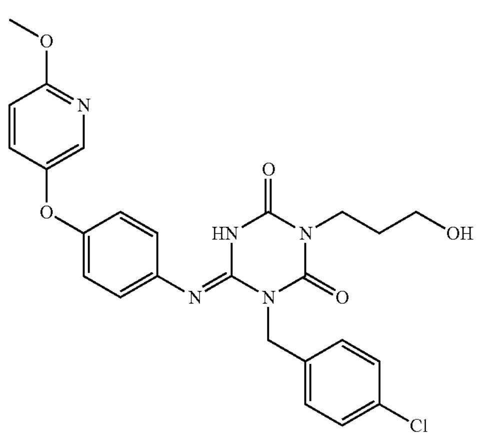 [SMILES: COc1ccc(Oc2ccc(/N=c3\[nH]c(=O)n(CCCO)c(=O)n3Cc3ccc(Cl)cc3)cc2)cn1] | I-1733 | 1.90 | 510 | 2 |

TABLE 350-continued

| Structure | Compound No. | Retention Time (min) | [M + H] | Method |
|---|---|---|---|---|
| 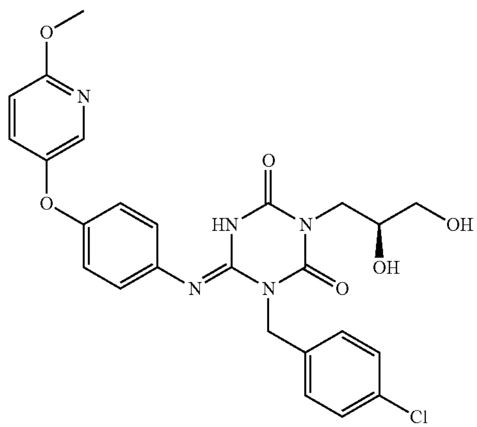 [SMILES: COc1ccc(Oc2ccc(/N=c3\[nH]c(=O)n(C[C@H](O)CO)c(=O)n3Cc3ccc(Cl)cc3)cc2)cn1] | I-1734 | 1.72 | 526 | 2 |
| 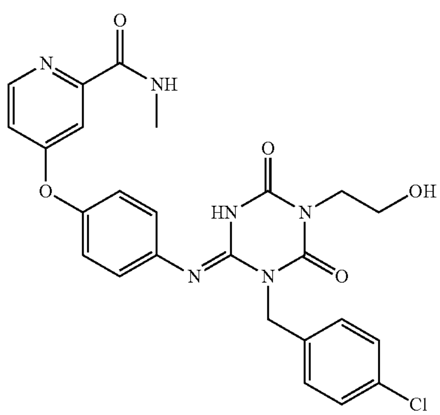 [SMILES: CNC(=O)c1cc(Oc2ccc(/N=c3\[nH]c(=O)n(CCO)c(=O)n3Cc3ccc(Cl)cc3)cc2)ccn1] | I-1735 | 1.64 | 523 | 2 |

TABLE 351

| Structure | Compound No. | Retention Time (min) | [M + H] | Method |
|---|---|---|---|---|
| 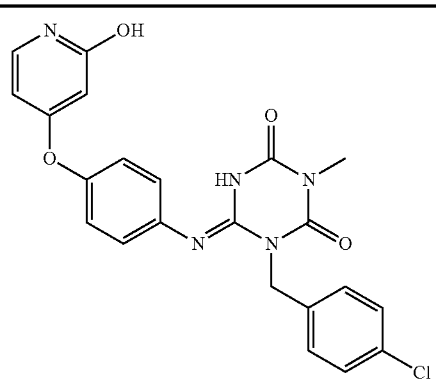 | I-1736 | 1.57 | 452 | 2 |

TABLE 351-continued

| Structure | Compound No. | Retention Time (min) | [M + H] | Method |
|---|---|---|---|---|
| 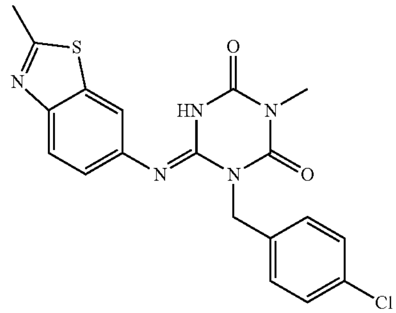 [SMILES: Cc1nc2ccc(/N=c3\[nH]c(=O)n(C)c(=O)n3Cc3ccc(Cl)cc3)cc2s1] | I-1737 | 1.81 | 414 | 2 |
| 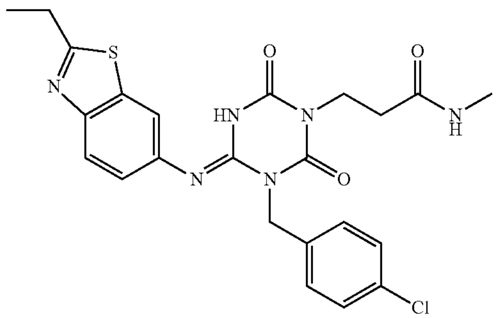 [SMILES: CCc1nc2ccc(/N=c3\[nH]c(=O)n(CCC(=O)NC)c(=O)n3Cc3ccc(Cl)cc3)cc2s1] | I-1738 | 1.97 | 499 | 3 |
| 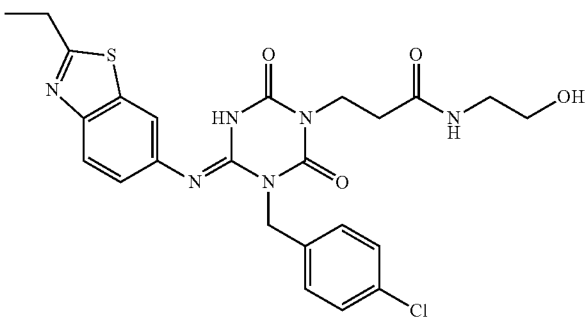 [SMILES: CCc1nc2ccc(/N=c3\[nH]c(=O)n(CCC(=O)NCCO)c(=O)n3Cc3ccc(Cl)cc3)cc2s1] | I-1739 | 1.86 | 529 | 3 |
| 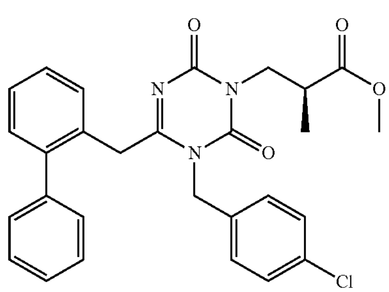 [SMILES: COC(=O)[C@@H](C)Cn1c(=O)nc(Cc2ccccc2-c2ccccc2)n(Cc2ccc(Cl)cc2)c1=O] | I-1740 | 2.42 | 504 | 2 |

TABLE 352
| Structure | Compound No. | Retention Time (min) | [M + H] | Method |
|---|---|---|---|---|
| 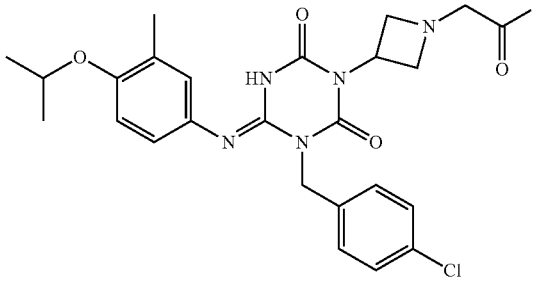 | I-1741 | 1.58 | 542 | 2 |
| 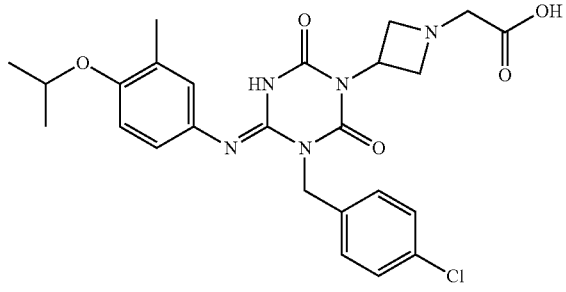 [SMILES: Cc1cc(/N=c2\[nH]c(=O)n(C3CN(CC(=O)O)C3)c(=O)n2Cc2ccc(Cl)cc2)ccc1OC(C)C] | I-1742 | 1.61 | 514 | 2 |
| 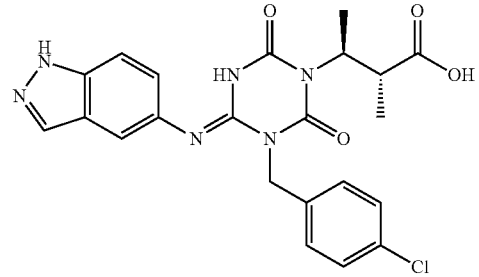 [SMILES: C[C@@H](C(=O)O)[C@H](C)n1c(=O)[nH]/c(=N\c2ccc3[nH]ncc3c2)n(Cc2ccc(Cl)cc2)c1=O] | I-1743 | 1.70 | 469 | 5 |
| 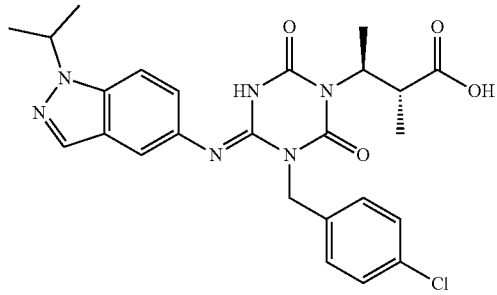 [SMILES: CC(C)n1ncc2cc(/N=c3\[nH]c(=O)n([C@@H](C)[C@@H](C)C(=O)O)c(=O)n3Cc3ccc(Cl)cc3)ccc21] | I-1744 | 2.10 | 511 | 5 |
| 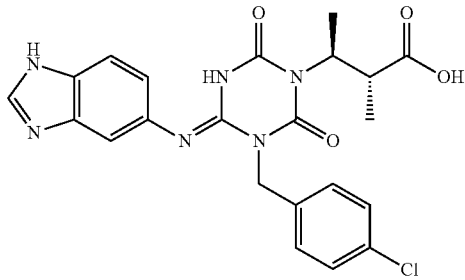 | I-1745 | 1.30 | 469 | 5 |

TABLE 353

| Structure | Compound No. | Retention Time (min) | [M + H] | Method |
|---|---|---|---|---|
| 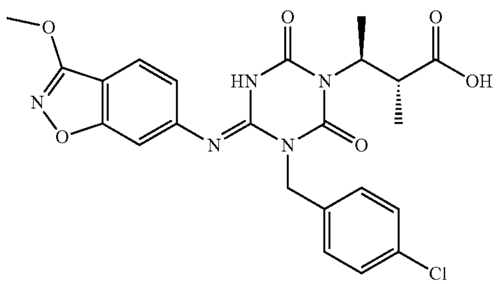 [SMILES: COc1noc2cc(/N=c3\[nH]c(=O)n([C@@H](C)[C@@H](C)C(=O)O)c(=O)n3Cc3ccc(Cl)cc3)ccc12] | I-1746 | 2.28 | 500 | 5 |
| 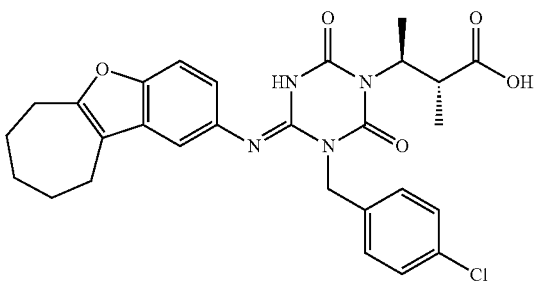 [SMILES: C[C@@H](C(=O)O)[C@H](C)n1c(=O)[nH]/c(=N\c2ccc3oc4c(c3c2)CCCCC4)n(Cc2ccc(Cl)cc2)c1=O] | I-1747 | 2.67 | 537 | 5 |
| 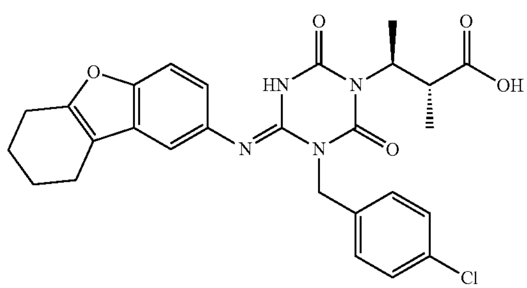 [SMILES: C[C@@H](C(=O)O)[C@H](C)n1c(=O)[nH]/c(=N\c2ccc3oc4c(c3c2)CCCC4)n(Cc2ccc(Cl)cc2)c1=O] | I-1748 | 2.55 | 523 | 5 |
| 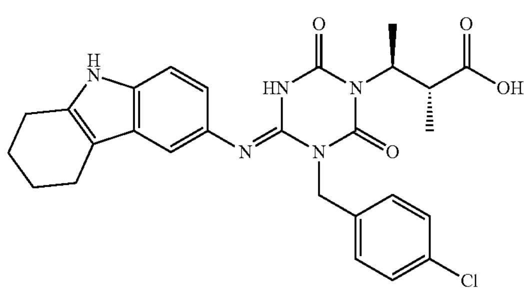 [SMILES: C[C@@H](C(=O)O)[C@H](C)n1c(=O)[nH]/c(=N\c2ccc3[nH]c4c(c3c2)CCCC4)n(Cc2ccc(Cl)cc2)c1=O] | I-1749 | 2.26 | 522 | 5 |
| 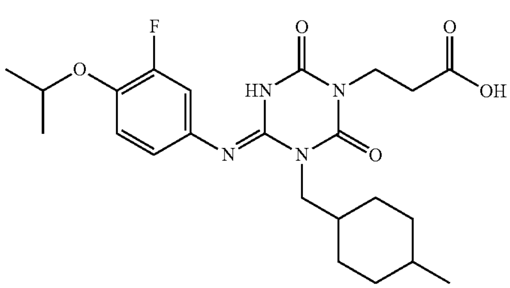 [SMILES: CC1CCC(Cn2c(=O)n(CCC(=O)O)c(=O)[nH]/c2=N\c2ccc(OC(C)C)c(F)c2)CC1] | I-1750 | 2.33 | 463 | 3 |

TABLE 354

| Structure | Compound No. | Retention Time (min) | [M + H] | Method |
|---|---|---|---|---|
| 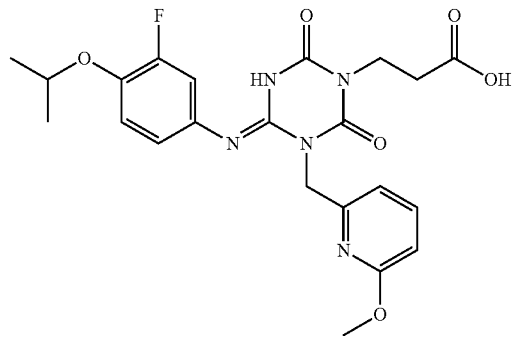 [SMILES: COc1cccc(Cn2c(=O)n(CCC(=O)O)c(=O)[nH]/c2=N\c2ccc(OC(C)C)c(F)c2)n1] | I-1751 | 1.95 | 474 | 3 |
| 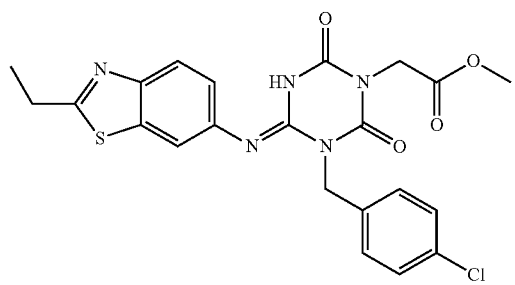 [SMILES: CCc1nc2ccc(/N=c3\[nH]c(=O)n(CC(=O)OC)c(=O)n3Cc3ccc(Cl)cc3)cc2s1] | I-1752 | 2.26 | 486 | 3 |
| 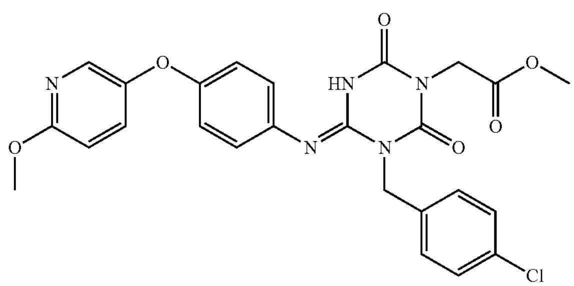 [SMILES: COC(=O)Cn1c(=O)[nH]/c(=N\c2ccc(Oc3ccc(OC)nc3)cc2)n(Cc2ccc(Cl)cc2)c1=O] | I-1753 | 2.32 | 524 | 3 |
| 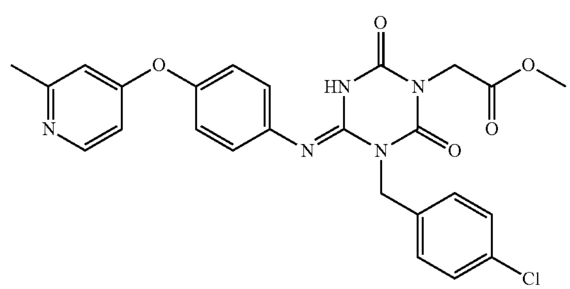 | I-1754 | 1.40 | 508 | 3 |
| 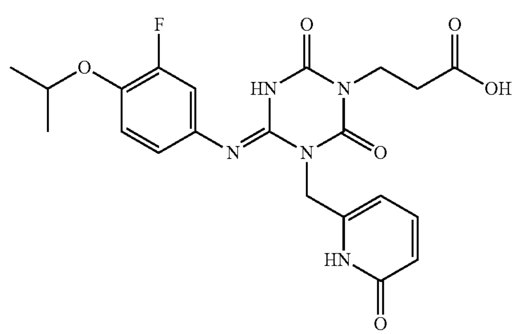 [SMILES: CC(C)Oc1ccc(/N=c2\[nH]c(=O)n(CCC(=O)O)c(=O)n2Cc2cccc(=O)[nH]2)cc1F] | I-1755 | 1.46 | 460 | 3 |

TABLE 355

| Structure | Compound No. | Retention Time (min) | [M + H] | Method |
|---|---|---|---|---|
| 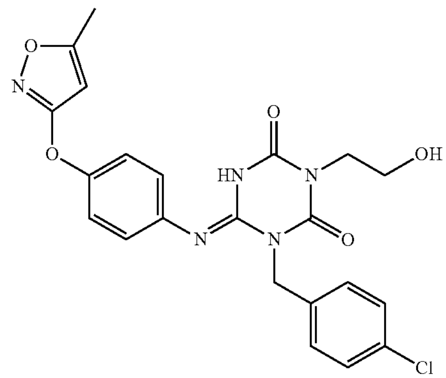 [SMILES: Cc1cc(Oc2ccc(/N=c3\[nH]c(=O)n(CCO)c(=O)n3Cc3ccc(Cl)cc3)cc2)no1] | I-1756 | 2.10 | 470 | 3 |
| 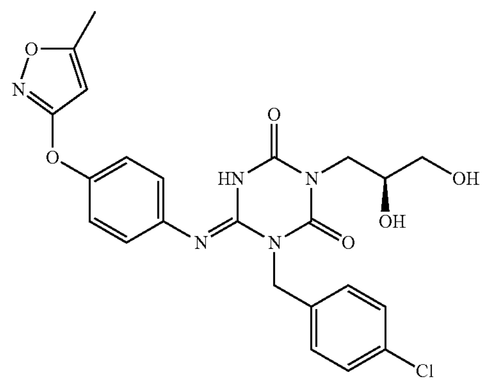 [SMILES: Cc1cc(Oc2ccc(/N=c3\[nH]c(=O)n(C[C@H](O)CO)c(=O)n3Cc3ccc(Cl)cc3)cc2)no1] | I-1757 | 1.88 | 500 | 3 |
| 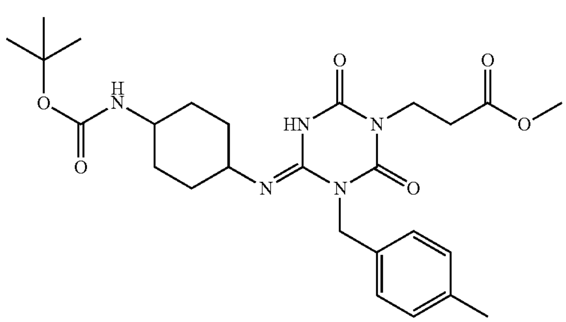 [SMILES: COC(=O)CCn1c(=O)[nH]/c(=N\C2CCC(NC(=O)OC(C)(C)C)CC2)n(Cc2ccc(C)cc2)c1=O] | I-1758 | 2.16 | 516 | 3 |
| 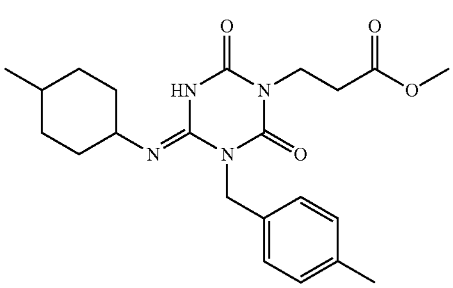 | I-1759 | 2.28 | 415 | 3 |

TABLE 355-continued

| Structure | Compound No. | Retention Time (min) | [M + H] | Method |
|---|---|---|---|---|
| 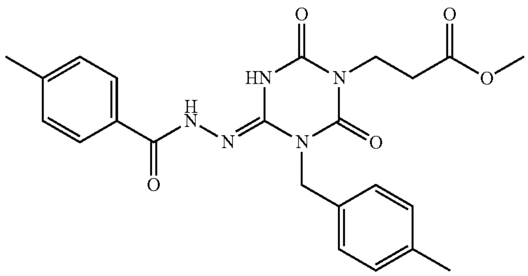 | I-1760 | 1.95 | 452 | 3 |

TABLE 356

| Structure | Compound No. | Retention Time (min) | [M + H] | Method |
|---|---|---|---|---|
| 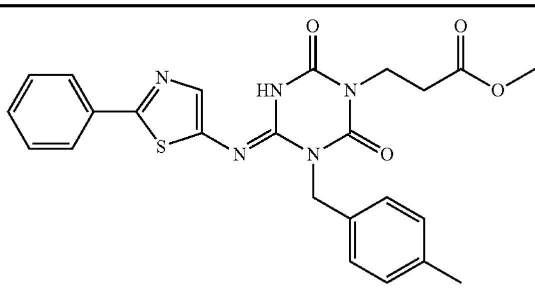 | I-1761 | 2.42 | 478 | 3 |
| 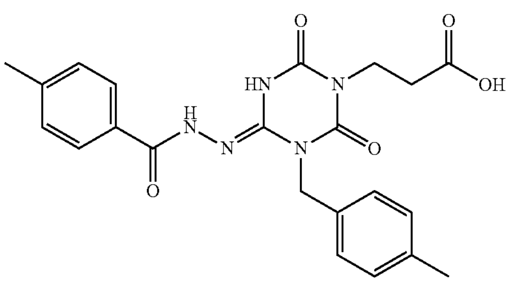 [SMILES: Cc1ccc(Cn2c(=O)n(CCC(=O)O)c(=O)[nH]/c2=N\NC(=O)c2ccc(C)cc2)cc1] | I-1762 | 1.73 | 438 | 3 |
| 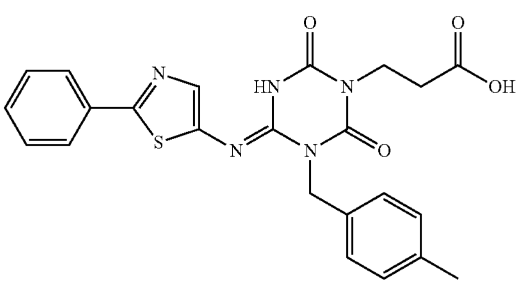 [SMILES: Cc1ccc(Cn2c(=O)n(CCC(=O)O)c(=O)[nH]/c2=N\c2cnc(-c3ccccc3)s2)cc1] | I-1763 | 2.16 | 464 | 3 |
| 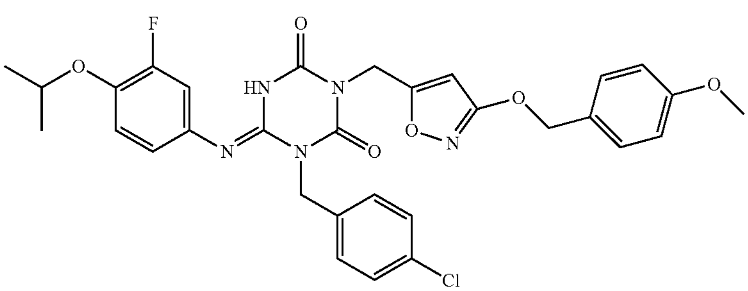 [SMILES: COc1ccc(COc2cc(Cn3c(=O)[nH]/c(=N\c4ccc(OC(C)C)c(F)c4)n(Cc4ccc(Cl)cc4)c3=O)on2)cc1] | I-1764 | 2.20 | 622 | 2 |

TABLE 356-continued

| Structure | Compound No. | Retention Time (min) | [M + H] | Method |
|---|---|---|---|---|
| 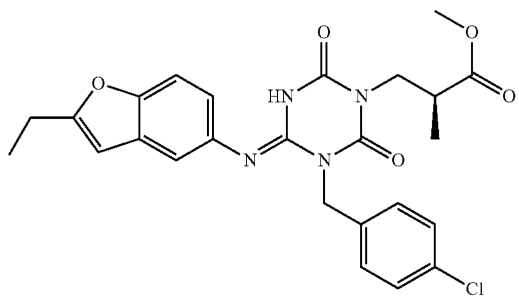 | I-1765 | 2.30 | 497 | 2 |

TABLE 357

| Structure | Compound No. | Retention Time (min) | [M + H] | Method |
|---|---|---|---|---|
| 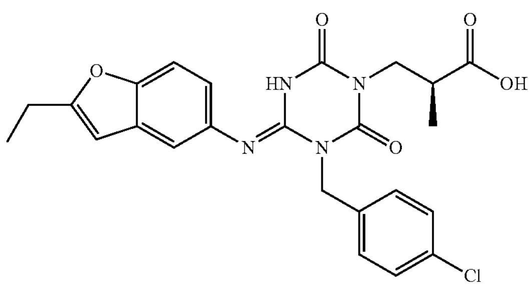 | I-1766 | 2.05 | 483 | 2 |
| 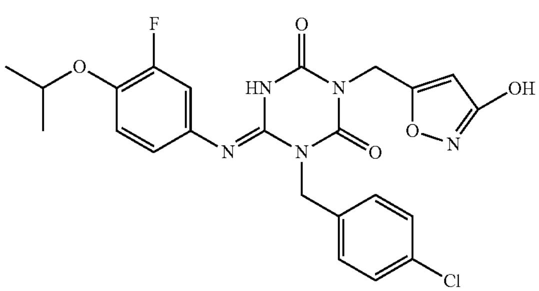 [SMILES: CC(C)Oc1ccc(/N=c2\[nH]c(=O)n(Cc3cc(O)no3)c(=O)n2Cc2ccc(Cl)cc2)cc1F] | I-1767 | 2.00 | 502 | 2 |
| 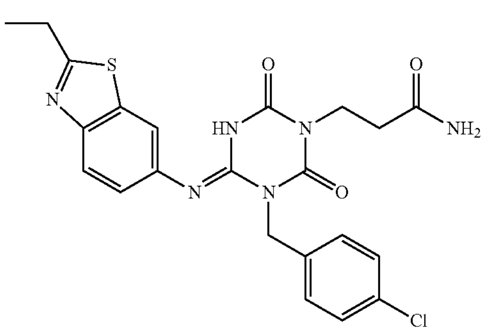 [SMILES: CCc1nc2ccc(/N=c3\[nH]c(=O)n(CCC(N)=O)c(=O)n3Cc3ccc(Cl)cc3)cc2s1] | I-1768 | 1.91 | 485 | 3 |

TABLE 357-continued

| Structure | Compound No. | Retention Time (min) | [M + H] | Method |
|---|---|---|---|---|
| 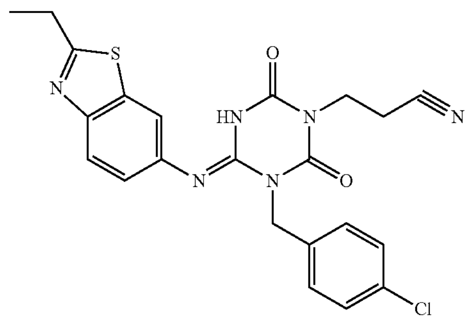 [SMILES: CCc1nc2ccc(/N=c3\[nH]c(=O)n(CCC#N)c(=O)n3Cc3ccc(Cl)cc3)cc2s1] | I-1769 | 2.21 | 467 | 3 |
| 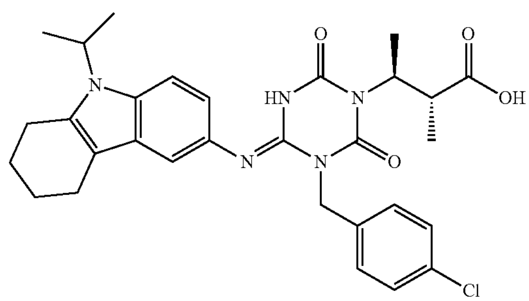 [SMILES: CC(C)n1c2c(c3cc(/N=c4\[nH]c(=O)n([C@@H](C)[C@@H](C)C(=O)O)c(=O)n4Cc4ccc(Cl)cc4)ccc31)CCCC2] | I-1770 | 2.63 | 564 | 5 |

TABLE 358

| Structure | Compound No. | Retention Time (min) | [M + H] | Method |
|---|---|---|---|---|
| 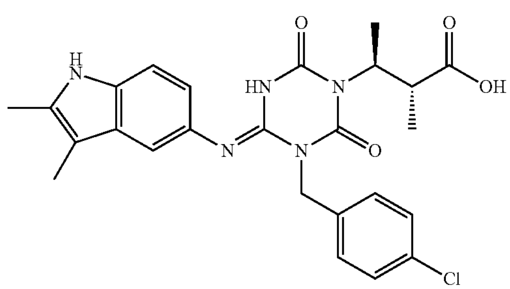 [SMILES: Cc1[nH]c2ccc(/N=c3\[nH]c(=O)n([C@@H](C)[C@@H](C)C(=O)O)c(=O)n3Cc3ccc(Cl)cc3)cc2c1C] | I-1771 | 2.05 | 496 | 5 |
| 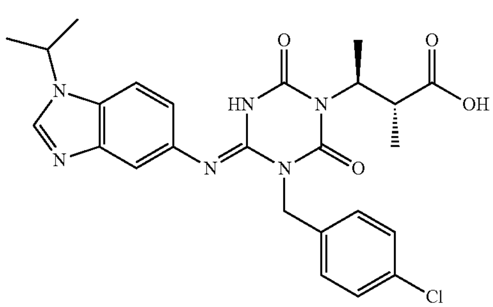 [SMILES: CC(C)n1cnc2cc(/N=c3\[nH]c(=O)n([C@@H](C)[C@@H](C)C(=O)O)c(=O)n3Cc3ccc(Cl)cc3)ccc21] | I-1772 | 2.05 | 511 | 5 |

TABLE 358-continued

| Structure | Compound No. | Retention Time (min) | [M + H] | Method |
|---|---|---|---|---|
| (structure) | I-1773 | 2.28 | 509 | 5 |
| (structure) | I-1774 | 1.92 | 548 | 5 |
| (structure) | I-1775 | 1.56 | 484 | 5 |

TABLE 359

| Structure | Compound No. | Retention Time (min) | [M + H] | Method |
|---|---|---|---|---|
| (structure) | I-1776 | 2.09 | 569 | 5 |

TABLE 359-continued

| Structure | Compound No. | Retention Time (min) | [M + H] | Method |
|---|---|---|---|---|
| 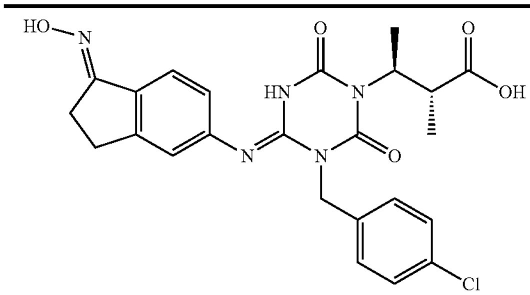 | I-1777 | 1.87 | 498 | 5 |
| 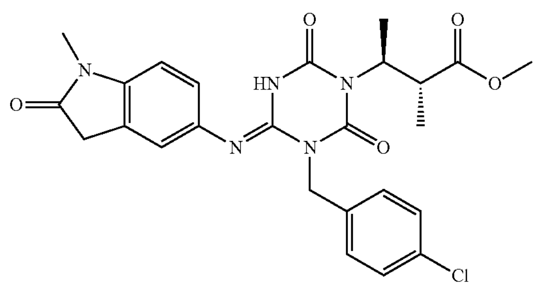 [SMILES: COC(=O)[C@H](C)[C@H](C)n1c(=O)[nH]/c(=N\c2ccc3c(c2)CC(=O)N3C)n(Cc2ccc(Cl)cc2)c1=O] | I-1778 | 1.81 | 512 | 5 |
| 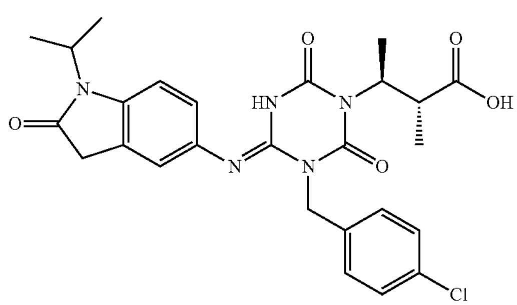 [SMILES: CC(C)N1C(=O)Cc2cc(/N=c3\[nH]c(=O)n([C@@H](C)[C@@H](C)C(=O)O)c(=O)n3Cc3ccc(Cl)cc3)ccc21] | I-1779 | 2.22 | 526 | 5 |
| 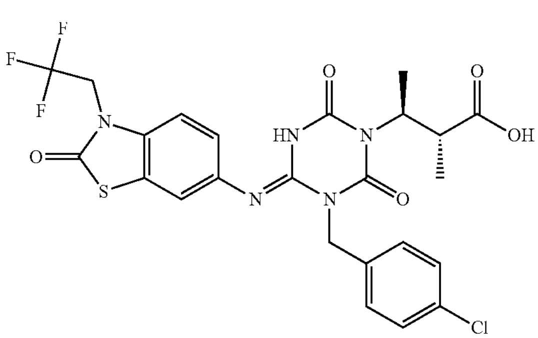 [SMILES: C[C@@H](C(=O)O)[C@H](C)n1c(=O)[nH]/c(=N\c2ccc3c(c2)sc(=O)n3CC(F)(F)F)n(Cc2ccc(Cl)cc2)c1=O] | I-1780 | 2.24 | 584 | 5 |

TABLE 360

| Structure | Compound No. | Retention Time (min) | [M + H] | Method |
|---|---|---|---|---|
| 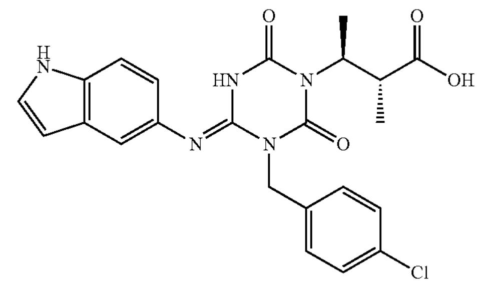 [SMILES: C[C@@H](C(=O)O)[C@H](C)n1c(=O)[nH]/c(=N\c2ccc3[nH]ccc3c2)n(Cc2ccc(Cl)cc2)c1=O] | I-1781 | 1.85 | 468 | 5 |
| 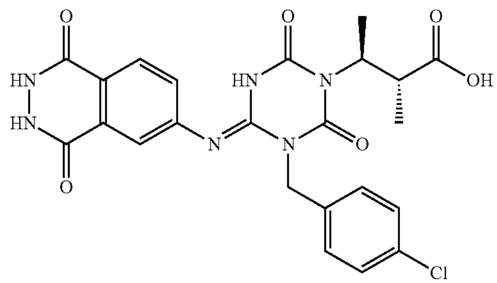 [SMILES: C[C@@H](C(=O)O)[C@H](C)n1c(=O)[nH]/c(=N\c2ccc3c(=O)[nH][nH]c(=O)c3c2)n(Cc2ccc(Cl)cc2)c1=O] | I-1782 | 1.66 | 513 | 5 |
| 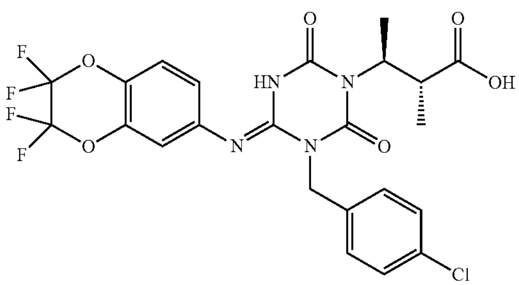 [SMILES: C[C@@H](C(=O)O)[C@H](C)n1c(=O)[nH]/c(=N\c2ccc3c(c2)OC(F)(F)C(F)(F)O3)n(Cc2ccc(Cl)cc2)c1=O] | I-1783 | 2.68 | 559 | 5 |
| 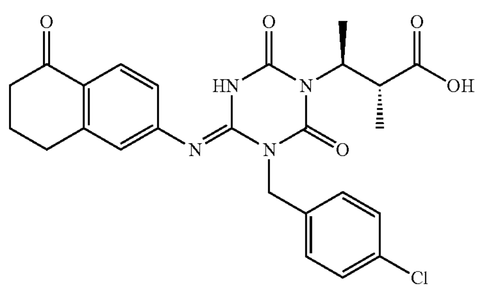 [SMILES: C[C@@H](C(=O)O)[C@H](C)n1c(=O)[nH]/c(=N\c2ccc3c(c2)CCCC3=O)n(Cc2ccc(Cl)cc2)c1=O] | I-1784 | 2.13 | 497 | 5 |
| 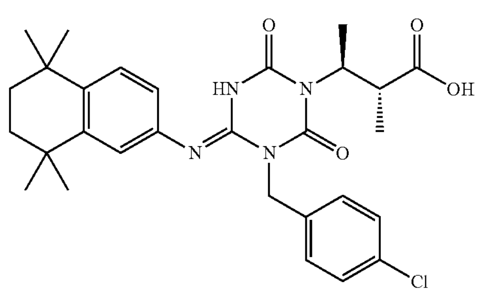 [SMILES: C[C@@H](C(=O)O)[C@H](C)n1c(=O)[nH]/c(=N\c2ccc3c(c2)C(C)(C)CCC3(C)C)n(Cc2ccc(Cl)cc2)c1=O] | I-1785 | 2.82 | 539 | 5 |

TABLE 361
| Structure | Compound No. | Retention Time (min) | [M + H] | Method |
|---|---|---|---|---|
| 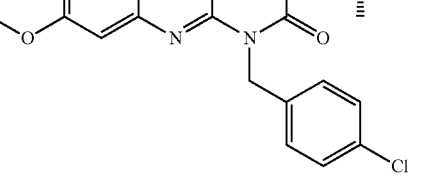 | I-1786 | 1.69 | 500 | 5 |
| 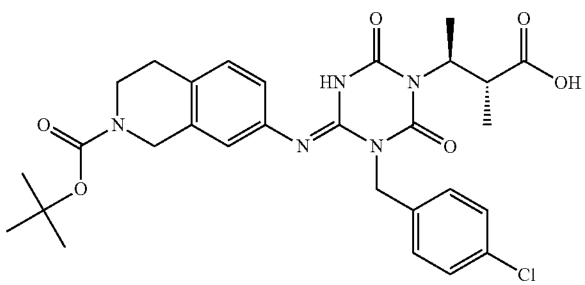 [SMILES: C[C@@H](C(=O)O)[C@H](C)n1c(=O)[nH]/c(=N\c2ccc3c(c2)CN(C(=O)OC(C)(C)C)CC3)n(Cc2ccc(Cl)cc2)c1=O] | I-1787 | 2.41 | 584 | 5 |
| 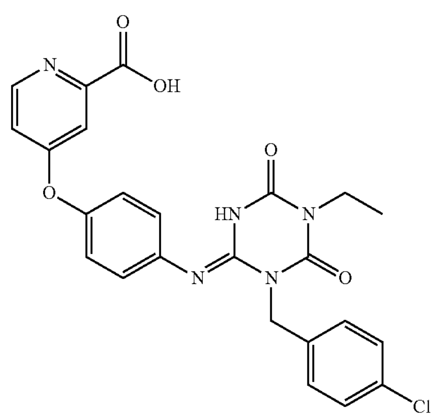 [SMILES: CCn1c(=O)[nH]/c(=N\c2ccc(Oc3ccnc(C(=O)O)c3)cc2)n(Cc2ccc(Cl)cc2)c1=O] | I-1788 | 1.51 | 494 | 2 |
| 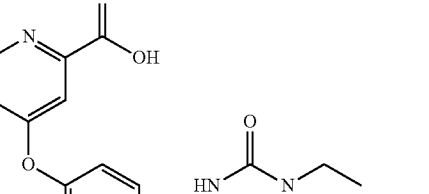 | I-1789 | 1.34 | 482 | 2 |

TABLE 361-continued

| Structure | Compound No. | Retention Time (min) | [M + H] | Method |
|---|---|---|---|---|
| 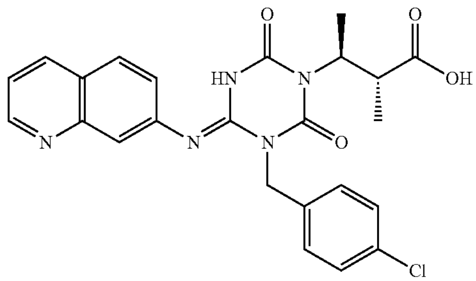 [SMILES: C[C@@H](C(=O)O)[C@H](C)n1c(=O)[nH]/c(=N\c2ccc3cccnc3c2)n(Cc2ccc(Cl)cc2)c1=O] | I-1790 | 1.53 | 480 | 5 |

TABLE 362

| Structure | Compound No. | Retention Time (min) | [M + H] | Method |
|---|---|---|---|---|
| 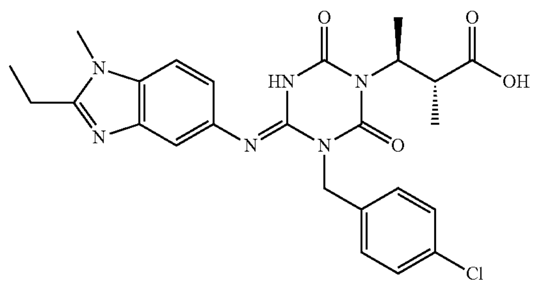 [SMILES: CCc1nc2cc(/N=c3\[nH]c(=O)n([C@@H](C)[C@@H](C)C(=O)O)c(=O)n3Cc3ccc(Cl)cc3)ccc2n1C] | I-1791 | 1.41 | 511 | 5 |
| 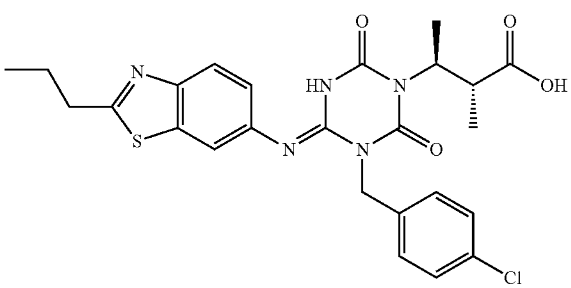 [SMILES: CCCc1nc2ccc(/N=c3\[nH]c(=O)n([C@@H](C)[C@@H](C)C(=O)O)c(=O)n3Cc3ccc(Cl)cc3)cc2s1] | I-1792 | 2.35 | 528 | 5 |
| 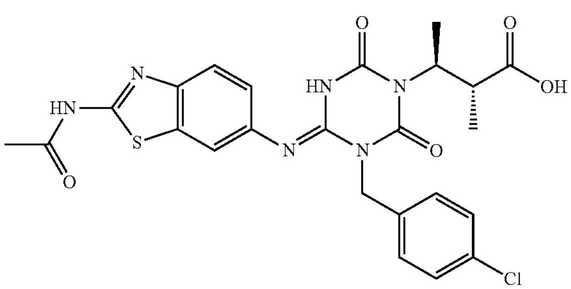 [SMILES: CC(=O)Nc1nc2ccc(/N=c3\[nH]c(=O)n([C@@H](C)[C@@H](C)C(=O)O)c(=O)n3Cc3ccc(Cl)cc3)cc2s1] | I-1793 | 1.82 | 543 | 5 |
| 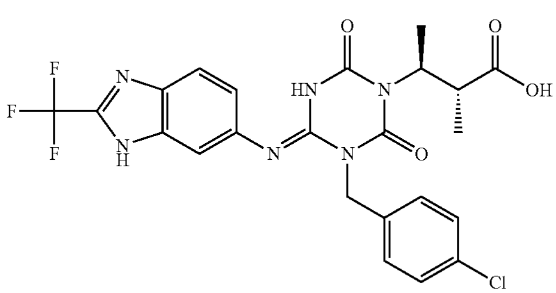 [SMILES: C[C@@H](C(=O)O)[C@H](C)n1c(=O)[nH]/c(=N\c2ccc3nc(C(F)(F)F)[nH]c3c2)n(Cc2ccc(Cl)cc2)c1=O] | I-1794 | 1.89 | 537 | 5 |

TABLE 362-continued

| Structure | Compound No. | Retention Time (min) | [M + H] | Method |
|---|---|---|---|---|
| 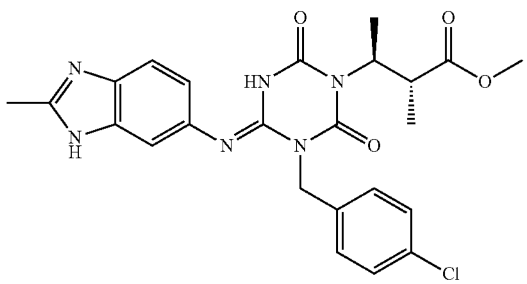 | I-1795 | 1.52 | 497 | 5 |

TABLE 363

| Structure | Compound No. | Retention Time (min) | [M + H] | Method |
|---|---|---|---|---|
| 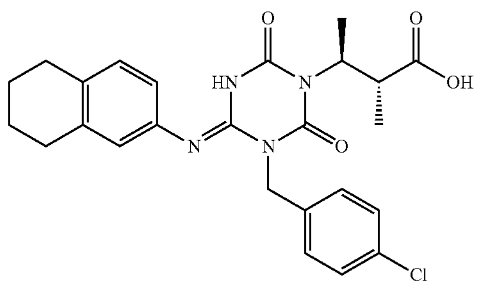 [SMILES: C[C@@H](C(=O)O)[C@H](C)n1c(=O)[nH]/c(=N\c2ccc3c(c2)CCCC3)n(Cc2ccc(Cl)cc2)c1=O] | I-1796 | 2.41 | 483 | 5 |
| 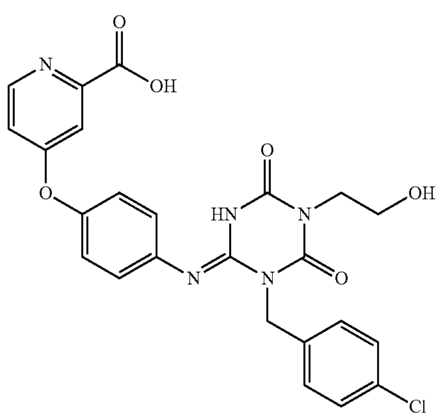 | I-1797 | 1.25 | 510 | 2 |
| 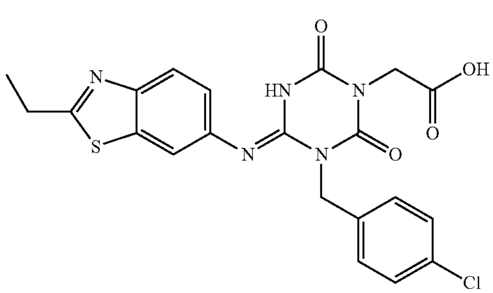 [SMILES: CCc1nc2ccc(/N=c3\[nH]c(=O)n(CC(=O)O)c(=O)n3Cc3ccc(Cl)cc3)cc2s1] | I-1798 | 2.03 | 472 | 3 |

TABLE 363-continued

| Structure | Compound No. | Retention Time (min) | [M + H] | Method |
|---|---|---|---|---|
| 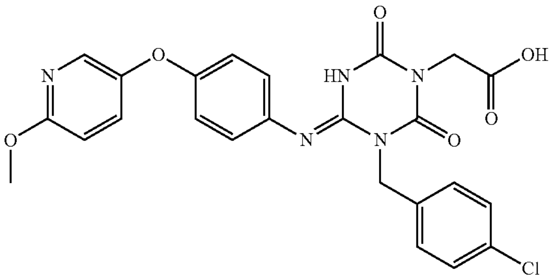 [SMILES: COc1ccc(Oc2ccc(/N=c3\[nH]c(=O)n(CC(=O)O)c(=O)n3Cc3ccc(Cl)cc3)cc2)cn1] | I-1799 | 2.11 | 510 | 3 |
| 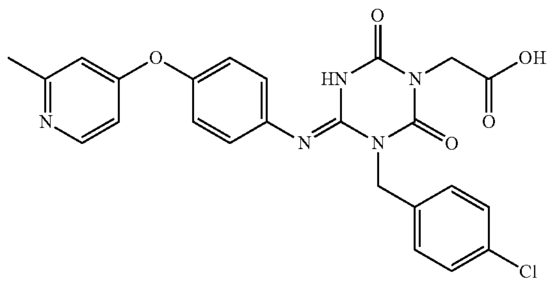 [SMILES: Cc1cc(Oc2ccc(/N=c3\[nH]c(=O)n(CC(=O)O)c(=O)n3Cc3ccc(Cl)cc3)cc2)ccn1] | I-1800 | 1.29 | 494 | 3 |

TABLE 364

| Structure | Compound No. | Retention Time (min) | [M + H] | Method |
|---|---|---|---|---|
| 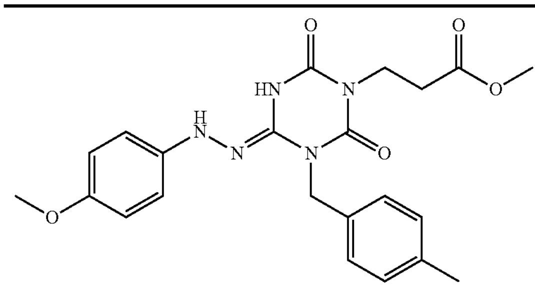 | I-1801 | 2.11 | 440 | 3 |
| 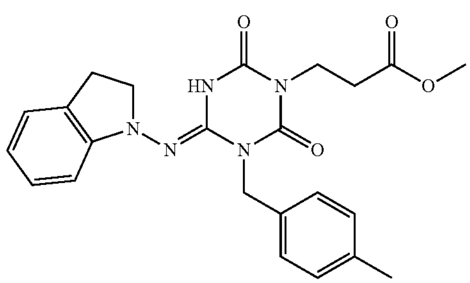 [SMILES: COC(=O)CCn1c(=O)[nH]/c(=N\N2CCc3ccccc32)n(Cc2ccc(C)cc2)c1=O] | I-1802 | 2.50 | 436 | 3 |
| 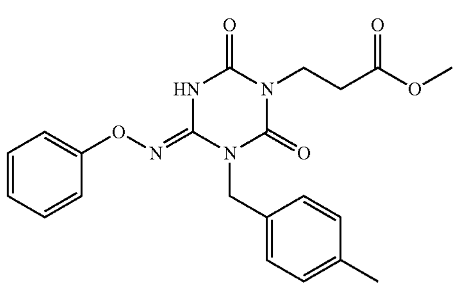 [SMILES: COC(=O)CCn1c(=O)[nH]/c(=N\Oc2ccccc2)n(Cc2ccc(C)cc2)c1=O] | I-1803 | 1.95 | 452 | 3 |

TABLE 364-continued
| Structure | Compound No. | Retention Time (min) | [M + H] | Method |
|---|---|---|---|---|
| 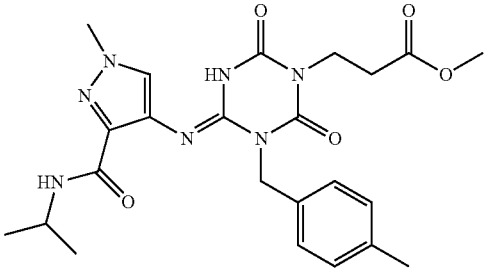 [SMILES: COC(=O)CCn1c(=O)[nH]/c(=N\c2cn(C)nc2C(=O)NC(C)C)n(Cc2ccc(C)cc2)c1=O] | I-1804 | 2.19 | 484 | 3 |
| 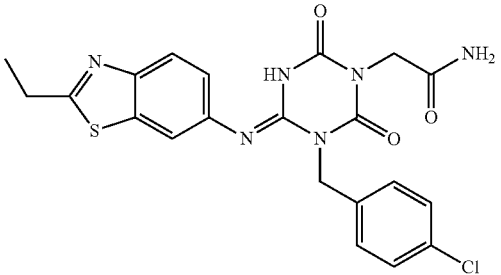 [SMILES: CCc1nc2ccc(/N=c3\[nH]c(=O)n(CC(N)=O)c(=O)n3Cc3ccc(Cl)cc3)cc2s1] | I-1805 | 1.87 | 471 | 3 |
TABLE 365
| Structure | Compound No. | Retention Time (min) | [M + H] | Method |
|---|---|---|---|---|
| 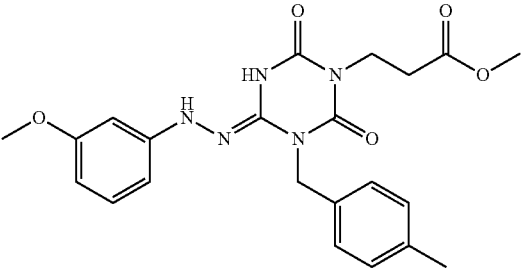 | I-1806 | 2.17 | 440 | 3 |
| 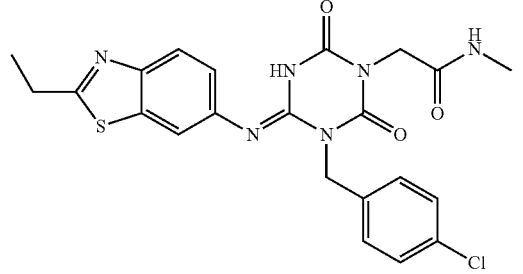 [SMILES: CCc1nc2ccc(/N=c3\[nH]c(=O)n(CC(=O)NC)c(=O)n3Cc3ccc(Cl)cc3)cc2s1] | I-1807 | 1.95 | 485 | 3 |
| 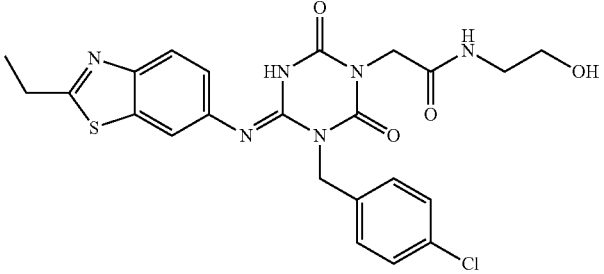 [SMILES: CCc1nc2ccc(/N=c3\[nH]c(=O)n(CC(=O)NCCO)c(=O)n3Cc3ccc(Cl)cc3)cc2s1] | I-1808 | 1.83 | 515 | 3 |

TABLE 365-continued

| Structure | Compound No. | Retention Time (min) | [M + H] | Method |
|---|---|---|---|---|
| 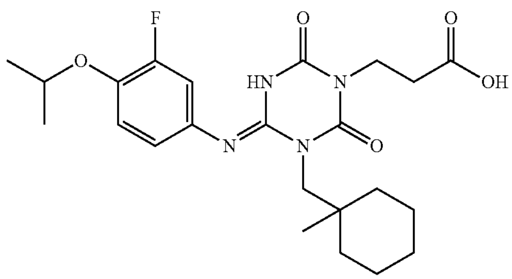 [SMILES: CC(C)Oc1ccc(/N=c2\[nH]c(=O)n(CCC(=O)O)c(=O)n2CC2(C)CCCCC2)cc1F] | I-1809 | 2.33 | 463 | 3 |
| 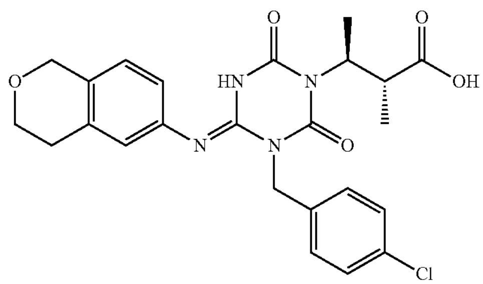 [SMILES: C[C@@H](C(=O)O)[C@H](C)n1c(=O)[nH]/c(=N\c2ccc3c(c2)CCOC3)n(Cc2ccc(Cl)cc2)c1=O] | I-1810 | 1.94 | 485 | 5 |

TABLE 366

| Structure | Compound No. | Retention Time (min) | [M + H] | Method |
|---|---|---|---|---|
| 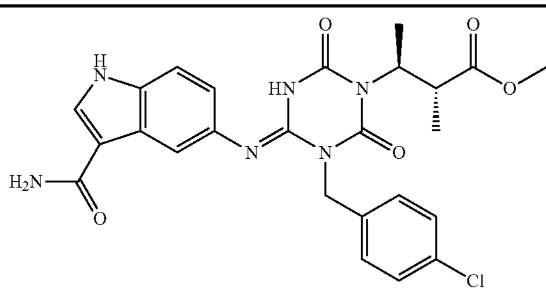 | I-1811 | 1.81 | 525 | 5 |
| 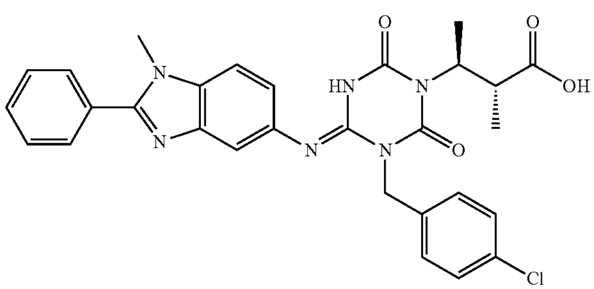 [SMILES: C[C@@H](C(=O)O)[C@H](C)n1c(=O)[nH]/c(=N\c2ccc3c(c2)nc(-c2ccccc2)n3C)n(Cc2ccc(Cl)cc2)c1=O] | I-1812 | 1.57 | 559 | 5 |
| 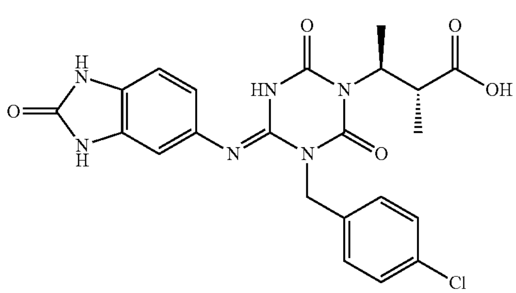 [SMILES: C[C@@H](C(=O)O)[C@H](C)n1c(=O)[nH]/c(=N\c2ccc3[nH]c(=O)[nH]c3c2)n(Cc2ccc(Cl)cc2)c1=O] | I-1813 | 1.49 | 485 | 5 |

TABLE 366-continued

| Structure | Compound No. | Retention Time (min) | [M + H] | Method |
|---|---|---|---|---|
| 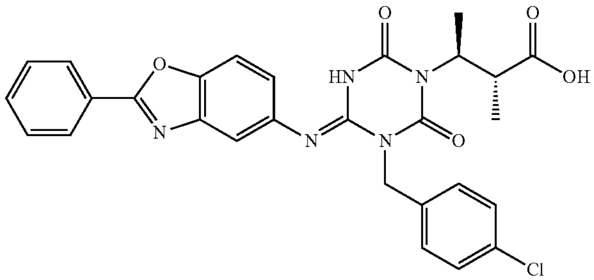 | I-1814 | 2.40 | 546 | 5 |
| 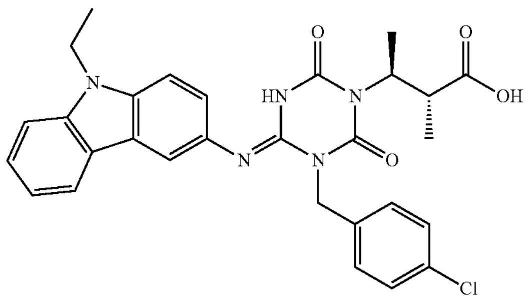 [SMILES: CCn1c2ccccc2c2cc(/N=c3\[nH]c(=O)n([C@@H](C)[C@@H](C)C(=O)O)c(=O)n3Cc3ccc(Cl)cc3)ccc21] | I-1815 | 2.44 | 546 | 5 |

TABLE 367

| Structure | Compound No. | Retention Time (min) | [M + H] | Method |
|---|---|---|---|---|
| 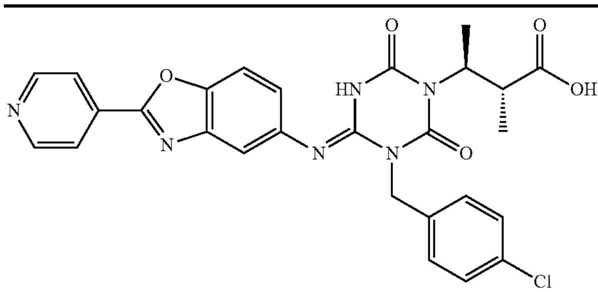 | I-1816 | 1.90 | 547 | 5 |
| 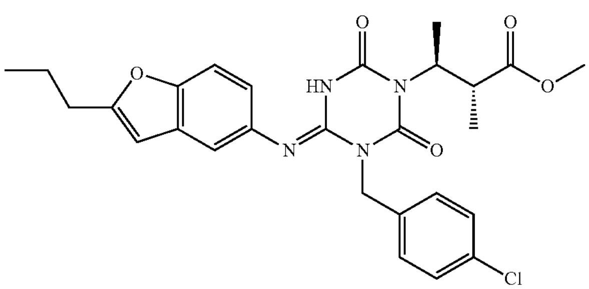 [SMILES: CCCc1cc2cc(/N=c3\[nH]c(=O)n([C@@H](C)[C@@H](C)C(=O)OC)c(=O)n3Cc3ccc(Cl)cc3)ccc2o1] | I-1817 | 2.81 | 525 | 5 |
| 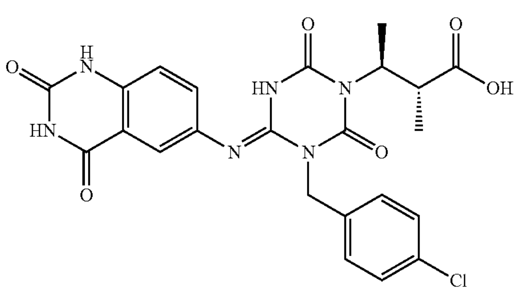 [SMILES: C[C@@H](C(=O)O)[C@H](C)n1c(=O)[nH]/c(=N\c2ccc3[nH]c(=O)[nH]c(=O)c3c2)n(Cc2ccc(Cl)cc2)c1=O] | I-1818 | 1.53 | 513 | 5 |

TABLE 367-continued
| Structure | Compound No. | Retention Time (min) | [M + H] | Method |
|---|---|---|---|---|
| 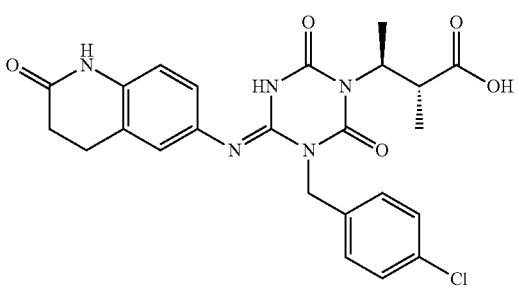 | I-1819 | 1.63 | 498 | 5 |
| 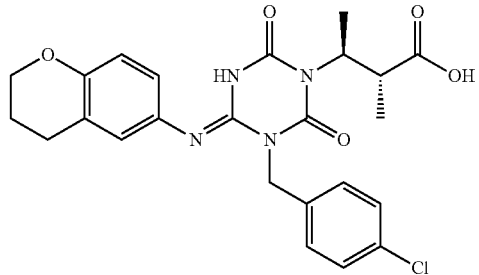 | I-1820 | 2.03 | 485 | 5 |
TABLE 368
| Structure | Compound No. | Retention Time (min) | [M + H] | Method |
|---|---|---|---|---|
| 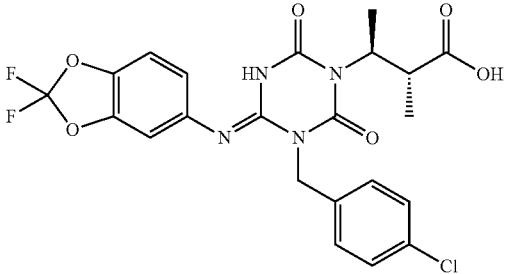 [SMILES: C[C@@H](C(=O)O)[C@H](C)n1c(=O)[nH]/c(=N\c2ccc3c(c2)OC(F)(F)O3)n(Cc2ccc(Cl)cc2)c1=O] | I-1821 | 2.41 | 509 | 5 |
| 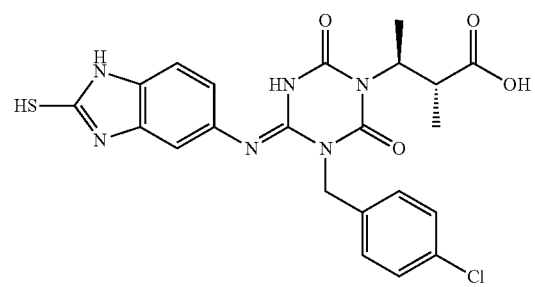 [SMILES: C[C@@H](C(=O)O)[C@H](C)n1c(=O)[nH]/c(=N\c2ccc3[nH]c(S)nc3c2)n(Cc2ccc(Cl)cc2)c1=O] | I-1822 | 1.60 | 501 | 5 |

TABLE 368-continued

| Structure | Compound No. | Retention Time (min) | [M + H] | Method |
|---|---|---|---|---|
| (structure) | I-1823 | 1.82 | 510 | 5 |
| (structure) | I-1824 | 1.81 | 519 | 5 |
| (structure) | I-1825 | 2.28 | 567 | 5 |

TABLE 369

| Structure | Compound No. | Retention Time (min) | [M + H] | Method |
|---|---|---|---|---|
| (structure) | I-1826 | 2.03 | 495 | 5 |
| (structure) | I-1827 | 2.86 | 533 | 5 |

TABLE 369-continued
| Structure | Compound No. | Retention Time (min) | [M + H] | Method |
|---|---|---|---|---|
| 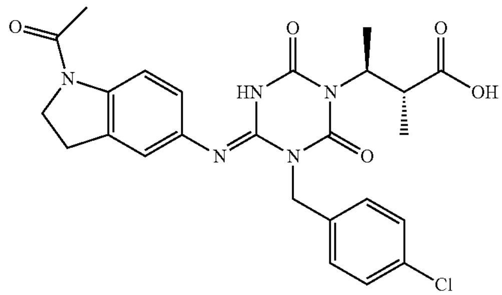 [SMILES: CC(=O)N1CCc2cc(/N=c3\[nH]c(=O)n([C@@H](C)[C@@H](C)C(=O)O)c(=O)n3Cc3ccc(Cl)cc3)ccc21] | I-1828 | 1.77 | 512 | 5 |
| 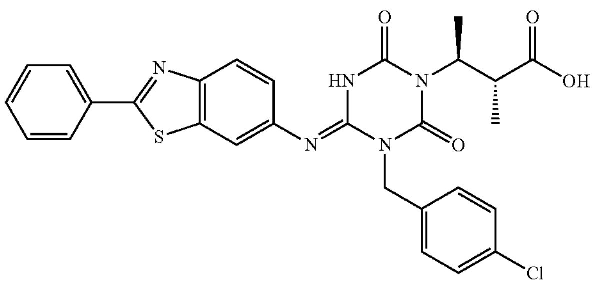 [SMILES: C[C@@H](C(=O)O)[C@H](C)n1c(=O)[nH]/c(=N\c2ccc3nc(-c4ccccc4)sc3c2)n(Cc2ccc(Cl)cc2)c1=O] | I-1829 | 2.59 | 562 | 5 |
| 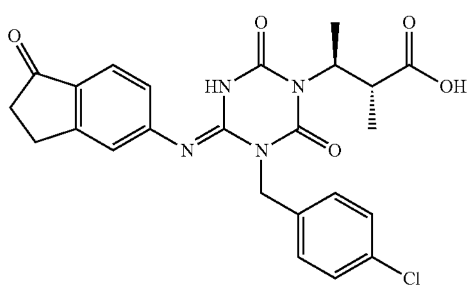 [SMILES: C[C@@H](C(=O)O)[C@H](C)n1c(=O)[nH]/c(=N\c2ccc3c(c2)CCC3=O)n(Cc2ccc(Cl)cc2)c1=O] | I-1830 | 2.00 | 483 | 5 |
TABLE 370
| Structure | Compound No. | Retention Time (min) | [M + H] | Method |
|---|---|---|---|---|
| 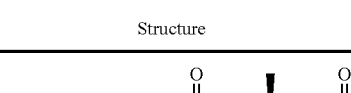 | I-1831 | 1.92 | 483 | 5 |

TABLE 370-continued

| Structure | Compound No. | Retention Time (min) | [M + H] | Method |
|---|---|---|---|---|
| 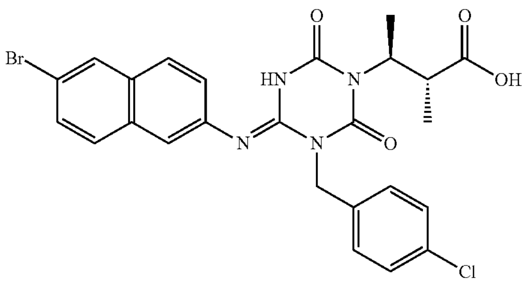 [SMILES: C[C@@H](C(=O)O)[C@H](C)n1c(=O)[nH]/c(=N\c2ccc3cc(Br)ccc3c2)n(Cc2ccc(Cl)cc2)c1=O] | I-1832 | 2.63 | 559 | 5 |
| 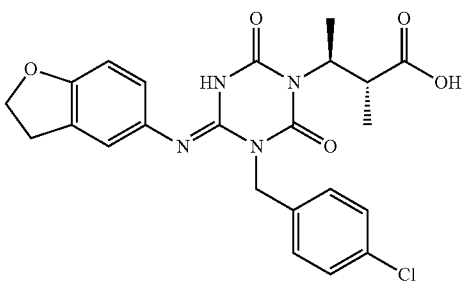 [SMILES: C[C@@H](C(=O)O)[C@H](C)n1c(=O)[nH]/c(=N\c2ccc3c(c2)CCO3)n(Cc2ccc(Cl)cc2)c1=O] | I-1833 | 1.91 | 471 | 5 |
| 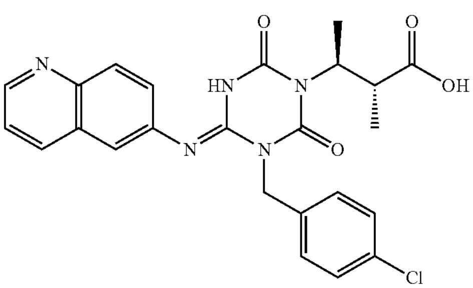 [SMILES: C[C@@H](C(=O)O)[C@H](C)n1c(=O)[nH]/c(=N\c2ccc3ncccc3c2)n(Cc2ccc(Cl)cc2)c1=O] | I-1834 | 1.57 | 480 | 5 |
| 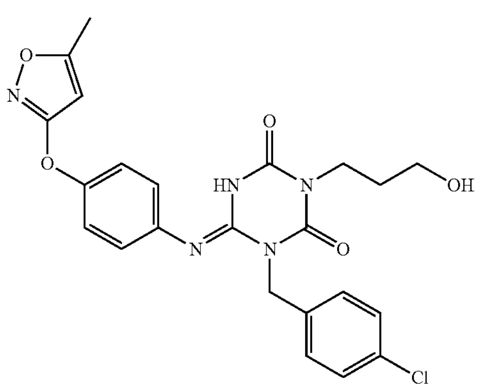 [SMILES: Cc1cc(Oc2ccc(/N=c3\[nH]c(=O)n(CCCO)c(=O)n3Cc3ccc(Cl)cc3)cc2)no1] | I-1835 | 2.05 | 484 | 3 |

TABLE 371

| Structure | Compound No. | Retention Time (min) | [M + H] | Method |
|---|---|---|---|---|
| 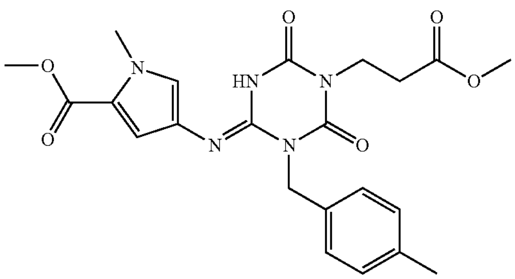 | I-1836 | 1.93 | 456 | 3 |
| 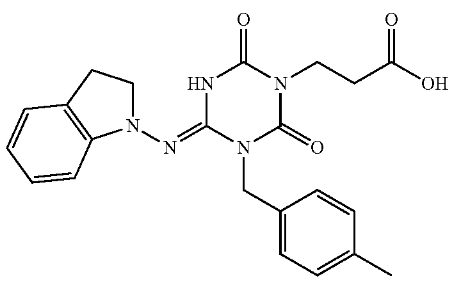 [SMILES: Cc1ccc(Cn2c(=O)n(CCC(=O)O)c(=O)[nH]/c2=N\N2CCc3ccccc32)cc1] | I-1837 | 2.22 | 422 | 3 |
| 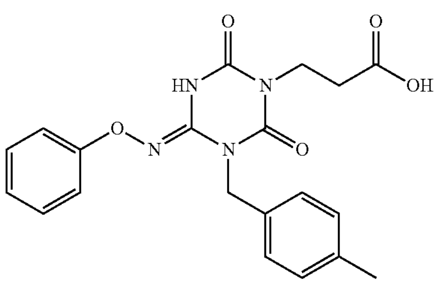 [SMILES: Cc1ccc(Cn2c(=O)n(CCC(=O)O)c(=O)[nH]/c2=N\Oc2ccccc2)cc1] | I-1838 | 2.17 | 397 | 3 |
| 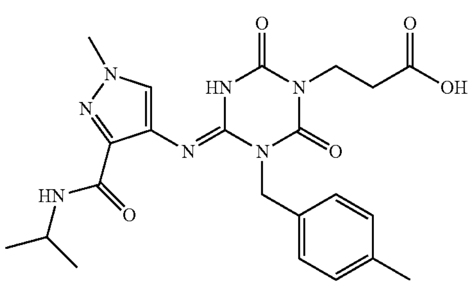 [SMILES: Cc1ccc(Cn2c(=O)n(CCC(=O)O)c(=O)[nH]/c2=N\c2cn(C)nc2C(=O)NC(C)C)cc1] | I-1839 | 1.92 | 470 | 3 |
| 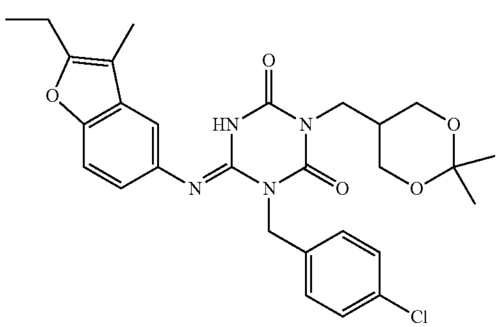 [SMILES: CCc1oc2ccc(/N=c3\[nH]c(=O)n(CC4COC(C)(C)OC4)c(=O)n3Cc3ccc(Cl)cc3)cc2c1C] | I-1840 | 2.66 | 539 | 3 |

TABLE 372
| Structure | Compound No. | Retention Time (min) | [M + H] | Method |
|---|---|---|---|---|
| 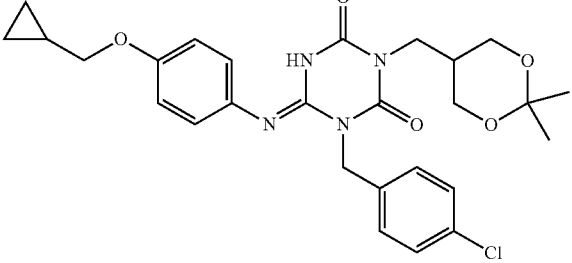 | I-1841 | 2.43 | 527 | 3 |
| 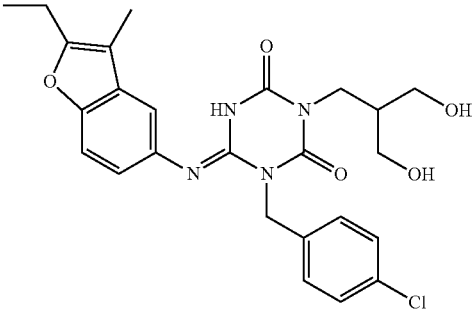 [SMILES: CCc1oc2ccc(/N=c3\[nH]c(=O)n(CC(CO)CO)c(=O)n3Cc3ccc(Cl)cc3)cc2c1C] | I-1842 | 2.19 | 499 | 3 |
| 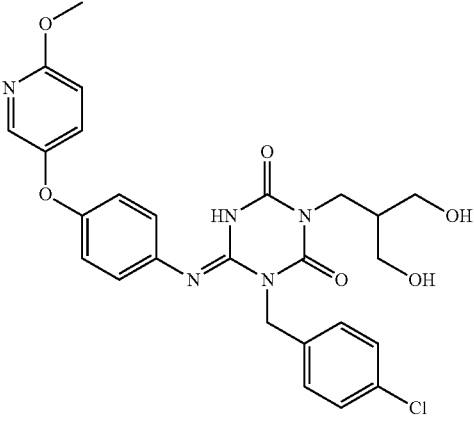 [SMILES: COc1ccc(Oc2ccc(/N=c3\[nH]c(=O)n(CC(CO)CO)c(=O)n3Cc3ccc(Cl)cc3)cc2)cn1] | I-1843 | 1.77 | 540 | 2 |
| 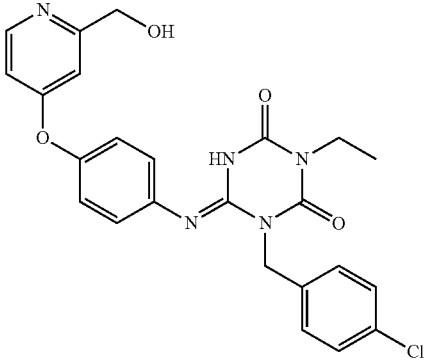 [SMILES: CCn1c(=O)[nH]/c(=N\c2ccc(Oc3ccnc(CO)c3)cc2)n(Cc2ccc(Cl)cc2)c1=O] | I-1844 | 1.41 | 480 | 2 |

TABLE 372-continued
| Structure | Compound No. | Retention Time (min) | [M + H] | Method |
|---|---|---|---|---|
| 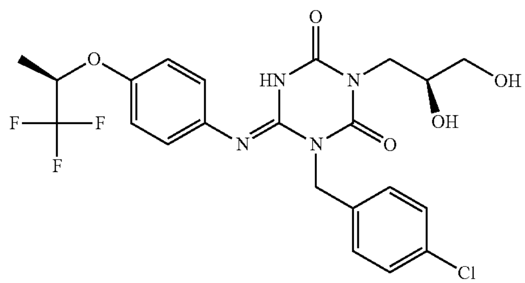 [SMILES: C[C@@H](Oc1ccc(/N=c2\[nH]c(=O)n(C[C@H](O)CO)c(=O)n2Cc2ccc(Cl)cc2)cc1)C(F)(F)F] | I-1845 | 1.85 | 515 | 2 |
TABLE 373
| Structure | Compound No. | Retention Time (min) | [M + H] | Method |
|---|---|---|---|---|
| 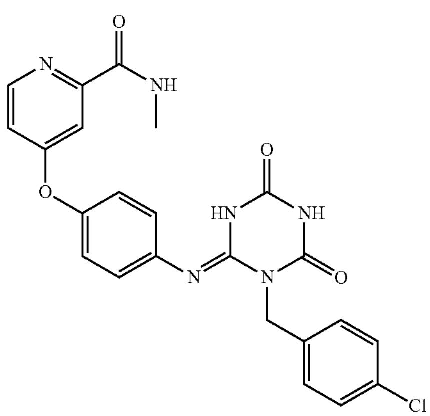 [SMILES: CNC(=O)c1cc(Oc2ccc(/N=c3\[nH]c(=O)[nH]c(=O)n3Cc3ccc(Cl)cc3)cc2)ccn1] | I-1846 | 1.71 | 479 | 2 |
| 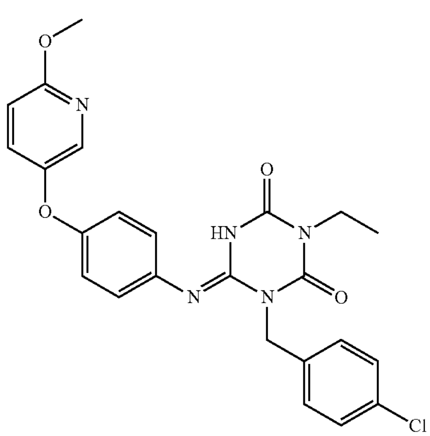 [SMILES: CCn1c(=O)[nH]/c(=N\c2ccc(Oc3ccc(OC)nc3)cc2)n(Cc2ccc(Cl)cc2)c1=O] | I-1847 | 2.18 | 480 | 2 |
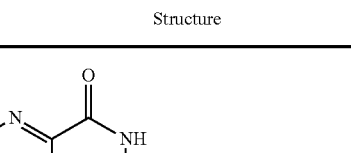

TABLE 373-continued

| Structure | Compound No. | Retention Time (min) | [M + H] | Method |
|---|---|---|---|---|
| (structure) | I-1848 | 1.61 | 466 | 2 |
| (structure) | I-1849 | 1.98 | 487 | 2 |
| (structure) | I-1850 | 2.10 | 440 | 2 |

TABLE 374

| Structure | Compound No. | Retention Time (min) | [M + H] | Method |
|---|---|---|---|---|
| (structure) | I-1851 | 1.79 | 544 | 2 |

TABLE 374-continued

| Structure | Compound No. | Retention Time (min) | [M + H] | Method |
|---|---|---|---|---|
| 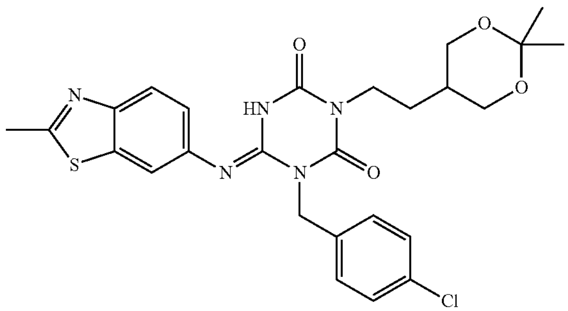 | I-1852 | 2.06 | 542 | 2 |
| 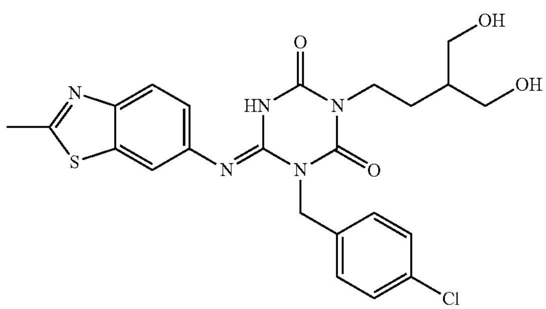 [SMILES: Cc1nc2ccc(/N=c3\[nH]c(=O)n(CCC(CO)CO)c(=O)n3Cc3ccc(Cl)cc3)cc2s1] | I-1853 | 1.55 | 502 | 2 |
| 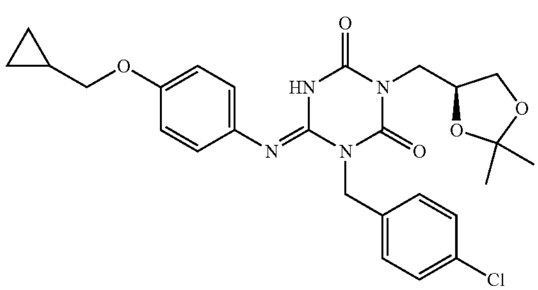 [SMILES: CC1(C)OC[C@H](Cn2c(=O)[nH]/c(=N\c3ccc(OCC4CC4)cc3)n(Cc3ccc(Cl)cc3)c2=O)O1] | I-1854 | 2.46 | 513 | 3 |
| 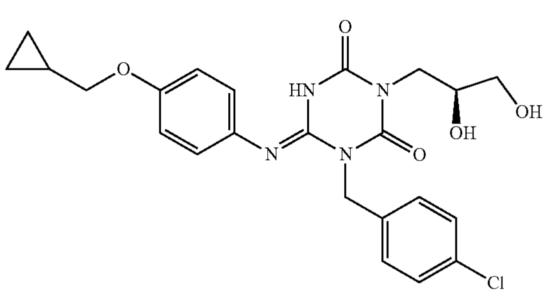 [SMILES: O=c1[nH]/c(=N\c2ccc(OCC3CC3)cc2)n(Cc2ccc(Cl)cc2)c(=O)n1C[C@H](O)CO] | I-1855 | 1.93 | 473 | 3 |

TABLE 375

| Structure | Compound No. | Retention Time (min) | [M + H] | Method |
|---|---|---|---|---|
| 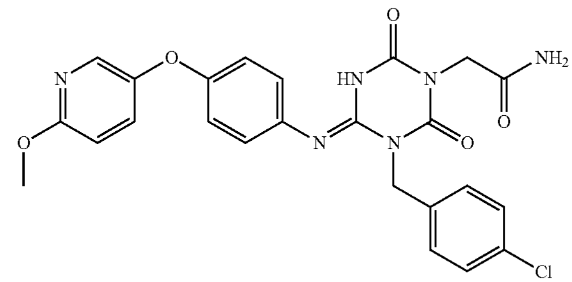 [SMILES: COc1ccc(Oc2ccc(/N=c3\[nH]c(=O)n(CC(N)=O)c(=O)n3Cc3ccc(Cl)cc3)cc2)cn1] | I-1856 | 1.96 | 509 | 3 |
| 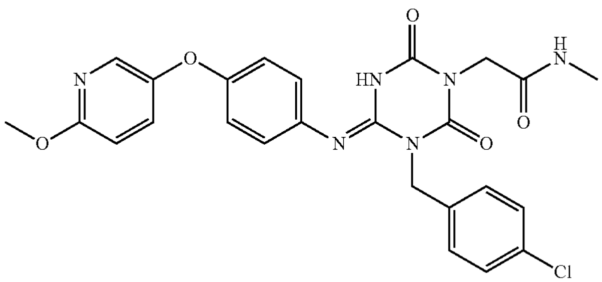 | I-1857 | 2.03 | 523 | 3 |
| 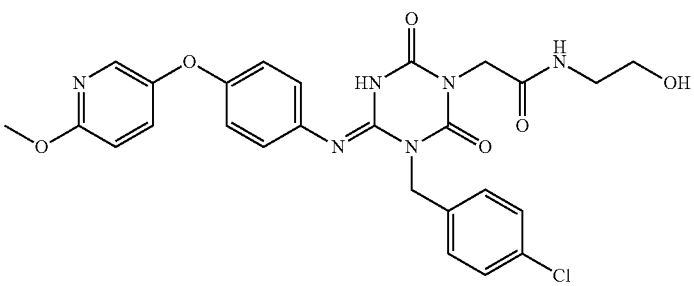 [SMILES: COc1ccc(Oc2ccc(/N=c3\[nH]c(=O)n(CC(=O)NCCO)c(=O)n3Cc3ccc(Cl)cc3)cc2)cn1] | I-1858 | 1.92 | 553 | 3 |
| 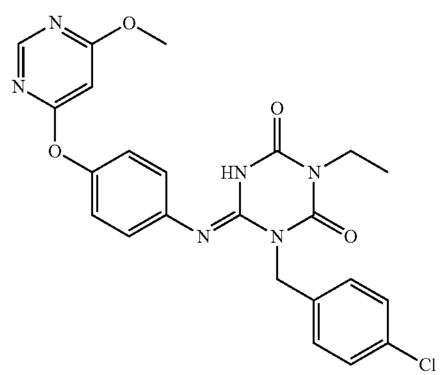 [SMILES: CCn1c(=O)[nH]/c(=N\c2ccc(Oc3cc(OC)ncn3)cc2)n(Cc2ccc(Cl)cc2)c1=O] | I-1859 | 2.39 | 481 | 3 |
| 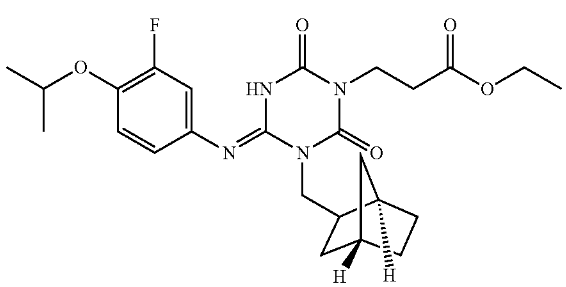 [SMILES: CCOC(=O)CCn1c(=O)[nH]/c(=N\c2ccc(OC(C)C)c(F)c2)n(CC2C[C@H]3CC[C@@H]2C3)c1=O] | I-1860 | 2.64 | 489 | 3 |

TABLE 376

| Structure | Compound No. | Retention Time (min) | [M + H] | Method |
|---|---|---|---|---|
| 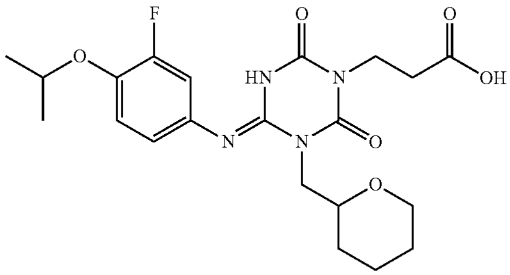 [SMILES: CC(C)Oc1ccc(/N=c2\[nH]c(=O)n(CCC(=O)O)c(=O)n2CC2CCCCO2)cc1F] | I-1861 | 2.04 | 451 | 3 |
| 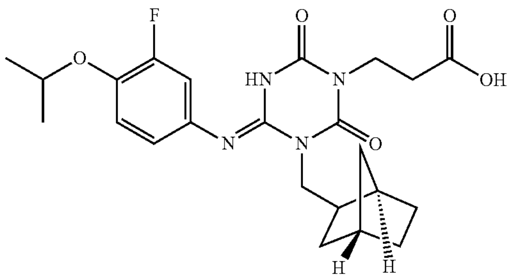 [SMILES: CC(C)Oc1ccc(/N=c2\[nH]c(=O)n(CCC(=O)O)c(=O)n2CC2C[C@H]3CC[C@@H]2C3)cc1F] | I-1862 | 2.25 | 461 | 3 |
| 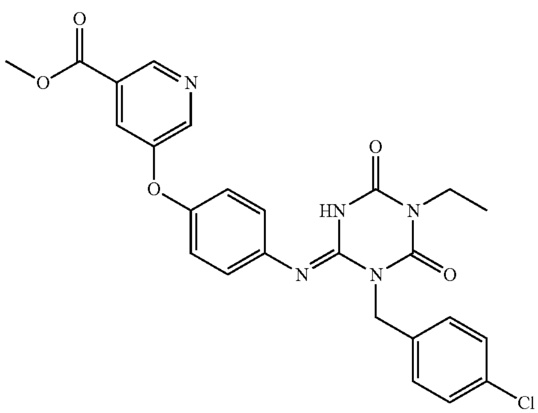 [SMILES: CCn1c(=O)[nH]/c(=N\c2ccc(Oc3cncc(C(=O)OC)c3)cc2)n(Cc2ccc(Cl)cc2)c1=O] | I-1863 | 2.07 | 508 | 2 |
| 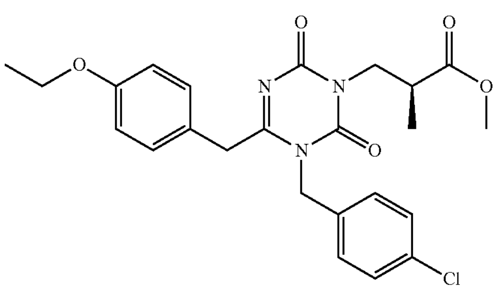 [SMILES: CCOc1ccc(Cc2nc(=O)n(C[C@H](C)C(=O)OC)c(=O)n2Cc2ccc(Cl)cc2)cc1] | I-1864 | 2.26 | 472 | 5 |
| 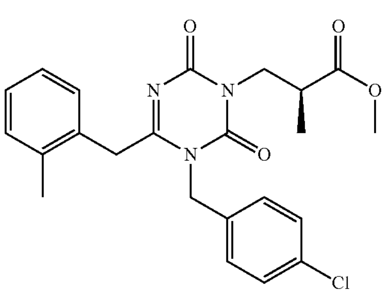 [SMILES: COC(=O)[C@@H](C)Cn1c(=O)nc(Cc2ccccc2C)n(Cc2ccc(Cl)cc2)c1=O] | I-1865 | 2.28 | 442 | 5 |

TABLE 377

| Structure | Compound No. | Retention Time (min) | [M + H] | Method |
|---|---|---|---|---|
| 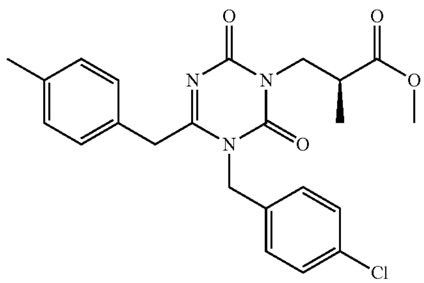 | I-1866 | 2.31 | 442 | 5 |
| 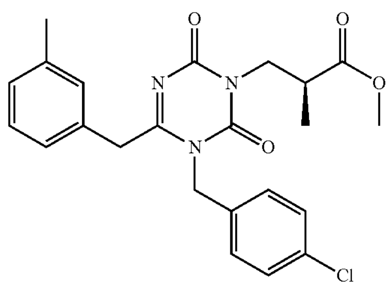 [SMILES: COC(=O)[C@@H](C)Cn1c(=O)nc(Cc2cccc(C)c2)n(Cc2ccc(Cl)cc2)c1=O] | I-1867 | 2.29 | 442 | 5 |
| 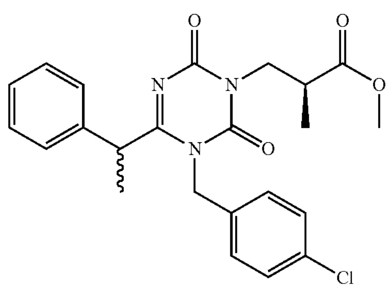 [SMILES: COC(=O)[C@@H](C)Cn1c(=O)nc(C(C)c2ccccc2)n(Cc2ccc(Cl)cc2)c1=O] | I-1868 | 2.31 | 442 | 5 |
| 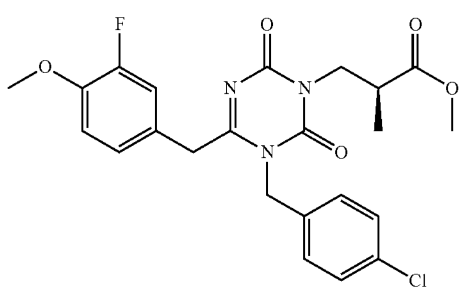 | I-1869 | 2.12 | 476 | 5 |
| 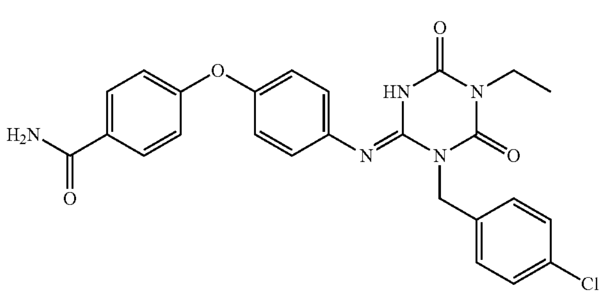 [SMILES: CCn1c(=O)[nH]/c(=N\c2ccc(Oc3ccc(C(N)=O)cc3)cc2)n(Cc2ccc(Cl)cc2)c1=O] | I-1870 | 2.06 | 492 | 3 |

TABLE 378

| Structure | Compound No. | Retention Time (min) | [M + H] | Method |
|---|---|---|---|---|
| 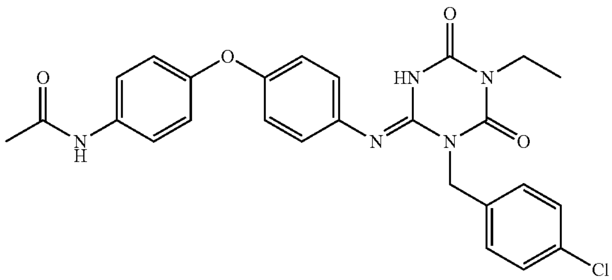 [SMILES: CCn1c(=O)[nH]/c(=N\c2ccc(Oc3ccc(NC(C)=O)cc3)cc2)n(Cc2ccc(Cl)cc2)c1=O] | I-1871 | 2.16 | 506 | 3 |
| 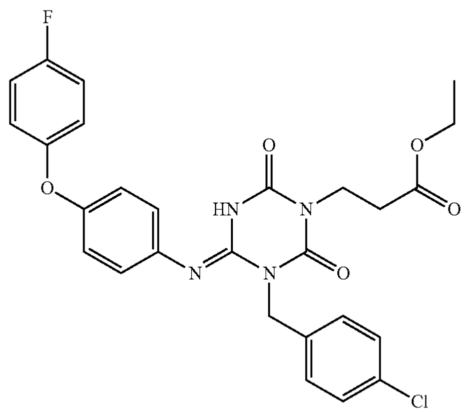 [SMILES: CCOC(=O)CCn1c(=O)[nH]/c(=N\c2ccc(Oc3ccc(F)cc3)cc2)n(Cc2ccc(Cl)cc2)c1=O] | I-1872 | 2.42 | 539 | 2 |
| 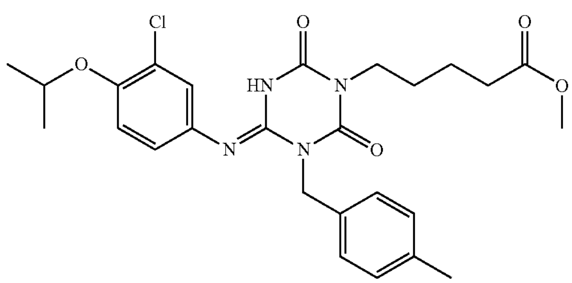 [SMILES: COC(=O)CCCCn1c(=O)[nH]/c(=N\c2ccc(OC(C)C)c(Cl)c2)n(Cc2ccc(C)cc2)c1=O] | I-1873 | 2.38 | 515 | 2 |
| 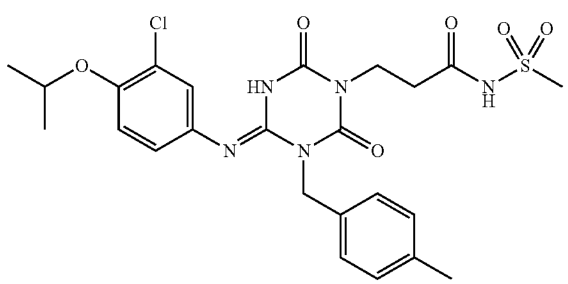 [SMILES: Cc1ccc(Cn2c(=O)n(CCC(=O)NS(C)(=O)=O)c(=O)[nH]/c2=N\c2ccc(OC(C)C)c(Cl)c2)cc1] | I-1874 | 2.23 | 550 | 3 |
| 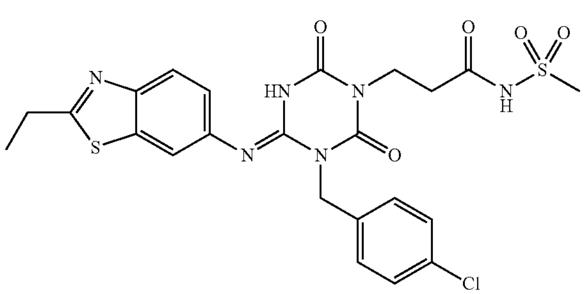 [SMILES: CCc1nc2ccc(/N=c3\[nH]c(=O)n(CCC(=O)NS(C)(=O)=O)c(=O)n3Cc3ccc(Cl)cc3)cc2s1] | I-1875 | 2.05 | 563 | 3 |

TABLE 379

| Structure | Compound No. | Retention Time (min) | [M + H] | Method |
|---|---|---|---|---|
| 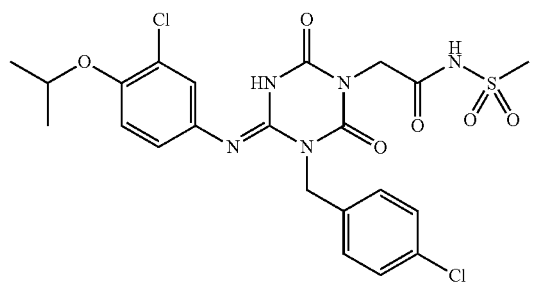 [SMILES: CC(C)Oc1ccc(/N=c2\[nH]c(=O)n(CC(=O)NS(C)(=O)=O)c(=O)n2Cc2ccc(Cl)cc2)cc1Cl] | I-1876 | 2.07 | 556 | 2 |
| 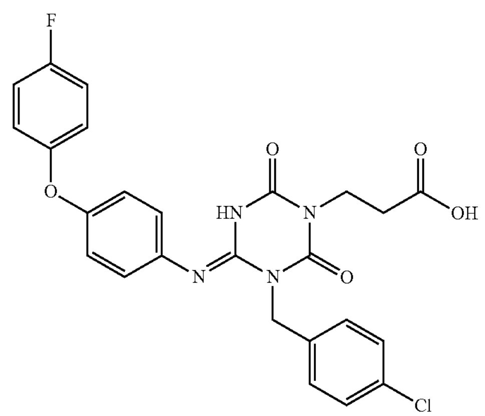 [SMILES: O=C(O)CCn1c(=O)[nH]/c(=N\c2ccc(Oc3ccc(F)cc3)cc2)n(Cc2ccc(Cl)cc2)c1=O] | I-1877 | 2.10 | 511 | 2 |
| 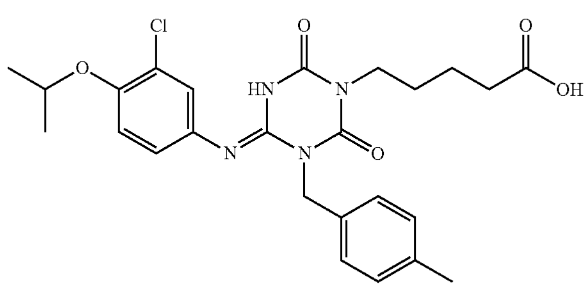 [SMILES: Cc1ccc(Cn2c(=O)n(CCCCC(=O)O)c(=O)[nH]/c2=N\c2ccc(OC(C)C)c(Cl)c2)cc1] | I-1878 | 2.11 | 501 | 2 |
| 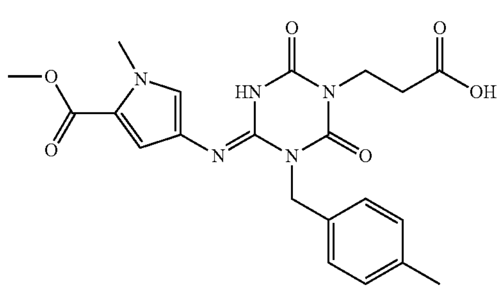 [SMILES: COC(=O)c1cc(/N=c2\[nH]c(=O)n(CCC(=O)O)c(=O)n2Cc2ccc(C)cc2)cn1C] | I-1879 | 1.69 | 442 | 3 |

TABLE 379-continued

| Structure | Compound No. | Retention Time (min) | [M + H] | Method |
|---|---|---|---|---|
| (structure) | I-1880 | 2.57 | 507 | 3 |

TABLE 380

| Structure | Compound No. | Retention Time (min) | [M + H] | Method |
|---|---|---|---|---|
| (structure) | I-1881 | 2.25 | 493 | 3 |
| (structure) | I-1882 | 1.88 | 529 | 2 |

TABLE 380-continued

| Structure | Compound No. | Retention Time (min) | [M + H] | Method |
|---|---|---|---|---|
| 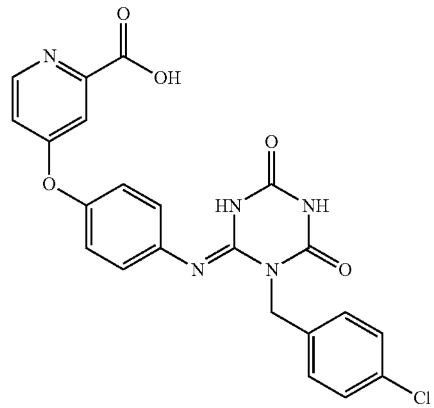 [SMILES: O=C(O)c1cc(Oc2ccc(/N=c3\[nH]c(=O)[nH]c(=O)n3Cc3ccc(Cl)cc3)cc2)ccn1] | I-1883 | 1.26 | 466 | 2 |
| 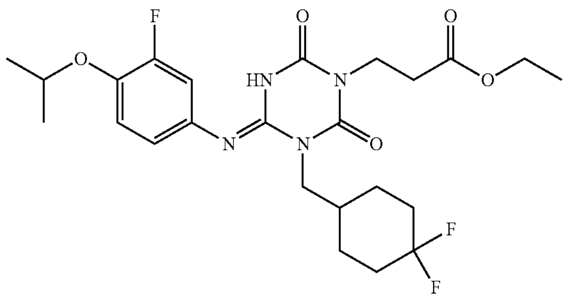 [SMILES: CCOC(=O)CCn1c(=O)[nH]/c(=N\c2ccc(OC(C)C)c(F)c2)n(CC2CCC(F)(F)CC2)c1=O] | I-1884 | 2.23 | 513 | 3 |
| 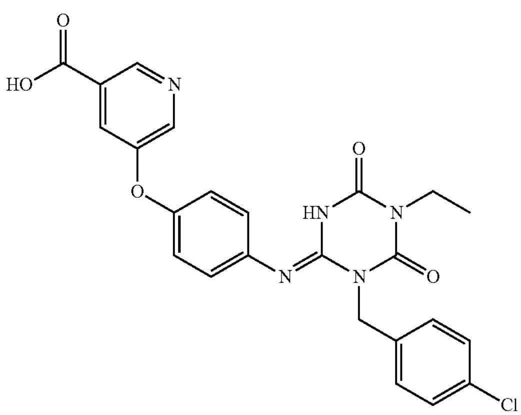 [SMILES: CCn1c(=O)[nH]/c(=N\c2ccc(Oc3cncc(C(=O)O)c3)cc2)n(Cc2ccc(Cl)cc2)c1=O] | I-1885 | 1.80 | 494 | 2 |

TABLE 381

| Structure | Compound No. | Retention Time (min) | [M + H] | Method |
|---|---|---|---|---|
| 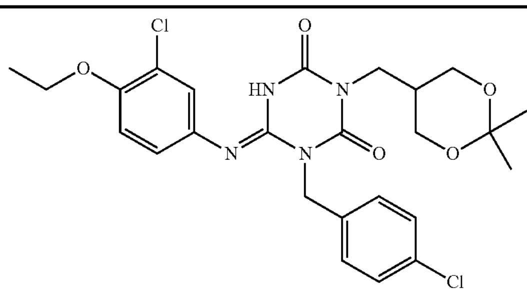 | I-1886 | 2.54 | 535 | 3 |

TABLE 381-continued

| Structure | Compound No. | Retention Time (min) | [M + H] | Method |
|---|---|---|---|---|
| 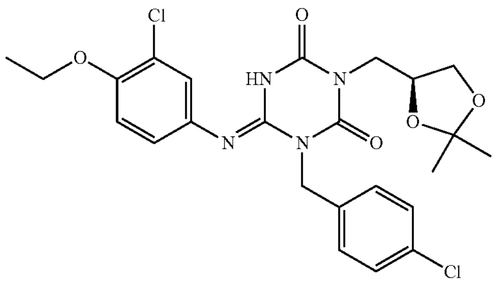 [SMILES: CCOc1ccc(/N=c2\[nH]c(=O)n(C[C@H]3COC(C)(C)O3)c(=O)n2Cc2ccc(Cl)cc2)cc1Cl] | I-1887 | 2.56 | 521 | 3 |
| 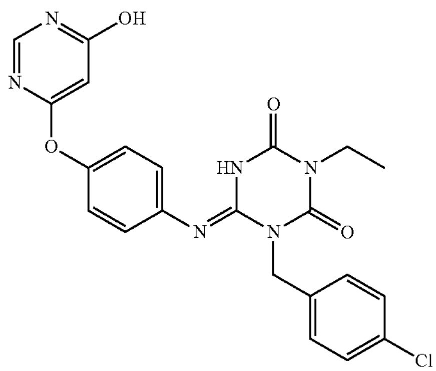 [SMILES: CCn1c(=O)[nH]/c(=N\c2ccc(Oc3cc(O)ncn3)cc2)n(Cc2ccc(Cl)cc2)c1=O] | I-1888 | 1.86 | 467 | 3 |
| 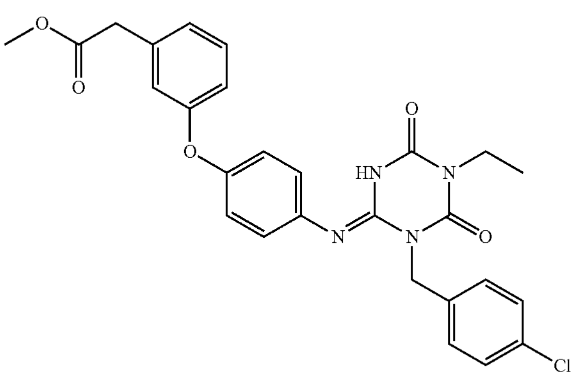 [SMILES: CCn1c(=O)[nH]/c(=N\c2ccc(Oc3cccc(CC(=O)OC)c3)cc2)n(Cc2ccc(Cl)cc2)c1=O] | I-1889 | 2.50 | 521 | 3 |
| 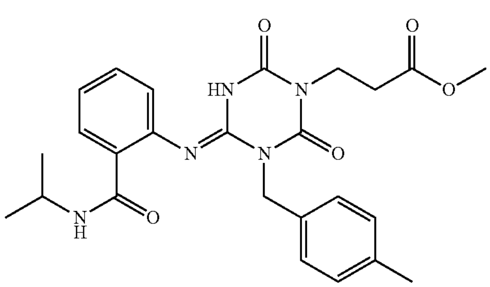 [SMILES: COC(=O)CCn1c(=O)[nH]/c(=N\c2ccccc2C(=O)NC(C)C)n(Cc2ccc(C)cc2)c1=O] | I-1890 | 2.22 | 480 | 3 |

TABLE 382

| Structure | Compound No. | Retention Time (min) | [M + H] | Method |
|---|---|---|---|---|
| 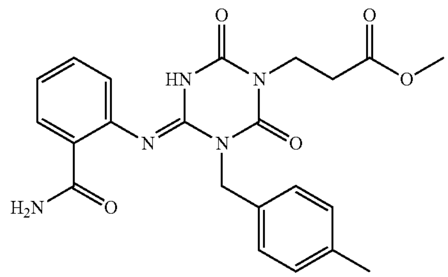 [SMILES: COC(=O)CCn1c(=O)[nH]/c(=N\c2ccccc2C(N)=O)n(Cc2ccc(C)cc2)c1=O] | I-1891 | 1.81 | 438 | 3 |
| 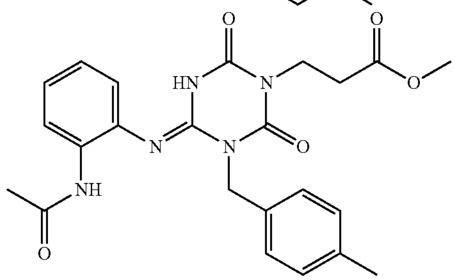 | I-1892 | 1.86 | 452 | 3 |
| 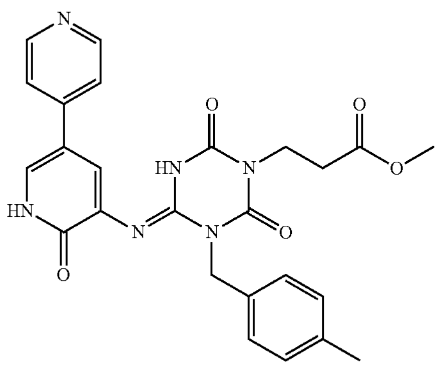 [SMILES: COC(=O)CCn1c(=O)[nH]/c(=N\c2cc(-c3ccncc3)c[nH]c2=O)n(Cc2ccc(C)cc2)c1=O] | I-1893 | 1.21 | 489 | 3 |
| 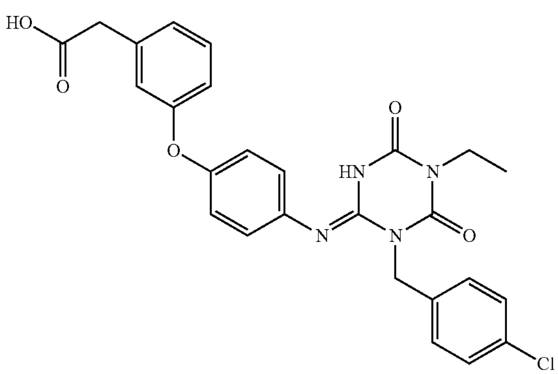 [SMILES: CCn1c(=O)[nH]/c(=N\c2ccc(Oc3cccc(CC(=O)O)c3)cc2)n(Cc2ccc(Cl)cc2)c1=O] | I-1894 | 2.22 | 507 | 3 |
| 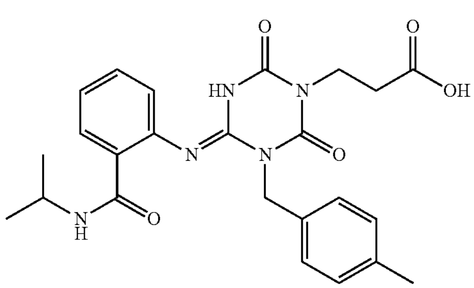 [SMILES: Cc1ccc(Cn2c(=O)n(CCC(=O)O)c(=O)[nH]/c2=N\c2ccccc2C(=O)NC(C)C)cc1] | I-1895 | 1.95 | 466 | 3 |

TABLE 383

| Structure | Compound No. | Retention Time (min) | [M + H] | Method |
|---|---|---|---|---|
| (structure of I-1896) | I-1896 | 1.60 | 465 | 2 |
| (structure of I-1897) | I-1897 | 1.54 | 509 | 2 |
| (structure of I-1898) | I-1898 | 2.02 | 547 | 2 |
| (structure of I-1899) | I-1899 | 2.58 | 529 | 3 |

TABLE 383-continued

| Structure | Compound No. | Retention Time (min) | [M + H] | Method |
|---|---|---|---|---|
| 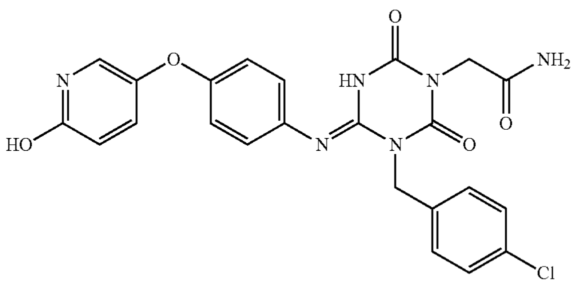 [SMILES: NC(=O)Cn1c(=O)[nH]/c(=N\c2ccc(Oc3ccc(O)nc3)cc2)n(Cc2ccc(Cl)cc2)c1=O] | I-1900 | 1.43 | 495 | 3 |

TABLE 384

| Structure | Compound No. | Retention Time (min) | [M +H] | Method |
|---|---|---|---|---|
| 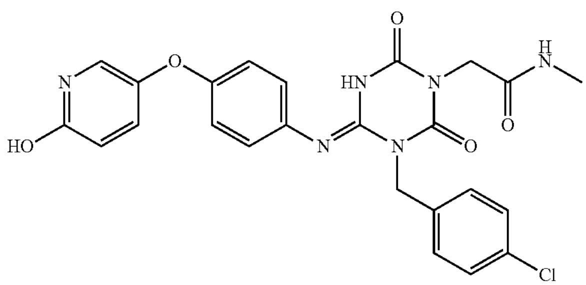 [SMILES: CNC(=O)Cn1c(=O)[nH]/c(=N\c2ccc(Oc3ccc(O)nc3)cc2)n(Cc2ccc(Cl)cc2)c1=O] | I-1901 | 1.49 | 509 | 3 |
| 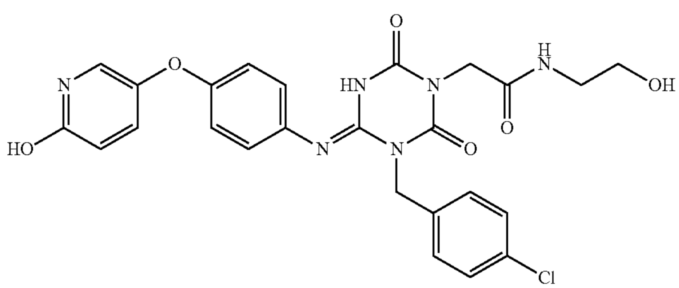 [SMILES: O=C(Cn1c(=O)[nH]/c(=N\c2ccc(Oc3ccc(O)nc3)cc2)n(Cc2ccc(Cl)cc2)c1=O)NCCO] | I-1902 | 1.40 | 539 | 3 |
| 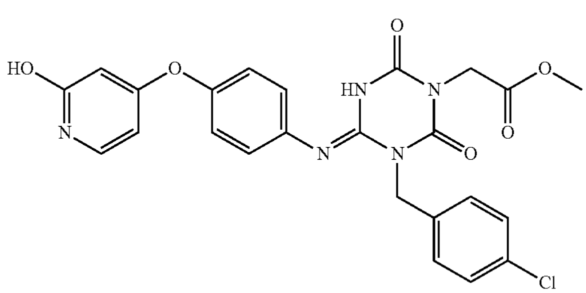 [SMILES: COC(=O)Cn1c(=O)[nH]/c(=N\c2ccc(Oc3ccnc(O)c3)cc2)n(Cc2ccc(Cl)cc2)c1=O] | I-1903 | 1.81 | 510 | 3 |

TABLE 384-continued

| Structure | Compound No. | Retention Time (min) | [M +H] | Method |
|---|---|---|---|---|
| 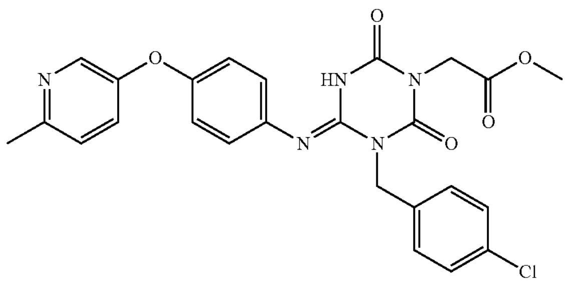 | I-1904 | 1.71 | 508 | 3 |
| 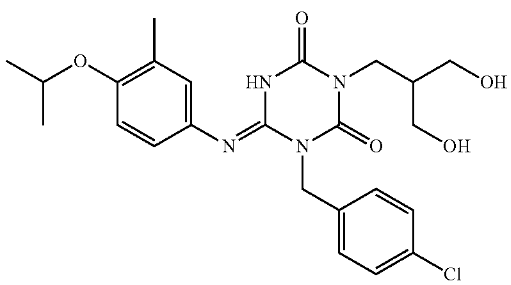 | I-1905 | 2.11 | 489 | 3 |

TABLE 385

| Structure | Compound No. | Retention Time (min) | [M + H] | Method |
|---|---|---|---|---|
| 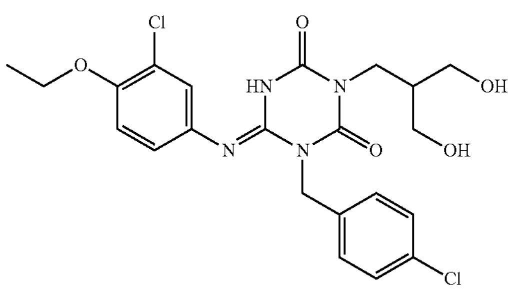 [SMILES: CCOc1ccc(/N=c2\[nH]c(=O)n(CC(CO)CO)c(=O)n2Cc2ccc(Cl)cc2)cc1Cl] | I-1906 | 2.04 | 495 | 3 |
| 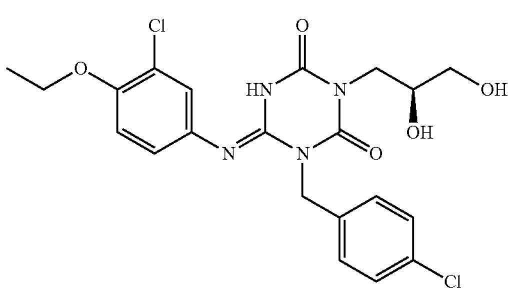 [SMILES: CCOc1ccc(/N=c2\[nH]c(=O)n(C[C@H](O)CO)c(=O)n2Cc2ccc(Cl)cc2)cc1Cl] | I-1907 | 2.01 | 481 | 3 |

TABLE 385-continued

| Structure | Compound No. | Retention Time (min) | [M + H] | Method |
|---|---|---|---|---|
| 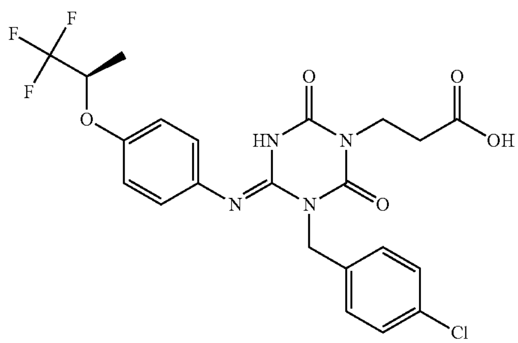 [SMILES: C[C@@H](Oc1ccc(/N=c2\[nH]c(=O)n(CCC(=O)O)c(=O)n2Cc2ccc(Cl)cc2)cc1)C(F)(F)F] | I-1908 | 2.00 | 513 | 2 |
| 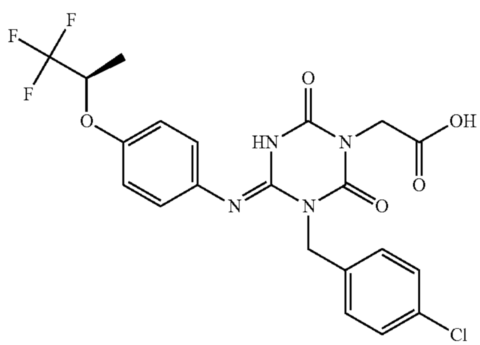 [SMILES: C[C@@H](Oc1ccc(/N=c2\[nH]c(=O)n(CC(=O)O)c(=O)n2Cc2ccc(Cl)cc2)cc1)C(F)(F)F] | I-1909 | 1.98 | 497 | 2 |
| 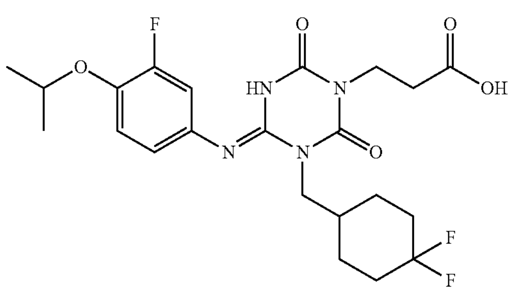 [SMILES: CC(C)Oc1ccc(/N=c2\[nH]c(=O)n(CCC(=O)O)c(=O)n2CC2CCC(F)(F)CC2)cc1F] | I-1910 | 2.04 | 485 | 3 |

TABLE 386

| Structure | Compound No. | Retention Time (min) | [M + H] | Method |
|---|---|---|---|---|
| 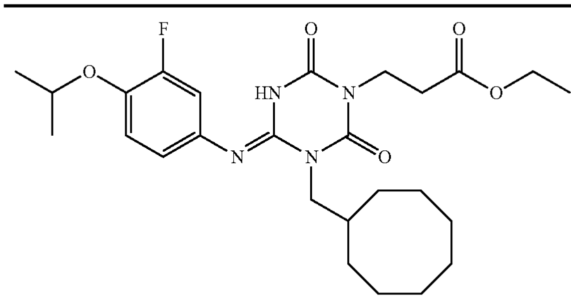 | I-1911 | 2.76 | 505 | 3 |

TABLE 386-continued

| Structure | Compound No. | Retention Time (min) | [M + H] | Method |
|---|---|---|---|---|
| 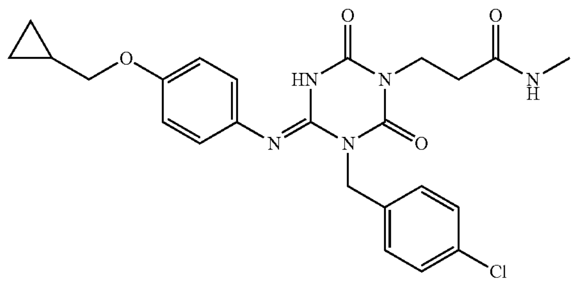 [SMILES: CNC(=O)CCn1c(=O)[nH]/c(=N\c2ccc(OCC3CC3)cc2)n(Cc2ccc(Cl)cc2)c1=O] | I-1912 | 2.00 | 484 | 3 |
| 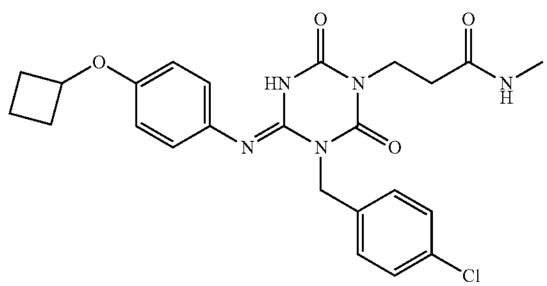 [SMILES: CNC(=O)CCn1c(=O)[nH]/c(=N\c2ccc(OC3CCC3)cc2)n(Cc2ccc(Cl)cc2)c1=O] | I-1913 | 2.06 | 484 | 3 |
| 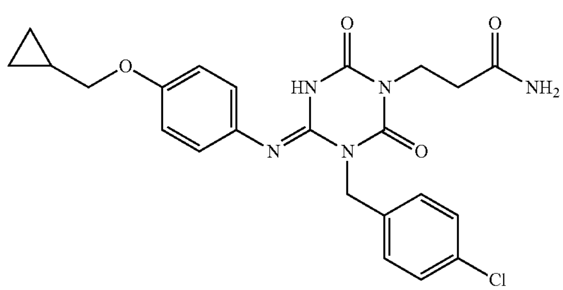 [SMILES: NC(=O)CCn1c(=O)[nH]/c(=N\c2ccc(OCC3CC3)cc2)n(Cc2ccc(Cl)cc2)c1=O] | I-1914 | 1.94 | 470 | 3 |
| 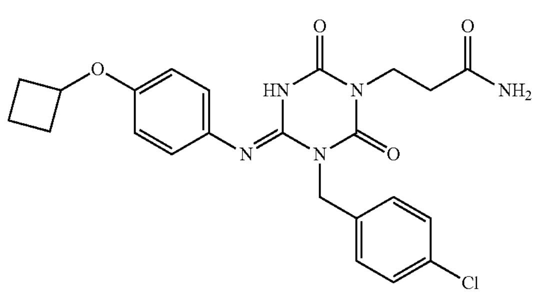 [SMILES: NC(=O)CCn1c(=O)[nH]/c(=N\c2ccc(OC3CCC3)cc2)n(Cc2ccc(Cl)cc2)c1=O] | I-1915 | 2.00 | 470 | 3 |

TABLE 387

| Structure | Compound No. | Retention Time (min) | [M + H] | Method |
|---|---|---|---|---|
| 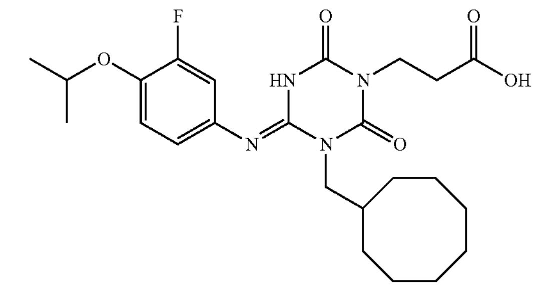 [SMILES: CC(C)Oc1ccc(/N=c2\[nH]c(=O)n(CCC(=O)O)c(=O)n2CC2CCCCCCC2)cc1F] | I-1916 | 2.41 | 477 | 3 |
| 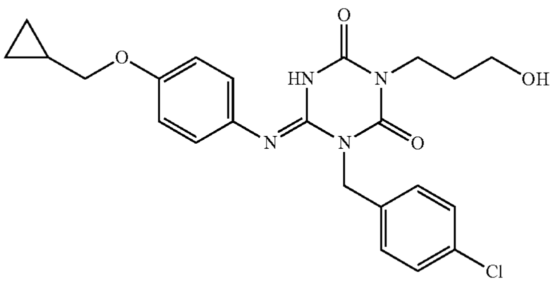 [SMILES: O=c1[nH]/c(=N\c2ccc(OCC3CC3)cc2)n(Cc2ccc(Cl)cc2)c(=O)n1CCCO] | I-1917 | 2.08 | 457 | 3 |
| 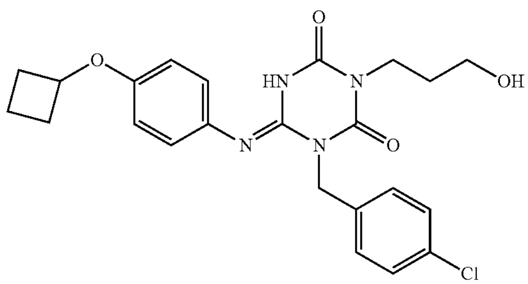 [SMILES: O=c1[nH]/c(=N\c2ccc(OC3CCC3)cc2)n(Cc2ccc(Cl)cc2)c(=O)n1CCCO] | I-1918 | 2.14 | 457 | 3 |
| 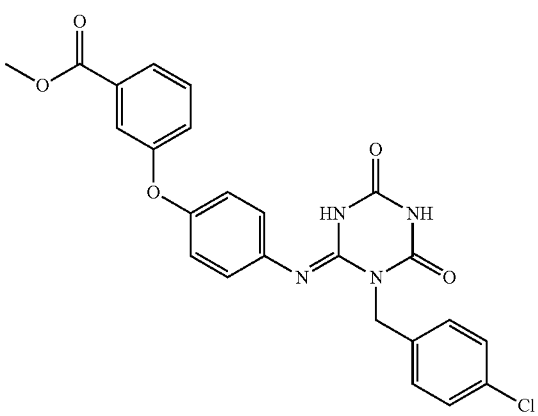 [SMILES: COC(=O)c1cccc(Oc2ccc(/N=c3\[nH]c(=O)[nH]c(=O)n3Cc3ccc(Cl)cc3)cc2)c1] | I-1919 | 2.29 | 479 | 3 |
| 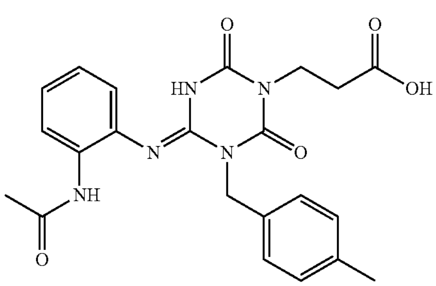 [SMILES: CC(=O)Nc1ccccc1/N=c1\[nH]c(=O)n(CCC(=O)O)c(=O)n1Cc1ccc(C)cc1] | I-1920 | 1.61 | 438 | 3 |

TABLE 388

| Structure | Compound No. | Retention Time (min) | [M + H] | Method |
|---|---|---|---|---|
| 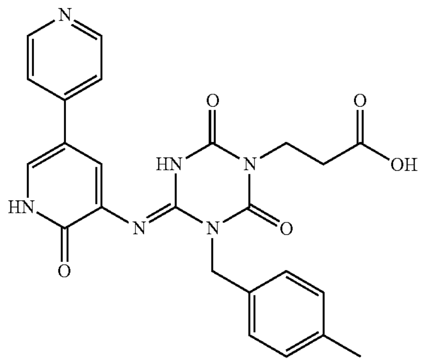 [SMILES: Cc1ccc(Cn2c(=O)n(CCC(=O)O)c(=O)[nH]/c2=N\c2cc(-c3ccncc3)c[nH]c2=O)cc1] | I-1921 | 1.03 | 475 | 3 |
| 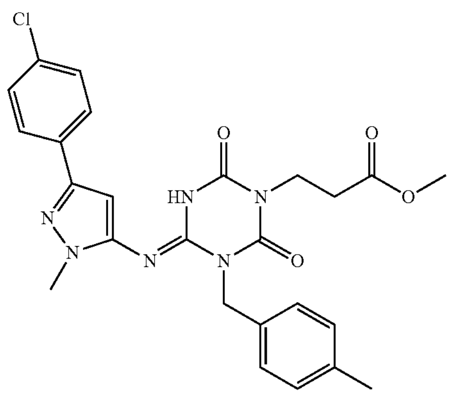 [SMILES: COC(=O)CCn1c(=O)[nH]/c(=N\c2cc(-c3ccc(Cl)cc3)nn2C)n(Cc2ccc(C)cc2)c1=O] | I-1922 | 2.57 | 509 | 3 |
| 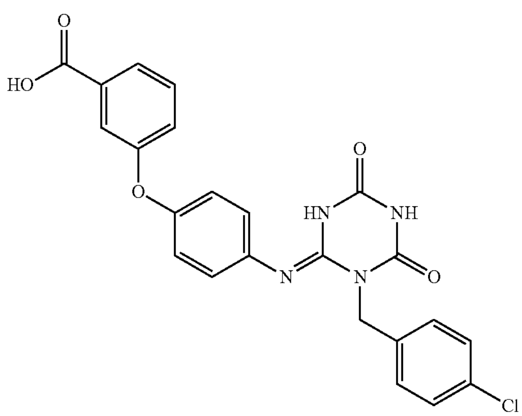 [SMILES: O=C(O)c1cccc(Oc2ccc(/N=c3\[nH]c(=O)[nH]c(=O)n3Cc3ccc(Cl)cc3)cc2)c1] | I-1923 | 1.96 | 465 | 3 |
| 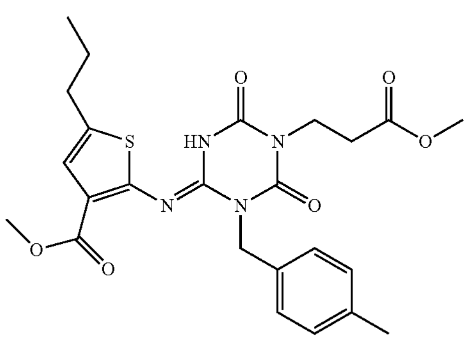 | I-1924 | 2.71 | 501 | 3 |

TABLE 388-continued
| Structure | Compound No. | Retention Time (min) | [M + H] | Method |
|---|---|---|---|---|
| 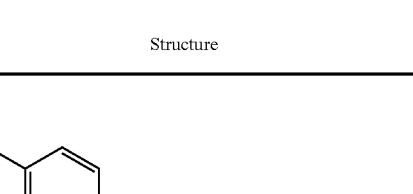 | I-1925 | 2.05 | 492 | 3 |
TABLE 389
| Structure | Compound No. | Retention Time (min) | [M + H] | Method |
|---|---|---|---|---|
| 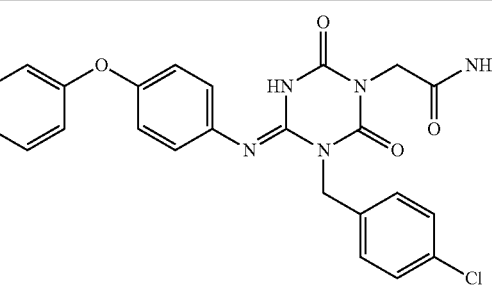 | I-1926 | 1.18 | 493 | 3 |
| 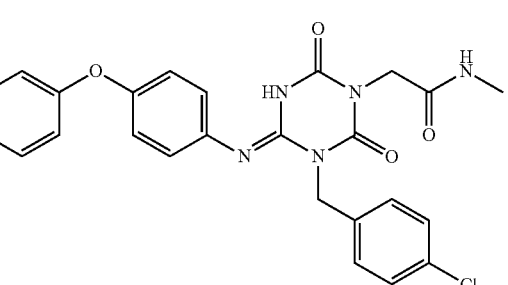 | I-1927 | 1.21 | 507 | 3 |
| 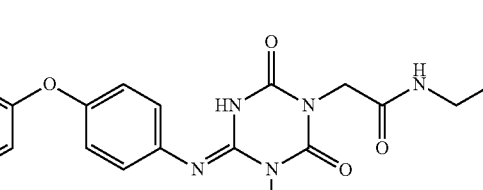 | I-1928 | 1.16 | 537 | 3 |

TABLE 389-continued

| Structure | Compound No. | Retention Time (min) | [M + H] | Method |
|---|---|---|---|---|
| (structure) | I-1928 | 2.23 | 437 | 3 |
| (structure) | I-1930 | 2.29 | 471 | 3 |

TABLE 390

| Structure | Compound No. | Retention Time (min) | [M + H] | Method |
|---|---|---|---|---|
| (structure) | I-1931 | 2.07 | 496 | 2 |
| (structure) | I-1932 | 1.62 | 496 | 3 |

TABLE 390-continued

| Structure | Compound No. | Retention Time (min) | [M + H] | Method |
|---|---|---|---|---|
| 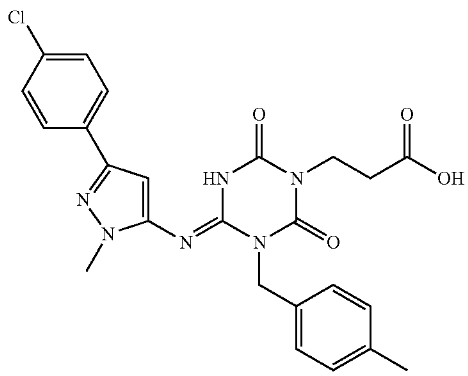 [SMILES: Cc1ccc(Cn2c(=O)n(CCC(=O)O)c(=O)[nH]/c2=N\c2cc(-c3ccc(Cl)cc3)nn2C)cc1] | I-1933 | 2.32 | 495 | 3 |
| 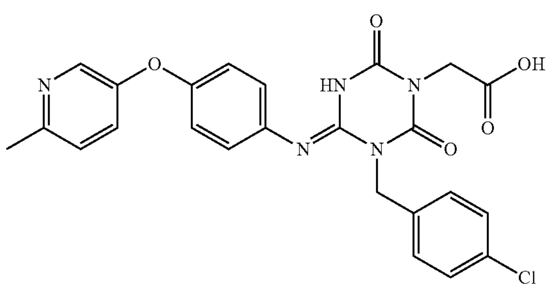 [SMILES: Cc1ccc(Oc2ccc(/N=c3\[nH]c(=O)n(CC(=O)O)c(=O)n3Cc3ccc(Cl)cc3)cc2)cn1] | I-1934 | 1.49 | 494 | 3 |
| 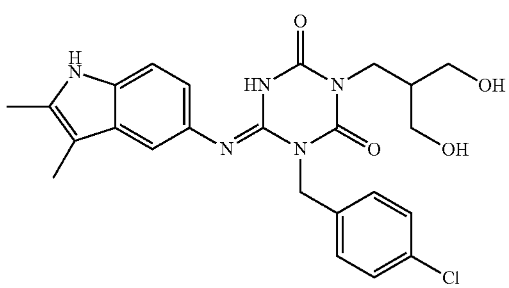 [SMILES: Cc1[nH]c2ccc(/N=c3\[nH]c(=O)n(CC(CO)CO)c(=O)n3Cc3ccc(Cl)cc3)cc2c1C] | I-1935 | 1.61 | 484 | 2 |

TABLE 391

| Structure | Compound No. | Retention Time (min) | [M + H] | Method |
|---|---|---|---|---|
| 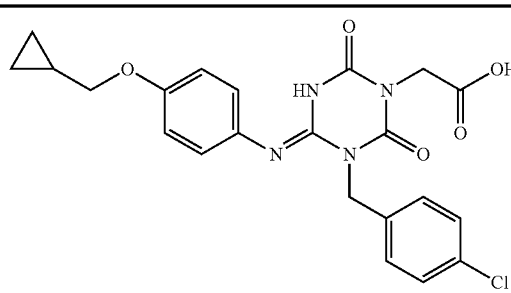 | I-1936 | 2.07 | 457 | 3 |

TABLE 391-continued

| Structure | Compound No. | Retention Time (min) | [M + H] | Method |
|---|---|---|---|---|
| 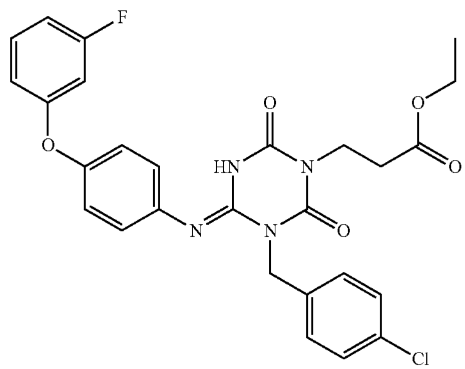 [SMILES: CCOC(=O)CCn1c(=O)[nH]/c(=N\c2ccc(Oc3cccc(F)c3)cc2)n(Cc2ccc(Cl)cc2)c1=O] | I-1937 | 2.46 | 539 | 2 |
| 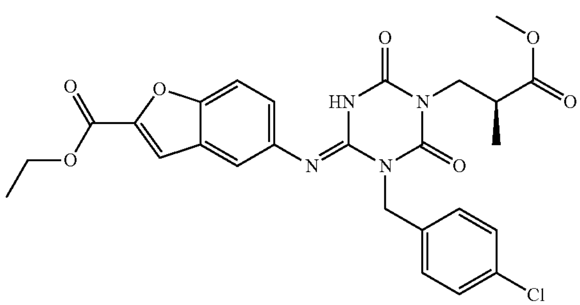 [SMILES: CCOC(=O)c1cc2cc(/N=c3\[nH]c(=O)n(C[C@H](C)C(=O)OC)c(=O)n3Cc3ccc(Cl)cc3)ccc2o1] | I-1938 | 2.21 | 541 | 2 |
| 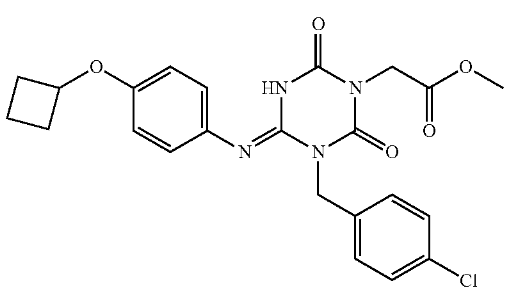 [SMILES: COC(=O)Cn1c(=O)[nH]/c(=N\c2ccc(OC3CCC3)cc2)n(Cc2ccc(Cl)cc2)c1=O] | I-1939 | 2.35 | 471 | 3 |
| 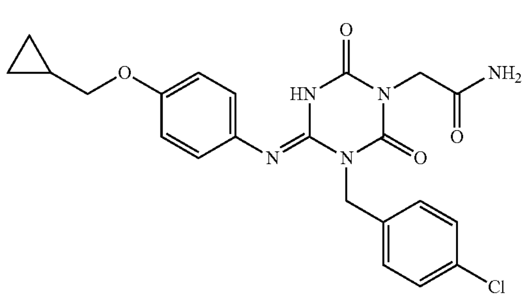 [SMILES: NC(=O)Cn1c(=O)[nH]/c(=N\c2ccc(OCC3CC3)cc2)n(Cc2ccc(Cl)cc2)c1=O] | I-1940 | 1.93 | 456 | 3 |

TABLE 392

| Structure | Compound No. | Retention Time (min) | [M + H] | Method |
|---|---|---|---|---|
| 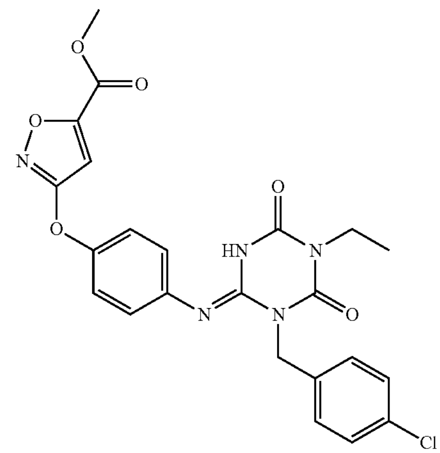 [SMILES: CCn1c(=O)[nH]/c(=N\c2ccc(Oc3cc(C(=O)OC)on3)cc2)n(Cc2ccc(Cl)cc2)c1=O] | I-1941 | 2.17 | 498 | 2 |
| 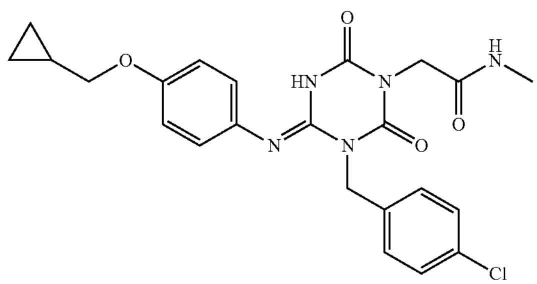 [SMILES: CNC(=O)Cn1c(=O)[nH]/c(=N\c2ccc(OCC3CC3)cc2)n(Cc2ccc(Cl)cc2)c1=O] | I-1942 | 1.99 | 470 | 3 |
| | I-1943 | 2.12 | 457 | 3 |
| 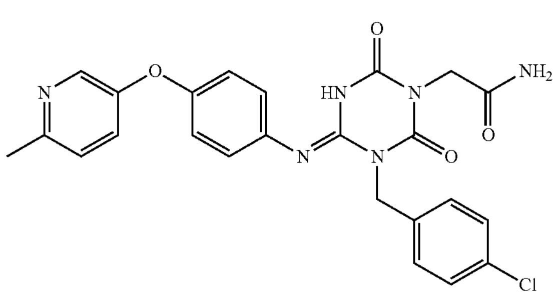 [SMILES: Cc1ccc(Oc2ccc(/N=c3\[nH]c(=O)n(CC(N)=O)c(=O)n3Cc3ccc(Cl)cc3)cc2)cn1] | I-1944 | 1.37 | 493 | 3 |

TABLE 392-continued

| Structure | Compound No. | Retention Time (min) | [M + H] | Method |
|---|---|---|---|---|
| 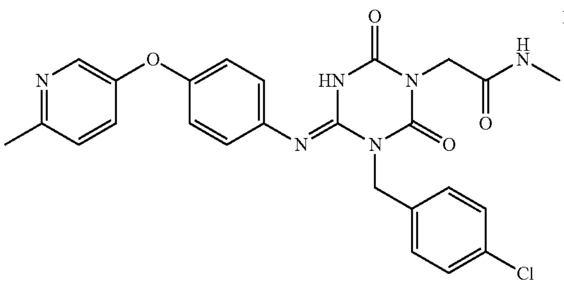 | I-1945 | 1.42 | 507 | 3 |

TABLE 393

| Structure | Compound No. | Retention Time (min) | [M + H] | Method |
|---|---|---|---|---|
| 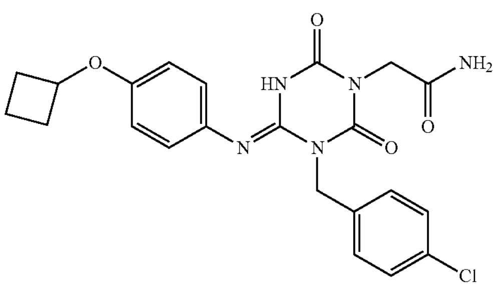 [SMILES: NC(=O)Cn1c(=O)[nH]/c(=N\c2ccc(OC3CCC3)cc2)n(Cc2ccc(Cl)cc2)c1=O] | I-1946 | 1.98 | 456 | 3 |
| | I-1947 | 2.47 | 513 | 2 |
| 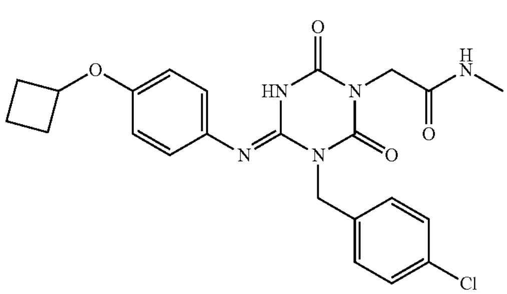 [SMILES: CNC(=O)Cn1c(=O)[nH]/c(=N\c2ccc(OC3CCC3)cc2)n(Cc2ccc(Cl)cc2)c1=O] | I-1948 | 2.06 | 470 | 3 |

TABLE 393-continued

| Structure | Compound No. | Retention Time (min) | [M + H] | Method |
|---|---|---|---|---|
| (structure) | I-1949 | 1.73 | 454 | 2 |
| (structure) | I-1950 | 1.74 | 468 | 2 |

TABLE 394

| Structure | Compound No. | Retention Time (min) | [M + H] | Method |
|---|---|---|---|---|
| (structure) | I-1952 | 2.12 | 511 | 2 |
| (structure) | I-1952 | 1.54 | 499 | 2 |

TABLE 394-continued
| Structure | Compound No. | Retention Time (min) | [M + H] | Method |
|---|---|---|---|---|
| 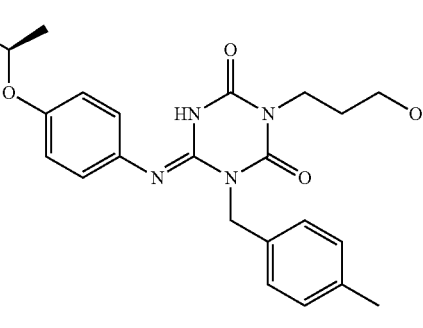 | I-1953 | 1.92 | 479 | 2 |
| 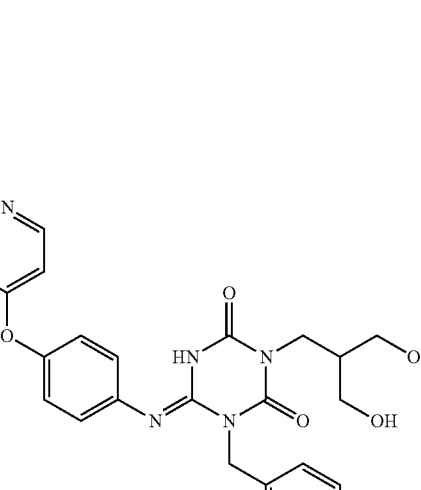 | I-1954 | 1.10 | 524 | 2 |
| 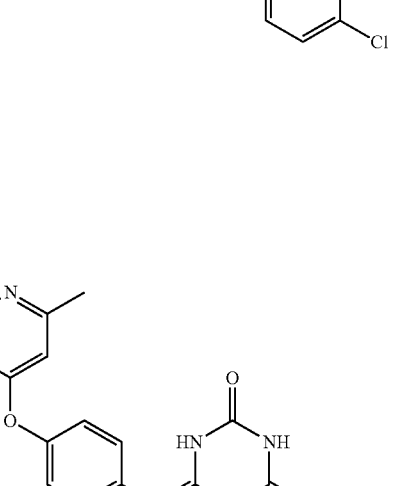 | I-1955 | 1.18 | 436 | 2 |

TABLE 395

| Structure | Compound No. | Retention Time (min) | [M + H] | Method |
|---|---|---|---|---|
| 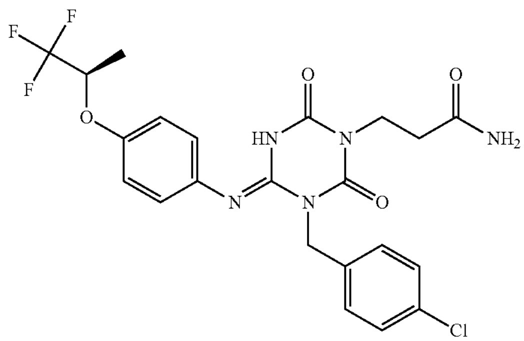 [SMILES: C[C@@H](Oc1ccc(/N=c2\[nH]c(=O)n(CCC(N)=O)c(=O)n2Cc2ccc(Cl)cc2)cc1)C(F)(F)F] | I-1956 | 1.87 | 512 | 2 |
| 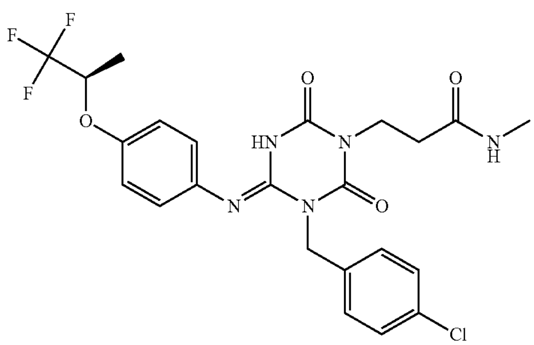 [SMILES: CNC(=O)CCn1c(=O)[nH]/c(=N\c2ccc(O[C@H](C)C(F)(F)F)cc2)n(Cc2ccc(Cl)cc2)c1=O] | I-1957 | 1.91 | 526 | 2 |
| 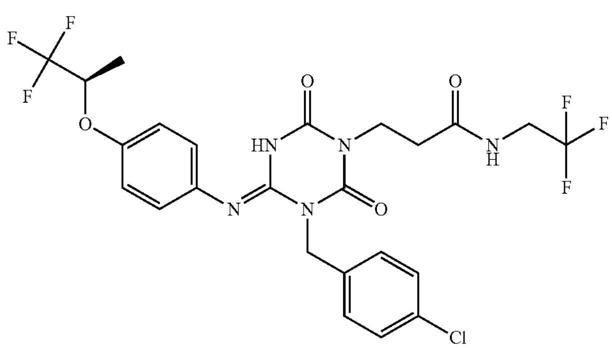 [SMILES: C[C@@H](Oc1ccc(/N=c2\[nH]c(=O)n(CCC(=O)NCC(F)(F)F)c(=O)n2Cc2ccc(Cl)cc2)cc1)C(F)(F)F] | I-1958 | 2.15 | 594 | 2 |
| 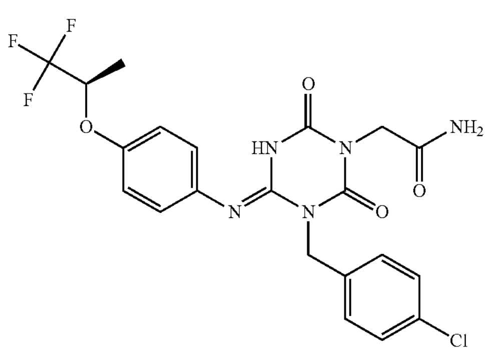 [SMILES: C[C@@H](Oc1ccc(/N=c2\[nH]c(=O)n(CC(N)=O)c(=O)n2Cc2ccc(Cl)cc2)cc1)C(F)(F)F] | I-1959 | 1.86 | 498 | 2 |

TABLE 395-continued

| Structure | Compound No. | Retention Time (min) | [M + H] | Method |
|---|---|---|---|---|
| 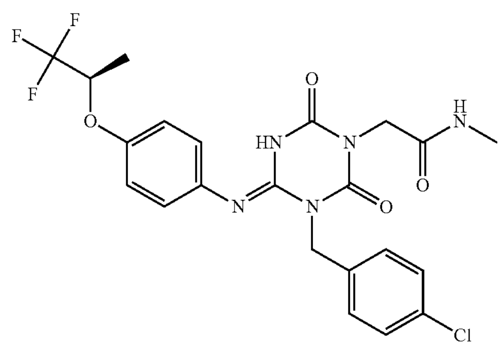 [SMILES: CNC(=O)Cn1c(=O)[nH]/c(=N\c2ccc(O[C@H](C)C(F)(F)F)cc2)n(Cc2ccc(Cl)cc2)c1=O] | I-1960 | 1.89 | 512 | 2 |

TABLE 396

| Structure | Compound No. | Retention Time (min) | [M + H] | Method |
|---|---|---|---|---|
| 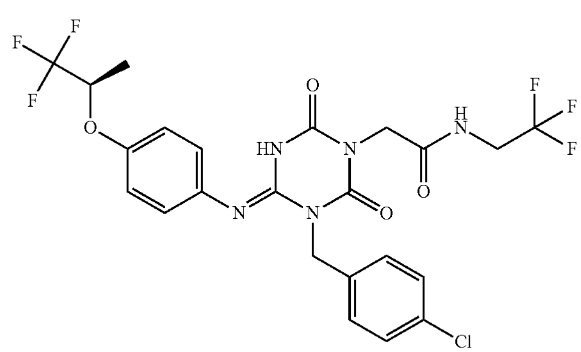 [SMILES: C[C@@H](Oc1ccc(/N=c2\[nH]c(=O)n(CC(=O)NCC(F)(F)F)c(=O)n2Cc2ccc(Cl)cc2)cc1)C(F)(F)F] | I-1961 | 2.14 | 582 | 2 |
| 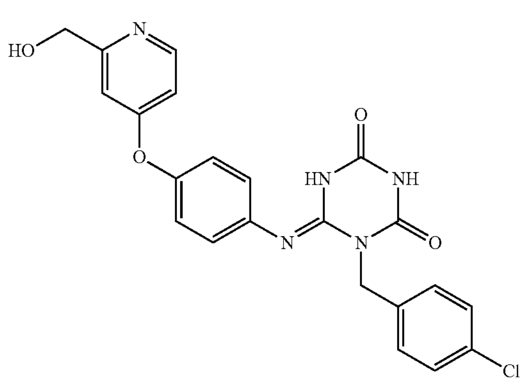 [SMILES: O=c1[nH]c(=O)n(Cc2ccc(Cl)cc2)/c(=N/c2ccc(Oc3ccnc(CO)c3)cc2)[nH]1] | I-1962 | 1.11 | 452 | 2 |

TABLE 396-continued

| Structure | Compound No. | Retention Time (min) | [M + H] | Method |
|---|---|---|---|---|
| 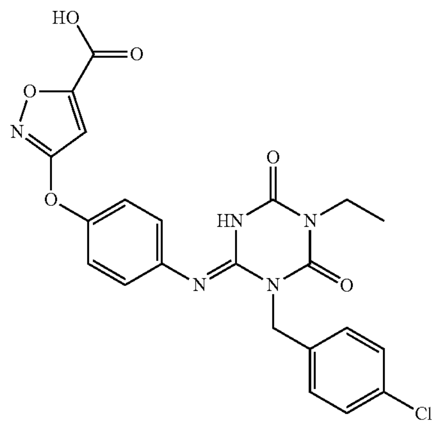 [SMILES: CCn1c(=O)[nH]/c(=N\c2ccc(Oc3cc(C(=O)O)on3)cc2)n(Cc2ccc(Cl)cc2)c1=O] | I-1963 | 1.74 | 484 | 2 |
| 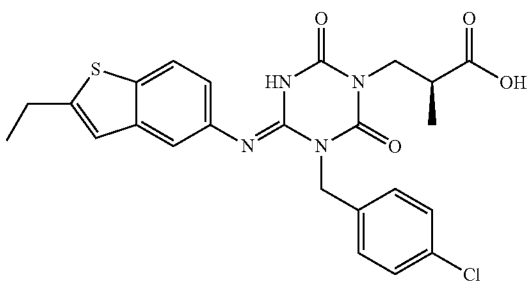 | I-1964 | 2.22 | 499 | 2 |
| 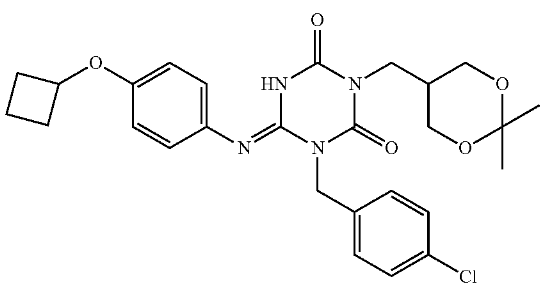 [SMILES: CC1(C)OCC(Cn2c(=O)[nH]/c(=N\c3ccc(OC4CCC4)cc3)n(Cc3ccc(Cl)cc3)c2=O)CO1] | I-1965 | 2.25 | 527 | 2 |

TABLE 397

| Structure | Compound No. | Retention Time (min) | [M + H] | Method |
|---|---|---|---|---|
| 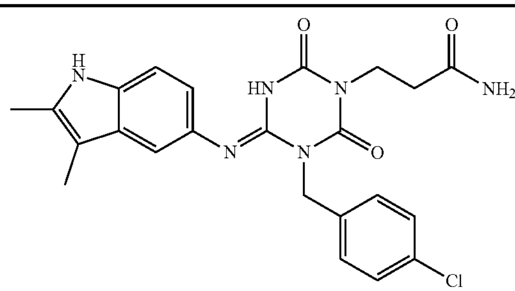 | I-1966 | 1.61 | 467 | 2 |

TABLE 397-continued

| Structure | Compound No. | Retention Time (min) | [M + H] | Method |
|---|---|---|---|---|
| 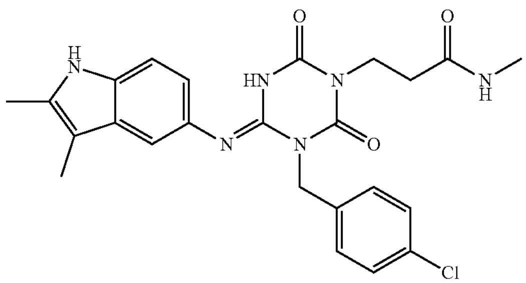 | I-1967 | 1.65 | 481 | 2 |
| 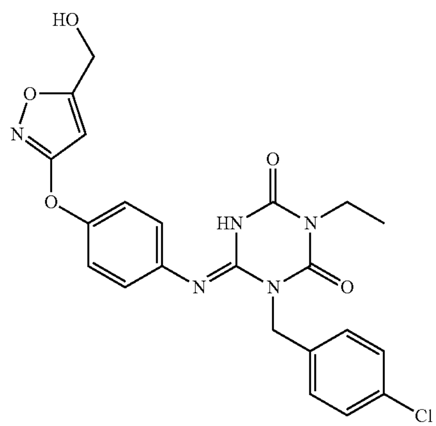 [SMILES: CCn1c(=O)[nH]/c(=N\c2ccc(Oc3cc(CO)on3)cc2)n(Cc2ccc(Cl)cc2)c1=O] | I-1968 | 1.84 | 470 | 2 |
| 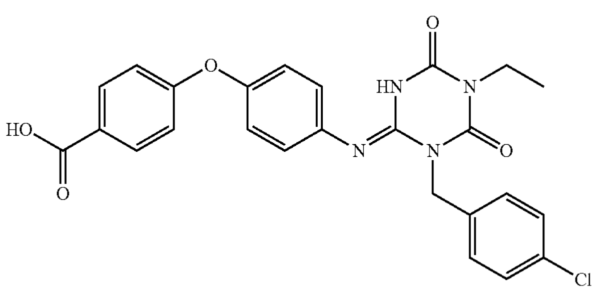 [SMILES: CCn1c(=O)[nH]/c(=N\c2ccc(Oc3ccc(C(=O)O)cc3)cc2)n(Cc2ccc(Cl)cc2)c1=O] | I-1969 | 2.02 | 493 | 2 |
| 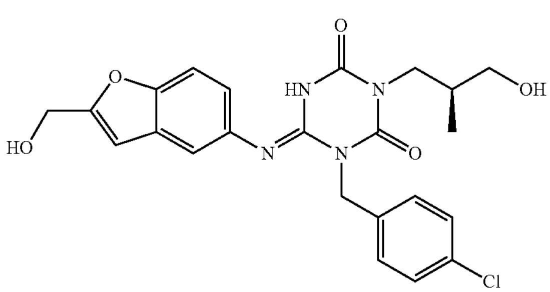 [SMILES: C[C@H](CO)Cn1c(=O)[nH]/c(=N\c2ccc3oc(CO)cc3c2)n(Cc2ccc(Cl)cc2)c1=O] | I-1970 | 1.57 | 471 | 2 |

TABLE 398
| Structure | Compound No. | Retention Time (min) | [M + H] | Method |
|---|---|---|---|---|
| 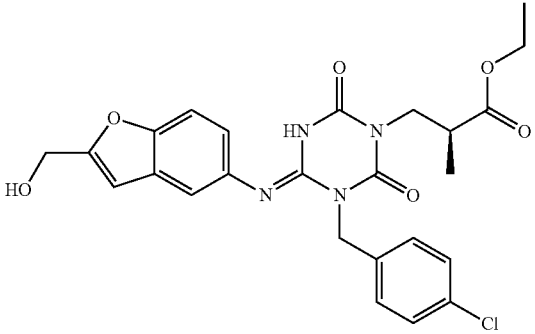 [SMILES: CCOC(=O)[C@@H](C)Cn1c(=O)[nH]/c(=N\c2ccc3oc(CO)cc3c2)n(Cc2ccc(Cl)cc2)c1=O] | I-1971 | 1.90 | 513 | 2 |
| 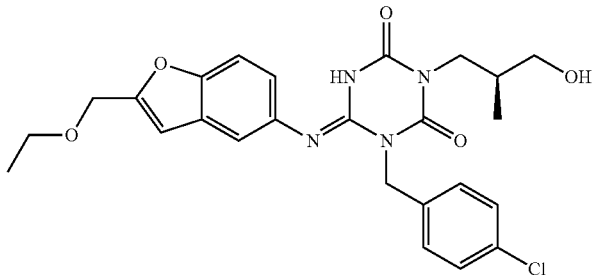 [SMILES: CCOCc1cc2cc(/N=c3\[nH]c(=O)n(C[C@H](C)CO)c(=O)n3Cc3ccc(Cl)cc3)ccc2o1] | I-1972 | 2.00 | 513 | 2 |
| 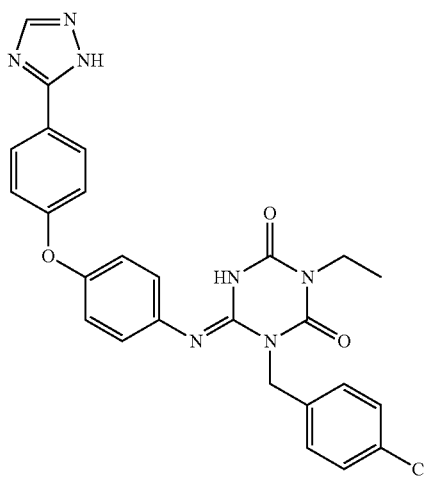 [SMILES: CCn1c(=O)[nH]/c(=N\c2ccc(Oc3ccc(-c4ncn[nH]4)cc3)cc2)n(Cc2ccc(Cl)cc2)c1=O] | I-1973 | 1.86 | 516 | 2 |
| 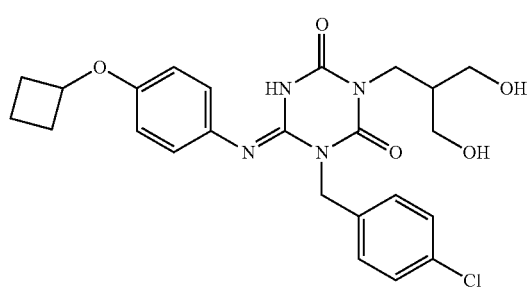 [SMILES: O=c1[nH]/c(=N\c2ccc(OC3CCC3)cc2)n(Cc2ccc(Cl)cc2)c(=O)n1CC(CO)CO] | I-1974 | 1.81 | 487 | 2 |

TABLE 398-continued

| Structure | Compound No. | Retention Time (min) | [M + H] | Method |
|---|---|---|---|---|
| (structure) | I-1975 | 1.63 | 448 | 3 |

TABLE 399

| Structure | Compound No. | Retention Time (min) | [M + H] | Method |
|---|---|---|---|---|
| (structure) | I-1976 | 1.38 | 494 | 3 |
| (structure) | I-1977 | 1.50 | 495 | 3 |
| (structure) | I-1978 | 1.56 | 509 | 3 |

TABLE 399-continued

| Structure | Compound No. | Retention Time (min) | [M + H] | Method |
|---|---|---|---|---|
| 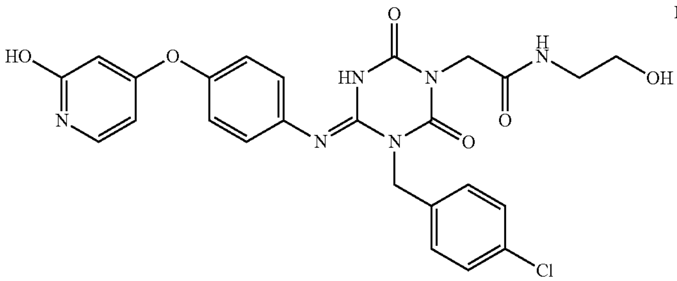 | I-1979 | 1.46 | 539 | 3 |
| 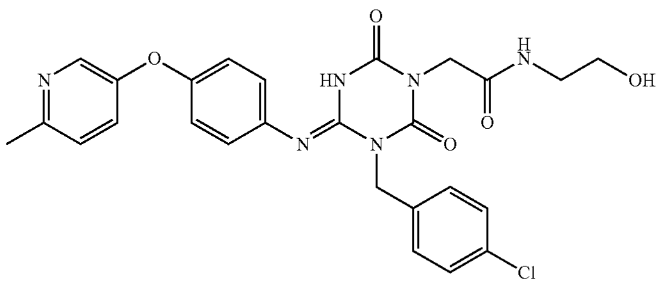 [SMILES: Cc1ccc(Oc2ccc(/N=c3\[nH]c(=O)n(CC(=O)NCCO)c(=O)n3Cc3ccc(Cl)cc3)cc2)cn1] | I-1980 | 1.32 | 537 | 3 |

TABLE 400

| Structure | Compound No. | Retention Time (min) | [M + H] | Method |
|---|---|---|---|---|
| 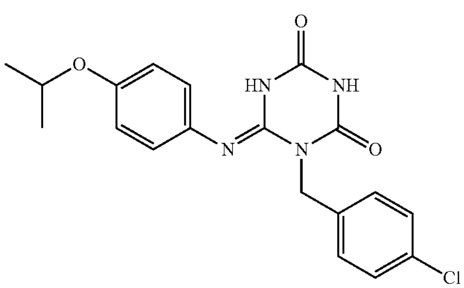 [SMILES: CC(C)Oc1ccc(/N=c2\[nH]c(=O)[nH]c(=O)n2Cc2ccc(Cl)cc2)cc1] | I-1981 | 2.05 | 387 | 3 |
| 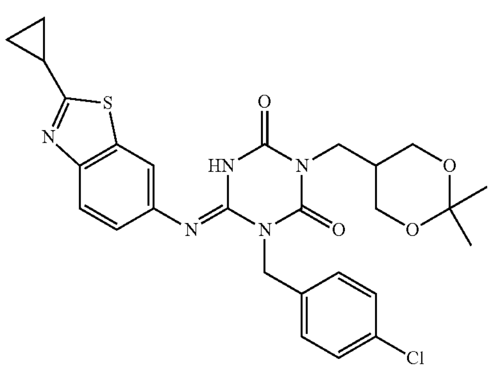 [SMILES: CC1(C)OCC(Cn2c(=O)[nH]/c(=N\c3ccc4nc(C5CC5)sc4c3)n(Cc3ccc(Cl)cc3)c2=O)CO1] | I-1982 | 2.20 | 554 | 2 |

TABLE 400-continued
| Structure | Compound No. | Retention Time (min) | [M + H] | Method |
|---|---|---|---|---|
| 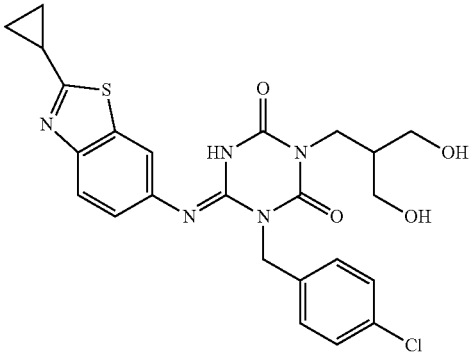 [SMILES: O=c1[nH]/c(=N\c2ccc3nc(C4CC4)sc3c2)n(Cc2ccc(Cl)cc2)c(=O)n1CC(CO)CO] | I-1983 | 1.94 | 514 | 3 |
| 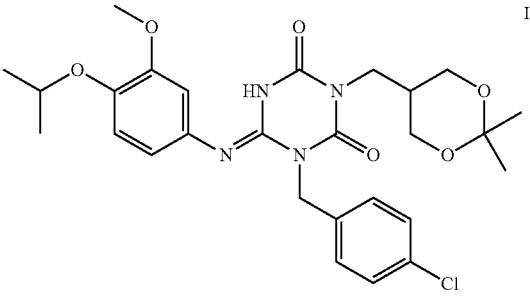 | I-1984 | 2.12 | 545 | 2 |
| 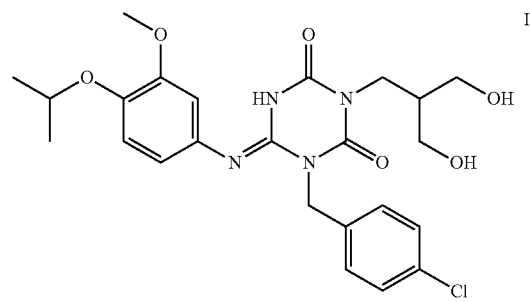 [SMILES: COc1cc(/N=c2\[nH]c(=O)n(CC3COC(C)(C)OC3)c(=O)n2Cc2ccc(Cl)cc2)ccc1OC(C)C] | I-1985 | 1.88 | 505 | 3 |
TABLE 401
| Structure | Compound No. | Retention Time (min) | [M + H] | Method |
|---|---|---|---|---|
| 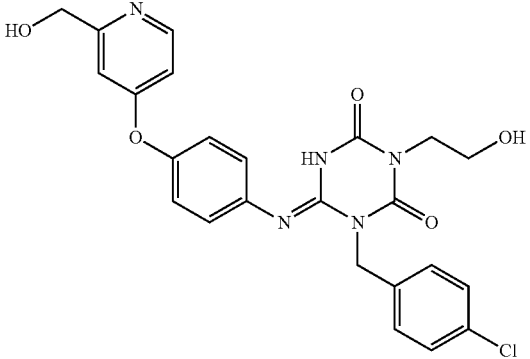 [SMILES: O=c1[nH]/c(=N\c2ccc(Oc3ccnc(CO)c3)cc2)n(Cc2ccc(Cl)cc2)c(=O)n1CCO] | I-1986 | 1.05 | 496 | 2 |

TABLE 401-continued

| Structure | Compound No. | Retention Time (min) | [M + H] | Method |
|---|---|---|---|---|
| 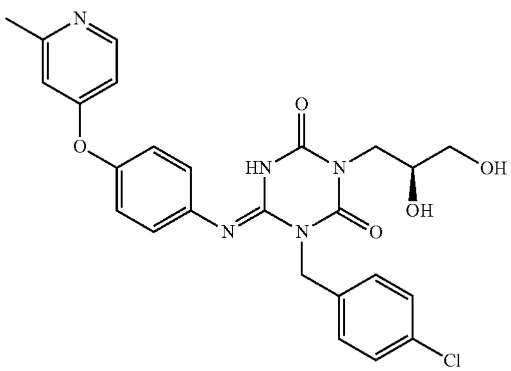 [SMILES: Cc1cc(Oc2ccc(/N=c3\[nH]c(=O)n(C[C@H](O)CO)c(=O)n3Cc3ccc(Cl)cc3)cc2)ccn1] | I-1987 | 1.08 | 510 | 2 |
| 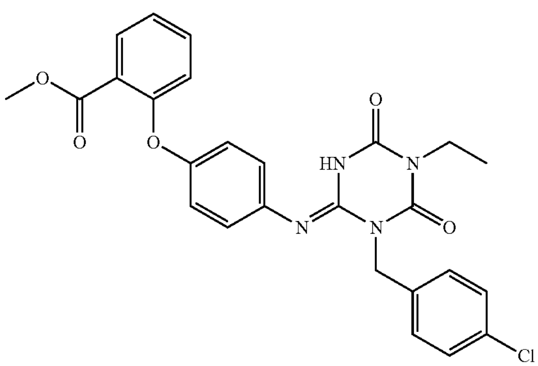 [SMILES: CCn1c(=O)[nH]/c(=N\c2ccc(Oc3ccccc3C(=O)OC)cc2)n(Cc2ccc(Cl)cc2)c1=O] | I-1988 | 2.45 | 507 | 3 |
| 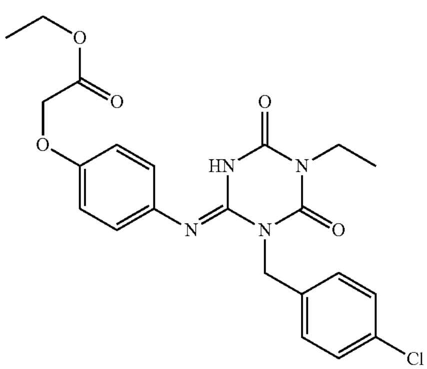 [SMILES: CCOC(=O)COc1ccc(/N=c2\[nH]c(=O)n(CC)c(=O)n2Cc2ccc(Cl)cc2)cc1] | I-1989 | 2.20 | 459 | 3 |
| 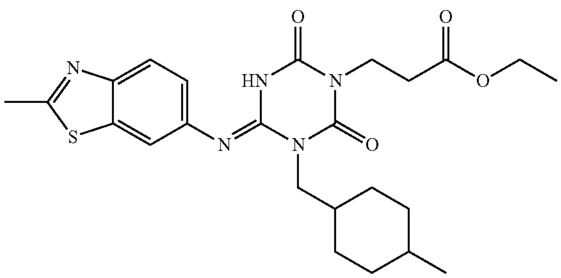 [SMILES: CCOC(=O)CCn1c(=O)[nH]/c(=N\c2ccc3nc(C)sc3c2)n(CC2CCC(C)CC2)c1=O] | I-1990 | 2.43 | 486 | 3 |

TABLE 402

| Structure | Compound No. | Retention Time (min) | [M + H] | Method |
|---|---|---|---|---|
| 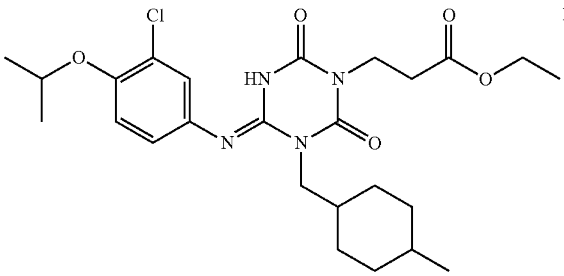 | I-1991 | 2.82 | 508 | 3 |
| 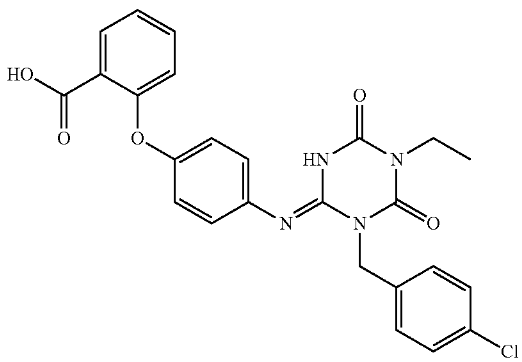 [SMILES: CCn1c(=O)[nH]/c(=N\c2ccc(Oc3ccccc3C(=O)O)cc2)n(Cc2ccc(Cl)cc2)c1=O] | I-1992 | 2.18 | 493 | 3 |
| 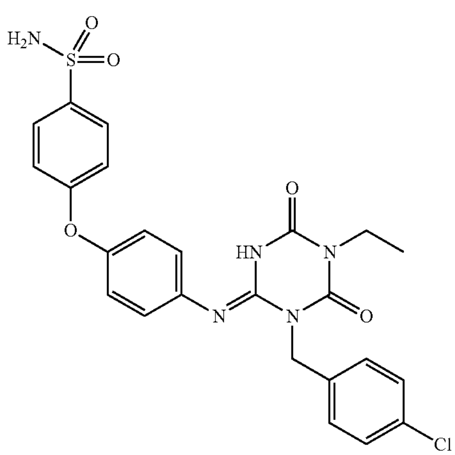 [SMILES: CCn1c(=O)[nH]/c(=N\c2ccc(Oc3ccc(S(N)(=O)=O)cc3)cc2)n(Cc2ccc(Cl)cc2)c1=O] | I-1993 | 2.10 | 528 | 3 |
| 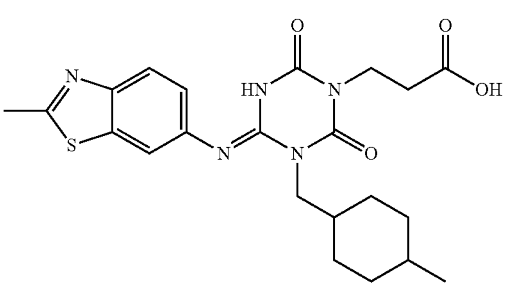 [SMILES: Cc1nc2ccc(/N=c3\[nH]c(=O)n(CCC(=O)O)c(=O)n3CC3CCC(C)CC3)cc2s1] | I-1994 | 2.01 | 458 | 3 |

TABLE 402-continued

| Structure | Compound No. | Retention Time (min) | [M + H] | Method |
|---|---|---|---|---|
| (structure) | I-1995 | 1.10 | 510 | 2 |

| Structure | Compound No. | Retention Time (min) | [M + H] | Method |
|---|---|---|---|---|
| (structure) | I-1996 | 1.67 | 493 | 2 |
| (structure) | I-1997 | 1.47 | 494 | 2 |

-continued

| Structure | Compound No. | Retention Time (min) | [M + H] | Method |
|---|---|---|---|---|
| 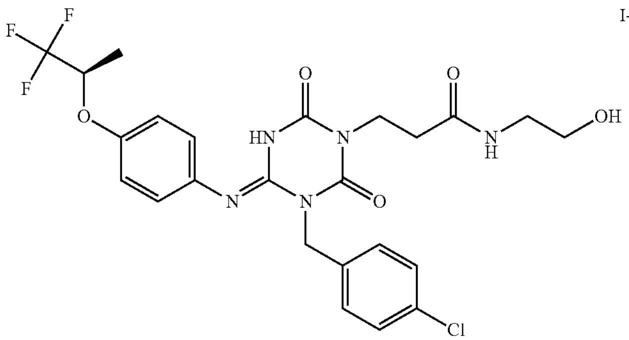 | I-1998 | 2.01 | 556 | 3 |
| 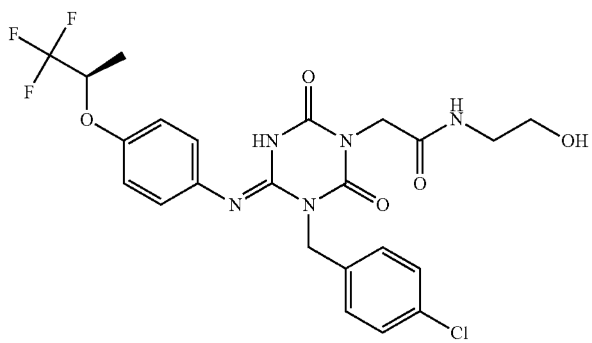 [SMILES: C[C@@H](Oc1ccc(/N=c2\[nH]c(=O)n(CC(=O)NCCO)c(=O)n2Cc2ccc(Cl)cc2)cc1)C(F)(F)F] | I-1999 | 1.99 | 542 | 3 |
| 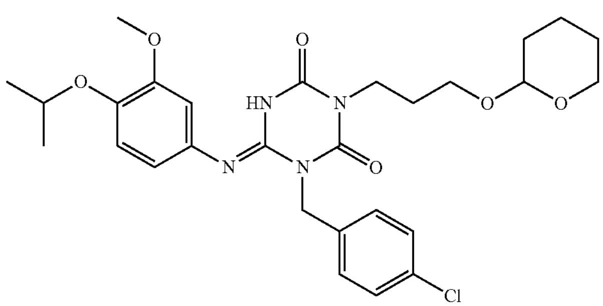 [SMILES: COc1cc(/N=c2\[nH]c(=O)n(CCCOC3CCCCO3)c(=O)n2Cc2ccc(Cl)cc2)ccc1OC(C)C] | I-2000 | 2.29 | 559 | 2 |

TABLE 404

| Structure | Compound No. | Retention Time (min) | [M + H] | Method |
|---|---|---|---|---|
| 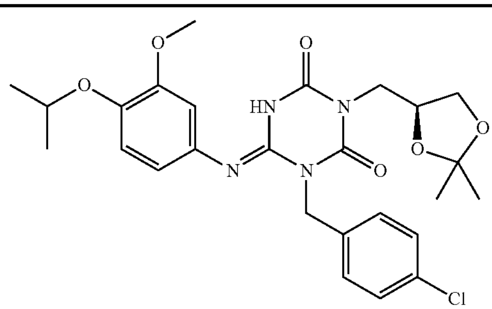 | I-2001 | 2.15 | 531 | 2 |

TABLE 404-continued
| Structure | Compound No. | Retention Time (min) | [M + H] | Method |
|---|---|---|---|---|
| 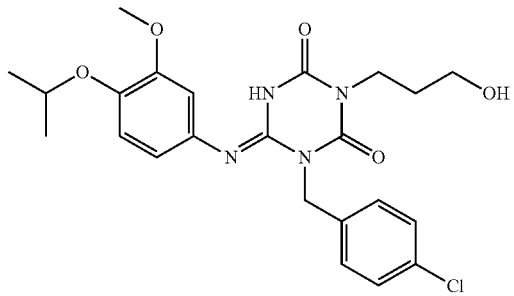 [SMILES: COc1cc(/N=c2\[nH]c(=O)n(CCCO)c(=O)n2Cc2ccc(Cl)cc2)ccc1OC(C)C] | I-2002 | 2.02 | 475 | 3 |
| 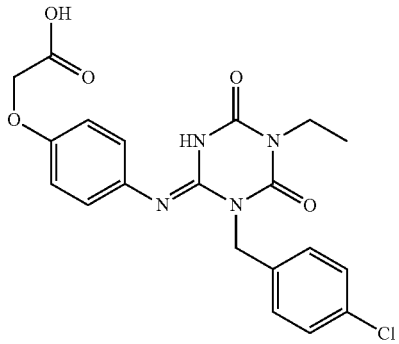 [SMILES: CCn1c(=O)[nH]/c(=N\c2ccc(OCC(=O)O)cc2)n(Cc2ccc(Cl)cc2)c1=O] | I-2003 | 1.84 | 431 | 3 |
| 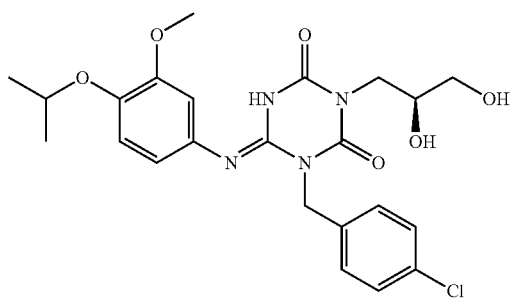 [SMILES: COc1cc(/N=c2\[nH]c(=O)n(C[C@H](O)CO)c(=O)n2Cc2ccc(Cl)cc2)ccc1OC(C)C] | I-2004 | 1.84 | 491 | 3 |
| 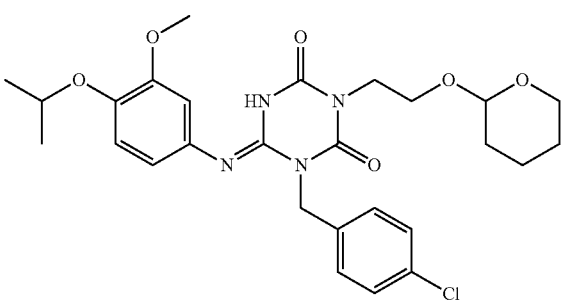 [SMILES: COc1cc(/N=c2\[nH]c(=O)n(CCOC3CCCCO3)c(=O)n2Cc2ccc(Cl)cc2)ccc1OC(C)C] | I-2005 | 2.22 | 545 | 2 |

TABLE 405

| Structure | Compound No. | Retention Time (min) | [M + H] | Method |
|---|---|---|---|---|
| 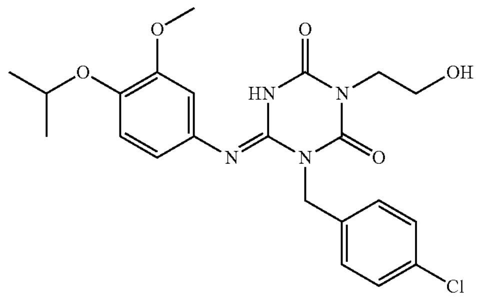 [SMILES: COc1cc(/N=c2\[nH]c(=O)n(CCO)c(=O)n2Cc2ccc(Cl)cc2)ccc1OC(C)C] | I-2006 | 1.97 | 461 | 3 |
| 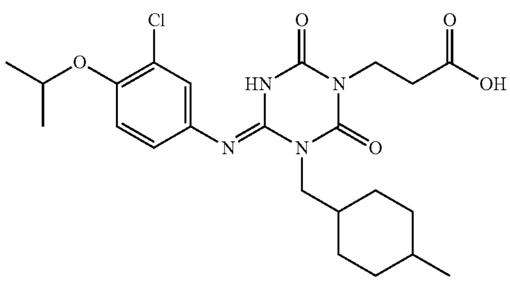 [SMILES: CC1CCC(Cn2c(=O)n(CCC(=O)O)c(=O)[nH]/c2=N\c2ccc(OC(C)C)c(Cl)c2)CC1] | I-2007 | 2.46 | 479 | 3 |
| 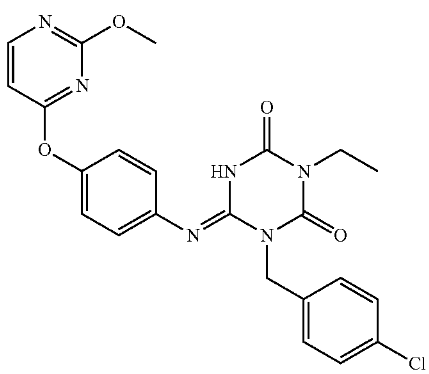 [SMILES: CCn1c(=O)[nH]/c(=N\c2ccc(Oc3ccnc(OC)n3)cc2)n(Cc2ccc(Cl)cc2)c1=O] | I-2008 | 2.29 | 481 | 3 |
| 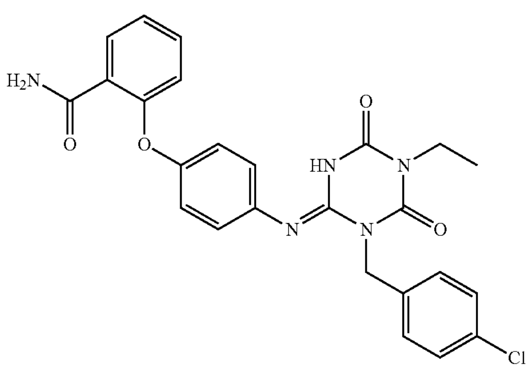 [SMILES: CCn1c(=O)[nH]/c(=N\c2ccc(Oc3ccccc3C(N)=O)cc2)n(Cc2ccc(Cl)cc2)c1=O] | I-2009 | 2.07 | 492 | 3 |

TABLE 405-continued
| Structure | Compound No. | Retention Time (min) | [M + H] | Method |
|---|---|---|---|---|
| 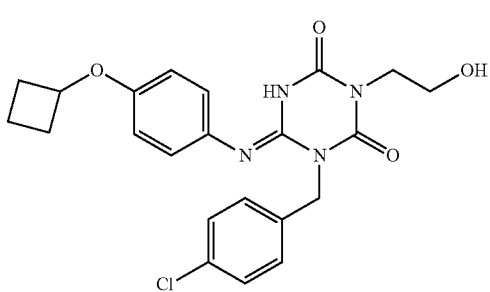 [SMILES: O=c1[nH]/c(=N\c2ccc(OC3CCC3)cc2)n(Cc2ccc(Cl)cc2)c(=O)n1CCO] | I-2010 | 2.10 | 443 | 3 |
TABLE 406
| Structure | Compound No. | Retention Time (min) | [M + H] | Method |
|---|---|---|---|---|
| 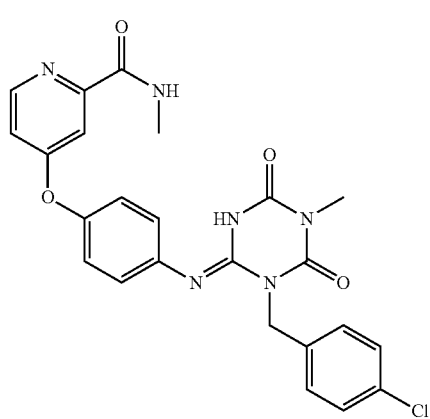 [SMILES: CNC(=O)c1cc(Oc2ccc(/N=c3\[nH]c(=O)n(C)c(=O)n3Cc3ccc(Cl)cc3)cc2)ccn1] | I-2011 | 1.83 | 493 | 2 |
| 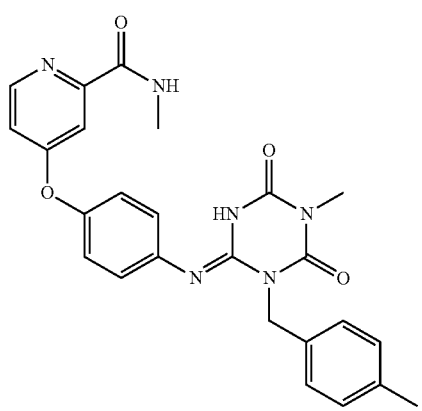 [SMILES: CNC(=O)c1cc(Oc2ccc(/N=c3\[nH]c(=O)n(C)c(=O)n3Cc3ccc(C)cc3)cc2)ccn1] | I-2012 | 1.74 | 473 | 2 |

TABLE 406-continued
| Structure | Compound No. | Retention Time (min) | [M + H] | Method |
|---|---|---|---|---|
| 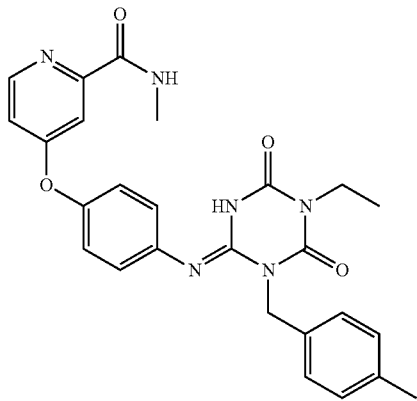 [SMILES: CCn1c(=O)[nH]/c(=N\c2ccc(Oc3ccnc(C(=O)NC)c3)cc2)n(Cc2ccc(C)cc2)c1=O] | I-2013 | 1.88 | 487 | 2 |
| 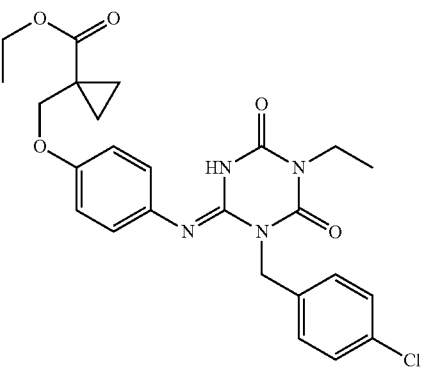 [SMILES: CCOC(=O)C1(COc2ccc(/N=c3\[nH]c(=O)n(CC)c(=O)n3Cc3ccc(Cl)cc3)cc2)CC1] | I-2014 | 2.42 | 499 | 3 |
| 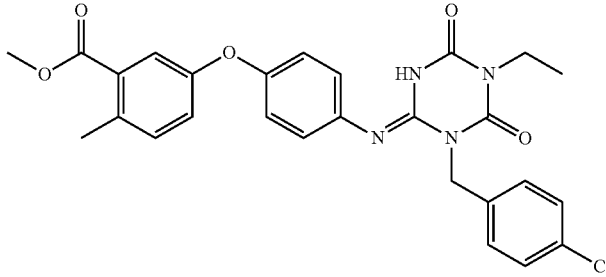 | I-2015 | 2.46 | 521 | 2 |

TABLE 407

| Structure | Compound No. | Retention Time (min) | [M + H] | Method |
|---|---|---|---|---|
| 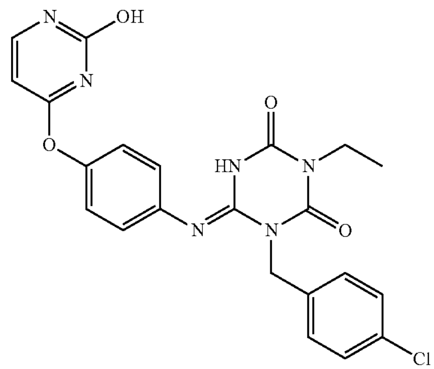 [SMILES: CCn1c(=O)[nH]/c(=N\c2ccc(Oc3ccnc(O)n3)cc2)n(Cc2ccc(Cl)cc2)c1=O] | I-2016 | 1.92 | 467 | 3 |
| 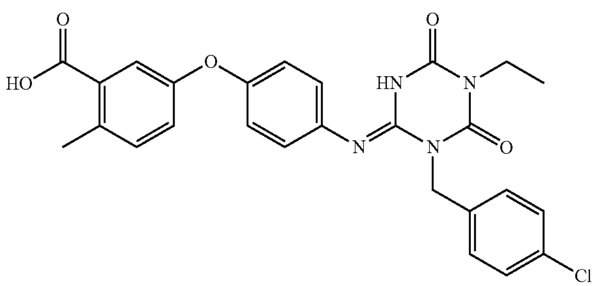 [SMILES: CCn1c(=O)[nH]/c(=N\c2ccc(Oc3ccc(C)c(C(=O)O)c3)cc2)n(Cc2ccc(Cl)cc2)c1=O] | I-2017 | 2.11 | 507 | 2 |
| 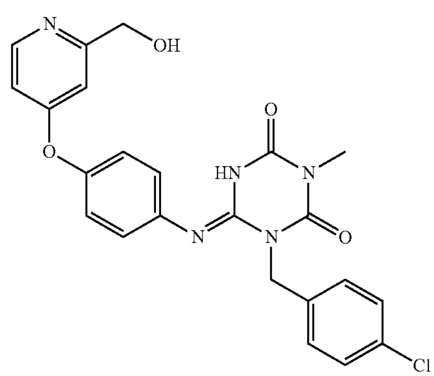 [SMILES: Cn1c(=O)[nH]/c(=N\c2ccc(Oc3ccnc(CO)c3)cc2)n(Cc2ccc(Cl)cc2)c1=O] | I-2018 | 1.34 | 466 | 3 |
| 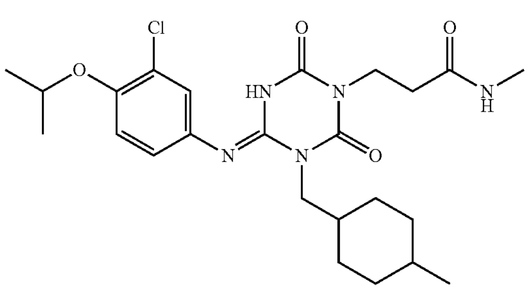 [SMILES: CNC(=O)CCn1c(=O)[nH]/c(=N\c2ccc(OC(C)C)c(Cl)c2)n(CC2CCC(C)CC2)c1=O] | I-2019 | 2.37 | 492 | 3 |

TABLE 407-continued
| Structure | Compound No. | Retention Time (min) | [M + H] | Method |
|---|---|---|---|---|
| 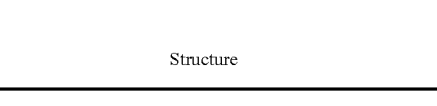 | I-2020 | 2.30 | 478 | 3 |
TABLE 408
| Structure | Compound No. | Retention Time (min) | [M + H] | Method |
|---|---|---|---|---|
| 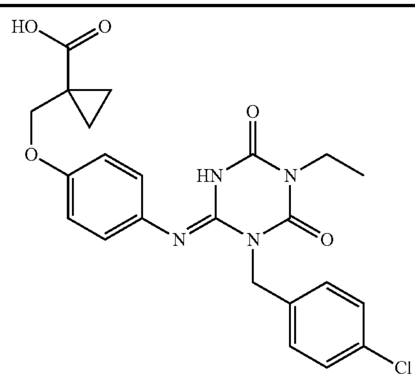 | I-2021 | 2.02 | 471 | 3 |
| 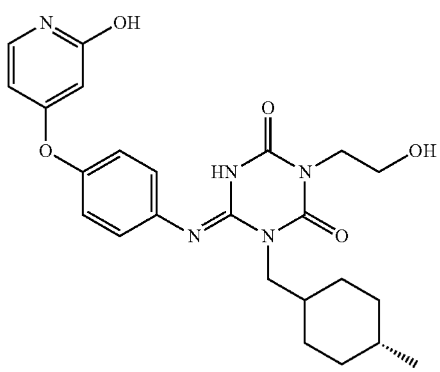 | I-2022 | 1.71 | 468 | 3 |
| 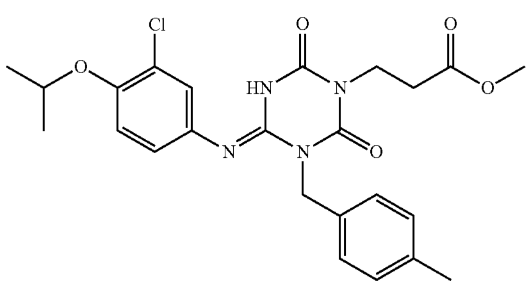 [SMILES: COC(=O)CCn1c(=O)[nH]/c(=N\c2ccc(OC(C)C)c(Cl)c2)n(Cc2ccc(C)cc2)c1=O] | I-2023 | 2.26 | 487 | 3 |

TABLE 408-continued

| Structure | Compound No. | Retention Time (min) | [M + H] | Method |
|---|---|---|---|---|
| 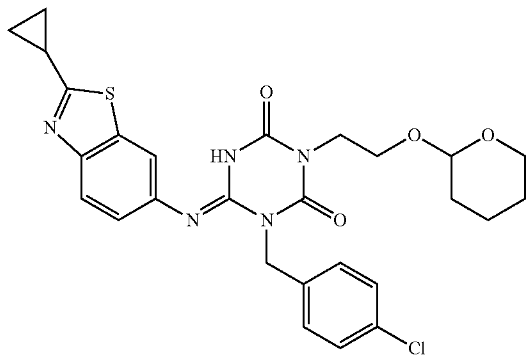 [SMILES: O=c1[nH]/c(=N\c2ccc3nc(C4CC4)sc3c2)n(Cc2ccc(Cl)cc2)c(=O)n1CCOC1CCCCO1] | I-2024 | 2.31 | 554 | 2 |
| 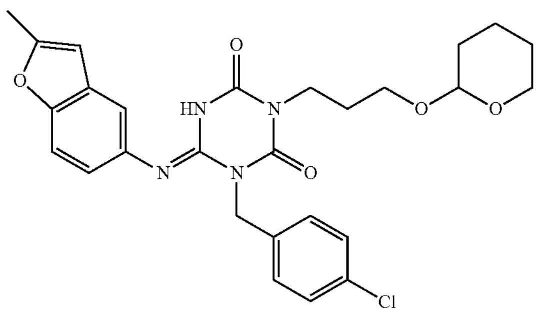 [SMILES: Cc1cc2cc(/N=c3\[nH]c(=O)n(CCCOC4CCCCO4)c(=O)n3Cc3ccc(Cl)cc3)ccc2o1] | I-2025 | 2.33 | 525 | 2 |

TABLE 409

| Structure | Compound No. | Retention Time (min) | [M + H] | Method |
|---|---|---|---|---|
| 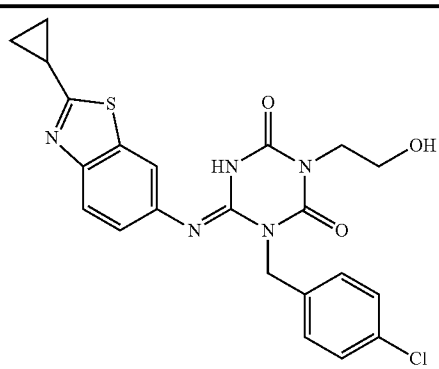 | I-2026 | 2.04 | 470 | 3 |
| 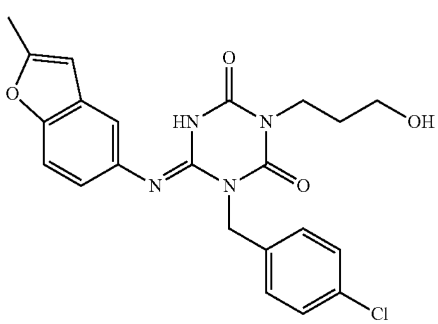 [SMILES: Cc1cc2cc(/N=c3\[nH]c(=O)n(CCCO)c(=O)n3Cc3ccc(Cl)cc3)ccc2o1] | I-2027 | 2.05 | 441 | 3 |

TABLE 409-continued

| Structure | Compound No. | Retention Time (min) | [M + H] | Method |
|---|---|---|---|---|
| 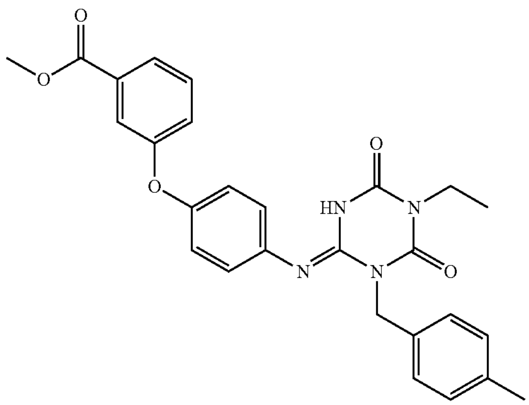 | I-2028 | 2.48 | 487 | 3 |
| 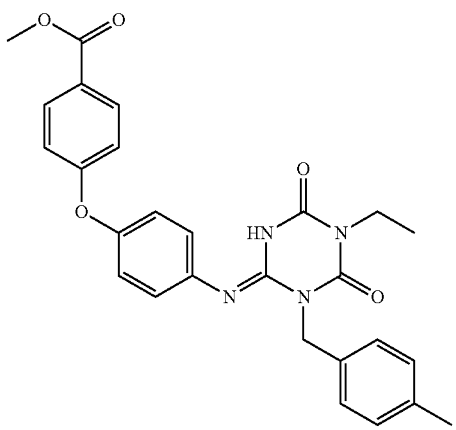 | I-2029 | 2.48 | 487 | 3 |
| 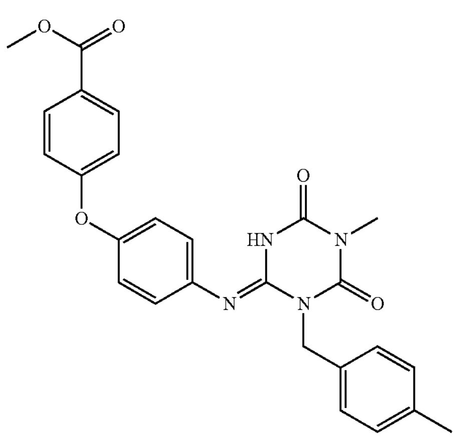 | I-2030 | 2.35 | 473 | 3 |

TABLE 410

| Structure | Compound No. | Retention Time (min) | [M + H] | Method |
|---|---|---|---|---|
| 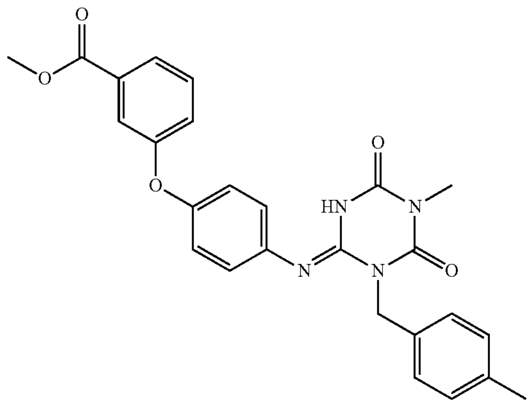 | I-2031 | 2.35 | 473 | 3 |
| 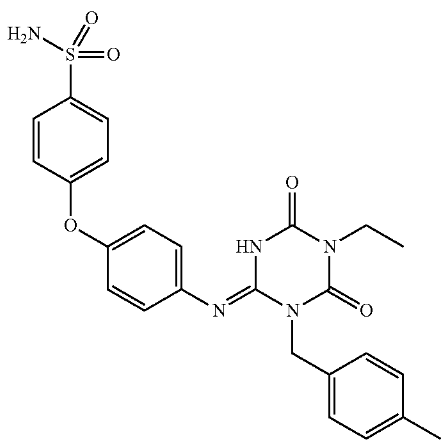 [SMILES: CCn1c(=O)[nH]/c(=N\c2ccc(Oc3ccc(S(N)(=O)=O)cc3)cc2)n(Cc2ccc(C)cc2)c1=O] | I-2032 | 2.02 | 508 | 3 |
| 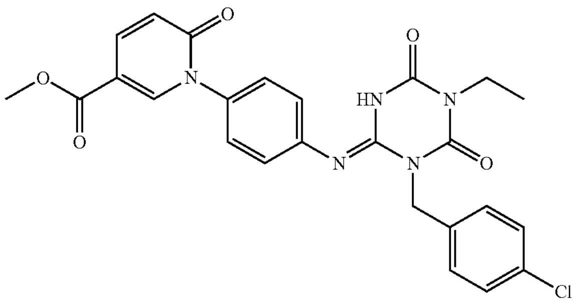 [SMILES: CCn1c(=O)[nH]/c(=N\c2ccc(-n3cc(C(=O)OC)ccc3=O)cc2)n(Cc2ccc(Cl)cc2)c1=O] | I-2033 | 2.15 | 508 | 3 |
| 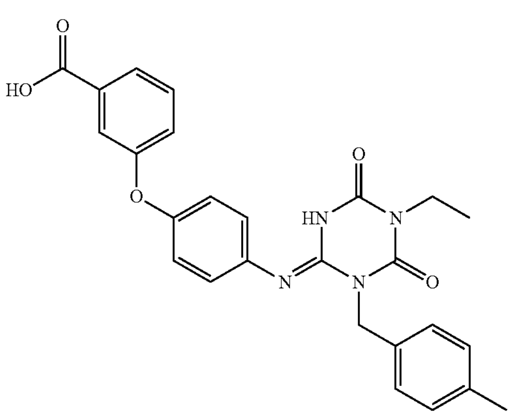 [SMILES: CCn1c(=O)[nH]/c(=N\c2ccc(Oc3cccc(C(=O)O)c3)cc2)n(Cc2ccc(C)cc2)c1=O] | I-2034 | 2.14 | 473 | 3 |

TABLE 410-continued

| Structure | Compound No. | Retention Time (min) | [M + H] | Method |
|---|---|---|---|---|
| (structure of I-2035) | I-2035 | 2.13 | 473 | 3 |

TABLE 411

| Structure | Compound No. | Retention Time (min) | [M + H] | Method |
|---|---|---|---|---|
| (structure of I-2036) | I-2036 | 1.42 | 473 | 2 |
| (structure of I-2037) | I-2037 | 2.20 | 513 | 2 |

TABLE 411-continued
| Structure | Compound No. | Retention Time (min) | [M + H] | Method |
|---|---|---|---|---|
| 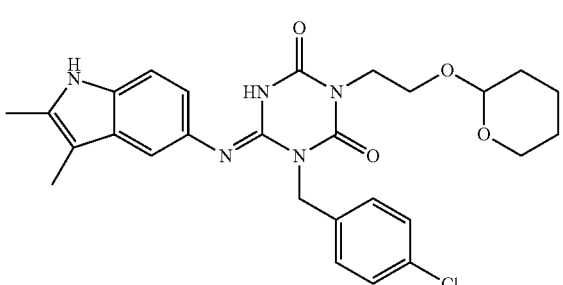 | I-2038 | 2.13 | 524 | 2 |
| 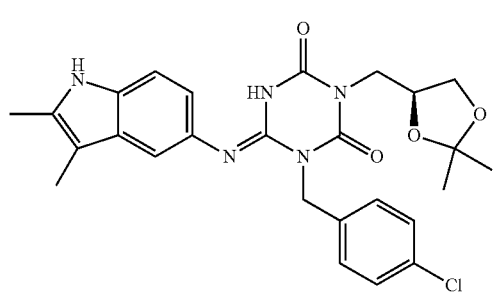 | I-2039 | 2.08 | 510 | 2 |
| 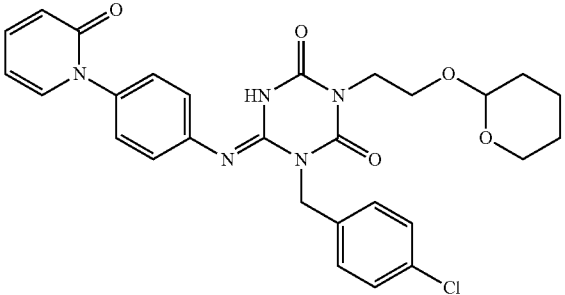 [SMILES: O=c1ccccn1-c1ccc(/N=c2\[nH]c(=O)n(CCOC3CCCCO3)c(=O)n2Cc2ccc(Cl)cc2)cc1] | I-2040 | 1.93 | 550 | 2 |
TABLE 412
| Structure | Compound No. | Retention Time (min) | [M + H] | Method |
|---|---|---|---|---|
| 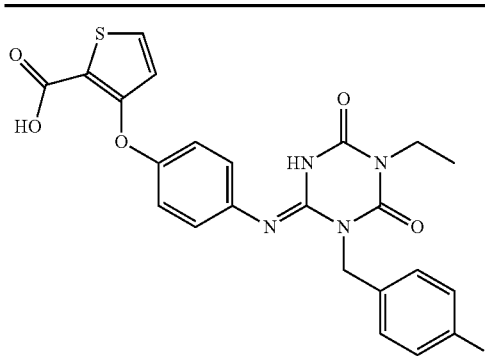 | I-2041 | 1.93 | 499 | 2 |

TABLE 412-continued

| Structure | Compound No. | Retention Time (min) | [M + H] | Method |
|---|---|---|---|---|
| 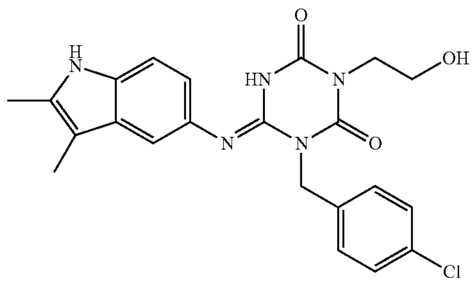 [SMILES: Cc1[nH]c2ccc(/N=c3\[nH]c(=O)n(CCO)c(=O)n3Cc3ccc(Cl)cc3)cc2c1C] | I-2042 | 1.69 | 440 | 2 |
| 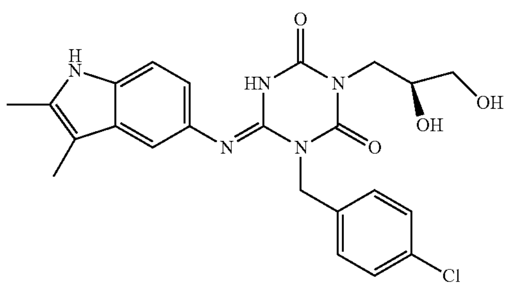 [SMILES: Cc1[nH]c2ccc(/N=c3\[nH]c(=O)n(C[C@H](O)CO)c(=O)n3Cc3ccc(Cl)cc3)cc2c1C] | I-2043 | 1.58 | 470 | 2 |
| 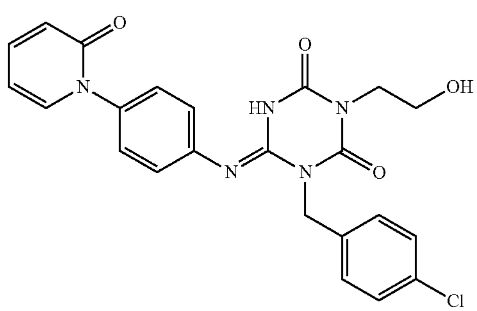 [SMILES: O=c1ccccn1-c1ccc(/N=c2\[nH]c(=O)n(CCO)c(=O)n2Cc2ccc(Cl)cc2)cc1] | I-2044 | 1.49 | 466 | 2 |
| 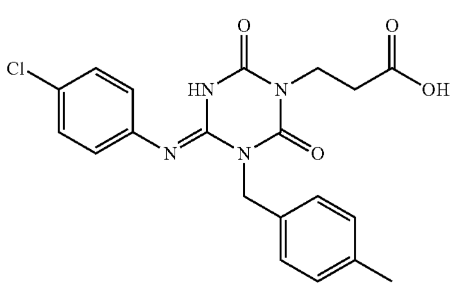 [SMILES: Cc1ccc(Cn2c(=O)n(CCC(=O)O)c(=O)[nH]/c2=N\c2ccc(Cl)cc2)cc1] | I-2045 | 1.97 | 415 | 5 |

TABLE 413

| Structure | Compound No. | Retention Time (min) | [M + H] | Method |
|---|---|---|---|---|
| (2-chlorophenyl imino triazinedione, N-(4-methylbenzyl), propanoic acid) | I-2046 | 2.00 | 415 | 5 |
| (3-chlorophenyl imino triazinedione, N-(4-methylbenzyl), propanoic acid) | I-2047 | 2.02 | 415 | 5 |
| (4-isopropoxy-2-methylphenyl imino triazinedione, N-(4-methylbenzyl), propanoic acid) | I-2048 | 2.02 | 453 | 5 |
| (4-isopropoxy-2-fluorophenyl imino triazinedione, N-(4-methylbenzyl), propanoic acid) | I-2049 | 2.06 | 457 | 5 |
| (2,3-dichlorophenyl imino triazinedione, N-(4-methylbenzyl), propanoic acid) | I-2050 | 2.30 | 449 | 5 |

TABLE 414

| Structure | Compound No. | Retention Time (min) | [M + H] | Method |
|---|---|---|---|---|
| 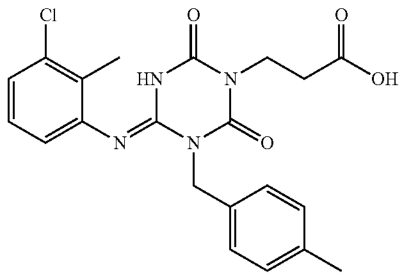 [SMILES: Cc1ccc(Cn2c(=O)n(CCC(=O)O)c(=O)[nH]/c2=N\c2cccc(Cl)c2C)cc1] | I-2051 | 2.19 | 429 | 5 |
| 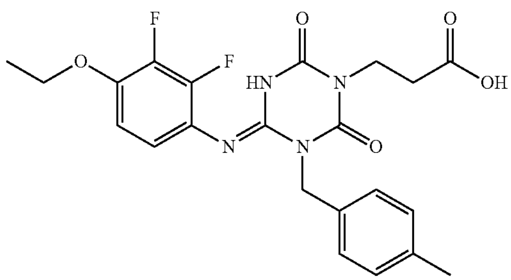 [SMILES: CCOc1ccc(/N=c2\[nH]c(=O)n(CCC(=O)O)c(=O)n2Cc2ccc(C)cc2)c(F)c1F] | I-2052 | 2.09 | 461 | 5 |
| 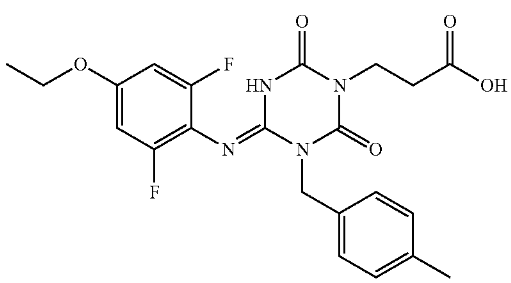 [SMILES: CCOc1cc(F)c(/N=c2\[nH]c(=O)n(CCC(=O)O)c(=O)n2Cc2ccc(C)cc2)c(F)c1] | I-2053 | 2.10 | 461 | 5 |
| 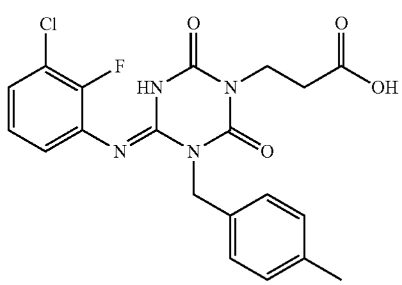 [SMILES: Cc1ccc(Cn2c(=O)n(CCC(=O)O)c(=O)[nH]/c2=N\c2cccc(Cl)c2F)cc1] | I-2054 | 2.15 | 433 | 5 |
| 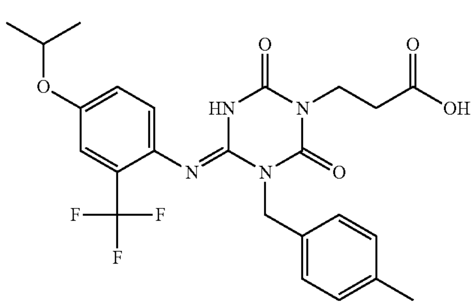 [SMILES: Cc1ccc(Cn2c(=O)n(CCC(=O)O)c(=O)[nH]/c2=N\c2ccc(OC(C)C)cc2C(F)(F)F)cc1] | I-2055 | 2.45 | 507 | 5 |

TABLE 415

| Structure | Compound No. | Retention Time (min) | [M + H] | Method |
|---|---|---|---|---|
| 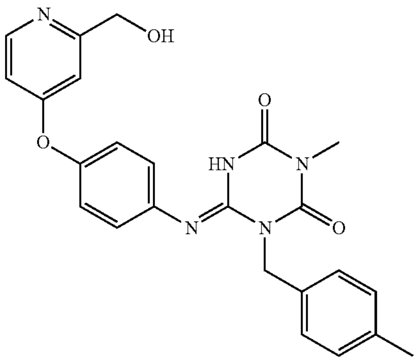 [SMILES: Cc1ccc(Cn2c(=O)n(C)c(=O)[nH]/c2=N\c2ccc(Oc3ccnc(CO)c3)cc2)cc1] | I-2056 | 1.26 | 446 | 3 |
| 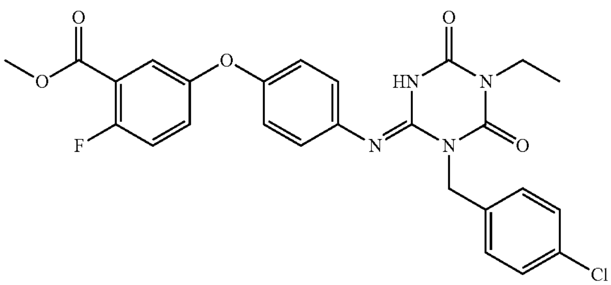 [SMILES: CCn1c(=O)[nH]/c(=N\c2ccc(Oc3ccc(F)c(C(=O)OC)c3)cc2)n(Cc2ccc(Cl)cc2)c1=O] | I-2057 | 2.32 | 525 | 2 |
| 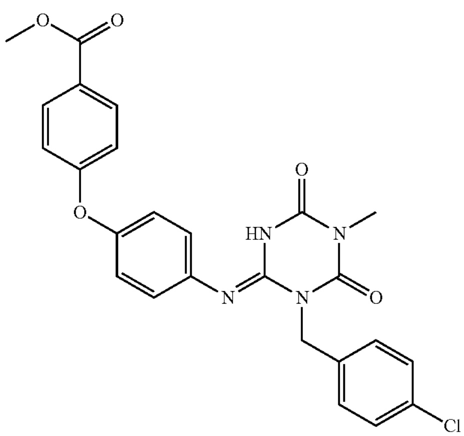 | I-2058 | 2.42 | 493 | 3 |
| 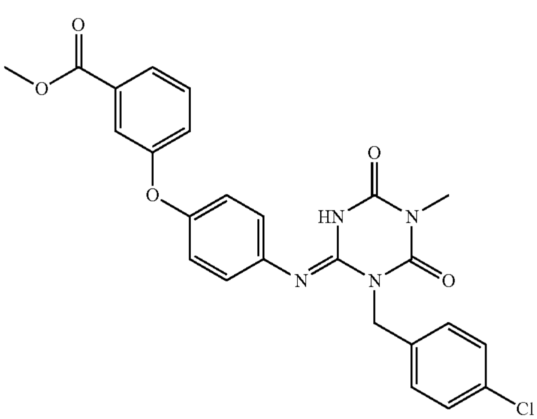 [SMILES: COC(=O)c1cccc(Oc2ccc(/N=c3\[nH]c(=O)n(C)c(=O)n3Cc3ccc(Cl)cc3)cc2)c1] | I-2059 | 2.42 | 493 | 3 |

TABLE 415-continued
| Structure | Compound No. | Retention Time (min) | [M + H] | Method |
|---|---|---|---|---|
| 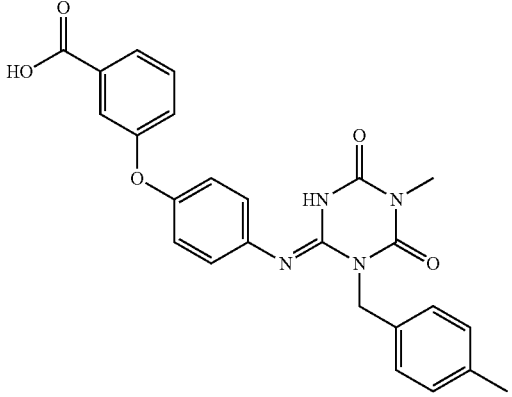 | I-2060 | 2.01 | 459 | 3 |
TABLE 416
| Structure | Compound No. | Retention Time (min) | [M + H] | Method |
|---|---|---|---|---|
| 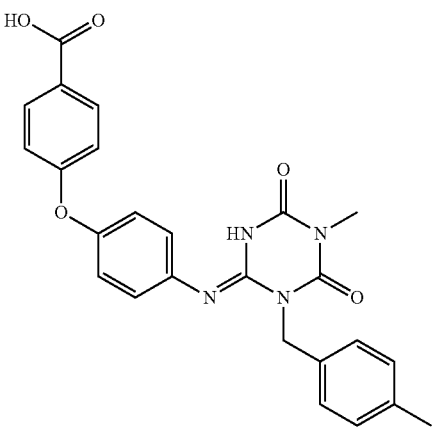 [SMILES: Cc1ccc(Cn2c(=O)n(C)c(=O)[nH]/c2=N\c2ccc(Oc3ccc(C(=O)O)cc3)cc2)cc1] | I-2061 | 1.99 | 459 | 3 |
| 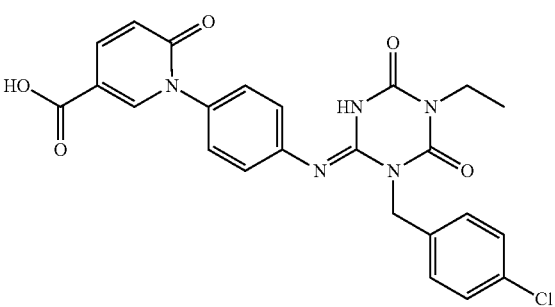 [SMILES: CCn1c(=O)[nH]/c(=N\c2ccc(-n3cc(C(=O)O)ccc3=O)cc2)n(Cc2ccc(Cl)cc2)c1=O] | I-2062 | 1.84 | 494 | 3 |

TABLE 416-continued

| Structure | Compound No. | Retention Time (min) | [M + H] | Method |
|---|---|---|---|---|
| 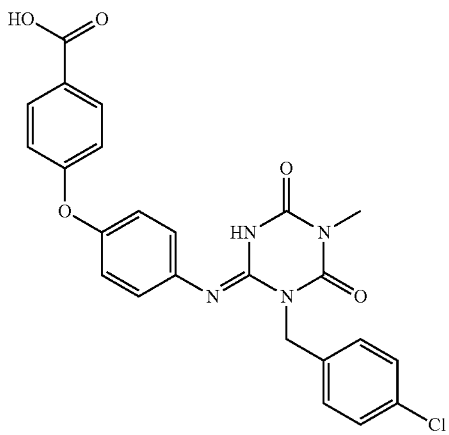 [SMILES: Cn1c(=O)[nH]/c(=N\c2ccc(Oc3ccc(C(=O)O)cc3)cc2)n(Cc2ccc(Cl)cc2)c1=O] | I-2063 | 2.08 | 479 | 3 |
| 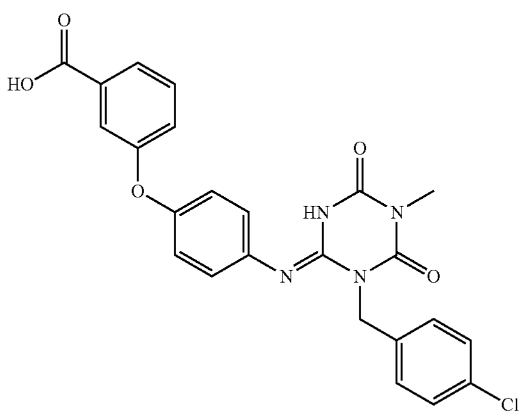 [SMILES: Cn1c(=O)[nH]/c(=N\c2ccc(Oc3cccc(C(=O)O)c3)cc2)n(Cc2ccc(Cl)cc2)c1=O] | I-2064 | 2.09 | 479 | 3 |
| 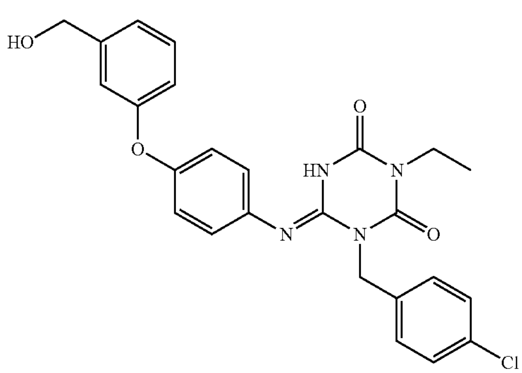 [SMILES: CCn1c(=O)[nH]/c(=N\c2ccc(Oc3cccc(CO)c3)cc2)n(Cc2ccc(Cl)cc2)c1=O] | I-2065 | 2.19 | 479 | 3 |

TABLE 417

| Structure | Compound No. | Retention Time (min) | [M + H] | Method |
|---|---|---|---|---|
| 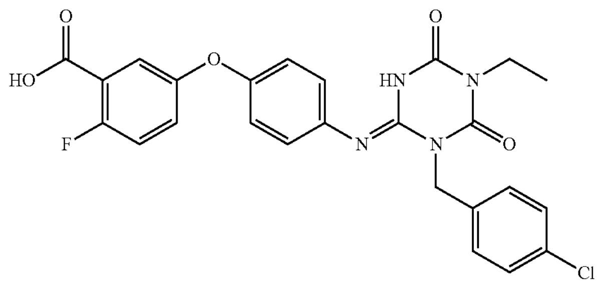 [SMILES: CCn1c(=O)[nH]/c(=N\c2ccc(Oc3ccc(F)c(C(=O)O)c3)cc2)n(Cc2ccc(Cl)cc2)c1=O] | I-2066 | 2.02 | 511 | 2 |
| 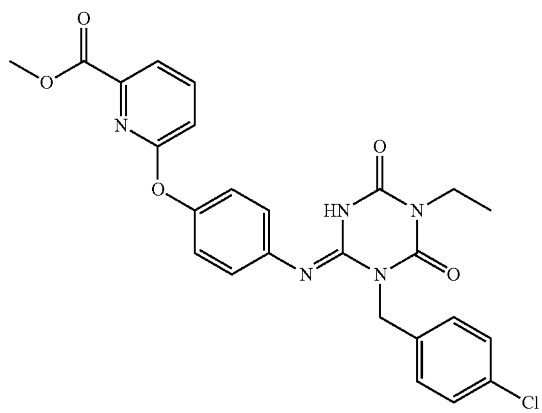 [SMILES: CCn1c(=O)[nH]/c(=N\c2ccc(Oc3cccc(C(=O)OC)n3)cc2)n(Cc2ccc(Cl)cc2)c1=O] | I-2067 | 2.38 | 508 | 3 |
| 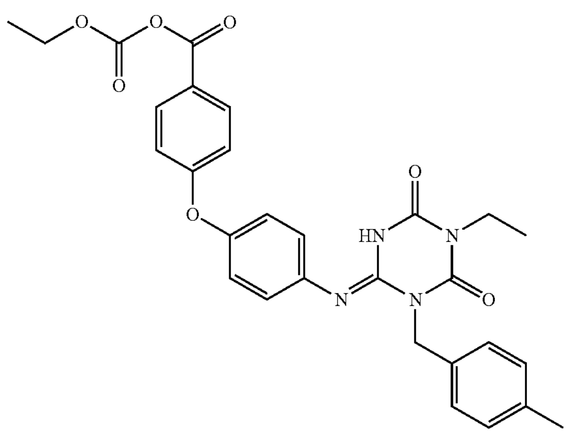 [SMILES: CCOC(=O)OC(=O)c1ccc(Oc2ccc(/N=c3\[nH]c(=O)n(CC)c(=O)n3Cc3ccc(C)cc3)cc2)cc1] | I-2068 | 2.61 | 545 | 3 |
| 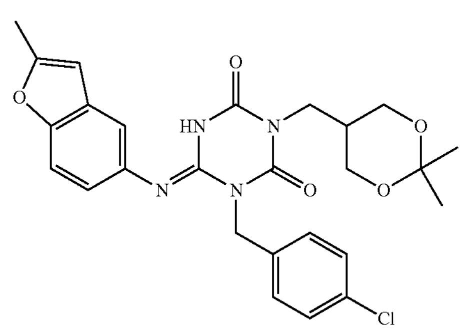 | I-2069 | 2.16 | 511 | 2 |

TABLE 417-continued

| Structure | Compound No. | Retention Time (min) | [M + H] | Method |
|---|---|---|---|---|
| 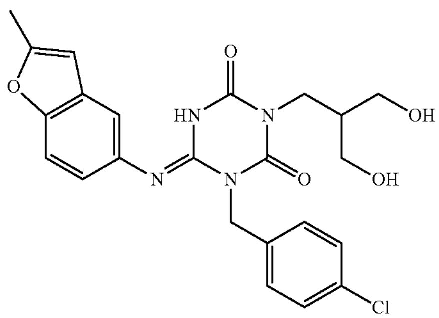 [SMILES: Cc1cc2cc(/N=c3\[nH]c(=O)n(CC(CO)CO)c(=O)n3Cc3ccc(Cl)cc3)ccc2o1] | I-2070 | 1.72 | 471 | 2 |

TABLE 418

| Structure | Compound No. | Retention Time (min) | [M + H] | Method |
|---|---|---|---|---|
| 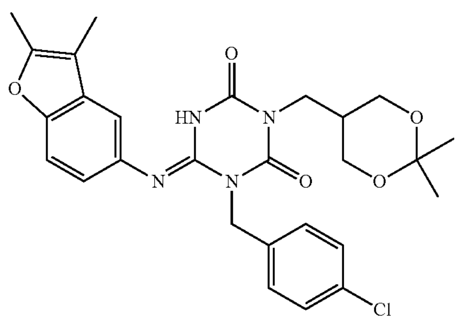 | I-2071 | 2.27 | 525 | 2 |
| 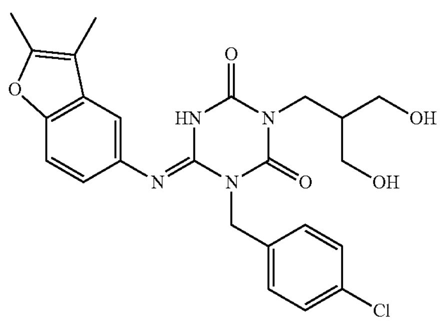 [SMILES: Cc1oc2ccc(/N=c3\[nH]c(=O)n(CC(CO)CO)c(=O)n3Cc3ccc(Cl)cc3)cc2c1C] | I-2072 | 1.80 | 485 | 2 |
| 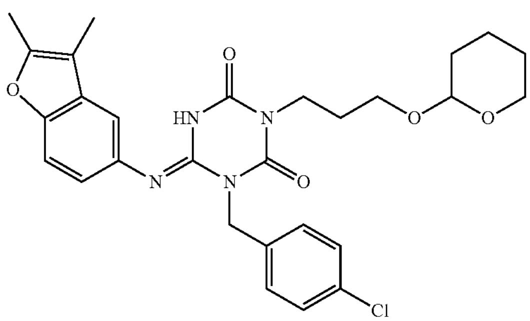 [SMILES: Cc1oc2ccc(/N=c3\[nH]c(=O)n(CCCOC4CCCCO4)c(=O)n3Cc3ccc(Cl)cc3)cc2c1C] | I-2073 | 2.45 | 539 | 2 |

TABLE 418-continued

| Structure | Compound No. | Retention Time (min) | [M + H] | Method |
|---|---|---|---|---|
| 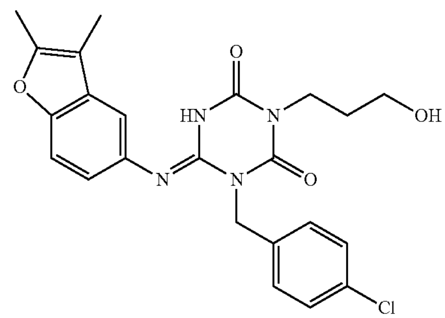 [SMILES: Cc1oc2ccc(/N=c3\[nH]c(=O)n(CCCO)c(=O)n3Cc3ccc(Cl)cc3)cc2c1C] | I-2074 | 2.17 | 455 | 3 |
| 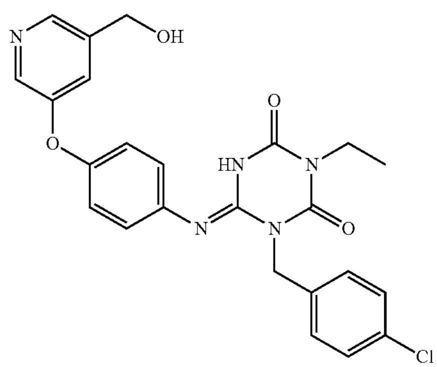 [SMILES: CCn1c(=O)[nH]/c(=N\c2ccc(Oc3cncc(CO)c3)cc2)n(Cc2ccc(Cl)cc2)c1=O] | I-2075 | 1.60 | 480 | 2 |

TABLE 419

| Structure | Compound No. | Retention Time (min) | [M + H] | Method |
|---|---|---|---|---|
| 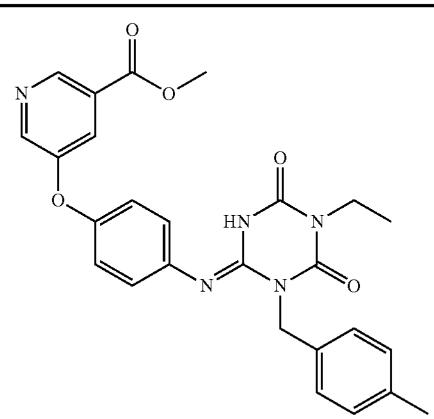 | I-2076 | 1.99 | 488 | 2 |

TABLE 419-continued

| Structure | Compound No. | Retention Time (min) | [M + H] | Method |
|---|---|---|---|---|
| 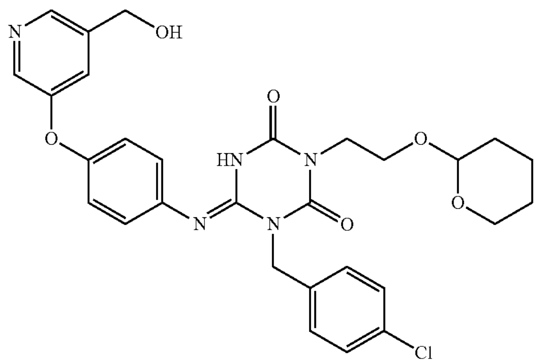 [SMILES: O=c1[nH]/c(=N\c2ccc(Oc3cncc(CO)c3)cc2)n(Cc2ccc(Cl)cc2)c(=O)n1CCOC1CCCCO1] | I-2077 | 1.69 | 580 | 2 |
| 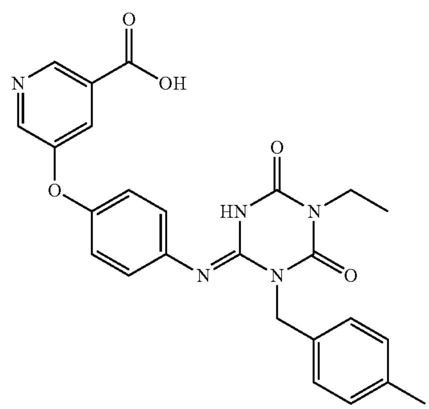 [SMILES: CCn1c(=O)[nH]/c(=N\c2ccc(Oc3cncc(C(=O)O)c3)cc2)n(Cc2ccc(C)cc2)c1=O] | I-2078 | 1.71 | 474 | 2 |
| 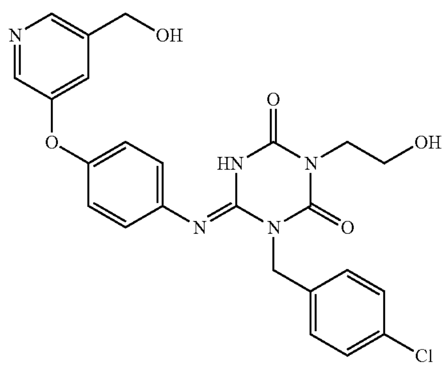 [SMILES: O=c1[nH]/c(=N\c2ccc(Oc3cncc(CO)c3)cc2)n(Cc2ccc(Cl)cc2)c(=O)n1CCO] | I-2079 | 1.26 | 496 | 2 |
| 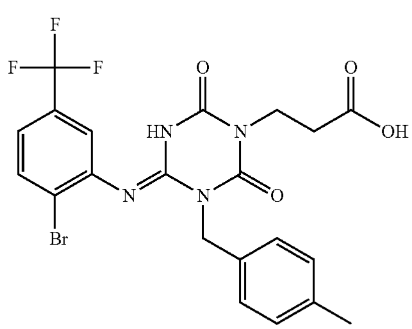 [SMILES: Cc1ccc(Cn2c(=O)n(CCC(=O)O)c(=O)[nH]/c2=N\c2cc(C(F)(F)F)ccc2Br)cc1] | I-2080 | 2.48 | 527 | 5 |

TABLE 420

| Structure | Compound No. | Retention Time (min) | [M + H] | Method |
|---|---|---|---|---|
| (structure) | I-2081 | 2.54 | 517 | 5 |
| (structure) | I-2082 | 2.28 | 463 | 5 |
| (structure) | I-2083 | 2.29 | 467 | 5 |
| (structure) | I-2084 | 2.44 | 483 | 5 |

TABLE 420-continued

| Structure | Compound No. | Retention Time (min) | [M + H] | Method |
|---|---|---|---|---|
| 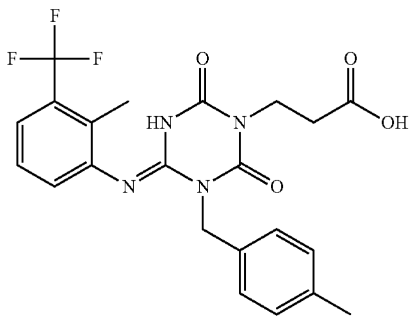 [SMILES: Cc1ccc(Cn2c(=O)n(CCC(=O)O)c(=O)[nH]/c2=N\c2cccc(C(F)(F)F)c2C)cc1] | I-2085 | 2.30 | 463 | 5 |

TABLE 421

| Structure | Compound No. | Retention Time (min) | [M + H] | Method |
|---|---|---|---|---|
| 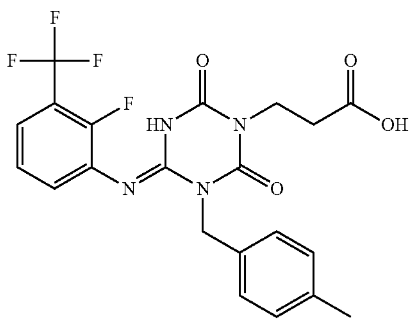 [SMILES: Cc1ccc(Cn2c(=O)n(CCC(=O)O)c(=O)[nH]/c2=N\c2cccc(C(F)(F)F)c2F)cc1] | I-2086 | 2.26 | 467 | 5 |
| 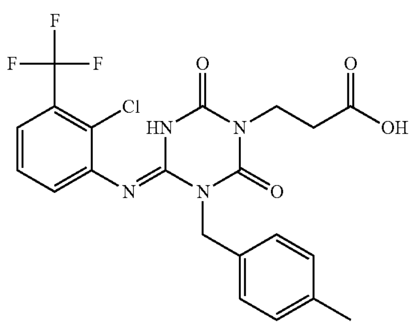 [SMILES: Cc1ccc(Cn2c(=O)n(CCC(=O)O)c(=O)[nH]/c2=N\c2cccc(C(F)(F)F)c2Cl)cc1] | I-2087 | 2.39 | 483 | 5 |
| 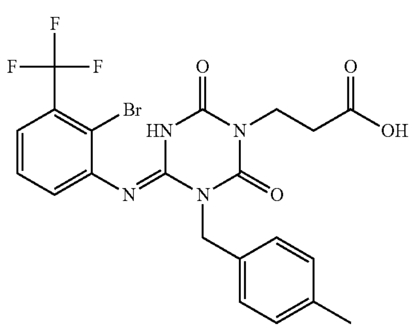 [SMILES: Cc1ccc(Cn2c(=O)n(CCC(=O)O)c(=O)[nH]/c2=N\c2cccc(C(F)(F)F)c2Br)cc1] | I-2088 | 2.42 | 529 | 5 |

TABLE 421-continued

| Structure | Compound No. | Retention Time (min) | [M + H] | Method |
|---|---|---|---|---|
| 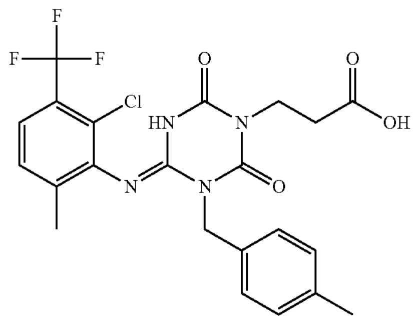 [SMILES: Cc1ccc(Cn2c(=O)n(CCC(=O)O)c(=O)[nH]/c2=N\c2c(C)ccc(C(F)(F)F)c2Cl)cc1] | I-2089 | 2.48 | 497 | 3 |
| 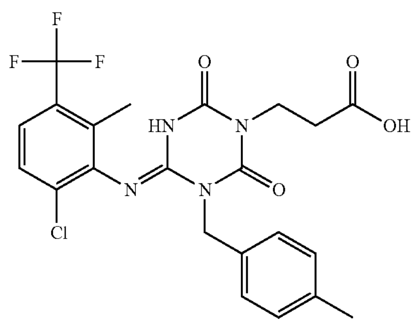 [SMILES: Cc1ccc(Cn2c(=O)n(CCC(=O)O)c(=O)[nH]/c2=N\c2c(Cl)ccc(C(F)(F)F)c2C)cc1] | I-2090 | 2.57 | 497 | 5 |

TABLE 422

| Structure | Compound No. | Retention Time (min) | [M + H] | Method |
|---|---|---|---|---|
| 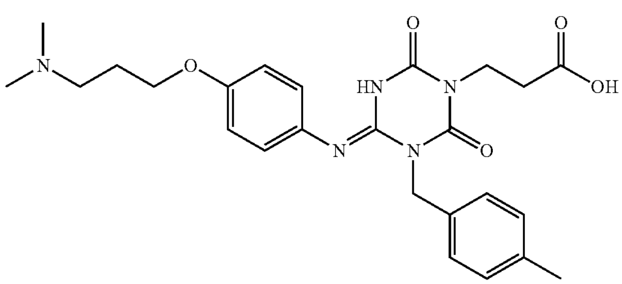 [SMILES: Cc1ccc(Cn2c(=O)n(CCC(=O)O)c(=O)[nH]/c2=N\c2ccc(OCCCN(C)C)cc2)cc1] | I-2091 | 1.21 | 482 | 5 |
| 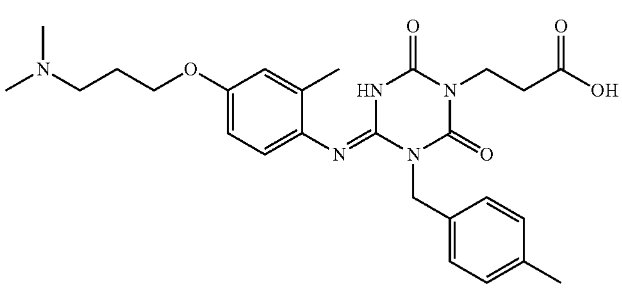 [SMILES: Cc1ccc(Cn2c(=O)n(CCC(=O)O)c(=O)[nH]/c2=N\c2ccc(OCCCN(C)C)cc2C)cc1] | I-2092 | 1.25 | 496 | 5 |

TABLE 422-continued
| Structure | Compound No. | Retention Time (min) | [M + H] | Method |
|---|---|---|---|---|
| 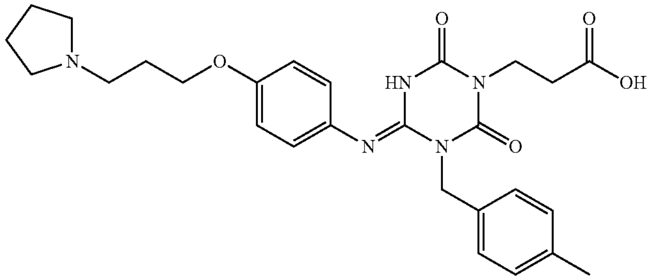 [SMILES: Cc1ccc(Cn2c(=O)n(CCC(=O)O)c(=O)[nH]/c2=N\c2ccc(OCCCN3CCCC3)cc2)cc1] | I-2093 | 1.19 | 508 | 5 |
| 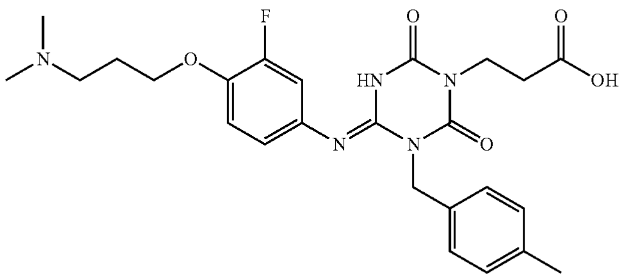 [SMILES: Cc1ccc(Cn2c(=O)n(CCC(=O)O)c(=O)[nH]/c2=N\c2ccc(OCCCN(C)C)c(F)c2)cc1] | I-2094 | 1.26 | 500 | 5 |
| 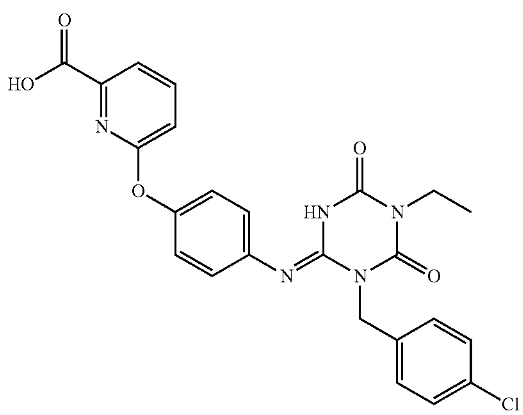 | I-2095 | 2.17 | 494 | 3 |
TABLE 423
| Structure | Compound No. | Retention Time (min) | [M + H] | Method |
|---|---|---|---|---|
| 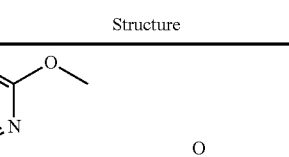 | I-2096 | 2.30 | 481 | 3 |

TABLE 423-continued
| Structure | Compound No. | Retention Time (min) | [M + H] | Method |
|---|---|---|---|---|
| 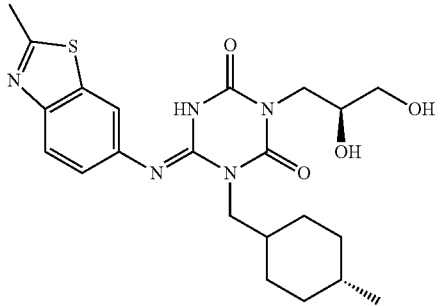 | I-2097 | 1.82 | 460 | 3 |
| 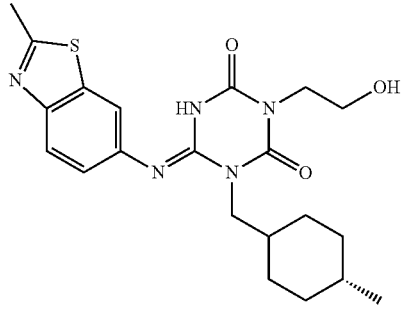 | I-2098 | 1.97 | 430 | 3 |
| 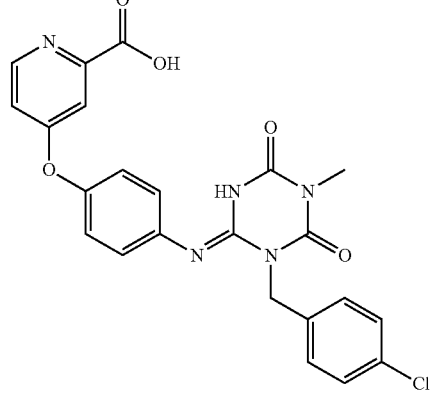 | I-2099 | 1.38 | 480 | 2 |
| 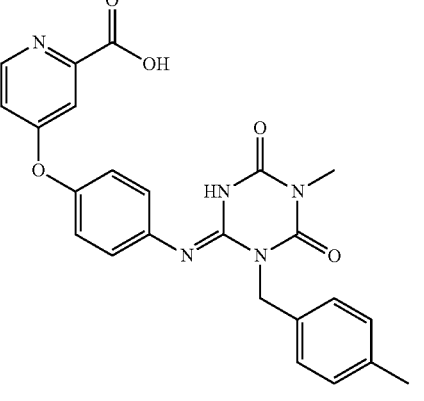 | I-2100 | 1.29 | 460 | 2 |

TABLE 424

| Structure | Compound No. | Retention Time (min) | [M + H] | Method |
|---|---|---|---|---|
| 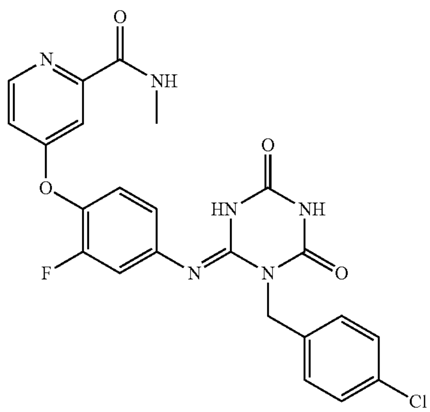 [SMILES: CNC(=O)c1cc(Oc2ccc(/N=c3\[nH]c(=O)[nH]c(=O)n3Cc3ccc(Cl)cc3)cc2F)ccn1] | I-2101 | 1.86 | 497 | 2 |
| 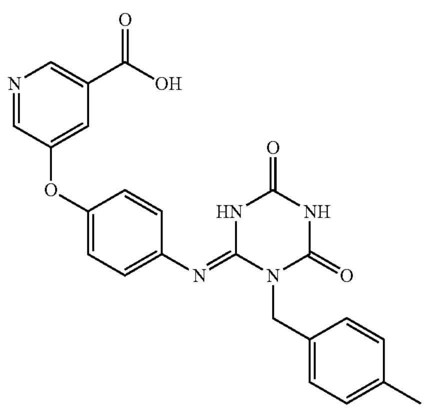 [SMILES: Cc1ccc(Cn2c(=O)[nH]c(=O)[nH]/c2=N\c2ccc(Oc3cncc(C(=O)O)c3)cc2)cc1] | I-2102 | 1.44 | 446 | 2 |
| 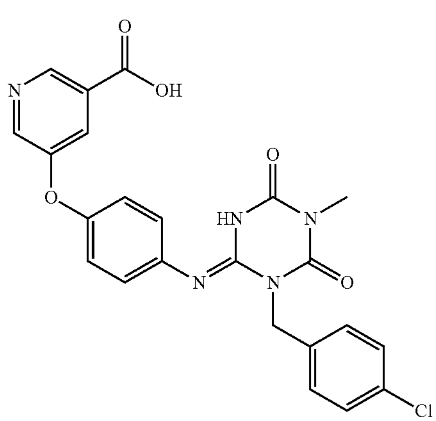 [SMILES: Cn1c(=O)[nH]/c(=N\c2ccc(Oc3cncc(C(=O)O)c3)cc2)n(Cc2ccc(Cl)cc2)c1=O] | I-2103 | 1.65 | 480 | 2 |

TABLE 424-continued
| Structure | Compound No. | Retention Time (min) | [M + H] | Method |
|---|---|---|---|---|
| 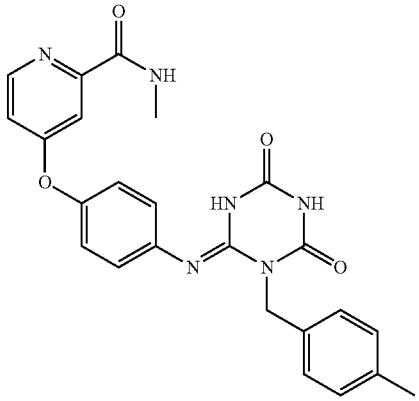 [SMILES: CNC(=O)c1cc(Oc2ccc(/N=c3\[nH]c(=O)[nH]c(=O)n3Cc3ccc(C)cc3)cc2)ccn1] | I-2104 | 1.64 | 457 | 2 |
| 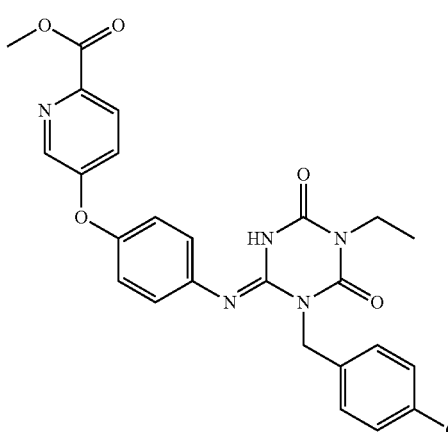 | I-2105 | 2.00 | 508 | 2 |
TABLE 425
| Structure | Compound No. | Retention Time (min) | [M + H] | Method |
|---|---|---|---|---|
| 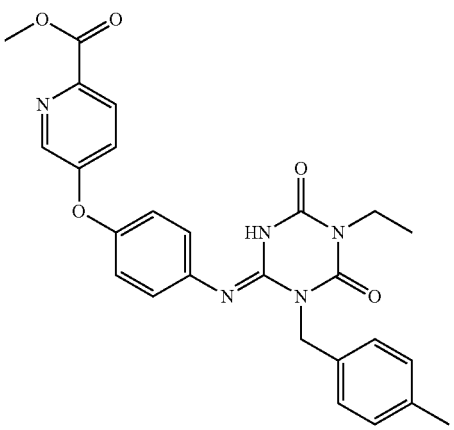 | I-2106 | 1.90 | 488 | 2 |

TABLE 425-continued

| Structure | Compound No. | Retention Time (min) | [M + H] | Method |
|---|---|---|---|---|
| 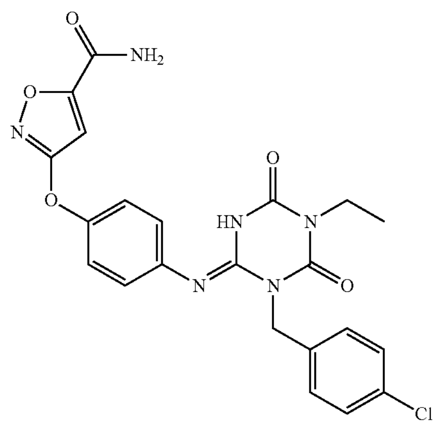 [SMILES: CCn1c(=O)[nH]/c(=N\c2ccc(Oc3cc(C(N)=O)on3)cc2)n(Cc2ccc(Cl)cc2)c1=O] | I-2107 | 1.79 | 483 | 2 |
| 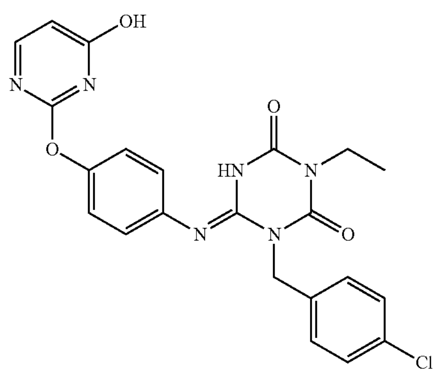 [SMILES: CCn1c(=O)[nH]/c(=N\c2ccc(Oc3nccc(O)n3)cc2)n(Cc2ccc(Cl)cc2)c1=O] | I-2108 | 1.84 | 467 | 3 |
| 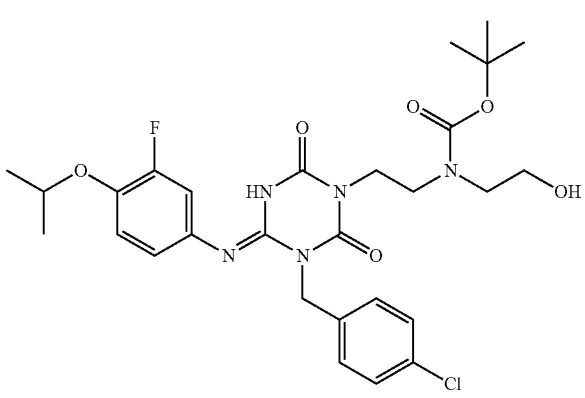 [SMILES: CC(C)Oc1ccc(/N=c2\[nH]c(=O)n(CCN(CCO)C(=O)OC(C)(C)C)c(=O)n2Cc2ccc(Cl)cc2)cc1F] | I-2109 | 2.47 | 592 | 3 |

TABLE 425-continued
| Structure | Compound No. | Retention Time (min) | [M + H] | Method |
|---|---|---|---|---|
| 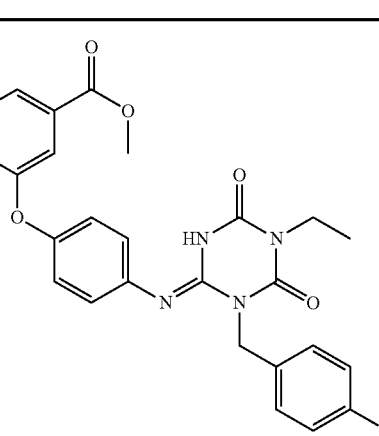 | I-2110 | 2.05 | 491 | 3 |
TABLE 426
| Structure | Compound No. | Retention Time (min) | [M + H] | Method |
|---|---|---|---|---|
| 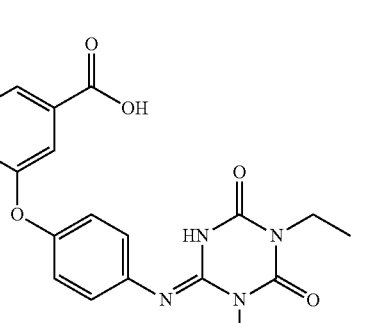 | I-2111 | 2.16 | 492 | 3 |
| 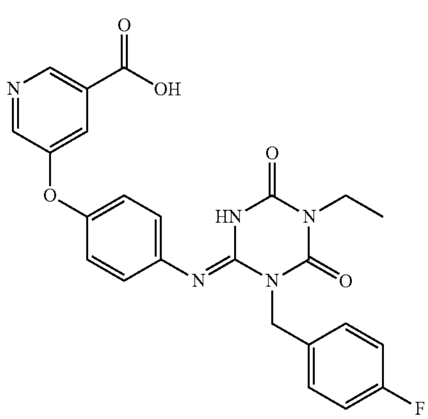 [SMILES: CCn1c(=O)[nH]/c(=N\c2ccc(Oc3cncc(C(=O)O)c3)cc2)n(Cc2ccc(F)cc2)c1=O] | I-2112 | 1.85 | 478 | 3 |

TABLE 426-continued

| Structure | Compound No. | Retention Time (min) | [M + H] | Method |
|---|---|---|---|---|
| 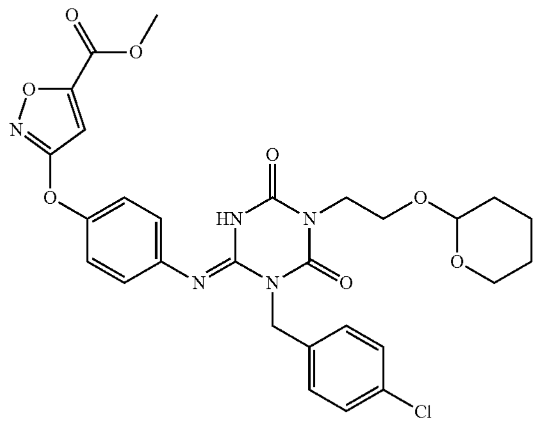 [SMILES: COC(=O)c1cc(Oc2ccc(/N=c3\[nH]c(=O)n(CCOC4CCCCO4)c(=O)n3Cc3ccc(Cl)cc3)cc2)no1] | I-2113 | 2.27 | 598 | 2 |
| 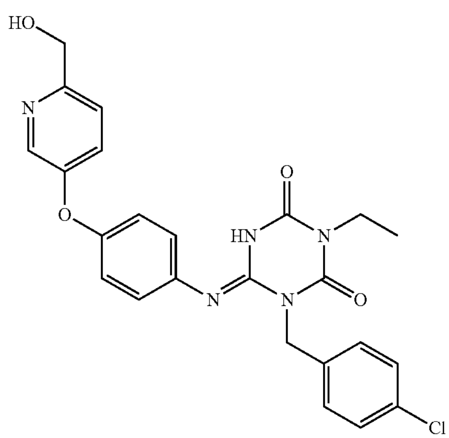 [SMILES: CCn1c(=O)[nH]/c(=N\c2ccc(Oc3ccc(CO)nc3)cc2)n(Cc2ccc(Cl)cc2)c1=O] | I-2114 | 1.62 | 480 | 2 |
| 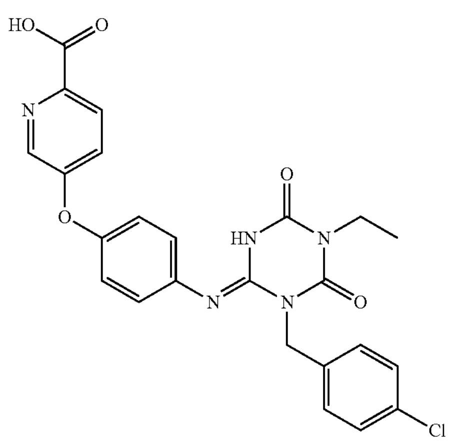 [SMILES: CCn1c(=O)[nH]/c(=N\c2ccc(Oc3ccc(C(=O)O)nc3)cc2)n(Cc2ccc(Cl)cc2)c1=O] | I-2115 | 1.78 | 494 | 2 |

TABLE 427

| Structure | Compound No. | Retention Time (min) | [M + H] | Method |
|---|---|---|---|---|
| 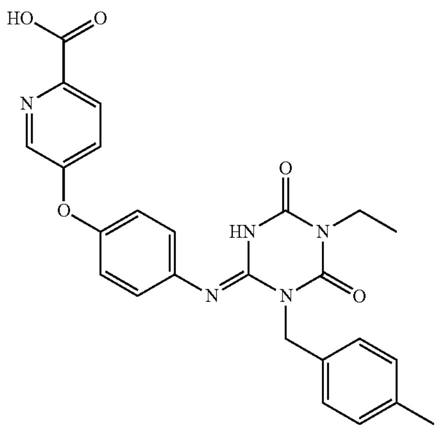 [SMILES: CCn1c(=O)[nH]/c(=N\c2ccc(Oc3ccc(C(=O)O)nc3)cc2)n(Cc2ccc(C)cc2)c1=O] | I-2116 | 1.70 | 474 | 2 |
| 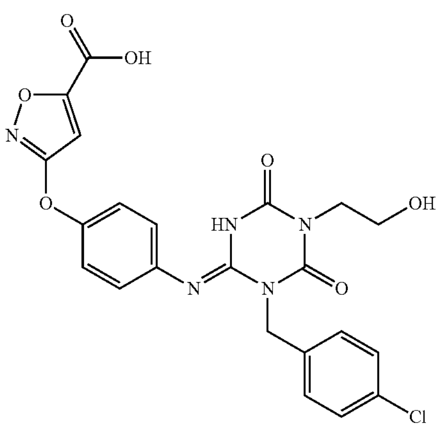 [SMILES: O=C(O)c1cc(Oc2ccc(/N=c3\[nH]c(=O)n(CCO)c(=O)n3Cc3ccc(Cl)cc3)cc2)no1] | I-2117 | 1.38 | 500 | 2 |
| 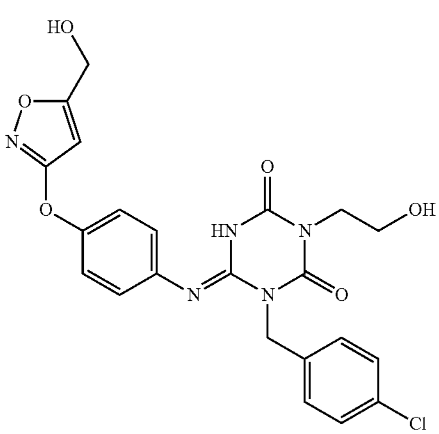 [SMILES: O=c1[nH]/c(=N\c2ccc(Oc3cc(CO)on3)cc2)n(Cc2ccc(Cl)cc2)c(=O)n1CCO] | I-2118 | 1.52 | 486 | 2 |

TABLE 427-continued

| Structure | Compound No. | Retention Time (min) | [M + H] | Method |
|---|---|---|---|---|
| 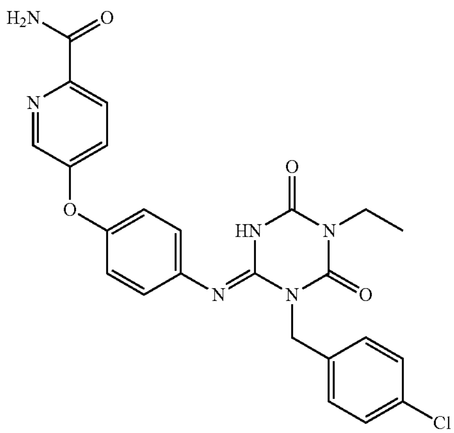 [SMILES: CCn1c(=O)[nH]/c(=N\c2ccc(Oc3ccc(C(N)=O)nc3)cc2)n(Cc2ccc(Cl)cc2)c1=O] | I-2119 | 1.84 | 493 | 2 |
| 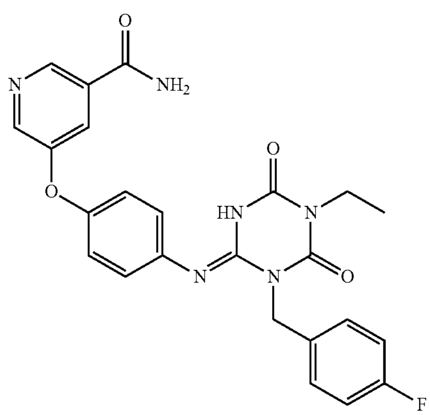 [SMILES: CCn1c(=O)[nH]/c(=N\c2ccc(Oc3cncc(C(N)=O)c3)cc2)n(Cc2ccc(F)cc2)c1=O] | I-2120 | 1.73 | 477 | 3 |

TABLE 428

| Structure | Compound No. | Retention Time (min) | [M + H] | Method |
|---|---|---|---|---|
| 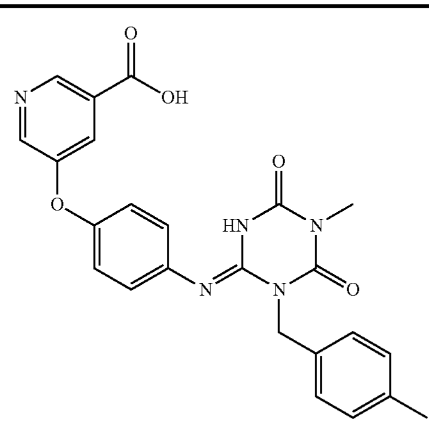 | I-2121 | 1.57 | 460 | 2 |

TABLE 428-continued

| Structure | Compound No. | Retention Time (min) | [M + H] | Method |
|---|---|---|---|---|
| 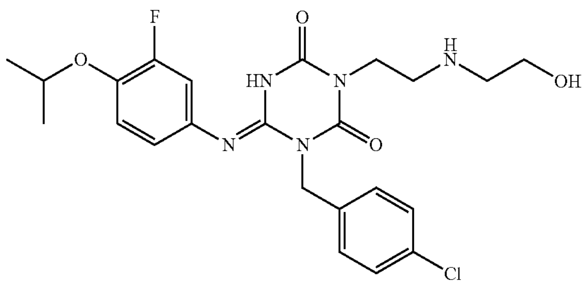 [SMILES: CC(C)Oc1ccc(/N=c2\[nH]c(=O)n(CCNCCO)c(=O)n2Cc2ccc(Cl)cc2)cc1F] | I-2122 | 1.49 | 492 | 3 |
| 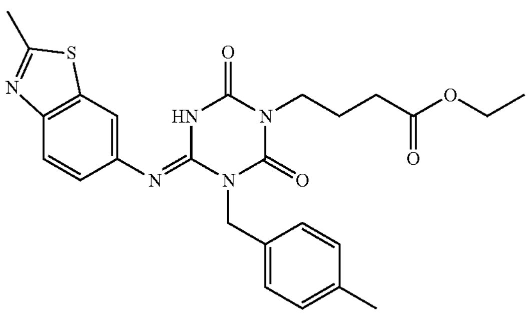 [SMILES: CCOC(=O)CCCn1c(=O)[nH]/c(=N\c2ccc3nc(C)sc3c2)n(Cc2ccc(C)cc2)c1=O] | I-2123 | 2.25 | 494 | 3 |
| 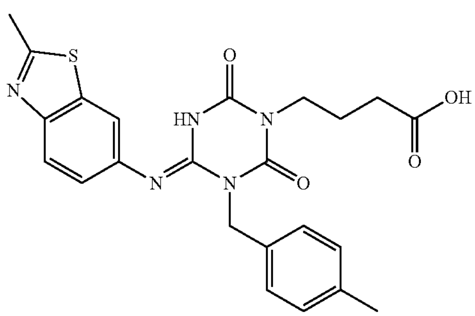 [SMILES: Cc1ccc(Cn2c(=O)n(CCCC(=O)O)c(=O)[nH]/c2=N\c2ccc3nc(C)sc3c2)cc1] | I-2124 | 1.84 | 466 | 3 |
| 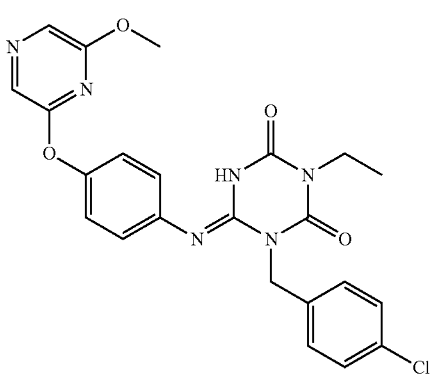 [SMILES: CCn1c(=O)[nH]/c(=N\c2ccc(Oc3cncc(OC)n3)cc2)n(Cc2ccc(Cl)cc2)c1=O] | I-2125 | 2.34 | 481 | 3 |

TABLE 429

| Structure | Compound No. | Retention Time (min) | [M + H] | Method |
|---|---|---|---|---|
| 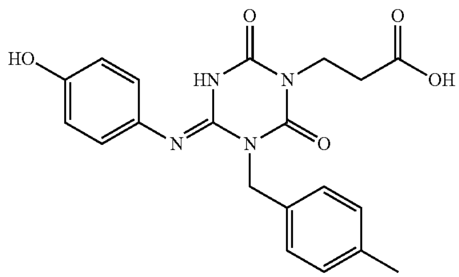 [SMILES: Cc1ccc(Cn2c(=O)n(CCC(=O)O)c(=O)[nH]/c2=N\c2ccc(O)cc2)cc1] | I-2126 | 1.40 | 397 | 5 |
| 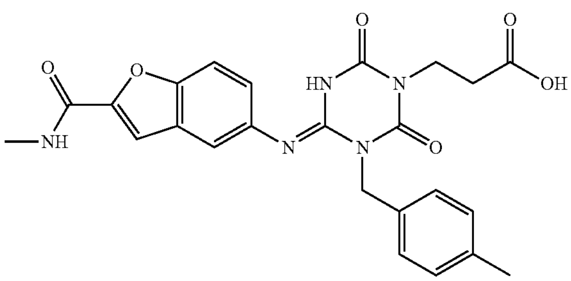 [SMILES: CNC(=O)c1cc2cc(/N=c3\[nH]c(=O)n(CCC(=O)O)c(=O)n3Cc3ccc(C)cc3)ccc2o1] | I-2127 | 1.37 | 478 | 2 |
| 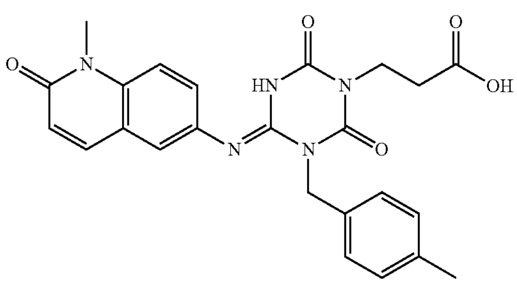 [SMILES: Cc1ccc(Cn2c(=O)n(CCC(=O)O)c(=O)[nH]/c2=N\c2ccc3c(ccc(=O)n3C)c2)cc1] | I-2128 | 1.56 | 462 | 3 |
| 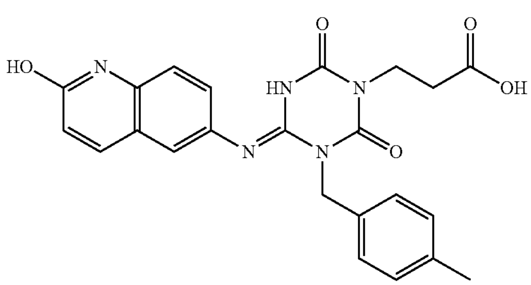 [SMILES: Cc1ccc(Cn2c(=O)n(CCC(=O)O)c(=O)[nH]/c2=N\c2ccc3nc(O)ccc3c2)cc1] | I-2129 | 1.35 | 448 | 5 |
| 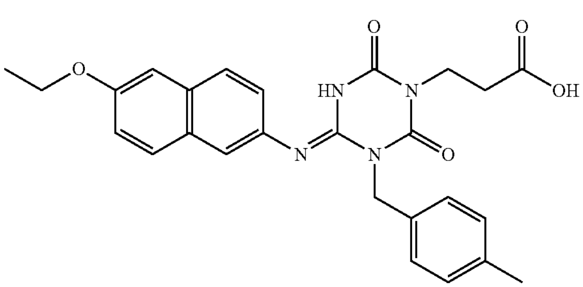 [SMILES: CCOc1ccc2cc(/N=c3\[nH]c(=O)n(CCC(=O)O)c(=O)n3Cc3ccc(C)cc3)ccc2c1] | I-2130 | 2.17 | 475 | 5 |

TABLE 430

| Structure | Compound No. | Retention Time (min) | [M + H] | Method |
|---|---|---|---|---|
| (structure) | I-2131 | 1.74 | 447 | 5 |
| (structure) | I-2132 | 1.54 | 476 | 5 |
| (structure) | I-2133 | 1.52 | 454 | 5 |
| (structure) | I-2134 | 1.81 | 434 | 5 |
| (structure) | I-2135 | 1.62 | 432 | 5 |

TABLE 431

| Structure | Compound No. | Retention Time (min) | [M + H] | Method |
|---|---|---|---|---|
| 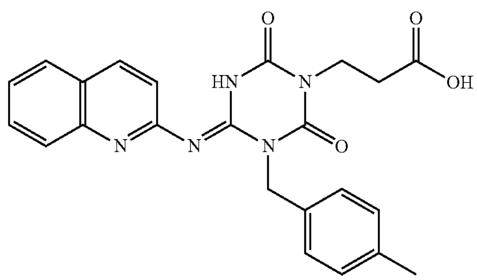 [SMILES: Cc1ccc(Cn2c(=O)n(CCC(=O)O)c(=O)[nH]/c2=N\c2ccc3ccccc3n2)cc1] | I-2136 | 2.11 | 432 | 5 |
| 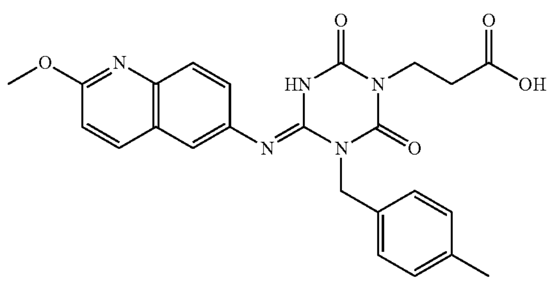 [SMILES: COc1ccc2cc(/N=c3\[nH]c(=O)n(CCC(=O)O)c(=O)n3Cc3ccc(C)cc3)ccc2n1] | I-2137 | 1.96 | 462 | 3 |
| 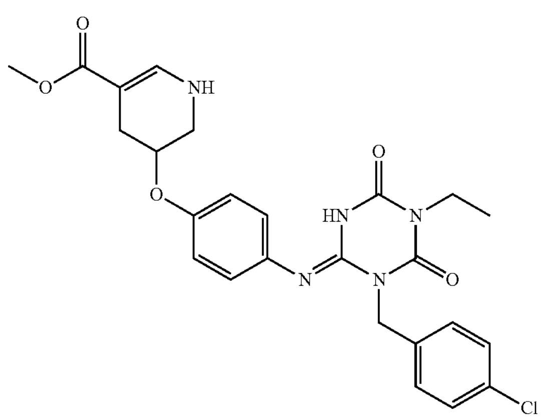 [SMILES: CCn1c(=O)[nH]/c(=N\c2ccc(OC3CNC=C(C(=O)OC)C3)cc2)n(Cc2ccc(Cl)cc2)c1=O] | I-2138 | 2.04 | 512 | 3 |
| 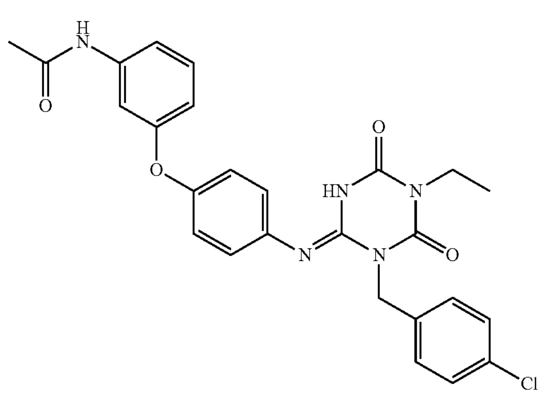 [SMILES: CCn1c(=O)[nH]/c(=N\c2ccc(Oc3cccc(NC(C)=O)c3)cc2)n(Cc2ccc(Cl)cc2)c1=O] | I-2139 | 2.19 | 506 | 3 |

TABLE 431-continued
| Structure | Compound No. | Retention Time (min) | [M + H] | Method |
|---|---|---|---|---|
| 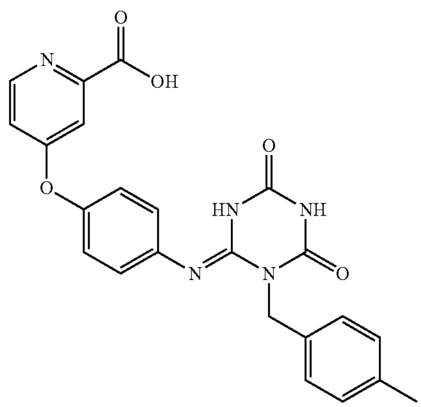 [SMILES: Cc1ccc(Cn2c(=O)[nH]c(=O)[nH]/c2=N\c2ccc(Oc3ccnc(C(=O)O)c3)cc2)cc1] | I-2140 | 1.19 | 446 | 2 |
TABLE 432
| Structure | Compound No. | Retention Time (min) | [M + H] | Method |
|---|---|---|---|---|
| 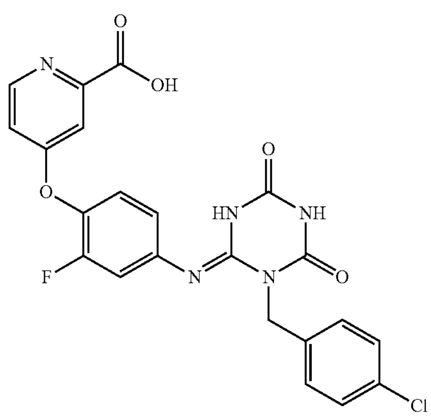 [SMILES: O=C(O)c1cc(Oc2ccc(/N=c3\[nH]c(=O)[nH]c(=O)n3Cc3ccc(Cl)cc3)cc2F)ccn1] | I-2141 | 1.41 | 484 | 2 |
| 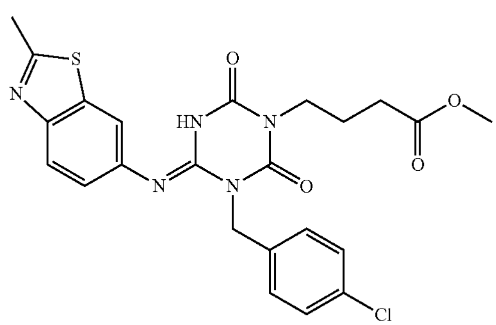 | I-2142 | 2.20 | 500 | 3 |
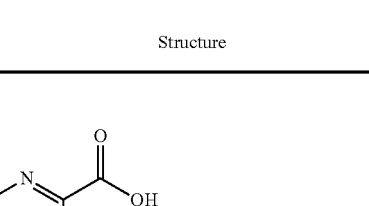

TABLE 432-continued

| Structure | Compound No. | Retention Time (min) | [M + H] | Method |
|---|---|---|---|---|
| 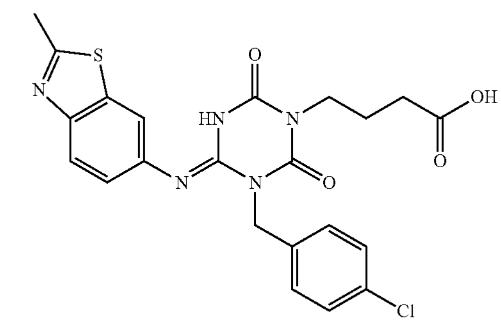 [SMILES: Cc1nc2ccc(/N=c3\[nH]c(=O)n(CCCC(=O)O)c(=O)n3Cc3ccc(Cl)cc3)cc2s1] | I-2143 | 1.92 | 486 | 3 |
| 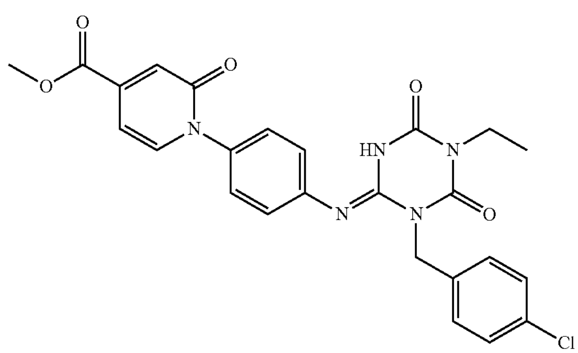 [SMILES: CCn1c(=O)[nH]/c(=N\c2ccc(-n3ccc(C(=O)OC)cc3=O)cc2)n(Cc2ccc(Cl)cc2)c1=O] | I-2144 | 2.14 | 508 | 3 |
| 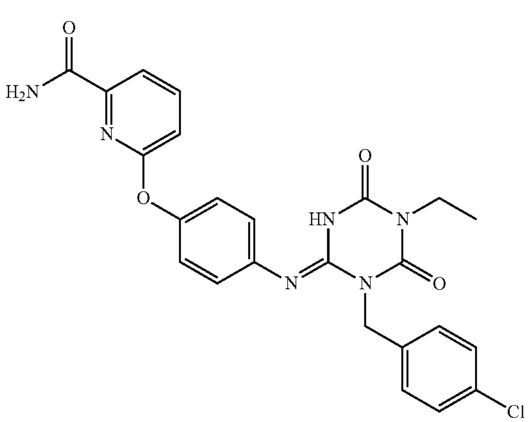 [SMILES: CCn1c(=O)[nH]/c(=N\c2ccc(Oc3cccc(C(N)=O)n3)cc2)n(Cc2ccc(Cl)cc2)c1=O] | I-2145 | 2.05 | 493 | 3 |

TABLE 433
| Structure | Compound No. | Retention Time (min) | [M + H] | Method |
|---|---|---|---|---|
| 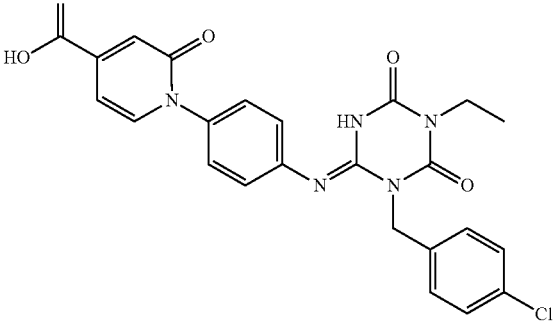 | I-2146 | 1.93 | 494 | 3 |
| 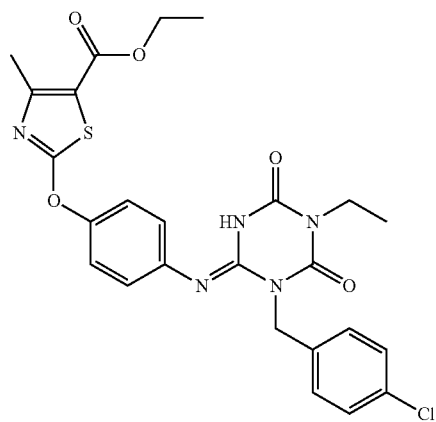 [SMILES: CCOC(=O)c1sc(Oc2ccc(/N=c3\[nH]c(=O)n(CC)c(=O)n3Cc3ccc(Cl)cc3)cc2)nc1C] | I-2147 | 2.53 | 542 | 2 |
| 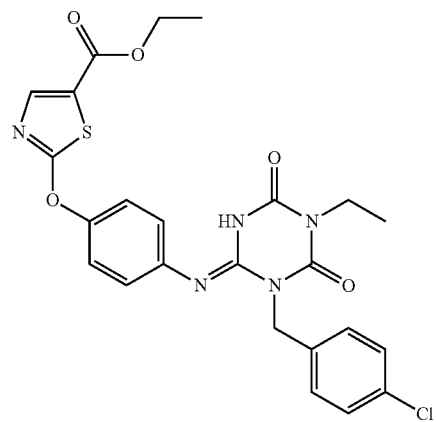 [SMILES: CCOC(=O)c1cnc(Oc2ccc(/N=c3\[nH]c(=O)n(CC)c(=O)n3Cc3ccc(Cl)cc3)cc2)s1] | I-2148 | 2.41 | 528 | 2 |
| 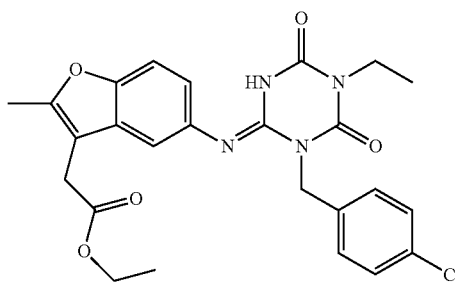 | I-2149 | 2.25 | 497 | 3 |

TABLE 433-continued

| Structure | Compound No. | Retention Time (min) | [M + H] | Method |
|---|---|---|---|---|
| 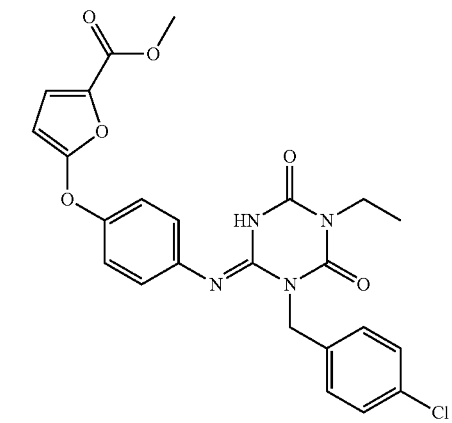 [SMILES: CCn1c(=O)[nH]/c(=N\c2ccc(Oc3ccc(C(=O)OC)o3)cc2)n(Cc2ccc(Cl)cc2)c1=O] | I-2150 | 2.23 | 497 | 2 |

TABLE 434

| Structure | Compound No. | Retention Time (min) | [M + H] | Method |
|---|---|---|---|---|
| 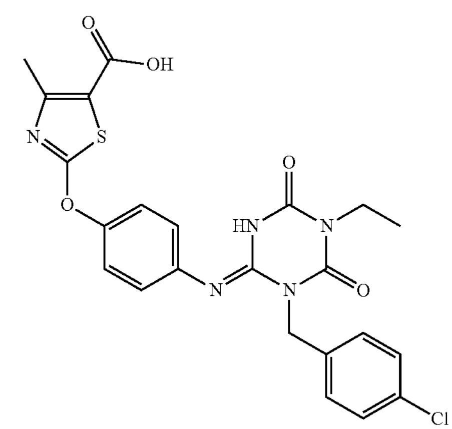 [SMILES: CCn1c(=O)[nH]/c(=N\c2ccc(Oc3nc(C)c(C(=O)O)s3)cc2)n(Cc2ccc(Cl)cc2)c1=O] | I-2151 | 2.04 | 514 | 2 |
| 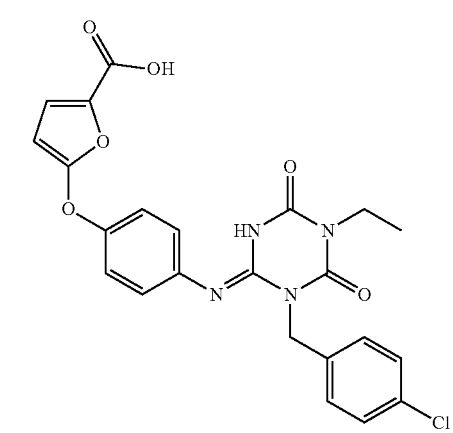 [SMILES: CCn1c(=O)[nH]/c(=N\c2ccc(Oc3ccc(C(=O)O)o3)cc2)n(Cc2ccc(Cl)cc2)c1=O] | I-2152 | 1.94 | 483 | 2 |

TABLE 434-continued

| Structure | Compound No. | Retention Time (min) | [M + H] | Method |
|---|---|---|---|---|
| 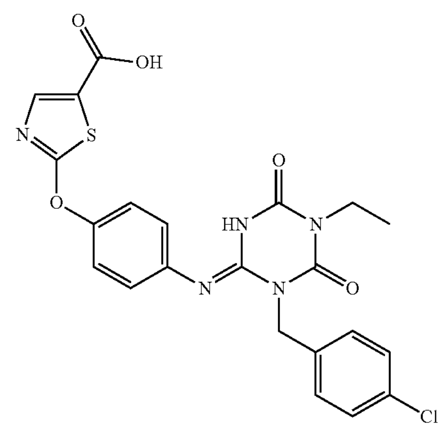 [SMILES: CCn1c(=O)[nH]/c(=N\c2ccc(Oc3ncc(C(=O)O)s3)cc2)n(Cc2ccc(Cl)cc2)c1=O] | I-2153 | 1.96 | 500 | 2 |
| 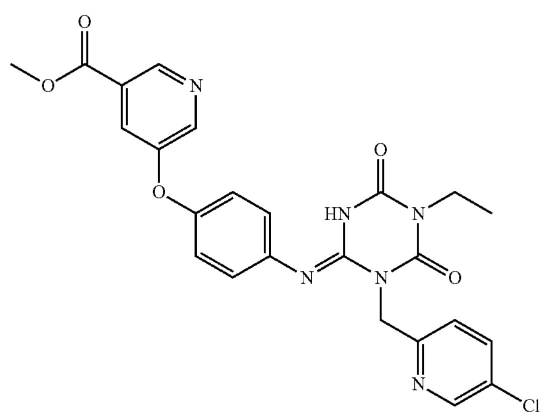 | I-2154 | 2.07 | 509 | 3 |
| 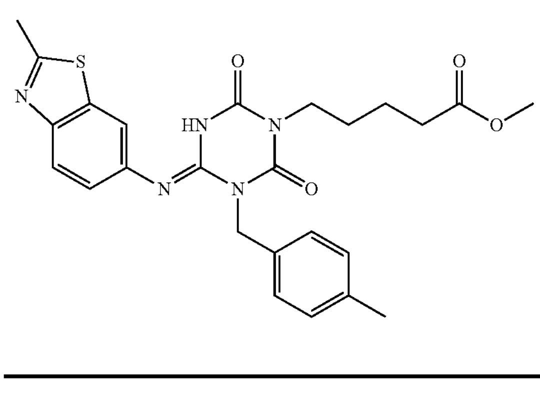 | I-2155 | 1.99 | 494 | 2 |

TABLE 435

| Structure | Compound No. | Retention Time (min) | [M + H] | Method |
|---|---|---|---|---|
| 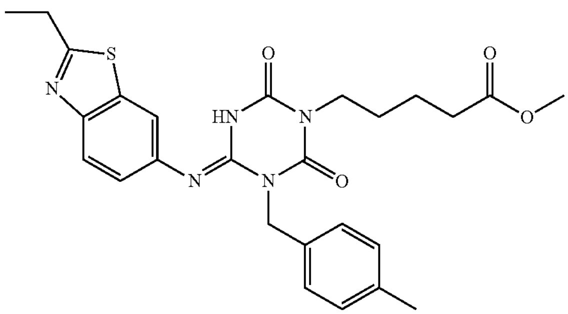 [SMILES: CCc1nc2ccc(/N=c3\[nH]c(=O)n(CCCCC(=O)OC)c(=O)n3Cc3ccc(C)cc3)cc2s1] | I-2156 | 2.13 | 508 | 2 |
| 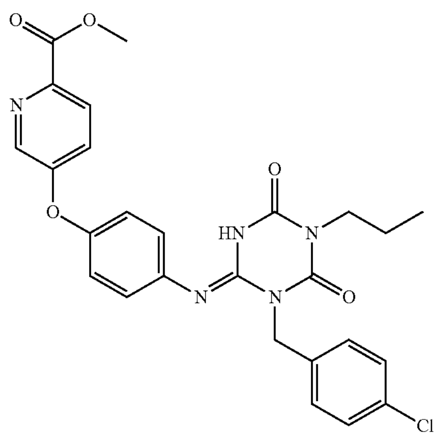 [SMILES: CCCn1c(=O)[nH]/c(=N\c2ccc(Oc3ccc(C(=O)OC)nc3)cc2)n(Cc2ccc(Cl)cc2)c1=O] | I-2157 | 2.15 | 522 | 2 |
| 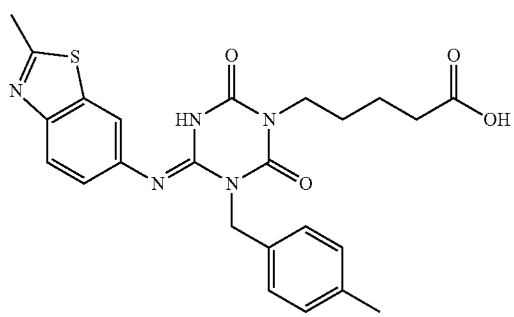 [SMILES: Cc1ccc(Cn2c(=O)n(CCCCC(=O)O)c(=O)[nH]/c2=N\c2ccc3nc(C)sc3c2)cc1] | I-2158 | 1.90 | 480 | 3 |
| 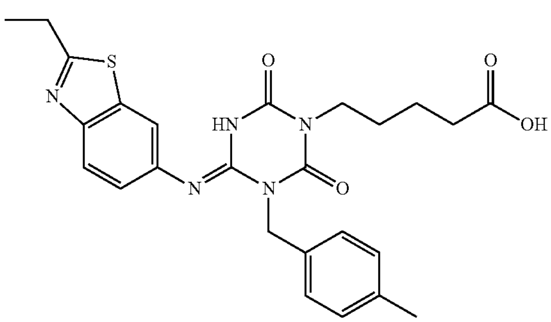 [SMILES: CCc1nc2ccc(/N=c3\[nH]c(=O)n(CCCCC(=O)O)c(=O)n3Cc3ccc(C)cc3)cc2s1] | I-2159 | 2.06 | 494 | 3 |

TABLE 435-continued

| Structure | Compound No. | Retention Time (min) | [M + H] | Method |
|---|---|---|---|---|
| (structure) | I-2160 | 2.32 | 522 | 3 |

TABLE 436

| Structure | Compound No. | Retention Time (min) | [M + H] | Method |
|---|---|---|---|---|
| (structure) | I-2161 | 2.15 | 508 | 3 |
| (structure) | I-2162 | 1.93 | 508 | 3 |

TABLE 436-continued

| Structure | Compound No. | Retention Time (min) | [M + H] | Method |
|---|---|---|---|---|
| 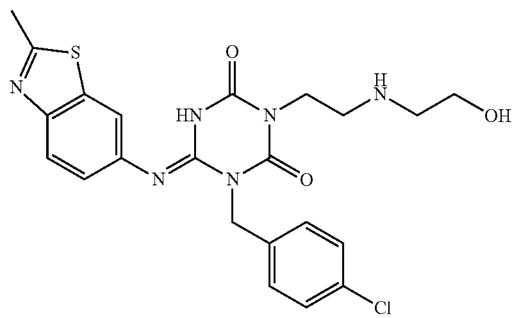 [SMILES: Cc1nc2ccc(/N=c3\[nH]c(=O)n(CCNCCO)c(=O)n3Cc3ccc(Cl)cc3)cc2s1] | I-2163 | 1.28 | 487 | 3 |
| 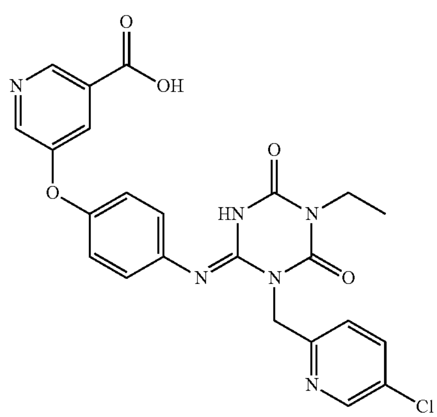 [SMILES: CCn1c(=O)[nH]/c(=N\c2ccc(Oc3cncc(C(=O)O)c3)cc2)n(Cc2ccc(Cl)cn2)c1=O] | I-2164 | 1.75 | 495 | 3 |
| 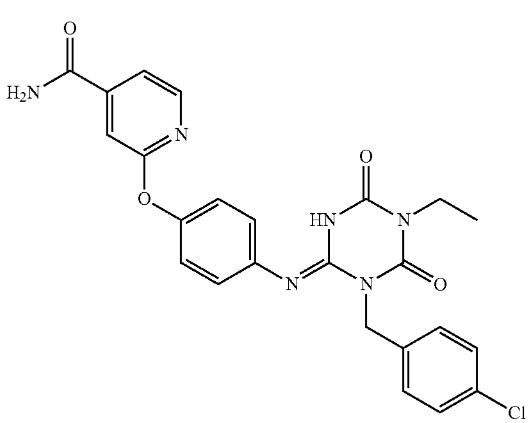 [SMILES: CCn1c(=O)[nH]/c(=N\c2ccc(Oc3cc(C(N)=O)ccn3)cc2)n(Cc2ccc(Cl)cc2)c1=O] | I-2165 | 1.75 | 493 | 3 |

TABLE 437

| Structure | Compound No. | Retention Time (min) | [M + H] | Method |
|---|---|---|---|---|
| 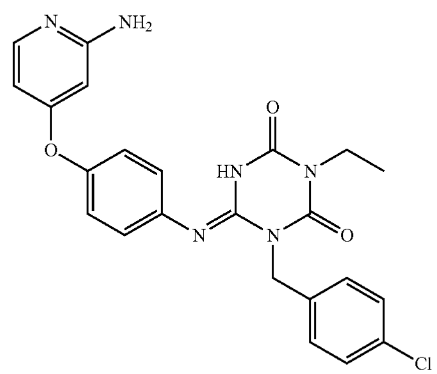 [SMILES: CCn1c(=O)[nH]/c(=N\c2ccc(Oc3ccnc(N)c3)cc2)n(Cc2ccc(Cl)cc2)c1=O] | I-2166 | 1.45 | 465 | 2 |
| 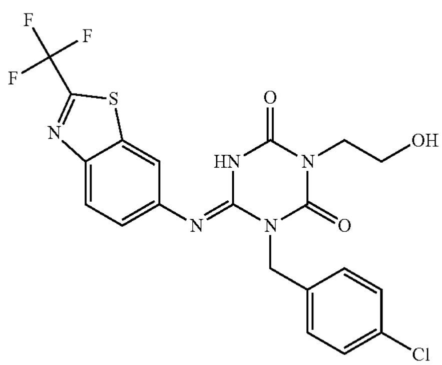 [SMILES: O=c1[nH]/c(=N\c2ccc3nc(C(F)(F)F)sc3c2)n(Cc2ccc(Cl)cc2)c(=O)n1CCO] | I-2167 | 2.16 | 498 | 2 |
| 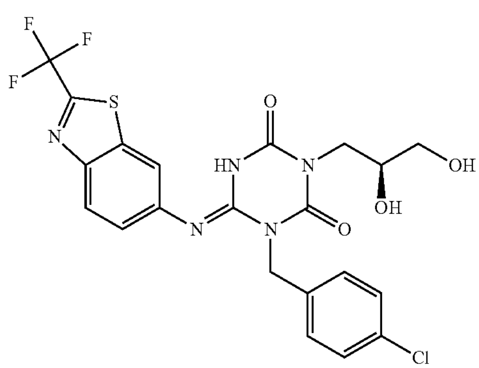 [SMILES: O=c1[nH]/c(=N\c2ccc3nc(C(F)(F)F)sc3c2)n(Cc2ccc(Cl)cc2)c(=O)n1C[C@H](O)CO] | I-2168 | 1.99 | 528 | 3 |
| 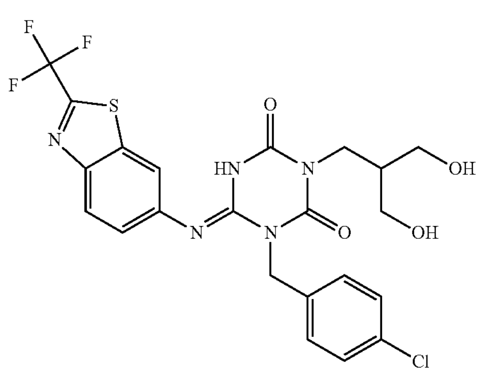 [SMILES: O=c1[nH]/c(=N\c2ccc3nc(C(F)(F)F)sc3c2)n(Cc2ccc(Cl)cc2)c(=O)n1CC(CO)CO] | I-2169 | 2.02 | 542 | 3 |

TABLE 437-continued

| Structure | Compound No. | Retention Time (min) | [M + H] | Method |
|---|---|---|---|---|
| 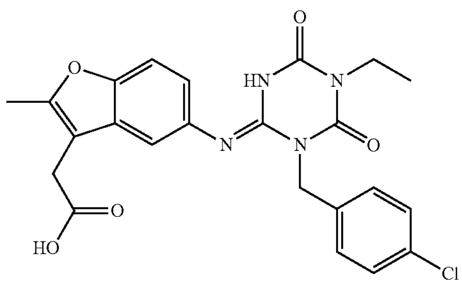 [SMILES: CCn1c(=O)[nH]/c(=N\c2ccc3oc(C)c(CC(=O)O)c3c2)n(Cc2ccc(Cl)cc2)c1=O] | I-2170 | 2.06 | 469 | 3 |

TABLE 438

| Structure | Compound No. | Retention Time (min) | [M + H] | Method |
|---|---|---|---|---|
| 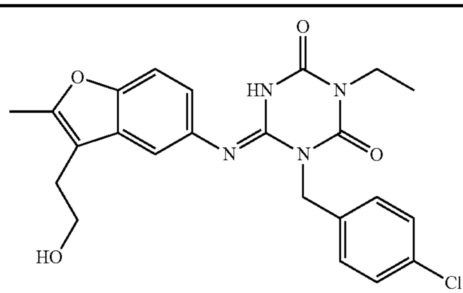 | I-2171 | 2.09 | 455 | 3 |
| 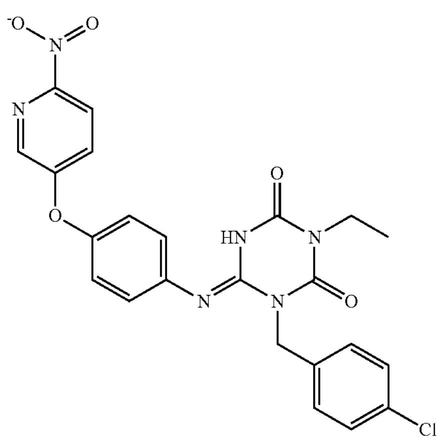 | I-2172 | 2.16 | 495 | 2 |
| 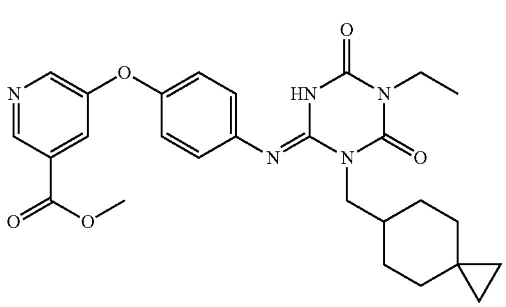 [SMILES: CCn1c(=O)[nH]/c(=N\c2ccc(Oc3cncc(C(=O)OC)c3)cc2)n(CC2CCC3(CC2)CC3)c1=O] | I-2173 | 2.25 | 506 | 2 |

TABLE 438-continued
| Structure | Compound No. | Retention Time (min) | [M + H] | Method |
|---|---|---|---|---|
| 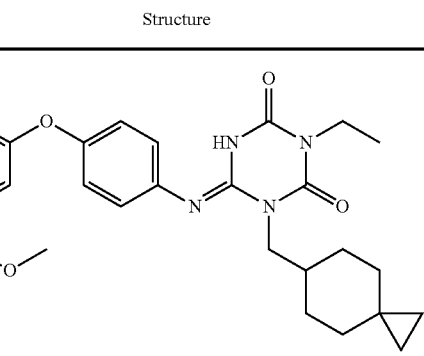 | I-2174 | 2.11 | 506 | 2 |
| 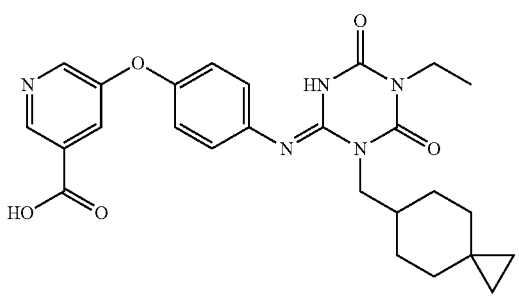 [SMILES: CCn1c(=O)[nH]/c(=N\c2ccc(Oc3cncc(C(=O)O)c3)cc2)n(CC2CCC3(CC2)CC3)c1=O] | I-2175 | 1.95 | 492 | 2 |
TABLE 439
| Structure | Compound No. | Retention Time (min) | [M + H] | Method |
|---|---|---|---|---|
| 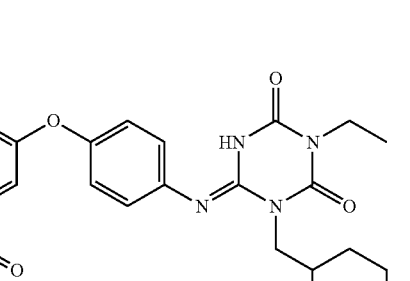 | I-2176 | 2.02 | 491 | 2 |
| 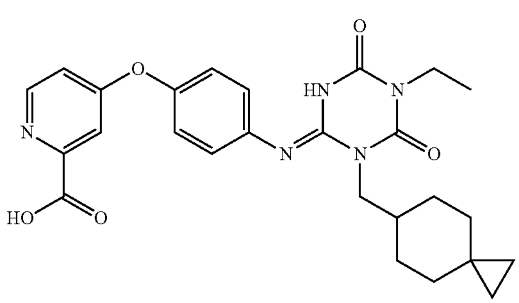 [SMILES: CCn1c(=O)[nH]/c(=N\c2ccc(Oc3ccnc(C(=O)O)c3)cc2)n(CC2CCC3(CC2)CC3)c1=O] | I-2177 | 1.64 | 492 | 2 |

TABLE 439-continued
| Structure | Compound No. | Retention Time (min) | [M + H] | Method |
|---|---|---|---|---|
| 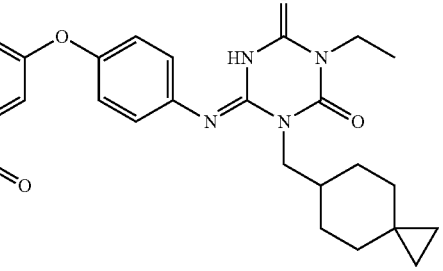 | I-2178 | 1.84 | 491 | 3 |
| 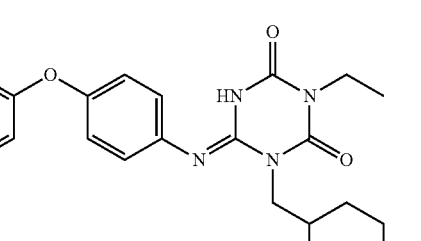 | I-2179 | 2.24 | 473 | 3 |
| 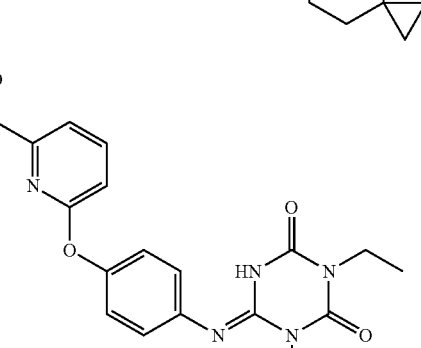 | I-2180 | 2.28 | 488 | 3 |
TABLE 440
| Structure | Compound No. | Retention Time (min) | [M + H] | Method |
|---|---|---|---|---|
| 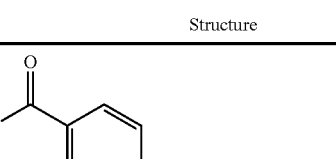 | I-2181 | 2.06 | 474 | 3 |

TABLE 440-continued

| Structure | Compound No. | Retention Time (min) | [M + H] | Method |
|---|---|---|---|---|
| 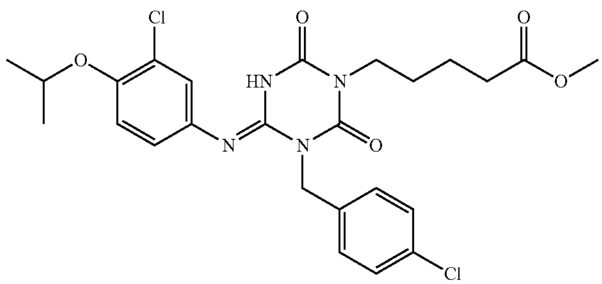 [SMILES: COC(=O)CCCCn1c(=O)[nH]/c(=N\c2ccc(OC(C)C)c(Cl)c2)n(Cc2ccc(Cl)cc2)c1=O] | I-2182 | 2.66 | 535 | 3 |
| 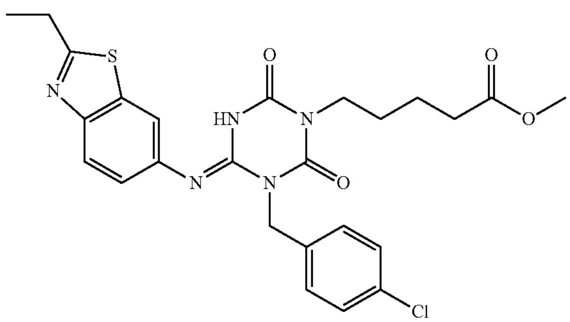 [SMILES: CCc1nc2ccc(/N=c3\[nH]c(=O)n(CCCCC(=O)OC)c(=O)n3Cc3ccc(Cl)cc3)cc2s1] | I-2183 | 2.45 | 528 | 3 |
| 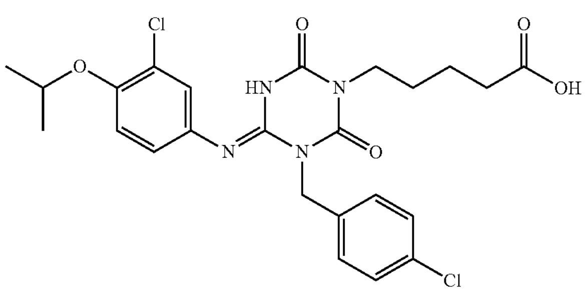 [SMILES: CC(C)Oc1ccc(/N=c2\[nH]c(=O)n(CCCCC(=O)O)c(=O)n2Cc2ccc(Cl)cc2)cc1Cl] | I-2184 | 2.39 | 521 | 3 |
| 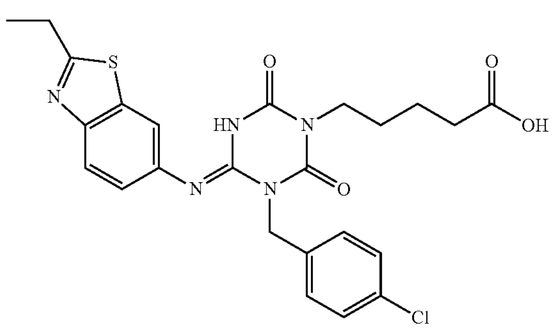 [SMILES: CCc1nc2ccc(/N=c3\[nH]c(=O)n(CCCCC(=O)O)c(=O)n3Cc3ccc(Cl)cc3)cc2s1] | I-2185 | 2.15 | 514 | 3 |

TABLE 441

| Structure | Compound No. | Retention Time (min) | [M + H] | Method |
|---|---|---|---|---|
| 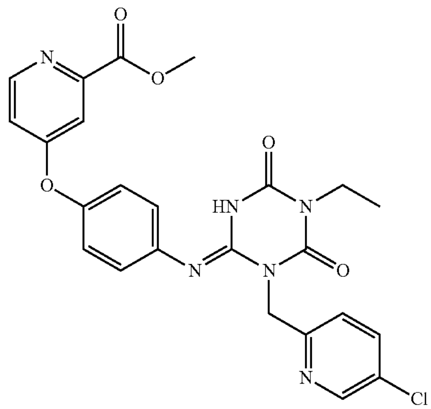 [SMILES: CCn1c(=O)[nH]/c(=N\c2ccc(Oc3ccnc(C(=O)OC)c3)cc2)n(Cc2ccc(Cl)cn2)c1=O] | I-2186 | 1.93 | 509 | 3 |
| 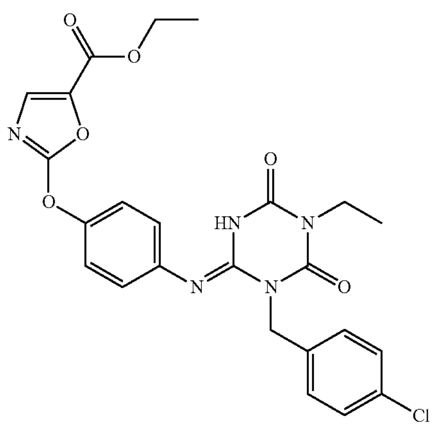 | I-2187 | 2.27 | 512 | 2 |
| 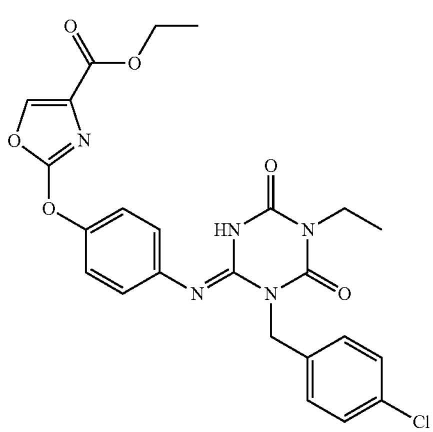 [SMILES: CCOC(=O)c1coc(Oc2ccc(/N=c3\[nH]c(=O)n(CC)c(=O)n3Cc3ccc(Cl)cc3)cc2)n1] | I-2188 | 2.25 | 512 | 2 |

TABLE 441-continued

| Structure | Compound No. | Retention Time (min) | [M + H] | Method |
|---|---|---|---|---|
| 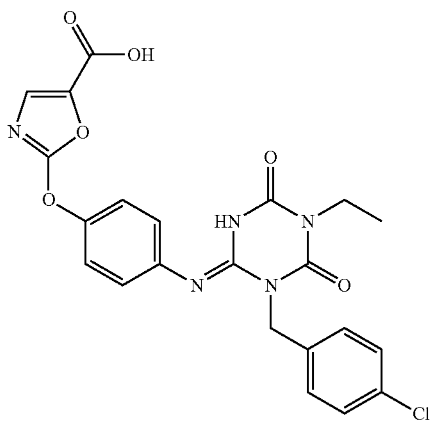 [SMILES: CCn1c(=O)[nH]/c(=N\c2ccc(Oc3ncc(C(=O)O)o3)cc2)n(Cc2ccc(Cl)cc2)c1=O] | I-2189 | 1.84 | 484 | 2 |
| 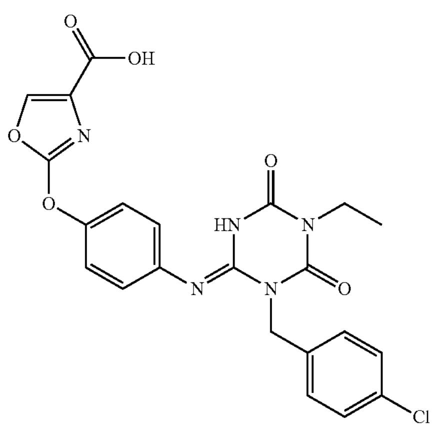 [SMILES: CCn1c(=O)[nH]/c(=N\c2ccc(Oc3nc(C(=O)O)co3)cc2)n(Cc2ccc(Cl)cc2)c1=O] | I-2190 | 1.92 | 484 | 2 |

TABLE 442

| Structure | Compound No. | Retention Time (min) | [M + H] | Method |
|---|---|---|---|---|
| 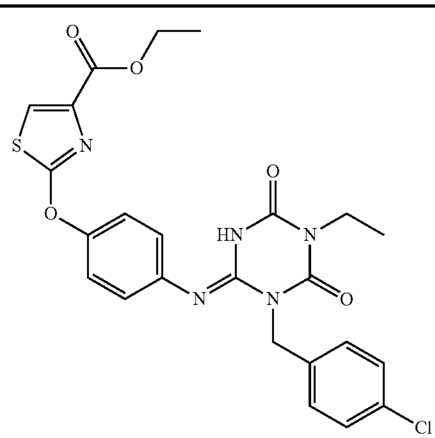 | I-2191 | 2.32 | 528 | 2 |

TABLE 442-continued

| Structure | Compound No. | Retention Time (min) | [M + H] | Method |
|---|---|---|---|---|
| 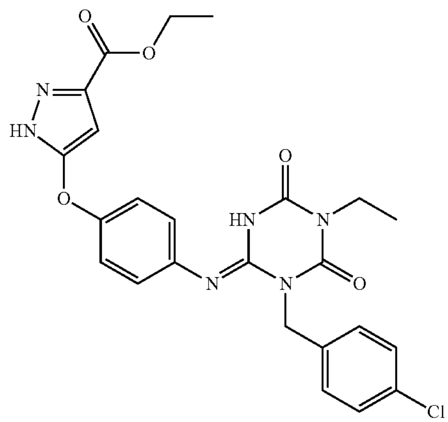 [SMILES: CCOC(=O)c1cc(Oc2ccc(/N=c3\[nH]c(=O)n(CC)c(=O)n3Cc3ccc(Cl)cc3)cc2)[nH]n1] | I-2192 | 2.09 | 511 | 2 |
| 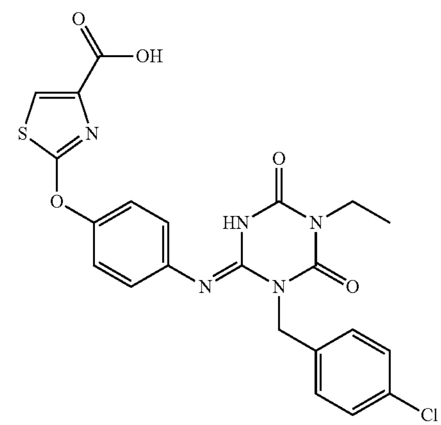 [SMILES: CCn1c(=O)[nH]/c(=N\c2ccc(Oc3nc(C(=O)O)cs3)cc2)n(Cc2ccc(Cl)cc2)c1=O] | I-2193 | 1.97 | 500 | 2 |
| 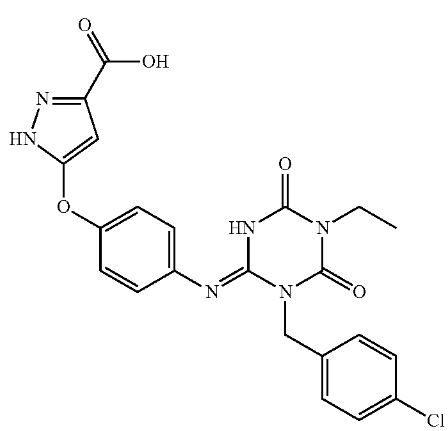 [SMILES: CCn1c(=O)[nH]/c(=N\c2ccc(Oc3cc(C(=O)O)n[nH]3)cc2)n(Cc2ccc(Cl)cc2)c1=O] | I-2194 | 1.74 | 483 | 2 |

TABLE 442-continued

| Structure | Compound No. | Retention Time (min) | [M + H] | Method |
|---|---|---|---|---|
| 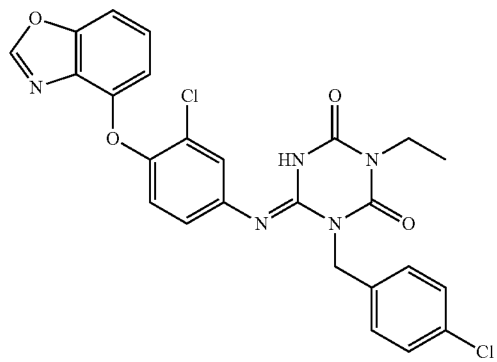 [SMILES: CCn1c(=O)[nH]/c(=N\c2ccc(Oc3cccc4ocnc34)c(Cl)c2)n(Cc2ccc(Cl)cc2)c1=O] | I-2195 | 2.64 | 524 | 5 |

TABLE 443

| Structure | Compound No. | Retention Time (min) | [M + H] | Method |
|---|---|---|---|---|
| 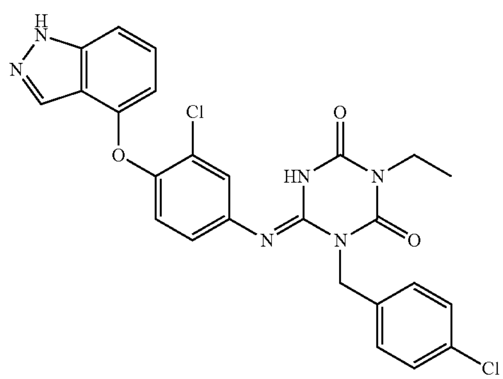 [SMILES: CCn1c(=O)[nH]/c(=N\c2ccc(Oc3cccc4[nH]ncc34)c(Cl)c2)n(Cc2ccc(Cl)cc2)c1=O] | I-2196 | 2.41 | 523 | 5 |
| 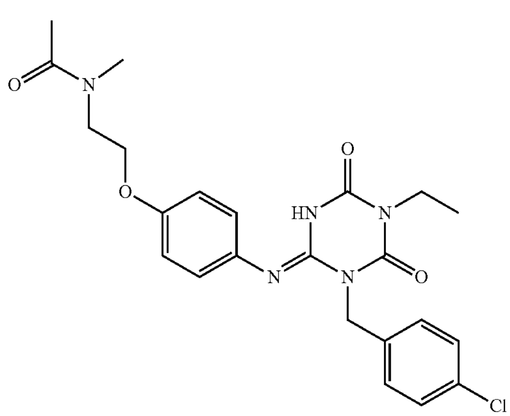 [SMILES: CCn1c(=O)[nH]/c(=N\c2ccc(OCCN(C)C(C)=O)cc2)n(Cc2ccc(Cl)cc2)c1=O] | I-2197 | 1.81 | 472 | 5 |

TABLE 443-continued

| Structure | Compound No. | Retention Time (min) | [M + H] | Method |
|---|---|---|---|---|
| 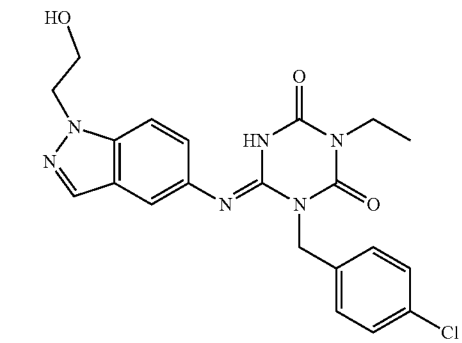 [SMILES: CCn1c(=O)[nH]/c(=N\c2ccc3c(cnn3CCO)c2)n(Cc2ccc(Cl)cc2)c1=O] | I-2198 | 1.58 | 441 | 2 |
| 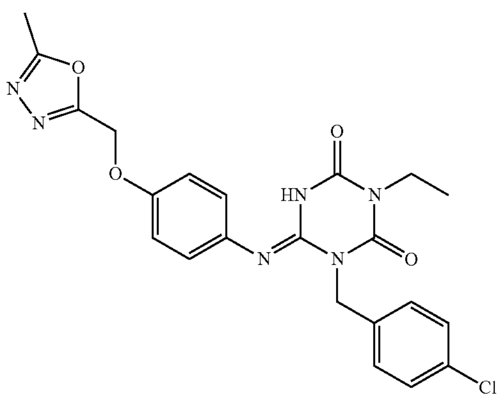 | I-2199 | 1.89 | 469 | 5 |
| 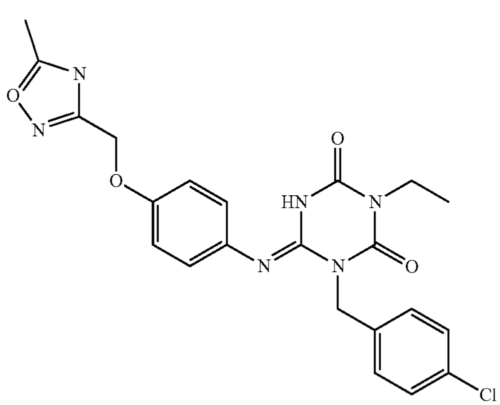 | I-2200 | 2.04 | 469 | 5 |

TABLE 444

| Structure | Compound No. | Retention Time (min) | [M + H] | Method |
|---|---|---|---|---|
| 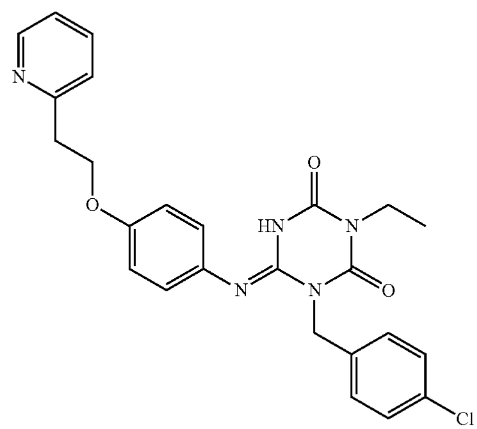 [SMILES: CCn1c(=O)[nH]/c(=N\c2ccc(OCCc3ccccn3)cc2)n(Cc2ccc(Cl)cc2)c1=O] | I-2201 | 1.54 | 478 | 5 |
| 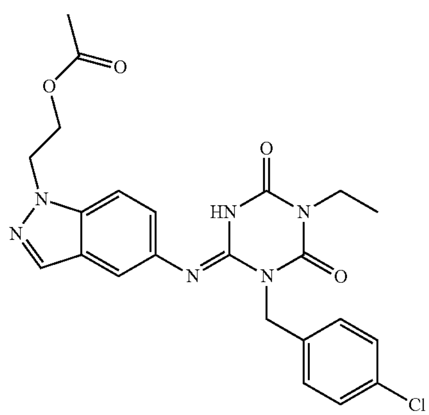 [SMILES: CCn1c(=O)[nH]/c(=N\c2ccc3c(cnn3CCOC(C)=O)c2)n(Cc2ccc(Cl)cc2)c1=O] | I-2202 | 1.98 | 483 | 5 |
| 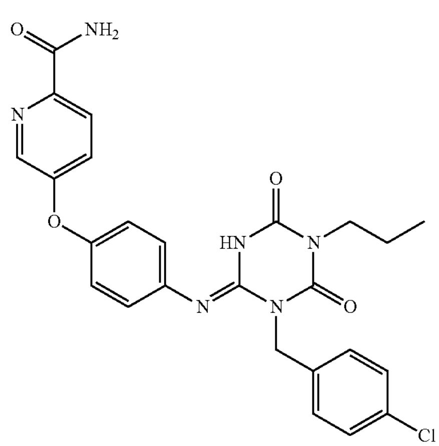 [SMILES: CCCn1c(=O)[nH]/c(=N\c2ccc(Oc3ccc(C(N)=O)nc3)cc2)n(Cc2ccc(Cl)cc2)c1=O] | I-2203 | 2.19 | 507 | 3 |

TABLE 444-continued

| Structure | Compound No. | Retention Time (min) | [M + H] | Method |
|---|---|---|---|---|
| 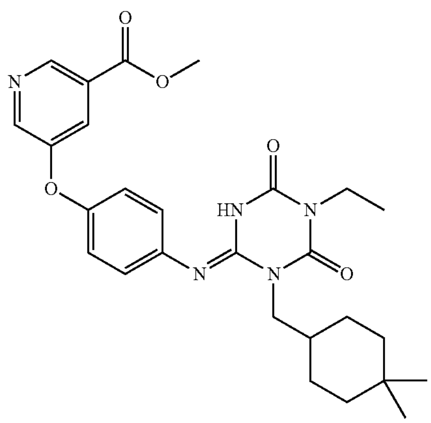 [SMILES: CCn1c(=O)[nH]/c(=N\c2ccc(Oc3cncc(C(=O)OC)c3)cc2)n(CC2CCC(C)(C)CC2)c1=O] | I-2204 | 2.56 | 508 | 3 |
| 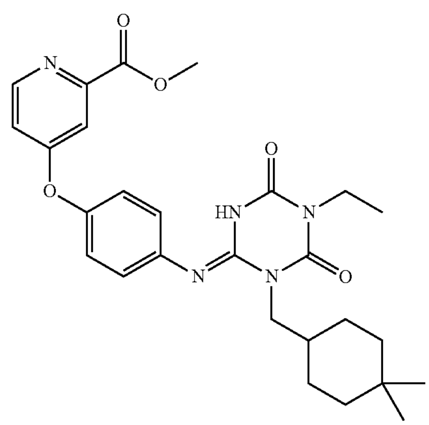 [SMILES: CCn1c(=O)[nH]/c(=N\c2ccc(Oc3ccnc(C(=O)OC)c3)cc2)n(CC2CCC(C)(C)CC2)c1=O] | I-2205 | 2.44 | 508 | 3 |

TABLE 445

| Structure | Compound No. | Retention Time (min) | [M + H] | Method |
|---|---|---|---|---|
| 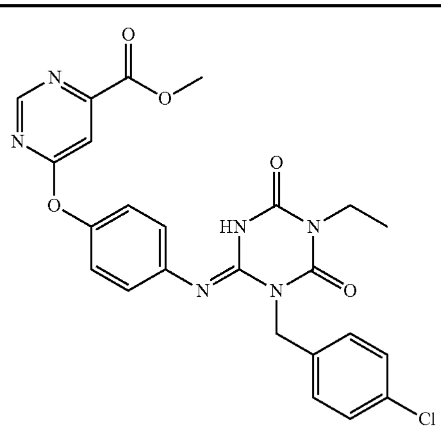 | I-2206 | 2.22 | 509 | 3 |

TABLE 445-continued

| Structure | Compound No. | Retention Time (min) | [M + H] | Method |
|---|---|---|---|---|
| 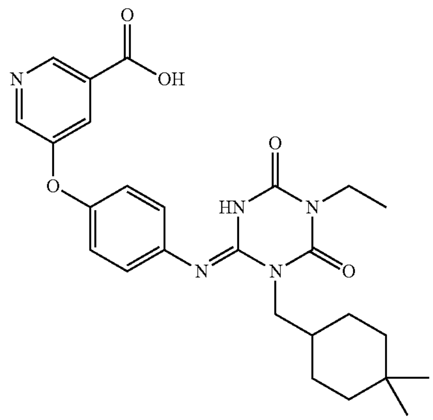 [SMILES: CCn1c(=O)[nH]/c(=N\c2ccc(Oc3cncc(C(=O)O)c3)cc2)n(CC2CCC(C)(C)CC2)c1=O] | I-2207 | 2.27 | 494 | 3 |
| 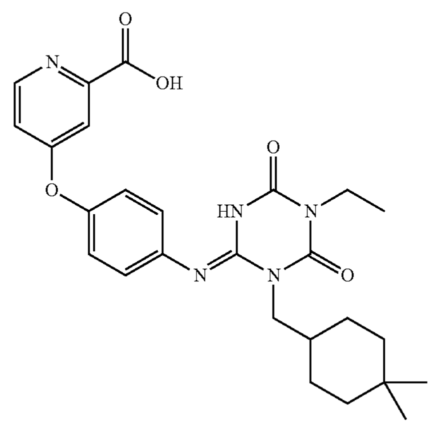 [SMILES: CCn1c(=O)[nH]/c(=N\c2ccc(Oc3ccnc(C(=O)O)c3)cc2)n(CC2CCC(C)(C)CC2)c1=O] | I-2208 | 1.94 | 494 | 3 |
| 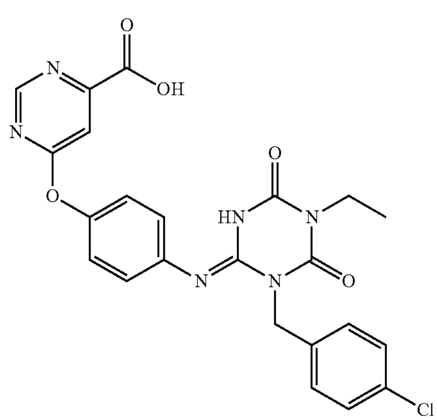 [SMILES: CCn1c(=O)[nH]/c(=N\c2ccc(Oc3cc(C(=O)O)ncn3)cc2)n(Cc2ccc(Cl)cc2)c1=O] | I-2209 | 2.03 | 495 | 3 |

TABLE 445-continued

| Structure | Compound No. | Retention Time (min) | [M + H] | Method |
|---|---|---|---|---|
| 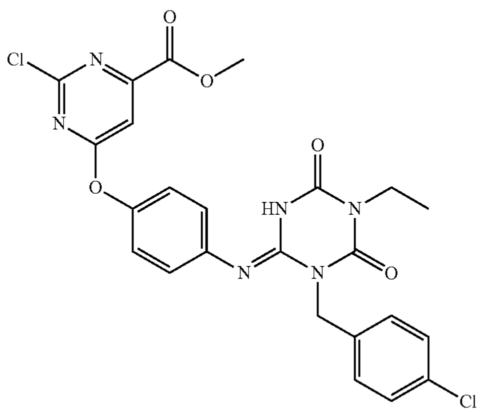 [SMILES: CCn1c(=O)[nH]/c(=N\c2ccc(Oc3cc(C(=O)OC)nc(Cl)n3)cc2)n(Cc2ccc(Cl)cc2)c1=O] | I-2210 | 2.40 | 543 | 3 |

TABLE 446

| Structure | Compound No. | Retention Time (min) | [M + H] | Method |
|---|---|---|---|---|
| 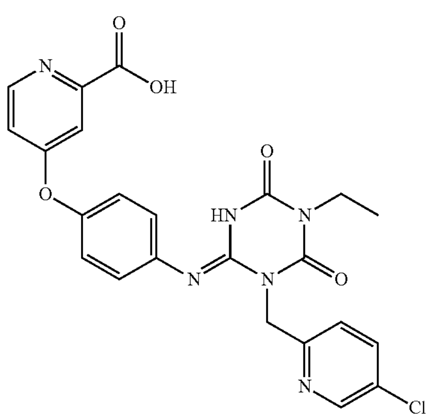 [SMILES: CCn1c(=O)[nH]/c(=N\c2ccc(Oc3ccnc(C(=O)O)c3)cc2)n(Cc2ccc(Cl)cn2)c1=O] | I-2211 | 1.43 | 495 | 3 |
| 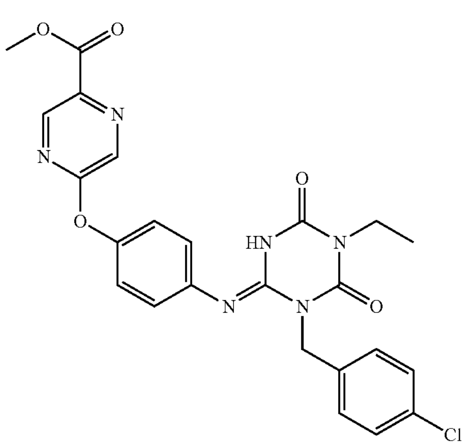 | I-2212 | 2.03 | 509 | 2 |

TABLE 446-continued

| Structure | Compound No. | Retention Time (min) | [M + H] | Method |
|---|---|---|---|---|
| 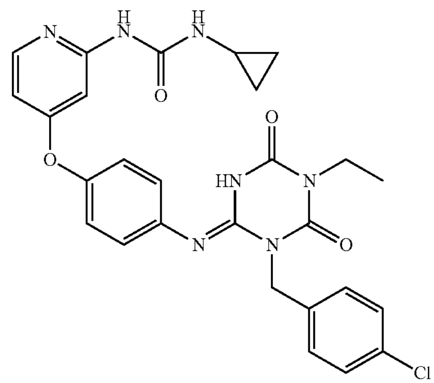 [SMILES: CCn1c(=O)[nH]/c(=N\c2ccc(Oc3ccnc(NC(=O)NC4CC4)c3)cc2)n(Cc2ccc(Cl)cc2)c1=O] | I-2213 | 1.68 | 548 | 2 |
| 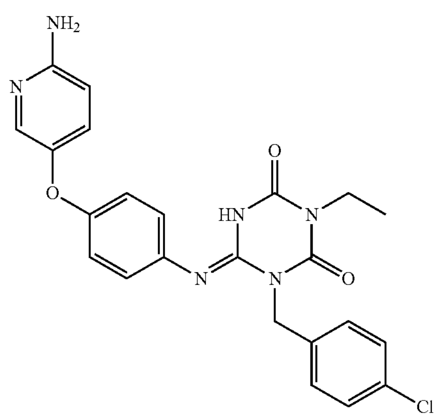 [SMILES: CCn1c(=O)[nH]/c(=N\c2ccc(Oc3ccc(N)nc3)cc2)n(Cc2ccc(Cl)cc2)c1=O] | I-2214 | 1.45 | 465 | 2 |
| 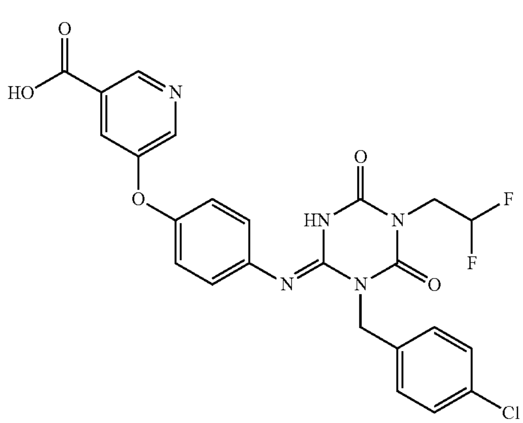 [SMILES: O=C(O)c1cncc(Oc2ccc(/N=c3\[nH]c(=O)n(CC(F)F)c(=O)n3Cc3ccc(Cl)cc3)cc2)c1] | I-2215 | 1.87 | 530 | 2 |

TABLE 447

| Structure | Compound No. | Retention Time (min) | [M + H] | Method |
|---|---|---|---|---|
| 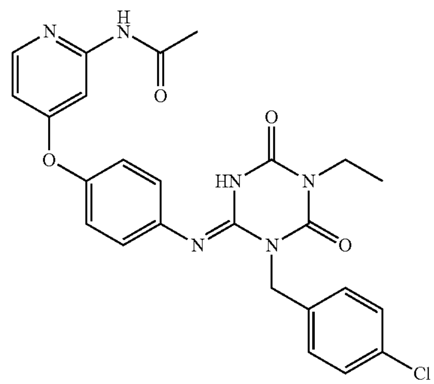 [SMILES: CCn1c(=O)[nH]/c(=N\c2ccc(Oc3ccnc(NC(C)=O)c3)cc2)n(Cc2ccc(Cl)cc2)c1=O] | I-2216 | 1.66 | 507 | 2 |
| 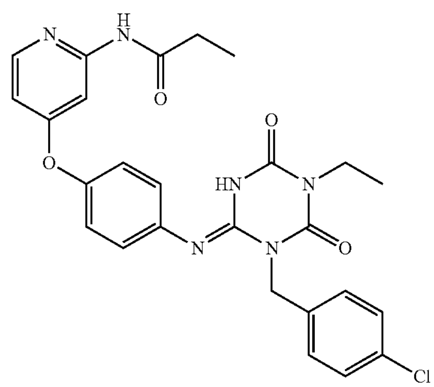 [SMILES: CCC(=O)Nc1cc(Oc2ccc(/N=c3\[nH]c(=O)n(CC)c(=O)n3Cc3ccc(Cl)cc3)cc2)ccn1] | I-2217 | 1.74 | 521 | 2 |
| 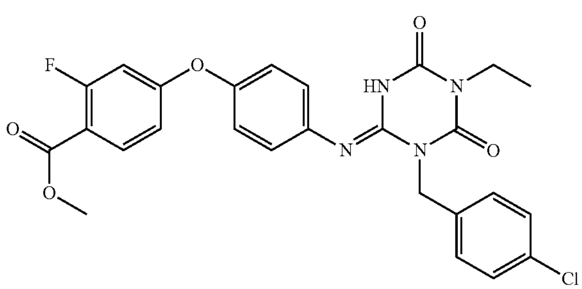 [SMILES: CCn1c(=O)[nH]/c(=N\c2ccc(Oc3ccc(C(=O)OC)c(F)c3)cc2)n(Cc2ccc(Cl)cc2)c1=O] | I-2218 | 2.40 | 525 | 2 |
| 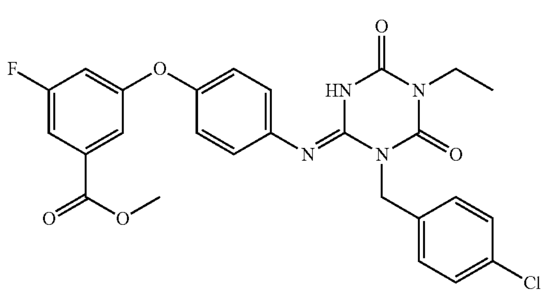 [SMILES: CCn1c(=O)[nH]/c(=N\c2ccc(Oc3cc(F)cc(C(=O)OC)c3)cc2)n(Cc2ccc(Cl)cc2)c1=O] | I-2219 | 2.47 | 525 | 2 |

TABLE 447-continued

| Structure | Compound No. | Retention Time (min) | [M + H] | Method |
|---|---|---|---|---|
| 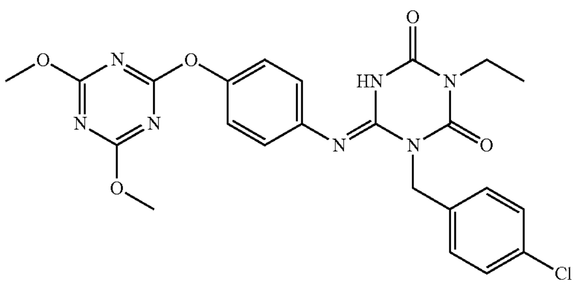 [SMILES: CCn1c(=O)[nH]/c(=N\c2ccc(Oc3nc(OC)nc(OC)n3)cc2)n(Cc2ccc(Cl)cc2)c1=O] | I-2220 | 2.09 | 512 | 2 |

TABLE 448

| Structure | Compound No. | Retention Time (min) | [M + H] | Method |
|---|---|---|---|---|
| 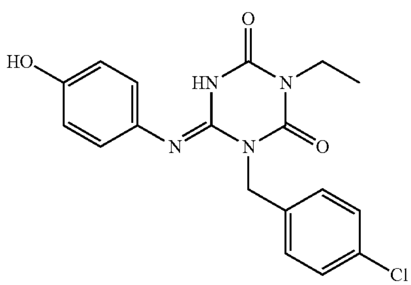 [SMILES: CCn1c(=O)[nH]/c(=N\c2ccc(O)cc2)n(Cc2ccc(Cl)cc2)c1=O] | I-2221 | 1.62 | 373 | 2 |
| 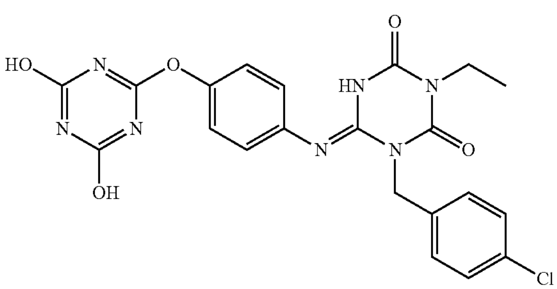 [SMILES: CCn1c(=O)[nH]/c(=N\c2ccc(Oc3nc(O)nc(O)n3)cc2)n(Cc2ccc(Cl)cc2)c1=O] | I-2222 | 1.61 | 484 | 2 |
| 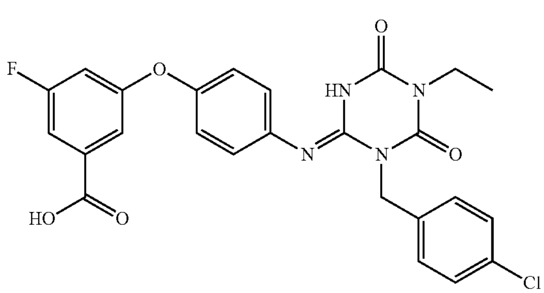 [SMILES: CCn1c(=O)[nH]/c(=N\c2ccc(Oc3cc(F)cc(C(=O)O)c3)cc2)n(Cc2ccc(Cl)cc2)c1=O] | I-2223 | 2.15 | 511 | 2 |

TABLE 448-continued

| Structure | Compound No. | Retention Time (min) | [M + H] | Method |
|---|---|---|---|---|
| 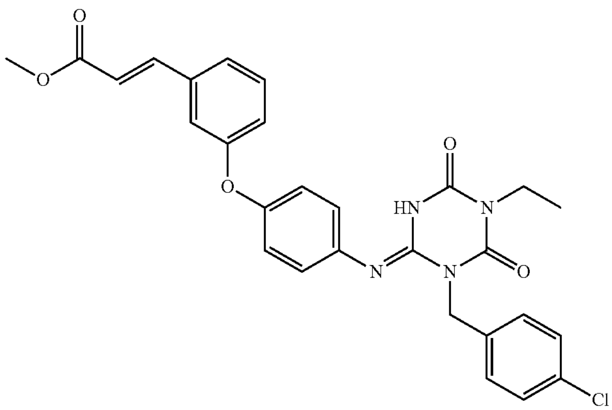 [SMILES: CCn1c(=O)[nH]/c(=N\c2ccc(Oc3cccc(/C=C/C(=O)OC)c3)cc2)n(Cc2ccc(Cl)cc2)c1=O] | I-2224 | 2.62 | 533 | 3 |
| 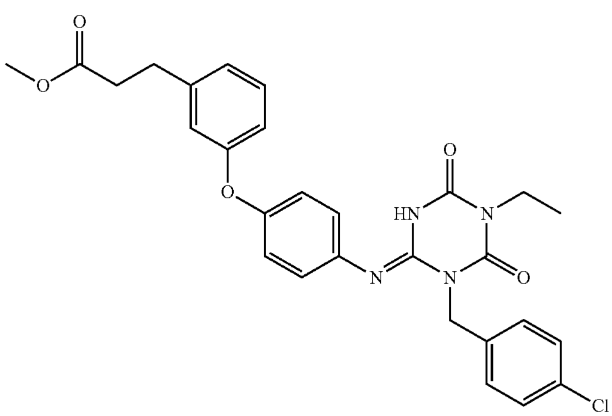 [SMILES: CCn1c(=O)[nH]/c(=N\c2ccc(Oc3cccc(CCC(=O)OC)c3)cc2)n(Cc2ccc(Cl)cc2)c1=O] | I-2225 | 2.57 | 535 | 3 |

TABLE 449

| Structure | Compound No. | Retention Time (min) | [M + H] | Method |
|---|---|---|---|---|
| 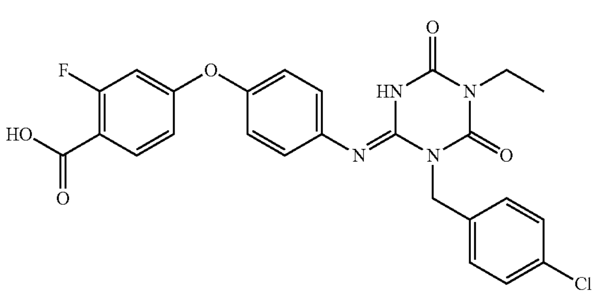 [SMILES: CCn1c(=O)[nH]/c(=N\c2ccc(Oc3ccc(C(=O)O)c(F)c3)cc2)n(Cc2ccc(Cl)cc2)c1=O] | I-2226 | 2.07 | 511 | 2 |

TABLE 449-continued
| Structure | Compound No. | Retention Time (min) | [M + H] | Method |
|---|---|---|---|---|
| 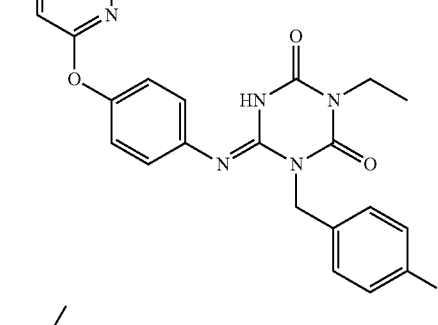 | I-2227 | 2.37 | 475 | 3 |
| 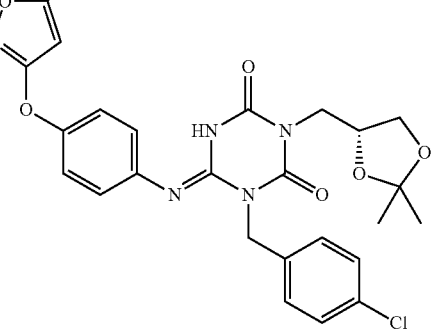 | I-2228 | 2.20 | 540 | 3 |
| 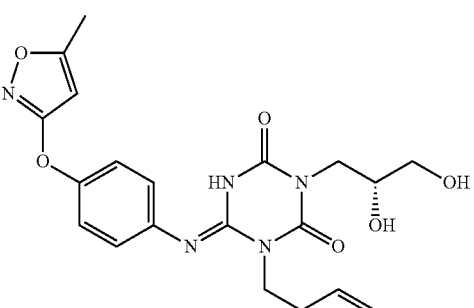 | I-2229 | 1.86 | 500 | 3 |
| 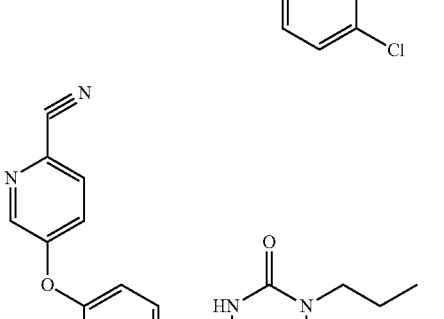 | I-2230 | 2.48 | 489 | 3 |

TABLE 450

| Structure | Compound No. | Retention Time (min) | [M + H] | Method |
|---|---|---|---|---|
| 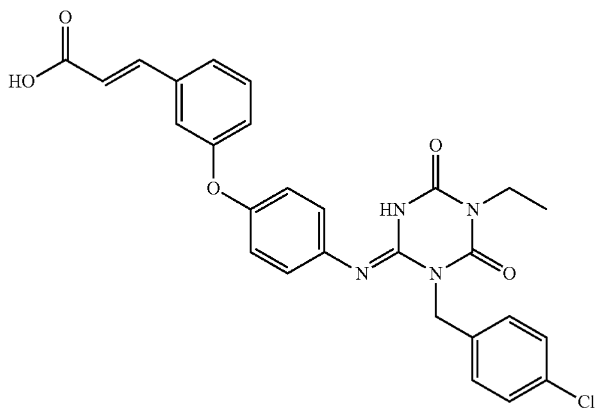 [SMILES: CCn1c(=O)[nH]/c(=N\c2ccc(Oc3cccc(/C=C/C(=O)O)c3)cc2)n(Cc2ccc(Cl)cc2)c1=O] | I-2231 | 230 | 519 | 3 |
| 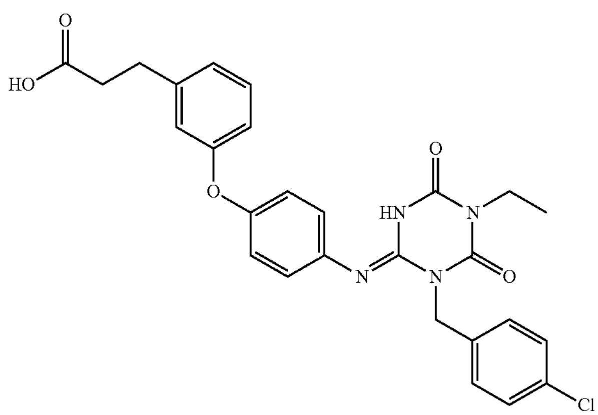 [SMILES: CCn1c(=O)[nH]/c(=N\c2ccc(Oc3cccc(CCC(=O)O)c3)cc2)n(Cc2ccc(Cl)cc2)c1=O] | I-2232 | 228 | 521 | 3 |
| 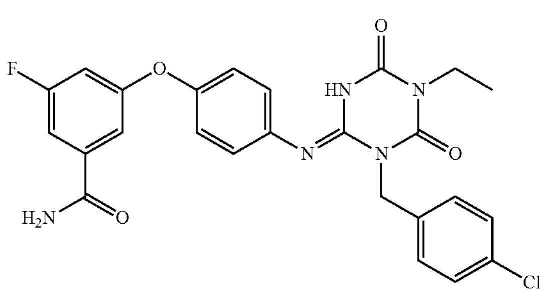 [SMILES: CCn1c(=O)[nH]/c(=N\c2ccc(Oc3cc(F)cc(C(N)=O)c3)cc2)n(Cc2ccc(Cl)cc2)c1=O] | I-2233 | 2.12 | 510 | 2 |
| 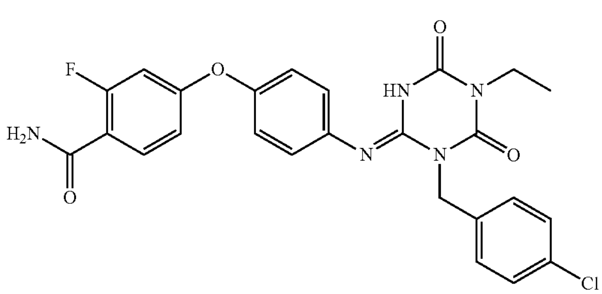 [SMILES: CCn1c(=O)[nH]/c(=N\c2ccc(Oc3ccc(C(N)=O)c(F)c3)cc2)n(Cc2ccc(Cl)cc2)c1=O] | I-2234 | 2.07 | 510 | 2 |

TABLE 450-continued
| Structure | Compound No. | Retention Time (min) | [M + H] | Method |
|---|---|---|---|---|
| 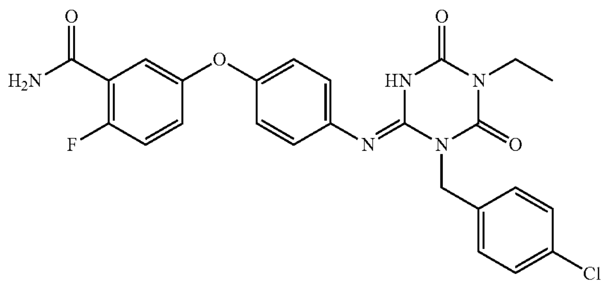 [SMILES: CCn1c(=O)[nH]/c(=N\c2ccc(Oc3ccc(F)c(C(N)=O)c3)cc2)n(Cc2ccc(Cl)cc2)c1=O] | I-2235 | 2.07 | 510 | 2 |
TABLE 451
| Structure | Compound No. | Retention Time (min) | [M + H] | Method |
|---|---|---|---|---|
| 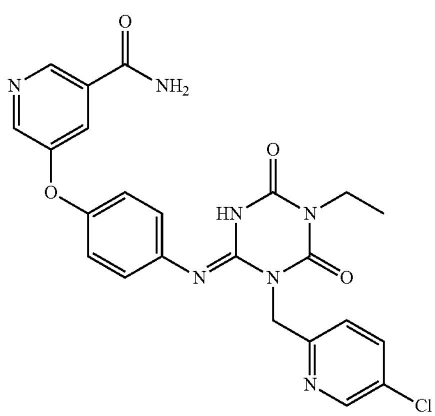 [SMILES: CCn1c(=O)[nH]/c(=N\c2ccc(Oc3cncc(C(N)=O)c3)cc2)n(Cc2ccc(Cl)cn2)c1=O] | I-2236 | 1.64 | 494 | 3 |
| 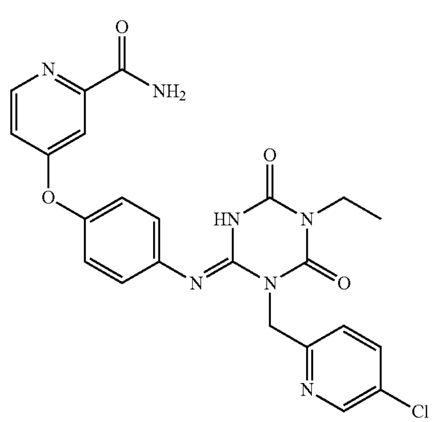 [SMILES: CCn1c(=O)[nH]/c(=N\c2ccc(Oc3ccnc(C(N)=O)c3)cc2)n(Cc2ccc(Cl)cn2)c1=O] | I-2237 | 1.81 | 494 | 3 |
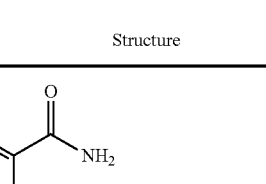

TABLE 451-continued
| Structure | Compound No. | Retention Time (min) | [M + H] | Method |
|---|---|---|---|---|
| 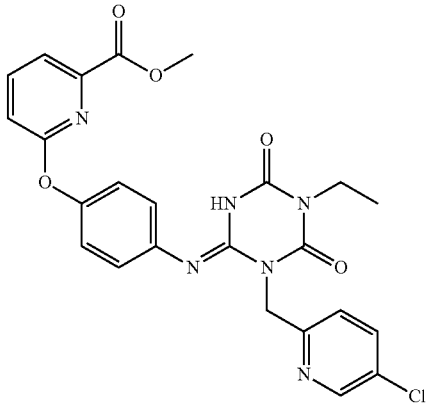 [SMILES: CCn1c(=O)[nH]/c(=N\c2ccc(Oc3cccc(C(=O)OC)n3)cc2)n(Cc2ccc(Cl)cn2)c1=O] | I-2238 | 2.11 | 509 | 3 |
| 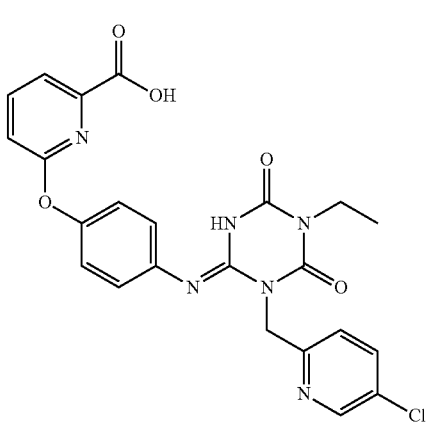 [SMILES: CCn1c(=O)[nH]/c(=N\c2ccc(Oc3cccc(C(=O)O)n3)cc2)n(Cc2ccc(Cl)cn2)c1=O] | I-2239 | 1.90 | 495 | 3 |
| 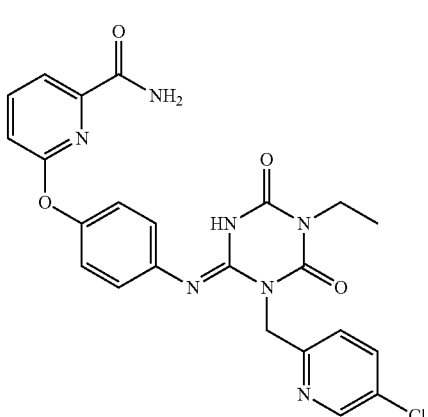 | I-2240 | 1.84 | 494 | 3 |

TABLE 452

| Structure | Compound No. | Retention Time (min) | [M + H] | Method |
|---|---|---|---|---|
| 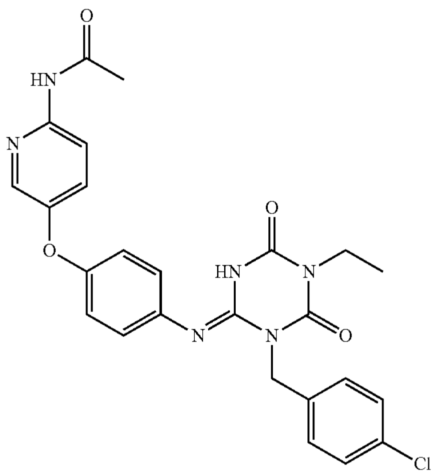 [SMILES: CCn1c(=O)[nH]/c(=N\c2ccc(Oc3ccc(NC(C)=O)nc3)cc2)n(Cc2ccc(Cl)cc2)c1=O] | I-2241 | 1.87 | 507 | 2 |
| 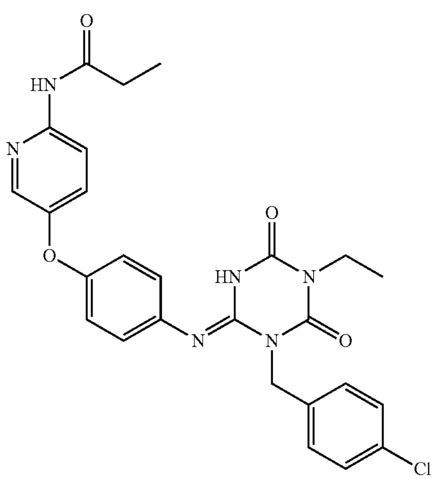 [SMILES: CCC(=O)Nc1ccc(Oc2ccc(/N=c3\[nH]c(=O)n(CC)c(=O)n3Cc3ccc(Cl)cc3)cc2)cn1] | I-2242 | 1.97 | 521 | 2 |
| 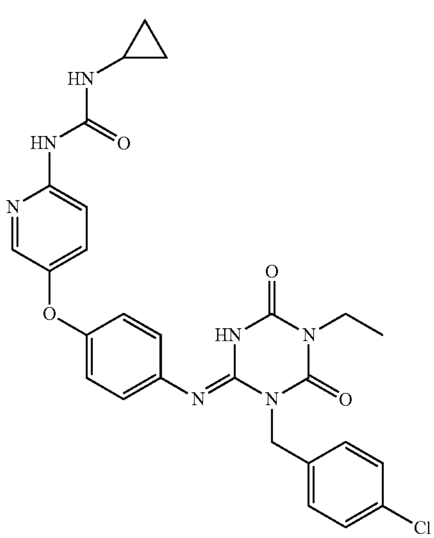 [SMILES: CCn1c(=O)[nH]/c(=N\c2ccc(Oc3ccc(NC(=O)NC4CC4)nc3)cc2)n(Cc2ccc(Cl)cc2)c1=O] | I-2243 | 1.95 | 548 | 2 |

TABLE 452-continued

| Structure | Compound No. | Retention Time (min) | [M + H] | Method |
|---|---|---|---|---|
| 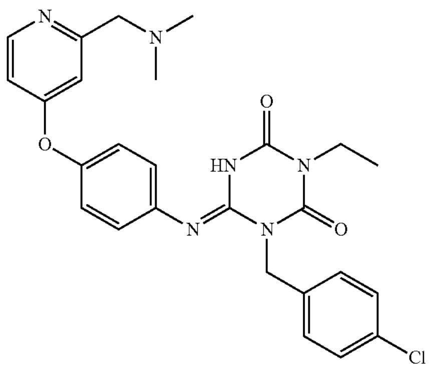 [SMILES: CCn1c(=O)[nH]/c(=N\c2ccc(Oc3ccnc(CN(C)C)c3)cc2)n(Cc2ccc(Cl)cc2)c1=O] | I-2244 | 1.34 | 507 | 2 |
| 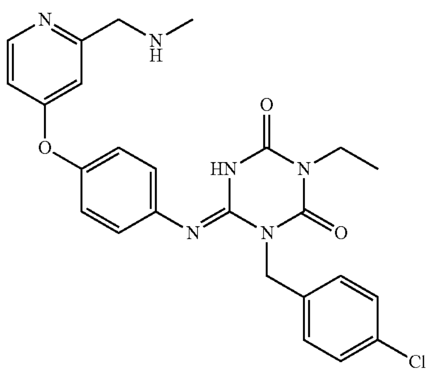 [SMILES: CCn1c(=O)[nH]/c(=N\c2ccc(Oc3ccnc(CNC)c3)cc2)n(Cc2ccc(Cl)cc2)c1=O] | I-2245 | 1.35 | 493 | 2 |

TABLE 453

| Structure | Compound No. | Retention Time (min) | [M + H] | Method |
|---|---|---|---|---|
| 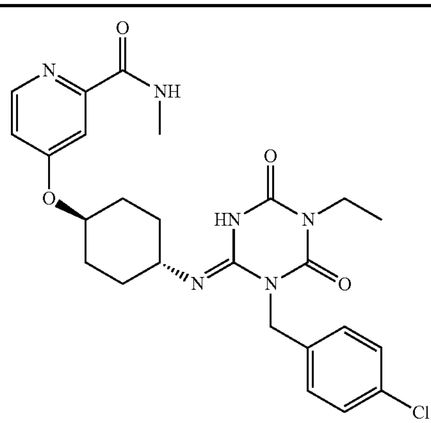 | I-2246 | 1.92 | 513 | 3 |

TABLE 453-continued

| Structure | Compound No. | Retention Time (min) | [M + H] | Method |
|---|---|---|---|---|
| 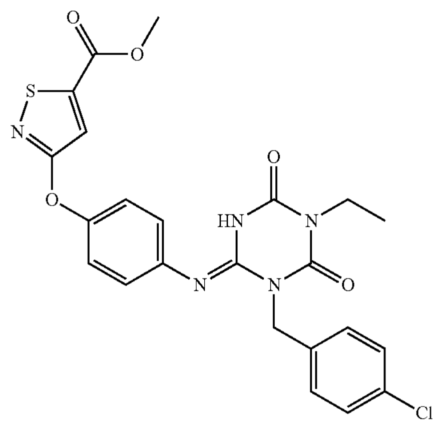 [SMILES: CCn1c(=O)[nH]/c(=N\c2ccc(Oc3cc(C(=O)OC)sn3)cc2)n(Cc2ccc(Cl)cc2)c1=O] | I-2247 | 2.48 | 514 | 5 |
| 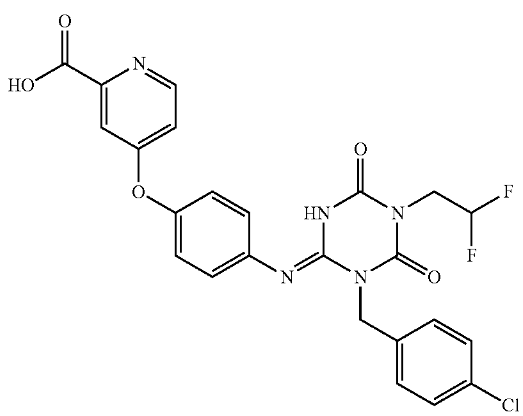 [SMILES: O=C(O)c1cc(Oc2ccc(/N=c3\[nH]c(=O)n(CC(F)F)c(=O)n3Cc3ccc(Cl)cc3)cc2)ccn1] | I-2248 | 1.57 | 530 | 2 |
| 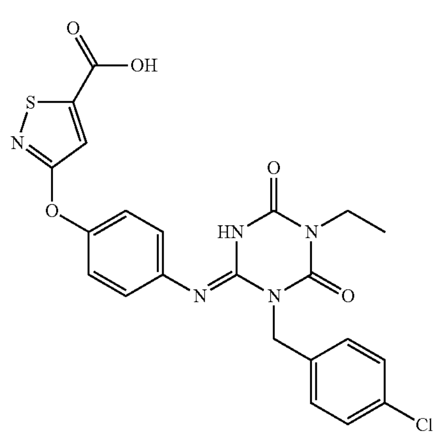 [SMILES: CCn1c(=O)[nH]/c(=N\c2ccc(Oc3cc(C(=O)O)sn3)cc2)n(Cc2ccc(Cl)cc2)c1=O] | I-2249 | 2.21 | 500 | 3 |

TABLE 453-continued

| Structure | Compound No. | Retention Time (min) | [M + H] | Method |
|---|---|---|---|---|
| 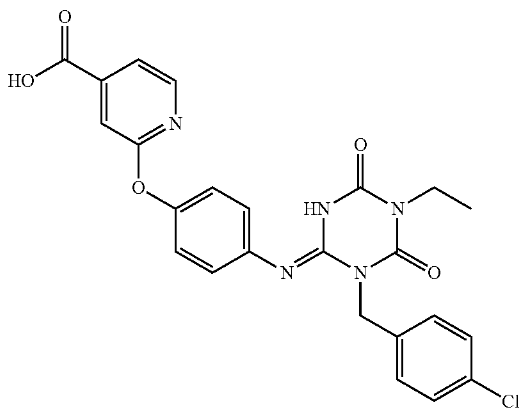 | I-2250 | 2.11 | 494 | 3 |

TABLE 454

| Structure | Compound No. | Retention Time (min) | [M + H] | Method |
|---|---|---|---|---|
| 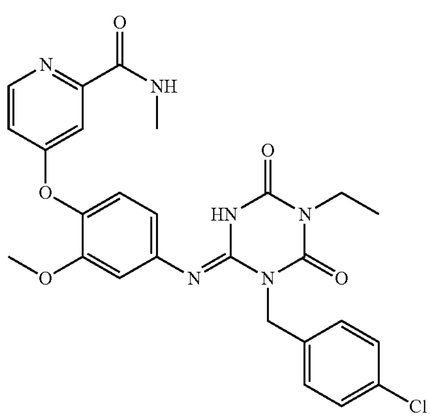 [SMILES: CCn1c(=O)[nH]/c(=N\c2ccc(Oc3ccnc(C(=O)NC)c3)c(OC)c2)n(Cc2ccc(Cl)cc2)c1=O] | I-2251 | 2.26 | 537 | 3 |
| 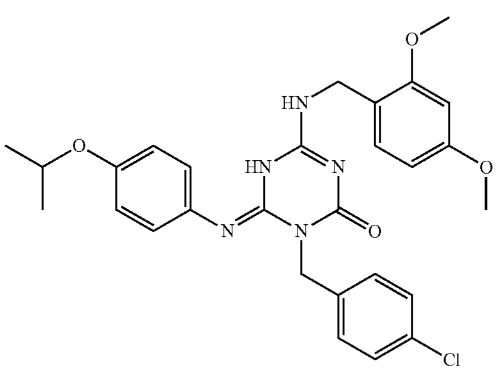 [SMILES: COc1ccc(CNc2nc(=O)n(Cc3ccc(Cl)cc3)/c(=N/c3ccc(OC(C)C)cc3)[nH]2)c(OC)c1] | I-2252 | 1.92 | 536 | 3 |

TABLE 454-continued
| Structure | Compound No. | Retention Time (min) | [M + H] | Method |
|---|---|---|---|---|
| 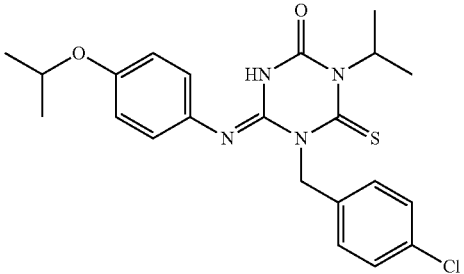 [SMILES: CC(C)Oc1ccc(/N=c2\[nH]c(=O)n(C(C)C)c(=S)n2Cc2ccc(Cl)cc2)cc1] | I-2253 | 2.92 | 445 | 3 |
| 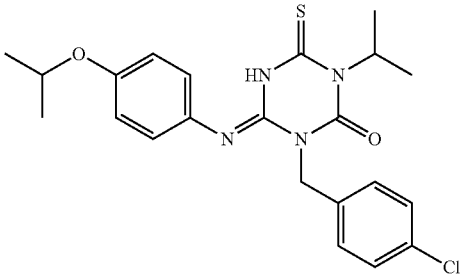 | I-2254 | 2.84 | 445 | 3 |
| 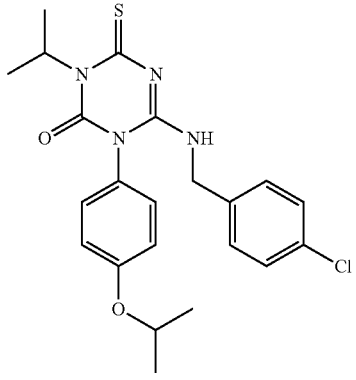 [SMILES: CC(C)Oc1ccc(-n2c(NCc3ccc(Cl)cc3)nc(=S)n(C(C)C)c2=O)cc1] | I-2255 | 2.58 | 445 | 3 |
TABLE 455
| Structure | Compound No. | Retention Time (min) | [M + H] | Method |
|---|---|---|---|---|
| 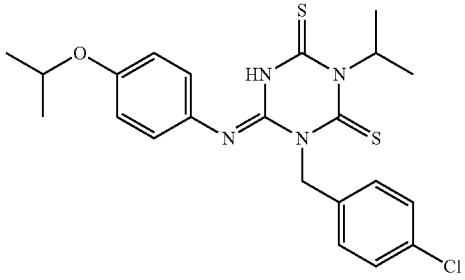 [SMILES: CC(C)Oc1ccc(/N=c2\[nH]c(=S)n(C(C)C)c(=S)n2Cc2ccc(Cl)cc2)cc1] | I-2256 | 3.08 | 461 | 3 |

TABLE 455-continued

| Structure | Compound No. | Retention Time (min) | [M + H] | Method |
|---|---|---|---|---|
| 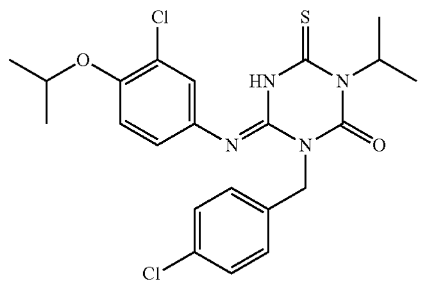 [SMILES: CC(C)Oc1ccc(/N=c2\[nH]c(=S)n(C(C)C)c(=O)n2Cc2ccc(Cl)cc2)cc1Cl] | I-2257 | 3.00 | 479 | 3 |
| 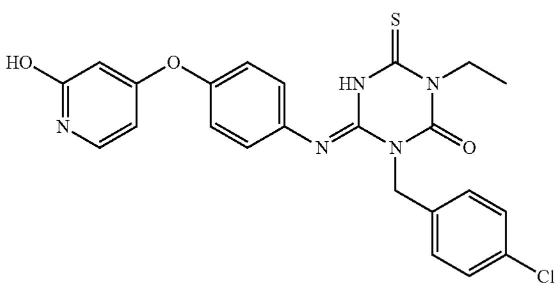 [SMILES: CCn1c(=S)[nH]/c(=N\c2ccc(Oc3ccnc(O)c3)cc2)n(Cc2ccc(Cl)cc2)c1=O] | I-2258 | 2.15 | 482 | 3 |
| 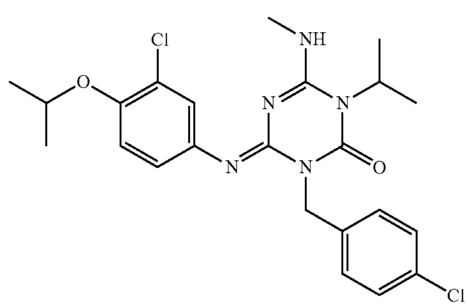 [SMILES: CNc1n/c(=N\c2ccc(OC(C)C)c(Cl)c2)n(Cc2ccc(Cl)cc2)c(=O)n1C(C)C] | I-2259 | 1.80 | 476 | 3 |
| 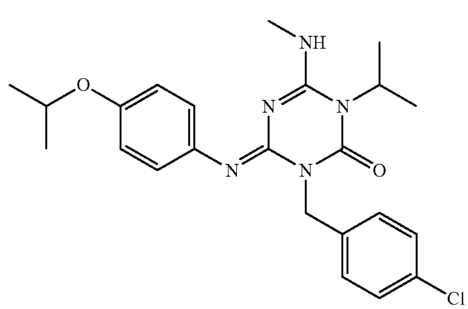 [SMILES: CNc1n/c(=N\c2ccc(OC(C)C)cc2)n(Cc2ccc(Cl)cc2)c(=O)n1C(C)C] | I-2260 | 1.73 | 442 | 3 |

TABLE 456

| Structure | Compound No. | Retention Time (min) | [M + H] | Method |
|---|---|---|---|---|
| 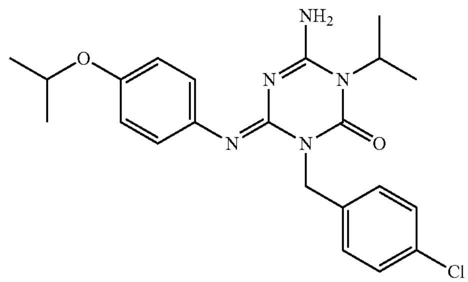 [SMILES: CC(C)Oc1ccc(/N=c2\nc(N)n(C(C)C)c(=O)n2Cc2ccc(Cl)cc2)cc1] | I-2261 | 1.65 | 428 | 3 |
| 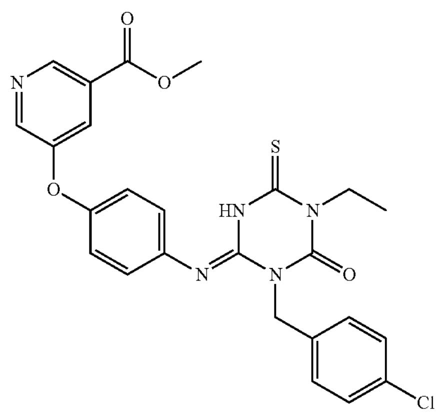 [SMILES: CCn1c(=S)[nH]/c(=N\c2ccc(Oc3cncc(C(=O)OC)c3)cc2)n(Cc2ccc(Cl)cc2)c1=O] | I-2262 | 2.59 | 524 | 3 |
| 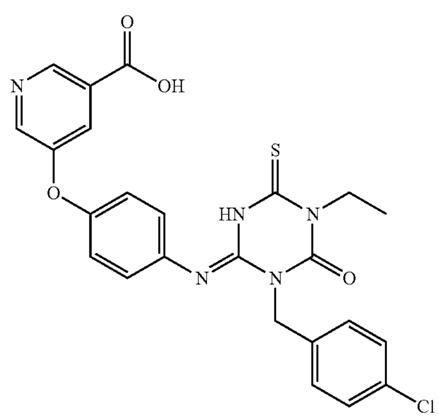 [SMILES: CCn1c(=S)[nH]/c(=N\c2ccc(Oc3cncc(C(=O)O)c3)cc2)n(Cc2ccc(Cl)cc2)c1=O] | I-2263 | 2.28 | 510 | 3 |
| 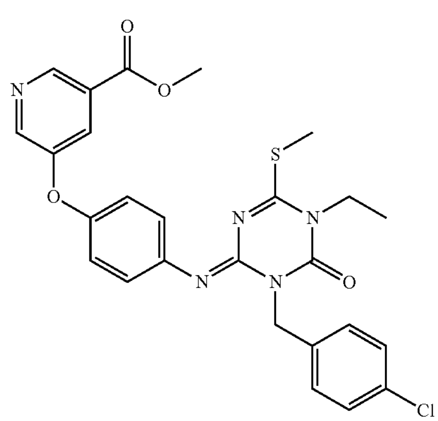 [SMILES: CCn1c(SC)n/c(=N\c2ccc(Oc3cncc(C(=O)OC)c3)cc2)n(Cc2ccc(Cl)cc2)c1=O] | I-2264 | 2.79 | 538 | 3 |

TABLE 456-continued

| Structure | Compound No. | Retention Time (min) | [M + H] | Method |
|---|---|---|---|---|
| 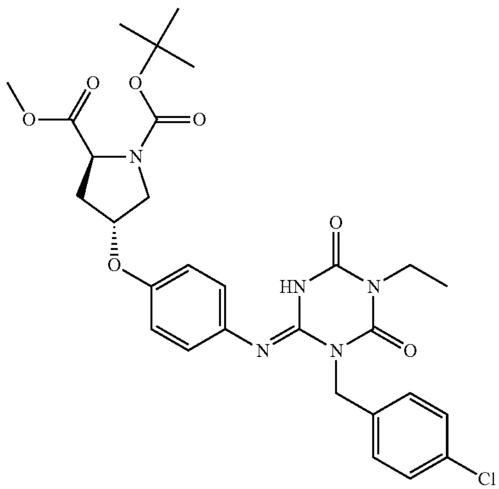 [SMILES: CCn1c(=O)[nH]/c(=N\c2ccc(O[C@@H]3C[C@@H](C(=O)OC)N(C(=O)OC(C)(C)C)C3)cc2)n(Cc2ccc(Cl)cc2)c1=O] | I-2265 | 2.46 | 600 | 3 |

TABLE 457

| Structure | Compound No. | Retention Time (min) | [M + H] | Method |
|---|---|---|---|---|
| 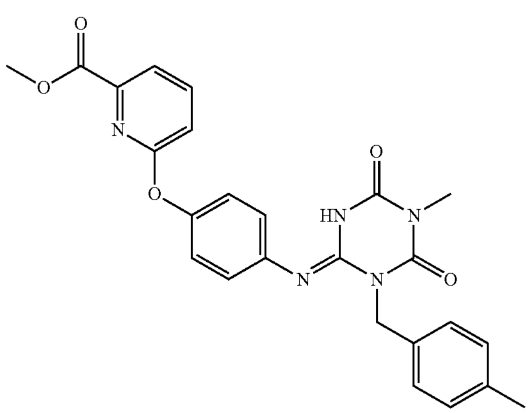 | I-2266 | 2.13 | 474 | 3 |
| 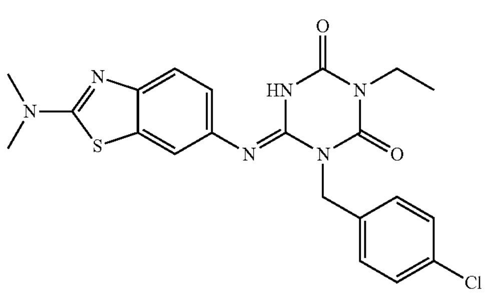 [SMILES: CCn1c(=O)[nH]/c(=N\c2ccc3nc(N(C)C)sc3c2)n(Cc2ccc(Cl)cc2)c1=O] | I-2267 | 1.80 | 457 | 2 |

TABLE 457-continued

| Structure | Compound No. | Retention Time (min) | [M + H] | Method |
|---|---|---|---|---|
| 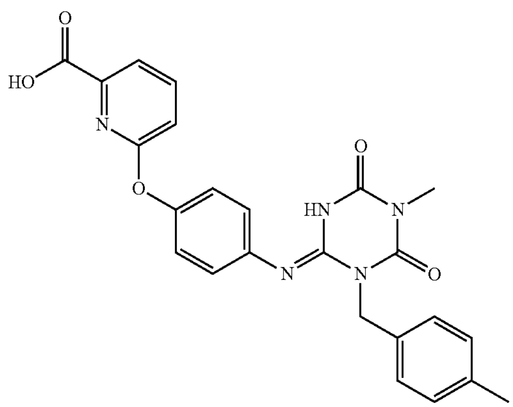 [SMILES: Cc1ccc(Cn2c(=O)n(C)c(=O)[nH]/c2=N\c2ccc(Oc3cccc(C(=O)O)n3)cc2)cc1] | I-2268 | 1.92 | 460 | 3 |
| 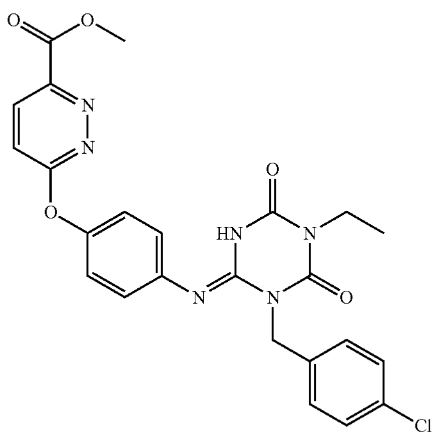 [SMILES: CCn1c(=O)[nH]/c(=N\c2ccc(Oc3ccc(C(=O)OC)nn3)cc2)n(Cc2ccc(Cl)cc2)c1=O] | I-2269 | 2.18 | 509 | 3 |
| 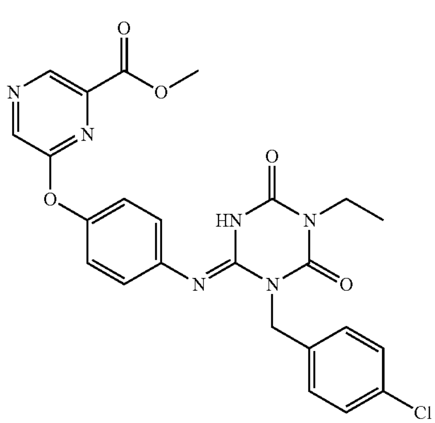 [SMILES: CCn1c(=O)[nH]/c(=N\c2ccc(Oc3cncc(C(=O)OC)n3)cc2)n(Cc2ccc(Cl)cc2)c1=O] | I-2270 | 2.30 | 509 | 3 |

TABLE 458

| Structure | Compound No. | Retention Time (min) | [M + H] | Method |
|---|---|---|---|---|
| (structure) | I-2271 | 2.25 | 494 | 3 |
| (structure) | I-2272 | 2.03 | 480 | 3 |
| (structure) | I-2273 | 2.02 | 495 | 3 |

TABLE 458-continued
| Structure | Compound No. | Retention Time (min) | [M + H] | Method |
|---|---|---|---|---|
| 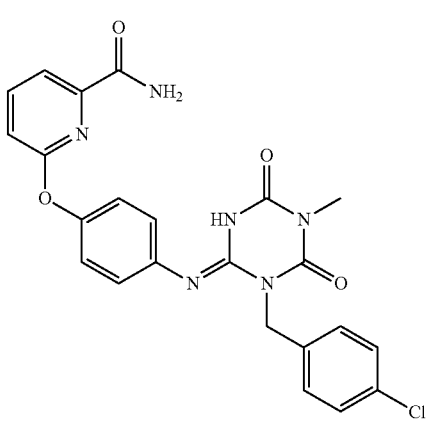 [SMILES: Cn1c(=O)[nH]/c(=N\c2ccc(Oc3cccc(C(N)=O)n3)cc2)n(Cc2ccc(Cl)cc2)c1=O] | I-2274 | 1.93 | 479 | 3 |
| 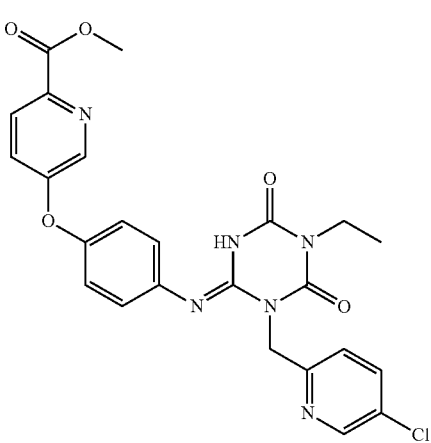 [SMILES: CCn1c(=O)[nH]/c(=N\c2ccc(Oc3ccc(C(=O)OC)nc3)cc2)n(Cc2ccc(Cl)cn2)c1=O] | I-2275 | 1.98 | 509 | 3 |
TABLE 459
| Structure | Compound No. | Retention Time (min) | [M + H] | Method |
|---|---|---|---|---|
| 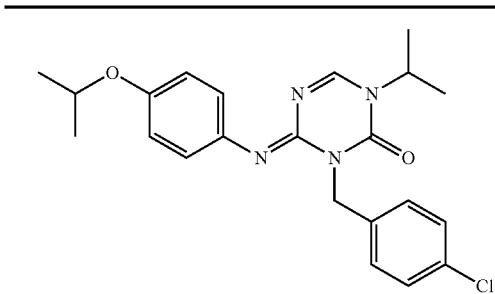 | I-2276 | 2.65 | 413 | 3 |

TABLE 459-continued

| Structure | Compound No. | Retention Time (min) | [M + H] | Method |
|---|---|---|---|---|
| 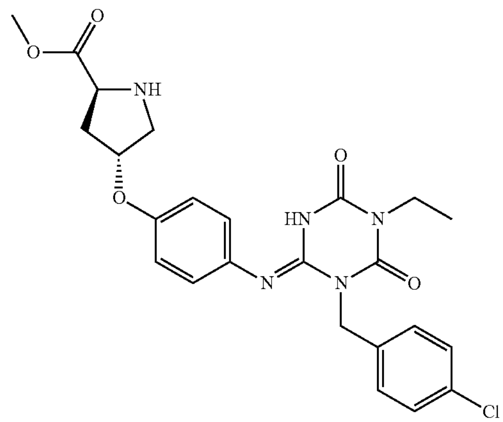 [SMILES: CCn1c(=O)[nH]/c(=N\c2ccc(O[C@H]3CN[C@H](C(=O)OC)C3)cc2)n(Cc2ccc(Cl)cc2)c1=O] | I-2277 | 1.38 | 500 | 3 |
| 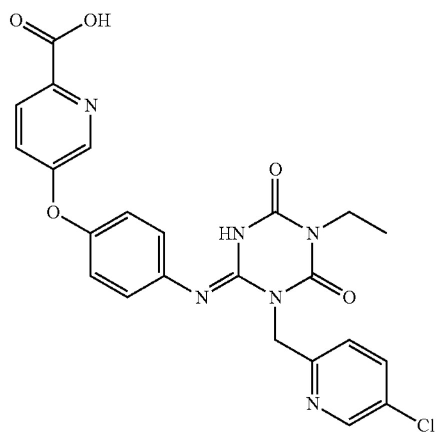 [SMILES: CCn1c(=O)[nH]/c(=N\c2ccc(Oc3ccc(C(=O)O)nc3)cc2)n(Cc2ccc(Cl)cn2)c1=O] | I-2278 | 1.75 | 495 | 3 |
| 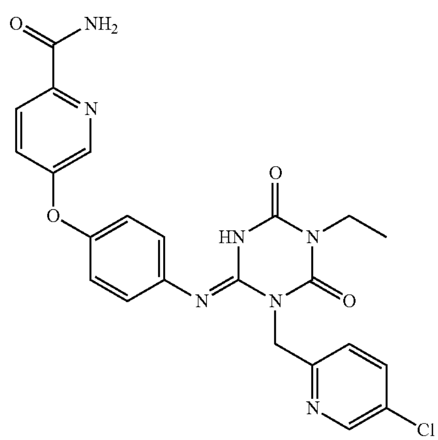 [SMILES: CCn1c(=O)[nH]/c(=N\c2ccc(Oc3ccc(C(N)=O)nc3)cc2)n(Cc2ccc(Cl)cn2)c1=O] | I-2279 | 1.81 | 494 | 3 |
| 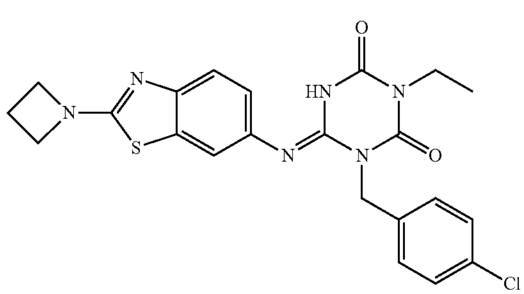 [SMILES: CCn1c(=O)[nH]/c(=N\c2ccc3nc(N4CCC4)sc3c2)n(Cc2ccc(Cl)cc2)c1=O] | I-2280 | 1.86 | 469 | 2 |

TABLE 460

| Structure | Compound No. | Retention Time (min) | [M + H] | Method |
|---|---|---|---|---|
| 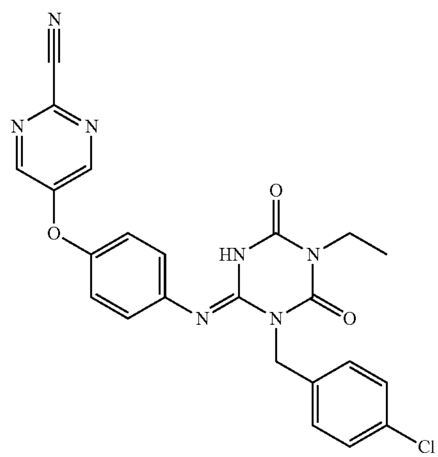 [SMILES: CCn1c(=O)[nH]/c(=N\c2ccc(Oc3cnc(C#N)nc3)cc2)n(Cc2ccc(Cl)cc2)c1=O] | I-2281 | 2.35 | 476 | 3 |
| 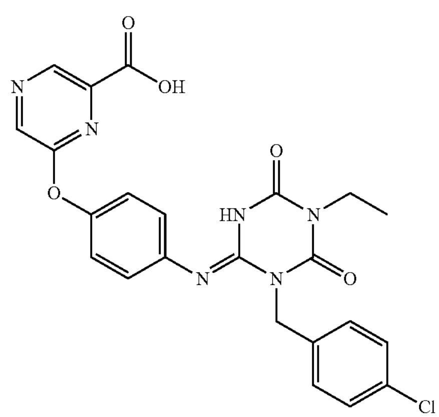 [SMILES: CCn1c(=O)[nH]/c(=N\c2ccc(Oc3cncc(C(=O)O)n3)cc2)n(Cc2ccc(Cl)cc2)c1=O] | I-2282 | 2.09 | 495 | 3 |
| 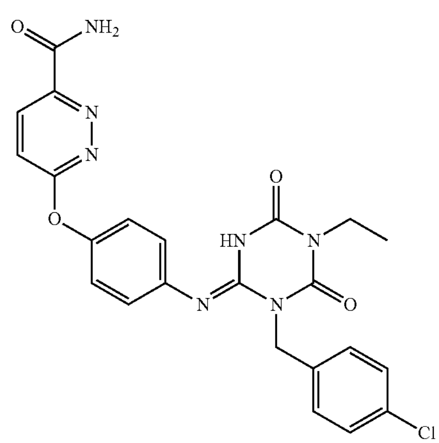 [SMILES: CCn1c(=O)[nH]/c(=N\c2ccc(Oc3ccc(C(N)=O)nn3)cc2)n(Cc2ccc(Cl)cc2)c1=O] | I-2283 | 1.99 | 494 | 3 |

TABLE 460-continued

| Structure | Compound No. | Retention Time (min) | [M + H] | Method |
|---|---|---|---|---|
| 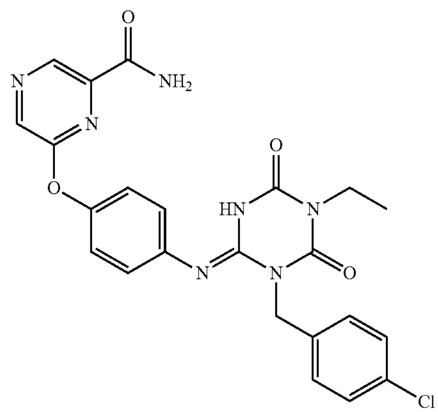 [SMILES: CCn1c(=O)[nH]/c(=N\c2ccc(Oc3cncc(C(N)=O)n3)cc2)n(Cc2ccc(Cl)cc2)c1=O] | I-2284 | 1.96 | 494 | 3 |
| 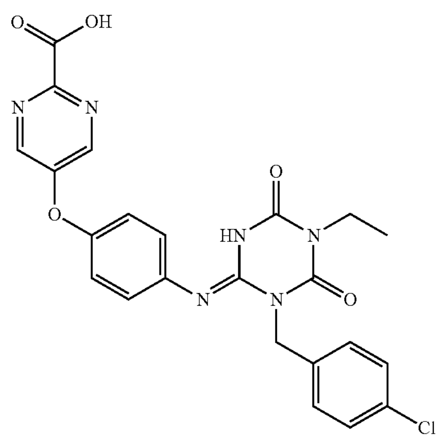 | I-2285 | 1.90 | 495 | 3 |

TABLE 461

| Structure | Compound No. | Retention Time (min) | [M + H] | Method |
|---|---|---|---|---|
| 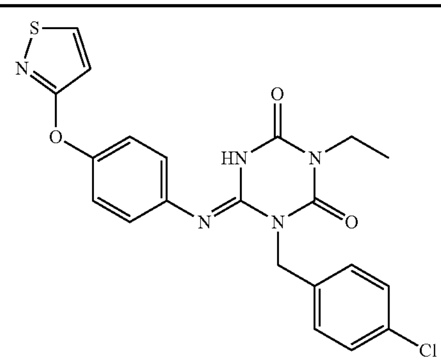 | I-2286 | 2.24 | 456 | 2 |

TABLE 461-continued

| Structure | Compound No. | Retention Time (min) | [M + H] | Method |
|---|---|---|---|---|
| 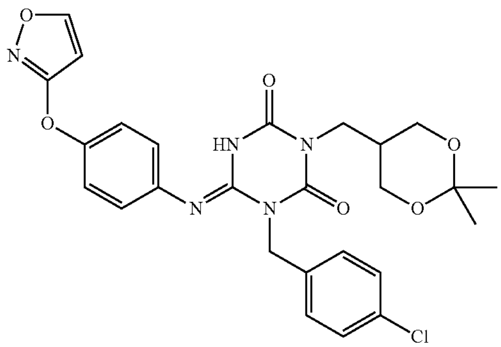 [SMILES: CC1(C)OCC(Cn2c(=O)[nH]/c(=N\c3ccc(Oc4ccon4)cc3)n(Cc3ccc(Cl)cc3)c2=O)CO1] | I-2287 | 2.16 | 540 | 2 |
| 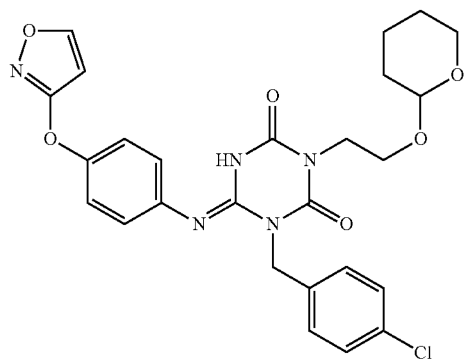 [SMILES: O=c1[nH]/c(=N\c2ccc(Oc3ccon3)cc2)n(Cc2ccc(Cl)cc2)c(=O)n1CCOC1CCCCO1] | I-2288 | 2.24 | 540 | 2 |
| 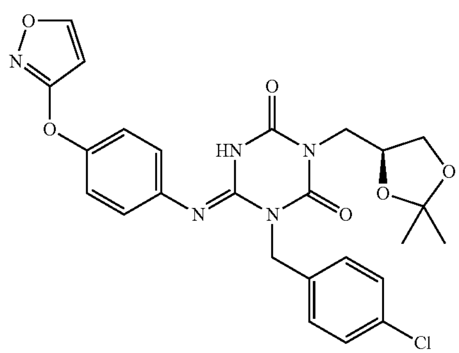 [SMILES: CC1(C)OC[C@H](Cn2c(=O)[nH]/c(=N\c3ccc(Oc4ccon4)cc3)n(Cc3ccc(Cl)cc3)c2=O)O1] | I-2289 | 2.19 | 526 | 2 |
| 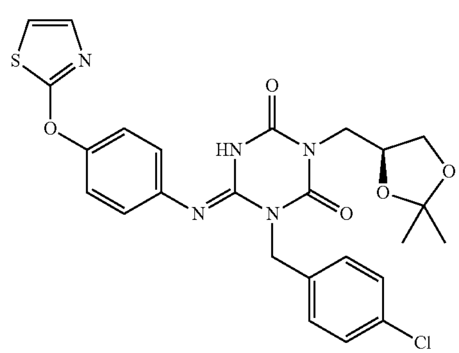 [SMILES: CC1(C)OC[C@H](Cn2c(=O)[nH]/c(=N\c3ccc(Oc4nccs4)cc3)n(Cc3ccc(Cl)cc3)c2=O)O1] | I-2290 | 2.27 | 542 | 2 |

TABLE 462

| Structure | Compound No | Retention Time (min) | [M + H] | Method |
|---|---|---|---|---|
| (isoxazol-3-yloxyphenyl)imino triazinedione with N-(2,3-dihydroxypropyl) and N-(4-chlorobenzyl) | I-2291 | 1.71 | 500 | 2 |
| (isoxazol-3-yloxyphenyl)imino triazinedione with N-(2-hydroxyethyl) and N-(4-chlorobenzyl) | I-2292 | 1.80 | 456 | 2 |
| (isoxazol-3-yloxyphenyl)imino triazinedione with N-((S)-2,3-dihydroxypropyl) and N-(4-chlorobenzyl) | I-2293 | 1.68 | 486 | 2 |
| (thiazol-2-yloxyphenyl)imino triazinedione with N-((S)-2,3-dihydroxypropyl) and N-(4-chlorobenzyl) | I-2294 | 1.77 | 502 | 2 |

TABLE 462-continued

| Structure | Compound No | Retention Time (min) | [M + H] | Method |
|---|---|---|---|---|
| 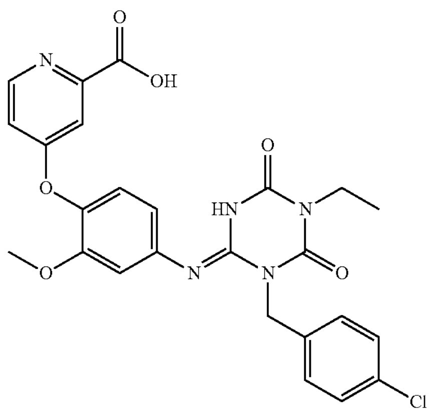 [SMILES: CCn1c(=O)[nH]/c(=N\c2ccc(Oc3ccnc(C(=O)O)c3)c(OC)c2)n(Cc2ccc(Cl)cc2)c1=O] | I-2295 | 1.68 | 524 | 2 |

TABLE 463

| Structure | Compound No. | Retention Time (min) | [M + H] | Method |
|---|---|---|---|---|
| 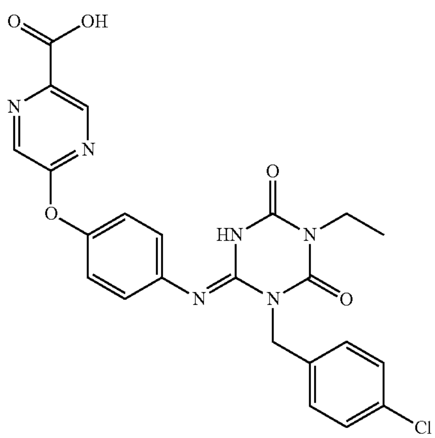 [SMILES: CCn1c(=O)[nH]/c(=N\c2ccc(Oc3cnc(C(=O)O)cn3)cc2)n(Cc2ccc(Cl)cc2)c1=O] | I-2296 | 1.97 | 495 | 2 |
| 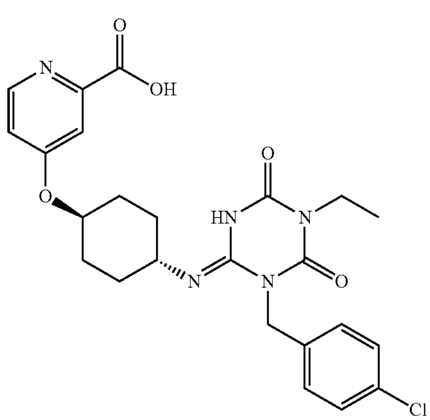 [SMILES: CCn1c(=O)[nH]/c(=N\[C@H]2CC[C@H](Oc3ccnc(C(=O)O)c3)CC2)n(Cc2ccc(Cl)cc2)c1=O] | I-2297 | 1.42 | 500 | 2 |

TABLE 463-continued

| Structure | Compound No. | Retention Time (min) | [M + H] | Method |
|---|---|---|---|---|
| 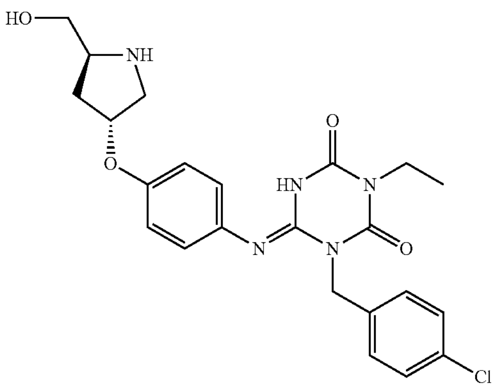 [SMILES: CCn1c(=O)[nH]/c(=N\c2ccc(O[C@H]3CN[C@H](CO)C3)cc2)n(Cc2ccc(Cl)cc2)c1=O] | I-2298 | 1.34 | 472 | 3 |
| 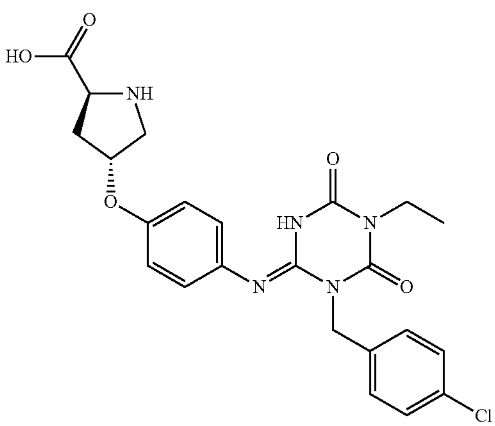 [SMILES: CCn1c(=O)[nH]/c(=N\c2ccc(O[C@H]3CN[C@H](C(=O)O)C3)cc2)n(Cc2ccc(Cl)cc2)c1=O] | I-2299 | 1.42 | 486 | 2 |

TABLE 464

| Structure | Compound No. | Retention Time (min) | [M + H] | Method |
|---|---|---|---|---|
| 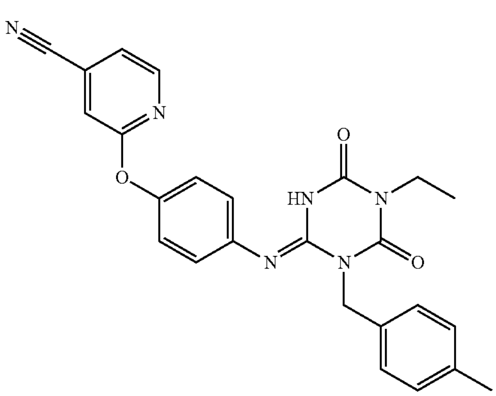 [SMILES: CCn1c(=O)[nH]/c(=N\c2ccc(Oc3cc(C#N)ccn3)cc2)n(Cc2ccc(C)cc2)c1=O] | I-2300 | 2.28 | 455 | 3 |

TABLE 464-continued

| Structure | Compound No. | Retention Time (min) | [M + H] | Method |
|---|---|---|---|---|
| 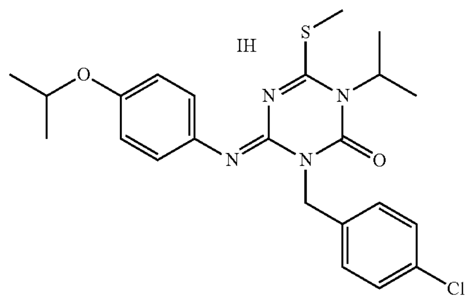 | I-2301 | 2.54 | 459 | 3 |
| 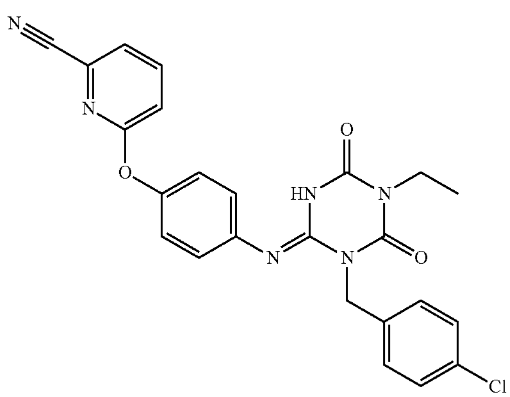 [SMILES: CCn1c(=O)[nH]/c(=N\c2ccc(Oc3cccc(C#N)n3)cc2)n(Cc2ccc(Cl)cc2)c1=O] | I-2302 | 2.35 | 475 | 3 |
| 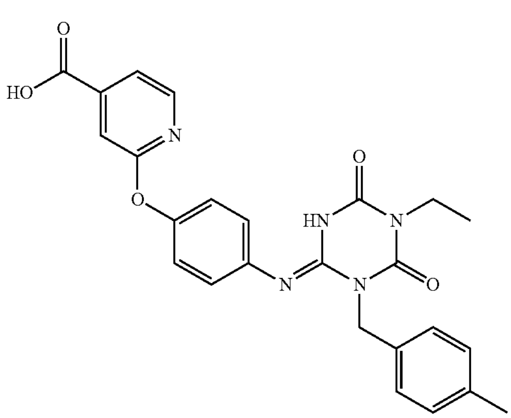 [SMILES: CCn1c(=O)[nH]/c(=N\c2ccc(Oc3cc(C(=O)O)ccn3)cc2)n(Cc2ccc(C)cc2)c1=O] | I-2303 | 2.02 | 474 | 3 |

TABLE 465

| Structure | Compound No. | Retention Time (min) | [M + H] | Method |
|---|---|---|---|---|
| 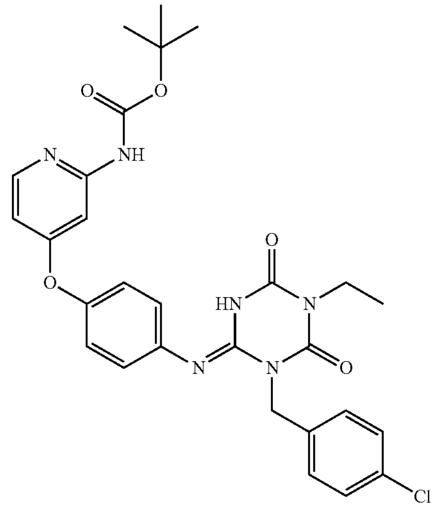 [SMILES: CCn1c(=O)[nH]/c(=N\c2ccc(Oc3ccnc(NC(=O)OC(C)(C)C)c3)cc2)n(Cc2ccc(Cl)cc2)c1=O] | I-2304 | 2.17 | 565 | 2 |
| 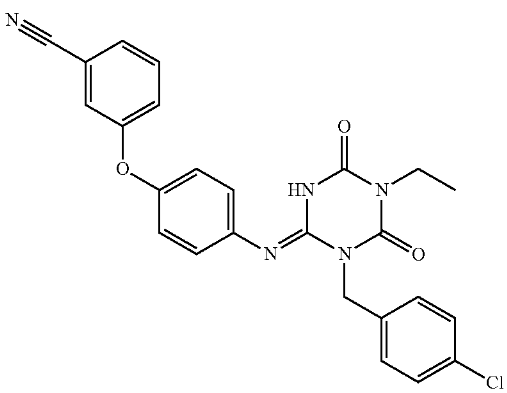 [SMILES: CCn1c(=O)[nH]/c(=N\c2ccc(Oc3cccc(C#N)c3)cc2)n(Cc2ccc(Cl)cc2)c1=O] | I-2305 | 2.49 | 474 | 3 |
| 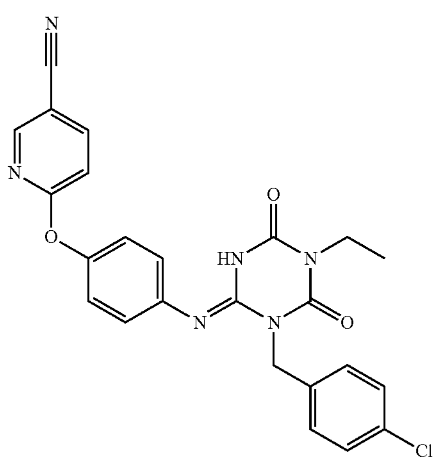 [SMILES: CCn1c(=O)[nH]/c(=N\c2ccc(Oc3ccc(C#N)cn3)cc2)n(Cc2ccc(Cl)cc2)c1=O] | I-2306 | 2.34 | 475 | 3 |

TABLE 465-continued

| Structure | Compound No. | Retention Time (min) | [M + H] | Method |
|---|---|---|---|---|
| 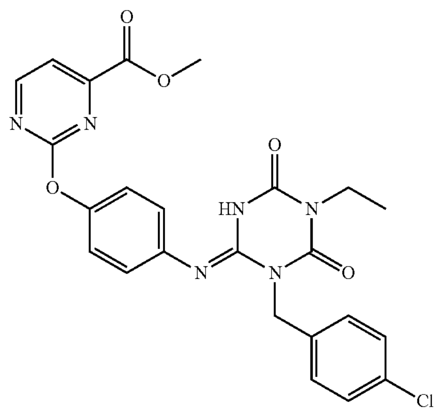 [SMILES: CCn1c(=O)[nH]/c(=N\c2ccc(Oc3nccc(C(=O)OC)n3)cc2)n(Cc2ccc(Cl)cc2)c1=O] | I-2307 | 2.2 | 409 | 3 |

TABLE 466

| Structure | Compound No. | Retention Time (min) | [M + H] | Method |
|---|---|---|---|---|
| 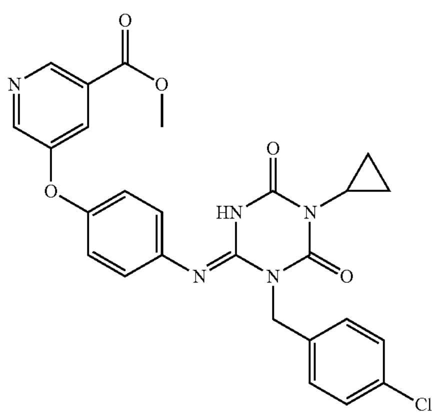 [SMILES: COC(=O)c1cncc(Oc2ccc(/N=c3\[nH]c(=O)n(C4CC4)c(=O)n3Cc3ccc(Cl)cc3)cc2)c1] | I-2308 | 2.09 | 520 | 2 |
| 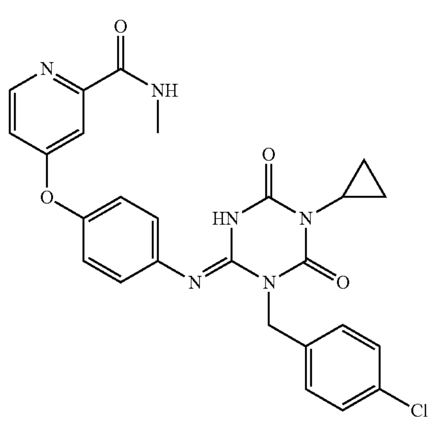 [SMILES: CNC(=O)c1cc(Oc2ccc(/N=c3\[nH]c(=O)n(C4CC4)c(=O)n3Cc3ccc(Cl)cc3)cc2)ccn1] | I-2309 | 1.99 | 519 | 2 |

TABLE 466-continued

| Structure | Compound No. | Retention Time (min) | [M + H] | Method |
|---|---|---|---|---|
| (structure of I-2310) | I-2310 | 2.28 | 476 | 3 |
| (structure of I-2311) | I-2311 | 1.94 | 494 | 3 |

TABLE 467

| Structure | Compound No. | Retention Time (min) | [M + H] | Method |
|---|---|---|---|---|
| (structure of I-2312) | I-2312 | 2.38 | 525 | 2 |
| (structure of I-2313) | I-2313 | 1.95 | 485 | 2 |

TABLE 467-continued

| Structure | Compound No. | Retention Time (min) | [M + H] | Method |
|---|---|---|---|---|
| (2-ethylbenzofuran-5-yl / 4-chlorobenzyl / 2,2-dimethyl-1,3-dioxolan-4-ylmethyl triazine) | I-2314 | 2.42 | 511 | 2 |
| (2-ethylbenzofuran-5-yl / 4-chlorobenzyl / 2,3-dihydroxypropyl triazine) | I-2315 | 2.01 | 471 | 3 |

TABLE 468

| Structure | Compound No. | Retention Time (min) | [M + H] | Method |
|---|---|---|---|---|
| (3-fluoro-4-isopropoxyphenyl / 4-chlorobenzyl / 3-(methylamino)propyl triazine) | I-2316 | 1.59 | 476 | 3 |
| (3-fluoro-4-isopropoxyphenyl / 4-chlorobenzyl / 3-(N-methylacetamido)propyl triazine) | I-2317 | 2.21 | 518 | 3 |

TABLE 468-continued

| Structure | Compound No. | Retention Time (min) | [M + H] | Method |
|---|---|---|---|---|
| 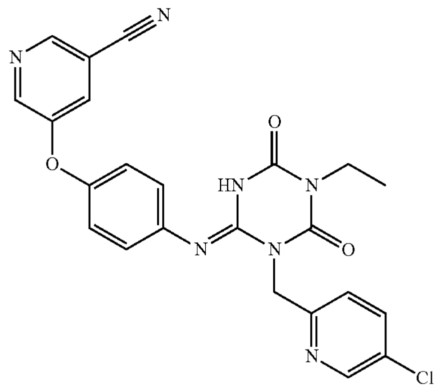 [SMILES: CCn1c(=O)[nH]/c(=N\c2ccc(Oc3cncc(C#N)c3)cc2)n(Cc2ccc(Cl)cn2)c1=O] | I-2318 | 2.04 | 476 | 3 |
| 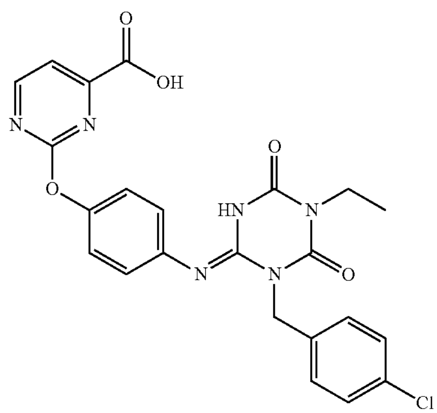 [SMILES: CCn1c(=O)[nH]/c(=N\c2ccc(Oc3nccc(C(=O)O)n3)cc2)n(Cc2ccc(Cl)cc2)c1=O] | I-2319 | 2.01 | 495 | 3 |

TABLE 469

| Structure | Compound No. | Retention Time (min) | [M + H] | Method |
|---|---|---|---|---|
| 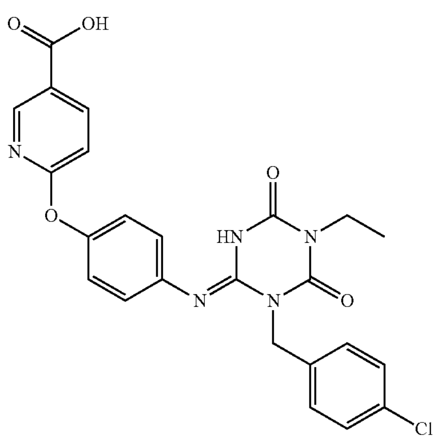 | I-2320 | 2.16 | 494 | 3 |

TABLE 469-continued

| Structure | Compound No. | Retention Time (min) | [M + H] | Method |
|---|---|---|---|---|
| 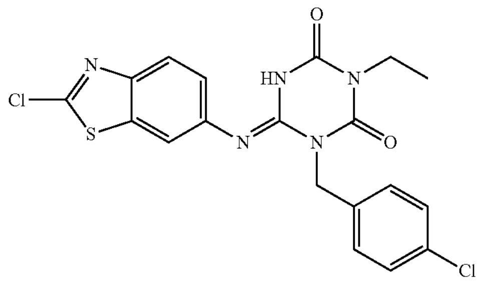 [SMILES: CCn1c(=O)[nH]/c(=N\c2ccc3nc(Cl)sc3c2)n(Cc2ccc(Cl)cc2)c1=O] | I-2321 | 2.40 | 448 | 2 |
| 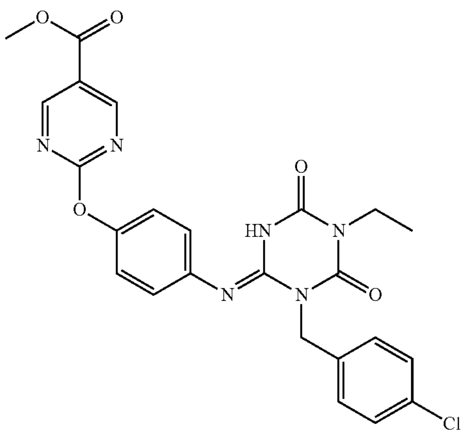 [SMILES: CCn1c(=O)[nH]/c(=N\c2ccc(Oc3ncc(C(=O)OC)cn3)cc2)n(Cc2ccc(Cl)cc2)c1=O] | I-2322 | 2.25 | 509 | 3 |
| 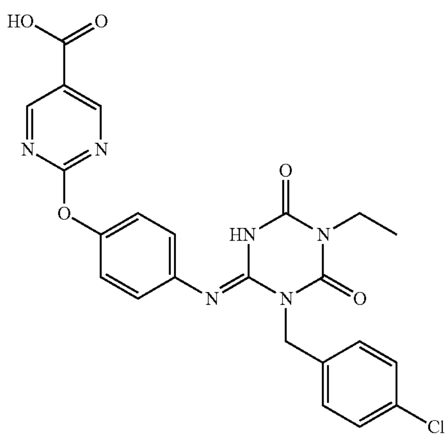 [SMILES: CCn1c(=O)[nH]/c(=N\c2ccc(Oc3ncc(C(=O)O)cn3)cc2)n(Cc2ccc(Cl)cc2)c1=O] | I-2323 | 2.03 | 495 | 3 |

TABLE 470

| Structure | Compound No. | Retention Time (min) | [M + H] | Method |
|---|---|---|---|---|
| 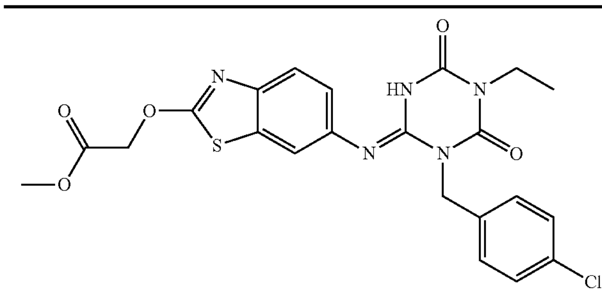 | I-2324 | 2.25 | 502 | 2 |

TABLE 470-continued

| Structure | Compound No. | Retention Time (min) | [M + H] | Method |
|---|---|---|---|---|
| 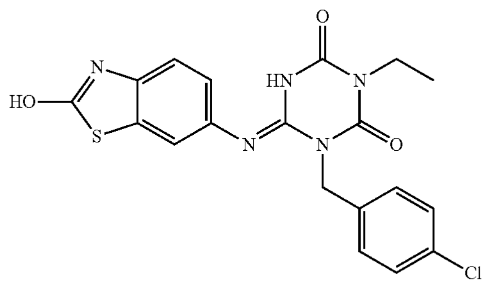 [SMILES: CCn1c(=O)[nH]/c(=N\c2ccc3nc(O)sc3c2)n(Cc2ccc(Cl)cc2)c1=O] | I-2325 | 1.90 | 430 | 2 |
| 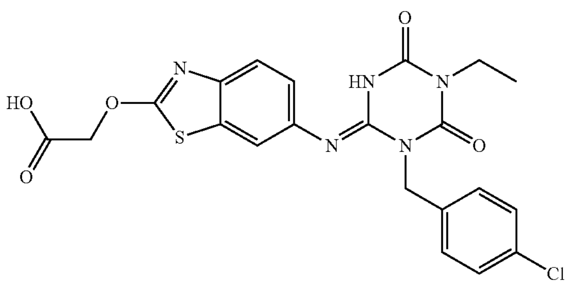 [SMILES: CCn1c(=O)[nH]/c(=N\c2ccc3nc(OCC(=O)O)sc3c2)n(Cc2ccc(Cl)cc2)c1=O] | I-2326 | 1.96 | 488 | 2 |
| 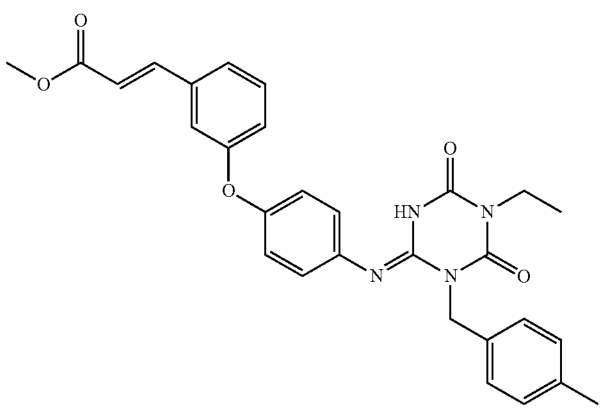 | I-2327 | 2.52 | 513 | 3 |

TABLE 471

| Structure | Compound No. | Retention Time (min) | [M + H] | Method |
|---|---|---|---|---|
| 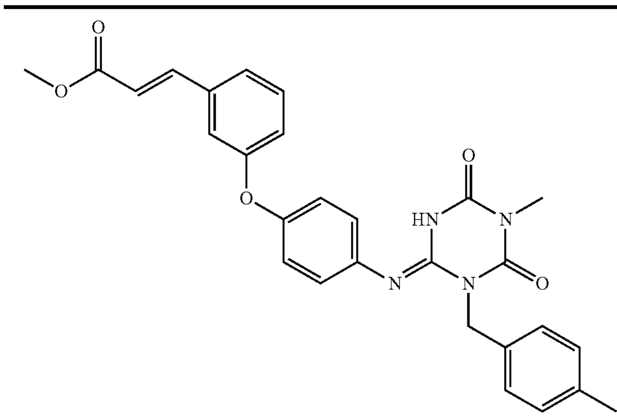 | I-2328 | 2.40 | 499 | 3 |

TABLE 471-continued

| Structure | Compound No. | Retention Time (min) | [M + H] | Method |
|---|---|---|---|---|
| 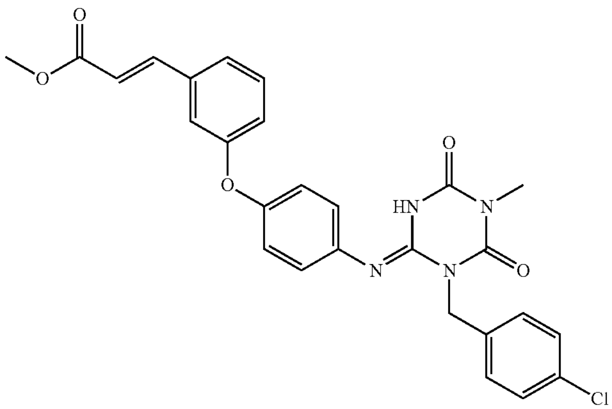 [SMILES: COC(=O)/C=C/c1cccc(Oc2ccc(/N=c3\[nH]c(=O)n(C)c(=O)n3Cc3ccc(Cl)cc3)cc2)c1] | I-2329 | 2.49 | 519 | 3 |
| 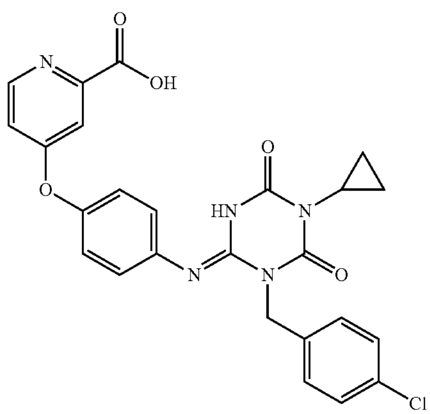 [SMILES: O=C(O)c1cc(Oc2ccc(/N=c3\[nH]c(=O)n(C4CC4)c(=O)n3Cc3ccc(Cl)cc3)cc2)ccn1] | I-2330 | 1.52 | 506 | 3 |
| 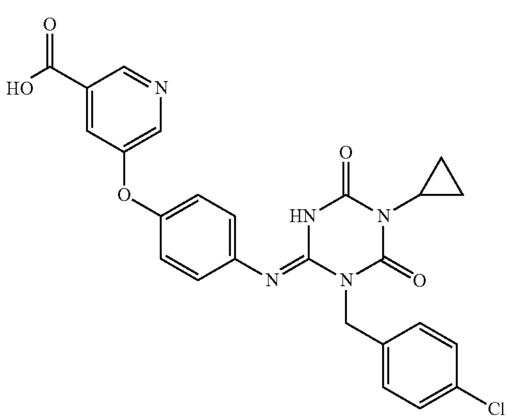 [SMILES: O=C(O)c1cncc(Oc2ccc(/N=c3\[nH]c(=O)n(C4CC4)c(=O)n3Cc3ccc(Cl)cc3)cc2)c1] | I-2331 | 1.82 | 506 | 2 |

TABLE 472

| Structure | Compound No. | Retention Time (min) | [M + H] | Method |
|---|---|---|---|---|
| 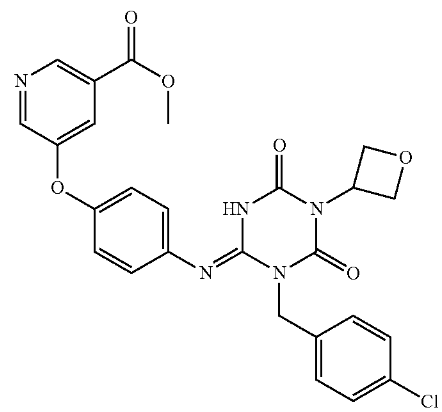 [SMILES: COC(=O)c1cncc(Oc2ccc(/N=c3\[nH]c(=O)n(C4COC4)c(=O)n3Cc3ccc(Cl)cc3)cc2)c1] | I-2332 | 2.04 | 536 | 2 |
| 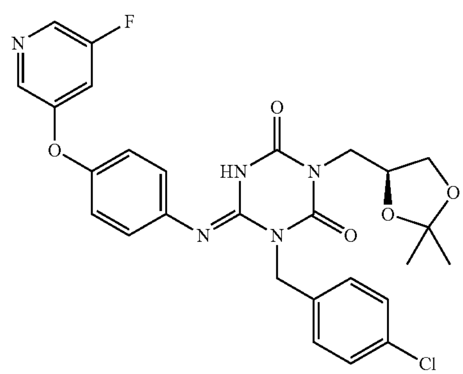 [SMILES: CC1(C)OC[C@H](Cn2c(=O)[nH]/c(=N\c3ccc(Oc4cncc(F)c4)cc3)n(Cc3ccc(Cl)cc3)c2=O)O1] | I-2333 | 2.26 | 554 | 2 |
| 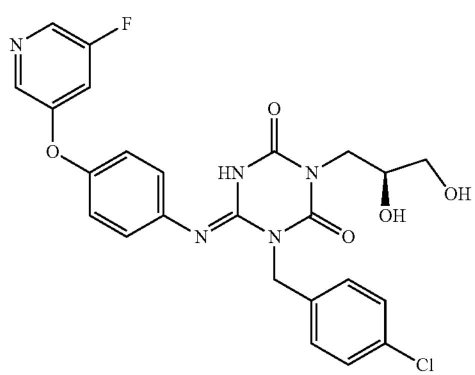 [SMILES: O=c1[nH]/c(=N\c2ccc(Oc3cncc(F)c3)cc2)n(Cc2ccc(Cl)cc2)c(=O)n1C[C@H](O)CO] | I-2334 | 1.84 | 514 | 3 |
| 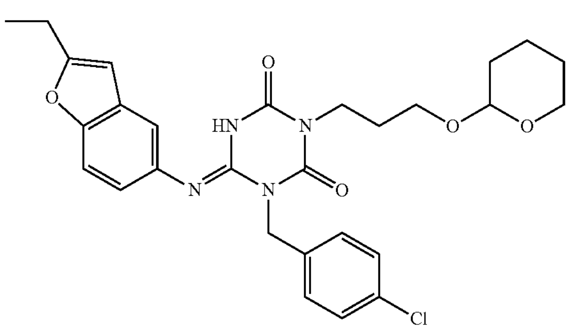 [SMILES: CCc1cc2cc(/N=c3\[nH]c(=O)n(CCCOC4CCCCO4)c(=O)n3Cc3ccc(Cl)cc3)ccc2o1] | I-2335 | 2.56 | 539 | 2 |

TABLE 473

| Structure | Compound No. | Retention Time (min) | [M + H] | Method |
|---|---|---|---|---|
| 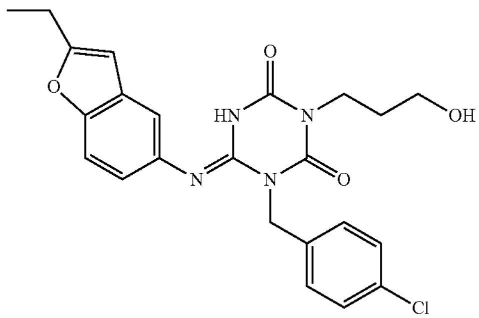 [SMILES: CCc1cc2cc(/N=c3\[nH]c(=O)n(CCCO)c(=O)n3Cc3ccc(Cl)cc3)ccc2o1] | I-2336 | 2.09 | 455 | 2 |
| 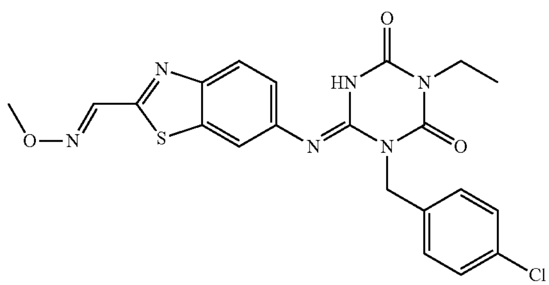 [SMILES: CCn1c(=O)[nH]/c(=N\c2ccc3nc(/C=N/OC)sc3c2)n(Cc2ccc(Cl)cc2)c1=O] | I-2337 | 2.40 | 471 | 2 |
| 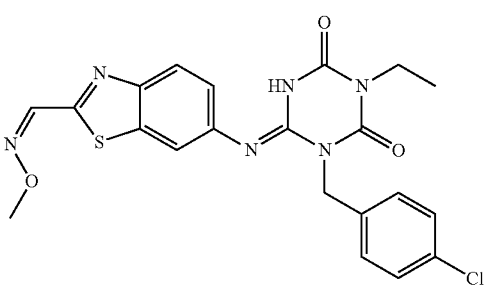 [SMILES: CCn1c(=O)[nH]/c(=N\c2ccc3nc(/C=N\OC)sc3c2)n(Cc2ccc(Cl)cc2)c1=O] | I-2338 | 2.35 | 471 | 2 |
| 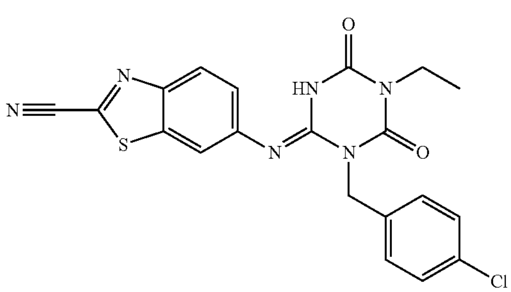 [SMILES: CCn1c(=O)[nH]/c(=N\c2ccc3nc(C#N)sc3c2)n(Cc2ccc(Cl)cc2)c1=O] | I-2339 | 2.35 | 439 | 2 |

TABLE 474
| Structure | Compound No. | Retention Time (min) | [M + H] | Method |
|---|---|---|---|---|
| 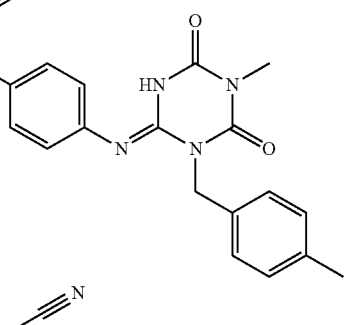 | I-2340 | 2.13 | 441 | 3 |
| 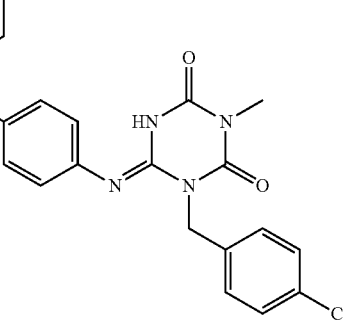 | I-2341 | 2.22 | 461 | 3 |
| 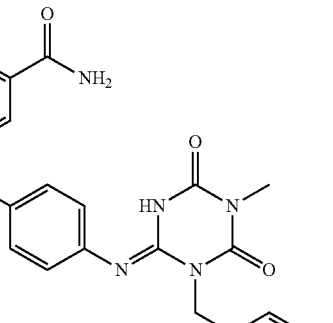 | I-2342 | 1.70 | 459 | 3 |
| 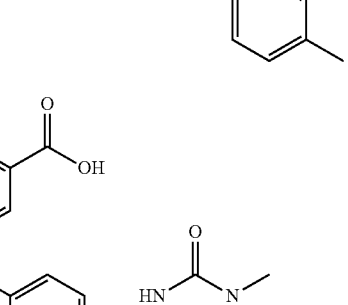 | I-2343 | 1.86 | 460 | 3 |

TABLE 475

| Structure | Compound No. | Retention Time (min) | [M + H] | Method |
|---|---|---|---|---|
| 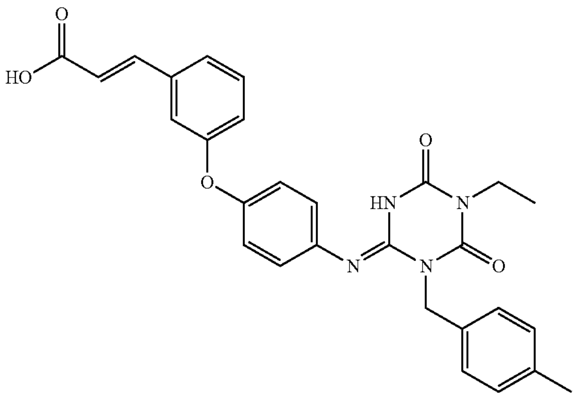 [SMILES: CCn1c(=O)[nH]/c(=N\c2ccc(Oc3cccc(/C=C/C(=O)O)c3)cc2)n(Cc2ccc(C)cc2)c1=O] | I-2344 | 2.20 | 499 | 3 |
| 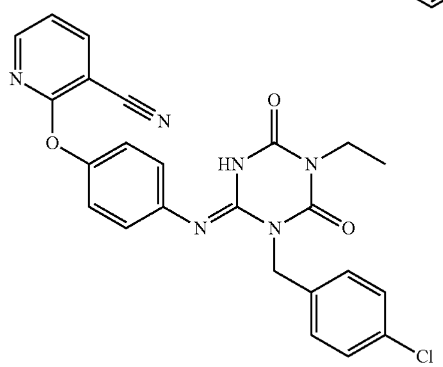 | I-2345 | 2.30 | 475 | 3 |
| 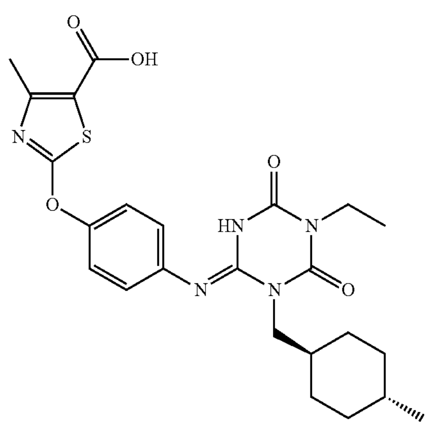 | I-2346 | 2.25 | 500 | 2 |
| 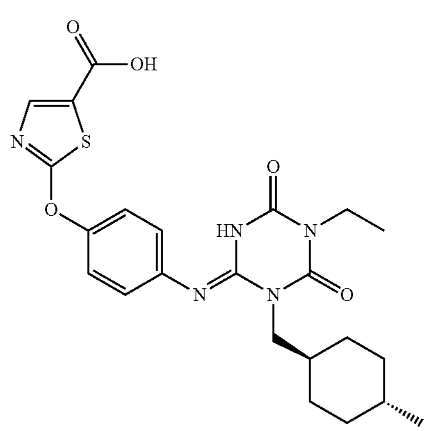 [SMILES: CCn1c(=O)[nH]/c(=N\c2ccc(Oc3ncc(C(=O)O)s3)cc2)n(C[C@H]2CC[C@H](C)CC2)c1=O] | I-2347 | 2.17 | 486 | 2 |

TABLE 476

| Structure | Compound No. | Retention Time (min) | [M + H] | Method |
|---|---|---|---|---|
| 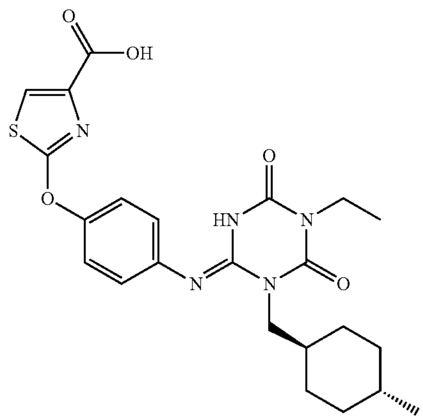 [SMILES: CCn1c(=O)[nH]/c(=N\c2ccc(Oc3nc(C(=O)O)cs3)cc2)n(C[C@H]2CC[C@H](C)CC2)c1=O] | I-2348 | 2.17 | 486 | 2 |
| 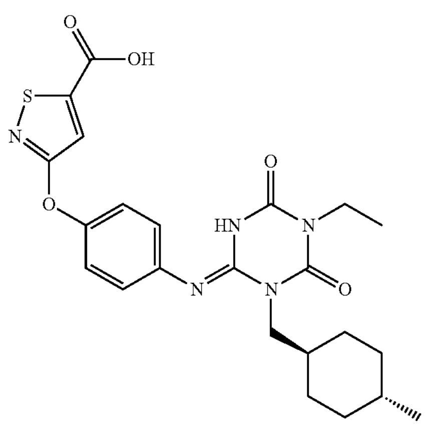 [SMILES: CCn1c(=O)[nH]/c(=N\c2ccc(Oc3cc(C(=O)O)sn3)cc2)n(C[C@H]2CC[C@H](C)CC2)c1=O] | I-2349 | 2.40 | 486 | 3 |
| 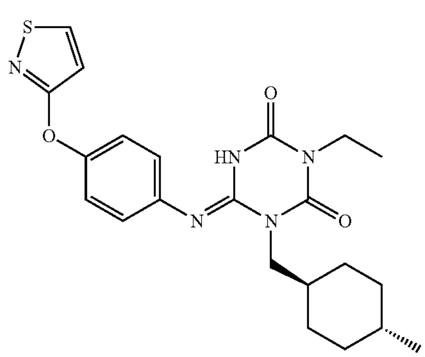 [SMILES: CCn1c(=O)[nH]/c(=N\c2ccc(Oc3ccsn3)cc2)n(C[C@H]2CC[C@H](C)CC2)c1=O] | I-2350 | 2.48 | 442 | 3 |

TABLE 476-continued

| Structure | Compound No. | Retention Time (min) | [M + H] | Method |
|---|---|---|---|---|
| 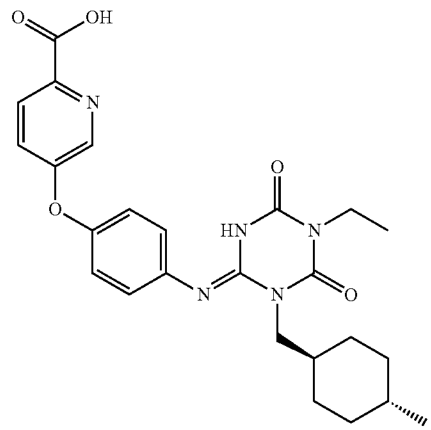 [SMILES: CCn1c(=O)[nH]/c(=N\c2ccc(Oc3ccc(C(=O)O)nc3)cc2)n(C[C@H]2CC[C@H](C)CC2)c1=O] | I-2351 | 2.15 | 480 | 3 |

TABLE 477

| Structure | Compound No. | Retention Time (min) | [M + H] | Method |
|---|---|---|---|---|
| 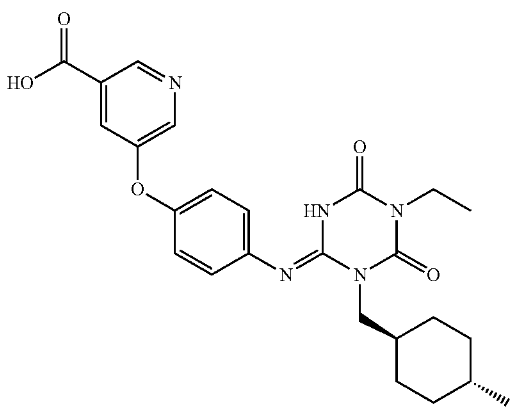 [SMILES: CCn1c(=O)[nH]/c(=N\c2ccc(Oc3cncc(C(=O)O)c3)cc2)n(C[C@H]2CC[C@H](C)CC2)c1=O] | I-2352 | 2.05 | 480 | 2 |
| 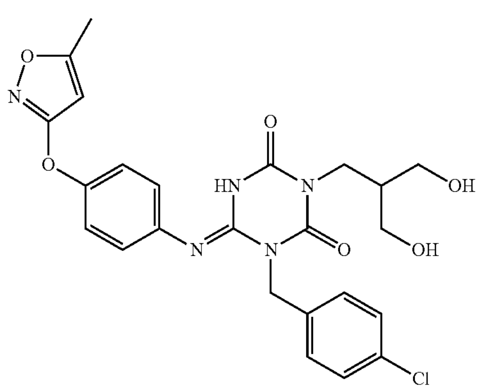 [SMILES: Cc1cc(Oc2ccc(/N=c3\[nH]c(=O)n(CC(CO)CO)c(=O)n3Cc3ccc(Cl)cc3)cc2)no1] | I-2353 | 1.80 | 514 | 2 |

TABLE 477-continued

| Structure | Compound No. | Retention Time (min) | [M + H] | Method |
|---|---|---|---|---|
| 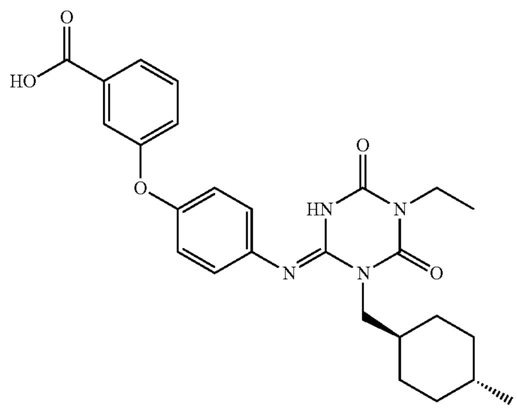 [SMILES: CCn1c(=O)[nH]/c(=N\c2ccc(Oc3cccc(C(=O)O)c3)cc2)n(C[C@H]2CC[C@H](C)CC2)c1=O] | I-2354 | 2.28 | 479 | 2 |
| 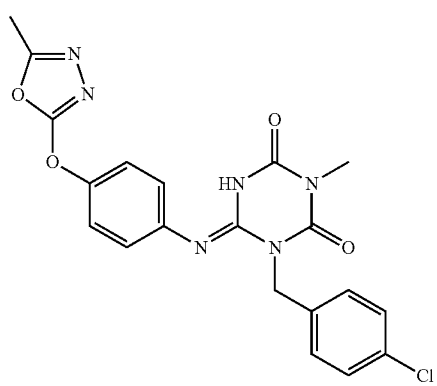 [SMILES: Cc1nnc(Oc2ccc(/N=c3\[nH]c(=O)n(C)c(=O)n3Cc3ccc(Cl)cc3)cc2)o1] | I-2355 | 1.87 | 441 | 2 |

TABLE 478

| Structure | Compound No. | Retention Time (min) | [M + H] | Method |
|---|---|---|---|---|
| 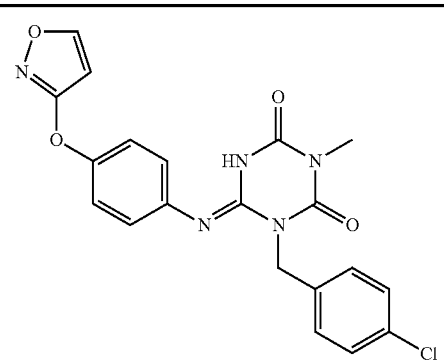 | I-2356 | 2.00 | 426 | 2 |

TABLE 478-continued

| Structure | Compound No. | Retention Time (min) | [M + H] | Method |
|---|---|---|---|---|
| 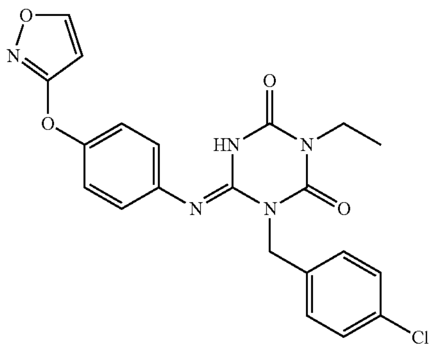 | I-2357 | 2.22 | 440 | 3 |
| 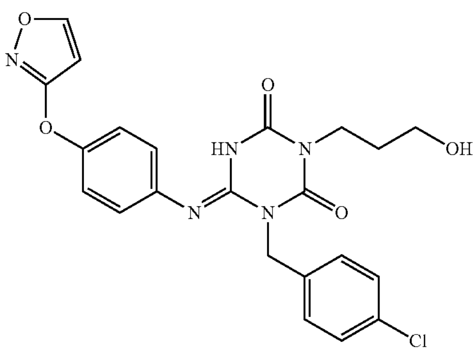 | I-2358 | 1.91 | 470 | 3 |
| 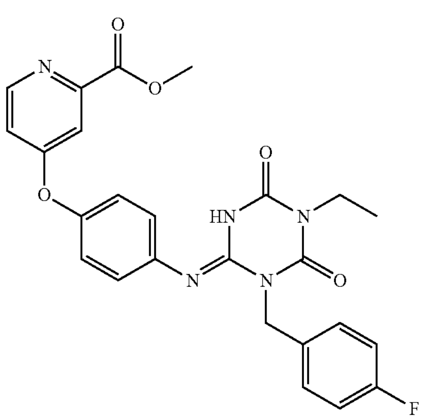 [SMILES: CCn1c(=O)[nH]/c(=N\c2ccc(Oc3ccnc(C(=O)OC)c3)cc2)n(Cc2ccc(F)cc2)c1=O] | I-2359 | 2.02 | 492 | 3 |

TABLE 479

| Structure | Compound No. | Retention Time (min) | [M + H] | Method |
|---|---|---|---|---|
| 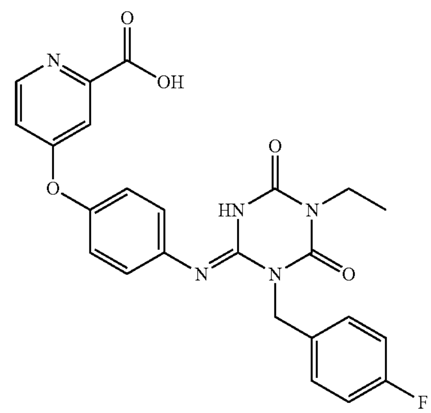 [SMILES: CCn1c(=O)[nH]/c(=N\c2ccc(Oc3ccnc(C(=O)O)c3)cc2)n(Cc2ccc(F)cc2)c1=O] | I-2360 | 1.54 | 478 | 3 |
| 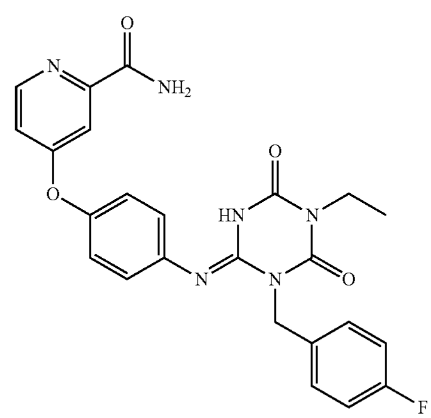 [SMILES: CCn1c(=O)[nH]/c(=N\c2ccc(Oc3ccnc(C(N)=O)c3)cc2)n(Cc2ccc(F)cc2)c1=O] | I-2361 | 1.91 | 477 | 3 |
| 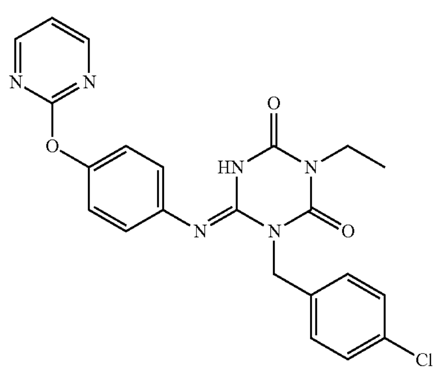 [SMILES: CCn1c(=O)[nH]/c(=N\c2ccc(Oc3ncccn3)cc2)n(Cc2ccc(Cl)cc2)c1=O] | I-2362 | 2.08 | 451 | 3 |

TABLE 479-continued

| Structure | Compound No. | Retention Time (min) | [M + H] | Method |
|---|---|---|---|---|
| 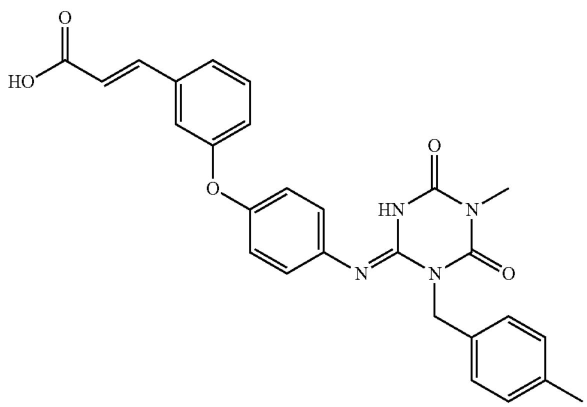 [SMILES: Cc1ccc(Cn2c(=O)n(C)c(=O)[nH]/c2=N\c2ccc(Oc3cccc(/C=C/C(=O)O)c3)cc2)cc1] | I-2363 | 2.08 | 485 | 3 |

TABLE 480

| Structure | Compound No. | Retention Time (min) | [M + H] | Method |
|---|---|---|---|---|
| 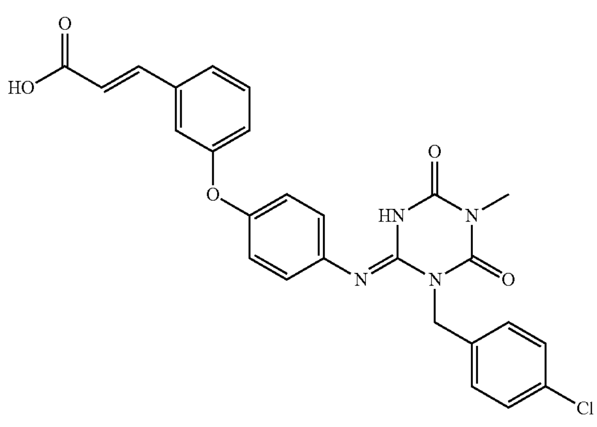 [SMILES: Cn1c(=O)[nH]/c(=N\c2ccc(Oc3cccc(/C=C/C(=O)O)c3)cc2)n(Cc2ccc(Cl)cc2)c1=O] | I-2364 | 2.15 | 505 | 3 |
| 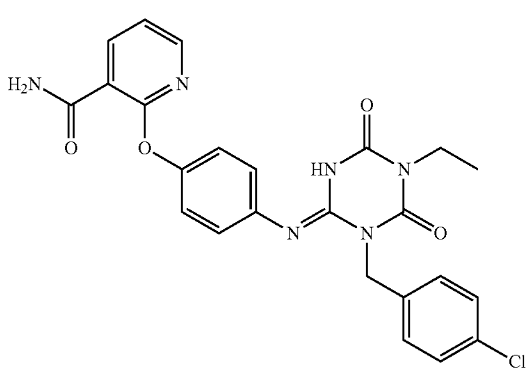 [SMILES: CCn1c(=O)[nH]/c(=N\c2ccc(Oc3ncccc3C(N)=O)cc2)n(Cc2ccc(Cl)cc2)c1=O] | I-2365 | 1.93 | 493 | 3 |

TABLE 480-continued

| Structure | Compound No. | Retention Time (min) | [M + H] | Method |
|---|---|---|---|---|
| 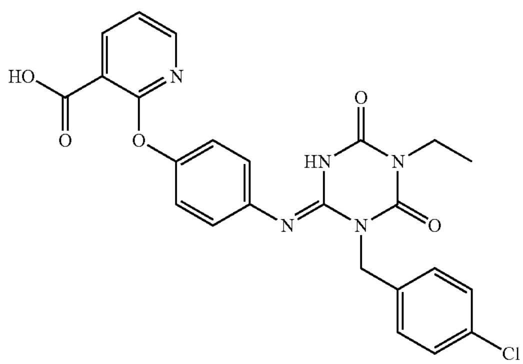 [SMILES: CCn1c(=O)[nH]/c(=N\c2ccc(Oc3ncccc3C(=O)O)cc2)n(Cc2ccc(Cl)cc2)c1=O] | I-2366 | 1.98 | 494 | 3 |
| 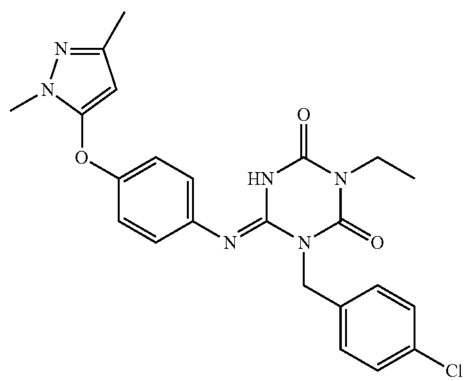 [SMILES: CCn1c(=O)[nH]/c(=N\c2ccc(Oc3cc(C)nn3C)cc2)n(Cc2ccc(Cl)cc2)c1=O] | I-2367 | 2.18 | 467 | 3 |

TABLE 481

| Structure | Compound No. | Retention Time (min) | [M + H] | Method |
|---|---|---|---|---|
| 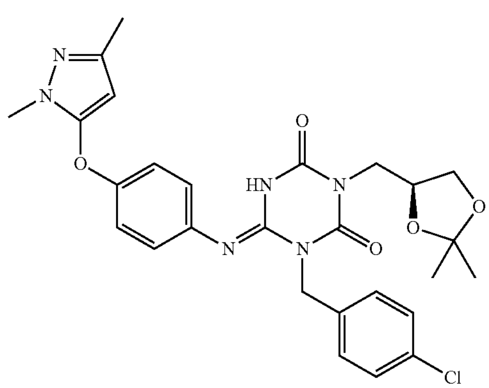 [SMILES: Cc1cc(Oc2ccc(/N=c3\[nH]c(=O)n(C[C@H]4COC(C)(C)O4)c(=O)n3Cc3ccc(Cl)cc3)cc2)n(C)n1] | I-2368 | 2.24 | 553 | 3 |

TABLE 481-continued

| Structure | Compound No. | Retention Time (min) | [M + H] | Method |
|---|---|---|---|---|
| 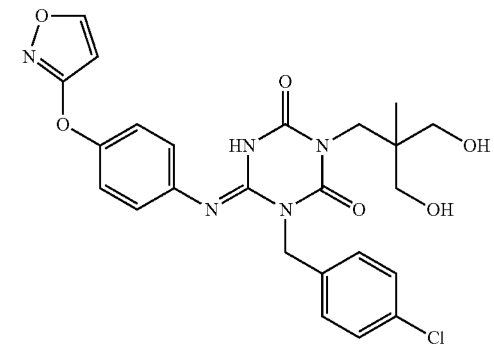 | I-2369 | 1.92 | 514 | 3 |
| 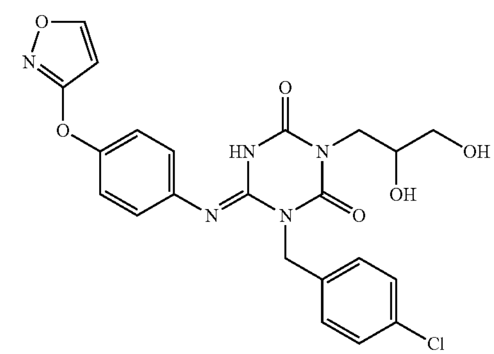 | I-2370 | 1.75 | 486 | 3 |
| 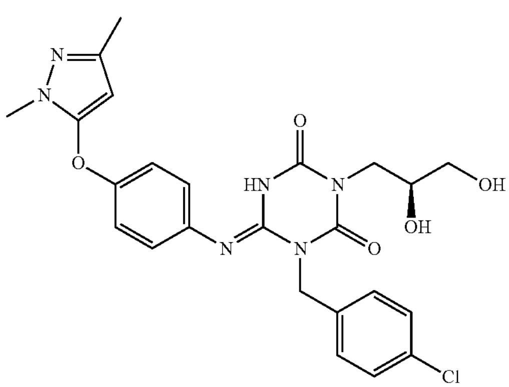 [SMILES: Cc1cc(Oc2ccc(/N=c3\[nH]c(=O)n(C[C@H](O)CO)c(=O)n3Cc3ccc(Cl)cc3)cc2)n(C)n1] | I-2371 | 1.72 | 513 | 3 |

TABLE 482
| Structure | Compound No. | Retention Time (min) | [M + H] | Method |
|---|---|---|---|---|
| 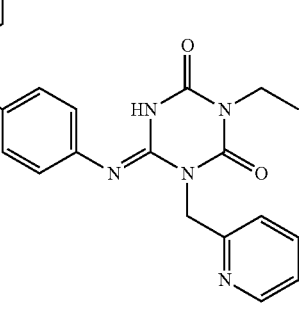 | I-2372 | 2.07 | 476 | 3 |
| 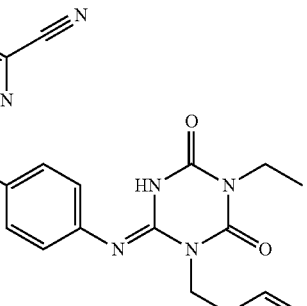 | I-2373 | 2.12 | 476 | 3 |
| 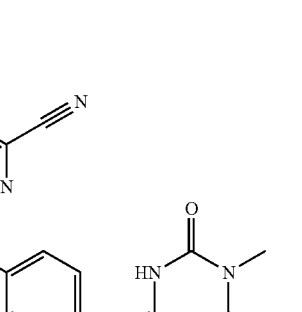 | I-2374 | 2.21 | 461 | 3 |

TABLE 482-continued
| Structure | Compound No. | Retention Time (min) | [M + H] | Method |
|---|---|---|---|---|
| 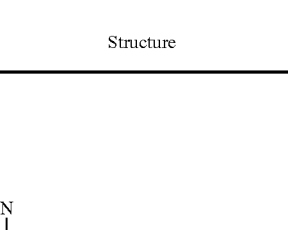 | I-2375 | 2.09 | 476 | 3 |
TABLE 483
| Structure | Compound No. | Retention Time (min) | [M + H] | Method |
|---|---|---|---|---|
| 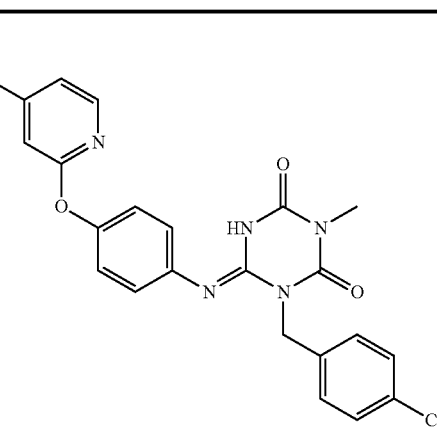 | I-2376 | 1.80 | 479 | 3 |
| 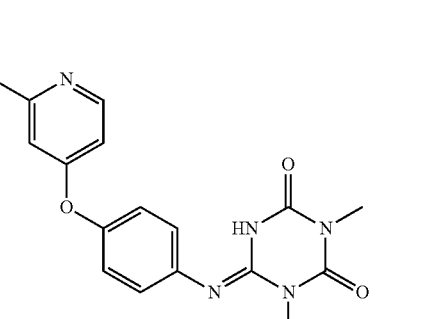 | I-2377 | 2.03 | 494 | 3 |

TABLE 483-continued
| Structure | Compound No. | Retention Time (min) | [M + H] | Method |
|---|---|---|---|---|
| 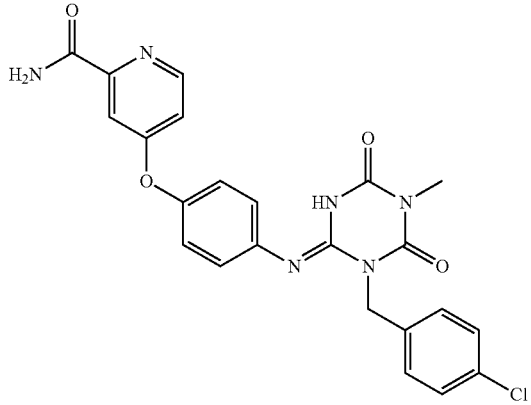 [SMILES: Cn1c(=O)[nH]/c(=N\c2ccc(Oc3ccnc(C(N)=O)c3)cc2)n(Cc2ccc(Cl)cc2)c1=O] | I-2378 | 1.92 | 479 | 3 |
| 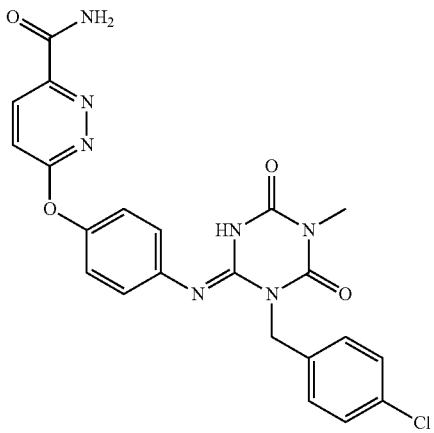 [SMILES: Cn1c(=O)[nH]/c(=N\c2ccc(Oc3ccc(C(N)=O)nn3)cc2)n(Cc2ccc(Cl)cc2)c1=O] | I-2379 | 1.84 | 480 | 3 |
TABLE 484
| Structure | Compound No. | Retention Time (min) | [M + H] | Method |
|---|---|---|---|---|
| 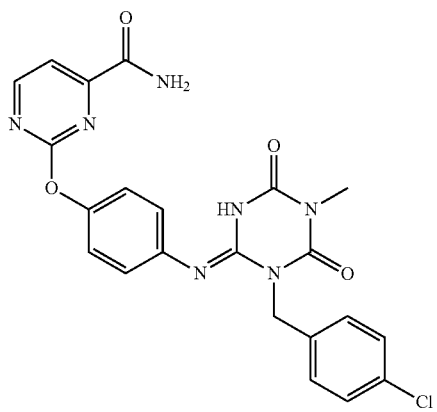 [SMILES: Cn1c(=O)[nH]/c(=N\c2ccc(Oc3nccc(C(N)=O)n3)cc2)n(Cc2ccc(Cl)cc2)c1=O] | I-2380 | 1.8 | 480 | 3 |

TABLE 484-continued

| Structure | Compound No. | Retention Time (min) | [M + H] | Method |
|---|---|---|---|---|
| 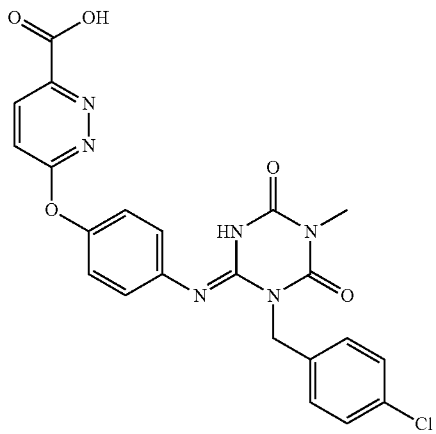 [SMILES: Cn1c(=O)[nH]/c(=N\c2ccc(Oc3ccc(C(=O)O)nn3)cc2)n(Cc2ccc(Cl)cc2)c1=O] | I-2381 | 1.88 | 481 | 3 |
| 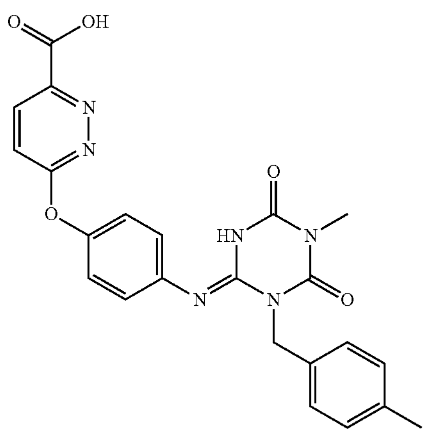 [SMILES: Cc1ccc(Cn2c(=O)n(C)c(=O)[nH]/c2=N\c2ccc(Oc3ccc(C(=O)O)nn3)cc2)cc1] | I-2382 | 1.78 | 461 | 3 |
| 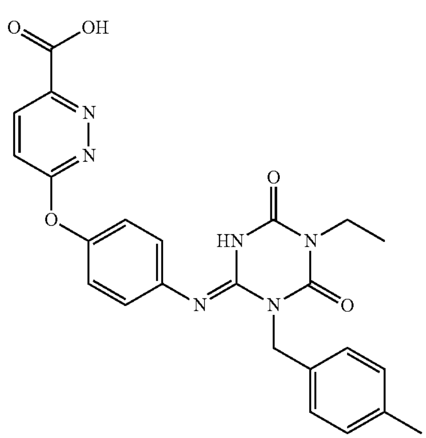 [SMILES: CCn1c(=O)[nH]/c(=N\c2ccc(Oc3ccc(C(=O)O)nn3)cc2)n(Cc2ccc(C)cc2)c1=O] | I-2383 | 1.92 | 475 | 3 |

TABLE 485

| Structure | Compound No. | Retention Time (min) | [M + H] | Method |
|---|---|---|---|---|
| (structure) | I-2384 | 1.82 | 475 | 2 |
| (structure) | I-2385 | 1.69 | 461 | 2 |
| (structure) | I-2386 | 1.79 | 481 | 2 |

TABLE 485-continued
| Structure | Compound No. | Retention Time (min) | [M + H] | Method |
|---|---|---|---|---|
| 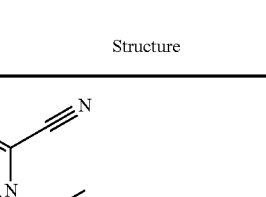 | I-2387 | 2.26 | 505 | 2 |
TABLE 486
| Structure | Compound No. | Retention Time (min) | [M + H] | Method |
|---|---|---|---|---|
| 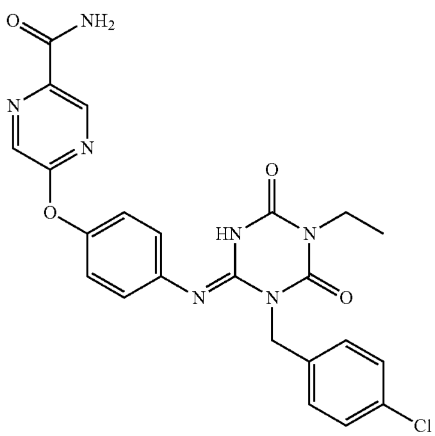 | I-2388 | 1.95 | 494 | 2 |
| 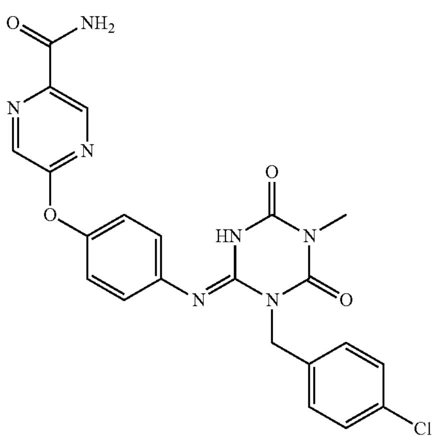 | I-2389 | 1.82 | 480 | 2 |

TABLE 486-continued

| Structure | Compound No. | Retention Time (min) | [M + H] | Method |
|---|---|---|---|---|
| 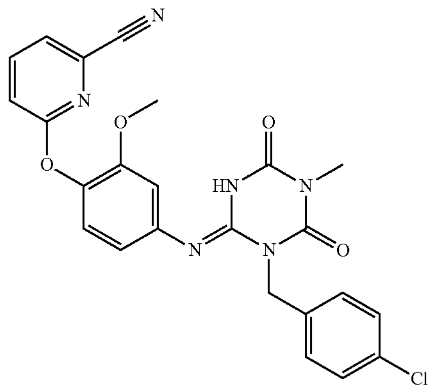 [SMILES: COc1cc(/N=c2\[nH]c(=O)n(C)c(=O)n2Cc2ccc(Cl)cc2)ccc1Oc1cccc(C#N)n1] | I-2390 | 2.15 | 491 | 2 |
| 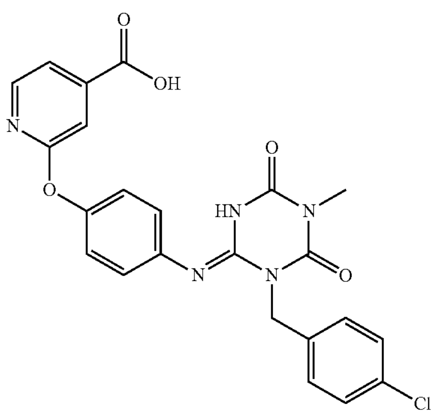 [SMILES: Cn1c(=O)[nH]/c(=N\c2ccc(Oc3cc(C(=O)O)ccn3)cc2)n(Cc2ccc(Cl)cc2)c1=O] | I-2391 | 1.96 | 480 | 3 |

TABLE 487

| Structure | Compound No. | Retention Time (min) | [M + H] | Method |
|---|---|---|---|---|
| 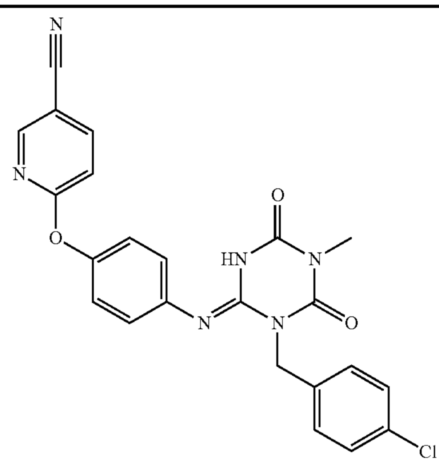 | I-2392 | 2.19 | 461 | 3 |

TABLE 487-continued
| Structure | Compound No. | Retention Time (min) | [M + H] | Method |
|---|---|---|---|---|
| 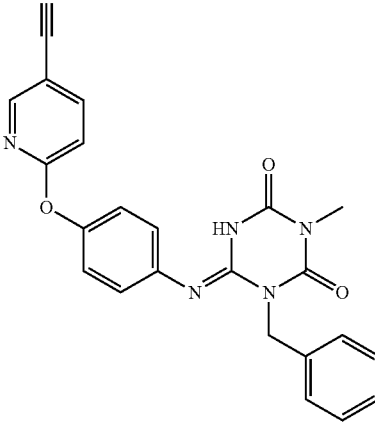 | I-2393 | 2.10 | 441 | 3 |
| 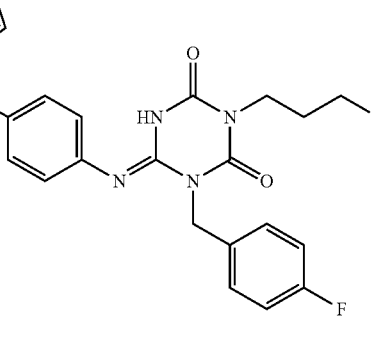 | I-2394 | 2.17 | 538 | 2 |
| 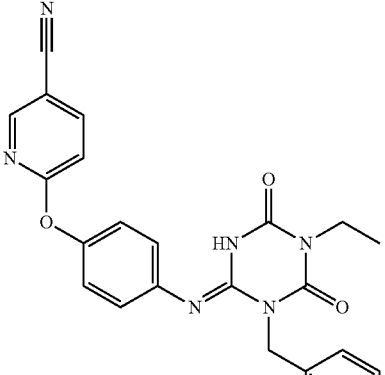 | I-2395 | 2.24 | 455 | 3 |

TABLE 488

| Structure | Compound No. | Retention Time (min) | [M + H] | Method |
|---|---|---|---|---|
| (structure) | I-2396 | 2.14 | 538 | 2 |
| (structure) | I-2397 | 1.78 | 454 | 3 |
| (structure) | I-2398 | 1.87 | 473 | 3 |
| (structure) | I-2399 | 1.78 | 498 | 3 |

TABLE 489

| Structure | Compound No. | Retention Time (min) | [M + H] | Method |
|---|---|---|---|---|
| (structure shown) | I-2400 | 2.06 | 474 | 3 |
| (structure shown) | I-2401 | 1.92 | 460 | 3 |
| (structure shown) | I-2402 | 2.06 | 494 | 3 |

TABLE 489-continued
| Structure | Compound No. | Retention Time (min) | [M + H] | Method |
|---|---|---|---|---|
| 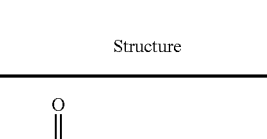 | I-2403 | 1.75 | 461 | 3 |
TABLE 490
| Structure | Compound No. | Retention Time (min) | [M + H] | Method |
|---|---|---|---|---|
| 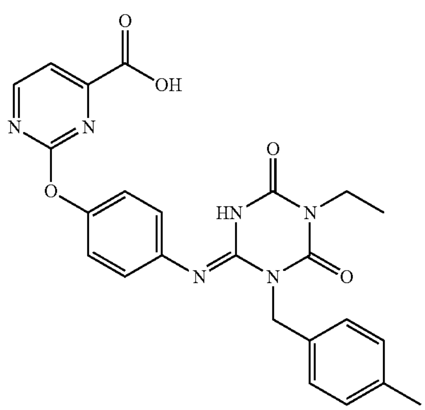 [SMILES: CCn1c(=O)[nH]/c(=N\c2ccc(Oc3nccc(C(=O)O)n3)cc2)n(Cc2ccc(C)cc2)c1=O] | I-2404 | 1.89 | 475 | 3 |
| 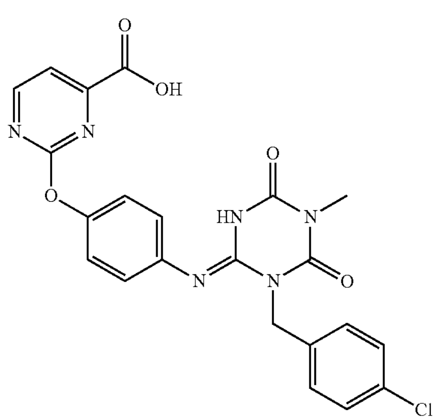 [SMILES: Cn1c(=O)[nH]/c(=N\c2ccc(Oc3nccc(C(=O)O)n3)cc2)n(Cc2ccc(Cl)cc2)c1=O] | I-2405 | 1.84 | 481 | 3 |

TABLE 490-continued

| Structure | Compound No. | Retention Time (min) | [M + H] | Method |
|---|---|---|---|---|
| 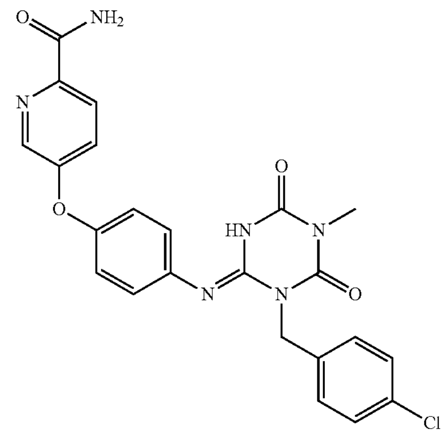 [SMILES: Cn1c(=O)[nH]/c(=N\c2ccc(Oc3ccc(C(N)=O)nc3)cc2)n(Cc2ccc(Cl)cc2)c1=O] | I-2406 | 1.88 | 479 | 3 |
| 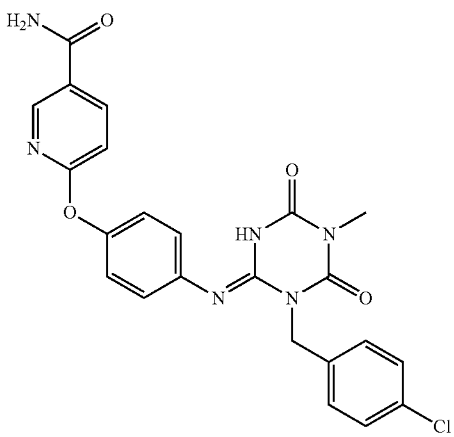 [SMILES: Cn1c(=O)[nH]/c(=N\c2ccc(Oc3ccc(C(N)=O)cn3)cc2)n(Cc2ccc(Cl)cc2)c1=O] | I-2407 | 1.83 | 479 | 3 |

TABLE 491

| Structure | Compound No. | Retention Time (min) | [M + H] | Method |
|---|---|---|---|---|
| 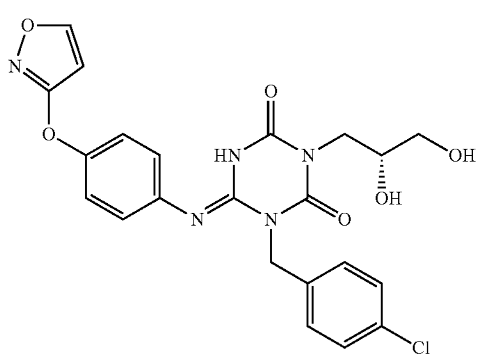 [SMILES: O=c1[nH]/c(=N\c2ccc(Oc3ccon3)cc2)n(Cc2ccc(Cl)cc2)c(=O)n1C[C@@H](O)CO] | I-2408 | 1.71 | 486 | 2 |

TABLE 491-continued

| Structure | Compound No. | Retention Time (min) | [M + H] | Method |
|---|---|---|---|---|
| 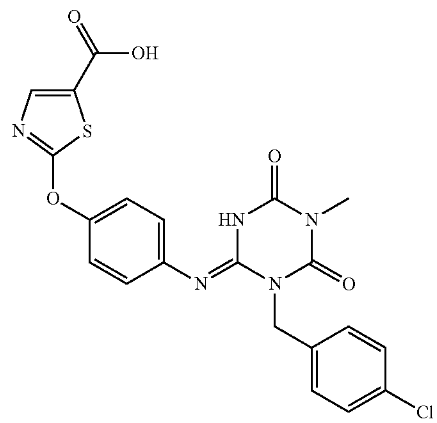 [SMILES: Cn1c(=O)[nH]/c(=N\c2ccc(Oc3ncc(C(=O)O)s3)cc2)n(Cc2ccc(Cl)cc2)c1=O] | I-2409 | 1.92 | 486 | 2 |
| 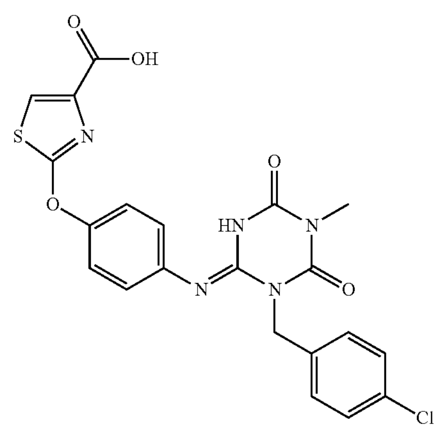 [SMILES: Cn1c(=O)[nH]/c(=N\c2ccc(Oc3nc(C(=O)O)cs3)cc2)n(Cc2ccc(Cl)cc2)c1=O] | I-2410 | 1.93 | 486 | 2 |
| 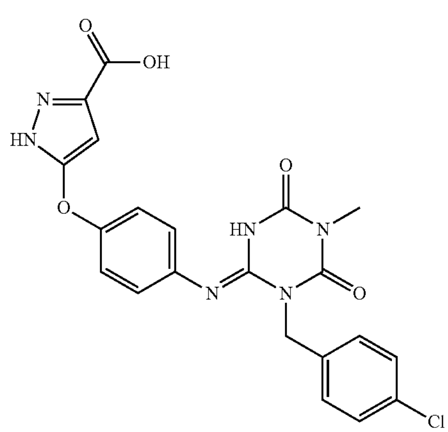 [SMILES: Cn1c(=O)[nH]/c(=N\c2ccc(Oc3cc(C(=O)O)n[nH]3)cc2)n(Cc2ccc(Cl)cc2)c1=O] | I-2411 | 1.73 | 469 | 2 |

TABLE 492

| Structure | Compound No. | Retention Time (min) | [M + H] | Method |
|---|---|---|---|---|
| 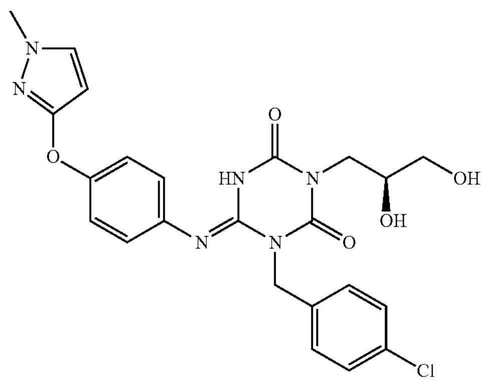 [SMILES: Cn1ccc(Oc2ccc(/N=c3\[nH]c(=O)n(C[C@H](O)CO)c(=O)n3Cc3ccc(Cl)cc3)cc2)n1] | I-2412 | 1.61 | 499 | 2 |
| 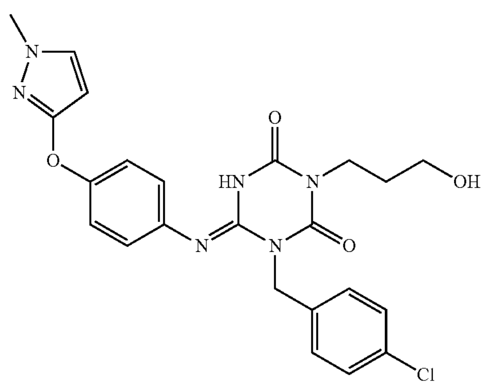 [SMILES: Cn1ccc(Oc2ccc(/N=c3\[nH]c(=O)n(CCCO)c(=O)n3Cc3ccc(Cl)cc3)cc2)n1] | I-2413 | 1.76 | 483 | 2 |
| 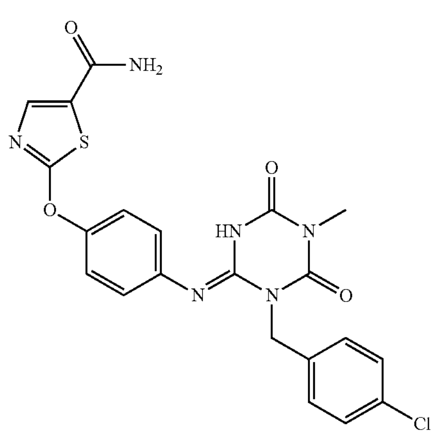 [SMILES: Cn1c(=O)[nH]/c(=N\c2ccc(Oc3ncc(C(N)=O)s3)cc2)n(Cc2ccc(Cl)cc2)c1=O] | I-2414 | 1.80 | 485 | 2 |

TABLE 492-continued

| Structure | Compound No. | Retention Time (min) | [M + H] | Method |
|---|---|---|---|---|
| 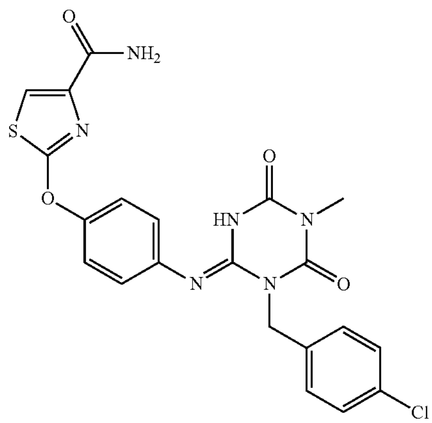 [SMILES: Cn1c(=O)[nH]/c(=N\c2ccc(Oc3nc(C(N)=O)cs3)cc2)n(Cc2ccc(Cl)cc2)c1=O] | I-2415 | 1.82 | 485 | 2 |

TABLE 493

| Structure | Compound No. | Retention Time (min) | [M + H] | Method |
|---|---|---|---|---|
| 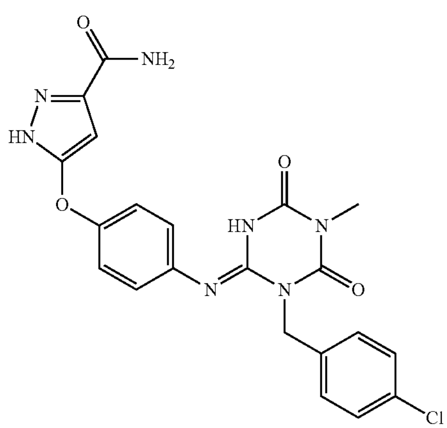 [SMILES: Cn1c(=O)[nH]/c(=N\c2ccc(Oc3cc(C(N)=O)n[nH]3)cc2)n(Cc2ccc(Cl)cc2)c1=O] | I-2416 | 1.64 | 468 | 2 |
| 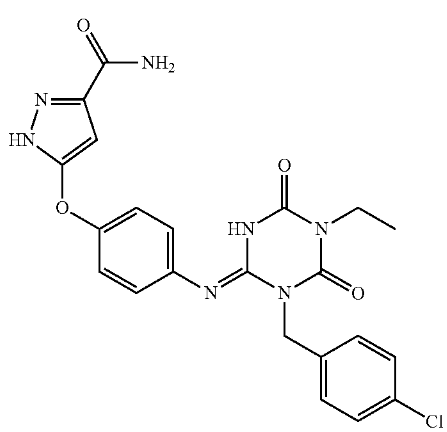 [SMILES: CCn1c(=O)[nH]/c(=N\c2ccc(Oc3cc(C(N)=O)n[nH]3)cc2)n(Cc2ccc(Cl)cc2)c1=O] | I-2417 | 1.77 | 482 | 2 |

TABLE 493-continued

| Structure | Compound No. | Retention Time (min) | [M + H] | Method |
|---|---|---|---|---|
| 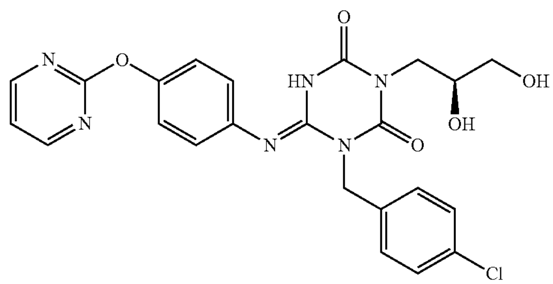 [SMILES: O=c1[nH]/c(=N\c2ccc(Oc3ncccn3)cc2)n(Cc2ccc(Cl)cc2)c(=O)n1C[C@H](O)CO] | I-2418 | 1.62 | 497 | 3 |
| 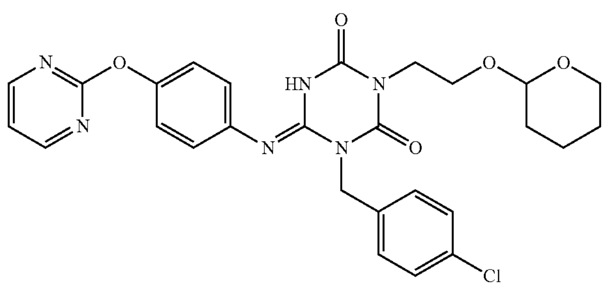 [SMILES: O=c1[nH]/c(=N\c2ccc(Oc3ncccn3)cc2)n(Cc2ccc(Cl)cc2)c(=O)n1CCOC1CCCCO1] | I-2419 | 2.22 | 467 | 3 |

TABLE 494

| Structure | Compound No. | Retention Time (min) | [M + H] | Method |
|---|---|---|---|---|
| 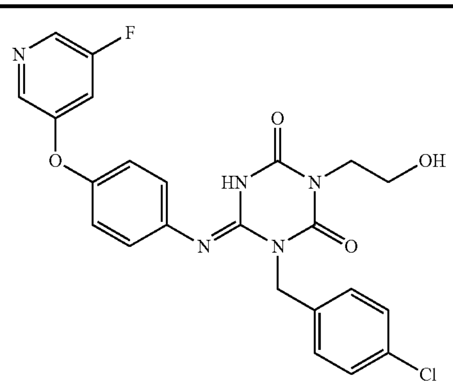 | I-2420 | 1.90 | 484 | 3 |
| 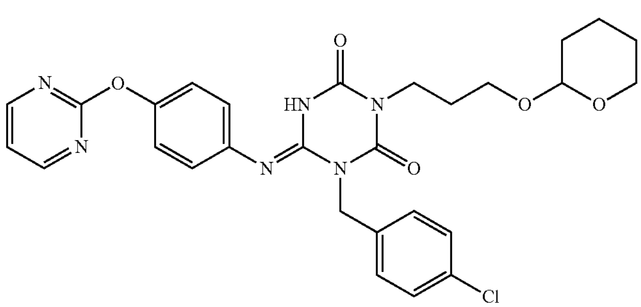 [SMILES: O=c1[nH]/c(=N\c2ccc(Oc3ncccn3)cc2)n(Cc2ccc(Cl)cc2)c(=O)n1CCCOC1CCCCO1] | I-2421 | 2.32 | 481 | 3 |

TABLE 494-continued

| Structure | Compound No. | Retention Time (min) | [M + H] | Method |
|---|---|---|---|---|
| 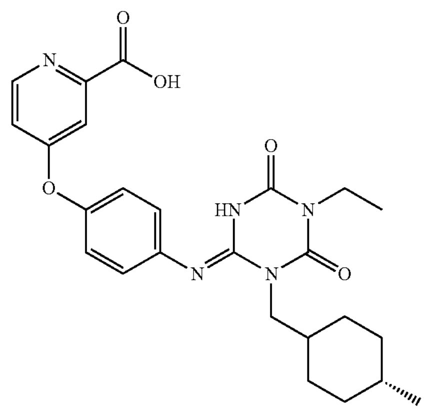 | I-2422 | 1.83 | 480 | 3 |
| 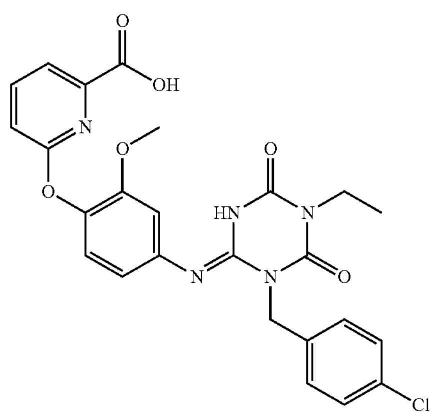 [SMILES: CCn1c(=O)[nH]/c(=N\c2ccc(Oc3cccc(C(=O)O)n3)c(OC)c2)n(Cc2ccc(Cl)cc2)c1=O] | I-2423 | 2.09 | 524 | 2 |

TABLE 495

| Structure | Compound No. | Retention Time (min) | [M + H] | Method |
|---|---|---|---|---|
| 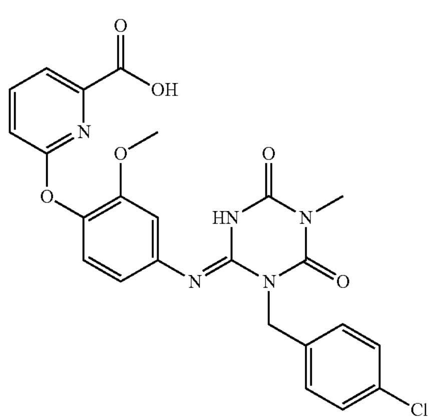 [SMILES: COc1cc(/N=c2\[nH]c(=O)n(C)c(=O)n2Cc2ccc(Cl)cc2)ccc1Oc1cccc(C(=O)O)n1] | I-2424 | 1.97 | 510 | 2 |

TABLE 495-continued

| Structure | Compound No. | Retention Time (min) | [M + H] | Method |
|---|---|---|---|---|
| 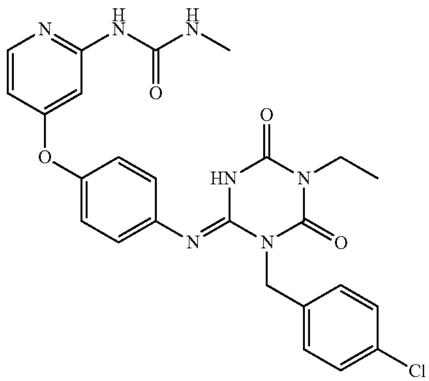 [SMILES: CCn1c(=O)[nH]/c(=N\c2ccc(Oc3ccnc(NC(=O)NC)c3)cc2)n(Cc2ccc(Cl)cc2)c1=O] | I-2425 | 1.70 | 522 | 2 |
| 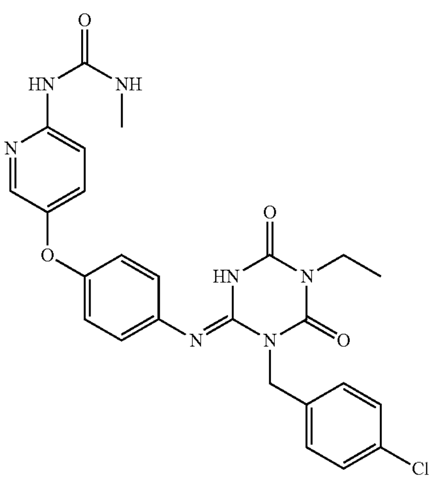 [SMILES: CCn1c(=O)[nH]/c(=N\c2ccc(Oc3ccc(NC(=O)NC)nc3)cc2)n(Cc2ccc(Cl)cc2)c1=O] | I-2426 | 1.96 | 522 | 2 |
| 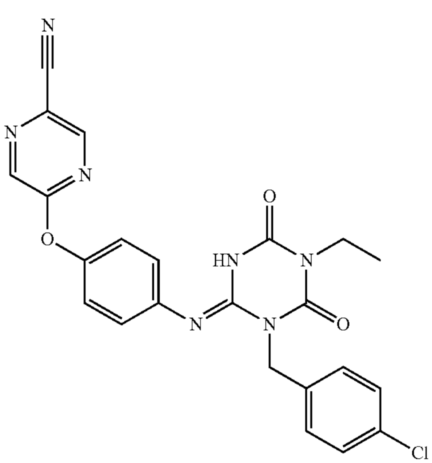 [SMILES: CCn1c(=O)[nH]/c(=N\c2ccc(Oc3cnc(C#N)cn3)cc2)n(Cc2ccc(Cl)cc2)c1=O] | I-2427 | 2.22 | 476 | 2 |

TABLE 496

| Structure | Compound No. | Retention Time (min) | [M + H] | Method |
|---|---|---|---|---|
| 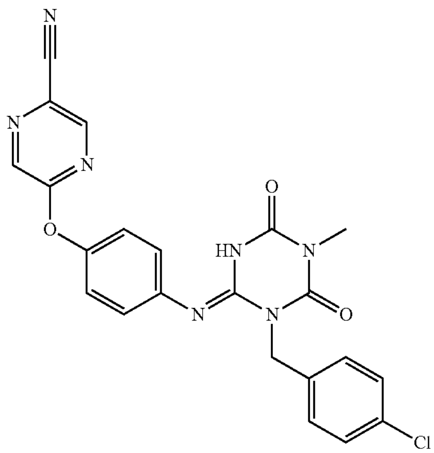 [SMILES: Cn1c(=O)[nH]/c(=N\c2ccc(Oc3cnc(C#N)cn3)cc2)n(Cc2ccc(Cl)cc2)c1=O] | I-2428 | 2.09 | 462 | 2 |
| 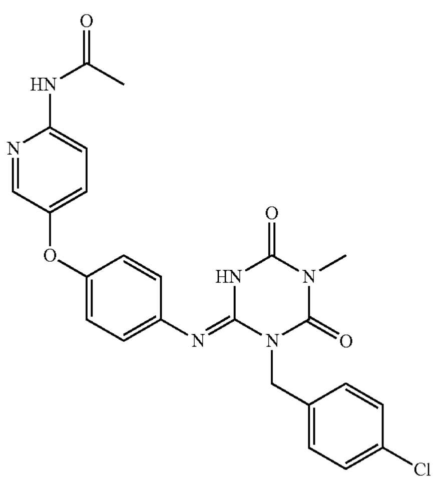 [SMILES: CC(=O)Nc1ccc(Oc2ccc(/N=c3\[nH]c(=O)n(C)c(=O)n3Cc3ccc(Cl)cc3)cc2)cn1] | I-2429 | 1.82 | 493 | 2 |
| 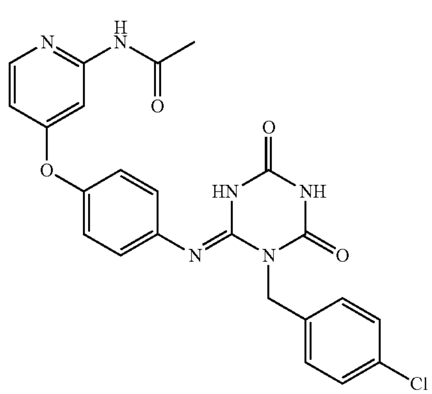 [SMILES: CC(=O)Nc1cc(Oc2ccc(/N=c3\[nH]c(=O)[nH]c(=O)n3Cc3ccc(Cl)cc3)cc2)ccn1] | I-2430 | 1.49 | 479 | 2 |

TABLE 496-continued

| Structure | Compound No. | Retention Time (min) | [M + H] | Method |
|---|---|---|---|---|
| (structure) | I-2431 | 1.60 | 493 | 2 |

TABLE 497

| Structure | Compound No. | Retention Time (min) | [M + H] | Method |
|---|---|---|---|---|
| (structure) | I-2432 | 2.34 | 525 | 3 |
| (structure) | I-2433 | 2.19 | 511 | 3 |

TABLE 497-continued
| Structure | Compound No. | Retention Time (min) | [M + H] | Method |
|---|---|---|---|---|
| 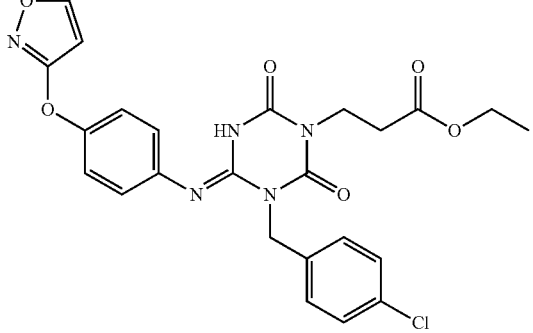 | I-2434 | 2.28 | 512 | 3 |
| 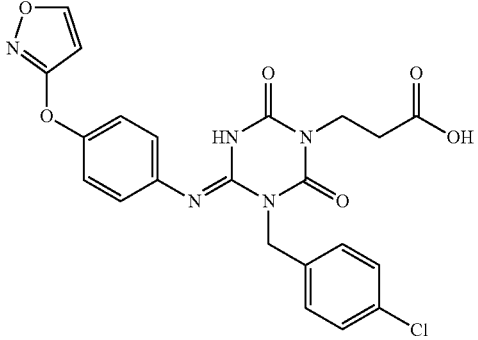 [SMILES: O=C(O)CCn1c(=O)[nH]/c(=N\c2ccc(Oc3ccon3)cc2)n(Cc2ccc(Cl)cc2)c1=O] | I-2435 | 1.91 | 484 | 3 |
TABLE 498
| Structure | Compound No. | Retention Time (min) | [M + H] | Method |
|---|---|---|---|---|
| 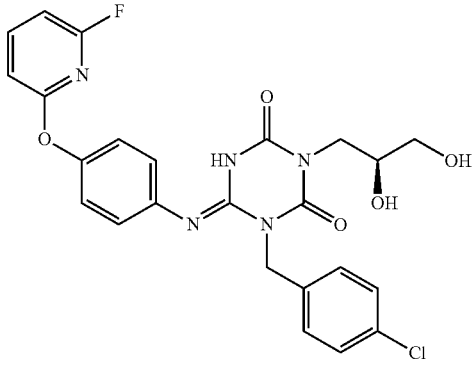 [SMILES: O=c1[nH]/c(=N\c2ccc(Oc3cccc(F)n3)cc2)n(Cc2ccc(Cl)cc2)c(=O)n1C[C@H](O)CO] | I-2436 |  | 514 | 3 |
| 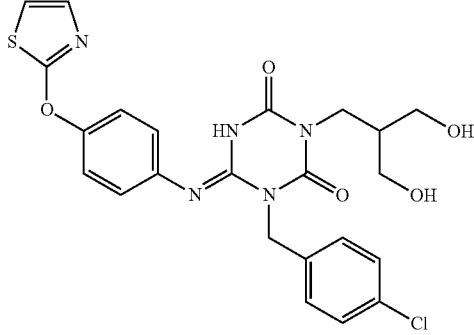 [SMILES: O=c1[nH]/c(=N\c2ccc(Oc3nccs3)cc2)n(Cc2ccc(Cl)cc2)c(=O)n1CC(CO)CO] | I-2437 | 1.89 | 516 | 3 |

TABLE 498-continued
| Structure | Compound No. | Retention Time (min) | [M + H] | Method |
|---|---|---|---|---|
| 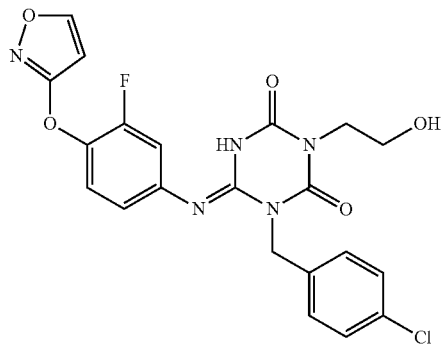 [SMILES: O=c1[nH]/c(=N\c2ccc(Oc3ccon3)c(F)c2)n(Cc2ccc(Cl)cc2)c(=O)n1CCO] | I-2438 | 1.94 | 474 | 2 |
| 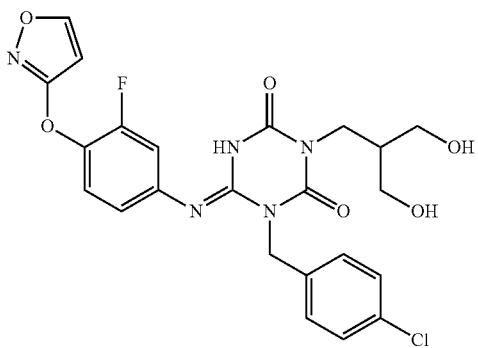 [SMILES: O=c1[nH]/c(=N\c2ccc(Oc3ccon3)c(F)c2)n(Cc2ccc(Cl)cc2)c(=O)n1CC(CO)CO] | I-2439 | 1.84 | 518 | 2 |
TABLE 499
| Structure | Compound No. | Retention Time (min) | [M + H] | Method |
|---|---|---|---|---|
| 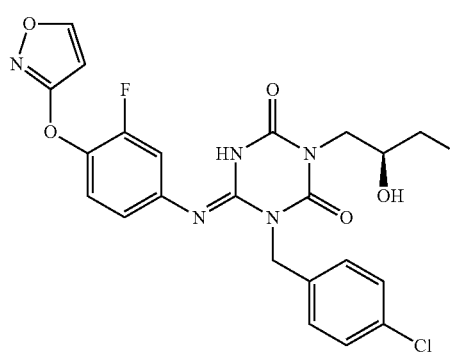 | I-2440 | 1.80 | 504 | 2 |

TABLE 499-continued

| Structure | Compound No. | Retention Time (min) | [M + H] | Method |
|---|---|---|---|---|
| 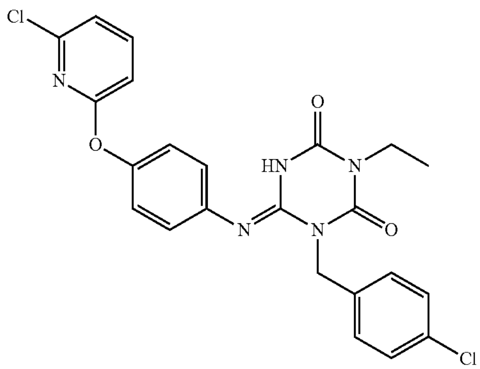 [SMILES: CCn1c(=O)[nH]/c(=N\c2ccc(Oc3cccc(Cl)n3)cc2)n(Cc2ccc(Cl)cc2)c1=O] | I-2441 | 2.50 | 484 | 3 |
| 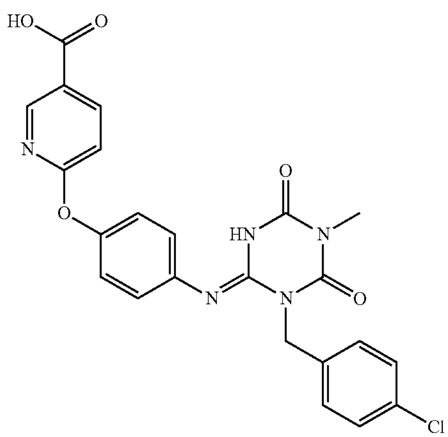 | I-2442 | 2.01 | 480 | 3 |
| 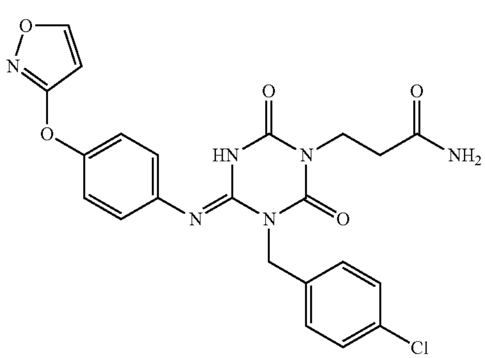 [SMILES: NC(=O)CCn1c(=O)[nH]/c(=N\c2ccc(Oc3ccon3)cc2)n(Cc2ccc(Cl)cc2)c1=O] | I-2443 | 1.77 | 483 | 3 |

TABLE 500

| Structure | Compound No. | Retention Time (min) | [M + H] | Method |
|---|---|---|---|---|
| 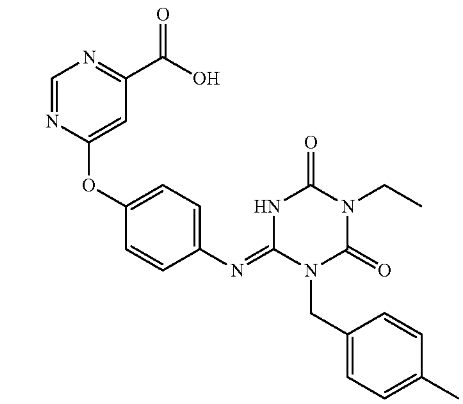 [SMILES: CCn1c(=O)[nH]/c(=N\c2ccc(Oc3cc(C(=O)O)ncn3)cc2)n(Cc2ccc(C)cc2)c1=O] | I-2444 | 1.9 | 475 | 3 |
| 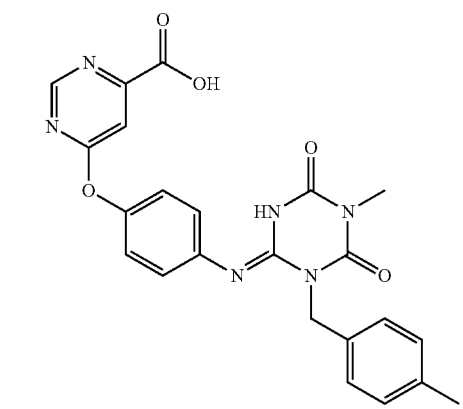 [SMILES: Cc1ccc(Cn2c(=O)n(C)c(=O)[nH]/c2=N\c2ccc(Oc3cc(C(=O)O)ncn3)cc2)cc1] | I-2445 | 1.75 | 461 | 3 |
| 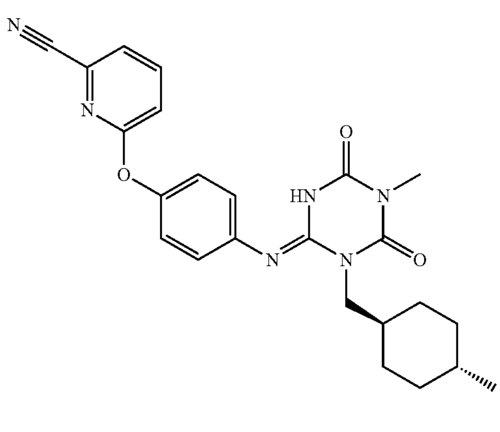 [SMILES: Cn1c(=O)[nH]/c(=N\c2ccc(Oc3cccc(C#N)n3)cc2)n(C[C@H]2CC[C@H](C)CC2)c1=O] | I-2446 | 2.35 | 447 | 3 |

TABLE 500-continued

| Structure | Compound No. | Retention Time (min) | [M + H] | Method |
|---|---|---|---|---|
| 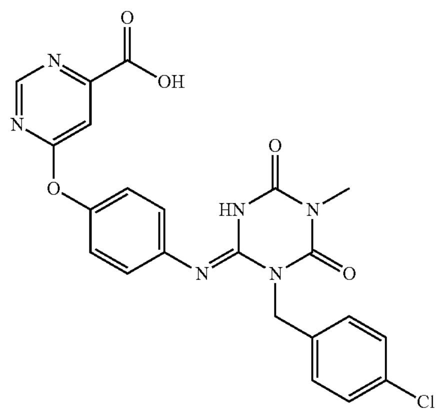 [SMILES: Cn1c(=O)[nH]/c(=N\c2ccc(Oc3cc(C(=O)O)ncn3)cc2)n(Cc2ccc(Cl)cc2)c1=O] | I-2447 | 1.83 | 481 | 3 |

TABLE 501

| Structure | Compound No. | Retention Time (min) | [M + H] | Method |
|---|---|---|---|---|
| 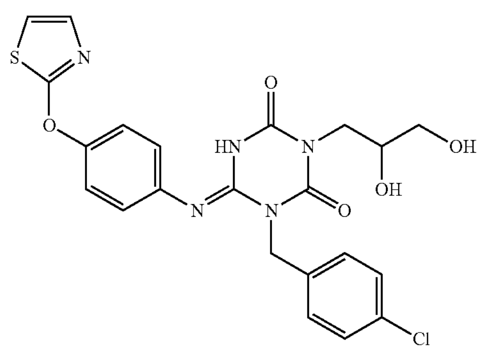 [SMILES: O=c1[nH]/c(=N\c2ccc(Oc3nccs3)cc2)n(Cc2ccc(Cl)cc2)c(=O)n1CC(O)CO] | I-2448 | 1.78 | 502 | 2 |
| 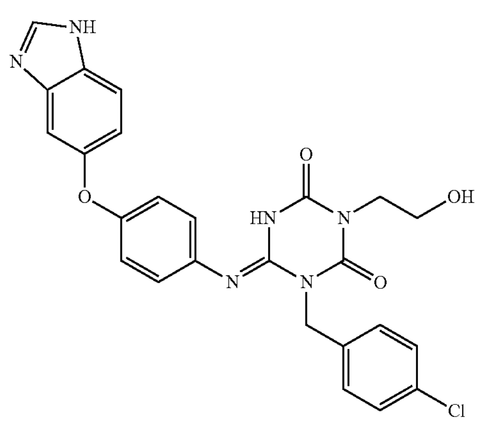 [SMILES: O=c1[nH]/c(=N\c2ccc(Oc3ccc4[nH]cnc4c3)cc2)n(Cc2ccc(Cl)cc2)c(=O)n1CCO] | I-2449 | 1.39 | 505 | 2 |

TABLE 501-continued
| Structure | Compound No. | Retention Time (min) | [M + H] | Method |
|---|---|---|---|---|
| 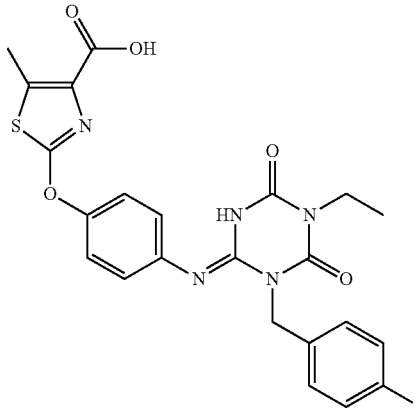 | I-2450 | 2.16 | 514 | 2 |
| 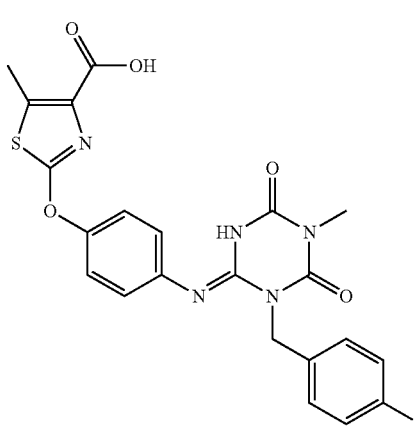 | I-2451 | 2.12 | 500 | 3 |
TABLE 502
| Structure | Compound No. | Retention Time (min) | [M + H] | Method |
|---|---|---|---|---|
| 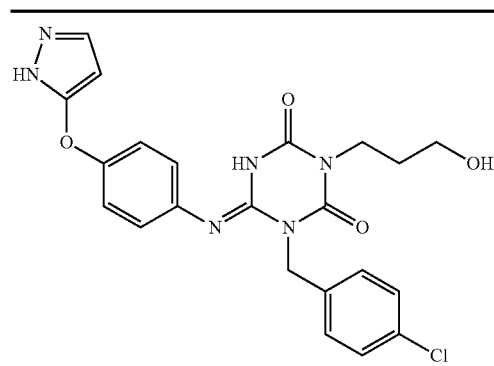 | I-2452 | 1.74 | 469 | 3 |

TABLE 502-continued

| Structure | Compound No. | Retention Time (min) | [M + H] | Method |
|---|---|---|---|---|
| 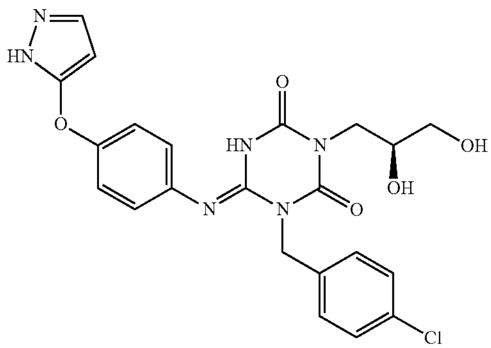 [SMILES: O=c1[nH]/c(=N\c2ccc(Oc3ccn[nH]3)cc2)n(Cc2ccc(Cl)cc2)c(=O)n1C[C@H](O)CO] | I-2453 | 1.59 | 485 | 3 |
| 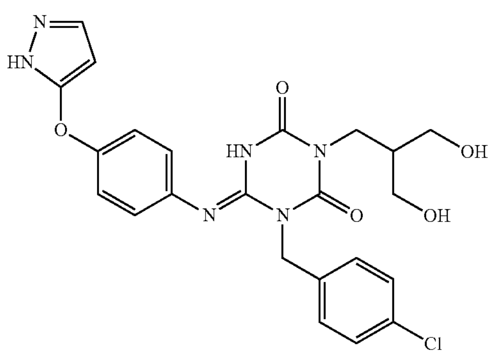 [SMILES: O=c1[nH]/c(=N\c2ccc(Oc3ccn[nH]3)cc2)n(Cc2ccc(Cl)cc2)c(=O)n1CC(CO)CO] | I-2454 | 1.57 | 499 | 2 |
| 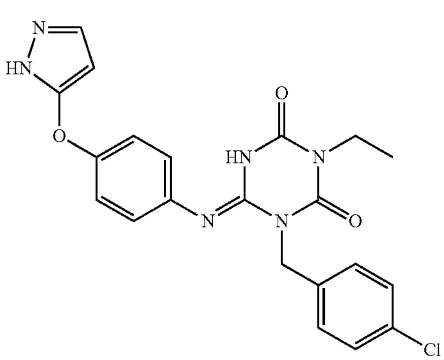 [SMILES: CCn1c(=O)[nH]/c(=N\c2ccc(Oc3ccn[nH]3)cc2)n(Cc2ccc(Cl)cc2)c1=O] | I-2455 | 1.94 | 439 | 2 |

TABLE 503

| Structure | Compound No. | Retention Time (min) | [M + H] | Method |
|---|---|---|---|---|
| 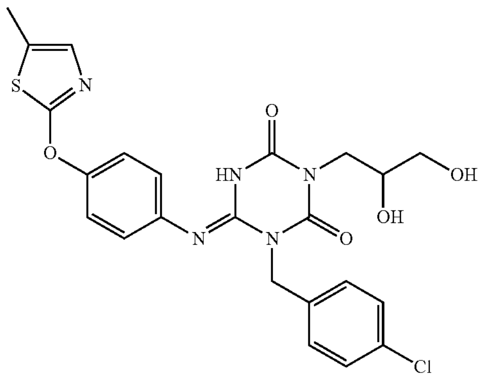 [SMILES: Cc1cnc(Oc2ccc(/N=c3\[nH]c(=O)n(CC(O)CO)c(=O)n3Cc3ccc(Cl)cc3)cc2)s1] | I-2456 | 1.91 | 516 | 2 |
| 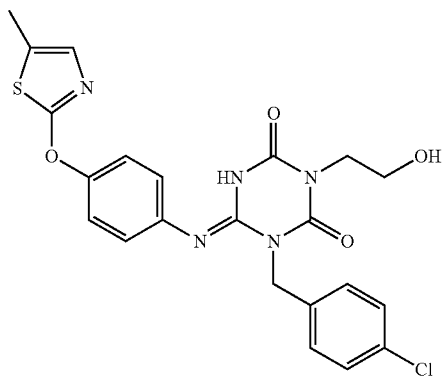 [SMILES: Cc1cnc(Oc2ccc(/N=c3\[nH]c(=O)n(CCO)c(=O)n3Cc3ccc(Cl)cc3)cc2)s1] | I-2457 | 2.13 | 486 | 3 |
| 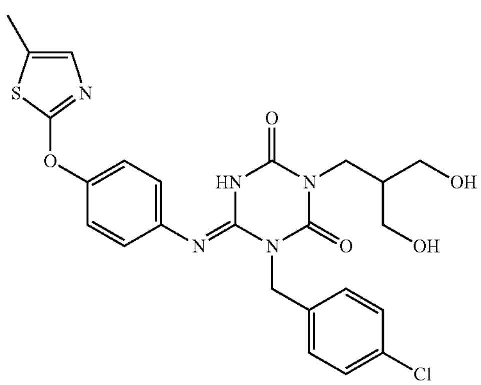 [SMILES: Cc1cnc(Oc2ccc(/N=c3\[nH]c(=O)n(CC(CO)CO)c(=O)n3Cc3ccc(Cl)cc3)cc2)s1] | I-2458 | 2.03 | 530 | 3 |
| 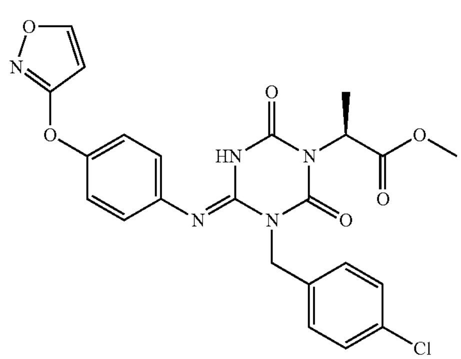 [SMILES: COC(=O)[C@H](C)n1c(=O)[nH]/c(=N\c2ccc(Oc3ccon3)cc2)n(Cc2ccc(Cl)cc2)c1=O] | I-2459 | 2.11 | 498 | 2 |

TABLE 504

| Structure | Compound No. | Retention Time (min) | [M + H] | Method |
|---|---|---|---|---|
| 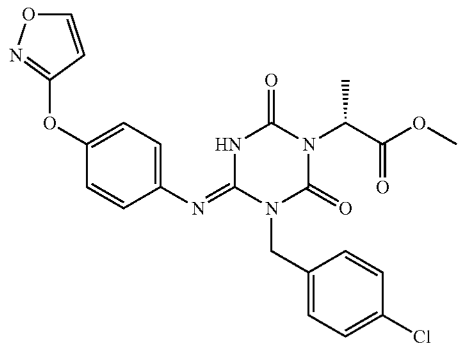 [SMILES: COC(=O)[C@@H](C)n1c(=O)[nH]/c(=N\c2ccc(Oc3ccon3)cc2)n(Cc2ccc(Cl)cc2)c1=O] | I-2460 | 2.10 | 498 | 2 |
| 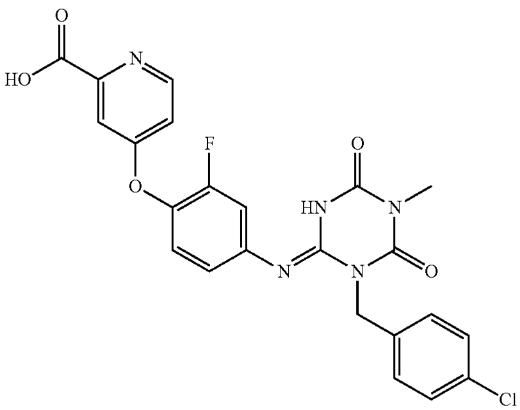 [SMILES: Cn1c(=O)[nH]/c(=N\c2ccc(Oc3ccnc(C(=O)O)c3)c(F)c2)n(Cc2ccc(Cl)cc2)c1=O] | I-2461 | 1.69 | 498 | 3 |
| 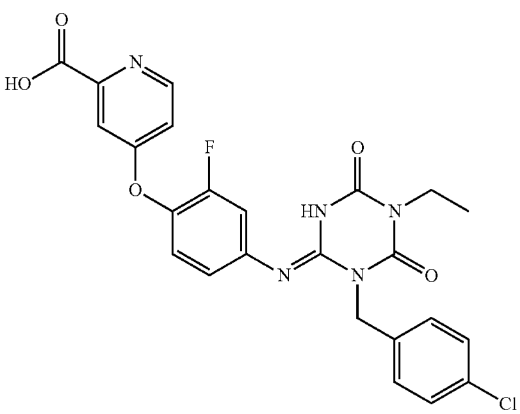 [SMILES: CCn1c(=O)[nH]/c(=N\c2ccc(Oc3ccnc(C(=O)O)c3)c(F)c2)n(Cc2ccc(Cl)cc2)c1=O] | I-2462 | 1.83 | 512 | 3 |
| 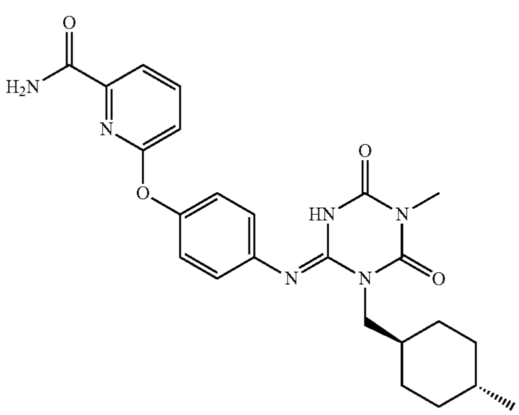 [SMILES: Cn1c(=O)[nH]/c(=N\c2ccc(Oc3cccc(C(N)=O)n3)cc2)n(C[C@H]2CC[C@H](C)CC2)c1=O] | I-2463 | 2.05 | 465 | 3 |

TABLE 505

| Structure | Compound No. | Retention Time (min) | [M + H] | Method |
|---|---|---|---|---|
| (structure) | I-2464 | 1.74 | 459 | 3 |
| (structure) | I-2465 | 2.14 | 466 | 3 |
| (structure) | I-2466 | 2.18 | 459 | 3 |

TABLE 505-continued

| Structure | Compound No. | Retention Time (min) | [M + H] | Method |
|---|---|---|---|---|
| 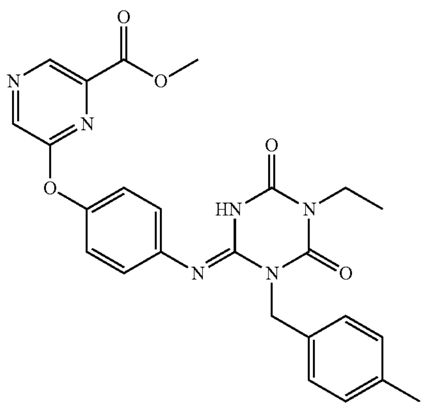 [SMILES: CCn1c(=O)[nH]/c(=N\c2ccc(Oc3cncc(C(=O)OC)n3)cc2)n(Cc2ccc(C)cc2)c1=O] | I-2467 | 2.2 | 489 | 3 |

TABLE 506

| Structure | Compound No. | Retention Time (min) | [M + H] | Method |
|---|---|---|---|---|
| 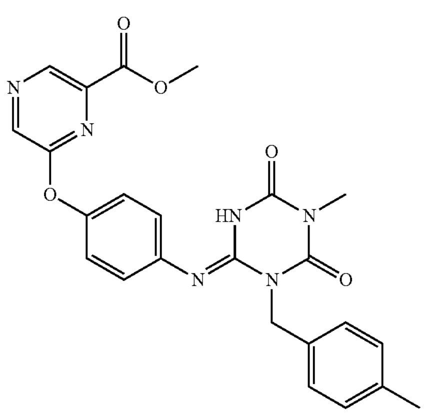 [SMILES: COC(=O)c1cncc(Oc2ccc(/N=c3\[nH]c(=O)n(C)c(=O)n3Cc3ccc(C)cc3)cc2)n1] | I-2468 | 2.05 | 475 | 3 |
| 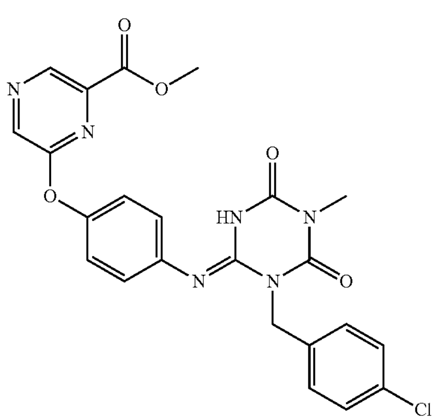 [SMILES: COC(=O)c1cncc(Oc2ccc(/N=c3\[nH]c(=O)n(C)c(=O)n3Cc3ccc(Cl)cc3)cc2)n1] | I-2469 | 2.14 | 495 | 3 |

TABLE 506-continued

| Structure | Compound No. | Retention Time (min) | [M + H] | Method |
|---|---|---|---|---|
| 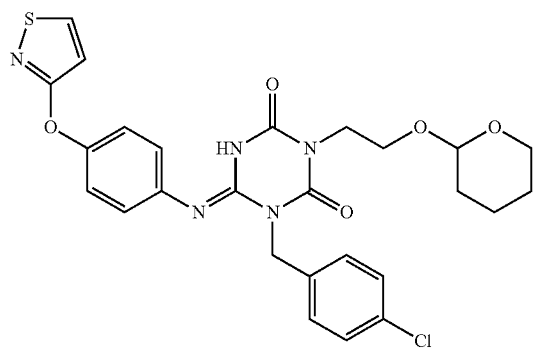 [SMILES: O=c1[nH]/c(=N\c2ccc(Oc3ccsn3)cc2)n(Cc2ccc(Cl)cc2)c(=O)n1CCOC1CCCCO1] | I-2470 | 2.48 | 472 | 3 |
| 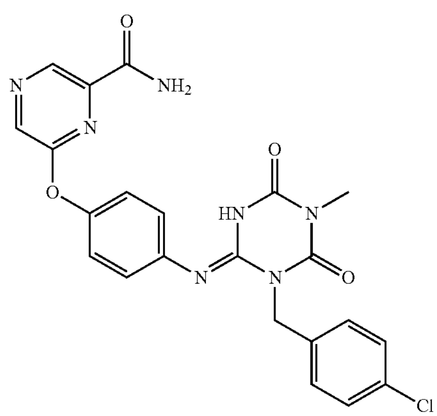 [SMILES: Cn1c(=O)[nH]/c(=N\c2ccc(Oc3cncc(C(N)=O)n3)cc2)n(Cc2ccc(Cl)cc2)c1=O] | I-2471 | 1.81 | 480 | 3 |

TABLE 507

| Structure | Compound No. | Retention Time (min) | [M + H] | Method |
|---|---|---|---|---|
| 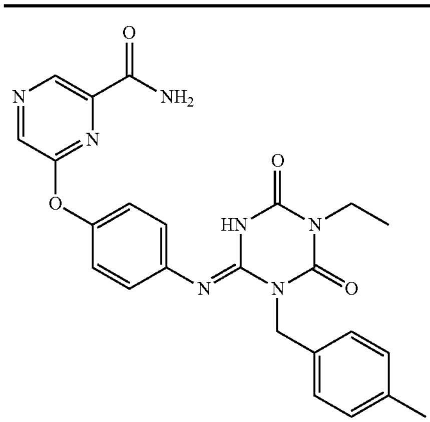 | I-2472 | 1.87 | 474 | 3 |

TABLE 507-continued

| Structure | Compound No. | Retention Time (min) | [M + H] | Method |
|---|---|---|---|---|
| 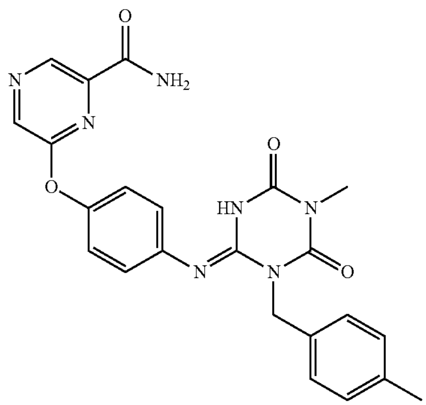 | I-2473 | 1.74 | 460 | 3 |
| 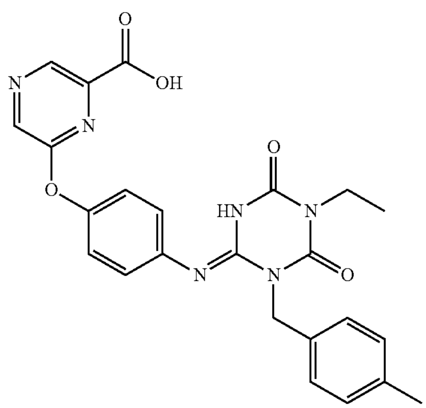 [SMILES: CCn1c(=O)[nH]/c(=N\c2ccc(Oc3cncc(C(=O)O)n3)cc2)n(Cc2ccc(C)cc2)c1=O] | I-2474 | 1.98 | 475 | 3 |
| 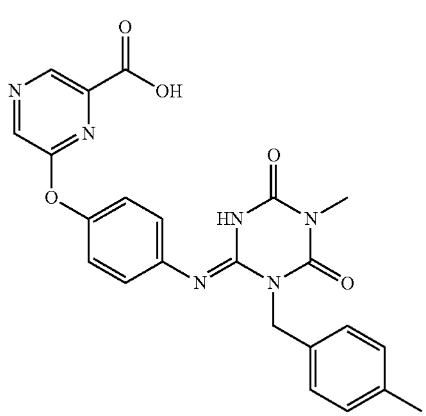 [SMILES: Cc1ccc(Cn2c(=O)n(C)c(=O)[nH]/c2=N\c2ccc(Oc3cncc(C(=O)O)n3)cc2)cc1] | I-2475 | 1.84 | 461 | 3 |

TABLE 508

| Structure | Compound No. | Retention Time (min) | [M + H] | Method |
|---|---|---|---|---|
| 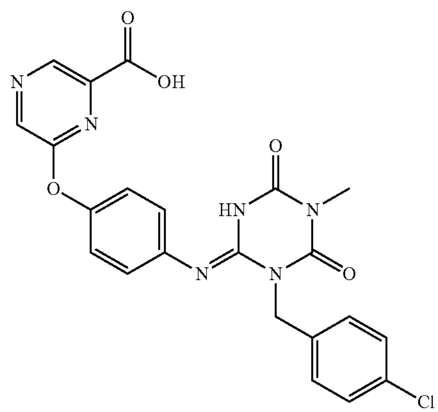 [SMILES: Cn1c(=O)[nH]/c(=N\c2ccc(Oc3cncc(C(=O)O)n3)cc2)n(Cc2ccc(Cl)cc2)c1=O] | I-2476 | 1.94 | 481 | 3 |
| 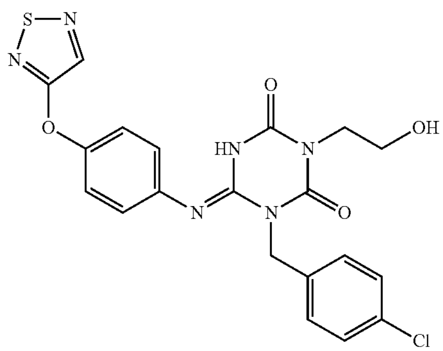 | I-2477 | 1.92 | 473 | 2 |
| 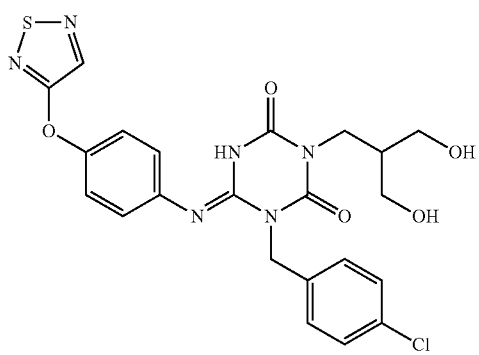 [SMILES: O=c1[nH]/c(=N\c2ccc(Oc3cnsn3)cc2)n(Cc2ccc(Cl)cc2)c(=O)n1CC(CO)CO] | I-2478 | 1.82 | 517 | 2 |
| 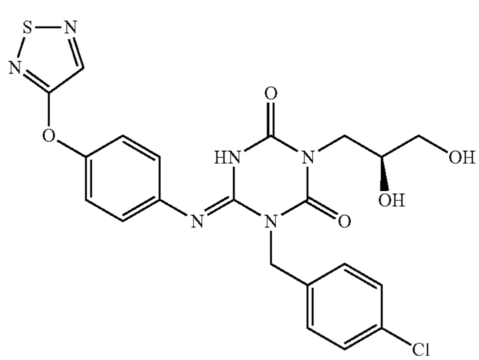 [SMILES: O=c1[nH]/c(=N\c2ccc(Oc3cnsn3)cc2)n(Cc2ccc(Cl)cc2)c(=O)n1C[C@H](O)CO] | I-2479 | 1.79 | 503 | 2 |

TABLE 509

| Structure | Compound No. | Retention Time (min) | [M + H] | Method |
|---|---|---|---|---|
| 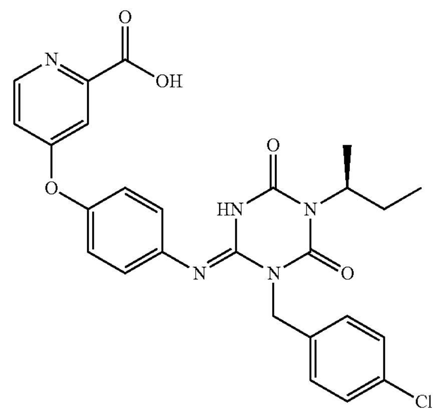 [SMILES: CC[C@H](C)n1c(=O)[nH]/c(=N\c2ccc(Oc3ccnc(C(=O)O)c3)cc2)n(Cc2ccc(Cl)cc2)c1=O] | I-2480 | 1.98 | 522 | 3 |
| 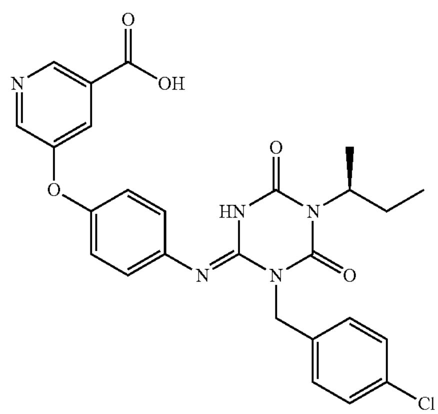 [SMILES: CC[C@H](C)n1c(=O)[nH]/c(=N\c2ccc(Oc3cncc(C(=O)O)c3)cc2)n(Cc2ccc(Cl)cc2)c1=O] | I-2481 | 2.29 | 522 | 3 |
| 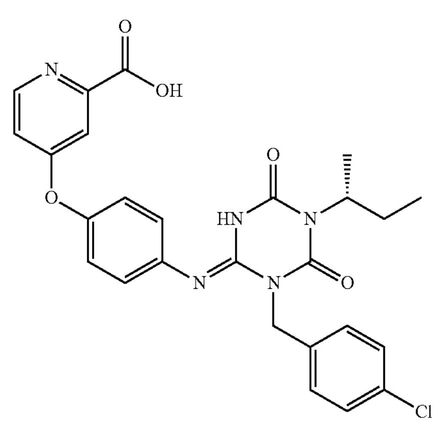 [SMILES: CC[C@@H](C)n1c(=O)[nH]/c(=N\c2ccc(Oc3ccnc(C(=O)O)c3)cc2)n(Cc2ccc(Cl)cc2)c1=O] | I-2482 | 1.96 | 522 | 3 |

TABLE 509-continued

| Structure | Compound No. | Retention Time (min) | [M + H] | Method |
|---|---|---|---|---|
| 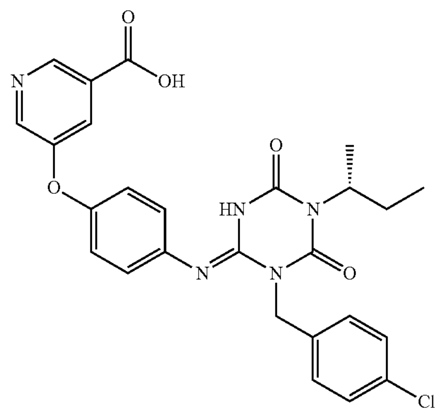 [SMILES: CC[C@@H](C)n1c(=O)[nH]/c(=N\c2ccc(Oc3cncc(C(=O)O)c3)cc2)n(Cc2ccc(Cl)cc2)c1=O] | I-2483 | 2.27 | 522 | 3 |

TABLE 510

| Structure | Compound No. | Retention Time (min) | [M + H] | Method |
|---|---|---|---|---|
| 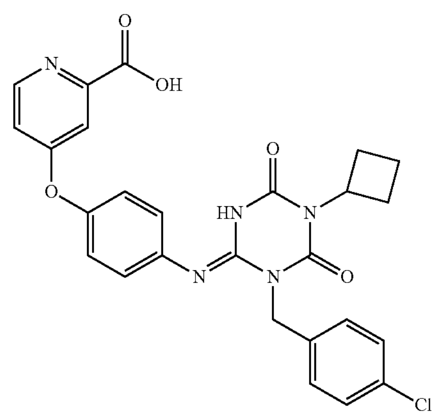 [SMILES: O=C(O)c1cc(Oc2ccc(/N=c3\[nH]c(=O)n(C4CCC4)c(=O)n3Cc3ccc(Cl)cc3)cc2)ccn1] | I-2484 | 1.90 | 520 | 3 |
| 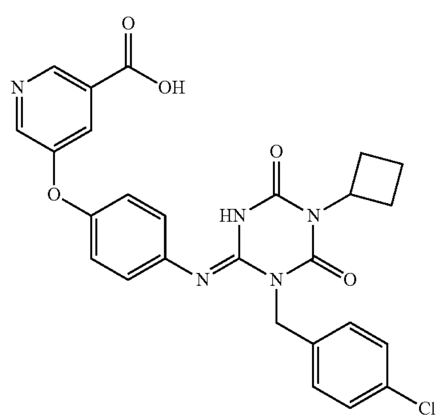 [SMILES: O=C(O)c1cncc(Oc2ccc(/N=c3\[nH]c(=O)n(C4CCC4)c(=O)n3Cc3ccc(Cl)cc3)cc2)c1] | I-2485 | 2.23 | 520 | 3 |

TABLE 510-continued

| Structure | Compound No. | Retention Time (min) | [M + H] | Method |
|---|---|---|---|---|
| 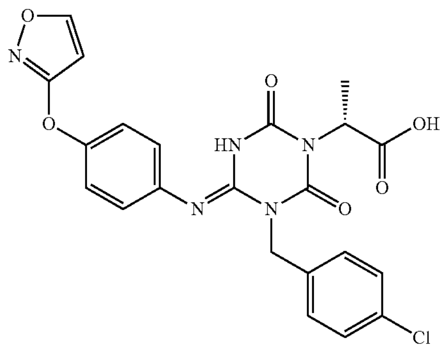 [SMILES: C[C@H](C(=O)O)n1c(=O)[nH]/c(=N\c2ccc(Oc3ccon3)cc2)n(Cc2ccc(Cl)cc2)c1=O] | I-2486 | 1.94 | 484 | 3 |
| 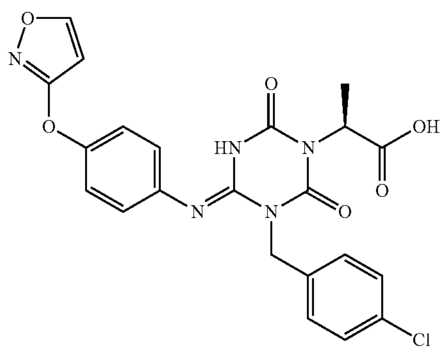 [SMILES: C[C@@H](C(=O)O)n1c(=O)[nH]/c(=N\c2ccc(Oc3ccon3)cc2)n(Cc2ccc(Cl)cc2)c1=O] | I-2487 | 1.94 | 484 | 3 |

TABLE 511

| Structure | Compound No. | Retention Time (min) | [M + H] | Method |
|---|---|---|---|---|
| 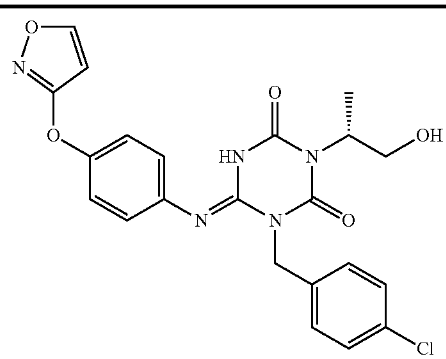 | I-2488 | 1.99 | 470 | 3 |
| 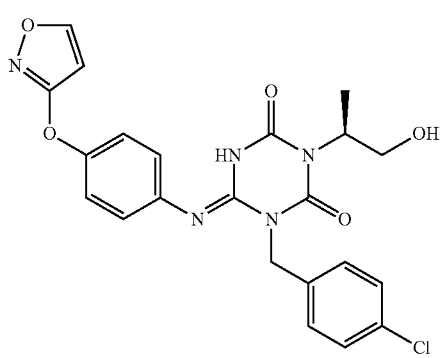 [SMILES: C[C@@H](CO)n1c(=O)[nH]/c(=N\c2ccc(Oc3ccon3)cc2)n(Cc2ccc(Cl)cc2)c1=O] | I-2489 | 1.99 | 470 | 3 |

TABLE 511-continued

| Structure | Compound No. | Retention Time (min) | [M + H] | Method |
|---|---|---|---|---|
| 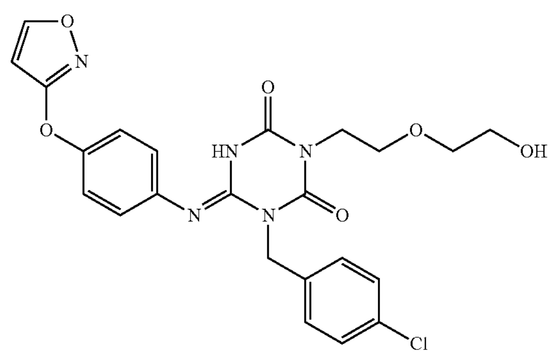 [SMILES: O=c1[nH]/c(=N\c2ccc(Oc3ccon3)cc2)n(Cc2ccc(Cl)cc2)c(=O)n1CCOCCO] | I-2490 | 1.89 | 500 | 3 |
| 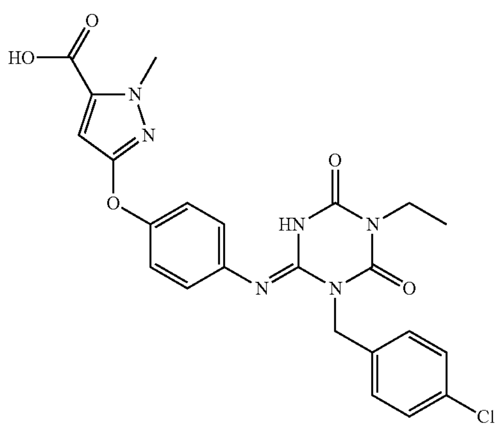 [SMILES: CCn1c(=O)[nH]/c(=N\c2ccc(Oc3cc(C(=O)O)n(C)n3)cc2)n(Cc2ccc(Cl)cc2)c1=O] | I-2491 | 1.96 | 497 | 3 |

TABLE 512

| Structure | Compound No. | Retention Time (min) | [M + H] | Method |
|---|---|---|---|---|
| 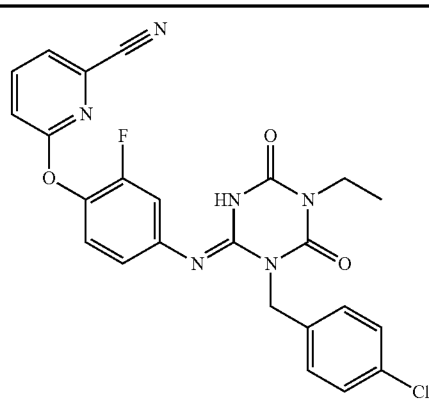 | I-2492 | 2.47 | 493 | 3 |

TABLE 512-continued
| Structure | Compound No. | Retention Time (min) | [M + H] | Method |
|---|---|---|---|---|
| 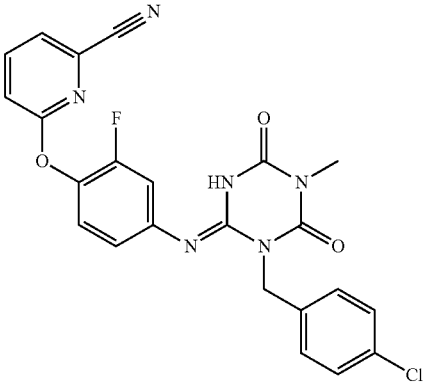 [SMILES: Cn1c(=O)[nH]/c(=N\c2ccc(Oc3cccc(C#N)n3)c(F)c2)n(Cc2ccc(Cl)cc2)c1=O] | I-2493 | 2.34 | 479 | 3 |
| 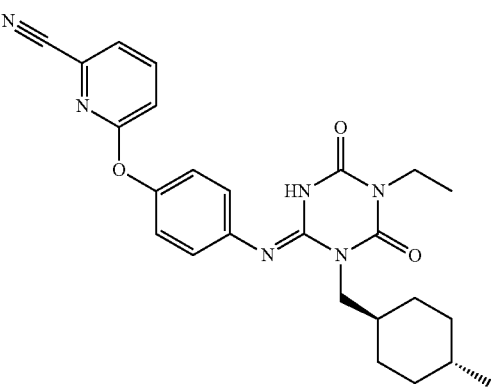 [SMILES: CCn1c(=O)[nH]/c(=N\c2ccc(Oc3cccc(C#N)n3)cc2)n(C[C@H]2CC[C@H](C)CC2)c1=O] | I-2494 | 2.49 | 461 | 3 |
| 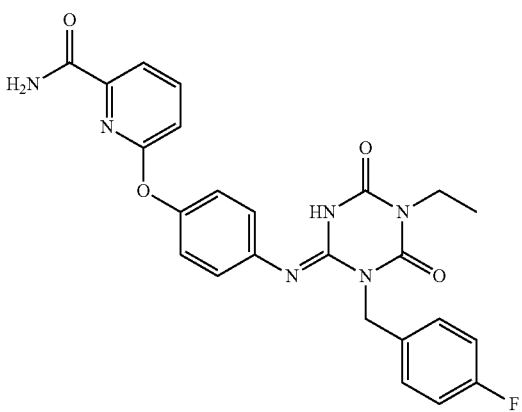 [SMILES: CCn1c(=O)[nH]/c(=N\c2ccc(Oc3cccc(C(N)=O)n3)cc2)n(Cc2ccc(F)cc2)c1=O] | I-2495 | 1.89 | 477 | 3 |

TABLE 513

| Structure | Compound No. | Retention Time (min) | [M + H] | Method |
|---|---|---|---|---|
| 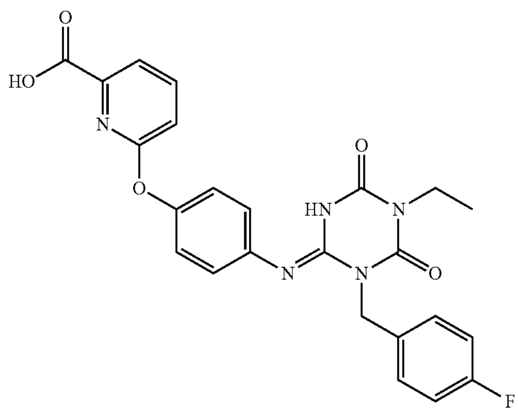 [SMILES: CCn1c(=O)[nH]/c(=N\c2ccc(Oc3cccc(C(=O)O)n3)cc2)n(Cc2ccc(F)cc2)c1=O] | I-2496 | 1.99 | 478 | 3 |
| 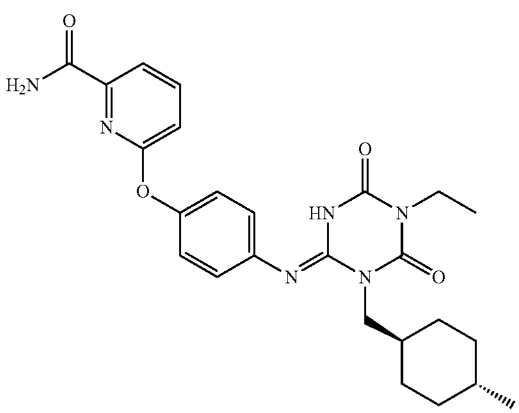 [SMILES: CCn1c(=O)[nH]/c(=N\c2ccc(Oc3cccc(C(N)=O)n3)cc2)n(C[C@H]2CC[C@H](C)CC2)c1=O] | I-2497 | 2.20 | 479 | 3 |
| 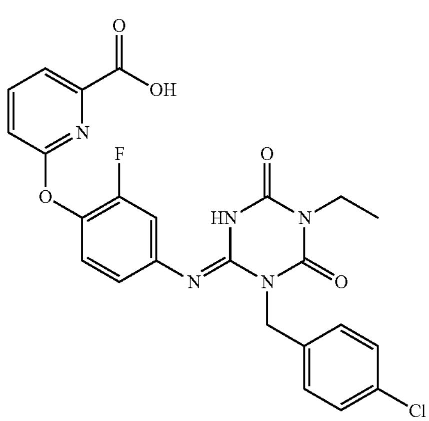 [SMILES: CCn1c(=O)[nH]/c(=N\c2ccc(Oc3cccc(C(=O)O)n3)c(F)c2)n(Cc2ccc(Cl)cc2)c1=O] | I-2498 | 2.34 | 512 | 3 |

TABLE 513-continued

| Structure | Compound No. | Retention Time (min) | [M + H] | Method |
|---|---|---|---|---|
| 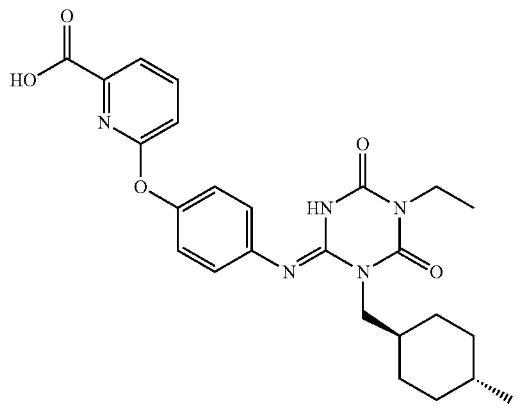 [SMILES: CCn1c(=O)[nH]/c(=N\c2ccc(Oc3cccc(C(=O)O)n3)cc2)n(C[C@H]2CC[C@H](C)CC2)c1=O] | I-2499 | 2.29 | 480 | 3 |

TABLE 514

| Structure | Compound No. | Retention Time (min) | [M + H] | Method |
|---|---|---|---|---|
| 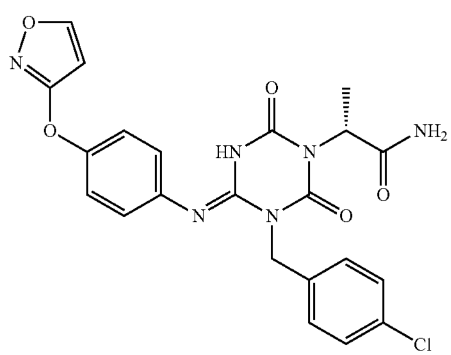 [SMILES: C[C@H](C(N)=O)n1c(=O)[nH]/c(=N\c2ccc(Oc3ccon3)cc2)n(Cc2ccc(Cl)cc2)c1=O] | I-2500 | 1.77 | 483 | 2 |
| 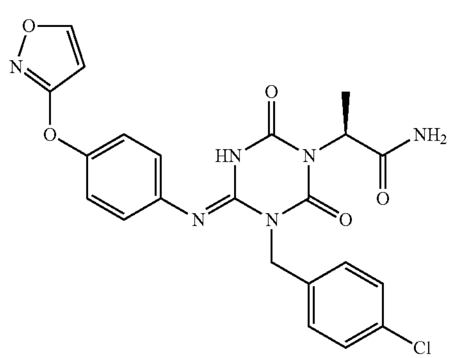 [SMILES: C[C@@H](C(N)=O)n1c(=O)[nH]/c(=N\c2ccc(Oc3ccon3)cc2)n(Cc2ccc(Cl)cc2)c1=O] | I-2501 | 1.77 | 483 | 2 |

TABLE 514-continued

| Structure | Compound No. | Retention Time (min) | [M + H] | Method |
|---|---|---|---|---|
| 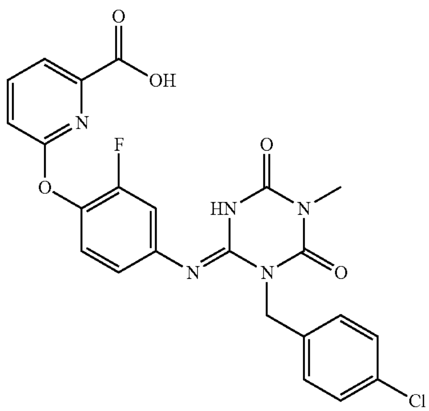 [SMILES: Cn1c(=O)[nH]/c(=N\c2ccc(Oc3cccc(C(=O)O)n3)c(F)c2)n(Cc2ccc(Cl)cc2)c1=O] | I-2502 | 2.21 | 498 | 3 |
| 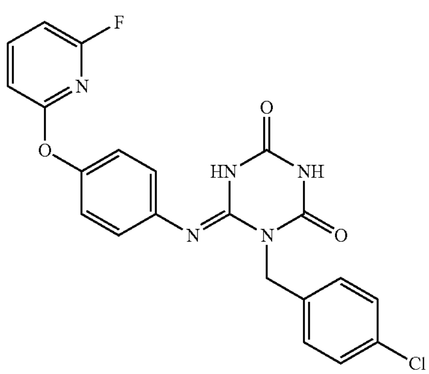 [SMILES: O=c1[nH]c(=O)n(Cc2ccc(Cl)cc2)/c(=N/c2ccc(Oc3cccc(F)n3)cc2)[nH]1] | I-2503 | 2.13 | 440 | 3 |

TABLE 515

| Structure | Compound No. | Retention Time (min) | [M + H] | Method |
|---|---|---|---|---|
| 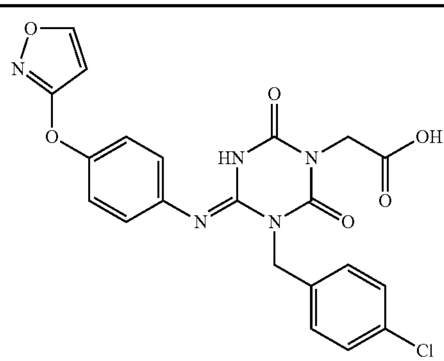 | I-2504 | 1.83 | 470 | 2 |

TABLE 515-continued

| Structure | Compound No. | Retention Time (min) | [M + H] | Method |
|---|---|---|---|---|
| 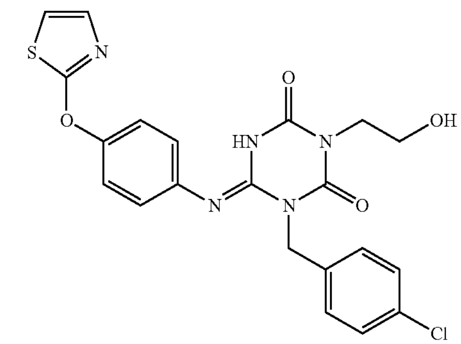 [SMILES: O=c1[nH]/c(=N\c2ccc(Oc3nccs3)cc2)n(Cc2ccc(Cl)cc2)c(=O)n1CCO] | I-2505 | 1.89 | 472 | 2 |
| 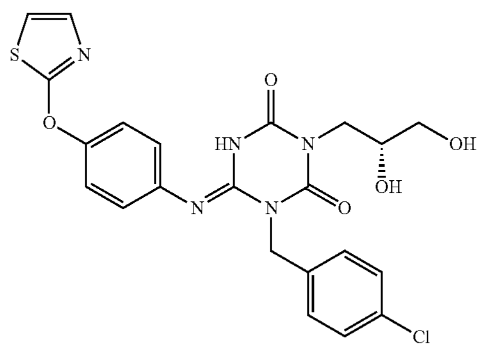 [SMILES: O=c1[nH]/c(=N\c2ccc(Oc3nccs3)cc2)n(Cc2ccc(Cl)cc2)c(=O)n1C[C@@H](O)CO] | I-2506 | 1.77 | 502 | 2 |
| 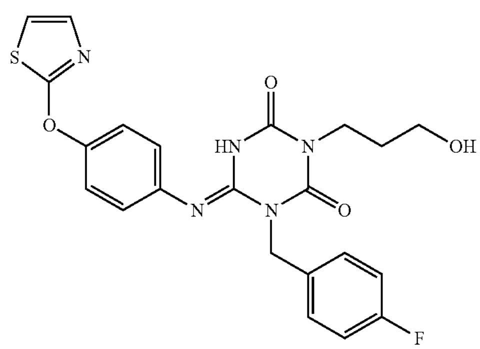 [SMILES: O=c1[nH]/c(=N\c2ccc(Oc3nccs3)cc2)n(Cc2ccc(F)cc2)c(=O)n1CCCO] | I-2507 | 1.80 | 470 | 2 |

TABLE 516

| Structure | Compound No. | Retention Time (min) | [M + H] | Method |
|---|---|---|---|---|
| 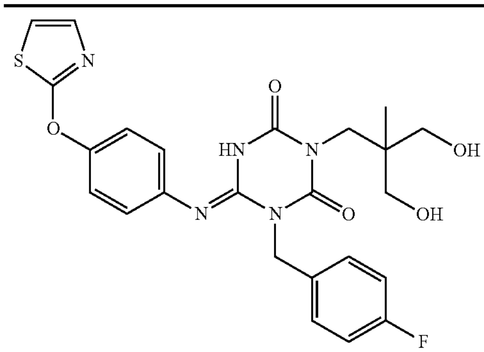 | I-2508 | 1.79 | 514 | 2 |

TABLE 516-continued

| Structure | Compound No. | Retention Time (min) | [M + H] | Method |
|---|---|---|---|---|
| 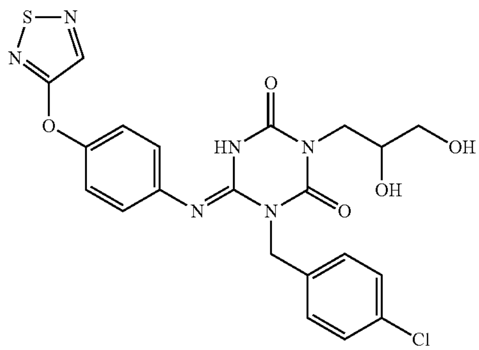 [SMILES: O=c1[nH]/c(=N\c2ccc(Oc3cnsn3)cc2)n(Cc2ccc(Cl)cc2)c(=O)n1CC(O)CO] | I-2509 | 1.80 | 502 | 2 |
| 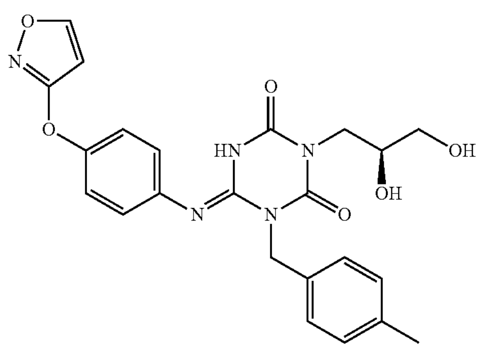 [SMILES: Cc1ccc(Cn2c(=O)n(C[C@H](O)CO)c(=O)[nH]/c2=N\c2ccc(Oc3ccon3)cc2)cc1] | I-2510 | 1.62 | 466 | 2 |
| 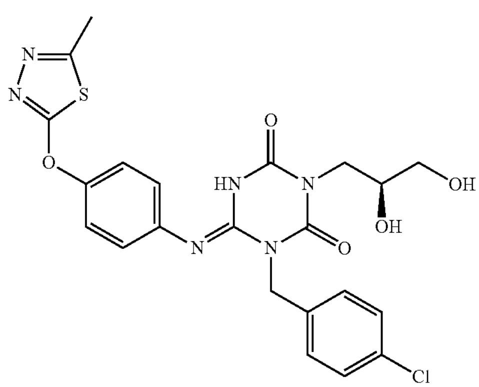 [SMILES: Cc1nnc(Oc2ccc(/N=c3\[nH]c(=O)n(C[C@H](O)CO)c(=O)n3Cc3ccc(Cl)cc3)cc2)s1] | I-2511 | 1.73 | 517 | 2 |

TABLE 517

| Structure | Compound No. | Retention Time (min) | [M + H] | Method |
|---|---|---|---|---|
| 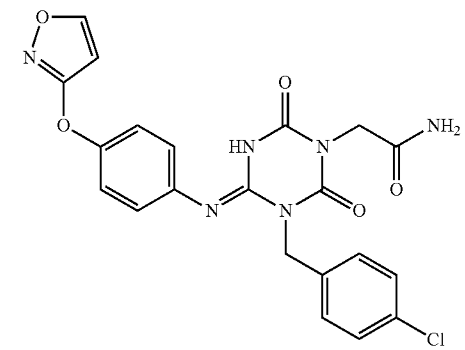 [SMILES: NC(=O)Cn1c(=O)[nH]/c(=N\c2ccc(Oc3ccon3)cc2)n(Cc2ccc(Cl)cc2)c1=O] | I-2512 | 1.70 | 469 | 2 |
| 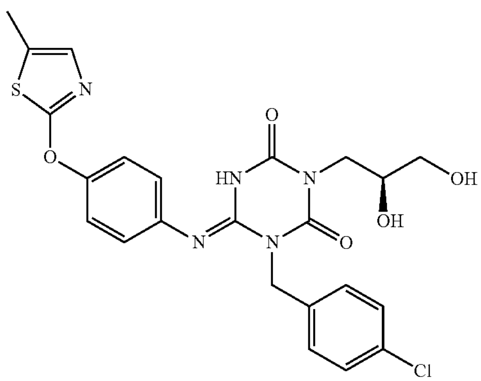 [SMILES: Cc1cnc(Oc2ccc(/N=c3\[nH]c(=O)n(C[C@H](O)CO)c(=O)n3Cc3ccc(Cl)cc3)cc2)s1] | I-2513 | 1.90 | 516 | 2 |
| 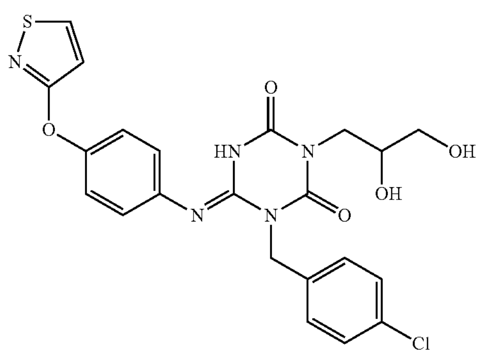 [SMILES: O=c1[nH]/c(=N\c2ccc(Oc3ccsn3)cc2)n(Cc2ccc(Cl)cc2)c(=O)n1CC(O)CO] | I-2514 | 1.78 | 502 | 2 |
| 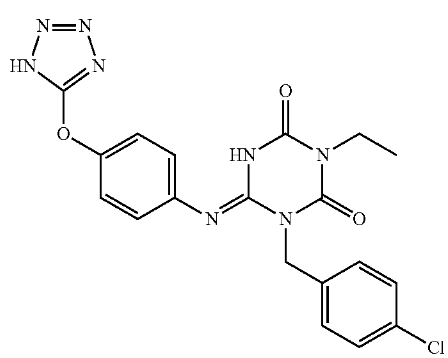 [SMILES: CCn1c(=O)[nH]/c(=N\c2ccc(Oc3nnn[nH]3)cc2)n(Cc2ccc(Cl)cc2)c1=O] | I-2515 | 1.84 | 441 | 2 |

TABLE 518

| Structure | Compound No. | Retention Time (min) | [M + H] | Method |
|---|---|---|---|---|
| 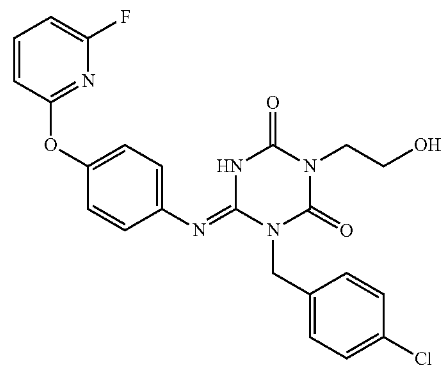 [SMILES: O=c1[nH]/c(=N\c2ccc(Oc3cccc(F)n3)cc2)n(Cc2ccc(Cl)cc2)c(=O)n1CCO] | I-2516 | 2.09 | 484 | 3 |
| 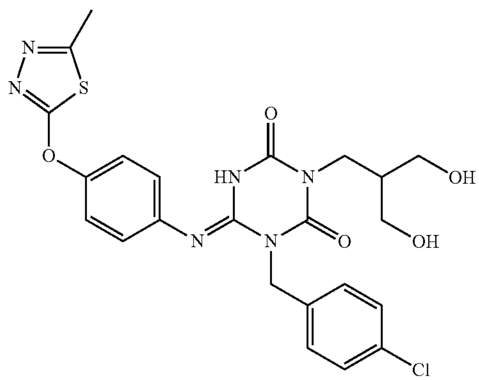 [SMILES: Cc1nnc(Oc2ccc(/N=c3\[nH]c(=O)n(CC(CO)CO)c(=O)n3Cc3ccc(Cl)cc3)cc2)s1] | I-2517 | 1.76 | 531 | 2 |
| 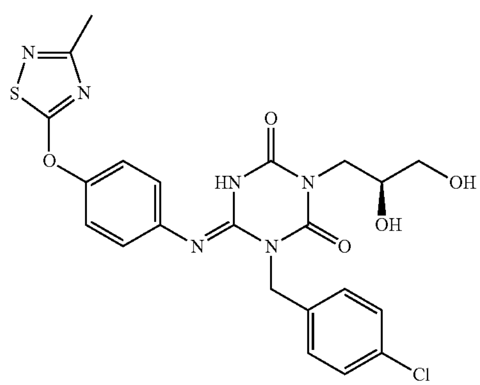 | I-2518 | 1.75 | 517 | 2 |
| 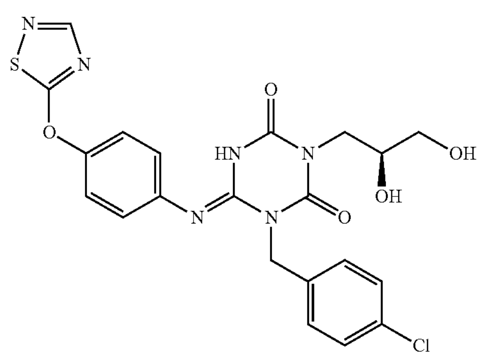 [SMILES: O=c1[nH]/c(=N\c2ccc(Oc3ncns3)cc2)n(Cc2ccc(Cl)cc2)c(=O)n1C[C@H](O)CO] | I-2519 | 1.70 | 503 | 2 |

TABLE 519

| Structure | Compound No. | Retention Time (min) | [M + H] | Method |
|---|---|---|---|---|
| 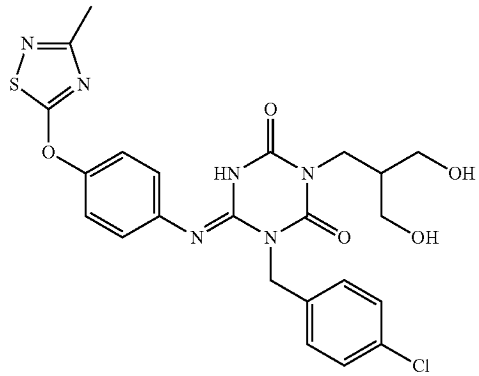 | I-2520 | 1.89 | 531 | 3 |
| 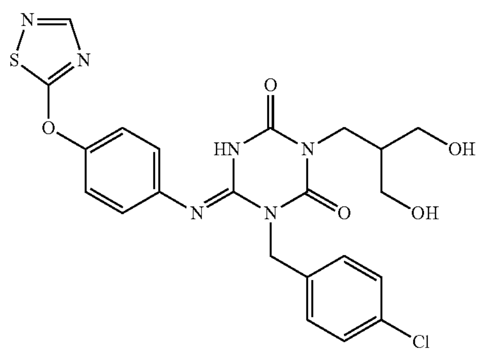 [SMILES: O=c1[nH]/c(=N\c2ccc(Oc3ncns3)cc2)n(Cc2ccc(Cl)cc2)c(=O)n1CC(CO)CO] | I-2521 | 1.81 | 517 | 3 |
| 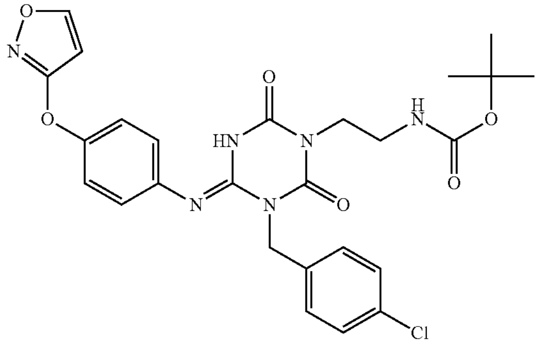 [SMILES: CC(C)(C)OC(=O)NCCn1c(=O)[nH]/c(=N\c2ccc(Oc3ccon3)cc2)n(Cc2ccc(Cl)cc2)c1=O] | I-2522 | 2.24 | 555 | 2 |
| 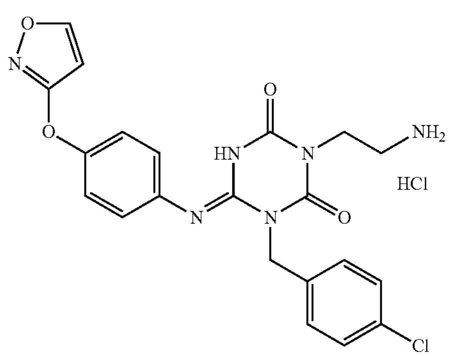 [SMILES: NCCn1c(=O)[nH]/c(=N\c2ccc(Oc3ccon3)cc2)n(Cc2ccc(Cl)cc2)c1=O ; Cl] | I-2523 | 1.37 | 455 | 2 |

TABLE 520

| Structure | Compound No. | Retention Time (min) | [M + H] | Method |
|---|---|---|---|---|
| (structure) | I-2524 | 1.75 | 497 | 2 |
| (structure) | I-2525 | 1.96 | 514 | 3 |
| (structure) | I-2526 | 1.98 | 526 | 3 |
| (structure) | I-2527 | 1.83 | 497 | 3 |

TABLE 521

| Structure | Compound No. | Retention Time (min) | [M + H] | Method |
|---|---|---|---|---|
| 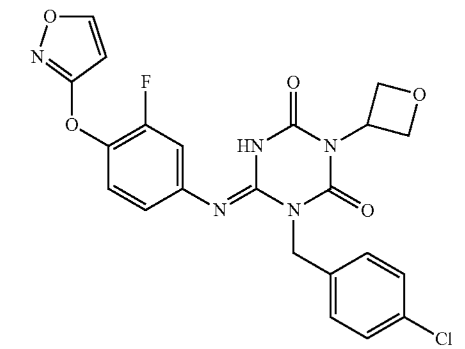 [SMILES: O=c1[nH]/c(=N\c2ccc(Oc3ccon3)c(F)c2)n(Cc2ccc(Cl)cc2)c(=O)n1C1COC1] | I-2528 | 2.19 | 486 | 3 |
| 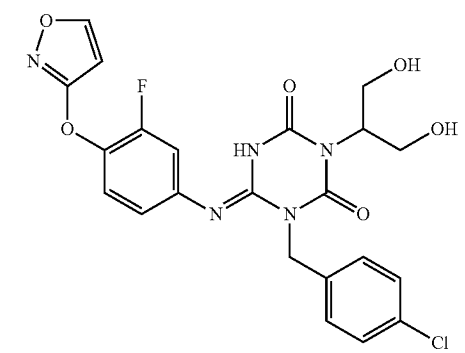 [SMILES: O=c1[nH]/c(=N\c2ccc(Oc3ccon3)c(F)c2)n(Cc2ccc(Cl)cc2)c(=O)n1C(CO)CO] | I-2529 | 1.88 | 504 | 3 |
| 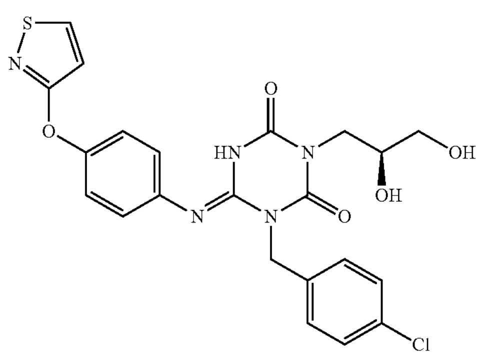 [SMILES: O=c1[nH]/c(=N\c2ccc(Oc3ccsn3)cc2)n(Cc2ccc(Cl)cc2)c(=O)n1C[C@H](O)CO] | I-2530 | 1.86 | 502 | 3 |
| 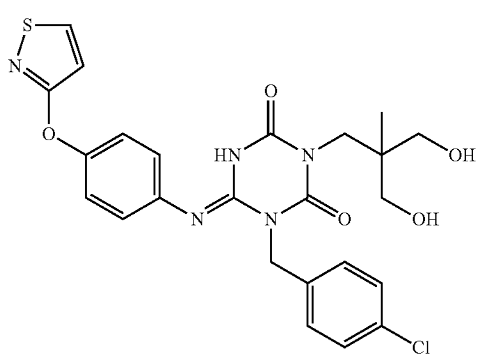 | I-2531 | 2.02 | 530 | 3 |

TABLE 522

| Structure | Compound No. | Retention Time (min) | [M + H] | Method |
|---|---|---|---|---|
| 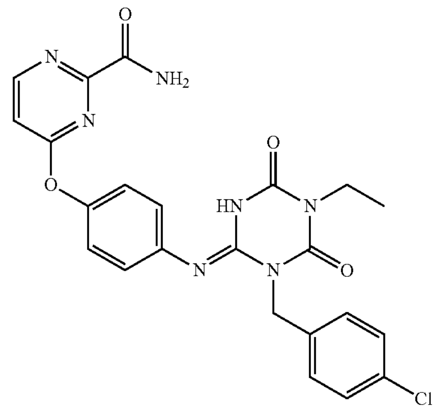 [SMILES: CCn1c(=O)[nH]/c(=N\c2ccc(Oc3ccnc(C(N)=O)n3)cc2)n(Cc2ccc(Cl)cc2)c1=O] | I-2532 | 1.94 | 494 | 3 |
| 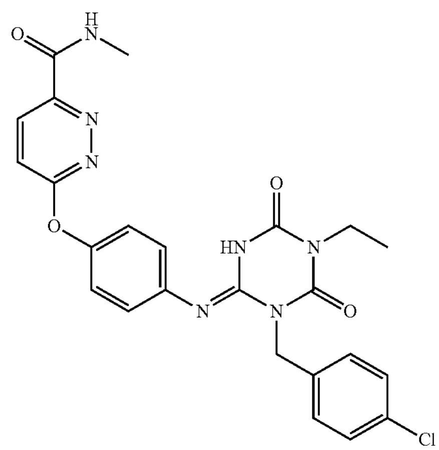 [SMILES: CCn1c(=O)[nH]/c(=N\c2ccc(Oc3ccc(C(=O)NC)nn3)cc2)n(Cc2ccc(Cl)cc2)c1=O] | I-2533 | 1.97 | 508 | 2 |
| 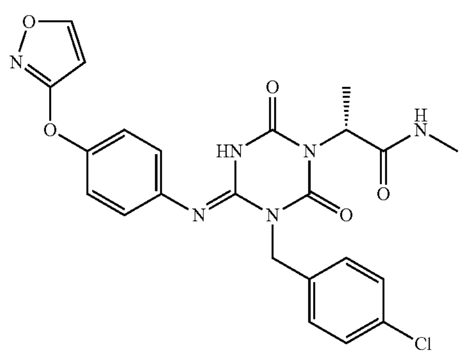 [SMILES: CNC(=O)[C@@H](C)n1c(=O)[nH]/c(=N\c2ccc(Oc3ccon3)cc2)n(Cc2ccc(Cl)cc2)c1=O] | I-2534 | 1.80 | 497 | 2 |
| 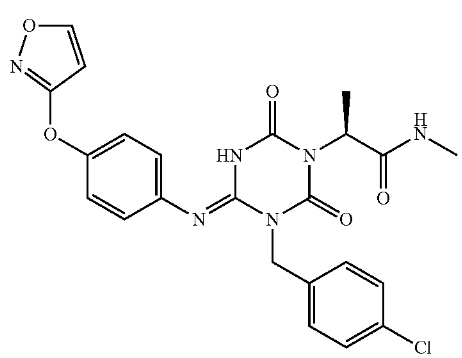 [SMILES: CNC(=O)[C@H](C)n1c(=O)[nH]/c(=N\c2ccc(Oc3ccon3)cc2)n(Cc2ccc(Cl)cc2)c1=O] | I-2535 | 1.81 | 497 | 2 |

TABLE 523
| Structure | Compound No. | Retention Time (min) | [M + H[ | Method |
|---|---|---|---|---|
| 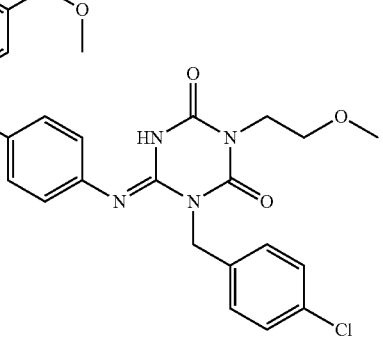 | I-2536 | 1.96 | 538 | 2 |
| 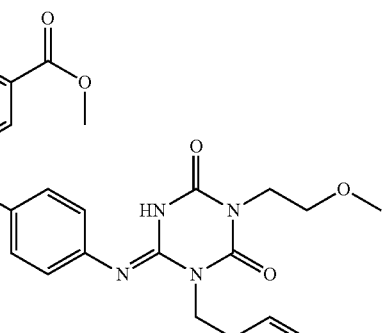 | I-2537 | 2.07 | 538 | 2 |
| 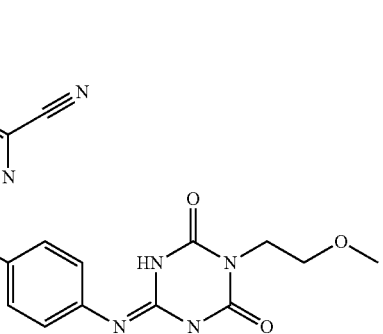 | I-2538 | 2.13 | 505 | 2 |

TABLE 523-continued
| Structure | Compound No. | Retention Time (min) | [M + H] | Method |
|---|---|---|---|---|
| 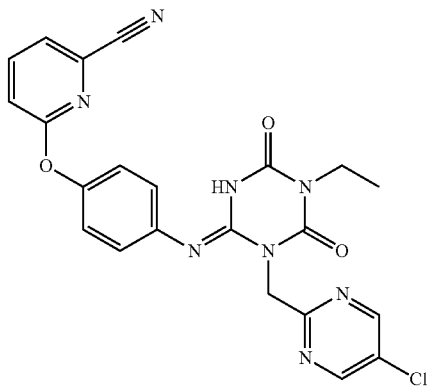 [SMILES: CCn1c(=O)[nH]/c(=N\c2ccc(Oc3cccc(C#N)n3)cc2)n(Cc2ncc(Cl)cn2)c1=O] | I-2539 | 1.82 | 477 | 2 |
TABLE 524
| Structure | Compoud No. | Retention Time (min) | [M + H] | Method |
|---|---|---|---|---|
| 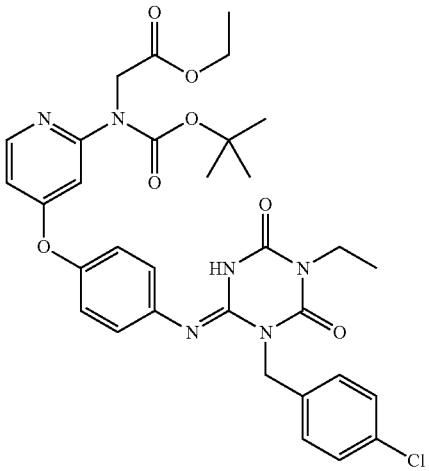 [SMILES: CCOC(=O)CN(C(=O)OC(C)(C)C)c1cc(Oc2ccc(/N=c3\[nH]c(=O)n(CC)c(=O)n3Cc3ccc(Cl)cc3)cc2)ccn1] | I-2540 | 2.68 | 651 | 2 |
| 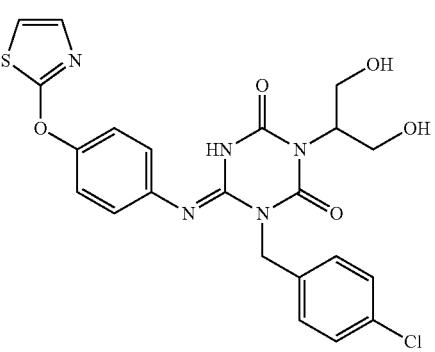 [SMILES: O=c1[nH]/c(=N\c2ccc(Oc3nccs3)cc2)n(Cc2ccc(Cl)cc2)c(=O)n1C(CO)CO] | I-2541 | 1.84 | 502 | 3 |

TABLE 524-continued

| Structure | Compound No. | Retention Time (min) | [M + H] | Method |
|---|---|---|---|---|
| 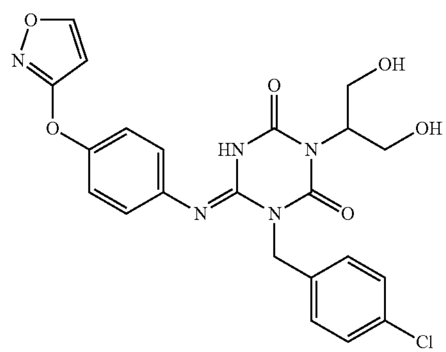 [SMILES: O=c1[nH]/c(=N\c2ccc(Oc3ccon3)cc2)n(Cc2ccc(Cl)cc2)c(=O)n1C(CO)CO] | I-2542 | 1.74 | 486 | 3 |
| 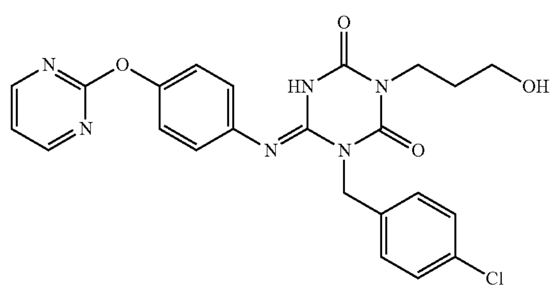 [SMILES: O=c1[nH]/c(=N\c2ccc(Oc3ncccn3)cc2)n(Cc2ccc(Cl)cc2)c(=O)n1CCCO] | I-2543 | 1.79 | 481 | 3 |

TABLE 525

| Structure | Compound No. | Retention Time (min) | [M + H] | Method |
|---|---|---|---|---|
| 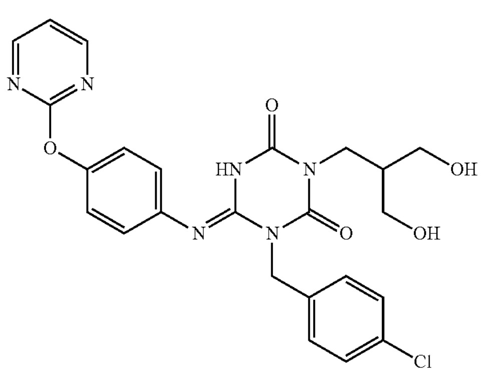 [SMILES: O=c1[nH]/c(=N\c2ccc(Oc3ncccn3)cc2)n(Cc2ccc(Cl)cc2)c(=O)n1CC(CO)CO] | I-2544 | 1.66 | 511 | 3 |

TABLE 525-continued

| Structure | Compound No. | Retention Time (min) | [M + H] | Method |
|---|---|---|---|---|
| 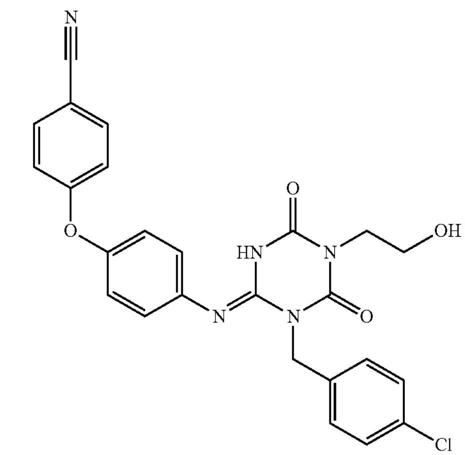 [SMILES: N#Cc1ccc(Oc2ccc(/N=c3\[nH]c(=O)n(CCO)c(=O)n3Cc3ccc(Cl)cc3)cc2)cc1] | I-2545 | 2.13 | 490 | 3 |
| 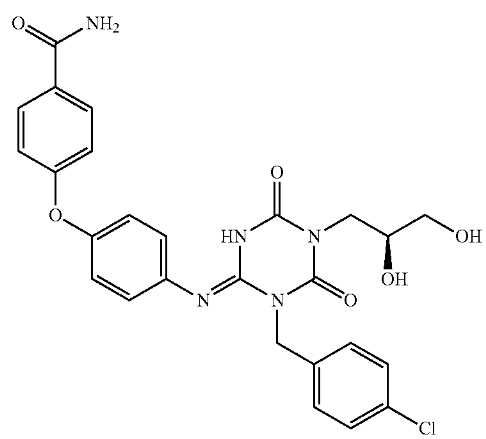 [SMILES: NC(=O)c1ccc(Oc2ccc(/N=c3\[nH]c(=O)n(C[C@H](O)CO)c(=O)n3Cc3ccc(Cl)cc3)cc2)cc1] | I-2546 | 1.60 | 538 | 3 |
| 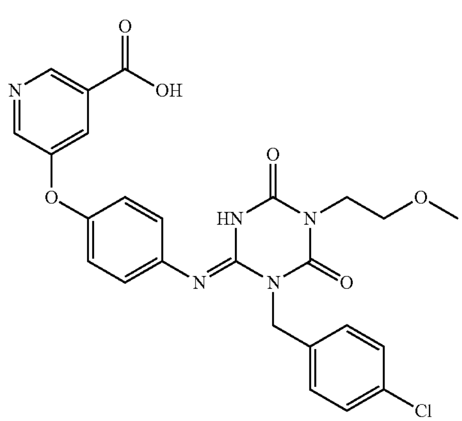 [SMILES: COCCn1c(=O)[nH]/c(=N\c2ccc(Oc3cncc(C(=O)O)c3)cc2)n(Cc2ccc(Cl)cc2)c1=O] | I-2547 | 1.82 | 524 | 2 |

TABLE 526

| Structure | Compoud No. | Retention Time (min) | [M + H] | Method |
|---|---|---|---|---|
| 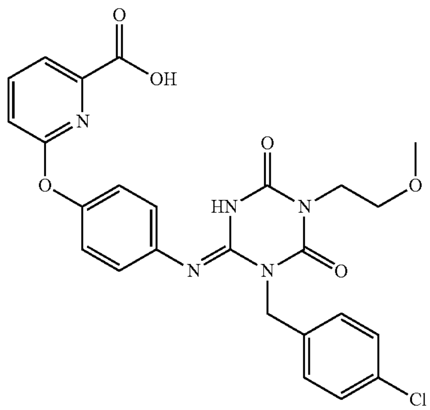 [SMILES: COCCn1c(=O)[nH]/c(=N\c2ccc(Oc3cccc(C(=O)O)n3)cc2)n(Cc2ccc(Cl)cc2)c1=O] | I-2548 | 1.98 | 524 | 2 |
| 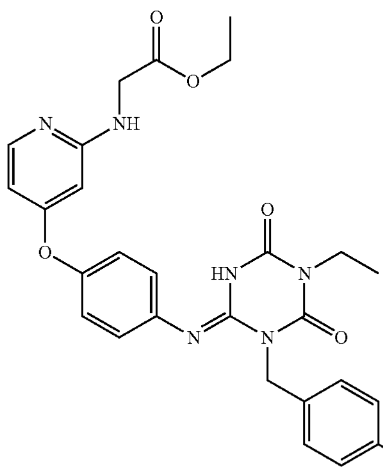 | I-2549 | 1.60 | 551 | 3 |
| 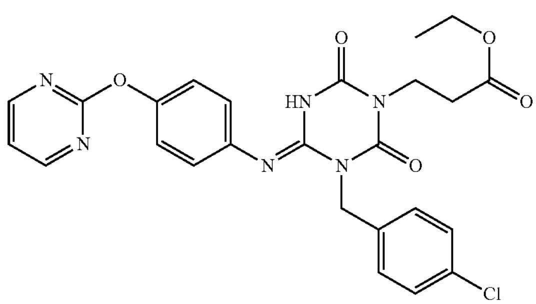 [SMILES: CCOC(=O)CCn1c(=O)[nH]/c(=N\c2ccc(Oc3ncccn3)cc2)n(Cc2ccc(Cl)cc2)c1=O] | I-2550 | 2.16 | 523 | 3 |
| 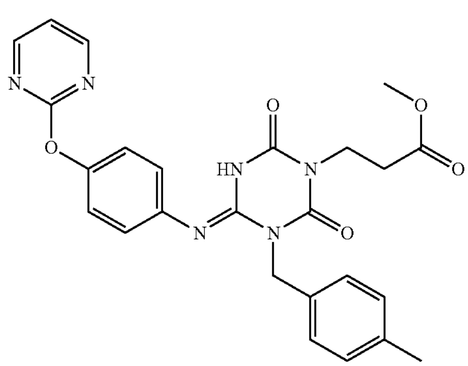 [SMILES: COC(=O)CCn1c(=O)[nH]/c(=N\c2ccc(Oc3ncccn3)cc2)n(Cc2ccc(C)cc2)c1=O] | I-2551 | 1.95 | 489 | 3 |

TABLE 527

| Structure | Compound No. | Retention Time (min) | [M + H] | Method |
|---|---|---|---|---|
| *(structure)* | I-2552 | 1.55 | 524 | 2 |
| *(structure)* | I-2553 | 1.62 | 496 | 2 |
| *(structure)* | I-2554 | 1.39 | 522 | 2 |

TABLE 527-continued

| Structure | Compound No. | Retention Time (min) | [M + H] | Method |
|---|---|---|---|---|
| 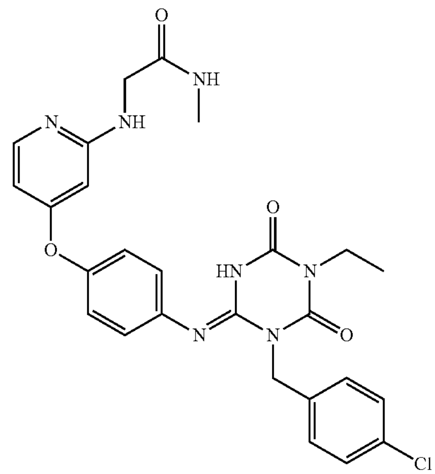 [SMILES: CCn1c(=O)[nH]/c(=N\c2ccc(Oc3ccnc(NCC(=O)NC)c3)cc2)n(Cc2ccc(Cl)cc2)c1=O] | I-2555 | 1.40 | 536 | 2 |

TABLE 528

| Structure | Compound No. | Retention Time (min) | [M + H] | Method |
|---|---|---|---|---|
| 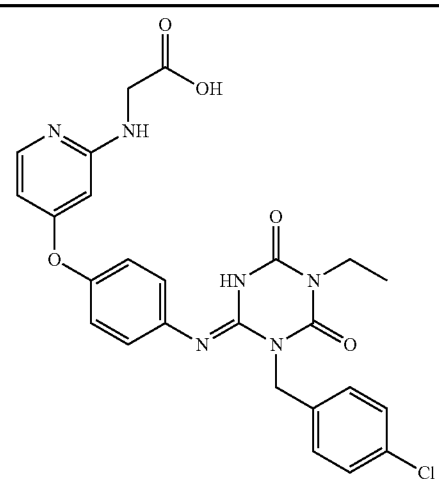 | I-2556 | 1.50 | 523 | 2 |
| 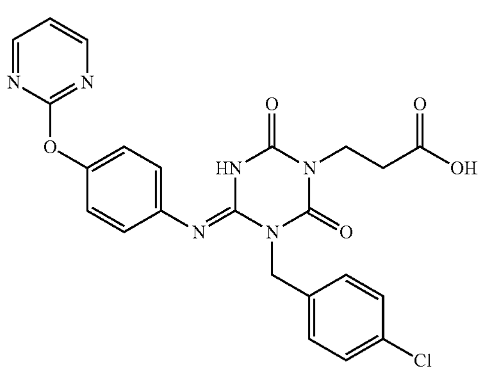 [SMILES: O=C(O)CCn1c(=O)[nH]/c(=N\c2ccc(Oc3ncccn3)cc2)n(Cc2ccc(Cl)cc2)c1=O] | I-2557 | 1.79 | 495 | 3 |

TABLE 528-continued
| Structure | Compound No. | Retention Time (min) | [M + H] | Method |
|---|---|---|---|---|
| 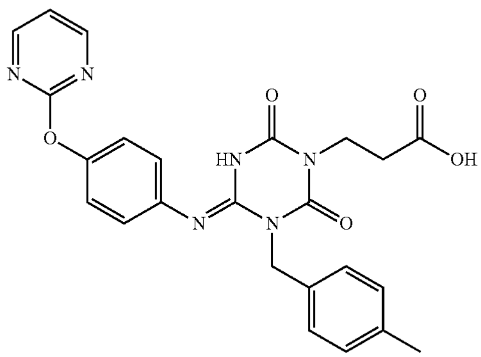 [SMILES: Cc1ccc(Cn2c(=O)n(CCC(=O)O)c(=O)[nH]/c2=N\c2ccc(Oc3ncccn3)cc2)cc1] | I-2558 | 1.71 | 475 | 3 |
| 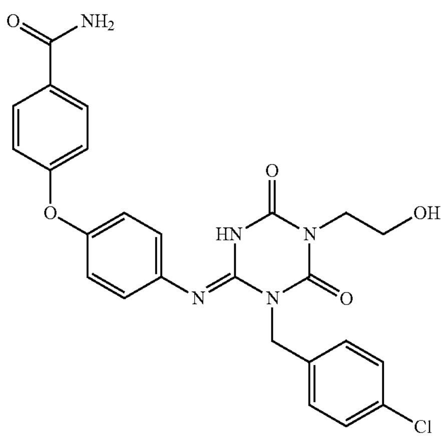 [SMILES: NC(=O)c1ccc(Oc2ccc(/N=c3\[nH]c(=O)n(CCO)c(=O)n3Cc3ccc(Cl)cc3)cc2)cc1] | I-2559 | 1.72 | 508 | 3 |
TABLE 529
| Structure | Compound No. | Retention Time (min) | [M + H] | Method |
|---|---|---|---|---|
| 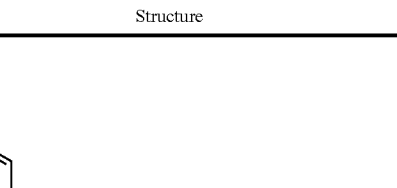 | I-2560 | 2.03 | 520 | 3 |

TABLE 529-continued

| Structure | Compoud No. | Retention Time (min) | [M + H] | Method |
|---|---|---|---|---|
| (structure) | I-2562 | 2.43 | 526 | 3 |
| (structure) | I-2563 | 2 | 472 | 3 |

TABLE 530

| Structure | Compoud No. | Retention Time (min) | [M + H] | Method |
|---|---|---|---|---|
| (structure) | I-2564 | 2.11 | 498 | 3 |

TABLE 530-continued

| Structure | Compound No. | Retention Time (min) | [M + H] | Method |
|---|---|---|---|---|
| 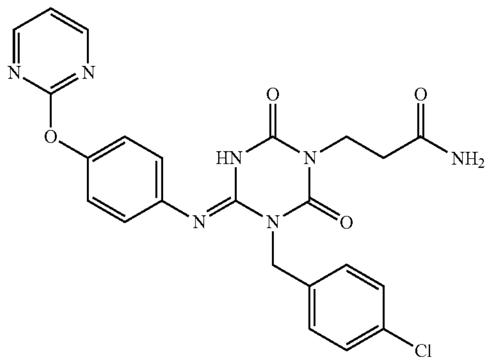 [SMILES: NC(=O)CCn1c(=O)[nH]/c(=N\c2ccc(Oc3ncccn3)cc2)n(Cc2ccc(Cl)cc2)c1=O] | I-2565 | 1.66 | 494 | 3 |
| 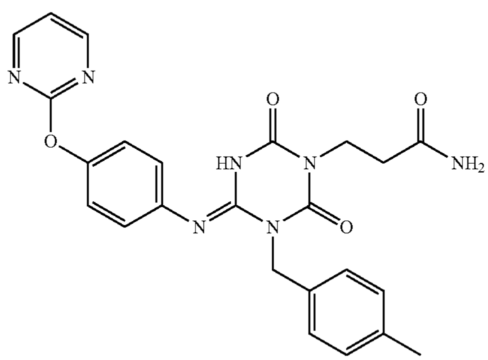 [SMILES: Cc1ccc(Cn2c(=O)n(CCC(N)=O)c(=O)[nH]/c2=N\c2ccc(Oc3ncccn3)cc2)cc1] | I-2566 | 1.57 | 474 | 3 |
| 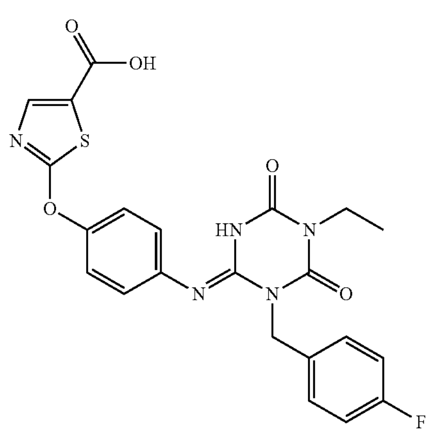 [SMILES: CCn1c(=O)[nH]/c(=N\c2ccc(Oc3ncc(C(=O)O)s3)cc2)n(Cc2ccc(F)cc2)c1=O] | I-2567 | 2.02 | 484 | 3 |

TABLE 531

| Structure | Compound No. | Retention Time (min) | [M + H] | Method |
|---|---|---|---|---|
| (structure) | I-2568 | 2.01 | 484 | 3 |
| (structure) | I-2569 | 1.26 | 429 | 3 |
| (structure) | I-2570 | 2.24 | 529 | 2 |
| (structure) | I-2571 | 1.78 | 529 | 2 |

TABLE 532

| Structure | Compoud No. | Retention Time (min) | [M + H] | Method |
|---|---|---|---|---|
| 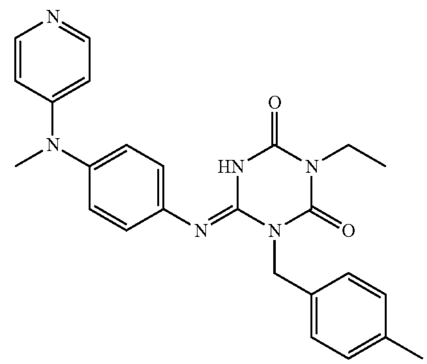 | I-2572 | 1.45 | 443 | 2 |
| 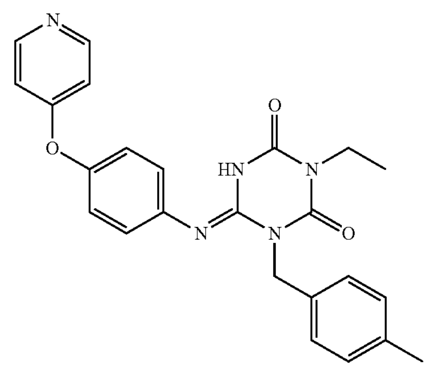 [SMILES: CCn1c(=O)[nH]/c(=N\c2ccc(Oc3ccncc3)cc2)n(Cc2ccc(C)cc2)c1=O] | I-2573 | 1.42 | 430 | 2 |
| 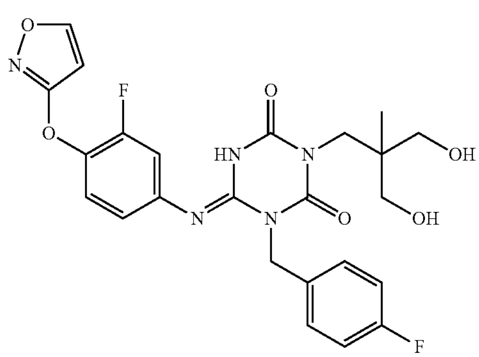 [SMILES: CC(CO)(CO)Cn1c(=O)[nH]/c(=N\c2ccc(Oc3ccon3)c(F)c2)n(Cc2ccc(F)cc2)c1=O] | I-2574 | 1.94 | 516 | 3 |
| 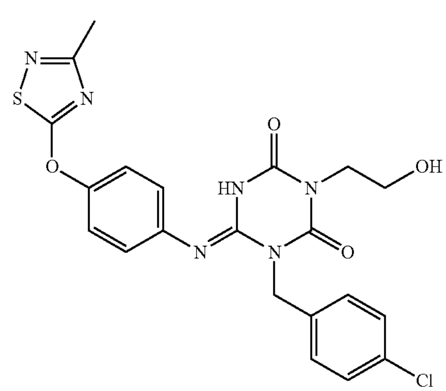 [SMILES: Cc1nsc(Oc2ccc(/N=c3\[nH]c(=O)n(CCO)c(=O)n3Cc3ccc(Cl)cc3)cc2)n1] | I-2575 | 2.01 | 487 | 3 |

TABLE 533

| Structure | Compound No. | Retention Time (min) | [M + H] | Method |
|---|---|---|---|---|
| 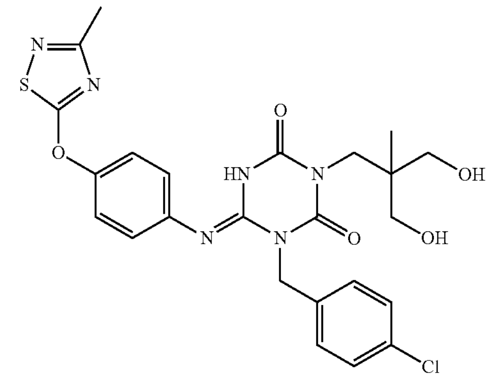 [SMILES: Cc1nsc(Oc2ccc(/N=c3\[nH]c(=O)n(CC(C)(CO)CO)c(=O)n3Cc3ccc(Cl)cc3)cc2)n1] | I-2576 | 1.92 | 545 | 2 |
| 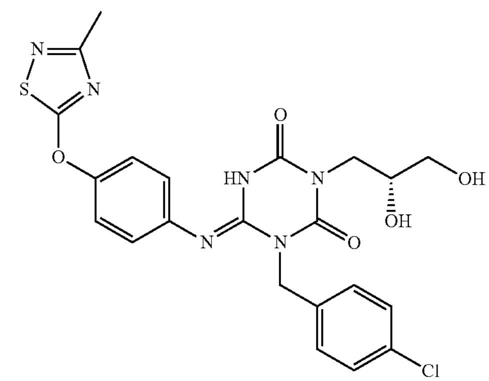 [SMILES: Cc1nsc(Oc2ccc(/N=c3\[nH]c(=O)n(C[C@@H](O)CO)c(=O)n3Cc3ccc(Cl)cc3)cc2)n1] | I-2577 | 1.77 | 517 | 2 |
| 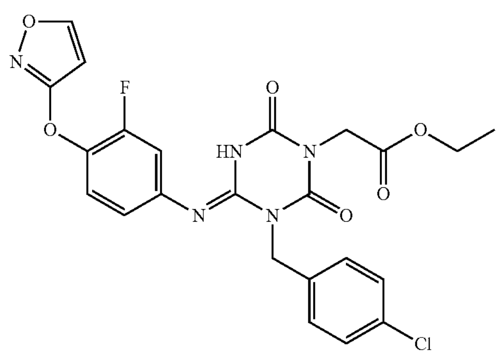 [SMILES: CCOC(=O)Cn1c(=O)[nH]/c(=N\c2ccc(Oc3ccon3)c(F)c2)n(Cc2ccc(Cl)cc2)c1=O] | I-2578 | 2.29 | 516 | 2 |
| 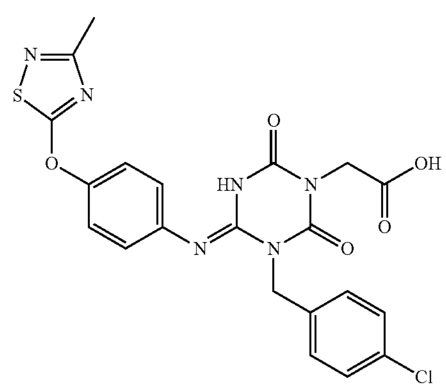 [SMILES: Cc1nsc(Oc2ccc(/N=c3\[nH]c(=O)n(CC(=O)O)c(=O)n3Cc3ccc(Cl)cc3)cc2)n1] | I-2579 | 1.91 | 501 | 2 |

TABLE 534

| Structure | Compound No. | Retention Time (min) | [M + H] | Method |
|---|---|---|---|---|
| 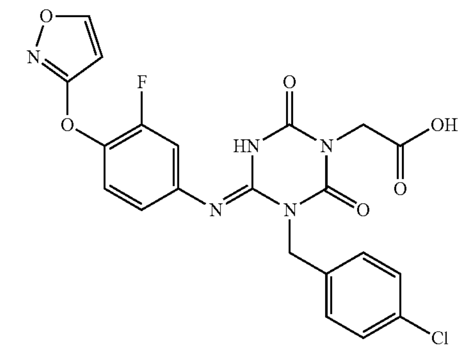 [SMILES: O=C(O)Cn1c(=O)[nH]/c(=N\c2ccc(Oc3ccon3)c(F)c2)n(Cc2ccc(Cl)cc2)c1=O] | I-2580 | 1.97 | 488 | 2 |
| 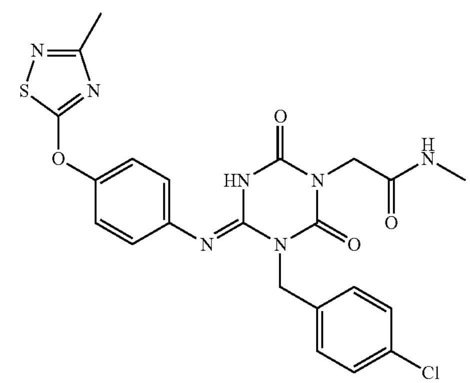 [SMILES: CNC(=O)Cn1c(=O)[nH]/c(=N\c2ccc(Oc3nc(C)ns3)cc2)n(Cc2ccc(Cl)cc2)c1=O] | I-2581 | 1.83 | 514 | 2 |
| 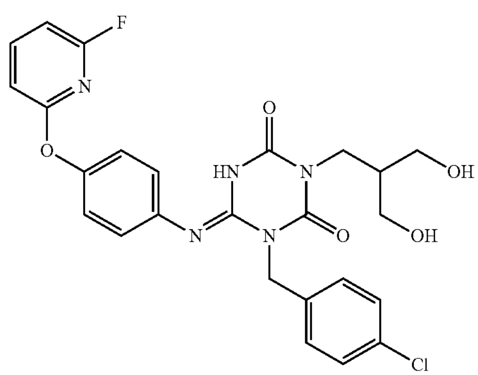 [SMILES: O=c1[nH]/c(=N\c2ccc(Oc3cccc(F)n3)cc2)n(Cc2ccc(Cl)cc2)c(=O)n1CC(CO)CO] | I-2582 | 2.01 | 528 | 3 |
| 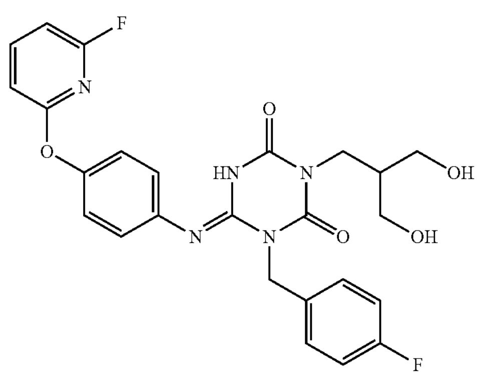 [SMILES: O=c1[nH]/c(=N\c2ccc(Oc3cccc(F)n3)cc2)n(Cc2ccc(F)cc2)c(=O)n1CC(CO)CO] | I-2583 | 1.88 | 512 | 3 |

TABLE 535

| Structure | Compound No. | Retention Time (min) | [M + H] | Method |
|---|---|---|---|---|
| 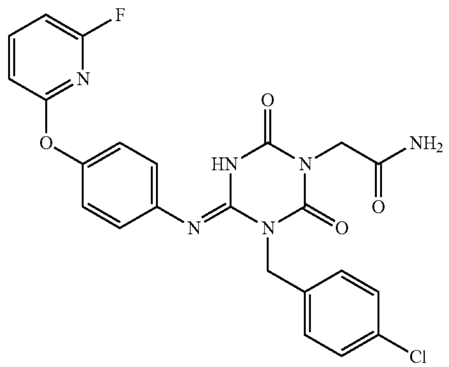 [SMILES: NC(=O)Cn1c(=O)[nH]/c(=N\c2ccc(Oc3cccc(F)n3)cc2)n(Cc2ccc(Cl)cc2)c1=O] | I-2584 | 1.97 | 497 | 3 |
| 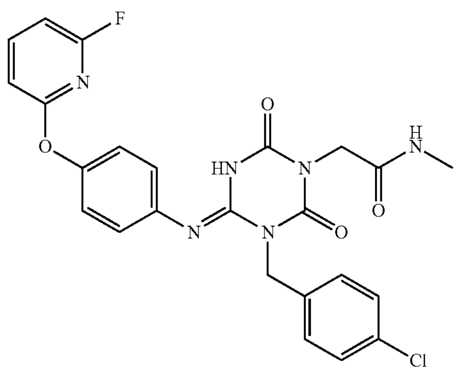 [SMILES: CNC(=O)Cn1c(=O)[nH]/c(=N\c2ccc(Oc3cccc(F)n3)cc2)n(Cc2ccc(Cl)cc2)c1=O] | I-2585 | 2.04 | 511 | 3 |
| 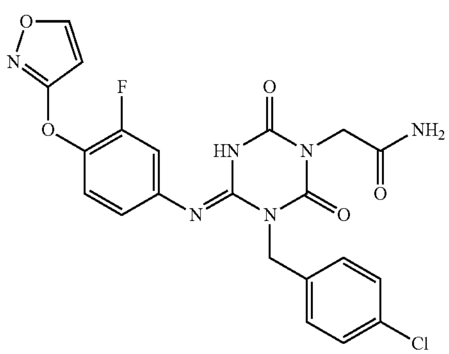 [SMILES: NC(=O)Cn1c(=O)[nH]/c(=N\c2ccc(Oc3ccon3)c(F)c2)n(Cc2ccc(Cl)cc2)c1=O] | I-2586 | 1.84 | 487 | 2 |
| 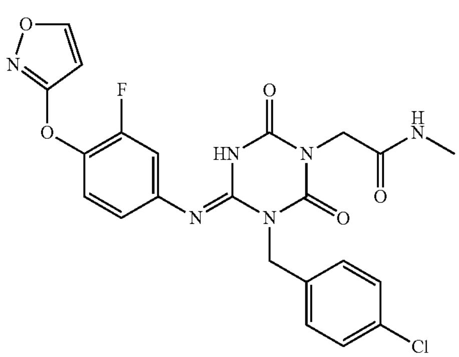 [SMILES: CNC(=O)Cn1c(=O)[nH]/c(=N\c2ccc(Oc3ccon3)c(F)c2)n(Cc2ccc(Cl)cc2)c1=O] | I-2587 | 1.90 | 501 | 2 |

TABLE 536

| Structure | Compound No. | Retention Time (min) | [M + H] | Method |
|---|---|---|---|---|
| 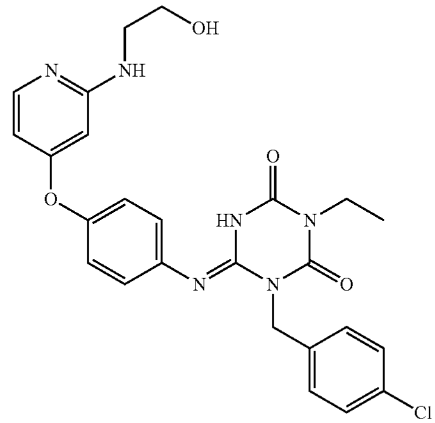 [SMILES: CCn1c(=O)[nH]/c(=N\c2ccc(Oc3ccnc(NCCO)c3)cc2)n(Cc2ccc(Cl)cc2)c1=O] | I-2588 | 1.43 | 509 | 2 |
| 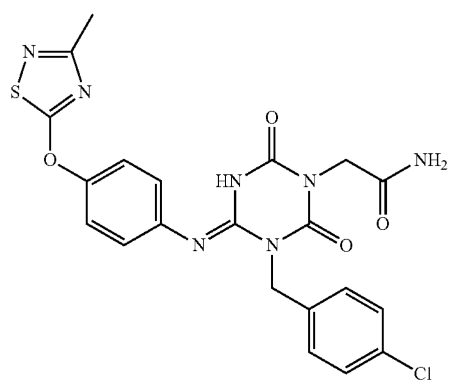 [SMILES: Cc1nsc(Oc2ccc(/N=c3\[nH]c(=O)n(CC(N)=O)c(=O)n3Cc3ccc(Cl)cc3)cc2)n1] | I-2589 | 1.77 | 500 | 2 |
| 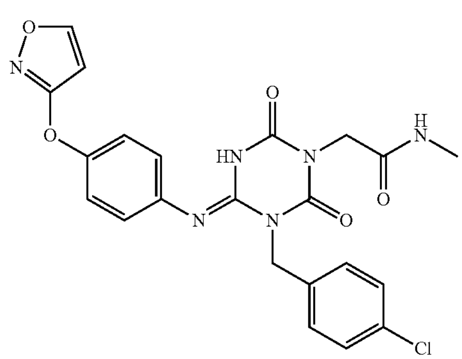 [SMILES: CNC(=O)Cn1c(=O)[nH]/c(=N\c2ccc(Oc3ccon3)cc2)n(Cc2ccc(Cl)cc2)c1=O] | I-2590 | 1.75 | 483 | 2 |

TABLE 536-continued

| Structure | Compound No. | Retention Time (min) | [M + H] | Method |
|---|---|---|---|---|
| 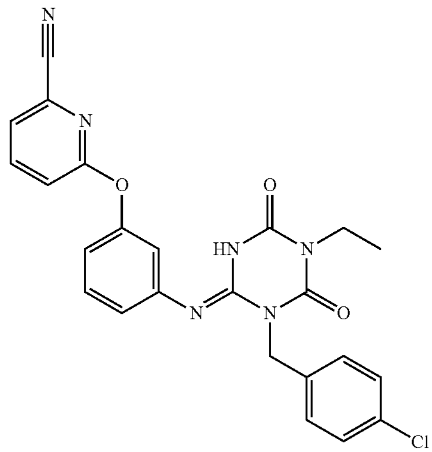 [SMILES: CCn1c(=O)[nH]/c(=N\c2cccc(Oc3cccc(C#N)n3)c2)n(Cc2ccc(Cl)cc2)c1=O] | I-2591 | 2.41 | 475 | 3 |

TABLE 537

| Structure | Compound No. | Retention Time (min) | [M + H] | Method |
|---|---|---|---|---|
| 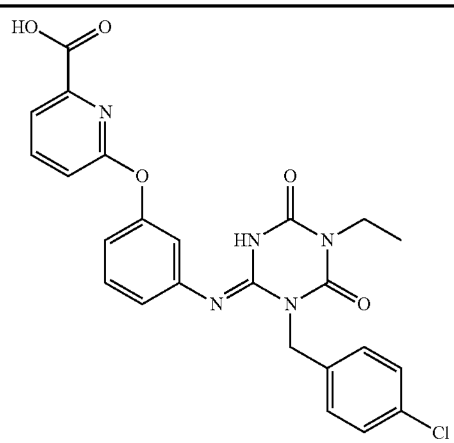 | I-2592 | 2.24 | 494 | 3 |
| 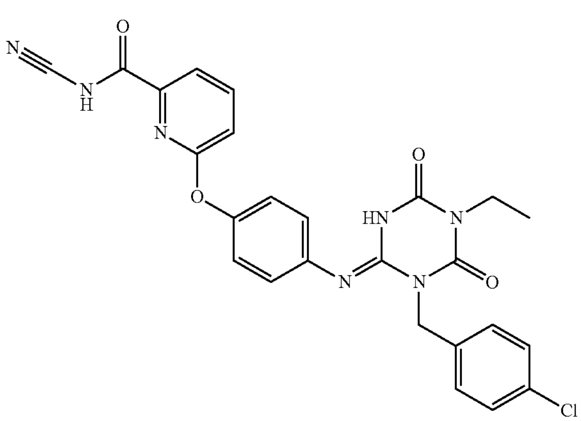 [SMILES: CCn1c(=O)[nH]/c(=N\c2ccc(Oc3cccc(C(=O)NC#N)n3)cc2)n(Cc2ccc(Cl)cc2)c1=O] | I-2593 | 2.18 | 518 | 2 |

TABLE 537-continued

| Structure | Compound No. | Retention Time (min) | [M + H] | Method |
|---|---|---|---|---|
| (structure) | I-2594 | 2.27 | 481 | 2 |
| (structure) | I-2595 | 1.88 | 541 | 2 |

TABLE 533

| Structure | Compound No. | Retention Time (min) | [M + H] | Method |
|---|---|---|---|---|
| (structure) | I-2596 | 1.85 | 527 | 2 |

TABLE 533-continued

| Structure | Compoud No. | Retention Time (min) | [M + H] | Method |
|---|---|---|---|---|
| 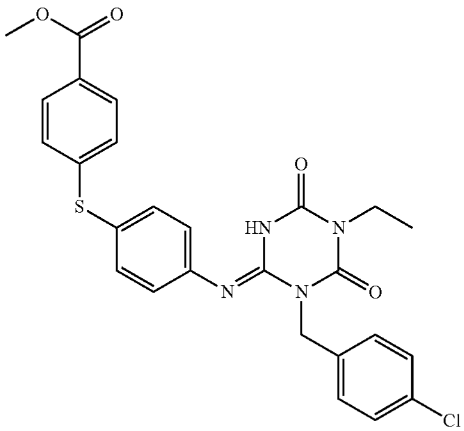 | I-2597 | 2.78 | 523 | 3 |
| 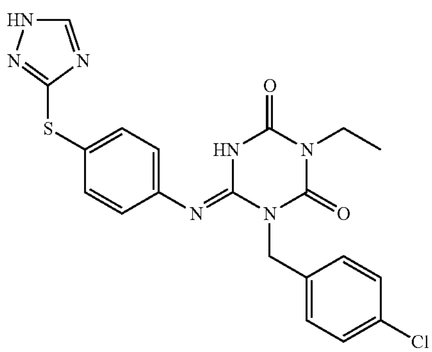 [SMILES: CCn1c(=O)[nH]/c(=N\c2ccc(Sc3nc[nH]n3)cc2)n(Cc2ccc(Cl)cc2)c1=O] | I-2598 | 2.04 | 456 | 3 |
| 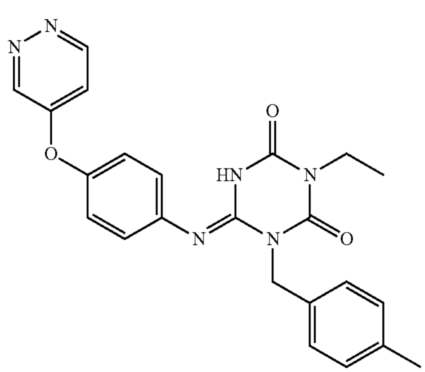 [SMILES: CCn1c(=O)[nH]/c(=N\c2ccc(Oc3ccnnc3)cc2)n(Cc2ccc(C)cc2)c1=O] | I-2599 | 1.84 | 431 | 3 |

TABLE 539

| Structure | Compound No. | Retention Time (min) | [M + H] | Method |
|---|---|---|---|---|
| 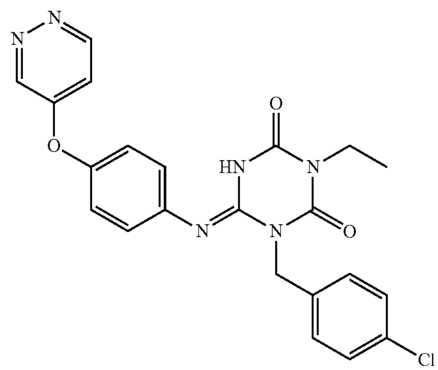 [SMILES: CCn1c(=O)[nH]/c(=N\c2ccc(Oc3ccnnc3)cc2)n(Cc2ccc(Cl)cc2)c1=O] | I-2600 | 1.93 | 451 | 3 |
| 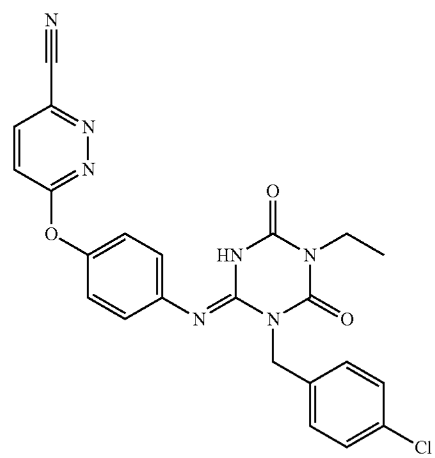 [SMILES: CCn1c(=O)[nH]/c(=N\c2ccc(Oc3ccc(C#N)nn3)cc2)n(Cc2ccc(Cl)cc2)c1=O] | I-2601 | 2.13 | 476 | 2 |
| 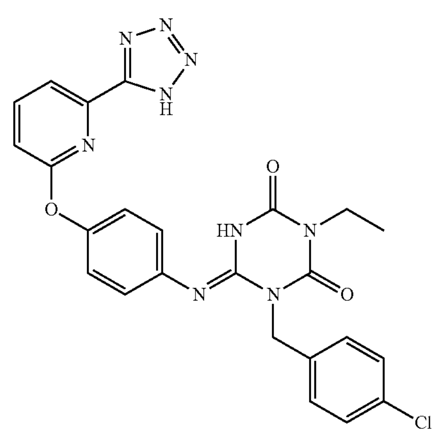 [SMILES: CCn1c(=O)[nH]/c(=N\c2ccc(Oc3cccc(-c4nnn[nH]4)n3)cc2)n(Cc2ccc(Cl)cc2)c1=O] | I-2602 | 2.09 | 518 | 2 |

TABLE 539-continued

| Structure | Compound No. | Retention Time (min) | [M + H] | Method |
|---|---|---|---|---|
| 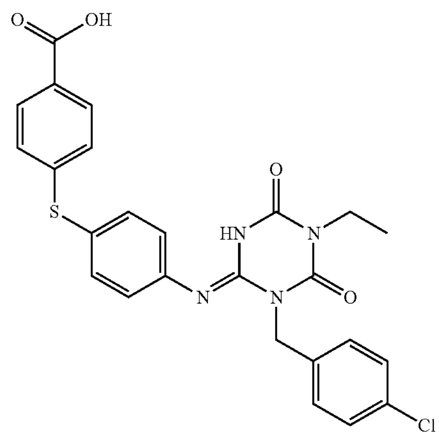 [SMILES: CCn1c(=O)[nH]/c(=N\c2ccc(Sc3ccc(C(=O)O)cc3)cc2)n(Cc2ccc(Cl)cc2)c1=O] | I-2603 | 2.43 | 509 | 3 |

TABLE 540

| Structure | Compound No. | Retention Time (min) | [M + H] | Method |
|---|---|---|---|---|
| 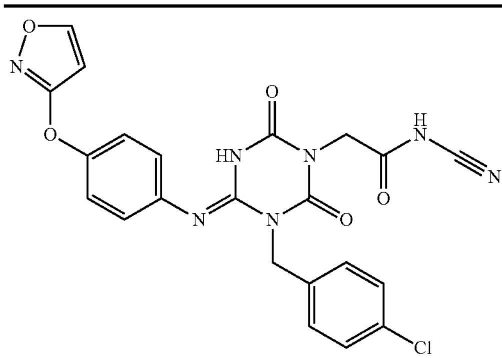 | I-2604 | 1.80 | 494 | 2 |
| 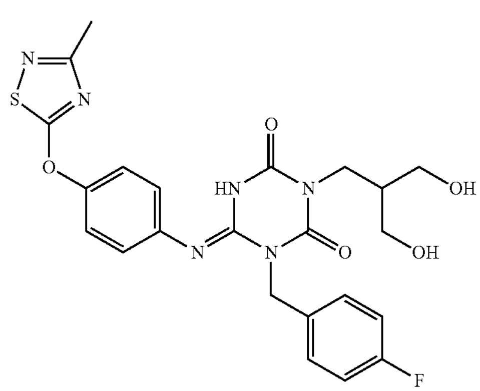 [SMILES: Cc1nsc(Oc2ccc(/N=c3\[nH]c(=O)n(CC(CO)CO)c(=O)n3Cc3ccc(F)cc3)cc2)n1] | I-2605 | 1.67 | 515 | 2 |

TABLE 540-continued

| Structure | Compound No. | Retention Time (min) | [M + H] | Method |
|---|---|---|---|---|
| *(structure)* | I-2606 | 1.80 | 485 | 2 |
| *(structure)* | I-2607 | 1.74 | 501 | 3 |

TABLE 541

| Structure | Compound No. | Retention Time (min) | [M + H] | Method |
|---|---|---|---|---|
| *(structure)* | I-2608 | 2.05 | 499 | 3 |

TABLE 541-continued
| Structure | Compound No. | Retention Time (min) | [M + H] | Method |
|---|---|---|---|---|
| 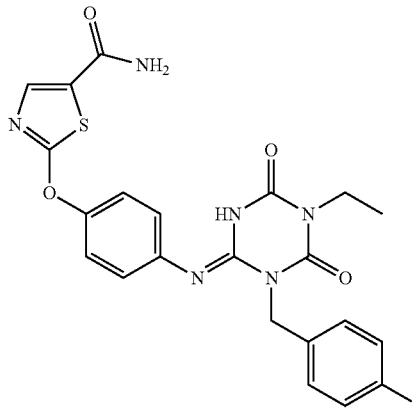 | I-2609 | 2.01 | 499 | 3 |
| 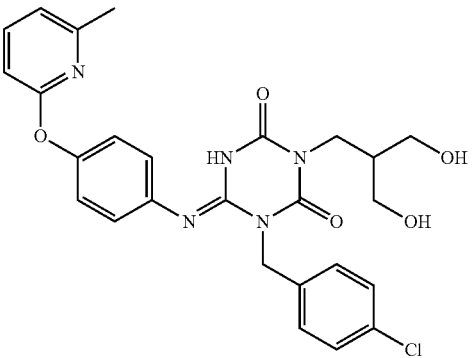 [SMILES: Cc1cccc(Oc2ccc(/N=c3\[nH]c(=O)n(CC(CO)CO)c(=O)n3Cc3ccc(Cl)cc3)cc2)n1] | I-2610 | 1.99 | 524 | 3 |
| 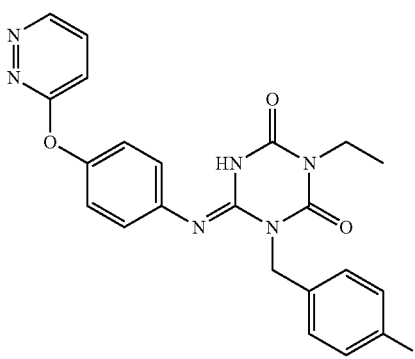 | I-2611 | 2.07 | 451 | 3 |

TABLE 542

| Structure | Compound No. | Retention Time (min) | [M + H] | Method |
|---|---|---|---|---|
| 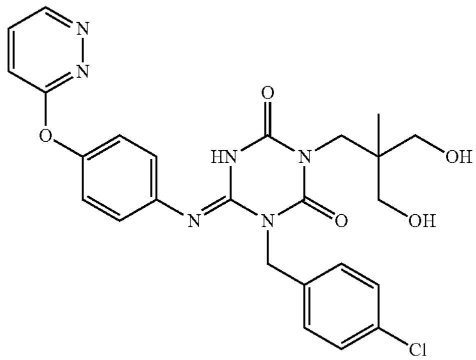 [SMILES: CC(CO)(CO)Cn1c(=O)[nH]/c(=N\c2ccc(Oc3cccnn3)cc2)n(Cc2ccc(Cl)cc2)c1=O] | I-2612 | 1.79 | 526 | 3 |
| 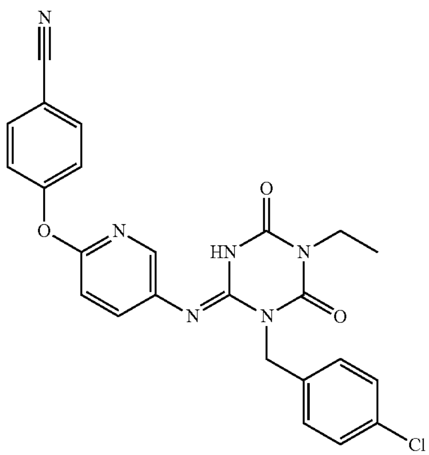 [SMILES: CCn1c(=O)[nH]/c(=N\c2ccc(Oc3ccc(C#N)cc3)nc2)n(Cc2ccc(Cl)cc2)c1=O] | I-2613 | 2.36 | 475 | 3 |
| 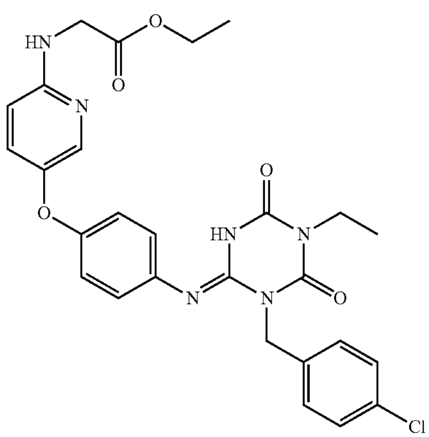 [SMILES: CCOC(=O)CNc1ccc(Oc2ccc(/N=c3\[nH]c(=O)n(CC)c(=O)n3Cc3ccc(Cl)cc3)cc2)cn1] | I-2614 | 1.93 | 551 | 2 |
| 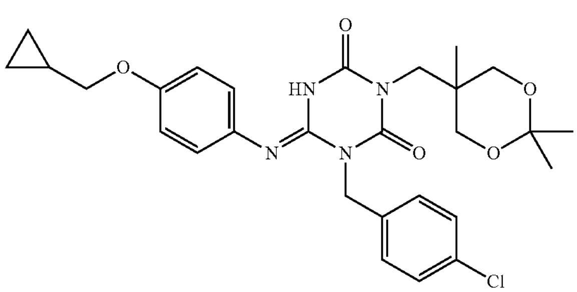 [SMILES: CC1(Cn2c(=O)[nH]/c(=N\c3ccc(OCC4CC4)cc3)n(Cc3ccc(Cl)cc3)c2=O)COC(C)(C)OC1] | I-2615 | 2.39 | 541 | 2 |

TABLE 543

| Structure | Compound No. | Retention Time (min) | [M + H] | Method |
|---|---|---|---|---|
| (structure) | I-2616 | 2.10 | 501 | 3 |
| (structure) | I-2617 | 1.96 | 485 | 3 |
| (structure) | I-2618 | 2.28 | 514 | 5 |
| (structure) | I-2619 | 2.42 | 528 | 5 |

TABLE 544
| Structure | Compound No. | Retention Time (min) | [M + H] | Method |
|---|---|---|---|---|
| 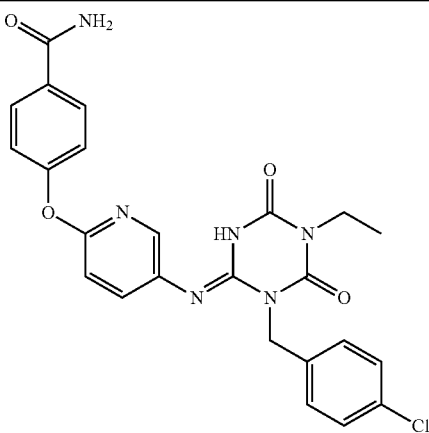 | I-2620 | 1.92 | 493 | 3 |
| 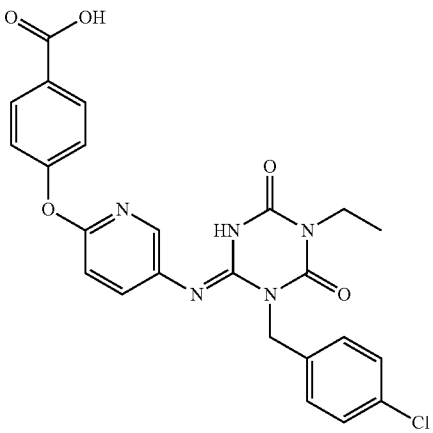 [SMILES: CCn1c(=O)[nH]/c(=N\c2ccc(Oc3ccc(C(=O)O)cc3)nc2)n(Cc2ccc(Cl)cc2)c1=O] | I-2621 | 2.11 | 494 | 3 |
| 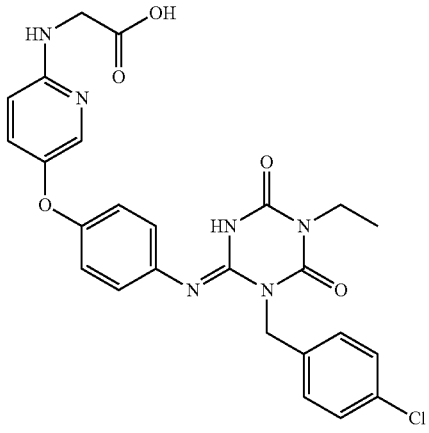 [SMILES: CCn1c(=O)[nH]/c(=N\c2ccc(Oc3ccc(NCC(=O)O)nc3)cc2)n(Cc2ccc(Cl)cc2)c1=O] | I-2622 | 1.61 | 523 | 2 |

TABLE 544-continued

| Structure | Compound No. | Retention Time (min) | [M + H] | Method |
|---|---|---|---|---|
| 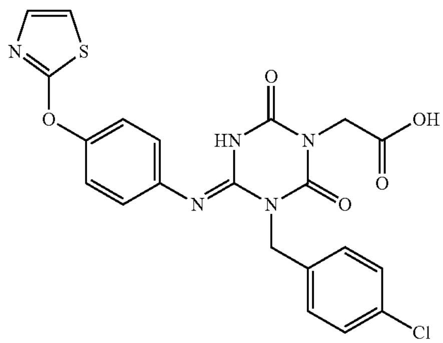 [SMILES: O=C(O)Cn1c(=O)[nH]/c(=N\c2ccc(Oc3nccs3)cc2)n(Cc2ccc(Cl)cc2)c1=O] | I-2823 | 1.93 | 486 | 5 |

TABLE 545

| Structure | Compound No. | Retention Time (min) | [M + H] | Method |
|---|---|---|---|---|
| 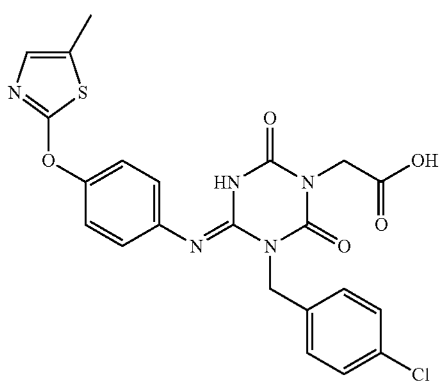 [SMILES: Cc1cnc(Oc2ccc(/N=c3\[nH]c(=O)n(CC(=O)O)c(=O)n3Cc3ccc(Cl)cc3)cc2)s1] | I-2624 | 2.07 | 500 | 5 |
| 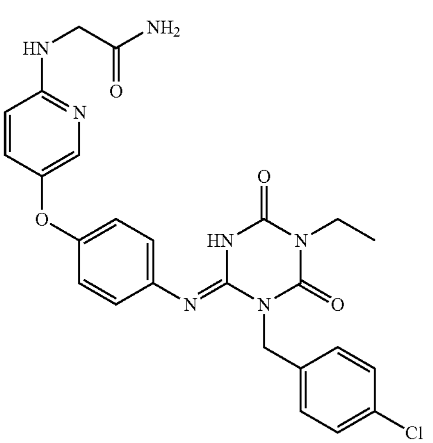 [SMILES: CCn1c(=O)[nH]/c(=N\c2ccc(Oc3ccc(NCC(N)=O)nc3)cc2)n(Cc2ccc(Cl)cc2)c1=O] | I-2625 | 1.53 | 522 | 2 |

TABLE 545-continued

| Structure | Compound No. | Retention Time (min) | [M + H] | Method |
|---|---|---|---|---|
| 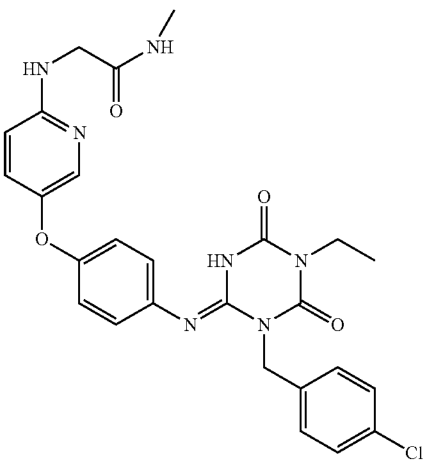 [SMILES: CCn1c(=O)[nH]/c(=N\c2ccc(Oc3ccc(NCC(=O)NC)nc3)cc2)n(Cc2ccc(Cl)cc2)c1=O] | I-2626 | 1.59 | 536 | 2 |
| 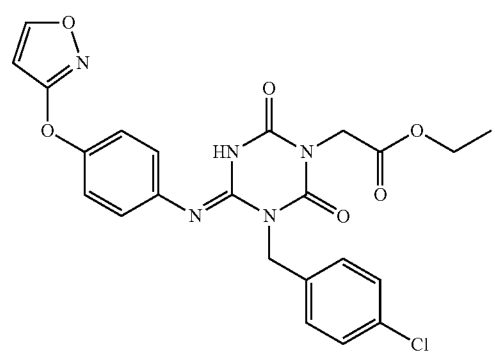 [SMILES: CCOC(=O)Cn1c(=O)[nH]/c(=N\c2ccc(Oc3ccon3)cc2)n(Cc2ccc(Cl)cc2)c1=O] | I-2627 | 2.19 | 498 | 5 |

TABLE 546

| Structure | Compound No. | Retention Time (min) | [M + H] | Method |
|---|---|---|---|---|
| 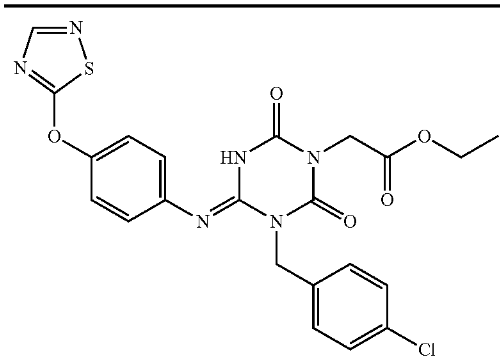 | I-2628 | 2.22 | 515 | 5 |

TABLE 546-continued

| Structure | Compound No. | Retention Time (min) | [M + H] | Method |
|---|---|---|---|---|
| 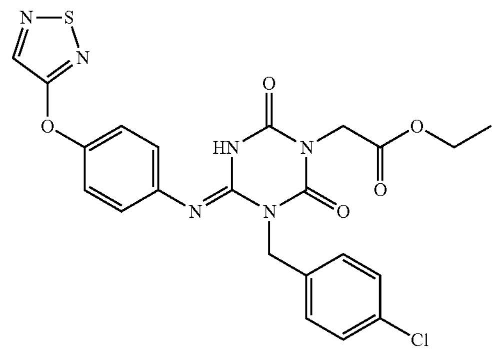 [SMILES: CCOC(=O)Cn1c(=O)[nH]/c(=N\c2ccc(Oc3cnsn3)cc2)n(Cc2ccc(Cl)cc2)c1=O] | I-2629 | 2.32 | 515 | 5 |
| 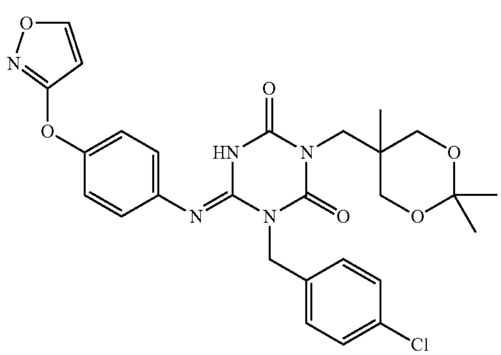 [SMILES: CC1(Cn2c(=O)[nH]/c(=N\c3ccc(Oc4ccon4)cc3)n(Cc3ccc(Cl)cc3)c2=O)COC(C)(C)OC1] | I-2630 | 2.28 | 554 | 2 |
| 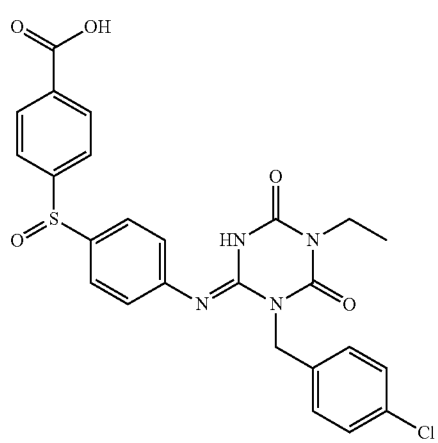 [SMILES: CCn1c(=O)[nH]/c(=N\c2ccc(S(=O)c3ccc(C(=O)O)cc3)cc2)n(Cc2ccc(Cl)cc2)c1=O] | I-2631 | 2.00 | 525 | 3 |

TABLE 547

| Structure | Compound No. | Retention Time (min) | [M + H] | Method |
|---|---|---|---|---|
| 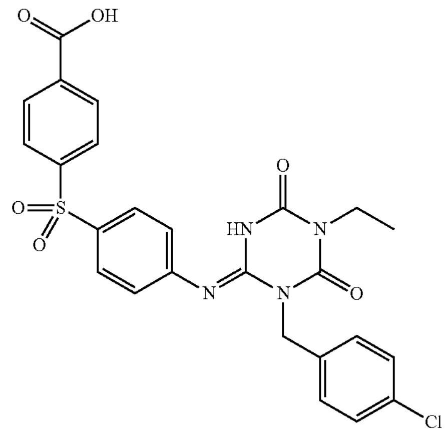 [SMILES: CCn1c(=O)[nH]/c(=N\c2ccc(S(=O)(=O)c3ccc(C(=O)O)cc3)cc2)n(Cc2ccc(Cl)cc2)c1=O] | I-2632 | 2.21 | 541 | 3 |
| 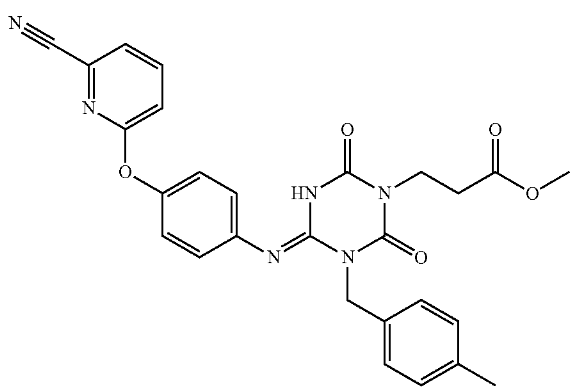 [SMILES: COC(=O)CCn1c(=O)[nH]/c(=N\c2ccc(Oc3cccc(C#N)n3)cc2)n(Cc2ccc(C)cc2)c1=O] | I-2633 | 2.21 | 513 | 3 |
| 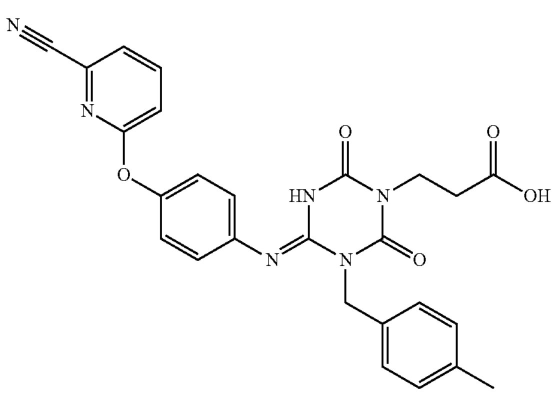 [SMILES: Cc1ccc(Cn2c(=O)n(CCC(=O)O)c(=O)[nH]/c2=N\c2ccc(Oc3cccc(C#N)n3)cc2)cc1] | I-2634 | 1.97 | 499 | 3 |

TABLE 547-continued
| Structure | Compound No. | Retention Time (min) | [M + H] | Method |
|---|---|---|---|---|
| 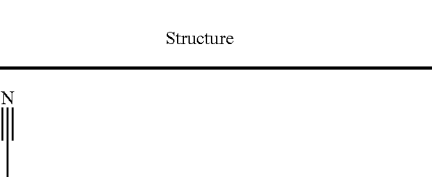 | I-2635 | 1.96 | 499 | 3 |
TABLE 548
| Structure | Compound No. | Retention Time (min) | [M + H] | Method |
|---|---|---|---|---|
| 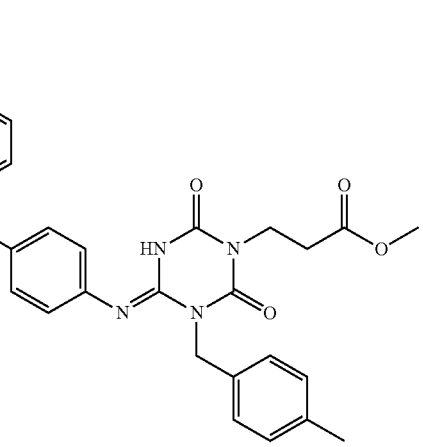 | I-2636 | 2.20 | 513 | 3 |
| 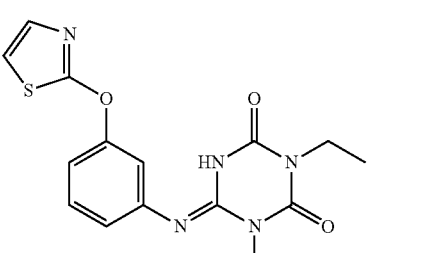 | I-2637 | 2.45 | 456 | 3 |

TABLE 548-continued
| Structure | Compound No. | Retention Time (min) | [M + H] | Method |
|---|---|---|---|---|
| 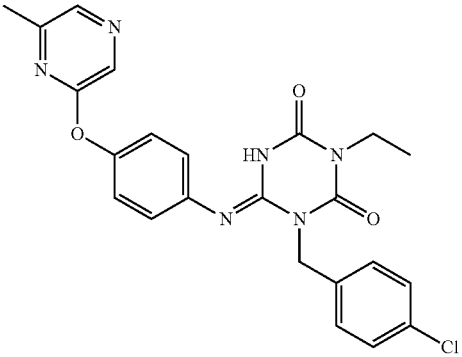 [SMILES: CCn1c(=O)[nH]/c(=N\c2ccc(Oc3cncc(C)n3)cc2)n(Cc2ccc(Cl)cc2)c1=O] | I-2638 | 2.29 | 465 | 3 |
| 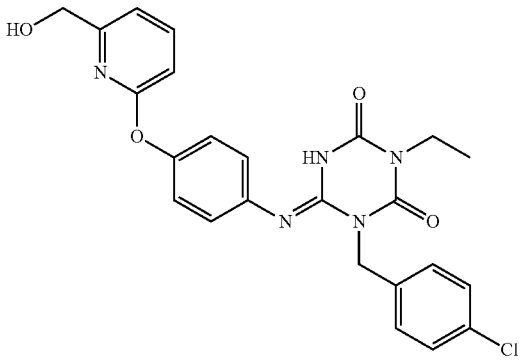 [SMILES: CCn1c(=O)[nH]/c(=N\c2ccc(Oc3cccc(CO)n3)cc2)n(Cc2ccc(Cl)cc2)c1=O] | I-2639 | 2.13 | 480 | 3 |
TABLE 549
| Structure | Compound No. | Retention Time (min) | [M + H] | Method |
|---|---|---|---|---|
| 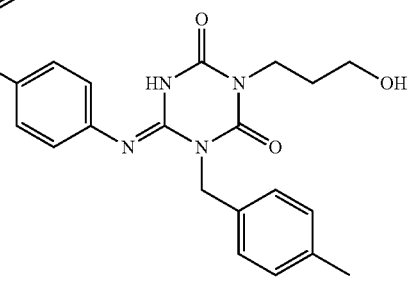 | I-2640 | 1.98 | 485 | 3 |

TABLE 549-continued

| Structure | Compound No. | Retention Time (min) | [M + H] | Method |
|---|---|---|---|---|
| 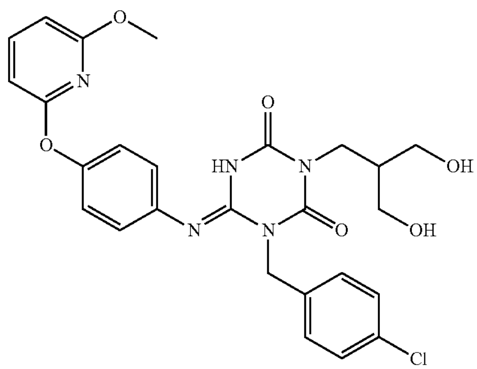 [SMILES: COc1cccc(Oc2ccc(/N=c3\[nH]c(=O)n(CC(CO)CO)c(=O)n3Cc3ccc(Cl)cc3)cc2)n1] | I-2641 | 2.08 | 540 | 3 |
| 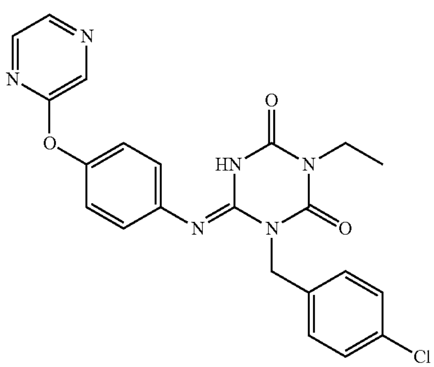 [SMILES: CCn1c(=O)[nH]/c(=N\c2ccc(Oc3cnccn3)cc2)n(Cc2ccc(Cl)cc2)c1=O] | I-2642 | 2.08 | 451 | 2 |
| 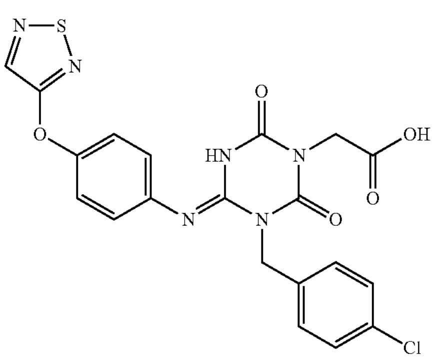 [SMILES: O=C(O)Cn1c(=O)[nH]/c(=N\c2ccc(Oc3cnsn3)cc2)n(Cc2ccc(Cl)cc2)c1=O] | I-2643 | 1.96 | 487 | 5 |

TABLE 550

| Structure | Compound No. | Retention Time (min) | [M + H] | Method |
|---|---|---|---|---|
| (structure) | I-2644 | 1.80 | 485 | 5 |
| (structure) | I-2645 | 1.87 | 499 | 5 |
| (structure) | I-2646 | 1.75 | 529 | 5 |
| (structure) | I-2647 | 1.95 | 499 | 5 |

TABLE 551

| Structure | Compound No. | Retention Time (min) | [M + H] | Method |
|---|---|---|---|---|
| 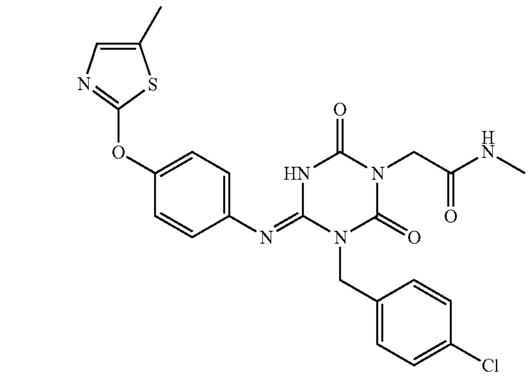 [SMILES: CNC(=O)Cn1c(=O)[nH]/c(=N\c2ccc(Oc3ncc(C)s3)cc2)n(Cc2ccc(Cl)cc2)c1=O] | I-2648 | 2.01 | 513 | 5 |
| 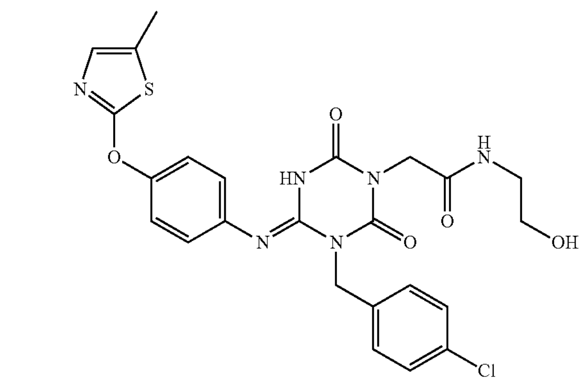 [SMILES: Cc1cnc(Oc2ccc(/N=c3\[nH]c(=O)n(CC(=O)NCCO)c(=O)n3Cc3ccc(Cl)cc3)cc2)s1] | I-2649 | 1.90 | 543 | 5 |
| 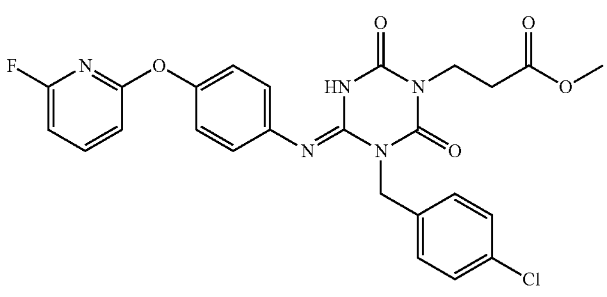 [SMILES: COC(=O)CCn1c(=O)[nH]/c(=N\c2ccc(Oc3cccc(F)n3)cc2)n(Cc2ccc(Cl)cc2)c1=O] | I-2650 | 2.37 | 526 | 5 |
| 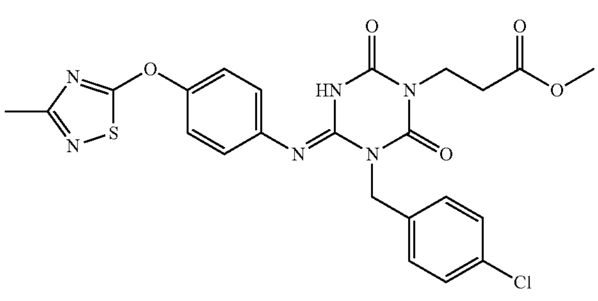 | I-2651 | 2.27 | 529 | 5 |

TABLE 552

| Structure | Compound No. | Retention Time (min) | [M + H] | Method |
|---|---|---|---|---|
| 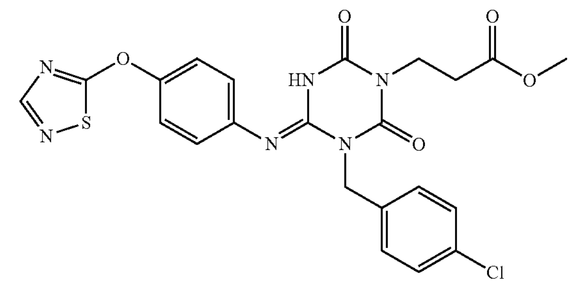 [SMILES: COC(=O)CCn1c(=O)[nH]/c(=N\c2ccc(Oc3ncns3)cc2)n(Cc2ccc(Cl)cc2)c1=O] | I-2652 | 2.20 | 515 | 5 |
| 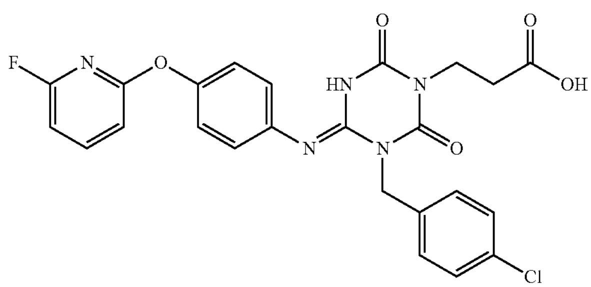 | I-2653 | 2.14 | 512 | 5 |
| 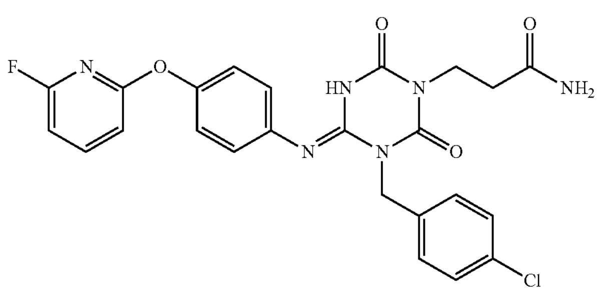 [SMILES: NC(=O)CCn1c(=O)[nH]/c(=N\c2ccc(Oc3cccc(F)n3)cc2)n(Cc2ccc(Cl)cc2)c1=O] | I-2654 | 1.98 | 511 | 5 |
| 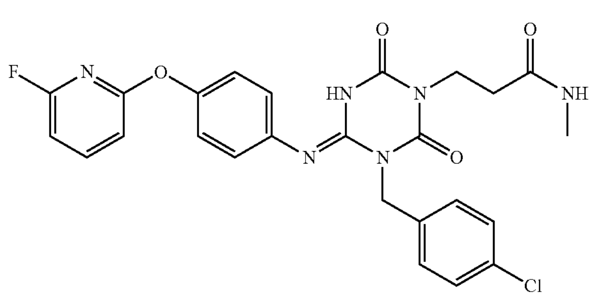 [SMILES: CNC(=O)CCn1c(=O)[nH]/c(=N\c2ccc(Oc3cccc(F)n3)cc2)n(Cc2ccc(Cl)cc2)c1=O] | I-2655 | 2.03 | 525 | 5 |

TABLE 553

| Structure | Compound No. | Retention Time (min) | [M + H] | Method |
|---|---|---|---|---|
| 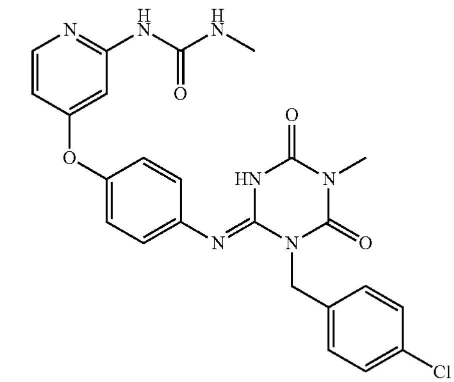 [SMILES: CNC(=O)Nc1cc(Oc2ccc(/N=c3\[nH]c(=O)n(C)c(=O)n3Cc3ccc(Cl)cc3)cc2)ccn1] | I-2656 | 1.51 | 508 | 2 |
| 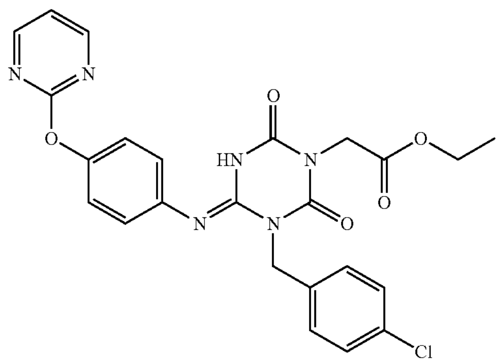 [SMILES: CCOC(=O)Cn1c(=O)[nH]/c(=N\c2ccc(Oc3ncccn3)cc2)n(Cc2ccc(Cl)cc2)c1=O] | I-2657 | 2.05 | 509 | 5 |
| 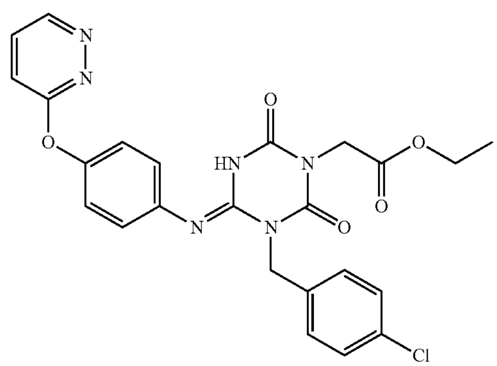 [SMILES: CCOC(=O)Cn1c(=O)[nH]/c(=N\c2ccc(Oc3cccnn3)cc2)n(Cc2ccc(Cl)cc2)c1=O] | I-2658 | 2.03 | 509 | 5 |
| 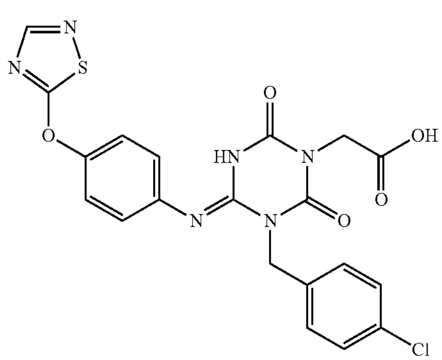 [SMILES: O=C(O)Cn1c(=O)[nH]/c(=N\c2ccc(Oc3ncns3)cc2)n(Cc2ccc(Cl)cc2)c1=O] | I-2659 | 1.85 | 487 | 5 |

TABLE 554

| Structure | Compound No. | Retention Time (min) | [M + H] | Method |
|---|---|---|---|---|
| 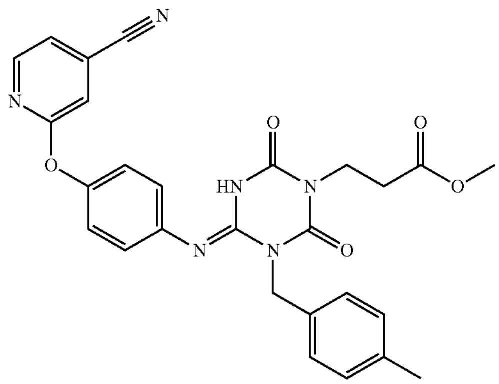 [SMILES: COC(=O)CCn1c(=O)[nH]/c(=N\c2ccc(Oc3cc(C#N)ccn3)cc2)n(Cc2ccc(C)cc2)c1=O] | I-2660 | 2.23 | 513 | 3 |
| 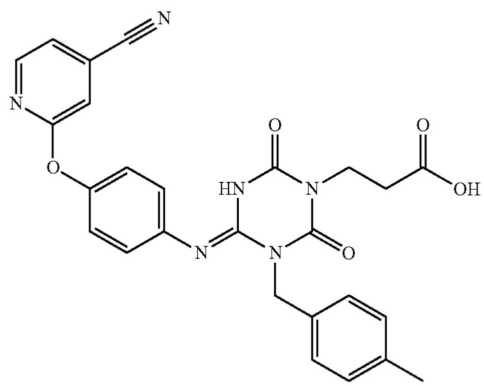 [SMILES: Cc1ccc(Cn2c(=O)n(CCC(=O)O)c(=O)[nH]/c2=N\c2ccc(Oc3cc(C#N)ccn3)cc2)cc1] | I-2661 | 1.99 | 499 | 3 |
| 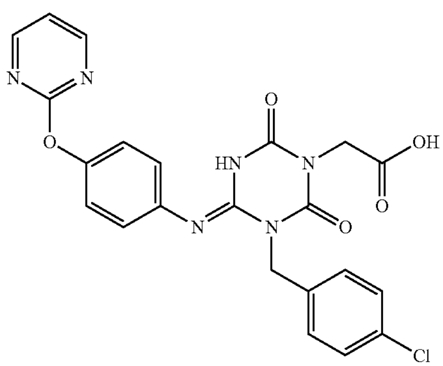 [SMILES: O=C(O)Cn1c(=O)[nH]/c(=N\c2ccc(Oc3ncccn3)cc2)n(Cc2ccc(Cl)cc2)c1=O] | I-2662 | 1.68 | 481 | 5 |
| 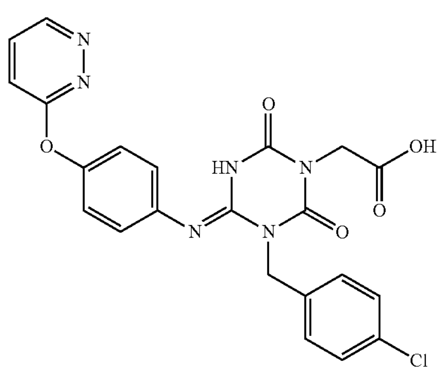 [SMILES: O=C(O)Cn1c(=O)[nH]/c(=N\c2ccc(Oc3cccnn3)cc2)n(Cc2ccc(Cl)cc2)c1=O] | I-2663 | 1.68 | 481 | 5 |

TABLE 555

| Structure | Compound No. | Retention Time (min) | [M + H] | Method |
|---|---|---|---|---|
| 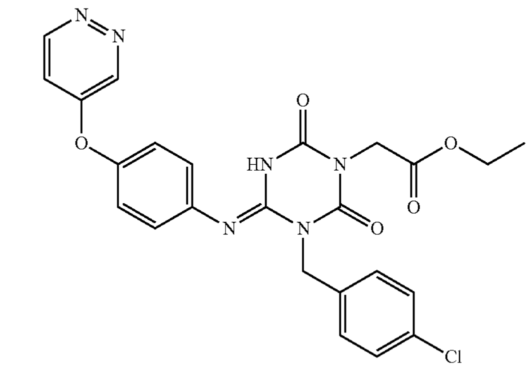 [SMILES: CCOC(=O)Cn1c(=O)[nH]/c(=N\c2ccc(Oc3ccnnc3)cc2)n(Cc2ccc(Cl)cc2)c1=O] | I-2664 | 1.88 | 509 | 5 |
| 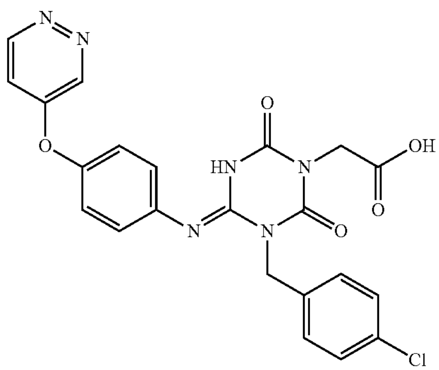 [SMILES: O=C(O)Cn1c(=O)[nH]/c(=N\c2ccc(Oc3ccnnc3)cc2)n(Cc2ccc(Cl)cc2)c1=O] | I-2665 | 1.52 | 481 | 5 |
| 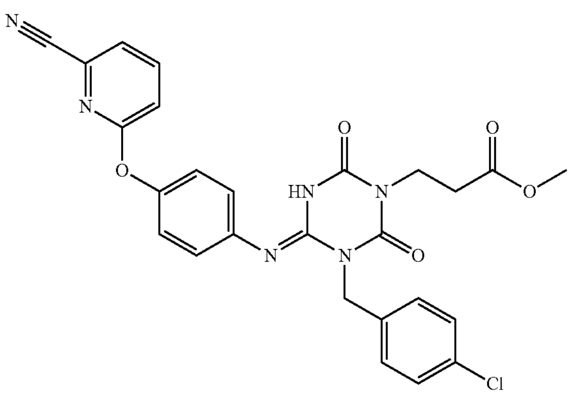 [SMILES: COC(=O)CCn1c(=O)[nH]/c(=N\c2ccc(Oc3cccc(C#N)n3)cc2)n(Cc2ccc(Cl)cc2)c1=O] | I-2666 | 2.29 | 533 | 3 |
| 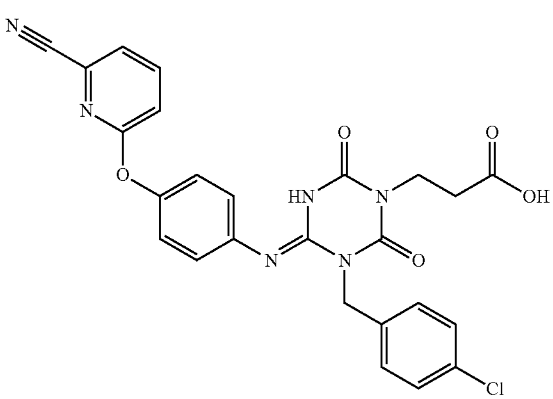 [SMILES: N#Cc1cccc(Oc2ccc(/N=c3\[nH]c(=O)n(CCC(=O)O)c(=O)n3Cc3ccc(Cl)cc3)cc2)n1] | I-2667 | 2.04 | 519 | 3 |

TABLE 556

| Structure | Compound No. | Retention Time (min) | [M + H] | Method |
|---|---|---|---|---|
| 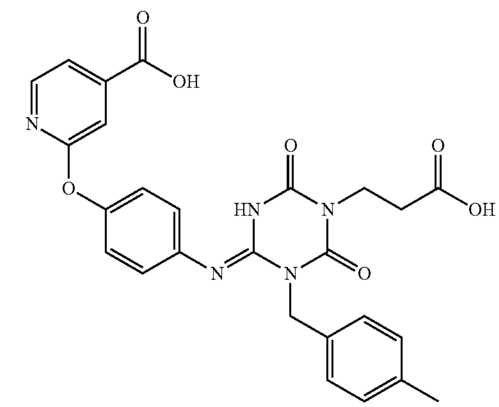 [SMILES: Cc1ccc(Cn2c(=O)n(CCC(=O)O)c(=O)[nH]/c2=N\c2ccc(Oc3cc(C(=O)O)ccn3)cc2)cc1] | I-2671 | 1.74 | 518 | 3 |
| 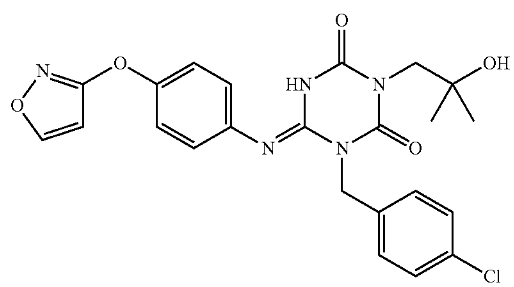 [SMILES: CC(C)(O)Cn1c(=O)[nH]/c(=N\c2ccc(Oc3ccon3)cc2)n(Cc2ccc(Cl)cc2)c1=O] | I-2672 | 2.04 | 484 | 5 |
| 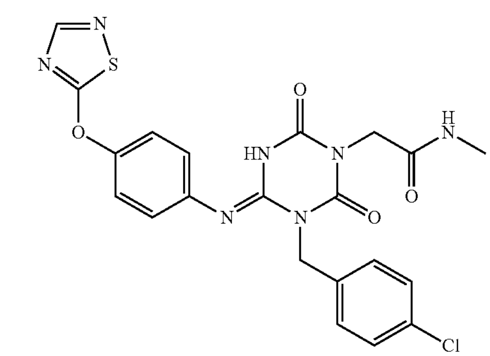 [SMILES: CNC(=O)Cn1c(=O)[nH]/c(=N\c2ccc(Oc3ncns3)cc2)n(Cc2ccc(Cl)cc2)c1=O] | I-2673 | 1.79 | 500 | 5 |
| 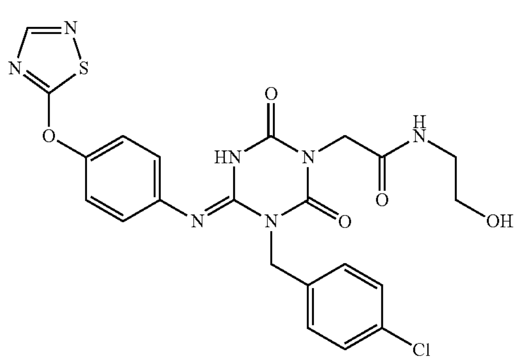 [SMILES: O=C(Cn1c(=O)[nH]/c(=N\c2ccc(Oc3ncns3)cc2)n(Cc2ccc(Cl)cc2)c1=O)NCCO] | I-2674 | 1.68 | 530 | 5 |

TABLE 557

| Structure | Compound No. | Retention Time (min) | [M + H] | Method |
|---|---|---|---|---|
| 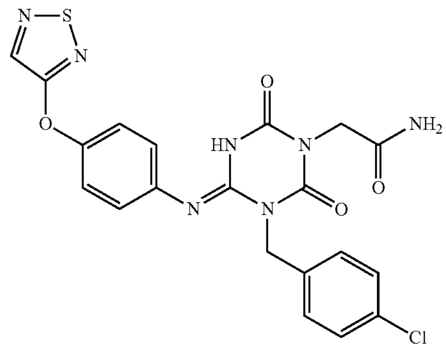 [SMILES: NC(=O)Cn1c(=O)[nH]/c(=N\c2ccc(Oc3cnsn3)cc2)n(Cc2ccc(Cl)cc2)c1=O] | I-2675 | 1.82 | 486 | 5 |
| 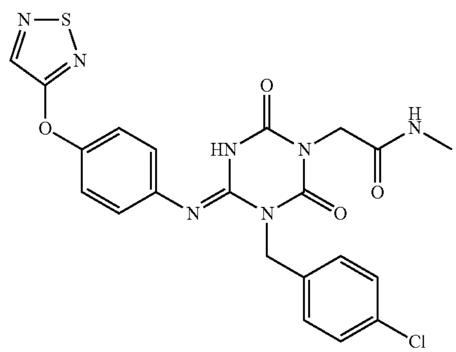 [SMILES: CNC(=O)Cn1c(=O)[nH]/c(=N\c2ccc(Oc3cnsn3)cc2)n(Cc2ccc(Cl)cc2)c1=O] | I-2676 | 1.89 | 500 | 5 |
| 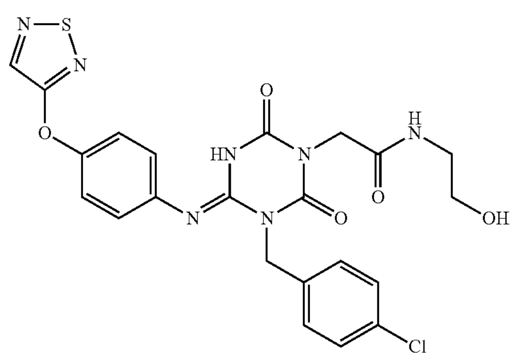 [SMILES: O=C(Cn1c(=O)[nH]/c(=N\c2ccc(Oc3cnsn3)cc2)n(Cc2ccc(Cl)cc2)c1=O)NCCO] | I-2677 | 1.79 | 530 | 5 |
| 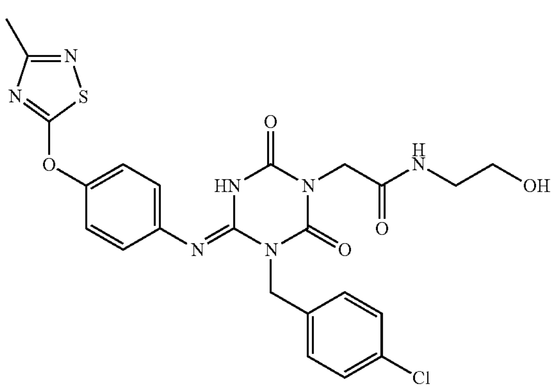 [SMILES: Cc1nsc(Oc2ccc(/N=c3\[nH]c(=O)n(CC(=O)NCCO)c(=O)n3Cc3ccc(Cl)cc3)cc2)n1] | I-2678 | 1.75 | 544 | 5 |

TABLE 558

| Structure | Compound No. | Retention Time (min) | [M + H] | Method |
|---|---|---|---|---|
| 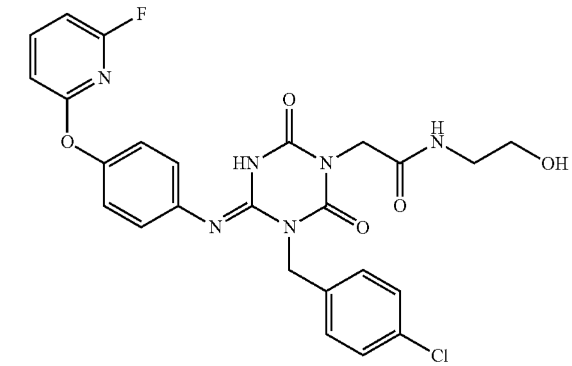 [SMILES: O=C(Cn1c(=O)[nH]/c(=N\c2ccc(Oc3cccc(F)n3)cc2)n(Cc2ccc(Cl)cc2)c1=O)NCCO] | I-2679 | 1.86 | 541 | 5 |
| 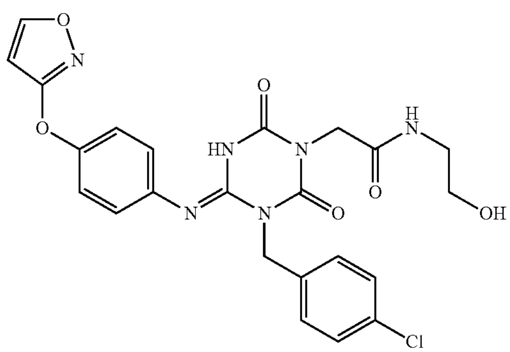 [SMILES: O=C(Cn1c(=O)[nH]/c(=N\c2ccc(Oc3ccon3)cc2)n(Cc2ccc(Cl)cc2)c1=O)NCCO] | I-2680 | 1.66 | 513 | 5 |
| 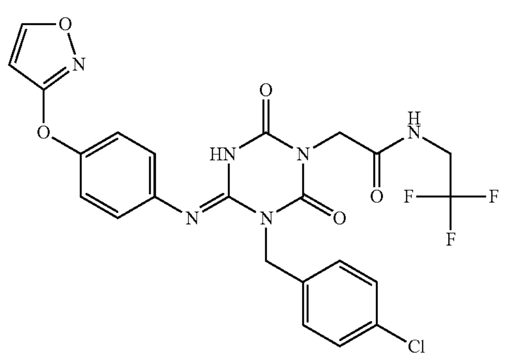 [SMILES: O=C(Cn1c(=O)[nH]/c(=N\c2ccc(Oc3ccon3)cc2)n(Cc2ccc(Cl)cc2)c1=O)NCC(F)(F)F] | I-2681 | 2.06 | 551 | 5 |
| 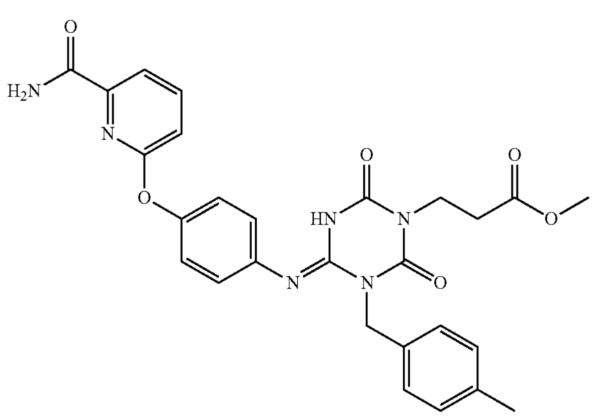 [SMILES: COC(=O)CCn1c(=O)[nH]/c(=N\c2ccc(Oc3cccc(C(N)=O)n3)cc2)n(Cc2ccc(C)cc2)c1=O] | I-2682 | 1.93 | 531 | 3 |

TABLE 559

| Structure | Compound No. | Retention Time (min) | [M + H] | Method |
|---|---|---|---|---|
| 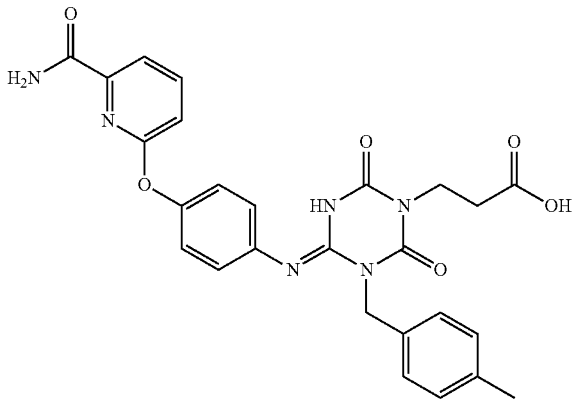 [SMILES: Cc1ccc(Cn2c(=O)n(CCC(=O)O)c(=O)[nH]/c2=N\c2ccc(Oc3cccc(C(N)=O)n3)cc2)cc1] | I-2683 | 1.72 | 517 | 3 |
| 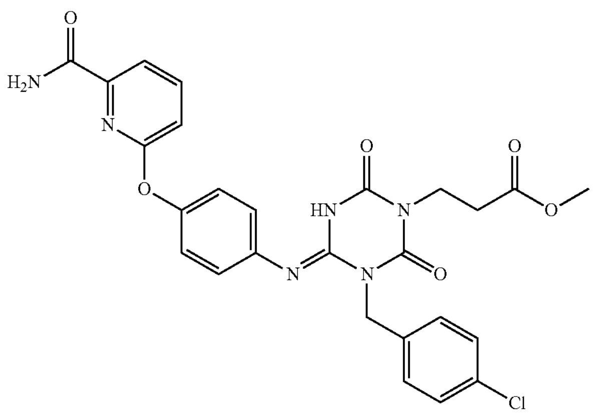 [SMILES: COC(=O)CCn1c(=O)[nH]/c(=N\c2ccc(Oc3cccc(C(N)=O)n3)cc2)n(Cc2ccc(Cl)cc2)c1=O] | I-2684 | 2 | 551 | 3 |
| 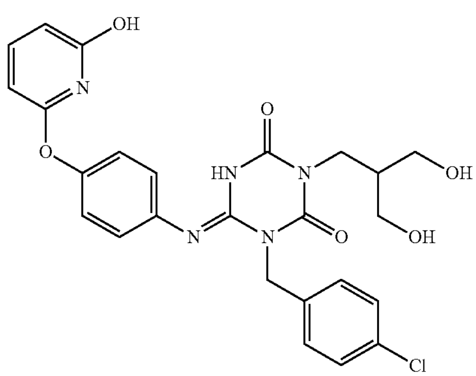 [SMILES: O=c1[nH]/c(=N\c2ccc(Oc3cccc(O)n3)cc2)n(Cc2ccc(Cl)cc2)c(=O)n1CC(CO)CO] | I-2685 | 1.65 | 526 | 3 |
| 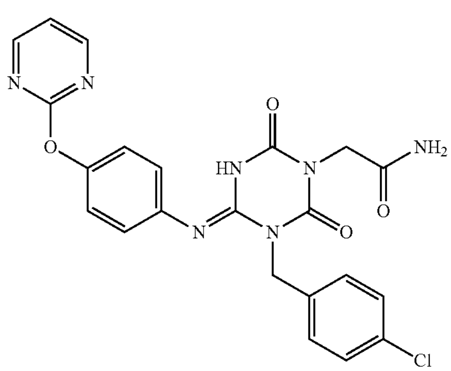 [SMILES: NC(=O)Cn1c(=O)[nH]/c(=N\c2ccc(Oc3ncccn3)cc2)n(Cc2ccc(Cl)cc2)c1=O] | I-2686 | 1.55 | 480 | 5 |

TABLE 560
| Structure | Compound No. | Retention Time (min) | [M + H] | Method |
|---|---|---|---|---|
| 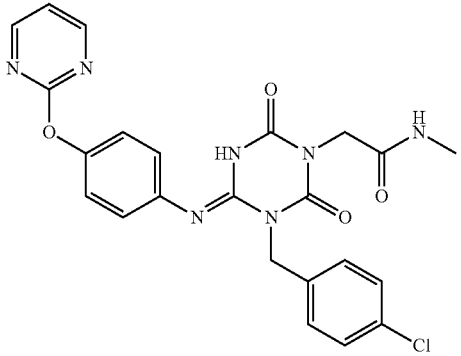 [SMILES: CNC(=O)Cn1c(=O)[nH]/c(=N\c2ccc(Oc3ncccn3)cc2)n(Cc2ccc(Cl)cc2)c1=O] | I-2687 | 1.61 | 494 | 5 |
| 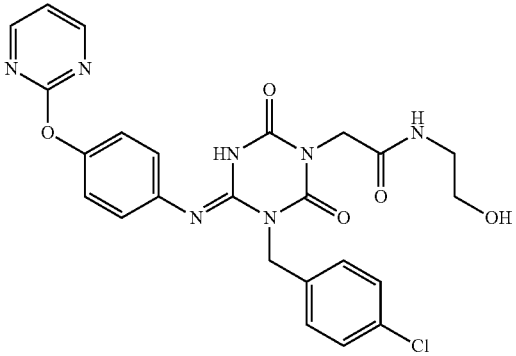 [SMILES: O=C(Cn1c(=O)[nH]/c(=N\c2ccc(Oc3ncccn3)cc2)n(Cc2ccc(Cl)cc2)c1=O)NCCO] | I-2688 | 1.52 | 524 | 5 |
| 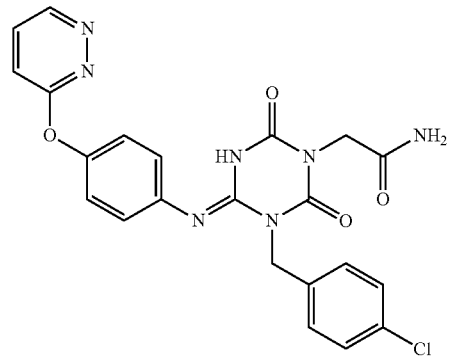 [SMILES: NC(=O)Cn1c(=O)[nH]/c(=N\c2ccc(Oc3cccnn3)cc2)n(Cc2ccc(Cl)cc2)c1=O] | I-2689 | 1.56 | 480 | 5 |
| 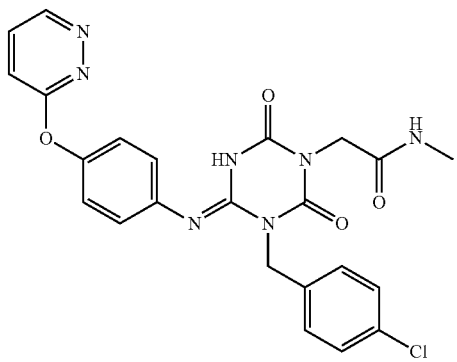 [SMILES: CNC(=O)Cn1c(=O)[nH]/c(=N\c2ccc(Oc3cccnn3)cc2)n(Cc2ccc(Cl)cc2)c1=O] | I-2690 | 1.62 | 494 | 5 |

TABLE 561
| Structure | Compound No. | Retention Time (min) | [M + H] | Method |
|---|---|---|---|---|
| 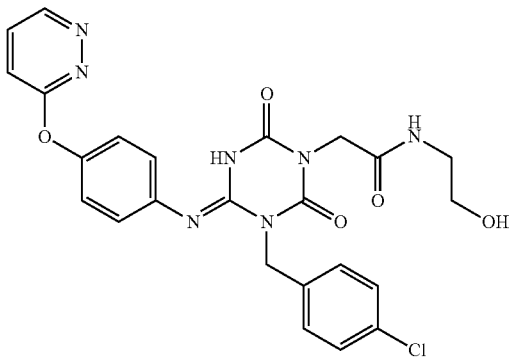 [SMILES: O=C(Cn1c(=O)[nH]/c(=N\c2ccc(Oc3cccnn3)cc2)n(Cc2ccc(Cl)cc2)c1=O)NCCO] | I-2691 | 1.53 | 524 | 5 |
| 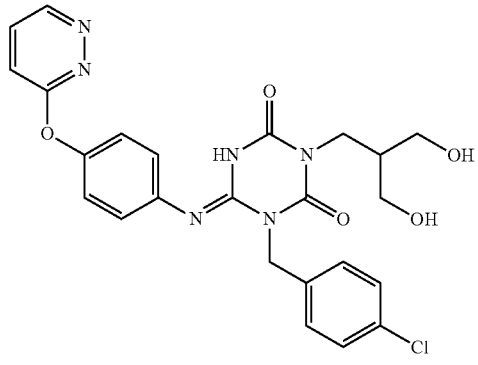 [SMILES: O=c1[nH]/c(=N\c2ccc(Oc3cccnn3)cc2)n(Cc2ccc(Cl)cc2)c(=O)n1CC(CO)CO] | I-2692 | 1.67 | 511 | 3 |
| 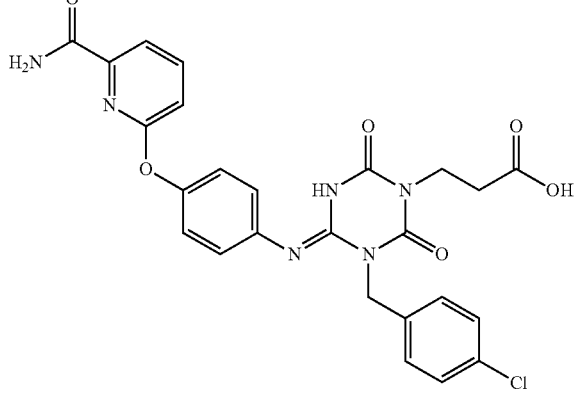 | I-2693 | 1.79 | 537 | 3 |
| 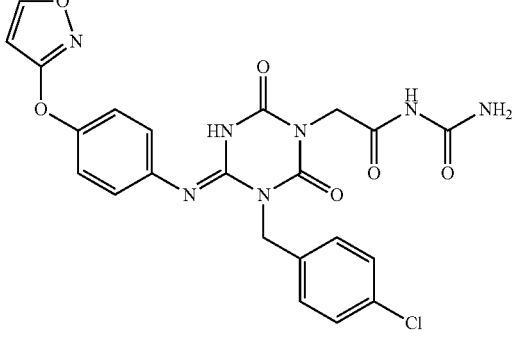 | I-2694 | 1.76 | 512 | 5 |

TABLE 562

| Structure | Compound No. | Retention Time (min) | [M + H] | Method |
|---|---|---|---|---|
| 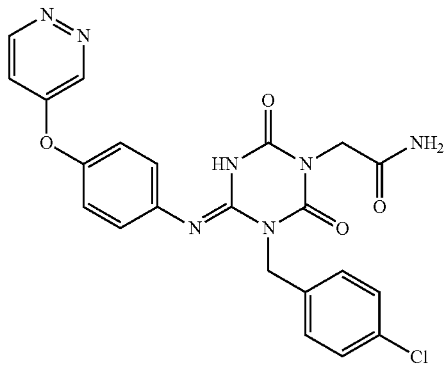 [SMILES: NC(=O)Cn1c(=O)[nH]/c(=N\c2ccc(Oc3ccnnc3)cc2)n(Cc2ccc(Cl)cc2)c1=O] | I-2695 | 1.41 | 480 | 5 |
| 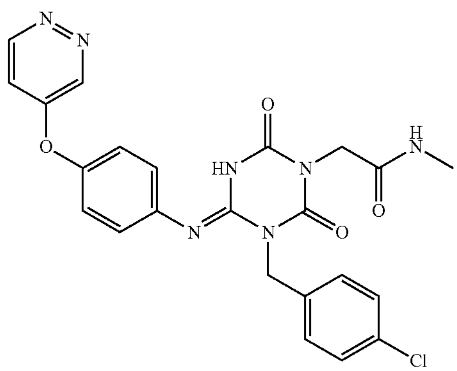 [SMILES: CNC(=O)Cn1c(=O)[nH]/c(=N\c2ccc(Oc3ccnnc3)cc2)n(Cc2ccc(Cl)cc2)c1=O] | I-2696 | 1.47 | 494 | 5 |
| 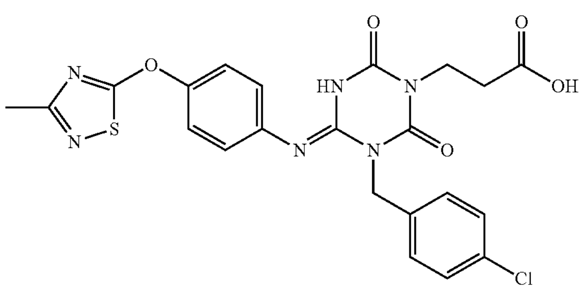 [SMILES: Cc1nsc(Oc2ccc(/N=c3\[nH]c(=O)n(CCC(=O)O)c(=O)n3Cc3ccc(Cl)cc3)cc2)n1] | I-2697 | 2.03 | 515 | 5 |
| 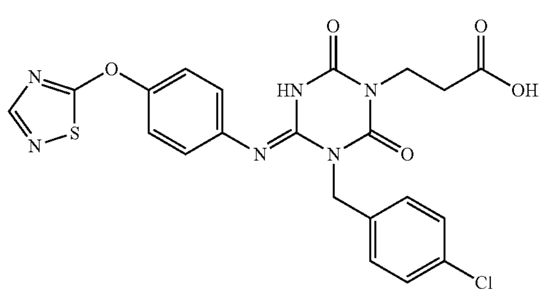 [SMILES: O=C(O)CCn1c(=O)[nH]/c(=N\c2ccc(Oc3ncns3)cc2)n(Cc2ccc(Cl)cc2)c1=O] | I-2698 | 1.96 | 501 | 5 |

TABLE 563

| Structure | Compound No. | Retention Time (min) | [M + H] | Method |
|---|---|---|---|---|
| 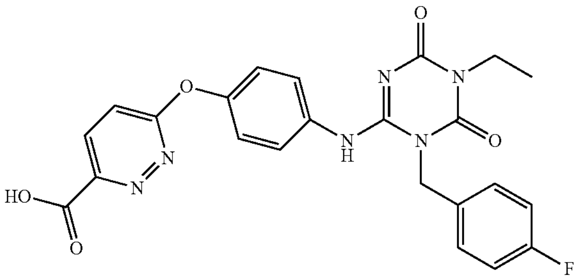 [SMILES: CCn1c(=O)nc(Nc2ccc(Oc3ccc(C(=O)O)nn3)cc2)n(Cc2ccc(F)cc2)c1=O] | I-2699 | 1.79 | 479 | 5 |
| 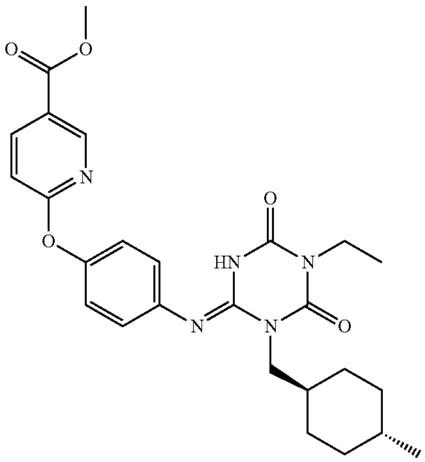 [SMILES: CCn1c(=O)[nH]/c(=N\c2ccc(Oc3ccc(C(=O)OC)cn3)cc2)n(C[C@H]2CC[C@H](C)CC2)c1=O] | I-2700 | 2.25 | 494 | 5 |
| 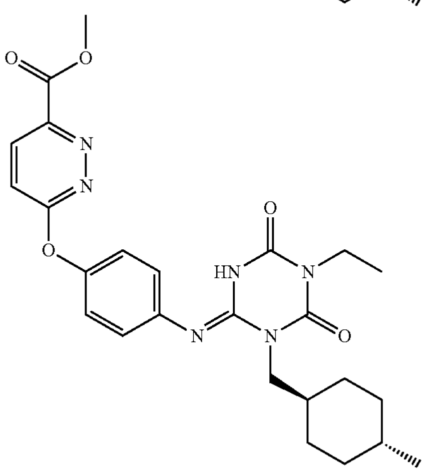 | I-2701 | 2.26 | 495 | 5 |
| 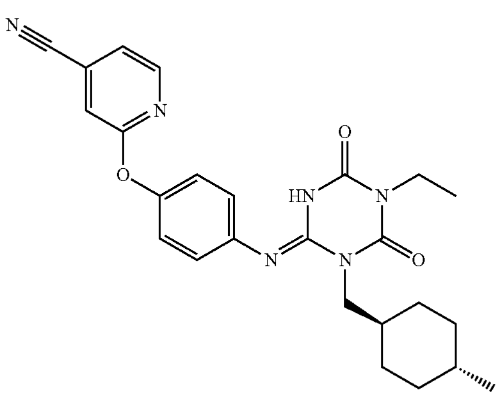 [SMILES: CCn1c(=O)[nH]/c(=N\c2ccc(Oc3cc(C#N)ccn3)cc2)n(C[C@H]2CC[C@H](C)CC2)c1=O] | I-2702 | 2.5 | 481 | 5 |

TABLE 564
| Structure | Compound No. | Retention Time (min) | [M + H] | Method |
|---|---|---|---|---|
| 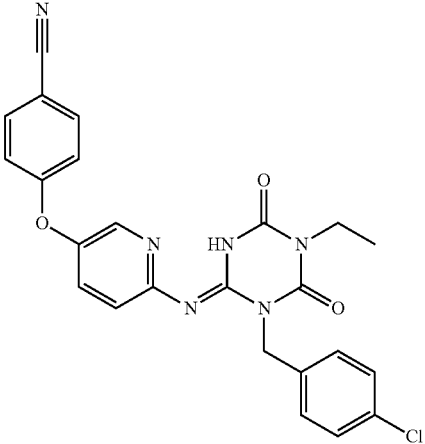 [SMILES: CCn1c(=O)[nH]/c(=N\c2ccc(Oc3ccc(C#N)cc3)cn2)n(Cc2ccc(Cl)cc2)c1=O] | I-2703 | 2.79 | 475 | 3 |
| 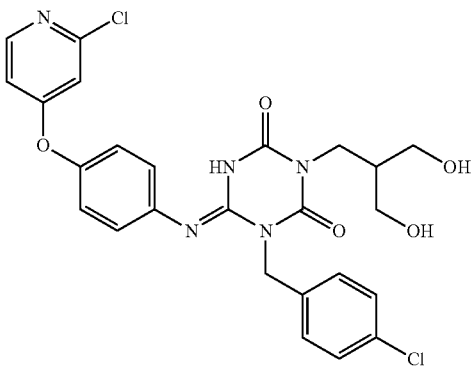 | I-2704 | 1.87 | 544 | 2 |
| 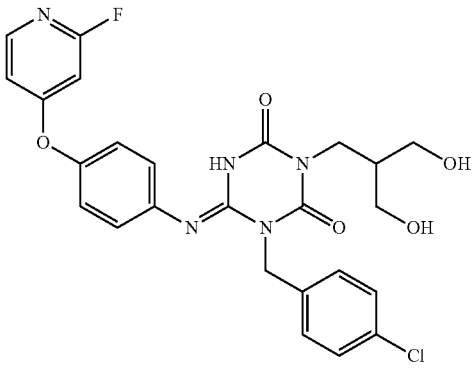 [SMILES: O=c1[nH]/c(=N\c2ccc(Oc3ccnc(F)c3)cc2)n(Cc2ccc(Cl)cc2)c(=O)n1CC(CO)CO] | I-2705 | 1.8 | 528 | 2 |
| 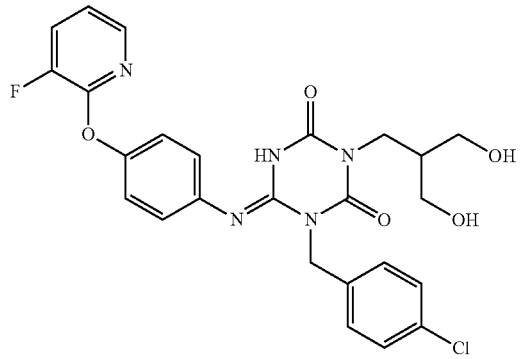 | I-2706 | 1.88 | 528 | 2 |

TABLE 565

| Structure | Compound No. | Retention Time (min) | [M + H] | Method |
|---|---|---|---|---|
| 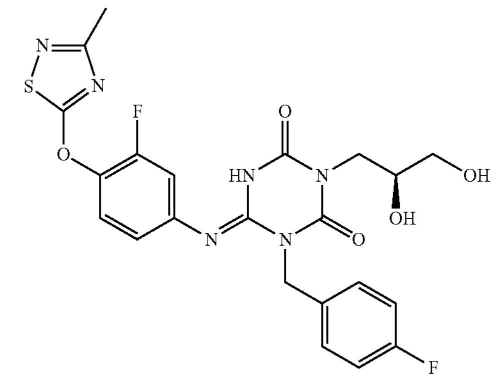 [SMILES: Cc1nsc(Oc2ccc(/N=c3\[nH]c(=O)n(C[C@H](O)CO)c(=O)n3Cc3ccc(Cl)cc3)cc2F)n1] | I-2707 | 1.8 | 519 | 2 |
| 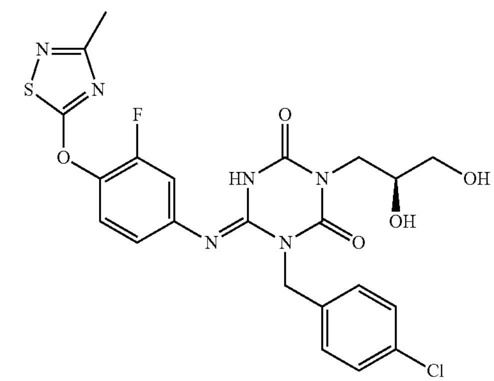 | I-2708 | 2.06 | 535 | 3 |
| 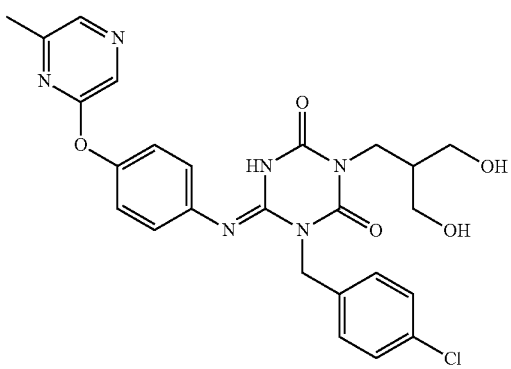 [SMILES: Cc1cncc(Oc2ccc(/N=c3\[nH]c(=O)n(CC(CO)CO)c(=O)n3Cc3ccc(Cl)cc3)cc2)n1] | I-2709 | 1.83 | 525 | 3 |
| 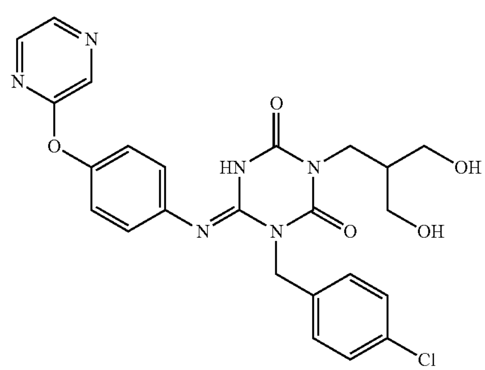 [SMILES: O=c1[nH]/c(=N\c2ccc(Oc3cnccn3)cc2)n(Cc2ccc(Cl)cc2)c(=O)n1CC(CO)CO] | I-2710 | 1.76 | 511 | 3 |

TABLE 566
| Structure (intermediate) | Compound No. | Retention Time (min) | [M + H] | Method |
|---|---|---|---|---|
| 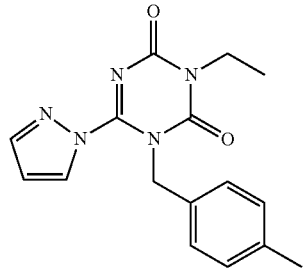 [SMILES: CCn1c(=O)nc(-n2cccn2)n(Cc2ccc(C)cc2)c1=O] | II-1 | 2.04 | 312 | 3 |
| 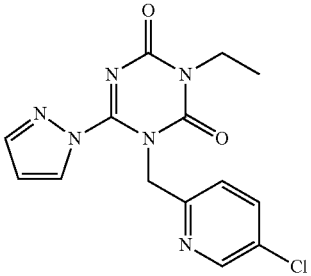 [SMILES: CCn1c(=O)nc(-n2cccn2)n(Cc2ccc(Cl)cn2)c1=O] | II-2 | 1.73 | 333 | 3 |
| 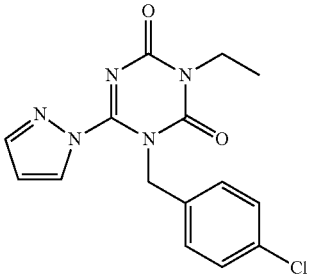 [SMILES: CCn1c(=O)nc(-n2cccn2)n(Cc2ccc(Cl)cc2)c1=O] | II-3 | 2.1 | 332 | 3 |
| 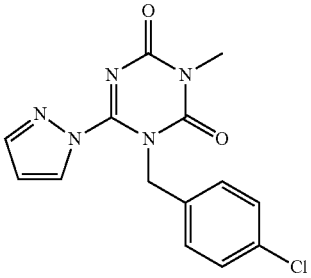 [SMILES: Cn1c(=O)nc(-n2cccn2)n(Cc2ccc(Cl)cc2)c1=O] | II-4 | 1.93 | 317 | 3 |
| 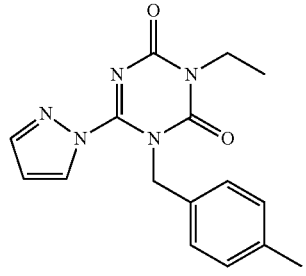 [SMILES: CCn1c(=O)nc(-n2cccn2)n(Cc2ccc(C)cc2)c1=O] | II-5 | 1.88 | 297 | 2 |

TABLE 567

| Structure (intermediate) | Compound No. | Retention Time (min) | [M + H] | Method |
|---|---|---|---|---|
| | II-11 | 2.96 | 390 | 2 |
| | II-12 | 1.88 | 316 | 3 |
| | II-13 | 1.01 | 266 | 2 |
| | II-14 | 2.08 | 390 | 2 |
| | II-15 | 1.92 | 370 | 2 |

TABLE 568

| Structure (intermediate) | Compound No. | Retention Time (min) | [M + H] | Method |
|---|---|---|---|---|
|  | II-16 | 0.86 | 266 | 3 |

TEST EXAMPLES

Test Example 1

Evaluation of Human P2X$_3$ Receptor Inhibitory Activity

Stably expressing cell line (C6BU-1 transfected with human P2X$_3$ receptor gene (GenBank accession number Y07683) was used. The cells were seeded in a 96-well microtiter plate at a concentration of 8000 cells/well and cultured in the medium (8.3% fetal bovine serum, 8.3% horse serum, 1% antibiotic and antifungal in DMEM) for one day at 37° C. under 5% carbon dioxide atmosphere. The medium was replaced with 4 μM Fluo-3-AM solution (20 mM HEPES, 137 mM NaCl, 2.7 mM KCl, 0.9 mM MgCl$_2$, 5.0 mM CaCl$_2$, 5.6 mM D-glucose, 2.5 mM probenecid, 10% BSA, and 0.08% Pluronic F-127, pH 7.5) and incubated at 37° C. under 5% dioxide carbon atmosphere for one hour. The plate was washed with washing buffer (20 mM HEPES, 137 mM NaCl, 2.7 KCl, 0.9 mM MgCl$_2$, 5.0 mM CaCl$_2$, 5.6 mM D-glucose, 2.5 mM probenecid, pH 7.5), each well was added with 40 μL of this buffer. The plate was placed in High-Throughput Screening System FDSS 3000 (Hamamatsu Photonics K.K.). Measurement of fluorescence intensity by FDSS 3000 was started, and 40 μl, of DMSO solutions containing different concentrations of the test, compound as prepared by dilution with dilution buffer (20 mM HEPES, 137 mM NaCl, 2.7 mM KCl, 0.9 mM MgCl$_2$, 5.0 mM CaCl$^2$, 5.6 mM D-glucose, 2.5 mM probenecid, 0.1.% Pluronic F-127, pH 7.5) were dispensed to each well through the built-in automatic dispenser. Five minutes after, 50 nM ATP solution (50 μL) prepared by dilution with the dilution buffer was dispensed through the built-in automatic dispenser, and the measurement of fluorescence intensity was continued for 3 min. For each well, the specific maximum fluorescence intensity was calculated as the ratio of the maximum fluorescence intensity after addition of the ATP solution to the fluorescence intensity at the starting of the measurement. The 50% inhibitory concentration (IC$_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. IC$_{50}$ was calculated using Microsoft Excel (Microsoft Corporation) and Ltd.)

The data of the compounds of the present invention are as shown in the following Tables.

TABLE 569

| Compound No. | P2X3 IC50 (μM) | Compound No. | P2X3 IC50 (μM) | Compound No. | P2X3 IC50 (μM) |
|---|---|---|---|---|---|
| I-0020 | 0.384 | I-0897 | 0.025 | I-1555 | 0.016 |
| I-0021 | 0.197 | I-0898 | 0.020 | I-1556 | 0.011 |
| I-0029 | 0.595 | I-0899 | 0.023 | I-1558 | 0.008 |
| I-0097 | 0.505 | I-0900 | 0.018 | I-1559 | 0.005 |
| I-0116 | 0.484 | I-0901 | 0.007 | I-1560 | 0.051 |
| I-0117 | 0.387 | I-0902 | 0.010 | I-1561 | 0.032 |
| I-0118 | 0.231 | I-0903 | 0.004 | I-1562 | 0.006 |
| I-0121 | 0.246 | I-0904 | 0.011 | I-1563 | 0.031 |
| I-0123 | 0.815 | I-0905 | 0.022 | I-1564 | 0.013 |
| I-0126 | 0.689 | I-0906 | 0.008 | I-1565 | 0.008 |
| I-0128 | 0.840 | I-0907 | 0.007 | I-1566 | 0.008 |
| I-0130 | 0.953 | I-0908 | 0.013 | I-1567 | 0.012 |
| I-0133 | 0.339 | I-0909 | 0.007 | I-1568 | 0.010 |
| I-0138 | 0.619 | I-0910 | 0.008 | I-1569 | 0.004 |
| I-0141 | 0.685 | I-0911 | 0.015 | I-1570 | 0.008 |
| I-0162 | 0.379 | I-0912 | 0.010 | I-1571 | 0.004 |
| I-0164 | 0.860 | I-0913 | 0.009 | I-1572 | 0.005 |
| I-0181 | 0.985 | I-0914 | 0.074 | I-1573 | 0.004 |
| I-0182 | 0.714 | I-0915 | 0.075 | I-1574 | 0.018 |
| I-0200 | 0.128 | I-0916 | 0.019 | I-1575 | 0.009 |
| I-0203 | 0.110 | I-0917 | 0.019 | I-1576 | 0.008 |
| I-0204 | 0.558 | I-0918 | 0.014 | I-1577 | 0.007 |
| I-0217 | 0.268 | I-0919 | 0.014 | I-1578 | 0.006 |
| I-0218 | 0.505 | I-0920 | 0.037 | I-1579 | 0.007 |
| I-0221 | 0.276 | I-0921 | 0.030 | I-1580 | 0.006 |
| I-0223 | 0.909 | I-0922 | 0.029 | I-1581 | 0.007 |
| I-0227 | 0.910 | I-0923 | 0.015 | I-1582 | 0.007 |
| I-0228 | 0.031 | I-0924 | 0.030 | I-1583 | 0.332 |
| I-0234 | 0.298 | I-0925 | 0.059 | I-1585 | 0.014 |
| I-0235 | 0.985 | I-0926 | 0.031 | I-1586 | 0.013 |
| I-0237 | 0.230 | I-0927 | 0.021 | I-1587 | 0.038 |
| I-0238 | 0.658 | I-0928 | 0.014 | I-1588 | 0.067 |
| I-0239 | 0.116 | I-0929 | 0.045 | I-1589 | 0.158 |
| I-0249 | 0.953 | I-0930 | 0.030 | I-1590 | 0.998 |
| I-0241 | 0.447 | I-0931 | 0.012 | I-1595 | 0.006 |
| I-0242 | 0.787 | I-0932 | 0.021 | I-1596 | 0.004 |
| I-0243 | 0.450 | I-0933 | 0.082 | I-1597 | 0.004 |
| I-0244 | 0.045 | I-0934 | 0.057 | I-1598 | 0.005 |
| I-0245 | 0.168 | I-0935 | 0.038 | I-1599 | 0.005 |
| I-0246 | 0.996 | I-0936 | 0.065 | I-1600 | 0.011 |
| I-0248 | 0.420 | I-0937 | 0.022 | I-1601 | 0.024 |
| I-0254 | 0.144 | I-0938 | 0.035 | I-1602 | 0.005 |
| I-0255 | 0.520 | I-0939 | 0.034 | I-1603 | 0.005 |
| I-0256 | 0.867 | I-0949 | 0.008 | I-1604 | 0.008 |
| I-0257 | 0.682 | I-0941 | 0.005 | I-1605 | 0.018 |
| I-0258 | 0.683 | I-0942 | 0.022 | I-1606 | 0.015 |
| I-0268 | 0.861 | I-0943 | 0.061 | I-1607 | 0.035 |
| I-0269 | 0.415 | I-0945 | 0.173 | I-1608 | 0.100 |
| I-0270 | 0.271 | I-0946 | 0.239 | I-1609 | 0.187 |
| I-0271 | 0.032 | I-0947 | 0.024 | I-1610 | 0.251 |
| I-0272 | 0.180 | I-0948 | 0.019 | I-1611 | 0.008 |
| I-0273 | 0.038 | I-0949 | 0.021 | I-1612 | 0.005 |
| I-0274 | 0.009 | I-0950 | 0.020 | I-1613 | 0.006 |
| I-0275 | 0.021 | I-0951 | 0.033 | I-1614 | 0.009 |
| I-0276 | 0.012 | I-0952 | 0.741 | I-1615 | 0.012 |

TABLE 570

| Compound No. | P2X3 IC50 (μM) | Compound No. | P2X3 IC50 (μM) | Compound No. | P2X3 IC50 (μM) |
|---|---|---|---|---|---|
| I-0277 | 0.038 | I-0953 | 0.042 | I-1616 | 0.007 |
| I-0278 | 0.931 | I-0954 | 0.023 | I-1617 | 0.027 |
| I-0280 | 0.030 | I-0955 | 0.028 | I-1618 | 0.008 |
| I-0281 | 0.012 | I-0956 | 0.139 | I-1619 | 0.006 |
| I-0282 | 0.027 | I-0957 | 0.025 | I-1620 | 0.014 |
| I-0283 | 0.019 | I-0958 | 0.030 | I-1621 | 0.004 |
| I-0284 | 0.629 | I-0959 | 0.007 | I-1622 | 0.004 |
| I-0285 | 0.014 | I-0960 | 0.070 | I-1623 | 0.007 |
| I-0286 | 0.277 | I-0961 | 0.074 | I-1624 | 0.008 |
| I-0287 | 0.222 | I-0962 | 0.031 | I-1625 | 0.006 |
| I-0288 | 0.093 | I-0963 | 0.662 | I-1626 | 0.018 |
| I-0289 | 0.066 | I-0964 | 0.344 | I-1627 | 0.009 |
| I-0290 | 0.266 | I-0965 | 0.021 | I-1628 | 0.683 |
| I-0291 | 0.009 | I-0966 | 0.017 | I-1629 | 0.004 |
| I-0292 | 0.034 | I-0967 | 0.019 | I-1630 | 0.015 |
| I-0293 | 0.351 | I-0968 | 0.107 | I-1631 | 0.008 |
| I-0294 | 0.040 | I-0969 | 0.047 | I-1632 | 0.389 |
| I-0295 | 0.046 | I-0970 | 0.020 | I-1633 | 0.016 |
| I-0296 | 0.176 | I-0971 | 0.030 | I-1635 | 0.005 |
| I-0297 | 0.045 | I-0972 | 0.038 | I-1636 | 0.009 |
| I-0298 | 0.027 | I-0973 | 0.019 | I-1637 | 0.012 |
| I-0299 | 0.046 | I-0974 | 0.029 | I-1638 | 0.013 |
| I-0300 | 0.025 | I-0975 | 0.043 | I-1639 | 0.014 |
| I-0301 | 0.048 | I-0976 | 0.069 | I-1640 | 0.013 |
| I-0305 | 0.946 | I-0977 | 0.015 | I-1641 | 0.020 |
| I-0307 | 0.250 | I-0978 | 0.013 | I-1642 | 0.551 |
| I-0309 | 0.357 | I-0979 | 0.006 | I-1643 | 0.005 |
| I-0310 | 0.389 | I-0980 | 0.011 | I-1644 | 0.005 |
| I-0311 | 0.142 | I-0981 | 0.010 | I-1646 | 0.043 |
| I-0312 | 0.104 | I-0982 | 0.017 | I-1947 | 0.677 |
| I-0313 | 0.178 | I-0983 | 0.007 | I-1648 | 0.160 |
| I-0314 | 0.555 | I-0984 | 0.021 | I-1649 | 0.285 |
| I-0315 | 0.183 | I-0985 | 0.026 | I-1650 | 0.009 |
| I-0316 | 0.712 | I-0986 | 0.031 | I-1651 | 0.054 |
| I-0317 | 0.137 | I-0987 | 0.015 | I-1653 | 0.014 |
| I-0320 | 0.083 | I-0988 | 0.093 | I-1654 | 0.066 |
| I-0321 | 0.033 | I-0989 | 0.068 | I-1655 | 0.667 |
| I-0322 | 0.112 | I-0990 | 0.051 | I-1656 | 0.007 |
| I-0323 | 0.148 | I-0991 | 0.022 | I-1657 | 0.009 |
| I-0324 | 0.309 | I-0992 | 0.024 | I-1658 | 0.006 |
| I-0325 | 0.665 | I-0993 | 0.020 | I-1659 | 0.006 |
| I-0326 | 0.011 | I-0994 | 0.020 | I-1660 | 0.005 |
| I-0328 | 0.124 | I-0995 | 0.276 | I-1661 | 0.006 |
| I-0329 | 0.266 | I-0996 | 0.032 | I-1662 | 0.011 |
| I-0330 | 0.594 | I-0997 | 0.680 | I-1663 | 0.008 |
| I-0331 | 0.066 | I-0998 | 0.024 | I-1665 | 0.007 |
| I-0332 | 0.008 | I-0999 | 0.174 | I-1666 | 0.010 |
| I-0333 | 0.192 | I-1000 | 0.116 | I-1668 | 0.309 |
| I-0334 | 0.099 | I-1001 | 0.292 | I-1670 | 0.007 |
| I-0335 | 0.007 | I-1002 | 0.298 | I-1671 | 0.006 |
| I-0338 | 0.053 | I-1003 | 0.229 | I-1673 | 0.014 |
| I-0339 | 0.775 | I-1004 | 0.085 | I-1674 | 0.971 |
| I-0340 | 0.336 | I-1005 | 0.031 | I-1676 | 0.854 |
| I-0341 | 0.149 | I-1006 | 0.118 | I-1677 | 0.017 |
| I-0342 | 0.005 | I-1007 | 0.015 | I-1678 | 0.111 |

TABLE 571

| Compound No. | P2X3 IC50 (μM) | Compound No. | P2X3 IC50 (μM) | Compound No. | P2X3 IC50 (μM) |
|---|---|---|---|---|---|
| I-0343 | 0.021 | I-1008 | 0.108 | I-1679 | 0.007 |
| I-0344 | 0.128 | I-1009 | 0.069 | I-1680 | 0.730 |
| I-0346 | 0.016 | I-1010 | 0.004 | I-1682 | 0.140 |
| I-0347 | 0.251 | I-1011 | 0.021 | I-1683 | 0.310 |
| I-0348 | 0.013 | I-1012 | 0.051 | I-1686 | 0.115 |
| I-0349 | 0.113 | I-1013 | 0.005 | I-1689 | 0.882 |
| I-0350 | 0.010 | I-1014 | 0.017 | I-1691 | 0.022 |
| I-0351 | 0.015 | I-1015 | 0.007 | I-1692 | 0.582 |
| I-0352 | 0.036 | I-1016 | 0.017 | I-1700 | 0.012 |
| I-0353 | 0.018 | I-1017 | 0.550 | I-1701 | 0.003 |
| I-0354 | 0.008 | I-1018 | 0.008 | I-1702 | 0.004 |
| I-0355 | 0.020 | I-1019 | 0.007 | I-1703 | 0.004 |
| I-0356 | 0.012 | I-1020 | 0.006 | I-1704 | 0.015 |
| I-0357 | 0.047 | I-1021 | 0.007 | I-1705 | 0.014 |
| I-0358 | 0.055 | I-1022 | 0.014 | I-1708 | 0.017 |
| I-0359 | 0.040 | I-1023 | 0.300 | I-1709 | 0.167 |
| I-0360 | 0.148 | I-1024 | 0.161 | I-1710 | 0.006 |
| I-0361 | 0.076 | I-1025 | 0.134 | I-1711 | 0.005 |
| I-0362 | 0.007 | I-1026 | 0.182 | I-1712 | 0.004 |
| I-0363 | 0.078 | I-1027 | 0.041 | I-1713 | 0.003 |
| I-0364 | 0.030 | I-1028 | 0.078 | I-1714 | 0.003 |
| I-0365 | 0.018 | I-1029 | 0.035 | I-1715 | 0.021 |
| I-0366 | 0.046 | I-1030 | 0.014 | I-1717 | 0.002 |
| I-0367 | 0.040 | I-1031 | 0.064 | I-1725 | 0.953 |
| I-0368 | 0.041 | I-1032 | 0.033 | I-1729 | 0.669 |
| I-0369 | 0.007 | I-1033 | 0.067 | I-1731 | 0.005 |
| I-0370 | 0.154 | I-1034 | 0.005 | I-1732 | 0.011 |
| I-0371 | 0.063 | I-1035 | 0.065 | I-1733 | 0.003 |
| I-0372 | 0.964 | I-1036 | 0.005 | I-1734 | 0.005 |
| I-0373 | 0.185 | I-1037 | 0.093 | I-1735 | 0.003 |
| I-0374 | 0.080 | I-1038 | 0.006 | I-1736 | 0.009 |
| I-0375 | 0.152 | I-1039 | 0.083 | I-1737 | 0.019 |
| I-0377 | 0.755 | I-1040 | 0.128 | I-1738 | 0.005 |
| I-0378 | 0.347 | I-1041 | 0.101 | I-1739 | 0.007 |
| I-0379 | 0.330 | I-1042 | 0.148 | I-1741 | 0.055 |
| I-0380 | 0.034 | I-1043 | 0.010 | I-1742 | 0.135 |
| I-0382 | 0.096 | I-1044 | 0.019 | I-1743 | 0.861 |
| I-0383 | 0.532 | I-1045 | 0.159 | I-1744 | 0.242 |
| I-0385 | 0.908 | I-1046 | 0.028 | I-1746 | 0.129 |
| I-0386 | 0.041 | I-1047 | 0.154 | I-1747 | 0.201 |
| I-0387 | 0.037 | I-1048 | 0.038 | I-1748 | 0.236 |
| I-0388 | 0.036 | I-1049 | 0.177 | I-1750 | 0.021 |
| I-0389 | 0.064 | I-1050 | 0.389 | I-1752 | 0.004 |
| I-0390 | 0.067 | I-1051 | 0.100 | I-1753 | 0.009 |
| I-0391 | 0.133 | I-1052 | 0.019 | I-1754 | 0.005 |
| I-0392 | 0.038 | I-1053 | 0.079 | I-1756 | 0.030 |
| I-0394 | 0.435 | I-1054 | 0.018 | I-1757 | 0.012 |
| I-0396 | 0.019 | I-1055 | 0.091 | I-1759 | 0.408 |
| I-0397 | 0.007 | I-1056 | 0.177 | I-1764 | 0.035 |
| I-0398 | 0.008 | I-1057 | 0.089 | I-1765 | 0.009 |
| I-0399 | 0.044 | I-1058 | 0.043 | I-1766 | 0.018 |
| I-0400 | 0.007 | I-1059 | 0.123 | I-1767 | 0.055 |
| I-0401 | 0.443 | I-1060 | 0.029 | I-1768 | 0.006 |
| I-0402 | 0.015 | I-1061 | 0.174 | I-1769 | 0.003 |
| I-0403 | 0.012 | I-1062 | 0.037 | I-1770 | 0.788 |

TABLE 572

| Compound No. | P2X3 IC50 (μM) | Compound No. | P2X3 IC50 (μM) | Compound No. | P2X3 IC50 (μM) |
|---|---|---|---|---|---|
| I-0404 | 0.032 | I-1063 | 0.152 | I-1771 | 0.014 |
| I-0405 | 0.030 | I-1064 | 0.257 | I-1772 | 0.297 |
| I-0406 | 0.027 | I-1065 | 0.085 | I-1773 | 0.029 |
| I-0407 | 0.010 | I-1066 | 0.425 | I-1774 | 0.255 |
| I-0408 | 0.012 | I-1067 | 0.093 | I-1777 | 0.636 |
| I-0409 | 0.044 | I-1068 | 0.541 | I-1779 | 0.203 |
| I-0410 | 0.061 | I-1069 | 0.111 | I-1780 | 0.932 |
| I-0412 | 0.099 | I-1070 | 0.471 | I-1781 | 0.518 |
| I-0413 | 0.007 | I-1071 | 0.998 | I-1783 | 0.170 |
| I-0414 | 0.314 | I-1072 | 0.252 | I-1784 | 0.950 |
| I-0415 | 0.035 | I-1073 | 0.092 | I-1786 | 0.621 |
| I-0416 | 0.035 | I-1074 | 0.086 | I-1788 | 0.005 |
| I-0417 | 0.200 | I-1076 | 0.177 | I-1789 | 0.030 |
| I-0418 | 0.071 | I-1077 | 0.064 | I-1792 | 0.020 |
| I-0419 | 0.053 | I-1078 | 0.218 | I-1793 | 0.984 |
| I-0420 | 0.019 | I-1080 | 0.066 | I-1794 | 0.380 |
| I-0421 | 0.006 | I-1081 | 0.030 | I-1795 | 0.795 |
| I-0422 | 0.004 | I-1082 | 0.063 | I-1796 | 0.587 |
| I-0423 | 0.049 | I-1083 | 0.125 | I-1797 | 0.006 |
| I-0424 | 0.016 | I-1084 | 0.392 | I-1798 | 0.150 |
| I-0425 | 0.211 | I-1085 | 0.034 | I-1799 | 0.382 |
| I-0426 | 0.678 | I-1086 | 0.291 | I-1800 | 0.510 |
| I-0428 | 0.779 | I-1087 | 0.071 | I-1801 | 0.687 |
| I-0430 | 0.004 | I-1088 | 0.548 | I-1804 | 0.162 |
| I-0431 | 0.026 | I-1089 | 0.487 | I-1805 | 0.005 |
| I-0432 | 0.199 | I-1090 | 0.135 | I-1807 | 0.006 |

TABLE 572-continued

| Compound No. | P2X3 IC50 (μM) | Compound No. | P2X3 IC50 (μM) | Compound No. | P2X3 IC50 (μM) |
|---|---|---|---|---|---|
| I-0434 | 0.079 | I-1091 | 0.179 | I-1808 | 0.004 |
| I-0438 | 0.398 | I-1092 | 0.069 | I-1809 | 0.339 |
| I-0440 | 0.943 | I-1093 | 0.038 | I-1810 | 0.682 |
| I-0441 | 0.034 | I-1094 | 0.103 | I-1812 | 0.630 |
| I-0442 | 0.349 | I-1095 | 0.144 | I-1814 | 0.299 |
| I-0443 | 0.407 | I-1096 | 0.094 | I-1815 | 0.367 |
| I-0444 | 0.006 | I-1097 | 0.141 | I-1816 | 0.300 |
| I-0445 | 0.008 | I-1098 | 0.074 | I-1817 | 0.052 |
| I-0446 | 0.006 | I-1099 | 0.070 | I-1818 | 0.829 |
| I-0447 | 0.005 | I-1100 | 0.043 | I-1819 | 0.873 |
| I-0448 | 0.018 | I-1101 | 0.053 | I-1820 | 0.204 |
| I-0449 | 0.055 | I-1102 | 0.148 | I-1821 | 0.429 |
| I-0450 | 0.011 | I-1103 | 0.423 | I-1822 | 0.332 |
| I-0451 | 0.117 | I-1104 | 0.011 | I-1826 | 0.751 |
| I-0452 | 0.207 | I-1105 | 0.152 | I-1827 | 0.913 |
| I-0453 | 0.017 | I-1106 | 0.007 | I-1829 | 0.092 |
| I-0454 | 0.008 | I-1107 | 0.043 | I-1830 | 0.869 |
| I-0455 | 0.020 | I-1108 | 0.050 | I-1831 | 0.739 |
| I-0456 | 0.279 | I-1109 | 0.430 | I-1832 | 0.032 |
| I-0457 | 0.388 | I-1110 | 0.397 | I-1833 | 0.580 |
| I-0459 | 0.036 | I-1111 | 0.161 | I-1834 | 0.325 |
| I-0460 | 0.016 | I-1112 | 0.872 | I-1835 | 0.008 |
| I-0461 | 0.003 | I-1113 | 0.123 | I-1836 | 0.787 |
| I-0462 | 0.005 | I-1114 | 0.214 | I-1839 | 0.107 |
| I-0463 | 0.024 | I-1115 | 0.516 | I-1840 | 0.007 |
| I-0464 | 0.030 | I-1118 | 0.387 | I-1841 | 0.006 |
| I-0465 | 0.008 | I-1120 | 0.534 | I-1842 | 0.005 |
| I-0466 | 0.003 | I-1122 | 0.008 | I-1843 | 0.004 |
| I-0467 | 0.004 | I-1123 | 0.014 | I-1844 | 0.004 |

TABLE 573

| Compound No. | P2X3 IC50 (μM) | Compound No. | P2X3 IC50 (μM) | Compound No. | P2X3 IC50 (μM) |
|---|---|---|---|---|---|
| I-0468 | 0.039 | I-1124 | 0.532 | I-1845 | 0.033 |
| I-0469 | 0.016 | I-1125 | 0.004 | I-1846 | 0.015 |
| I-0470 | 0.009 | I-1126 | 0.008 | I-1847 | 0.006 |
| I-0471 | 0.004 | I-1127 | 0.068 | I-1848 | 0.014 |
| I-0472 | 0.074 | I-1128 | 0.021 | I-1849 | 0.007 |
| I-0473 | 0.564 | I-1129 | 0.011 | I-1851 | 0.004 |
| I-0474 | 0.057 | I-1130 | 0.133 | I-1852 | 0.005 |
| I-0475 | 0.037 | I-1131 | 0.105 | I-1853 | 0.004 |
| I-0476 | 0.037 | I-1132 | 0.586 | I-1854 | 0.004 |
| I-0477 | 0.137 | I-1133 | 0.051 | I-1855 | 0.021 |
| I-0478 | 0.101 | I-1134 | 0.035 | I-1856 | 0.008 |
| I-0479 | 0.080 | I-1135 | 0.018 | I-1857 | 0.007 |
| I-0480 | 0.024 | I-1136 | 0.204 | I-1858 | 0.005 |
| I-0481 | 0.047 | I-1137 | 0.678 | I-1859 | 0.005 |
| I-0482 | 0.583 | I-1139 | 0.052 | I-1860 | 0.150 |
| I-0483 | 0.014 | I-1140 | 0.044 | I-1862 | 0.552 |
| I-0484 | 0.571 | I-1141 | 0.911 | I-1863 | 0.005 |
| I-0485 | 0.035 | I-1142 | 0.802 | I-1864 | 0.186 |
| I-0486 | 0.056 | I-1143 | 0.024 | I-1865 | 0.357 |
| I-0487 | 0.629 | I-1144 | 0.764 | I-1869 | 0.328 |
| I-0488 | 0.007 | I-1146 | 0.009 | I-1870 | 0.004 |
| I-0489 | 0.012 | I-1147 | 0.010 | I-1871 | 0.006 |
| I-0490 | 0.012 | I-1148 | 0.086 | I-1872 | 0.015 |
| I-0492 | 0.100 | I-1149 | 0.065 | I-1873 | 0.002 |
| I-0493 | 0.290 | I-1150 | 0.551 | I-1874 | 0.013 |
| I-0494 | 0.198 | I-1151 | 0.046 | I-1875 | 0.013 |
| I-0495 | 0.042 | I-1152 | 0.110 | I-1876 | 0.035 |
| I-0496 | 0.027 | I-1153 | 0.071 | I-1877 | 0.036 |
| I-0497 | 0.124 | I-1154 | 0.131 | I-1878 | 0.010 |
| I-0498 | 0.010 | I-1155 | 0.009 | I-1879 | 0.128 |
| I-0499 | 0.046 | I-1156 | 0.006 | I-1880 | 0.015 |
| I-0500 | 0.027 | I-1157 | 0.052 | I-1881 | 0.006 |
| I-0501 | 0.102 | I-1158 | 0.063 | I-1882 | 0.016 |
| I-0502 | 0.952 | I-1159 | 0.043 | I-1883 | 0.007 |
| I-0503 | 0.034 | I-1160 | 0.973 | I-1884 | 0.296 |
| I-0504 | 0.125 | I-1161 | 0.148 | I-1885 | 0.007 |
| I-0505 | 0.125 | I-1162 | 0.179 | I-1886 | 0.003 |
| I-0506 | 0.458 | I-1163 | 0.823 | I-1887 | 0.003 |
| I-0507 | 0.009 | I-1166 | 0.126 | I-1888 | 0.010 |

TABLE 573-continued

| Compound No. | P2X3 IC50 (μM) | Compound No. | P2X3 IC50 (μM) | Compound No. | P2X3 IC50 (μM) |
|---|---|---|---|---|---|
| I-0508 | 0.137 | I-1168 | 0.004 | I-1889 | 0.023 |
| I-0509 | 0.013 | I-1171 | 0.025 | I-1892 | 0.113 |
| I-0510 | 0.191 | I-1172 | 0.097 | I-1893 | 0.178 |
| I-0511 | 0.020 | I-1173 | 0.009 | I-1894 | 0.023 |
| I-0512 | 0.050 | I-1174 | 0.027 | I-1896 | 0.014 |
| I-0513 | 0.015 | I-1175 | 0.883 | I-1897 | 0.024 |
| I-0514 | 0.120 | I-1176 | 0.834 | I-1898 | 0.011 |
| I-0515 | 0.279 | I-1177 | 0.273 | I-1899 | 0.004 |
| I-0516 | 0.301 | I-1178 | 0.017 | I-1900 | 0.016 |
| I-0517 | 0.511 | I-1179 | 0.033 | I-1901 | 0.015 |
| I-0518 | 0.652 | I-1182 | 0.056 | I-1902 | 0.008 |
| I-0519 | 0.098 | I-1183 | 0.047 | I-1903 | 0.004 |
| I-0524 | 0.006 | I-1184 | 0.138 | I-1904 | 0.008 |
| I-0525 | 0.005 | I-1185 | 0.116 | I-1905 | 0.005 |
| I-0526 | 0.015 | I-1186 | 0.033 | I-1906 | 0.006 |
| I-0527 | 0.007 | I-1187 | 0.058 | I-1907 | 0.008 |

TABLE 574

| Compound No. | P2X3 IC50 (μM) | Compound No. | P2X3 IC50 (μM) | Compound No. | P2X3 IC50 (μM) |
|---|---|---|---|---|---|
| I-0528 | 0.012 | I-1188 | 0.131 | I-1908 | 0.070 |
| I-0529 | 0.080 | I-1189 | 0.033 | I-1911 | 0.253 |
| I-0530 | 0.004 | I-1190 | 0.005 | I-1912 | 0.029 |
| I-0531 | 0.029 | I-1191 | 0.022 | I-1913 | 0.019 |
| I-0532 | 0.072 | I-1192 | 0.020 | I-1914 | 0.046 |
| I-0533 | 0.060 | I-1193 | 0.040 | I-1915 | 0.023 |
| I-0534 | 0.054 | I-1194 | 0.031 | I-1916 | 0.995 |
| I-0535 | 0.024 | I-1195 | 0.221 | I-1917 | 0.023 |
| I-0536 | 0.033 | I-1197 | 0.008 | I-1918 | 0.012 |
| I-0537 | 0.053 | I-1198 | 0.035 | I-1919 | 0.214 |
| I-0538 | 0.022 | I-1199 | 0.036 | I-1923 | 0.084 |
| I-0539 | 0.034 | I-1200 | 0.045 | I-1925 | 0.006 |
| I-0540 | 0.010 | I-1201 | 0.788 | I-1926 | 0.010 |
| I-0541 | 0.029 | I-1202 | 0.093 | I-1927 | 0.007 |
| I-0542 | 0.010 | I-1203 | 0.532 | I-1928 | 0.005 |
| I-0543 | 0.018 | I-1204 | 0.005 | I-1930 | 0.029 |
| I-0544 | 0.052 | I-1205 | 0.002 | I-1931 | 0.009 |
| I-0545 | 0.046 | I-1206 | 0.043 | I-1932 | 0.095 |
| I-0546 | 0.019 | I-1207 | 0.015 | I-1934 | 0.198 |
| I-0547 | 0.016 | I-1208 | 0.021 | I-1935 | 0.009 |
| I-0548 | 0.007 | I-1209 | 0.006 | I-1937 | 0.022 |
| I-0549 | 0.027 | I-1210 | 0.037 | I-1938 | 0.312 |
| I-0550 | 0.058 | I-1211 | 0.030 | I-1939 | 0.030 |
| I-0551 | 0.096 | I-1212 | 0.090 | I-1940 | 0.055 |
| I-0552 | 0.172 | I-1213 | 0.104 | I-1941 | 0.005 |
| I-0553 | 0.601 | I-1214 | 0.070 | I-1942 | 0.049 |
| I-0554 | 0.006 | I-1215 | 0.027 | I-1943 | 0.258 |
| I-0555 | 0.459 | I-1216 | 0.013 | I-1944 | 0.011 |
| I-0556 | 0.011 | I-1217 | 0.005 | I-1945 | 0.008 |
| I-0557 | 0.012 | I-1218 | 0.061 | I-1946 | 0.025 |
| I-0558 | 0.019 | I-1219 | 0.029 | I-1947 | 0.353 |
| I-0559 | 0.033 | I-1220 | 0.013 | I-1948 | 0.022 |
| I-0560 | 0.034 | I-1221 | 0.117 | I-1949 | 0.005 |
| I-0561 | 0.023 | I-1222 | 0.017 | I-1950 | 0.029 |
| I-0562 | 0.034 | I-1223 | 0.297 | I-1951 | 0.025 |
| I-0563 | 0.139 | I-1224 | 0.054 | I-1952 | 0.781 |
| I-0564 | 0.013 | I-1225 | 0.082 | I-1953 | 0.016 |
| I-0565 | 0.005 | I-1226 | 0.122 | I-1954 | 0.005 |
| I-0566 | 0.019 | I-1227 | 0.030 | I-1955 | 0.097 |
| I-0567 | 0.005 | I-1228 | 0.009 | I-1956 | 0.034 |
| I-0568 | 0.097 | I-1229 | 0.004 | I-1957 | 0.022 |
| I-0569 | 0.007 | I-1230 | 0.004 | I-1958 | 0.016 |
| I-0570 | 0.008 | I-1231 | 0.036 | I-1959 | 0.065 |
| I-0571 | 0.027 | I-1232 | 0.005 | I-1960 | 0.054 |
| I-0572 | 0.040 | I-1233 | 0.325 | I-1961 | 0.013 |
| I-0573 | 0.048 | I-1234 | 0.230 | I-1962 | 0.065 |
| I-0574 | 0.015 | I-1235 | 0.214 | I-1963 | 0.013 |
| I-0576 | 0.568 | I-1236 | 0.013 | I-1964 | 0.277 |
| I-0577 | 0.430 | I-1237 | 0.183 | I-1965 | 0.003 |
| I-0578 | 0.254 | I-1238 | 0.002 | I-1966 | 0.011 |
| I-0579 | 0.614 | I-1239 | 0.732 | I-1967 | 0.008 |
| I-0581 | 0.145 | I-1240 | 0.018 | I-1968 | 0.015 |

TABLE 574-continued

| Compound No. | P2X3 IC50 (μM) | Compound No. | P2X3 IC50 (μM) | Compound No. | P2X3 IC50 (μM) |
|---|---|---|---|---|---|
| I-0582 | 0.365 | I-1241 | 0.108 | I-1969 | 0.021 |
| I-0583 | 0.038 | I-1242 | 0.015 | I-1970 | 0.082 |
| I-0584 | 0.248 | I-1243 | 0.012 | I-1971 | 0.061 |

TABLE 575

| Compound No. | P2X3 IC50 (μM) | Compound No. | P2X3 IC50 (μM) | Compound No. | P2X3 IC50 (μM) |
|---|---|---|---|---|---|
| I-0586 | 0.611 | I-1244 | 0.473 | I-1972 | 0.243 |
| I-0587 | 0.299 | I-1245 | 0.003 | I-1973 | 0.002 |
| I-0589 | 0.006 | I-1246 | 0.006 | I-1974 | 0.007 |
| I-0590 | 0.004 | I-1247 | 0.028 | I-1976 | 0.017 |
| I-0593 | 0.004 | I-1248 | 0.006 | I-1977 | 0.005 |
| I-0596 | 0.010 | I-1249 | 0.021 | I-1978 | 0.005 |
| I-0597 | 0.507 | I-1250 | 0.054 | I-1979 | 0.004 |
| I-0599 | 0.038 | I-1251 | 0.017 | I-1980 | 0.007 |
| I-0600 | 0.013 | I-1252 | 0.023 | I-1981 | 0.354 |
| I-0601 | 0.031 | I-1253 | 0.281 | I-1982 | 0.009 |
| I-0602 | 0.020 | I-1254 | 0.045 | I-1983 | 0.010 |
| I-0603 | 0.012 | I-1255 | 0.048 | I-1984 | 0.009 |
| I-0604 | 0.013 | I-1256 | 0.018 | I-1985 | 0.011 |
| I-0605 | 0.025 | I-1257 | 0.009 | I-1986 | 0.016 |
| I-0606 | 0.021 | I-1258 | 0.008 | I-1987 | 0.007 |
| I-0607 | 0.012 | I-1259 | 0.011 | I-1988 | 0.391 |
| I-0608 | 0.006 | I-1260 | 0.031 | I-1989 | 0.619 |
| I-0609 | 0.031 | I-1261 | 0.018 | I-1990 | 0.002 |
| I-0610 | 0.035 | I-1262 | 0.163 | I-1991 | 0.006 |
| I-0611 | 0.037 | I-1263 | 0.025 | I-1992 | 0.240 |
| I-0612 | 0.038 | I-1264 | 0.031 | I-1993 | 0.006 |
| I-0613 | 0.011 | I-1265 | 0.022 | I-1994 | 0.010 |
| I-0614 | 0.010 | I-1266 | 0.049 | I-1995 | 0.005 |
| I-0615 | 0.005 | I-1267 | 0.009 | I-1996 | 0.004 |
| I-0616 | 0.010 | I-1268 | 0.052 | I-1997 | 0.004 |
| I-0617 | 0.067 | I-1269 | 0.008 | I-1998 | 0.034 |
| I-0618 | 0.121 | I-1270 | 0.012 | I-1999 | 0.028 |
| I-0619 | 0.014 | I-1271 | 0.032 | I-2000 | 0.003 |
| I-0620 | 0.044 | I-1272 | 0.007 | I-2001 | 0.005 |
| I-0621 | 0.058 | I-1273 | 0.007 | I-2002 | 0.008 |
| I-0622 | 0.030 | I-1274 | 0.006 | I-2004 | 0.013 |
| I-0623 | 0.020 | I-1275 | 0.006 | I-2005 | 0.003 |
| I-0624 | 0.042 | I-1276 | 0.078 | I-2006 | 0.036 |
| I-0625 | 0.066 | I-1277 | 0.015 | I-2007 | 0.017 |
| I-0626 | 0.022 | I-1278 | 0.033 | I-2008 | 0.007 |
| I-0627 | 0.091 | I-1279 | 0.158 | I-2009 | 0.472 |
| I-0628 | 0.061 | I-1280 | 0.027 | I-2010 | 0.054 |
| I-0629 | 0.127 | I-1281 | 0.006 | I-2011 | 0.010 |
| I-0630 | 0.030 | I-1282 | 0.004 | I-2012 | 0.009 |
| I-0631 | 0.010 | I-1283 | 0.004 | I-2013 | 0.003 |
| I-0632 | 0.011 | I-1284 | 0.015 | I-2014 | 0.360 |
| I-0633 | 0.004 | I-1285 | 0.051 | I-2015 | 0.032 |
| I-0634 | 0.011 | I-1286 | 0.034 | I-2016 | 0.005 |
| I-0635 | 0.019 | I-1289 | 0.510 | I-2017 | 0.041 |
| I-0636 | 0.010 | I-1291 | 0.683 | I-2018 | 0.022 |
| I-0637 | 0.069 | I-1292 | 0.445 | I-2019 | 0.005 |
| I-0638 | 0.006 | I-1296 | 0.918 | I-2020 | 0.006 |
| I-0639 | 0.216 | I-1297 | 0.026 | I-2021 | 0.230 |
| I-0640 | 0.005 | I-1298 | 0.026 | I-2022 | 0.007 |
| I-0641 | 0.026 | I-1299 | 0.051 | I-2023 | 0.004 |
| I-0642 | 0.005 | I-1300 | 0.018 | I-2024 | 0.005 |
| I-0643 | 0.054 | I-1301 | 0.514 | I-2025 | 0.005 |
| I-0644 | 0.040 | I-1302 | 0.169 | I-2026 | 0.022 |
| I-0645 | 0.102 | I-1303 | 0.066 | I-2027 | 0.017 |
| I-0646 | 0.028 | I-1304 | 0.574 | I-2028 | 0.013 |

TABLE 576

| Compound No. | P2X3 IC50 (μM) | Compound No. | P2X3 IC50 (μM) | Compound No. | P2X3 IC50 (μM) |
|---|---|---|---|---|---|
| I-0647 | 0.316 | I-1305 | 0.227 | I-2029 | 0.004 |
| I-0648 | 0.336 | I-1306 | 0.080 | I-2030 | 0.006 |
| I-0649 | 0.021 | I-1307 | 0.007 | I-2031 | 0.052 |
| I-0650 | 0.020 | I-1308 | 0.029 | I-2032 | 0.004 |
| I-0651 | 0.097 | I-1309 | 0.021 | I-2033 | 0.622 |
| I-0652 | 0.102 | I-1310 | 0.066 | I-2034 | 0.009 |
| I-0653 | 0.037 | I-1311 | 0.023 | I-2035 | 0.022 |
| I-0654 | 0.026 | I-1312 | 0.045 | I-2036 | 0.006 |
| I-0655 | 0.067 | I-1313 | 0.062 | I-2037 | 0.340 |
| I-0656 | 0.100 | I-1314 | 0.059 | I-2038 | 0.013 |
| I-0657 | 0.471 | I-1315 | 0.040 | I-2039 | 0.009 |
| I-0658 | 0.109 | I-1316 | 0.054 | I-2040 | 0.023 |
| I-0659 | 0.134 | I-1317 | 0.105 | I-2041 | 0.109 |
| I-0660 | 0.011 | I-1318 | 0.544 | I-2042 | 0.023 |
| I-0661 | 0.007 | I-1320 | 0.365 | I-2043 | 0.009 |
| I-0662 | 0.022 | I-1321 | 0.007 | I-2044 | 0.125 |
| I-0663 | 0.005 | I-1322 | 0.020 | I-2045 | 0.975 |
| I-0664 | 0.006 | I-1323 | 0.033 | I-2047 | 0.384 |
| I-0665 | 0.004 | I-1324 | 0.009 | I-2048 | 0.491 |
| I-0666 | 0.008 | I-1325 | 0.028 | I-2049 | 0.085 |
| I-0667 | 0.020 | I-1326 | 0.217 | I-2052 | 0.068 |
| I-0669 | 0.193 | I-1327 | 0.073 | I-2053 | 0.952 |
| I-0670 | 0.008 | I-1328 | 0.012 | I-2054 | 0.611 |
| I-0671 | 0.015 | I-1329 | 0.049 | I-2056 | 0.026 |
| I-0672 | 0.008 | I-1330 | 0.009 | I-2057 | 0.021 |
| I-0673 | 0.008 | I-1331 | 0.056 | I-2058 | 0.007 |
| I-0674 | 0.126 | I-1332 | 0.054 | I-2059 | 0.056 |
| I-0675 | 0.037 | I-1333 | 0.052 | I-2060 | 0.022 |
| I-0676 | 0.030 | I-1334 | 0.011 | I-2061 | 0.148 |
| I-0677 | 0.173 | I-1335 | 0.030 | I-2063 | 0.120 |
| I-0678 | 0.008 | I-1336 | 0.071 | I-2064 | 0.040 |
| I-0679 | 0.032 | I-1337 | 0.014 | I-2065 | 0.054 |
| I-0680 | 0.026 | I-1338 | 0.036 | I-2066 | 0.023 |
| I-0681 | 0.049 | I-1339 | 0.030 | I-2067 | 0.021 |
| I-0682 | 0.023 | I-1340 | 0.057 | I-2068 | 0.016 |
| I-0683 | 0.009 | I-1341 | 0.036 | I-2069 | 0.007 |
| I-0684 | 0.030 | I-1342 | 0.010 | I-2070 | 0.019 |
| I-0685 | 0.008 | I-1343 | 0.035 | I-2071 | 0.008 |
| I-0686 | 0.605 | I-1344 | 0.033 | I-2072 | 0.008 |
| I-0687 | 0.012 | I-1345 | 0.069 | I-2073 | 0.010 |
| I-0688 | 0.005 | I-1346 | 0.812 | I-2074 | 0.007 |
| I-0689 | 0.005 | I-1348 | 0.918 | I-2075 | 0.021 |
| I-0691 | 0.048 | I-1349 | 0.015 | I-2076 | 0.007 |
| I-0692 | 0.029 | I-1350 | 0.028 | I-2077 | 0.003 |
| I-0693 | 0.013 | I-1351 | 0.041 | I-2078 | 0.008 |
| I-0694 | 0.013 | I-1352 | 0.026 | I-2079 | 0.038 |
| I-0696 | 0.129 | I-1353 | 0.041 | I-2082 | 0.833 |
| I-0697 | 0.057 | I-1354 | 0.139 | I-2085 | 0.852 |
| I-0698 | 0.026 | I-1355 | 0.177 | I-2086 | 0.234 |
| I-0699 | 0.037 | I-1356 | 0.048 | I-2095 | 0.005 |
| I-0700 | 0.006 | I-1357 | 0.025 | I-2096 | 0.035 |
| I-0701 | 0.035 | I-1358 | 0.009 | I-2097 | 0.005 |
| I-0702 | 0.107 | I-1359 | 0.724 | I-2098 | 0.004 |
| I-0703 | 0.015 | I-1360 | 0.032 | I-2099 | 0.008 |
| I-0704 | 0.023 | I-1361 | 0.015 | I-2100 | 0.007 |

TABLE 577

| Compound No. | P2X3 IC50 (μM) | Compound No. | P2X3 IC50 (μM) | Compound No. | P2X3 IC50 (μM) |
|---|---|---|---|---|---|
| I-0705 | 0.011 | I-1362 | 0.054 | I-2101 | 0.026 |
| I-0706 | 0.014 | I-1363 | 0.056 | I-2102 | 0.034 |
| I-0707 | 0.021 | I-1364 | 0.043 | I-2103 | 0.020 |
| I-0708 | 0.966 | I-1365 | 0.094 | I-2104 | 0.040 |
| I-0709 | 0.007 | I-1366 | 0.020 | I-2105 | 0.001 |
| I-0710 | 0.019 | I-1367 | 0.014 | I-2106 | 0.002 |
| I-0711 | 0.040 | I-1368 | 0.005 | I-2107 | 0.007 |
| I-0712 | 0.025 | I-1369 | 0.003 | I-2108 | 0.026 |
| I-0713 | 0.016 | I-1370 | 0.019 | I-2109 | 0.011 |
| I-0714 | 0.030 | I-1371 | 0.009 | I-2110 | 0.012 |
| I-0715 | 0.013 | I-1372 | 0.005 | I-2111 | 0.044 |
| I-0716 | 0.102 | I-1373 | 0.004 | I-2112 | 0.047 |
| I-0717 | 0.021 | I-1374 | 0.017 | I-2113 | 0.001 |
| I-0718 | 0.093 | I-1375 | 0.005 | I-2114 | 0.007 |
| I-0719 | 0.115 | I-1376 | 0.015 | I-2115 | 0.018 |

TABLE 577-continued

| Compound No. | P2X3 IC50 (μM) | Compound No. | P2X3 IC50 (μM) | Compound No. | P2X3 IC50 (μM) |
|---|---|---|---|---|---|
| I-0721 | 0.013 | I-1377 | 0.007 | I-2116 | 0.015 |
| I-0722 | 0.014 | I-1378 | 0.012 | I-2117 | 0.023 |
| I-0723 | 0.024 | I-1379 | 0.010 | I-2118 | 0.035 |
| I-0724 | 0.250 | I-1380 | 0.026 | I-2119 | 0.001 |
| I-0725 | 0.014 | I-1381 | 0.020 | I-2120 | 0.033 |
| I-0726 | 0.016 | I-1382 | 0.257 | I-2121 | 0.021 |
| I-0727 | 0.012 | I-1384 | 0.050 | I-2122 | 0.093 |
| I-0728 | 0.014 | I-1386 | 0.028 | I-2123 | 0.004 |
| I-0729 | 0.007 | I-1387 | 0.044 | I-2124 | 0.027 |
| I-0730 | 0.023 | I-1388 | 0.009 | I-2125 | 0.007 |
| I-0731 | 0.012 | I-1389 | 0.012 | I-2128 | 0.287 |
| I-0732 | 0.041 | I-1390 | 0.015 | I-2130 | 0.790 |
| I-0733 | 0.287 | I-1391 | 0.016 | I-2133 | 0.182 |
| I-0735 | 0.007 | I-1392 | 0.018 | I-2137 | 0.134 |
| I-0736 | 0.131 | I-1393 | 0.035 | I-2138 | 0.171 |
| I-0737 | 0.140 | I-1394 | 0.044 | I-2139 | 0.022 |
| I-0738 | 0.019 | I-1395 | 0.023 | I-2140 | 0.007 |
| I-0739 | 0.029 | I-1396 | 0.004 | I-2141 | 0.007 |
| I-0740 | 0.221 | I-1397 | 0.003 | I-2142 | 0.006 |
| I-0741 | 0.050 | I-1398 | 0.025 | I-2143 | 0.023 |
| I-0742 | 0.038 | I-1399 | 0.050 | I-2145 | 0.008 |
| I-0743 | 0.013 | I-1400 | 0.013 | I-2147 | 0.014 |
| I-0744 | 0.053 | I-1401 | 0.022 | I-2148 | 0.002 |
| I-0745 | 0.125 | I-1402 | 0.033 | I-2149 | 0.791 |
| I-0746 | 0.140 | I-1403 | 0.050 | I-2150 | 0.044 |
| I-0747 | 0.012 | I-1404 | 0.024 | I-2151 | 0.012 |
| I-0748 | 0.295 | I-1405 | 0.026 | I-2152 | 0.041 |
| I-0749 | 0.027 | I-1406 | 0.064 | I-2153 | 0.006 |
| I-0750 | 0.022 | I-1407 | 0.036 | I-2154 | 0.133 |
| I-0751 | 0.021 | I-1408 | 0.016 | I-2155 | 0.004 |
| I-0752 | 0.034 | I-1409 | 0.017 | I-2156 | 0.002 |
| I-0753 | 0.011 | I-1410 | 0.056 | I-2157 | 0.001 |
| I-0754 | 0.016 | I-1411 | 0.058 | I-2158 | 0.029 |
| I-0755 | 0.024 | I-1412 | 0.011 | I-2159 | 0.047 |
| I-0756 | 0.131 | I-1413 | 0.072 | I-2160 | 0.003 |
| I-0757 | 0.035 | I-1414 | 0.986 | I-2161 | 0.014 |
| I-0758 | 0.019 | I-1415 | 0.532 | I-2162 | 0.006 |
| I-0760 | 0.037 | I-1416 | 0.141 | I-2163 | 0.054 |
| I-0761 | 0.015 | I-1417 | 0.207 | I-2164 | 0.125 |
| I-0762 | 0.082 | I-1419 | 0.304 | I-2165 | 0.979 |

TABLE 578

| Compound No. | P2X3 IC50 (μM) | Compound No. | P2X3 IC50 (μM) | Compound No. | P2X3 IC50 (μM) |
|---|---|---|---|---|---|
| I-0763 | 0.080 | I-1420 | 0.607 | I-2166 | 0.010 |
| I-0764 | 0.254 | I-1421 | 0.883 | I-2167 | 0.054 |
| I-0765 | 0.040 | I-1422 | 0.529 | I-2168 | 0.057 |
| I-0766 | 0.438 | I-1423 | 0.041 | I-2189 | 0.051 |
| I-0767 | 0.088 | I-1424 | 0.035 | I-2170 | 0.819 |
| I-0769 | 0.207 | I-1425 | 0.050 | I-2171 | 0.296 |
| I-0770 | 0.405 | I-1426 | 0.050 | I-2172 | 0.001 |
| I-0772 | 0.477 | I-1427 | 0.008 | I-2173 | 0.012 |
| I-0773 | 0.790 | I-1428 | 0.926 | I-2174 | 0.006 |
| I-0774 | 0.054 | I-1429 | 0.232 | I-2175 | 0.013 |
| I-0775 | 0.041 | I-1430 | 0.709 | I-2176 | 0.004 |
| I-0777 | 0.116 | I-1431 | 0.242 | I-2177 | 0.014 |
| I-0778 | 0.084 | I-1432 | 0.002 | I-2178 | 0.005 |
| I-0779 | 0.016 | I-1434 | 0.002 | I-2179 | 0.003 |
| I-0780 | 0.015 | I-1435 | 0.061 | I-2180 | 0.011 |
| I-0781 | 0.009 | I-1436 | 0.054 | I-2181 | 0.004 |
| I-0782 | 0.192 | I-1438 | 0.063 | I-2182 | 0.003 |
| I-0783 | 0.065 | I-1439 | 0.039 | I-2183 | 0.001 |
| I-0784 | 0.022 | I-1440 | 0.006 | I-2184 | 0.010 |
| I-0785 | 0.011 | I-1441 | 0.009 | I-2185 | 0.015 |
| I-0786 | 0.015 | I-1442 | 0.008 | I-2186 | 0.104 |
| I-0787 | 0.024 | I-1443 | 0.006 | I-2187 | 0.044 |
| I-0788 | 0.032 | I-1444 | 0.004 | I-2188 | 0.009 |
| I-0789 | 0.181 | I-1445 | 0.004 | I-2189 | 0.047 |
| I-0790 | 0.013 | I-1447 | 0.006 | I-2190 | 0.033 |
| I-0791 | 0.266 | I-1448 | 0.012 | I-2191 | 0.005 |
| I-0792 | 0.170 | I-1449 | 0.004 | I-2192 | 0.008 |
| I-0794 | 0.168 | I-1450 | 0.448 | I-2193 | 0.006 |

TABLE 578-continued

| Compound No. | P2X3 IC50 (μM) | Compound No. | P2X3 IC50 (μM) | Compound No. | P2X3 IC50 (μM) |
|---|---|---|---|---|---|
| I-0795 | 0.724 | I-1451 | 0.005 | I-2194 | 0.052 |
| I-0796 | 0.386 | I-1452 | 0.014 | I-2195 | 0.014 |
| I-0797 | 0.701 | I-1453 | 0.013 | I-2196 | 0.446 |
| I-0798 | 0.465 | I-1454 | 0.023 | I-2197 | 0.215 |
| I-0799 | 0.281 | I-1455 | 0.032 | I-2199 | 0.515 |
| I-0800 | 0.021 | I-1456 | 0.014 | I-2200 | 0.545 |
| I-0801 | 0.010 | I-1457 | 0.014 | I-2201 | 0.092 |
| I-0802 | 0.021 | I-1458 | 0.025 | I-2203 | 0.001 |
| I-0804 | 0.132 | I-1459 | 0.034 | I-2204 | 0.028 |
| I-0805 | 0.029 | I-1460 | 0.272 | I-2205 | 0.009 |
| I-0806 | 0.012 | I-1461 | 0.025 | I-2206 | 0.012 |
| I-0807 | 0.013 | I-1462 | 0.003 | I-2207 | 0.069 |
| I-0808 | 0.203 | I-1463 | 0.632 | I-2208 | 0.012 |
| I-0809 | 0.034 | I-1464 | 0.070 | I-2209 | 0.008 |
| I-0810 | 0.016 | I-1465 | 0.006 | I-2210 | 0.014 |
| I-0811 | 0.040 | I-1466 | 0.121 | I-2211 | 0.014 |
| I-0812 | 0.033 | I-1467 | 0.012 | I-2212 | 0.002 |
| I-0818 | 0.018 | I-1468 | 0.010 | I-2213 | 0.002 |
| I-0814 | 0.017 | I-1469 | 0.009 | I-2214 | 0.022 |
| I-0815 | 0.189 | I-1470 | 0.010 | I-2215 | 0.006 |
| I-0816 | 0.037 | I-1471 | 0.007 | I-2216 | 0.005 |
| I-0817 | 0.027 | I-1473 | 0.012 | I-2217 | 0.006 |
| I-0818 | 0.529 | I-1474 | 0.138 | I-2218 | 0.003 |
| I-0819 | 0.022 | I-1475 | 0.039 | I-2219 | 0.014 |
| I-0820 | 0.035 | I-1476 | 0.262 | I-2220 | 0.037 |
| I-0821 | 0.050 | I-1477 | 0.068 | I-2222 | 0.005 |
| I-0822 | 0.026 | I-1478 | 0.019 | I-2223 | 0.006 |

TABLE 579

| Compound No. | P2X3 IC50 (μM) | Compound No. | P2X3 IC50 (μM) | Compound No. | P2X3 IC50 (μM) |
|---|---|---|---|---|---|
| I-0823 | 0.011 | I-1479 | 0.020 | I-2224 | 0.033 |
| I-0824 | 0.018 | I-1480 | 0.002 | I-2225 | 0.061 |
| I-0825 | 0.025 | I-1481 | 0.039 | I-2226 | 0.012 |
| I-0826 | 0.019 | I-1482 | 0.098 | I-2227 | 0.004 |
| I-0827 | 0.026 | I-1483 | 0.087 | I-2228 | 0.005 |
| I-0828 | 0.025 | I-1484 | 0.006 | I-2229 | 0.023 |
| I-0829 | 0.216 | I-1485 | 0.235 | I-2230 | 0.002 |
| I-0830 | 0.089 | I-1486 | 0.043 | I-2231 | 0.003 |
| I-0831 | 0.077 | I-1487 | 0.106 | I-2232 | 0.013 |
| I-0832 | 0.103 | I-1488 | 0.652 | I-2233 | 0.002 |
| I-0833 | 0.015 | I-1489 | 0.254 | I-2234 | 0.002 |
| I-0834 | 0.018 | I-1491 | 0.284 | I-2235 | 0.004 |
| I-0835 | 0.078 | I-1492 | 0.461 | I-2236 | 0.062 |
| I-0836 | 0.095 | I-1493 | 0.444 | I-2237 | 0.020 |
| I-0837 | 0.017 | I-1494 | 0.571 | I-2238 | 0.148 |
| I-0838 | 0.033 | I-1495 | 0.026 | I-2239 | 0.049 |
| I-0839 | 0.012 | I-1496 | 0.009 | I-2240 | 0.021 |
| I-0840 | 0.017 | I-1497 | 0.619 | I-2241 | 0.001 |
| I-0841 | 0.150 | I-1498 | 0.022 | I-2242 | <0.004 |
| I-0843 | 0.183 | I-1499 | 0.019 | I-2243 | 0.006 |
| I-0845 | 0.024 | I-1500 | 0.897 | I-2244 | 0.059 |
| I-0846 | 0.035 | I-1501 | 0.011 | I-2245 | 0.108 |
| I-0847 | 0.031 | I-1502 | 0.107 | I-2246 | 0.790 |
| I-0848 | 0.060 | I-1503 | 0.012 | I-2247 | 0.003 |
| I-0849 | 0.078 | I-1504 | 0.005 | I-2248 | 0.007 |
| I-0850 | 0.062 | I-1505 | 0.004 | I-2249 | 0.006 |
| I-0851 | 0.024 | I-1506 | 0.002 | I-2250 | 0.008 |
| I-0852 | 0.038 | I-1507 | 0.015 | I-2251 | 0.005 |
| I-0853 | 0.013 | I-1508 | 0.018 | I-2252 | 0.769 |
| I-0854 | 0.032 | I-1509 | 0.014 | I-2254 | 0.078 |
| I-0855 | 0.010 | I-1510 | 0.013 | I-2255 | 0.543 |
| I-0856 | 0.012 | I-1511 | 0.029 | I-2257 | 0.151 |
| I-0857 | 0.019 | I-1512 | 0.013 | I-2258 | 0.003 |
| I-0858 | 0.022 | I-1513 | 0.010 | I-2262 | 0.017 |
| I-0859 | 0.017 | I-1514 | 0.024 | I-2263 | 0.004 |
| I-0860 | 0.062 | I-1515 | 0.157 | I-2264 | 0.558 |
| I-0861 | 0.019 | I-1516 | 0.049 | I-2265 | 0.299 |
| I-0862 | 0.010 | I-1517 | 0.240 | I-2266 | 0.044 |
| I-0864 | 0.035 | I-1518 | 0.002 | I-2267 | 0.331 |
| I-0865 | 0.017 | I-1519 | 0.002 | I-2268 | 0.006 |
| I-0866 | 0.002 | I-1520 | 0.032 | I-2269 | 0.002 |

TABLE 579-continued

| Compound No. | P2X3 IC50 (μM) | Compound No. | P2X3 IC50 (μM) | Compound No. | P2X3 IC50 (μM) |
|---|---|---|---|---|---|
| I-0867 | 0.006 | I-1521 | 0.022 | I-2270 | <0.004 |
| I-0868 | 0.023 | I-1522 | 0.005 | I-2271 | 0.036 |
| I-0869 | 0.574 | I-1523 | 0.003 | I-2272 | 0.008 |
| I-0870 | 0.530 | I-1527 | 0.005 | I-2273 | 0.012 |
| I-0871 | 0.040 | I-1528 | 0.032 | I-2274 | 0.005 |
| I-0872 | 0.081 | I-1529 | 0.026 | I-2275 | 0.010 |
| I-0873 | 0.047 | I-1530 | 0.093 | I-2276 | 0.778 |
| I-0874 | 0.086 | I-1531 | 0.025 | I-2277 | 0.107 |
| I-0875 | 0.014 | I-1532 | 0.025 | I-2278 | 0.136 |
| I-0876 | 0.023 | I-1533 | 0.016 | I-2279 | 0.033 |
| I-0877 | 0.028 | I-1534 | 0.005 | I-2280 | 0.127 |
| I-0878 | 0.022 | I-1535 | 0.028 | I-2281 | 0.002 |
| I-0879 | 0.058 | I-1536 | 0.024 | I-2282 | <0.004 |
| I-0880 | 0.049 | I-1537 | 0.003 | I-2283 | <0.004 |

TABLE 580

| Compound No. | P2X3 IC50 (μM) | Compound No. | P2X3 IC50 (μM) | Compound No. | P2X3 IC50 (μM) |
|---|---|---|---|---|---|
| I-0881 | 0.127 | I-1538 | 0.017 | I-2284 | <0.004 |
| I-0882 | 0.100 | I-1539 | 0.004 | I-2285 | 0.015 |
| I-0883 | 0.024 | I-1540 | 0.052 | I-2286 | 0.005 |
| I-0884 | 0.016 | I-1542 | 0.004 | I-2287 | <0.004 |
| I-0885 | 0.087 | I-1543 | 0.006 | I-2288 | 0.001 |
| I-0886 | 0.076 | I-1544 | 0.004 | I-2289 | <0.004 |
| I-0887 | 0.023 | I-1545 | 0.003 | I-2090 | <0.004 |
| I-0888 | 0.030 | I-1546 | 0.007 | I-2291 | 0.004 |
| I-0889 | 0.053 | I-1547 | 0.003 | I-2292 | 0.012 |
| I-0890 | 0.032 | I-1548 | 0.005 | I-2293 | 0.006 |
| I-0891 | 0.013 | I-1549 | 0.008 | I-2294 | 0.005 |
| I-0892 | 0.018 | I-1550 | 0.833 | I-2295 | <0.004 |
| I-0893 | 0.202 | I-1551 | 0.009 | I-2296 | 0.005 |
| I-0894 | 0.028 | I-1552 | 0.015 | I-2297 | 0.065 |
| I-0895 | 0.047 | I-1553 | 0.011 | | |
| I-0896 | 0.016 | I-1554 | 0.014 | | |

TABLE 581

| Compound No. | P2X3 IC50 (μM) |
|---|---|
| I-2300 | 0.003 |
| I-2301 | 0.437 |
| I-2302 | 0.002 |
| I-2303 | 0.007 |
| I-2304 | 0.029 |
| I-2305 | 0.004 |
| I-2306 | 0.002 |
| I-2307 | 0.015 |
| I-2308 | 0.003 |
| I-2309 | 0.002 |
| I-2310 | 0.005 |
| I-2311 | 0.008 |
| I-2312 | 0.005 |
| I-2313 | 0.008 |
| I-2314 | 0.007 |
| I-2315 | 0.017 |
| I-2316 | 0.051 |
| I-2317 | 0.003 |
| I-2318 | 0.018 |
| I-2319 | 0.017 |
| I-2320 | 0.006 |
| I-2321 | 0.011 |
| I-2322 | 0.006 |
| I-2323 | 0.016 |
| I-2324 | 0.115 |
| I-2325 | 0.047 |
| I-2326 | 0.108 |
| I-2327 | 0.008 |
| I-2328 | 0.034 |
| I-2329 | 0.070 |

TABLE 581-continued

| Compound No. | P2X3 IC50 (μM) |
|---|---|
| I-2330 | 0.007 |
| I-2331 | 0.007 |
| I-2332 | 0.218 |
| I-2333 | 0.003 |
| I-2334 | 0.005 |
| I-2335 | 0.006 |
| I-2336 | 0.010 |
| I-2338 | 0.260 |
| I-3339 | 0.043 |
| I-2340 | 0.013 |
| I-2341 | 0.010 |
| I-2342 | 0.016 |
| I-2343 | 0.019 |
| I-2344 | 0.003 |
| I-2345 | 0.020 |
| I-2346 | 0.004 |
| I-2347 | 0.005 |
| I-2348 | 0.004 |
| I-2349 | 0.004 |
| I-2350 | 0.002 |
| I-2351 | 0.009 |
| I-2352 | 0.006 |
| I-2353 | 0.008 |
| I-2354 | 0.003 |
| I-2355 | 0.071 |
| I-2356 | 0.024 |
| I-2357 | 0.012 |
| I-2358 | 0.006 |
| I-2359 | 0.026 |
| I-2360 | 0.011 |
| I-2361 | 0.015 |
| I-2362 | 0.010 |
| I-2363 | 0.009 |
| I-2364 | 0.008 |
| I-2365 | 0.211 |
| I-2366 | 0.090 |
| I-2367 | 0.128 |
| I-2368 | 0.013 |
| I-2369 | 0.003 |
| I-2370 | 0.011 |
| I-2371 | 0.102 |
| I-2372 | 0.032 |
| I-2373 | 0.033 |
| I-2374 | 0.008 |
| I-2375 | 0.022 |
| I-2376 | 0.020 |
| I-2377 | 0.015 |
| I-2378 | 0.006 |
| I-2379 | 0.009 |
| I-2380 | 0.029 |
| I-2381 | 0.054 |
| I-2382 | 0.054 |
| I-2383 | 0.015 |
| I-2384 | 0.005 |
| I-2385 | 0.013 |
| I-2386 | 0.013 |
| I-2387 | 0.002 |
| I-2388 | 0.003 |
| I-2389 | 0.010 |
| I-2390 | 0.007 |
| I-2391 | 0.029 |
| I-2392 | 0.011 |
| I-2393 | 0.010 |
| I-2394 | 0.021 |
| I-2395 | 0.004 |
| I-2396 | 0.006 |
| I-2397 | 0.039 |
| I-2398 | 0.003 |
| I-2399 | 0.020 |
| I-2400 | 0.006 |
| I-2401 | 0.018 |
| I-2402 | 0.003 |
| I-2403 | 0.061 |
| I-2404 | 0.016 |
| I-2405 | 0.062 |
| I-2406 | 0.010 |
| I-2407 | 0.009 |

TABLE 581-continued

| Compound No. | P2X3 IC50 (μM) |
|---|---|
| I-2408 | 0.014 |
| I-2409 | 0.014 |
| I-2410 | 0.036 |
| I-2411 | 0.166 |
| I-2412 | 0.084 |
| I-2413 | 0.036 |
| I-2414 | 0.003 |
| I-2415 | 0.009 |
| I-2416 | 0.054 |
| I-2417 | 0.041 |
| I-2418 | 0.012 |
| I-2419 | 0.003 |
| I-2420 | 0.009 |
| I-2421 | 0.003 |
| I-2422 | 0.007 |
| I-2423 | 0.007 |
| I-2424 | 0.020 |
| I-2425 | 0.002 |
| I-2426 | 0.011 |
| I-2427 | 0.002 |
| I-2428 | 0.005 |
| I-2429 | 0.005 |
| I-2430 | 0.048 |
| I-2431 | 0.018 |
| I-2432 | 0.002 |
| I-2433 | 0.005 |
| I-2434 | 0.004 |
| I-2435 | 0.037 |
| I-2436 | 0.004 |
| I-2437 | 0.006 |
| I-2438 | 0.007 |
| I-2439 | 0.004 |
| I-2440 | 0.005 |
| I-2441 | 0.010 |
| I-2442 | 0.018 |
| I-2443 | 0.024 |
| I-2444 | 0.008 |
| I-2445 | 0.013 |
| I-2446 | 0.001 |
| I-2447 | 0.010 |
| I-2448 | 0.011 |
| I-2449 | 0.009 |
| I-2450 | 0.008 |

TABLE 582

| Compound No. | P2X3 IC50 (μM) |
|---|---|
| I-2451 | 0.025 |
| I-2452 | 0.036 |
| I-2453 | 0.064 |
| I-2454 | 0.035 |
| I-2455 | 0.063 |
| I-2456 | 0.008 |
| I-2457 | 0.013 |
| I-2458 | 0.003 |
| I-2459 | 0.007 |
| I-2460 | 0.035 |
| I-2461 | 0.007 |
| I-2462 | 0.007 |
| I-2463 | 0.003 |
| I-2464 | 0.010 |
| I-2465 | 0.004 |
| I-2466 | 0.016 |
| I-2467 | 0.007 |
| I-2468 | 0.020 |
| I-2469 | 0.019 |
| I-2470 | 0.000 |
| I-2471 | 0.005 |
| I-2472 | 0.003 |
| I-2473 | 0.008 |
| I-2474 | 0.007 |
| I-2475 | 0.012 |

TABLE 582-continued

| Compound No. | P2X3 IC50 (μM) |
|---|---|
| I-2476 | 0.013 |
| I-2477 | 0.015 |
| I-2478 | 0.005 |
| I-2479 | 0.008 |
| I-2480 | 0.006 |
| I-2481 | 0.008 |
| I-2482 | 0.011 |
| I-2483 | 0.008 |
| I-2484 | 0.008 |
| I-2485 | 0.008 |
| I-2486 | 0.381 |
| I-2488 | 0.037 |
| I-2489 | 0.050 |
| I-2490 | 0.010 |
| I-2491 | 0.074 |
| I-2492 | 0.004 |
| I-2493 | 0.005 |
| I-2494 | 0.001 |
| I-2495 | 0.021 |
| I-2496 | 0.030 |
| I-2497 | 0.001 |
| I-2498 | 0.003 |
| I-2499 | 0.005 |
| I-2500 | 0.067 |
| I-2501 | 0.057 |
| I-2502 | 0.007 |
| I-2503 | 0.039 |
| I-2504 | 0.370 |
| I-2505 | 0.017 |
| I-2506 | 0.014 |
| I-2507 | 0.035 |
| I-2508 | 0.013 |
| I-2509 | 0.009 |
| I-2510 | 0.010 |
| I-2511 | 0.235 |
| I-2512 | 0.011 |
| I-2513 | 0.006 |
| I-2514 | 0.011 |
| I-2515 | 0.346 |
| I-2516 | 0.009 |
| I-2517 | 0.167 |
| I-2518 | 0.004 |
| I-2519 | 0.004 |
| I-2520 | 0.002 |
| I-2521 | 0.005 |
| I-2522 | 0.011 |
| I-2523 | 0.169 |
| I-2524 | 0.034 |
| I-2525 | 0.010 |
| I-2526 | 0.008 |
| I-2527 | 0.026 |
| I-2529 | 0.073 |
| I-2530 | 0.016 |
| I-2531 | 0.004 |
| I-2532 | 0.005 |
| I-2533 | 0.004 |
| I-2534 | 0.105 |
| I-2535 | 0.044 |
| I-2536 | 0.005 |
| I-2537 | 0.005 |
| I-2538 | 0.003 |
| I-2539 | 0.076 |
| I-2540 | 0.104 |
| I-2541 | 0.118 |
| I-2542 | 0.186 |
| I-2543 | 0.010 |
| I-2544 | 0.011 |
| I-2545 | 0.007 |
| I-2546 | 0.006 |
| I-2547 | 0.008 |
| I-2548 | 0.006 |
| I-2549 | 0.012 |
| I-2550 | 0.004 |
| I-2551 | 0.004 |
| I-2552 | 0.005 |
| I-2553 | 0.216 |
| I-2554 | 0.007 |

TABLE 582-continued

| Compound No. | P2X3 IC50 (μM) |
|---|---|
| I-2555 | 0.016 |
| I-2556 | 0.005 |
| I-2557 | 0.019 |
| I-2558 | 0.022 |
| I-2559 | 0.008 |
| I-2560 | 0.005 |
| I-2561 | 0.065 |
| I-2562 | 0.004 |
| I-2563 | 0.015 |
| I-2564 | 0.269 |
| I-2565 | 0.017 |
| I-2566 | 0.017 |
| I-2567 | 0.038 |
| I-2568 | 0.087 |
| I-2569 | 0.162 |
| I-2570 | 0.005 |
| I-2571 | 0.007 |
| I-2573 | 0.006 |
| I-2574 | 0.011 |
| I-2575 | 0.006 |
| I-2576 | 0.003 |
| I-2577 | 0.008 |
| I-2578 | 0.006 |
| I-2579 | 0.071 |
| I-2580 | 0.204 |
| I-2581 | 0.005 |
| I-2582 | 0.003 |
| I-2583 | 0.015 |
| I-2584 | 0.008 |
| I-2585 | 0.008 |
| I-2586 | 0.007 |
| I-2587 | 0.007 |
| I-2588 | 0.011 |
| I-2589 | 0.006 |
| I-2590 | 0.017 |
| I-2591 | 0.051 |
| I-2592 | 0.350 |
| I-2593 | 0.001 |
| I-2594 | 0.075 |
| I-2595 | 0.027 |
| I-2596 | 0.051 |
| I-2597 | 0.215 |
| I-2598 | 0.341 |
| I-2599 | 0.004 |
| I-2600 | 0.004 |
| I-2601 | 0.012 |
| I-2602 | 0.002 |

TABLE 583

| Compound No. | P2X3 IC50 (μM) |
|---|---|
| I-2603 | 0.125 |
| I-2604 | 0.021 |
| I-2605 | 0.014 |
| I-2606 | 0.014 |
| I-2607 | 0.020 |
| I-2608 | 0.006 |
| I-2609 | 0.002 |
| I-2610 | 0.012 |
| I-2611 | 0.014 |
| I-2612 | 0.004 |
| I-2613 | 0.137 |
| I-2614 | 0.027 |
| I-2615 | 0.007 |
| I-2616 | 0.012 |
| I-2617 | 0.042 |
| I-2618 | 0.007 |
| I-2619 | 0.006 |
| I-2620 | 0.110 |
| I-2621 | 0.265 |
| I-2622 | 0.005 |
| I-2623 | 0.506 |

TABLE 583-continued

| Compound No. | P2X3 IC50 (μM) |
|---|---|
| I-2624 | 0.368 |
| I-2625 | 0.003 |
| I-2626 | 0.005 |
| I-2627 | 0.007 |
| I-2628 | 0.004 |
| I-2629 | 0.006 |
| I-2630 | 0.003 |
| I-2631 | 0.475 |
| I-2633 | 0.002 |
| I-2634 | 0.011 |
| I-2635 | 0.008 |
| I-2636 | 0.002 |
| I-2637 | 0.177 |
| I-2638 | 0.015 |
| I-2639 | 0.026 |
| I-2640 | 0.002 |
| I-2641 | 0.012 |
| I-2642 | 0.011 |
| I-2643 | 0.491 |
| I-2644 | 0.017 |
| I-2645 | 0.018 |
| I-2646 | 0.008 |
| I-2647 | 0.016 |
| I-2648 | 0.014 |
| I-2649 | 0.006 |
| I-2650 | 0.003 |
| I-2651 | 0.002 |
| I-2652 | 0.003 |
| I-2653 | 0.009 |
| I-2654 | 0.009 |
| I-2655 | 0.005 |
| I-2656 | 0.006 |
| I-2657 | 0.007 |
| I-2658 | 0.005 |
| I-2659 | 0.277 |
| I-2660 | 0.003 |
| I-2661 | 0.015 |
| I-2663 | 0.330 |
| I-2664 | 0.003 |
| I-2665 | 0.085 |
| I-2666 | 0.002 |
| I-2667 | 0.010 |
| I-2671 | 0.036 |
| I-2672 | 0.011 |
| I-2673 | 0.007 |
| I-2674 | 0.005 |
| I-2675 | 0.013 |
| I-2676 | 0.013 |
| I-2677 | 0.007 |
| I-2678 | 0.003 |
| I-2679 | 0.005 |
| I-2680 | 0.012 |
| I-2681 | 0.004 |
| I-2682 | 0.002 |
| I-2683 | 0.012 |
| I-2684 | 0.002 |
| I-2685 | 0.012 |
| I-2686 | 0.036 |
| I-2687 | 0.035 |
| I-2688 | 0.018 |
| I-2689 | 0.020 |
| I-2690 | 0.018 |
| I-2691 | 0.008 |
| I-2692 | 0.008 |
| I-2693 | 0.012 |
| I-2694 | 0.003 |
| I-2695 | 0.010 |
| I-2696 | 0.008 |
| I-2697 | 0.019 |
| I-2698 | 0.025 |
| I-2699 | 0.134 |
| I-2700 | 0.353 |
| I-2701 | 0.001 |
| I-2702 | 0.003 |
| I-2704 | 0.004 |
| I-2705 | 0.003 |
| I-2706 | 0.006 |

TABLE 583-continued

| Compound No. | P2X3 IC50 (µM) |
|---|---|
| I-2707 | 0.007 |
| I-2708 | 0.002 |
| I-2709 | 0.006 |
| I-2710 | 0.006 |

TABLE 584

| Compound No. | rat P2X3 IC50 (µM) |
|---|---|
| I-0837 | 0.019 |
| I-2291 | 0.003 |
| I-1788 | 0.005 |
| I-1679 | 0.006 |

Test Example 2

Evaluation of Rat $P2X_3$ Receptor Inhibitory Activity

Rat $P2X_3$ receptor gene (GenBank accession number NM_031075) was expressed in C6BU-1 cell. The cells stably expressing rat $P2X_3$ were seeded in a 96-well microtiter plate at a concentration of 8000 cells/well and cultured in the medium (8.3% fetal bovine serum. 8.3% horse serum, 1% antibiotic and antifungal in DMEM) for one day at 37° C. under 5% carbon dioxide atmosphere. In transiently expressing system, the C6BU-1 cells were seeded in a 90-well microliter plate at a concentration of 2500 cells/well and cultured in the medium for one day at 37° C. under 5% carbon dioxide atmosphere. The plasmid was transfected into the cells using transfection reagent FuGENE6 (Roche). The transfected cells were cultured in the medium for one day at 37° C. under 5% carbon dioxide atmosphere. The medium was replaced with 4 µM Fluo-3-AM solution (pH 7.5) containing 20 mM HEPES, 137 mM NaCl, 2.7 mM KCl, 0.9 mM $MgCl_2$, 5.0 mM $CaCl_2$, 5.6 mM D-glucose, 2.5 mM probenecid, 10% BSA, and 0.08% Pluronic F-127, and incubated at 37° C. under 5% dioxide carbon atmosphere for one hour. The plate was washed with washing buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.5), and each well was added with 40 µL of this buffer. The plate was placed in High-Throughput Screening System FDSS 3000 (Hamamatsu Photonics K.K.). Measurement of fluorescence intensity by FDSS 3000 was started, and 40 µL of DMSO solutions containing different concentrations of the test compound as prepared by dilution with dilution buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, 0.1% Pluronic F-127, pH 7.5) were dispensed to each well through the built-in automatic dispenser. Five minutes after, 50 mM ATP solution (50 µL) prepared by dilution with the dilution buffer was dispensed through the built-in automatic dispenser, and the measurement of fluorescence intensity was continued for 3 min. For each well, the specific maximum fluorescence intensity was calculated as the ratio of the maximum fluorescence intensity after addition of the ATP solution to the fluorescence intensity at the starting of the measurement. The 50% inhibitory concentration ($IC_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. $IC_{50}$ was calculated using Microsoft Excel (Microsoft Corporation) and XLfit (idbs Ltd.).

The data of the compounds of the present invention are as shown in the following Table.

Test Example 3

Evaluation of Rat $P2X_3$ receptor inhibitory activity in the presence of Rat Serum Albumin (RSA)

Rat $P2X_3$ receptor gene (GenBank accession number NM_031075) was expressed in C6BU-1 cell. The cells stably expressing rat $P2X_3$ were seeded in a 96-well microtiter plate at a :concentration of 8000 cells/well and cultured in the medium (8.3% fetal bovine serum, 8.3% horse serum, 1% antibiotic and antifungal in DMEM) for one day at 37° C. under 5% carbon dioxide atmosphere. In transiently expressing system, the C6BU-1 cells were seeded in a 96-well microtiter plate at a concentration of 2500 cells/well and cultured in the medium for one day at 37° C. under 5% carbon dioxide atmosphere. The plasmid was transfected into the cells using transfection reagent FuGENE6 (Roche). The transfected cells were cultured in the medium for one day at 37° C. under 5% carbon dioxide atmosphere. The medium was replaced with 4 µM Fluo-3-AM solution (pH 7.5) containing 20 mM HEPES, 137 mM NaCl, 2.7 mM KCl, 0.9 mM $MgCl_2$, 5.0 mM $CaCl_2$, 5.6 mM D-glucose, 2.5 mM probenecid, 10% BSA, and 0.08% Pluronic F-127, and incubated at 37° C. under 5% carbon dioxide atmosphere for one hour. The plate was washed with washing buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.5), and each well was added with 40 µL of this buffer. The plate was placed in High-Throughput Screening System FDSS 3000 (Hamamatsu Photonics K.K.). Measurement of fluorescence intensity by FDSS 3000 was started, and 40 µL of DMSO solutions containing 1% RSA (final concentrations) and different concentrations of the test compound as prepared by dilution with dilution buffer (20 mM HEPES, 137 mM NaCl, 2.7 mM KCl, 0.9 mM $MgCl_2$, 5.0 mM $CaCl_2$, 5.0 mM D-glucose, 2.5 mM probenecid, 0.1% Pluronic F-127, pH 7.5) were dispensed to each well through the built-in automatic dispenser. Five minutes after, 50 nM ATP solution (50 µL) prepared by dilution with the dilution buffer was dispensed through the built-in automatic dispenser, and the measurement of fluorescence intensity was continued for 3 min. For each well, the specific maximum fluorescence intensity was calculated as the ratio of the maximum fluorescence intensity after addition of the ATP solution to the fluorescence intensity at the starting of the measurement. The 50% inhibitory concentration ($IC_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. $IC_{50}$ was calculated using Microsoft Excel (Microsoft Corporation) and XLfit (idbs Ltd.).

The data of the compounds of the present invention are as shown in the following Table.

TABLE 585

| Compound No. | rat P2X3 (+RSA) IC50 (μ/M) |
|---|---|
| I-0837 | 0.044 |
| I-2291 | 0.020 |
| I-1788 | 0.059 |
| I-1679 | 0.023 |

Test Example 4

Evaluation of the Urinary Function in a Rat Model of Cystitis Surgery for Cystemetry A rat was fixed in the supine position after being given anesthesia through the inhalation of 2% isoflurane (Anesthetic background: Nitrous oxide: Oxygen=7:3). A midline incision was made in its abdomen to expose the bladder. A cannula (made by) processing a polyethylene tube (PE-50: Becton Dickinson)) was inserted through a small incision on top of the bladder and fixed to create a bladder fistula. The other end of the cannula was led through the hypodermal tissue to the back, and the muscular coat and skin were sutured. The cannula, which was led to the back, was protected with a stainless spring in the middle and connected to the cannula swivel.

Acetic Acid Infusion

Two days alter the surgery, 0.3% acetic acid was infused into the bladder through the indwelled cannula at a rate of 4 mL/hr for 30 minutes to induce cystitis. The animals, where acetic acid was not infused, were used as normal animals.

Cystometry Measurement

Three days after the acetic acid infusion, the other end of the cannula inserted into the bladder was connected to a T shape stopcock and then the intravesical pressure was recorded continuously using a pressure amplifier while infusing warmed normal saline solution at a rate of 3.0 mL/hr from one side and through a pressure transducer on the other side. The baseline of the intravesical pressure was measured (for approximately 40 minutes) after a measurement for stable duration (for approximately 20 minutes). After that, a vehicle, positive control compound or test compound wore administered, and the value after administration was measured for approximately 120 minutes. At the same time, the voided urine was received on scales under the cage to measure the variation in weight simultaneously.

Data Adoption Criteria

Based on the voiding interval, normal animals whose voiding interval was 10 minutes or longer were adopted and those whose voiding interval was shorter than that were excluded. In the case of the animals into which acetic acid was infused, those whose voiding interval was less than half the average value of the normal animals were adopted as animals with cystitis and those whose voiding interval was longer than that were excluded.

Collection of Residual Urine

After the completion of the measurement, the infusion of normal saline solution was stopped immediately after urination to collect the residual urine under pentoarbital sodium anesthesia. The collected residual urine was transferred to the voided urine receiver and recorded on the chart.

Analysis Items

Intravesical pressure one to two hours after the start of the measurement (pressure during rest and pressure during urination), voiding interval, voided volume per urination, and residual urine volume The following value was used as an indicator of the effect of the voiding interval:

Improvement rate of the urinary function=(Voiding interval of an animal with cystitis after drug treatment−Voiding interval of an animal with cystitis before drug treatment)/(Mean voiding interval of normal animals before drug treatment−Voiding interval of an animal with cystitis before drug treatment)

The following value was used as an indicator of the effect on the voided volume per urination:

Improvement rate of the voided volume per urination=(Voided volume per urination of a rat with cystitis after drug treatment−Voided volume per urination of an animal with cystitis before drug treatment)/(Mean voided volume per urination of normal animals before drug treatment−Voided volume per urination of an animal with cystitis before drug treatment)

In the a hove-mentioned test, the compound I-0364 showed improvements in the urinary function in the voiding interval of 74.8% and in the voided volume per urination of 88% after oral administration of 30 mg/kg.

Test Example 5

Analgesic Effect in a Seltzer Model

Preparation of Partial Sciatic Nerve Ligation Model in Rats

Rats were anaesthetized using isoflurane/O2 inhalation anaesthesia. After induction of anesthesia, the left thigh was shaved. An incision was made in the skin just below the hip bone. The muscle was bluntly dissected to expose the sciatic nerve. One third (⅓) to one half (½) of the sciatic nerve thickness was tightly ligated and the wound was closed. The right thigh is used as a sham-operated control. The right thigh undergoes an identical procedure with the left hind limb, however, the sciatic nerve is not manipulated or ligated.

Evaluation (1)

Two weeks after nerve ligation, the effect on mechanical allodynia was assessed using a series of von Frey filaments. For habituation, the rats were placed into a plastic cage on a wire mesh bottom. The mechanical sensitivity (mechanical threshold) of the hind paws was estimated with a series of von Frey filaments (0.4-20 g). The measurement of mechanical sensitivity of the right and left hind paws was performed to obtain predose mechanical sensitivity. The rats showing thee threshold change from 0.6 to 2 g (in nerve ligated side) and 8 to 15 g (in sham operated side) were used in the experiments. On the day belone the experiment, the rats were evaluated with a series of von Frey filaments to familiarize them with the test procedure. The adopted animal was administrated with the test compounds. The test compounds were homogenized with mortar and pestle and suspended or diluted in 0.5% Methyl Cellulose to prepare 0.1-2.0 mg/mL/kg suspension and orally administered to rat using a syringe attached with a sonde. Post-dose mechanical sensitivities of the right and left hind paws were measured at approximately 1 to 5 hours after drug administration. Percent reversal of mechanical allodynia for each rat was calculated using the following formula. The analgesic effects of the compounds were compared.

$$\% \text{ Reversal} = \frac{\text{Log}_{10}(\text{Postdose mechanical sensitivity in nerve ligated side}) - \text{Log}_{10}(\text{Predose mechanical sensitivity in nerve ligated side})}{\text{Log}_{10}(\text{Predose mechanical sensitivity in sham operated side}) - \text{Log}_{10}(\text{Predose mechanical sensitivity in nerve ligated side})}$$

In the above examination, the analgesic effect of the oral administration of compound I-0364 at dose of 10 mg/kg was 41.2% reversal at 3 hours.

The analgesic effects of the compounds of the present invention after single administration of 3 mg/kg at 3 hours are as shown in the following Table.

Oral administration of I-0826, I-0931, I-1373, I-1849, i-2291, I-2292, I-2293, I-1757, I-2153, I-2272, I-2283, I-2369 and I-2428 at dose of 3 mg/kg produced analges ic effect more than 30% reversal.

Evaluation (2)

Mechanical hyperalgesia was eavaluated using an analgesy meter. Two weeks after nerve ligation, the paw pressure test was performed using an analgesy meter (stimulus pressure increased 16 g per second) to obtain paw withdrawal thresholds (PWT). Measurements were made on both sides of the hind paw and to obtain pre-dose PWT. The rats showing the threshold change from 60 to 90 g (in nerve ligated side) and 100 to 175 g (in sham operated side) were used in the experiments. On the day before the experiment, the rats have their hind paws set on the apparatus to familiarize them with the test procedure. The adopted animal was administrated with the test compounds. The test compounds were homogenized with mortar and pestle and suspended or diluted in 0.5% Methyl Cellulose to prepare 0.03-100 mg/2mL/kg suspension and orally administered to rat using a syringe attached with a sonde. Post-dose PWT of the right and left hind paws were measured at approximately 1 to 5 hours after drug administration. Percent reversal of mechanical hyperalgesia for each rat was calculated using the following formula. The analgesic effects of the compounds were compared.

$$\% \text{ Reversal} = \frac{\text{Postdose } PWT \text{ in nerve ligated side} - \text{Predose } PWT \text{ in nerve ligated side}}{\text{Predose } PWT \text{ in sham operated side} - \text{Predose } PWT \text{ in nerve ligated side}}$$

In the above examination, the analgesic effect of the oral administration of compound I-0364 at dose of 10 mg/kg was 56.7% reversal at 3 hours.

Test Example 6

CYP3A4 Fluorescent MBI Test

The CYP3A4 fluorescent MBI test is a test of investigating enhancement or CYP3A4 inhibition of a compound by a metabolism reaction, and the test was performed using, as CYP3A4 enzyme expressed in *Escherichia coli* and employlng, as an index, a reaction in which 7-benzyloxytrifluoromethylchmarin (BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 1.5625, 3.125, 6.25, 12.5, 25, 50 µmol/L (six points).

An enzyme in a K-Pi buffer (pH 7.4) and a test drug solution as a pre-reaction. solution were added to a 96-well plate at the composition of the pre-reaction, a part of it was transferred to another 96-well plate so that it was ⅒ diluted by a substrate in a K-Pi buffer, NADPH as a co-factor was added to initiate a reaction as an index (without preincubation) and, after a predetermined time of a reaction, acetonitrile:0.5 mol/L Tris (trishydroxyaminomethane)=4:1 was added to stop the reaction. In addition, NADPH was added to a remaining preincubation solution to initiate a preincubation (with preincubation) and, after a predetermined time of a preincubation, a part was transferred to another plate so that it was ⅒ diluted with a substrate and a K-Pi buffer to initiate a reaction as an index. After a predetermined time of a reaction, acetonitrile:0.5 mol/L Tris (trishydroxyaminomethane)=4:1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

(Result)

Compound No. I-0837: (−)

Test Example 7

CYP Inhibition Test

Using commercially available pooled human hepatic microsome, and employlng, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4) reaction time, 15 minutes; reaction temperature, 37° C; enzyme, pooled human hepatic microsome 0.2 mg protein/mL; test drug concentration, 1.0, 5.0, 10, 20 µmol/L (four points).

Each five kinds of substrates, human hepatic microsome, or a test drug in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

(Results)
Compound No. I-0837: five kinds>20 μmol/L
Compound No. I-2291: five kinds>20 μmol/L
Compound No. I-1788: five kinds>20 μmol/L
Compound No. I-1079: five kinds>20 μmol/L Test Example 8

FAT Test

20 μl, of freezing-stored rat typhoid bacillus (*Salmonella typhimurium* TAD98 strain. TA100 strain) is inoculated on 10 mL of a liquid nutrient medium (2.5% Oxoid nutrient broth No. 2), and this is cultured before shaking at 37° C. for 10 hours. 9 mL of a bacterial solution of the TA98 strain is centrifuged (2000× g, 10 minutes) to remove a culturing solution, the bacteria is suspended in 9 mL of a Micro F buffer ($K_2HPO_4$: 3.5 g/L, $KH_2PO_4$: 1 g/L, $(NH_4)SO_4$: 1 g/L, trisodium citrate dihydrate: 0.25 g/L, $MgSO_4 \cdot 7H_2O$: 0.1 g/L), the suspension is added to 110 mL of an Exposure medium (Micro F buffer containing Biotin: 8 μg/mL, histidine: 0.2 μg/mL, glucose: 8 mg/mL), and the TA100 strain is added to 120 mL of the Exposure medium relative to 3.16 mL of the bacterial solution to prepare a test bacterial solution. Each 12 μL of a test substance DMSO solution (8 stage dilution from maximum dose 50 mg/mL is at 2-fold ratio), DMSO as a negative control, 50 μg/mL of 4-nitroquinoline-1-oxide DMSO solution for the TA98 strain, 0.25 μg/mL of 2-(furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of 89 mix under the metabolism activating condition) are mixed, and this is shaking-cultured at 37° C. for 90 minutes. 460 μL of the bacterial solution exposed to the test substance is mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group. (−) means that mutagenicity is negative and (+) is positive.

Test Example 9

Solubility Test

The solubility of a compound was determined under a condition in which 1% DMSO was added. 10 mmol/L compound solution was prepared using DMSO, and then 6 μL of the compound solution was added to 594 μL of artificial intestinal juice in pH 6.8 (to 250 mL of 0.2 mol/L potassium dihydrogen phosphate reagent solution was added 118 mL of 0.2 mol/L NaOH reagent solution and water to provide a final volume of 1000 mL). After standing at 25 degrees Celsius for 16 hours, the mixed solution was filtrated with suction. The filtrate was diluted twice with methanol/water (½) and then a concentration in the filtration was measured with HPLC or LC/MS/MS by the absolute calibration method.

(Results)
Compound No. I-0837:>50 μmol/L
Compound No. I-2291:>50 μmol/L
Compound No. I-1788:>50 μmol/L
Compound No. I-1679:>50 μmol/L Test Example 10

Metabolism Stability Test

Using commercially available pooled human hepatic microsomes, a test compound is reacted for a constant time, a remaining rate is calculated by comparing a reacted sample and an unreacted sample, thereby, a degree of metabolism in liver is assessed.

A reaction was performed (oxidative reaction) at 37° C. for 0 minute or 30 minutes in the presence of 1 mmol/L NADPH in 0.2 mL of a buffer (50 mmol/L tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v), mixed and centrifuged at 3000 rpm for 15 minutes. The test compound in the supernatant was quantified by LC/MS/MS, and a remaining amount of the test compound after the reaction was calculated, letting a compound amount at 0 minute reaction time to be 100%.

(Results) The remaining rate at the compound concentration 0.5 μmol/L are shown below.
Compound No. I-0837: 99%
Compound No. I-2291: 94%
Compound No. I-1788: >99.9%

Test Example 11 hERG Test

For the purpose of assessing risk of an electrocardiogram QT interval prolongation, effects on delayed rectifier K+ current ($I_{K_r}$), which plays an important role in the ventricular repolarization process, is studied using HEK293 cells expressing human ether-a-go-go related gene (hERG) channel.

After a cell was retained at: a membrane potential of −80 mV by whole cell patch clamp method using an automated patch clamp system (PatchXpress 7000A, Axon Instruments Inc.), $I_{K_r}$ induced by depolarization pulse stimulation at +50 mV for 2 seconds and, further, repolarization pulse stimulation at −50 mV for 2 seconds is recorded. After the generated current is stabilized, extracellular solution (NaCl: 137 mmol/L, KCl: 4 mmol/L, $CaCl_2 \cdot 2H_2O$: 1.8 mmol/L, $MgCl_2 \cdot 6H_2O$: 1 mmol/L, glucose: 10 mmol/L, HEPES (4-(2-hydroxyethyl)-1-piperazineethanesulfonic acid): 10 mmol/L, pH=7.4) in which the test compound had been dissolved at an objective concentration (1.0 μmol/L) is applied to the cell under the room temperature condition for 10 minutes. From the recording $I_{K_r}$, an absolute value of the tail peak current is measured based on the current value at the resting membrane potential using an analysis software (DataXpress ver. 1, Molecular Devices Corporation). Further, the % inhibition relative to the tail peak current before application of the test substance is calculated, and compared with the vehicle-applied group (0.1% dimethyl sulfoxide solution) to assess influence of the test substance on $I_{K_r}$.

Test Example 12

Metabolic Stability Test

The test compound is reacted for a given period of time using cryopreserved rat hepatneytes that are prepared and the residual ratio is calculated based on the comparison between reacted and unreacted samples to evaluate the degree of hepatic metabolism.

The compound is reacted in the Williams E medium containing $1.0 \times 10^6$ cells/mL of cryopreserved rat hepatocytes at a temperature of 37° C. for 0, 1 or 2 hours. After reaction, 50 μL of reaction solution is added to and mixed with 100 μL of a solution containing methanol and acetonitrile in the proportion of one to one (v/v) and the mixture is centrifuged at 3000 rpm for 15 minutes. The test compound contained in the centrifugal supernatant is quantitated using a LC/MS/MS system and the residual ratio of the test compound after reaction is calculated regarding the amount of compound after the reaction for 0 minute as 100%.

Test Example 13

Protein Binding Test

The unbound fraction the present compound in serum was measured using serum of various species.

The reactive conditions are as follows: Evaluation method, Equilibrium dialysis; Reaction time, 24 hours; Reaction temperature, 37° C.; Concentration of the present compound, 2 μg/mL.

The test solution was added to each serum and the mixture was agitated to prepare the serum samples at the concentration mentioned above. Each serum sample was added into one side or the cell and phosphate buffered saline (PBS) was added into the other side to perform equilibrium dialysis at 37° C. for 24 hours. Then, the concentration of the compounds in the samples that were obtained from both sides was measured by LC/MS/MS.

(Result) The ratio of PBS concentration to serum concentration is expressed as unbound fraction.

Compound No. I-0837: 2.1%
Compound No. I-2291: 4.5%
Compound No. I-1679: 1.8%
Compound No. I-2011: 0.5%

Test Example 14

Bioavailability (BA) Test

Materials and Methods for Experiment of BA
(1) Animals: Mice or SD rats were used
(2) Breeding conditions: Mice or SD rats were allowed to freely take solid food and sterilized tap water.
(3) Dose and grouping: orally or intravenously administered at a predetermined dose; grouping was as follows (Dose depends one the compound)
Oral administration: 0.3 to 30 mg/kg (n=2 to 3)
Intravenous administration: 0.5 to 10 mg/kg (n=2 to 3)

(4) Preparation of dosing solution: for oral administration, in a solution or a suspension state: for intravenous administration, in a solubilized state
(5) Administration method: in oral administration, forcedly administer into ventriculus with oral probe; in intravenous administration, administer from caudal vein with a needle-equipped syringe
(6) Evaluation items: blood was collected over time, and the plasma concentration of drug was measured by by LC/MS/MS
(7) Statistical analysis: regarding the transition of the plasma concentration or the present compound, the area under the plasma concentration-time curve (AUC) was calculated by non-linear least squares program WinNonlin (Registered trade name), and the bioavailability (BA) was calculated the AUCs of the oral administration group and intravenous administration group (Results)
Compound No. I-0837: 46%
Compound No. I-2291: 83%
Compound No. I-1788: 31%
Compound No. I-1079: >99.9%

Preparation Example 1

A granule containing the following ingredient is prepared.

| Ingredient | Compound of the formula (I) | 10 mg |
|---|---|---|
| | Lactose | 700 mg |
| | Corn starch | 274 mg |
| | HPC—L | 16 mg |

The compound of the formula (I) and lactose are passed through a 60 mesh sieve. Corn starch is passed through a 120 mesh sieve. Those are mixed with a V-type mixing machine. An aqueous solution of HPC-L (low viscosity hydroxypropylcellulose) is added to a mixture powder, and this is kneaded, granulated (extrusion granulation, pore diameter 0.5 to 1 mm), and dried. The resulting dry granule is sieved with a vibration sieve (12/60 mesh) to obtain as granule.

Preparation Example 2

A powder for filling into a capsule containing the following ingredients is prepared.

| Ingredient | Compound of the formula (I) | 15 mg |
|---|---|---|
| | Lactose | 90 mg |
| | Corn starch | 42 mg |
| | HPC—L | 3 mg |

The compound of the formula (1), and lactose are passed through as 60 mesh sieve. Corn starch is passed through a 120 mesh sieve. These are mixed, a HPC-L solution is added to the mixed powder, this is kneaded, granulated, and dried. The resulting dry granule is adjusted in a size, and 150 mg of it is filled into a No. 4 hard gelatin capsule.

Preparation Example 3

A tablet containing the following ingredients is prepared.

| Ingredient | Compound of the formula (I) | 10 mg |
|---|---|---|
| | Lactose | 90 mg |
| | Microcrystaline cellulose | 30 mg |

-continued

| | | |
|---|---|---|
| CMC—Na | 15 mg | |
| Magnesium stearate | 5 mg | |

The compound of the formula (Ia), lactose, microcrystalline cellulose, CMC-Na (carboxymethylcellulose sodium salt) are passed through a 60 mesh sieve, and mixed. Magnesium stearate is mixed into a mixture powder to obtain a mixture powder for tabletting. The present mixed powder is directly compressed to obtain a 150 mg tablet.

Formulation Example 4

The following ingredients are warmed, mixed, and sterilized to obtain an injectable.

| Ingredient | Compound of the formula (I) | 3 mg |
|---|---|---|
| | Nonionic surfactant | 15 mg |
| | Purified water for injection | 1 ml |

Formulation Example 5

A cataplasm containing the following ingredients is prepared.

| Ingredient | Compound of the formula (I) | 50 mg |
|---|---|---|
| | aqueous-based (5% ethanol/5% butylene glycol/90% purified water) | 950 mg |
| | glycerin | |
| | kaoline | |
| | aqueous polyvinyl alcohol | |

The compound of the formula (I) is added to aqueous-based. The mixture is irradiated by ultrasonic for 15 minutes and then is sufficiently stirred to obtain a solution. 5 part of glycerin, 1 part of kaoline and 5 part of aqueous polyvinyl alcohol are homogeneously mixed and 1 part of the resulting solution is added to the above solution including the compound of the formula (I). The obtained solution is mixed and to give a paste form and the resulting paste is applied to an non-woven fabric. The resulting composition a covered by polyester film to give a cataplasm.

As shown, the compounds described in the present specification showed inhibiting activity on $P2X_3$ receptor and analgesic activity and treating effect on overactive bladder. Furthermore, as the compounds of the invention are effective on $P2X_3$ subtype, the compounds are also considered to have inhibiting activity on $P2X_{2/3}$ receptor, which comprises $P2X_3$ subtype.

[Industrial Applicability]

The compounds of the general formula (I), the general formula (II), the general formula (III), the general formula (IV), the general formula (VII), the general formula (VIII) and the general formula (IX) have an antagonistic effect on $P2X_3$ and/or $P2X_{2/3}$ receptor and are useful in the treatment of diseases or conditions associated with a $P2X_3$ and/or $P2X_{2/3}$ receptor, such as chronic pain, urination disorder, etc.

The invention claimed is:

1. A compound selected from

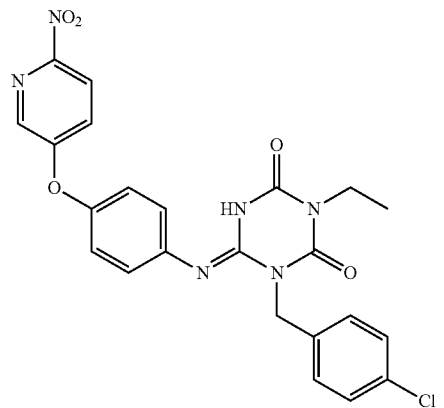

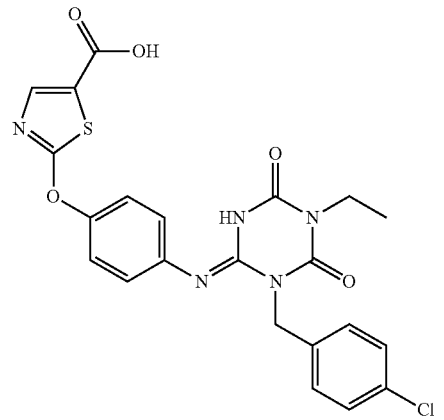

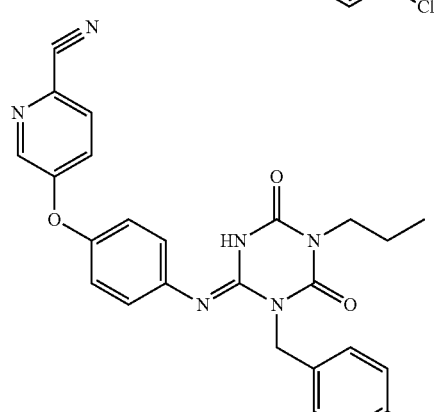

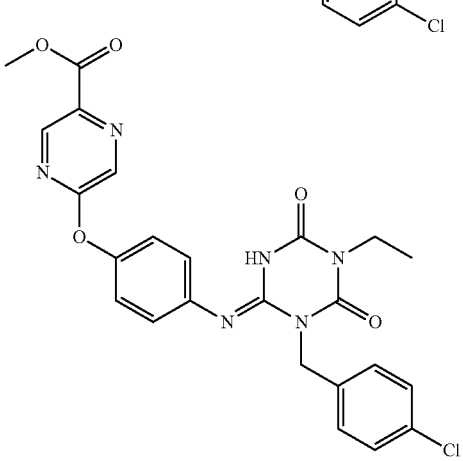

1567
-continued
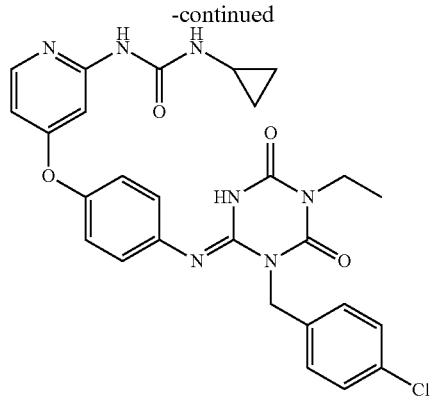
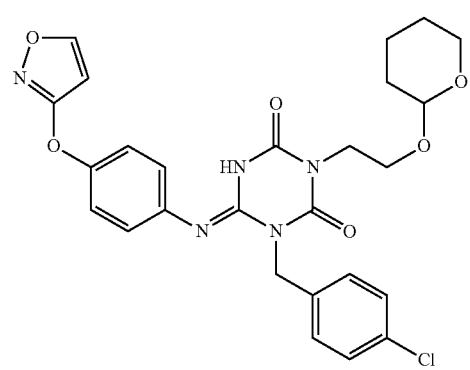
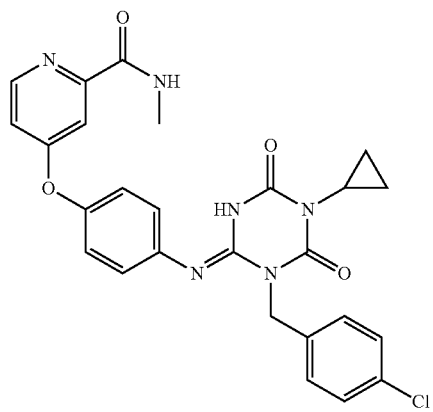
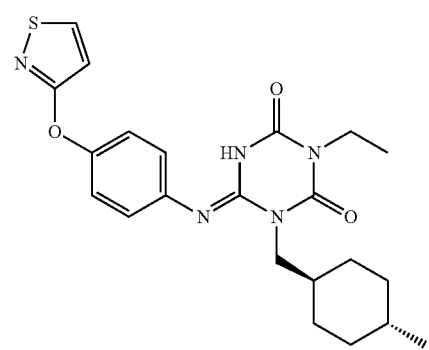
1568
-continued
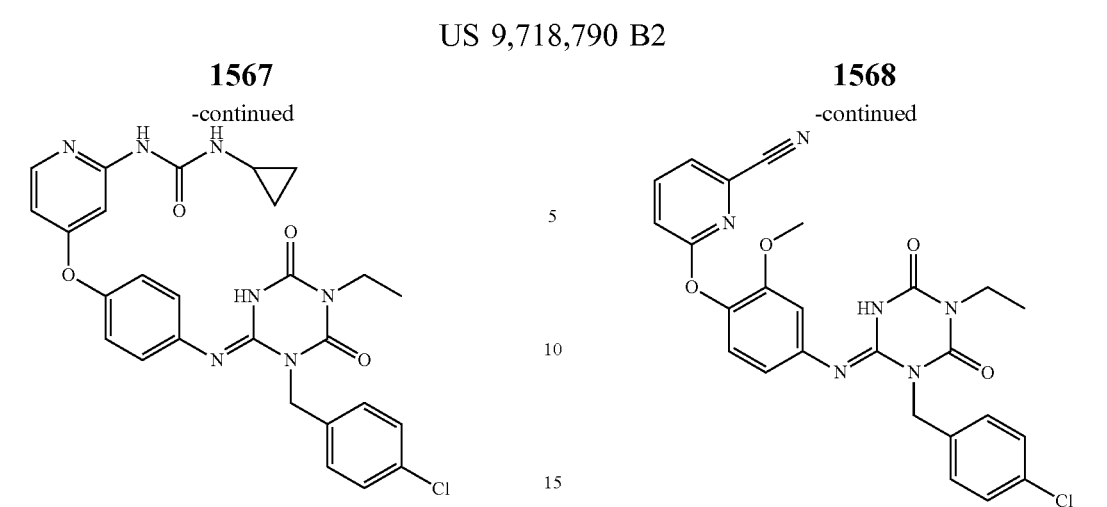
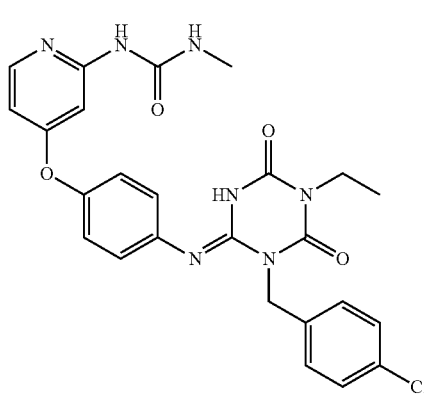
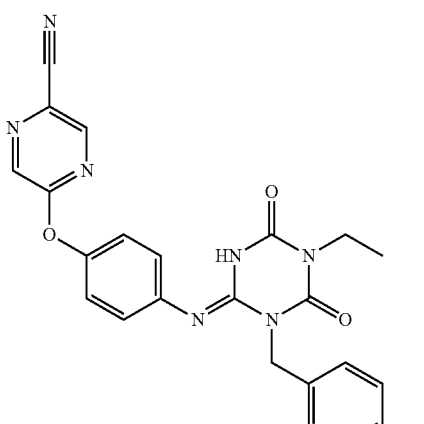
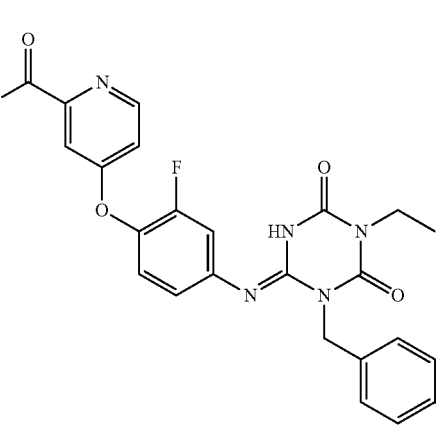

1569

-continued

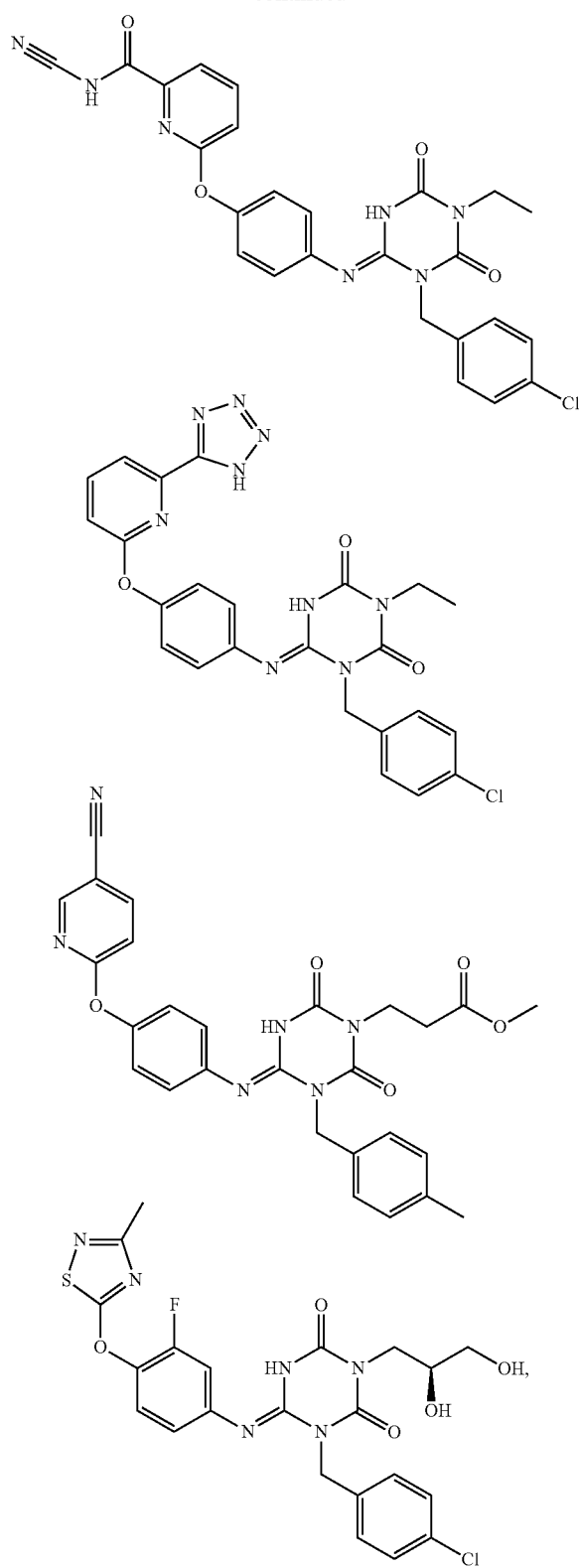

or a pharmaceutically acceptable salt thereof. or a solvate thereof.

2. A pharmaceutical composition comprising at least one compound according to claim 1, or its pharmaceutically acceptable salt, or solvate thereof.

3. The pharmaceutical composition according to claim 2, wherein the composition has a $P2X_3$ and/or $P2X_{2/3}$ receptor antagonistic effect.

4. The compound according to claim 1, having the formula:

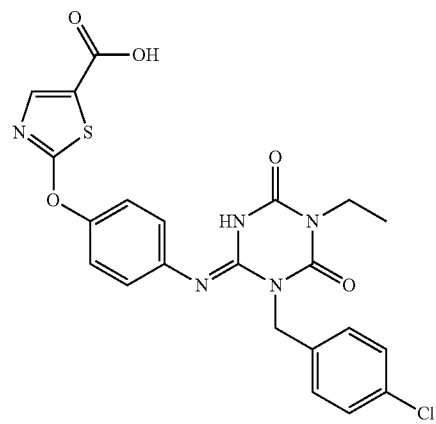

or its pharmaceutically acceptable salt, or solvate thereof.

5. The compound according to claim 1, having the formula:

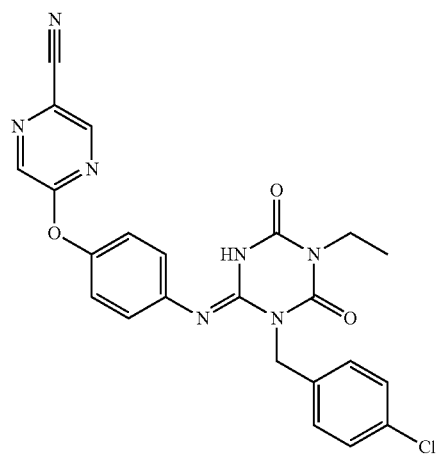 [SMILES: CCn1c(=O)[nH]/c(=N\c2ccc(Oc3cnc(C#N)cn3)cc2)n(Cc2ccc(Cl)cc2)c1=O]

or its pharmaceutically acceptable salt, or solvate thereof.

6. The compound according to claim 1, having the formula:

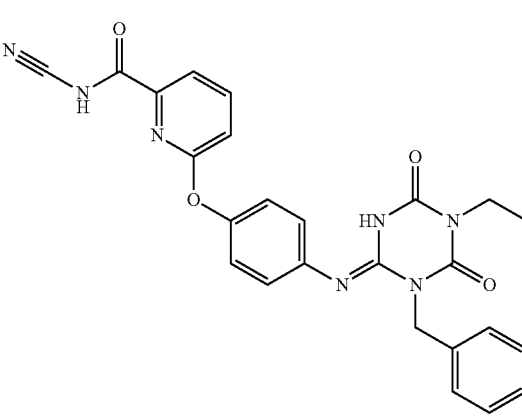

or its pharmaceutically acceptable salt, or solvate thereof.

7. The compound according to claim 1, having the formula:

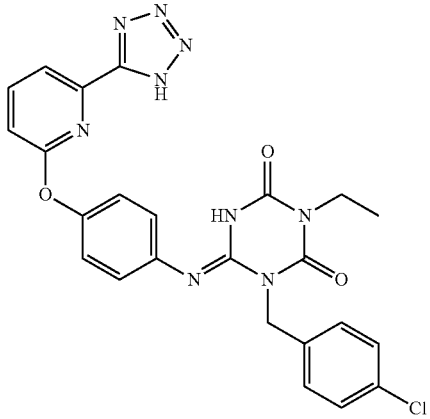 [SMILES: CCn1c(=O)[nH]/c(=N\c2ccc(Oc3cccc(-c4nnn[nH]4)n3)cc2)n(Cc2ccc(Cl)cc2)c1=O]

or its pharmaceutically acceptable salt, or solvate thereof.

8. The compound according to claim 1, having the formula:

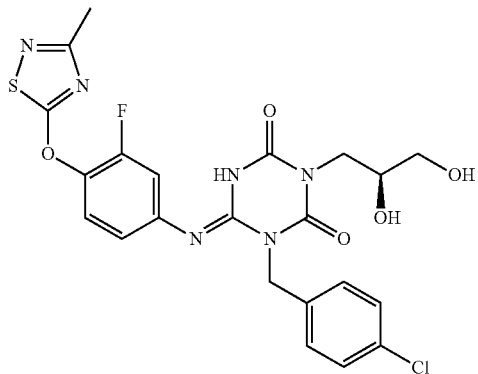 [SMILES: Cc1nsc(Oc2ccc(/N=c3\[nH]c(=O)n(C[C@H](O)CO)c(=O)n3Cc3ccc(Cl)cc3)cc2F)n1]

or its pharmaceutically acceptable salt, or solvate thereof.

9. A pharmaceutical composition comprising a compound according to claim 4, or its pharmaceutically acceptable salt, or solvate thereof.

10. The pharmaceutical composition according to claim 9 wherein the composition has a $P2X_3$ and/or $P2X_{2/3}$ receptor antagonistic effect.

* * * * *